(12) United States Patent
Han et al.

(10) Patent No.: US 12,280,124 B2
(45) Date of Patent: Apr. 22, 2025

(54) ANTIBODY-DRUG CONJUGATES COMPRISING GLP1 PEPTIDOMIMETICS AND USES THEREOF

(71) Applicant: REGENERON PHARMACEUTICALS, INC., Tarrytown, NY (US)

(72) Inventors: Amy Han, Hockessin, DE (US); Haruka Okamoto, New York, NY (US); William Olson, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/475,248

(22) Filed: Sep. 14, 2021

(65) Prior Publication Data
US 2022/0096648 A1    Mar. 31, 2022

Related U.S. Application Data

(60) Provisional application No. 63/077,983, filed on Sep. 14, 2020.

(51) Int. Cl.
*A61K 47/68* (2017.01)
*A61P 3/04* (2006.01)

(52) U.S. Cl.
CPC ...... *A61K 47/6849* (2017.08); *A61K 47/6811* (2017.08); *A61P 3/04* (2018.01)

(58) Field of Classification Search
CPC .... A61K 47/6849; A61K 47/6811; A61P 3/04
See application file for complete search history.

(56) References Cited

U.S. PATENT DOCUMENTS

| 2006/0275288 A1 | 12/2006 | Grihalde et al. |
| 2012/0148586 A1 | 6/2012 | Chou et al. |
| 2018/0311372 A1 | 11/2018 | Cheng et al. |
| 2018/0333504 A1 | 11/2018 | Han et al. |
| 2019/0070306 A1 | 3/2019 | Han et al. |

FOREIGN PATENT DOCUMENTS

| EP | 3034514 A1 | 6/2016 | |
| GB | 2551945 A * | 1/2018 | ............. A61K 38/08 |
| WO | 2021231366 A1 | 11/2021 | |
| WO | 2022056494 A1 | 3/2022 | |

OTHER PUBLICATIONS

PA5-111834, from Invitrogen, p. 1, accessed Dec. 4, 2023.*
International Search Report and Written Opinion dated Jan. 4, 2022, from corresponding International Application No. PCT/US2021/050337.
Caina Li et al., "Glutazumab, a novel long-lasting GLP-1/anti-GLP-1R antibody fusion protein, exerts anti-diabetic effects through targeting dual receptor binding sites", Biochemical Pharmacology, vol. 150, Feb. 3, 2018, pp. 46-53.
International Search Report and Written Opinion dated Jul. 18, 2023 from corresponding International Application No. PCT/US2023/064203 (16 pages).
Written Opinion of the International Preliminary Examining Authority dated Feb. 7, 2024 for corresponding International Application No. PCT/US2023/064203 (12 pages).

* cited by examiner

*Primary Examiner* — Li N Komatsu
(74) *Attorney, Agent, or Firm* — Troutman Pepper Locke LLP

(57) ABSTRACT

Described herein are protein-drug conjugates and compositions thereof that are useful, for example, for targeting glucagon-like peptide 1 receptor (GLP1R). In certain embodiments, provided are peptidomimetic payloads and linker-payloads and methods of making same. More specifically, GLP1 peptidomimetics, antibody-drug conjugates, and compositions which comprise anti-GLP1R antibodies and GLP1 peptidomimetic payloads and methods of treating GLP1R-associated conditions are provided.

33 Claims, 101 Drawing Sheets

Specification includes a Sequence Listing.

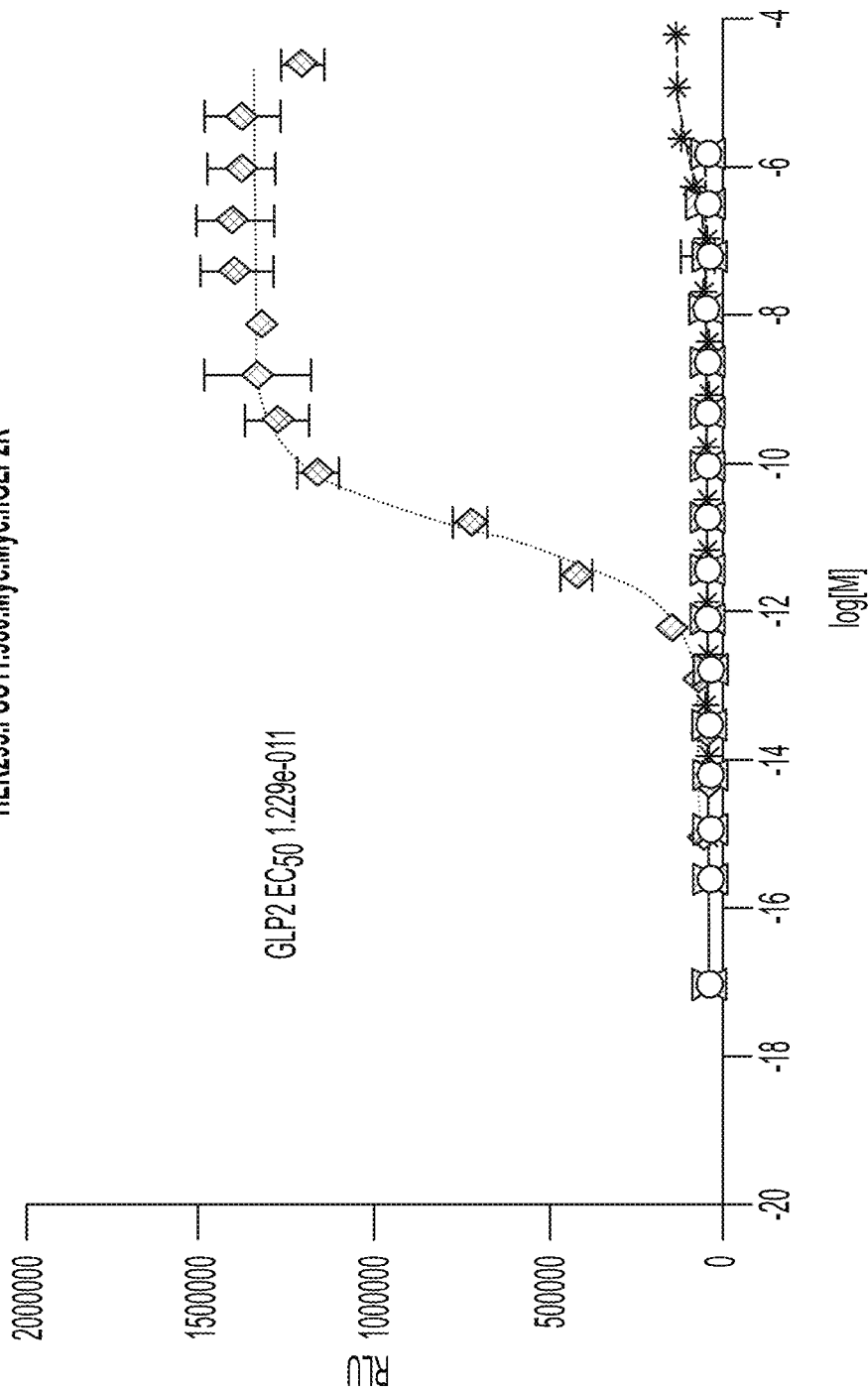

| ATDC | hGLP1R* EC$_{50}$ (nM) | Ratio |
|---|---|---|
| Anti-GLP1R mAb1-4 PEG-GLP1R agonist | 2.8E-11 | 90X |
| Isotype control mAb3-4 PEG-GLP1R agonist | 2.5E-09 | |
| Anti-GLP1R mAb1-8 PEG-GLP1R agonist | 2.2E-11 | 136X |
| Isotype control mAb3-8 PEG-GLP1R agonist | 2.9E-09 | |
| Anti-GLP1R mAb1-12 PEG-GLP1R agonist | 4.4E-11 | 53X |
| Isotype control mAb3-12 PEG-GLP1R agonist | 2.3E-09 | |
| Anti-GLP1R mAb1-24PEG-GLP1R agonist | 4.9E-11 | 30X |
| Isotype control mAb3-24PEG-GLP1R agonist | 1.9E-09 | |
| GLP-1 | 4.7E-11 | |
| Dulaglutide | 9.5E-11 | |

FIG. 7A

| Assay | | Linker-Payload 11 (LP11) |
|---|---|---|
| GLP1R LUC $EC_{50}$ (nM) | | 0.016 nM |
| GLP2R, GIPR, or GCGR $EC_{50}$ (nM) | | Completely inactive |
| c-AMP $EC_{50}$ | | 0.318 nM |
| Plasma Stability | Mouse T1/2 | > 7 days |
| | Monkey T1/2 | > 2 days |
| | Human T1/2 | > 7 days |
| Liver microsome | T1/2 | >145 min |
| | $CL_{int}$(mic) | < 9.6 μL/min/mg |
| | $CL_{int}$(liver) | <8.6 mL/min/kg |
| Water solubility | | 60 nM |
| Protein binding | | 97.97% |
| hERG $IC_{50}$ | | > 100 μM |
| Ames (TA98 and TA100) in the presence and absence of S9 | | Negative for mutagenicity |

FIG. 8

| Description | DAR | GLP1R LUC EC50(pM) |
|---|---|---|
| Anti-GLP1R mAb2-VL-Qtag-LP11 (GLP1R-ATDC) | 1.2 | 27 |
| Isotype Control mAb2-VL-Qtag-LP11 (control ATDC) | 1.6 | 12000 |
| Anti-GLP1R mAb6-VH-Qtag-LP11 (GLP1R-ATDC) | 1.8 | 110 |
| Isotype Control mAb1-VH-Qtag-LP11 (Control ATDC) | 1.6 | 75000 |
| Linker-Payload | | 37 |
| Payload | | 16 |
| Control | | 28 |

FIG. 10
CONTINUED

| Reagent | ATDC + mAb EC$_{50}$ (M) | EC$_{50}$ fold change compared to 0 nM anti-GLP1R parental mAb |
|---|---|---|
| Anti-GLP1R mAb2-LP11 (VL-Qtag-ATDC) + 100 nM mAb | 1.2E-10 | 4.0 |
| + 10 nM mAb | 4.4E-11 | 1.5 |
| + 1 nM mAb | 2.9E-11 | 1.0 |
| + 0.1 nM mAb | 2.7E-11 | 0.9 |
| + 0.01 nM mAb | 2.4E-11 | 0.8 |
| | 3.0E-11 | 1.0 |

ANTIBODY-DRUG CONJUGATES COMPRISING GLP1 PEPTIDOMIMETICS AND USES THEREOF

CROSS-REFERENCE TO RELATED APPLICATIONS

This application claims priority to U.S. Provisional Patent Application No. 63/077,983, filed Sep. 14, 2020, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Jun. 21, 2024, is named 250298_000251_SL.txt and is 116,101 bytes in size.

FIELD OF THE DISCLOSURE

The present disclosure relates to protein-drug conjugates (e.g., antibody-drug conjugates), pharmaceutical compositions, and methods of treating disease therewith. Also provided are peptidomimetic payloads and linker-payloads and methods of making same. More specifically, the present disclosure relates to protein-drug conjugates (e.g., antibody-drug conjugates) comprising GLP1 peptidomimetics and methods of treating GLP1R-associated conditions therewith.

BACKGROUND OF THE DISCLOSURE

Diabetes is a chronic disease of abnormal glucose metabolism. 425 million people are estimated to be living with diabetes worldwide. Global diabetes drugs include insulin, DPP-4 inhibitors, glucagon-like peptide 1 receptor (GLP1R) agonists, but most patients do not achieve combined treatment goal to manage hyperglycaemia and cardiovascular risk factors.

Glucagon-Like Peptide 1 Receptor (GLP1R) is the receptor for glucagon-like peptide 1 (GLP1) and is expressed in the pancreatic beta cells. GLP1R is also expressed in the brain where it functions in the control of appetite, memory and learning. GLP1R is a member of the secretin family (Class B) of G protein-coupled receptors (GPCRs). Upon binding of its ligand, GLP1, GLP1R initiates a downstream signaling cascade through Gαs G-proteins that raises intracellular cyclic AMP (cAMP) levels, which leads to the transcriptional regulation of genes (Donnelly 2011). Activation of GLP1R results in increased insulin synthesis and release of insulin.

GLP1R and GLP1 are highly validated targets for obesity and type 2 diabetes. Marketed GLP1R agonists increase insulin secretion, thereby lowering blood glucose levels, but they require weekly or more frequent administration.

Accordingly, there is a need in the art for GLP1R agonists with longer duration and better safety. In certain embodiments, the present disclosure meets the needs and provides other advantages.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE DISCLOSURE

Various non-limiting aspects and embodiments of the disclosure are described below.

In one aspect, compound having a structure of Formula (A):

$$BA\text{-}(L\text{-}P)_m \qquad (A),$$

wherein:

BA is an antibody or an antigen-binding fragment thereof;
L is a non-cleavable linker;
P is a payload having the structure selected from the group consisting of:

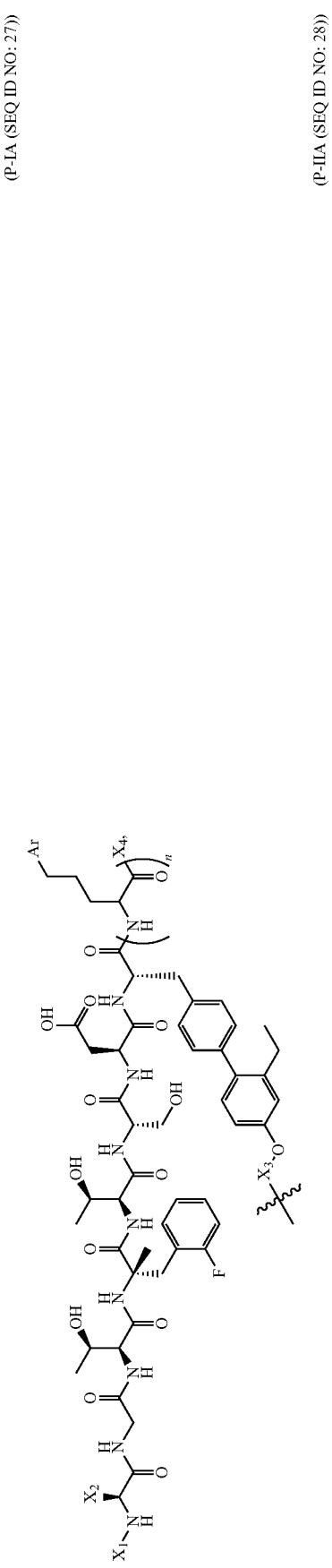
(P-IA (SEQ ID NO: 27))
(P-IIA (SEQ ID NO: 28))
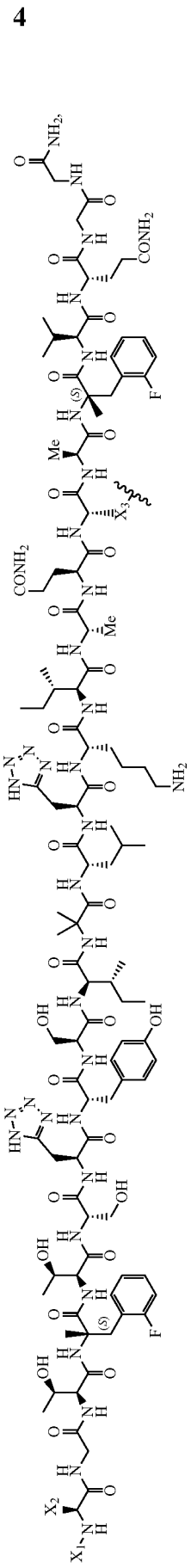
(P-IIIA (SEQ ID NO: 29))

wherein

is the point of attachment of the payload to L;
$X_1$ is selected from H;

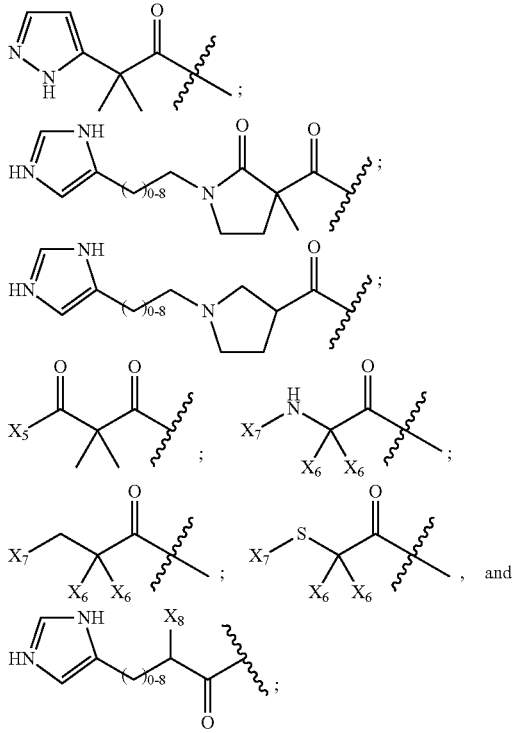

$X_2$ is selected from

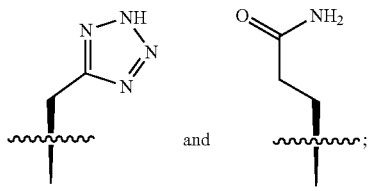

$X_3$ is selected from a bond, —$(CH_2)_{2-6}$—NH—, —$(CH_2)_{2-6}$—Tr—, and —$(CH_2)_{2-6}$—Tr—$(CH_2)_{1-6}$—NH, where Tr is a triazole moiety;
n is 0 or 1;
$X_4$ is selected from —$NH_2$, —OH and —N(H)(phenyl);
$X_5$ is selected from —OH, —$NH_2$, —NH—OH, and

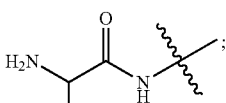

$X_6$ is independently at each occurrence selected from H, —OH, —$CH_3$, and —$CH_2OH$;

$X_7$ is selected from H,

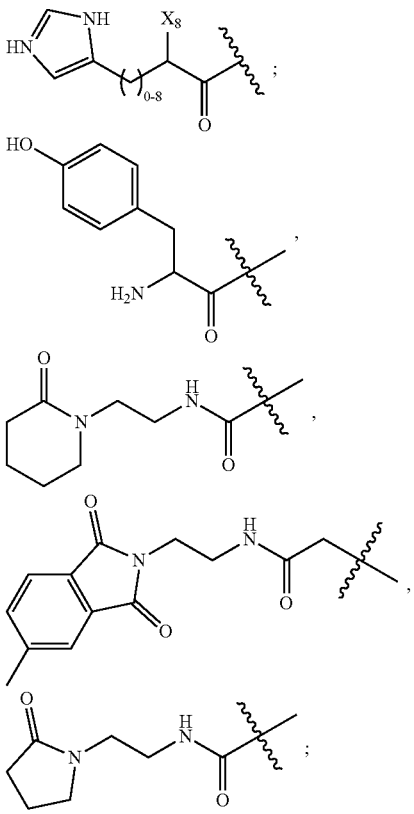

$X_8$ is selected from H, —OH, —$NH_2$, and

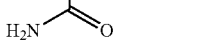

Ar is selected from and

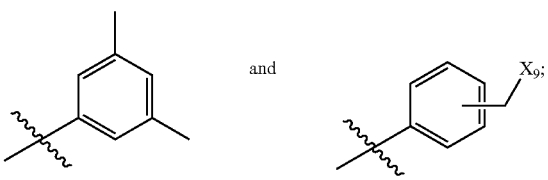

$X_9$ is selected from —$NH_2$,

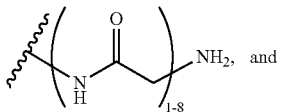

-continued

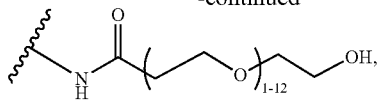

and m is an integer from 1 to 4 or a pharmaceutically acceptable salt thereof.

In another aspect, provided herein is a compound having a structure of Formula (I):

BA-L-P     (I), wherein:

BA is an antibody or an antigen-binding fragment thereof;

L is a non-cleavable linker;

P is a payload having the structure selected from the group consisting of:

wherein $$\xi$$

is the point of attachment of the payload P to L;

$X_1$ is selected from H;

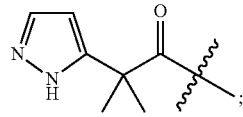

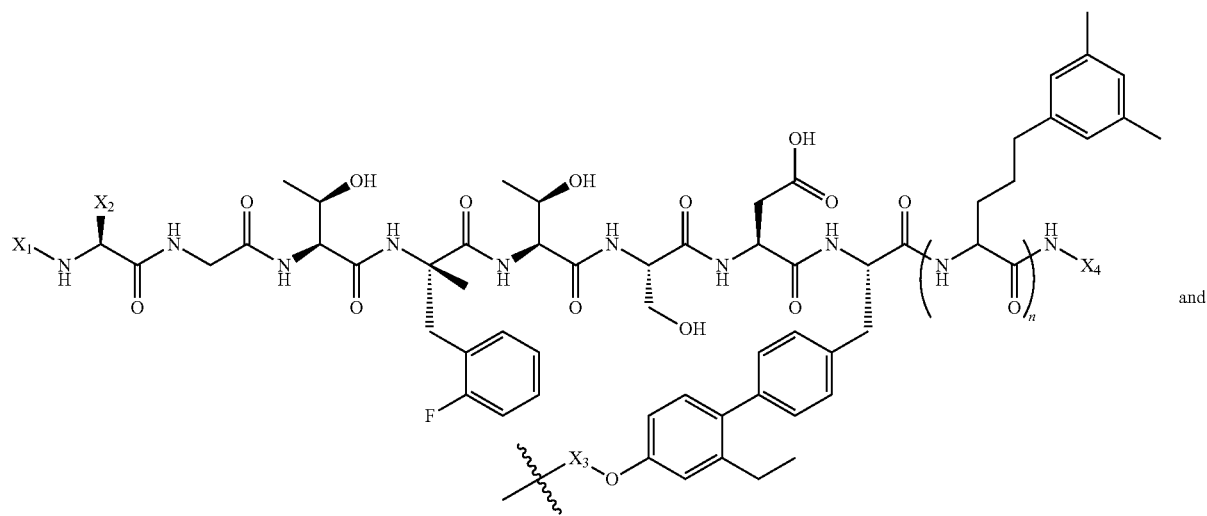

(P-I (SEQ ID NO: 30))

and

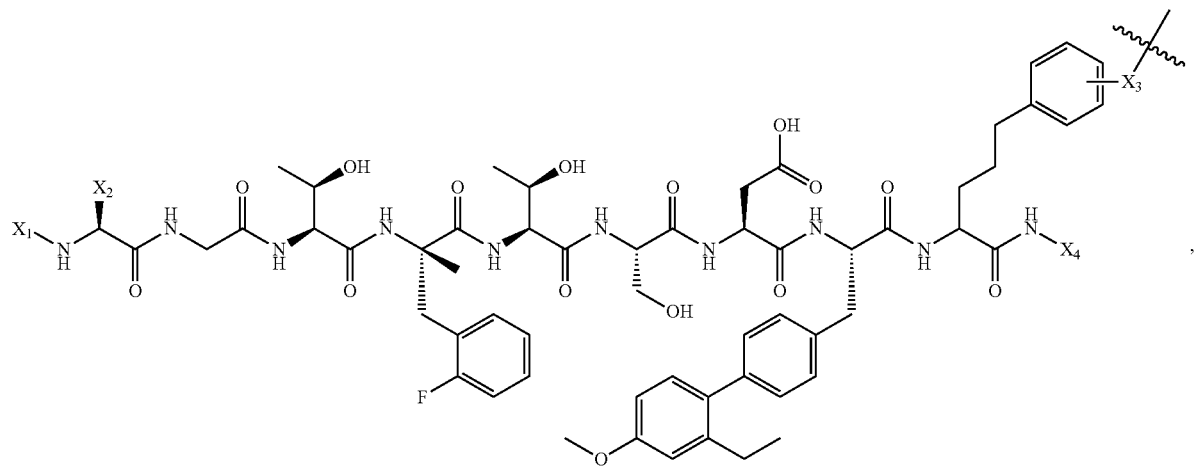

(P-II (SEQ ID NO: 28))

,

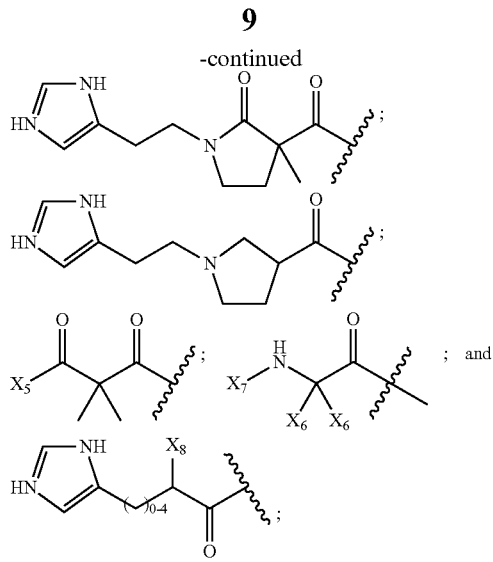

$X_2$ is selected from

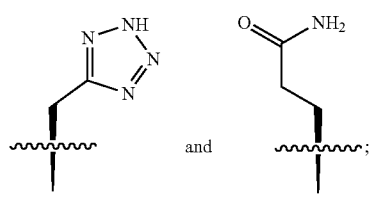

$X_3$ is selected from —$(CH_2)_{2-6}$—NH— and —$(CH_2)_{2-6}$—Tr-, where Tr is a triazole moiety;

n is 0 or 1;

$X_4$ is selected from H and phenyl;

$X_5$ is selected from —OH, —$NH_2$, —NH—OH, and

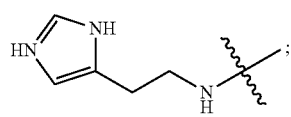 [SMILES: *NCCc1cnc[nH]1]

$X_6$ is independently at each occurrence selected from H, —OH, —$CH_3$, and —$CH_2OH$;

$X_7$ is selected from H,

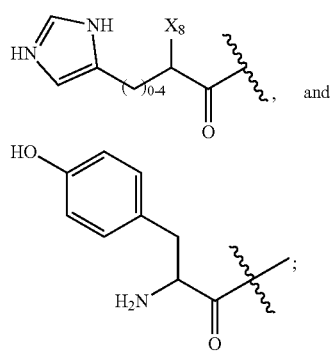

$X_3$ is selected from H, —OH, —$NH_2$, and

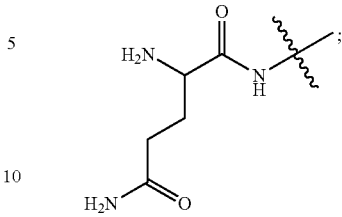

or a pharmaceutically acceptable salt thereof.

In some embodiments of the compound described herein, BA is a Glucagon-like peptide-1 receptor (GLP1R)-targeting antibody or an antigen-binding fragment thereof. In some embodiments, the GLP1R-targeting antibody is a GLP1R agonist antibody. In some embodiments, the GLP1R-targeting antibody is 5A10, 9A10, AB9433-1, h38C2, PA5-111834, NLS1205, MAB2814, EPR21819, or glutazumab.

In some embodiments, the linker L is attached to one or both heavy chains of the BA. In some embodiments, the linker L is attached to one or both heavy chain variable domains of the BA. In some embodiments, the linker L is attached to one or both light chains of the BA. In some embodiments, the linker L is attached to one or both light chain variable domains of the BA.

In some embodiments, the linker L is attached to BA via a glutamine residue. In some embodiments, the glutamine residue is introduced to the N-terminus of one or both heavy chains of the BA. In some embodiments, the glutamine residue is introduced to the N-terminus of one or both light chains of the BA. In some embodiments, the glutamine residue is naturally present in a CH2 or CH3 domain of the BA. In some embodiments, the glutamine residue is introduced to the BA by modifying one or more amino acids. In some embodiments, the glutamine residue is Q295 or N297Q.

In some embodiments, the linker L is attached to BA via a lysine residue.

In some embodiments, the antibody or antigen-binding fragment thereof is aglycosylated. In some embodiments, the antibody or antigen-binding fragment thereof is deglycosylated. In some embodiments, the antigen-binding fragment is an Fab fragment.

In one embodiment, m is 1. In one embodiment, m is an integer from 2 to 4. In one embodiment, m is 2.

In some embodiments, more than one L-P is attached to the BA. In some embodiments, two L-Ps are attached to the BA.

In some embodiments, the linker L has the structure of formula (L'):

—La—Y—Lp-         (L'), wherein La is a first linker covalently attached to the BA;

Y is a group comprising a triazole, and

Lp is absent or a second linker covalently attached to the P, wherein when Lp is absent, Y is also absent.

In some embodiments, Y has a structure selected from the group consisting of:

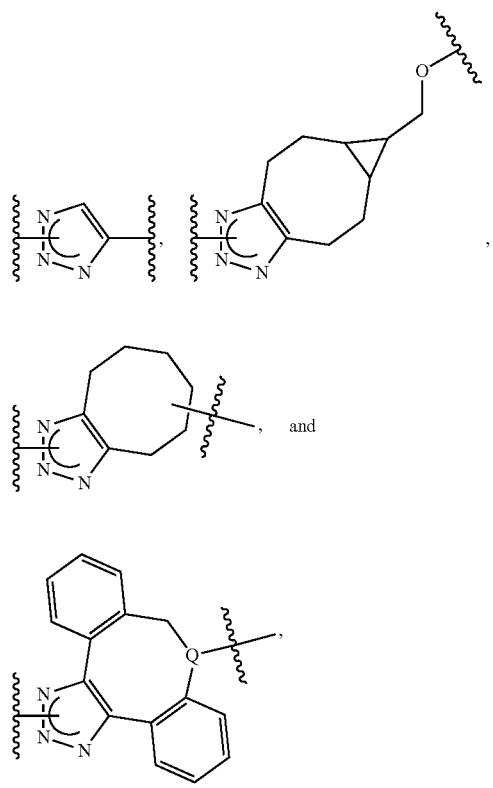

wherein Q is C or N.

In some embodiments, Lp comprises a polyethylene glycol (PEG) segment having 1 to 36 —CH$_2$CH$_2$O— (EG) units. In some embodiments, the PEG segment comprises between 2 and 30 EG units. In some embodiments, the PEG segment comprises between 4 and 24 EG units. In some embodiments, the PEG segment comprises 4 EG units, or 8 EG units, or 12 EG units, or 24 EG units. In some embodiments, the PEG segment comprises 4 EG units. In some embodiments, the PEG segment comprises 8 EG units.

In some embodiments, Y-Lp has a structure selected from the group consisting of:

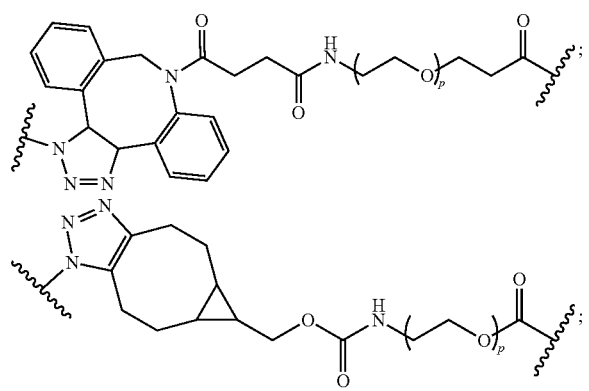

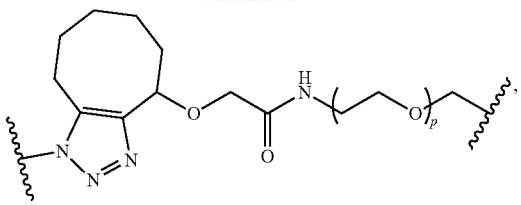

or a triazole regioisomer thereof,
wherein p is an integer from 1 to 36.

In some embodiments, the Lp comprises one or more amino acids selected from glycine, serine, glutamic acid, alanine, valine, and proline and combinations thereof. In some embodiments, the Lp comprises 1 to 10 glycines. In some embodiments, the Lp comprises 1 to 6 serines. In some embodiments, the Lp comprises 1 to 10 glycines and 1 to 6 serines. In some embodiments, the Lp comprises 4 glycines and 1 serine. In some embodiments, the Lp is selected from the group consisting of Gly-Gly-Gly-Gly-Ser (G$_4$S) (SEQ ID NO: 1), Ser-Gly-Gly-Gly-Gly (SG$_4$) (SEQ ID NO: 2), and Gly-Gly-Gly-Gly-Ser-Gly-Gly-Gly-Gly-Ser (G$_4$S-G$_4$S) (SEQ ID NO: 3).

In some embodiments, the Lp comprises a combination of a PEG segment having 1 to 36 EG units and one or more amino acids selected from glycine, serine, glutamic acid, alanine, valine, and proline and combinations thereof. In some embodiments, the serine residue comprises a carbohydrate group. In some embodiments, the serine residue comprises a glucose group.

In some embodiments, Lp has a structure selected from the group consisting of:

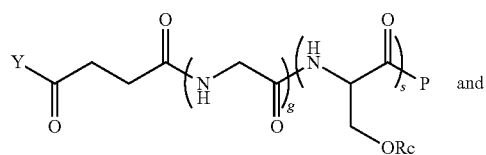

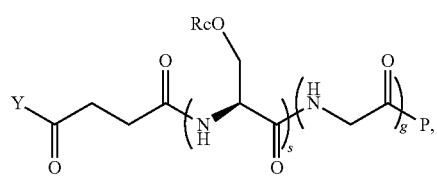

wherein Y is the group comprising a triazole and P is the payload, and wherein Rc is selected from H and glucose, g is an integer from 1 to 10 and s is an integer from 0 to 4.

In some embodiments, Y-Lp has a structure selected from the group consisting of: (SEQ ID NOS 31-36, respectively, in order of appearance)

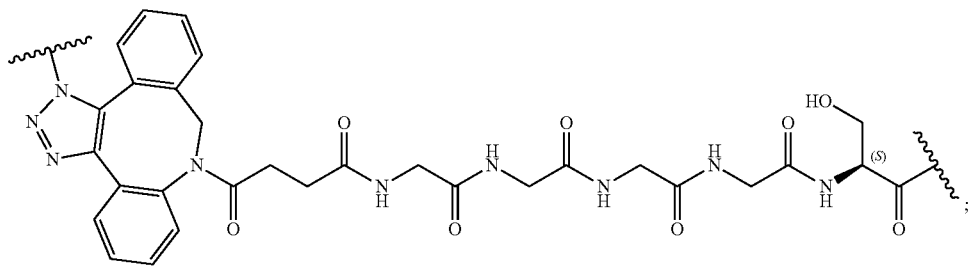
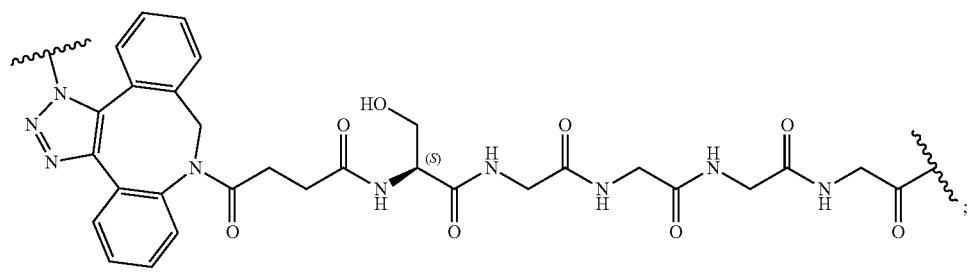
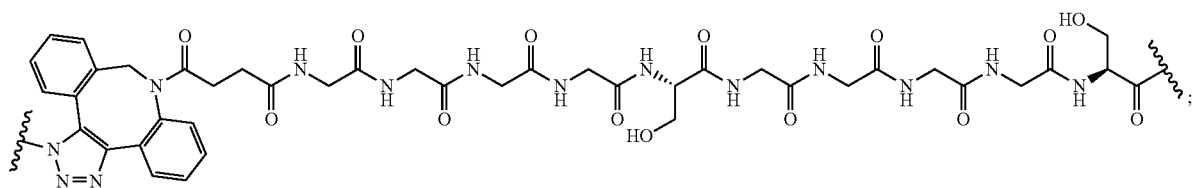
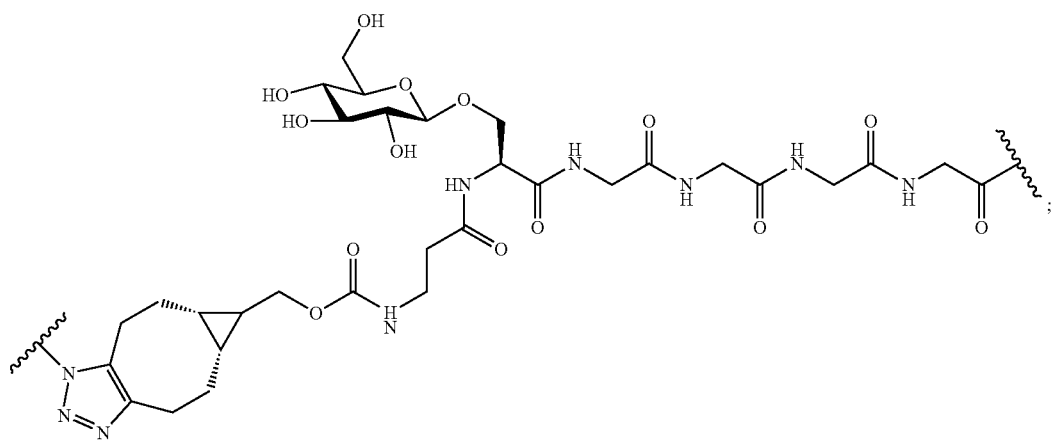
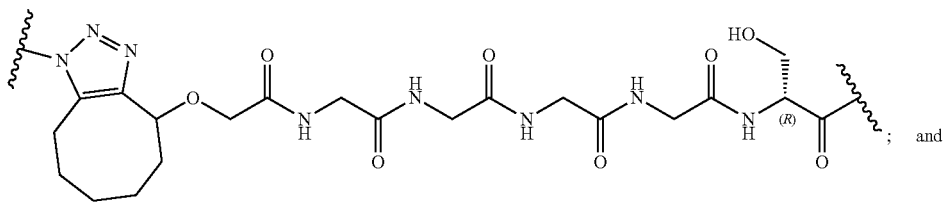

-continued

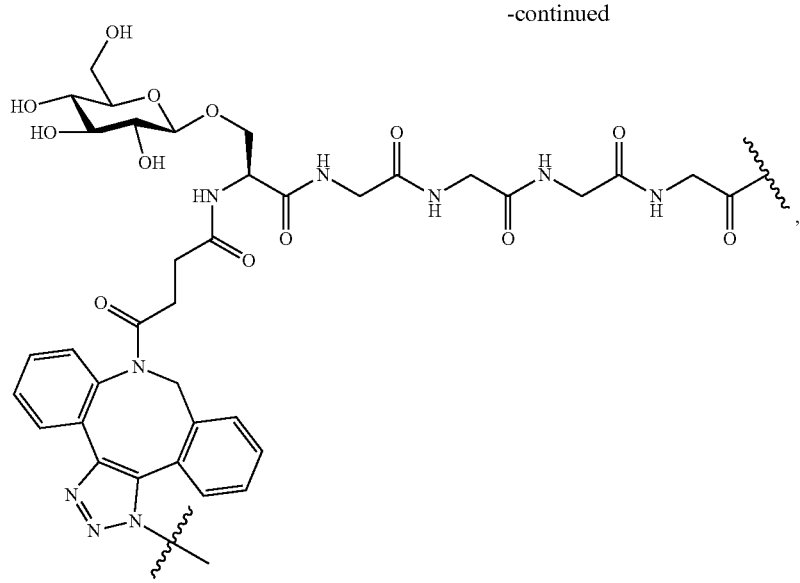

or a triazole regioisomer thereof.

In some embodiments, La comprises a polyethylene glycol (PEG) segment having 1 to 36 —CH$_2$CH$_2$O— (EG) units. In some embodiments, the PEG segment comprises 4 EG units, or 8 EG units, or 12 EG units, or 24 EG units. In some embodiments, the PEG segment comprises 8 EG units. In some embodiments, La has a structure selected from the group consisting of

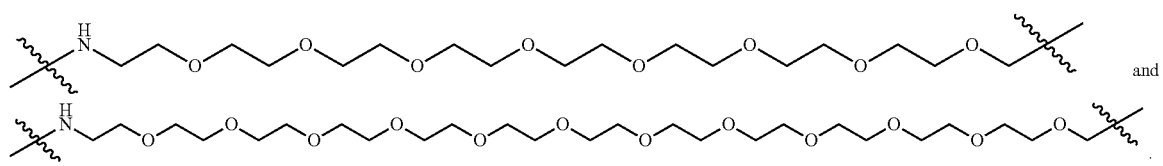

In some embodiments, La comprises one or more amino acids selected from glycine, threonine, serine, glutamine, glutamic acid, alanine, valine, leucine, and proline and combinations thereof. In some embodiments, La comprises 1 to 10 glycines and 1 to 6 serines. In some embodiments, La comprises 4 glycines and 1 serine. In some embodiments, La is selected from the group consisting of Gly-Gly-Gly-Gly-Ser (G$_4$S) (SEQ ID NO: 1), Ser-Gly-Gly-Gly-Gly (SG$_4$) (SEQ ID NO: 2), Gly-Gly-Ser-Gly-Gly-Ser-Gly-Gly (G$_2$S-G$_2$S-G$_2$) (SEQ ID NO: 25), and Gly-Gly-Gly-Gly-Ser-Gly-Gly-Gly-Gly (G$_4$S-G$_4$) (SEQ ID NO: 26).

In some embodiments, La comprises a combination of a PEG segment having 1 to 36 EG units and one or more amino acids selected from glycine, threonine, serine, glutamine, glutamic acid, alanine, valine, leucine, and proline and combinations thereof. In some embodiments, La is selected from the group consisting of (SEQ ID NOS 37-38, respectively, in order of appearance):

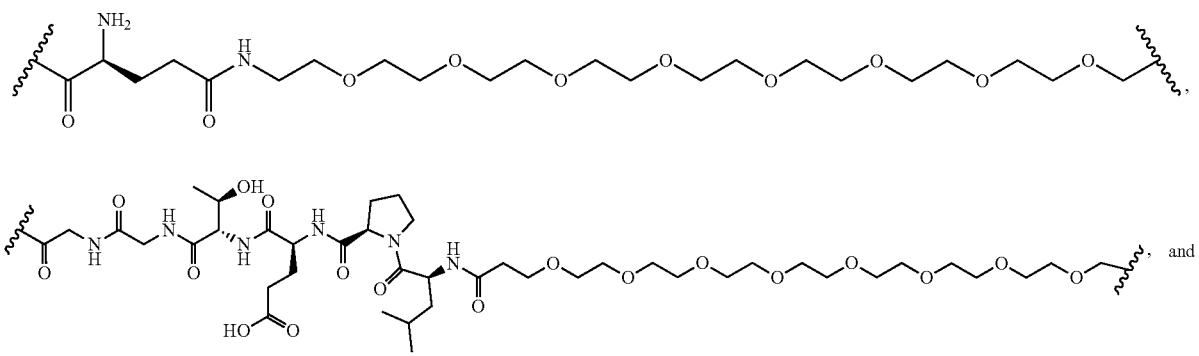

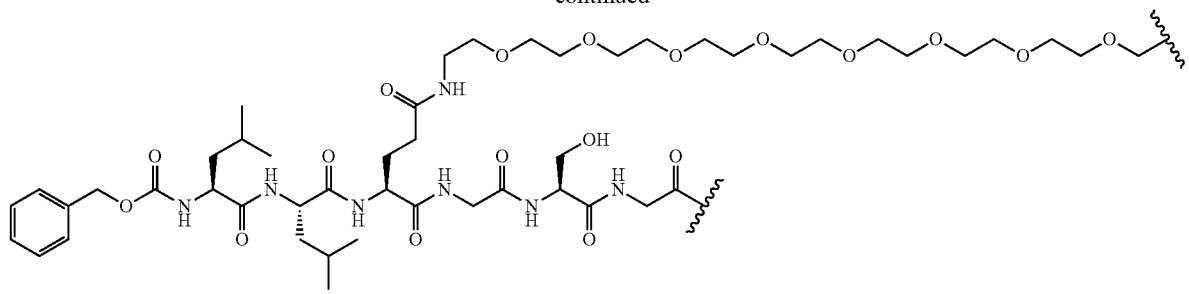

In some embodiments, La comprises a —(CH$_2$)$_{2-24}$— chain. In some embodiments, In some embodiments, La comprises a combination of a —(CH$_2$)$_{2-24}$— chain, a PEG segment having 1 to 36 EG units and one or more amino acids selected from glycine, threonine, serine, glutamine, glutamic acid, alanine, valine, leucine, and proline and combinations thereof. La is selected from the group consisting of (SEQ ID NOS 39-40, respectively, in order of appearance):

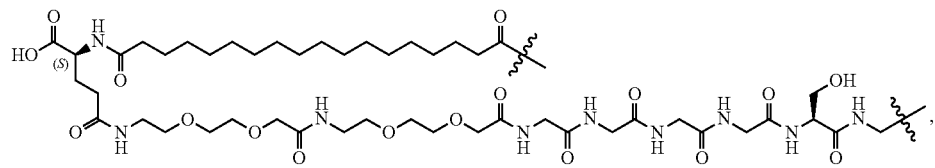

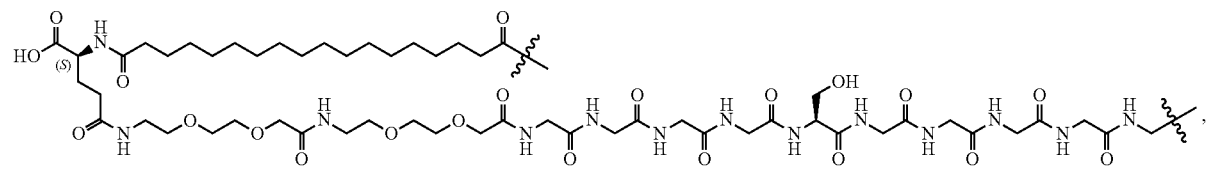

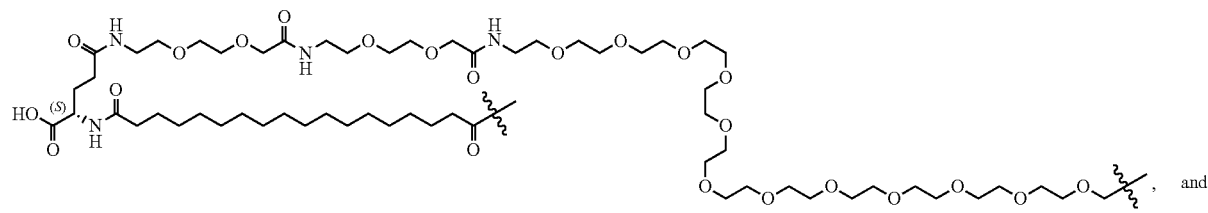, and

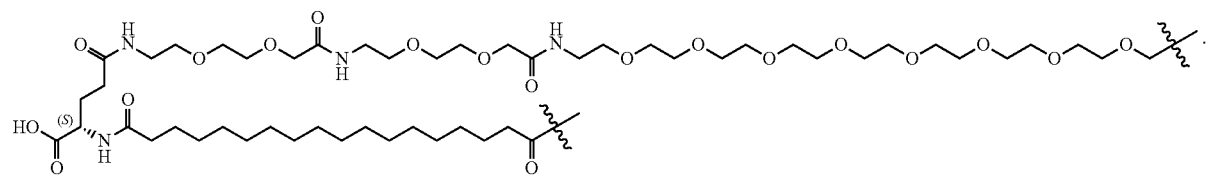.

In various embodiments of the compound described herein, P has the structure (P-I (SEQ ID NO: 30))

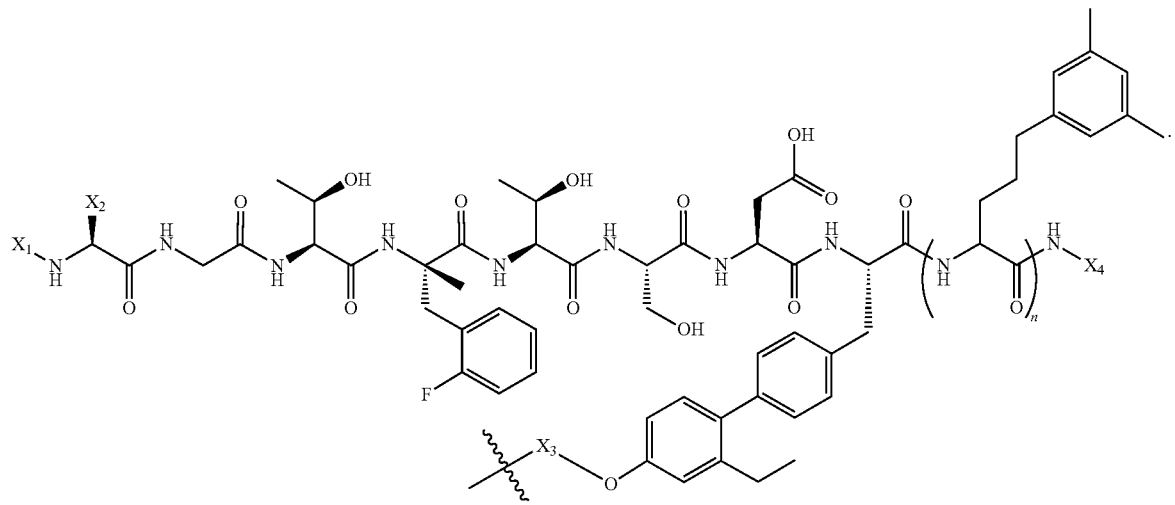

In some embodiments, $X_1$ is H; $X_2$ is

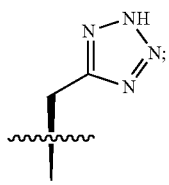

$X_3$ is selected from —(CH$_2$)$_{2-6}$—NH— and —(CH$_2$)$_{2-6}$—Tr-, where Tr is a triazole moiety; n is 1, and $X_4$ is H.

In some embodiments, $X_1$ is

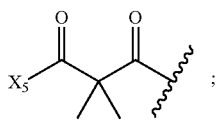

$X_2$ is

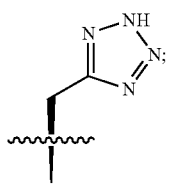

$X_3$ is —(CH$_2$)$_{2-6}$—NH—; n is 1; $X_4$ is H, and $X_5$ is selected from —OH, —NH$_2$, —NH—OH, and

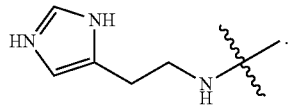

In some embodiments, $X_1$ is

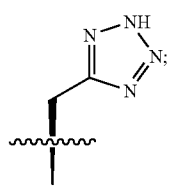

$X_2$ is

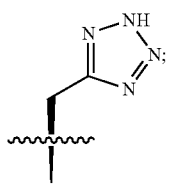

$X_3$ is —(CH$_2$)$_{2-6}$—NH—; n is 1, and $X_4$ is H.

In some embodiments, $X_1$ is

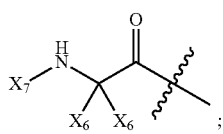

X₂ is

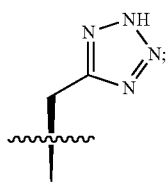

X₃ is —(CH₂)₂₋₆—NH—; n is 1; X₄ is H; X₆ is independently at each occurrence selected from H and —CH₂OH, and X₇ is H.

In some embodiments, X₁ is

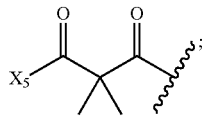

X₂ is

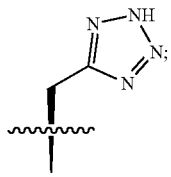

X₃ is —(CH₂)₂₋₆—Tr-, where Tr is a triazole moiety; n is 1; X₄ is H, and X₅ is

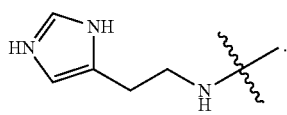 [SMILES: *NCCc1cnc[nH]1]

In some embodiments, X₁ is

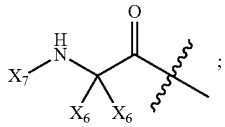

X₂ is

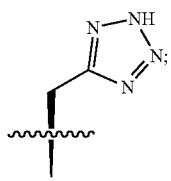

X₃ is —(CH₂)₂₋₆—NH—; n is 1; X₄ is H; X₆ is independently at each occurrence selected from H and —CH₃; X₇ is

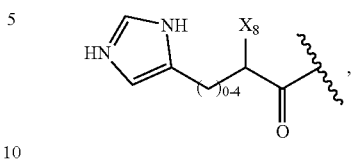

and X₈ is —NH₂.

In some embodiments, X₁ is

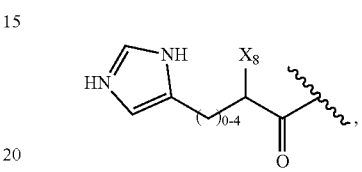

X₂ is

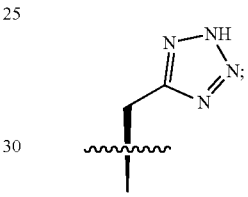

X₃ is —(CH₂)₂₋₆—NH—; n is 1; X₄ is H, and X₃ is H.

In some embodiments, X₁ is

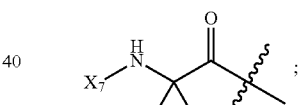

X₂ is

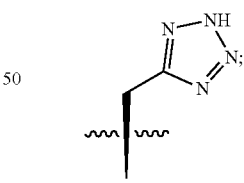

X₃ is —(CH₂)₂₋₆—NH—; n is 1; X₄ is H; X₆ is H at each occurrence; X₇ is

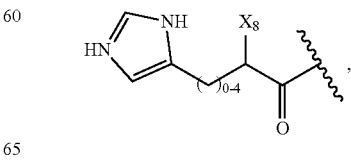

and X₃ is H.

In some embodiments, $X_1$ is

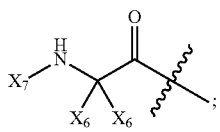

$X_2$ is

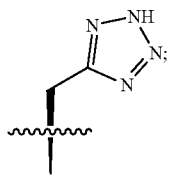

$X_3$ is —$(CH_2)_{2-6}$—NH—; n is 1; $X_4$ is H; $X_6$ is independently at each occurrence selected from H and —$CH_3$; $X_7$ is

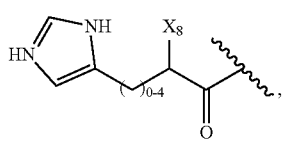

and $X_8$ is

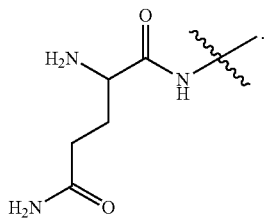

In some embodiments, $X_1$ is

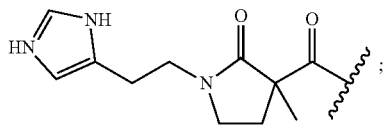 [SMILES: *C(=O)C1(C)CCN(CCc2cnc[nH]2)C1=O ; ";"]

$X_2$ is

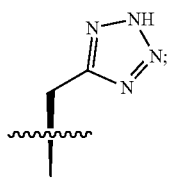

$X_3$ is —$(CH_2)_{2-6}$—NH—; n is 1, and $X_4$ is H.

In some embodiments, $X_1$ is

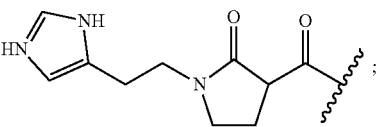 [SMILES: *C(=O)C1CCN(CCc2cnc[nH]2)C1=O ; ";"]

$X_2$ is

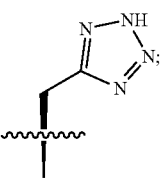

$X_3$ is —$(CH_2)_{2-6}$—NH—; n is 1, and $X_4$ is H.

In some embodiments, $X_1$ is

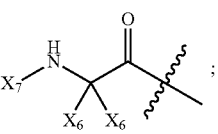

$X_2$ is

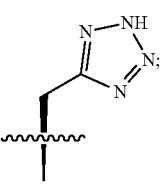

$X_3$ is —$(CH_2)_{2-6}$—NH—; n is 1; $X_4$ is H; $X_6$ is independently at each occurrence selected from H and —$CH_3$, and $X_7$ is

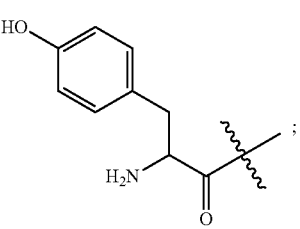 [SMILES: *C(=O)C(N)Cc1ccc(O)cc1]

In some embodiments, $X_1$ is H; $X_2$ is

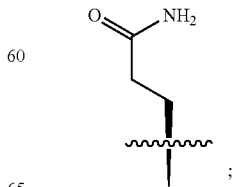

$X_3$ is —$(CH_2)_{2-6}$—NH—; n is 1, and $X_4$ is H.

In some embodiments, $X_1$ is
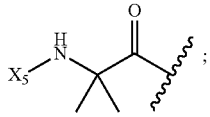
$X_2$ is
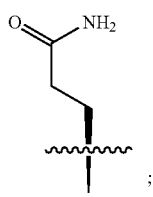
$X_3$ is —$(CH_2)_{2-6}$—NH—; n is 1; $X_4$ is H, and $X_5$ is
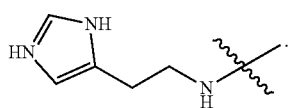
In some embodiments, $X_1$ is
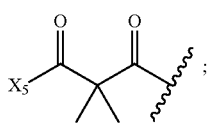
$X_2$ is
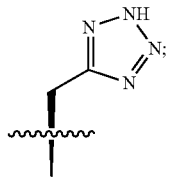
$X_3$ is —$(CH_2)_{2-6}$—NH—; n is 0; $X_4$ is phenyl, and $X_5$ is
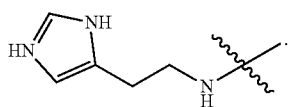
In some embodiments, $X_1$ is
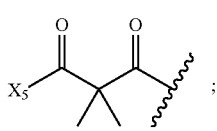
$X_2$ is
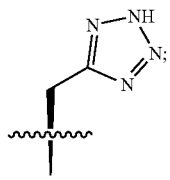
$X_3$ is —$(CH_2)_{2-6}$—NH—; n is 1; $X_4$ is phenyl, and $X_5$ is
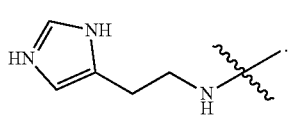 [SMILES: *NCCc1cnc[nH]1]

In various embodiments of the compound described herein, P has the structure
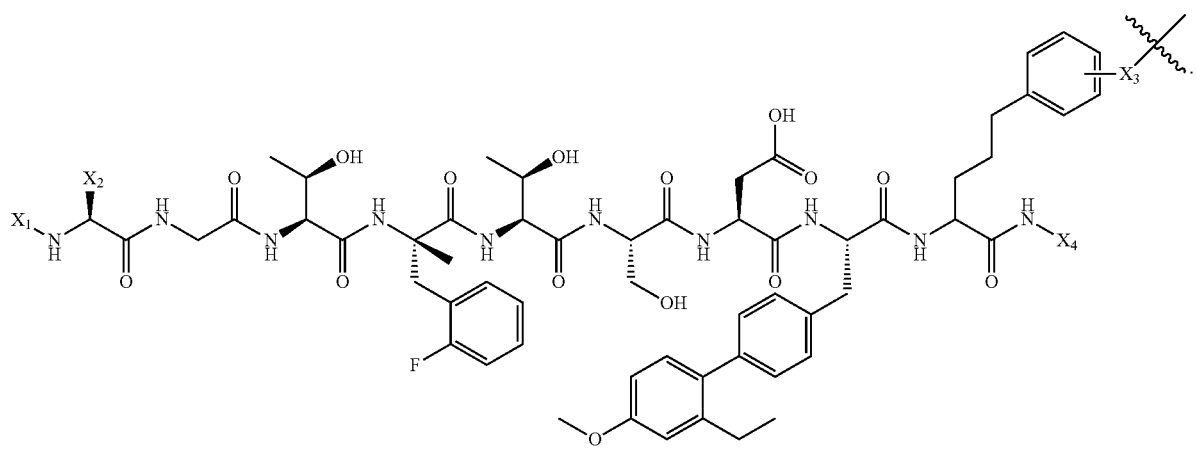
(P-II (SEQ ID NO: 28))
In some embodiments, $X_1$ is
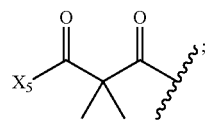
$X_2$ is
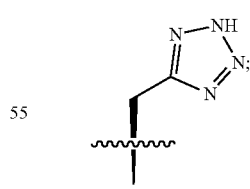
$X_3$ is —$(CH_2)_{2-6}$—NH—; $X_4$ is H, and $X_5$ is
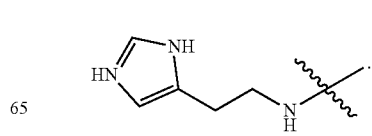

In various embodiments of the compound described herein, P has the structure selected from the group consisting of:
Structure
(SEQ ID NO: 41)
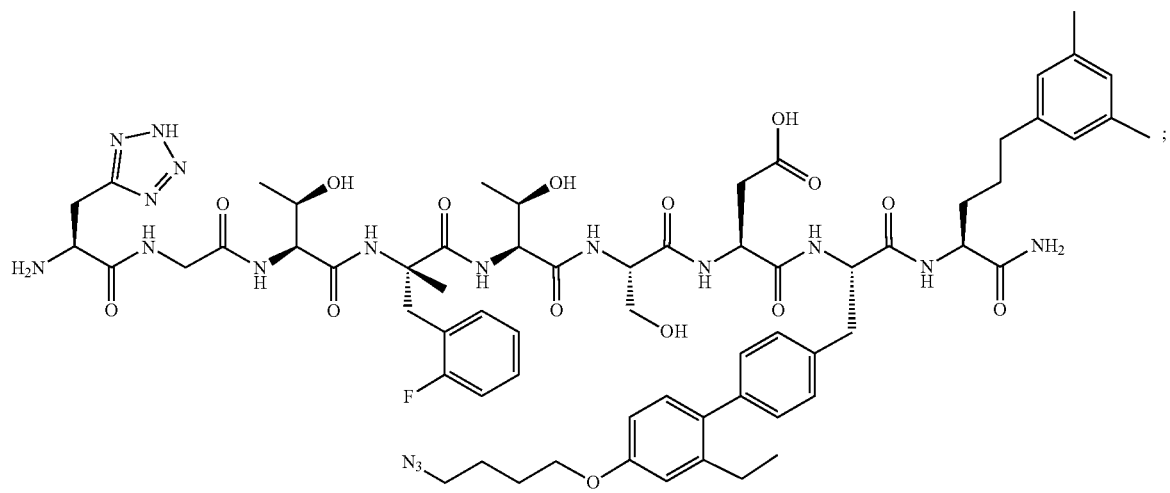
(SEQ ID NO: 42)
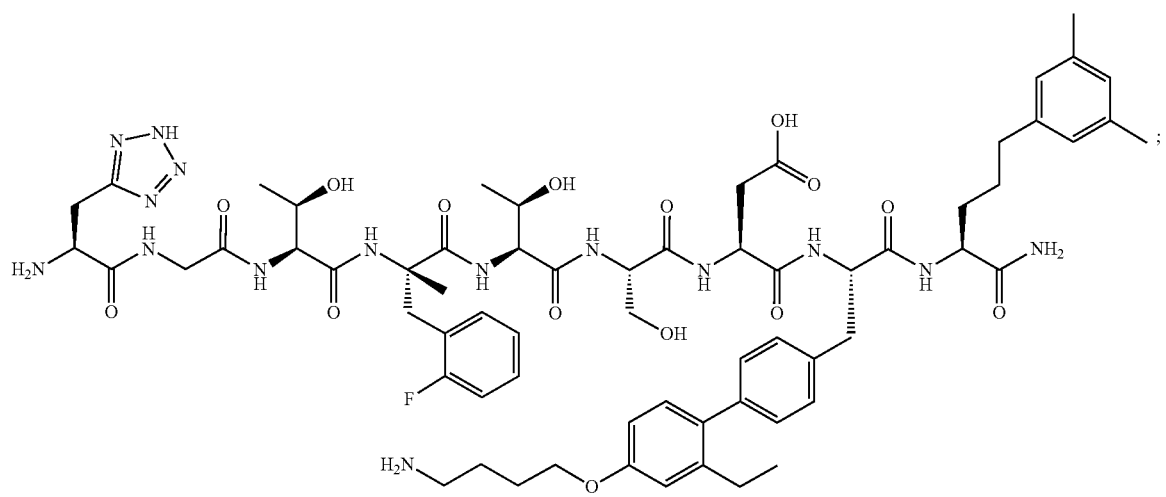
(SEQ ID NO: 43)
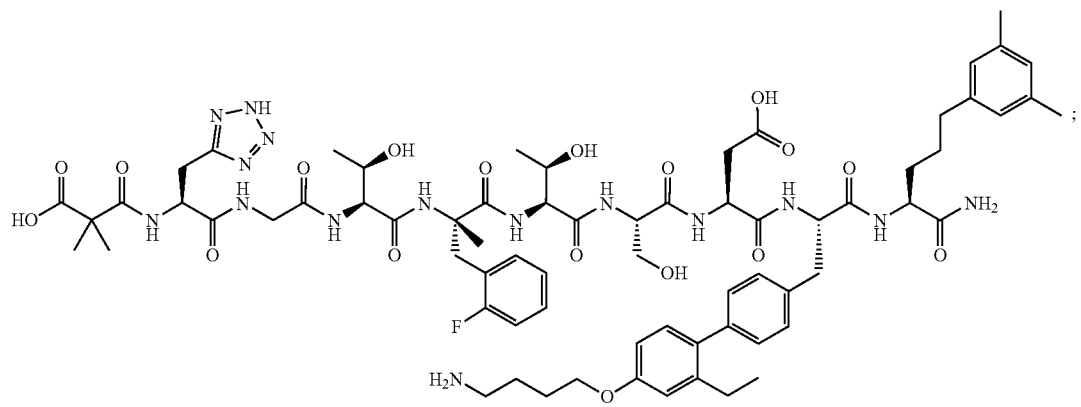

-continued
(SEQ ID NO: 44)
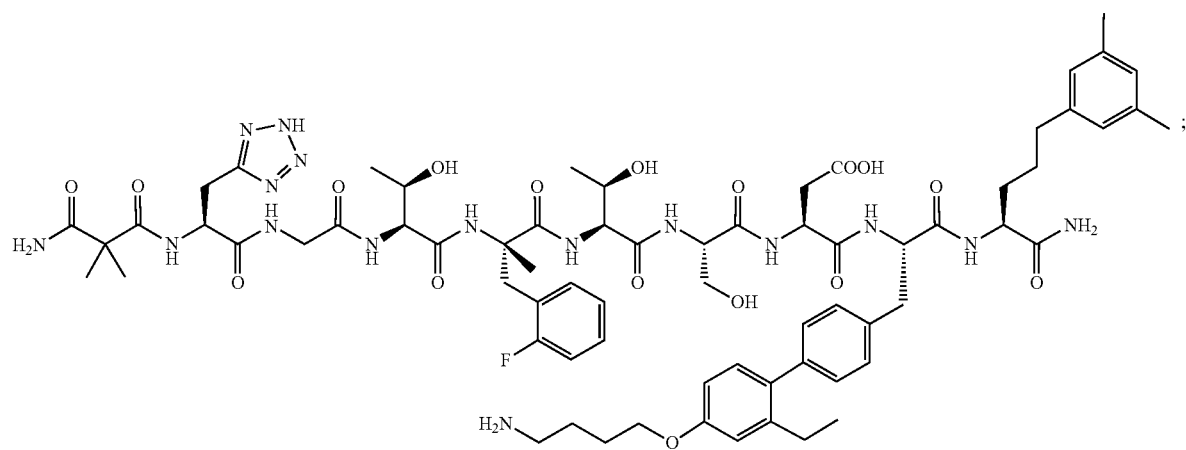
(SEQ ID NO: 45)
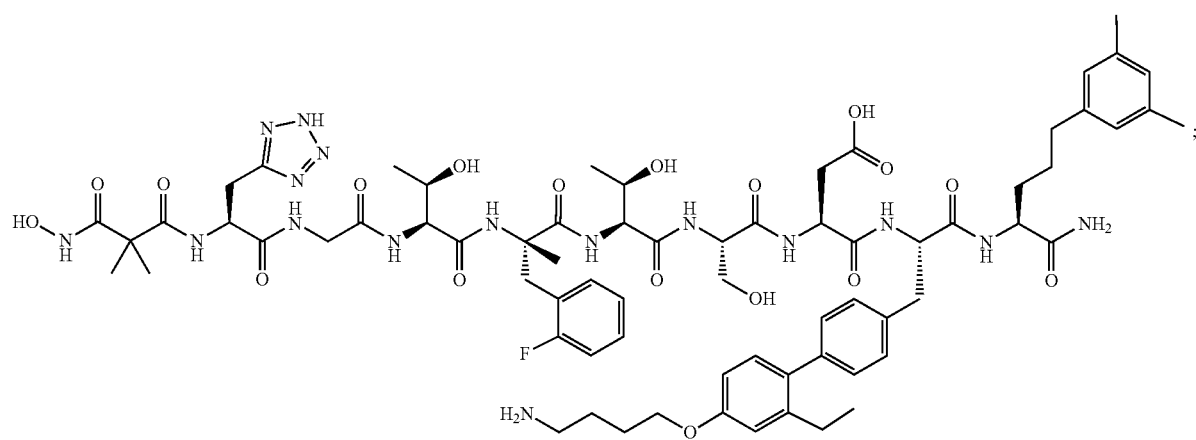
(SEQ ID NO: 46)
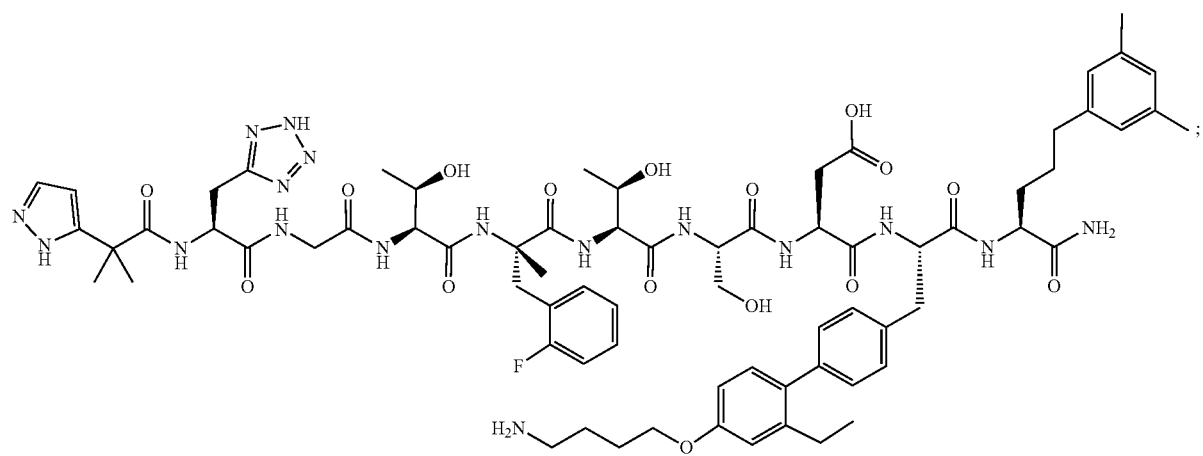

-continued
(SEQ ID NO: 47)
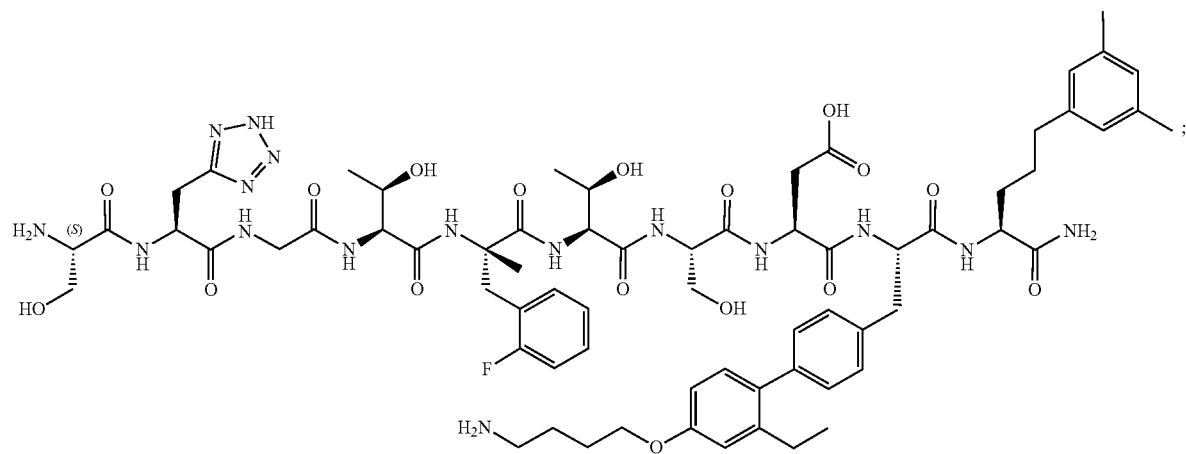
(SEQ ID NO: 48)
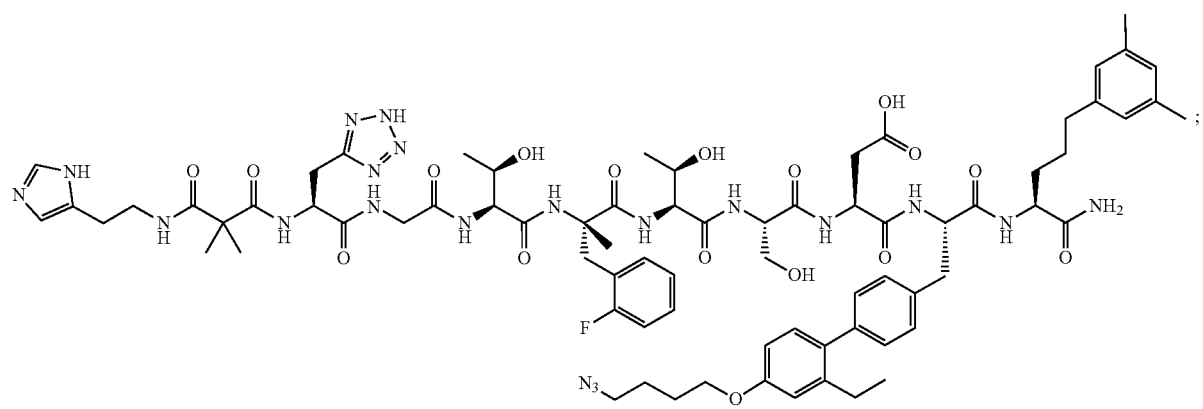
(SEQ ID NO: 49)
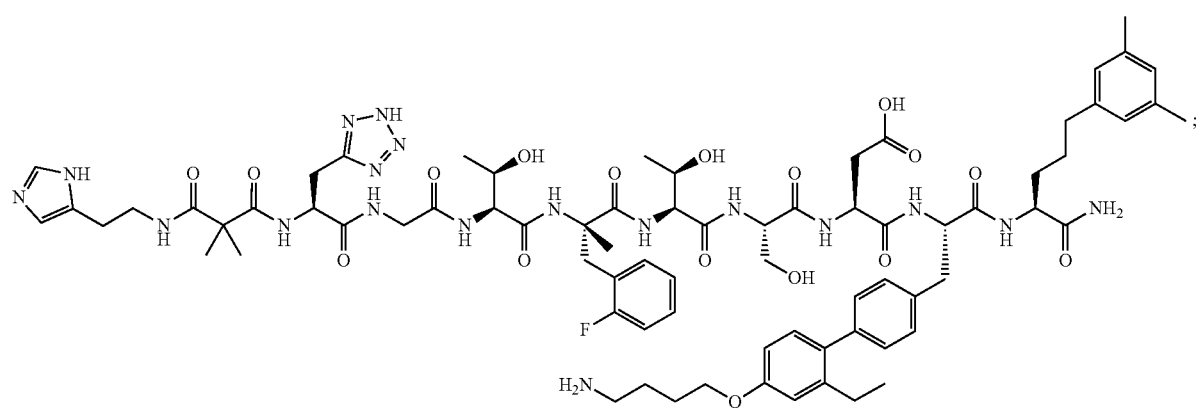

(SEQ ID NO: 50)
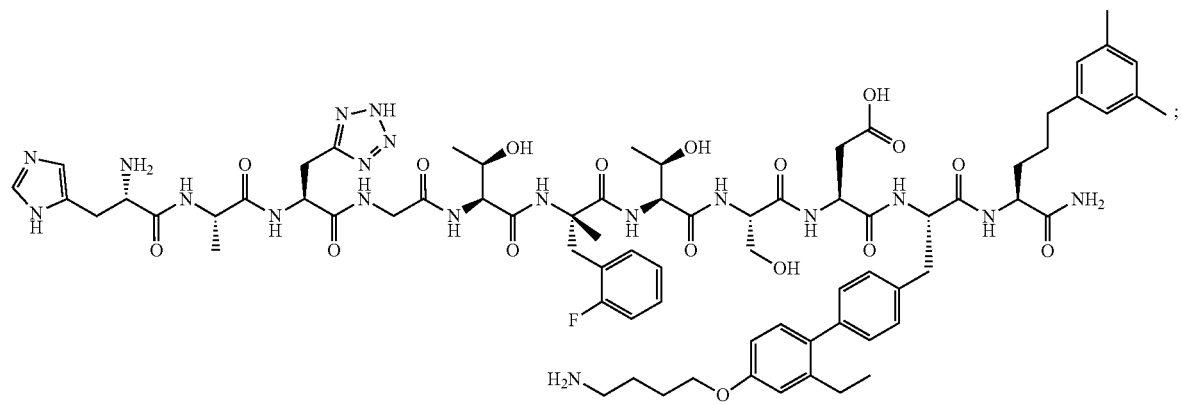
(SEQ ID NO: 51)
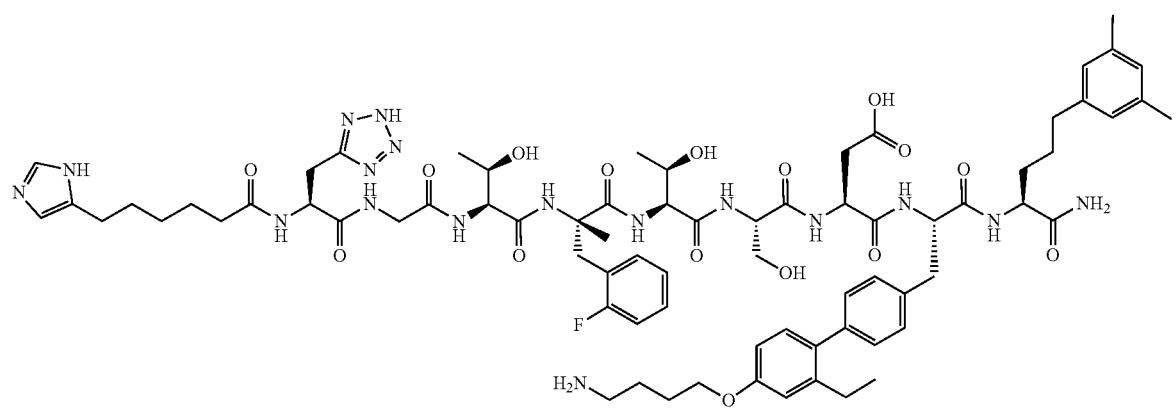
(SEQ ID NO: 52)
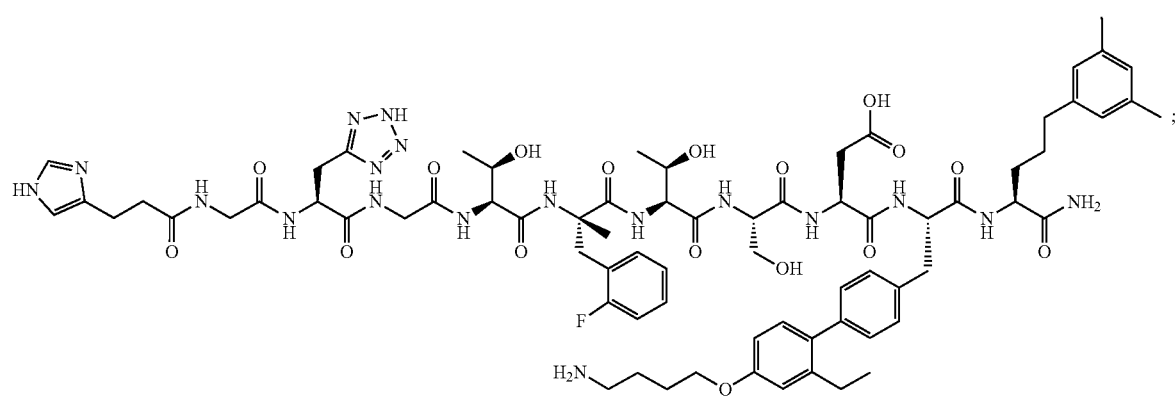
(SEQ ID NO: 53)
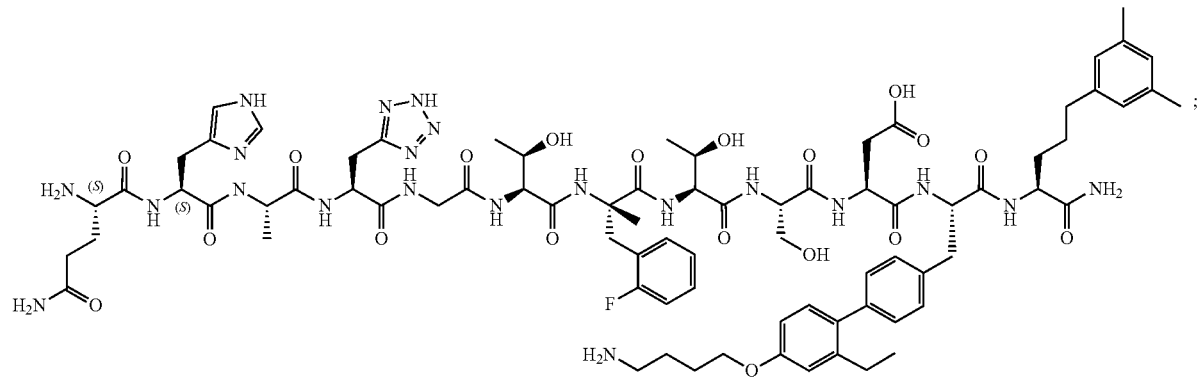

(SEQ ID NO: 54)
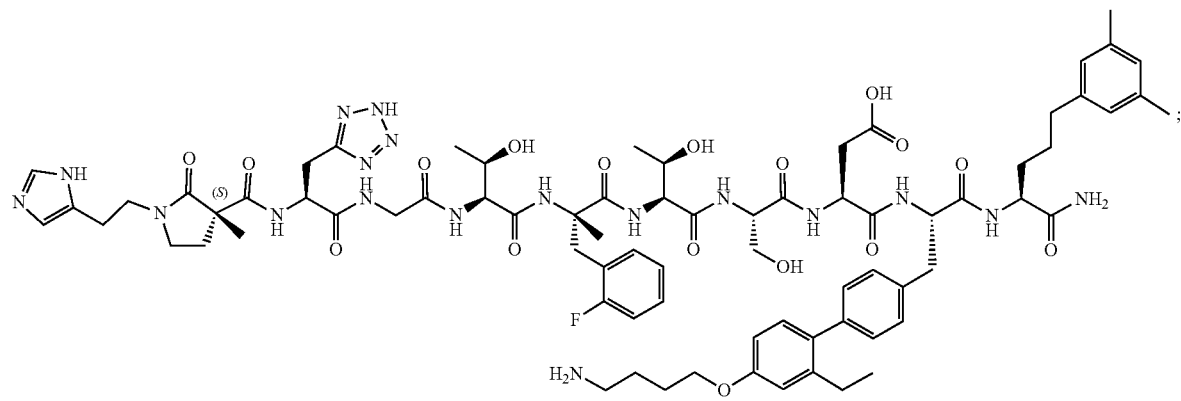
(SEQ ID NO: 55)
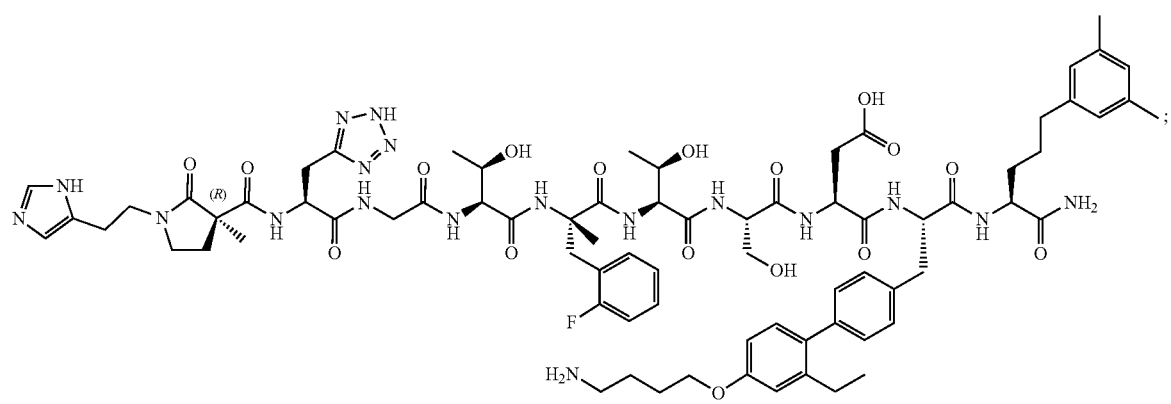
(SEQ ID NO: 56)
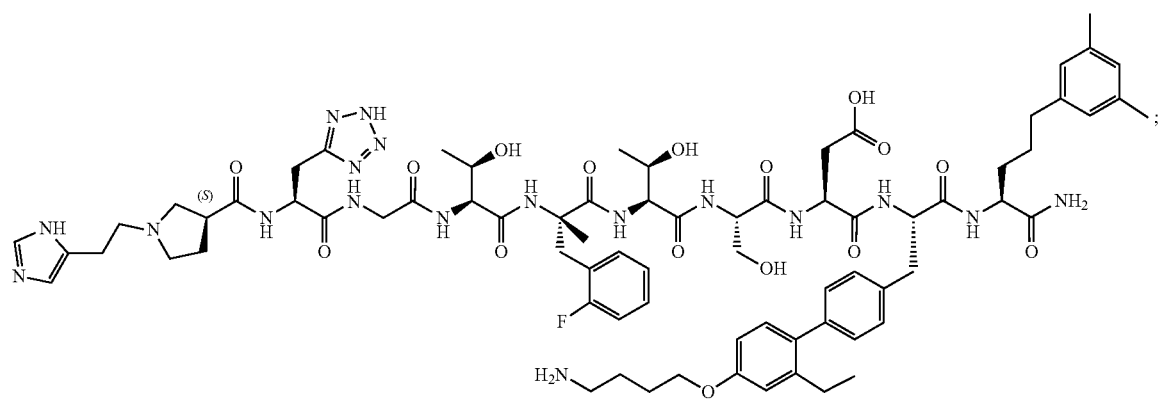

-continued
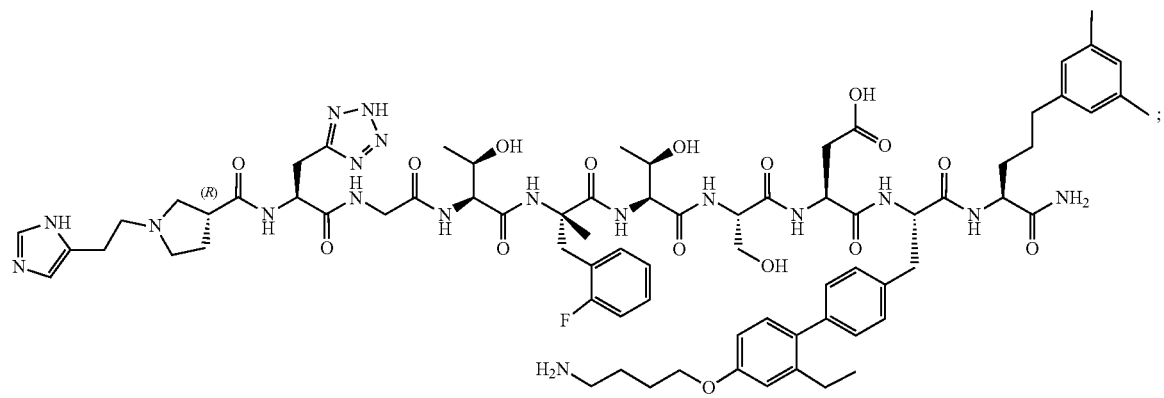
(SEQ ID NO: 57)
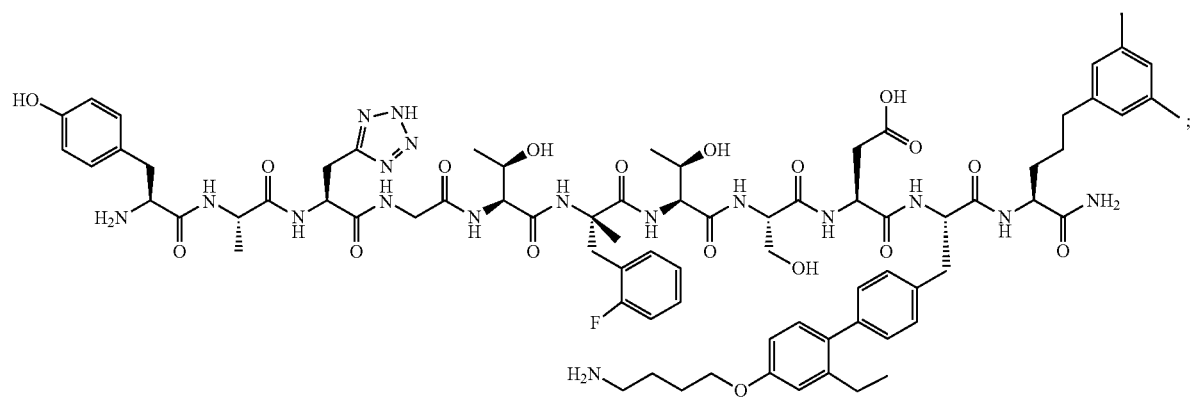
(SEQ ID NO: 58)
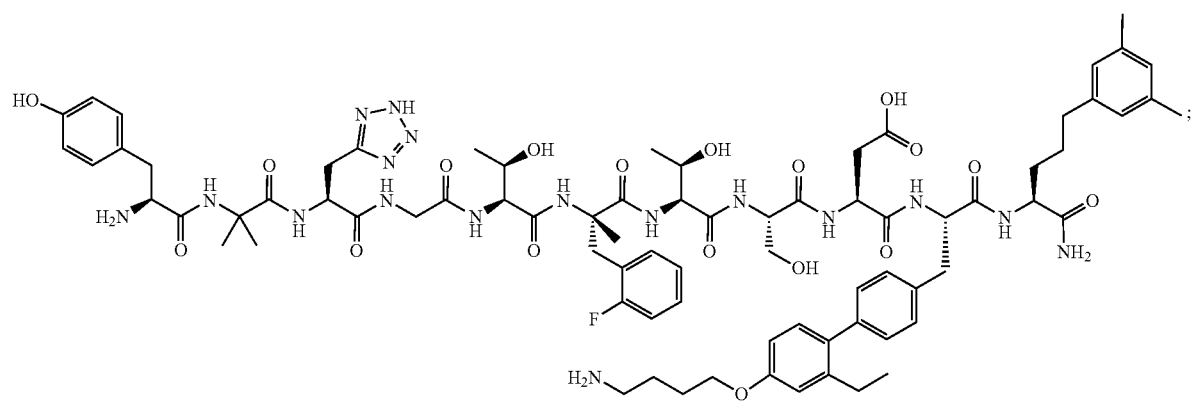
(SEQ ID NO: 59)

(SEQ ID NO: 60)
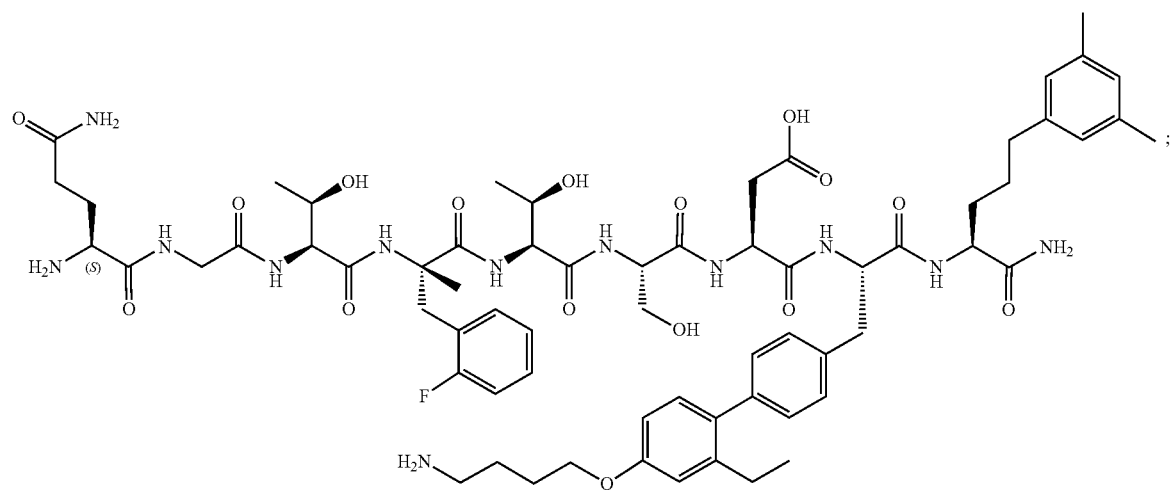
(SEQ ID NO: 61)
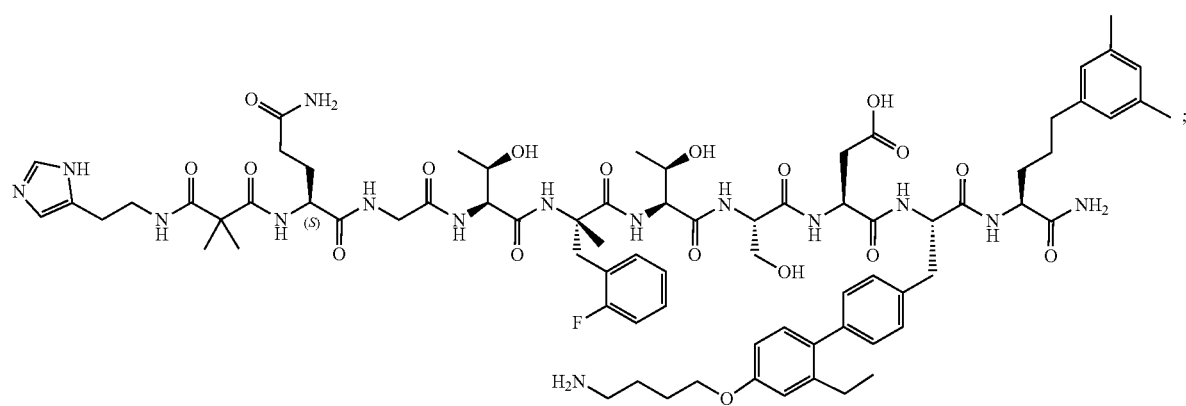
(SEQ ID NO: 62)
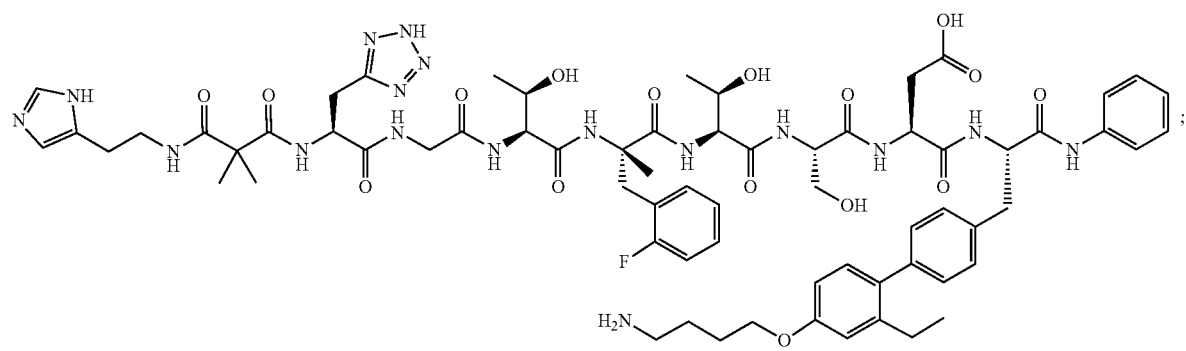

-continued
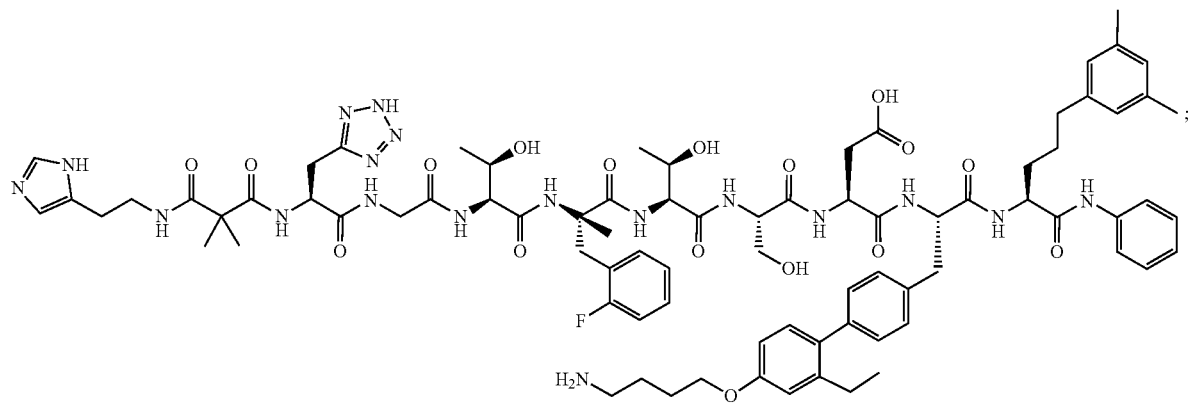
(SEQ ID NO: 63)
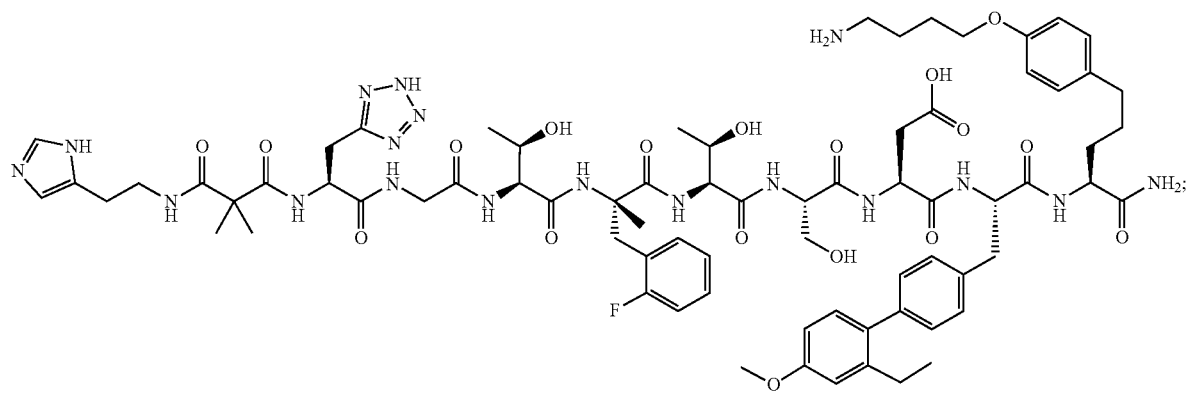
(SEQ ID NO: 64)
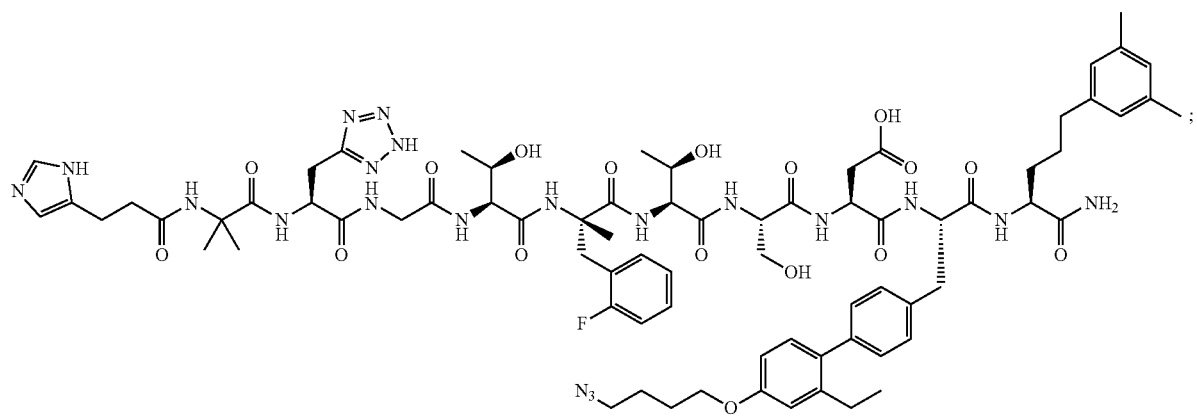
(SEQ ID NO: 65)

(SEQ ID NO: 66)
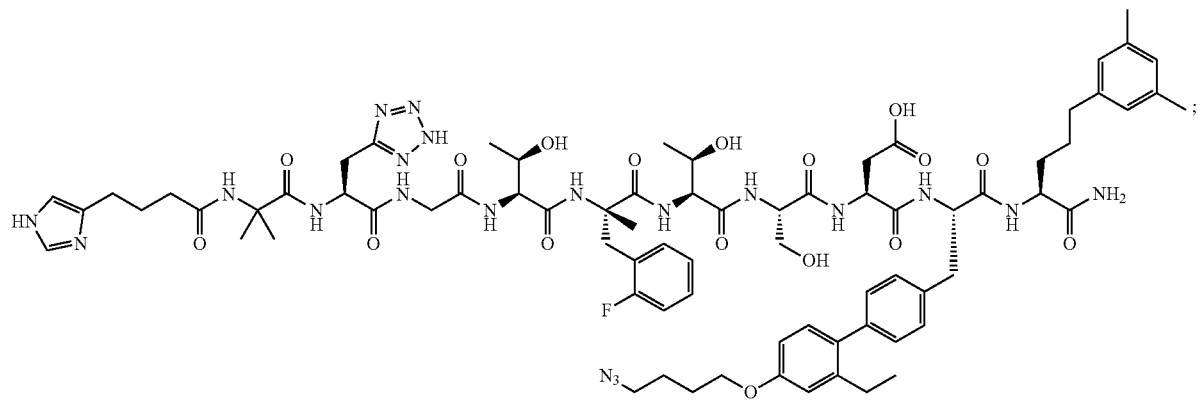
(SEQ ID NO: 67)
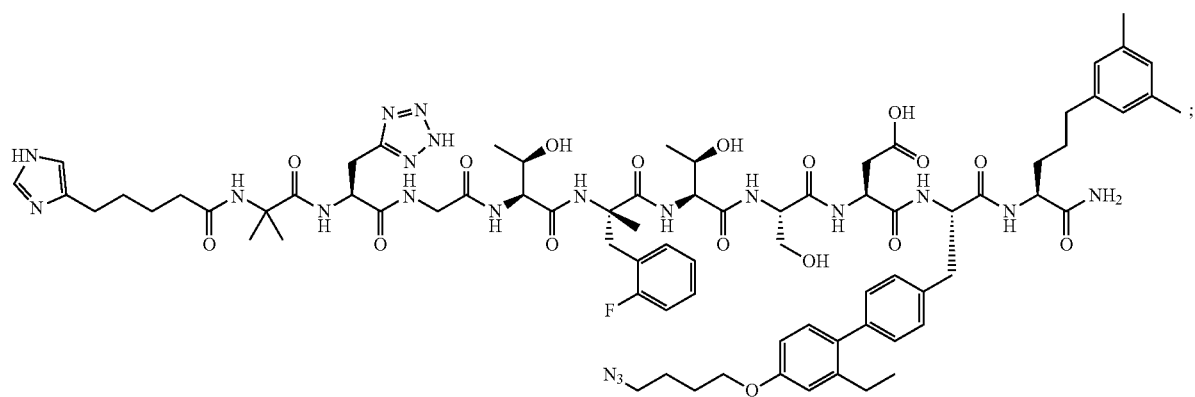
(SEQ ID NO: 68)
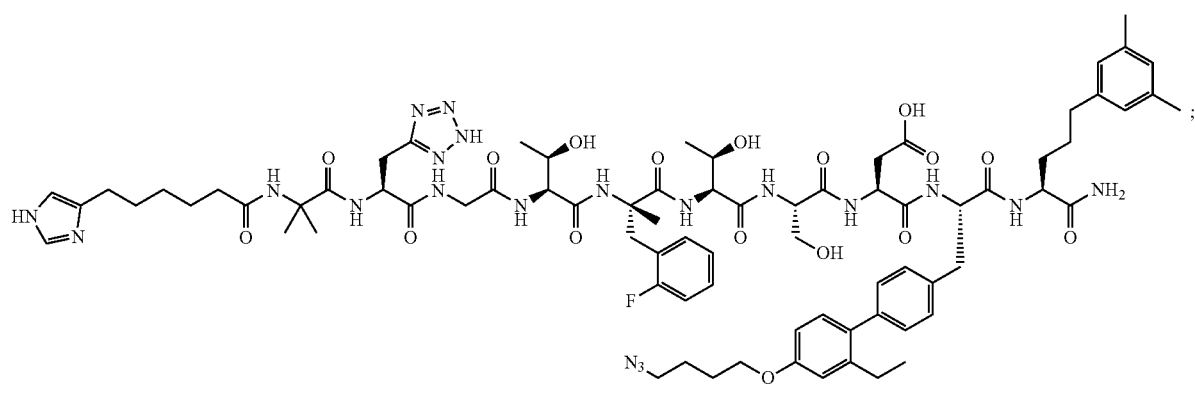
(SEQ ID NO: 69)
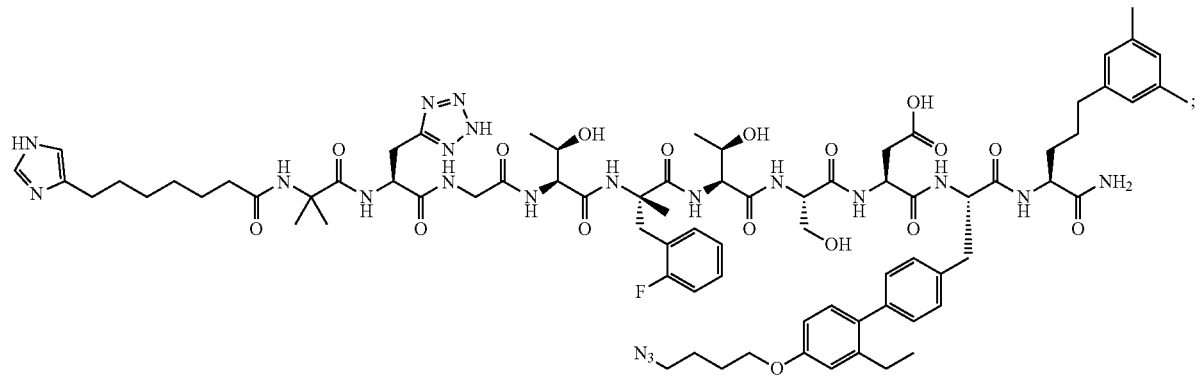

(SEQ ID NO: 70)
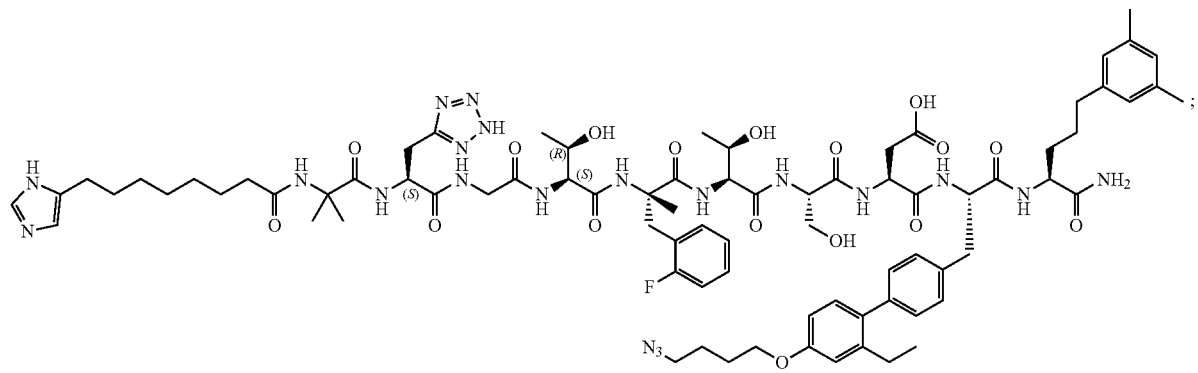
(SEQ ID NO: 71)
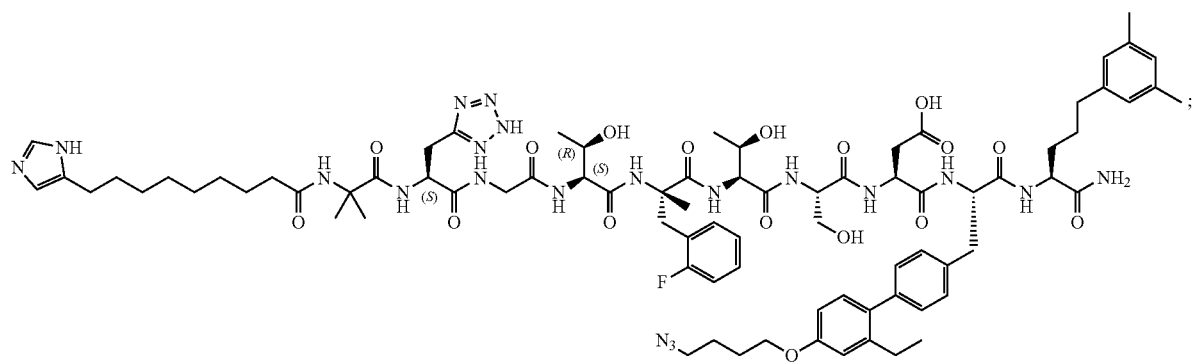
(Main Structure: SEQ ID NO: 72; Branched Sequence: SEQ ID NO: 154)
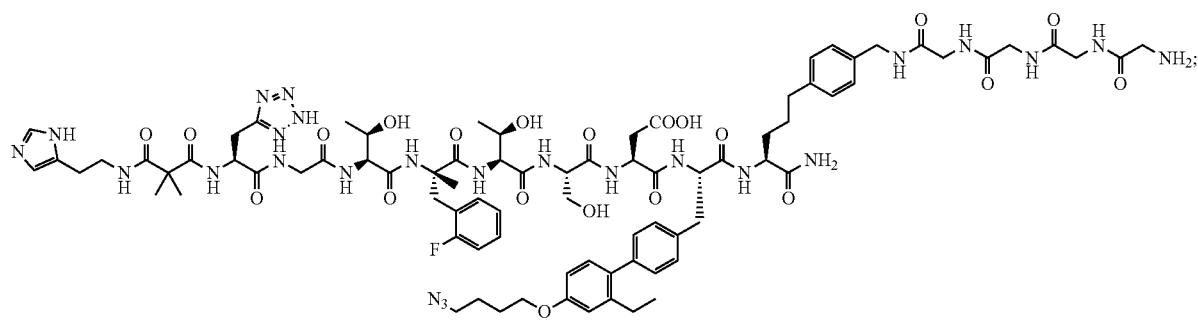
(SEQ ID NO: 73)
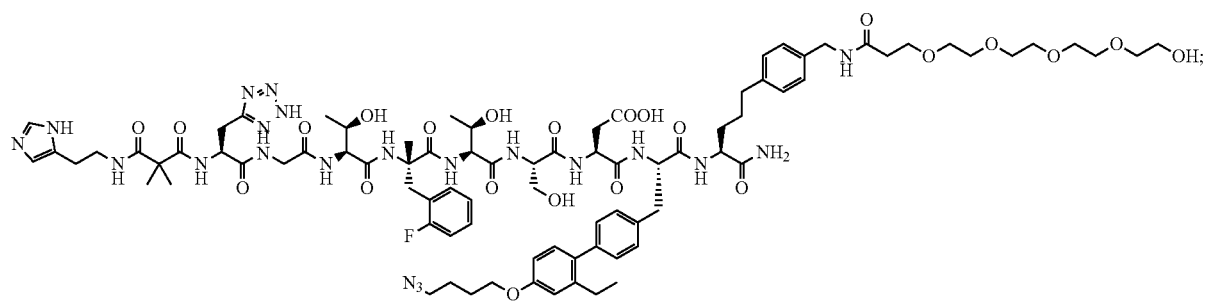

-continued

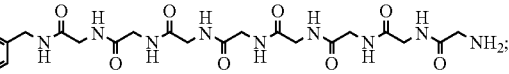
(Main Structure: SEQ ID NO: 74; Branched Sequence: SEQ ID NO: 155)

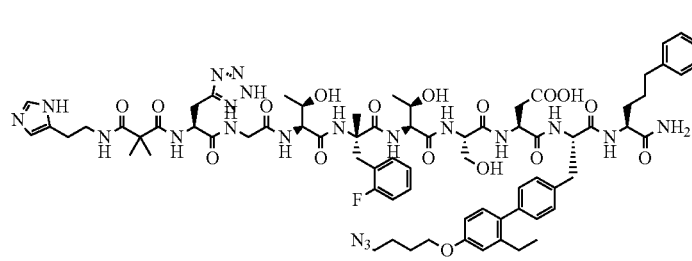

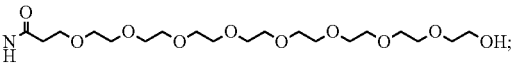
(SEQ ID NO: 75)

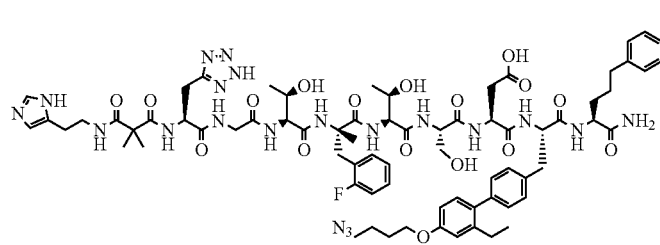

In various embodiments of the compound described herein, the compound has a half life of longer than 7 days in plasma.

In various embodiments of the compound described herein, the compound does not bind to G protein-coupled receptors (GPCRs) other than GLP1R.

In another aspect, provided herein is a pharmaceutical composition comprising the compound of any of the embodiments described herein.

In another aspect, provided herein is a pharmaceutical dosage form comprising the compound of any of the embodiments described herein.

In another aspect, provided herein is a method of selectively targeting GLP1R on a surface of a cell with the compound of any of the embodiments described herein. In some embodiments, the cell is a mammalian cell. In some embodiments, the cell is a human cell. In some embodiments, the cell is a pancreatic cell, a brain cell, a heart cell, a vascular tissue cell, a kidney cell, an adipose tissue cell, a liver cell, or a muscle cell.

In another aspect, provided herein is a method of enhancing GLP1R activity in an individual in need thereof comprising administering to the individual an effective amount of the compound of any of the embodiments described herein, the composition described herein, or the dosage form described herein.

In another aspect, provided herein is a method of lowering blood glucose levels in an individual in need thereof comprising administering to the individual an effective amount of the compound of any of the embodiments described herein, the composition described herein, or the dosage form described herein.

In another aspect, provided herein is a method of lowering body weight in an individual in need thereof comprising administering to the individual an effective amount of the compound of any of the embodiments described herein, the composition described herein, or the dosage form described herein.

In another aspect, provided herein is a method of treating a GLP1R-associated condition in an individual in need thereof comprising administering to the individual an effective amount of the compound of any of the embodiments described herein, the composition described herein, or the dosage form described herein. In some embodiments, the GLP1R-associated condition is type II diabetes, obesity, liver disease, coronary artery disease, or kidney disease. In some embodiments, the GLP1R-associated condition is type II diabetes and/or obesity.

In various embodiments of any of the method described herein, the compound, the composition, or the dosage form of the present disclosure is administered subcutaneously, intravenously, intradermally, intraperitoneally, or intramuscularly. In another aspect, provided herein is a method of producing the compound described herein having a structure of Formula (A):

BA-(L-P)$_m$ (A), the method comprising the steps of:
a) contacting, in the presence of a transglutaminase, the BA comprising at least m glutamine residues Gln with at least m equivalents of compound L-P, and
b) isolating the produced compound of Formula (A)

In another aspect, provided herein is a method of producing the compound described herein having a structure of Formula (I):

BA-L-P (I), the method comprising the steps of:
a) contacting, in the presence of a transglutaminase, the BA comprising at least one glutamine residue Gln with a compound L-P, and
b) isolating the produced compound of Formula (I).

In another aspect, provided herein is a method of producing the compound of claim 1 having a structure of Formula (A):

BA-(L-P)$_m$ (A), wherein the linker L has has the structure of formula (L'):

—La—Y-Lp- (L'), wherein La is a first linker covalently attached to the BA;
Y is a group comprising a triazole, and
Lp is a second linker covalently attached to the P, the method comprising the steps of:
a) contacting, in the presence of a transglutaminase, the BA comprising at least m glutamine residues Gln with the first linker La comprising an azide or an alkyne moiety;
b) contacting the product of step a) with at least m equivalents of compound Lp-P, wherein the second linker Lp comprises an azide or an alkyne moiety, wherein La and Lp are capable of reacting to produce a triazole, and
c) isolating the produced compound of Formula (A).

In another aspect, provided herein is a method of producing the compound described herein having a structure of Formula (I):

$$BA\text{-}L\text{-}P \tag{I}$$

wherein the linker L has has the structure of formula (L'):

$$-La-Y-Lp- \tag{L'}$$

wherein La is a first linker covalently attached to the BA;

Y is a group comprising a triazole, and

Lp is a second linker covalently attached to the P, the method comprising the steps of:
a) contacting, in the presence of a transglutaminase, the BA comprising at least one glutamine residue Gln with the first linker La comprising an azide or an alkyne moiety;
b) contacting the product of step a) with a compound Lp-P, wherein the second linker Lp comprises an azide or an alkyne moiety, wherein La and Lp are capable of reacting to produce a triazole, and
c) isolating the produced compound of Formula (I).

In another aspect, provided herein is a compound having a structure selected from the group consisting of Formula (P-IB), Formula (P-IIB), and Formula (P-IIIB):

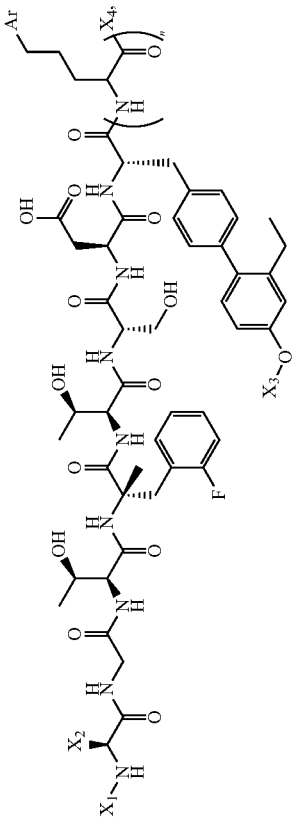
(P-IB (SEQ ID NO: 83))
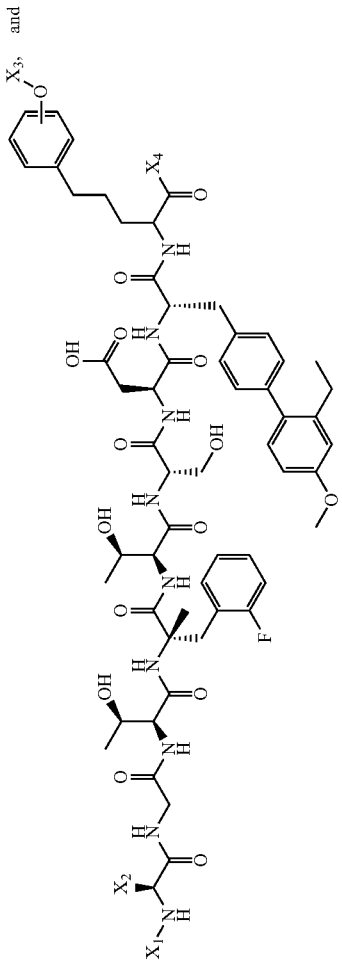
(P-IIB (SEQ ID NO: 84))
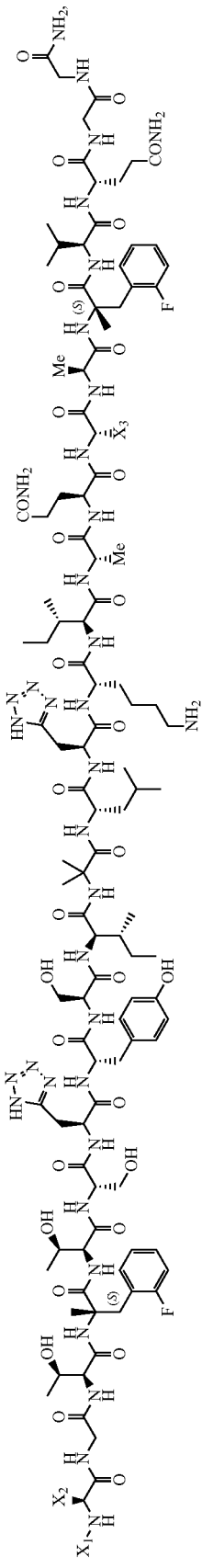
(P-IIIB (SEQ ID NO: 29))

wherein:

$X_1$ is selected from H;

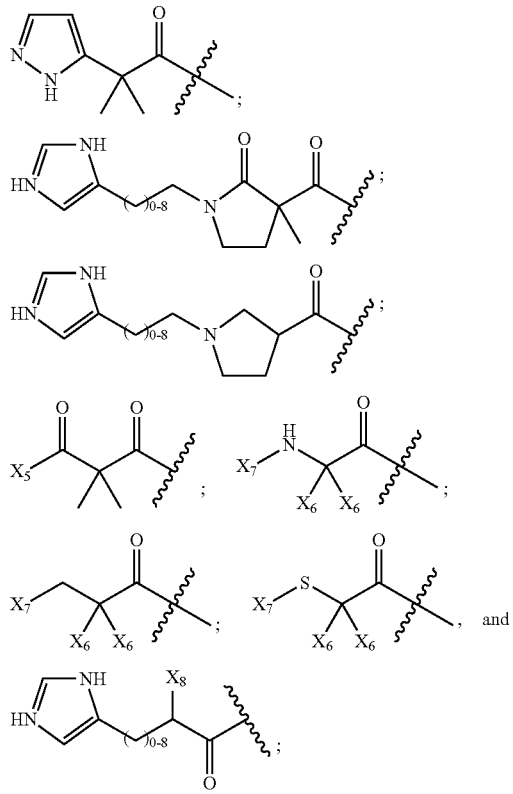

$X_2$ is selected from

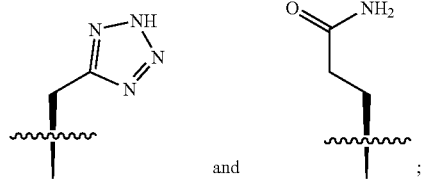

$X_3$ is selected from —$CH_3$, —$(CH_2)_{2-6}$—$NH_2$, —$(CH_2)_{2-6}$—$N_3$, and —$(CH_2)_{2-6}$—Tr-$(CH_2)_{1-6}$—$NH_2$, where Tr is a triazole moiety;

n is 0 or 1;

$X_4$ is selected from —$NH_2$, —OH and —N(H)(phenyl);

$X_5$ is selected from —OH, —$NH_2$, —NH—OH, and

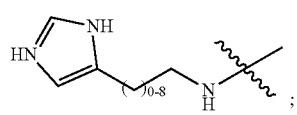

$X_6$ is independently at each occurrence selected from H, —OH, —$CH_3$, and —$CH_2OH$;

$X_7$ is selected from H

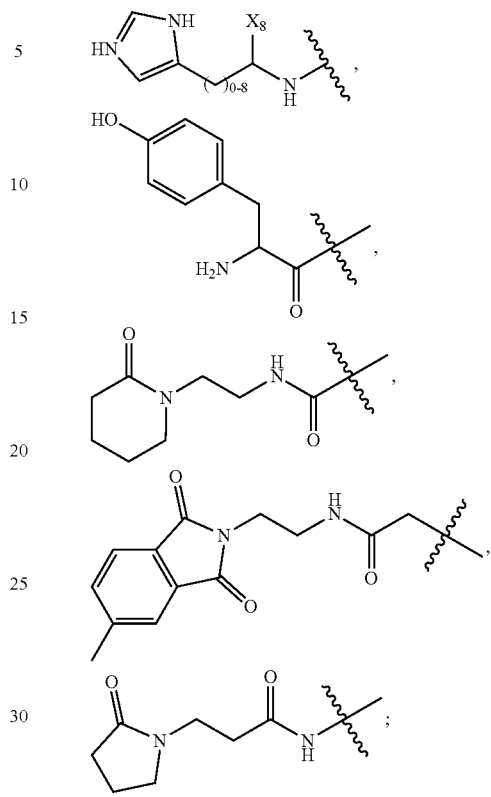

$X_8$ is selected from H, —OH, —$NH_2$, and

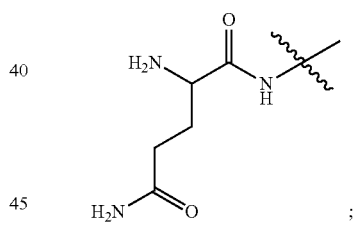

Ar is selected from

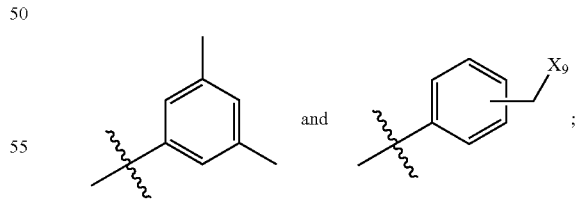

$X_9$ is selected from —$NH_2$,

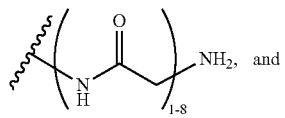

-continued

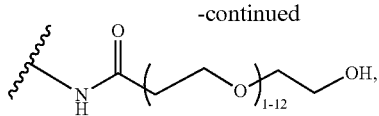

and m is an integer from 1 to 4 or a pharmaceutically acceptable salt thereof.

In another aspect, provided herein is a compound having a structure of Formula (II):

$X_2$ is selected from,

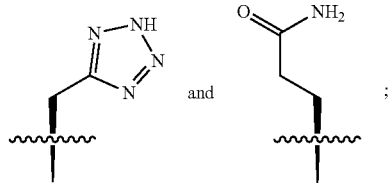

(II (SEQ ID NO: 85))

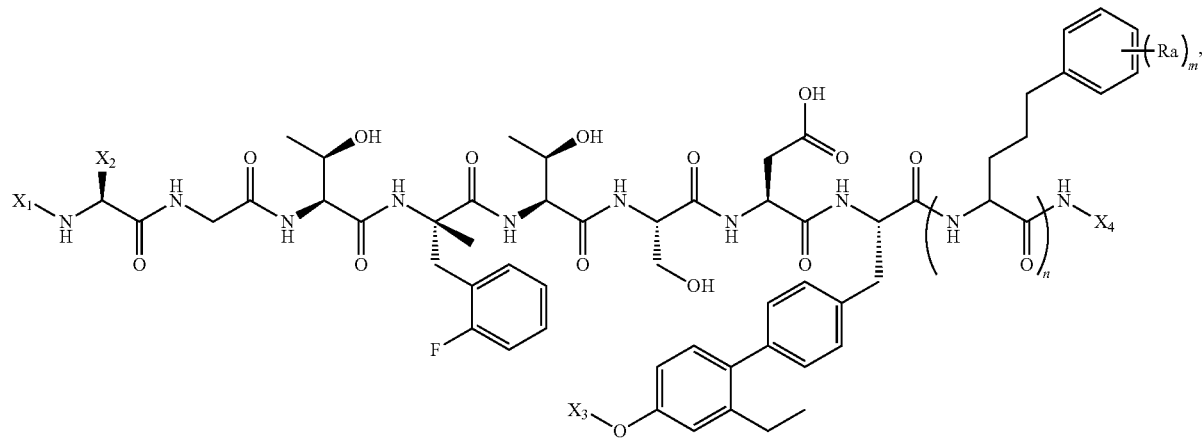

wherein:

$X_1$ is selected from H;

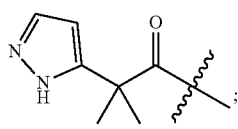

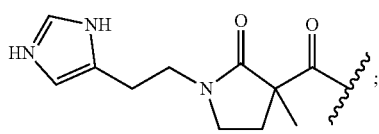

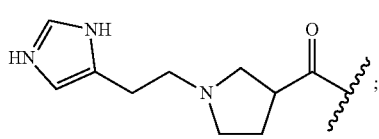

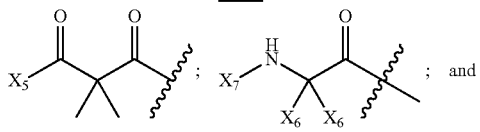

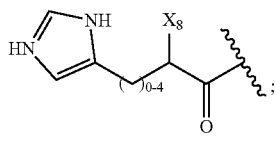

$X_3$ is selected from —$(CH_2)_{2-6}$—$NH_2$, —$(CH_2)_{2-6}$—$N_3$, and —$CH_3$, with the proviso that when $X_3$ is —$CH_3$, n is 1 and Ra in at least one occurrence is selected from —$(CH_2)_{2-6}$—$NH_2$ and —$(CH_2)_{2-6}$—$N_3$;

n is 0 or 1;

m is an integer from 0 to 3;

Ra is independently at each occurrence selected from —$CH_3$, —$(CH_2)_{2-6}$—$NH_2$, and —$(CH_2)_{2-6}$—$N_3$;

$X_4$ is selected from H and phenyl;

$X_5$ is selected from —OH, —$NH_2$, —NH—OH, and

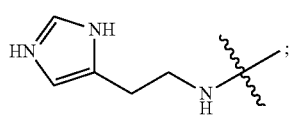 [SMILES: *NCCc1cnc[nH]1]

$X_6$ is independently at each occurrence selected from H, —OH, —$CH_3$, and —$CH_2OH$;

$X_7$ is selected from H,

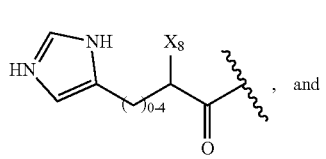

and

-continued
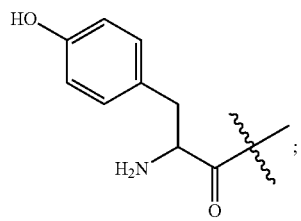
;
$X_3$ is selected from H, —OH, —NH$_2$, and
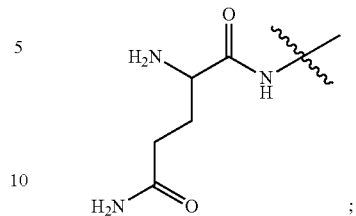
;
and pharmaceutically acceptable salts thereof.
In some embodiments, P has the structure selected from the group consisting of:
Structure
(SEQ ID NO: 41)
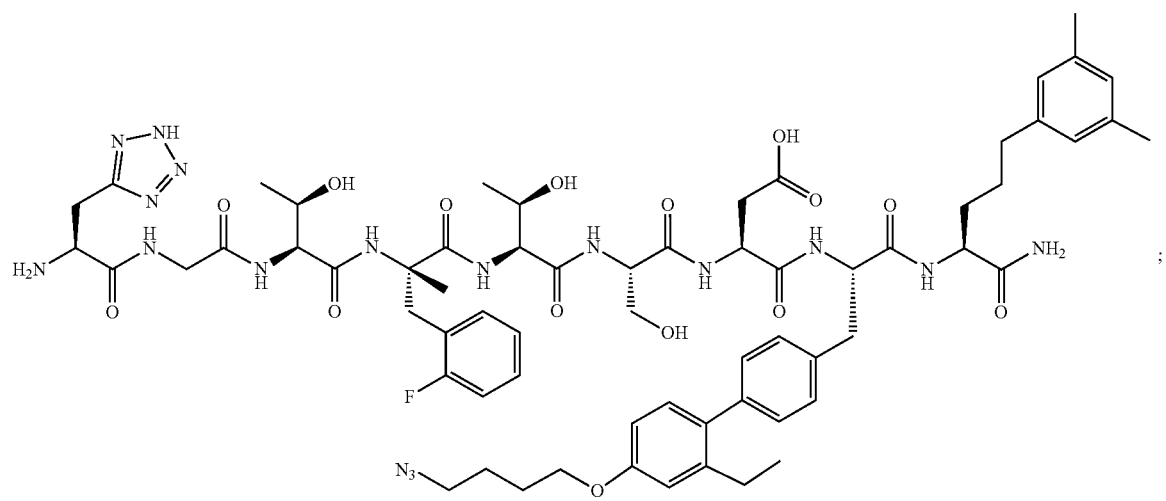
;
(SEQ ID NO: 42)
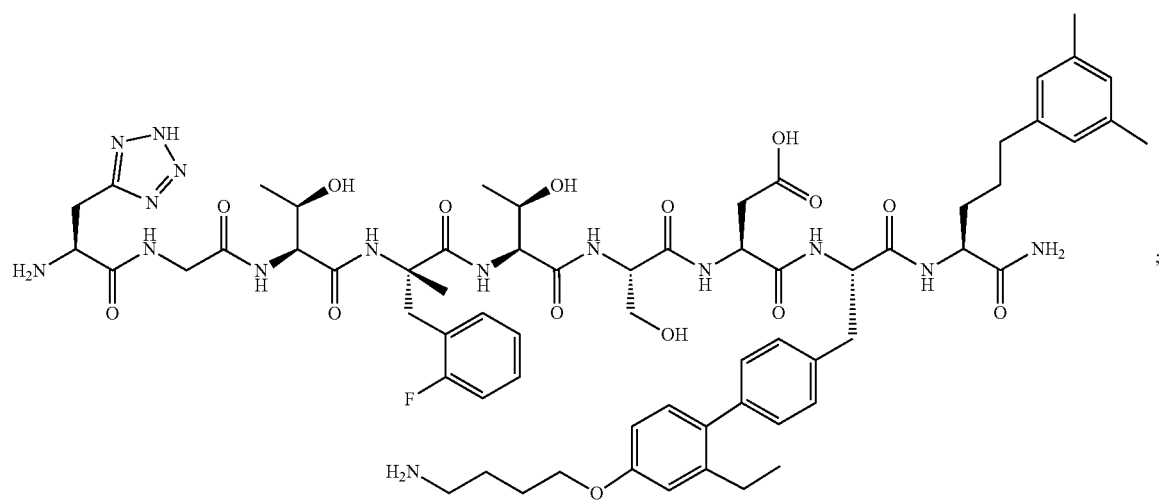
;

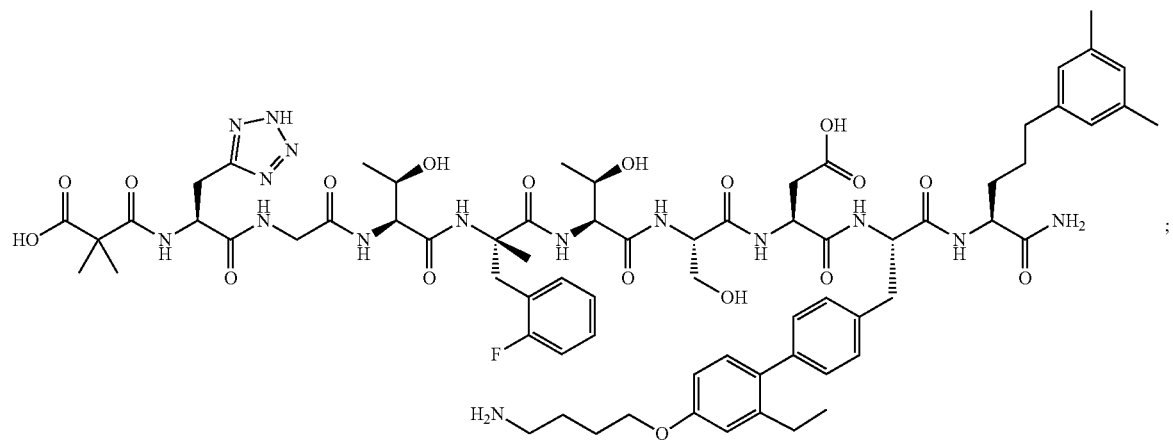
(SEQ ID NO: 43)
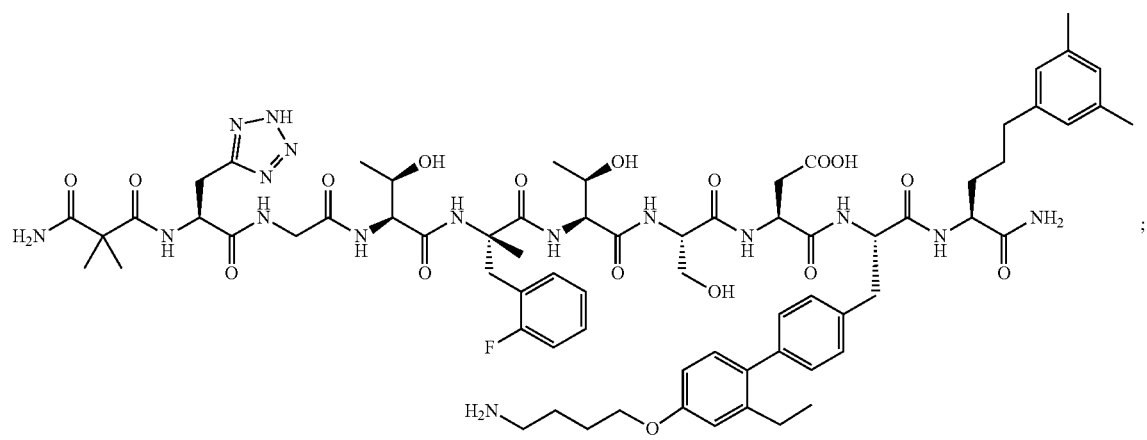
(SEQ ID NO: 44)
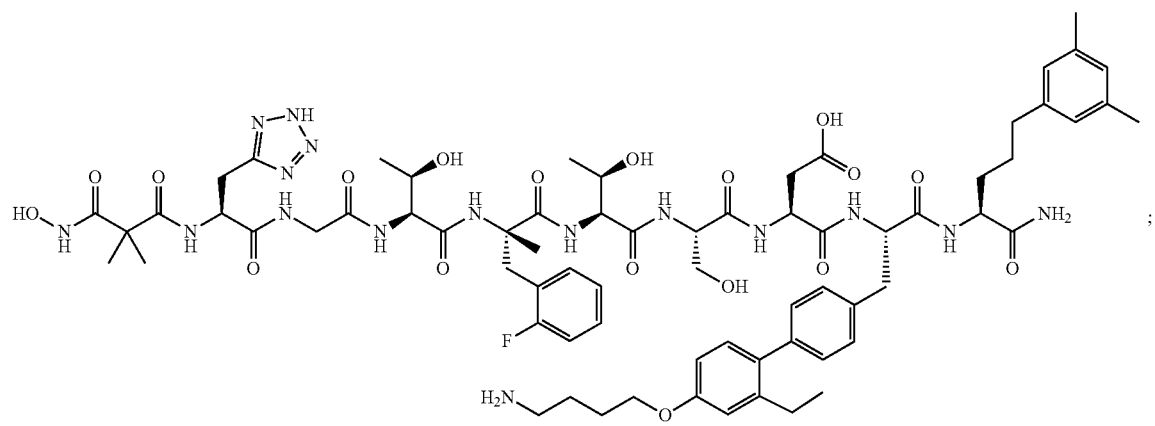
(SEQ ID NO: 45)

-continued
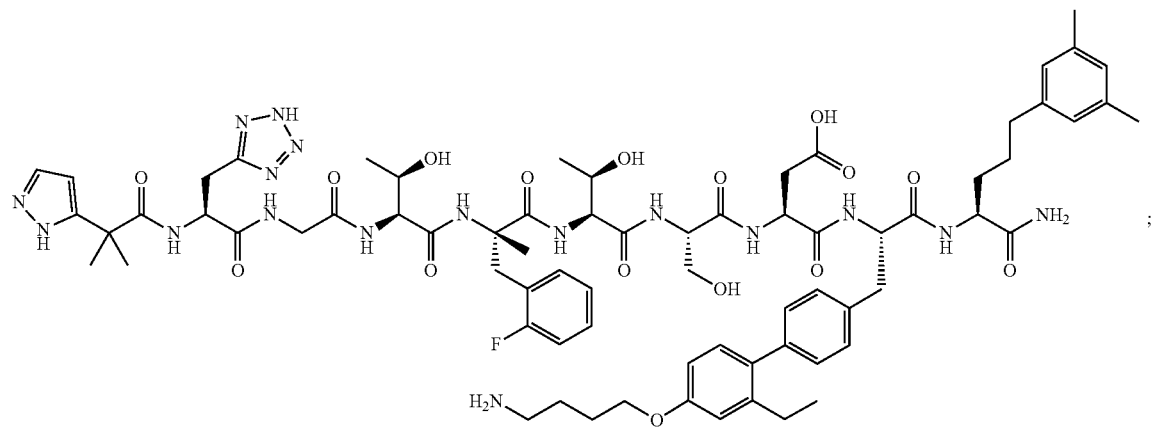
(SEQ ID NO: 46)
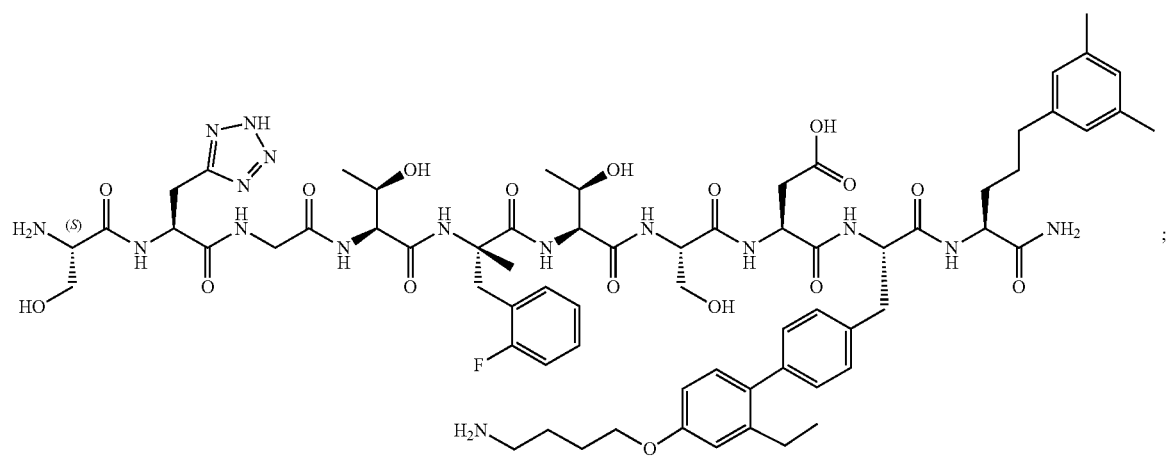
(SEQ ID NO: 47)
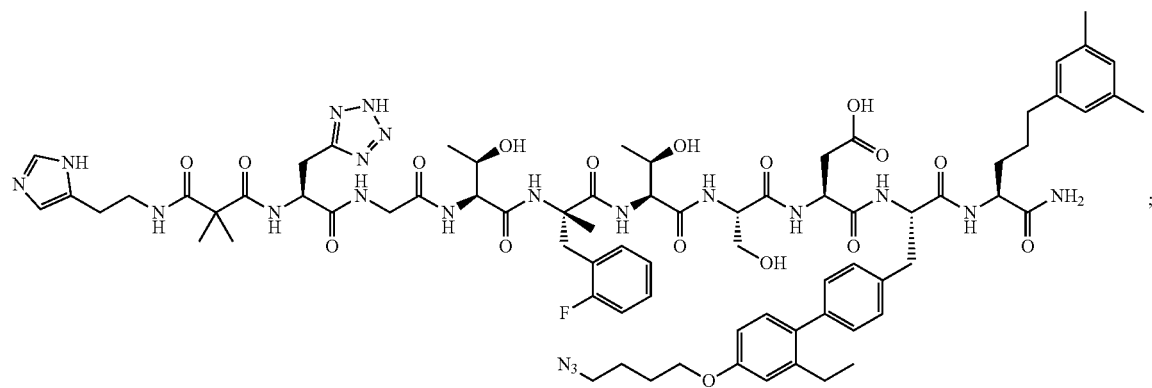
(SEQ ID NO: 48)

(SEQ ID NO: 49)
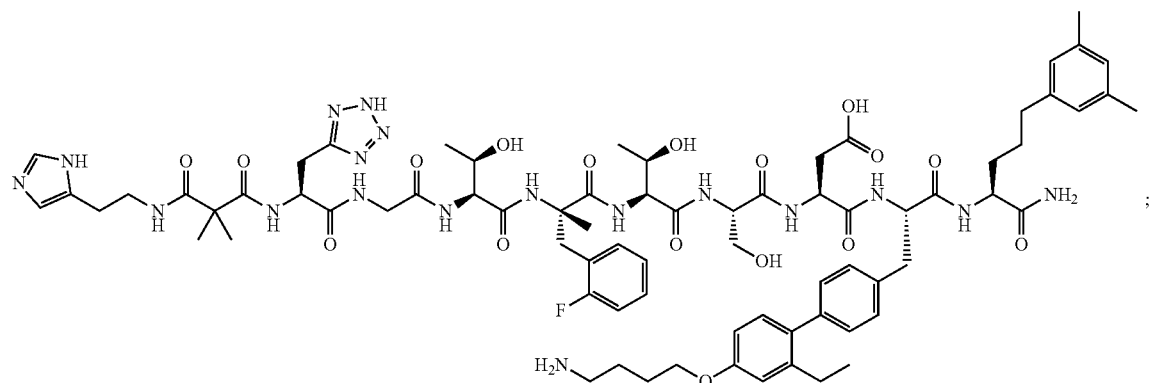
(SEQ ID NO: 50)
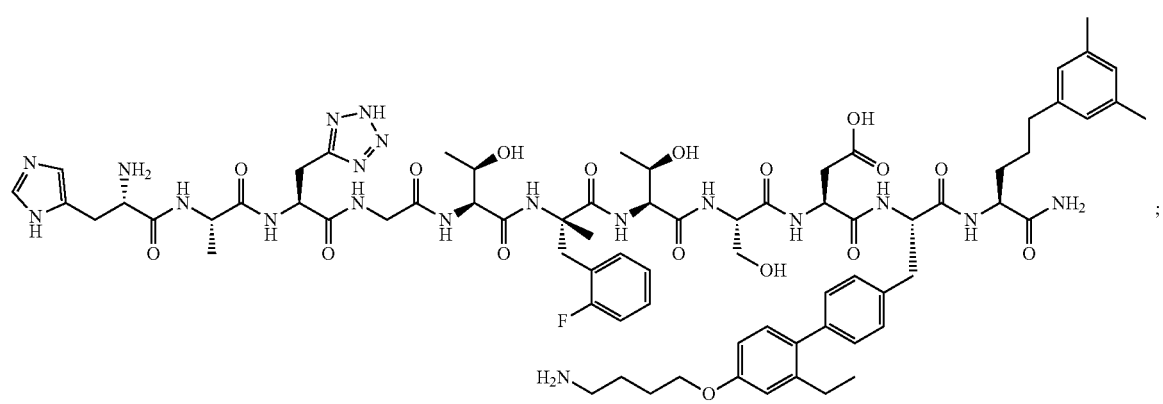
(SEQ ID NO: 51)
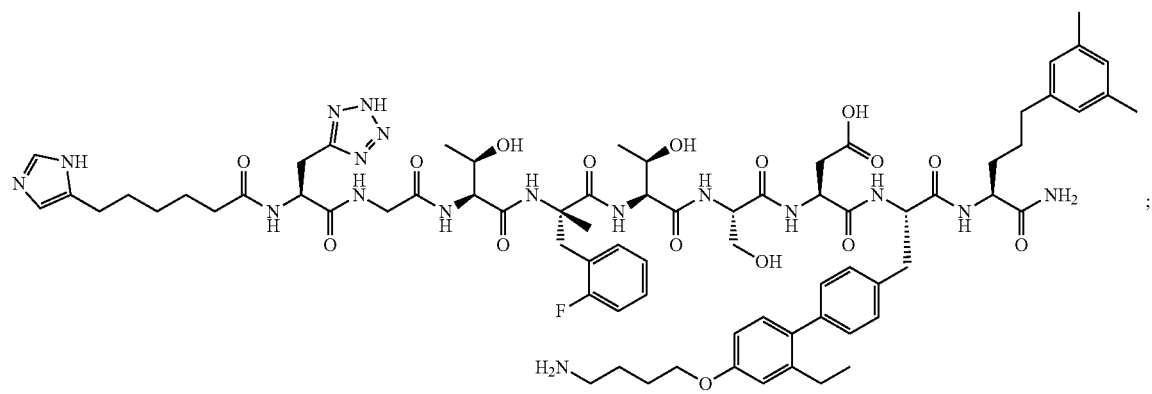
(SEQ ID NO: 52)
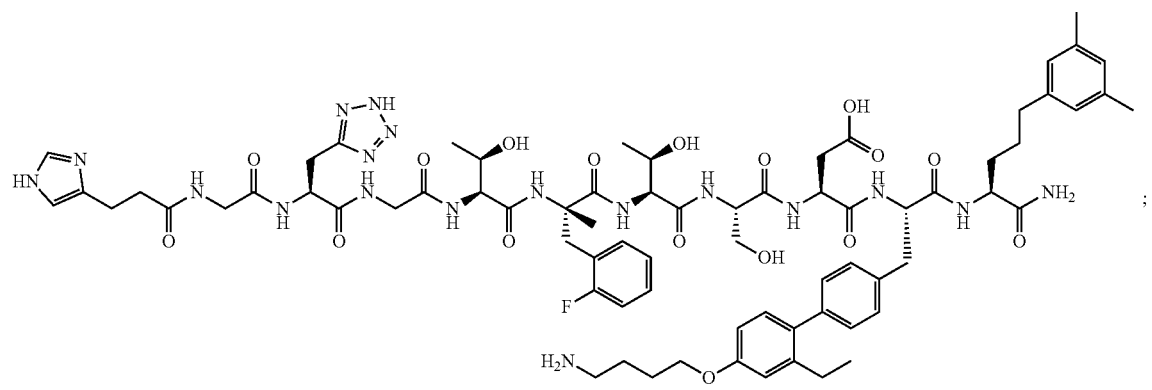

(SEQ ID NO: 53)
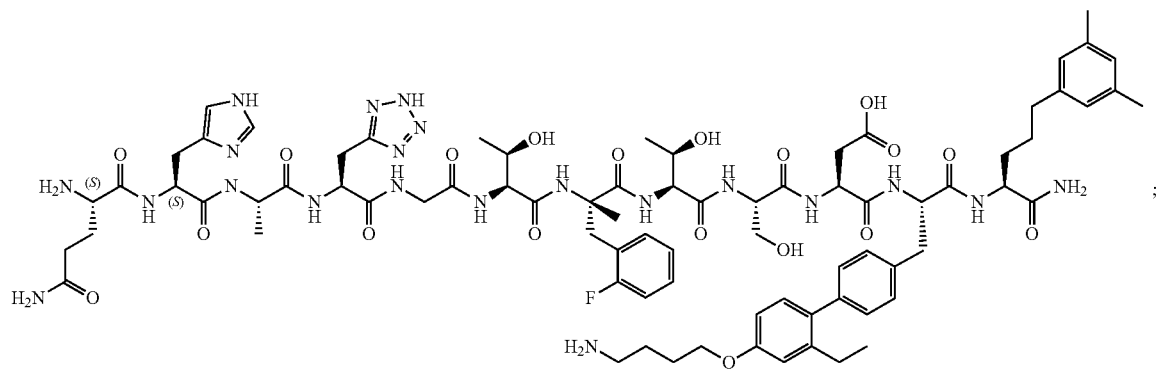
(SEQ ID NO: 54)

(SEQ ID NO: 55)
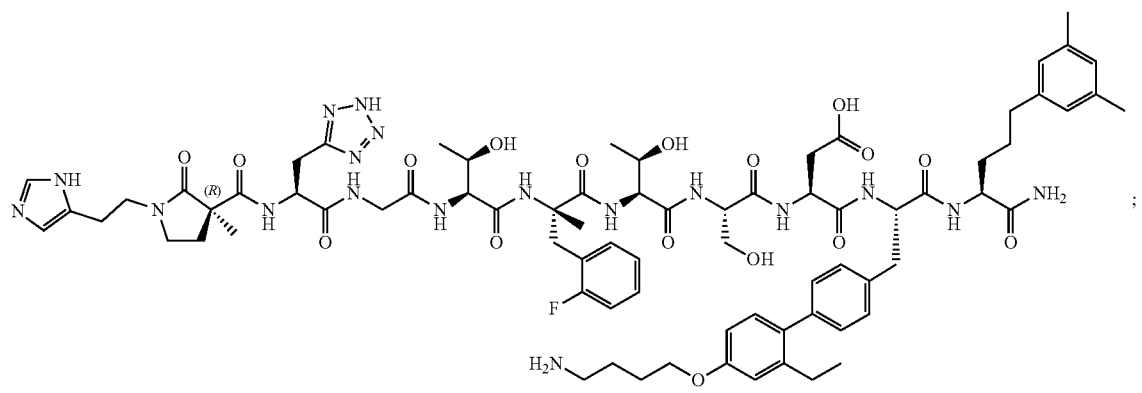
(SEQ ID NO: 56)
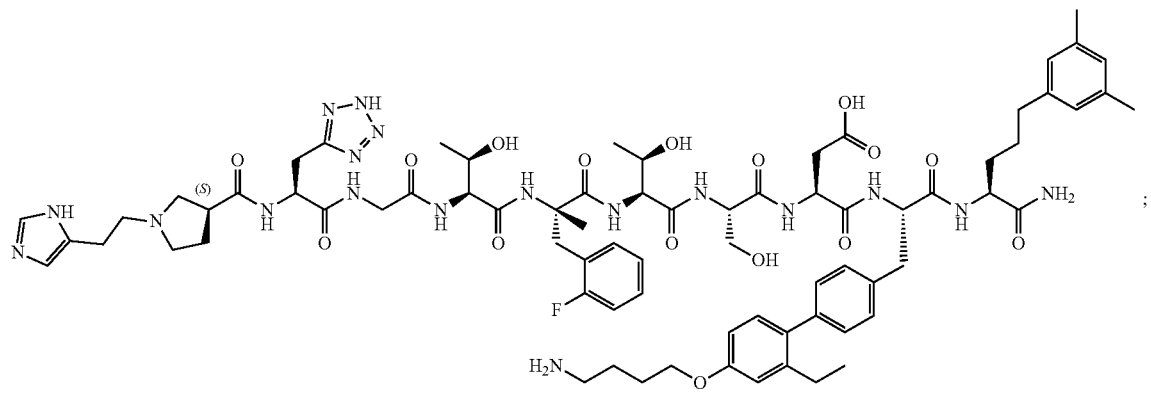

(SEQ ID NO: 57)
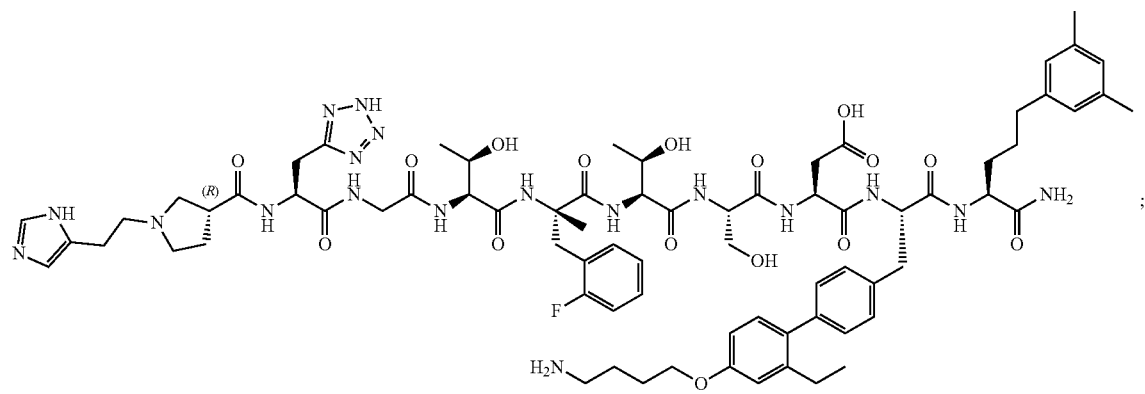
;
(SEQ ID NO: 58)
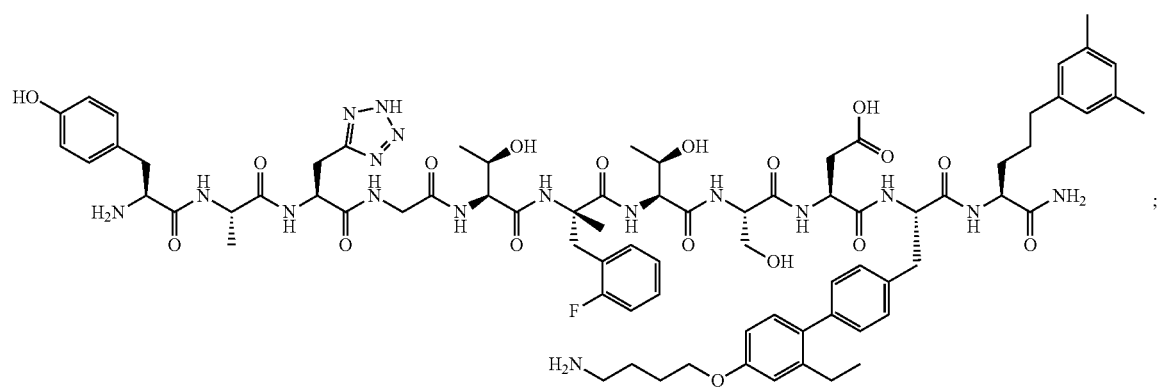
;
(SEQ ID NO: 59)
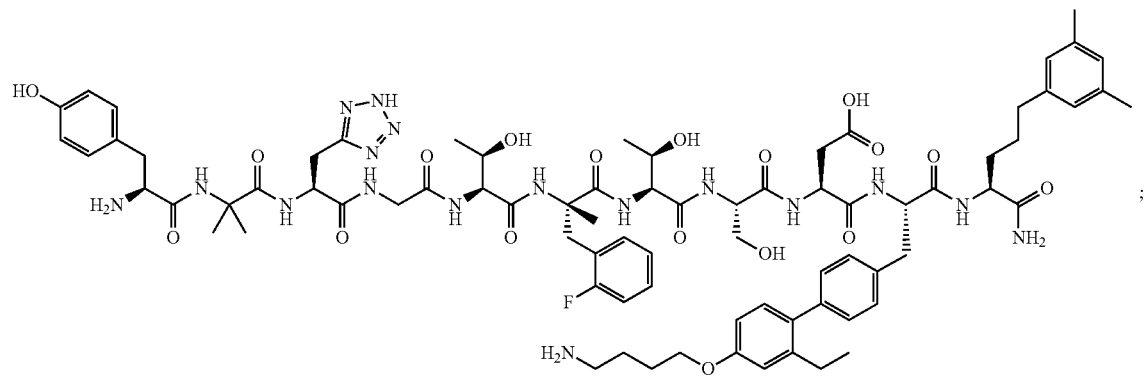
;

(SEQ ID NO: 60)
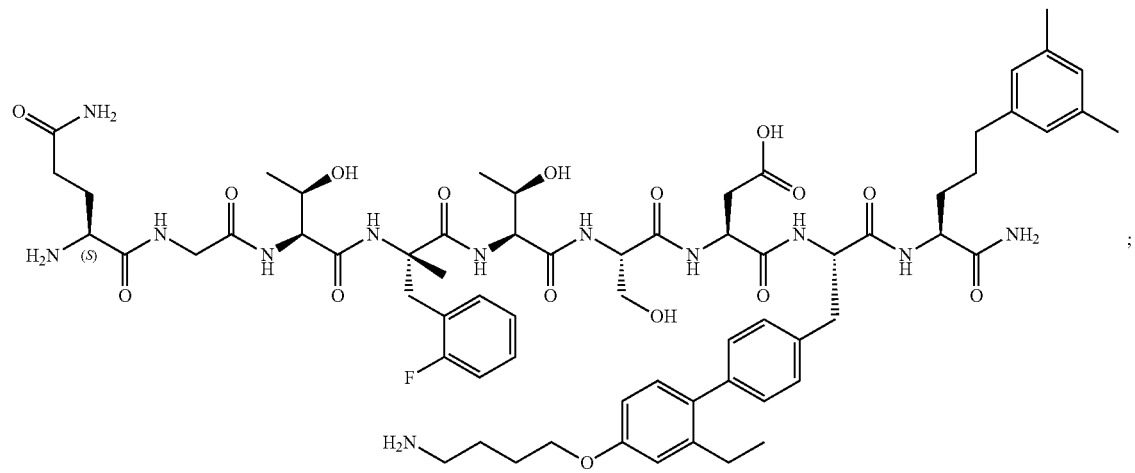
(SEQ ID NO: 61)
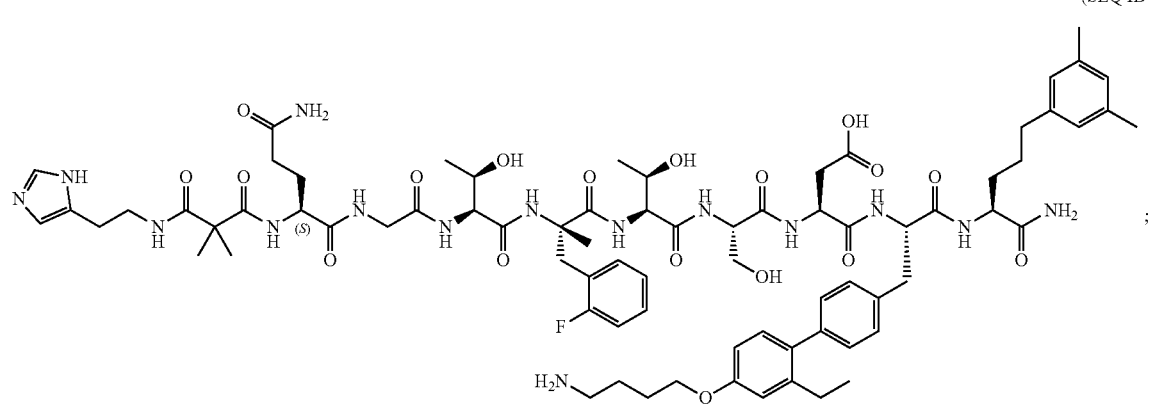
(SEQ ID NO: 62)
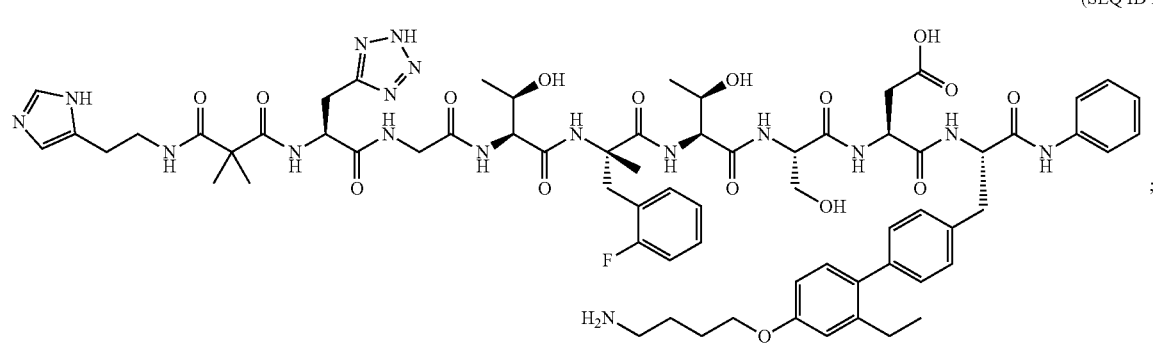
(SEQ ID NO: 63)
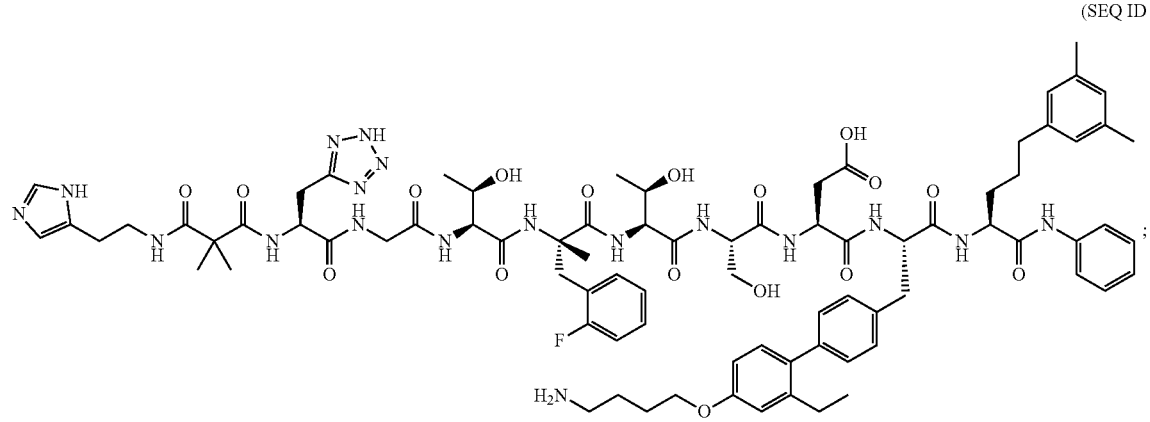

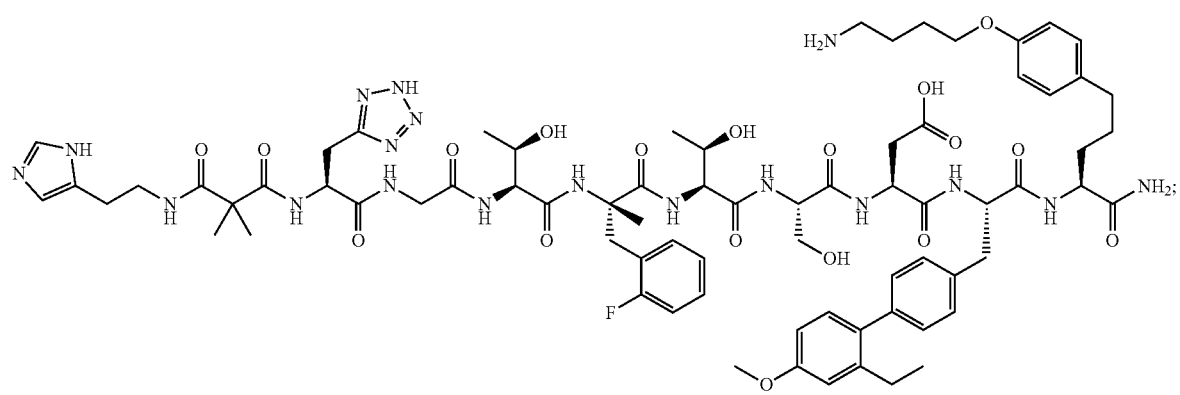
(SEQ ID NO: 64)
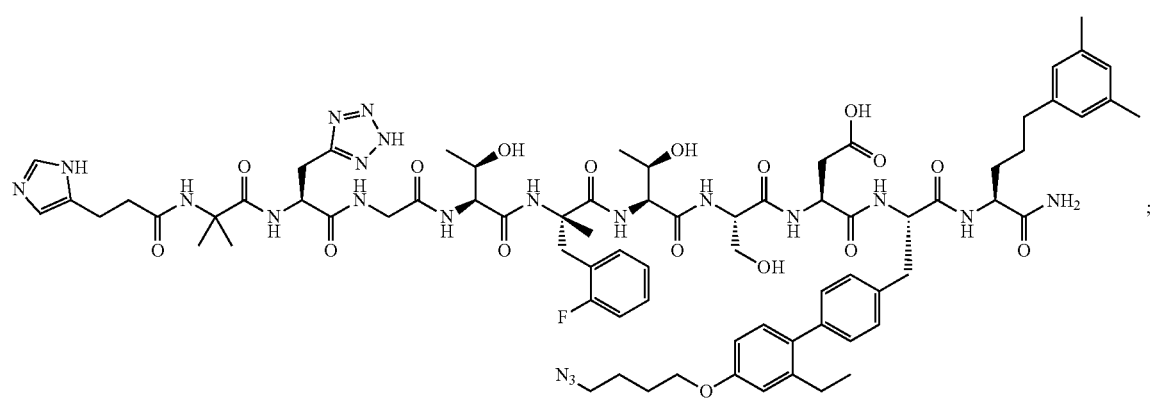
(SEQ ID NO: 65)
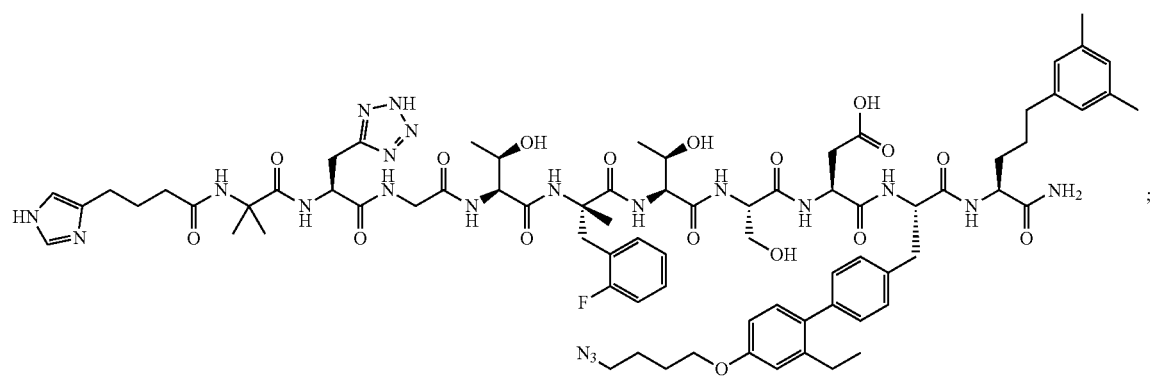
(SEQ ID NO: 66)

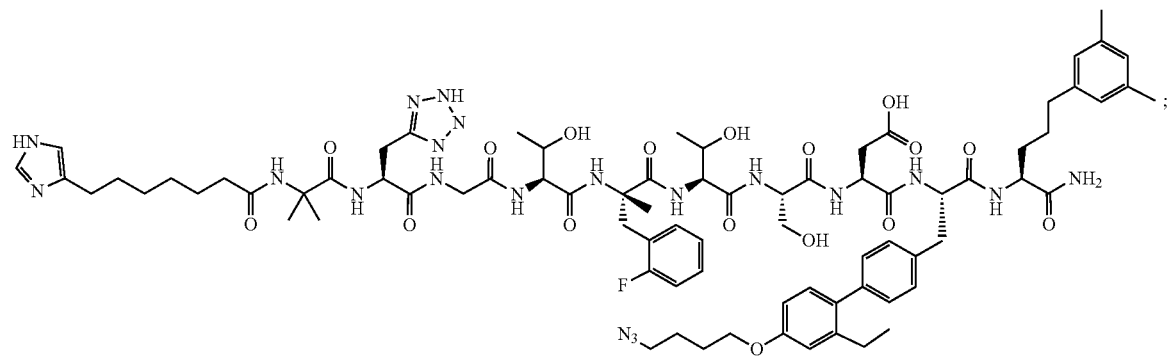
(SEQ ID NO: 67)
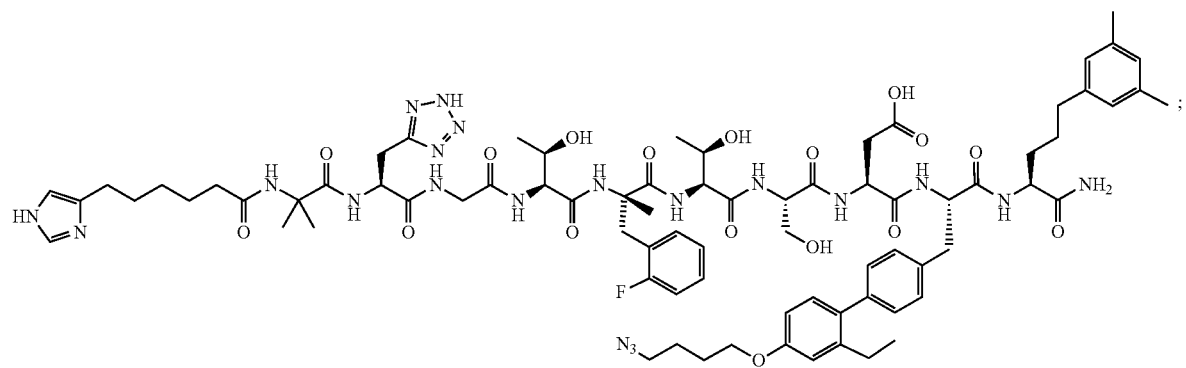
(SEQ ID NO: 68)
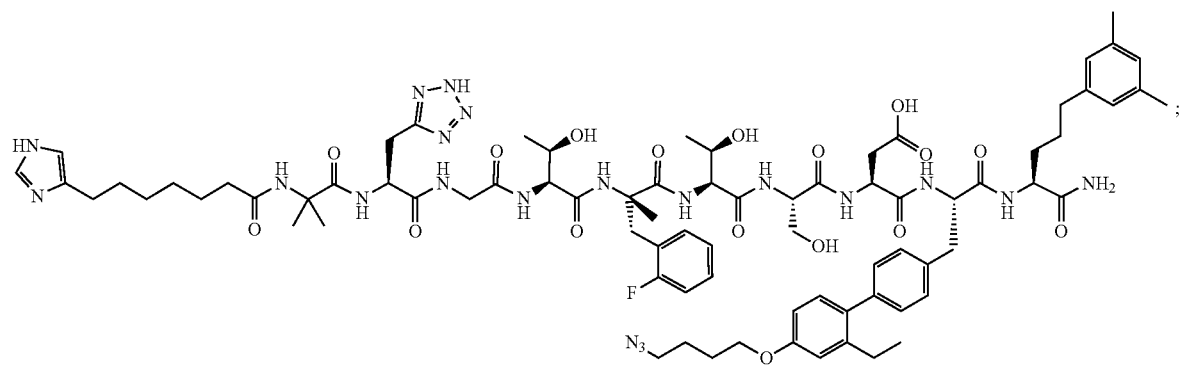
(SEQ ID NO: 69)
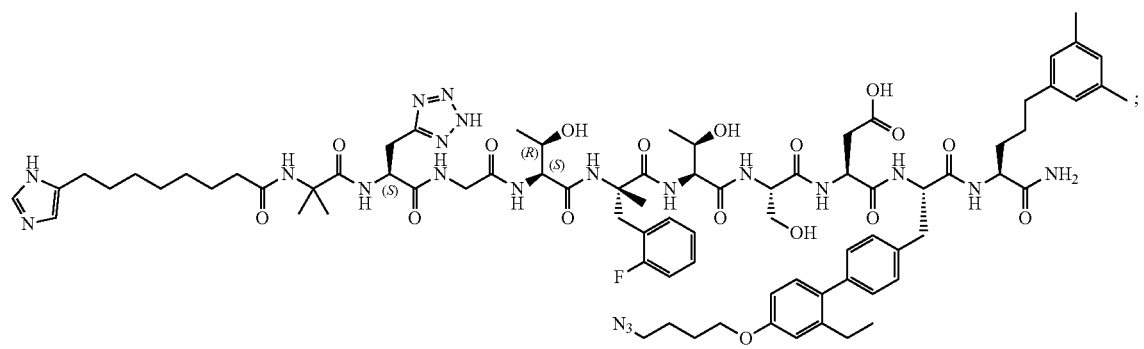
(SEQ ID NO: 70)

(SEQ ID NO: 71)
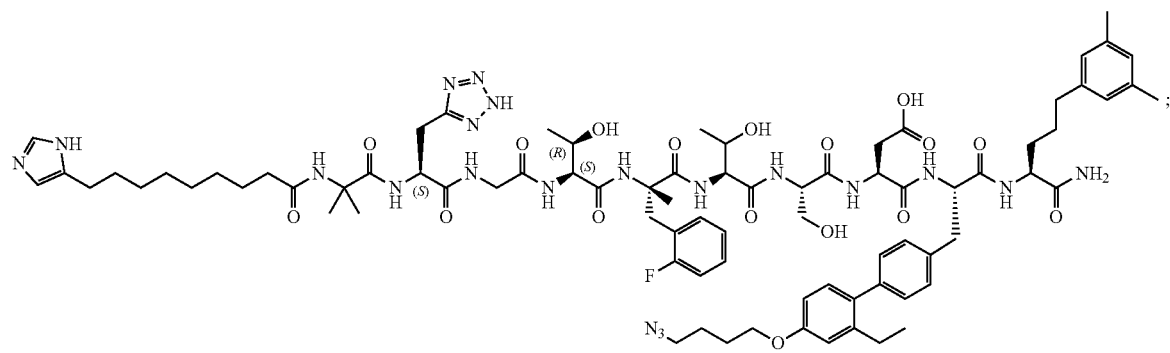
(Main Structure: SEQ ID NO: 72; Branched Sequence: SEQ ID NO: 154)
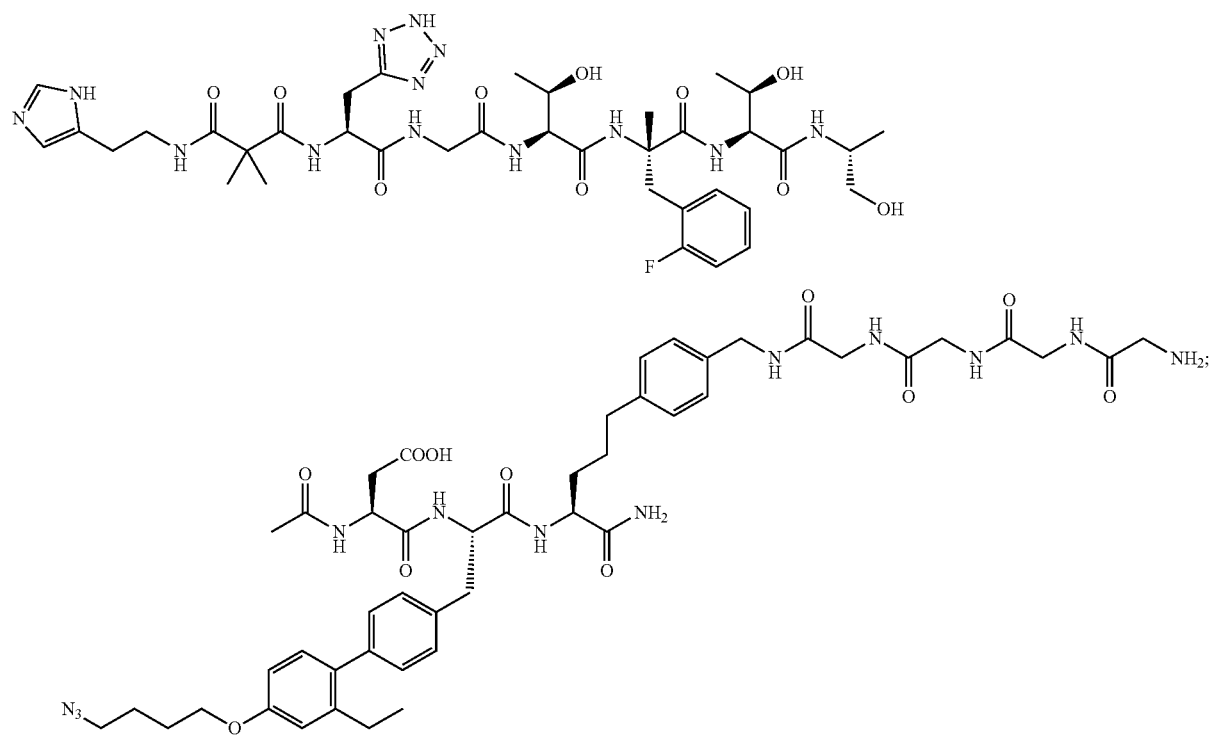
(SEQ ID NO: 73)
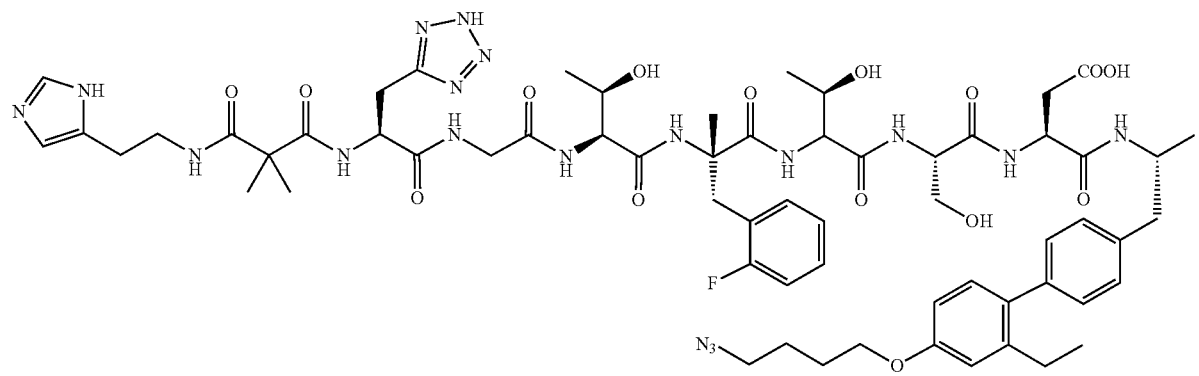

-continued
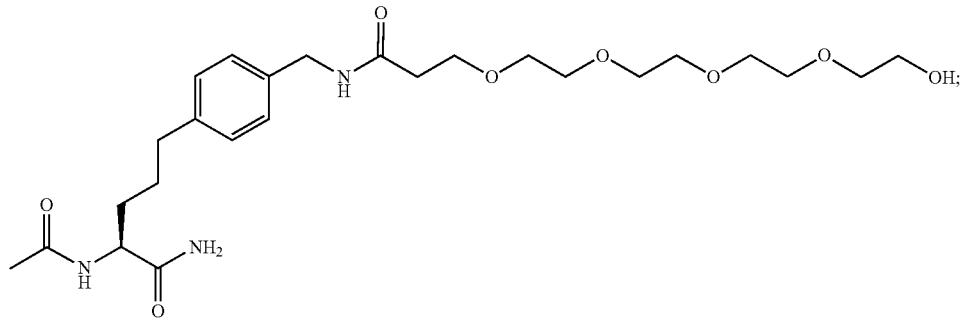
(Main Structure: SEQ ID NO: 74; Branched Sequence: SEQ ID NO: 155)
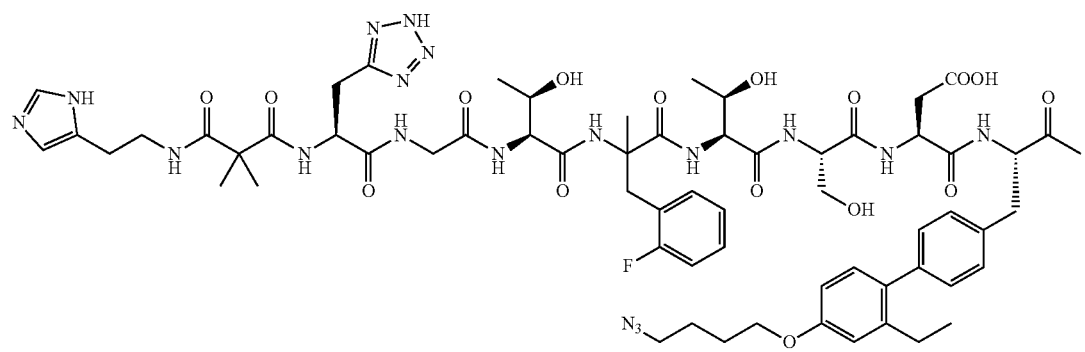
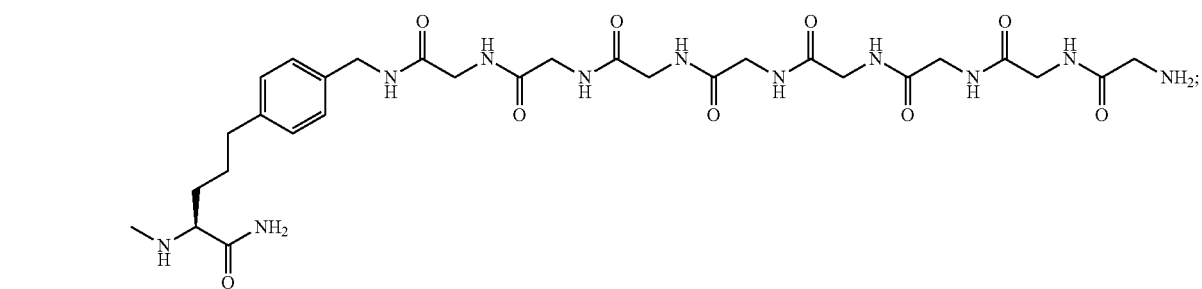
(SEQ ID NO: 75)
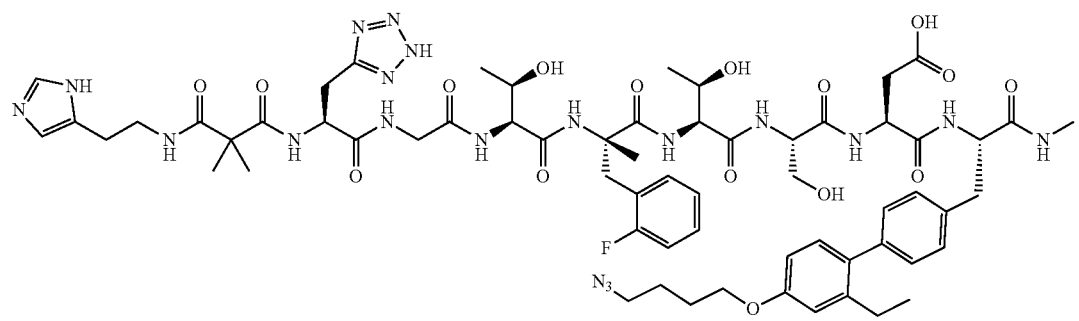
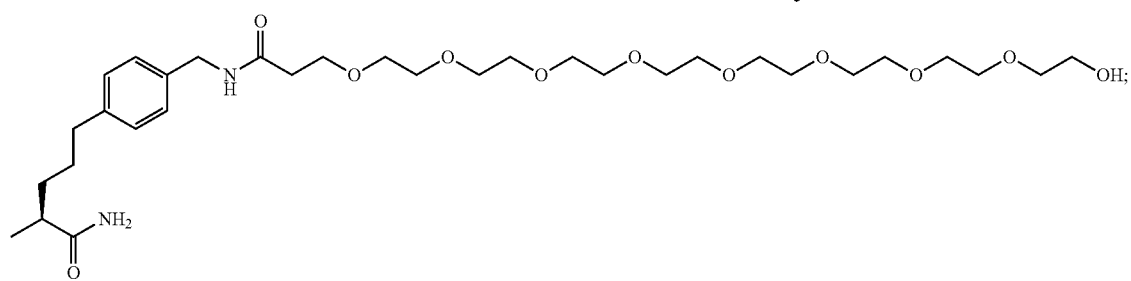

(SEQ ID NO: 76)
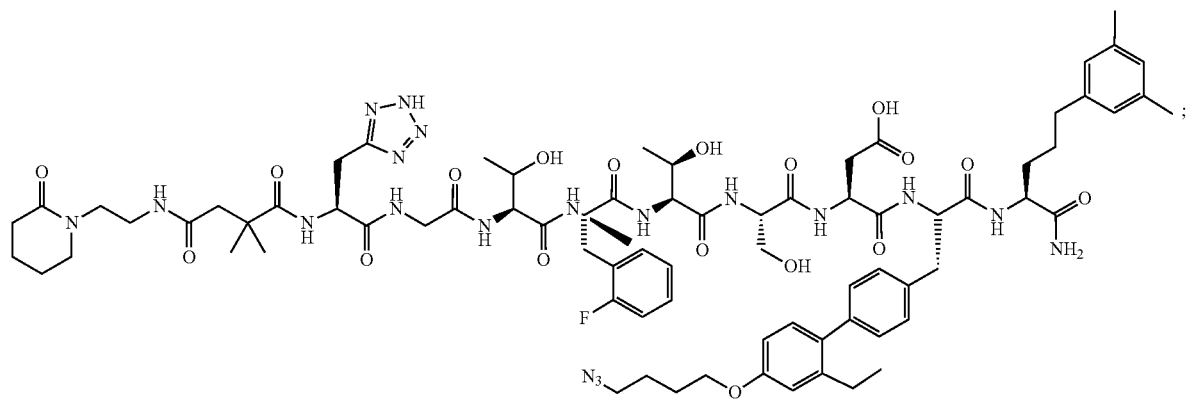
(SEQ ID NO: 77)
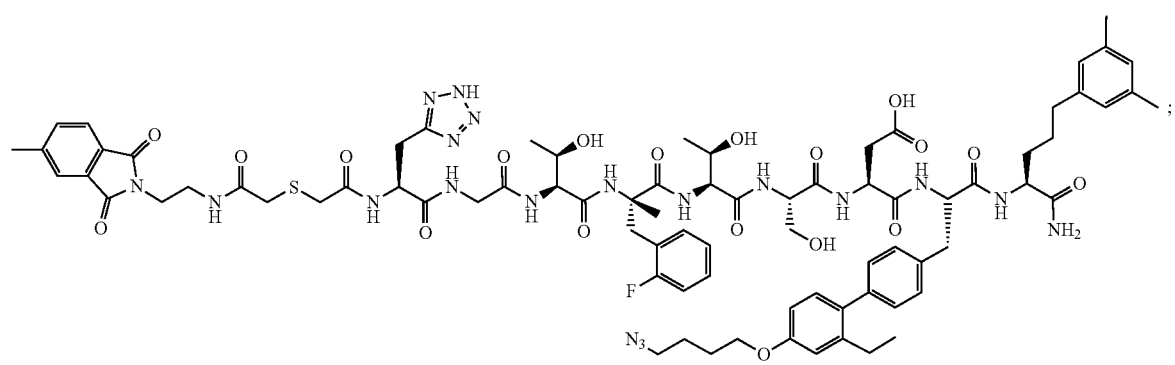
(SEQ ID NO: 78)
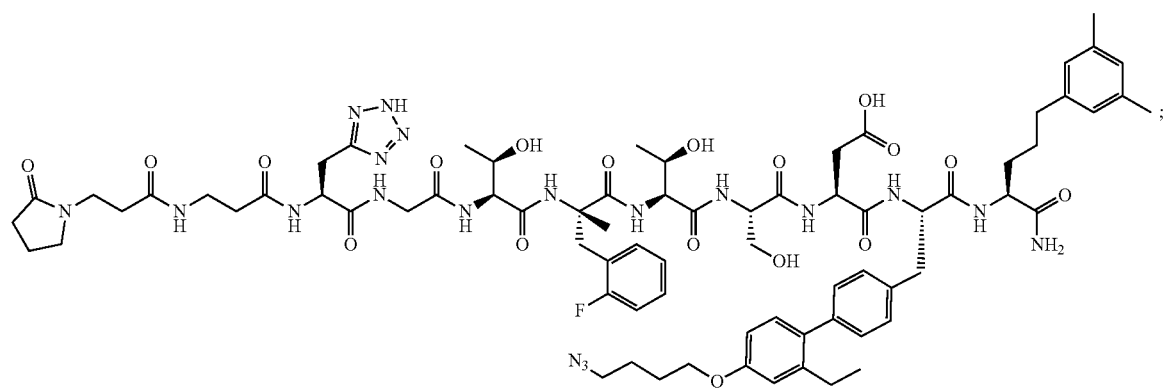
(SEQ ID NO: 79)
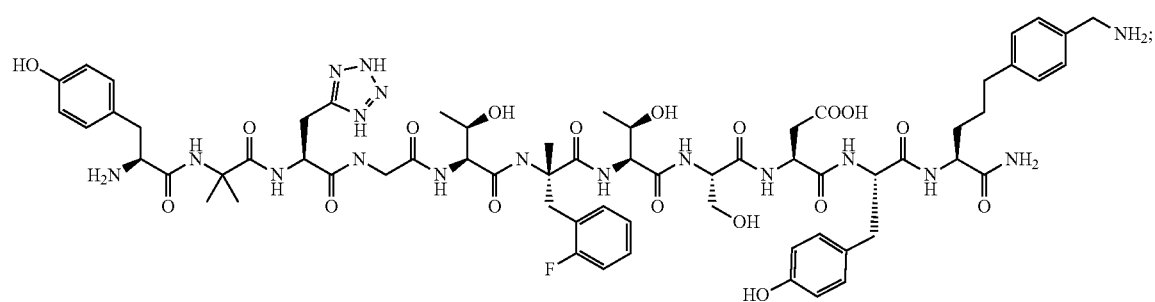

(SEQ ID NO: 80)
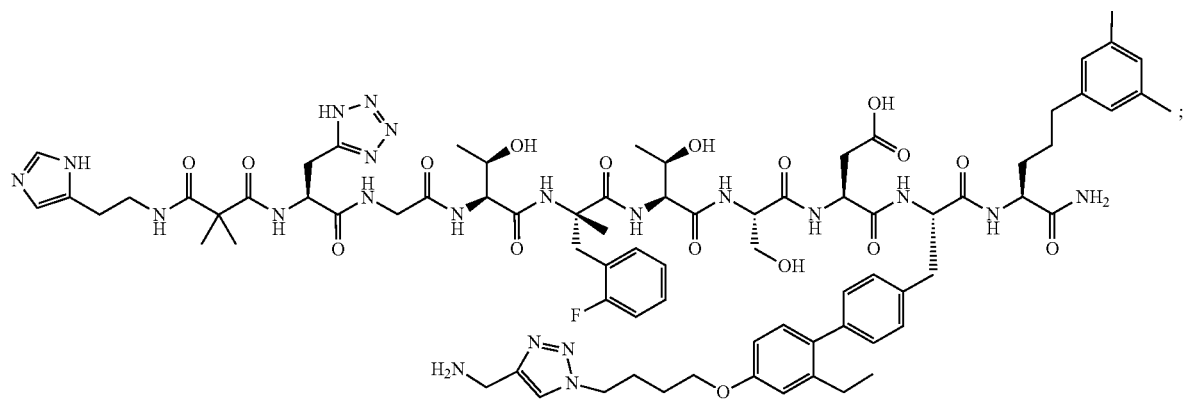
(SEQ ID NO: 81)
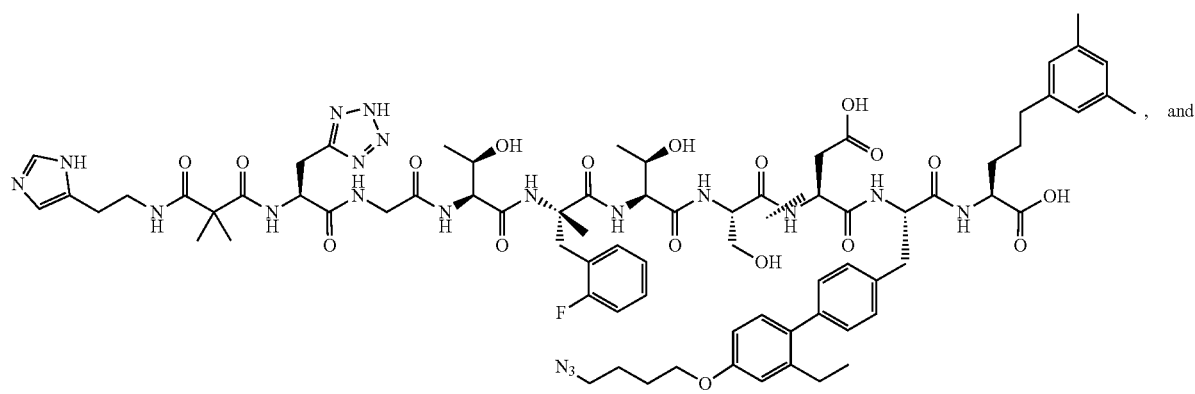
, and
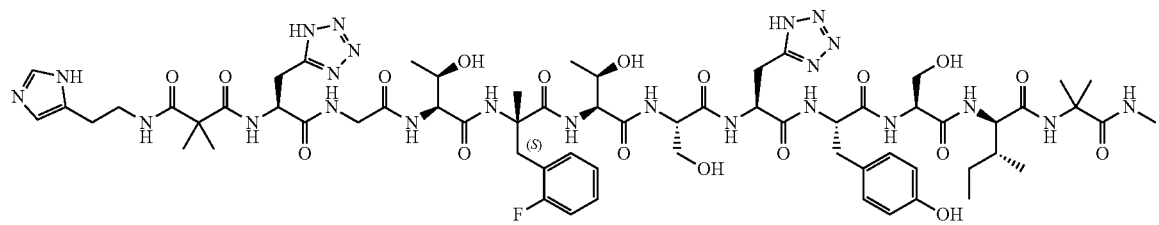
(SEQ ID NO: 82)
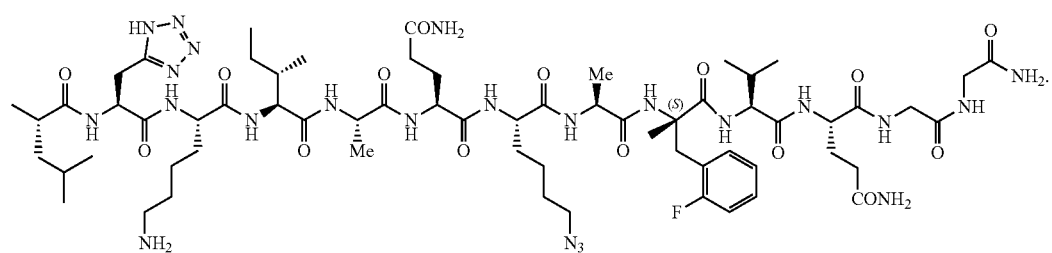

In another aspect, provided herein is a compound having a structure of Formula (C):

(C (SEQ ID NO: 27))

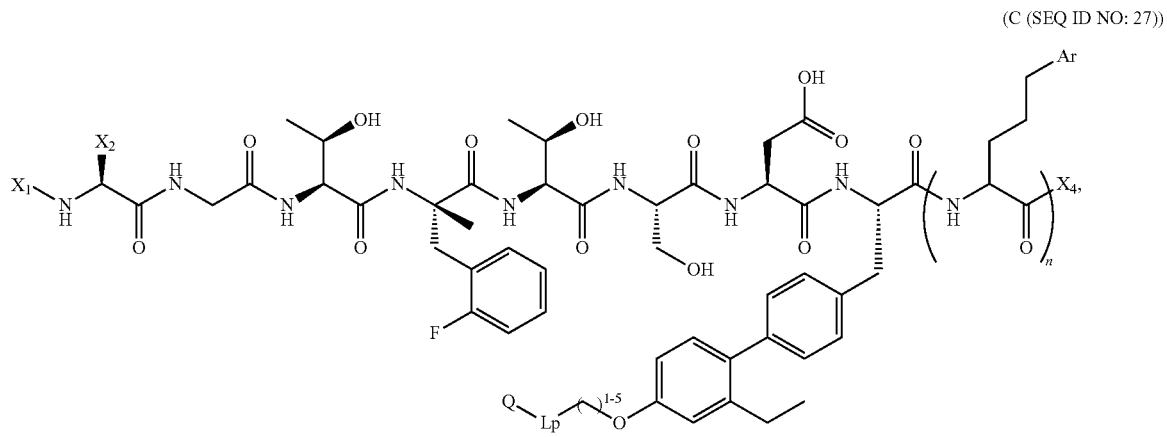

wherein:

Lp is absent or a linker comprising one or more of

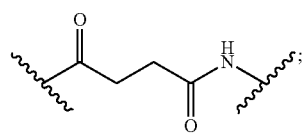 [SMILES: *NC(=O)CCC(*)=O]

a carbamate group; a cyclodextrin; a polyethylene glycol (PEG) segment having 1 to 36 —CH$_2$CH$_2$O— (EG) units; a —(CH$_2$)$_{2-24}$— chain; a triazole; one or more amino acids selected from glycine, serine, glutamic acid, alanine, valine, and proline, and combinations thereof;

Q is a moiety selected from —NH$_2$, —N$_3$,

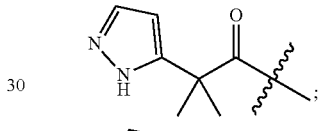

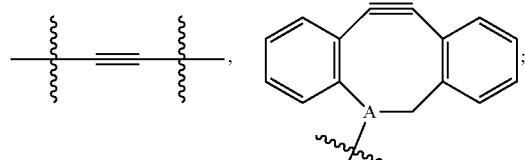

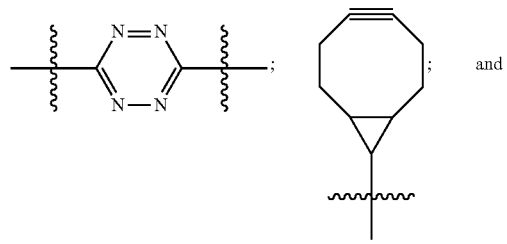

where A is C or N;

X$_1$ is selected from H;

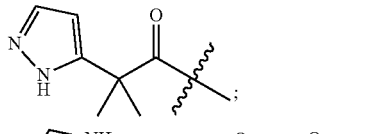

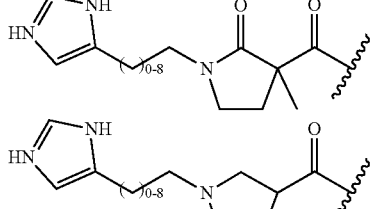

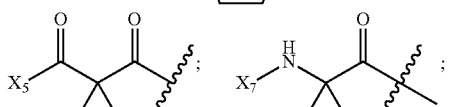

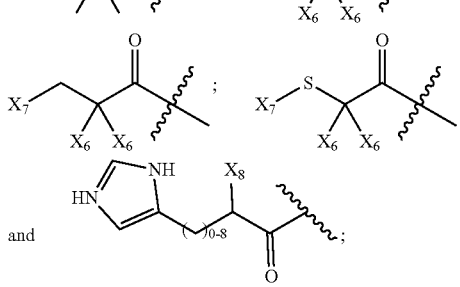

X$_2$ is selected from

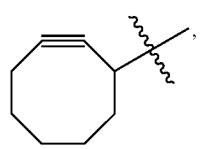  and  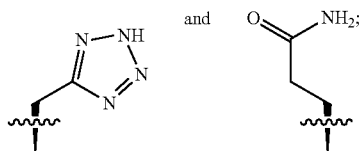

n is 0 or 1;

$X_4$ is selected from —$NH_2$, —OH and —N(H)(phenyl);

$X_5$ is selected from —OH, —$NH_2$, —NH—OH, and

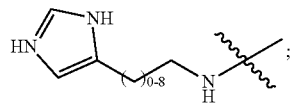

$X_6$ is independently at each occurrence selected from H, —OH, —$CH_3$, and —$CH_2OH$;

$X_7$ is selected from H,

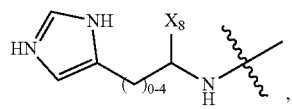

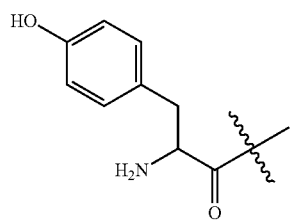

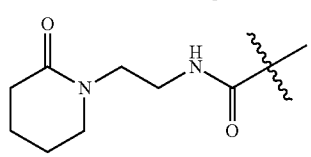

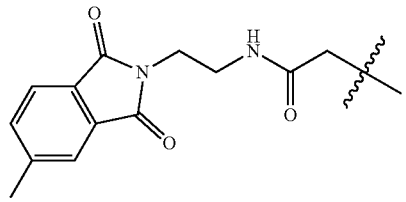

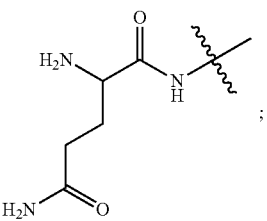 [SMILES: *NC(=O)C(N)CCC(N)=O ; ";"]

$X_8$ is selected from H, —OH, —$NH_2$, and

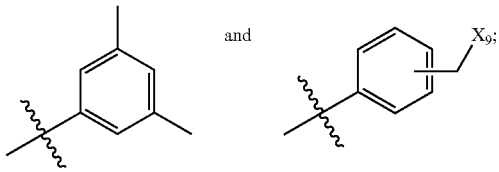

Ar is selected from

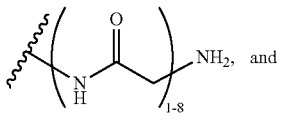

$X_9$ is selected from —$NH_2$,

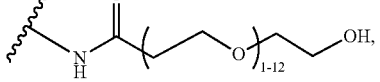

or a pharmaceutically acceptable salt thereof

In another aspect, provided herein is a compound having a structure of Formula (III):

(III (SEQ ID NO: 86))

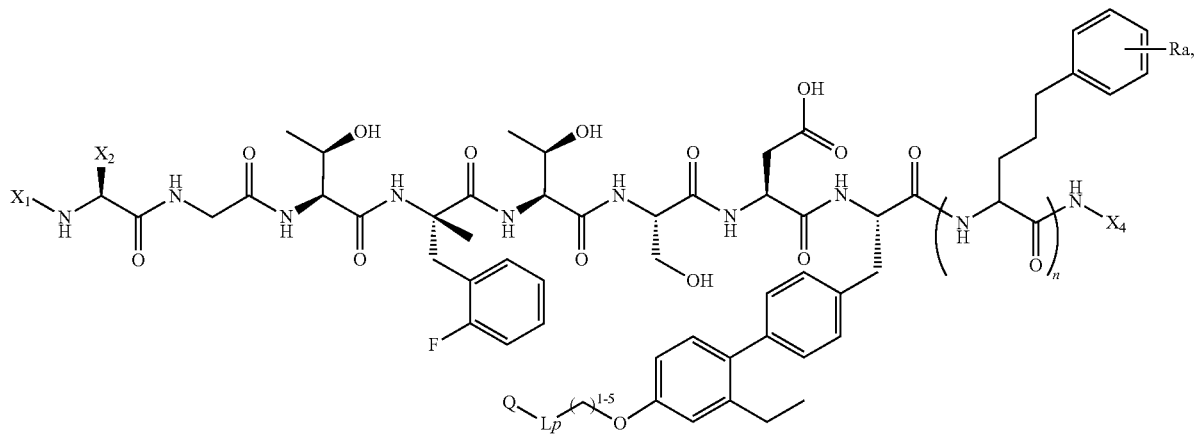

wherein:

$L_p$ is absent or a linker comprising one or more of

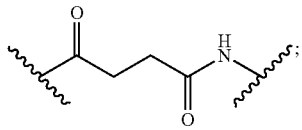 [SMILES: *NC(=O)CCC(*)=O]

a carbamate group; a cyclodextrin; a polyethylene glycol (PEG) segment having 1 to 36 —CH$_2$CH$_2$O— (EG) units; one or more amino acids selected from glycine, serine, glutamic acid, alanine, valine, and proline, and combinations thereof;

Q is a moiety selected from —N$_3$,

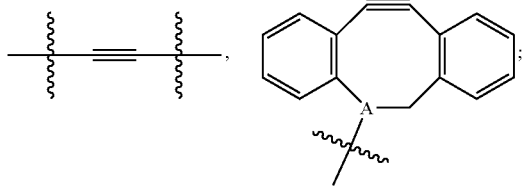

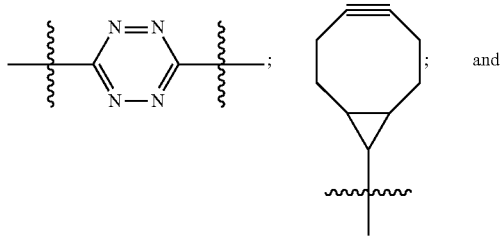

where A is C or N;

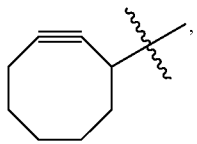

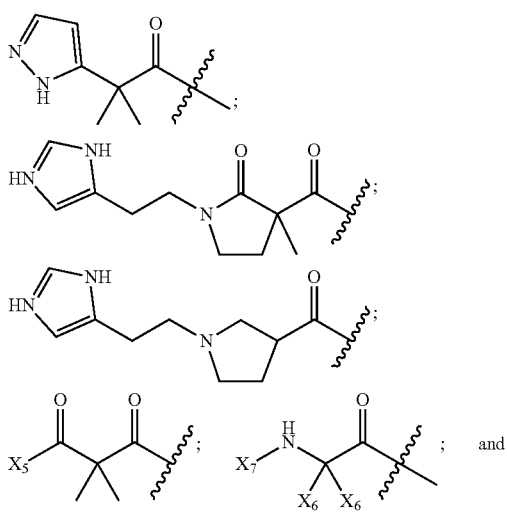

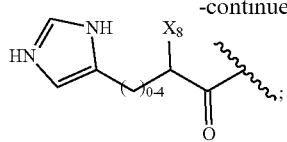

$X_1$ is selected from H;
$X_2$ is selected from

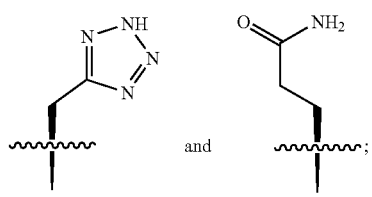

$X_3$ is selected from —(CH$_2$)$_{2-6}$—NH$_2$, —(CH$_2$)$_{2-6}$—N$_3$, and —CH$_3$, with the proviso that when $X_3$ is —CH$_3$, n is 1 and Ra in at least one occurrence is selected from —(CH$_2$)$_{2-6}$—NH$_2$ and —(CH$_2$)$_{2-6}$—N$_3$;

n is 0 or 1;

Ra is independently at each occurrence selected from H, —CH$_3$, —(CH$_2$)$_{2-6}$—NH$_2$, and —(CH$_2$)$_{2-6}$—N$_3$;

$X_4$ is selected from H and phenyl;
$X_5$ is selected from —OH, —NH$_2$, —NH—OH, and

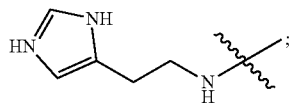

$X_6$ is independently at each occurrence selected from H, —OH, —CH$_3$, and —CH$_2$OH;

$X_7$ is selected from H,

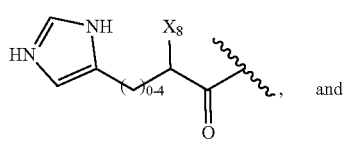 and

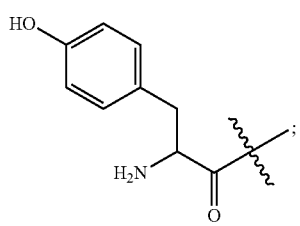

$X_3$ is selected from H, —OH, —NH$_2$, and
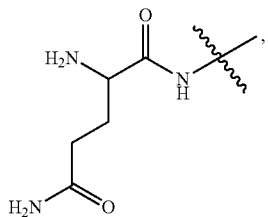
and pharmaceutically acceptable salts thereof.
In some embodiments, The compound described above has a structure selected from the group consisting of:

Structure (SEQ ID NO: 179)
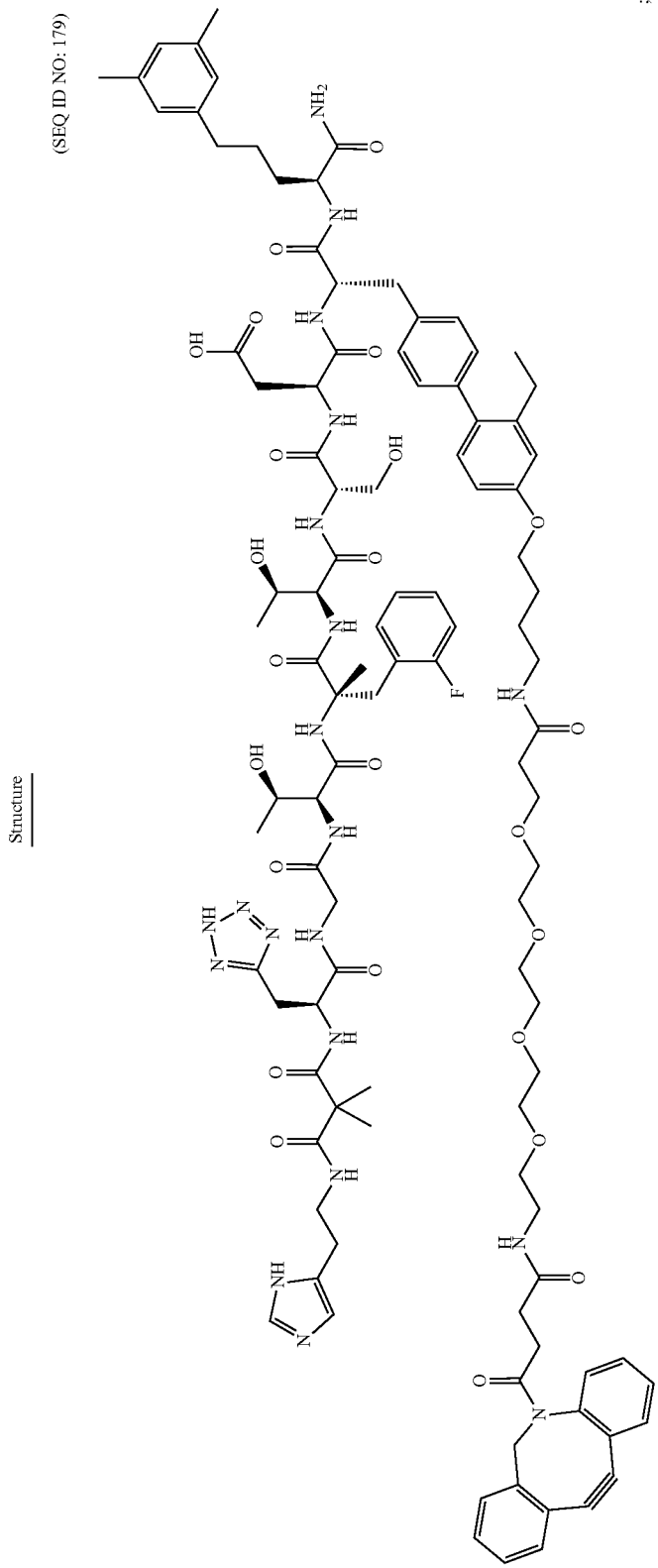

(SEQ ID NO: 180)
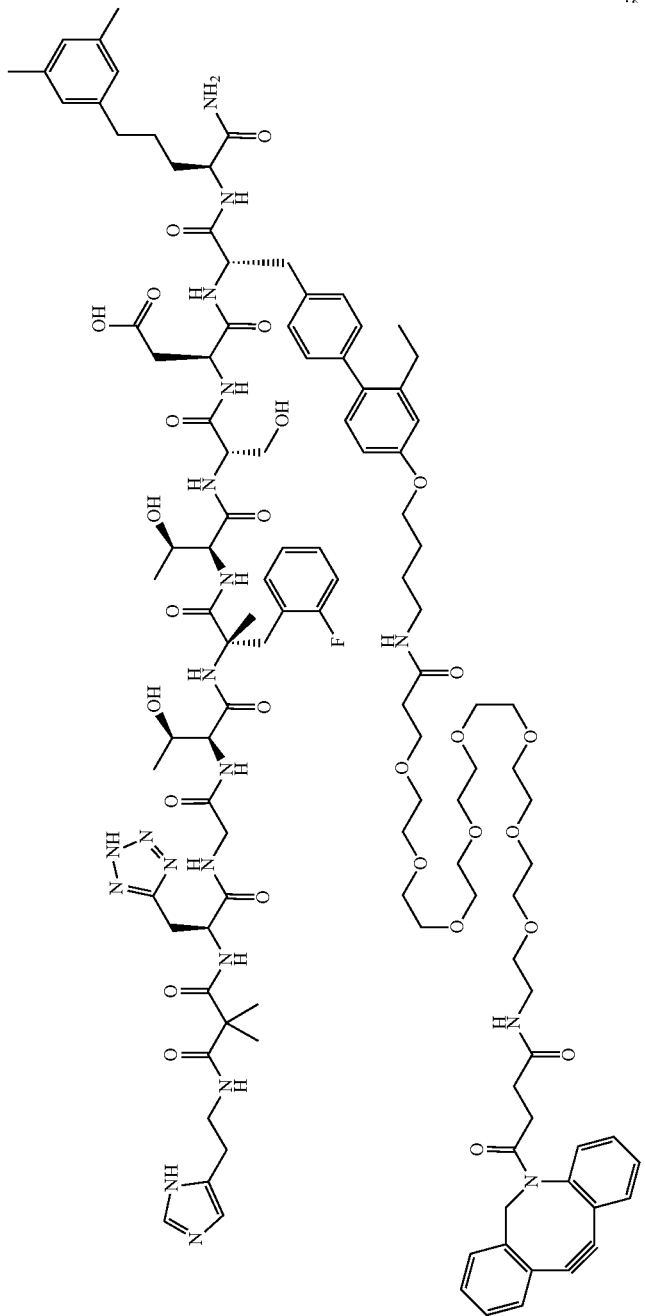

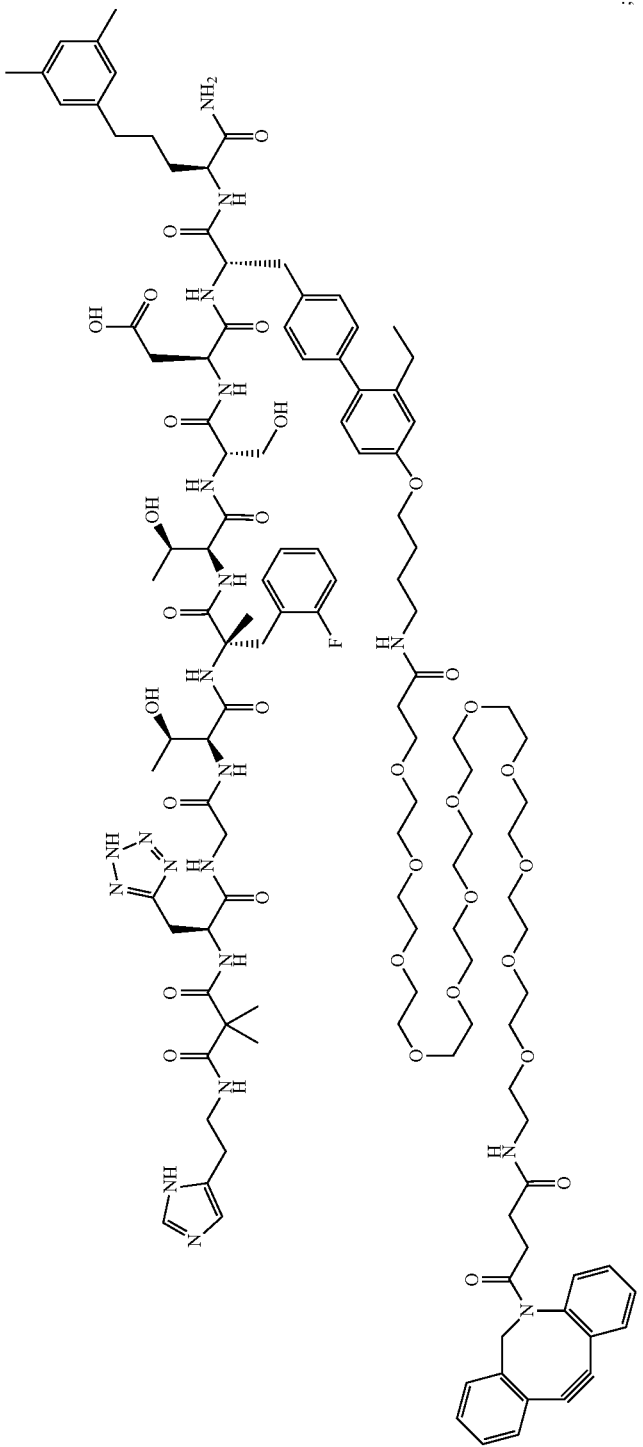
(SEQ ID NO: 181)

-continued
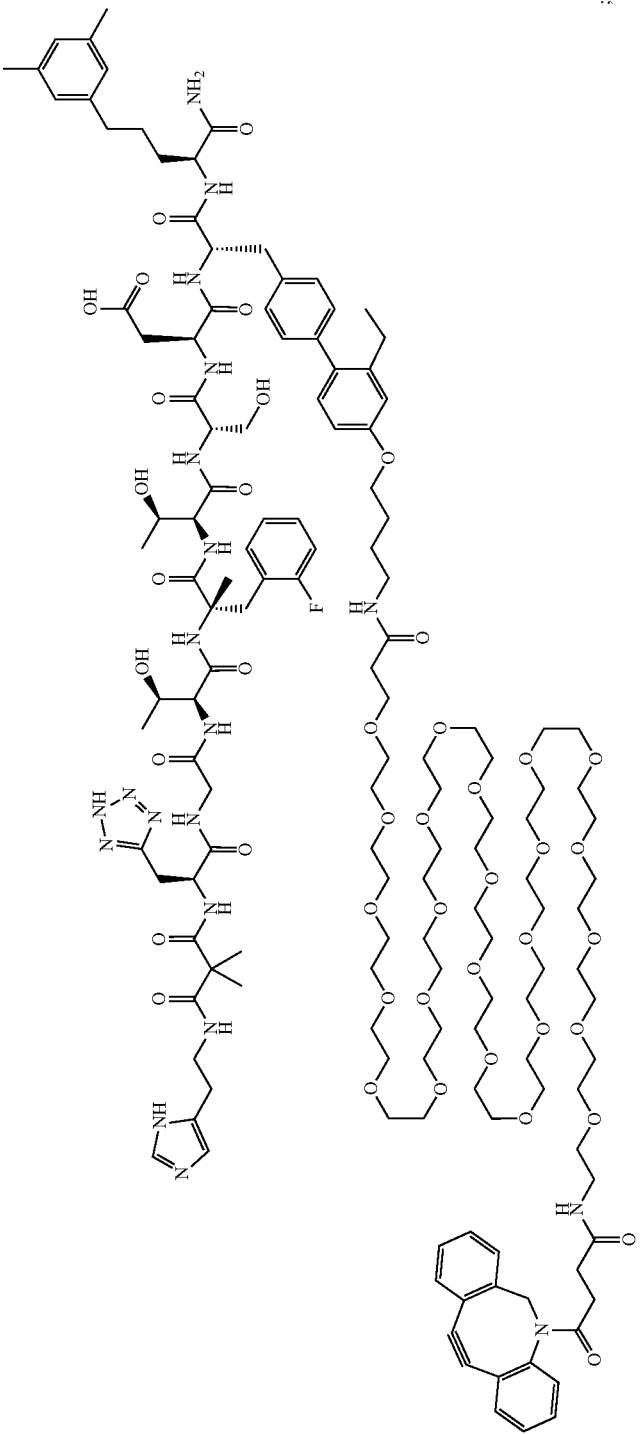
(SEQ ID NO: 182)

(SEQ ID NO: 183)
-continued
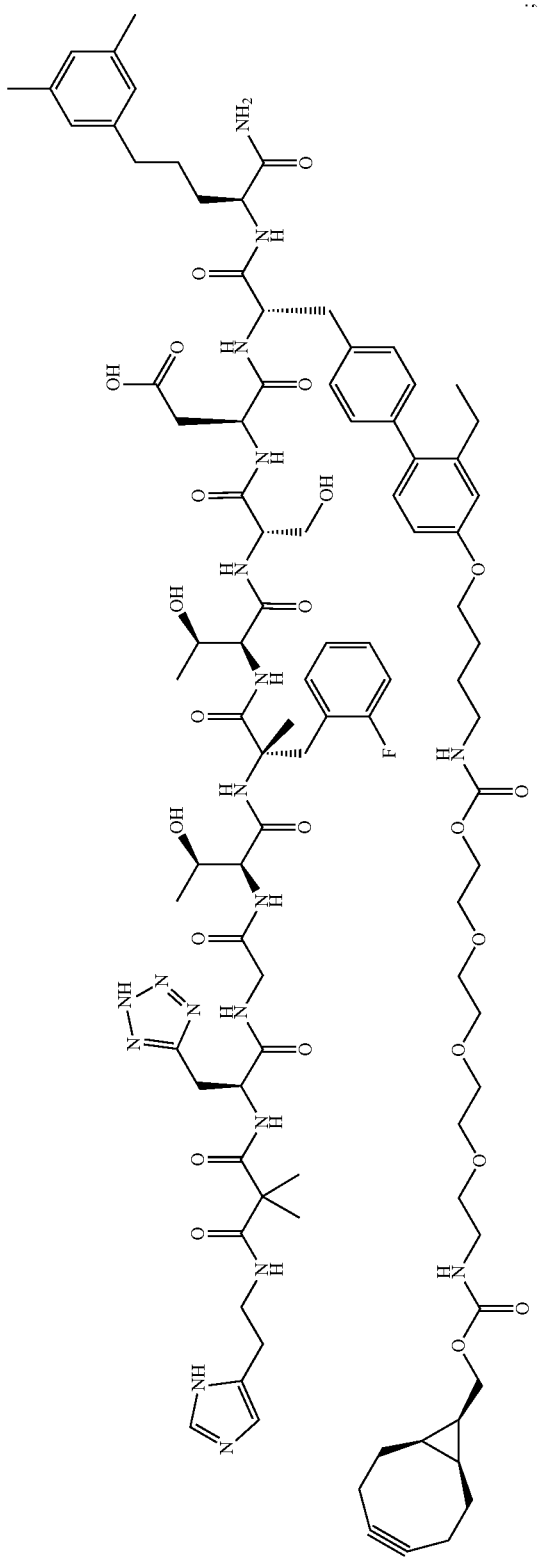

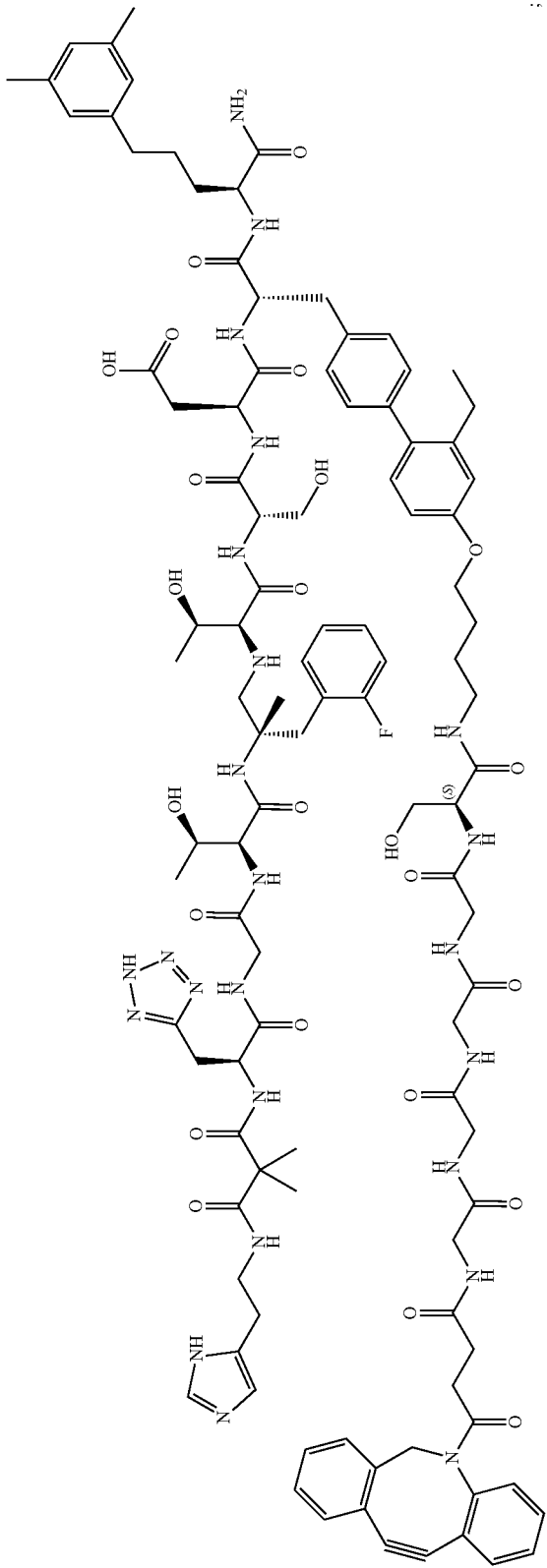

(Main Structure: SEQ ID NO: 89; Branched Sequence: SEQ ID NO: 157)
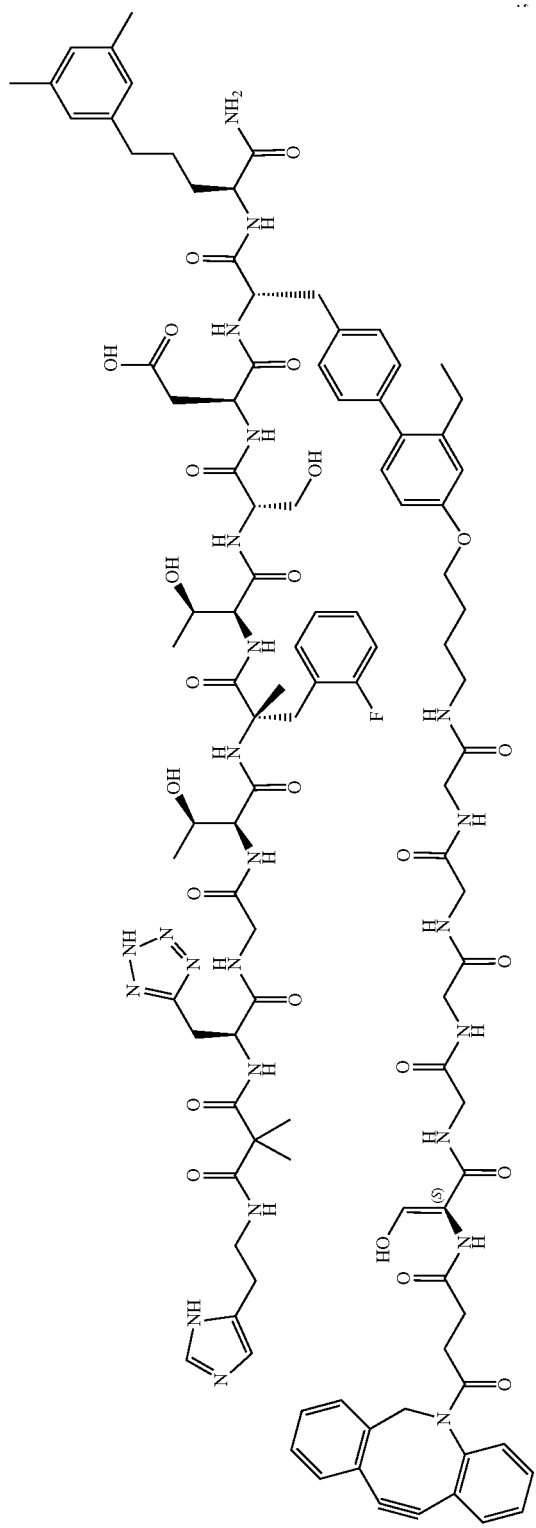

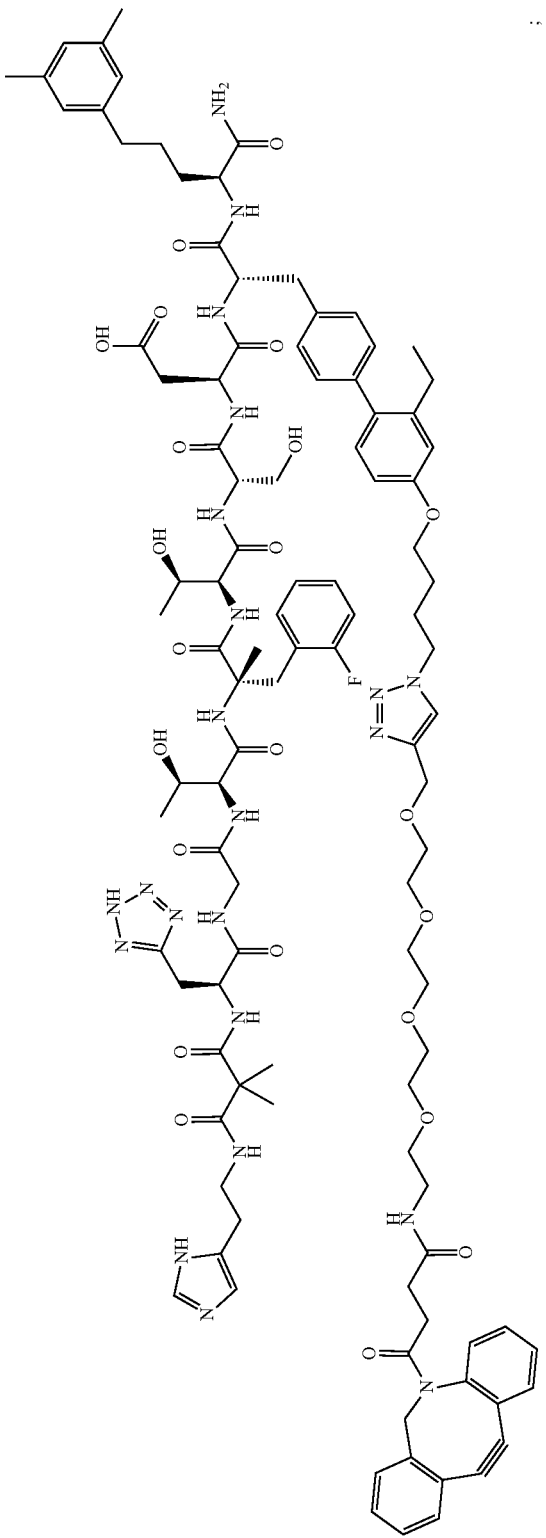
(SEQ ID NO: 184)
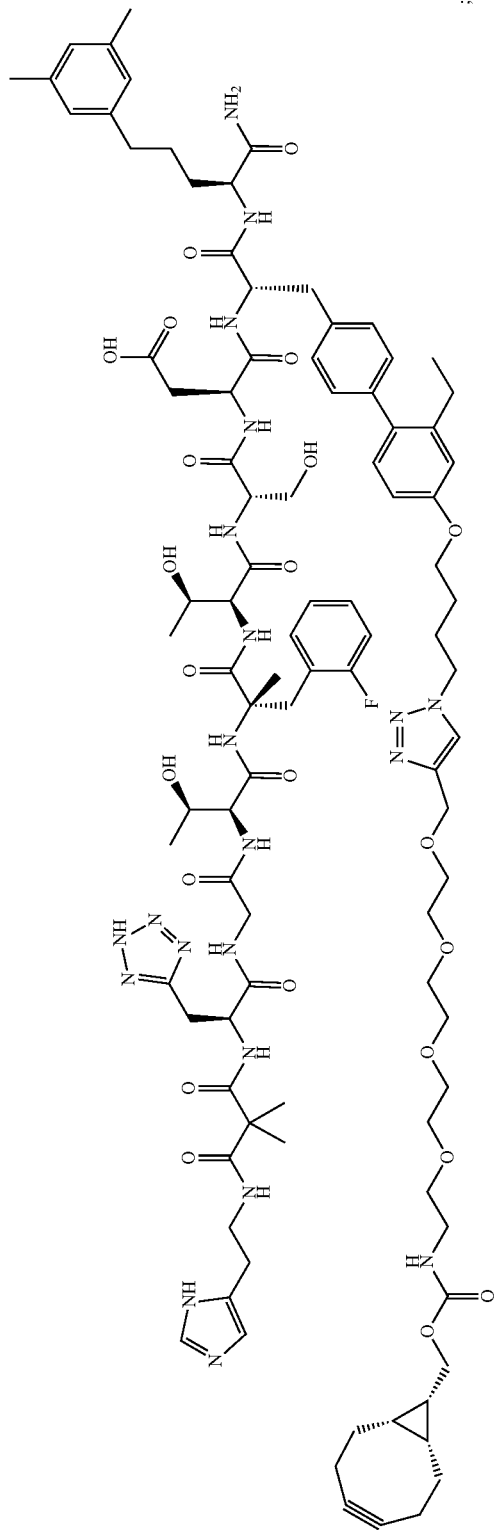
(SEQ ID NO: 185)

(SEQ ID NO: 186)
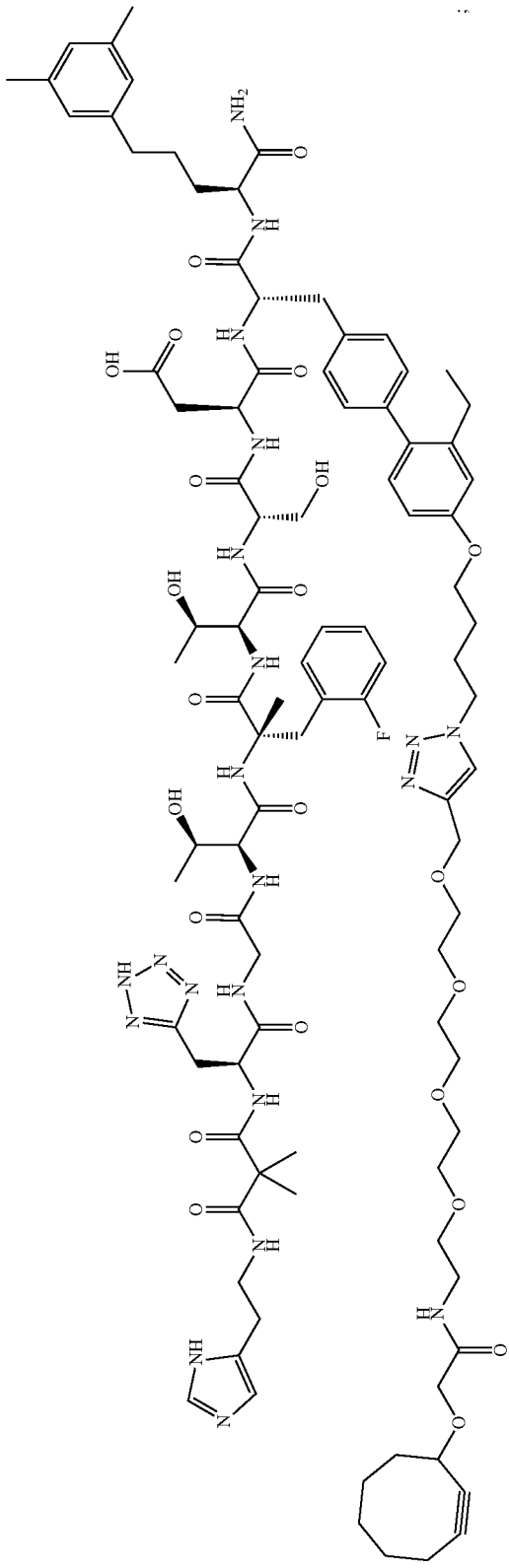
(SEQ ID NO: 91)
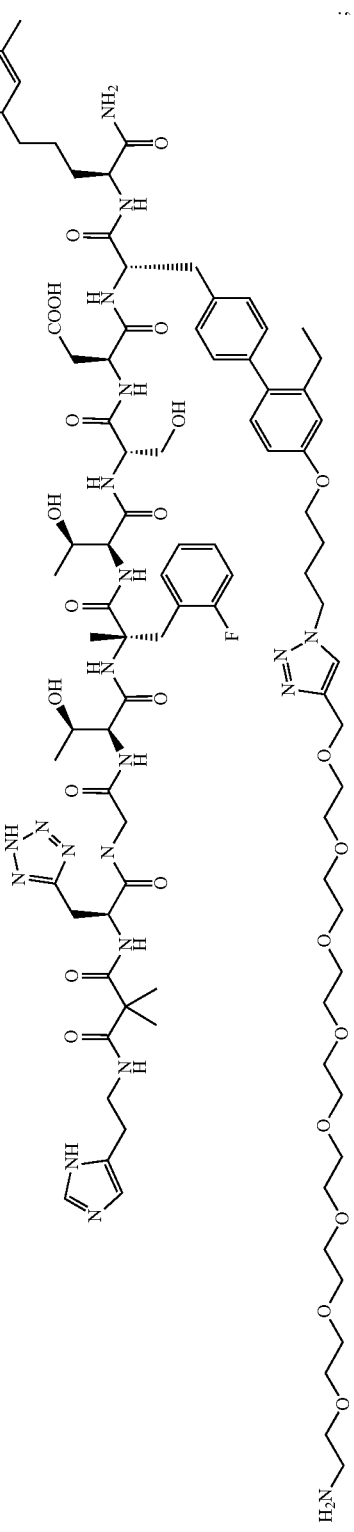

-continued
(SEQ ID NO: 92)
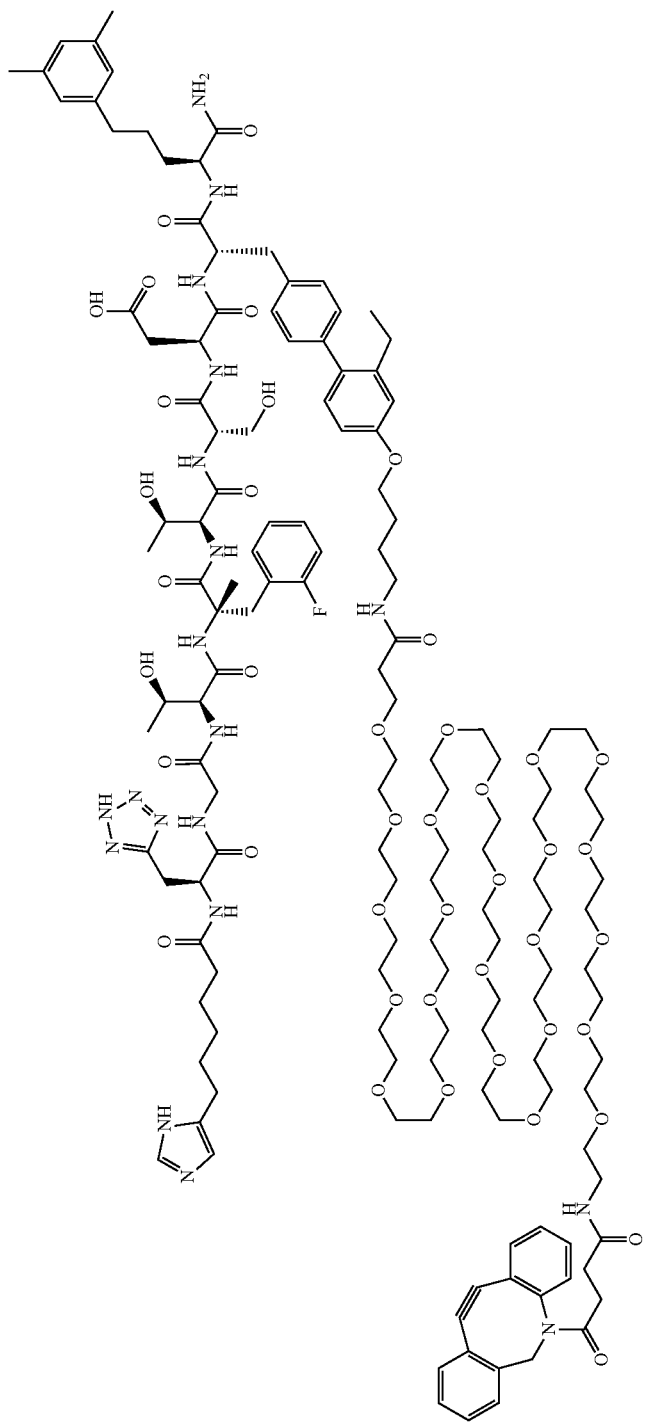

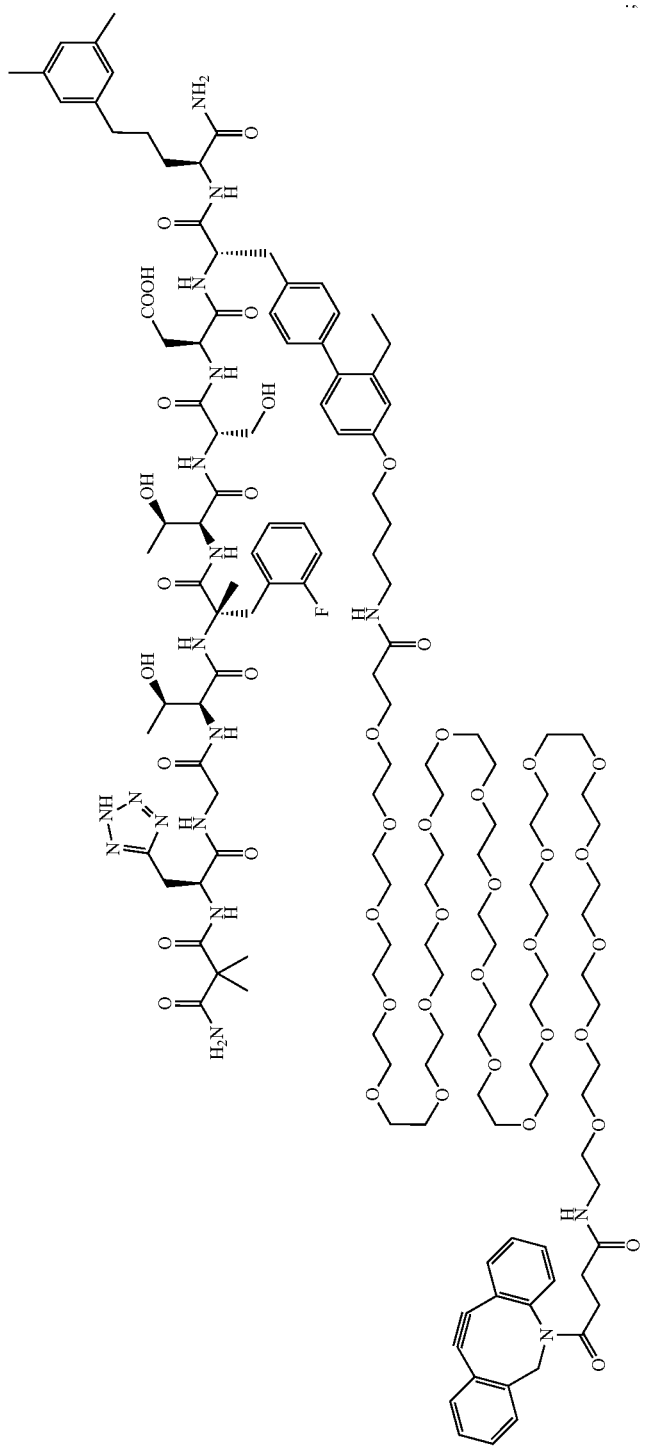
(SEQ ID NO: 93)

-continued
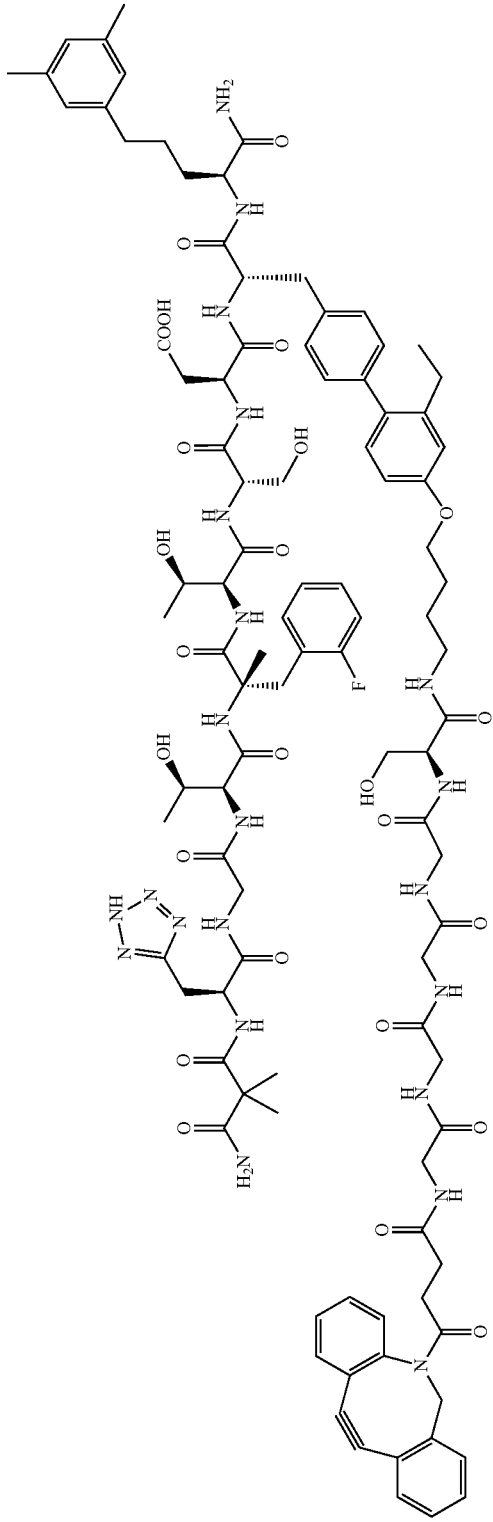
(Main Structure: SEQ ID NO: 94; Branched Sequence: SEQ ID NO: 158)
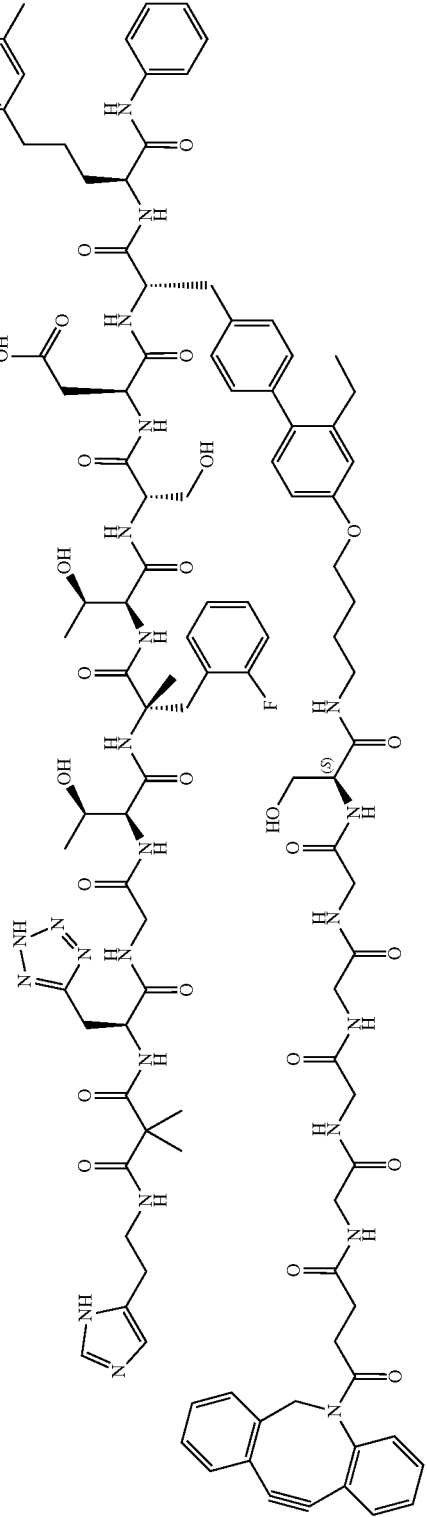
(Main Structure: SEQ ID NO: 95; Branched Sequence: SEQ ID NO: 159)

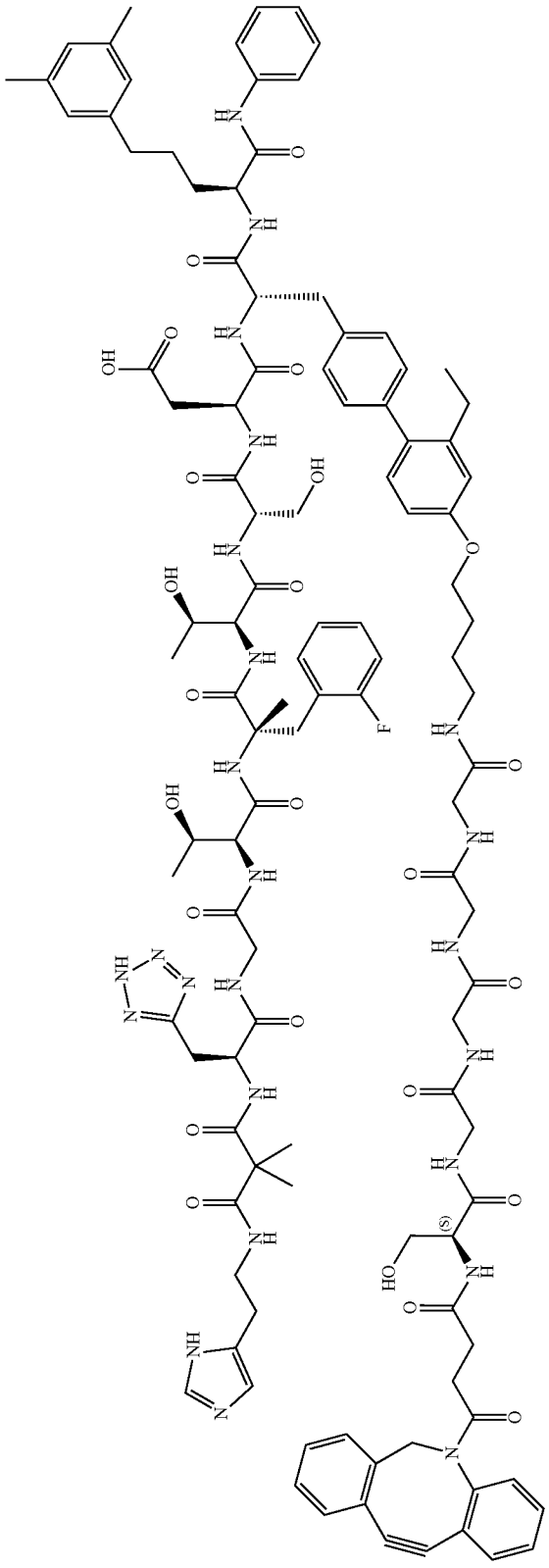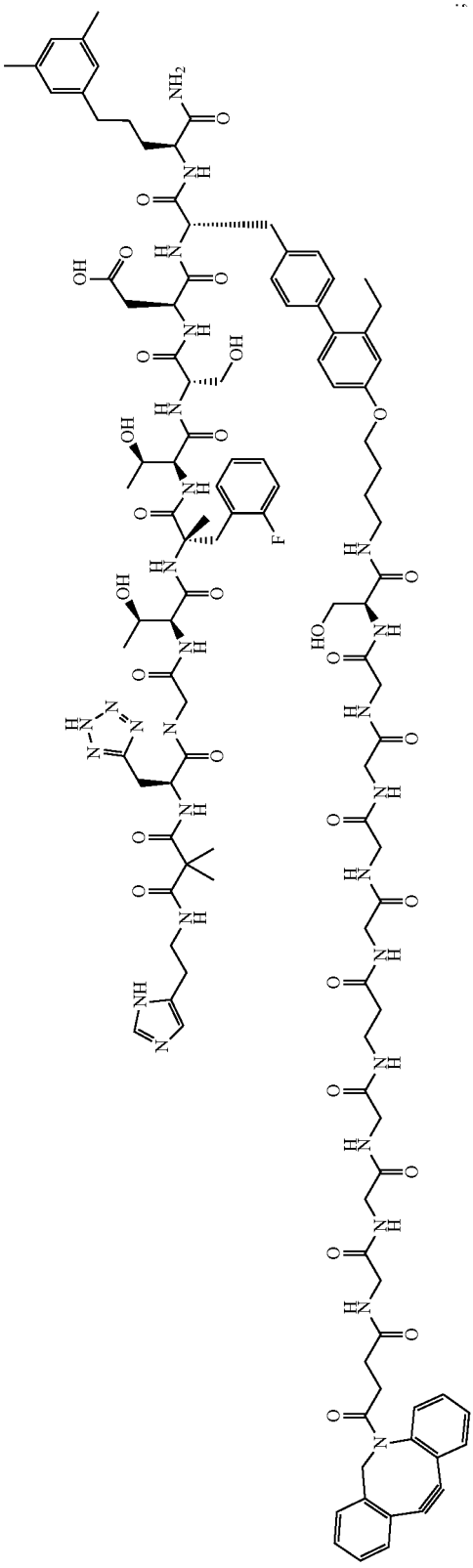

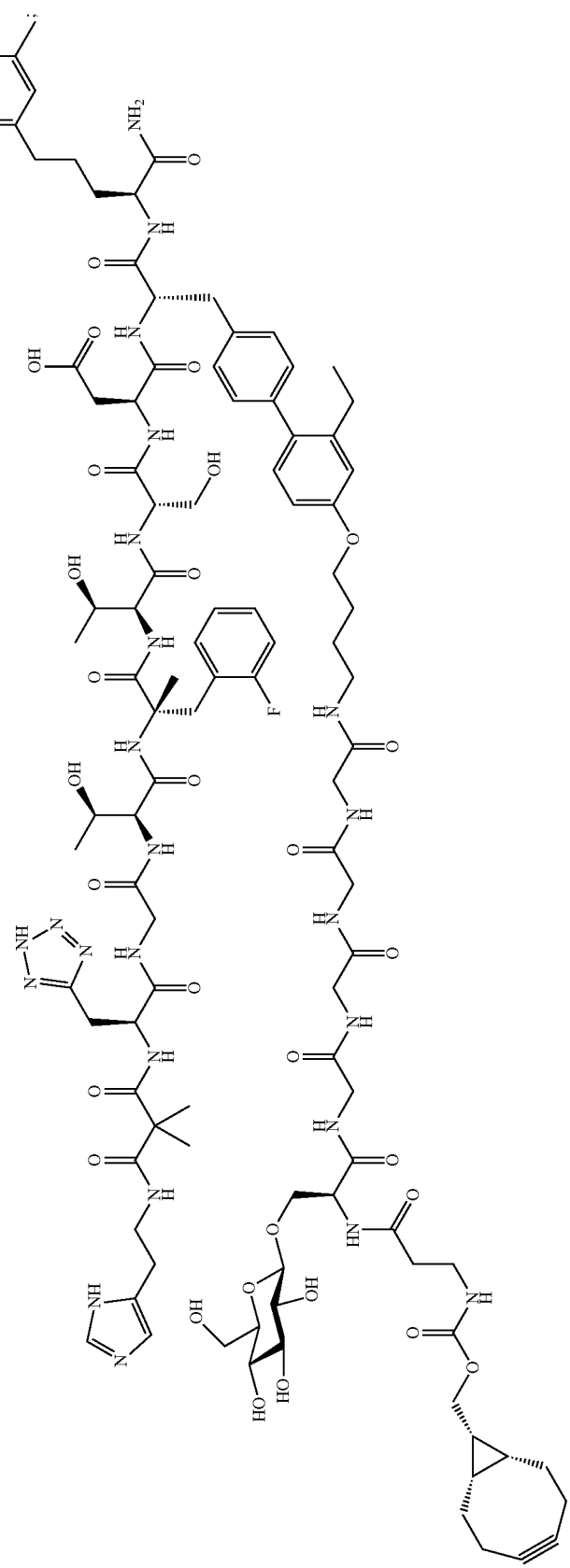
(Main Structure: SEQ ID NO: 98; Branched Sequence: SEQ ID NO: 162)

-continued
(Main Structure: SEQ ID NO: 99; Branched Sequence: SEQ ID NO: 163)
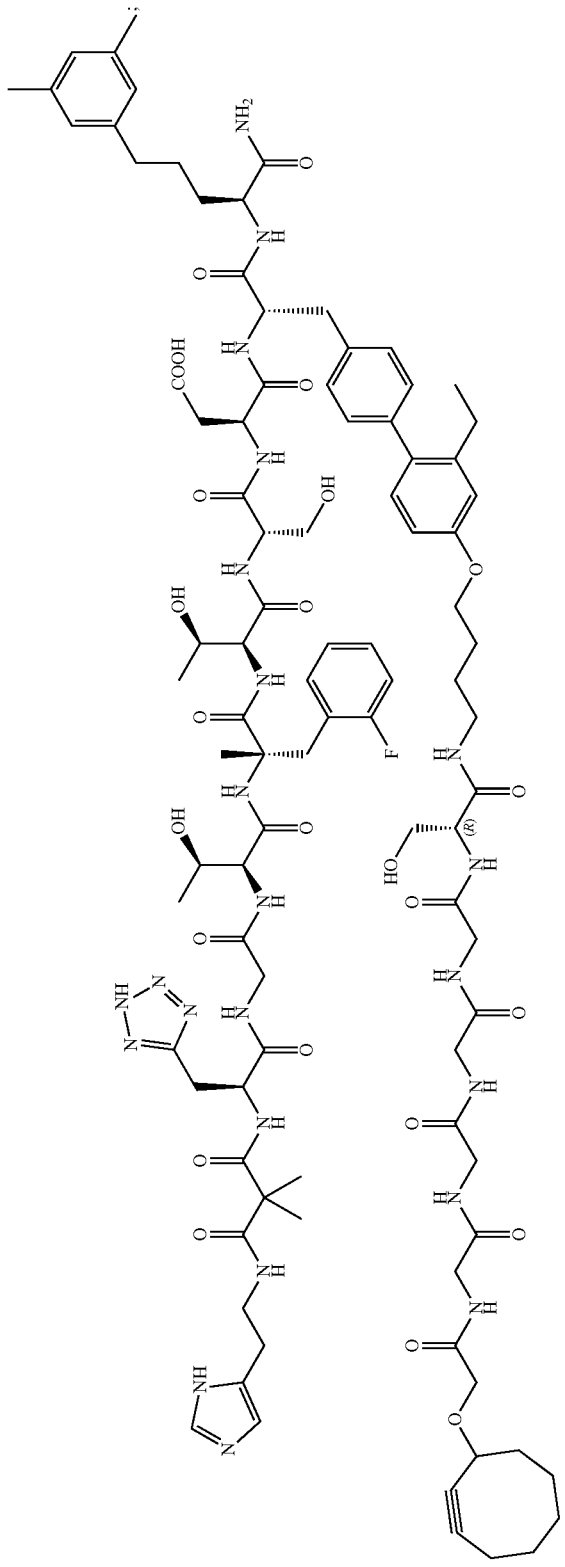

-continued
(Main Structure: SEQ ID NO: 100; Branched Sequence: SEQ ID NO: 164)
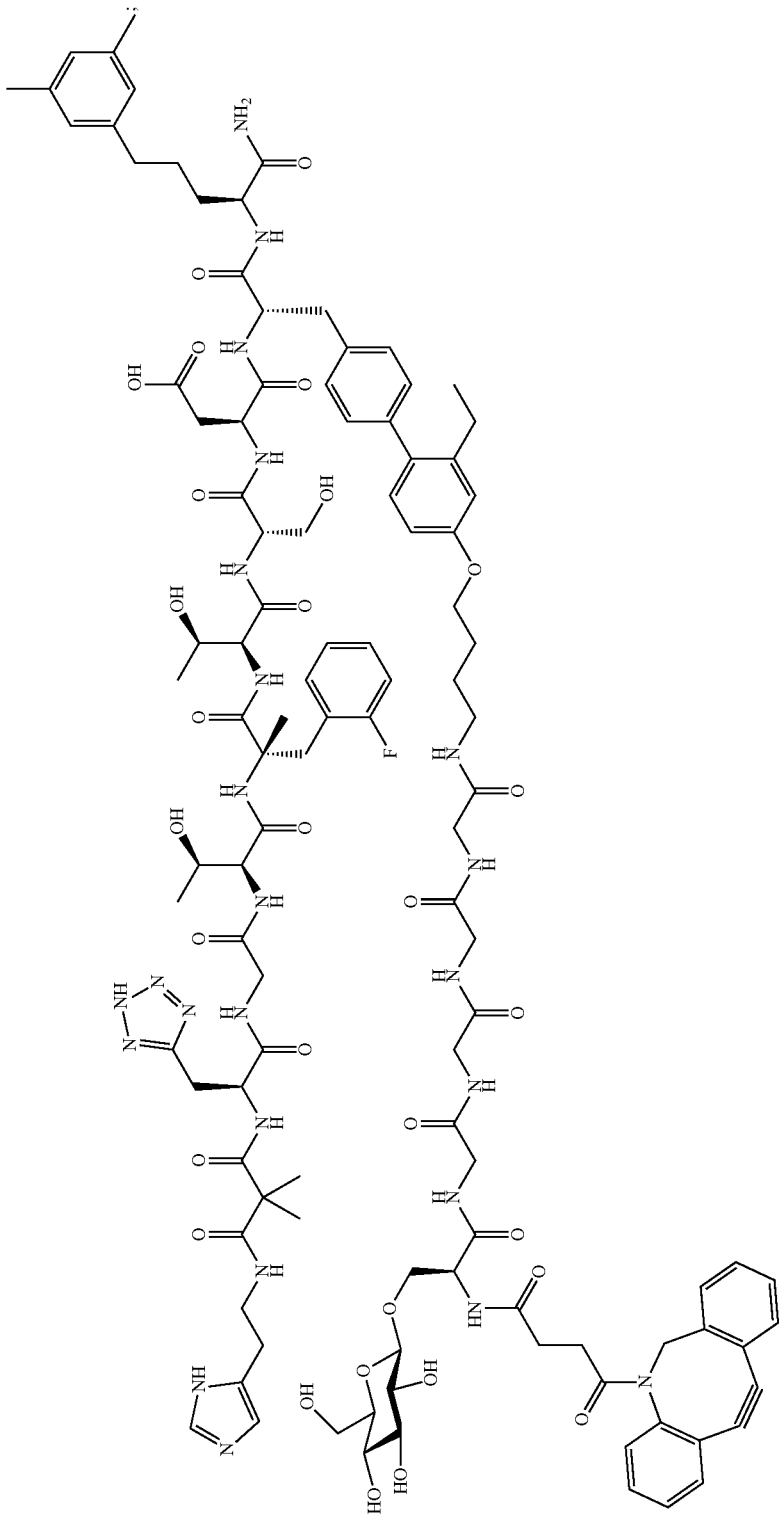

(SEQ ID NO: 101)
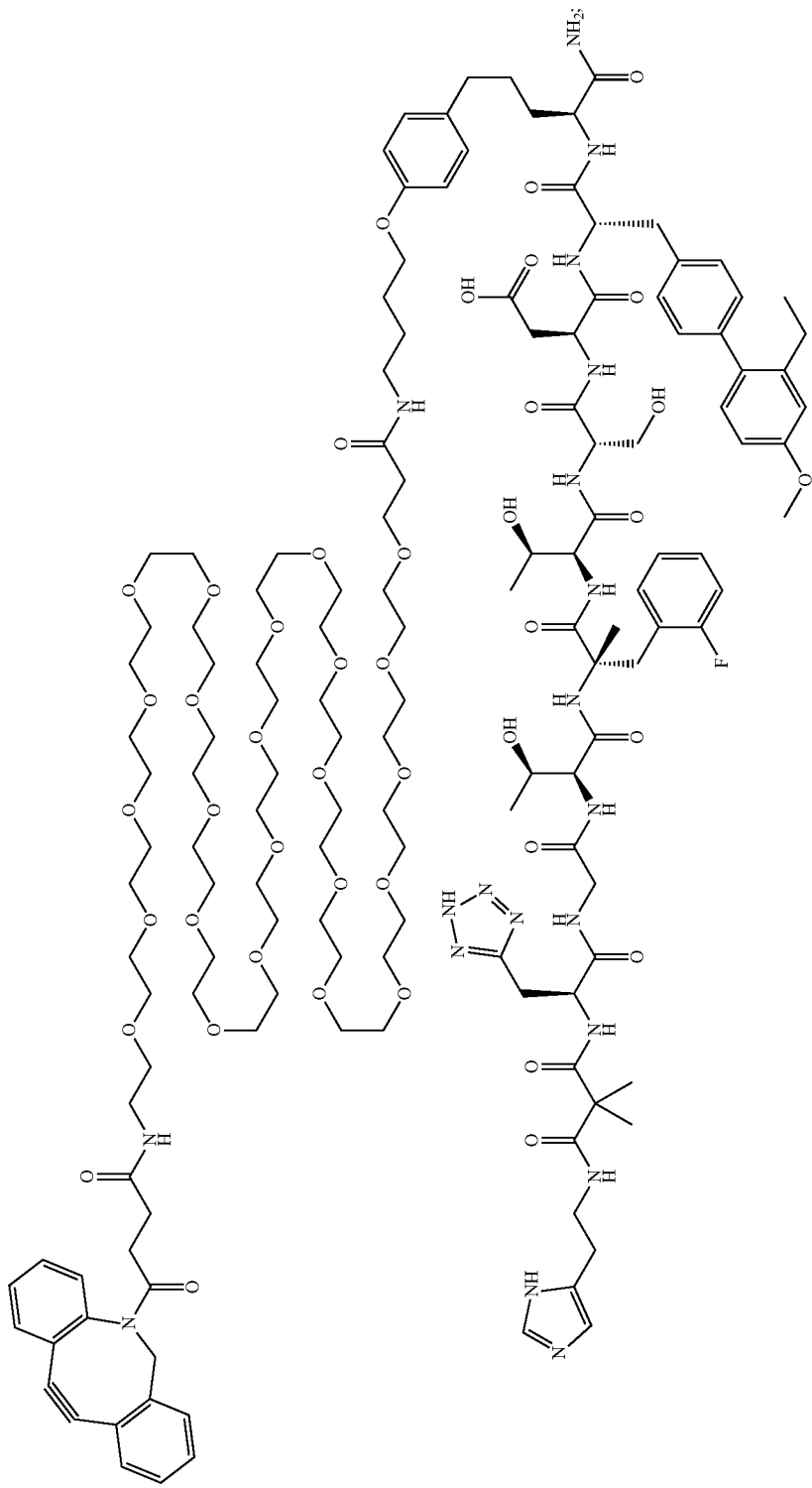

-continued
(SEQ ID NO: 102)
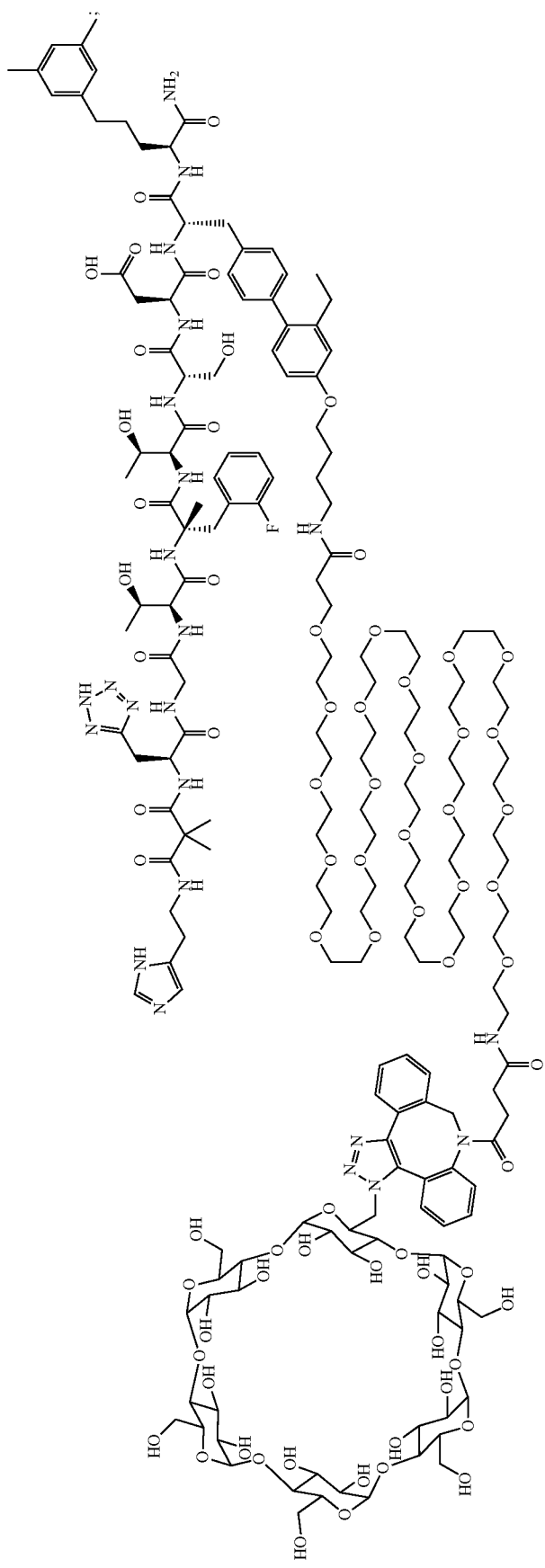

(SEQ ID NO: 103)
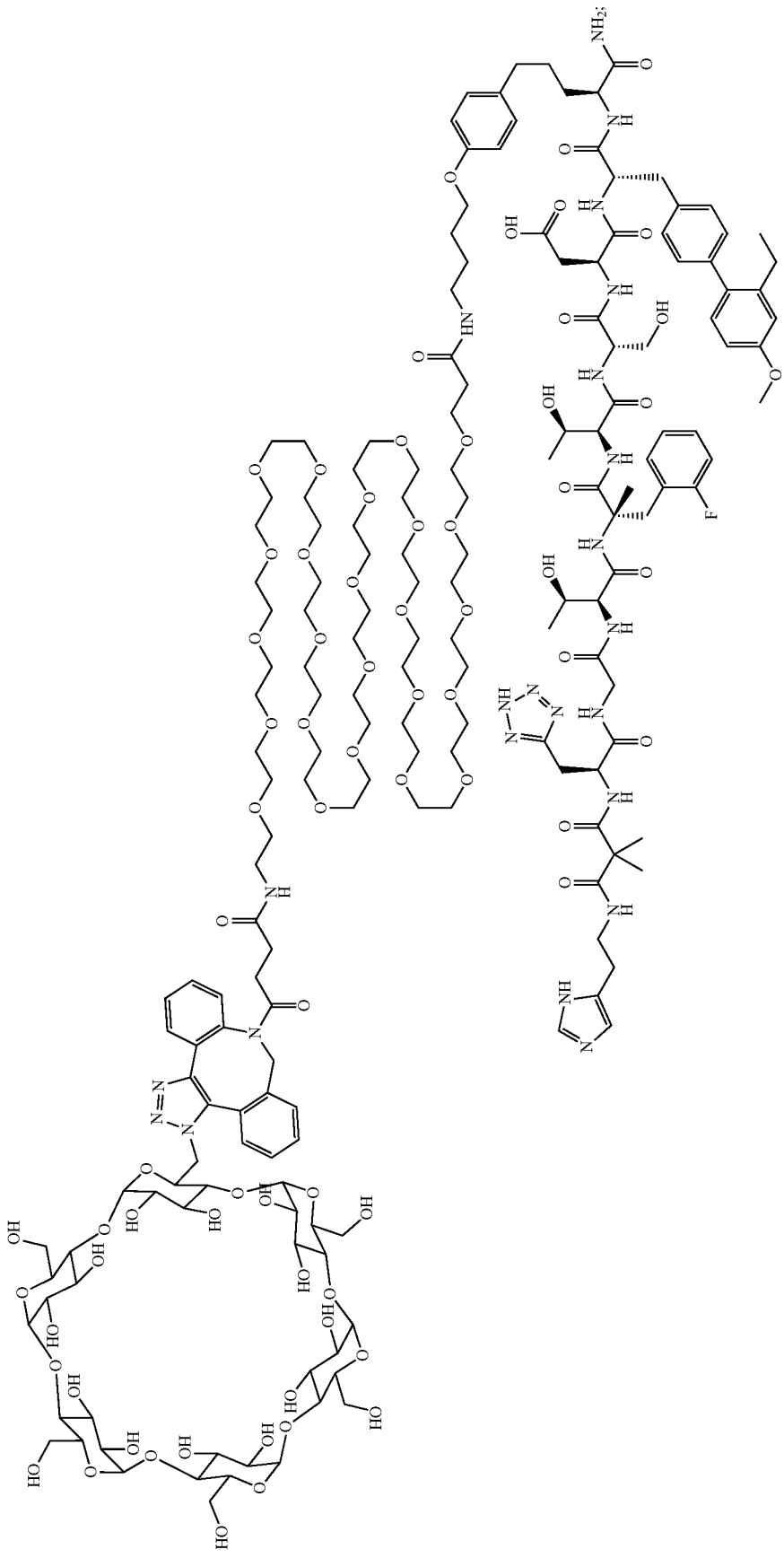

131 (SEQ ID NO: 104)
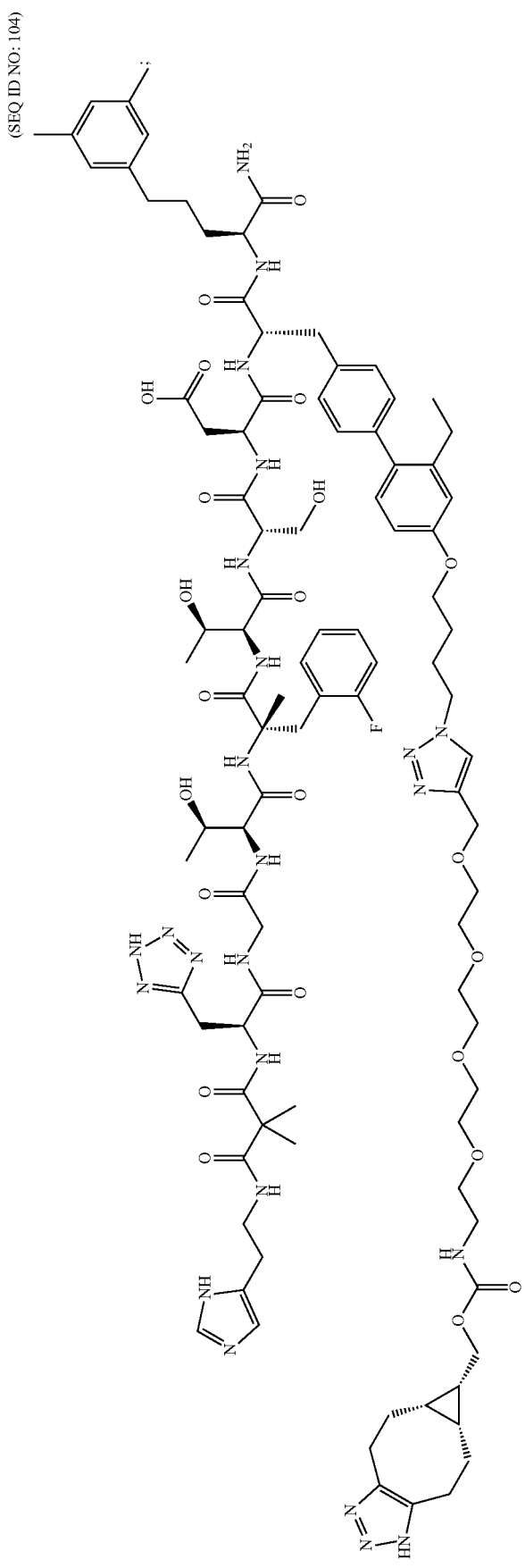
132 (SEQ ID NO: 105)
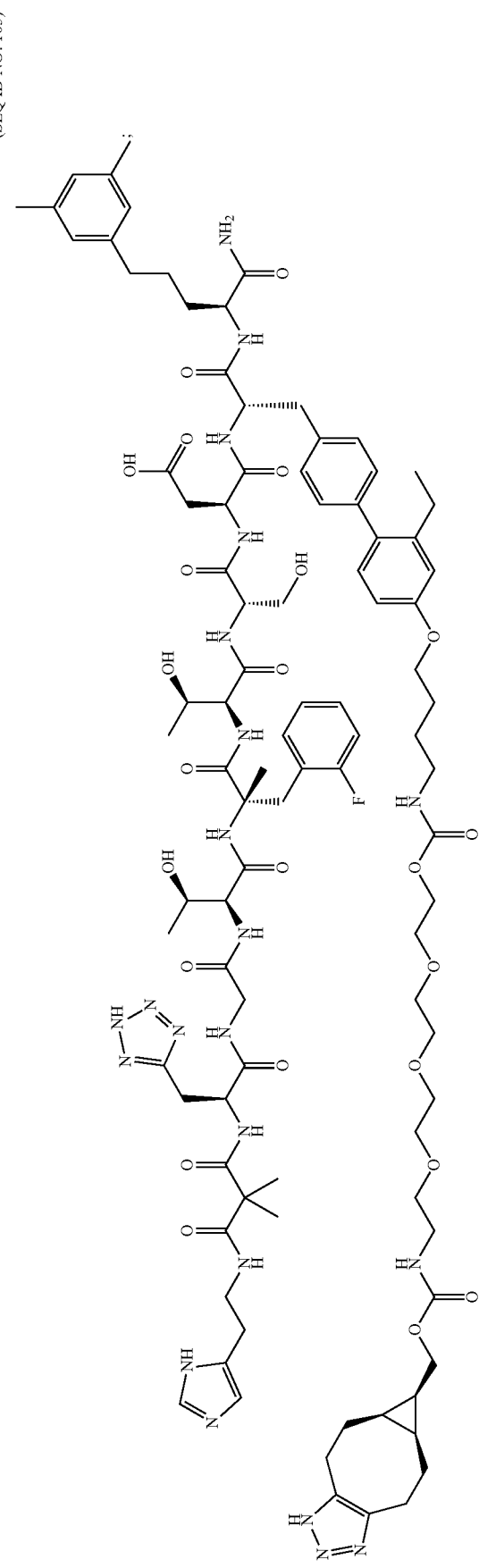

133
(Main Structure: SEQ ID NO: 106; Branched Sequence: SEQ ID NO: 165)
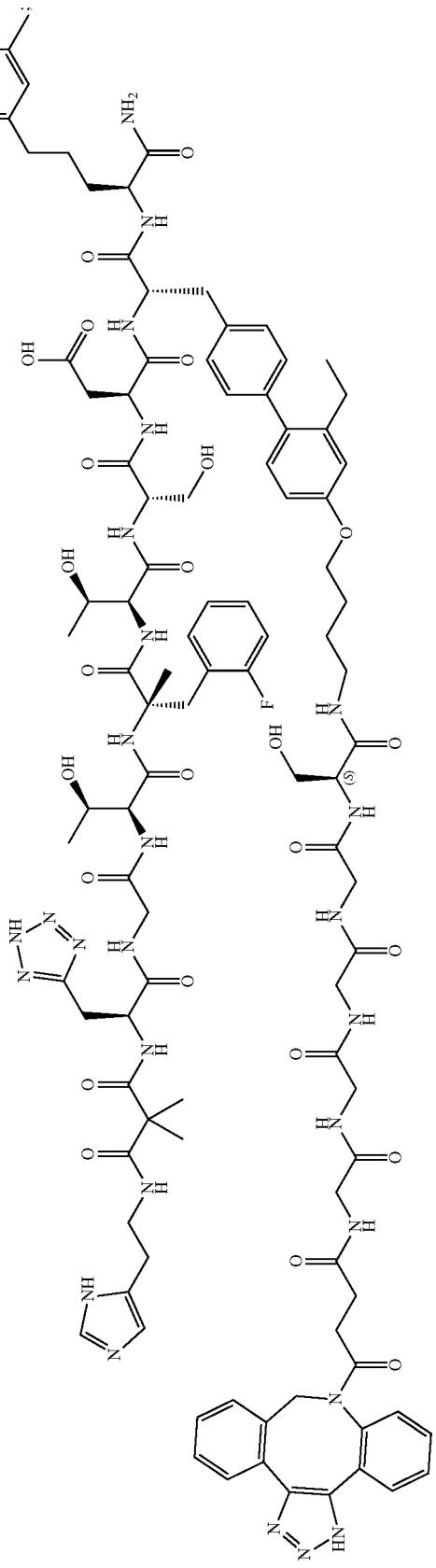
134
(SEQ ID NO: 187)
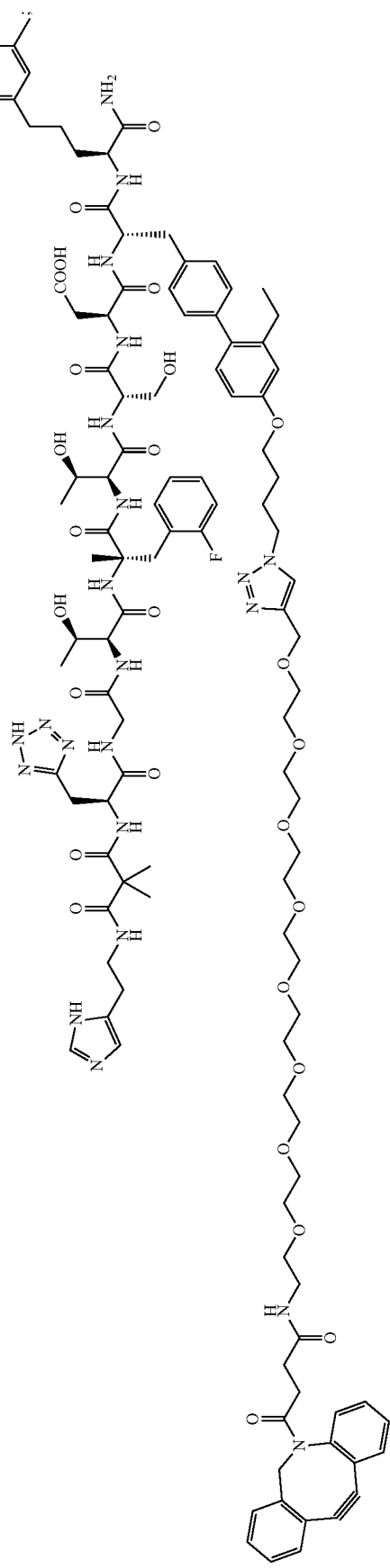

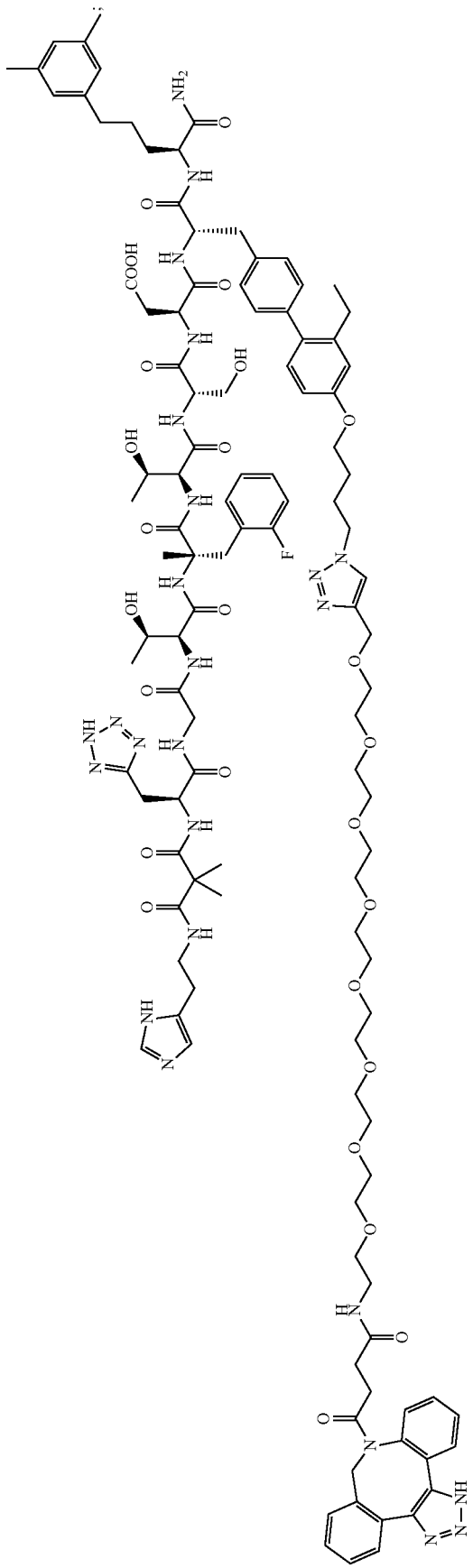
135 (SEQ ID NO: 188)
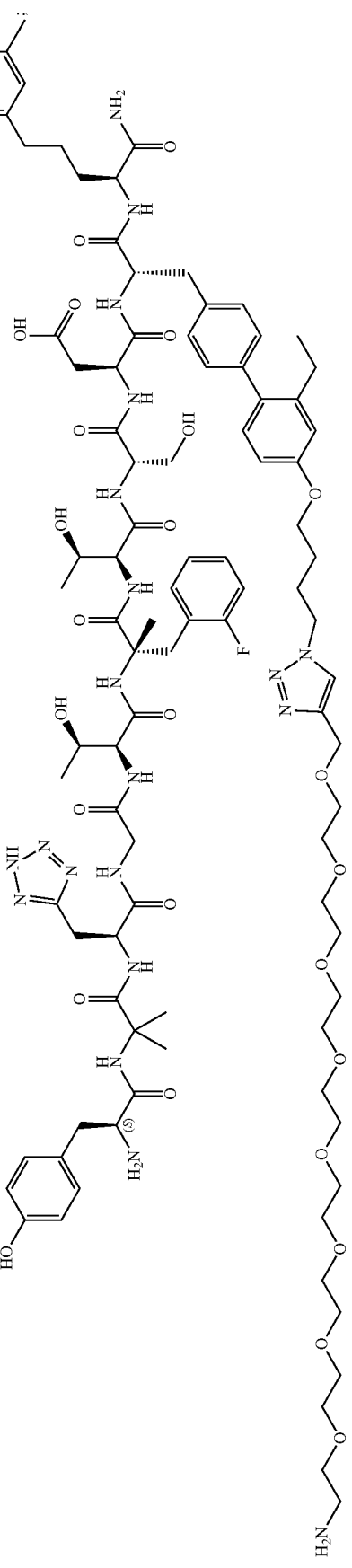
136 (SEQ ID NO: 108)

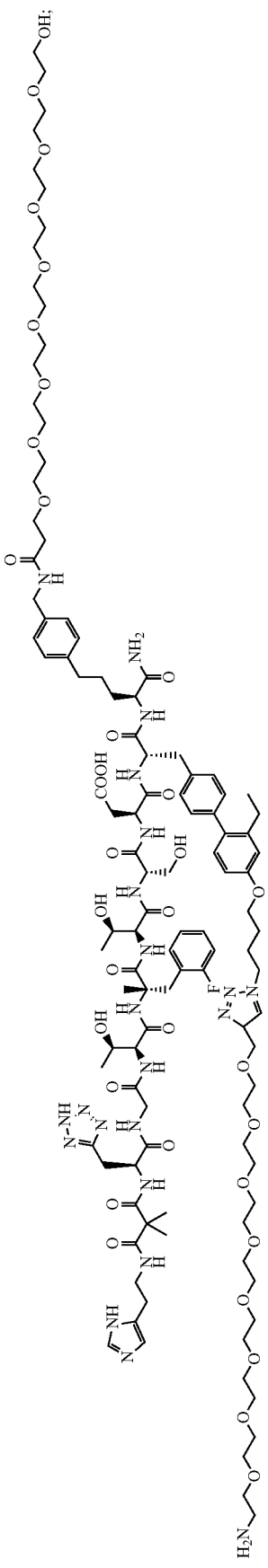 (SEQ ID NO: 109)
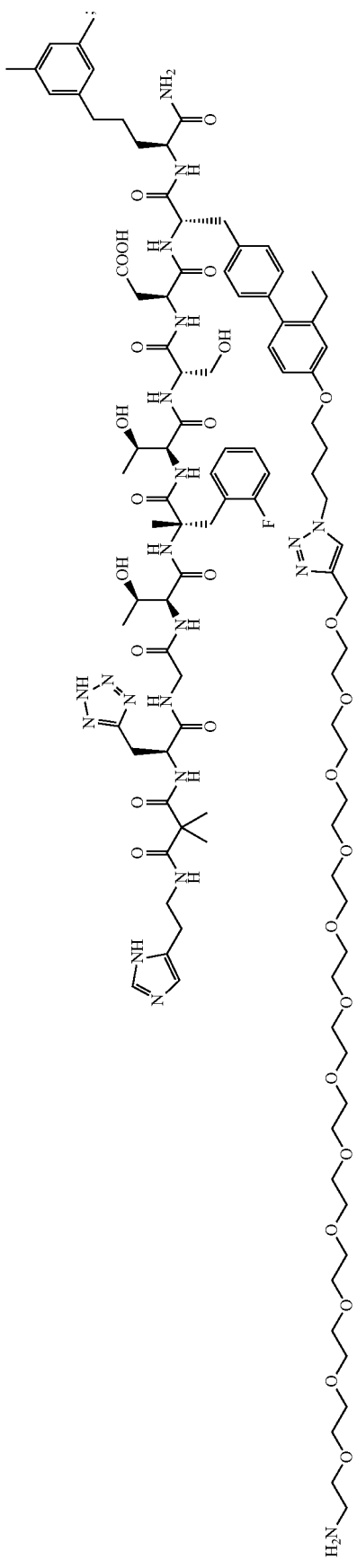 (SEQ ID NO: 110)

139 (SEQ ID NO: 189)
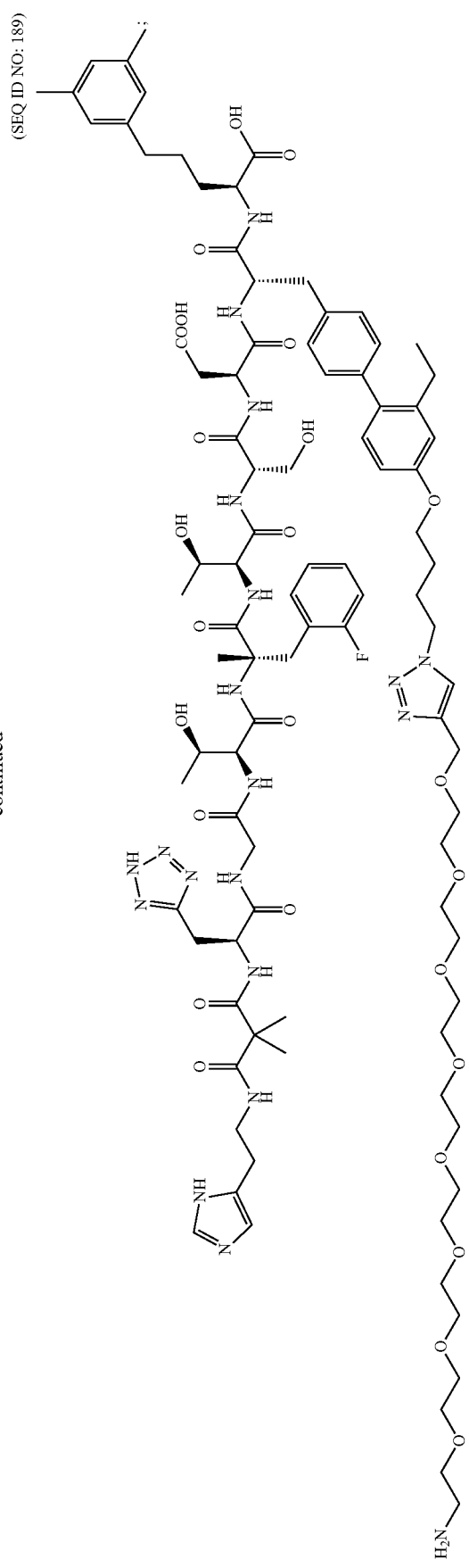
140 (SEQ ID NO: 190)
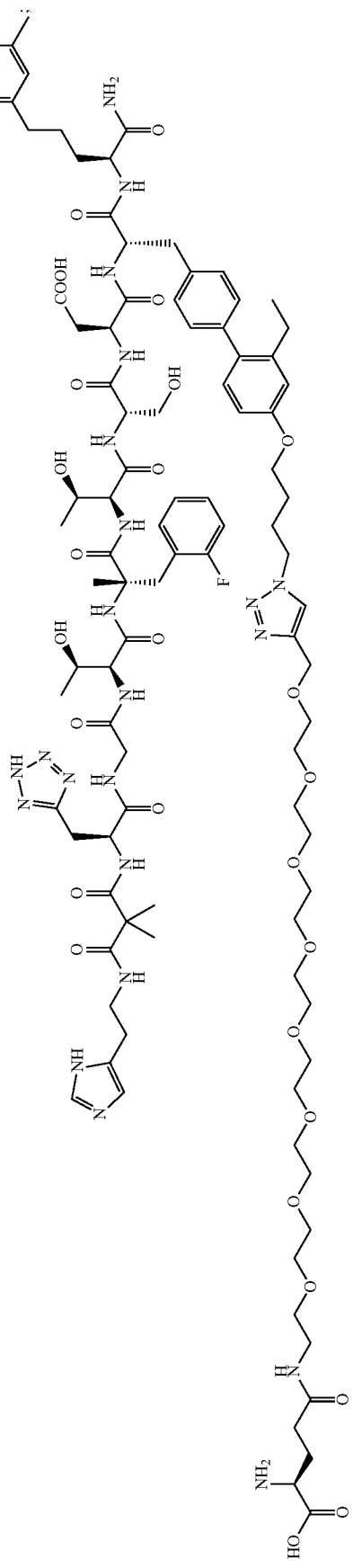

141
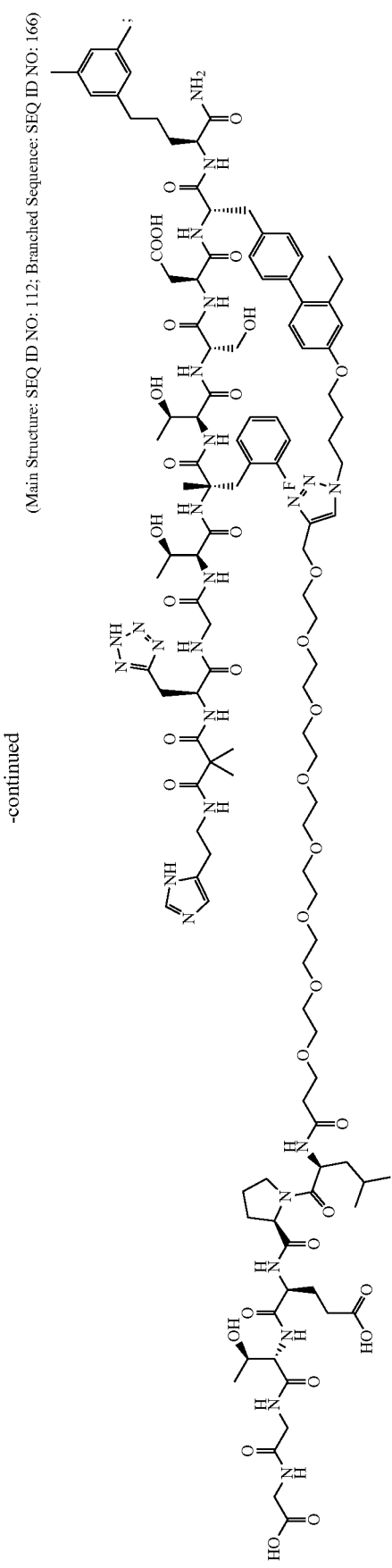
(Main Structure: SEQ ID NO: 112; Branched Sequence: SEQ ID NO: 166)
-continued
142
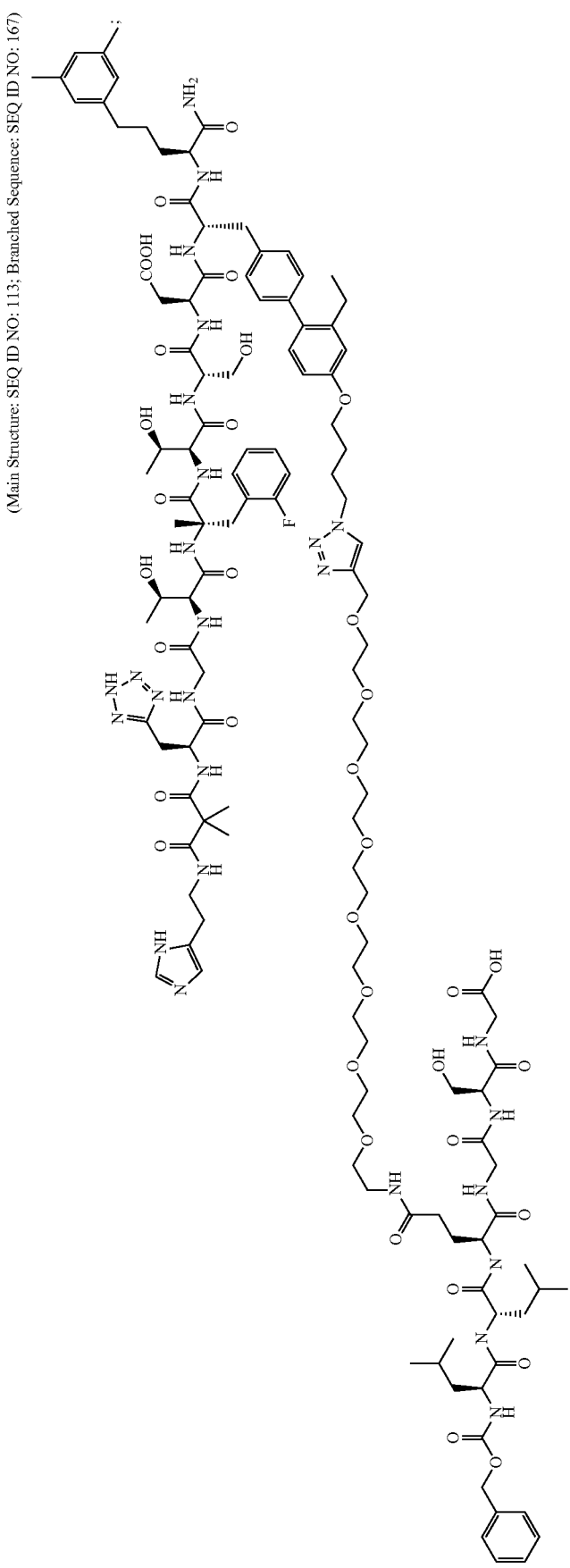
(Main Structure: SEQ ID NO: 113; Branched Sequence: SEQ ID NO: 167)

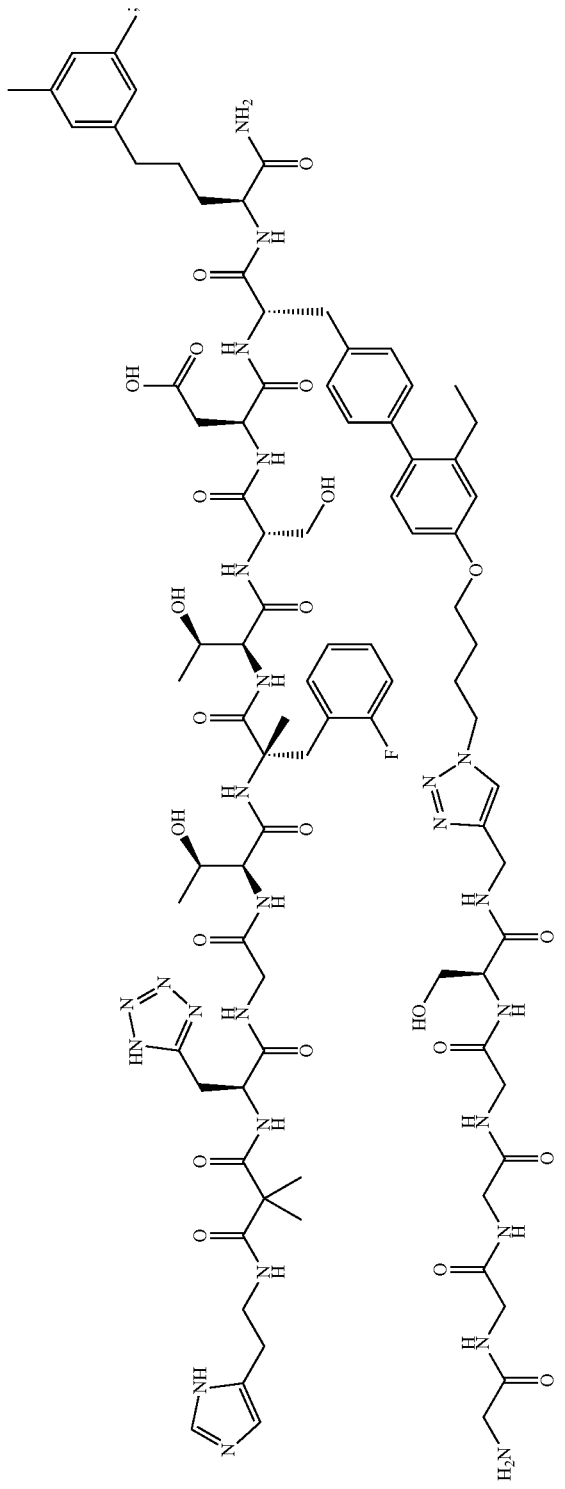
(Main Structure: SEQ ID NO: 114; Branched Sequence: SEQ ID NO: 168)

(Main Structure: SEQ ID NO: 115; Branched Sequence: SEQ ID NO: 169)
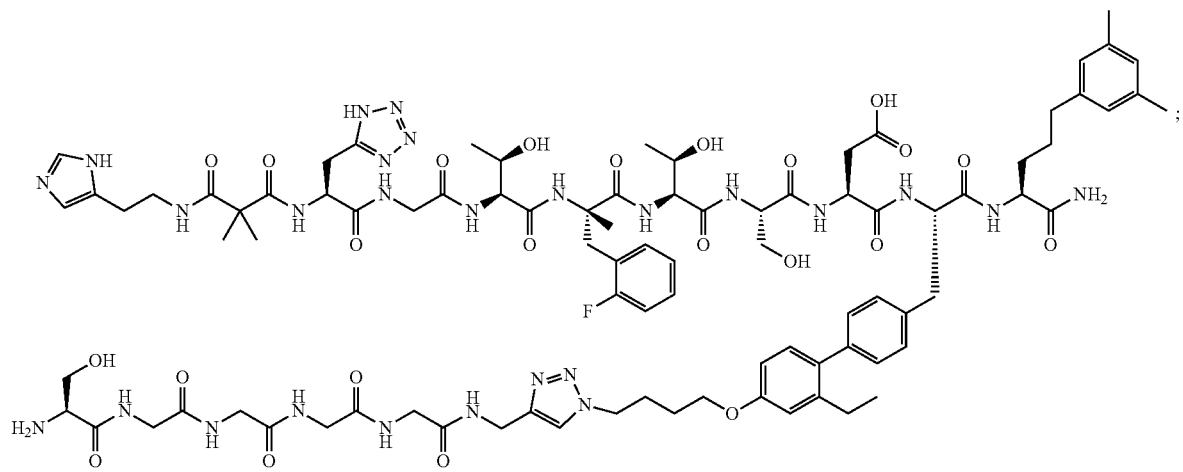
(Main Structure: SEQ ID NO: 116; Branched Sequence: SEQ ID NO: 170)
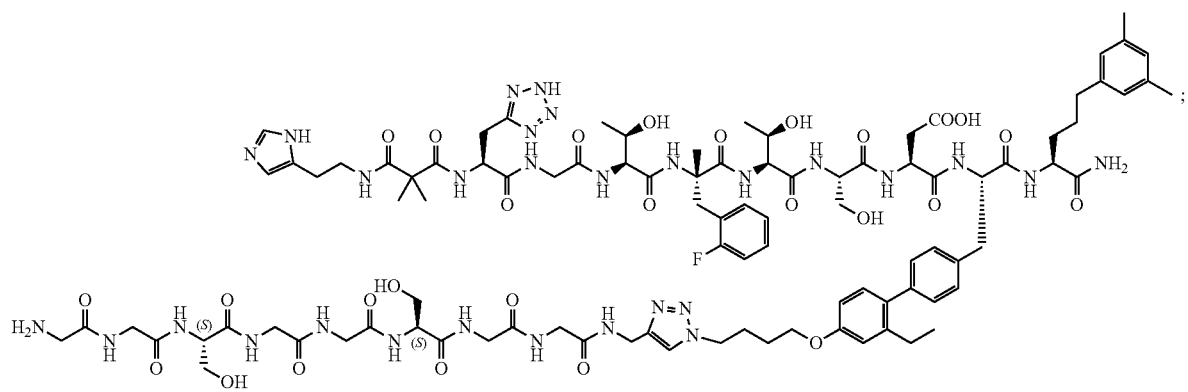
(Main Structure: SEQ ID NO: 117; Branched Sequence: SEQ ID NO: 171)
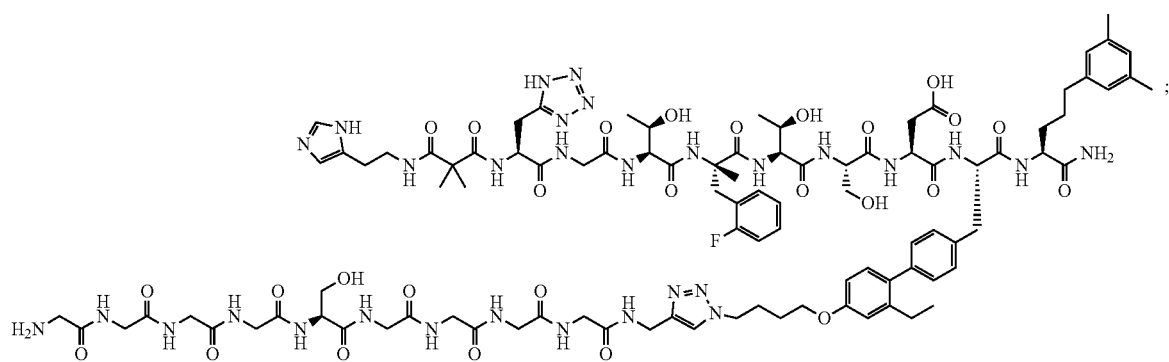
(Main Structure: SEQ ID NO: 118; Branched Sequence: SEQ ID NO: 172)
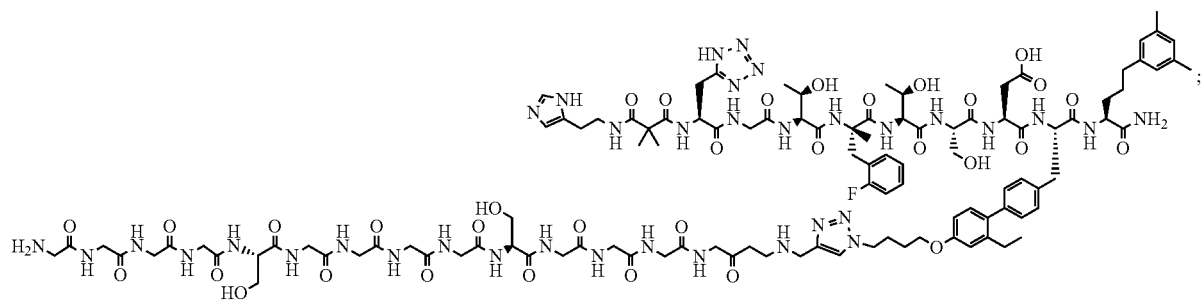

-continued
(Main Structure: SEQ ID NO: 119; Branched Sequence: SEQ ID NO: 173)
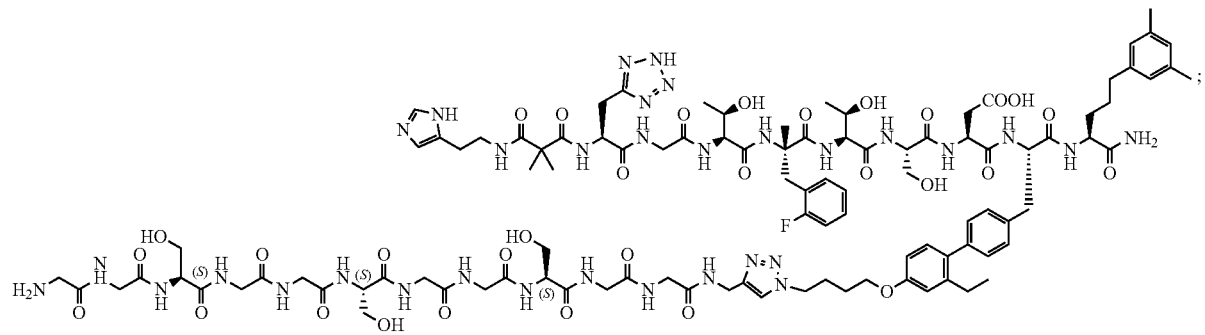
(Main Structure: SEQ ID NO: 120; Branched Sequence: SEQ ID NO: 174)
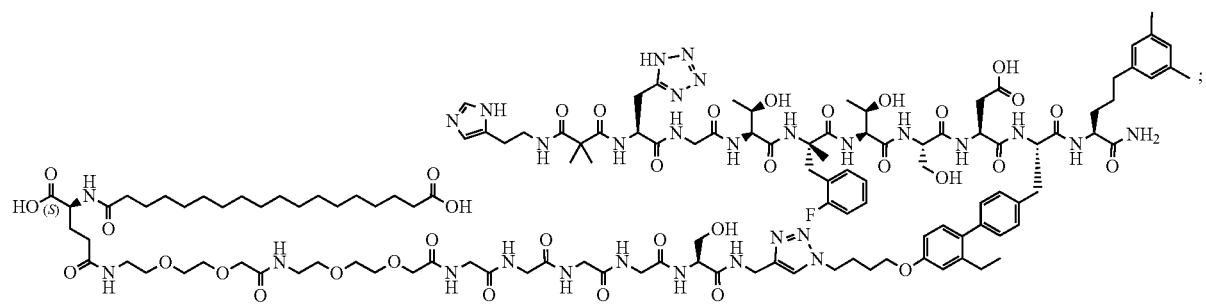
(Main Structure: SEQ ID NO: 121; Branched Sequence: SEQ ID NO: 175)
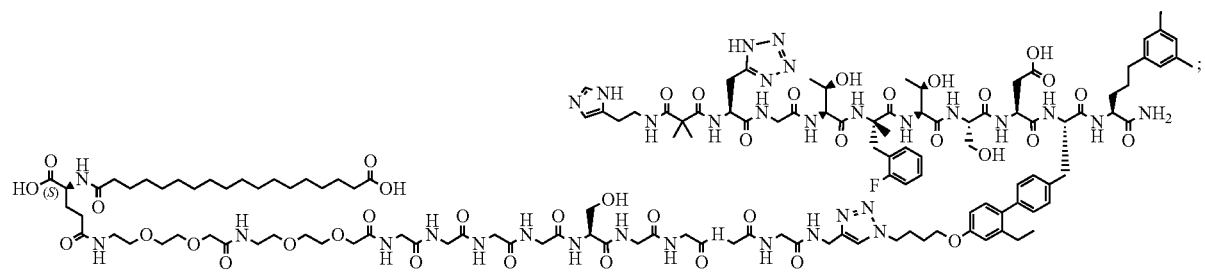
(SEQ ID NO: 122)
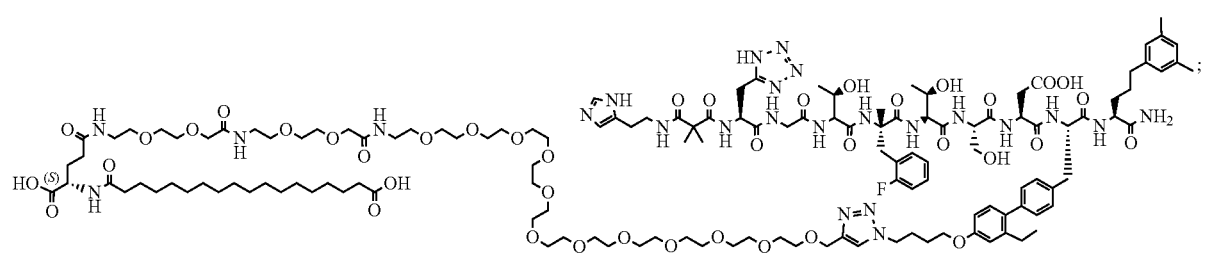

(SEQ ID NO: 123)

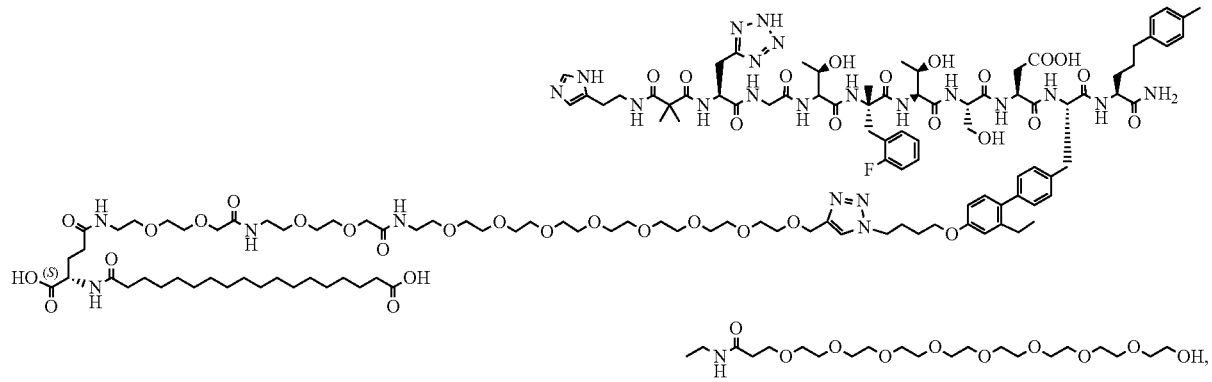

or a pharmaceutically acceptable salt thereof.

In another aspect, provided herein is an antibody-drug conjugate comprising a Glucagon-like peptide-1 receptor (GLP1R)-targeting antibody or an antigen-binding fragment thereof conjugated, optionally through a linker, to a payload having the structure selected from the group consisting of:

Structure

Structure (SEQ ID NO: 41)

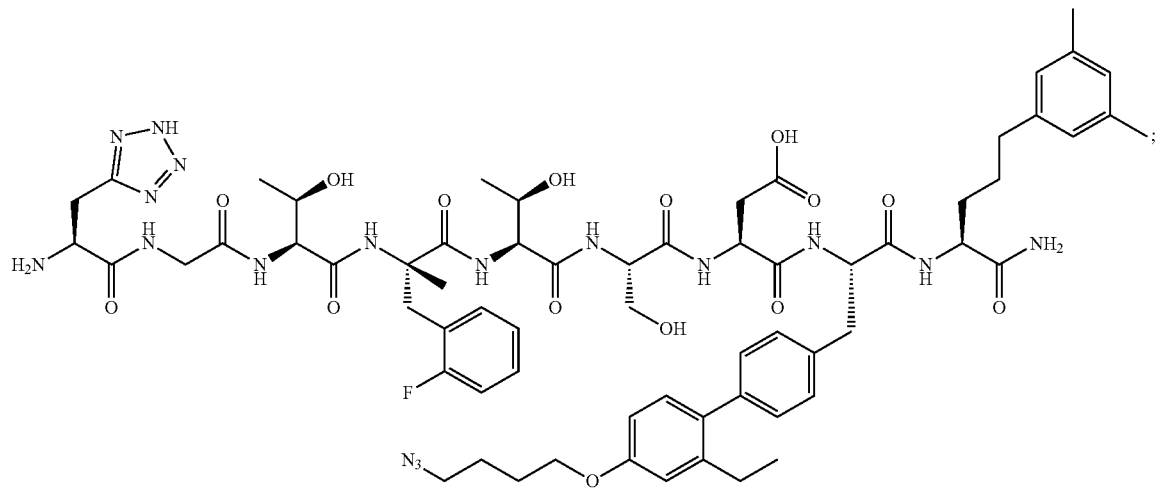

(SEQ ID NO: 42)

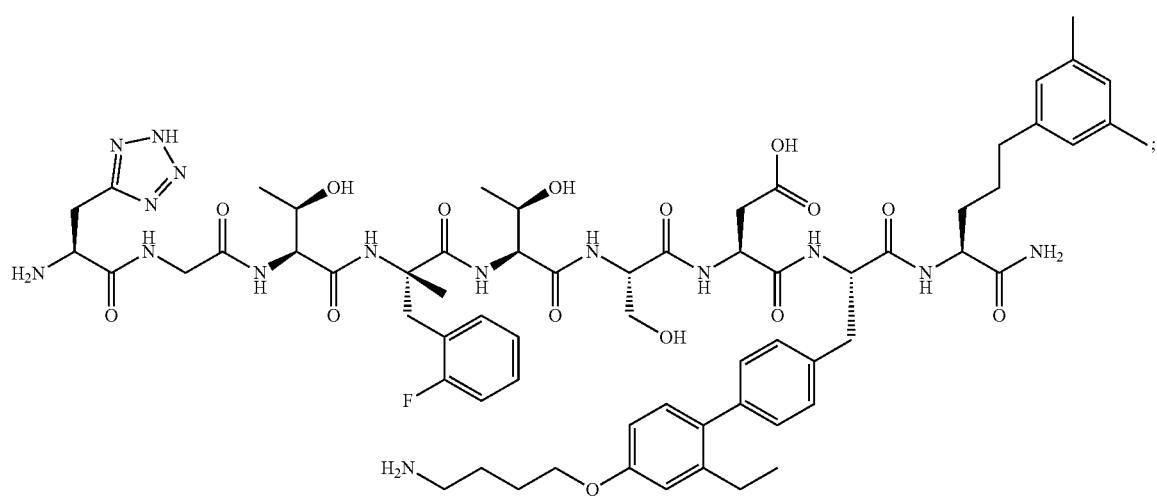

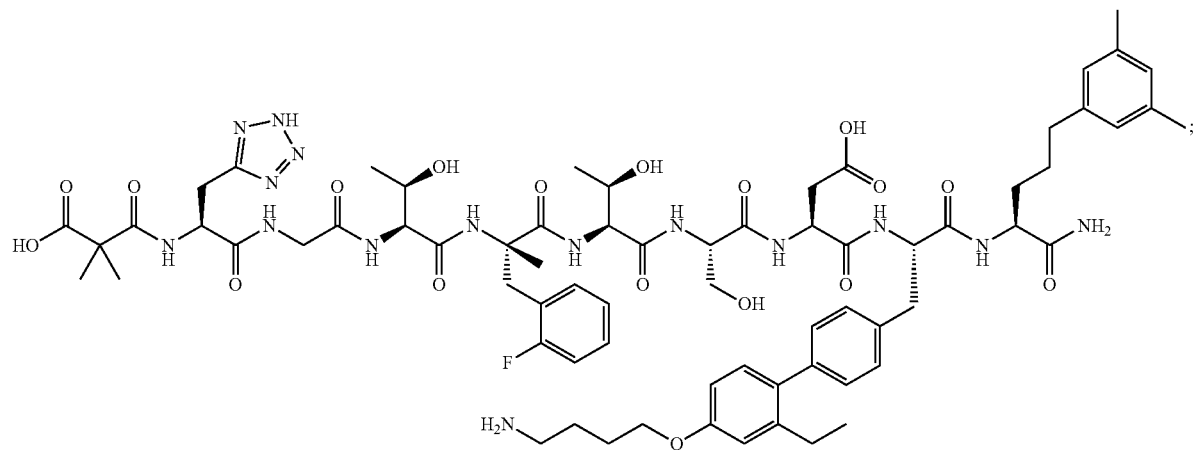
(SEQ ID NO: 43)
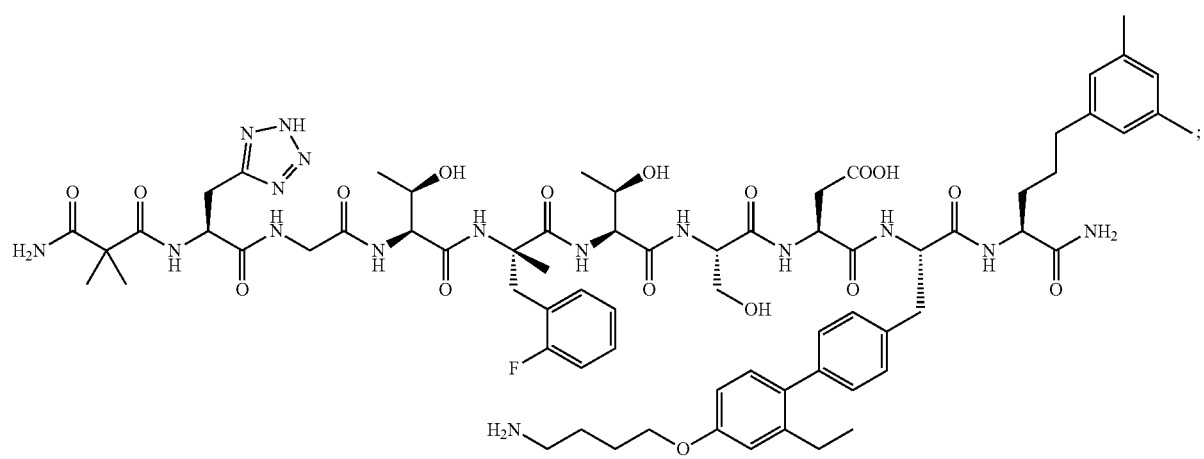
(SEQ ID NO: 44)
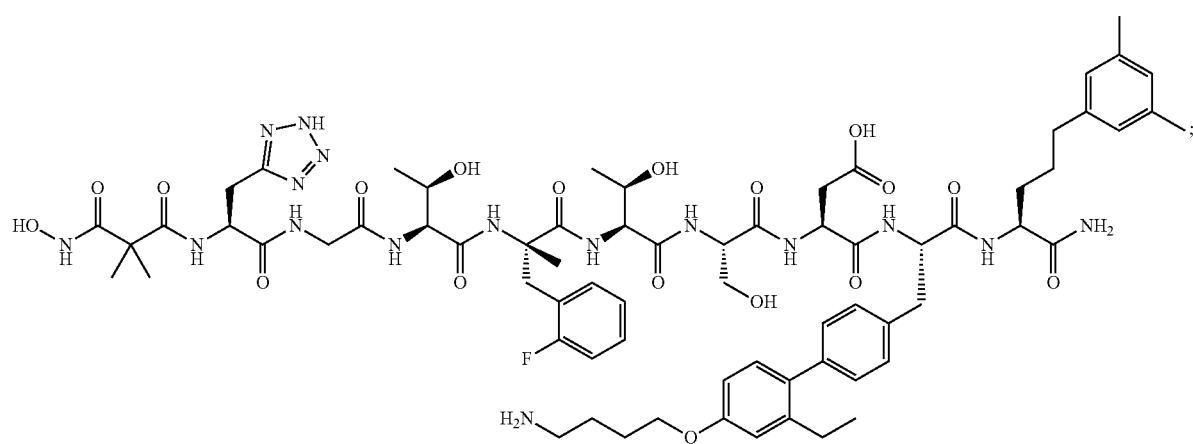
(SEQ ID NO: 45)

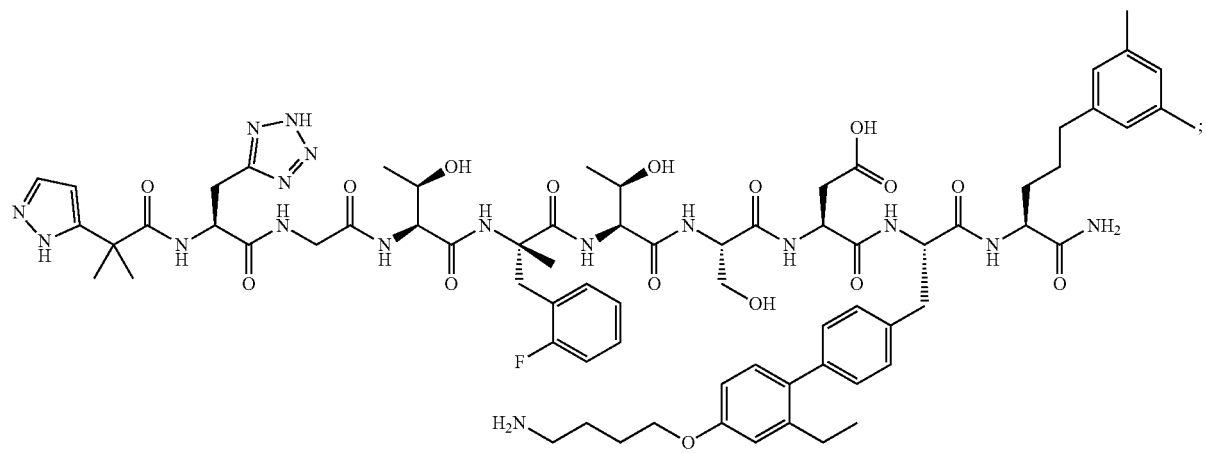
(SEQ ID NO: 46)
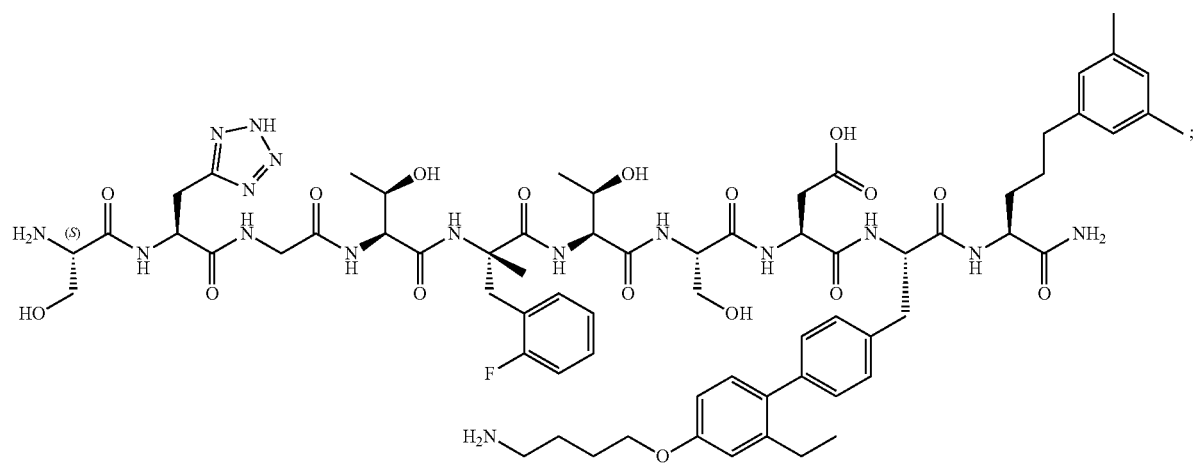
(SEQ ID NO: 47)
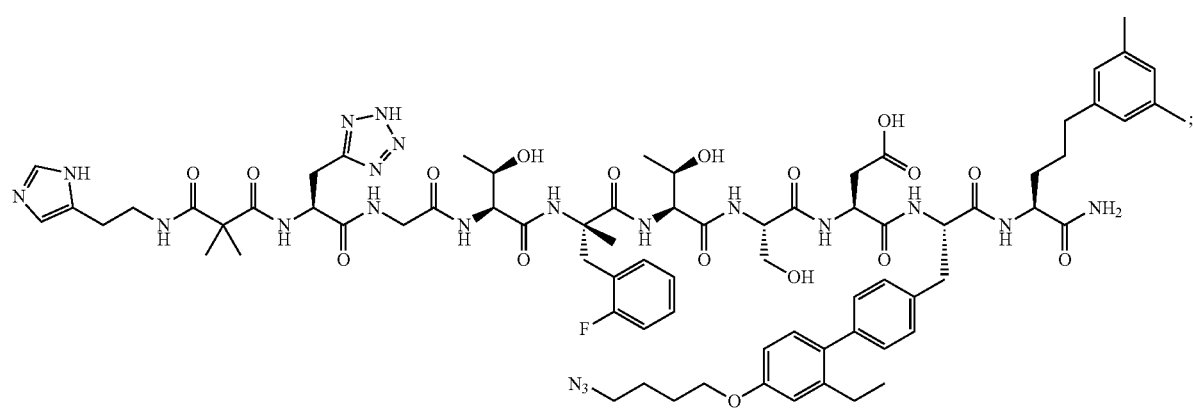
(SEQ ID NO: 48)

(SEQ ID NO: 49)
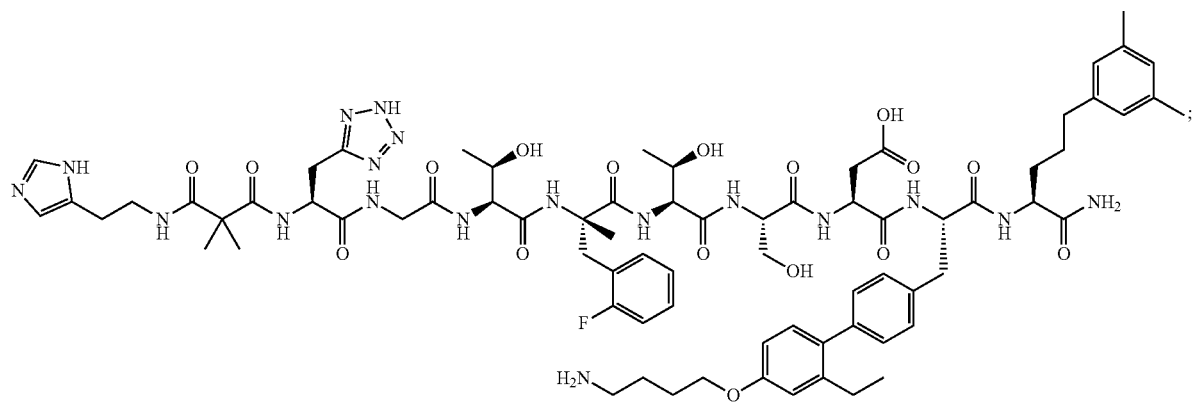
(SEQ ID NO: 50)
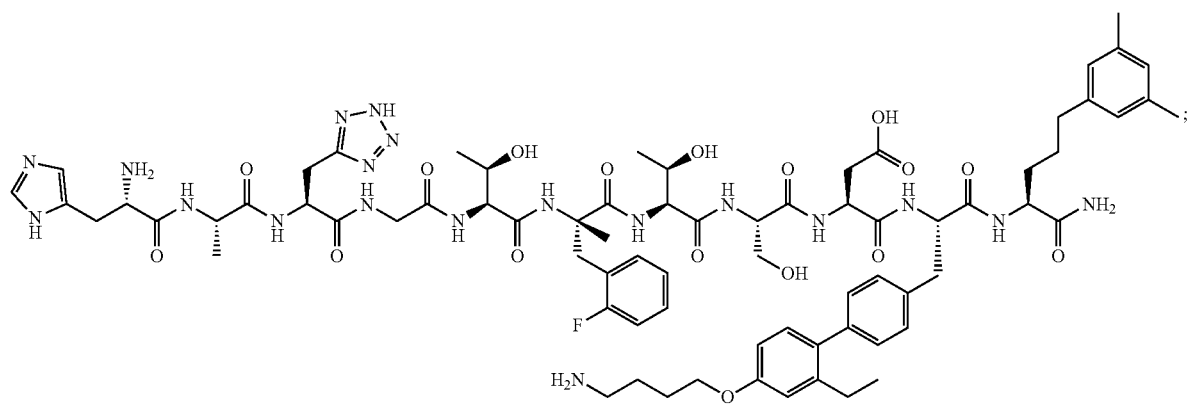
(SEQ ID NO: 51)
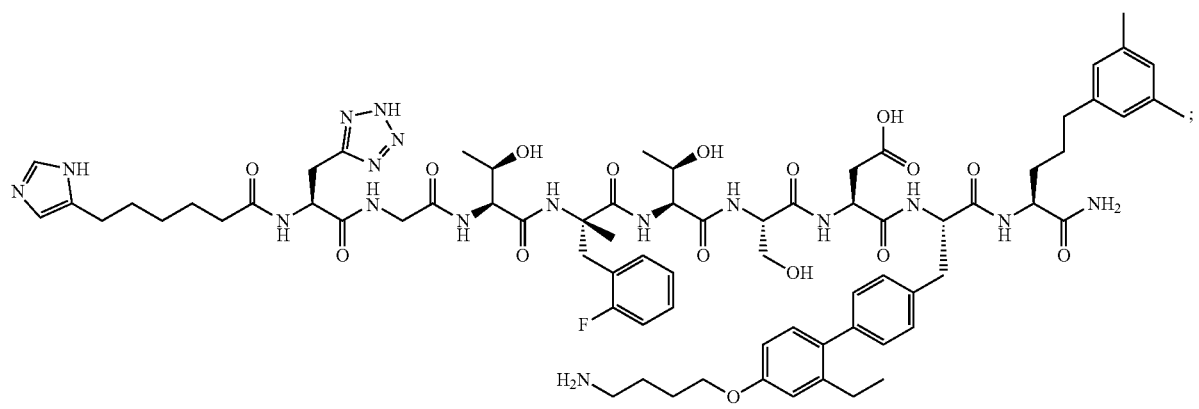

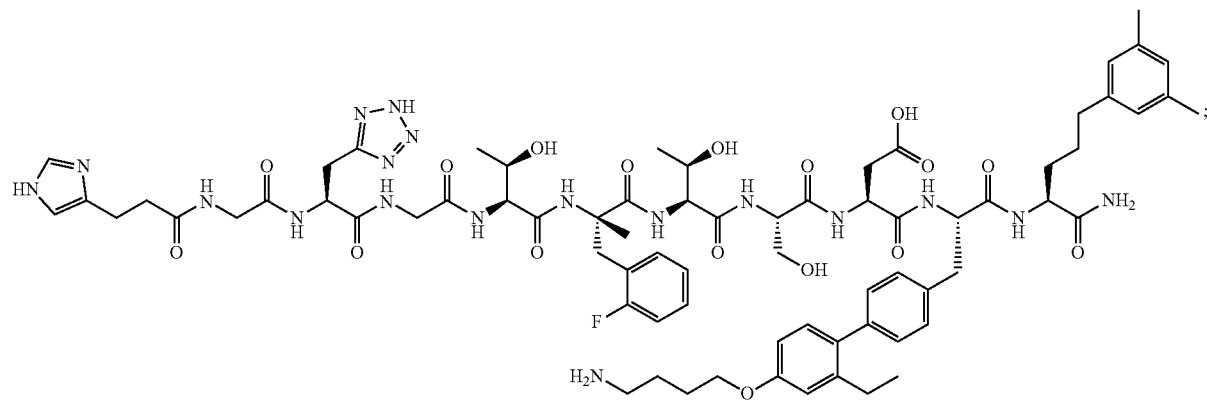
(SEQ ID NO: 52)
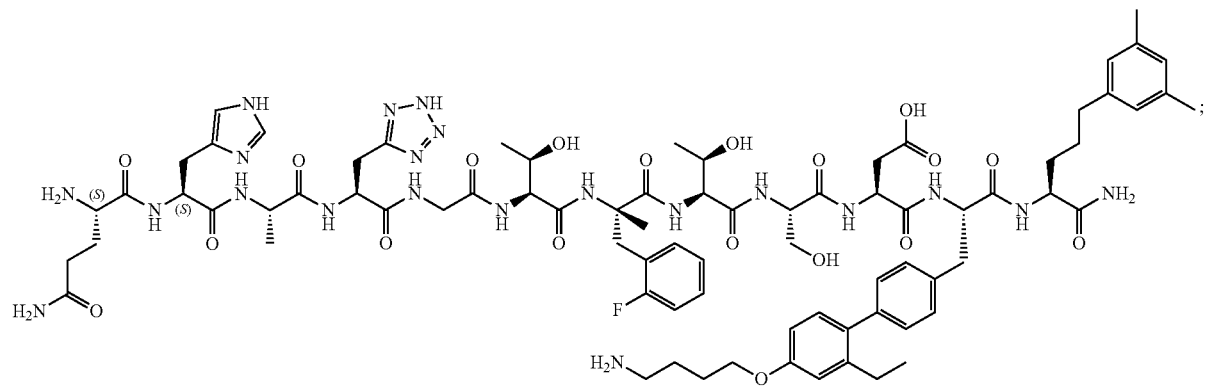
(SEQ ID NO: 53)
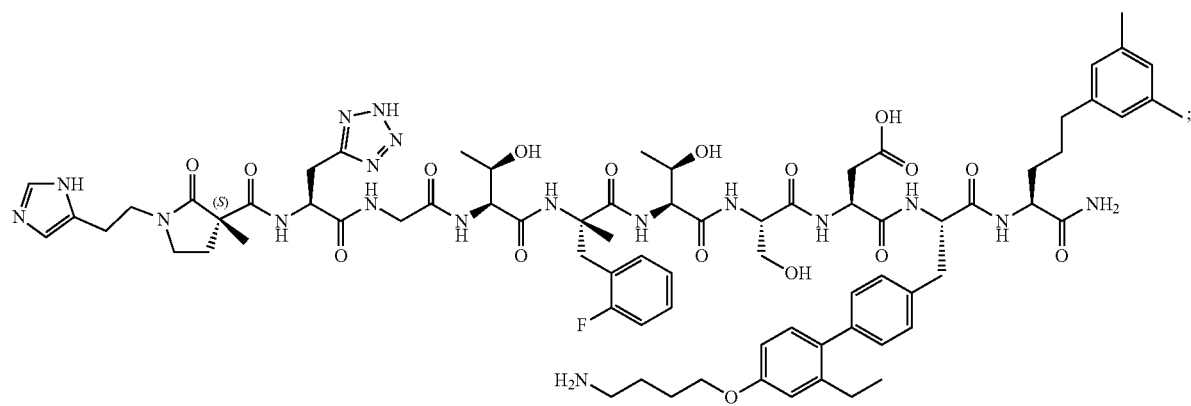
(SEQ ID NO: 54)

(SEQ ID NO: 55)
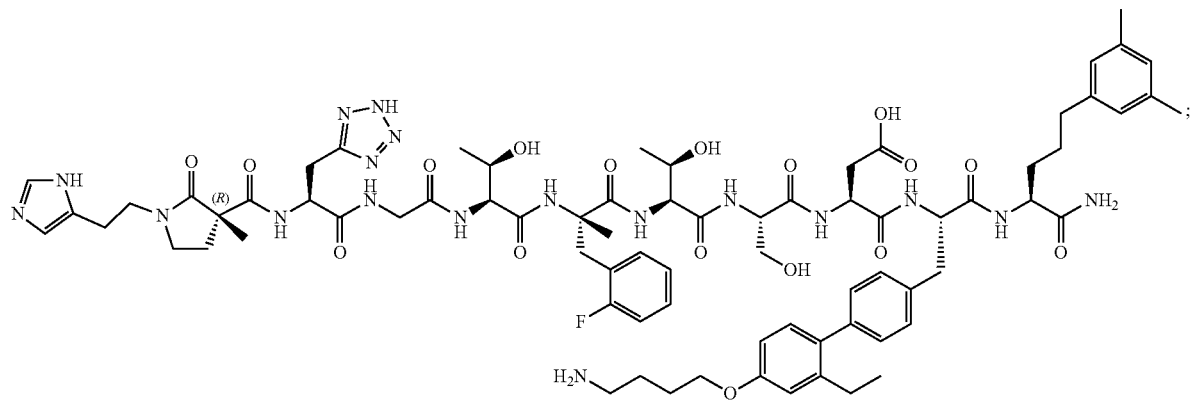
(SEQ ID NO: 56)
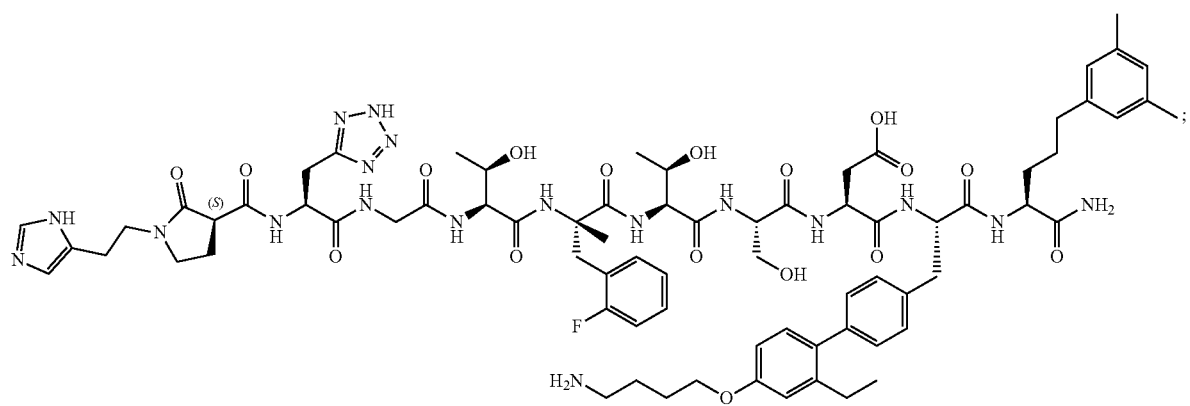
(SEQ ID NO: 57)
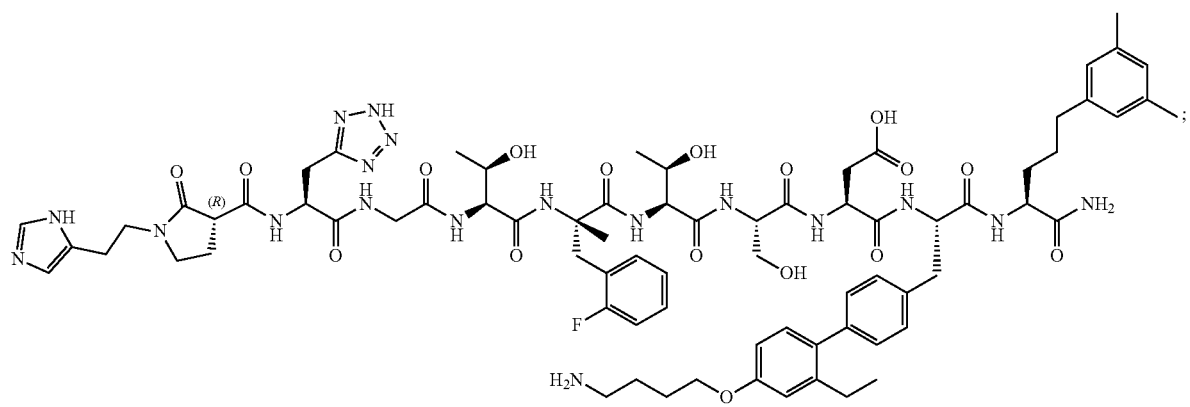

(SEQ ID NO: 58)
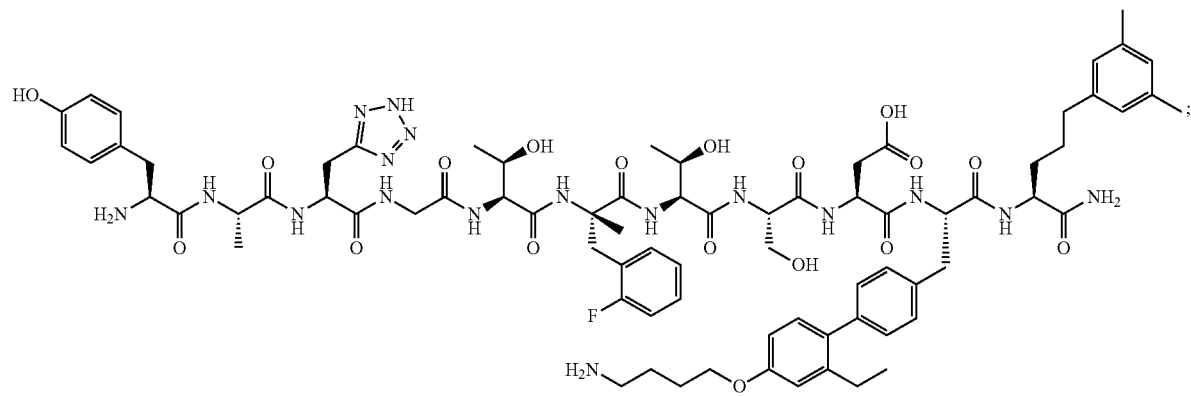
(SEQ ID NO: 59)
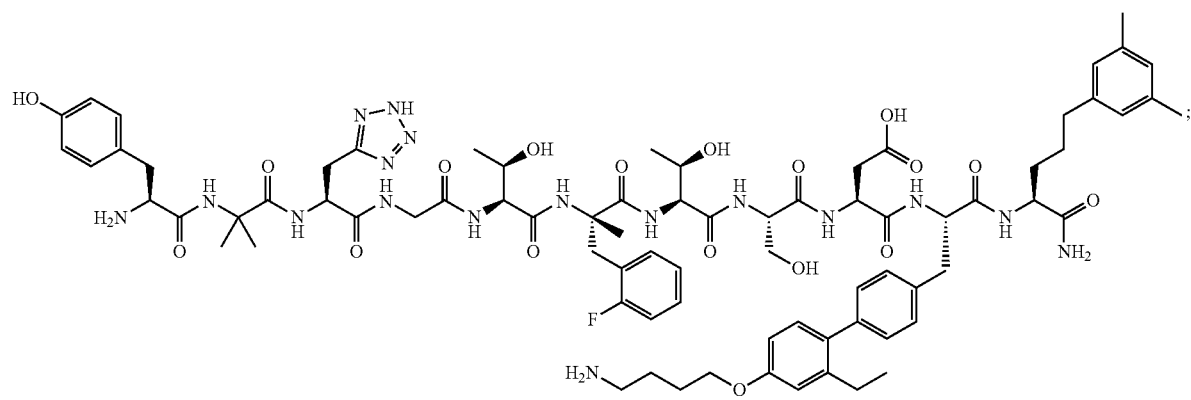
(SEQ ID NO: 60)
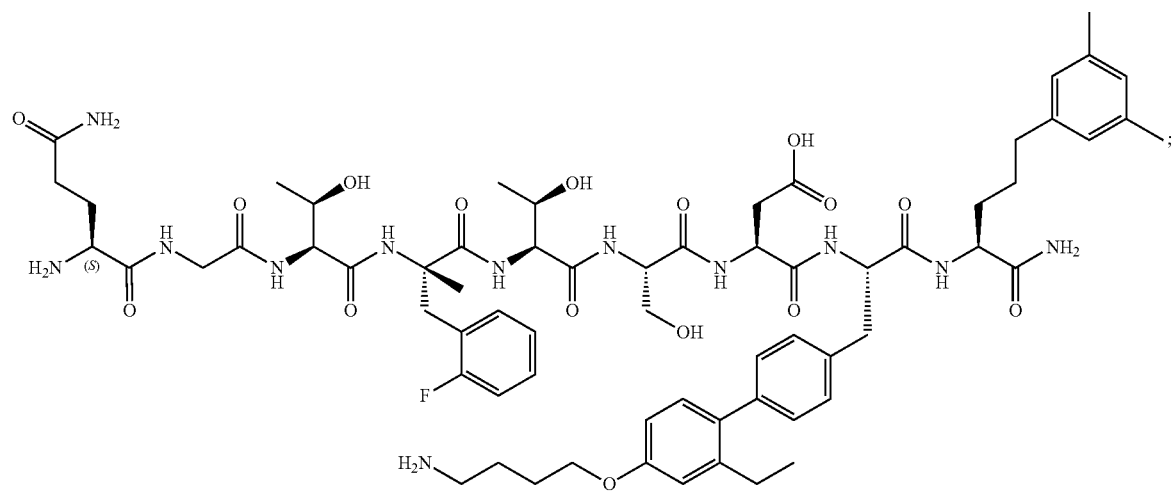

(SEQ ID NO: 61)
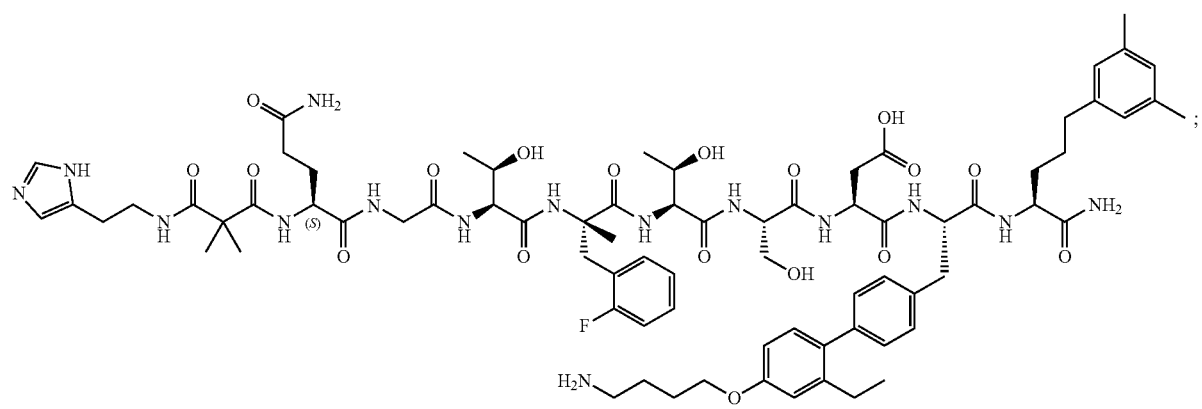
(SEQ ID NO: 62)
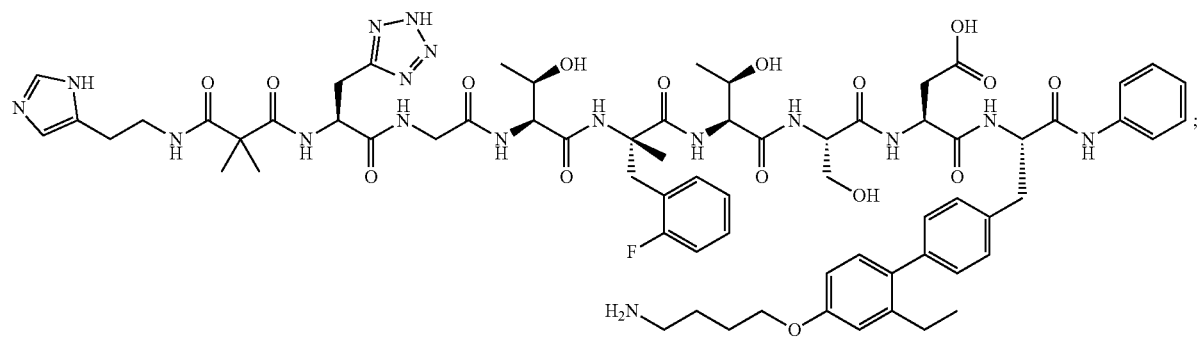
(SEQ ID NO: 63)
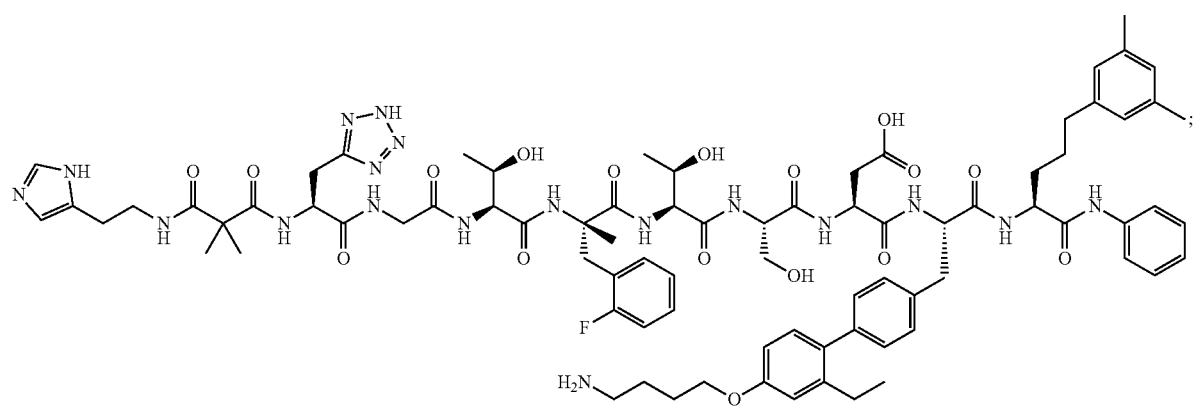
(SEQ ID NO: 64)
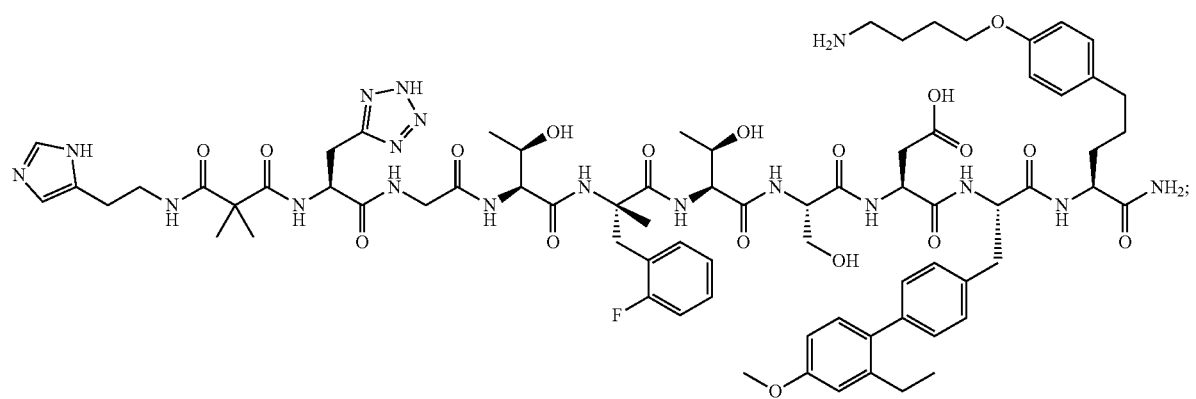

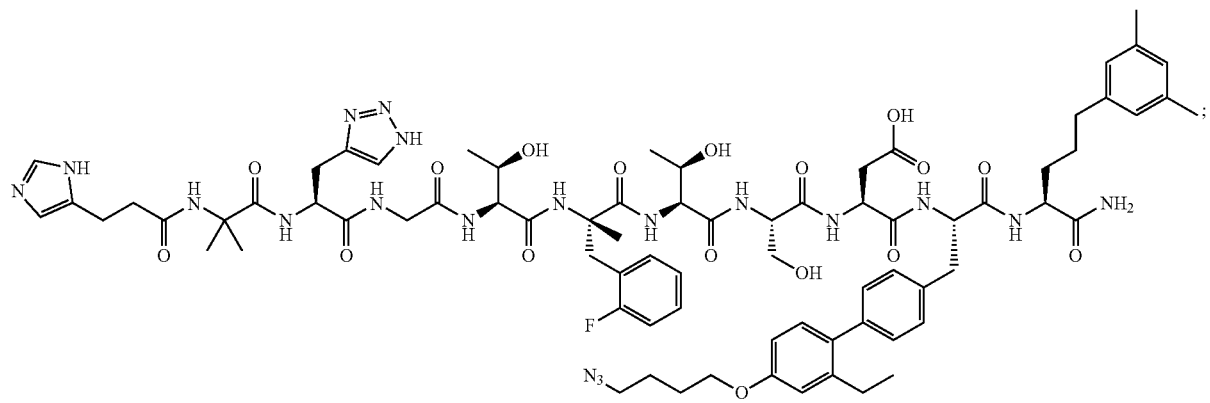
(SEQ ID NO: 65)
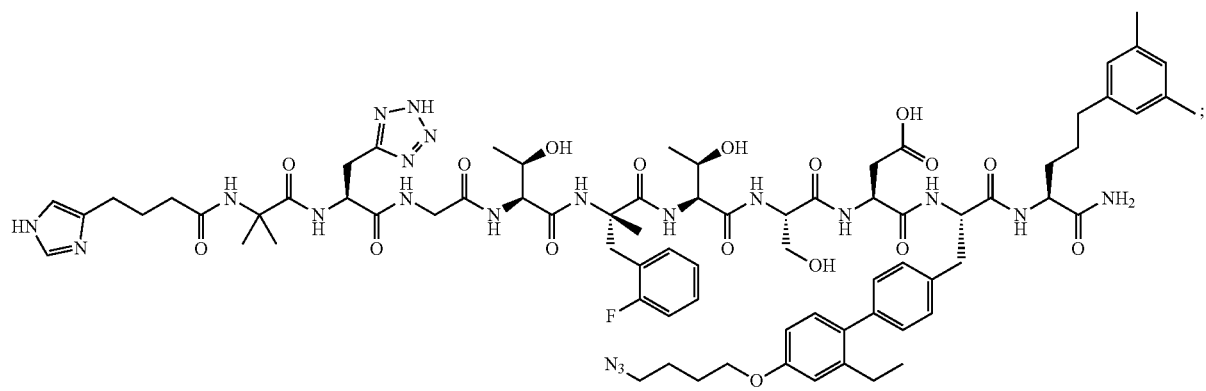
(SEQ ID NO: 66)
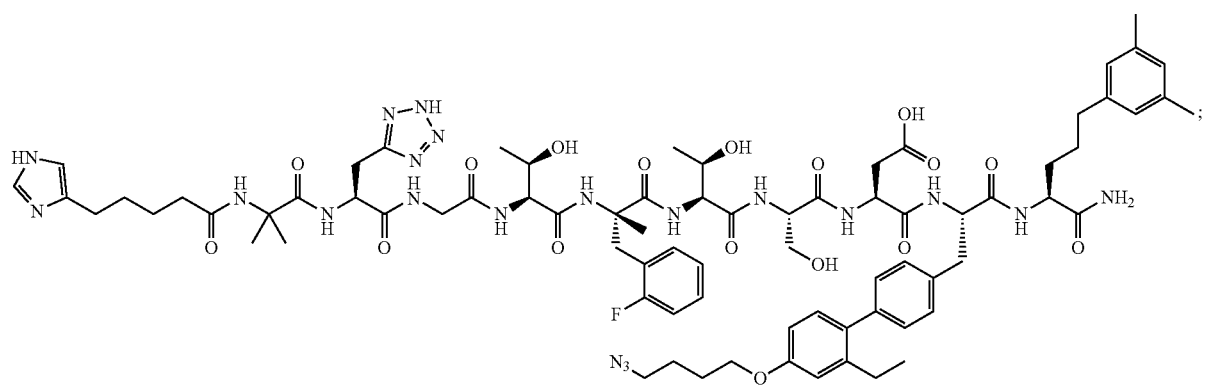
(SEQ ID NO: 67)
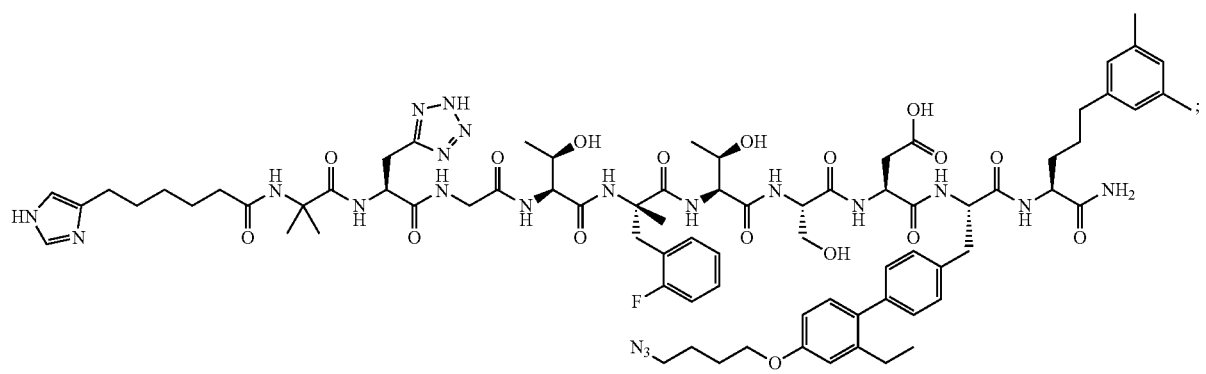
(SEQ ID NO: 68)

(SEQ ID NO: 69)
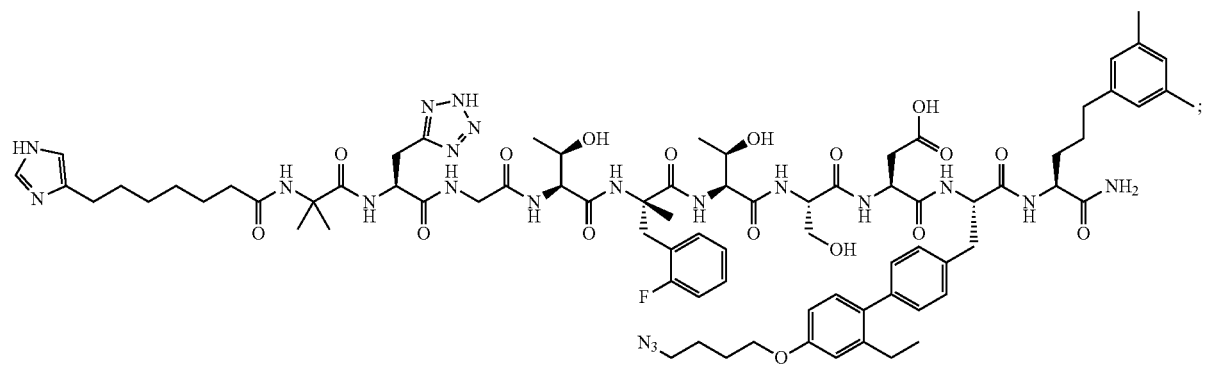
(SEQ ID NO: 70)
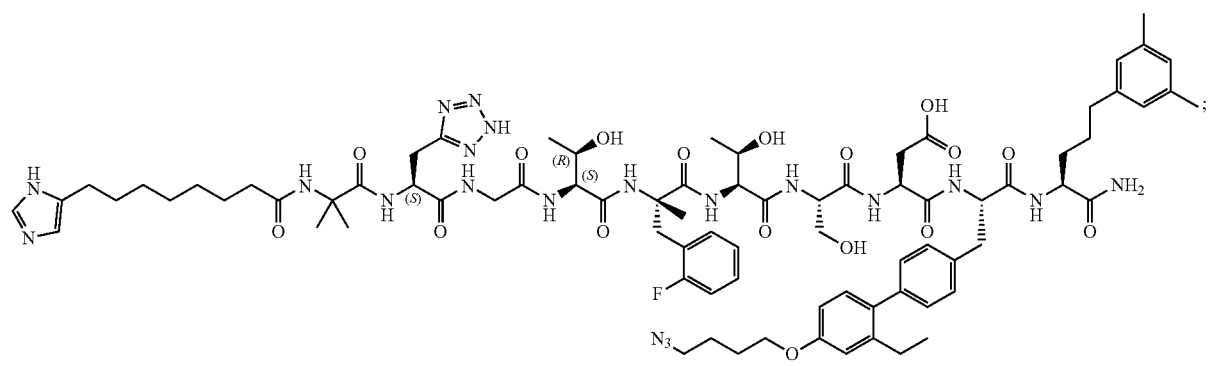
(SEQ ID NO: 71)
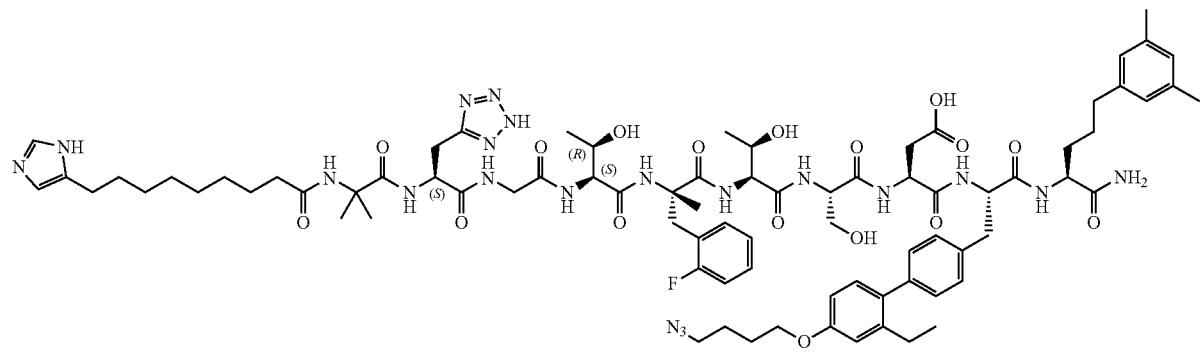
(Main Structure: SEQ ID NO: 72; Branched Sequence: SEQ ID NO: 154)
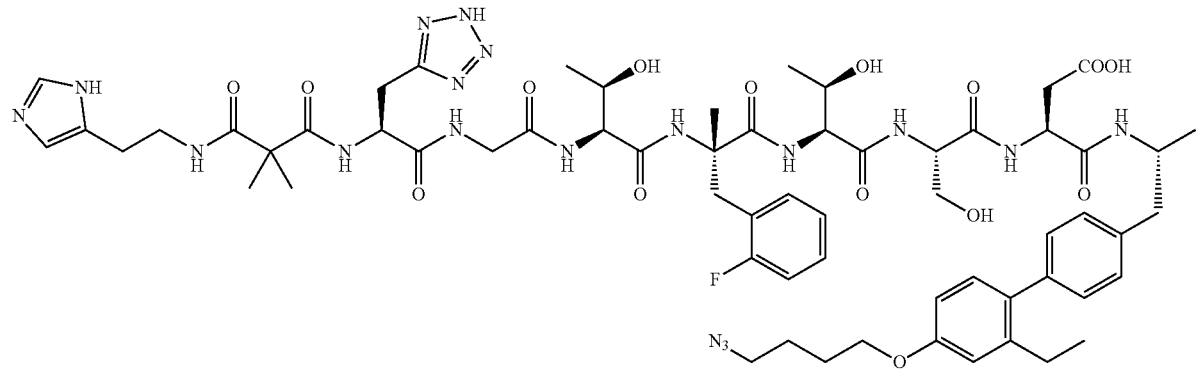

-continued
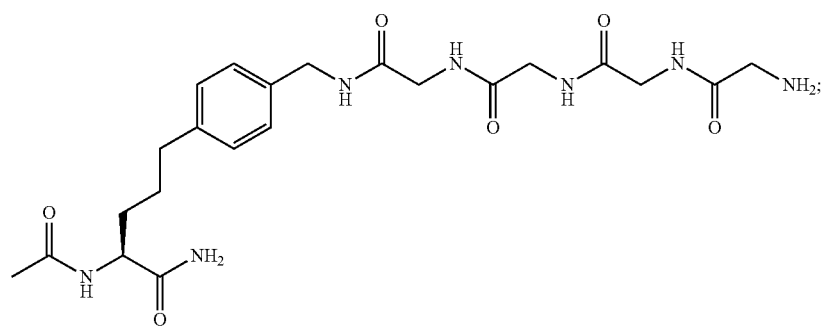
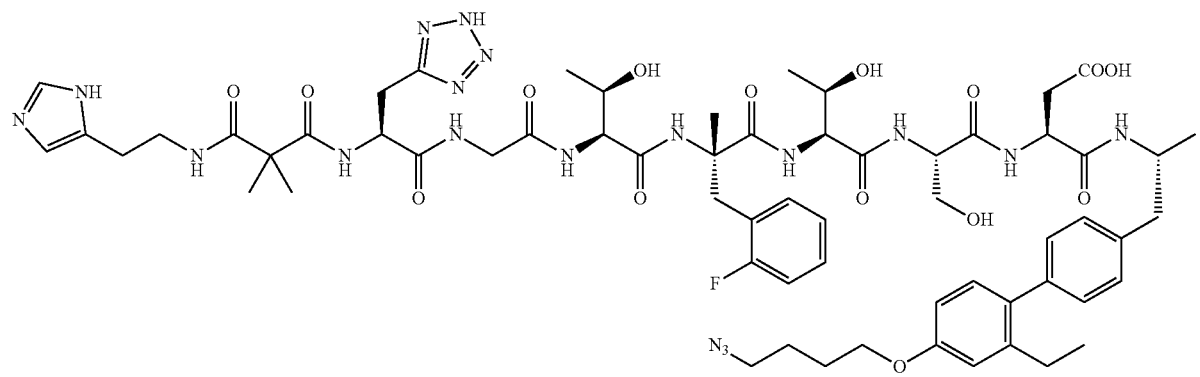
(SEQ ID NO: 73)
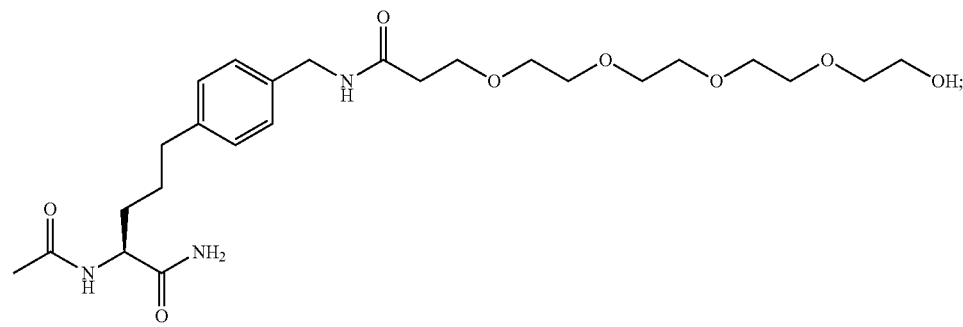
(Main Structure: SEQ ID NO: 74; Branched Sequence: SEQ ID NO: 155)
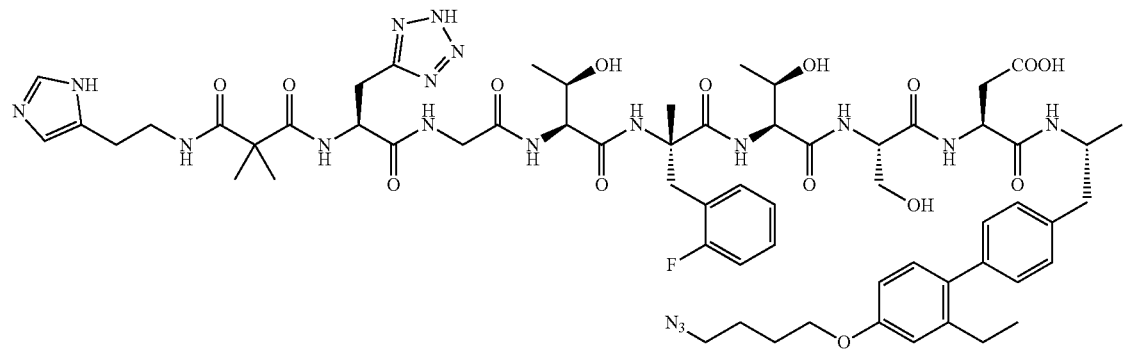

171 172
-continued
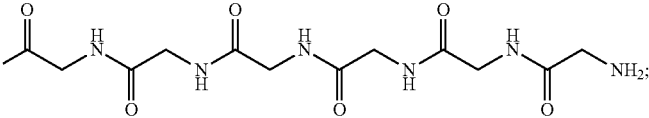
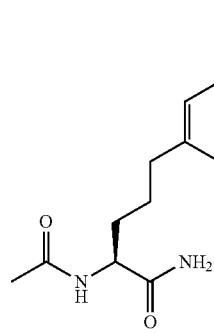
(SEQ ID NO: 75)
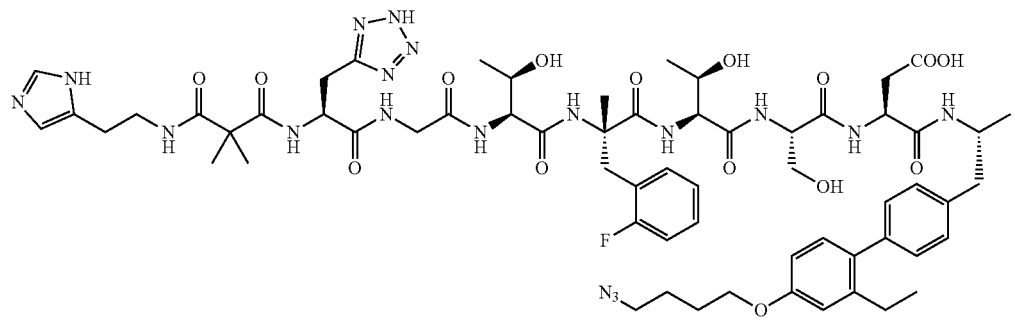
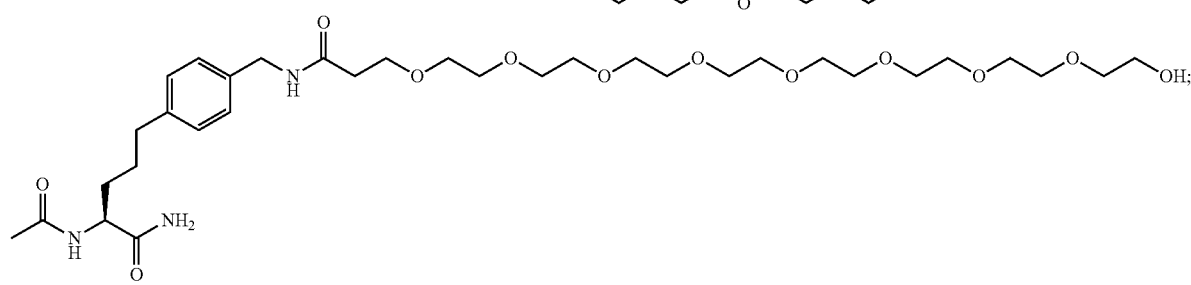
(SEQ ID NO: 76)
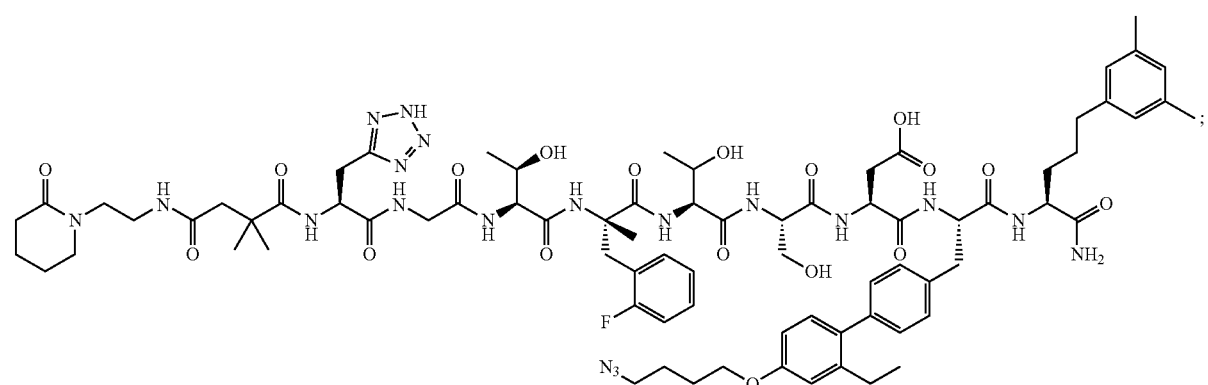
(SEQ ID NO: 77)
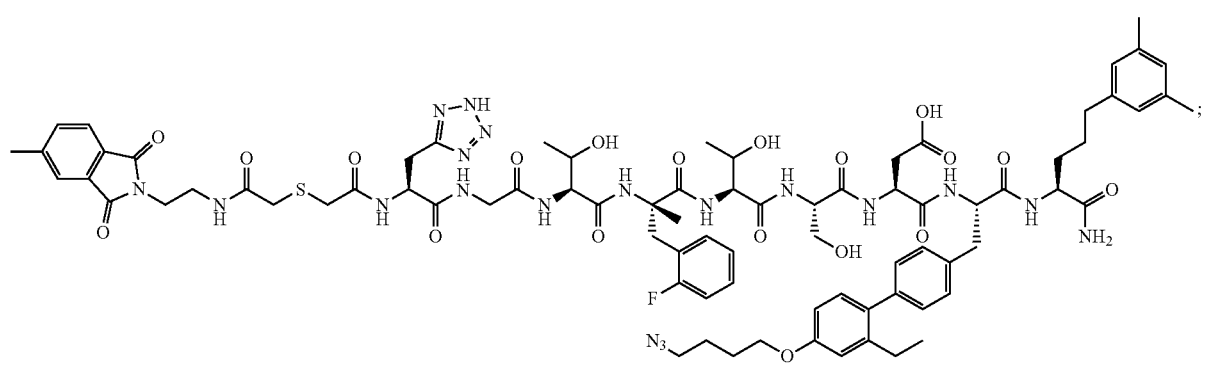

-continued
(SEQ ID NO: 78)
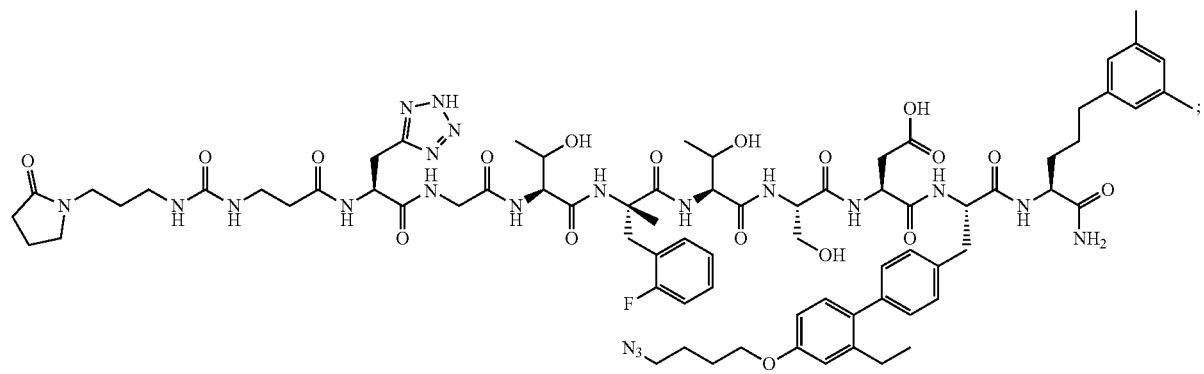
(SEQ ID NO: 79)
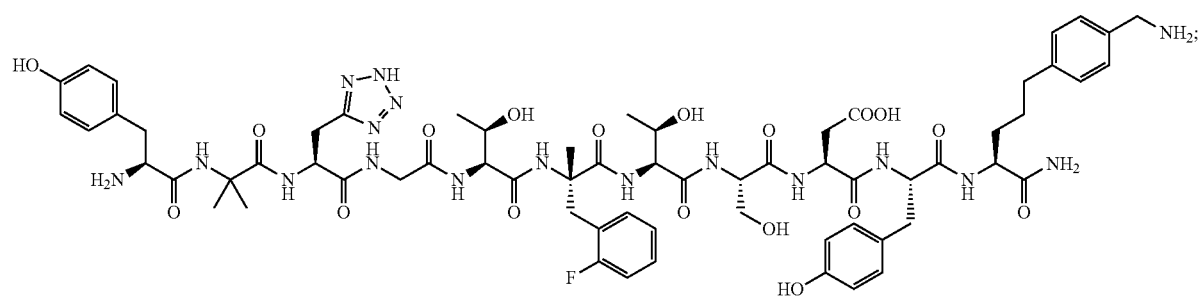
(SEQ ID NO: 80)
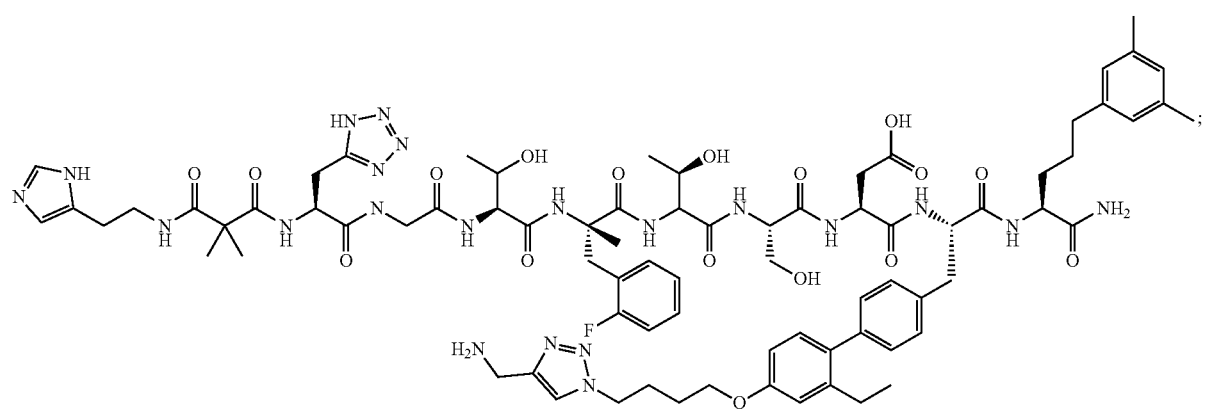
(SEQ ID NO: 81)
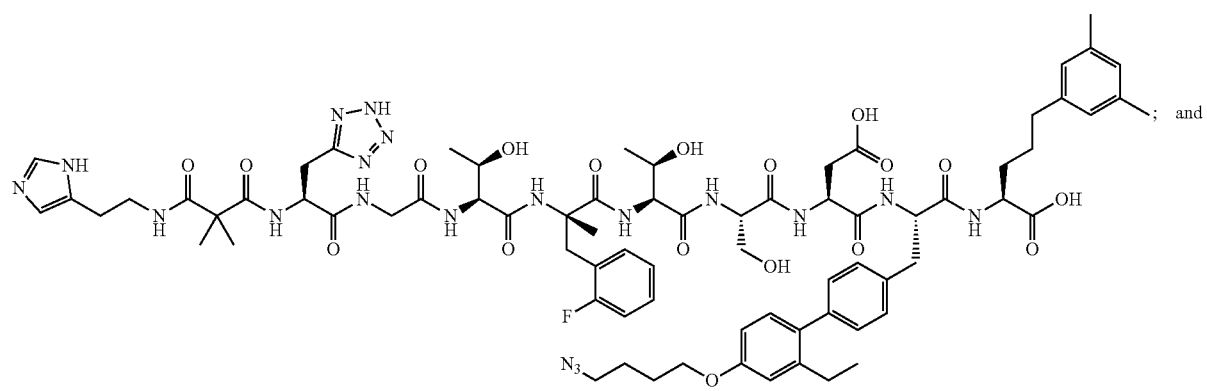

(SEQ ID NO: 82)

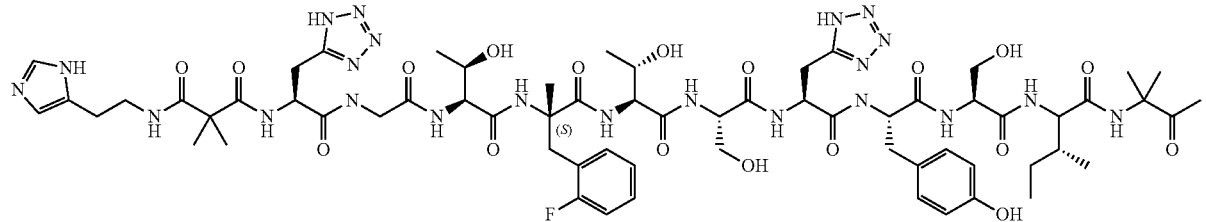

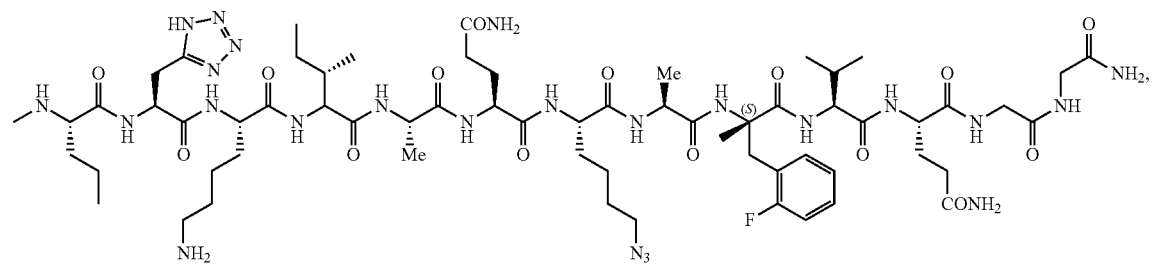

or a pharmaceutically acceptable salt thereof.

In yet another aspect, provided herein is an antibody-drug conjugate comprising a Glucagon-like peptide-1 receptor (GLP1R)-targeting antibody or an antigen-binding fragment thereof and a payload having the structure (SEQ ID NO: 124):

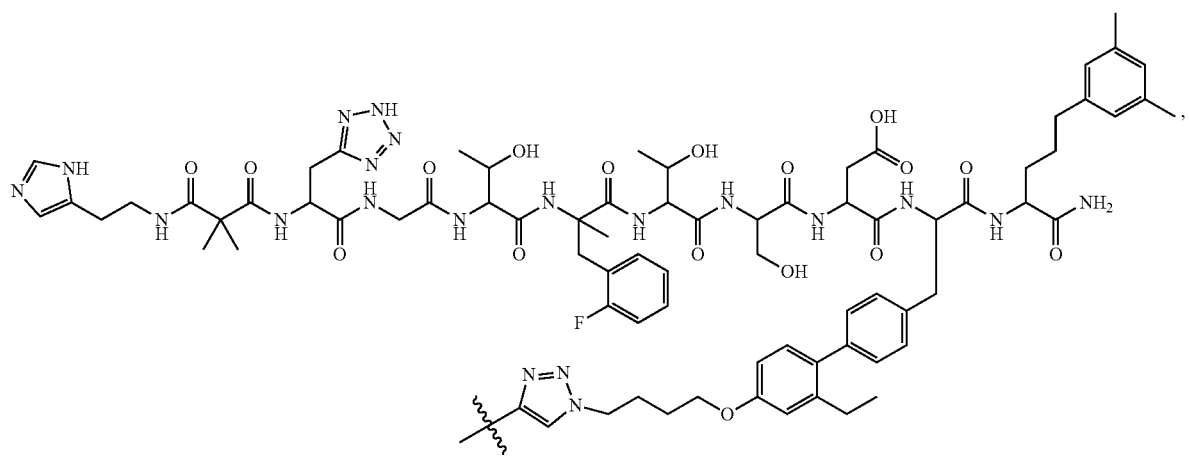 [SMILES: *c1cn(CCCCOc2ccc(-c3ccc(CC(NC(=O)C(CC(=O)O)NC(=O)C(CO)NC(=O)C(NC(=O)C(C)(Cc4ccccc4F)NC(=O)C(NC(=O)CNC(=O)C(Cc4nn[nH]n4)NC(=O)C(C)(C)C(=O)NCCc4cnc[nH]4)C(C)O)C(C)O)C(=O)NC(CCCc4cc(C)cc(C)c4)C(N)=O)cc3)c(CC)c2)nn1]

wherein

is the point of attachment of the payload to the antibody or the antigen-binding fragment thereof directly or through a linker.

In one embodiment, the payload has the structure (SEQ ID NO: 90):

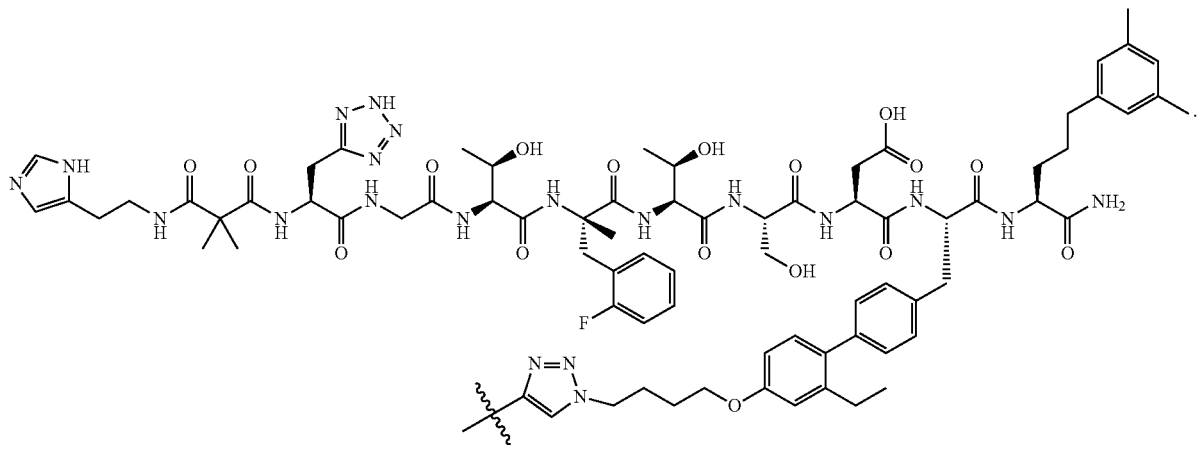 [SMILES: *c1cn(CCCCOc2ccc(-c3ccc(C[C@H](NC(=O)[C@H](CC(=O)O)NC(=O)[C@H](CO)NC(=O)[C@@H](NC(=O)[C@](C)(Cc4ccccc4F)NC(=O)[C@@H](NC(=O)CNC(=O)[C@H](Cc4nn[nH]n4)NC(=O)C(C)(C)C(=O)NCCc4cnc[nH]4)[C@@H](C)O)[C@@H](C)O)C(=O)N[C@@H](CCCc4cc(C)cc(C)c4)C(N)=O)cc3)c(CC)c2)nn1]

In yet another aspect, provided herein is an antibody-drug conjugate comprising a Glucagon-like peptide-1 receptor (GLP1R)-targeting antibody or an antigen-binding fragment thereof and a linker-payload having the structure (SEQ ID NO: 125):

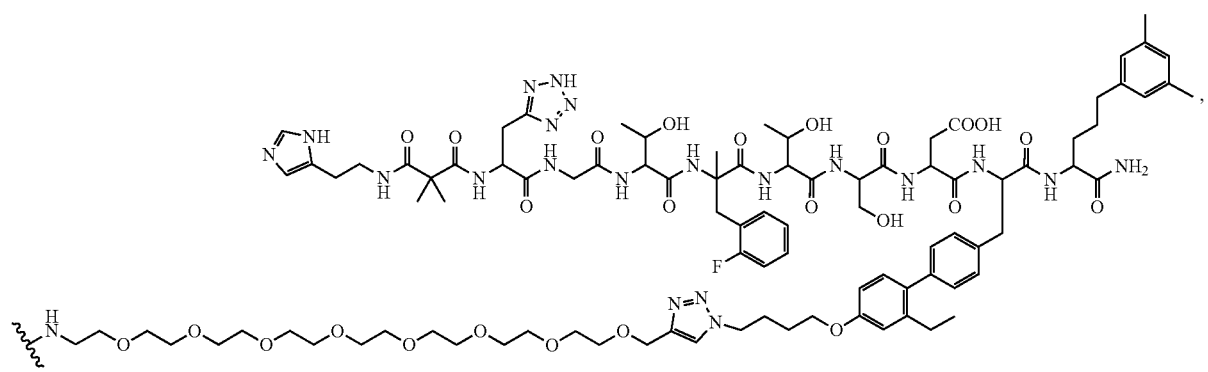 [SMILES: *NCCOCCOCCOCCOCCOCCOCCOCCOCc1cn(CCCCOc2ccc(-c3ccc(CC(NC(=O)C(CC(=O)O)NC(=O)C(CO)NC(=O)C(NC(=O)C(C)(Cc4ccccc4F)NC(=O)C(NC(=O)CNC(=O)C(Cc4nn[nH]n4)NC(=O)C(C)(C)C(=O)NCCc4cnc[nH]4)C(C)O)C(C)O)C(=O)NC(CCCc4cc(C)cc(C)c4)C(N)=O)cc3)c(CC)c2)nn1]

wherein

is the point of attachment of the linker-payload to the antibody or the antigen-binding fragment thereof.

In one embodiments, the linker-payload has the structure (SEQ ID NO: 126):

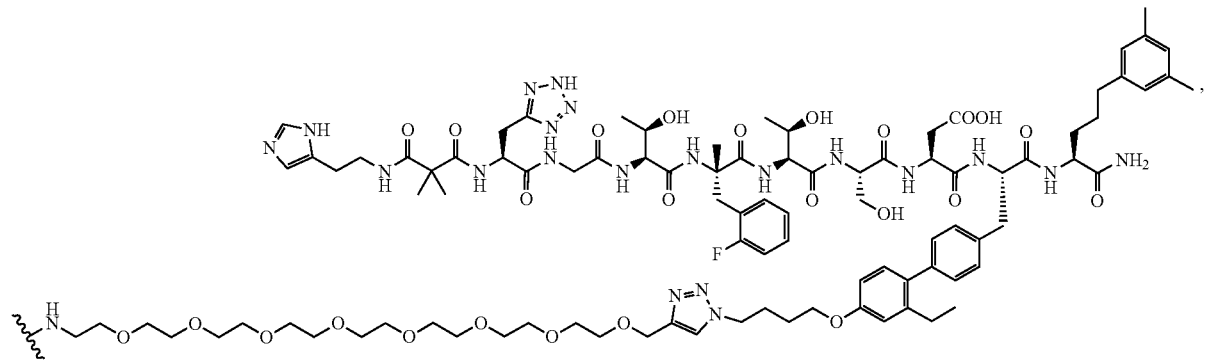

These and other aspects of the present disclosure will become apparent to those skilled in the art after a reading of the following detailed description of the disclosure, including the appended claims.

BRIEF DESCRIPTION OF THE DRAWINGS

FIGS. 6A-6D demonstrate that the GLP1R peptidomimetic payloads of the present disclosure showed no activation in related GPCRs bioassays.

FIGS. 7A-7B show that shorter linker GLP1R ATDCs showed greater potency over the control ATDCs.

FIG. 8 shows that the lead linker-payload showed optimal in vitro ADME profile with no in vitro cardiotoxicity and mutagenic potential and its ATDC is highly stable in plasmas.

FIG. 11B shows the data corresponding to the graphs in FIG. 11A.

FIGS. 17A and 17B show a sequence for solid-supported synthesis of GLP1 peptidomimetic payloads P10, P12, P18, P19, P25, P26, P27, P28, P29, P30, P31, P36, P37, and P38 according to the disclosure.

DETAILED DESCRIPTION

Figure 1A:
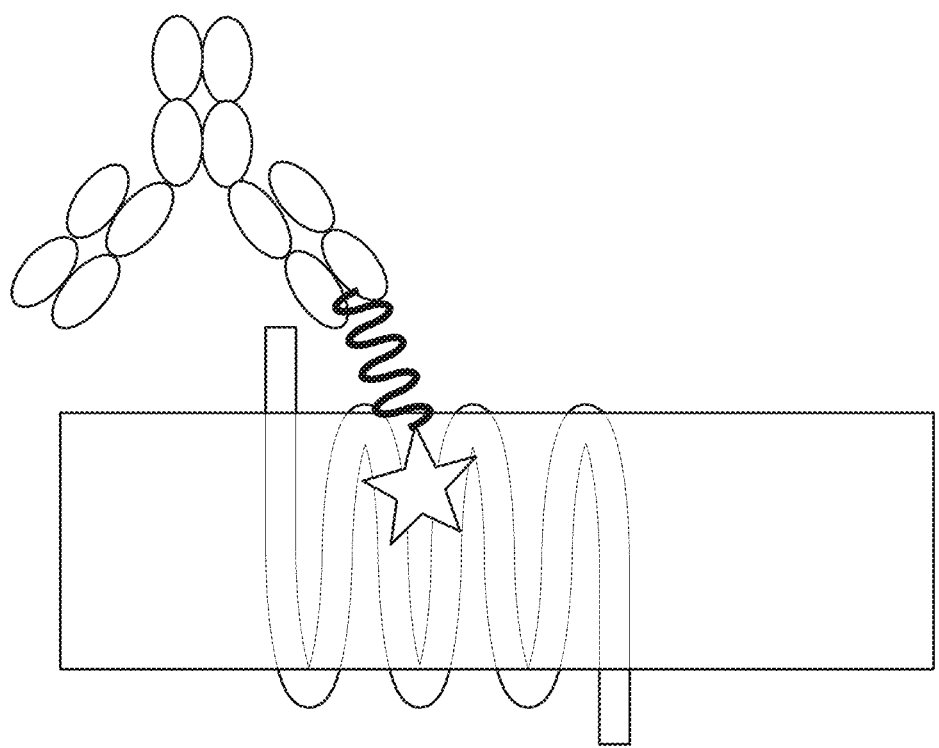
FIG. 1A shows a schematic representation of an exemplary antibody-tethered drug conjugate (ATDC) design and its mechanism of action.
Figure 1B:
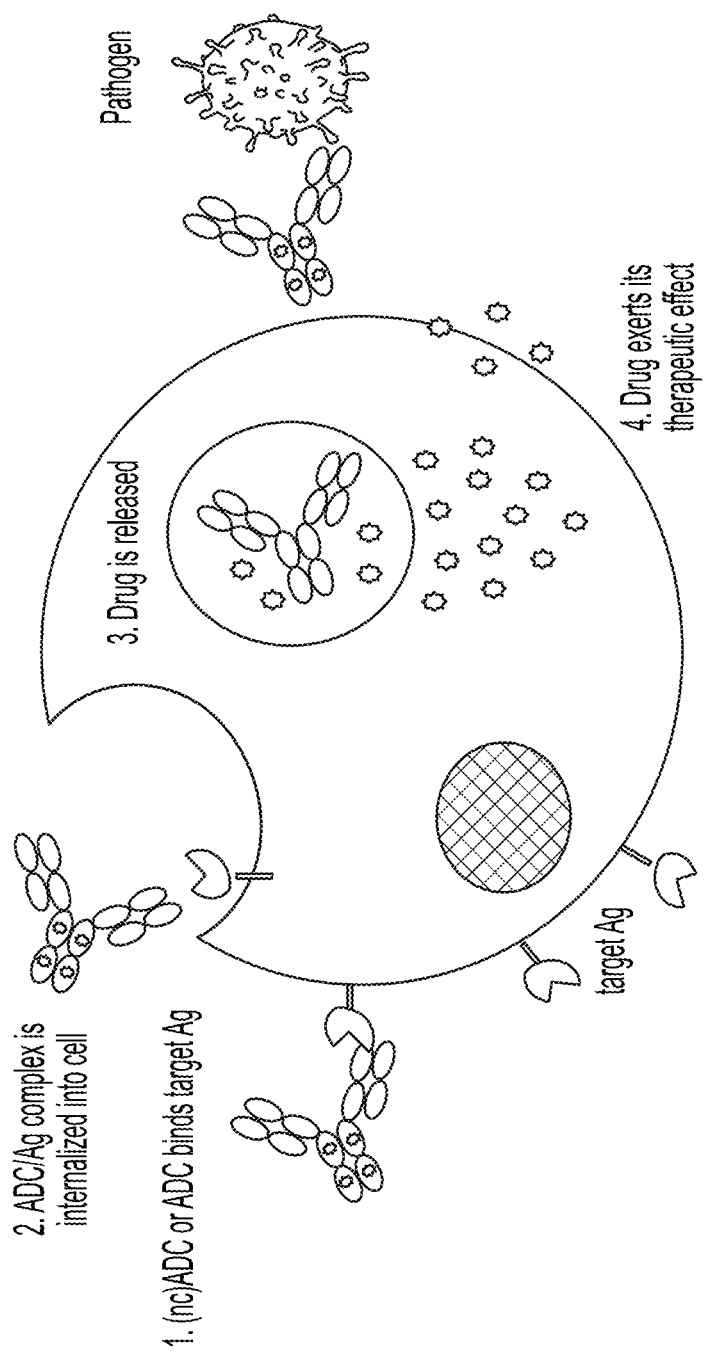
FIG. 1B shows a schematic representation of a conventional antibody-drug conjugate (ADC) design and its mechanism of action.
Figure 2:
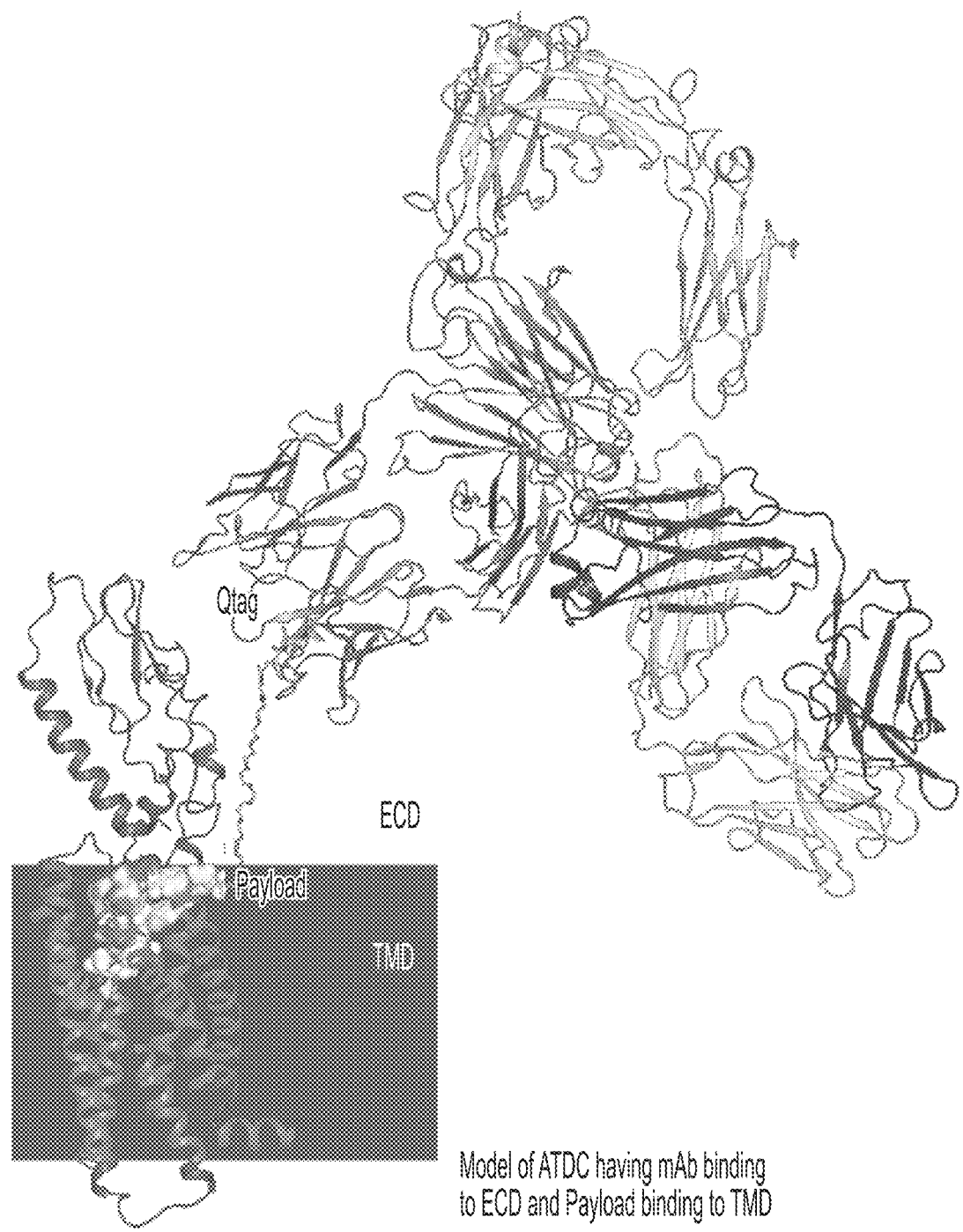
FIG. 2 shows a model of an antibody-tethered drug conjugate having an antibody binding to extracellular domain (ECD) and a payload binding to the transmembrane domain (TMD).
Figure 3A:
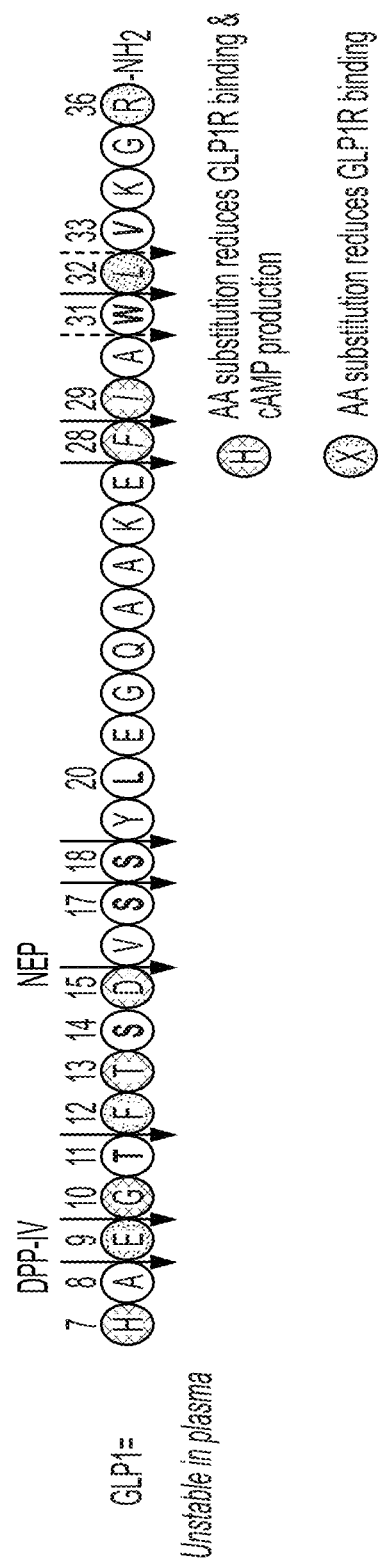
FIG. 3A shows a schematic representation of GLP1 (7-36) amide (SEQ ID NO: 4). The numbers above the sequence correspond to the amino acid positions in the proglucagon propeptide. The blue arrow indicates the dipeptidyl peptidase-4 (DPP-IV) cleavage site. The red arrows indicate the neutral endopeptidase (NEP) cleavage sites. The dashed arrows indicate cleavage sites by unknown endoprotease(s). The residues in orange are amino acids which, when substituted, reduce GLP1R binding and cAMP production. The residues in green are amino acids which, when substituted, reduce GLP1R binding.
Figure 3B:
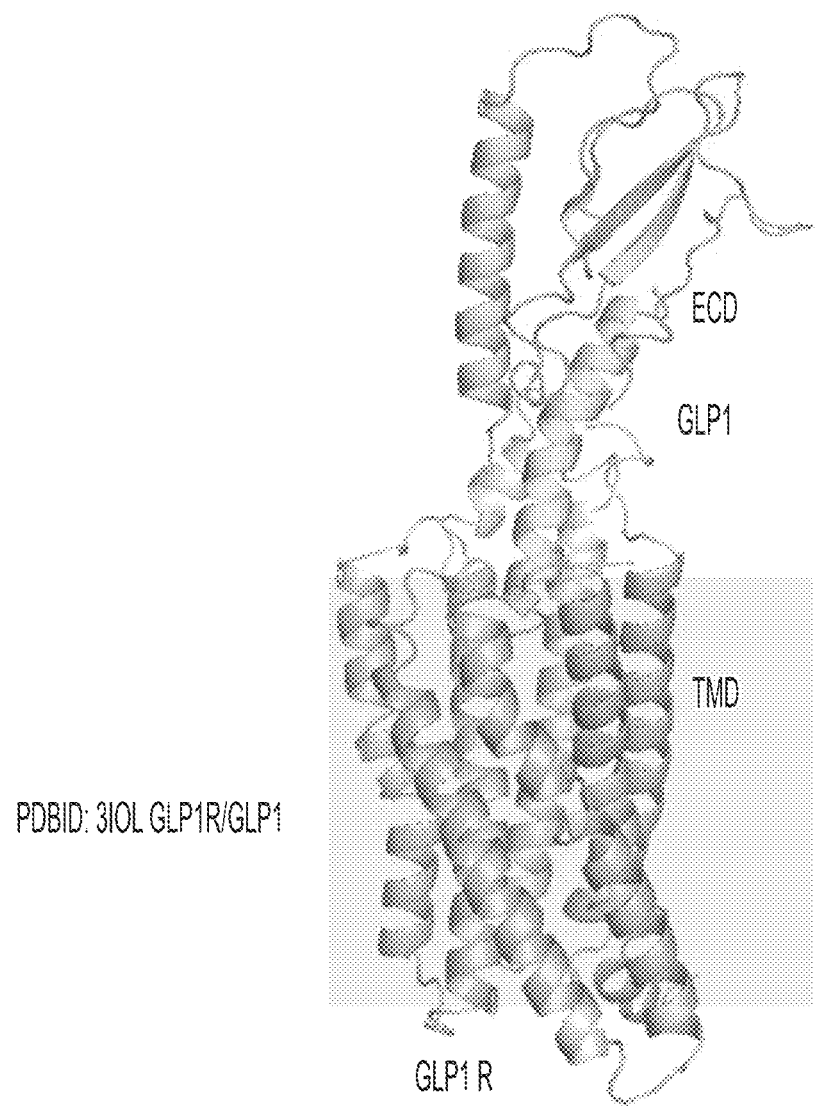
FIG. 3B shows a structure of GLP1R bound to GLP1 (Protein Data Bank ID: 3IOL). References of this structure may be found in Zhang et al. Nature 2017, Chepurny et al. JBC 2019, De Graaf et al. Pharmacological reviews 2016, and Manandhar and Ahn Journal of Medical Chemistry 2014, each of which is incorporated herein by reference in its entirety.
Figure 4A:
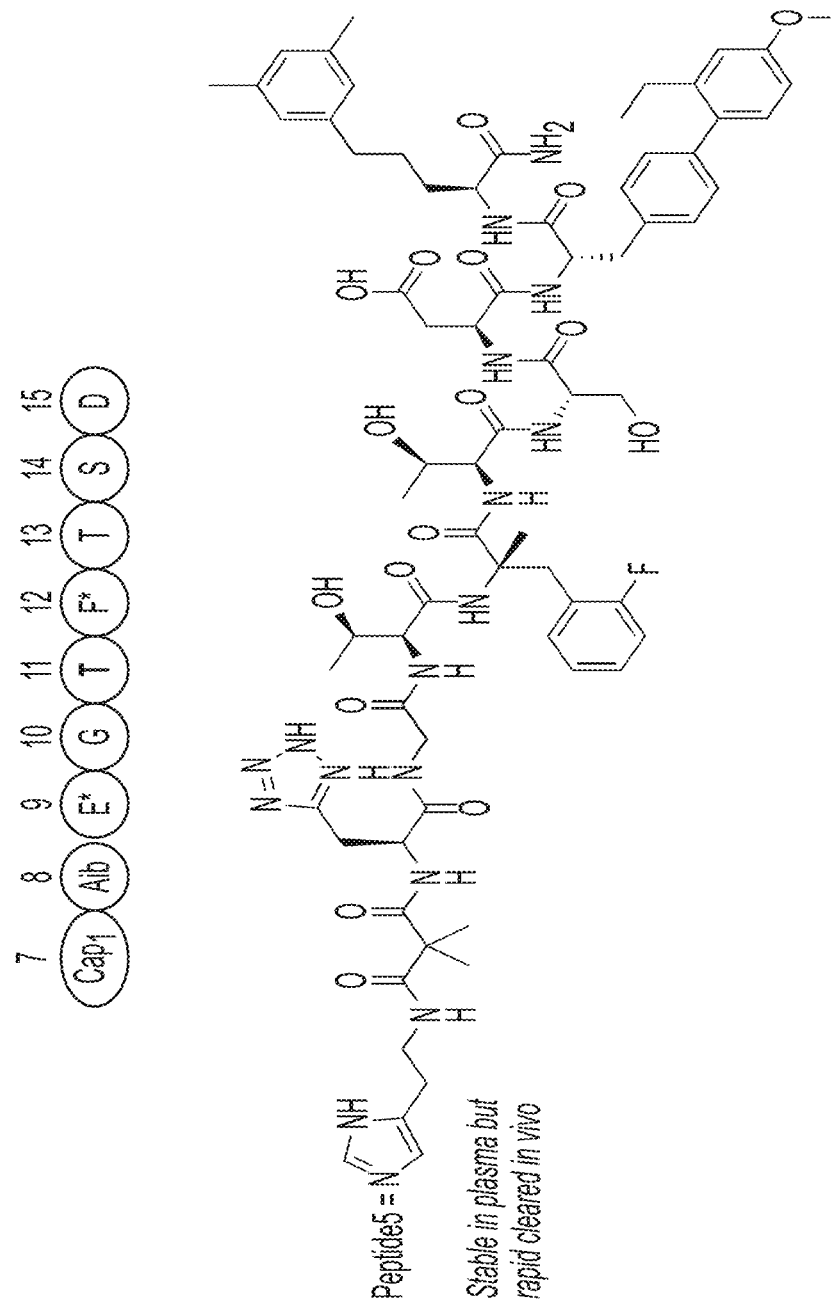
FIG. 4A shows the sequence and structure of a GLP1 peptidomimetic, Peptide 5 (SEQ ID NO: 5). The numbers above the sequence correspond to the amino acid positions in the proglucagon propeptide.
Figure 4B:
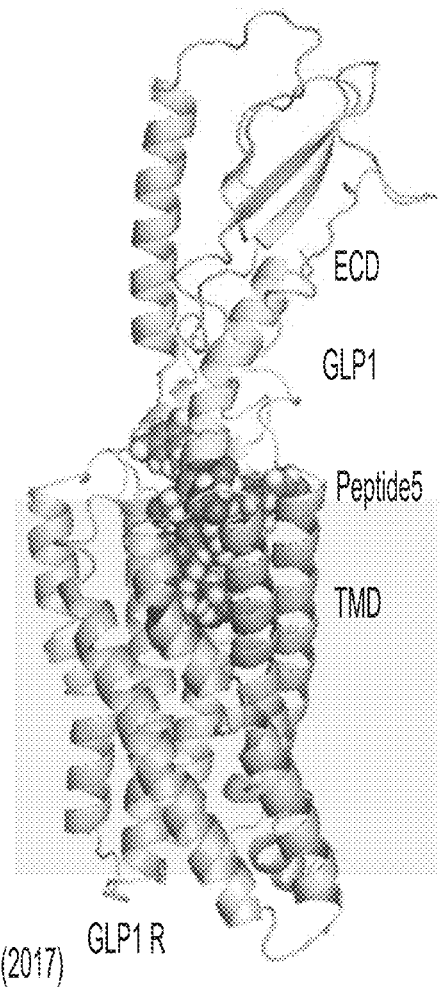
FIG. 4B shows superimposed structures of GLP1R bound to Peptide 5 (Protein Data Bank ID: 5NX2) and GLP1R bound to GLP1 (Protein Data Bank ID: 3IOL) using the GLP1R in 5NX2 as the template. Reference of the 5NX2 structure can be found in Jazayeri A, et al. Nature volume 546, pages 254-258 (2017), which is incorporated herein by reference in its entirety.
Figure 5:
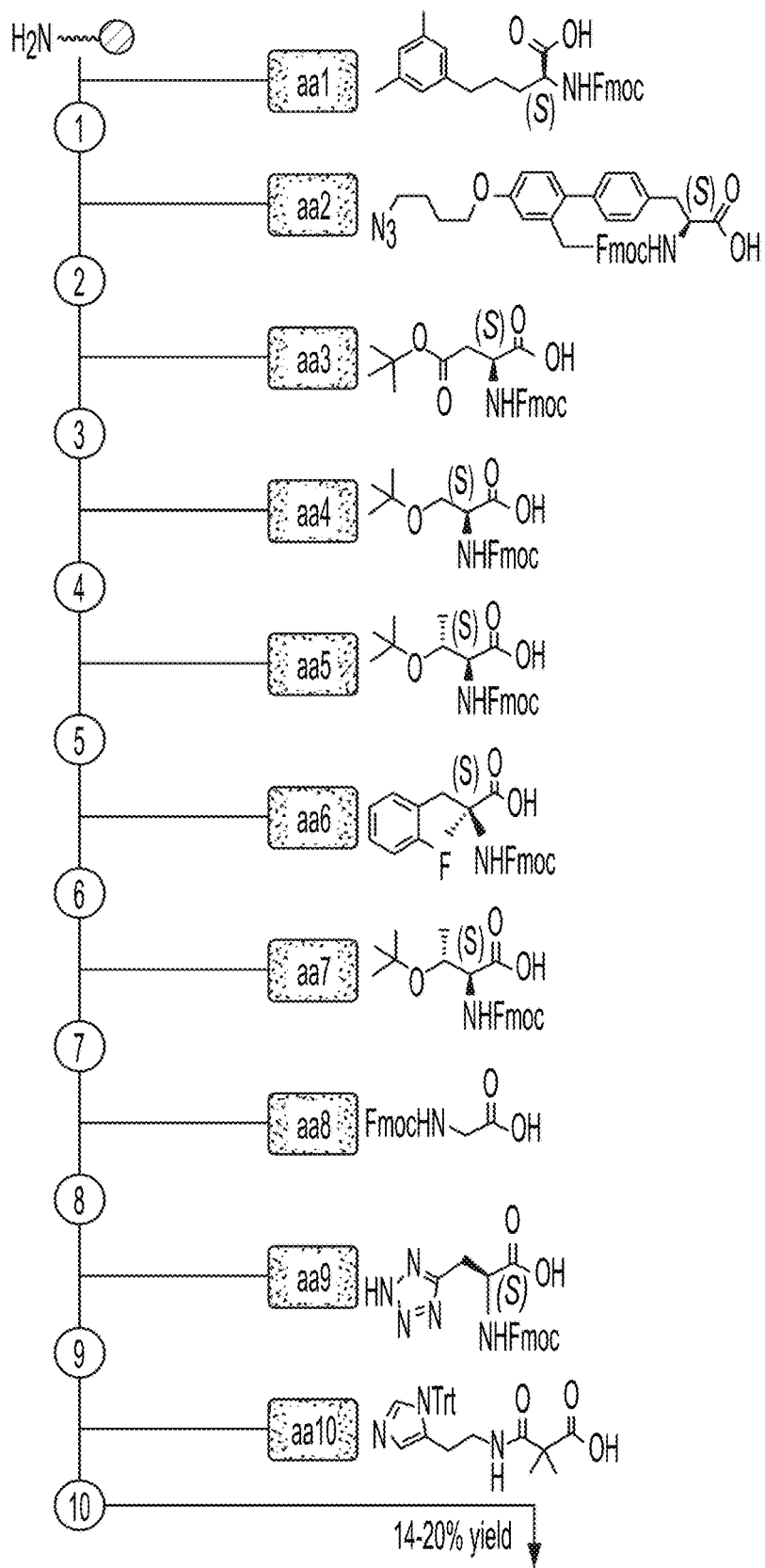
FIG. 5 shows a synthetic scheme for making GLP1 peptidomimetic payloads of the present disclosure. Solid Phase Peptide Synthesis on resin was established which efficiently generated the payloads of the present disclosure with good yields. Additional GLP1R peptidomimetic payloads were generated via systematic R1/R2/R3-modifications.
Figure 5:
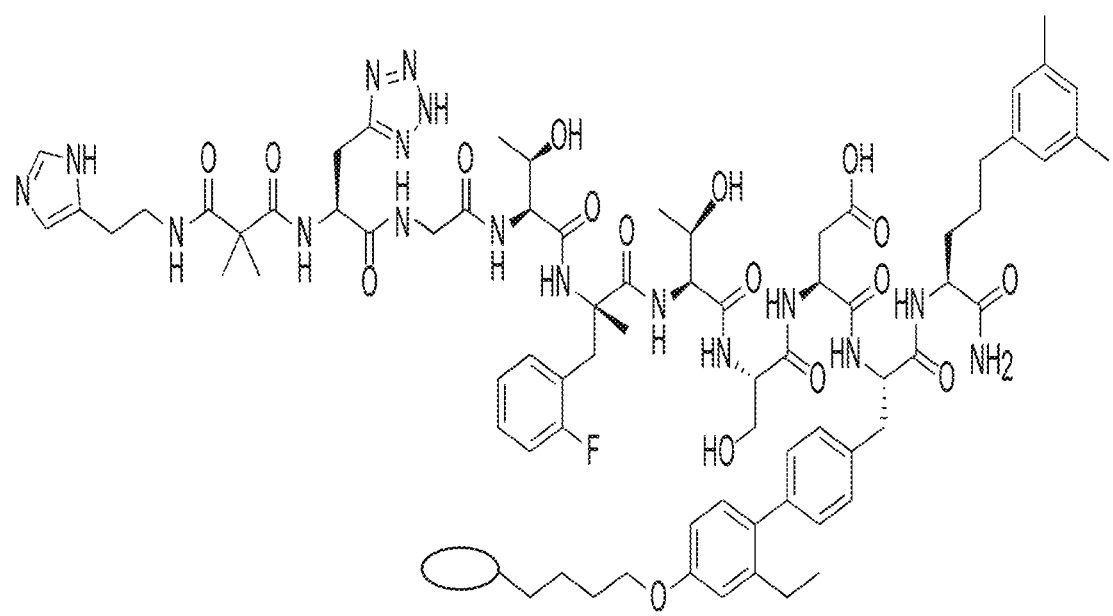
Figure 6A:
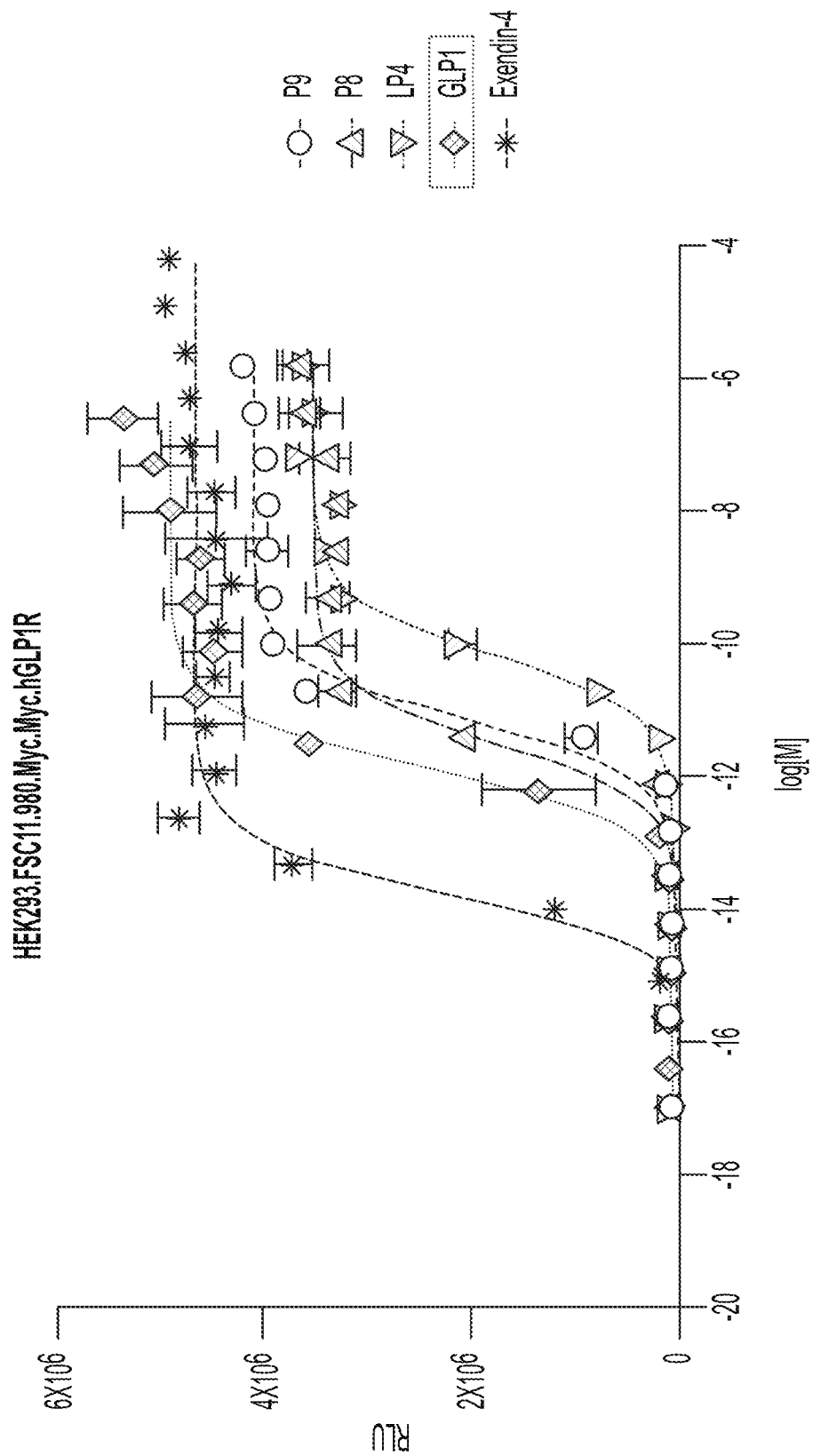
Figure 6B:
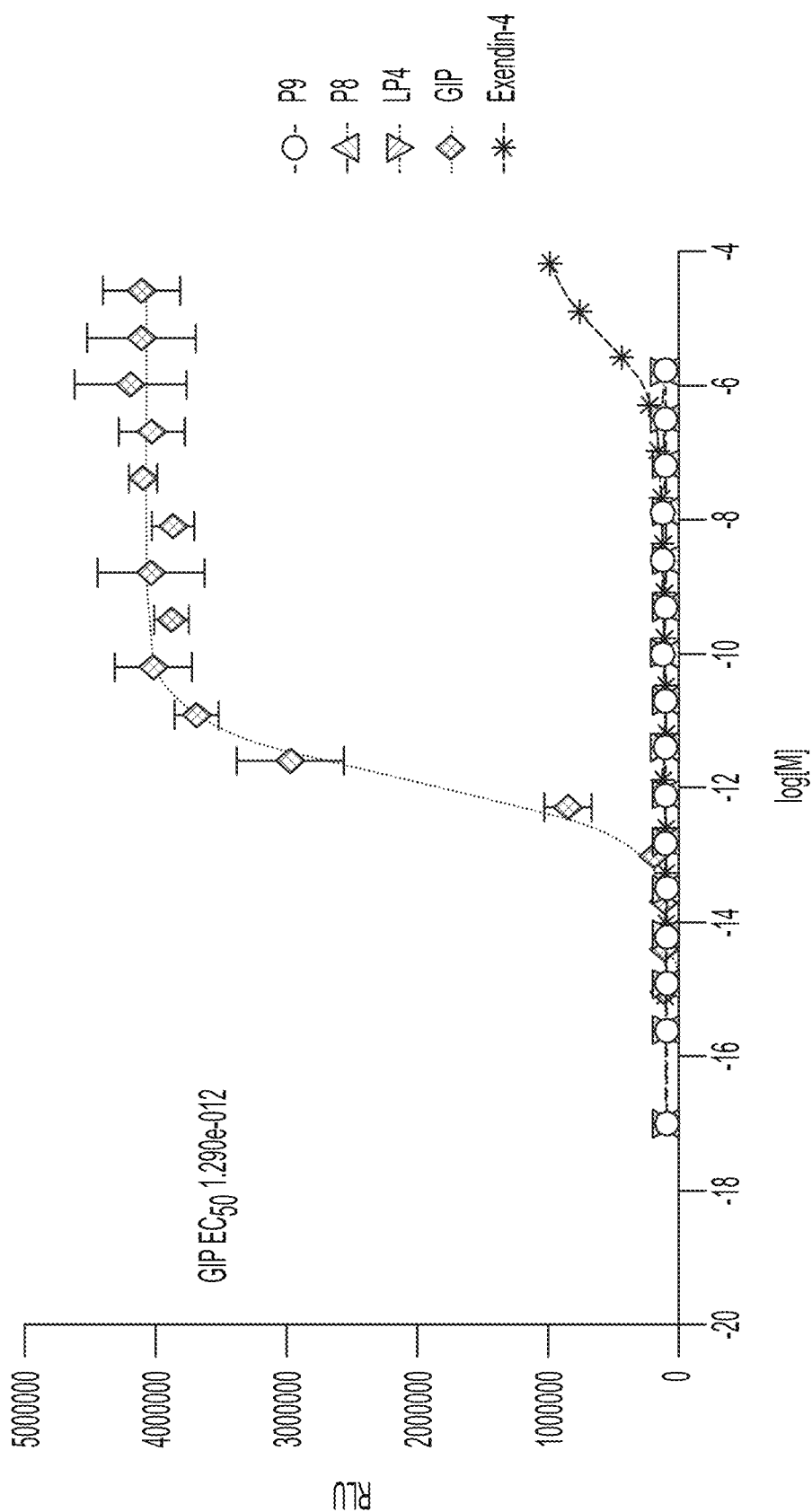
Figure 6D:
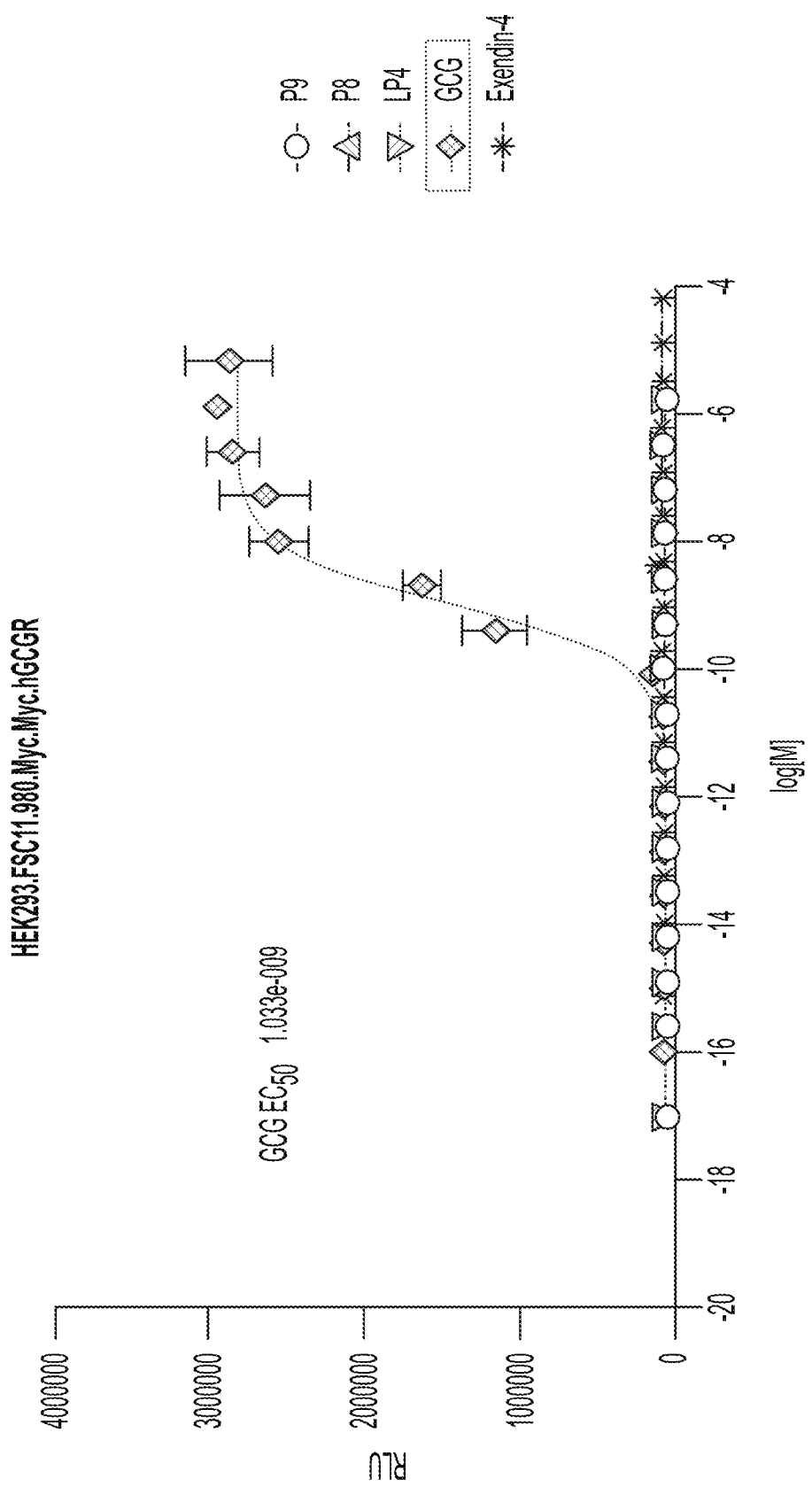
Figure 7B:
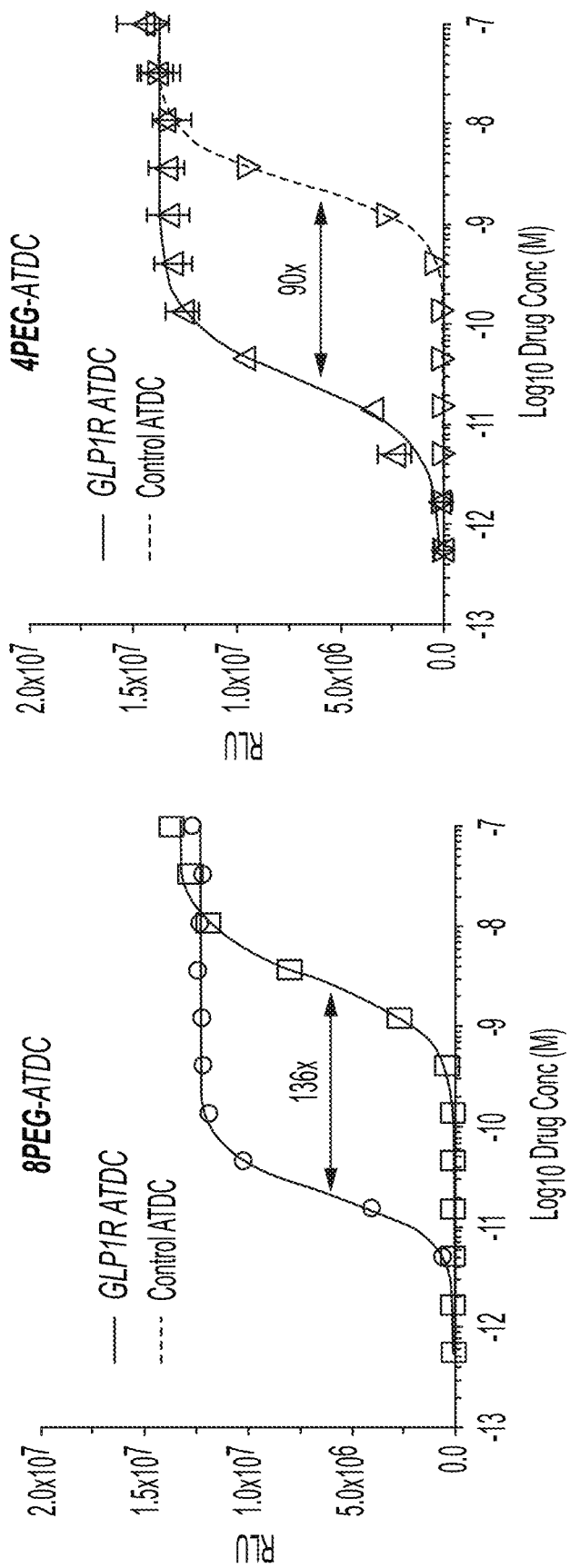
Figure 7B:
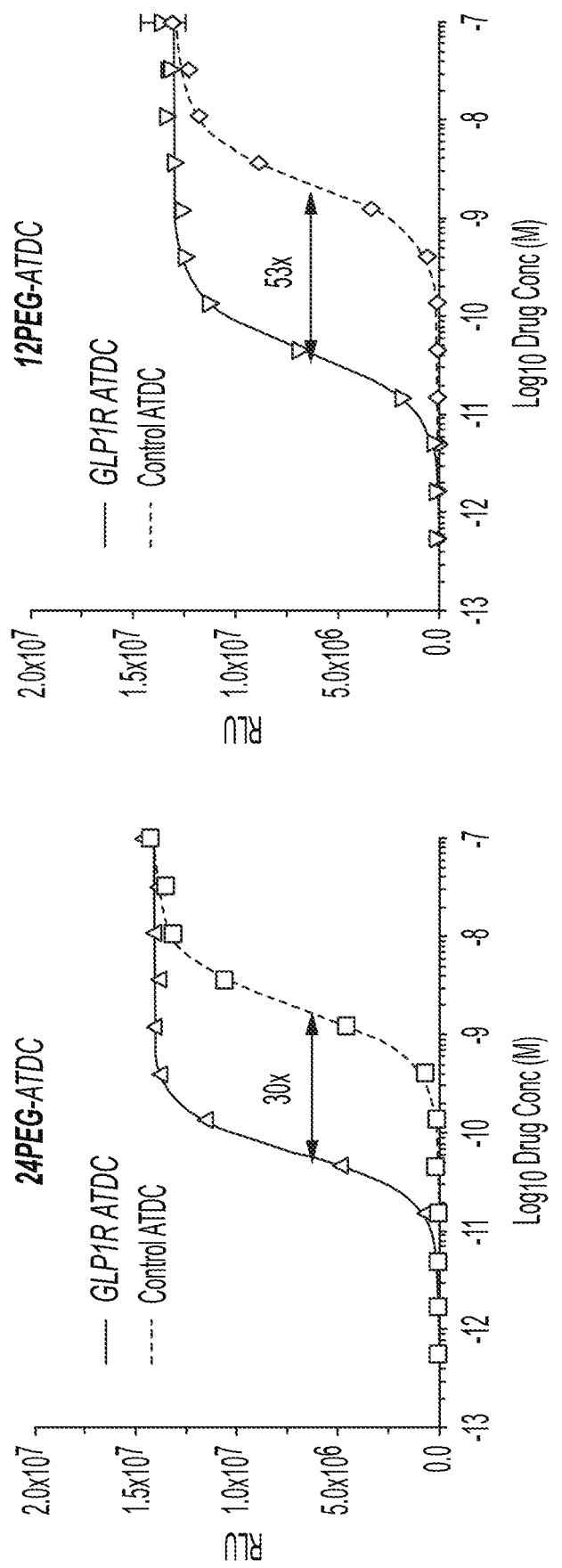
Figure 9A:
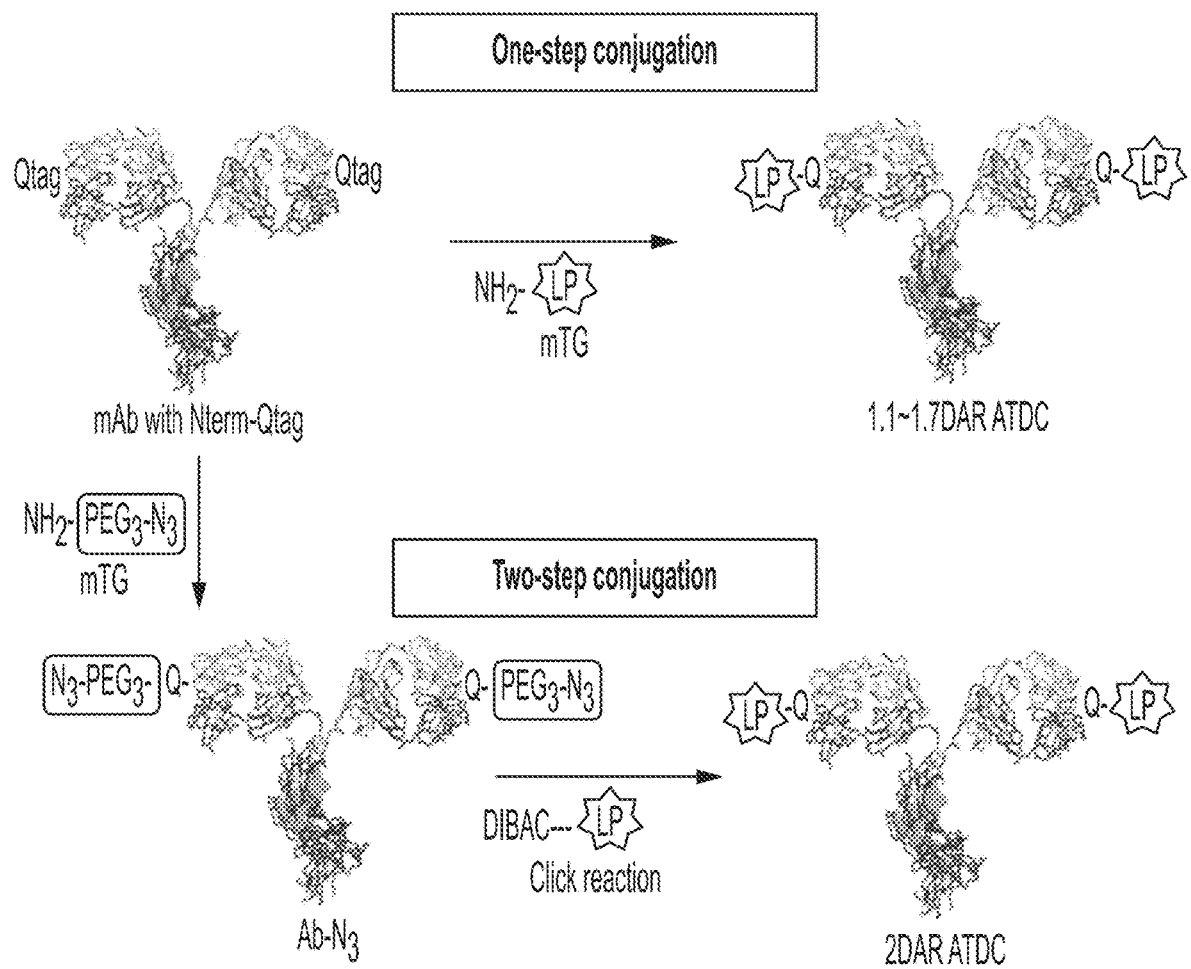
FIG. 9A shows two methods for conjugating linker-payloads to an antibody of the present disclosure.
Figure 9B:
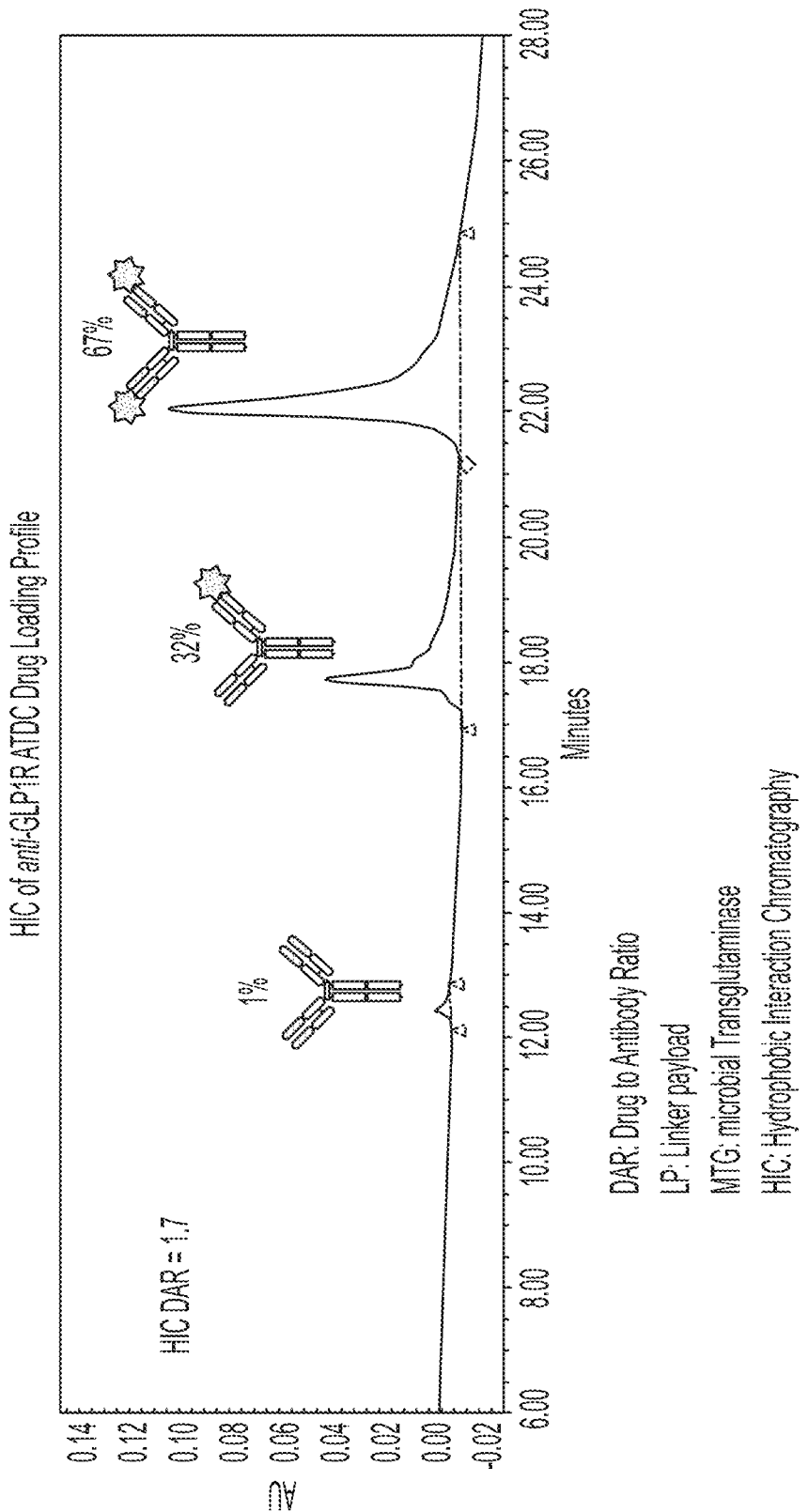
FIG. 9B shows a representative hydrophobic interaction chromatography (HIC) graph of anti-GLP1R ATDC drug loading profile. HIC was used in the conjugatability screening to triage ATDCs that show low conjugation yields, low DAR, high aggregates and poor Biacore-binding.

The present disclosure provides, in some aspects, antibody-drug conjugates that specifically bind the glucagon-like peptide 1 receptor (GLP1R) protein. As described in the Background section above, GLP1R and its ligand GLP1 are highly validated targets for obesity and type 2 diabetes. However, no direct agonist antibodies have been identified for type 2 diabetes treatment. Single peptides with agonist activities on GLP1R are effective therapeutic agents for glucose control and body weight loss, but in-line peptide-antibody fusions are susceptible to proteolysis. In certain embodiments of the present disclosure, antibody-drug conjugates were generated that combine an antibody, or antigen-binding fragment thereof, specifically targeting the extracellular domain of GLP1R, with a GLP1 peptidomimetic functionally activating GLP1R. In certain embodiments, antibody-drug conjugates of the present disclosure have a longer drug duration with comparable or better weight and glucose reducing efficacy and minimized off-target side effects.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive. Therefore, specific structural and functional details disclosed herein are not to be interpreted as limiting, but merely as a representative basis for teaching one skilled in the art to variously employ the present disclosure.

Definitions

Unless defined otherwise, all technical and scientific terms used herein have the same meaning as commonly understood by one of ordinary skill in the art to which this disclosure belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician. In some embodiments, treatment comprises methods wherein cells are ablated in such manner where disease is indirectly impacted. In certain embodiments, treatment comprises depleting immune cells as a hematopoietic conditioning regimen prior to therapy.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable salt", as used in connection with compositions of the disclosure, refers to any salt suitable for administration to a patient. Suitable salts include, but are not limited to, those disclosed in. Berge et al., "Pharmaceutical Salts", J. Pharm. Sci., 1977, 66:1, incorporated herein by reference. Examples of salts include, but are not limited to, acid derived, base derived, organic, inorganic, amine, and alkali or alkaline earth metal salts, including but not limited to calcium salts, magnesium salts, potassium salts, sodium salts, salts of hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methane sulfonic acid, ethane sulfonic acid, p toluene sulfonic acid, salicylic acid, and the like. In some examples, a payload described herein comprises a tertiary amine, where the nitrogen atom in the tertiary amine is the atom through which the payload is bonded to a linker or a linker-spacer. In such instances, bonding to the tertiary amine of the payload yields a quaternary amine in the linker-payload molecule. The positive charge on the quaternary amine can be balanced by a counter ion (e.g., chloro, bromo, iodo, or any other suitably charged moiety such as those described herein).

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10 carbon atoms, or about 1 to 6 carbon atoms. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "halogen" means F, Cl, Br, or I; the term "halide" refers to a halogen radical or substituent, namely —F, —Cl, —Br, or —I.

The term "adduct", e.g., "a Diels-Alder adduct" of the present disclosure encompasses any moiety comprising the product of an addition reaction, e.g., a Diels-Alder reaction, independent of the synthetic steps taken to produce the moiety.

The term "covalent attachment" means formation of a covalent bond, i.e., a chemical bond that involves sharing of one or more electron pairs between two atoms. Covalent bonding may include different interactions, including but not limited to σ-bonding, π-bonding, metal-to-metal bonding, agostic interactions, bent bonds, and three-center two-electron bonds. When a first group is said to be "capable of covalently attaching" to a second group, this means that the first group is capable of forming a covalent bond with the second group, directly or indirectly, e.g., through the use of a catalyst or under specific reaction conditions. Non-limiting examples of groups capable of covalently attaching to each other may include, e.g., an amine and a carboxylic acid (forming an amide bond), a diene and a dienophile (via a Diels-Alder reaction), a maleimide and a thiol (forming a thio-maleimide), and an azide and an alkyne (forming a triazole via a 1,3-cycloaddition reaction).

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds.

The term "stable," as used herein, refers to compounds that are not substantially altered when subjected to conditions to allow for their production, detection, and, in certain embodiments, their recovery, purification, and use for one or more of the purposes disclosed herein.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, cyclic adducts, e.g., products of a cycloaddition reaction, e.g., an azide-acetylene cycloaddition reaction or a Diels-Alder reaction, depicted herein include all regioisomers, i.e., structural isomers that differ only in the position of a functional group or a substituent. By way of an example, the following structures represent triazole regioisomers, which differ only in the position of the substituent on the triazole ring:

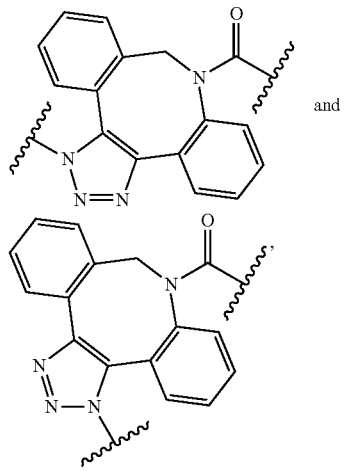

Triazole regioisomers may also be represented by the following structure:

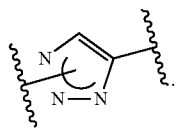

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this disclosure.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Unless otherwise stated, all crystalline forms of the compounds of the disclosure and salts thereof are also within the scope of the disclosure. The compounds of the disclosure may be isolated in various amorphous and crystalline forms, including without limitation forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (PXRD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

In some embodiments, the compounds of the disclosure are substantially isolated. By "substantially isolated" is meant that a particular compound is at least partially isolated from impurities. For example, in some embodiments a compound of the disclosure comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated compound including, for example, other crystalline forms and other substances.

Certain groups, moieties, substituents, and atoms are depicted with a wavy line. The wavy line can intersect or cap a bond or bonds. The wavy line indicates the atom through which the groups, moieties, substituents, or atoms are bonded. For example, a phenyl group that is substituted with a propyl group depicted as:

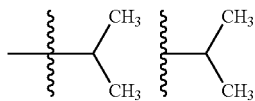

has the following structure:

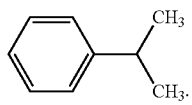

The term "GLP1R" refers to the glucagon-like peptide 1 receptor and includes recombinant GLP1R protein or a fragment thereof. GLP1R has a sequence of 463 residues. Donnelly, Br J Pharmacol, 166(1):27-41 (2011). Glucagon-like peptide 1 (GLP1) is a 31-amino acid peptide hormone released from intestinal L cells following nutrient consumption. The binding of GLP1 to GLP1R potentiates glucose-induced secretion of insulin from pancreatic beta cells, increases insulin expression, inhibits beta-cell apoptosis, promotes beta-cell neogenesis, reduces glucagon secretion, delays gastric emptying, promotes satiety and increases peripheral glucose disposal.

The phrase "an antibody that binds GLP1R" or an "anti-GLP1R antibody" includes antibodies and antigen-binding fragments thereof that specifically recognize GLP1R.

An "agonist antibody," as used herein (or an "antibody that increases or enhances GLP1R activity"), is intended to refer to an antibody whose binding to GLP1R results in activation of at least one biological activity of GLP1R. For example, an agonist antibody of GLP1R may elicit stimulation of the adenylate cyclase pathway resulting in increased synthesis of cyclic AMP and release of insulin if the cell is a mammalian pancreatic beta cell. An agonist antibody of GLP1R may also reduce glucose levels upon administration to a subject in need thereof.

All amino acid abbreviations used in this disclosure are those accepted by the United States Patent and Trademark Office as set forth in 37 C.F.R. § 1.822 (B)(J).

The term "protein" means any amino acid polymer having more than about 20 amino acids covalently linked via amide bonds. As used herein, "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, nanobodies, recombinant antibody chimeras, scFv fusion proteins, cytokines, chemokines, peptide hormones, and the like. Proteins can be produced using recombinant cell-based production systems, such as the insect bacculovirus system, yeast systems (e.g, *Pichia* sp.), mammalian systems (e.g., CHO cells and CHO derivatives like CHO-K1 cells).

All references to proteins, polypeptides and protein fragments herein are intended to refer to the human version of the respective protein, polypeptide or protein fragment unless explicitly specified as being from a non-human species. Thus, the expression "GLP1R" means human GLP1R unless specified as being from a non-human species, e.g., "mouse GLP1R," "monkey GLP1R," etc.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., Dev. Comp. *Immunol.*, 2003, 27:55-77 ("IMGT" numbering scheme); and Honegge and Pluckthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "glutaminyl-modified antibody" refers to an antibody with at least one covalent linkage from a glutamine side chain to a primary amine compound of the present disclosure. In particular embodiments, the primary amine compound is linked through an amide linkage on the glutamine side chain. In certain embodiments, the glutamine is an endogenous glutamine. In other embodiments, the glutamine is an endogenous glutamine made reactive by polypeptide engineering (e.g., via amino acid deletion, insertion, substitution, or mutation on the polypeptide). In additional embodiments, the glutamine is polypeptide engineered with an acyl donor glutamine-containing tag (e.g., glutamine-containing peptide tags, Q-tags or TGase recognition tag).

The term "TGase recognition tag" refers to a sequence of amino acids comprising an acceptor glutamine residue and that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The recognition tag may be a peptide sequence that is not naturally present in the polypeptide comprising the TGase recognition tag. In some embodiments, the TGase recognition tag comprises at least one Gln. In some embodiments, the TGase recognition tag comprises an amino acid sequence XXQX, wherein X is any amino acid (e.g., conventional amino acid Leu, Ala, Gly, Ser, Val, Phe, Tyr, His, Arg, Asn, Glu, Asp, Cys, Gin, He, Met, Pro, Thr, Lys, or Trp or nonconventional amino acid). In some embodiments, the acyl donor glutamine-containing tag comprises an amino acid sequence selected from the group consisting of LLQGG (SEQ ID NO: 6), LLQG (SEQ ID NO: 7), LSLSQG (SEQ ID NO: 8), GGGLLQGG (SEQ ID NO: 9), GLLQG (SEQ ID NO: 10), LLQ, GSPLAQSHGG (SEQ ID NO: 11), GLLQGGG (SEQ ID NO: 12), GLLQGG (SEQ ID NO: 13), GLLQ (SEQ ID NO: 14), LLQLLQGA (SEQ ID NO: 15), LLQGA (SEQ ID NO: 16), LLQYQGA (SEQ ID NO: 17), LLQGSG (SEQ ID NO: 18), LLQYQG (SEQ ID NO: 19), LLQLLQG (SEQ ID NO: 20), SLLQG (SEQ ID NO: 21), LLQLQ (SEQ ID NO: 22), LLQLLQ (SEQ ID NO: 23), and LLQGR (SEQ ID NO: 24). See for example, WO2012059882, the entire contents of which are incorporated herein.

The term "antibody," as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2, and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments, the FRs of the antibody (or antigen-binding portion thereof) can be identical to the human germline sequences, or can be naturally or artificially modified. An amino acid consensus sequence can be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody can be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA can be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain can be of any size or amino acid composition and will generally comprise at least one CDR which is adjacent to or in frame with one or more framework sequences. In antigen-binding fragments having a VH domain associated with a VL domain, the VH and VL domains can be situated relative to one another in any suitable arrangement. For example, the variable region can be dimeric and contain VH-VH, VH-VL or VL-VL dimers.

Alternatively, the antigen-binding fragment of an antibody can contain a monomeric VH or VL domain.

In certain embodiments, an antigen-binding fragment of an antibody can contain at least one variable domain covalently linked to at least one constant domain. Non-limiting, exemplary configurations of variable and constant domains that can be found within an antigen-binding fragment of an antibody of the present description include: (i) VH-CH1; (ii) VH-CH2; (iii) VH-CH3; (iv) VH-CH1-CH2; (V) VH-CH1-CH2—CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed herein, the variable and constant domains can be either directly linked to one another or can be linked by a full or partial hinge or linker region. A hinge region can consist of at least 2 (e.g., 5, 10, 15, 20, 40, 60, or more) amino acids which result in a flexible or semi-flexible linkage between adjacent variable and/or constant domains in a single polypeptide molecule.

Moreover, an antigen-binding fragment of an antibody of the present description can comprise a homo-dimer or hetero-dimer (or other multimer) of any of the variable and constant domain configurations listed herein in non-covalent association with one another and/or with one or more monomeric VH or VL domain (e.g., by disulfide bond(s)).

As with full antibody molecules, antigen-binding fragments can be monospecific or multispecific (e.g., bispecific).

A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, can be adapted for use in the context of an antigen-binding fragment of an antibody of the present description using routine techniques available in the art.

In certain embodiments, the antibodies of the description, e.g., anti-GLP1R antibodies, are human antibodies. The term "human antibody," as used herein, is intended to include antibodies having variable and constant regions derived from human germline immunoglobulin sequences. The human antibodies of the description can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies can, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (See, e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) *Molecular Immunology* 30: 105) to levels typically observed using a human IgG1 hinge. The instant description encompasses antibodies having one or more mutations in the hinge, CH2 or CH3 region which can be desirable, for example, in production, to improve the yield of the desired antibody form.

The antibodies of the description can be isolated or purified antibodies. An "isolated antibody" or "purified antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present description. For example, an antibody that has been purified from at least one component of a reaction or reaction sequence, is a "purified antibody" or results from purifying the antibody. An isolated antibody also includes an antibody in situ within a recombinant cell. Isolated antibodies are antibodies that have been subjected to at least one purification or isolation step. According to certain embodiments, an isolated antibody or purified antibody can be substantially free of other cellular material and/or chemicals.

The antibodies disclosed herein can comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present description includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with given heavy and light chain variable region sequences, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present description can contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, improved drug-to-antibody ratio (DAR) for antibody-drug conjugates, etc. Antibodies and antigen-binding fragments obtained in this general manner are encompassed within the present description.

The term "aglycosylated antibody" refers to an antibody that does not comprise a glycosylation sequence that might interfere with a transglutamination reaction, for instance an antibody that does not have saccharide group at N297 on one or more heavy chains. In particular embodiments, an antibody heavy chain has an N297 mutation. In other words, the antibody is mutated to no longer have an asparagine residue at position 297 according to the EU numbering system as disclosed by Kabat et al. In particular embodiments, an antibody heavy chain has an N297Q or an N297D mutation. Such an antibody can be prepared by site-directed mutagenesis to remove or disable a glycosylation sequence or by site-directed mutagenesis to insert a glutamine residue at site apart from any interfering glycosylation site or any other interfering structure. Such an antibody also can be isolated from natural or artificial sources. Aglycosylated antibodies also include antibodies comprising a T299 or S298P or other mutations, or combinations of mutations that result in a lack of glycosylation.

The term "deglycosylated antibody" refers to an antibody in which a saccharide group at is removed to facilitate transglutaminase-mediated conjugation. Saccharides include, but are not limited to, N-linked oligosaccharides. In some embodiments, deglycosylation is performed at residue N297. In some embodiments, removal of saccharide groups is accomplished enzymatically, included but not limited to via PNGase.

The term "epitope" refers to an antigenic determinant that interacts with a specific antigen binding site in the variable region of an antibody molecule known as a paratope. A single antigen can have more than one epitope. Thus, different antibodies can bind to different areas on an antigen and can have different biological effects. Epitopes can be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope can include moieties of saccharides, phosphoryl groups, or sulfonyl groups on the antigen.

The terms "conjugated protein" or "conjugated antibody" as used herein refers to a protein or an antibody covalently linked to one or more chemical moieties. The chemical moiety can include an amine compound of the present disclosure. Linkers (L) and payloads (P) suitable for use with the present disclosure are described in detail herein. In particular embodiments, a conjugated antibody comprising a therapeutic moiety is an antibody-drug conjugate (ADC), also referred to as an antibody-payload conjugate, or an antibody-linker-payload conjugate.

The term "Drug-to-Antibody Ratio" or (DAR) is the average number of therapeutic moieties, e.g., drugs, conjugated to a binding agent of the present disclosure.

The term "Linker Antibody Ratio" or (LAR), also denoted as the lower case, in some embodiments, is the average number of reactive primary amine compounds conjugated to a binding agent of the present disclosure. Such binding agents, e.g., antibodies, can be conjugated with primary amine compounds comprising, e.g., a suitable azide or alkyne. The resulting binding agent, which is functionalized with an azide or an alkyne can subsequently react with a therapeutic moiety comprising the corresponding azide or alkyne via the 1,3-cycloaddition reaction.

The phrase "pharmaceutically acceptable amount" refers to an amount effective or sufficient in treating, reducing, alleviating, or modulating the effects or symptoms of at least one health problem in a subject in need thereof. For example, a pharmaceutically acceptable amount of an antibody or antibody-drug conjugate is an amount effective for modulating a biological target using the antibody or antibody-drug-conjugates provided herein. Suitable pharmaceutically acceptable amounts include, but are not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% of an antibody or antibody-drug-conjugate provided herein.

The phrase "reaction pH" refers to the pH of a reaction after all reaction components or reactants have been added.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule can, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity can be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In some embodiments, conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) *Science* 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another particular algorithm when comparing a sequence of the description to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) *Nucleic Acids Res.* 25:3389-402.

Protein-Drug Conjugate Compounds

According to the foregoing objective and others, the present disclosure provides protein-drug conjugate compounds, e.g., antibody-drug conjugate compounds, and precursors and intermediates thereof, pharmaceutical compositions, and methods for treating certain diseases in a subject in need of such treatment. According to the disclosure, the protein-drug conjugate compounds provided herein comprise a binding agent conjugated with a therapeutic moiety, e.g., GLP1 peptidomimetics, as described herein.

In one aspect, the present disclosure provides compounds comprising a binding agent according to the present disclosure, (e.g., an antibody or a fragment thereof), conjugated to one or more GLP1 peptidomimetics via non-cleavable linker. Illustrative non-limiting examples include Formula (I) described herein. In specific embodiments of a protein-drug conjugate according to the disclosure, wherein the binding agent is an antibody, (e.g., a monoclonal antibody), the term "antibody drug conjugate" or ADC is optionally used.

In various embodiments, antibody drug conjugate or ADC of the disclosure is an antibody-tethered drug conjugate or ATDC. An ATDC is an antibody-drug conjugate wherein the drug is tethered to the antibody by a non-cleavable linker. In some embodiments, the non-cleavable linker in an ATDC of the present disclosure is stable after the ATDC is administered into the body, e.g., a human body. For example, the non-cleavable linker can be stable in plasma, e.g., in human plasma, stable upon binding cell surface, or stable upon antibody binding its target antigen and/or GLP1 peptidomimetic binding GLP1R. In some embodiments, the non-cleavable linker is more stable in vivo than either the payload or the antibody under the same physiological conditions. In some embodiments, an ATDC of the present disclosure may be degraded in the lysosome to release the payload, the linker-payload, and/or its ATDC metabolites/catabolites, which in certain embodiments are effective for GLP1R activation either locally or systematically.

In some embodiments, the ATDC is stable in plasma and degrades in the lysosome. In some embodiments, the ATDC is stable in plasma and does not degrade in the lysosome.

In one aspect, provided herein is a compound having a structure of Formula (A):

BA-(L-P)$_m$     (A), wherein:

BA is an antibody or an antigen-binding fragment thereof;

L is a non-cleavable linker;

P is a payload having the structure selected from the group consisting of:

(P-IA (SEQ ID NO: 27))

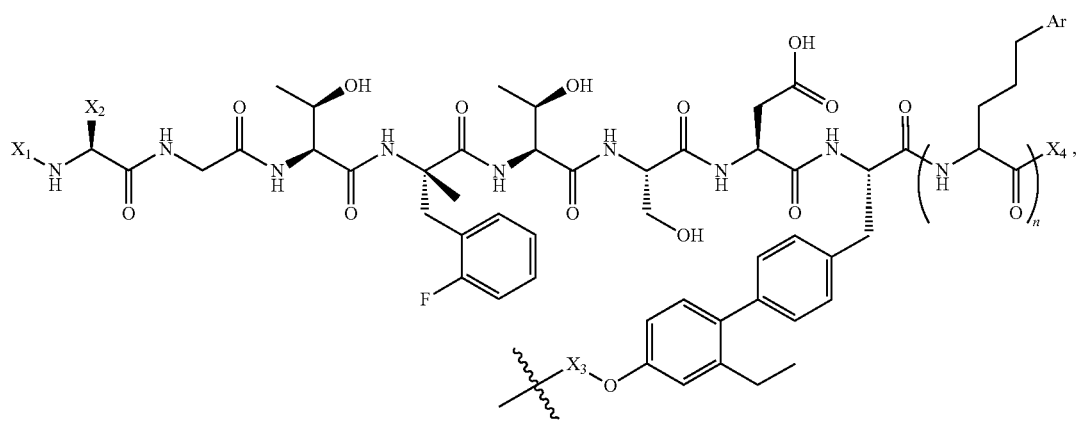

(P-IIA (SEQ ID NO: 28))
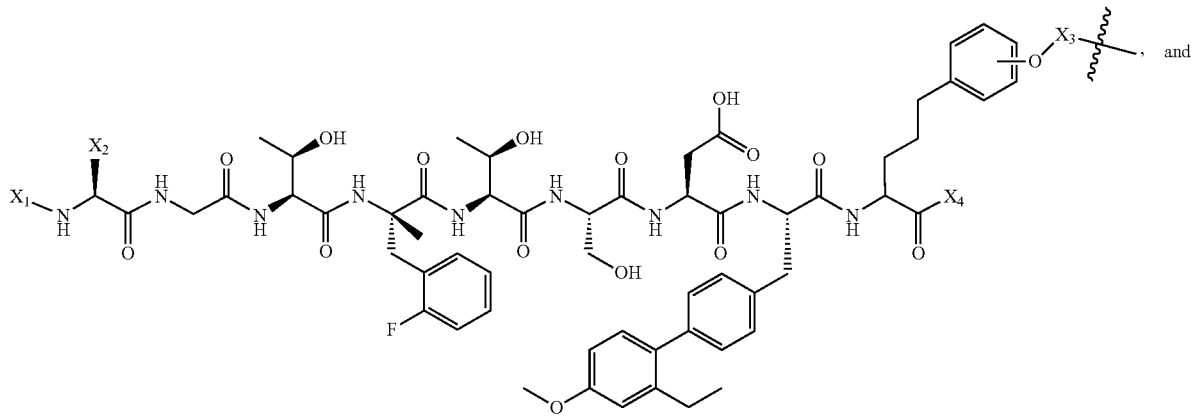
(P-IIIA (SEQ ID NO: 29))
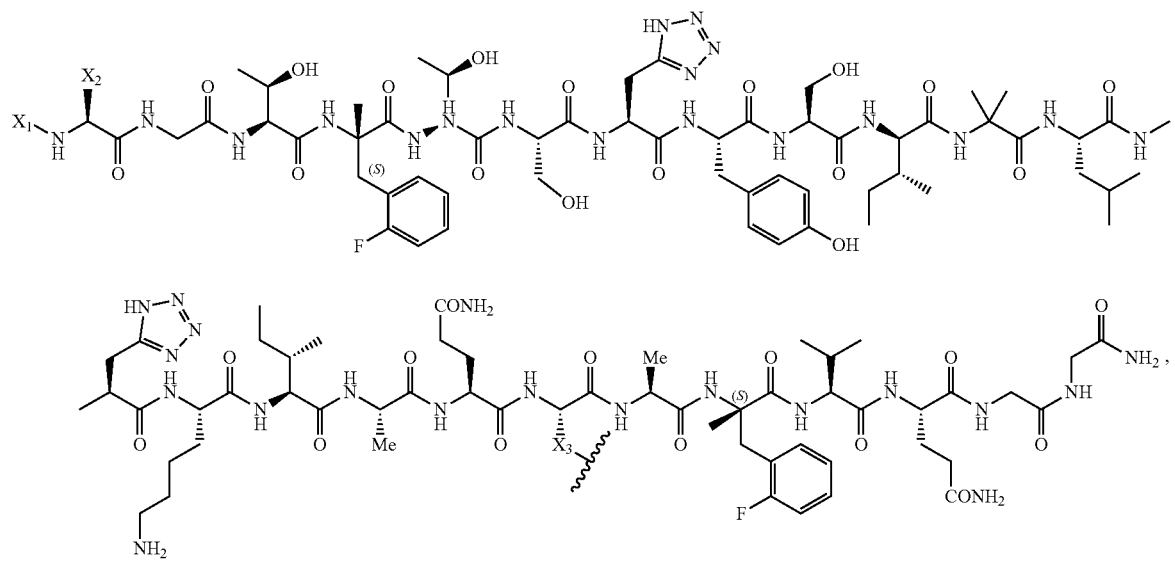
wherein
is the point of attachment of the payload to L;
$X_1$ is selected from H;
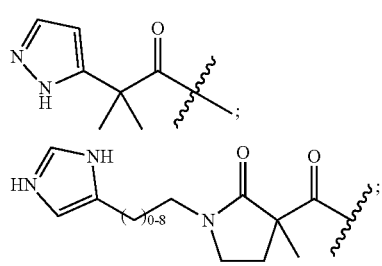
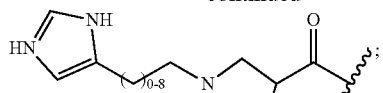
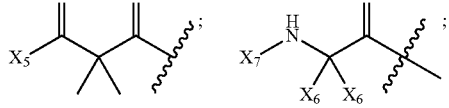
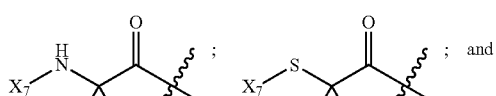
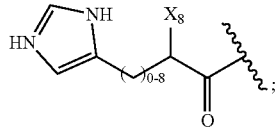

$X_2$ is selected from

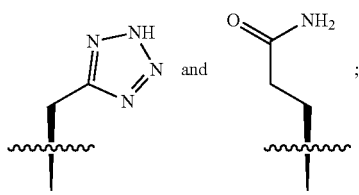

$X_3$ is selected from a bond, —(CH$_2$)$_{2-6}$—NH—, —(CH$_2$)$_{2-6}$—Tr-, and —(CH$_2$)$_{2-6}$—Tr-(CH$_2$)$_{1-6}$—NH, where Tr is a triazole moiety;
n is 0 or 1;
$X_4$ is selected from —NH$_2$, —OH and —N(H)(phenyl);
$X_5$ is selected from —OH, —NH$_2$, —NH—OH, and

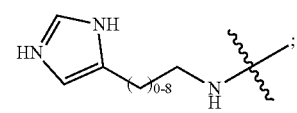

$X_6$ is independently at each occurrence selected from H, —OH, —CH$_3$, and —CH$_2$OH;
$X_7$ is selected from H,

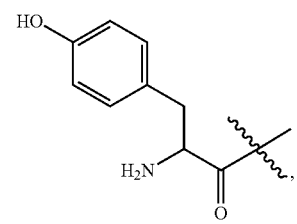

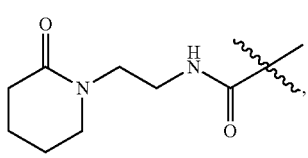

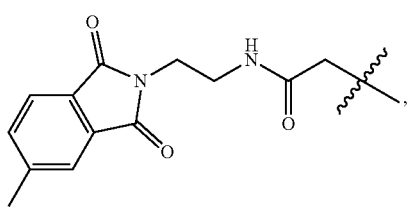

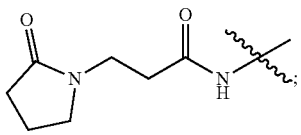

$X_8$ is selected from H, —OH, —NH$_2$, and

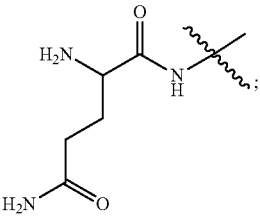 [SMILES: *NC(=O)C(N)CCC(N)=O]

Ar is selected from

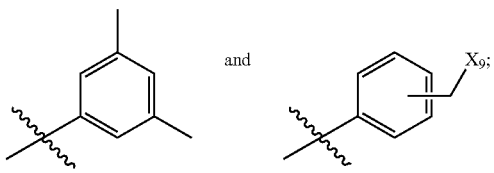

$X_9$ is selected from —NH$_2$,

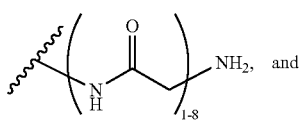

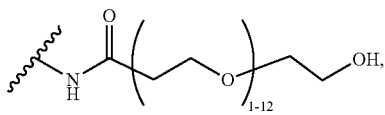

and
m is an integer from 1 to 4
or a pharmaceutically acceptable salt thereof.

In one embodiment, m is 1. In one embodiment, m is an integer from 2 to 4. In one embodiment, m is 2.

In one aspect, the present disclosure provides a compound having a structure of Formula (I):

$$BA-L-P \qquad (I),$$

wherein:
BA is an antibody or an antigen-binding fragment thereof;
L is a non-cleavable linker;

P is a payload having the structure selected from the group consisting of:
(P-I (SEQ ID NO: 30))
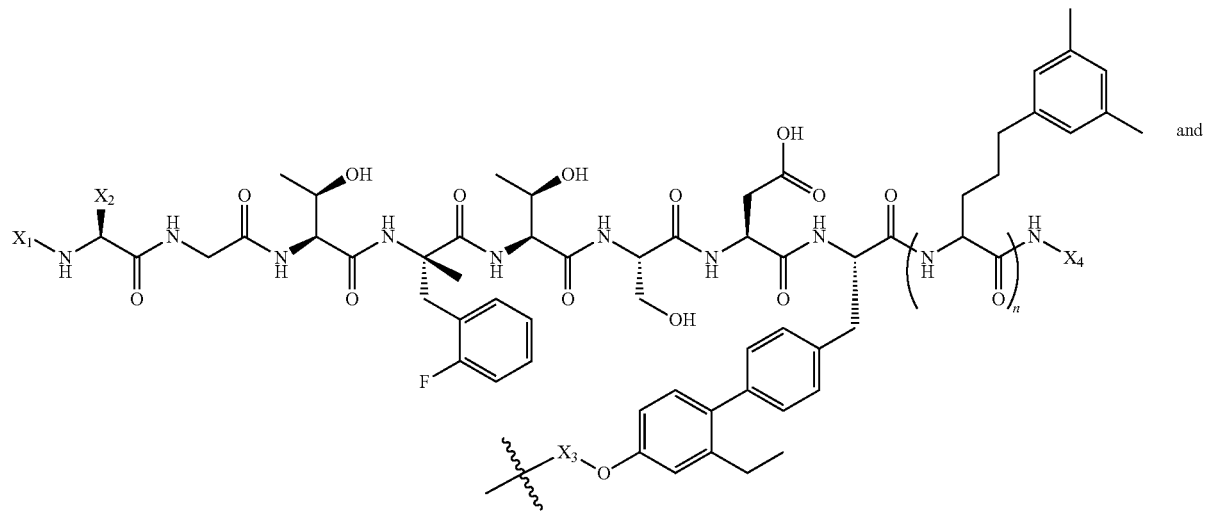
(P-II (SEQ ID NO: 28))
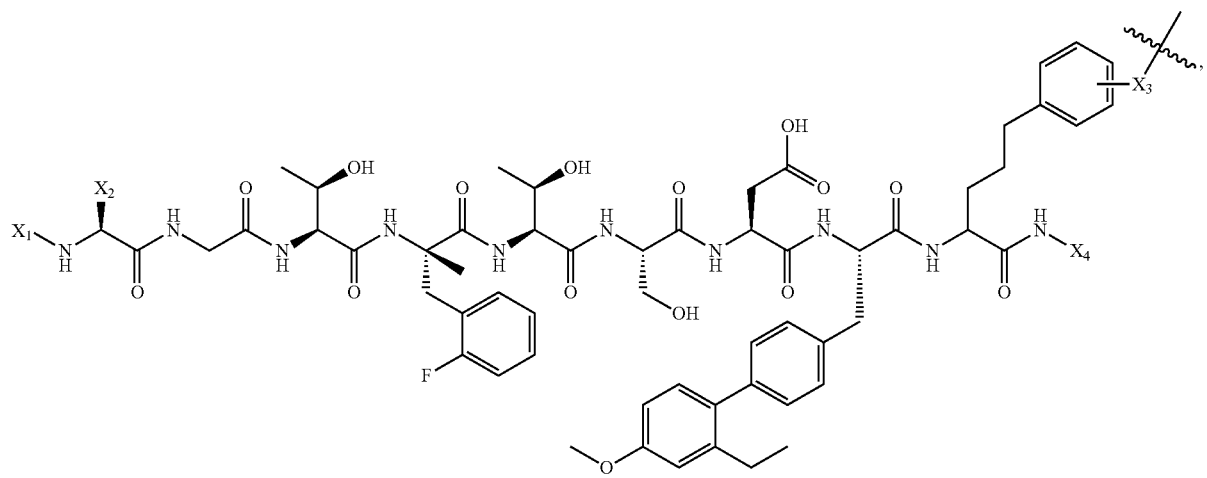
wherein
is the point of attachment of the payload to L;
X₁ is selected from H;
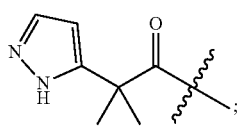
-continued
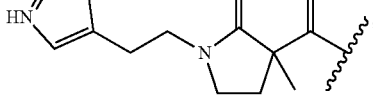

$X_2$ is selected from

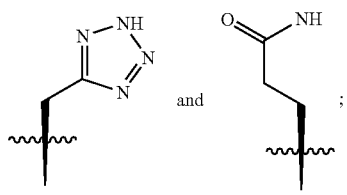

and ;

$X_3$ is selected from —$(CH_2)_{2-6}$—NH— and —$(CH_2)_{2-6}$—Tr-, where Tr is a triazole moiety;
n is 0 or 1;
$X_4$ is selected from H and phenyl;
$X_5$ is selected from —OH, —$NH_2$, —NH—OH, and

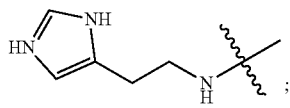 [SMILES: *NCCc1cnc[nH]1]

$X_6$ is independently at each occurrence selected from H, —OH, —$CH_3$, and —$CH_2OH$;
$X_7$ is selected from H,

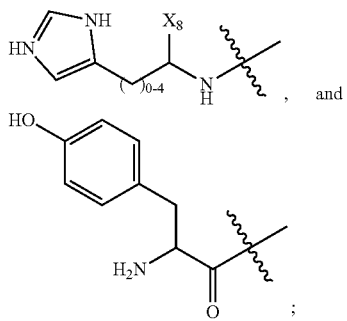

$X_3$ is selected from H, —OH, —$NH_2$, and

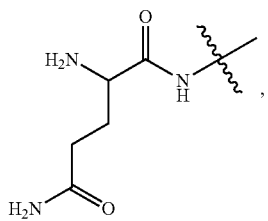

or a pharmaceutically acceptable salt thereof.

Linker L

In one embodiment, the linker L is a non-cleavable linker, i.e., a linker which is stable and provides a covalent connection between the antibody and the drug, e.g., between a GLP1R-targeting antibody and a GLP1 peptidomimetic payload P according to the present disclosure. In some embodiments, the non-cleavable linker L of the present disclosure is stable after the ATDC is administered into the body, e.g., a human body. For example, the linker L can be stable in plasma, e.g., in human plasma, stable upon binding cell surface, or stable upon antibody binding its target antigen and/or GLP1 peptidomimetic binding GLP1R. In some embodiments, the linker L is more stable in vivo than either the payload or the antibody under the same physiological conditions.

In one embodiment, the linker L has the structure of formula (L'):

wherein La is a first linker covalently attached to the antibody or an antigen-binding fragment thereof;
Y is a group comprising a triazole, a Diels-Alder adduct, or a thiol-maleimide adduct, and
Lp is absent or a second linker covalently attached to the payload P according to the present disclosure, wherein when Lp is absent Y is also absent.

In one embodiment, Y is a group comprising a triazole.

In another embodiment, Y is a group comprising a Diels-Alder adduct.

In one embodiment, the linker L has the structure of formula (L'):

wherein La is a first linker covalently attached to the antibody or an antigen-binding fragment thereof;
Y is a group comprising a triazole, and
Lp is absent or a second linker covalently attached to the payload P according to the present disclosure.

In one embodiment, La comprises $C_{1-6}$ alkyl, phenyl, —NH—, —C(O)—, —$(CH_2)_u$—NH—C(O)—, —$(CH_2)_u$—C(O)—NH—, —$(CH_2—CH_2—O)_v$—, —$(CH_2)_u$—(O—$CH_2—CH_2)_v$—C(O)—NH—, a peptide unit comprising from 2 to 4 amino acids, or combinations thereof, each of which may be optionally substituted with one or more of —S—, —$S(O_2)$—, —C(O)—, —$C(O_2)$—; and $CO_2H$, wherein subscripts u and v are independently an integer from 1 to 8.

In one embodiment, La is selected from the group consisting of:

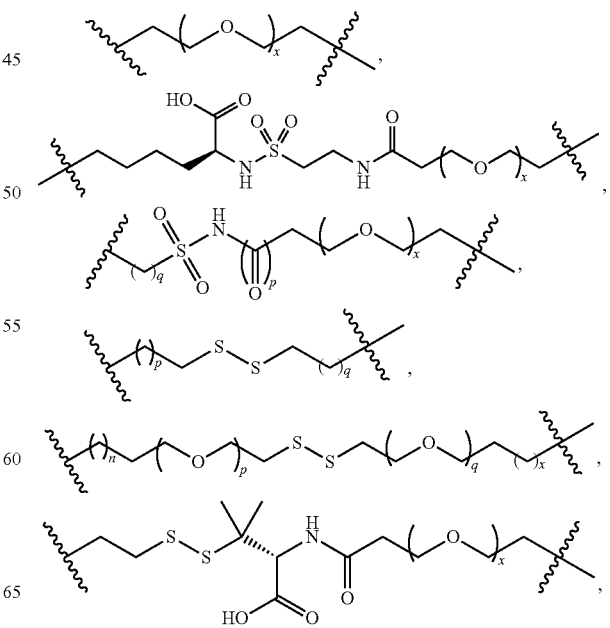

205

-continued

, and

206

-continued

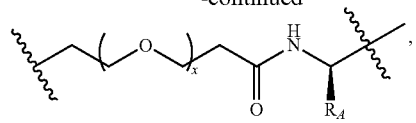, wherein $R_A$ is a group comprising an alkyne, an azide, a tetrazine, a trans-cyclooctene, a maleimide, an amine, a ketone, an aldehyde, a carboxylic acid, an ester, a thiol, a sulfonic acid, a tosylate, a halide, a silane, a cyano group, a carbohydrate group, a biotin group, a lipid residue and wherein subscripts x, n, p and q are independently an integer from 0 to 12, and combinations thereof.

In one embodiment, —La— is selected from the group consisting of:

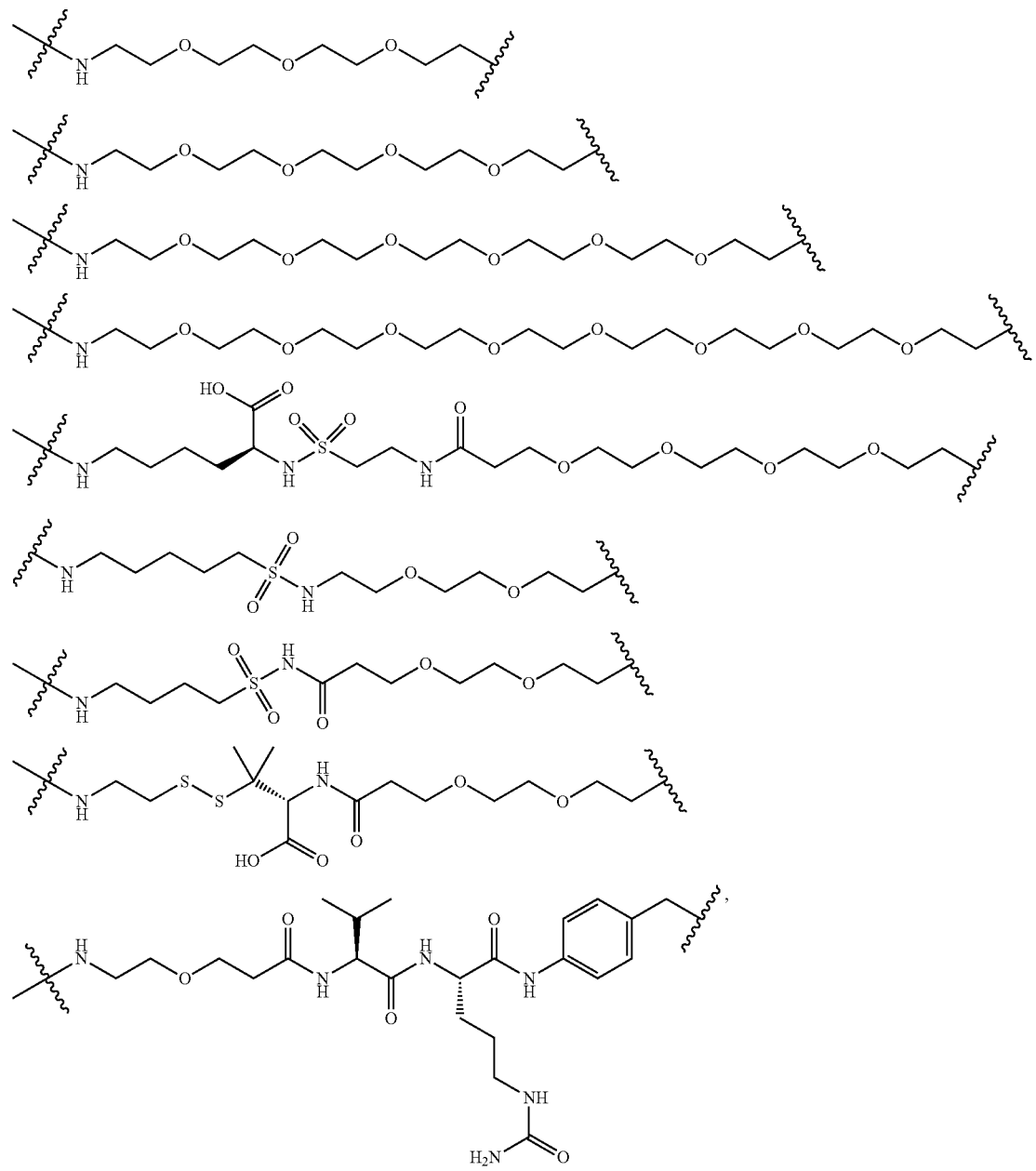

where the
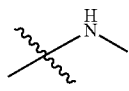
is the amino point of attachment to a residue (e.g., a glutamine residue) of the antibody and/or the antigen-containing fragment thereof.
In one embodiment, —La— is
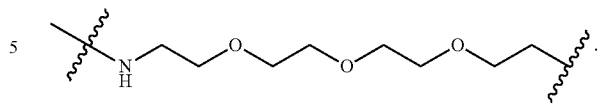
In another embodiment, —La— is selected from the group consisting of:
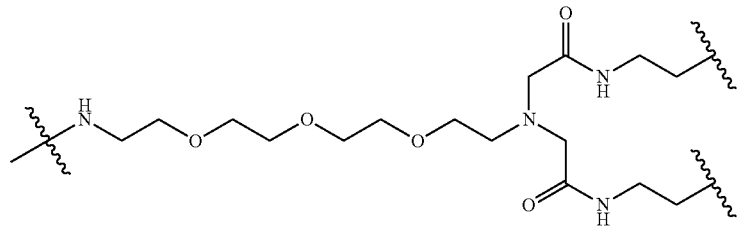
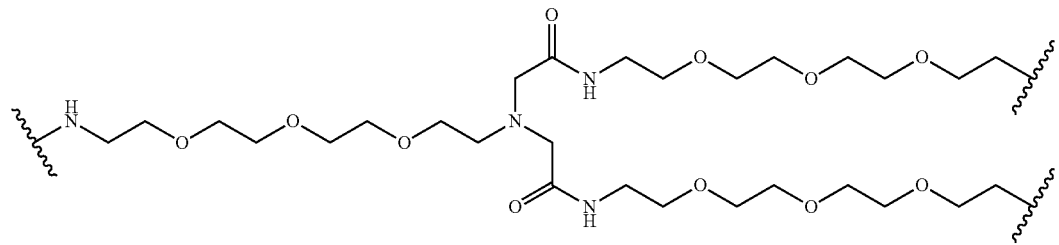
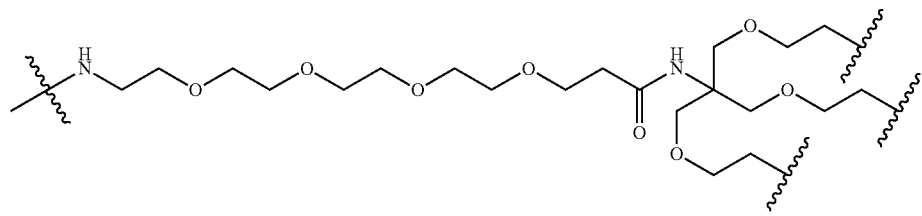
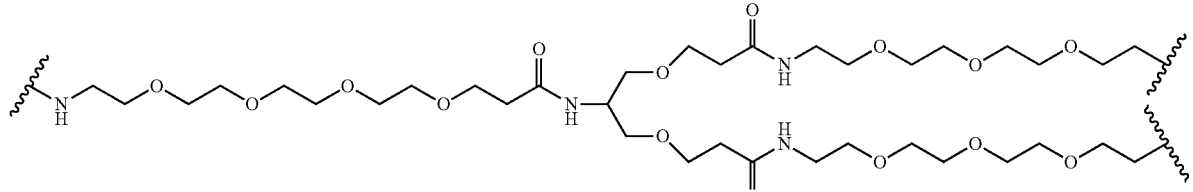
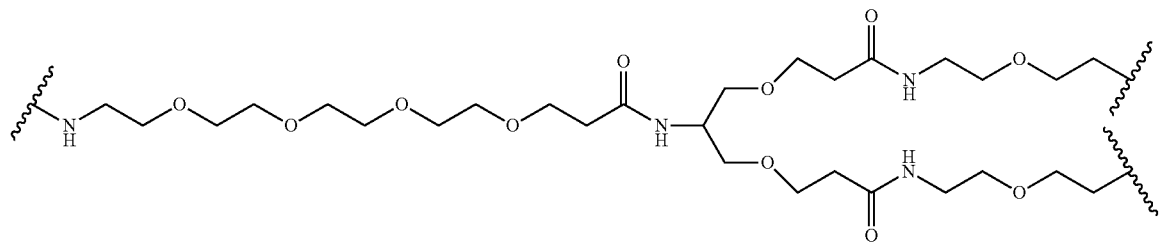

209
210
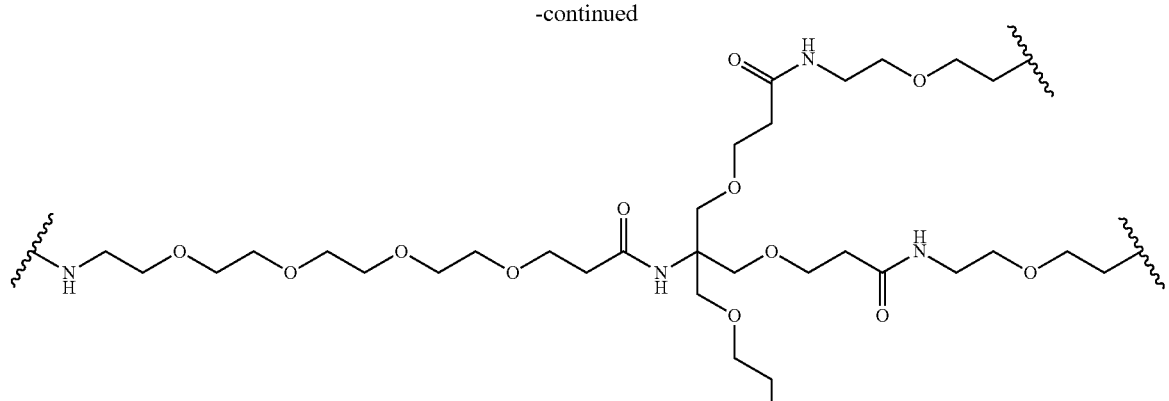
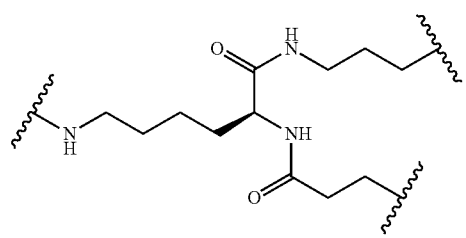
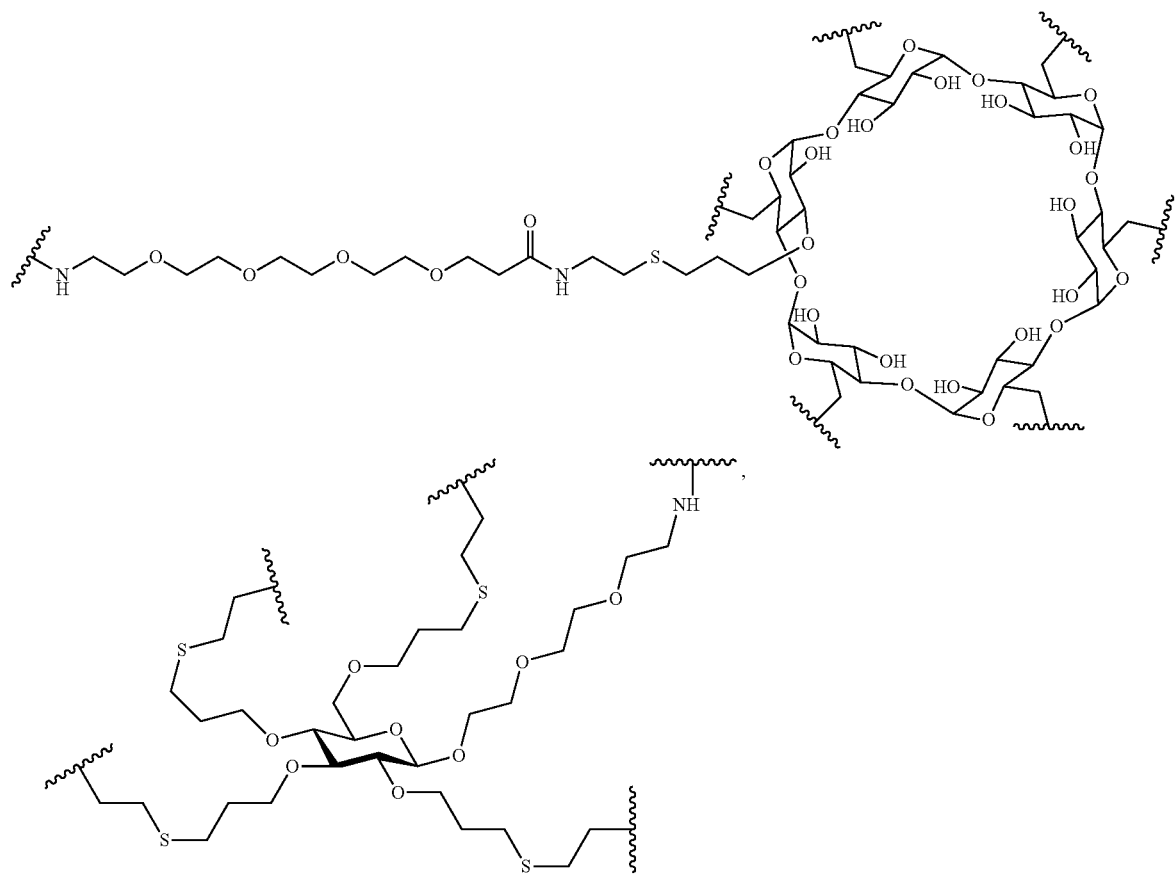

where the

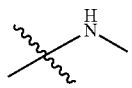

is the amino point of attachment to a residue (e.g., a glutamine residue) of the antibody and/or the antigen-containing fragment thereof.

In some embodiments, La comprises a polyethylene glycol (PEG) segment having 1 to 36 —$CH_2CH_2O$— (EG) units. In some embodiments, the PEG segment comprises 4 EG units, or 8 EG units, or 12 EG units, or 24 EG units. In some embodiments, the PEG segment comprises 8 EG units. In some embodiments, La has a structure selected from the group consisting of

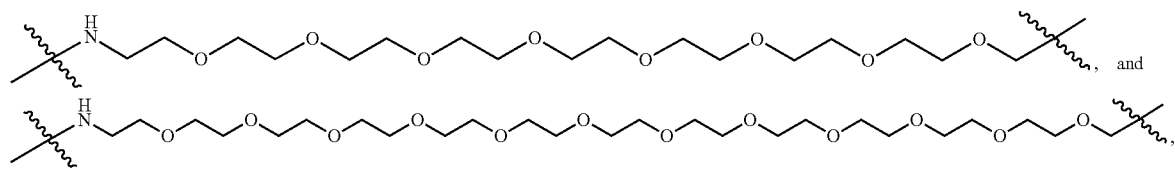

In some embodiments, La comprises one or more amino acids selected from glycine, threonine, serine, glutamine, glutamic acid, alanine, valine, leucine, and proline and combinations thereof. In some embodiments, La comprises 1 to 10 glycines and 1 to 6 serines. In some embodiments, La comprises 4 glycines and 1 serine. In some embodiments, La is selected from the group consisting of Gly-Gly-Gly-Gly-Ser ($G_4S$) (SEQ ID NO: 1), Ser-Gly-Gly-Gly-Gly ($SG_4$) (SEQ ID NO: 2), Gly-Gly-Ser-Gly-Gly-Ser-Gly-Gly ($G_2S$-$G_2S$-$G_2$) (SEQ ID NO: 25), and Gly-Gly-Gly-Gly-Ser-Gly-Gly-Gly-Gly ($G_4S$-$G_4$) (SEQ ID NO: 3).

In some embodiments, La comprises a combination of a PEG segment having 1 to 36 EG units and one or more amino acids selected from glycine, threonine, serine, glutamine, glutamic acid, alanine, valine, leucine, and proline and combinations thereof. In some embodiments, La is selected from the group consisting of (SEQ ID NOS 37-38, respectively, in order of appearance):

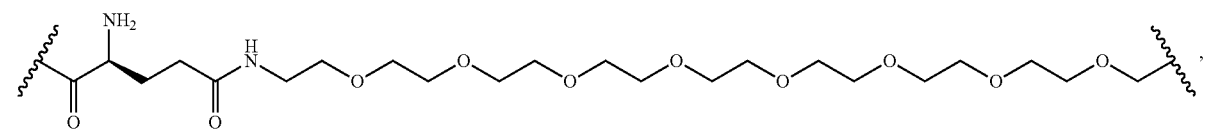

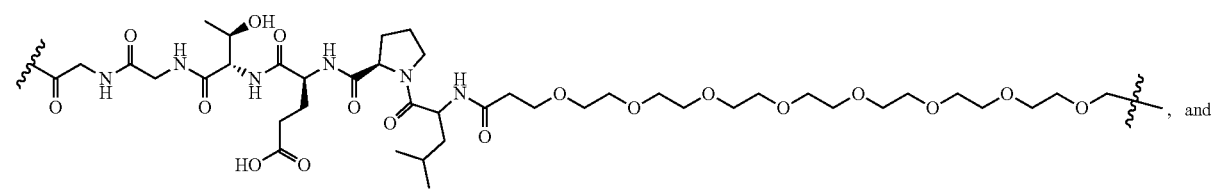

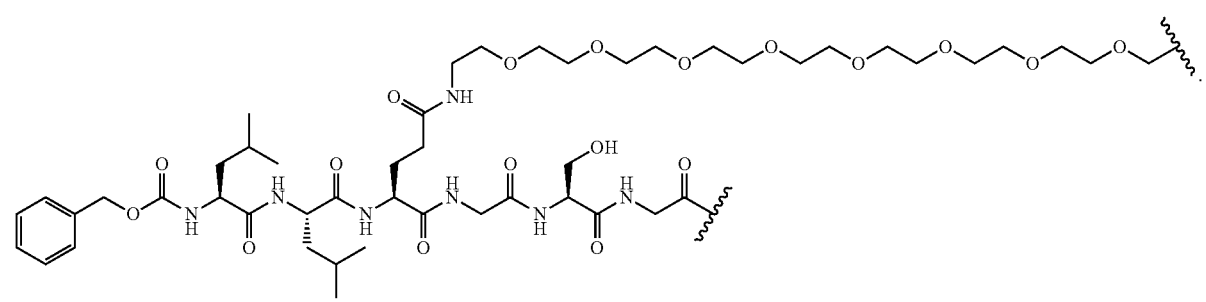

In some embodiments, La comprises a —(CH₂)₂₋₂₄— chain. In some embodiments, In some embodiments, La comprises a combination of a —(CH₂)₂₋₂₄— chain, a PEG segment having 1 to 36 EG units and one or more amino acids selected from glycine, threonine, serine, glutamine, glutamic acid, alanine, valine, leucine, and proline and combinations thereof. La is selected from the group consisting of (SEQ ID NOS 127-128, respectively, in order of appearance):

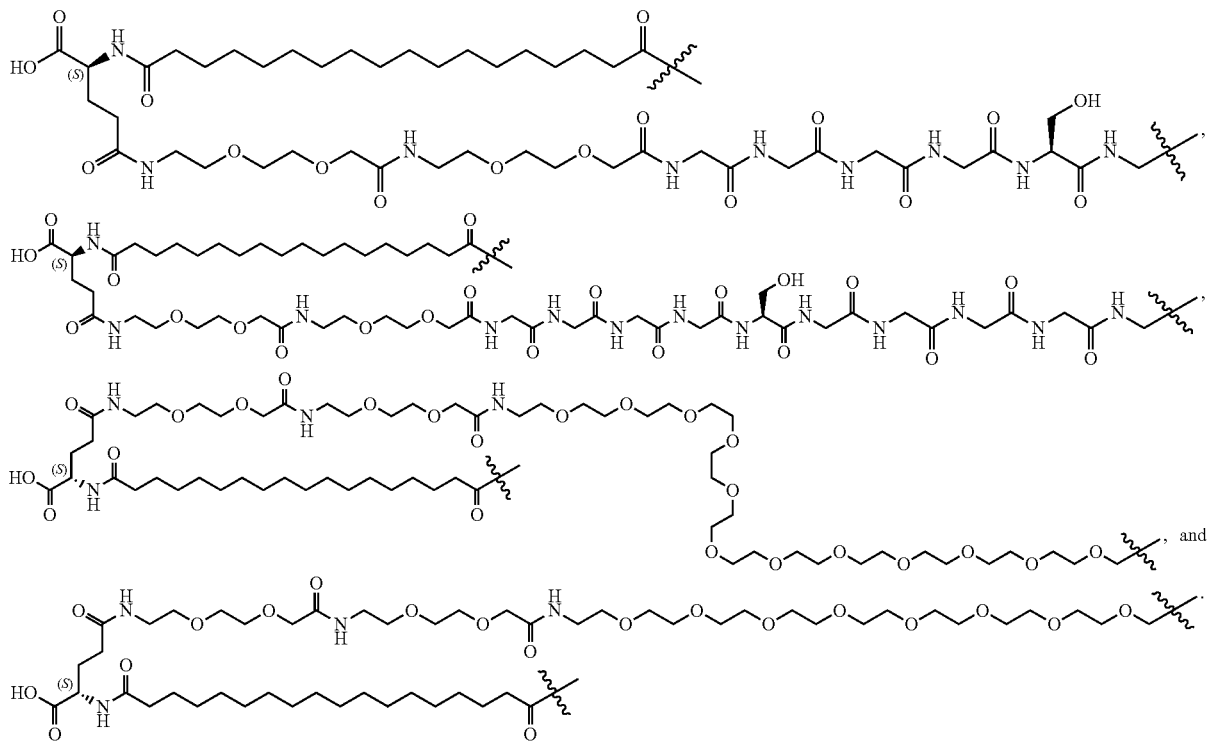

In one embodiment, Y has a structure selected from the group consisting of:

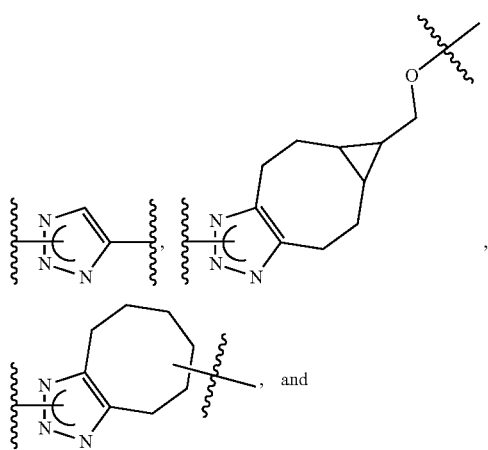

-continued

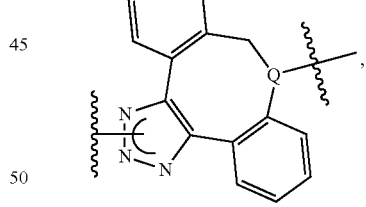

wherein Q is C or N.

In one embodiment, the linker L, or the first linker La, or the second linker Lp, comprises a polyethylene glycol (PEG) segment having 1 to 36 —CH₂CH₂O— (EG) units.

In one embodiment, the PEG segment comprises between 2 and 30 EG units, or between 4 and 24 EG units. In one embodiment, the PEG segment comprises 2 EG units, or 4 EG units, or 6 EG units, or 8 EG units, or 10 EG units, or 12 EG units, or 14 EG units, or 16 EG units, or 18 EG units, or 20 EG units, or 22 EG units, or 24 EG units.

In one embodiment, the PEG segment comprises 4 EG units. In one embodiment, the PEG segment comprises 8 EG units. In one embodiment, the PEG segment comprises 12 EG units. In one embodiment, the PEG segment comprises 24 EG units.

In one embodiment, the PEG segment comprises 4 to 8 EG units. In one embodiment, the PEG segment comprises 4 EG units or 8 EG units.

In one embodiment, La comprises a PEG segment having 3 EG units.

In one embodiment, Lp comprises a PEG segment having 4 EG units. In one embodiment, Lp comprises a PEG segment having 8 EG units.

In one embodiments, the Y-Lp has a structure selected from the group consisting of:

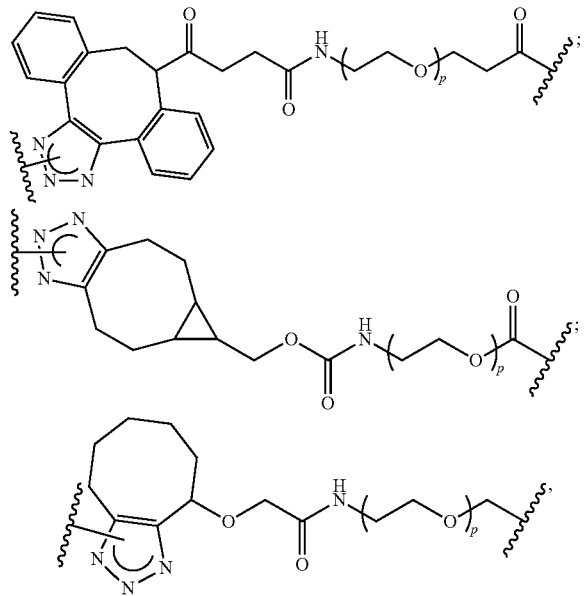

wherein p is an integer from 1 to 36.

In one embodiment, the Y-Lp has a structure selected from the group consisting of:

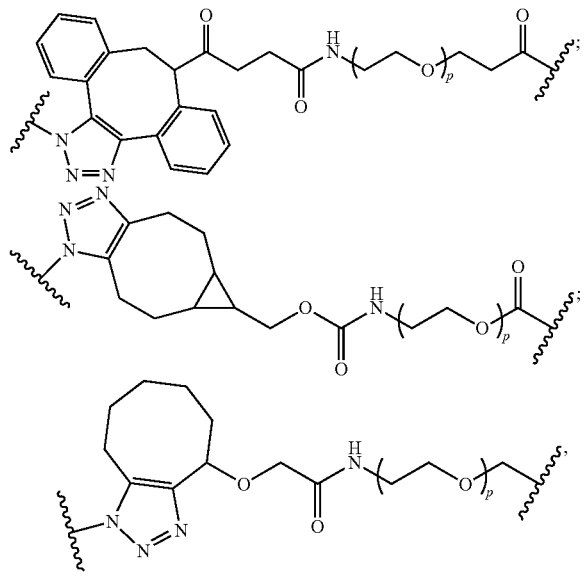

or a triazole regioisomer thereof, wherein p is an integer from 1 to 36.

In another embodiment, the linker L or the first linker La, or the second linker Lp, comprises one or more amino acids selected from glycine, serine, glutamic acid, alanine, valine, and proline and combinations thereof.

In one embodiment, the linker L or the first linker La, or the second linker Lp, comprises from 1 to 10 glycines, or 1 glycine, or 2 glycines, or 3 glycines, or 4 glycines, or 5 glycines, or 6 glycines, or 7 glycines, or 8 glycines, or 9 glycines, or 10 glycines.

In one embodiment, the linker L or the first linker La, or the second linker Lp, comprises from 1 to 6 serines, or 1 serine, or 2 serines, or 3 serines, or 4 serines, or 5 serines, or 6 serines.

In one embodiment, the linker L or the first linker La, or the second linker Lp, comprises 1 to 10 glycines and 1 to 6 serines.

In one embodiment, the linker L or the first linker La, or the second linker Lp, comprises 4 glycines and 1 serine.

In one embodiment, the linker L or the first linker La, or the second linker Lp, is selected from the group consisting of Gly-Gly-Gly-Gly-Ser (G4S) (SEQ ID NO: 1), Ser-Gly-Gly-Gly-Gly (SG4) (SEQ ID NO: 2), and Gly-Gly-Gly-Gly-Ser-Gly-Gly-Gly-Gly-Ser (G4S-G4S) (SEQ ID NO: 3).

In some embodiments, one or more serine residues comprise a carbohydrate group, e.g., a glucose group.

In one embodiment, the linker L or the first linker La, or the second linker Lp, comprises from 1 to 10 glutamic acids and from 1 to 10 glycines.

In some embodiments, the linker L or the first linker La, or the second linker Lp, comprises a combination of a polyethylene glycol (PEG) segment having 1 to 36 —$CH_2CH_2O$— (EG) units and one or more amino acids selected from glycine, serine, glutamic acid, alanine, valine, and proline and combinations thereof.

In one embodiment, the linker L or the first linker La, or the second linker Lp, comprises a combination of a PEG segment having 1 to 36 EG units and 1 to 10 glycines. In one embodiment, the linker L or the first linker La, or the second linker Lp, comprises a combination of a PEG segment having 1 to 36 EG units and a group selected from Gly-Gly-Gly-Gly-Ser (G4S) (SEQ ID NO: 1), Ser-Gly-Gly-Gly-Gly (SG4) (SEQ ID NO: 2), and Gly-Gly-Gly-Gly-Ser-Gly-Gly-Gly-Gly-Ser (G4S-G4S) (SEQ ID NO: 3).

In one embodiment, the linker L or the first linker La, or the second linker Lp, has a structure selected from the group consisting of:

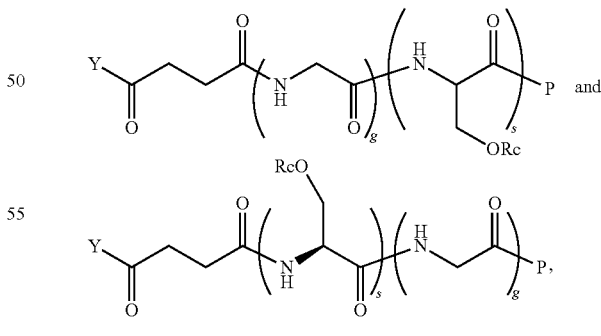

wherein Y is the group comprising a triazole, e.g., as shown above, and P is the payload, and wherein Rc is selected from hydrogen (H) and glucose, g is an integer from 1 to 10 and s is an integer from 0 to 4.

In one embodiment, the Y-Lp has a structure selected from the group consisting of (SEQ ID NOS 31-36, respectively, in order of appearance):

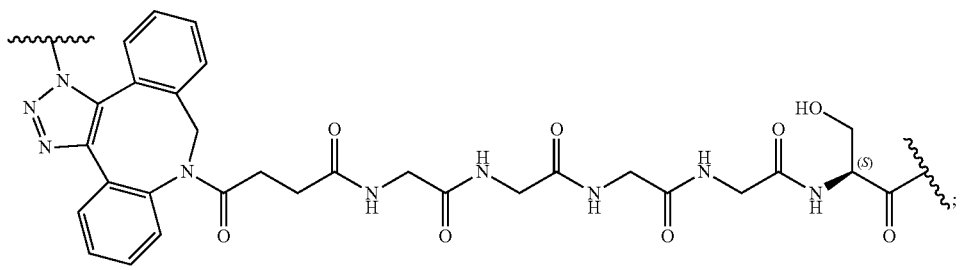
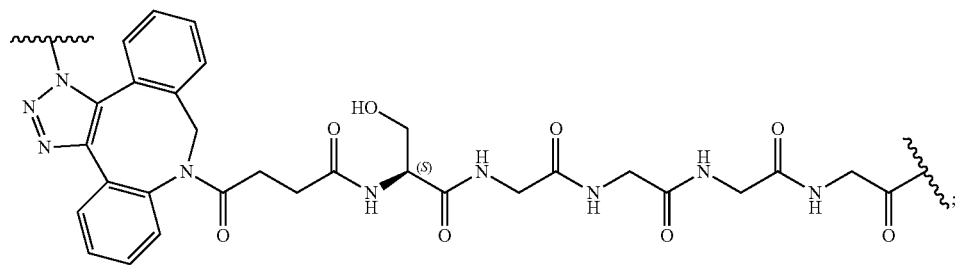
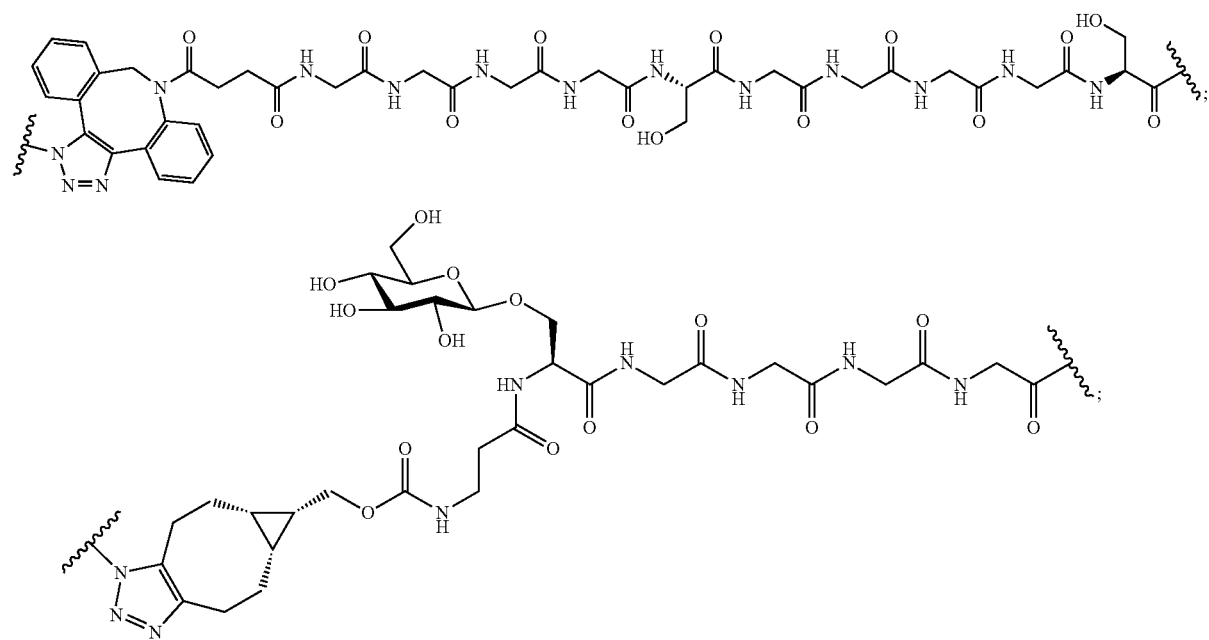
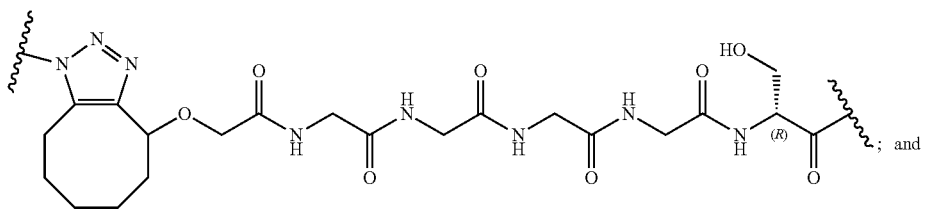

-continued

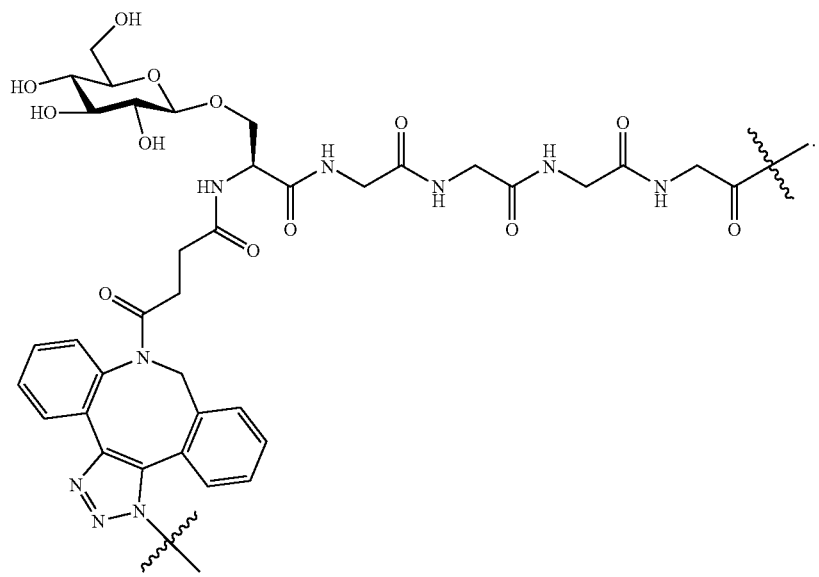

In one embodiment, the linker L comprises a cyclodextrin moiety.

In some embodiments, the linker L is attached to the antibody or an antigen-binding fragment thereof via a glutamine residue. In some embodiments, the linker L is attached to the antibody or an antigen-binding fragment thereof via a lysine residue. In some embodiments, the linker L is attached to the antibody or an antigen-binding fragment thereof via a cysteine residue.

Payloads P

In one aspect, the payloads P according to the present disclosure have a structure of Formula selected from the group consisting of Formula (P-IB), Formula (P-IIB), and Formula (P-IIIB):

(P-IB (SEQ ID NO: 83))

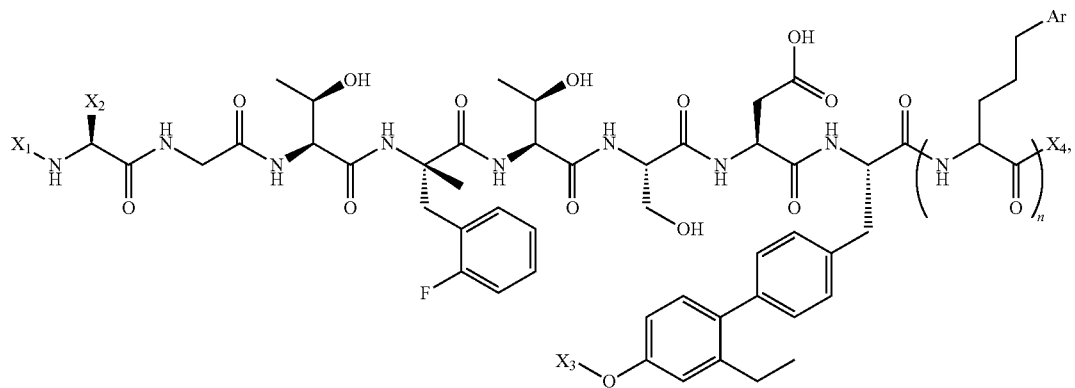

(P-IIB (SEQ ID NO: 84))
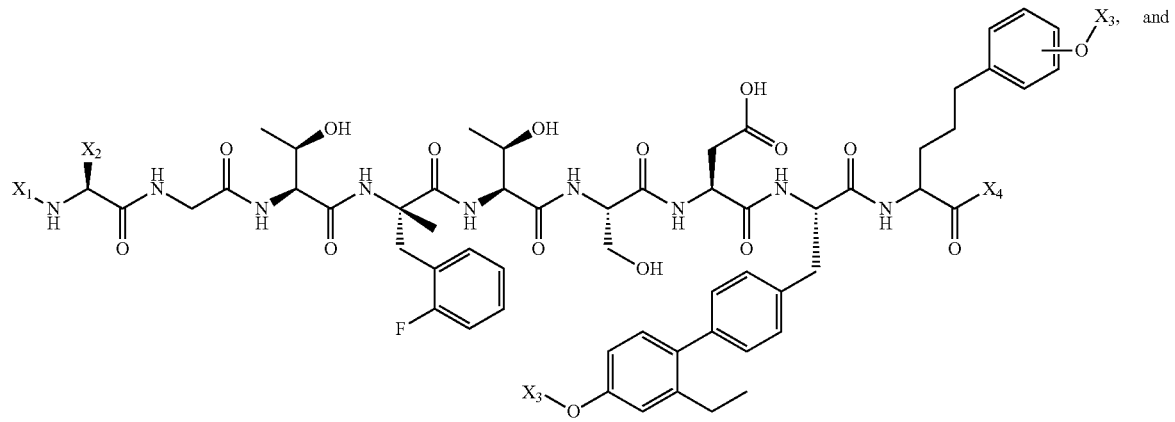
(P-IIIB (SEQ ID NO: 29))
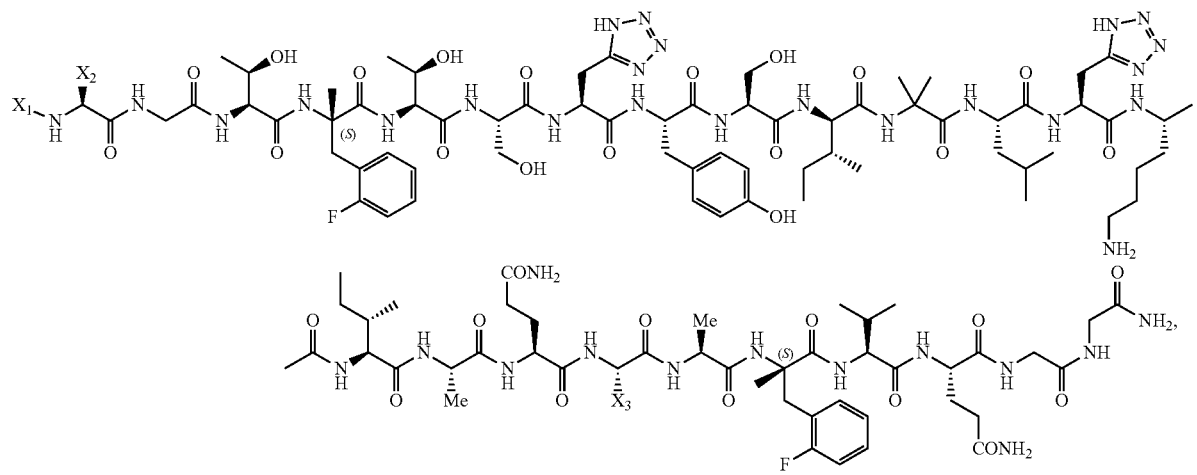
wherein:
$X_1$ is selected from H;
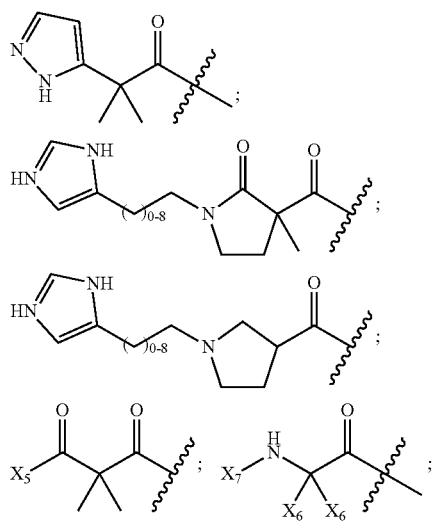
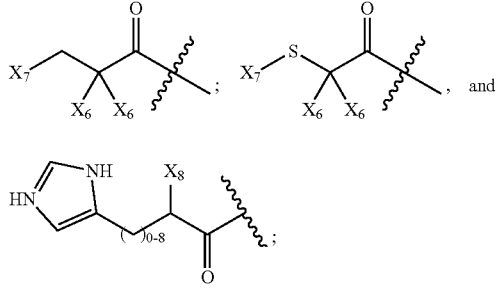
$X_2$ is selected from
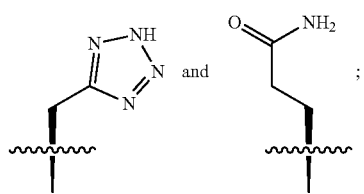

X₃ is selected from —CH₃, —(CH₂)₂₋₆—NH₂, —(CH₂)₂₋₆—N₃, and —(CH₂)₂₋₆—Tr-(CH₂)₁₋₆—NH₂, where Tr is a triazole moiety;

n is 0 or 1;

X₄ is selected from —NH₂, —OH and —N(H)(phenyl);

X₅ is selected from —OH, —NH₂, —NH—OH, and

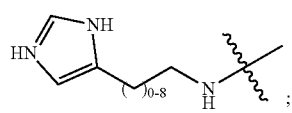

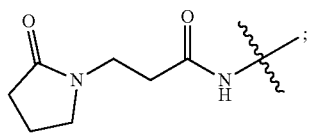

X₈ is selected from H, —OH, —NH₂, and

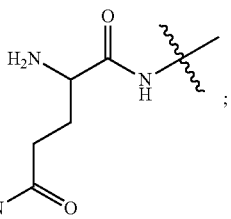

X₆ is independently at each occurrence selected from H, —OH, —CH₃, and —CH₂OH;

X₇ is selected from H,

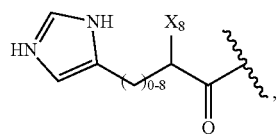

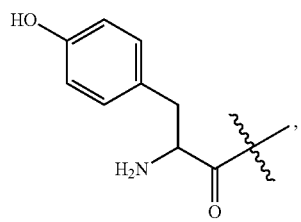

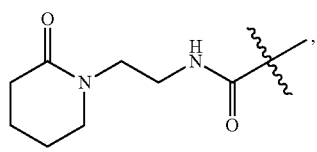

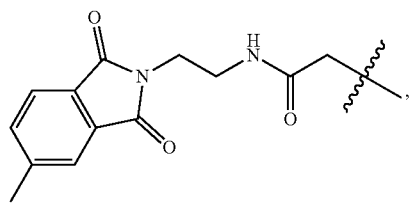

Ar is selected from

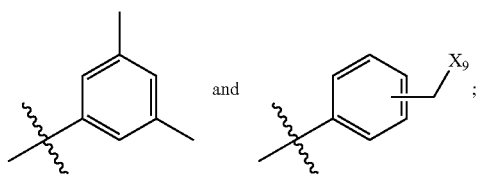

X₉ is selected from —NH₂,

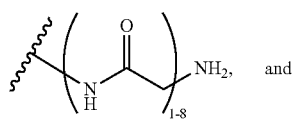

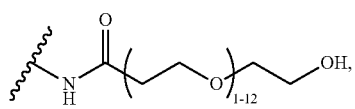

and m is an integer from 1 to 4, or a pharmaceutically acceptable salt thereof.

In one embodiment, the payloads P according to the present disclosure have a structure of Formula (II) (SEQ ID NO: 85):

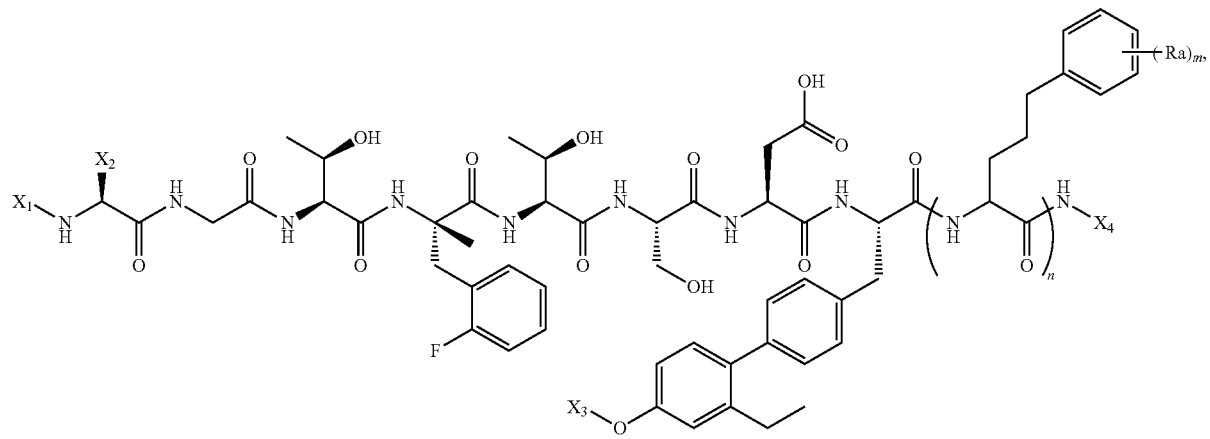

(II)

wherein:
X₁ is selected from H

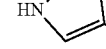

X₂ is selected from

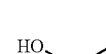

X₃ is selected from —(CH₂)₂₋₆—NH₂, —(CH₂)₂₋₆—N₃, and —CH₃, with the proviso that when X₃ is —CH₃, n is 1 and Ra in at least one occurrence is selected from —(CH₂)₂₋₆—NH₂ and —(CH₂)₂₋₆—N₃;
n is 0 or 1;
m is an integer from 0 to 3;

Ra is independently at each occurrence selected from —CH₃, —(CH₂)₂₋₆—NH₂, and —(CH₂)₂₋₆—N₃;
X₄ is selected from H and phenyl;
X₅ is selected from —OH, —NH₂, —NH—OH, and

X₆ is independently at each occurrence selected from H, —OH, —CH₃, and —CH₂OH;
X₇ is selected from H,

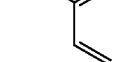

X₈ is selected from H, —OH, —NH₂, and and pharmaceutically acceptable salts thereof.

In one embodiment, the payload P has a structure selected from:
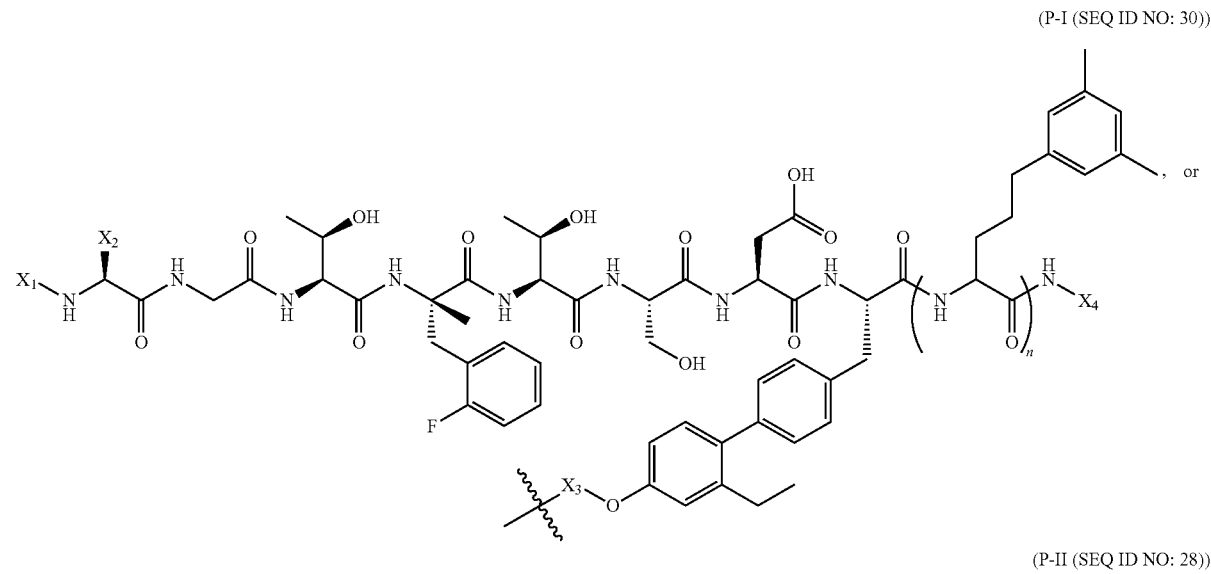
where
indicates the point of attachment to a linker.
In one embodiment, the payload has the structure of formula (P-I), shown above, wherein
$X_1$ is H; $X_2$ is
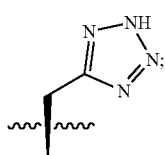
$X_3$ is selected from —$(CH_2)_{2-6}$—NH— and —$(CH_2)_{2-6}$—Tr-, where Tr is a triazole moiety; n is 1, and $X_4$ is H;
$X_1$ is
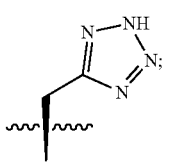
$X_2$ is
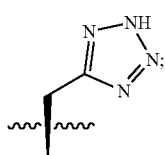

$X_3$ is —(CH$_2$)$_{2-6}$—NH—; n is 1; $X_4$ is H, and $X_5$ is selected from —OH, —NH$_2$, —NH—OH, and

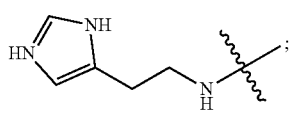 [SMILES: *NCCc1cnc[nH]1]

$X_1$ is

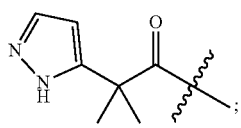

$X_2$ is

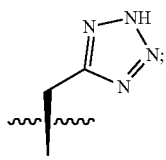

$X_3$ is —(CH$_2$)$_{2-6}$—NH—; n is 1, and $X_4$ is H;
$X_1$ is

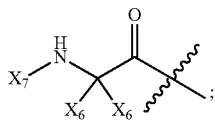

$X_2$ is

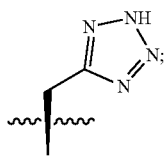

$X_3$ is —(CH$_2$)$_{2-6}$—NH—; n is 1; $X_4$ is H; $X_6$ is independently at each occurrence selected from H and —CH$_2$OH, and $X_7$ is H;
$X_1$ is

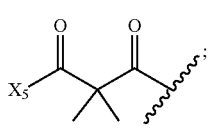

$X_2$ is

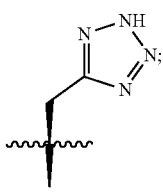

$X_3$ is —(CH$_2$)$_{2-6}$—Tr-, where Tr is a triazole moiety; n is 1; $X_4$ is H, and $X_5$ is

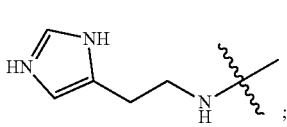 [SMILES: *NCCc1cnc[nH]1]

$X_1$ is

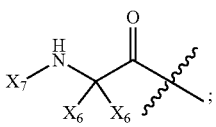

$X_2$ is

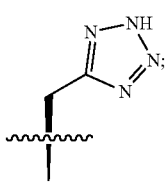

$X_3$ is —(CH$_2$)$_{2-6}$—NH—; n is 1; $X_4$ is H; $X_6$ is independently at each occurrence selected from H and —CH$_3$; $X_7$ is

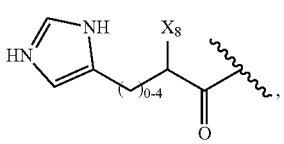

and $X_8$ is —NH$_2$;
$X_1$ is

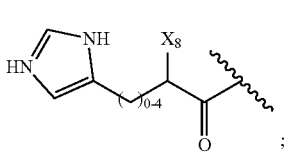

$X_2$ is
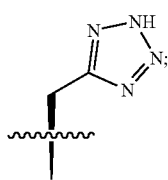
$X_3$ is —$(CH_2)_{2-6}$—NH—; n is 1; $X_4$ is H, and $X_3$ is H;
 $X_1$ is
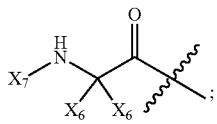
$X_2$ is
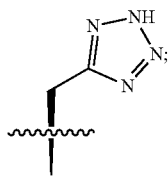
$X_3$ is —$(CH_2)_{2-6}$—NH—; n is 1; $X_4$ is H; $X_6$ is H at each occurrence; $X_7$ is
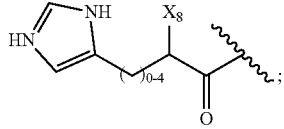
and $X_3$ is H;
 $X_1$ is
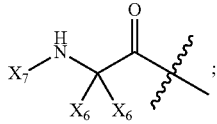
$X_2$ is
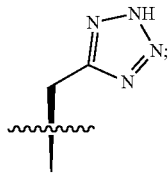
$X_3$ is —$(CH_2)_{2-6}$—NH—; n is 1; $X_4$ is H; $X_6$ is independently at each occurrence selected from H and —$CH_3$; $X_7$ is
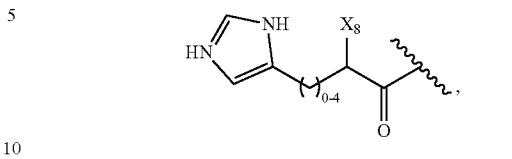
and $X_8$ is
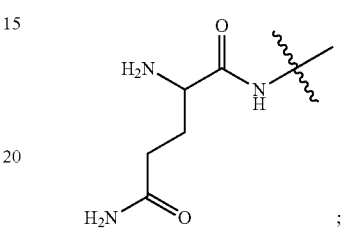
$X_1$ is
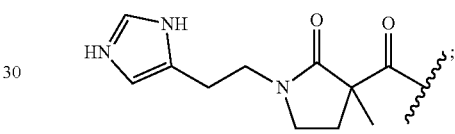
$X_2$ is
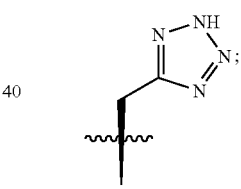
$X_3$ is —$(CH_2)_{2-6}$—NH—; n is 1, and $X_4$ is H;
 $X_1$ is
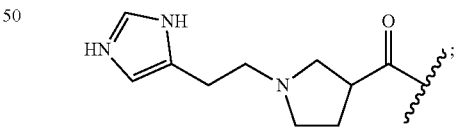
$X_2$ is
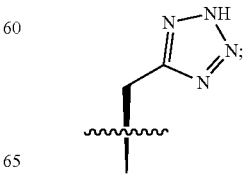

$X_3$ is —$(CH_2)_{2-6}$—NH—; n is 1; $X_4$ is H; $X_1$ is
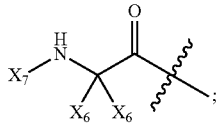
$X_2$ is
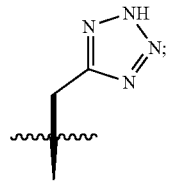
$X_3$ is —$(CH_2)_{2-6}$—NH—; n is 1, and $X_4$ is H; $X_6$ is independently at each occurrence selected from H and —$CH_3$, and $X_7$ is
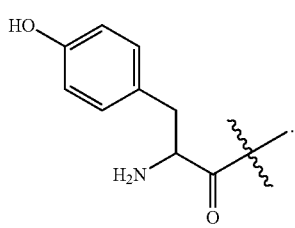 [SMILES: *C(=O)C(N)Cc1ccc(O)cc1]
$X_1$ is H; $X_2$ is
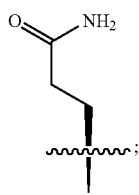
$X_3$ is —$(CH_2)_{2-6}$—NH—; n is 1, and $X_4$ is H; $X_1$ is
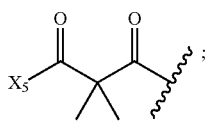
$X_2$ is
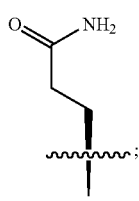
$X_3$ is —$(CH_2)_{2-6}$—NH—; n is 1; $X_4$ is H, and $X_5$ is
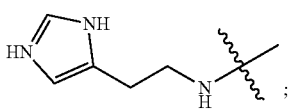 [SMILES: *NCCc1cnc[nH]1]
$X_1$ is
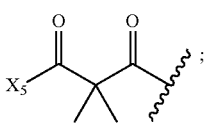
$X_2$ is
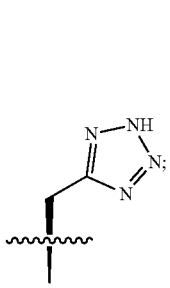
$X_3$ is —$(CH_2)_{2-6}$—NH—; n is 0; $X_4$ is phenyl, and $X_5$ is
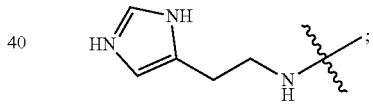
and
$X_1$ is
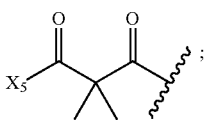
$X_2$ is
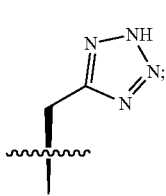

$X_3$ is —$(CH_2)_{2-6}$—NH—; n is 1; $X_4$ is phenyl, and $X_5$ is
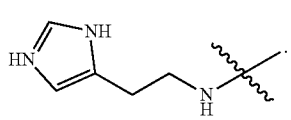 [SMILES: *NCCc1cnc[nH]1]
In one embodiment, the payload has the structure of formula (P-II), shown above, wherein $X_1$ is
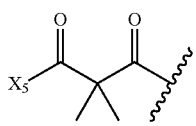
$X_2$ is
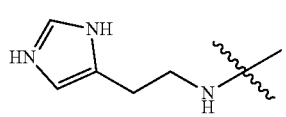
$X_3$ is —$(CH_2)_{2-6}$—NH—; $X_4$ is H, and $X_5$ is
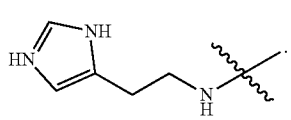 [SMILES: *NCCc1cnc[nH]1]
In one embodiment, the payloads P according to the present disclosure have a structure selected from:
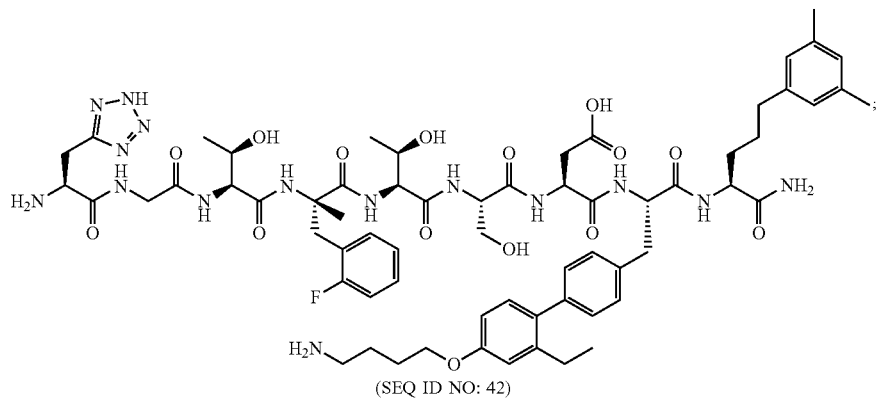

-continued
| P# | Structure |
|---|---|
| P3 | 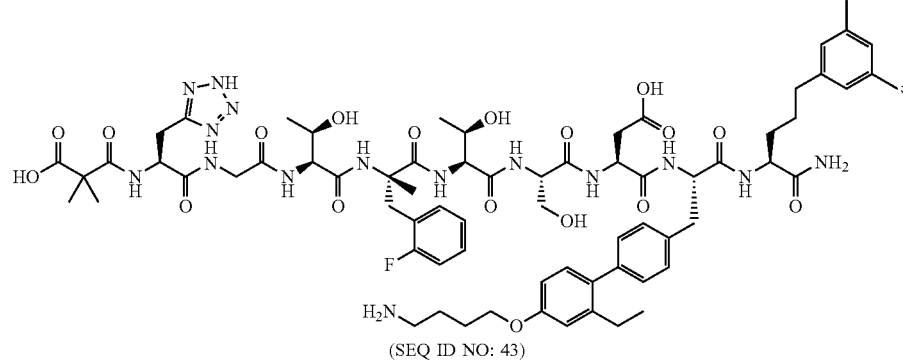<br>(SEQ ID NO: 43) |
| P4 | 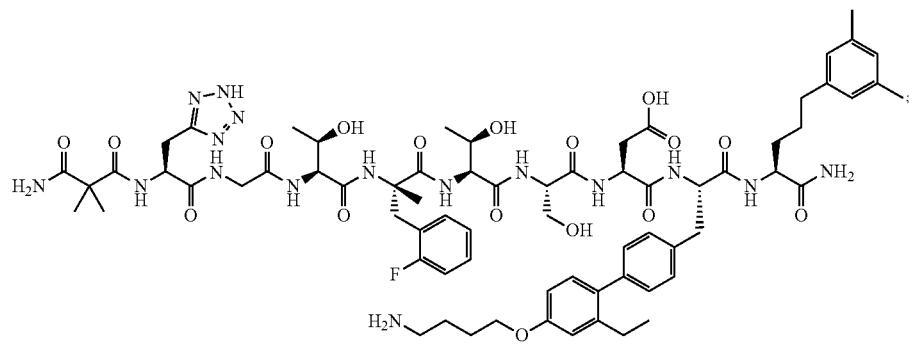 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(N)=O)[C@@H](C)O)[C@@H](C)O)C(=O)N[C@@H](CCCc2cc(C)cc(C)c2)C(N)=O)cc1]<br>(SEQ ID NO: 44) |
| P5 | 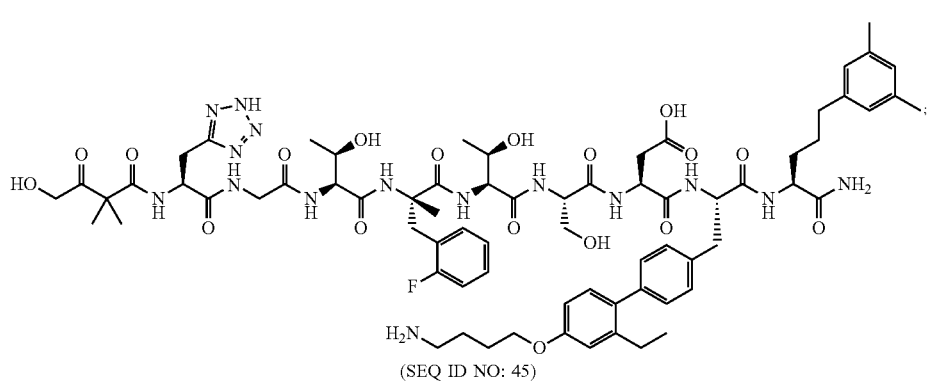<br>(SEQ ID NO: 45) |
| P6 | 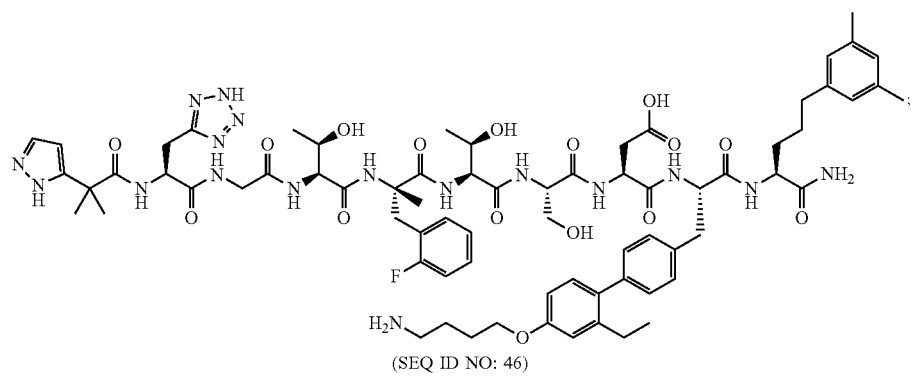<br>(SEQ ID NO: 46) |

| P# | Structure |
|---|---|
| P7 | 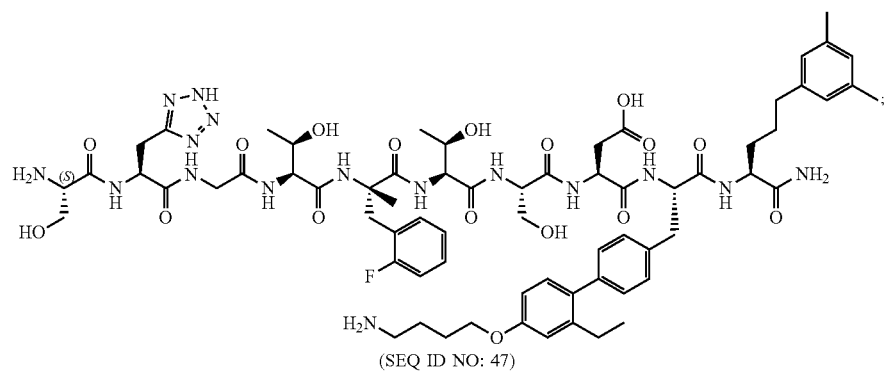<br>(SEQ ID NO: 47) |
| P8 | 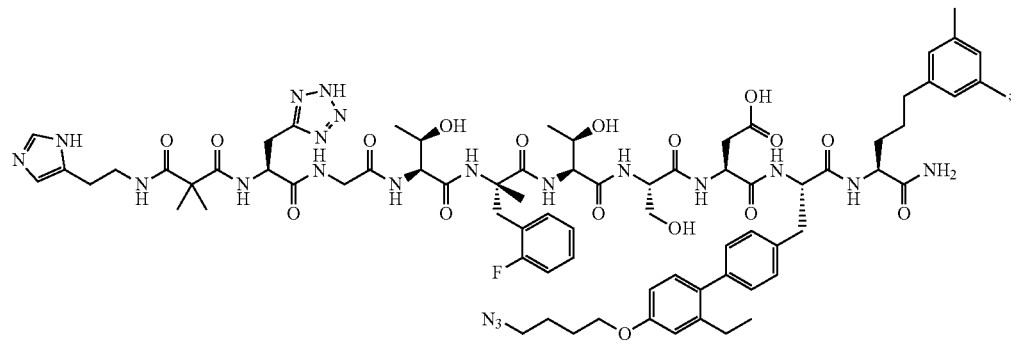 [SMILES: CCc1cc(OCCCCN=[N+]=[N-])ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1]<br>(SEQ ID NO: 48) |
| P9 | 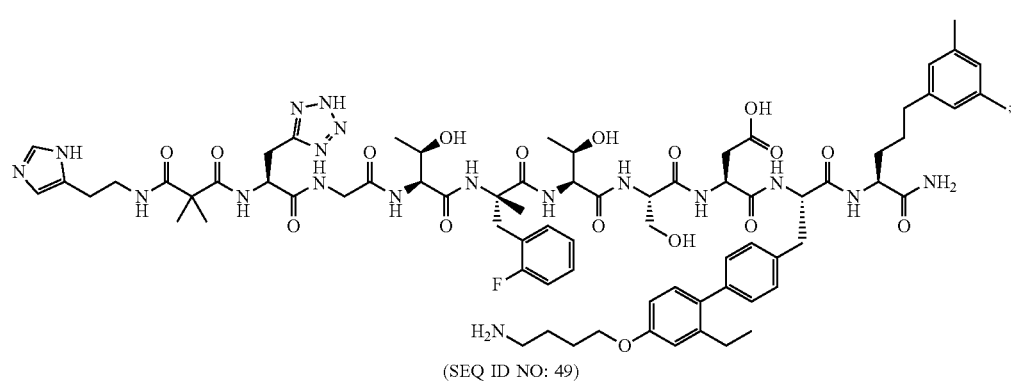<br>(SEQ ID NO: 49) |
| P10 | 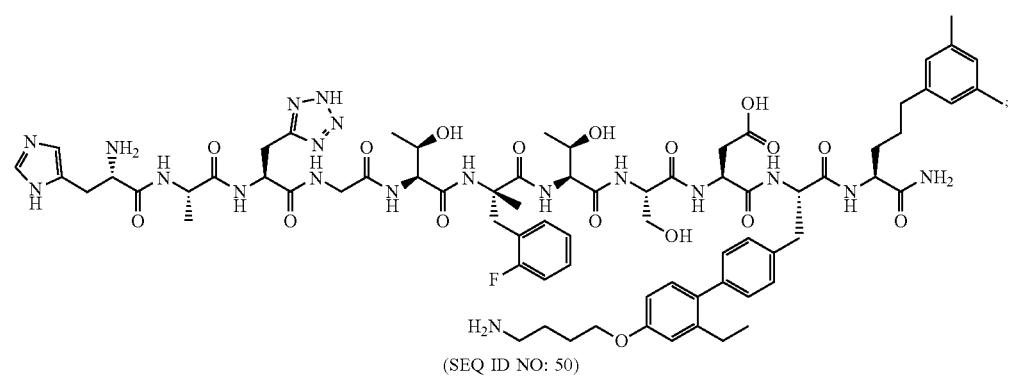<br>(SEQ ID NO: 50) |

| P# | Structure |
|---|---|
| P11 | 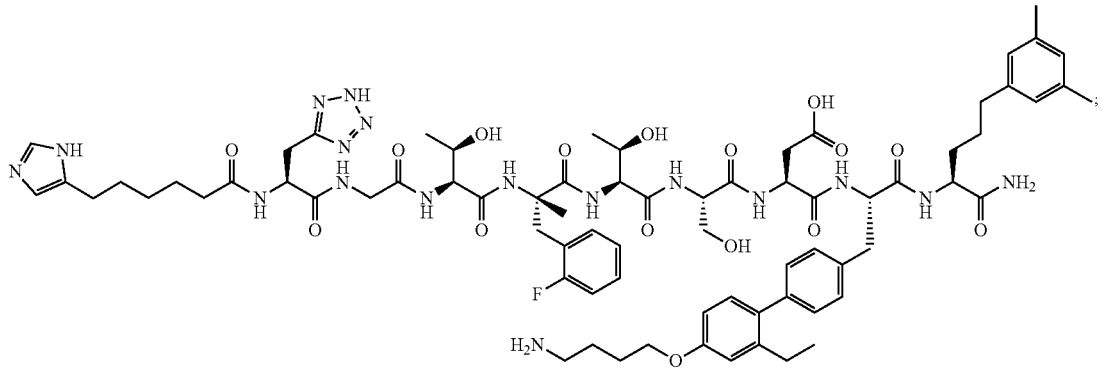 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)CCCCCc2cnc[nH]2)[C@@H](C)O)[C@@H](C)O)C(=O)N[C@@H](CCCc2cc(C)cc(C)c2)C(N)=O)cc1] (SEQ ID NO: 51) |
| P12 | 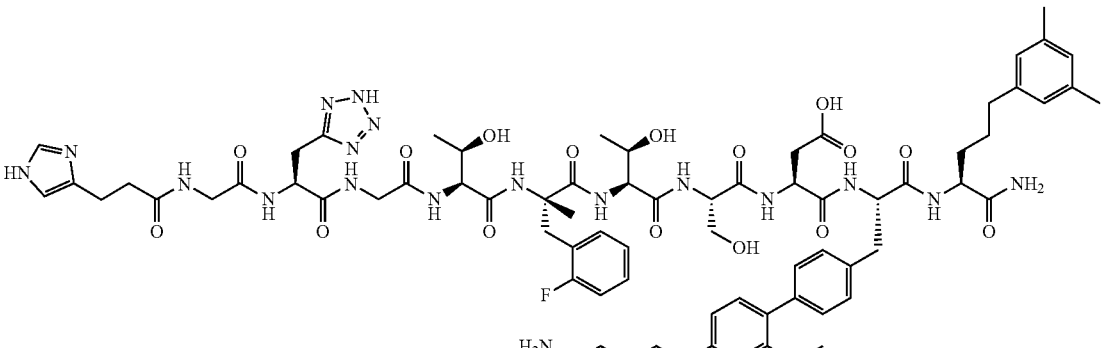 (SEQ ID NO: 52) |
| P13 | 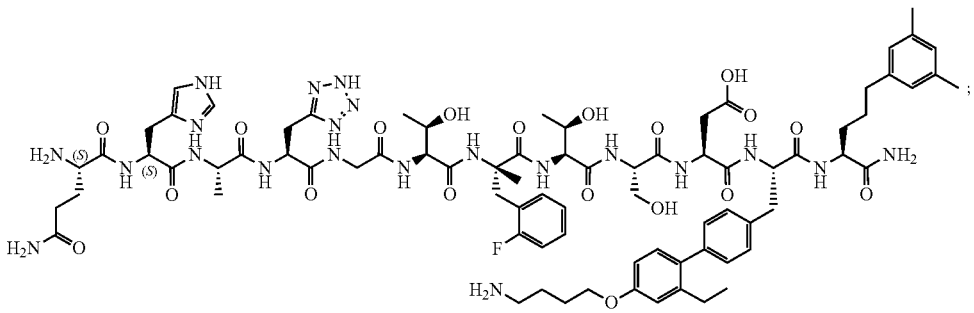 (SEQ ID NO: 53) |
| P14 | 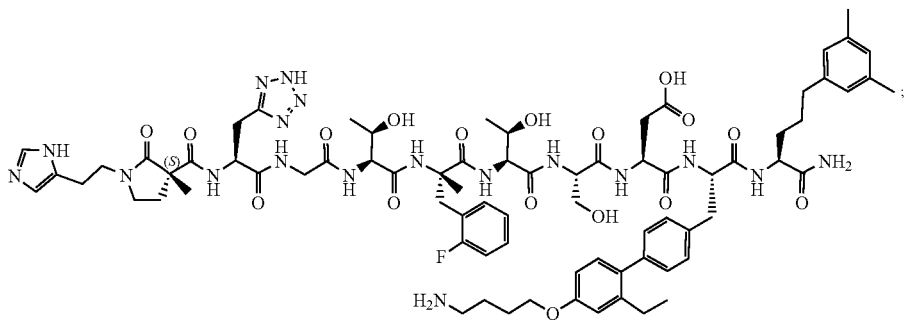 (SEQ ID NO: 54) |

| P# | Structure |
|---|---|
| P15 | 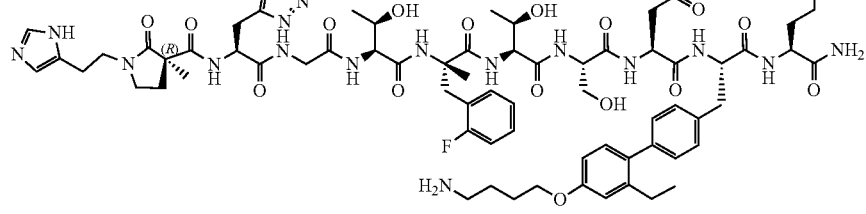<br>(SEQ ID NO: 55) |
| P16 | 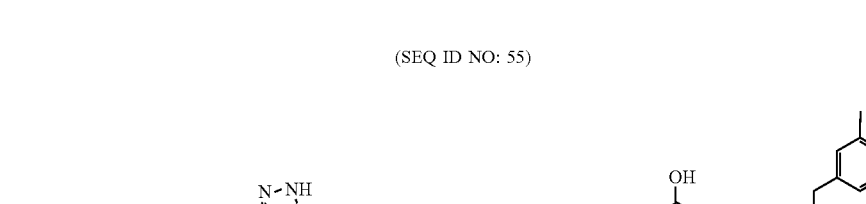<br>(SEQ ID NO: 56) |
| P17 | 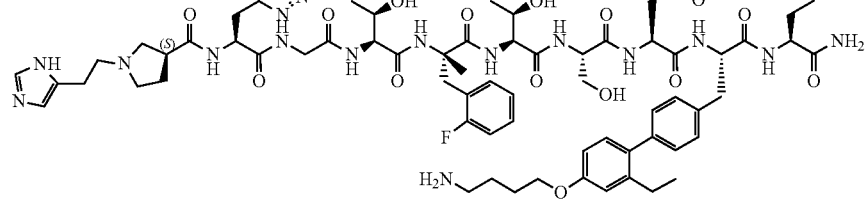<br>(SEQ ID NO: 57) |
| P18 | 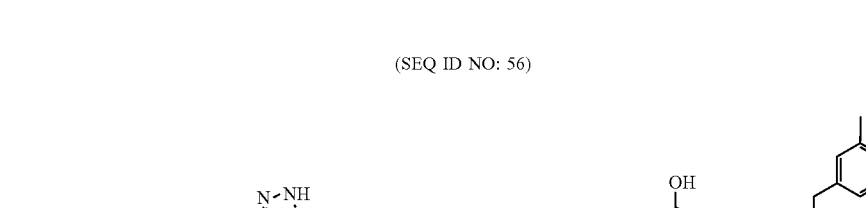<br>(SEQ ID NO: 58) |

| P# | Structure |
|---|---|
| P19 | 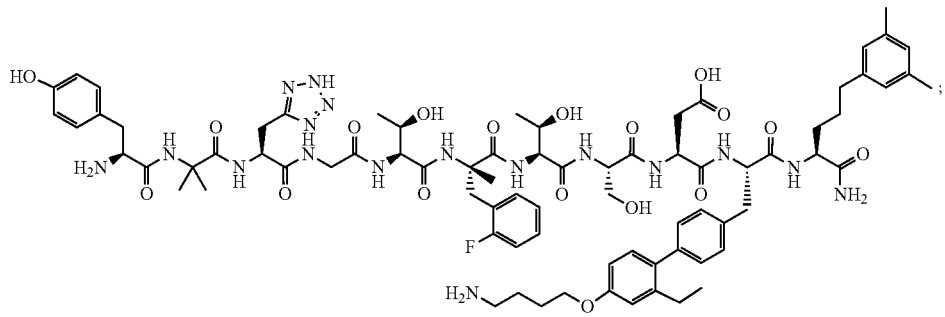 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)NC(=O)[C@@H](N)Cc2ccc(O)cc2)[C@@H](C)O)[C@@H](C)O)C(=O)N[C@@H](CCCc2cc(C)cc(C)c2)C(N)=O)cc1]
(SEQ ID NO: 59) |
| P20 | 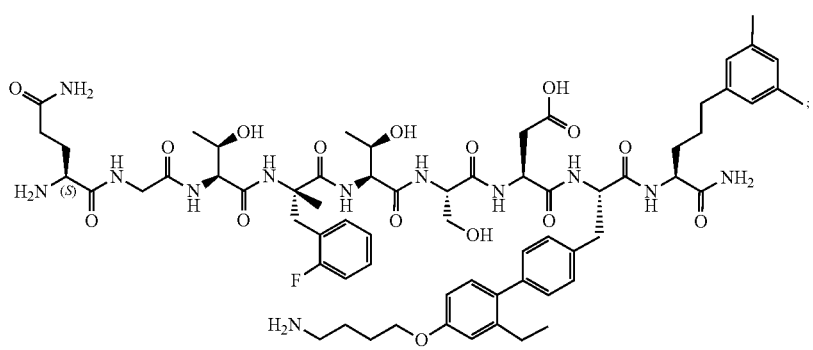
(SEQ ID NO: 60) |
| P21 | 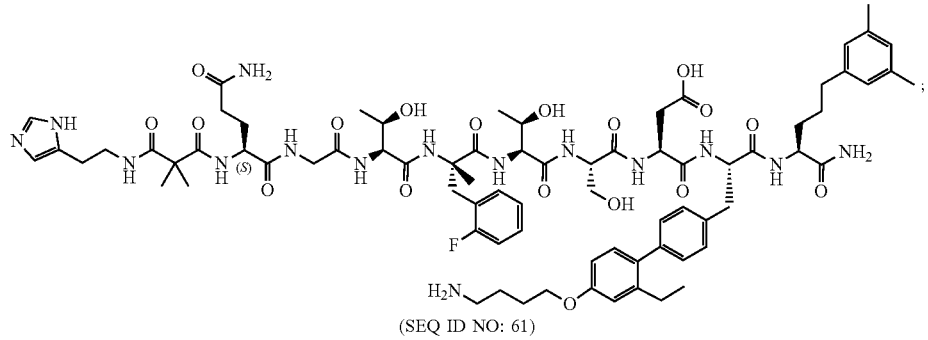
(SEQ ID NO: 61) |
| P22 | 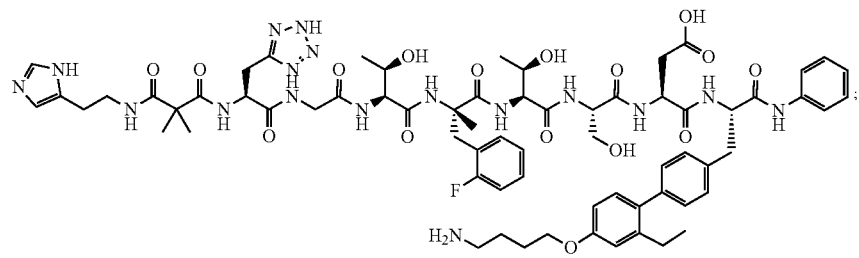
(SEQ ID NO: 62) |

-continued
| P# | Structure |
|---|---|
| P23 | 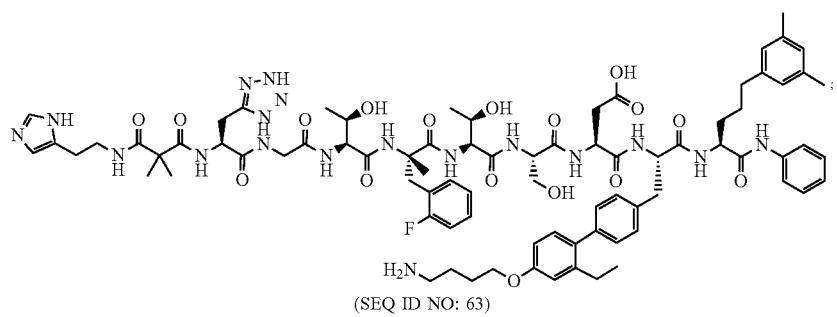<br>(SEQ ID NO: 63) |
| P24 | 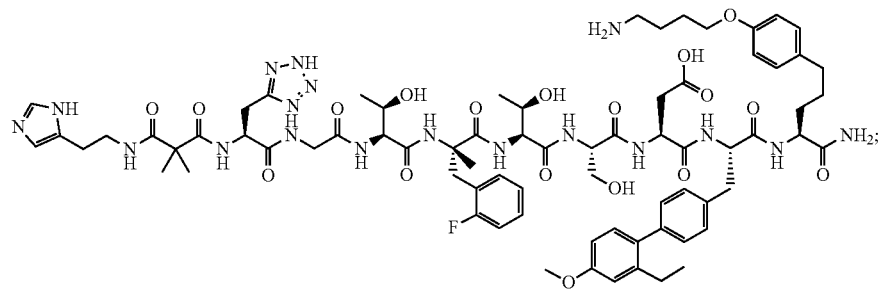 [SMILES: CCc1cc(OC)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2ccc(OCCCCN)cc2)C(N)=O)cc1]<br>(SEQ ID NO: 64) |
| P25 | 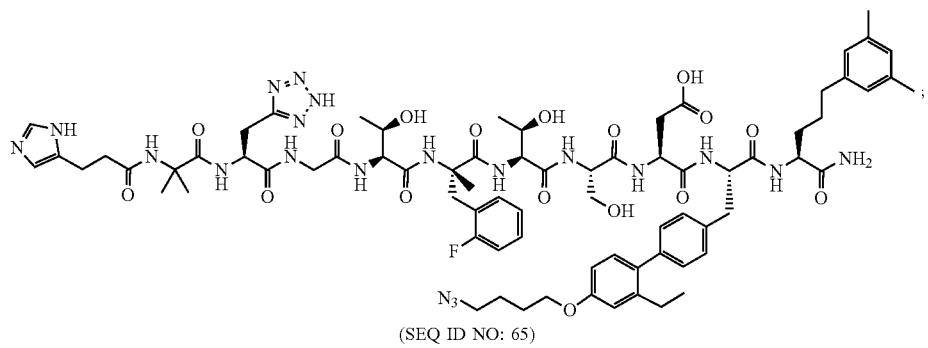<br>(SEQ ID NO: 65) |
| P26 | 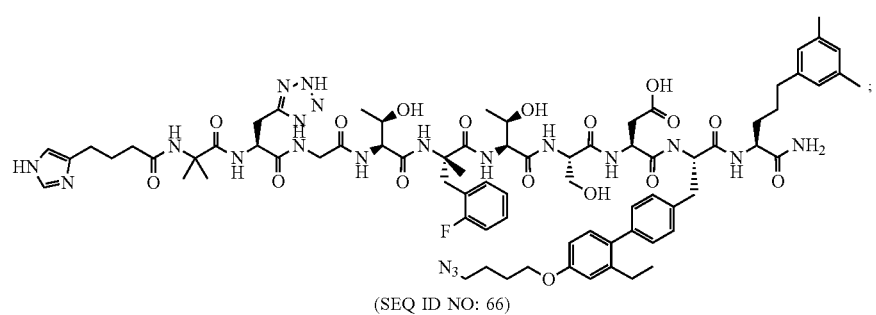<br>(SEQ ID NO: 66) |
| P27 | 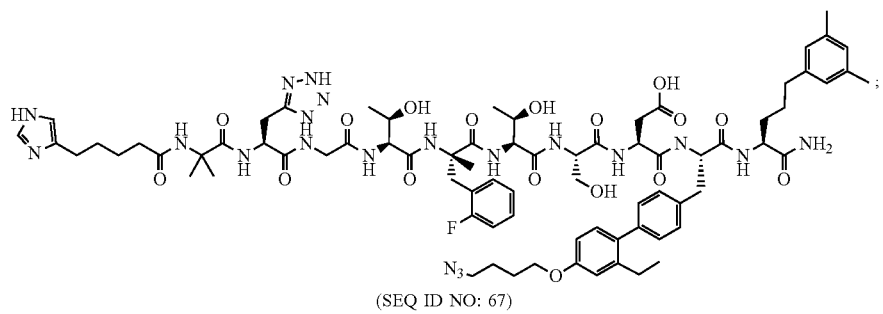<br>(SEQ ID NO: 67) |

-continued
| P# | Structure |
|---|---|
| P28 | 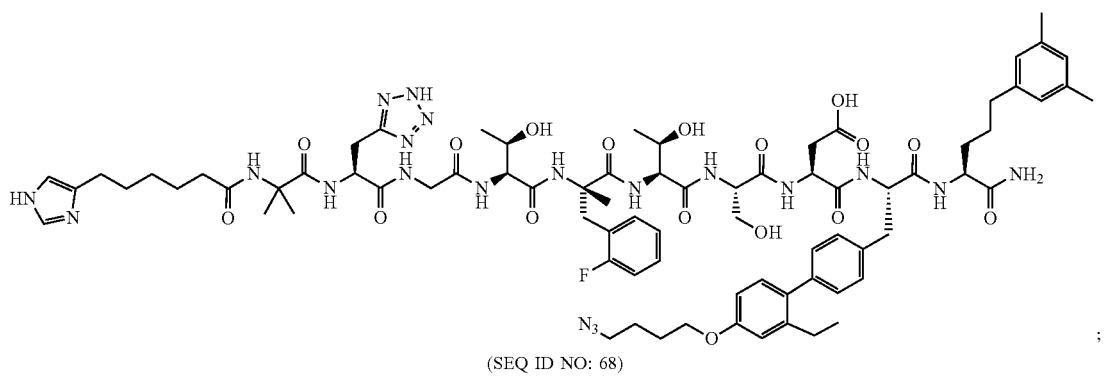 (SEQ ID NO: 68) |
| P29 | 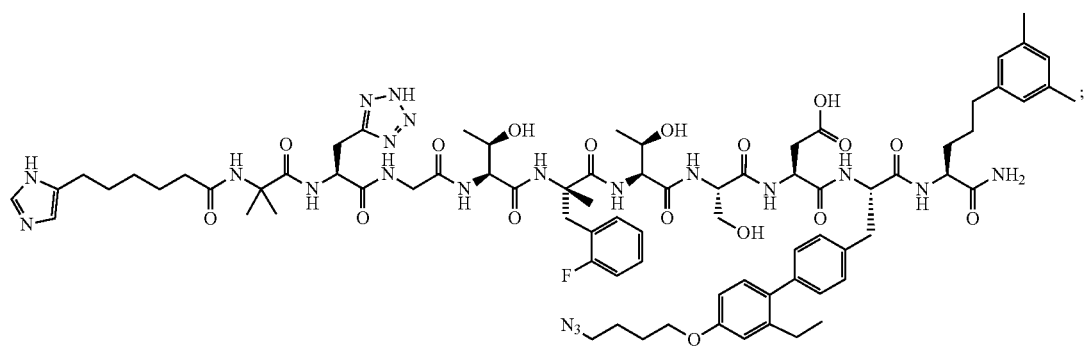 (SEQ ID NO: 69) |
| P30 | 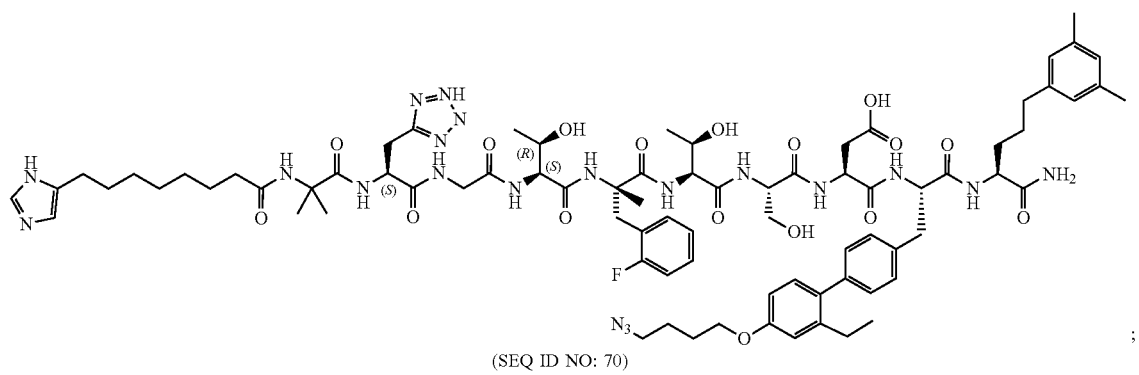 (SEQ ID NO: 70) |
| P31 | 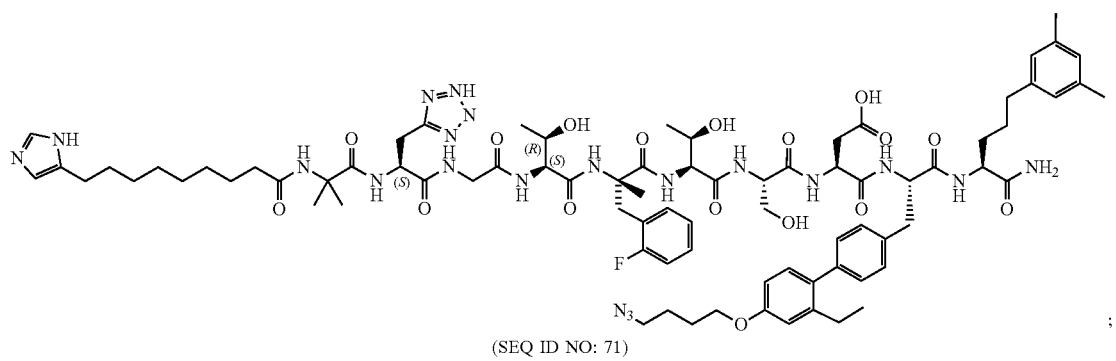 (SEQ ID NO: 71) |

| P# | Structure |
|---|---|
| P32 | 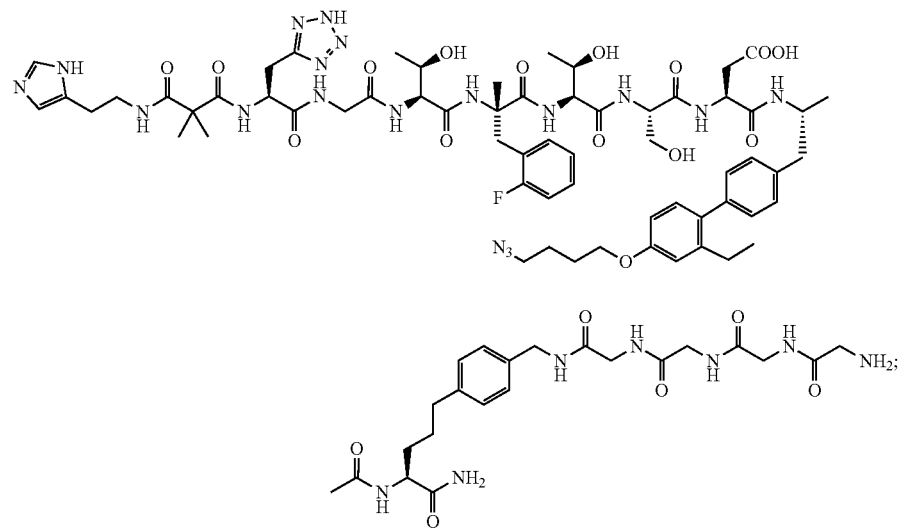<br>(Main Structure: SEQ ID NO: 72; Branched Sequence: SEQ ID NO: 154) |
| P33 | 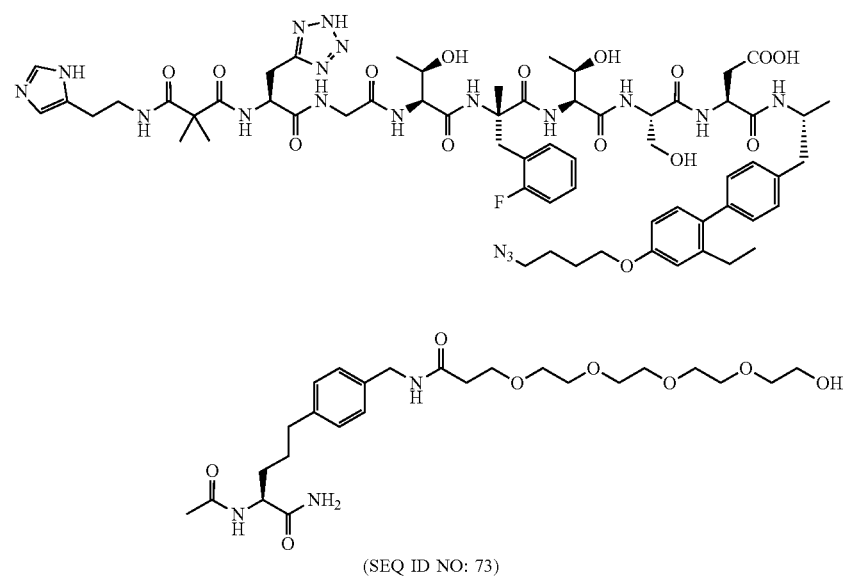<br>(SEQ ID NO: 73) |

| P# | Structure |
|---|---|
| P34 | 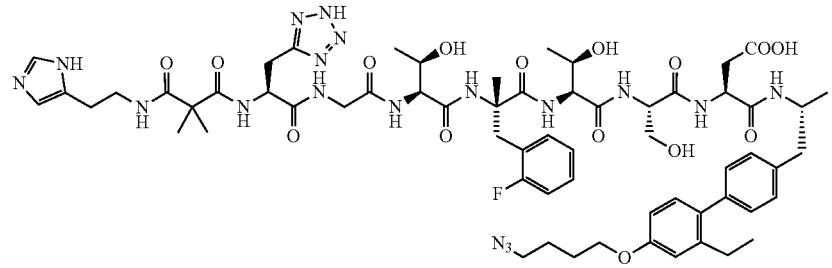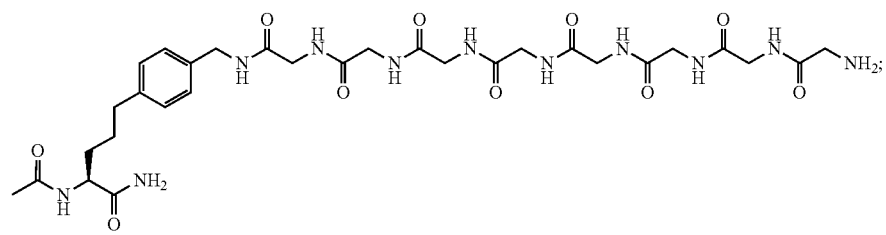
(Main Structure: SEQ ID NO: 74; Branched Sequence: SEQ ID NO: 155) |
| P35 | 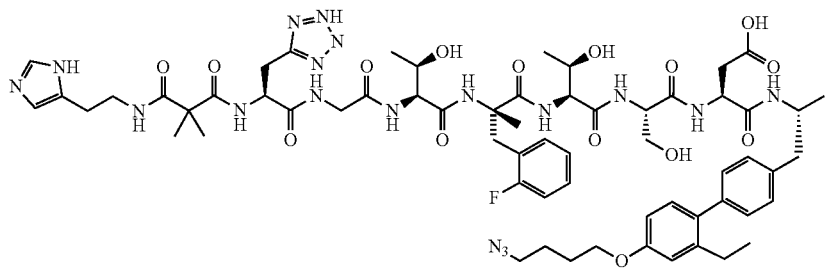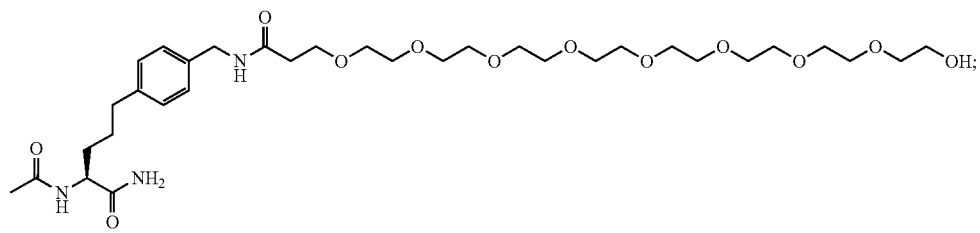
(SEQ ID NO: 75) |
| P36 | 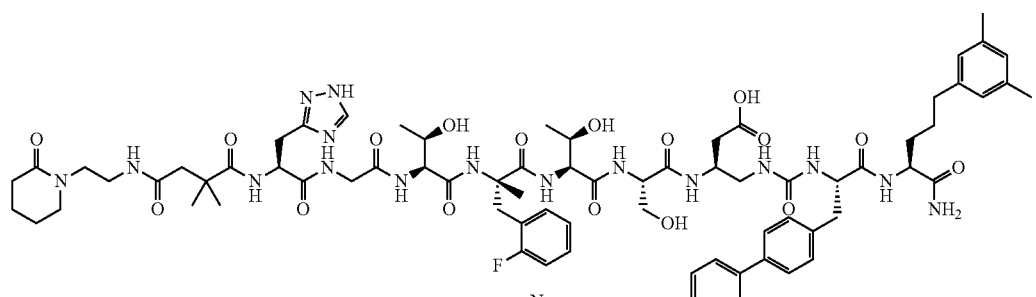
(SEQ ID NO: 76) |

-continued
| P# | Structure |
|---|---|
| P37 | 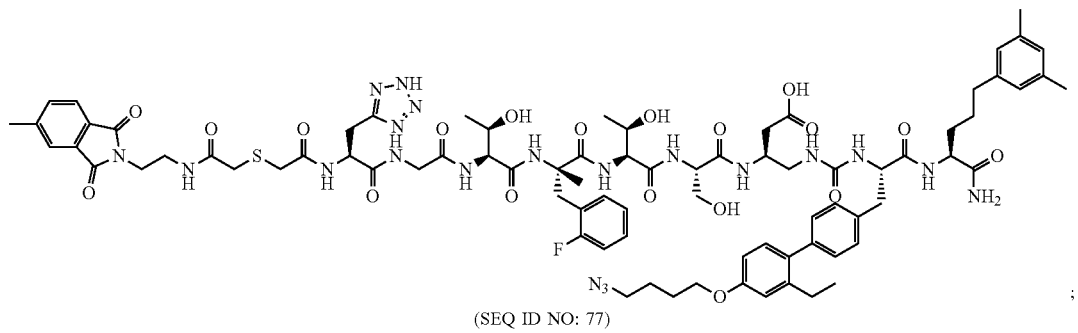<br>(SEQ ID NO: 77) |
| P38 | 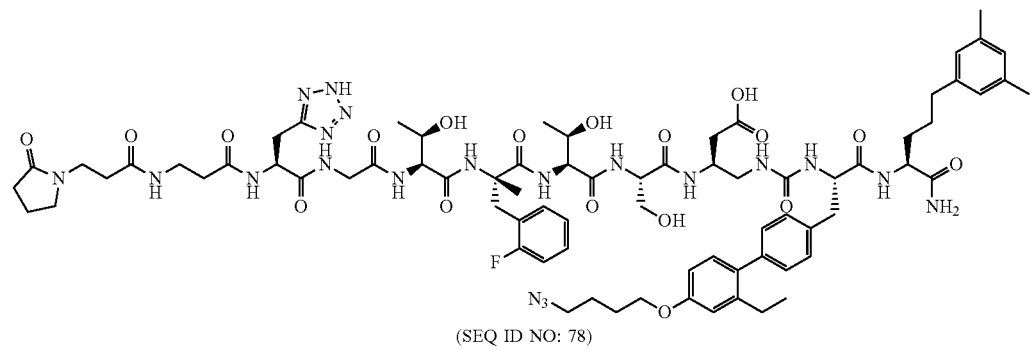<br>(SEQ ID NO: 78) |
| P39 | 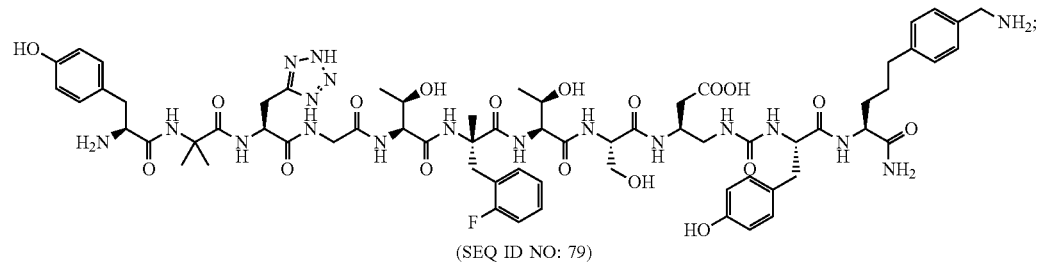<br>(SEQ ID NO: 79) |
| P40 | 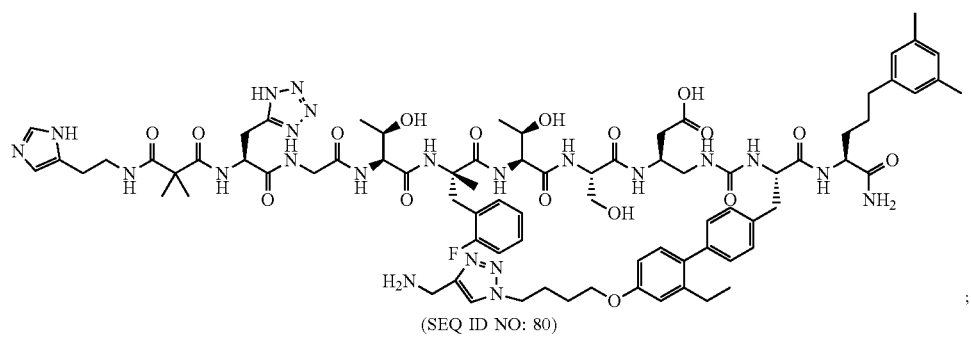<br>(SEQ ID NO: 80) |
| P41 | 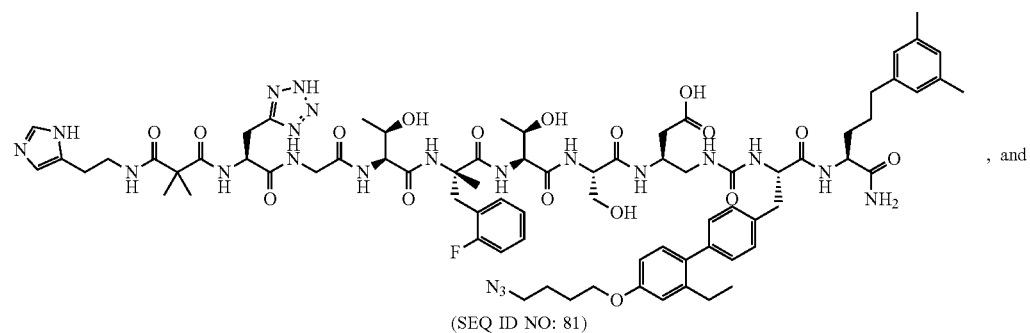<br>(SEQ ID NO: 81) |
;
;
;
, and -continued

| P# | Structure |
|---|---|
| P42 | 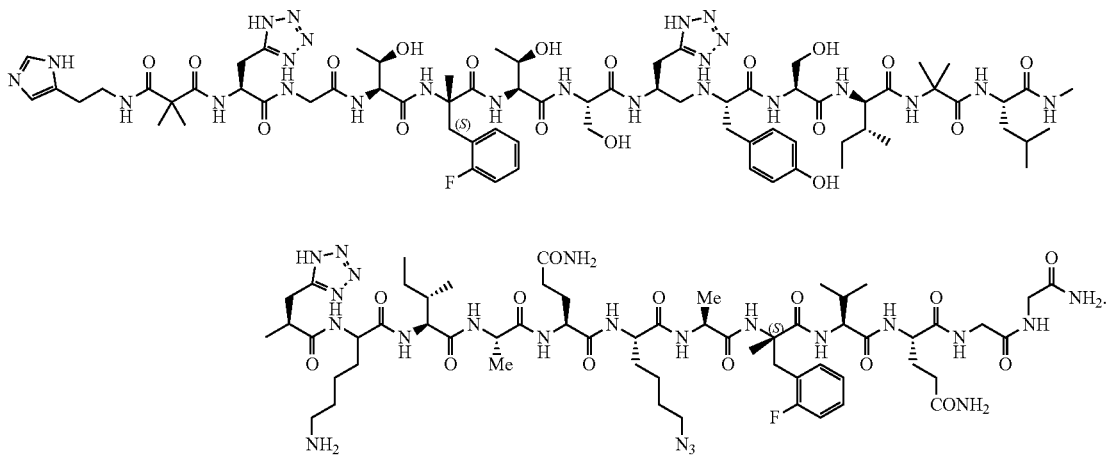<br>(SEQ ID NO: 82) |

In one embodiment, the payloads as described above have the following properties:

| P# | Molecular Formula | MW | M/Z 100% (M + H) | RT on HPLC (15 min) | CLogP | Plasma stability t½ (hr) |
|---|---|---|---|---|---|---|
| P1 | $C_{65}H_{86}FN_{17}O_{15}$ | 1364.48 | 860.2 $[M + 2H]^{2+}$ 1365.6 $[M + H]^+$ | 10.15 | 4.94 ± 0.99 | |
| P2 | $C_{65}H_{88}FN_{15}O_{15} \cdot 2CF_3COOH$ | 1566.53 | 670.0 $[M + 2H]^{2+}$ | 7.77 | 4.08 ± 0.98 | 10.7 |
| P3 | $C_{70}H_{94}FN_{15}O_{18} \cdot CF_3COOH$ | 1566.61 | 1454.1 $[M + H]^+$ 727.3 $[M + 2H]^{2+}$ | 8.10 | 4.54 ± 1.00 | >57.8 |
| P4 | $C_{70}H_{95}FN_{16}O_{17} \cdot CF_3COOH$ | 1565.62 | 1452.4 $[M + H]^+$ 726.7 $[M + 2H]^{2+}$ | 7.90 | 3.59 ± 1.00 | >57.8 |
| P5 | $C_{70}H_{95}FN_{16}O_{18}$ | 1467.6 | 1468.0 $[M + H]^+$ 735.2 $[M + 2H]^{2+}$ | 8.00 | 3.23 ± 1.00 | |
| P6 | $C_{72}H_{96}FN_{17}O_{16} \cdot 2CF_3COOH$ | 1702.68 | 738.2 $[M + 2H]^{2+}$ | 8.16 | 4.38 ± 1.00 | >57.8 |
| P7 | $C_{68}H_{93}FN_{16}O_{17} \cdot 2CF_3COOH$ | 1653.61 | 713.8 $[M + 2H]^{2+}$ | 7.58 | 3.16 ± 1.00 | |
| P8 | $C_{75}H_{99}FN_{20}O_{17}$ | 1571.71 | 786.38 $[M + 2H]^{2+}$ 1571.76 $[M + H]^+$ | 10.14 | 4.43 ± 1.02 | |
| P9 | $C_{75}H_{101}FN_{18}O_{17} \cdot 2CF_3COOH$ | 1773.76 | 773.9 $[M + 2H]^{2+}$ | 7.44 | 3.57 ± 1.01 | >57.8 |
| P10 | $C_{74}H_{100}FN_{19}O_{17} \cdot 3CF_3COOH$ | 1888.77 | 516.4 $[M + 3H]^{3+}$ 774.2 $[M + 2H]^{2+}$ | 7.46 | 2.95 ± 1.02 | 1.8 |
| P11 | $C_{74}H_{100}FN_{17}O_{16} \cdot 2CF_3COOH$ | 1730.74 | 752.3 $[M + 2H]^{2+}$ | 7.72 | 5.04 ± 0.99 | >57.8 |
| P12 | $C_{73}H_{97}FN_{18}O_{17} \cdot 2CF_3COOH$ | 1745.71 | 759.8 $[M + 2H]^{2+}$ | 7.65 | 3.03 ± 1.01 | >57.8 |

-continued

| P# | Molecular Formula | MW | M/Z 100% (M + H) | RT on HPLC (15 min) | CLogP | Plasma stability t½ (hr) |
|---|---|---|---|---|---|---|
| P13 | $C_{79}H_{108}FN_{21}O_{19} \cdot 3CF_3COOH$ | 2016.9 | 559.1 $[M + 3H]^{3+}$ 838.3 $[M + 2H]^{2+}$ | 7.37 | 1.81 ± 1.04 | 16.9 |
| P14 | $C_{76}H_{101}FN_{18}O_{17}$ | 1557.72 | 779.9 $[M + 2H]^{2+}$ | 7.60 | 3.68 ± 1.01 | |
| P15 | $C_{76}H_{101}FN_{18}O_{17} \cdot 2(CF_3COOH)$ | 1785.77 | 779.8 $[M + 2H]^{2+}$ | 7.62 | 3.68 ± 1.01 | |
| P16 | $C_{75}H_{101}FN_{18}O_{16} \cdot 2(CF_3COOH)$ | 1757.76 | 765.7 $[M + 2H]^{2+}$ | 7.18 | 3.68 ± 1.01 | |
| P17 | $C_{75}H_{101}FN_{18}O_{16} \cdot 2(CF_3COOH)$ | 1757.76 | 766.3 $[M + 2H]^{2+}$ | 7.36 | 3.68 ± 1.01 | |
| P18 | $C_{77}H_{102}FN_{17}O_{18}$ | 1572.74 | 787.3 $[M + 2H]^{2+}$ | 7.68 | 4.60 ± 1.01 | |
| P19 | $C_{78}H_{104}FN_{17}O_{18}$ | 1586.76 | 794.4 $[M + 2H]^{2+}$ | 7.81 | 4.95 ± 1.01 | >57.8 |
| P20 | $C_{66}H_{91}FN_{12}O_{16}$ | 1327.5 | 1327.7 $[M + H]^{+}$ | 7.40 | 3.41 ± 1.00 | |
| P21 | $C_{76}H_{104}FN_{15}O_{18} \cdot 2CF_3COOH$ | 1762.77 | 768.3 $[M + 2H]^{2+}$ | 7.44 | 3.92 ± 0.97 | >57.8 |
| P22 | $C_{68}H_{88}FN_{17}O_{16}$ | 1418.53 | 710.2 $[M + 2H]^{2+}$ | 7.06 | 3.03 ± 0.99 | |
| P23 | $C_{81}H_{105}FN_{18}O_{17}$ | 1621.81 | 811.9 $[M + 2H]^{2+}$ | 8.30 | 6.00 ± 1.01 | |
| P24 | $C_{74}H_{99}FN_{18}O_{18} \cdot 2CF_3COOH$ | 1775.73 | 774.8 $[M + 2H]^{2+}$ | 11.00 (20 min) | 2.56 ± 1.01 | |
| P25 | $C_{75}H_{99}FN_{20}O_{17}$ | 1570.8 | 786.7 $[M + 2H]^{2+}$ | 9.54 | 4.58 ± 1.01 | |
| P26 | $C_{76}H_{101}FN_{20}O_{17}$ | 1584.8 | 793.7 $[M + 2H]^{2+}$ | 9.55 | 5.09 ± 1.01 | |
| P27 | $C_{77}H_{103}FN_{20}O_{17}$ | 1598.8 | 800.39 $[M + 2H]^{2+}$ | 9.58 | 5.54 ± 1.01 | |
| P28 | $C_{78}H_{105}FN_{20}O_{17}$ | 1612.8 | 807.40 $[M + 2H]^{2+}$ | 9.60 | 5.98 ± 1.01 | |
| P29 | $C_{79}H_{107}FN_{20}O_{17}$ | 1626.8 | 814.40 $[M + 2H]^{2+}$ | 9.61 | 6.51 ± 1.01 | |
| P30 | $C_{81}H_{111}FN_{20}O_{17}$ | 1768.8 | 821.4 $[M + 2H]^{2+}$ | 9.63 | 7.57 ± 1.01 | |
| P31 | $C_{81}H_{111}FN_{20}O_{17}$ | 1654.8 | 828.8 $[M + 2H]^{2+}$ | 9.80 | 7.57 ± 1.01 | |
| P32 | $C_{82}H_{110}FN_{25}O_{21}$ | 1799.8 | 900.91 $[M + 2H]^{2+}$ | 7.23 | -0.30 ± 1.06 | |
| P33 | $C_{85}H_{118}FN_{21}O_{23}$ | 1819.9 | 911.40 $[M + 2H]^{2+}$ | 7.96 | 0.25 ± 1.05 | |
| P34 | $C_{90}H_{122}FN_{29}O_{25}$ | 2027.9 | 1015.2 $[M + 2H]^{2+}$ | 7.15 | -2.76 ± 1.10 | |
| P35 | $C_{93}H_{134}FN_{21}O_{27}$ | 1996.0 | 999.4 $[M + 2H]^{2+}$ | 7.88 | -1.18 ± 1.07 | |
| P36 | $C_{78}H_{106}FN_{19}O_{18}$ | 1615.8 | 809.3 $[M + 2H]^{2+}$ | 5.25 | 4.76 ± 1.02 | |
| P37 | $C_{80}H_{100}FN_{19}O_{19}S$ | 1681.7 | 842.3 $[M + 2H]^{2+}$ | 4.84 | 7.01 ± 1.03 | |
| P38 | $C_{75}H_{100}FN_{19}O_{18}$ | 1573.8 | 788.20 $[M + 2H]^{2+}$ | 9.93 | 3.49 ± 1.02 | |
| P39 | $C_{65}H_{86}FN_{17}O_{18}$ | 1411.63 | 1412.7 $[M + H]^{+}$, 707.3 $[M + 2H]^{2+}$ | 6.89 | -0.24 ± 1.01 | |
| P40 | $C_{78}H_{104}FN_{21}O_{17}$ | 1625.79 | 814.2 $[M + 2H]^{2+}$ | 6.94 | 2.98 +/- 1.40 | |
| P41 | $C_{75}H_{98}FN_{19}O_{18}$ | 1571.73 | 787.3 $[M + 2H]^{2+}$ | 9.66 | 5.40 +/- 1.02 | |
| P42 | $C_{126}H_{190}F_2N_{46}O_{33}$ | 2913.46 | 1458.2 $[M + 2H]^{2+}$ | 7.17 | -3.08 +/- 1.57 | |

In some embodiments, the payloads of the present disclosure are amenable to conjugation with a binding agent (e.g., antibody).

Linker-Payloads (L-P)

In one embodiment, the present disclosure provides reactive linker-payloads comprising payloads P as described above and linkers capable of covalently attaching to an antibody or an antigen-binding fragment thereof.

In one embodiment, the linker-payload according to the present disclosure has a structure of Formula (C) (SEQ ID NO: 27):

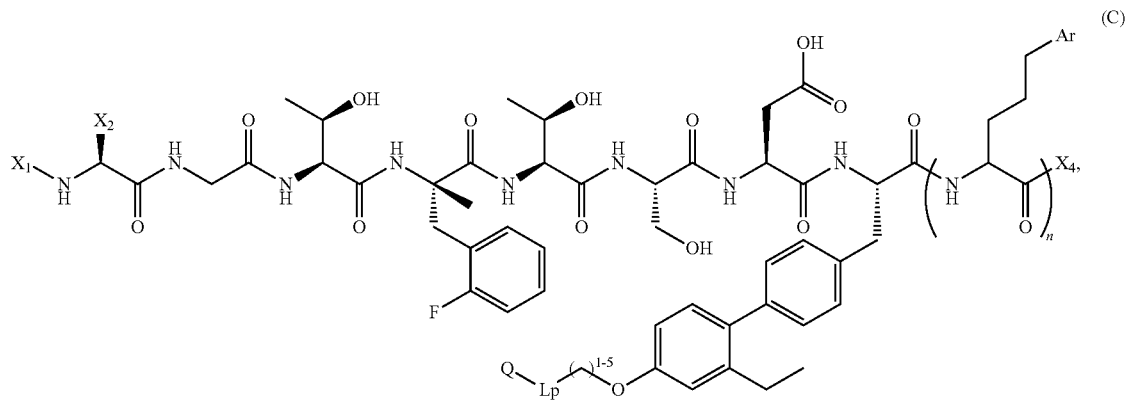

wherein:

L$_p$ is absent or a linker comprising one or more of

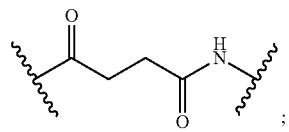 [SMILES: *NC(=O)CCC(*)=O]

a carbamate group; a cyclodextrin; a polyethylene glycol (PEG) segment having 1 to 36 —CH$_2$CH$_2$O— (EG) units; a —(CH$_2$)$_{2-24}$— chain; a triazole; one or more amino acids selected from glycine, serine, glutamic acid, alanine, valine, and proline, and combinations thereof;

Q is a moiety selected from —NH$_2$, —N$_3$,

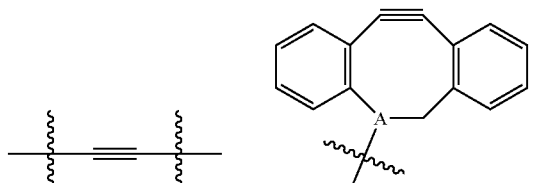

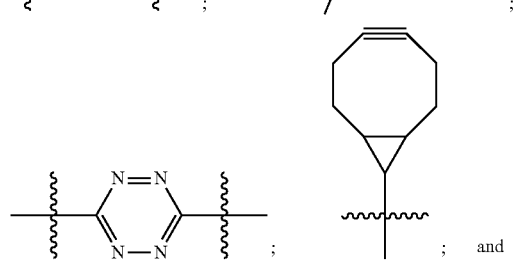

-continued

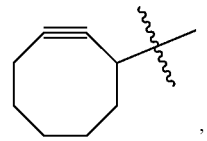

where A is C or N;

X$_1$ is selected from H

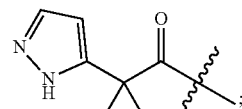

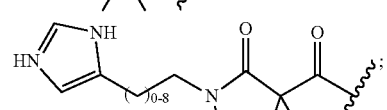

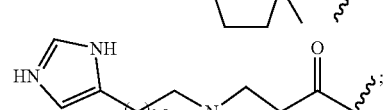

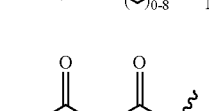 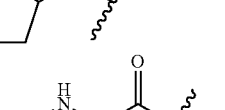

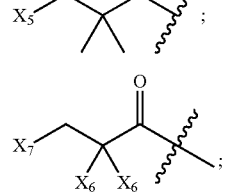

and

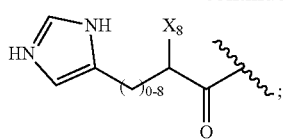

$X_2$ is selected from

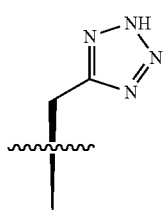 and 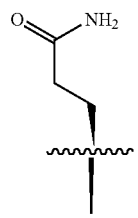;

n is 0 or 1;
$X_4$ is selected from —NH$_2$, —OH and —N(H)(phenyl);
$X_5$ is selected from —OH, —NH$_2$, —NH—OH, and

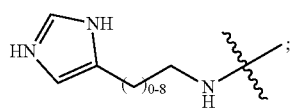

$X_6$ is independently at each occurrence selected from H, —OH, —CH$_3$, and —CH$_2$OH;
$X_7$ is selected from H,

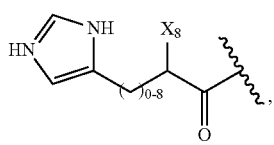

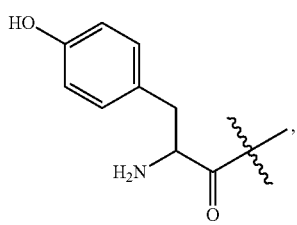

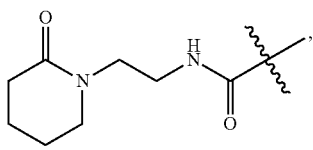

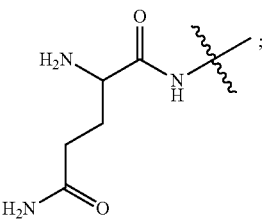

$X_8$ is selected from H, —OH, —NH$_2$, and

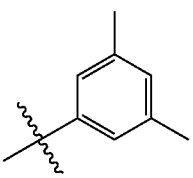

Ar is selected from

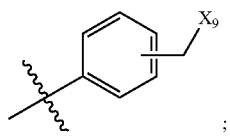 and 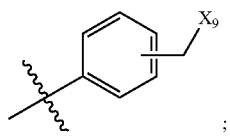;

$X_9$ is selected from —NH$_2$,

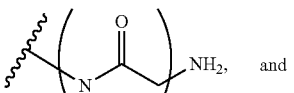 and

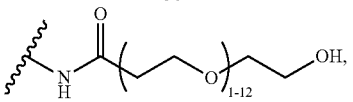

or a pharmaceutically acceptable salt thereof.

In one embodiment, the linker-payload according to the present disclosure has a structure of Formula (III) (SEQ ID NO: 86):

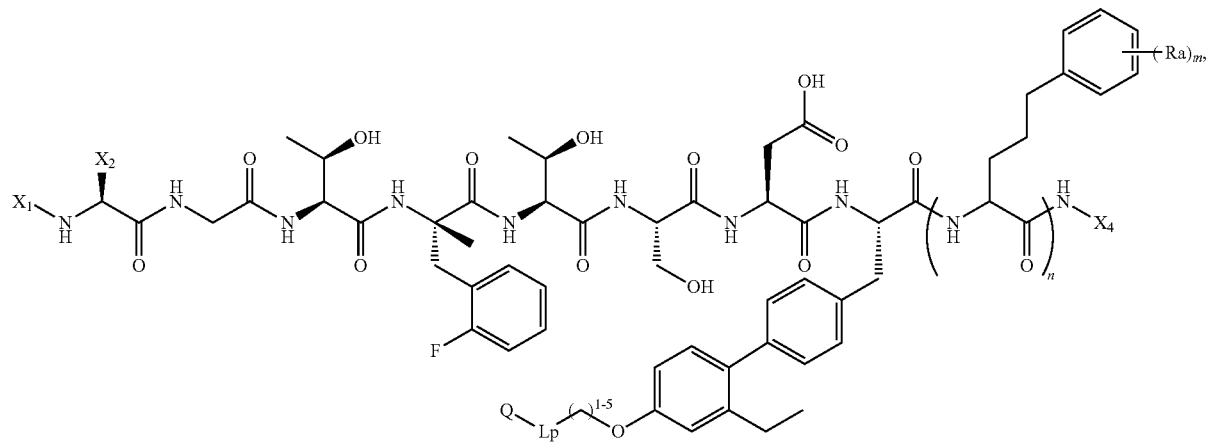

(III)

wherein:

$L_p$ is absent or a linker comprising one or more of

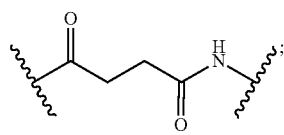

a carbamate group; a cyclodextrin; a polyethylene glycol (PEG) segment having 1 to 36 —CH$_2$CH$_2$O— (EG) units; one or more amino acids selected from glycine, serine, glutamic acid, alanine, valine, and proline, and combinations thereof;

Q is a moiety selected from —N$_3$,

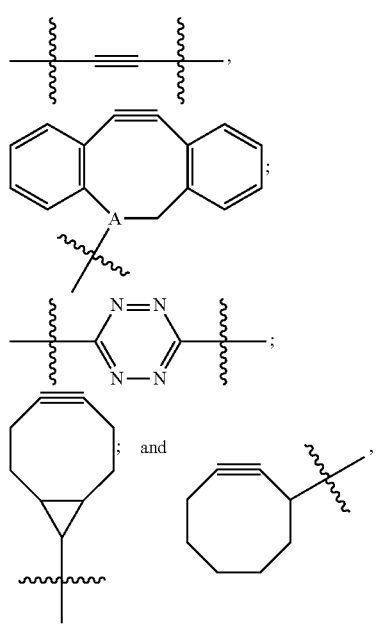

where A is C or N;

$X_1$ is selected from H;

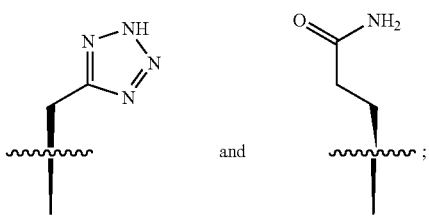

$X_2$ is selected from and ;

$X_3$ is selected from —(CH$_2$)$_{2-6}$—NH$_2$, —(CH$_2$)$_{2-6}$—N$_3$, and —CH$_3$, with the proviso that when $X_3$ is —CH$_3$, n is 1 and Ra in at least one occurrence is selected from —(CH$_2$)$_{2-6}$—NH$_2$ and —(CH$_2$)$_{2-6}$—N$_3$;

n is 0 or 1;

Ra is independently at each occurrence selected from H, —CH₃, —(CH₂)₂₋₆—NH₂, and —(CH₂)₂₋₆—N₃;

X₄ is selected from H and phenyl;

X₅ is selected from —OH, —NH₂, —NH—OH, and

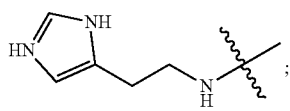 [SMILES: *NCCc1cnc[nH]1]

X₆ is independently at each occurrence selected from H, —OH, —CH₃, and —CH₂OH;

X₇ is selected from H,

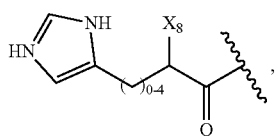

and

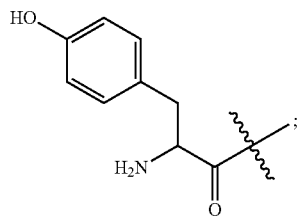

X₃ is selected from H, —OH, —NH₂, and

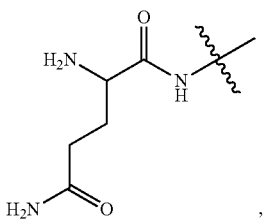 [SMILES: *NC(=O)C(N)CCC(N)=O]

and pharmaceutically acceptable salts thereof.

In one embodiment, the linker-payload LP comprises a cyclodextrin moiety. In some embodiments, the linker-payload LP comprising a cyclodextrin moiety exhibits GLP1R agonism activity.

In one embodiment, the linker-payloads LP according to the present disclosure have the structure selected from the group consisting of:

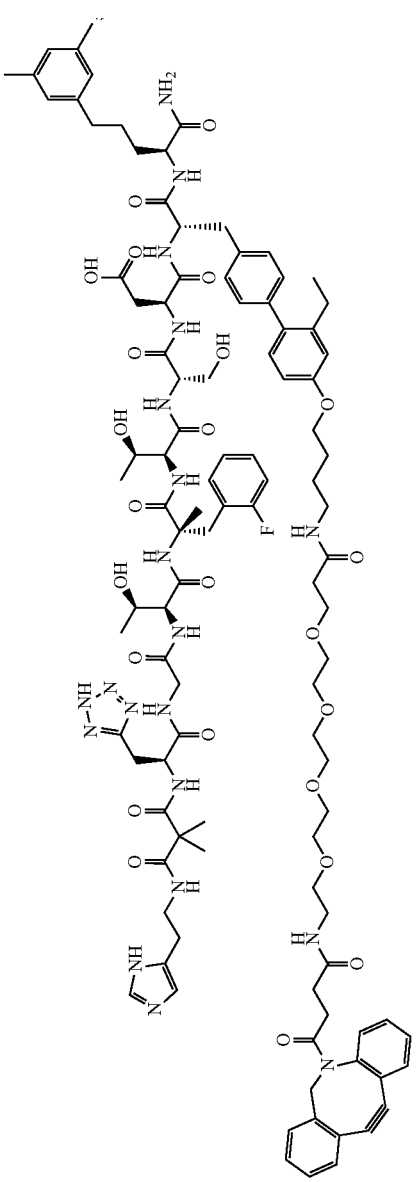

| LP# | Name | Structure |
|---|---|---|
| LP3 (SEQ ID NO: 87) | DIBAC-suc-PEG12-P9 | 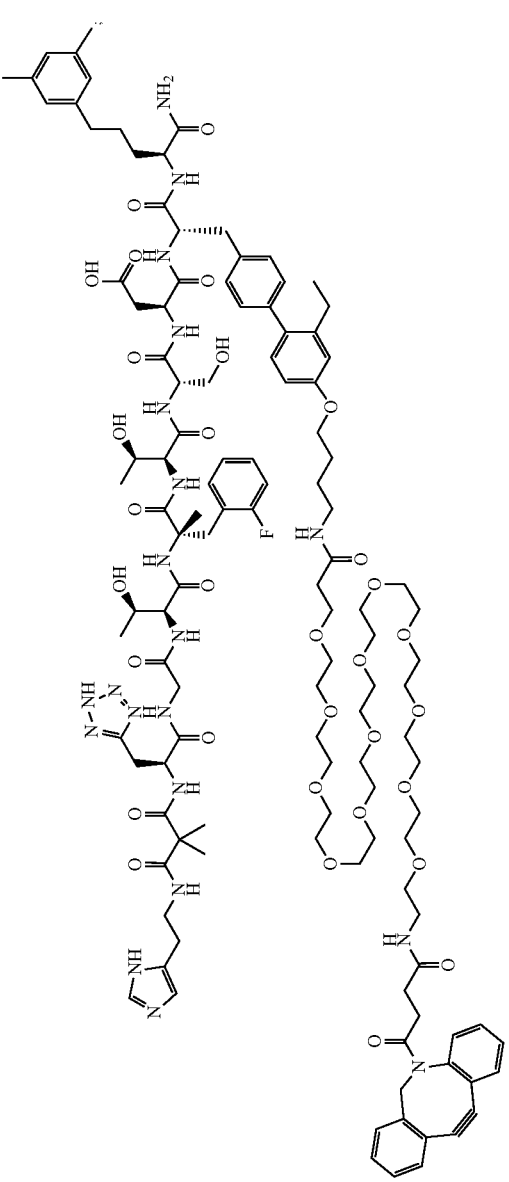 |
| LP4 (SEQ ID NO: 87) | DIBAC-suc-PEG24-P9 | 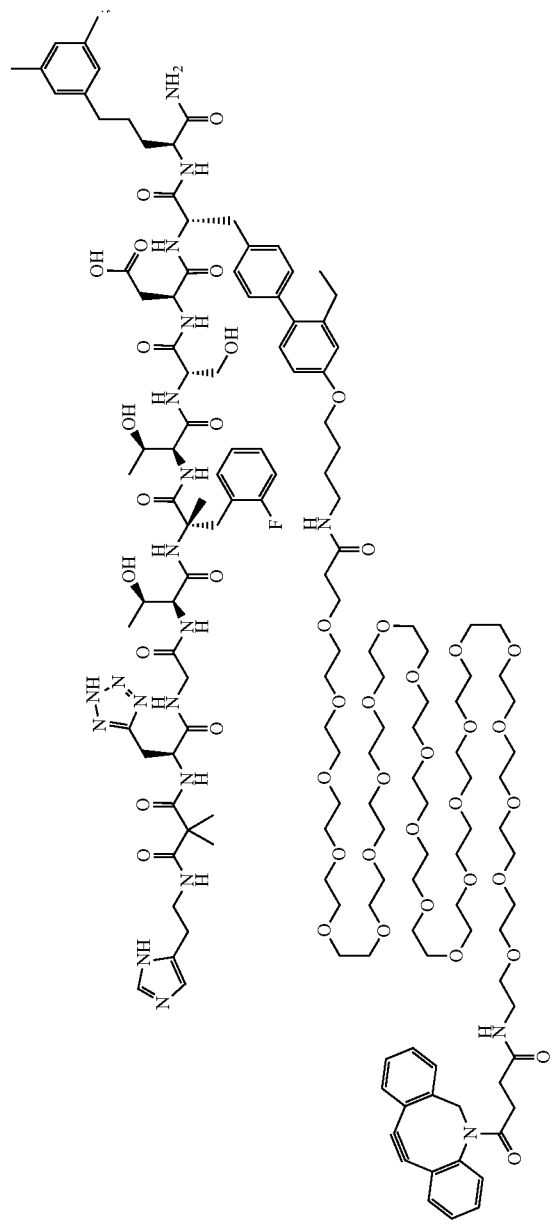 |

| LP# | Name | Structure |
|---|---|---|
| LP5 (SEQ ID NO: 87) | BCN-PEG4-carbamate-P9 | 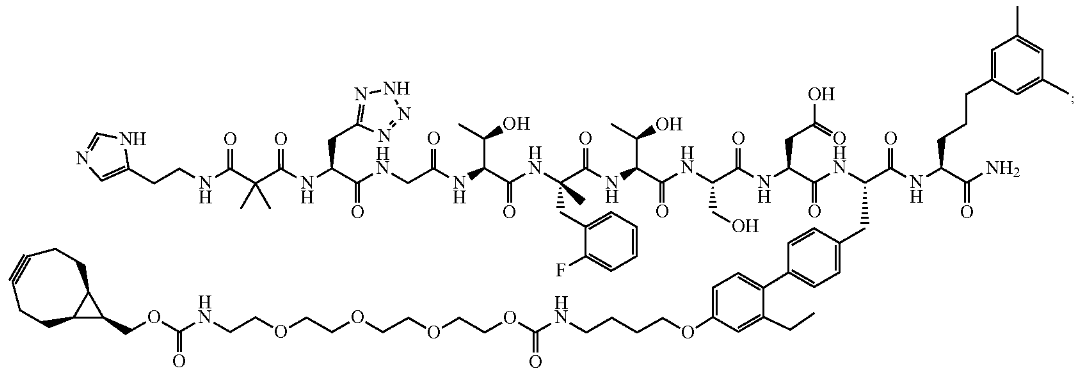 [SMILES: CCc1cc(OCCCCNC(=O)OCCOCCOCCOCCNC(=O)OC[C@@H]2[C@@H]3CCC#CCC[C@@H]32)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1] |
| LP6 (SEQ ID NOS 88 and 156, respectively, in order of appearance) | DIBAC-suc-G4S-P9 | 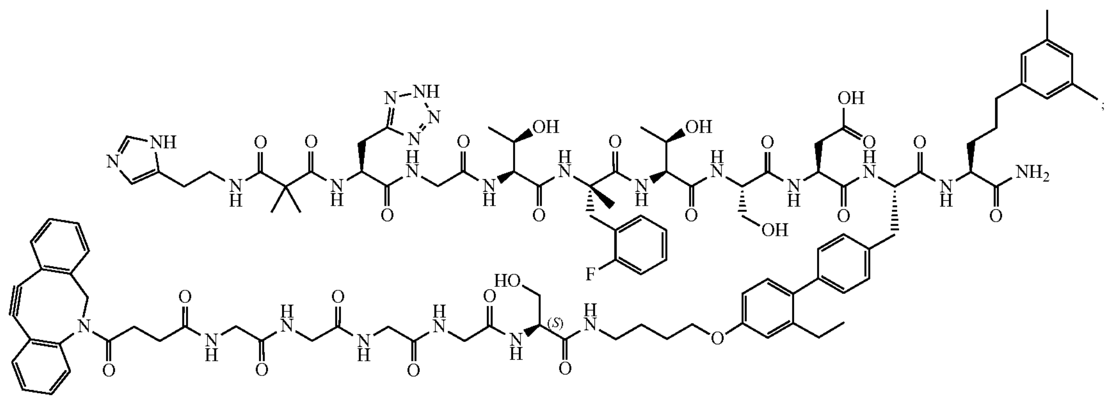 |

-continued
| LP# | Name | Structure |
|---|---|---|
| LP7 (SEQ ID NOS 89 and 157, respectively, in order of appearance) | DIBAC-suc-SG4-P9 | 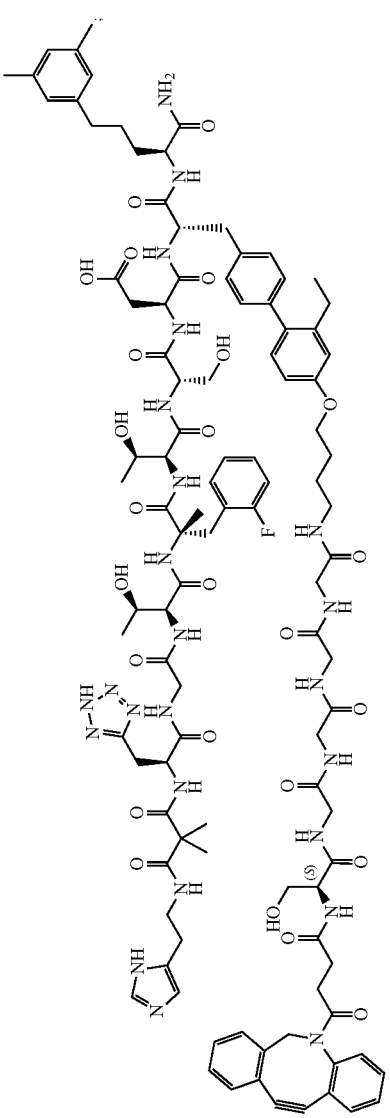 |
| LP8 (SEQ ID NO: 90) | DIBAC-suc-PEG4-triazole-P8 | 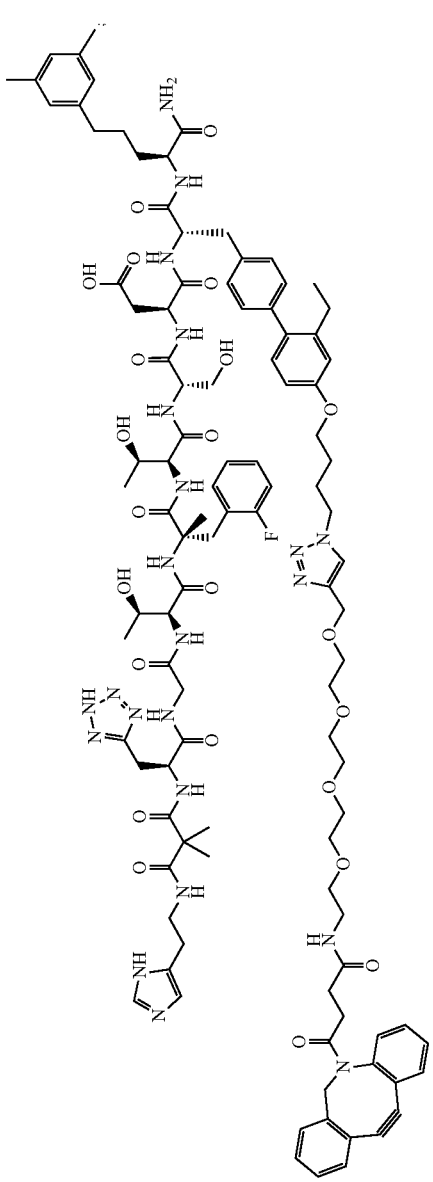 |

-continued

| LP# | Name | Structure |
|---|---|---|
| LP9 (SEQ ID NO: 90) | BCN-PEG4-triazole-P8 | 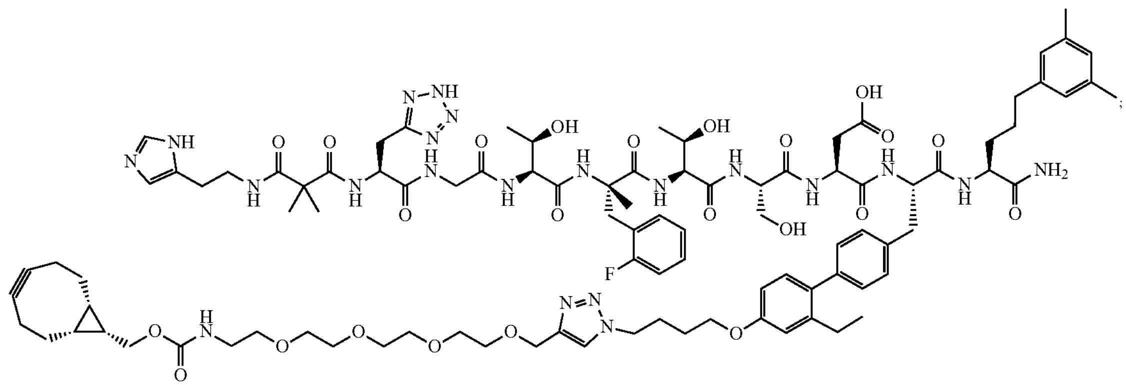 [SMILES: CCc1cc(OCCCCn2cc(COCCOCCOCCOCCNC(=O)OC[C@@H]3[C@@H]4CCC#CCC[C@@H]43)nn2)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1] |
| LP10 (SEQ ID NO: 90) | COT-PEG4-triazole-P8 | 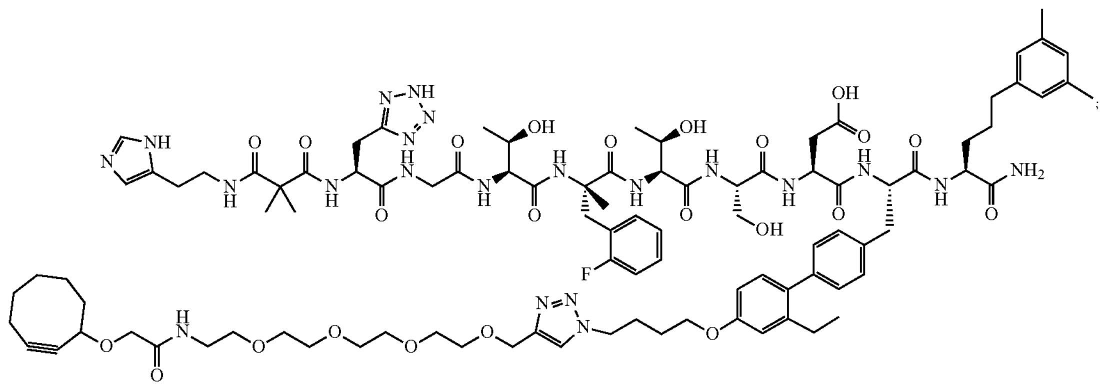 [SMILES: CCc1cc(OCCCCn2cc(COCCOCCOCCOCCNC(=O)COC3C#CCCCCC3)nn2)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1] |

-continued
| LP# | Name | Structure |
|---|---|---|
| LP11 (SEQ ID NO: 91) | NH2-PEG8-triazole-P8 | 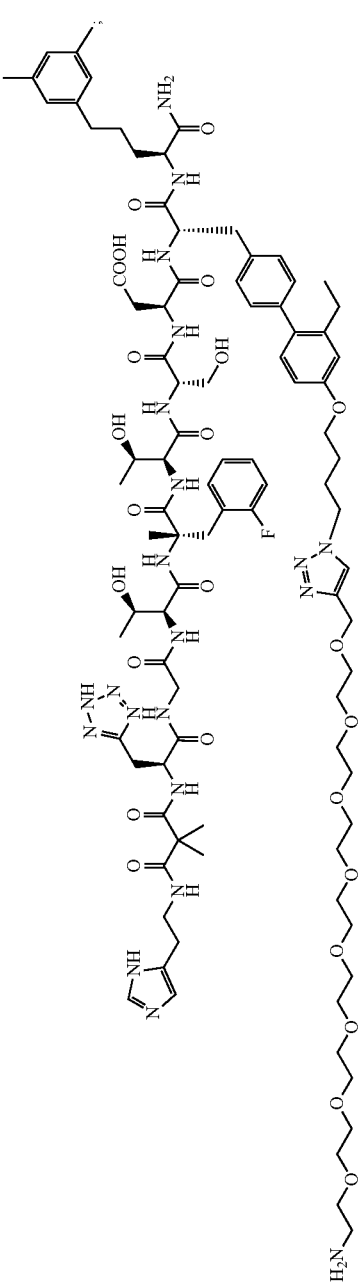 |
| LP12 (SEQ ID NO: 92) | DIBAC-suc-PEG24-P11 | 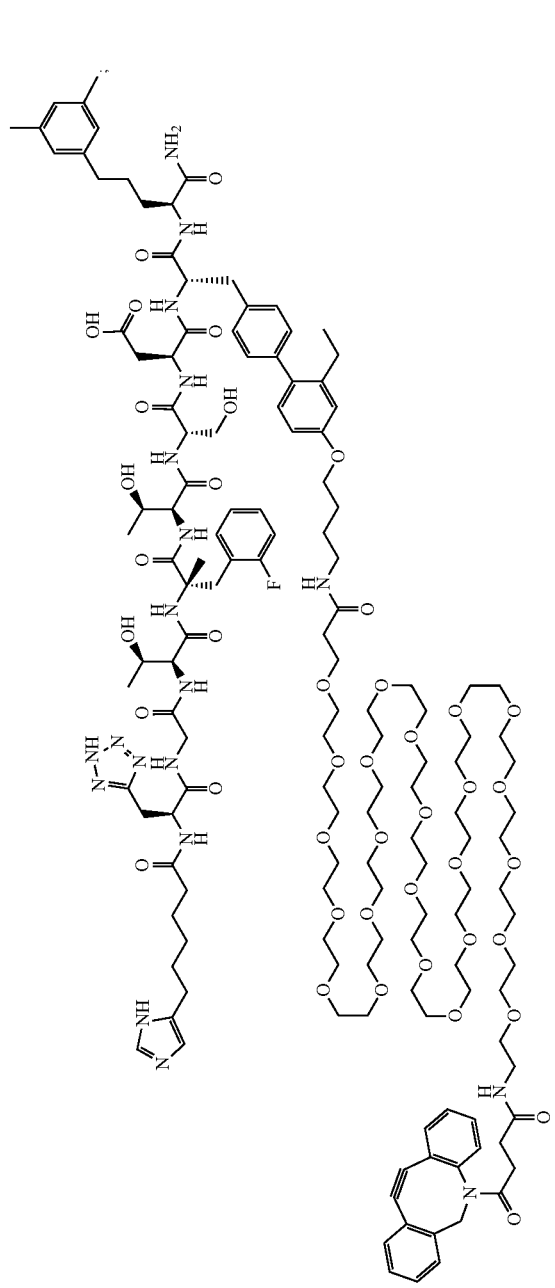 |

| LP# | Name | Structure |
|---|---|---|
| LP13 (SEQ ID NO: 93) | DIBAC-suc-PEG-P4 | 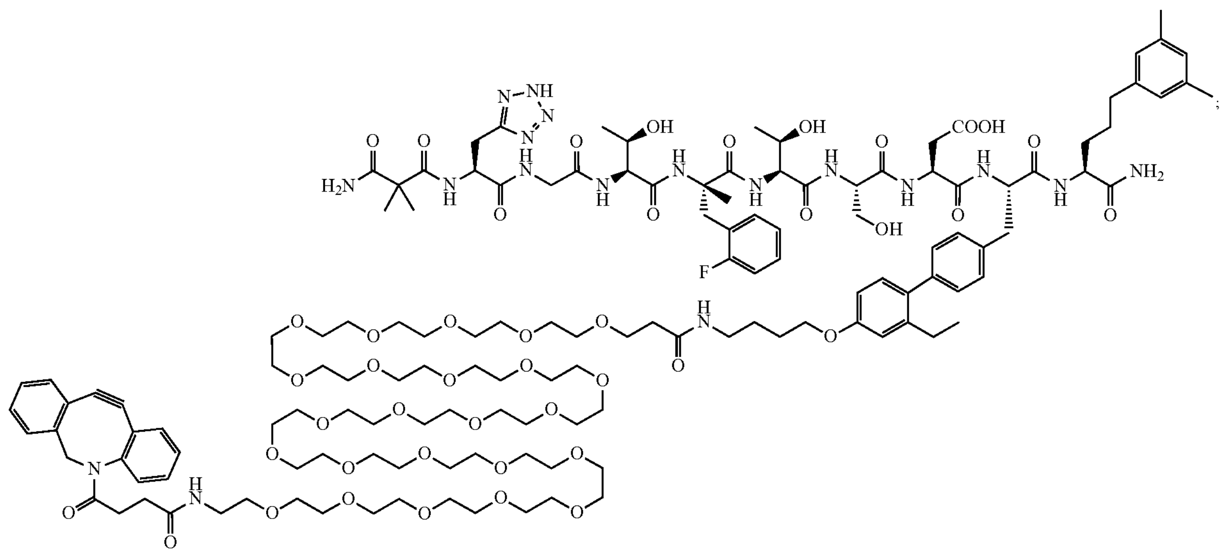 [SMILES: CCc1cc(OCCCCNC(=O)CCOCCOCCOCCOCCOCCOCCOCCOCCOCCOCCOCCOCCOCCOCCOCCOCCOCCOCCOCCOCCOCCOCCOCCOCCNC(=O)CCC(=O)N2Cc3ccccc3C#Cc3ccccc32)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(N)=O)[C@@H](C)O)[C@@H](C)O)C(=O)N[C@@H](CCCc2cc(C)cc(C)c2)C(N)=O)cc1] |
| LP14 (SEQ ID NOS 94 and 158, respectively, in order of appearance) | DIBAC-suc-G4S-P4 | 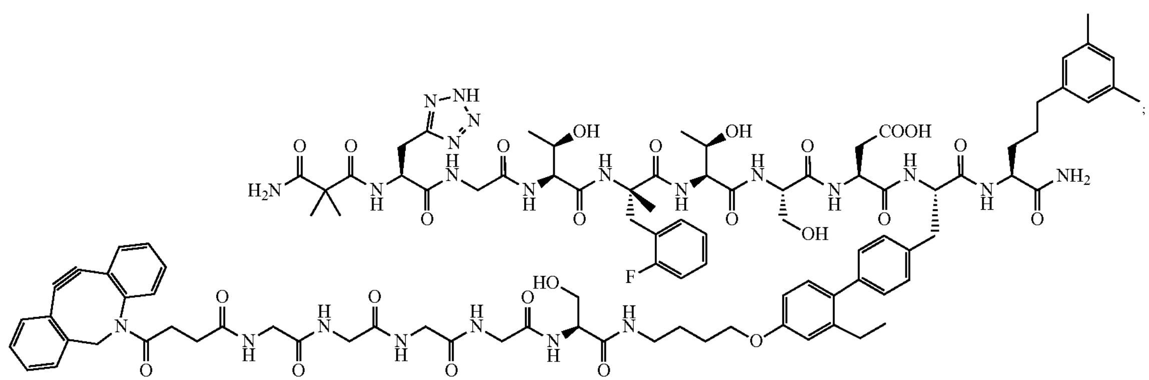 [SMILES: CCc1cc(OCCCCNC(=O)[C@H](CO)NC(=O)CNC(=O)CNC(=O)CNC(=O)CNC(=O)CCC(=O)N2Cc3ccccc3C#Cc3ccccc32)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(N)=O)[C@@H](C)O)[C@@H](C)O)C(=O)N[C@@H](CCCc2cc(C)cc(C)c2)C(N)=O)cc1] |

| LP# | Name | Structure |
|---|---|---|
| LP15 (SEQ ID NOS 95 and 159, respectively, in order of appearance) | DIBAC-suc-G4S-P23 | 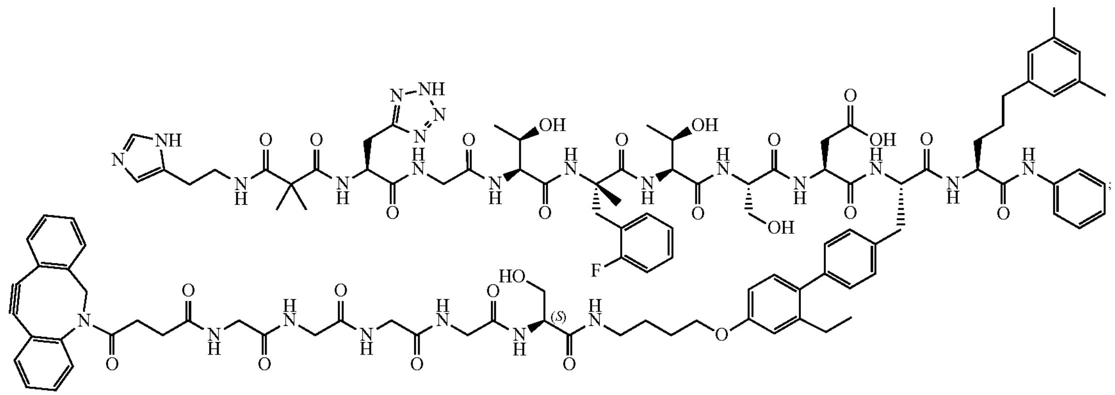 |
| LP16 (SEQ ID NOS 96 and 160, respectively, in order of appearance) | DIBAC-suc-SG4-P23 | 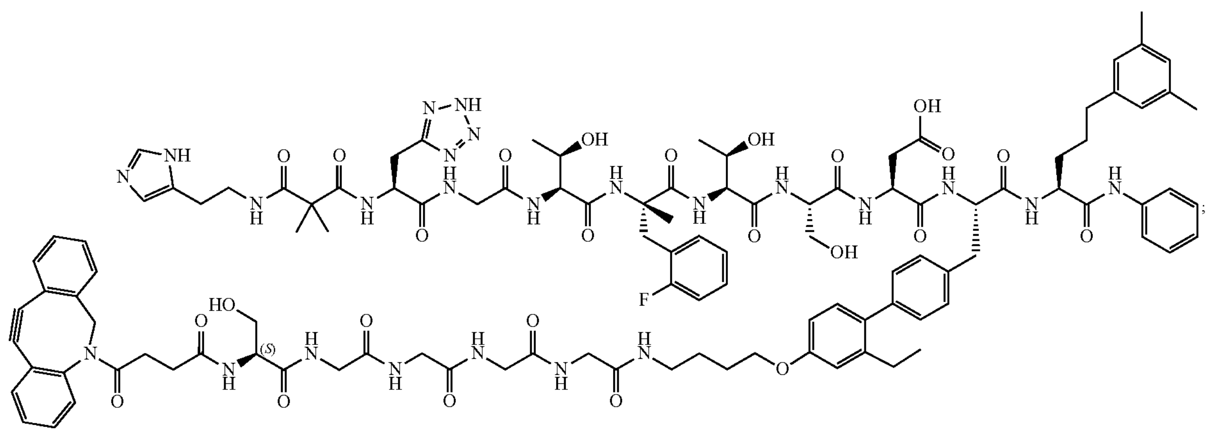 |

| LP# | Name | Structure |
|---|---|---|
| LP17 (SEQ ID NOS 97 and 161, respectively, in order of appearance) | DIBAC-suc-G₄S-G₄S-P9 | 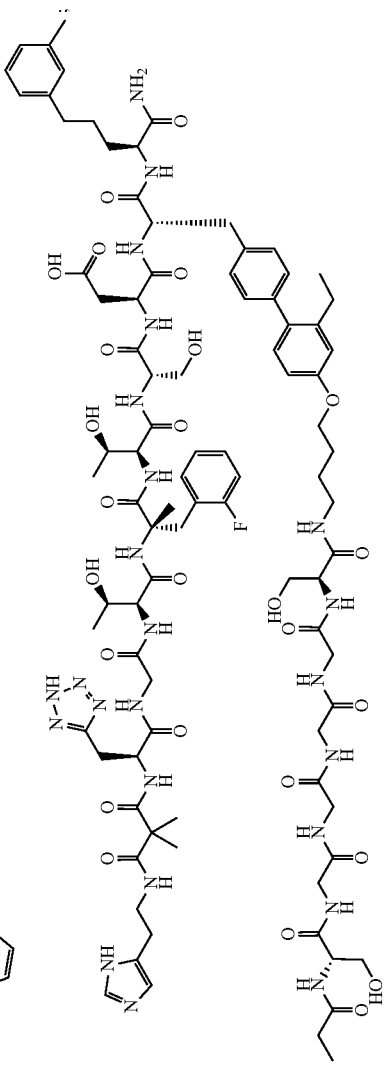 |
| LP18 (SEQ ID NOS 98 and 162, respectively, in order of appearance) | BCN-NHC₂H₄CO-(glucose) SG₄-P9 | 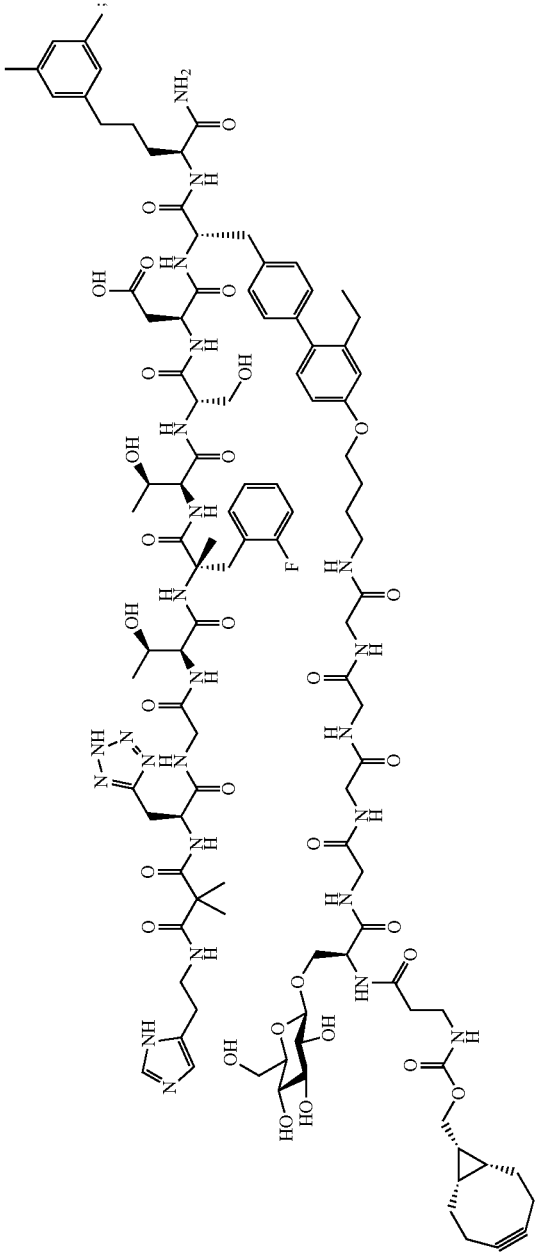 |

| LP# | Name | Structure |
|---|---|---|
| LP19 (SEQ ID NOS 99 and 163, respectively, in order of appearance) | COT-G$_4$-(R)Ser-P9 | 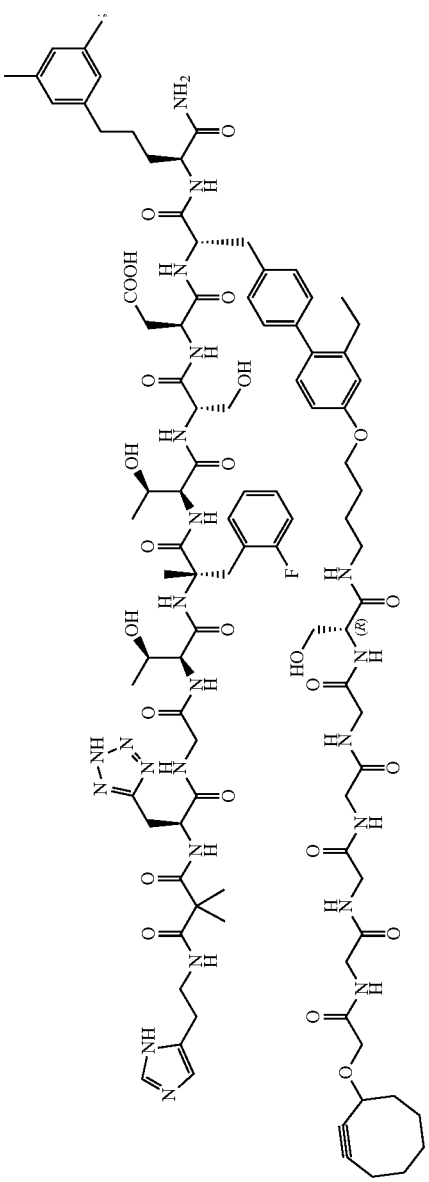 |
| LP20 (SEQ ID NOS 100 and 164, respectively, in order of appearance) | DIBAC-suc-(glucose) SG$_4$-P9 | 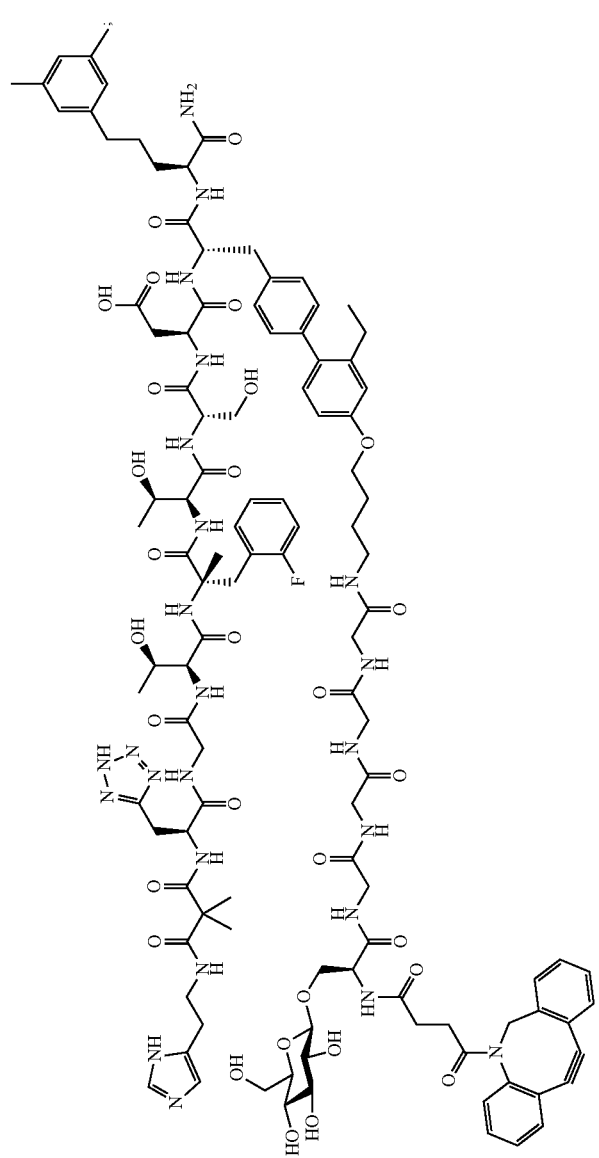 |

-continued
| LP# | Name | Structure |
|---|---|---|
| LP21 (SEQ ID NO: 101) | DIBAC-suc-PEG24-P24 | 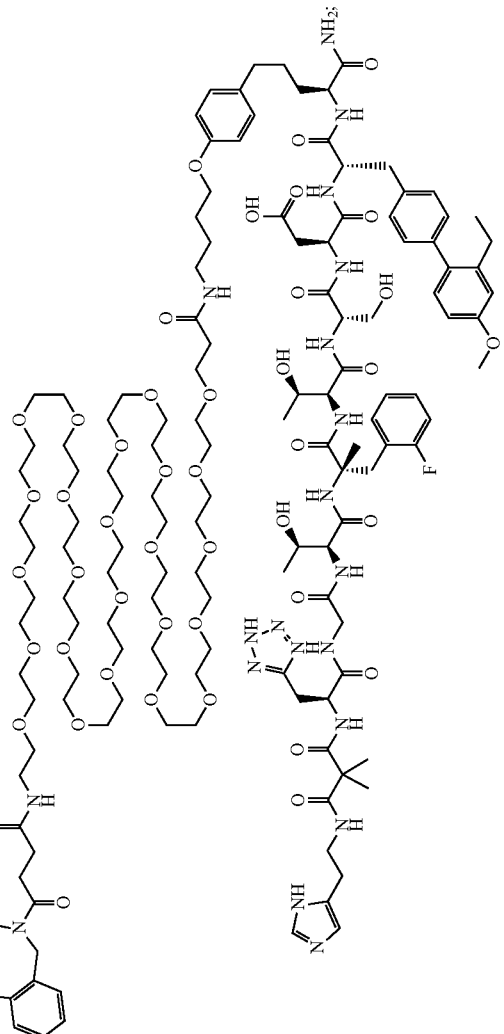 |

| LP# | Name | Structure |
|---|---|---|
| LP22 | cyclodextrin-(SEQ ID NO: 102)triazole-DIBAC-suc-PEG24-P9 | 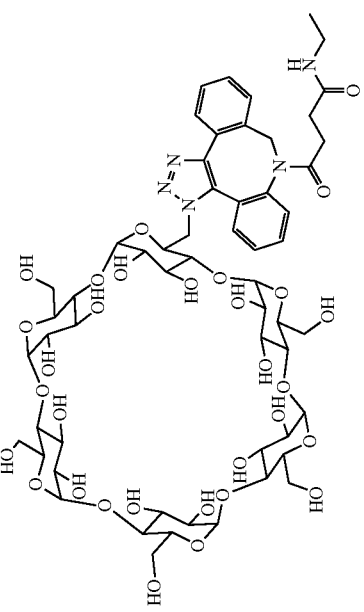 |

| LP# | Name | Structure |
|---|---|---|
| LP23 (SEQ ID NOS 103 and 178, respectively, in order of appearance) | cyclodextrin-triazole-DIBAC-suc-PEG24-P24 | 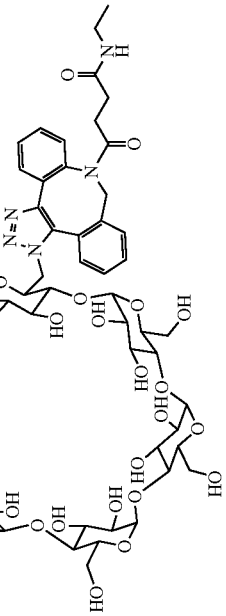 |

-continued

| LP# | Name | Structure |
|---|---|---|
| LP24 (SEQ ID NO: 104) | triazole-BCN-PEG4-triazole-P8 | 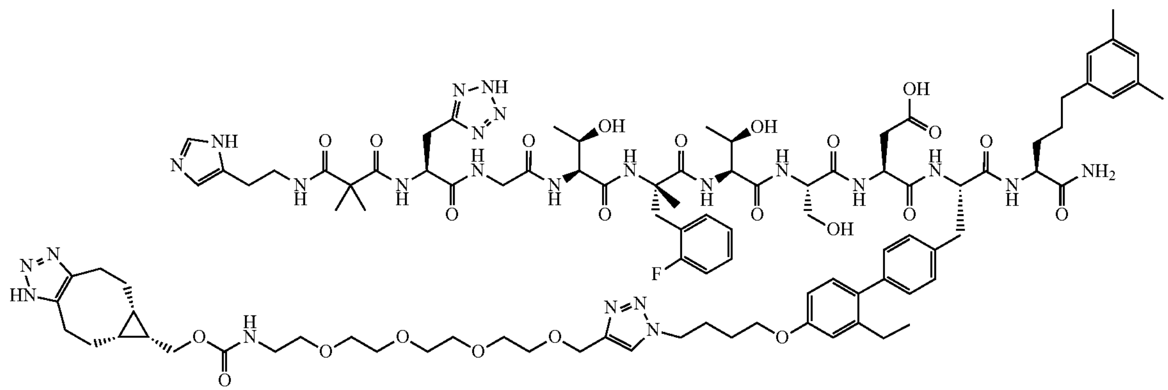 [SMILES: CCc1cc(OCCCCn2cc(COCCOCCOCCOCCNC(=O)OC[C@@H]3[C@@H]4CCc5[nH]nnc5CC[C@@H]43)nn2)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1] |
| LP25 (SEQ ID NO: 105) | triazole-BCN-PEG4-carbamate-P9 | 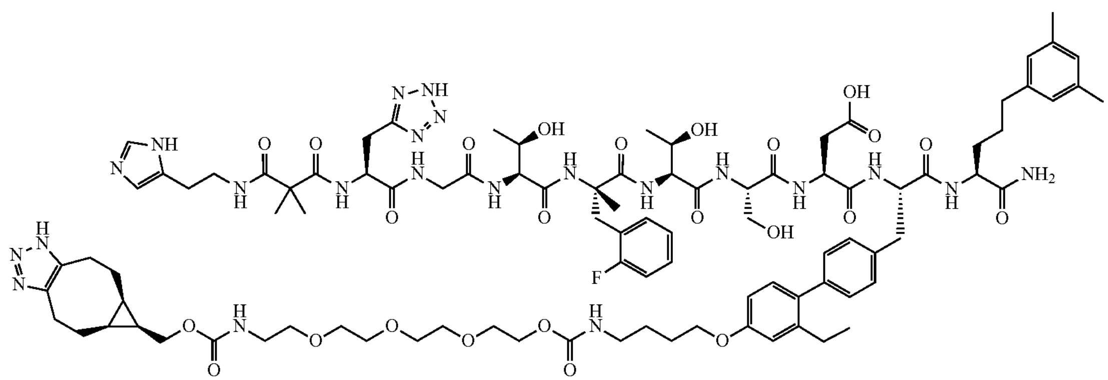 [SMILES: CCc1cc(OCCCCNC(=O)OCCOCCOCCOCCNC(=O)OC[C@@H]2[C@@H]3CCc4[nH]nnc4CC[C@@H]32)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2cc(C)cc(C)c2)C(N)=O)cc1] |

-continued
| LP# | Name | Structure |
|---|---|---|
| LP26 (SEQ ID NOS 106 G4S-P9 and 165, respectively, in order of appearance) | triazole-DABAC- | 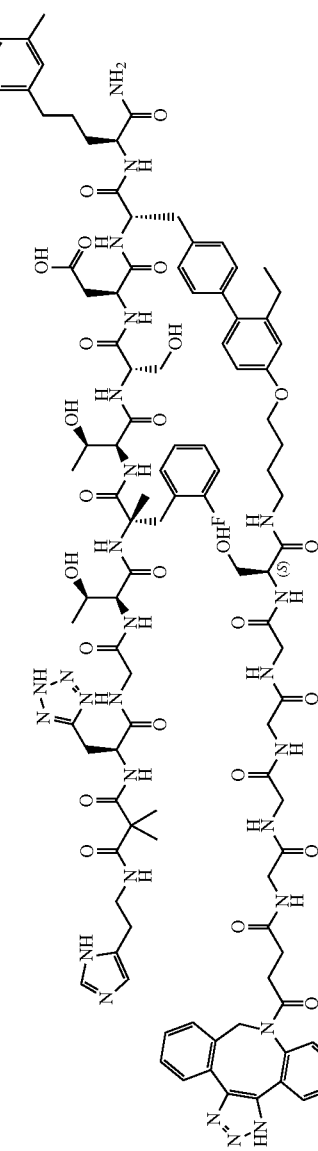 |
| LP27 (SEQ ID NO: 107) | DIBAC-suc-PEG8-triazole-P8 | 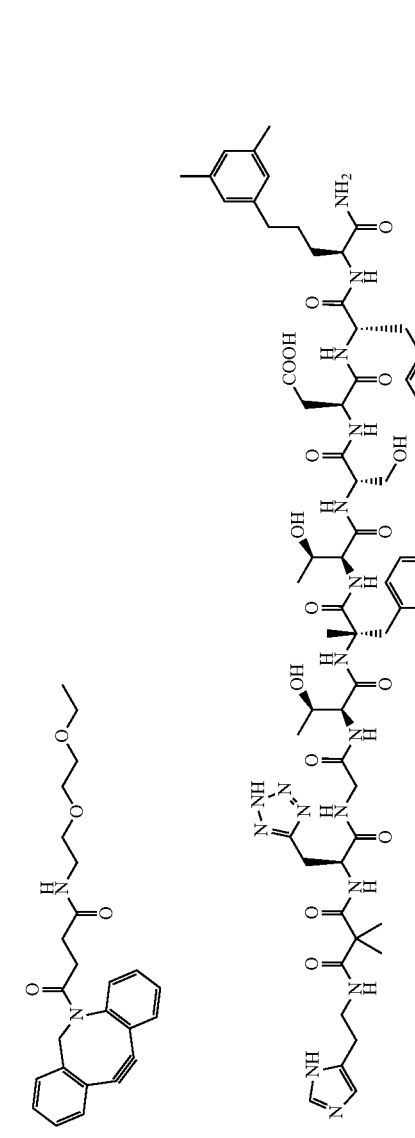 |

-continued

| LP# | Name | Structure |
|---|---|---|
| LP28 (SEQ ID NO: 107) | triazole-DIBAC-suc-PEG8-triazole-P8 | 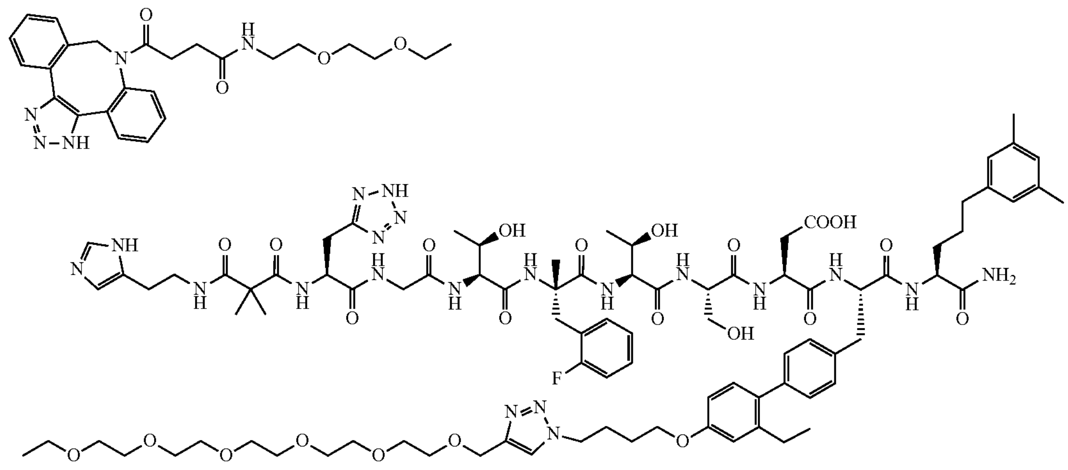 |
| LP29 (SEQ ID NO: 108) | NH2-PEG8-triazole-P19 | |

| LP# | Name | Structure |
|---|---|---|
| LP30 (SEQ ID NO: 109) | NH2-PEG8-triazole-P35 | 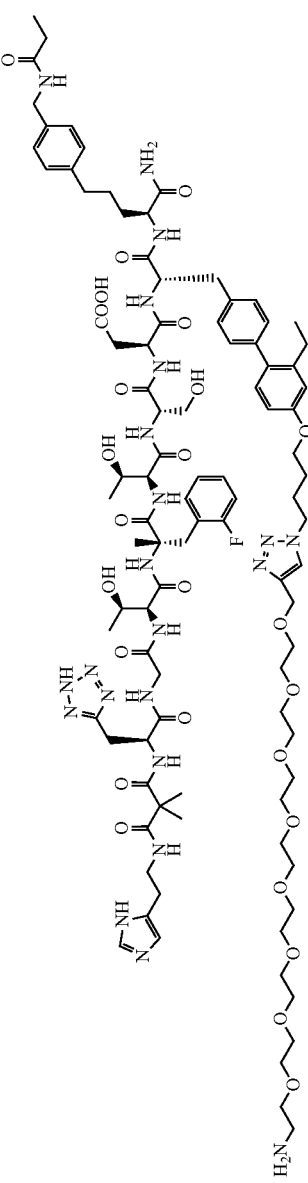 |
| LP31 (SEQ ID NO: 110) | NH2-PEG8-triazole-P8 | 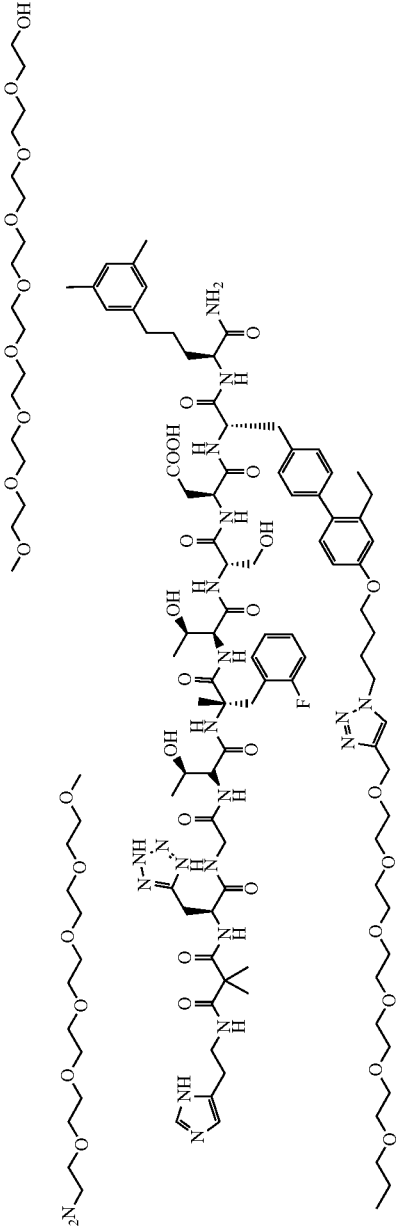 |

| LP# | Name | Structure |
|---|---|---|
| LP32 (SEQ ID NO: 111) | NH2-PEG8-triazole-P8 acid | 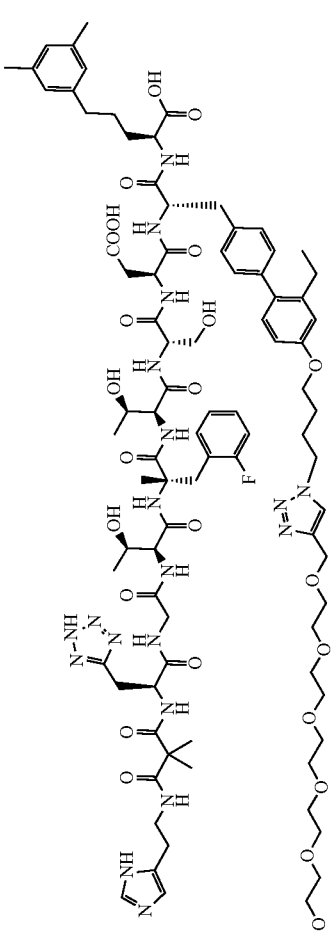 |
| LP33 (SEQ ID NO: 111) | E-PEG8-triazole-P8 | 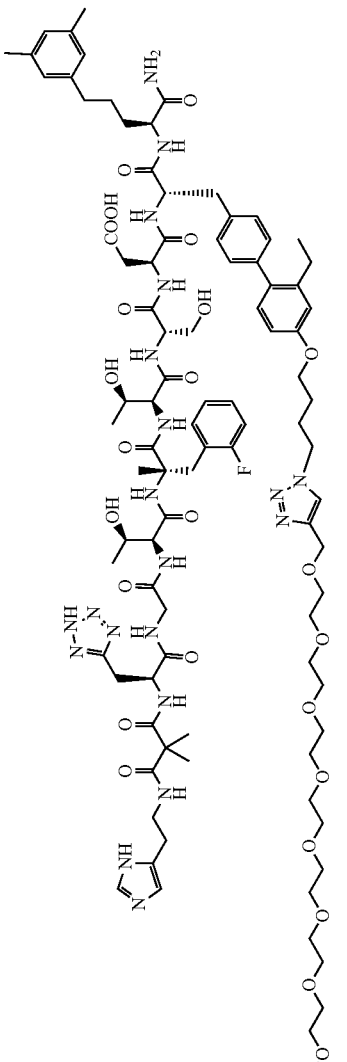 |
| LP33 (SEQ ID NOS 112 and 166, respectively, in order of appearance) | GGTEPL-PEG8-triazole-P8 | 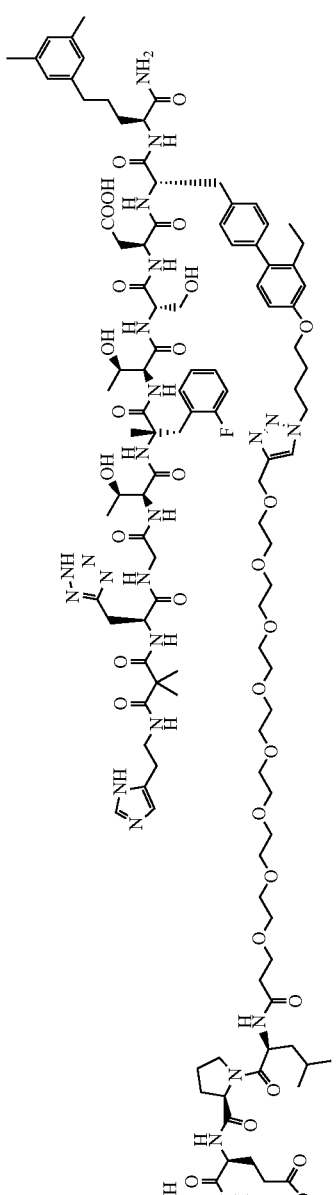 |

-continued
| LP# | Name | Structure |
|---|---|---|
| LP35 (SEQ ID NOS 113 and 167, respectively, in order of appearance) | Cbz-LLQGSG-PEG8-triazole-P8 | 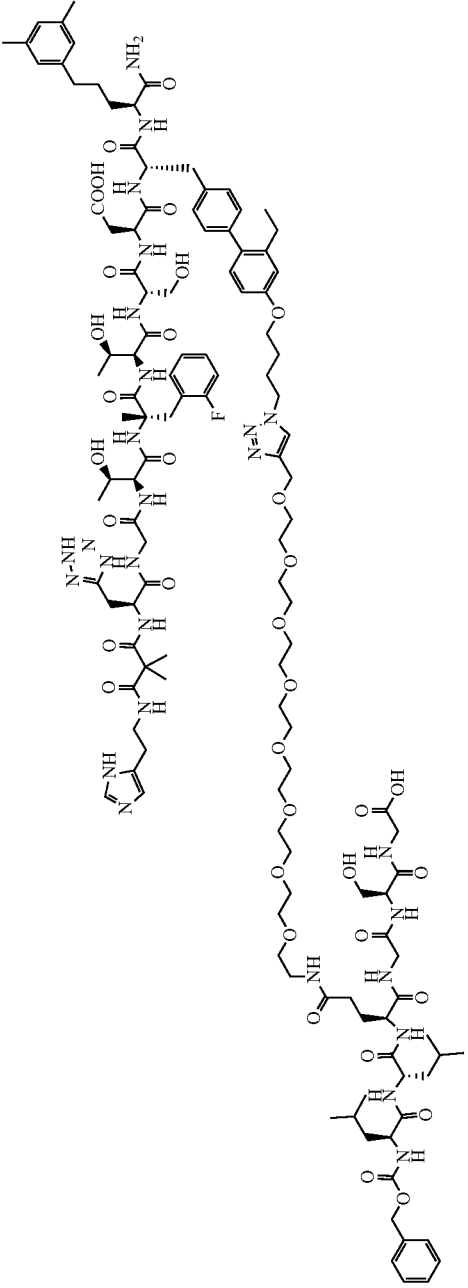 |
| LP36 (SEQ ID NOS 114 and 168, respectively, in order of appearance) | G4S-triazole-P40 | 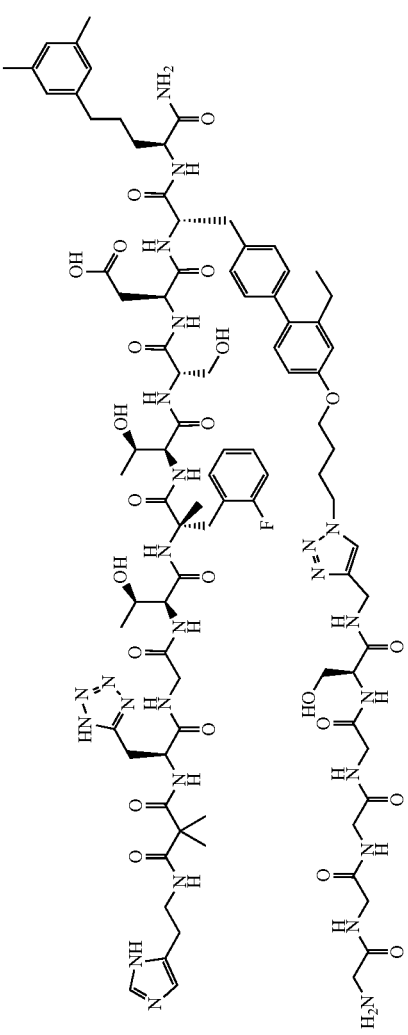 |

| LP# | Name | Structure |
|---|---|---|
| LP37 (SEQ ID NOS 115 and 169, respectively, in order of appearance) | SG4-triazole-P40 | 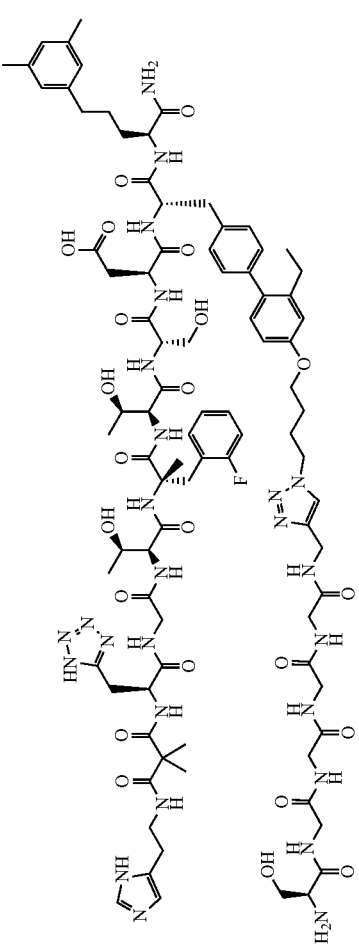 |
| LP38 (SEQ ID NOS 116 and 170, respectively, in order of appearance) | G2SG2SG2 triazole-P40 | 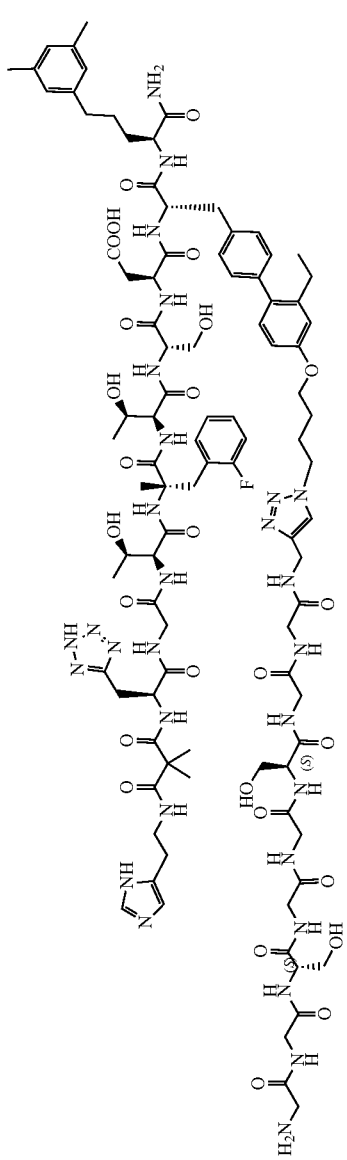 |

| LP# | Name | Structure |
|---|---|---|
| LP39 (SEQ ID NOS 117 and 171, respectively, in order of appearance) | G4SG4 triazole-P40 | 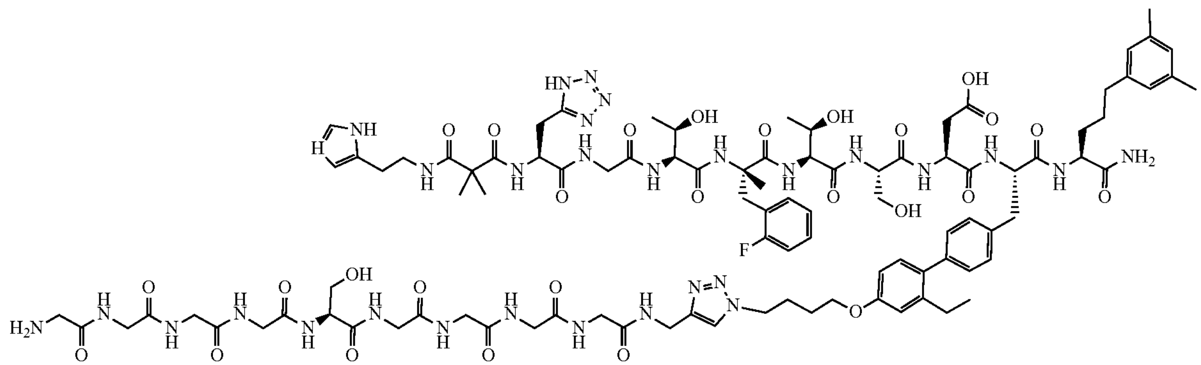 |
| LP40 (SEQ ID NOS 118 and 172, respectively, in order of appearance) | G4SG4SG4 triazole-P40 | 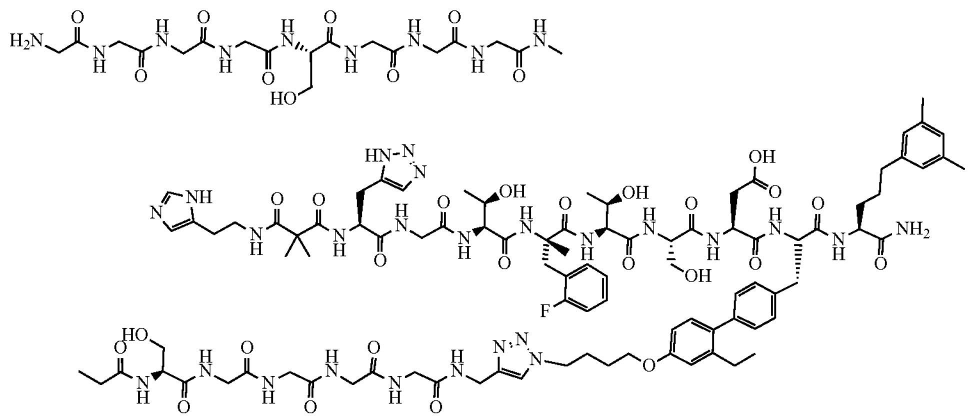 |

| LP# | Name | Structure |
|---|---|---|
| LP41 (SEQ ID NOS 119 and 173, respectively, in order of appearance) | G2SG2SG2SG2 triazole-P40 | 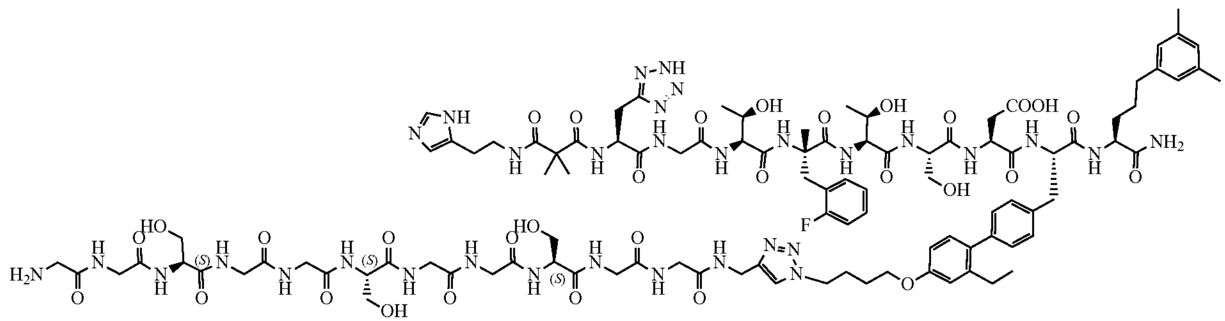 |
| LP42 (SEQ ID NOS 120 and 174, respectively, in order of appearance) | C18-diacid-Glu-(AEEA)2-G4SG4-triazole-P40 | 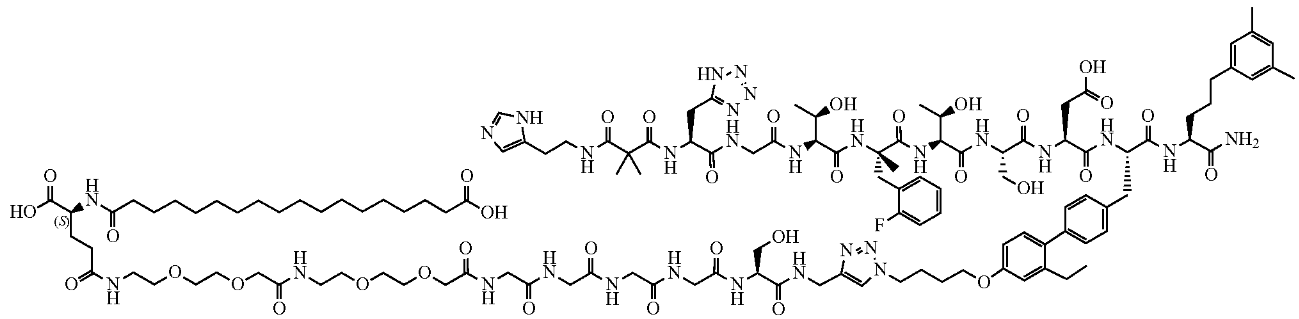 |

-continued

| LP# | Name | Structure |
|---|---|---|
| LP43 (SEQ ID NOS 121 and 175, respectively, in order of appearance) | C18-diacid-Glu-(AEEA)2-G4SG4-triazole-P40 | 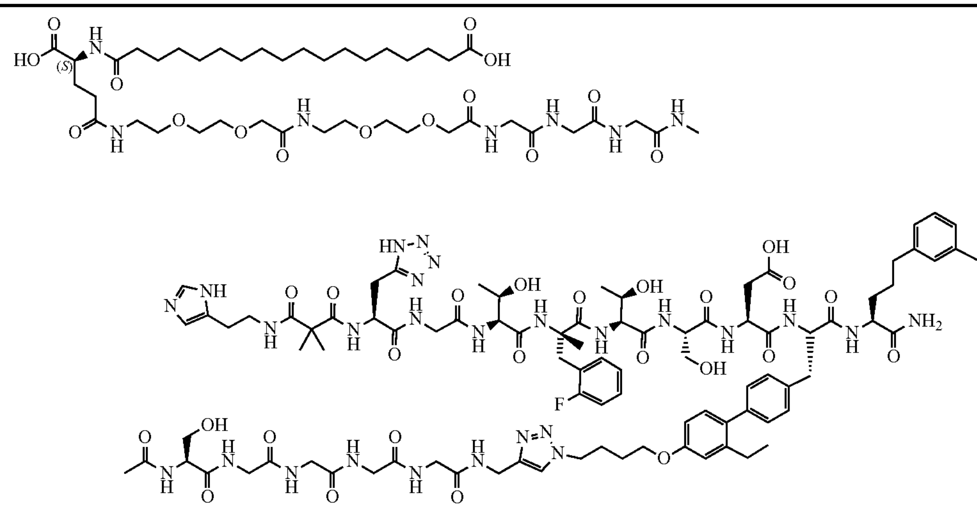 |
| LP44 (SEQ ID NO: 122) | C18-diacid-Glu-(AEEA)2-NH2-PEG12-P40 | 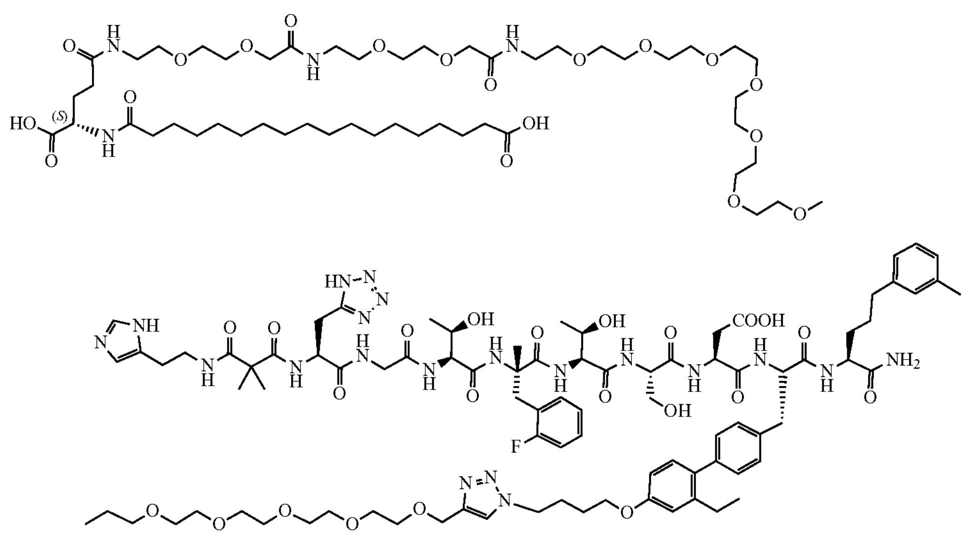 |

| LP# | Name | Structure |
|---|---|---|
| LP45 (SEQ ID NO: 122) | C18-diacid-Glu-(AEEA)2-NH2-PEG8-P35 | 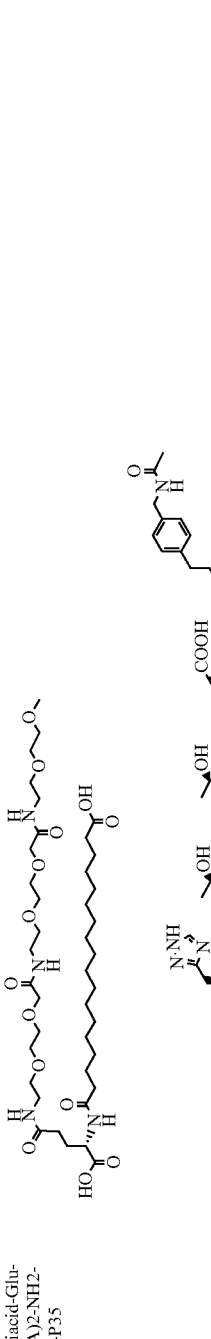 |

In one embodiment, the linker-payloads as described above have the following properties:

| LP# | Molecular Formula | MW | M/Z 100% (M + H) | RT on HPLC (min) | CLogP | Corresponding Payload |
|---|---|---|---|---|---|---|
| LP1 | $C_{105}H_{135}FN_{20}O_{24}$ | 2080.31 | 1041 [M + 2H]$^{2+}$ | 15.16 (A) | 5.55 ± 1.08 | P9 |
| LP2 | $C_{113}H_{151}FN_{20}O_{28}$ | 2256.52 | 1129.2 [M + 2H]$^{2+}$ 753.0 [M + 3H]$^{3+}$ | 15.27 (A) | 4.12 ± 1.10 | P9 |
| LP3 | $C_{121}H_{167}FN_{20}O_{32}$ | 2432.73 | 811.8 [M + 3H]$^{3+}$ 1217.2 [M + 2H]$^{2+}$ | 15.12 (A) | 2.68 ± 1.12 | P9 |
| LP4 | $C_{145}H_{215}FN_{20}O_{44}$ | 2961.36 | 741.3 [M + 4H]$^{4+}$ 988.3 [M + 3H]$^{3+}$ | 14.76 (A) | −1.61 ± 1.17 | P9 |
| LP5 | $C_{95}H_{130}FN_{19}O_{24}$ | 1941.16 | 971.5 [M + 2H]$^{2+}$ | 10.12 (D) | 5.48 ± 1.05 | P9 |
| LP6 | $C_{105}H_{131}FN_{24}O_{25}$ | 2148.31 | 716.9 [M + 3H]$^{3+}$ | 3.58 (E) | 4.24 ± 1.10 | P9 |
| LP7 | $C_{105}H_{131}FN_{24}O_{25}$ | 2148.31 | 1074.5 [M + 2H]$^{2+}$ | 3.55 (E) | 4.24 ± 1.10 | P9 |
| LP8 | $C_{105}H_{133}FN_{22}O_{23}$ | 2090.31 | 1045.5 [M + 2H]$^{2+}$ | 2.86 (E) | 5.95 ± 1.47 | P8 |
| LP9 | $C_{97}H_{132}FN_{21}O_{23}$ | 1979.21 | 990.5 [M + 2H]$^{2+}$ 660.7 [M + 3H]$^{3+}$ | 9.89 (D) | 4.59 ± 1.44 | P8 |
| LP10 | $C_{96}H_{132}FN_{21}O_{23}$ | 1967.2 | 984.7 [M + 2H]$^{2+}$ | 9.74 (D) | 7.75 ± 1.55 | P8 |
| LP11 | $C_{94}H_{136}FN_{21}O_{25} \cdot 2(CF_3COOH)$ | 2207.26 | 990.6 [M + 2H]$^{2+}$ 660.8 [M + 3H]$^{3+}$ 495.8 [M + 4H]$^{4+}$ | 9.40 (B) | 0.52 ± 1.46 | P8 |
| LP12 | $C_{144}H_{214}FN_{19}O_{43}$ | 2918.34 | 974 [M + 3H]$^{3+}$ 1459.6 [M + 2H]$^{2+}$ 717.8 [M + 4H]$^{4+}$ | 2.53 (E) | −0.14 ± 1.16 | P11 |
| LP13 | $C_{140}H_{209}FN_{18}O_{44}$ | 2867.25 | 956.9 [M + 3H]$^{3+}$ 1434.7 [M + 2H]$^{2+}$ | 3.97 (E) | −1.59 ± 1.16 | P4 |
| LP14 | $C_{100}H_{125}FN_{22}O_{25}$ | 2054.19 | 1028.5 [M + 2H]$^{2+}$ | 3.57 (E) | 4.26 ± 1.09 | P4 |
| LP15 | $C_{111}H_{135}FN_{24}O_{25}$ | 2224.4 | 1113.1 [M + 2H]$^{2+}$ | 2.76 (E) | 6.67 ± 1.09 | P23 |
| LP16 | $C_{111}H_{135}FN_{24}O_{25}$ | 2224.4 | 1112.9 [M + 2H]$^{2+}$ | 3.73 (E) | 6.67 ± 1.09 | P23 |
| LP17 | $C_{116}H_{148}FN_{29}O_{31}$ | 2463.59 | 1232.4 [M + 2H]$^{2+}$ | 2.17 (E) | 0.93 ± 1.14 | P9 |
| LP18 | $C_{106}H_{145}FN_{24}O_{31}$ | 2270.43 | 757.7 [M + 3H]$^{3+}$ 1136.0 [M + 2H]$^{2+}$ | 8.17 (D) | 0.36 ± 1.09 | P9 |
| LP19 | $C_{96}H_{130}FN_{23}O_{25}$ | 2025.2 | 1013.7 [M + 2H]$^{2+}$ | 8.70 (B) | 2.38 ± 1.09 | P9 |
| LP20 | $C_{111}H_{141}FN_{24}O_{30}$ | 2310.45 | 1156.0 [M + 2H]$^{2+}$ | 2.28 (E) | 2.54 ± 1.10 | P9 |
| LP21 | $C_{144}H_{213}FN_{20}O_{45}$ | 2963.34 | 741.6 [M + 4H]$^{4+}$ 988.5 [M + 3H]$^{3+}$ | 14.49 (A) | −2.62 ± 1.17 | P24 |
| LP22 | $C_{181}H_{274}FN_{23}O_{73}$ | 3959.22 | 1321.0 [M + 3H]$^{3+}$ 991.3 [M + 4H]$^{4+}$ | 11.97 (A) | N/A | P9 |
| LP23 | $C_{180}H_{272}FN_{23}O_{74}$ | 3961.2 | 991.4 [M + 4H]$^{4+}$ 1321.5 [M + 3H]$^{3+}$ | 8.14 (D) | N/A | P24 |
| LP24 | $C_{97}H_{133}FN_{24}O_{23}$ | 2022.2 | 675.1 [M + 3H]$^{3+}$ | 3.56 (F) | 2.82 ± 1.45 | P8 |

-continued

| LP# | Molecular Formula | MW | M/Z 100% (M + H) | RT on HPLC (min) | CLogP | Corresponding Payload |
|---|---|---|---|---|---|---|
| LP25 | $C_{95}H_{131}FN_{22}O_{24}$ | 1984.2 | 1012.0 $[M + 2H]^{2+}$ 662.4 $[M + 3H]^{3+}$ | 3.57 (F) | 3.71 ± 1.43 | P9 |
| LP26 | $C_{105}H_{132}FN_{27}O_{25}$ | 2191.3 | 1012.0 $[M + 2H]^{2+}$ 1096.7 $[M + 2H]^{2+}$ | 3.26 (F) | 2.54 ± 1.53 | P9 |
| LP27 | C113H149FN22O27 | 2266.5 | 756.03 $[M + 3H]^{3+}$ | 9.17 (E) | 4.52 ± 1.49 | P8 |
| LP28 | C113H150FN25O27• | 2423.57 | 2309.11 $[M + H]^{+}$ 1155.56 $[M + 2H]^{2+}$ | 4.20 (F) | 3.81 +/− 1.50 | P8 |
| LP29 | $C_{97}H_{139}FN_{20}O_{26}$• | 2248.3 | 1011.0 $[M + 2H]^{2+}$ | 3.73 (F) | 1.90 ± 1.46 | P19 |
| LP30 | $C_{112}H_{171}FN_{22}O_{35}$• | 2632.7 | 802.20 $[M + 3H]^{3+}$ | 6.32 (D) | −5.09 ± 1.51 | P35 |
| LP31 | $C_{102}H_{152}FN_{21}O_{29}$• | 2383.5 | 1078.6 $[M + 2H]^{2+}$ | 7.48 (D) | −0.92 ± 1.48 | P8 |
| LP32 | $C_{94}H_{135}FN_{20}O_{26}$• | 2208.24 | 991.0 $[M + 2H]^{2+}$ | 7.56 (D) | 1.49 +/− 1.46 | P41 |
| LP33 | $C_{99}H_{143}FN_{22}O_{28}$ | 2108.32 | 1054.9 $[M + 2H]^{2+}$ | 3.27 (E) | −0.23 +/− 1.49 | P8 |
| LP34 | $C_{119}H_{173}FN_{26}O_{36}$• | 2659.81 | 1282.6 $[M + 2H]^{2+}$ | 4.34 (E) | −0.48 +/− 1.56 | P8 |
| LP35 | $C_{126}H_{182}FN_{27}O_{36}$• | 2783.97 | 1335.7 $[M + 2H]^{2+}$ 890.9 $[M + 3H]^{3+}$ 668.4 $[M + 4H]^{4+}$ | 7.15 (D) | 2.72 +/− 1.54 | P8 |
| LP36 | C89H121FN26O23• | 2170.12 | 971.9 $[M + 2H]^{2+}$ | 6.62 (D) | −0.54 +/− 1.47 | P40 |
| LP37 | $C_{89}H_{121}FN_{26}O_{23}$• | 2170.12 | 971.0 $[M + 2H]^{2+}$ | 6.61 (D) | −0.61 +/− 1.47 | P40 |
| LP38 | $C_{96}H_{132}FN_{29}O_{27}$ | 2143.25 | 1072.30 $[M + 2H]^{2+}$ 715.30 $[M + 3H]^{3+}$ | 8.96 (D) | −2.88 +/− 1.49 | P40 |
| LP39 | $C_{97}H_{133}FN_{30}O_{27}$ | 2170.28 | 1085.60 $[M + 2H]^{2+}$ 725.30 $[M + 3H]^{3+}$ | 8.97 (D) | −3.00 +/− 1.50 | P40 |
| LP40 | $C_{108}H_{150}FN_{35}O_{33}$ | 2485.56 | 1243.05 $[M + 2H]^{2+}$ 829.03 $[M + 3H]^{3+}$ | 6.50 (D) | −6.31 +/− 1.55 | P40 |
| LP41 | $C_{103}H_{143}FN_{32}O_{31}$ | 2344.43 | 1173.21 $[M + 2H]^{2+}$ 782.47 $[M + 3H]^{3+}$ | 6.54 (D) | −4.96 +/− 1.52 | P40 |
| LP42 | $C_{124}H_{182}FN_{29}O_{35}$• | 2657.94 | 1329.17 $[M + 2H]^{2+}$ | 8.53 (D) | 3.04 +/− 1.54 | P40 |
| LP43 | $C_{132}H_{194}FN_{33}O_{39}$• | 2886.15 | 1443.21 $[M + 2H]2+$ | 8.30 (D) | 0.58 +/− 1.57 | P40 |
| LP44 | $C_{137}H_{213}FN_{24}O_{41}$• | 2985.32 | 1436.4 $[M + 2H]^{2+}$ | 9.30 (D) | 2.56 +/− 1.56 | P40 |
| LP45 | $C_{147}H_{232}FN_{25}O_{47}$• | 3120.55 | 781.1 $[M + 4H]^{4+}$ | 8.14 (D) | −1.88 +/− 1.58 | P35 |

Binding Agents

In one embodiment, the effectiveness of the protein-drug conjugate embodiments described herein depend on the selectivity of the binding agent to bind its binding partner. In one embodiment of the present disclosure, the binding agent is any molecule capable of binding with some specificity to a given binding partner. In one embodiment, the binding agent is within a mammal where the interaction can result in a therapeutic use. In an alternative embodiment, the binding agent is in vitro where the interaction can result in a diagnostic use. In some aspects, the binding agent is capable of binding to a cell or cell population.

Suitable binding agents of the present disclosure include proteins that bind to a binding partner. Suitable binding agents include, but are not limited to, antibodies, lymphokines, hormones, growth factors, viral receptors, interleukins, or any other cell binding or peptide binding molecules or substances.

In one embodiment the binding agent is an antibody. In certain embodiments, the antibody is selected from monoclonal antibodies, polyclonal antibodies, antibody fragments (Fab, Fab', and F(ab)2, minibodies, diabodies, tribodies, and the like). Antibodies herein can be humanized using methods described in U.S. Pat. No. 6,596,541 and US Publication No. 2012/0096572, each incorporated by reference in their entirety. In certain embodiments of the protein-drug conjugate compounds of the present disclosure, BA is a humanized monoclonal antibody. For example, BA can be a monoclonal antibody that binds GLP1R.

In the present disclosure, the antibody can be any antibody deemed suitable to the practitioner of skill. In some embodiments, a linker or linker-payload is attached to one or both heavy chains of the antibody or antigen-binding fragment thereof. In some embodiments, a linker or linker-payload is attached to one or both heavy chain variable domains of the antibody or antigen-binding fragment thereof.

In some embodiments, a linker or linker-payload is attached to the N-terminus of one or both heavy chain variable domains of the antibody or antigen-binding fragment thereof. In some embodiments, a linker or linker-payload is attached to the N-terminus of both heavy chain variable domains of the antibody or antigen-binding fragment thereof. In some embodiments, a linker or linker-payload is attached to one or both light chains of the antibody or antigen-binding fragment thereof. In some embodiments, a linker or linker-payload is attached to one or both light chain variable domains of the antibody or antigen-binding fragment thereof. In some embodiments, a linker or linker-payload is attached to the N-terminus of one or both light chain variable domains of the antibody or antigen-binding fragment thereof. In some embodiments, a linker or linker-payload is attached to the N-terminus of both light chain variable domains of the antibody or antigen-binding fragment thereof.

In some embodiments, a linker or linker-payload is attached to the C-terminus of one or both heavy chain variable domains of the antibody or antigen-binding fragment thereof. In some embodiments, a linker or linker-payload is attached to the C-terminus of both heavy chain variable domains of the antibody or antigen-binding fragment thereof. In some embodiments, a linker or linker-payload is attached to one or both light chains of the antibody or antigen-binding fragment thereof. In some embodiments, a linker or linker-payload is attached to one or both light chain variable domains of the antibody or antigen-binding fragment thereof. In some embodiments, a linker or linker-payload is attached to the C-terminus of one or both light chain variable domains of the antibody or antigen-binding fragment thereof. In some embodiments, a linker or linker-payload is attached to the C-terminus of both light chain variable domains of the antibody or antigen-binding fragment thereof.

In some embodiments, the antibody comprises at least one glutamine residue in at least one polypeptide chain sequence. In certain embodiments, the antibody comprises one or more Gln295 residues. In certain embodiments, the antibody comprises two heavy chain polypeptides, each with one Gln295 residue. In further embodiments, the antibody comprises one or more glutamine residues at a site other than a heavy chain 295. Such antibodies can be isolated from natural sources or engineered to comprise one or more glutamine residues. Techniques for engineering glutamine residues into an antibody polypeptide chain are within the skill of the practitioners in the art. In certain embodiments, a glutamine residue is introduced to the N-terminus of an antibody polypeptide chain. In one embodiment, a glutamine residue is introduced to the N-terminus of one or both heavy chains of the antibody. In one embodiment, a glutamine residue is introduced to the N-terminus of both heavy chains of the antibody. In another embodiment, the glutamine residue is introduced to the N-terminus of one or both light chains of the antibody. In one embodiment, a glutamine residue is introduced to the N-terminus of both light chains of the antibody. In another embodiment, a glutamine residue is introduced to the N-terminus of one or both heavy chains and one or both light chains of the antibody.

In certain embodiments, a glutamine residue is introduced to the C-terminus of an antibody polypeptide chain. In one embodiment, a glutamine residue is introduced to the C-terminus of one or both heavy chains of the antibody. In one embodiment, a glutamine residue is introduced to the C-terminus of both heavy chains of the antibody. In another embodiment, the glutamine residue is introduced to the C-terminus of one or both light chains of the antibody. In one embodiment, a glutamine residue is introduced to the C-terminus of both light chains of the antibody. In another embodiment, a glutamine residue is introduced to the C-terminus of one or both heavy chains and one or both light chains of the antibody.

In certain embodiments, the antibody or antigen-binding fragment thereof has been modified to comprise a TGase recognition tag. Suitable TGase recognition tags include those described herein.

In certain embodiments, the antibody or antigen-binding fragment thereof has been modified to comprise a Q-tag at the N-terminus of one or both antibody light chains. In certain embodiments, the antibody or antigen-binding fragment thereof has been modified to comprise a Q-tag at the N-terminus of both antibody light chains.

In certain embodiments, the antibody or antigen-binding fragment thereof has been modified to comprise a Q-tag at the N-terminus of one or both antibody heavy chains. In certain embodiments, the antibody or antigen-binding fragment thereof has been modified to comprise a Q-tag at the N-terminus of both antibody heavy chains.

In certain embodiments, the antibody or antigen-binding fragment thereof has been modified to comprise a Q-tag at the C-terminus of one or both antibody light chains. In certain embodiments, the antibody or antigen-binding fragment thereof has been modified to comprise a Q-tag at the C-terminus of both antibody light chains.

In certain embodiments, the antibody or antigen-binding fragment thereof has been modified to comprise a Q-tag at the C-terminus of one or both antibody heavy chains. In certain embodiments, the antibody or antigen-binding fragment thereof has been modified to comprise a Q-tag at the C-terminus of both antibody heavy chains.

In certain embodiments, the antibody or antigen-binding fragment thereof is aglycosylated. In certain embodiments, the antibody antigen-binding fragment thereof is deglycosylated. In certain embodiments, the antibody antigen-binding fragment is a Fab fragment.

The antibody can be in any form known to those of skill in the art. In certain embodiments, the antibody comprises a light chain. In certain embodiments, the light chain is a kappa light chain. In certain embodiments, the light chain is a lambda light chain.

In certain embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')2 fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as GLP1R.

Some embodiments herein are target specific for therapeutic or diagnostic use.

In some embodiments, the binding agent is an anti-glucagon-like peptide 1 receptor (GLP1R), i.e., an anti-GLP1R antibody, or an antigen-binding fragment thereof. In some embodiments, the binding agent is an anti-GLP1R agonist antibody, or an antigen-binding fragment thereof.

In some embodiments, suitable anti-GLP1R antibodies are those disclosed in US Publication No. US20060275288A1, which is incorporated herein by reference in its entirety. Exemplary anti-GLP1R antibodies according to the present disclosure include 5A10 and 9A10.

In some embodiments, suitable anti-GLP1R antibodies include, but not limited to, AB9433-1, h38C2, PA5-111834, NLS1205, MAB2814, EPR21819, and glutazumab.

The present disclosure also provides nucleic acid molecules encoding anti-GLP1R antibodies or portions thereof. Also included within the scope of the present disclosure are recombinant expression vectors capable of expressing a polypeptide comprising a heavy or light chain variable region of an anti-GLP1R antibody. For example, the present disclosure includes recombinant expression vectors comprising any of the nucleic acid molecules mentioned above. Further included within the scope of the present disclosure are host cells into which such vectors have been introduced, as well as methods of producing the antibodies or portions thereof by culturing the host cells under conditions permitting production of the antibodies or antibody fragments, and recovering the antibodies and antibody fragments so produced.

In some embodiments, the present disclosure includes anti-GLP1R antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the disclosure provides a pharmaceutical composition comprising a recombinant human antibody or fragment thereof which specifically binds GLP1R and a pharmaceutically acceptable carrier. In a related aspect, the disclosure includes a composition which is a combination of an anti-GLP1R antibody and a second therapeutic agent. In one embodiment, the second therapeutic agent is any agent that is advantageously combined with an anti-GLP1R antibody. Additional combination therapies and co-formulations involving the anti-GLP1R antibodies of the present disclosure are disclosed elsewhere herein.

In another aspect, the disclosure provides therapeutic methods for targeting cells expressing GLP1R using an anti-GLP1R antibody of the disclosure, wherein the therapeutic methods comprise administering a therapeutically effective amount of a pharmaceutical composition comprising an anti-GLP1R antibody of the disclosure to a subject in need thereof. In some embodiments, the cell is a mammalian cell. In some embodiments, the cell is a human cell. In some embodiments, the cell is a pancreatic cell, a brain cell, a heart cell, a vascular tissue cell, a kidney cell, an adipose tissue cell, a liver cell, or a muscle cell. In one embodiment, the cell is a pancreatic cell or a brain cell.

In some cases, the anti-GLP1R antibodies (or antigen-binding fragments thereof) can be used to enhance GLP1R activity in the cells.

The present disclosure also includes the use of an anti-GLP1R antibody of the disclosure in the manufacture of a medicament for the treatment of a disease or disorder (e.g., type II diabetes and/or obesity) associated with GLP1R-expressing cells. In one aspect, the disclosure relates to a compound comprising an anti-GLP1R antibody or antigen-binding fragment, as disclosed herein, for use in medicine. In one aspect, the disclosure relates to a compound comprising an antibody-drug conjugate (ADC) as disclosed herein, for use in medicine.

In yet another aspect, the disclosure provides monospecific anti-GLP1R antibodies for diagnostic applications, such as, e.g., imaging reagents.

The disclosure further includes an antibody or antigen-binding fragment that competes for binding to human GLP1R with an antibody described herein.

The disclosure furthermore includes an antibody or antigen-binding fragment, wherein the antibody or antigen-binding fragment thereof binds to the same epitope on human GLP1R as an antibody described herein.

In one aspect, the present disclosure provides antibody-drug conjugates comprising an anti-GLP1R antibody or antigen-binding fragment thereof as described above and a therapeutic agent (e.g., a GLP1 peptidomimetic). In some embodiments, the antibody or antigen-binding fragment and the payload are covalently attached via a linker, as discussed above. In various embodiments, the anti-GLP1R antibody or antigen-binding fragment can be any of the anti-GLP1R antibodies or fragments described herein. In some embodiments, the antibody-drug conjugates of the present disclosure are stable in plasma. Plasma stability may be determined using an in vitro or in vivo plasma stability assay, such as those set forth in Example 8.2 or Example 10 below. In some embodiments, the antibody-drug conjugates of the present disclosure have a half life of longer than 4 days, longer than 5 days, longer than 6 days, longer than 7 days, longer than 8 days, longer than 9 days, longer than 10 days, longer than 11 days, longer than 12 days, longer than 13 days, longer than 2 weeks, longer than 3 weeks, longer than 4 weeks, about 1 week, about 2 weeks, about 3 weeks, about 4 weeks, about 1 month, about 2 month, about 3 month, about 4 month, about 5 month, about 6 month, between 5-10 days, between 8-12 days, between 10-15 days, between 12-18 days, between 15-20 days, between 20-30 days, between 1-2 weeks, between 2-3 weeks, between 3-4 weeks, between 4-6 weeks, between 5-8 weeks, between 6-10 weeks, between 1-2 months, between 1.5-3 months, between 2-4 months, between 2.5-5 months, between 3-6 months, or between 4-6 months in plasma.

In some embodiments, the antibody-drug conjugates of the present disclosure bind to GLP1R with at least a 10-fold greater affinity than other G protein-coupled receptors (GPCRs). In some embodiments, the antibody-drug conjugates of the present disclosure bind to GLP1R with at least a 20-fold, 50-fold, 100-fold, 500-fold, 1000-fold, 10,000-fold greater affinity than other G protein-coupled receptors (GPCRs). In some embodiments, such antibody-drug conjugates exhibit essentially undetectable binding against GPCRs other than GLP1R. Binding of the antibody-drug conjugates to a target molecule can be measured using a standard binding assay available in the relevant art, such as luciferase reporter assay, surface plasmon resonance assay, enzyme-linked immunosorbent assay (ELISA), radioimmunoassay (RIA), FACS analysis, or Western blot assay. Examples of GPCRs other than GLP1R include, but are not limited to, GIPR, GLP2R and GCGR.

In certain embodiments, an antibody drug conjugate of the present disclosure comprises an anti-GLP1R antibody, or antigen-binding fragment thereof, conjugated with a linker payload, wherein the linker payload is attached to the antibody, or antigen-binding fragment thereof, at the N-terminus of a light chain. In one embodiment, an antibody drug conjugate of the present disclosure comprises an anti-GLP1R antibody, or antigen-binding fragment thereof, conjugated at the N-terminus of a light chain with a linker payload, wherein the payload has the following structure (SEQ ID NO: 129):

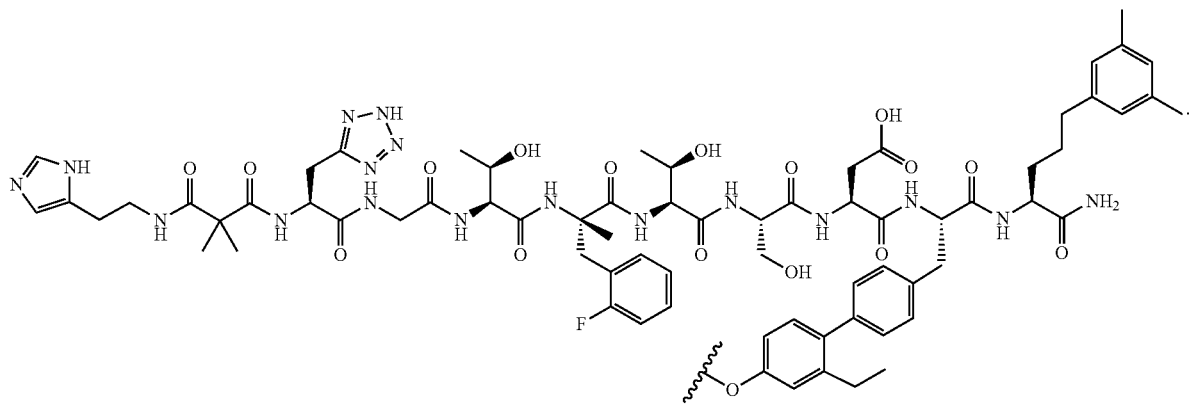 [SMILES: *Oc1ccc(-c2ccc(C[C@H](NC(=O)[C@H](CC(=O)O)NC(=O)[C@H](CO)NC(=O)[C@@H](NC(=O)[C@](C)(Cc3ccccc3F)NC(=O)[C@@H](NC(=O)CNC(=O)[C@H](Cc3nn[nH]n3)NC(=O)C(C)(C)C(=O)NCCc3cnc[nH]3)[C@@H](C)O)[C@@H](C)O)C(=O)N[C@@H](CCCc3cc(C)cc(C)c3)C(N)=O)cc2)c(CC)c1]

In certain embodiments, an antibody drug conjugate of the present disclosure comprises an anti-GLP1R antibody, or antigen-binding fragment thereof, conjugated with two linker payloads, wherein each linker payload is attached to the antibody, or antigen-binding fragment thereof, at the N-terminus of a light chain. In one embodiment, an antibody drug conjugate of the present disclosure comprises an anti-GLP1R antibody, or antigen-binding fragment thereof, conjugated at the N-terminus of each light chain with a linker payload for a total of two linker payloads per each antibody, wherein the payload has the following structure (SEQ ID NO: 129):

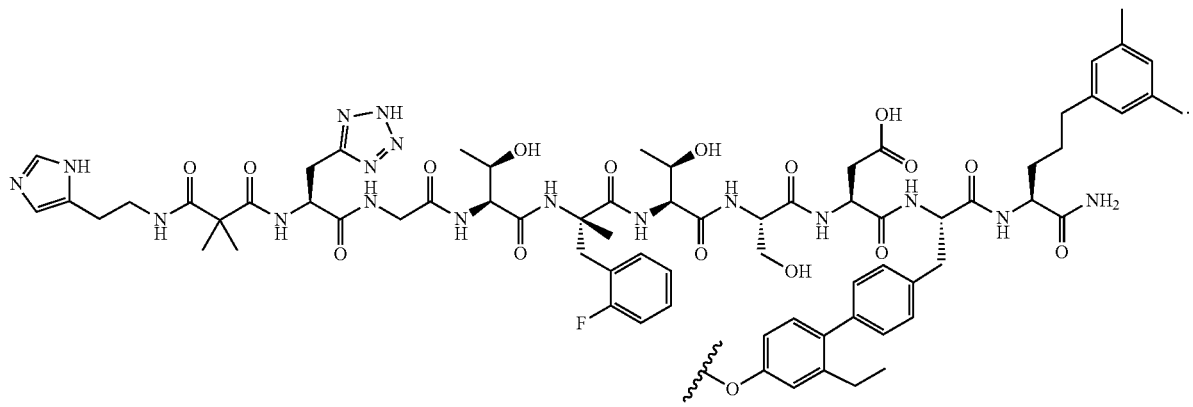 [SMILES: *Oc1ccc(-c2ccc(C[C@H](NC(=O)[C@H](CC(=O)O)NC(=O)[C@H](CO)NC(=O)[C@@H](NC(=O)[C@](C)(Cc3ccccc3F)NC(=O)[C@@H](NC(=O)CNC(=O)[C@H](Cc3nn[nH]n3)NC(=O)C(C)(C)C(=O)NCCc3cnc[nH]3)[C@@H](C)O)[C@@H](C)O)C(=O)N[C@@H](CCCc3cc(C)cc(C)c3)C(N)=O)cc2)c(CC)c1]

In yet another aspect, provided herein is an antibody-drug conjugate comprising a Glucagon-like peptide-1 receptor (GLP1R)-targeting antibody or an antigen-binding fragment thereof and a payload having the structure (SEQ ID NO: 124):

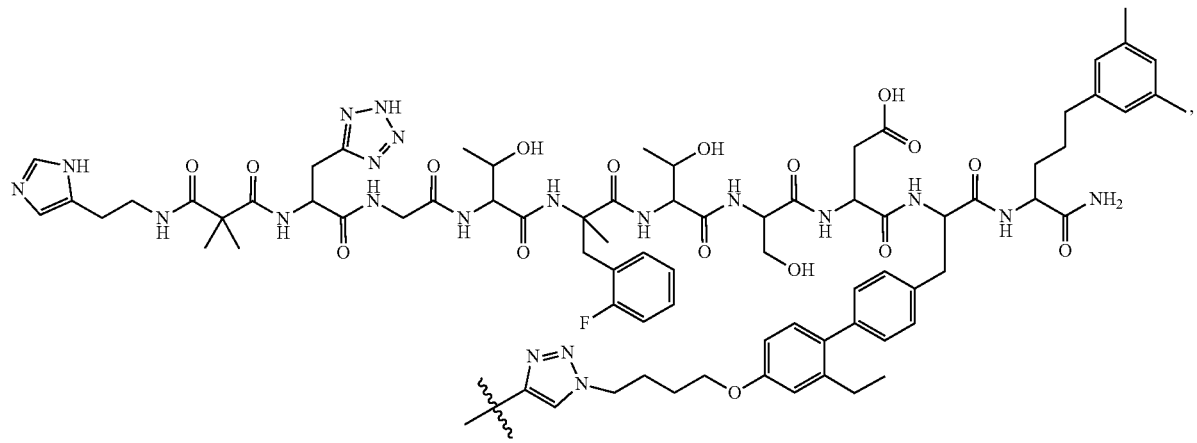 [SMILES: *c1cn(CCCCOc2ccc(-c3ccc(CC(NC(=O)C(CC(=O)O)NC(=O)C(CO)NC(=O)C(NC(=O)C(C)(Cc4ccccc4F)NC(=O)C(NC(=O)CNC(=O)C(Cc4nn[nH]n4)NC(=O)C(C)(C)C(=O)NCCc4cnc[nH]4)C(C)O)C(C)O)C(=O)NC(CCCc4cc(C)cc(C)c4)C(N)=O)cc3)c(CC)c2)nn1]

wherein

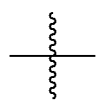

is the point of attachment of the payload to the antibody or the antigen-binding fragment thereof directly or through a linker.

In one embodiment, the payload has the structure (SEQ ID NO: 90):

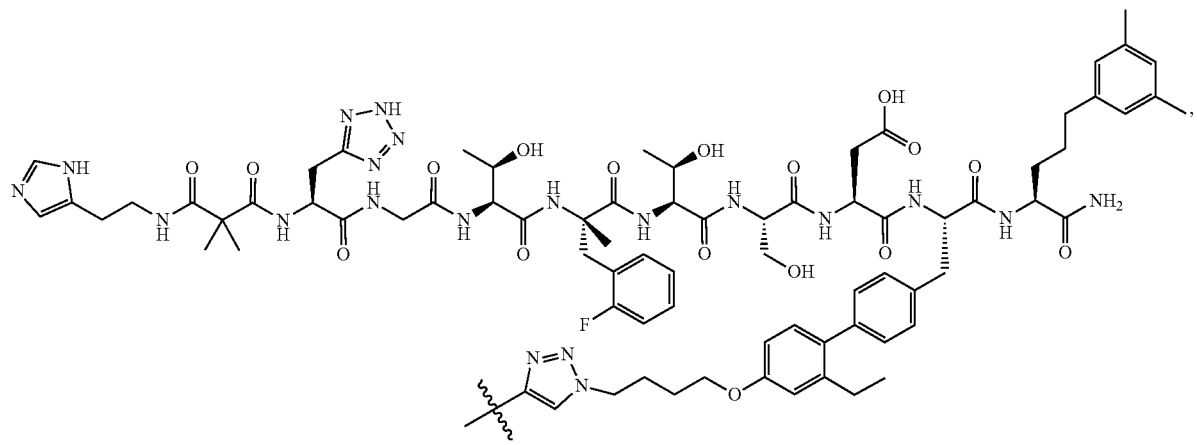 [SMILES: *c1cn(CCCCOc2ccc(-c3ccc(C[C@H](NC(=O)[C@H](CC(=O)O)NC(=O)[C@H](CO)NC(=O)[C@@H](NC(=O)[C@](C)(Cc4ccccc4F)NC(=O)[C@@H](NC(=O)CNC(=O)[C@H](Cc4nn[nH]n4)NC(=O)C(C)(C)C(=O)NCCc4cnc[nH]4)[C@@H](C)O)[C@@H](C)O)C(=O)N[C@@H](CCCc4cc(C)cc(C)c4)C(N)=O)cc3)c(CC)c2)nn1]

In yet another aspect, provided herein is an antibody-drug conjugate comprising a Glucagon-like peptide-1 receptor (GLP1R)-targeting antibody or an antigen-binding fragment thereof and a linker-payload having the structure (SEQ ID NO: 125):

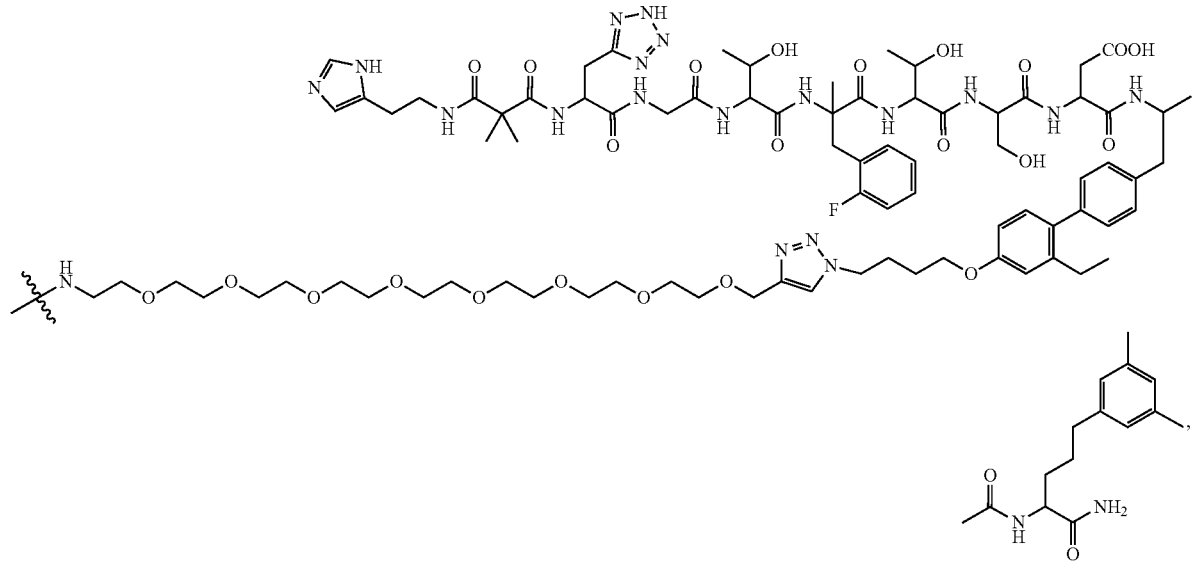

wherein

is the point of attachment of the linker-payload to the antibody or the antigen-binding fragment thereof.

In one embodiments, the linker-payload has the structure (SEQ ID NO: 126):

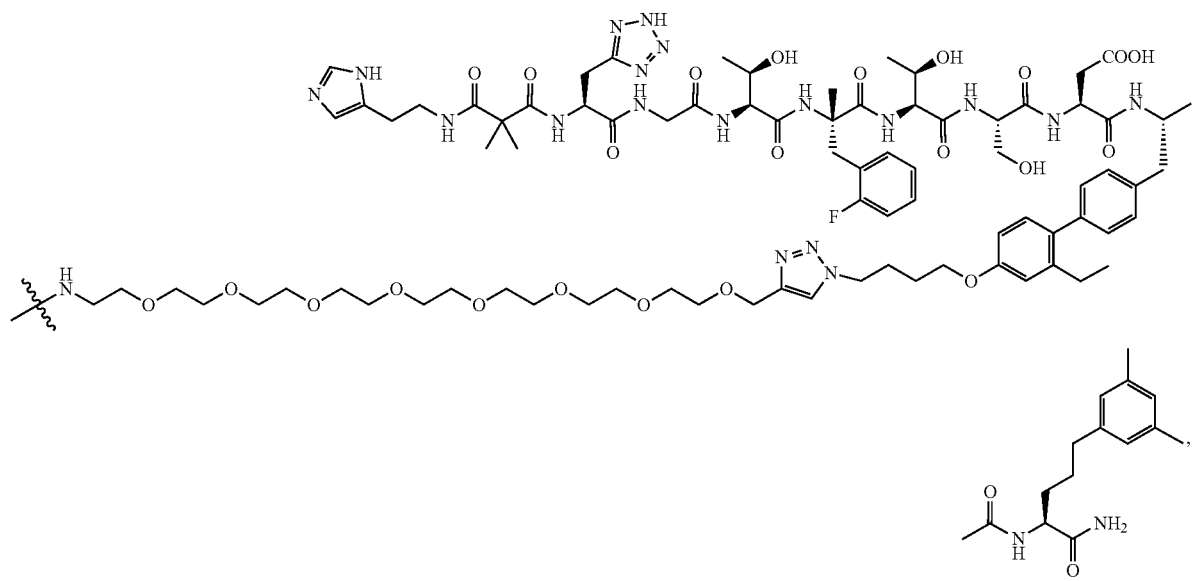

Antibody Conjugation

Techniques and linkers for conjugating to residues of an antibody or antigen binding fragment are known in the art. Exemplary amino acid attachments that can be used in the context of this aspect, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci.*, USA, 2008, 105:12451-12456), formyl glycine (see, e.g., Carrico et al., *Nat. Chem. Biol.*, 2007, 3:321-322; Agarwal et al., *Proc. Natl. Acad. Sci.*, USA, 2013, 110:46-51, and Rabuka et al., Nat. Protocols, 2012, 10:1052-1067), non-natural amino acids (see, e.g., WO 2013/068874, and WO 2012/166559), and acidic amino acids (see, e.g., WO 2012/05982). Lysine conjugation can also proceed through NHS (N-hydroxy succinimide). Linkers can also be conjugated to cysteine residues, including cysteine residues of a cleaved interchain disulfide bond, by forming a carbon bridge between thiols (see, e.g., U.S. Pat. Nos. 9,951,141, 9,950,076). Linkers can also be conjugated to an antigen-binding protein via attachment to carbohydrates (see, e.g., US 2008/0305497, WO 2014/065661, and Ryan et al., *Food & Agriculture Immunol.*, 2001, 13:127-130) and disulfide linkers (see, e.g., WO 2013/085925, WO 2010/010324, WO 2011/018611, and Shaunak et al., *Nat. Chem. Biol.*, 2006, 2:312-313). Site specific conjugation techniques can also be employed to direct conjugation to particular residues of the antibody or antigen binding protein (see, e.g., Schumacher et al. *J Clin Immunol* (2016) 36 (Suppl 1): 100). In specific embodiments discussed in more detail below, Site specific conjugation techniques, include glutamine conjugation via transglutaminase (see e.g., Schibli, Angew Chemie Inter Ed. 2010, 49,9995).

Payloads according to the disclosure linked through lysine and/or cysteine, e.g., via a maleimide or amide conjugation, are included within the scope of the present disclosure.

In some embodiments, the protein-drug conjugates of the present disclosure are produced according to a two-step process, where Step 1 is lysine-based linker conjugation, e.g., with an NHS-ester linker, and Step 2 is a payload conjugation reaction (e.g., a 1,3-cycloaddition reaction).

In some embodiments, the protein-drug conjugates of the present disclosure are produced according to a two-step process, where Step 1 is cysteine-based linker conjugation, e.g., with a maleimide linker, and Step 2 is a payload conjugation reaction (e.g., a 1,3-cycloaddition reaction).

In some embodiments, the protein-drug conjugates of the present disclosure are produced according to a two-step process, where Step 1 is transglutaminase-mediated site specific conjugation and Step 2 is a payload conjugation reaction (e.g., a 1,3-cycloaddition reaction).

Step 1: Transglutaminase Mediated Site Specific Conjugation

In some embodiments, proteins (e.g., antibodies) may be modified in accordance with known methods to provide glutaminyl modified proteins. Techniques for conjugating antibodies and primary amine compounds are known in the art. Site specific conjugation techniques are employed herein to direct conjugation to glutamine using glutamine conjugation via transglutaminase (see e.g., Schibli, *Angew Chemie* Inter Ed. 2010, 49, 9995).

Primary amine-comprising compounds (e.g., linkers La) of the present disclosure can be conjugated to one or more glutamine residues of a binding agent (e.g., a protein, e.g., an antibody, e.g., an anti-GLP1R antibody) via transglutaminase-based chemo-enzymatic conjugation (see, e.g., Dennler et al., *Protein Conjugate Chem.* 2014, 25, 569-578, and WO 2017/147542). For example, in the presence of transglutaminase, one or more glutamine residues of an antibody can be coupled to a primary amine linker compound. Briefly, in some embodiments, a binding agent having a glutamine residue (e.g., a Gln295, i.e. Q295 residue) is treated with a primary amine-containing linker La in the presence of the enzyme transglutaminase. In certain embodiments, the binding agent is aglycosylated. In certain embodiments, the binding agent is deglycosylated.

In certain embodiments, the binding agent (e.g., a protein, e.g., an antibody) comprises at least one glutamine residue in at least one polypeptide chain sequence. In certain embodiments, the binding agent comprises two heavy chain polypeptides, each with one Gln295 residue. In further embodiments, the binding agent comprises one or more glutamine residues at a site other than a heavy chain 295.

In some embodiments, a binding agent, such as an antibody, can be prepared by site-directed mutagenesis to insert a glutamine residue at a site without resulting in disabled antibody function or binding. For example, included herein are antibodies bearing Asn297Gln (N297Q) mutation(s) as described herein. In some embodiments, an antibody having a Gln295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the binding agent, e.g., antibody, conjugated via transglutaminase can have a higher than expected LAR value (e.g., a LAR higher than 4). Any such antibodies can be isolated from natural or artificial sources.

Step 2: Payload Conjugation Reaction

In certain embodiments, linkers La according to the present disclosure comprise at least one first reactive group capable of further reaction after transglutamination. In these embodiments, the glutaminyl-modified protein (e.g., antibody) is capable of further reaction with a reactive payload compound P or a reactive linker-payload compound (e.g., Lp-P as disclosed herein), to form a protein-payload conjugate. More specifically, the reactive linker-payload compound Lp-P may comprise a second reactive group that is capable of reacting with the first reactive group of the linker La. In certain embodiments, a first or second reactive group according to the present disclosure comprises a moiety that is capable of undergoing a 1,3-cycloaddition reaction. In certain embodiments, the reactive group is an azide. In certain embodiments, the reactive group comprises an alkyne (e.g., a terminal alkyne, or an internal strained alkyne). In certain embodiments of the present disclosure the reactive group is compatible with the binding agent and transglutamination reaction conditions.

In certain embodiments of the disclosure, linker La molecules comprise a first reactive group. In certain embodiments of the disclosure, linker La molecules comprise more than one reactive group.

In certain embodiments, the reactive linker-payload Lp-P comprises one payload molecule (n=1). In certain other embodiments, the reactive linker-payload Lp-P comprises two or more payload molecules (n 2).

In certain embodiments of the disclosure, the drug-antibody ratio or DAR is from about 1 to about 30, or from about 1 to about 24, or from about 1 to about 20, or from about 1 to about 16, or from about 1 to about 12, or from about 1 to about 10, or from about 1 to about 8, or about 1, 2, 3, 4, 5, 6, 7, or 8 payload molecules per antibody. In some embodiments, the DAR is from 1 to 30. In some embodiments, the DAR is from 1 to 16. In some embodiments, the DAR is from 1 to 8. In some embodiments, the DAR is from 1 to 6. In certain embodiments, the DAR is from 2 to 4. In some cases, the DAR is from 2 to 3. In certain cases, the DAR is from 0.5 to 3.5. In some embodiments, the DAR is about 1, or about 1.5, or about 2, or about 2.5, or about 3, or about 3.5. In some embodiments, the DAR is 2. In some embodiments, the DAR is 4. In some embodiments, the DAR is 8.

In one aspect, the present disclosure provides a method of producing the compound having a structure of Formula (A):

BA-(L-P)$_m$ (A), the method comprising the steps of:
a) contacting, in the presence of a transglutaminase, the BA comprising at least m glutamine residues Gln with at least m equivalents of compound L-P, and
b) isolating the produced compound of Formula (A).

In one aspect, the present disclosure provides a method of producing the compound having a structure of Formula (A):

BA-(L-P)$_m$ (A), wherein the linker L has has the structure of formula (L'):

—La—Y-Lp- (L'), wherein La is a first linker covalently attached to the BA;
Y is a group comprising a triazole, and
Lp is a second linker covalently attached to the P,
the method comprising the steps of:
a) contacting, in the presence of a transglutaminase, the BA comprising at least m glutamine residues Gln with the first linker La comprising an azide or an alkyne moiety;
b) contacting the product of step a) with at least m equivalents of compound Lp-P, wherein the second linker Lp comprises an azide or an alkyne moiety, wherein La and Lp are capable of reacting to produce a triazole, and
c) isolating the produced compound of Formula (A).

In one aspect, the present disclosure provides a method of producing a compound having a structure according to Formula (I):

BA-L-P (I), the method comprising the steps of:
a) contacting, in the presence of a transglutaminase, the BA comprising at least one glutamine residue Gln with a compound L-P, and
b) isolating the produced compound of Formula (I),
wherein BA is an antibody or an antigen-binding fragment thereof;
L is a non-cleavable linker;
P is a payload having the structure selected from the group consisting of:

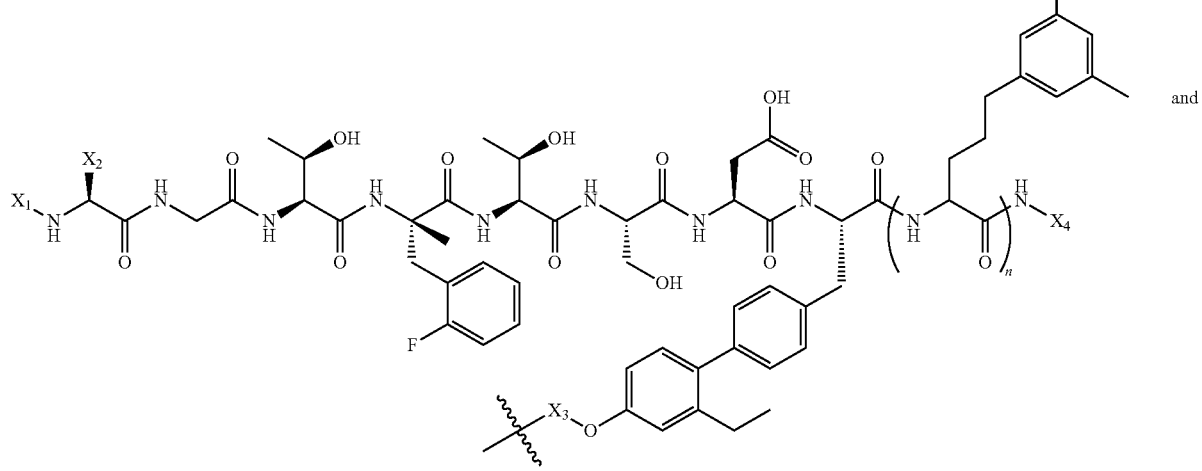

(P1 (SEQ ID NO: 30))

and

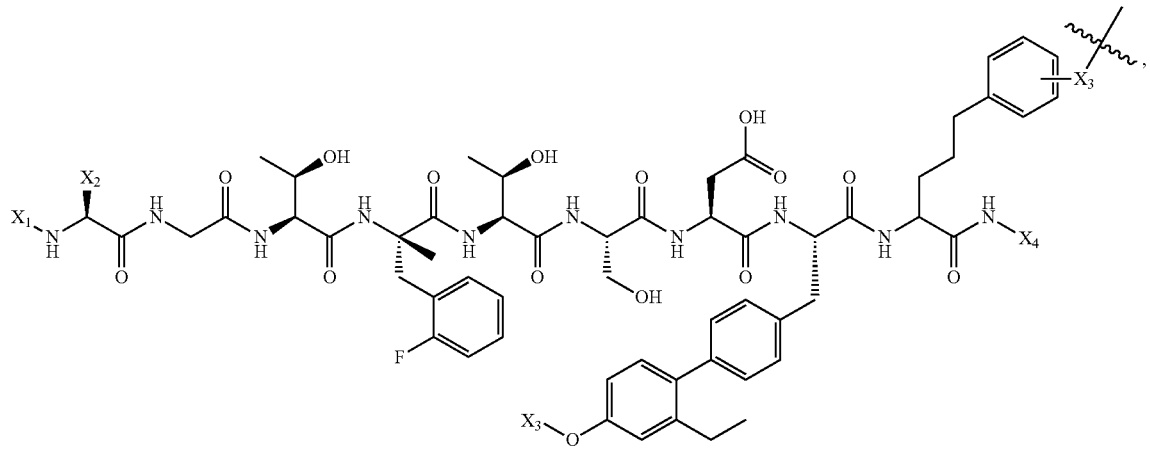
(P2 (SEQ ID NO: 28))
wherein
is the point of attachment of the payload to L;
X₁ is selected from H;
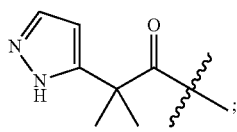
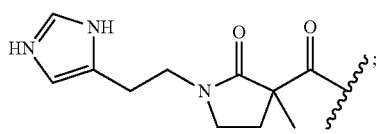
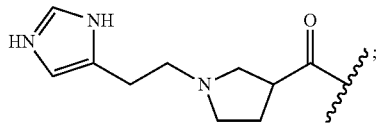
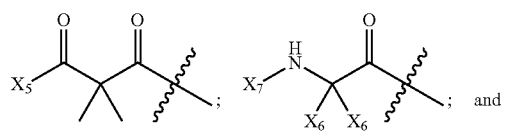
and
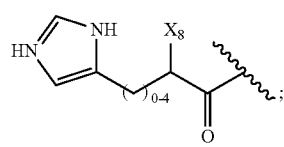
X₂ is selected from
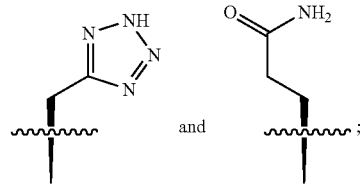
and
X₃ is selected from —(CH₂)₂₋₆—NH— and —(CH₂)₂₋₆—Tr-, where Tr is a triazole moiety;
n is 0 or 1;
X₄ is selected from H and phenyl;

$X_5$ is selected from —OH, —NH$_2$, —NH—OH, and

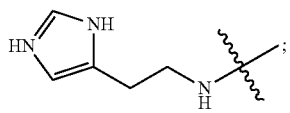 [SMILES: *NCCc1cnc[nH]1]

$X_6$ is independently at each occurrence selected from H, —OH, —CH$_3$, and —CH$_2$OH;

$X_7$ is selected from H,

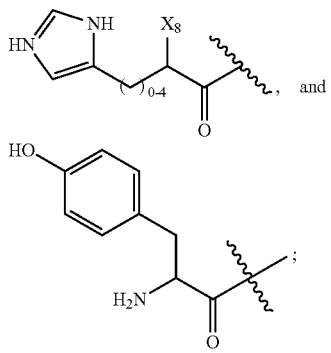

$X_8$ is selected from H, —OH, —NH$_2$, and

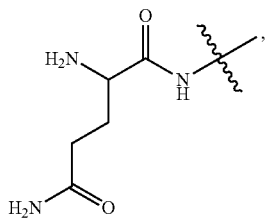

or a pharmaceutically acceptable salt thereof.

In another aspect, the present disclosure provides a method of producing a compound having a structure according to Formula (I):

$$BA\text{-}L\text{-}P \quad (I),$$

wherein the linker L has has the structure of formula (L'):

$$-La-Y-Lp- \quad (L'),$$

wherein La is a first linker covalently attached to the BA;

Y is a group comprising a triazole, a Diels-Alder adduct, or a thio-maleimide adduct, and Lp is a second linker covalently attached to the P, the method comprising the steps of:

a) contacting, in the presence of a transglutaminase, the BA comprising at least one glutamine residue Gln with the first linker La comprising an azide or an alkyne moiety;

b) contacting the product of step a) with a compound Lp-P, wherein the second linker Lp comprises an azide or an alkyne moiety, wherein La and Lp are capable of reacting to produce a triazole, and c) isolating the produced compound of Formula (I), wherein BA, L', and P are as defined above.

In one embodiment, Y is a group comprising a triazole.

In one embodiment, the glutamine residue Gln is naturally present in a CH2 or CH3 domain of the BA. In another embodiment, the glutamine residue Gln is introduced to the BA by modifying one or more amino acids. In one embodiment, the Gln is Q295 or N297Q.

In one embodiment, the transglutaminase is microbial transglutaminase (MTG). In one embodiment, the transglutaminase is bacterial transglutaminase (BTG).

In one embodiment, the compound L-P for use in any of the above methods of producing the compounds of Formula (I) has a structure selected from the group consisting of:

Structure (SEQ ID NO: 179)

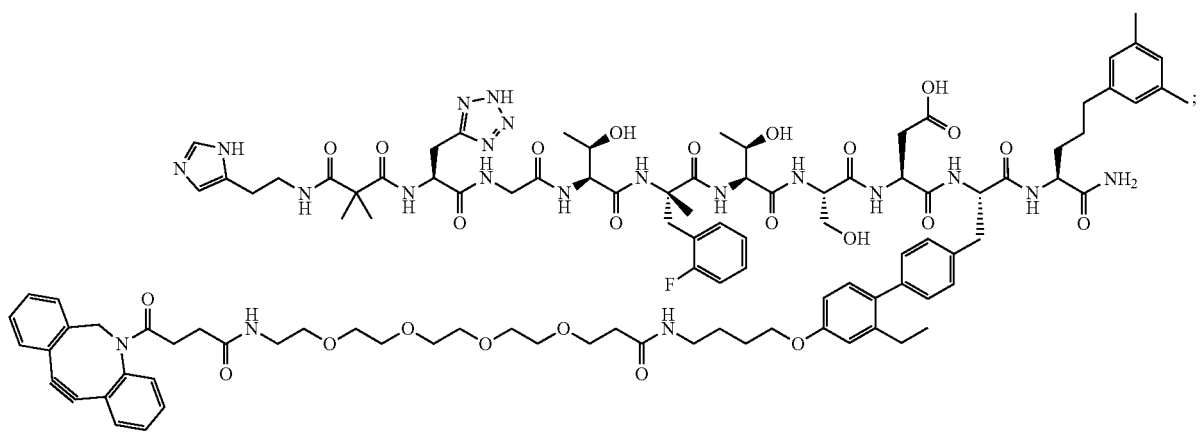

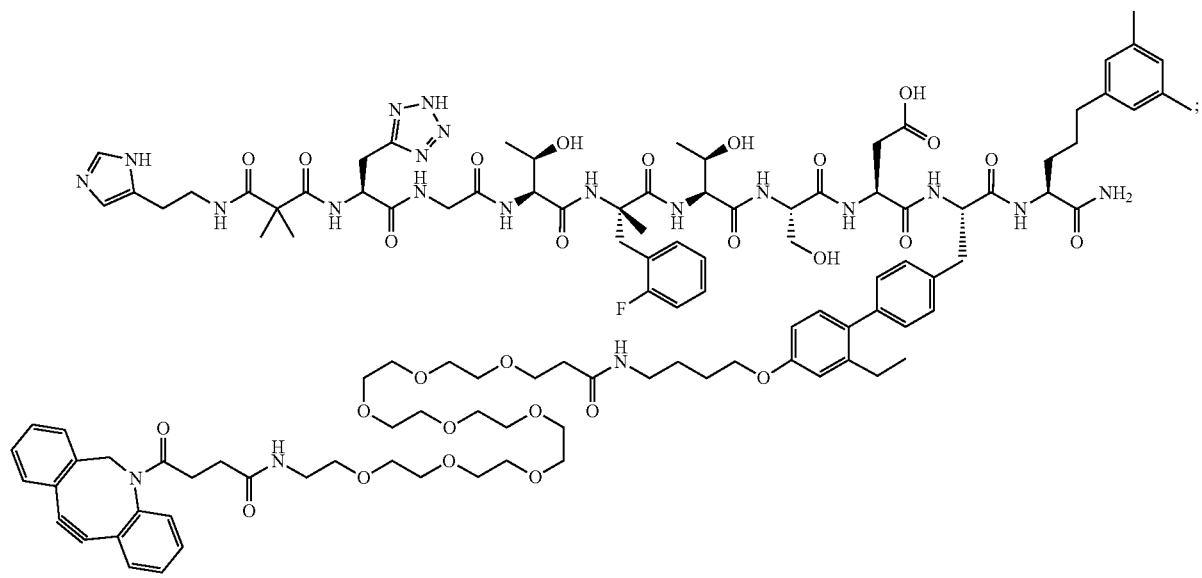
(SEQ ID NO: 180)
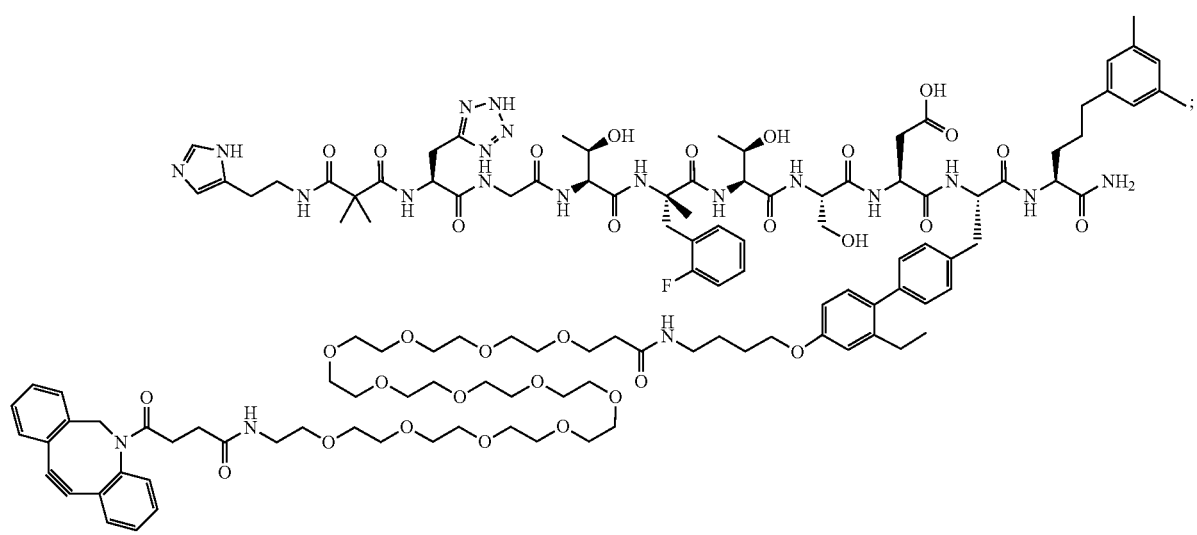
(SEQ ID NO: 181)

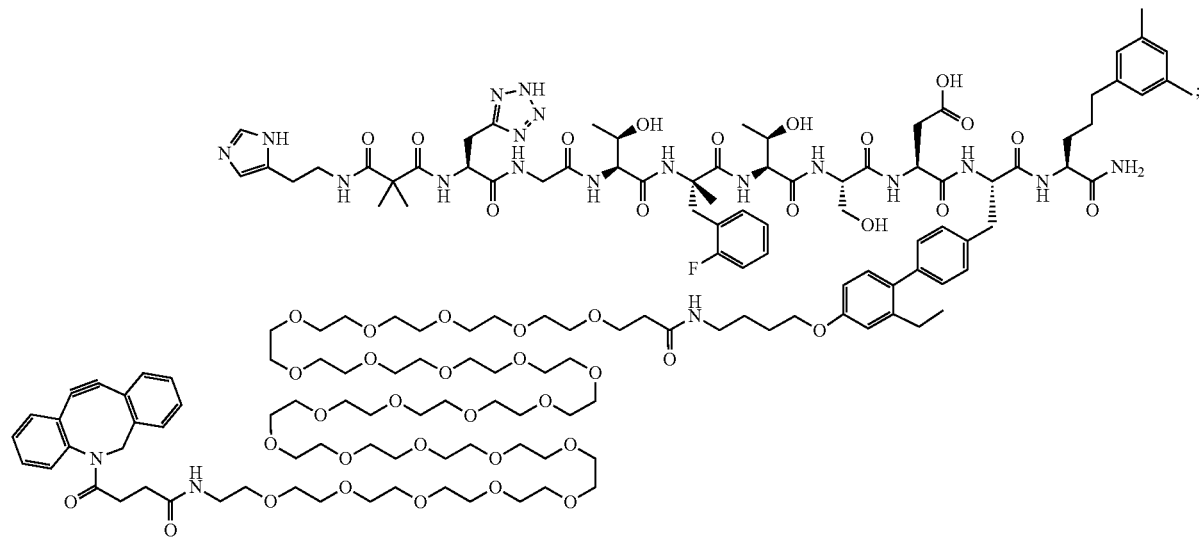
(SEQ ID NO: 182)
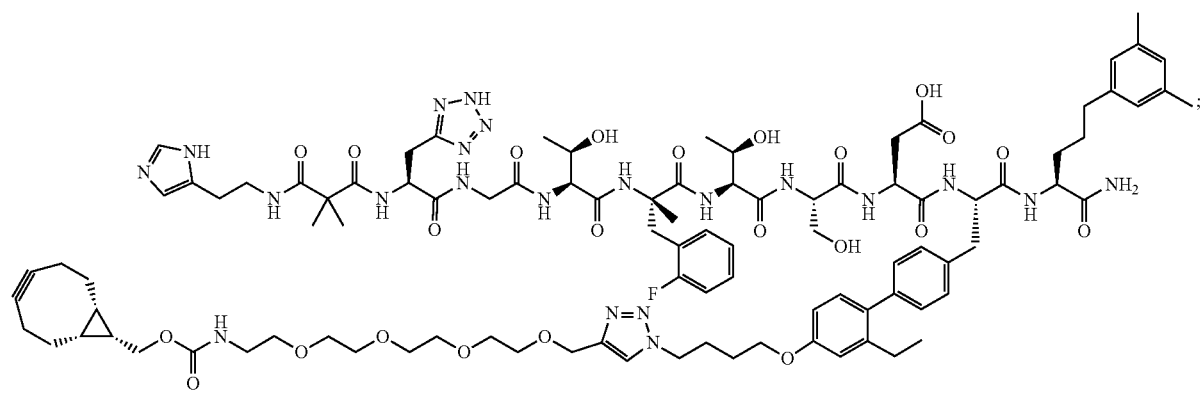
(SEQ ID NO: 185)
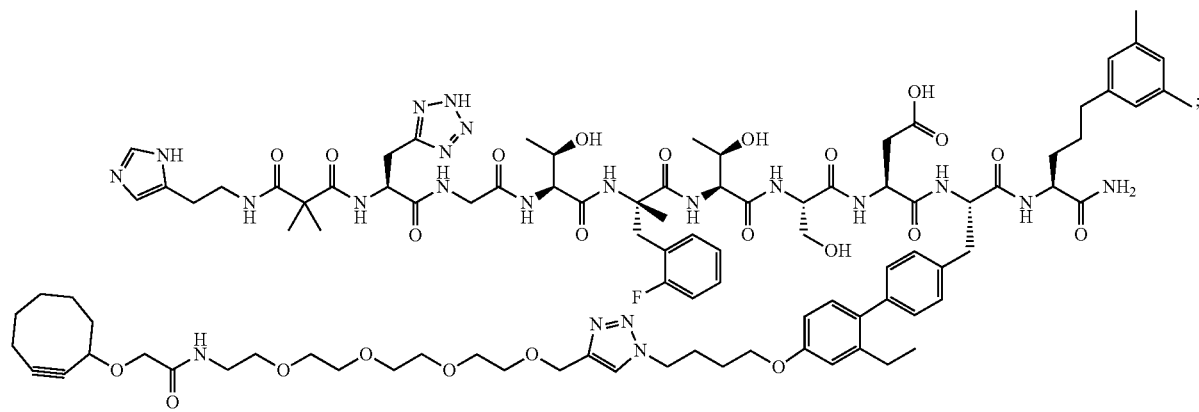
(SEQ ID NO: 186)

(SEQ ID NO: 91)
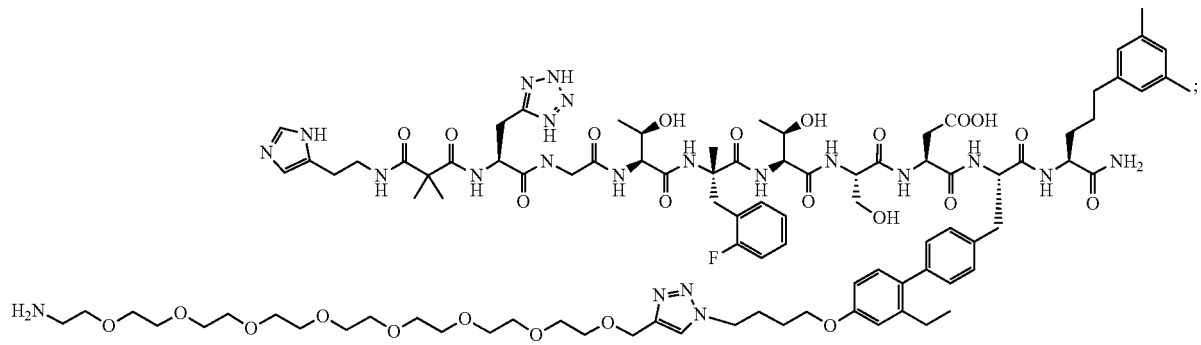
(SEQ ID NO: 92)
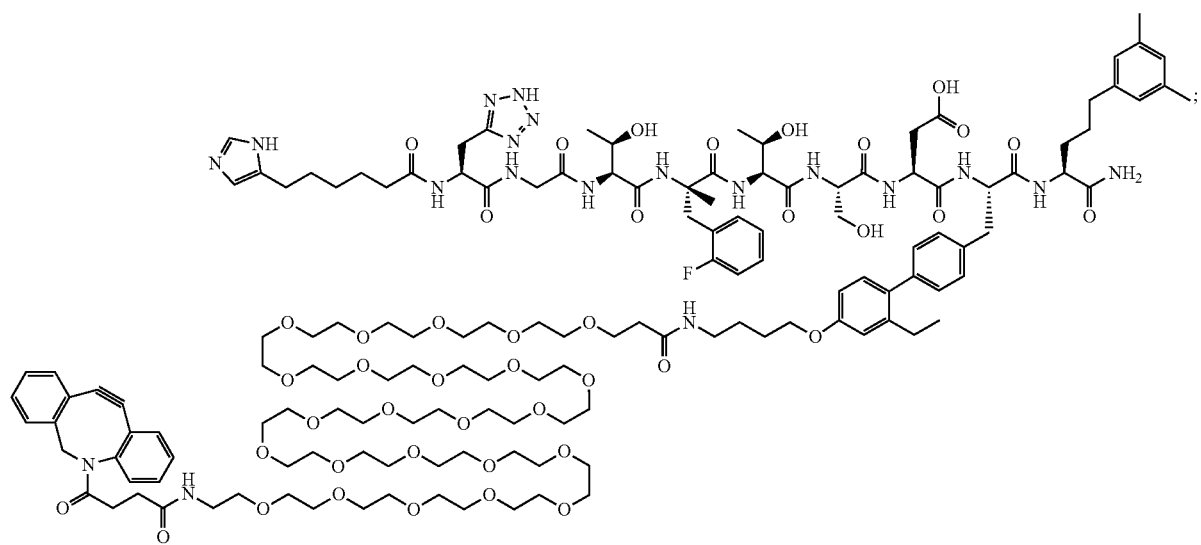
(SEQ ID NO: 93)
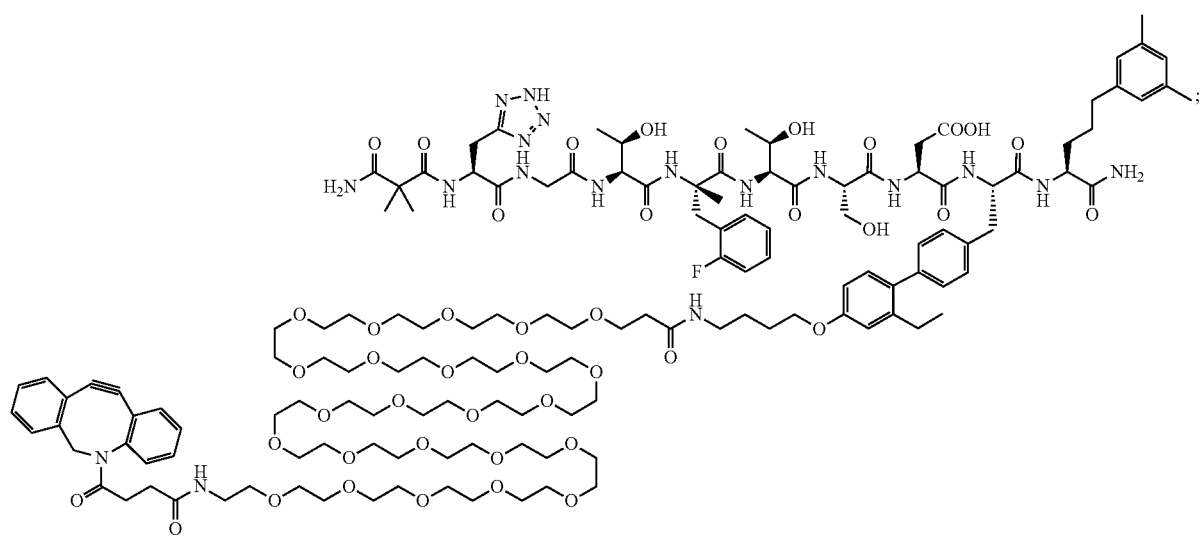

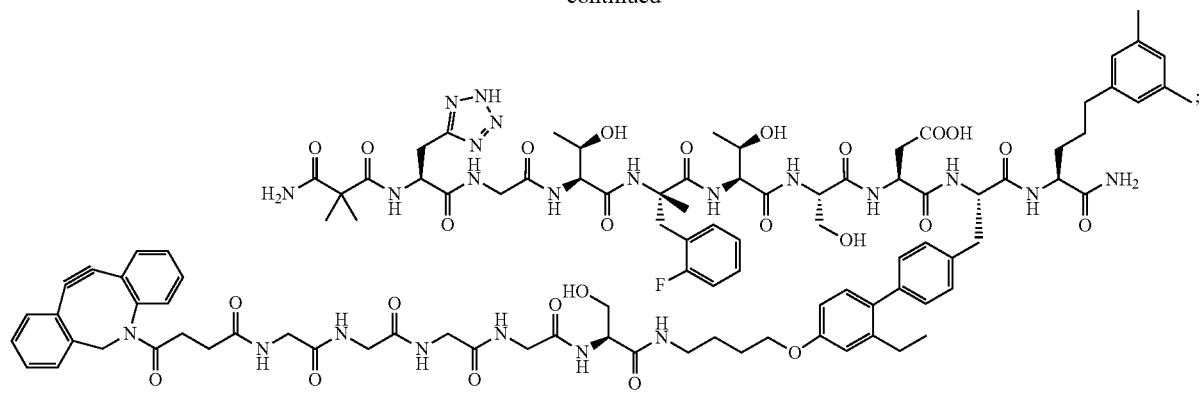
(Main Structure: SEQ ID NO: 94; Branched Sequence: SEQ ID NO: 158)
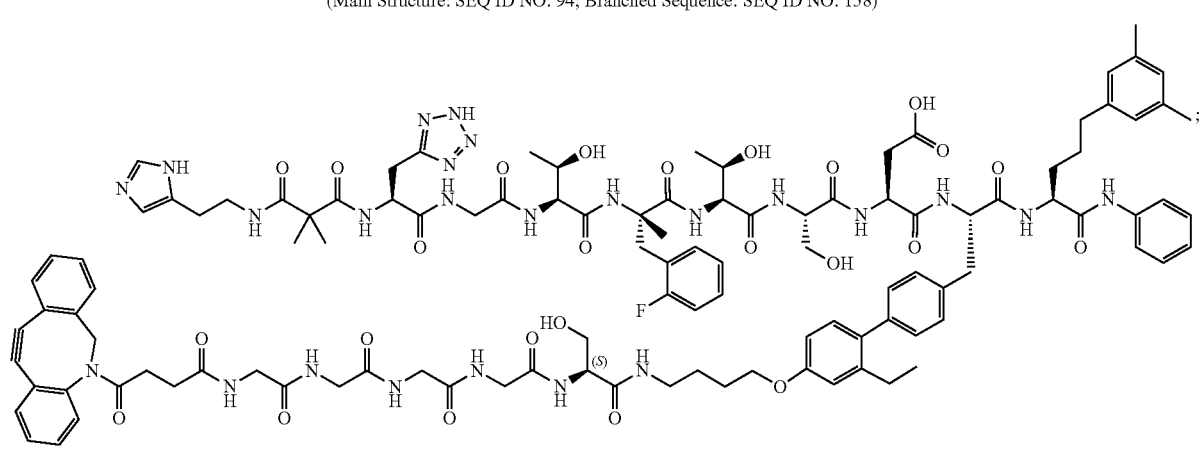
(Main Structure: SEQ ID NO: 95; Branched Sequence: SEQ ID NO: 159)
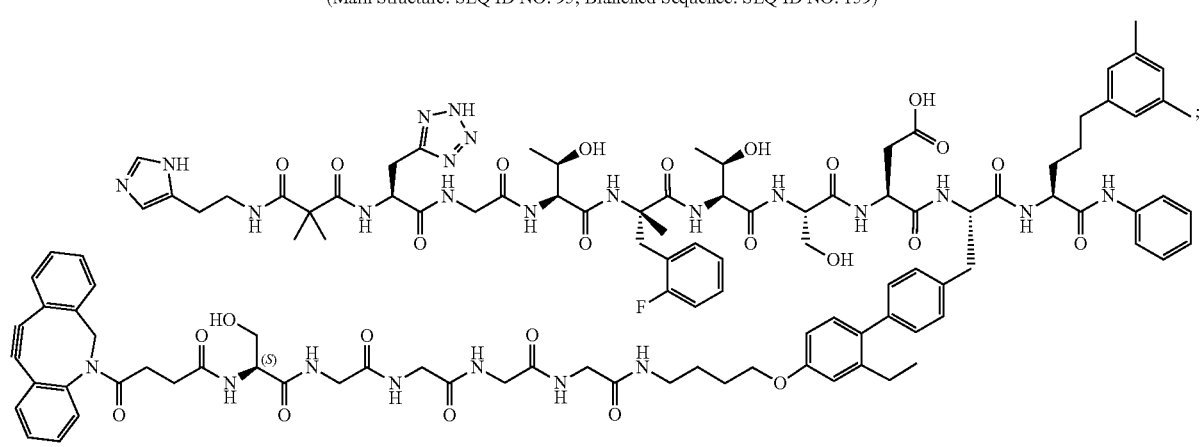
(Main Structure: SEQ ID NO: 96; Branched Sequence: SEQ ID NO: 160)
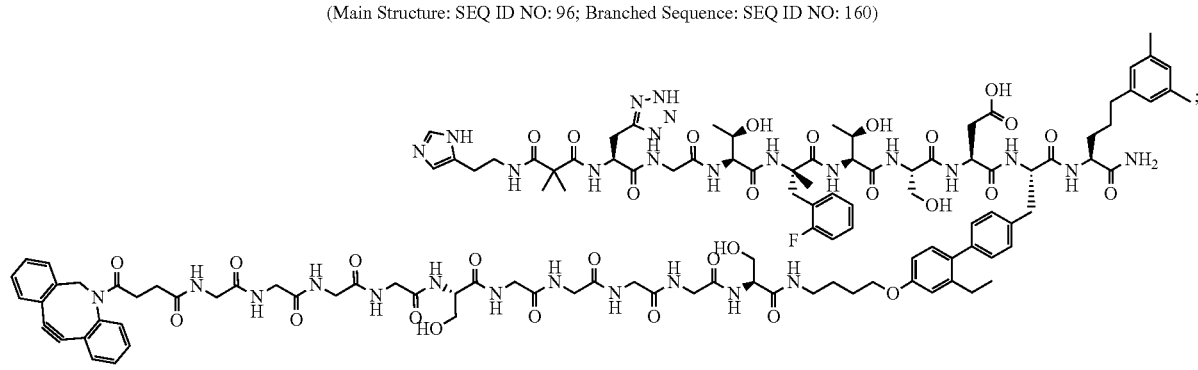
(Main Structure: SEQ ID NO: 97; Branched Sequence: SEQ ID NO: 161)

-continued
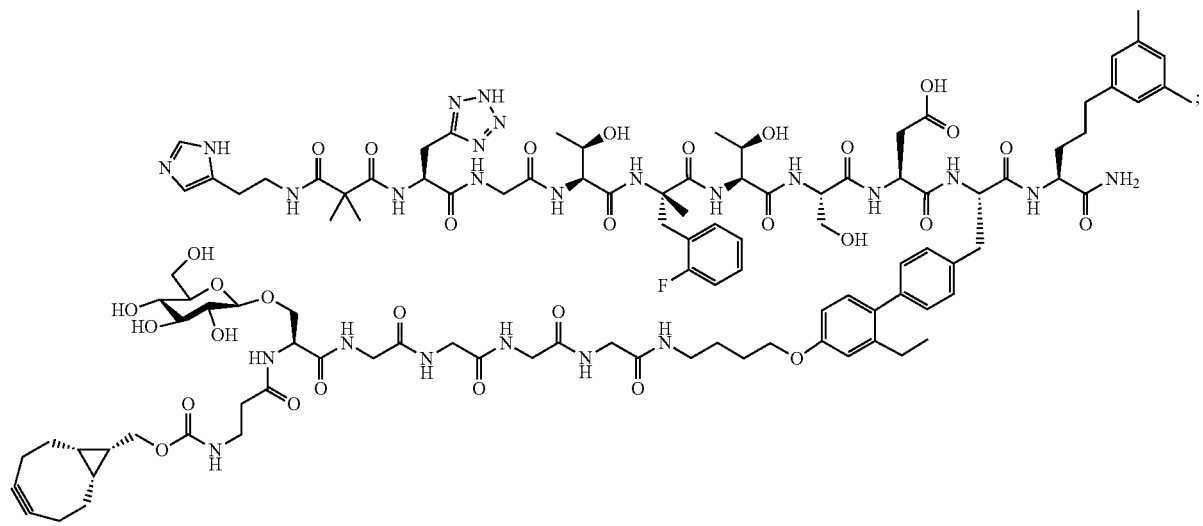
(Main Structure: SEQ ID NO: 98; Branched Sequence: SEQ ID NO: 162)
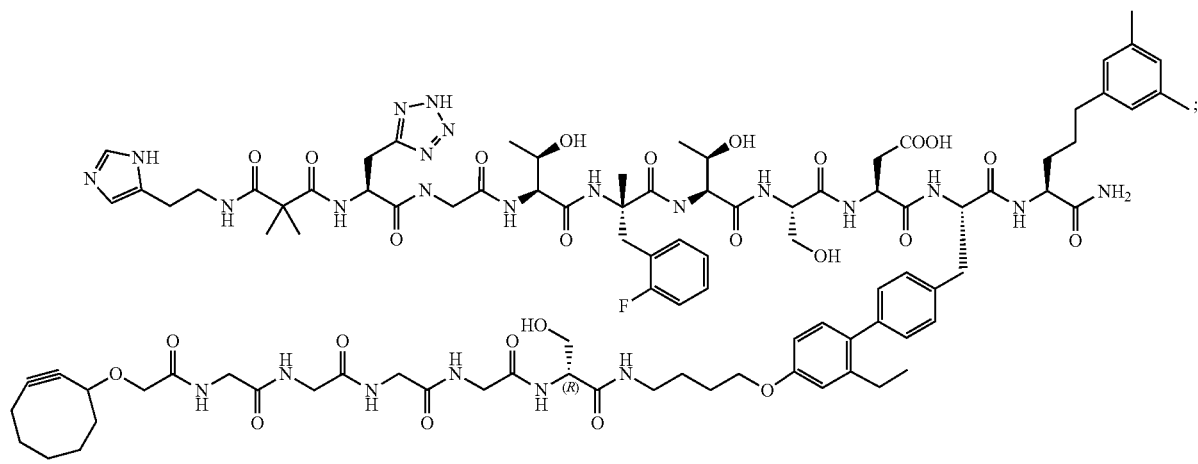
(Main Structure: SEQ ID NO: 99; Branched Sequence: SEQ ID NO: 163)
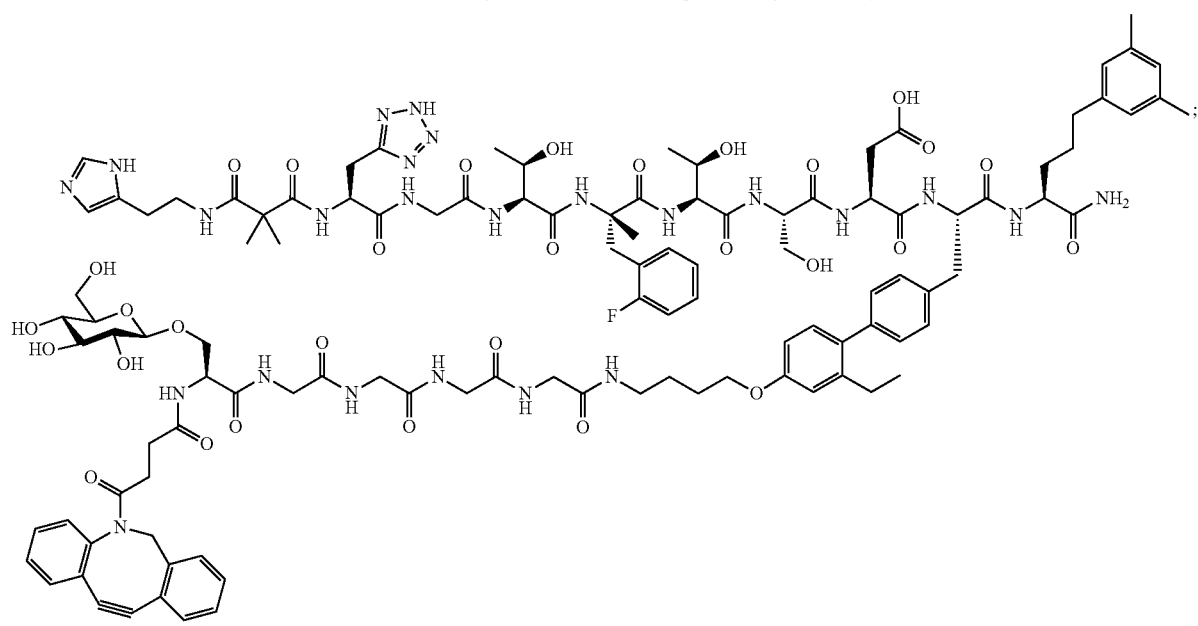
(Main Structure: SEQ ID NO: 100; Branched Sequence: SEQ ID NO: 164)

(SEQ ID NO: 101)
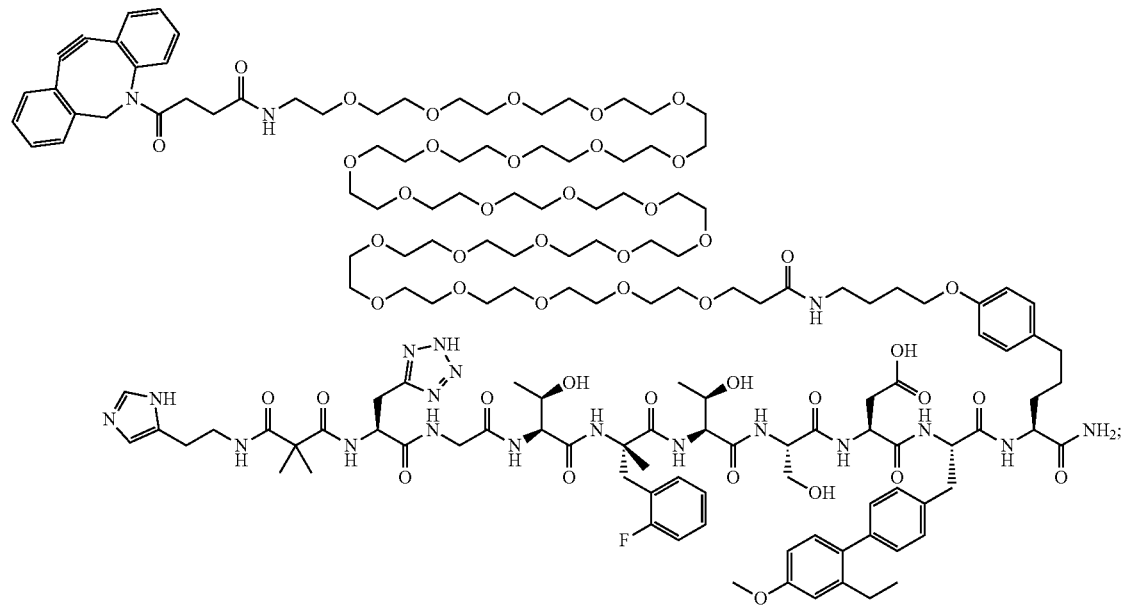
(SEQ ID NO: 102)
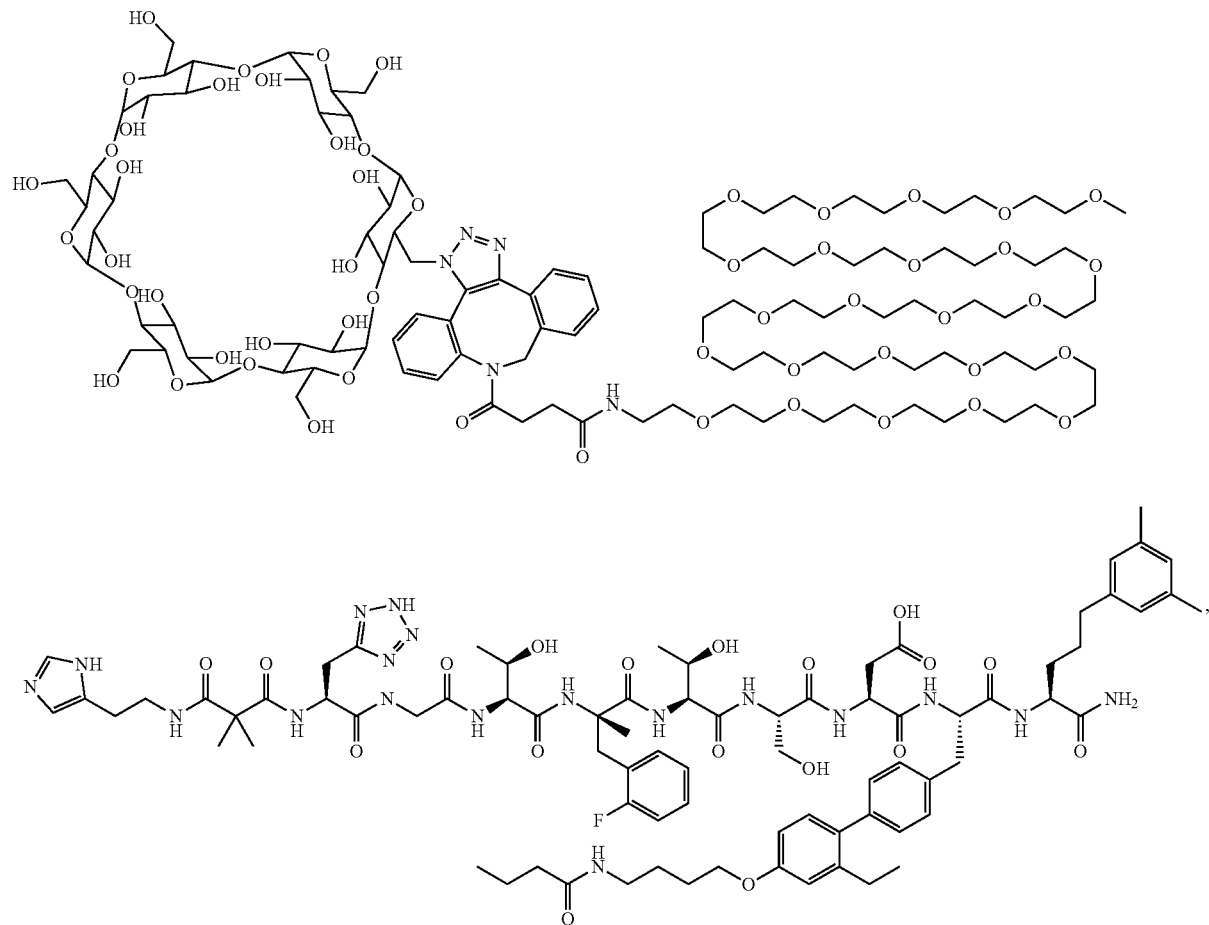
or a pharmaceutically acceptable salt thereof.

Therapeutic Formulation and Administration

The present disclosure provides pharmaceutical compositions comprising the protein-drug conjugates of the present disclosure.

In one aspect, the present disclosure provides compositions comprising a population of protein-drug conjugates according to the present disclosure having a drug-antibody ratio (DAR) of about 0.5 to about 30.0.

In one embodiment, the composition has a DAR of about 1.0 to about 2.5.

In one embodiment, the composition has a DAR of about 2.

In one embodiment, the composition has a DAR of about 3.0 to about 4.5.

In one embodiment, the composition has a DAR of about 4.

In one embodiment, the composition has a DAR of about 6.5 to about 8.5.

In one embodiment, the composition has a DAR of about 8.

The compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of a protein-drug conjugate administered to a patient may vary depending upon the age and the size of the patient, target disease, conditions, route of administration, and the like. The suitable dose is typically calculated according to body weight or body surface area. When a protein-drug conjugate of the present disclosure is used for therapeutic purposes in an adult patient, it may be advantageous to intravenously administer the protein-drug conjugate of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a protein-drug conjugate may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ 1, ‖ and Ill (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™ OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Protein-Drug Conjugates, Linker-Payloads and Payloads

In another aspect, the compounds (e.g., an antibody-drug conjugate, a linker-payload and/or a payload), disclosed herein are useful, inter alia, for the treatment, prevention and/or amelioration of a disease, disorder or condition in need of such treatment.

In one aspect, the present disclosure provides a method of treating a condition in a subject in need thereof comprising administering to the subject a therapeutically effective amount of a compound (e.g., an antibody-drug conjugate, a linker-payload and/or a payload) according to the disclosure, or the composition comprising any compound according to the present disclosure.

In some embodiments, the compounds (e.g., an antibody-drug conjugate, a linker-payload and/or a payload) disclosed herein are useful for treating any disease or disorder in which stimulation, activation and/or targeting of GLP1R would be beneficial. In particular, the anti-GLP1R antibody-drug conjugates of the present disclosure can be used for the treatment, prevention and/or amelioration of any disease or disorder associated with or mediated by GLP1R expression or activity.

In some embodiments, the compounds (e.g., an antibody-drug conjugate, a linker-payload and/or a payload) disclosed herein are useful for treating a GLP1R-associated condition. In some embodiments, the GLP1R-associated condition is Type 1 or Type 2 diabetes mellitus. The administered compound (e.g., an antibody-drug conjugate, a linker-payload and/or a payload) may cause at least one of the following results: induction of insulin secretion, suppression of glucagon release, reduction of blood sugar, improvement of glycemic control, promotion of islet neogenesis, and delay of gastric emptying or potentiation of glucose resistant islets.

In some embodiments, the GLP1R-associated condition is a neurodegenerative disorder, a cognitive disorder, memory disorder or learning disorder. The neurodegenerative disorder may be, for example, dementia, senile dementia, mild cognitive impairment, Alzheimer-related dementia, Huntington's chores, tardive dyskinesia, hyperkinesias, mania, Morbus Parkinson, steel-Richard syndrome, Down's syndrome, myasthenia gravis, nerve trauma, brain trauma, vascular amyloidosis, cerebral hemorrhage I with amyloidosis, brain inflammation, Friedrich's ataxia, acute confusion disorder, amyotrophic lateral sclerosis, glaucoma and Alzheimer's disease.

In some embodiments, the GLP1R-associated condition is a liver disease. The liver disease may be, for example, non-alcoholic fatty liver disease (NAFLD), fatty liver, non-alcoholic steatohepatitis (NASH), and cirrhosis.

In some embodiments, the GLP1R-associated condition is a coronary artery disease. The coronary artery disease may be, for example, cardiomyopathy and myocardial infarction.

In some embodiments, the GLP1R-associated condition is a kidney disease. The kidney disease may be, for example, hypertension, or chronic kidney failure.

In some embodiments, the GLP1R-associated condition is an eating disorder. The eating disorder may be, for example, binge eating.

Without wishing to be bound by theory, the compounds (e.g., an antibody-drug conjugate, a linker-payload and/or a payload) disclosed herein may be employed to attenuate the effects of apoptosis-mediated degenerative diseases of the central nervous system such as Alzheimer's Disease, Creutzfeld-Jakob Disease and bovine spongiform encephalopathy, chronic wasting syndrome and other prion mediated apoptotic neural diseases (see, e.g., Perry and Grieg (2004) Current Drug Targets 6:565-571). Administration of a compound (e.g., an antibody-drug conjugate, a linker-payload and/or a payload) disclosed herein may also lead to down-modulation of βAPP and thereby ameliorate Aβ mono- or oligomer-mediated pathologies associated with Alzheimer's Disease (see, e.g., Perry et al. (2003) Journal of Neuroscience Research 72:603-612).

It is also contemplated that the compounds (e.g., an antibody-drug conjugate, a linker-payload and/or a payload) disclosed herein may be used to improve learning and memory, for example, by enhancing neuronal plasticity and facilitation of cellular differentiation (see, During et al. (2003) Nature Medicine 9:1173-1179). Further, the compounds (e.g., an antibody-drug conjugate, a linker-payload and/or a payload) disclosed herein may also be used to preserve dopamine neurons and motor function in Morbus Parkinson (see, e.g., Greig et al. (2005) Abstract 897.6, Society for Neuroscience, Washington, D.C.).

In some embodiments, the compounds (e.g., an antibody-drug conjugate, a linker-payload and/or a payload) disclosed herein may also be used to treat a metabolic disorder. The metabolic disorder may be, for example, obesity, dyslipidemia, metabolic syndrome X, and pathologies emanating from islet insufficiency.

Additional diseases that may be treated by a compound (e.g., an antibody-drug conjugate, a linker-payload and/or a payload) of the present disclosure include autoimmune diseases, in particular, those associated with inflammation, including, but not limited to, autoimmune diabetes, adult onset diabetes, morbid obesity, Metabolic Syndrome X and dyslipidemia. For example, the anti-GLP1R antibody-drug conjugate can be employed as a growth factor for the promotion of islet growth in persons with autoimmune diabetes. The compounds (e.g., an antibody-drug conjugate, a linker-payload and/or a payload) described herein may also be useful in the treatment of congestive heart failure.

In one aspect, the present disclosure provides a method of selectively targeting an antigen (e.g., GLP1R) on a surface of a cell with a compound. In one embodiment, the method of selectively targeting an antigen (e.g., GLP1R) on a surface of a cell with a compound comprises linking the compound to a targeted antibody. In one embodiment, the compound is a payload as described above. In one embodiment, the cell is a mammalian cell. In one embodiment, the cell is a human cell. In one embodiment, the cell is a pancreatic cell or a brain cell. In certain embodiments, the present disclosure provides a method of selectively targeting an antigen on a surface of a cell with a compound having the structure selected from the group consisting of:
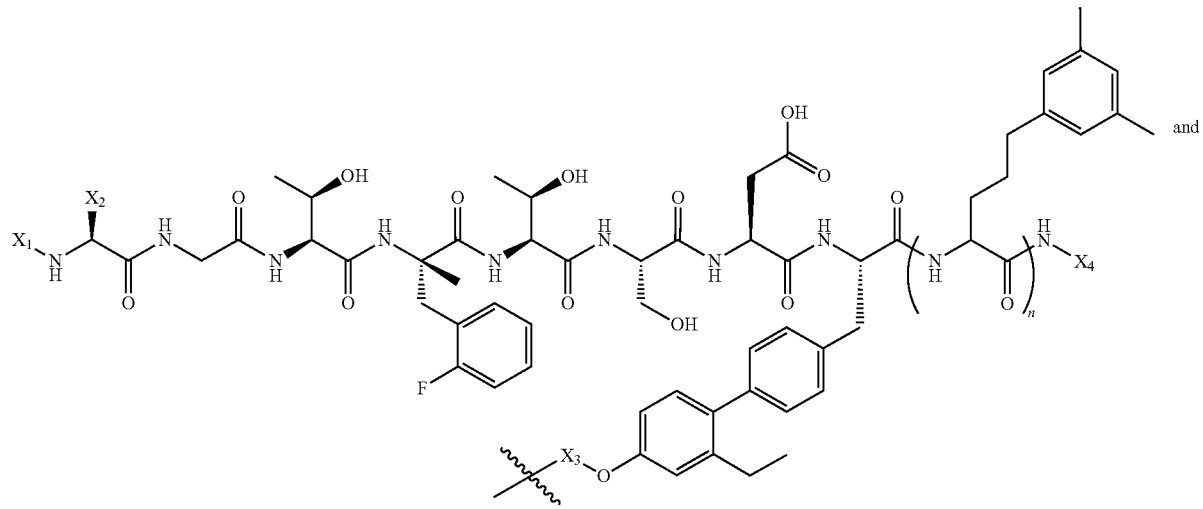
(P-I (SEQ ID NO: 30))
and
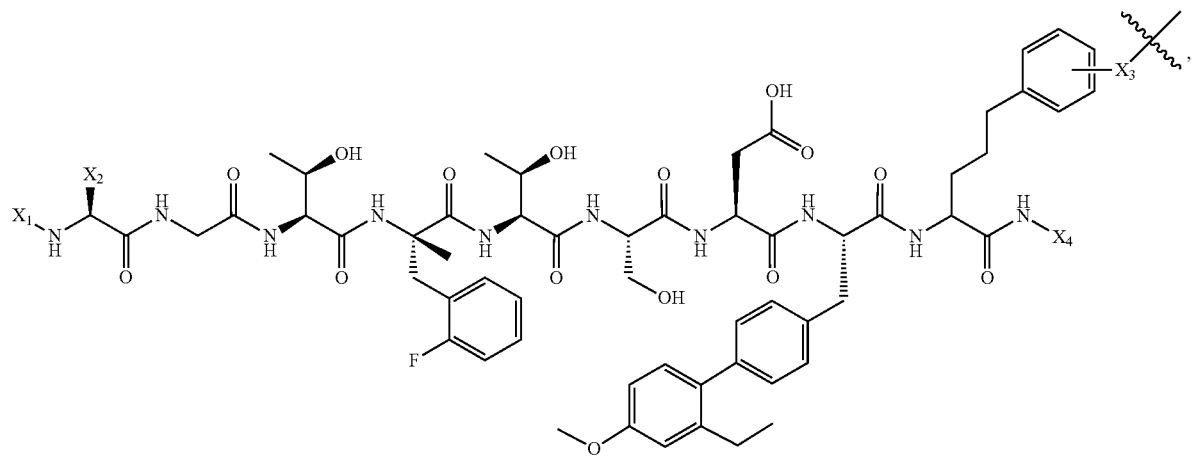
(P-II (SEQ ID NO: 28))
wherein
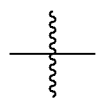
is the point of attachment of the compound to a linker L;
$X_1$ is selected from H;
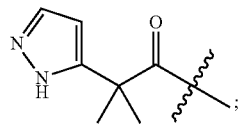
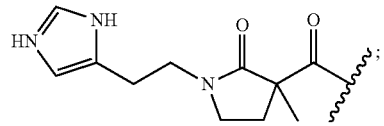
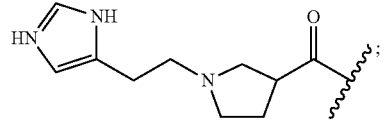
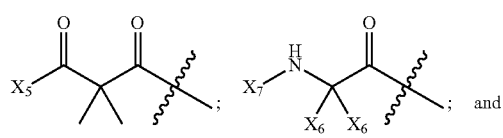
and

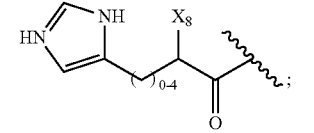

X₂ is selected from

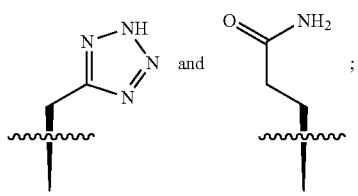

X₃ is selected from —(CH₂)₂₋₆—NH— and —(CH₂)₂₋₆—Tr-, where Tr is a triazole moiety;
n is 0 or 1;
X₄ is selected from H and phenyl;
X₅ is selected from —OH, —NH₂, —NH—OH, and

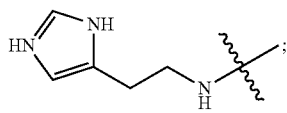 [SMILES: *NCCc1cnc[nH]1]

X₆ is independently at each occurrence selected from H, —OH, —CH₃, and —CH₂OH;
X₇ is selected from H

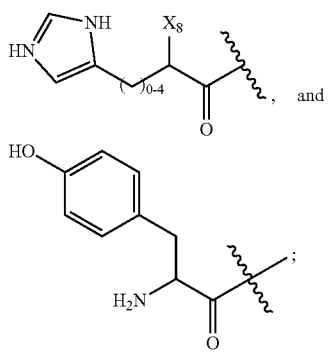

X₈ is selected from H, —OH, —NH₂, and

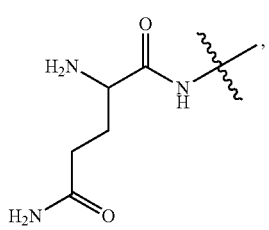

or a pharmaceutically acceptable salt thereof.

In certain embodiments, the present disclosure also includes the use of a compound (e.g., an antibody-drug conjugate, a linker-payload and/or a payload) of the present disclosure in the manufacture of a medicament for the treatment of a disease or disorder (e.g., cancer) related to or caused by GLP1R-expressing cells. In one aspect, the present disclosure relates to a protein-drug conjugate comprising an anti-GLP1R antibody or antigen-binding fragment, as disclosed herein, for use in medicine. In one aspect, the present disclosure relates to a compound comprising an antibody-drug conjugate (ADC) as disclosed herein, for use in medicine.

Combination Therapies and Formulations

The present disclosure provides methods which comprise administering a pharmaceutical composition comprising any of the exemplary protein-drug conjugates (e.g., antibody-drug conjugates), linker-payloads and payloads described herein in combination with one or more additional therapeutic agents.

Exemplary additional therapeutic agents that may be combined with or administered in combination with protein-drug conjugates (e.g., antibody-drug conjugates), linker-payloads and payloads of the present disclosure include, other GLP1R agonists (e.g., an anti-GLP1R antibody or a small molecule agonist of GLP1R or an anti-GLP1R antibody-drug conjugate). Non-limiting examples of GLP1R agonists include exenatide (Byetta, Bydureon), liraglutide (Victoza, Saxenda), lixisenatide (Lyxumia in Europe, Adlyxin in the United States), albiglutide (Tanzeum), dulaglutide (Trulicity), semaglutide (Ozempic), and taspoglutide.

Exemplary additional therapeutic agents may include dual or triple-agonists, including GLP1R/GIPR dual agonists, such as GLP1R/GCGR dual agonists, GLP1R/GIPR/GCGR triple-agonists.

Other agents that may be beneficially administered in combination with the protein-drug conjugates (e.g., antibody-drug conjugates), linker-payloads and payloads of the disclosure include those that are useful in the treatment of diabetes (e.g., type II diabetes), obesity, and/or other related metabolic diseases.

In some embodiments, the additional therapeutic agent is an antidiabetic agent. Any suitable antidiabetic agents can be used. Non-limiting examples of antidiabetic agents include insulin, insulin analogs (including insulin lispro, insulin aspart, insulin glulisine, isophane insulin, insulin zinc, insulin glargine, and insulin detemir), biguanides (including metformin, phenformin, and buformin), thiazolidinediones or TZDs (including rosiglitazone, pioglitazone, and troglitazone), sulfonylureas (including tolbutamide, acetohexamide, tolazamide, chlorpropamide, glipizide, glibenclamide, glimepiride, gliclazide, glyclopyramide, and gliquidone), meglitinides (including repaglinide and nateglinide), alpha-glucosidase inhibitors (including miglitol, acarbose, and voglibose), glucagon-like peptide analogs and agonists (including exenatide, liraglutide, semaglutide, taspoglutide, lixisenatide, albuglutide, and dulaglutide), gastric inhibitory peptide analogs, dipeptidyl peptidase-4 (DPP-4) inhibitors (including vildagliptin, sitagliptin, saxagliptin, linagliptin, alogliptin, septagliptin, teneligliptin, and gemigliptin), amylin agonist analogs, sodium/glucose cotransporter 2 (SGLT2) inhibitors, glucokinase activators, squalene synthase inhibitors, other lipid lowering agents and aspirin. In some such embodiments, the antidiabetic agent is an oral antidiabetic agents (OAA) such as metformin, acarbose, or TZDs. In some such embodiments, the antidiabetic agent is metformin.

In some embodiments, the GLP1R agonist and one or more antidiabetic agents may be formulated into the same dosage form, such as a solution or suspension for parenteral administration.

The additional therapeutically active component(s) may be administered just prior to, concurrent with, or shortly after the administration of a compound of the present disclosure; (for purposes of the present disclosure, such administration regimens are considered the administration of an antigen-binding molecule "in combination with" an additional therapeutically active component).

The present disclosure includes pharmaceutical compositions in which protein-drug conjugates (e.g., antibody-drug conjugates), linker-payloads and/or payloads of the present disclosure are co-formulated with one or more of the additional therapeutically active component(s) as described elsewhere herein.

Administration Regimens

According to certain embodiments of the present disclosure, multiple doses of a protein-drug conjugate (e.g., an anti-GLP1R antibody-drug conjugate), linker-payload and/or a payload may be administered to a subject over a defined time course. The methods according to this aspect of the disclosure comprise sequentially administering to a subject multiple doses of a protein-drug conjugate (e.g., an anti-GLP1R antibody-drug conjugate), linker-payload and/or a payload of the disclosure. As used herein, "sequentially administering" means that each dose of a protein-drug conjugate (e.g., an anti-GLP1R antibody-drug conjugate), linker-payload and/or a payload is administered to the subject at a different point in time, e.g., on different days separated by a predetermined interval (e.g., hours, days, weeks or months). The present disclosure includes methods which comprise sequentially administering to the patient a single initial dose of a protein-drug conjugate (e.g., an anti-GLP1R antibody-drug conjugate), linker-payload and/or a payload, followed by one or more secondary doses of the protein-drug conjugate (e.g., an anti-GLP1R antibody-drug conjugate), linker-payload and/or payload, and optionally followed by one or more tertiary doses of the a protein-drug conjugate (e.g., an anti-GLP1R antibody-drug conjugate), linker-payload and/or payload.

The terms "initial dose," "secondary doses," and "tertiary doses," refer to the temporal sequence of administration of the protein-drug conjugate (e.g., an anti-GLP1R antibody-drug conjugate), linker-payload and/or payload of the disclosure. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the protein-drug conjugate (e.g., an anti-GLP1R antibody-drug conjugate), linker-payload and/or payload, but generally may differ from one another in terms of frequency of administration. In certain embodiments, however, the amount of the protein-drug conjugate (e.g., an anti-GLP1R antibody-drug conjugate), linker-payload and/or payload contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present disclosure, each secondary and/or tertiary dose is administered 1 to 26 (e.g., 1, 1%, 2, 2%, 3, 3%, 4, 4%, 5, 5%, 6, 6%, 7, 7%, 8, 8%, 9, 9%, 10, 10%, 11, 11%, 12, 12%, 13, 13%, 14, 14%, 15, 15%, 16, 16%, 17, 17%, 18, 18%, 19, 19%, 20, 20%, 21, 21%, 22, 22%, 23, 23%, 24, 24%, 25, 25%, 26, 26%, or more) weeks after the immediately preceding dose. The phrase "the immediately preceding dose," as used herein, means, in a sequence of multiple administrations, the dose of a protein-drug conjugate (e.g., an anti-GLP1R antibody-drug conjugate), linker-payload and/or payload which is administered to a patient prior to the administration of the very next dose in the sequence with no intervening doses.

The methods according to this aspect of the disclosure may comprise administering to a patient any number of secondary and/or tertiary doses of a protein-drug conjugate (e.g., an anti-GLP1R antibody-drug conjugate), linker-payload and/or payload. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples illustrate specific aspects of the instant description. The examples should not be construed as limiting, as the examples merely provide specific understanding and practice of the embodiments and their various aspects.

The abbreviations used in the Examples and throughout the specification are as follows:

| Abbreviation | Term |
| --- | --- |
| aa# (e.g., aa1) | amino acid number (e.g., amino acid 1) |
| Ac | acetyl |
| ADC | antibody-drug conjugation |
| aq. | aqueous |
| Boc | t-butoxycarbonyl |
| CD | cyclodextrin |

-continued

| Abbreviation | Term |
|---|---|
| DCC | dicyclohexylcarbodiimide |
| DCM | dichloromethane |
| DIPEA | diisopropylethylamine |
| DMAP | 4-Dimethylaminopyridine |
| DMF | N,N-Dimethylformamide |
| DMSO | dimethylsulfoxide |
| EDCl | 1-ethyl-3-(3-dimethylaminopropyl)carbodiimide hydrochloride |
| Et | ethyl |
| EtOAc | Ethyl acetate |
| EtOH | ethanol |
| Et$_3$N | Triethylamine |
| Fmoc | 9-fluorenylmethoxycarbonyl |
| FmocCl | 9-Fluorenylmethyl chloroformate |
| FmocOSu | N-(9-Fluorenylmethoxycarbonyloxy)succinimide |
| HATU | O-(7-azabenzotriazol-1-yl)-N,N,N',N'-tetramethyluronium hexafluorophosphate |
| HOBt (HOBT) | 1-hydroxybenzotriazole |
| HOSu | N-hydroxysuccinimide |
| HPLC | high-pressure liquid chromatography |
| HRMS | High-resolution mass spectrometry |
| LCMS | Liquid chromatography-mass spectrometry |
| Me | methyl |
| MPM (PMB) | p-methoxybenzyl |
| Ms | mesyl (methanesulfonyl) |
| MS | mass spectrometry |
| 4A MS | 4A molecular sieves |
| MW | Molecule weight |
| MeOH | methanol |
| NMR | nuclear magnetic resonance |
| PEG | polyethylene glycol |
| Ph | phenyl |
| Pr | propyl |
| psi | pounds per square inch |
| Py (pyr) | pyridine |
| PE | Petroleum ether |
| Resin | MBHA resin (0.3~0.8 mmol/g, 100~200 mesh, 1% DVB) |
| R$_f$ | retention factor in chromatography |
| t-Bu (tBu) | tert-butyl |
| t-BuOMe (MTBE, TBME) | Methyl tert-butyl ether |
| TEA | triethylamine |
| TES | triethylsilyl |
| TFA | trifluoroacetic acid |
| Tfa | trifluoroacetamide |
| THF | tetrahydrofuran |
| Tr (Trt) | trityl (triphenylmethyl) |
| TRTCl | triphenylmethyl chloride |
| Ts (Tos) | p-toluenesulfonyl |
| Rink Amide Linker | 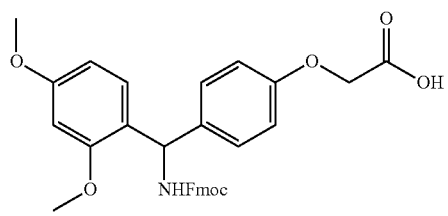 |
| Fmoc-Rink Amide MBHA Resin | 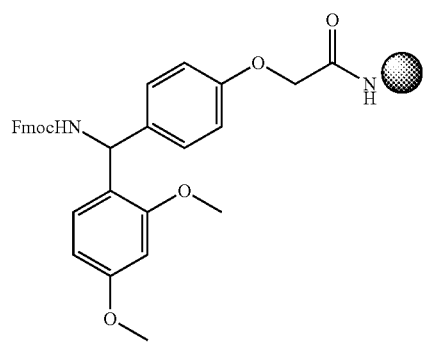 |

-continued

| Abbreviation | Term |
|---|---|
| Rink Amide MBHA Resin | (structure) |
| DIBAC-PEG₄-acid | (structure) |
| DIBAC-PEG₄-NHS | (structure) |
| DIBAC-PEG₈-acid | (structure) |
| DIBAC-PEG₈-NHS | (structure) |
| DIBAC-PEG₁₂-acid | (structure) |

| Abbreviation | Term |
|---|---|
| DIBAC-PEG$_{12}$-NHS | 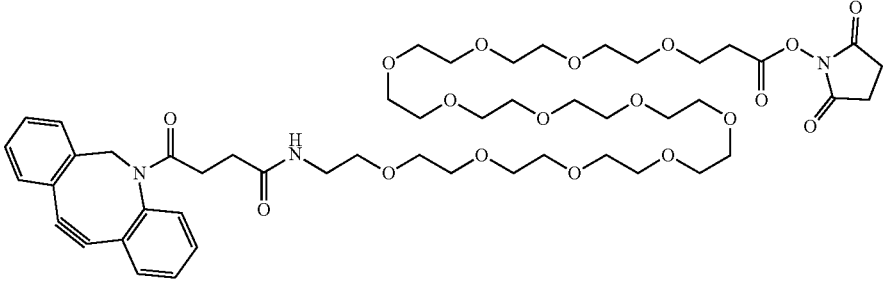 [SMILES: O=C(CCC(=O)N1Cc2ccccc2C#Cc2ccccc21)NCCOCCOCCOCCOCCOCCOCCOCCOCCOCCOCCOCCOCCC(=O)ON1C(=O)CCC1=O] |
| DIBAC-PEG$_{24}$-acid | 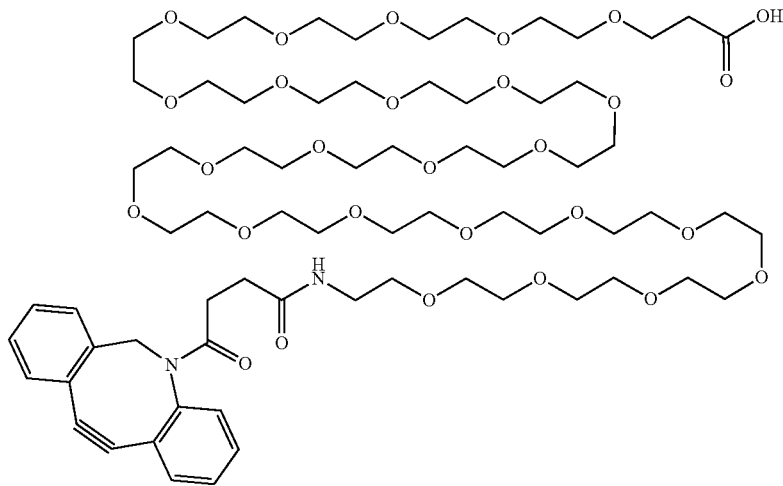 [SMILES: O=C(O)CCOCCOCCOCCOCCOCCOCCOCCOCCOCCOCCOCCOCCOCCOCCOCCOCCOCCOCCOCCOCCOCCOCCOCCOCCNC(=O)CCC(=O)N1Cc2ccccc2C#Cc2ccccc21] |
| DIBAC-PEG$_{24}$-NHS | 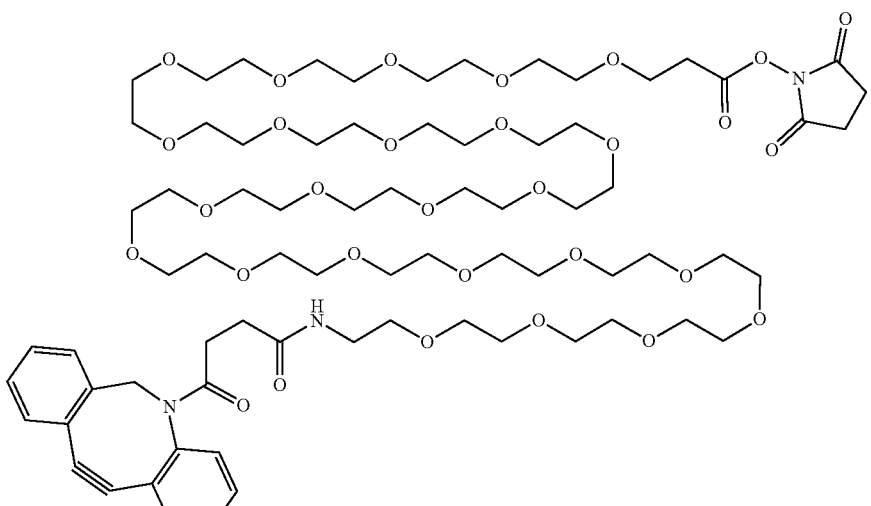 |

-continued

| Abbreviation | Term |
|---|---|
| Azido-DIBAC-PEG$_{24}$-linker | (structure) |
| CD-N$_3$ | (structure) |
| CD-N$_3$-DIBAC-PEG$_{24}$-linker | (structure) |

Example 1. Synthesis of Small Molecular Payloads and Linker-Payloads

1.1 Solid Phase Peptide Synthesis of Peptidomimetic Payloads

General Procedure of Preparation of Peptidomimetics (Payloads) Using SPPS Approach Scheme 1 depicts an assembly of peptidomimetic payloads according to the disclosure on resin. The peptides were assembled manually by a roller-mixer onto Fmoc SPPS (Solid phase peptide synthesis) using polypropylene columns equipped with a filter disc. A sufficient quantity of Rink amide MBHA resin (loading: 0.5-0.6 mmol/g) was swollen in DMF or $CH_2Cl_2$ for 15 min Scheme 1: General Scheme for assembling polypeptide payloads using SPPS strategy

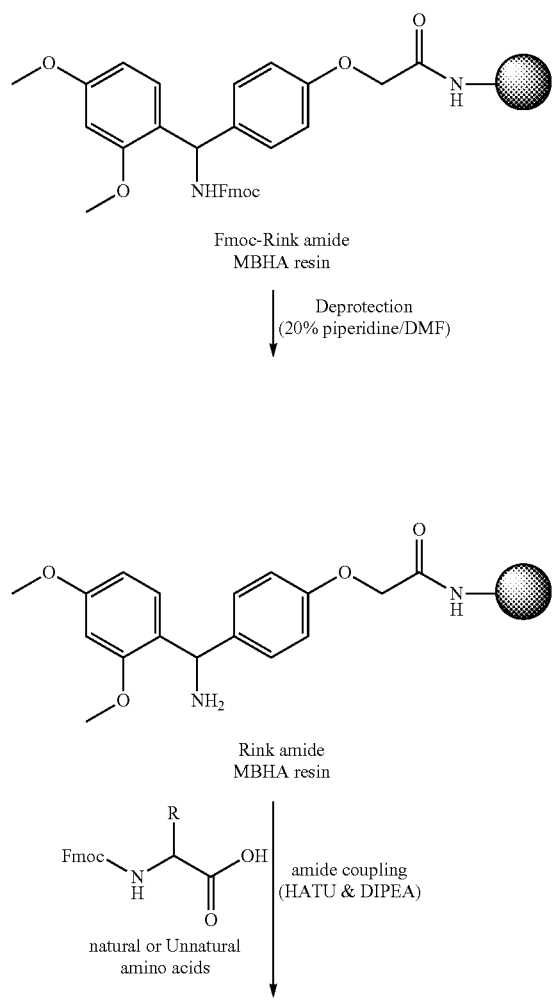

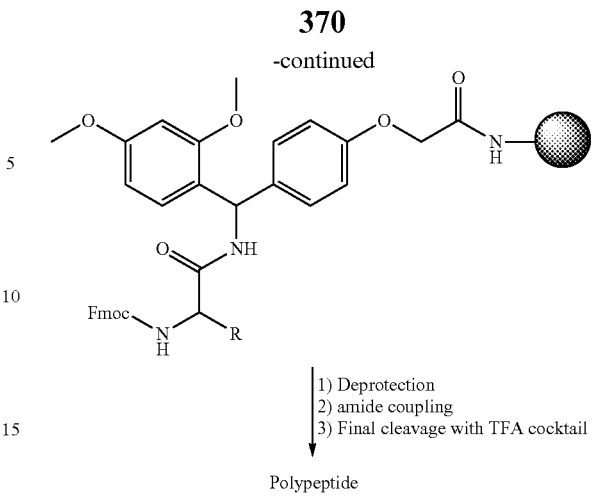

Step 1: General Procedure for Removal of Fmoc from Fmoc-Rink Amide MBHA Resin

The Fmoc-group on the resin was removed by incubation of resin with 20% piperidine in DMF (10-30 ml/100 mg of resin) for 5 to 15 min. The deprotected resin was filtered and washed with excess of DMF and DCM. After washing three times, the resin was incubated in a freshly distilled DMF (1 mL/100 mg of resin), under nitrogen atmosphere for 5 min.

Step 2: General Procedure for Amide Coupling on Rink Amide MBHA Resin

For the amide coupling reaction with the SPPS-reactant, a DMF solution containing HATU (1.5-4 eq.), Fmoc-protected amino acid (1.5-5 eq. at 0.5M concentration), and DIPEA (5-10 eq.) were added to the resin. For the amide coupling reaction with a natural amino acid as a reactant, the Fmoc-amino acid (5 eq.), HATU (4.5 eq.) and DIPEA (10 eq.) were mixed with the resin; for the amide coupling reaction with an unnatural amino acid as a reactant, the Fmoc-amino acid (1.5-2 eq.), HATU (1.5 eq.) and DIPEA (5.0 eq.) were mixed with the resin. The mixed resin mixture was then shaken for 1-3 hours under nitrogen atmosphere, and the coupling reactions were monitored using a ninhydrin test qualitative analysis. After attachment of the Fmoc-protected amino acid, the resin was then washed with DMF and DCM to generate the corresponding peptide bound resin.

Step 3: General Procedure for Cleavage from Resin Followed by Global Deprotection The resin-bound peptidomimetic payloads were subjected to cleavage and deprotection with TFA cocktail as follows. A solution of TFA/water/triisopropylsilane (95:2.5:2.5) (10 mL per 100 mg of peptidyl-resin) was added to peptidyl-resins and the mixture was kept at room temperature. After 2-3 hours, the resin was filtered and rinsed by a cleavage solution. The combined filtrate was treated with cold t-BuOMe to precipitate the peptide. The suspension was centrifuged for 10 min (5000 R). The crude white powder was combined and purified by preparative HPLC.

The peptide chain elongation was performed by a number of iterations consisting of deprotection, washing, coupling, and washing procedures, (i.e. the resin was subjected to the reaction conditions for 1 hour each time, and the solution was drained and the resin was re-subjected to fresh reagents each time), as depicted in Scheme 1. Finally, the resulting Fmoc-protected peptidyl-resin was deprotected by 20% piperidine as described above and washed with DMF and DCM four times each. The resin bound peptide was dried under nitrogen flow for 10-15 minutes and subjected to cleavage/deprotection. Using the above protocol and suitable variations thereof, the peptidomimetics designed in the present disclosure were prepared, using Fmoc-SPPS approach. Furthermore, the resin bound peptidomimetics were cleaved and deprotected, purified and characterized using the following protocol.

1.2 Preparative HPLC Purification of the Crude Peptidomimetics

The preparative HPLC was carried out on a Shimadzu LC-8a Liquid chromatograph. A solution of crude peptide dissolved in DMF or water was injected into a column and eluted with a linear gradient of ACN in water. Different methods were used. (See General Information). The desired product eluted were in fractions and the pure peptidomimetics were obtained as amorphous with powders by lyophilization of respective HPLC fractions. In general, after the prep-HPLC purification, the overall recovery was found to be in the range of 40~50% yield.

Preparative HPLC method A: using FA condition (column: Xtimate C18 150*25 mm*5 µm; mobile phase: [water (0.225% FA)-ACN]; B %: 40%-70%, 7 min) to afford a pure product.

Preparative HPLC method B: using TFA condition (column: YMC-Exphere C18 10 µm 300*50 mm 12 nm; mobile phase: [water (0.1% TFA)-ACN]; B %: 15%-45%, 55 min) to afford a pure product.

Preparative HPLC method C: using neutral condition (column: Phenomenex Gemini-NX 150*30 mm*5 µm; mobile phase: [water (10 mM $NH_4HCO_3$)-ACN]; B %: 21%-51%, 11 min) to afford a pure product.

Preparative HPLC method D: using neutral condition (column: Waters Xbridge 150*255u; mobile phase: [water (10 mM $NH_4HCO_3$)-ACN]; B %: 20%-50%, 7 min) to afford a pure product.

Preparative HPLC method E: using FA condition (column: Phenomenex Luna C18 250*50 mm*10 µm; mobile phase: [water (0.225% FA)-ACN]; B %: 55%-86%, 21 min) to afford a pure product.

1.3 HPLC Analysis of the Purified Peptidomimetics

After purification by preparation HPLC as described above, each peptide was analyzed by analytical HPLC with using methods A, B, C, D, E, or F. The acquisition of chromatogram was carried out at 220 nm, using a PDA detector, in general, the purity of pure peptidomimetics obtained after Prep-HPLC purification was found to be >95%.

HPLC method A (20 min): Mobile Phase: 4.0 mL TFA in 4 L water (solvent A) and 3.2 mL TFA in 4 L acetonitrile (solvent B), using the elution gradient 10%-80% (solvent B) over 20 minutes and holding at 80% for 3.5 minutes at a flow rate of 1.0 mL/minutes; Column: Gemini-NX 5 µm 150*4.6 mm, C18, 110A Wavelength: UV 220 nm, 254 nm; Column temperature: 30° C.

HPLC method B (15 min): Mobile Phase: 2.75 mL/4L TFA in water (solvent A) and 2.5 mL/4L TFA in acetonitrile (solvent B), using the elution gradient 10%-80% (solvent B) over 10 minutes and holding at 80% for 5 minutes at a flow rate of 1.5 mL/min; Column: WELCH Ultimate LP-C18 150*4.6 mm 5 µm; Wavelength: UV 220 nm, 215 nm, 254 nm; Column temperature: 40° C.

HPLC method C (8 min): Mobile Phase: 2.75 mL/4L TFA in water (solvent A) and 2.5 mL/4L TFA in acetonitrile (solvent B), using the elution gradient 10%-80% (solvent B) over 7 minutes and holding at 80% for 0.48 minutes at a flow rate of 1.5 mL/min; Column: Ultimate XB-C18.3 µm, 3.0*50 mm; Wavelength: 220 nm, 215 nm, 254 nm; Column temperature: 40° C.

HPLC method D (15 min): Mobile Phase: water containing 0.04% TFA (solvent A). and acetonitrile containing 0.02% TFA (solvent B), using the elution gradient 10% to 80% (solvent B) over 15 minutes and holding at 80% for 3.5 minutes at a flow rate of 1.5 mL/minutes; Column: YMC-Pack ODS-A 150*4.6 mm Wavelength: UV 220 nm, 254 nm; Column temperature: 30° C.

HPLC method E (8 min): Mobile Phase: 0.2 mL/1L $NH3*H_2O$ in water (solvent A) and acetonitrile (solvent B), using the elution gradient 0%-60% (solvent B) over 5 minutes and holding at 60% for 2 minutes at a flow rate of 1.2 ml/min; Column: Xbridge Shield RP-18, 5 µm, 2.1*50 mm. Wavelength: UV 220 nm, 254 nm; Column temperature: 30° C.

HPLC method F (7 min): Mobile Phase: 1.5 mL/4L TFA in water (solvent A) and 0.75 mL/4L TFA in acetonitrile (solvent B), using the elution gradient 10%-80% (solvent B). Column: Xtimate C18 2.1*30 mm; Wavelength: UV 220 nm, 254 nm; Column temperature: 50° C.

1.4 Characterization by Mass Spectrometry:

Each peptide was characterized by electrospray ionization mass spectrometry (ESI-MS), either in flow injection or LC/MS mode. In all cases, the experimentally measured molecular weight was within 0.5 Daltons of the calculated monoisotopic molecular weight. Using the above described protocol, all the crude/pure peptidomimetics were characterized by mass spectroscopy and in general, observed mass of peptidomimetic agreed with the calculated/theoretical mass, which confirms successful synthesis of desired peptidomimetics.

LC-MS method A: a MERCK (RP-18e 25-2 mm) column, with a flow rate of 1.5 mL/min, eluting with a gradient of 5% to 95% acetonitrile containing 0.02% TFA (solvent B) and water containing 0.04% TFA (solvent A).

LC-MS method B: a Xtimate (C18 2.1*30 mm, 3 µm) column, with a flow rate of 0.8 mL/min, eluting with a gradient of 10% to 80% acetonitrile containing 0.02% TFA (solvent B) and water containing 0.04% TFA (solvent A).

LC-MS method C: a Chromolith (Flash RP-18e 25-3 mm) column, with a flow rate of 1.5 mL/min, eluting with a gradient of 5% to 95% acetonitrile containing 0.04% TFA (solvent B) and water containing 0.06% TFA (solvent A).

LC-MS method D: Agilent, a Pursuit (5 C18 20*2.0 mm) column, flow rate 1.5 mL/min, eluting with a gradient of 5% to 95% acetonitrile containing 0.02% TFA (solvent B) and water containing 0.04% TFA (solvent A).

LC-MS method E: Waters Xbridge C18 30*2.0 mm, 3.5 µm column, with a flow rate of 1.0 mL/min, eluting with a gradient of 5% to 95%. Mobile phase: A) 0.05% $N_{H3}H_2O$ in Water; B) ACN. Gradient: 0% B increase to 95% B within 5.8 min; hold at 95% B for 1.1 min; then back to 0% B at 6.91 min and hold for 0.09 min.

LC-MS method F: XBridge C18 3.5 µm 2.1*30 mm Column, with a flow rate of 1.0 mL/min, Mobile phase: 0.8 mL/4L $NH_3·H_2O$ in water (solvent A) and acetonitrile (solvent B), using the gradient 10%-80% (solvent B) over 2 minutes and holding at 80% for 0.48 minutes.

1.5 HRMS Analysis was Performed on an Agilent 6200 Series TOF and 6500 Series Q-TOF LC/MS System The mobile phase: 0.1% FA in water (solvent A) and ACN (solvent B); Elution Gradient: 5%-95% (solvent B) over 3 minutes and holding at 95% for 1 minute at a flow rate of 1 ml/minute; Column: Xbridge Shield RP 18 5 μm, 2.1*50 mm Ion Source: AJS ESI source; Ion Mode: Positive; Nebulization Gas: Nitrogen; Drying Gas (N2) Flow: 8 L/min; Nebulizer Pressure: 35 psig; Gas Temperature: 325° C.; Sheath gas Temperature: 350° C.; Sheath gas flow: 11 L/min; Capillary Voltage: 3.5 KV; Fragmentor Voltage: 175 V.

Example 2. Synthesis of Unnatural Amino Acids

TABLE 1

Structures of natural and unnatural amino acids aa1-aa30

| No. | Structure | Source* | MF | ESI-MS Calcd. M/Z | Found |
|---|---|---|---|---|---|
| aa1 | 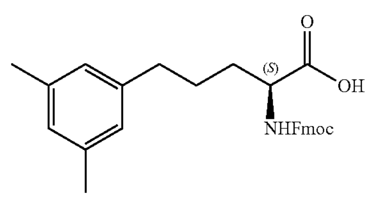 | GB2551945a Jazayeri, A. et al. *Nature*. 2017, 546, 254-258 | $C_{28}H_{29}NO_4$ | 443.2 | 466.1 [M + Na]$^+$ |
| aa1b | 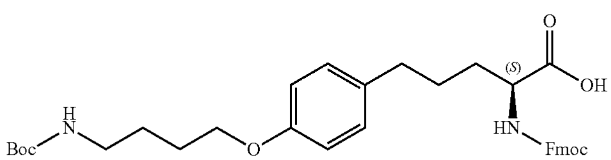 | Prepared | $C_{35}H_{42}N_2O_7$ | 602.2 | 625.1 [M + Na]$^+$ |
| aa2 | 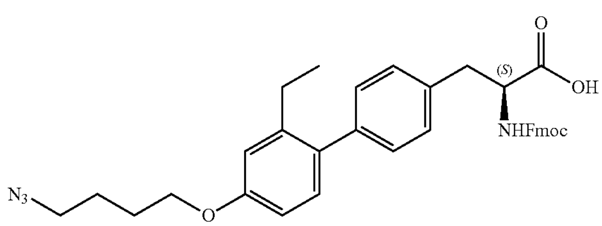 | Prepared | $C_{36}H_{36}N_4O_5$ | 604.2 | 627.3 [M + Na]$^+$ |
| aa2b | 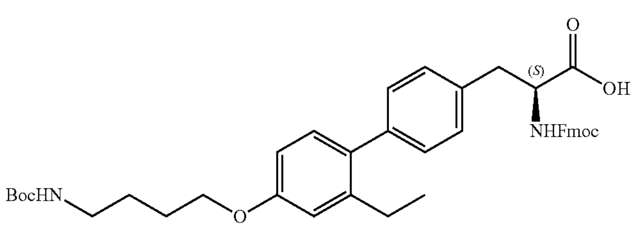 | Prepared | $C_{41}H_{46}N_2O_7$ | 678.3 | 701.3 [M + Na]$^+$ |
| aa2c | 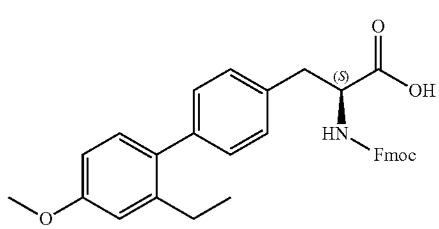 | Prepared | $C_{40}H_{43}N_2O_7$ | 662.77 | 663.5 [M + H]$^+$ |
| aa3 | 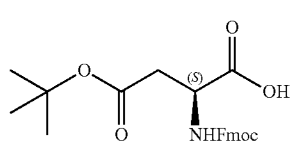 | Commercial | | | |

TABLE 1-continued

Structures of natural and unnatural amino acids aa1-aa30

| No. | Structure | Source* | MF | ESI-MS Calcd. M/Z | Found |
|---|---|---|---|---|---|
| aa4 | | Commercial | | | |
| aa5 | | Commercial | | | |
| aa6 | | Commercial | | | |
| aa7 | | Commercial | | | |
| aa8 | | Commercial | | | |
| aa9 | | Ceretti, S. et al *Eur. J. Org. Chem.* 2004, 4188-4196 | $C_{19}H_{17}N_5O_4$ | 379.1 | 402.0 [M + Na]$^+$ |
| aa9a | | Prepared | $C_{38}H_{31}N_5O_4$ | 621.2 | |
| aa9d | | Prepared | $C_{28}H_{27}N_5O_6$ | 529.20 | 530.4 [M + H]$^+$ |
| aa10 | | CB2551945a | $C_{29}H_{30}N_3O_3$ | 467.2 | 468.1 [M + H]$^+$ |

TABLE 1-continued

Structures of natural and unnatural amino acids aa1-aa30

| No. | Structure | Source* | MF | ESI-MS Calcd. M/Z | Found |
|---|---|---|---|---|---|
| aa11 | | Commercial | | | |
| aa12 | | WO2010/ 052253 | | | |
| aa13 | | Prepared | | | |
| aa14 | | Prepared | $C_7H_{11}N_2O_2$ | 154.1 | 155.0 [M + H]$^+$ |
| aa15 | | Commercial | | | |
| aa16 | | Commercial | | | |
| aa17 | | US2003/114668 | $C_{28}H_{27}N_2O_2$ | 422.22 | 423.2 [M − H]$^-$ |
| aa18 | | Crich, D. et al, *Org. Lett.* 2007, 9, 4423- 4426 | $C_{25}H_{23}N_2O_2$ | 382.18 | 383.2 [M + H]$^+$ |
| aa19 | | Commercial | | | |
| aa20 | | Prepared | $C_{30}H_{30}N_3O_3$ | 479.2 | 480.3 [M + H]$^+$ SFC- HPLC: RT = 2.346 min |

TABLE 1-continued

Structures of natural and unnatural amino acids aa1-aa30

| No. | Structure | Source* | MF | ESI-MS Calcd. M/Z | Found |
|---|---|---|---|---|---|
| aa21 | 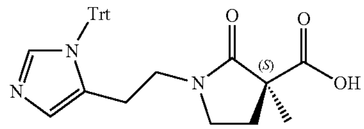 | Prepared | $C_{30}H_{30}N_3O_3$ | 479.2 | 480.3 [M + H]$^+$ SFC-HPLC: RT = 3.607 min |
| aa22 | 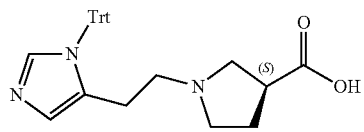 | Prepared | $C_{29}H_{30}N_3O_2$ | 451.2 | 452.3 [M + H]$^+$ |
| aa23 | 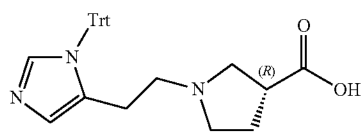 | Prepared | $C_{29}H_{30}N_3O_2$ | 451.2 | 452.2 [M + H]$^+$ |
| aa24 | 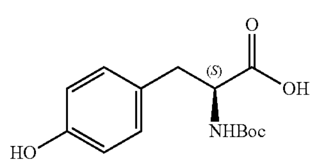 | Commercial | | | |
| aa25 | 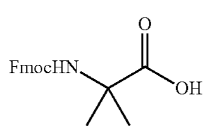 | Commercial | | | |
| aa26 | 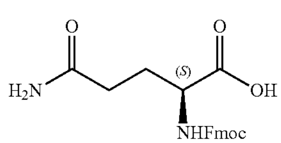 | Commercial | | | |
| aa27 | 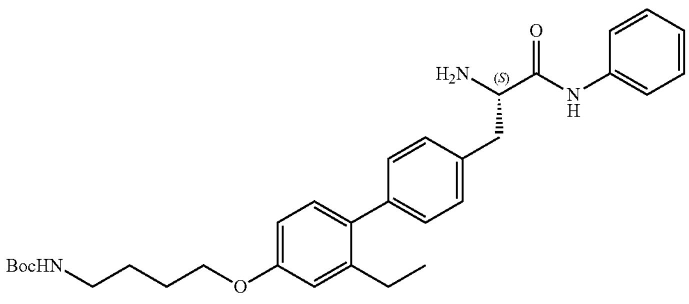 | Prepared | $C_{32}H_{41}N_3O_4$ | 531.3 | 554.1 [M + Na]$^+$ |

TABLE 1-continued

Structures of natural and unnatural amino acids aa1-aa30

| No. | Structure | Source* | MF | ESI-MS Calcd. M/Z | Found |
|---|---|---|---|---|---|
| aa28 | 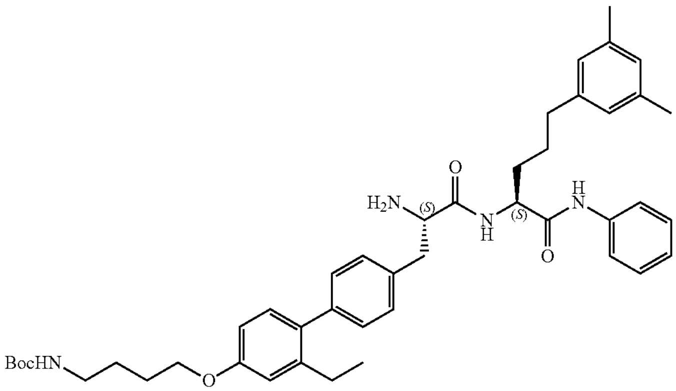 | Prepared | $C_{45}H_{58}N_4O_5$ | 734.4 | 757.5 [M + Na]$^+$. |
| aa29 | 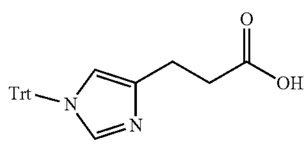 | Prepared | $C_{25}H_{22}N_2O_2$ | 382.17 | 381.17 [M − H]$^-$ |
| aa30 | 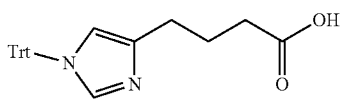 | Prepared | $C_{26}H_{24}N_2O_2$ | 396.18 | 397.20 [M − H]$^-$ |
| aa31 | 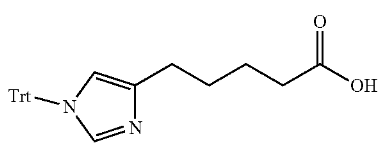 | Prepared | $C_{27}H_{26}N_2O_2$ | 410.20 | 411.3 [M − H]$^-$ |
| aa32 | 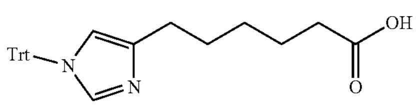 | Prepared | $C_{28}H_{28}N_2O_2$ | 424.22 | 425.22 [M − H]$^-$ |
| aa33 | 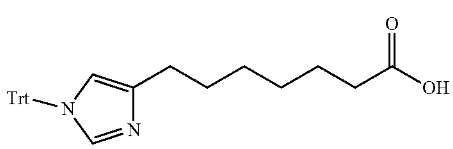 | Prepared | $C_{29}H_{30}N_2O_2$ | 438.23 | 439.23 [M − H]$^-$ |
| aa34 | 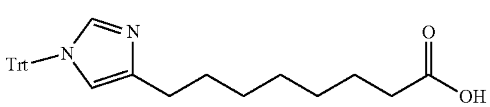 | Prepared | $C_{30}H_{32}N_2O_2$ | 452.25 | 453.23 [M − H]$^-$ |
| aa35 | 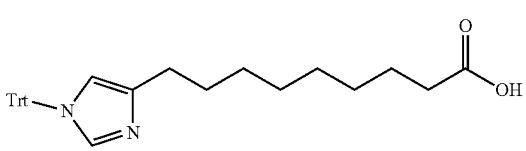 | Prepared | $C_{31}H_{34}N_2O_2$ | 466.26 | 465.25 [M − H]$^-$ |
| aa36 | 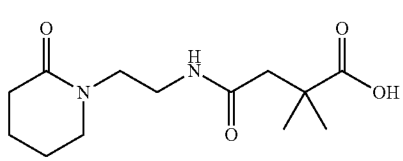 [SMILES: CC(C)(CC(=O)NCCN1CCCCC1=O)C(=O)O] | Prepared | $C_{13}H_{22}N_2O_4$ | 270.16 | 271.2 [M + H]$^+$ |

TABLE 1-continued
Structures of natural and unnatural amino acids aa1-aa30
| No. | Structure | Source* | MF | ESI-MS Calcd. M/Z | Found |
|---|---|---|---|---|---|
| aa37 | | Prepared | $C_{15}H_{16}N_2O_5S$ | 336.08 | 358.9 [M + Na]+ |
| aa38 | | Commercial | $C_{18}H_{17}NO_4$ | 311.12 | / |
| aa39 | | Commercial | $C_7H_{11}NO_3$ | 157.07 | / |
2.1 Synthesis of Unnatural Amino Acid (aa1b)
Scheme 2 outlines the synthesis of unnatural amino acid (aa1b):
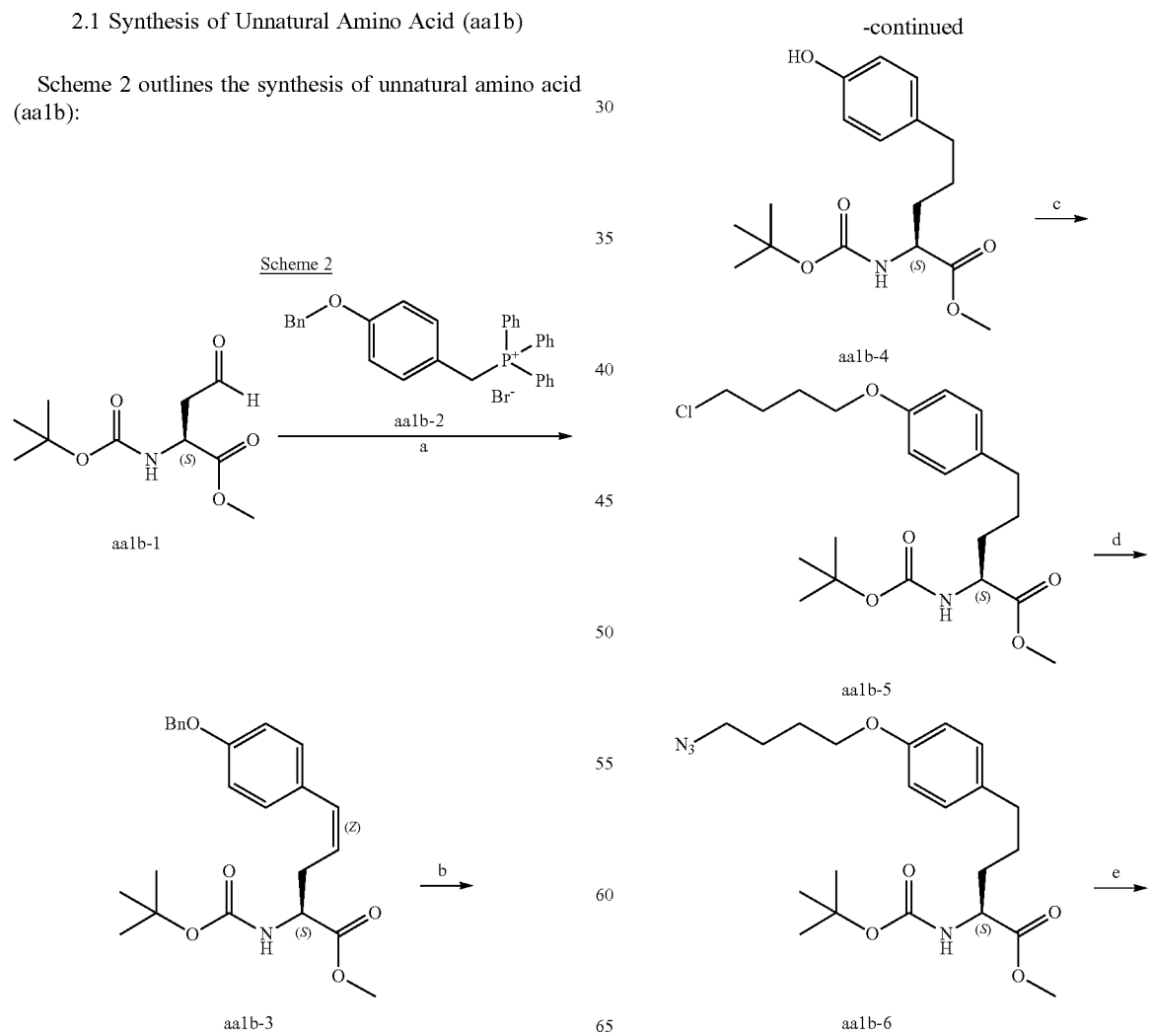

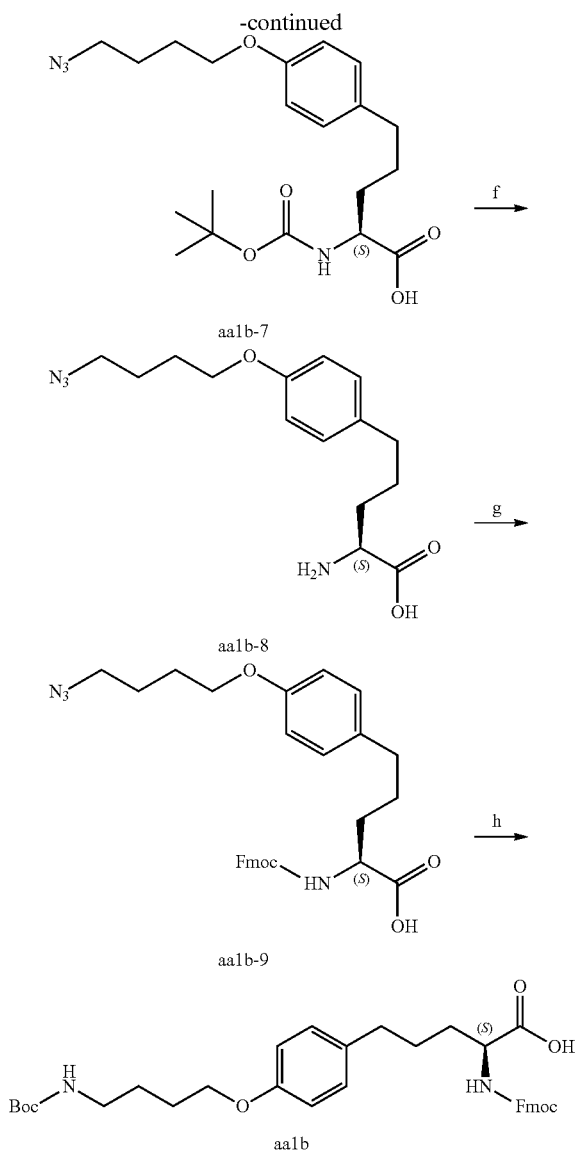

Reagents and conditions: a) 1-(benzyloxy)-4-(bromomethyl)benzene (aa1b-4) (1.0 eq.), t-BuOK (1.0 eq.), THF, 0-10° C., 1 h, 67.93%; b) Pd/C (10%), H₂ (50 Psi), MeOH, 40° C., 44 h; 94.24%; c) 1-chloro-4-iodobutane (1.5 eq.), K₂CO₃ (2.0 eq.), DMF, 50° C., 16 h, 83.44%; d) NaN₃ (2.17 eq.), K₂CO₃ (2.0 eq.), DMF, 65° C., 16 h, 98.44%; e) LiOH·H₂O (2.0 eq.), THF/H₂O, 22° C., 1 h, 100%; f) HCl/EtOAc, 22° C., 1 h, 85.04%; g) aq. NaHCO₃ (0.43 M), Fmoc-osu, THF, 0-22° C., 16 h, 92.11%; h) (Boc)₂O (3.0 eq.), DIPEA (3.0 eq.), Pd/C (10%), H₂ (15 Psi), 4 h, 22.50%.

Aa1b-2 were prepared according to the detailed synthetic procedure found in Wu, X. Y.; Stockdill, J. L.; Park, P. K.; Samuel J. Danishefsky, S. J. Expanding the Limits of Isonitrile-Mediated Amidations: On the Remarkable Stereosubtleties of Macrolactam Formation from Synthetic Seco-Cyclosporins. *J. Am. Chem. Soc.* 2012, 134, 2378-2384. Preparation of aa1b-1 was referred to at Du, J. J.; Gao, X. F.; Xin, L. M.; Lei, Z.; Liu, Z.; and Guo, J. Convergent Synthesis of N-Linked Glycopeptides via Aminolysis of w-Asp p-Nitrophenyl Thioesters in Solution. *Org. Lett.* 2016, 18, 4828-4831.

Step 1: Synthesis of (S,Z)-methyl 5-(4-(benzyloxy)phenyl)-2-((tert-butoxycarbonyl)amino)pent-4-enoate (aa1b-3)

To a suspension of aa1b-2 (17.50 g, 32.43 mmol, 1.0 eq.) in THF (100 mL) was added t-BuOK (3.64 g, 32.43 mmol, 1.0 eq.) under nitrogen at 0° C. The mixture was stirred at 0° C. for 30 min. A solution of aa1b-1 (7.5 g, 32.43 mmol, 1.0 eq.) in THF (50 mL) was added dropwise to the mixture. The reaction was warmed to 10° C. and stirred for 1 hr. Light yellow suspension was observed. The reaction was added to ice-water (300 mL) and extracted with EtOAc (200 mL×2). The organic layers were combined and washed with brine (200 mL), dried over Na2SO4, filtered and concentrated to give crude as yellow oil. The residue was purified by flash silica gel chromatography (ISCO®; 80 g SepaFlash® Silica Flash Column, Eluent of 0-18% Ethylacetate/Petroleum ether gradient @ 50 mL/min) for 1.5 h with total volume 2.5 L to give aa1b-3 (9.7 g, 23.57 mmol, 67.93% yield) as a light yellow oil.

$^1$H NMR (400 MHz, CHLOROFORM-d) δ =7.45-7.26 (m, 6H), 7.18 (br d, J=8.6 Hz, 1H), 6.92 (dd, J=8.7, 11.4 Hz, 2H), 6.56-6.34 (m, 1H), 5.98-5.83 (m, 1H), 5.55-5.42 (m, 1H), 5.07 (d, J=2.2 Hz, 3H), 4.48-4.36 (m, 1H), 3.77-3.68 (m, 3H), 2.94-2.56 (m, 2H), 1.43 (s, 9H)

Step 2: Synthesis of (S)-methyl 2-((tert-butoxycarbonyl)amino)-5-(4-hydroxyphenyl) pentanoate (aa1b-4)

A solution of methyl aa1b-3 (9.7 g, 23.57 mmol, 1.0 eq.) and Pd/C (10% palladium on activated carbon, 1.0 g, 9.40 mmol) in MeOH (100 mL) was stirred at 40° C. under 50 Psi of hydrogen for 44 hr. Black suspension was observed. The reaction was filtered through a pad of Celite, the cake was washed with MeOH (50 mL×3). The filtrate was concentrated in vacuum to give aa1b-4 (7.5 g, 22.22 mmol, 94.24% yield, 95.788% purity) as a gray solid.

$^1$H NMR (400 MHz, CHLOROFORM-d) δ =7.05-6.92 (m, J=8.3 Hz, 2H), 6.79-6.70 (m, J=8.3 Hz, 2H), 5.59 (br s, 1H), 5.03 (br d, J=7.8 Hz, 1H), 4.37-4.26 (m, 1H), 3.71 (s, 3H), 2.61-2.47 (m, 2H), 1.81 (br s, 1H), 1.68-1.54 (m, 3H), 1.44 (s, 9H). LCMS (ESI): RT=0.927 min, mass calcd. for $C_{17}H_{25}NO_5$ 323.17, m/z found 345.9 [M+Na]⁺. Reverse phase LC-MS was carried out using method C.

Step 3: Synthesis of (S)-methyl 2-((tert-butoxycarbonyl)amino)-5-(4-(4-chlorobutoxy)phenyl) pentanoate (aa1b-5)

A solution of aa1b-10 (7 g, 21.65 mmol, 1.0 eq.), 1-chloro-4-iodobutane (7.09 g, 32.47 mmol, 1.5 eq.) and K₂CO₃ (5.98 g, 43.29 mmol, 2.0 eq.) in DMF (70 mL) was stirred at 50° C. for 16 hr. The combined reaction was added to ice-water (200 mL) and extracted with EtOAc (150 mL×3). The organic layers were combined and washed with brine (150 mL×2), dried over Na₂SO₄, filtered and concentrated to give crude as yellow oil. The residue was purified by flash silica gel chromatography (ISCO®; 80 g SepaFlash® Silica Flash Column, Eluent of 0-20% Ethyl acetate/Petroleum ether gradient @ 50 mL/min) for 1.5 h with total volume 2.5 L to give aa1b-5 (8 g, 19.33 mmol, 83.44% yield) as a colorless oil.

$^1$H NMR (400 MHz, CHLOROFORM-d) δ =7.04 (d, J=8.6 Hz, 2H), 6.79 (d, J=8.6 Hz, 2H), 4.95 (br d, J=7.3 Hz, 1H), 4.34-4.22 (m, 1H), 3.98-3.92 (m, 2H), 3.70 (s, 3H), 3.60 (t, J=6.2 Hz, 2H), 2.62-2.48 (m, 2H), 2.04-1.84 (m, 4H), 1.83-1.59 (m, 4H), 1.42 (s, 9H)

Step 4: Synthesis of (S)-methyl 5-(4-(4-azidobutoxy)phenyl)-2-((tert-butoxycarbonyl)amino) pentanoate (aa1b-6)

A mixture of aa1b-5 (7.5 g, 18.12 mmol, 1.0 eq.), NaN$_3$ (2.56 g, 39.32 mmol, 2.17 eq.), K$_2$CO$_3$ (5.01 g, 36.24 mmol, 2.0 eq.) and KI (300.78 mg, 1.81 mmol, 0.1 eq.) in DMF (75 mL) was stirred at 65° C. for 16 hr. The reaction was added to ice-water (200 mL) and extracted with EtOAc (100 mL×3). The organic layers were combined and washed with brine (100 mL×3), dried over Na$_2$SO$_4$, filtered and concentrated to give aa1b-6 (7.5 g, 17.84 mmol, 98.44% yield) as a yellow oil.

Step 5: Synthesis of (S)-5-(4-(4-azidobutoxy)phenyl)-2-((tert-butoxycarbonyl)amino)pentanoic acid (aa1b-7)

A solution of aa1b-6 (7.5 g, 17.84 mmol, 1.0 eq.) and LiOH·H$_2$O (1 M, 35.67 mL, 2.0 eq.) in THF (70 mL) was stirred at 22° C. for 1 hr. No change was observed. The reaction was concentrated in vacuum to remove THF. The reaction was adjusted to pH=5 with 1N HCl and extracted with EtOAc (10 mL×2). The organic layers were combined and washed with brine (10 mL), dried over Na$_2$SO$_4$, filtered and concentrated to give aa1b-7 (7.25 g, 17.84 mmol, 100.00% yield) as a colorless oil.

Step 6: Synthesis of (S)-2-amino-5-(4-(4-azidobutoxy)phenyl)pentanoic acid hydrochloride (aa1b-8)

A solution of aa1b-7 (7.25 g, 17.84 mmol, 1.0 eq.) in 4M HCl/EtOAc (75 mL) was stirred at 22° C. for 1 hr. The reaction was concentrated in vacuum to give aa1b-8 (5.2 g, 15.17 mmol, 85.04% yield, HCl) as a white solid.

Step 7: Synthesis of (S)-2-((((9H-fluoren-9-yl)methoxy)carbonyl)amino)-5-(4-(4-azidobutoxy)phenyl)pentanoic acid (aa1b-9)

To a solution of aa1b-8 (5 g, 14.58 mmol, 1.0 eq., HCl) in THF (116 mL) was added NaHCO$_3$ (2.45 g, 29.17 mmol, 2.0 eq.) in H$_2$O (58 mL), and then Fmoc-OSu (5.41 g, 16.04 mmol, 1.1 eq.) was added at 0° C. The reaction mixture was stirred at 22° C. for 16 hr. No change was observed. The reaction was adjusted to pH=6 with 1 N HCl and extracted with EtOAc (50 mL×3). The organic layers were combined and washed with brine (50 mL), dried over Na$_2$SO$_4$, filtered and concentrated to give crude as yellow oil. The residue was purified by flash silica gel chromatography (ISCO®; 80 g SepaFlash® Silica Flash Column, Eluent of 0-5% MeOH/DCM gradient @ 50 mL/min) for 2.5 h with total volume 3 L to give aa1b-9 (7 g, 12.20 mmol, 83.64% yield, 92.113% purity) as a yellow oil.

$^1$H NMR (400 MHz, CHLOROFORM-d) δ =7.75 (br d, J=7.3 Hz, 2H), 7.60-7.49 (m, 2H), 7.41-7.34 (m, 2H), 7.29 (br t, J=7.5 Hz, 2H), 7.05 (br d, J=8.3 Hz, 2H), 6.78 (br d, J=8.3 Hz, 2H), 5.18 (br d, J=8.3 Hz, 1H), 4.40 (br d, J=6.8 Hz, 3H), 4.21 (br t, J=7.0 Hz, 1H), 3.98-3.88 (m, 2H), 3.34 (t, J=6.5 Hz, 2H), 2.57 (br d, J=6.1 Hz, 2H), 1.98-1.60 (m, 8H)

Step 8: Synthesis of (S)-2-((((9H-fluoren-9-yl)methoxy)carbonyl)amino)-5-(4-(4-((tert-butoxycarbonyl) amino) butoxy)phenyl)pentanoic acid (aa1b)

A mixture of aa1b-15 (7 g, 13.24 mmol, 1.0 eq.), DIPEA (5.13 g, 39.73 mmol, 6.92 mL, 3.0 eq.) and Boc$_2$O (8.67 g, 39.73 mmol, 9.13 mL, 3.0 eq.) and Pd/C (10% palladium on activated carbon, 3.5 g, 32.9 mmol) in EtOAc (100 mL) was stirred at 25° C. under 15 PSi of H$_2$ for 4 hr. Black suspension was observed. The reaction was filtered through a pad of Celite, the cake was washed with EtOAc (50 mL×3). The filtrate was washed with aq·NH$_4$Cl (100 mL×3), brine (100 mL), dried over Na$_2$SO$_4$, filtered and concentrated in vacuum to give crude as colorless oil. The crude was purified by prep-HPLC (column: Phenomenex Luna(2) C18 250*50 10 μm; mobile phase: [water(0.225% FA)-ACN]; B %: 45%-78%, 21.5 min) to give aa1b (1.8 g, 2.99 mmol, 22.50% yield) as a yellow oil. LCMS (ESI): RT=0.954 min, mass calcd. for C$_{35}$H$_{42}$N$_2$O$_7$Na 625.29, m/z found 625.1 [M+Na]$^+$. Reverse phase LC-MS was carried out using method A.

$^1$H NMR (400 MHz, CHLOROFORM-d) δ =7.75 (br d, J=7.6 Hz, 2H), 7.60-7.55 (m, 2H), 7.38 (br t, J=6.7 Hz, 2H), 7.29 (t, J=7.1 Hz, 2H), 7.04 (br d, J=8.1 Hz, 2H), 6.78 (d, J=7.4 Hz, 2H), 5.24 (br s, 1H), 4.40 (br d, J=6.6 Hz, 2H), 4.23-4.18 (m, 1H), 3.92 (br s, 2H), 3.21-3.07 (m, 2H), 2.61-2.51 (m, 2H), 1.97-1.84 (m, 2H), 1.82-1.54 (m, 8H), 1.43 (s, 9H)

2.2 the Synthesis of Unnatural Amino Acid (Aa2)

Scheme 3 outlines the synthesis of unnatural amino acid (aa2):

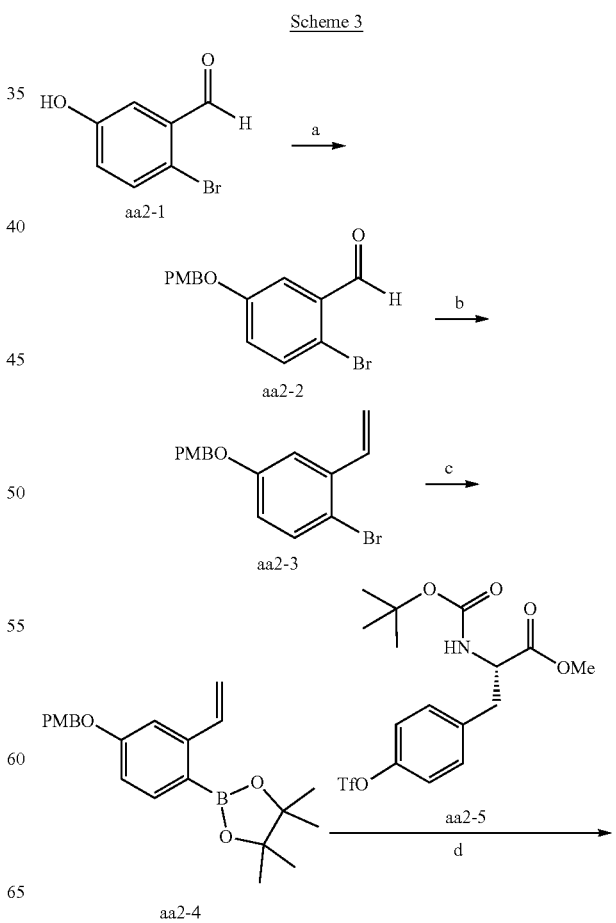

Scheme 3

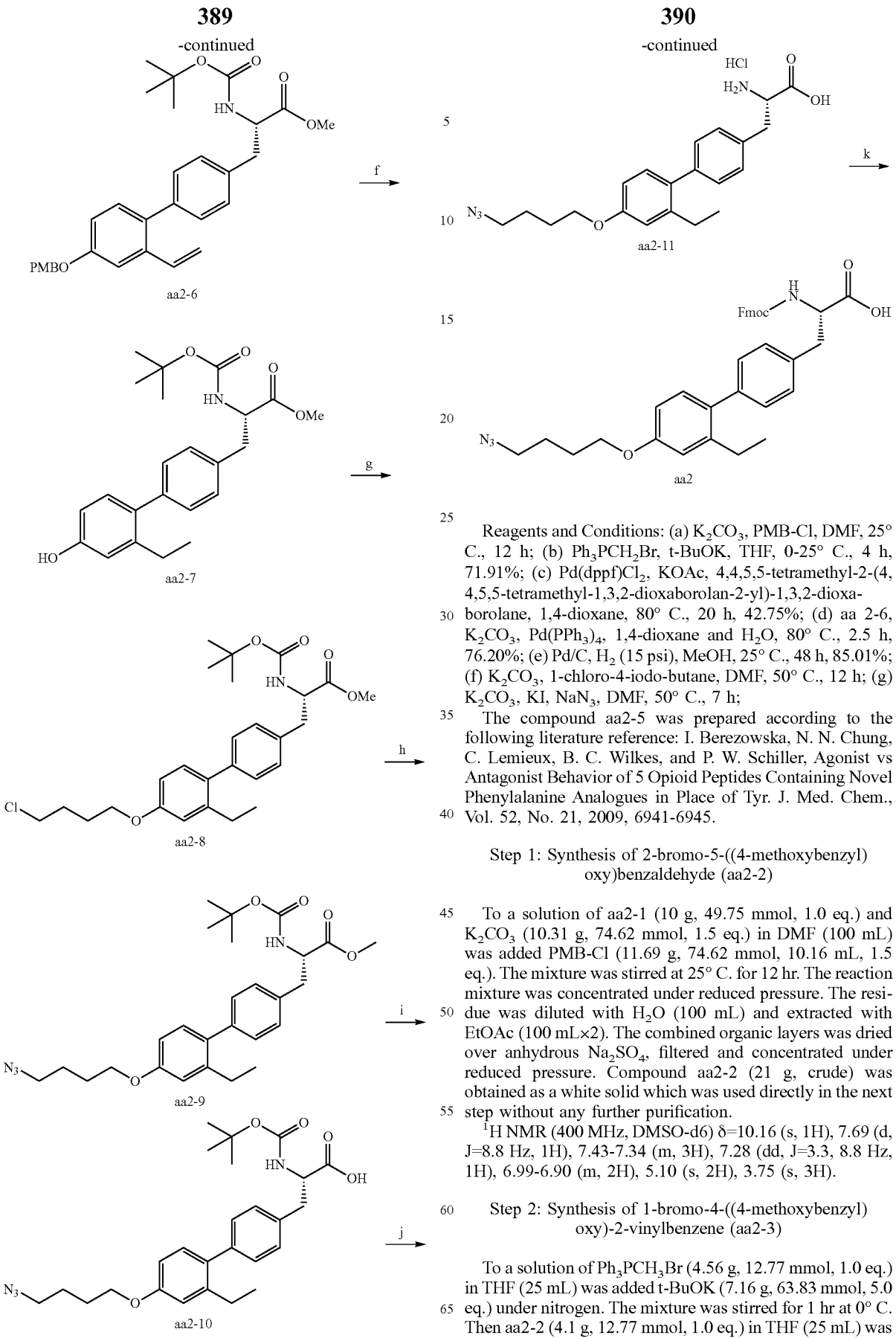

Reagents and Conditions: (a) K₂CO₃, PMB-Cl, DMF, 25° C., 12 h; (b) Ph₃PCH₂Br, t-BuOK, THF, 0-25° C., 4 h, 71.91%; (c) Pd(dppf)Cl₂, KOAc, 4,4,5,5-tetramethyl-2-(4,4,5,5-tetramethyl-1,3,2-dioxaborolan-2-yl)-1,3,2-dioxaborolane, 1,4-dioxane, 80° C., 20 h, 42.75%; (d) aa 2-6, K₂CO₃, Pd(PPh₃)₄, 1,4-dioxane and H₂O, 80° C., 2.5 h, 76.20%; (e) Pd/C, H₂ (15 psi), MeOH, 25° C., 48 h, 85.01%; (f) K₂CO₃, 1-chloro-4-iodo-butane, DMF, 50° C., 12 h; (g) K₂CO₃, KI, NaN₃, DMF, 50° C., 7 h;

The compound aa2-5 was prepared according to the following literature reference: I. Berezowska, N. N. Chung, C. Lemieux, B. C. Wilkes, and P. W. Schiller, Agonist vs Antagonist Behavior of 5 Opioid Peptides Containing Novel Phenylalanine Analogues in Place of Tyr. J. Med. Chem., Vol. 52, No. 21, 2009, 6941-6945.

Step 1: Synthesis of 2-bromo-5-((4-methoxybenzyl)oxy)benzaldehyde (aa2-2)

To a solution of aa2-1 (10 g, 49.75 mmol, 1.0 eq.) and K₂CO₃ (10.31 g, 74.62 mmol, 1.5 eq.) in DMF (100 mL) was added PMB-Cl (11.69 g, 74.62 mmol, 10.16 mL, 1.5 eq.). The mixture was stirred at 25° C. for 12 hr. The reaction mixture was concentrated under reduced pressure. The residue was diluted with H₂O (100 mL) and extracted with EtOAc (100 mL×2). The combined organic layers was dried over anhydrous Na₂SO₄, filtered and concentrated under reduced pressure. Compound aa2-2 (21 g, crude) was obtained as a white solid which was used directly in the next step without any further purification.

¹H NMR (400 MHz, DMSO-d6) δ=10.16 (s, 1H), 7.69 (d, J=8.8 Hz, 1H), 7.43-7.34 (m, 3H), 7.28 (dd, J=3.3, 8.8 Hz, 1H), 6.99-6.90 (m, 2H), 5.10 (s, 2H), 3.75 (s, 3H).

Step 2: Synthesis of 1-bromo-4-((4-methoxybenzyl)oxy)-2-vinylbenzene (aa2-3)

To a solution of Ph₃PCH₃Br (4.56 g, 12.77 mmol, 1.0 eq.) in THF (25 mL) was added t-BuOK (7.16 g, 63.83 mmol, 5.0 eq.) under nitrogen. The mixture was stirred for 1 hr at 0° C. Then aa2-2 (4.1 g, 12.77 mmol, 1.0 eq.) in THF (25 mL) was added dropwise. The mixture was stirred for 3 hr at 25° C.

The reaction mixture was diluted with H₂O (100 mL) and extracted with EtOAc (100 mL×2). The combined organic layers were dried over anhydrous Na₂SO₄, filtered and concentrated under reduced pressure. The residue was purified by flash silica gel chromatography (ISCO®; 40 g SepaFlash® Silica Flash Column, Eluent of 0~5% Ethyl acetate/Petroleum ether gradient @ 30 mL/min) for 24 min with total volume 0.9 L. Compound aa2-3 (2.93 g, 9.18 mmol, 71.91% yield) was obtained as a white solid.

$^1$H NMR (400 MHz, CHLOROFORM-d) δ =7.46-7.29 (m, 3H), 7.18-7.09 (m, 1H), 7.06-6.96 (m, 1H), 6.95-6.86 (m, 2H), 6.81-6.70 (m, 1H), 5.72-5.59 (m, 1H), 5.40-5.29 (m, 1H), 5.03-4.90 (m, 2H), 3.86-3.74 (m, 3H).

Step 3: Synthesis of 2-(4-((4-methoxybenzyl)oxy)-2-vinylphenyl)-4,4,5,5-tetramethyl-1,3,2-dioxaborolane (aa2-4)

A solution of aa2-3 (200 mg, 626.58 µmol, 1 eq.) in 1,4-dioxane (3 mL) was treated with Pd(PPh₃)₄ (72.41 mg, 62.66 µmol, 0.1 eq.) and KOAc (122.99 mg, 1.25 mmol, 2 eq.), and then 4,4,5,5-tetramethyl-2-(4,4,5,5-tetramethyl-1,3,2-dioxaborolan-2-yl)-1,3,2-dioxaborolane (477.34 mg, 1.88 mmol, 3 eq.) was added. The mixture was stirred at 80° C. for 12 hr under nitrogen. The reaction mixture was diluted with brine (30 mL) and extracted with EtOAc (30 mL×2). The combined organic layers were dried over anhydrous Na₂SO₄, filtered and concentrated under reduced pressure. The residue was purified by flash silica gel chromatography (ISCO®; 4 g SepaFlash® Silica Flash Column, Eluent of 0~10% Ethyl acetate/Petroleum ether gradient @ 18 mL/min). Compound aa2-4 (190 mg, 518.76 µmol, 82.79% yield) was obtained as a white solid.

$^1$H NMR (400 MHz, CHLOROFORM-d) δ =7.75 (d, J=8.4 Hz, 1H), 7.55 (dd, J=10.9, 17.5 Hz, 1H), 7.36 (d, J=8.6 Hz, 2H), 7.22 (d, J=2.4 Hz, 1H), 6.97-6.89 (m, 2H), 6.87 (dd, J=2.4, 8.4 Hz, 1H), 5.67 (d, J=17.4 Hz, 1H), 5.26 (d, J=11.0 Hz, 1H), 5.03 (s, 2H), 3.82 (s, 3H), 1.34 (s, 12H).

Step 4: Synthesis of (S)-methyl 2-((tert-butoxycarbonyl)amino)-3-(4'-((4-methoxybenzyl)oxy)-2'-vinyl-[1,1'-biphenyl]-4-yl)propanoate (aa2-6)

A solution of aa2-4 (100 mg, 273.03 µmol, 1 eq.) in 1,4-dioxane (3 mL) and H₂O (1 mL) was treated with K₂CO₃ (56.60 mg, 409.55 µmol, 1.5 eq.) and Pd(PPh₃)₄ (31.55 mg, 27.30 µmol, 0.1 eq.), and then aa2-5 (116.69 mg, 273.03 µmol, 1 eq.) was added. The mixture was stirred at 80° C. for 2.5 hr under nitrogen. The reaction mixture was diluted with brine (30 mL) and extracted with EtOAc (30 mL×2). The combined organic layers were dried over anhydrous Na₂SO₄, filtered and concentrated under reduced pressure. The residue was purified by flash silica gel chromatography (ISCO®; 4 g SepaFlash® Silica Flash Column, Eluent of 0~10% Ethyl acetate/Petroleum ether gradient @ 18 mL/min) for 14 min with total volume 0.3 L. Compound aa2-6 (100 mg, 193.20 µmol, 70.76% yield) was obtained as a yellow oil.

LCMS (ESI): RT=0.950 min, mass calcd. for C₃₁H₃₅NO₆Na 540.24, [M+Na]⁺, m/z found 540.1 [M+Na]⁺. Reverse phase LC-MS was carried out using method A.

$^1$H NMR (400 MHz, CHLOROFORM-d) δ =7.39 (d, J=8.6 Hz, 2H), 7.27-7.25 (m, 2H), 7.23 (s, 2H), 7.17 (dd, J=8.3, 16.2 Hz, 3H), 6.97-6.91 (m, 3H), 6.67 (dd, J=11.0, 17.4 Hz, 1H), 5.67 (dd, J=1.1, 17.4 Hz, 1H), 5.22-5.15 (m, 1H), 5.05 (s, 2H), 3.83 (s, 3H), 3.74 (s, 3H), 1.47-1.35 (m, 1H), 1.43 (s, 8H).

Step 5: Synthesis of (S)-methyl 2-((tert-butoxycarbonyl)amino)-3-(2'-ethyl-4'-hydroxy-[1,1'-biphenyl]-4-yl)propanoate (aa2-7)

To a solution of aa2-6 (2.8 g, 5.41 mmol, 1.0 eq.) in MeOH (25 mL) was added Pd/C (300 mg, 10% palladium on activated carbon) and stirred for 48 hr at 25° C. under hydrogen (15 psi). The reaction mixture was filtered and concentrated under reduced pressure. The residue was purified by flash silica gel chromatography (ISCO®; 40 g SepaFlash® Silica Flash Column, Eluent of 0~30% Ethyl acetate/Petroleum ether, gradient @ 35 mL/min) for 22 min with total volume 0.9 L. Compound aa2-7 (1.85 g, 4.60 mmol, 85.01% yield, 99.3% purity) was obtained as a colorless oil.

LCMS (ESI): RT=0.935 min, mass calcd. for C₂₃H₂₉NO₅Na 422.20 [M+Na]⁺, m/z found 422.1 [M+Na]⁺. Reverse phase LC-MS was carried out using method A.

$^1$H NMR (400 MHz, CHLOROFORM-d) δ =7.22-7.11 (m, 4H), 7.04 (d, J=8.2 Hz, 1H), 6.78 (d, J=2.6 Hz, 1H), 6.69 (dd, J=2.6, 8.2 Hz, 1H), 5.24 (s, 1H), 5.05 (br d, J=8.4 Hz, 1H), 4.70-4.58 (m, 1H), 3.73 (s, 3H), 3.20-3.11 (m, 1H), 3.11-3.02 (m, 1H), 2.53 (q, J=7.6 Hz, 2H), 1.42 (s, 9H), 1.08 (t, J=7.5 Hz, 3H).

Step 6: Synthesis of (S)-methyl 2-((tert-butoxycarbonyl)amino)-3-(4'-(4-chlorobutoxy)-2'-ethyl-[1,1'-biphenyl]-4-yl)propanoate (aa2-8)

To a solution of aa2-7 (350 mg, 876.14 µmol, 1 eq.) and K₂CO₃ (242.18 mg, 1.75 mmol, 2.0 eq.) in DMF (5 mL) was added 1-chloro-4-iodo-butane (287.11 mg, 1.31 mmol, 1.5 eq.) at 25° C. The mixture was stirred at 50° C. for 12 hr. The residue was diluted with brine (50 mL) and extracted with EtOAc (50 mL×2). The combined organic layers were dried over anhydrous Na₂SO₄, filtered and concentrated under reduced pressure. The residue was purified by flash silica gel chromatography (ISCO®; 12 g SepaFlash® Silica Flash Column, Eluent of 0 30% Ethyl acetate/Petroleum ether gradient @ 35 mL/min) for 14 min with total volume 0.4 L. Compound aa2-8 (340 mg, crude) was obtained as a yellow oil.

LCMS (ESI): RT=1.145 min, mass calcd. for C₂₇H₃₆ClNO₅Na 512.22 [M+Na]⁺, m/z found 512.2 [M+Na]⁺. Reverse phase LC-MS was carried out using method A.

Step 7: Synthesis of (S)-methyl 3-(4'-(4-azidobutoxy)-2'-ethyl-[1,1'-biphenyl]-4-yl)-2-((tert-butoxycarbonyl)amino)propanoate (aa2-9)

To a solution of aa2-8 (1.6 g, 3.27 mmol, 1.0 eq.) in DMF (15 mL) was added K₂CO₃ (902.51 mg, 6.53 mmol, 2.0 eq.), KI (54.20 mg, 326.51 µmol, 0.1 eq.) and NaN₃ (460 mg, 7.08 mmol, 2.1 eq.). The mixture was stirred at 50° C. for 7 hr. The reaction mixture was diluted with brine 50 mL and extracted with EtOAc (50 mL×2). The combined organic layers were dried over anhydrous Na₂SO₄, filtered and concentrated under reduced pressure. The water layers were quenched by addition of aqueous NaClO (1.0 M, 100 mL). Compound aa2-9 (1.7 g, crude) was obtained as a yellow oil.

LCMS (ESI): RT=1.140 min, mass calcd. for C$_{27}$H$_{36}$N$_4$O$_5$Na 519.27, m/z found 519.3 [M+Na]$^+$. Reverse phase LC-MS was carried out using method A.

Step 8: Synthesis of (S)-3-(4'-(4-azidobutoxy)-2'-ethyl-[1,1'-biphenyl]-4-yl)-2-((tert-butoxycarbonyl)amino)propanoic acid (aa2-10)

To a solution of aa2-9 (1.7 g, 3.42 mmol, 1.0 eq.) in THF (12 mL) was added LiOH·H$_2$O (287.31 mg, 6.85 mmol, 2.0 eq.) in H$_2$O (6 mL) at 0° C., and then the mixture was allowed to gradually warm to 25° C. and was stirred for 2 hr. The mixture was treated with EtOAc (30 mL) and extracted with water (25 mL×2). The combined aqueous layers were acidified (1 M aqueous HCl) and extracted with EtOAc (50 mL×3). The combined organic layer was dried by anhydrous Na$_2$SO$_4$, filtered and concentrated under reduced pressure. Compound aa2-10 (2.01 g, crude) was obtained as a yellow oil which was used directly in the next step without any further purification.

Step 9: Synthesis of (S)-2-amino-3-(4'-(4-azidobutoxy)-2'-ethyl-[1,1'-biphenyl]-4-yl)propanoic acid hydrochloride (aa2-11)

Compound aa2-10 (2.01 g, 4.17 mmol, 1.0 eq.) was dissolved in 4.0 M HCl/EtOAc (20 mL). The mixture was stirred at 25° C. for 1 hr. The reaction mixture was filtered. The filter cake was washed with EtOAc (30 ml) and dried under vacuum. Compound aa2-11 (1 g, crude) was obtained as a white solid which was used directly in the next step without any further purification.

LCMS (ESI): RT=1.121 min, mass calcd. for C$_{21}$H$_{27}$N$_4$O$_3$ 383.21 [M+H]$^+$, m/z found 383.2 [M+H]$^+$. Reverse phase LC-MS was carried out using method A.

Step 10: Synthesis of (S)-2-((((9H-fluoren-9-yl)methoxy)carbonyl)amino)-3-(4'-(4-azidobutoxy)-2'-ethyl-[1, 1'-biphenyl]-4-yl)propanoic acid (aa2)

To a solution of aa2-11 (1 g, 2.39 mmol, 1.0 eq.) in THF (15 mL) was added NaHCO$_3$ (401.07 mg, 4.77 mmol, 2.0 eq.) in H$_2$O (8 mL), and then (2,5-dioxopyrrolidin-1-yl) 9H-fluoren-9-ylmethyl carbonate (805.23 mg, 2.39 mmol, 1.0 eq.) was added at 0° C. The mixture was stirred for 12 hr at 25° C. The reaction mixture was diluted with brine (100 mL) and acidified (1 M aqueous HCl) to pH=2-3. The reaction mixture was extracted with EtOAc (30 mL×2). The combined organic layers were dried over anhydrous Na$_2$SO$_4$, filtered and concentrated under reduced pressure. The residue was purified by flash silica gel chromatography (ISCO®; 40 g SepaFlash® Silica Flash Column, Eluent of 0~10% Methanol/Dichloromethane @ 30 mL/min) for 16 min with total volume 0.6 L. Product aa2 (1.3 g, 2.14 mmol, 89.52% yield, 99.4% purity) was obtained as a white foam.

LCMS (ESI): RT=1.113 min, mass calcd. for C$_{36}$H$_{36}$N$_4$O$_5$Na 627.26 [M+Na]$^+$, m/z found 627.3 [M+Na]$^+$. Reverse phase LC-MS was carried out using method A.

$^1$H NMR (400 MHz, DMSO-d$_6$) δ=7.88 (d, J=7.5 Hz, 2H), 7.81 (d, J=8.6 Hz, 1H), 7.66 (t, J=6.9 Hz, 2H), 7.40 (dt, J=2.3, 7.3 Hz, 2H), 7.34-7.25 (m, 4H), 7.14 (d, J=8.2 Hz, 2H), 6.97 (d, J=8.4 Hz, 1H), 6.83 (d, J=2.4 Hz, 1H), 6.76 (dd, J=2.5, 8.5 Hz, 1H), 4.27-4.17 (m, 3H), 4.17-4.13 (m, 1H), 4.03-3.98 (m, 2H), 3.42 (t, J=6.7 Hz, 2H), 3.13 (br dd, J=3.9, 13.8 Hz, 1H), 2.96-2.87 (m, 1H), 2.52 (d, J=1.8 Hz, 2H), 2.43 (q, J=7.4 Hz, 2H), 1.82-1.74 (m, 2H), 1.73-1.66 (m, 2H), 0.98-0.90 (m, 3H).

SFC: ee %=97.95%-2.05%=95.9%; Method Comments: Column: Chiralcel OJ-3 100×4.6 mm I.D., 3 μm; Mobile phase: A: CO2 B: ethanol (0.05% DEA); Gradient: from 5% to 40% of B in 4 min and hold 40% for 2.5 min, then 5% of B for 1.5 min; Flow rate: 2.8 mL/min; Column temp.: 35° C.; ABPR: 1500 psi.

2.3 the Synthesis of Unnatural Amino Acid (aa2b)

Scheme 4 outlines the synthesis of unnatural amino acid (aa1b):

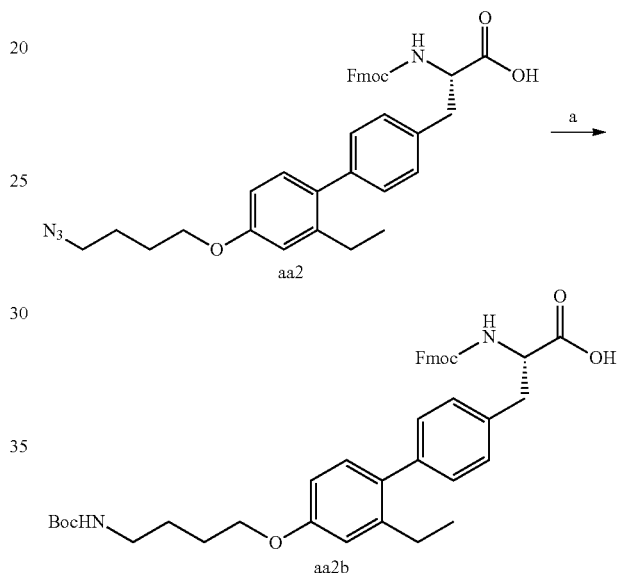

Scheme 4

Reagents and Conditions: (a) H$_2$, Pd/C, (Boc)$_2$O, DIPEA, MeOH, 20° C., 12 h, 47%.

Step 1: Synthesis of (R)-2-((((9H-fluoren-9-y) methoxy) carbonyl) amino)-3-(4'-(4-((tert-butoxycarbonyl)amino)butoxy)-2'-ethyl-[1, 1'-biphenyl]-4-yl) propanoic acid (aa2b)

To a solution of aa2 (3.2 g, 5.29 mmol, 1.0 eq.) in MeOH (30 mL) was added Pd/C (700 mg, 10% palladium on activated carbon), DIPEA (1.37 g, 10.60 mmol, 1.84 mL, 2.0 eq) and Boc$_2$O (2.31 g, 10.58 mmol, 2.43 mL, 2.0 eq). The mixture was stirred at 20° C. for 12 hr under hydrogen (15 psi). The reaction mixture was filtered through a small pad of Celite and the cake was rinsed with 40*5 mL of EtOAc (40 mL*5). Then brine (400 mL) was added and extracted with EtOAc (300 mL*2). The combined organic layers were dried over Na$_2$SO$_4$, filtered and concentrated under reduced pressure to give a residue. The residue was purified by prep-HPLC (column: Phenomenex Luna C18 250*50 mm*10 um; mobile phase: [water (0.225% FA)-ACN]; B %: 55%-86%, 21 min), the product was suspended in water (150 mL), the mixture frozen in a dry-ice/ethanol bath to afford the product aa2b (3.4 g, 5.01 mmol, 47.32% yield, 100% purity) as a white solid.

LCMS (ESI): RT=0.922 min, mass calcd. for $C_{41}H_{46}N_2O_7Na$ 701.33 [M+Na]$^+$, m/z found 701.3 [M+Na]$^+$. Reverse phase LC-MS was carried out using method C.

$^1$H NMR (400 MHz, DMSO-d6) δ =7.87 (d, J=7.6 Hz, 2H), 7.69-7.60 (m, 2H), 7.43-7.36 (m, 2H), 7.33-7.20 (m, 4H), 7.15-7.05 (m, 3H), 6.95 (br d, J=8.3 Hz, 1H), 6.89-6.70 (m, 4H), 4.28 (br dd, J=5.9, 9.0 Hz, 1H), 4.17-4.09 (m, 2H), 4.00-3.91 (m, 3H), 3.19-3.09 (m, 2H), 3.02-2.88 (m, 2H), 2.46-2.38 (m, 2H), 1.73-1.62 (m, 2H), 1.56-1.48 (m, 2H), 1.37 (s, 9H), 0.93 (br t, J=7.6 Hz, 3H).

2.4 the Synthesis of Unnatural Amino Acid (Aa13)

Scheme 5 outlines the synthesis of unnatural amino acid (aa13):

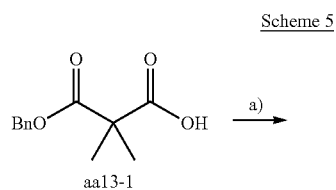

Reagents and conditions: (a) HATU (1.5 eq), DHP (1.0 eq), DIPEA (3.0 eq), DCM, 25° C., 2 h; (b) 10% Pd/C, MeOH, 25° C., 5h.

aa13-1 was prepared according to WO2010/052253, the content of which are incorporated by reference herein in their entirety.

Step 1: Synthesis of benzyl 2,2-dimethyl-3-oxo-3-(((tetrahydro-2H-pyran-2-yl)oxy)amino) propanoate (aa13-2)

To a solution of aa13-1 (200 mg, 899.94 μmol, 1 eq), HATU (513.28 mg, 1.35 mmol, 1.5 eq) and DIPEA (348.93 mg, 2.70 mmol, 470.26 μL, 3 eq) in DCM (10 mL) was stirred at 25° C. for 10 min. Otetrahydropyran-2-ylhydroxylamine (105.42 mg, 899.94 μmol, 1 eq) was added to the mixture and stirred at 25° C. for 2 hr. The reaction was added DCM (5 mL) and washed with aq. NH$_4$Cl (5 mL). The aqueous layer was separated and extracted with DCM (5 mL). The organic layers were combined and washed with brine (5 mL), dried over anhydrous Na$_2$SO$_4$, filtered and concentrated in vacuum to give crude as yellow oil, which was purified by flash silica gel chromatography (ISCO®; 20 g SepaFlash® Silica Flash Column, Eluent of 0-35% Ethylacetate/Petroleum ethergradient @ 30 mL/min) to give aa13-2 (230 mg, 715.69 μmol, 79.53% yield) as a colorless oil.

$^1$H NMR (400 MHz, CHLOROFORM-d) δ =9.28-9.14 (m, 1H), 7.38-7.30 (m, 5H), 5.16 (s, 2H), 4.87 (br s, 1H), 3.93-3.80 (m, 1H), 3.59 (br d, J=1.5 Hz, 1H), 1.76 (br s, 3H), 1.65-1.58 (m, 1H), 1.56-1.52 (m, 2H), 1.48 (s, 6H)

Step 2: Synthesis of 2,2-dimethyl-3-oxo-3-(((tetrahydro-2H-pyran-2-yl)oxy)amino)propanoic acid (aa13)

A black suspension of aa13-2 (230 mg, 715.69 μmol, 1 eq) and 10% Pd/C (23 mg) in MeOH (5 mL) was stirred at 25° C. under 15 Psi of H$_2$ for 5 hr. The reaction was filtered through a pad of Celite, the cake was washed with MeOH (5 mL*3). The filtrate was concentrated in vacuum to give aa13 (120 mg, 518.93 μmol, 72.51% yield) as colorless oil.

$^1$H NMR (400 MHz, METHANOL-d4) δ =4.90-4.88 (m, 1H), 4.05 (br s, 1H), 3.59-3.53 (m, 1H), 1.85-1.68 (m, 3H), 1.68-1.51 (m, 3H), 1.40 (s, 6H).

2.5 the Synthesis of Unnatural Amino Acid (Aa14)

Scheme 6 outlines the synthesis of unnatural amino acid (aa14):

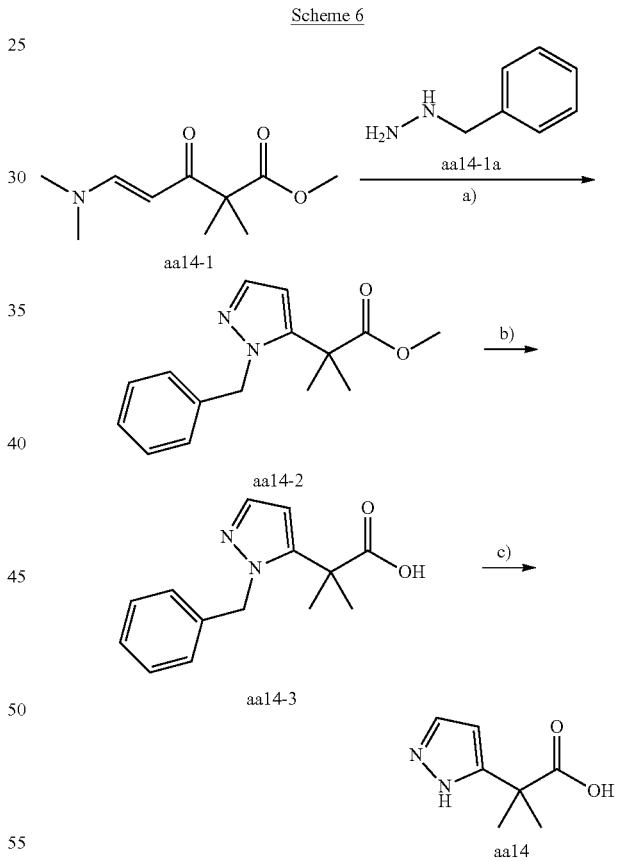

Reagents and conditions: (a) aa-14-1a (1.0 eq), dioxane, 50° C., 15 h; (b) LiOH·H$_2$O (2.0 eq), THF/H2O=1/1, 50° C., 16 h; (c) 10% Pd/C, cat. TFA, EtOH The compound aa14-1 was prepared according to US2015/380666.

Step 1: Synthesis of methyl 2-(1-benzyl-1H-pyrazol-5-yl)-2-methylpropanoate (aa14-3)

A mixture of aa14-1 (2.76 g, 13.85 mmol, 1 eq) and aa14-1a (2.20 g, 13.85 mmol, 1 eq) in dioxane (30 mL) was stirred at 50° C. for 15 hr. The reaction was filtered and the filtrate was concentrated in vacuum to give crude as brown oil. The residue was purified by flash silica gel chromatography (ISCO®; 20 g SepaFlash® Silica Flash Column, Eluent of 0-20% Ethylacetate/Petroleum ether gradient @ 25 mL/min) to give aa14-2 (0.9 g, 3.48 mmol, 25.15% yield) as a light yellow oil.

$^1$H NMR (400 MHz, CHLOROFORM-d) δ =7.53 (s, 1H), 7.29-7.26 (m, 1H), 7.23-7.16 (m, 1H), 6.98 (d, J=7.4 Hz, 2H), 6.22 (s, 1H), 5.23 (s, 2H), 3.26 (s, 3H), 1.56 (s, 6H)

Step 2: Synthesis of methyl 2-(1-benzyl-1H-pyrazol-5-yl)-2-methylpropanoate (aa14-3)

A mixture of aa14-2 (700 mg, 2.71 mmol, 1 eq) and LiOH·H$_2$O (1 M, 5.42 mL, 2 eq) in THF (5.4 mL) was stirred at 50° C. for 16 hr. The reaction was concentrated in vacuum to remove the THF. The reaction was diluted with water (5 mL) and MTBE (5 mL). The aqueous layer was separated and adjusted to pH=6 with 1N HCl. The organic layer was discarded. The aqueous layer was extracted with EtOAc (5 mL*3). The organic layers were combined and washed with brine (5 mL), dried over anhydrous Na$_2$SO$_4$, filtered and concentrated in vacuum to give aa14-3 (600 mg, 2.46 mmol, 90.64% yield) as a white solid.

$^1$H NMR (400 MHz, CHLOROFORM-d) δ =7.53 (s, 1H), 7.26-7.17 (m, 3H), 6.97 (d, J=7.4 Hz, 2H), 6.24 (s, 1H), 5.23 (s, 2H), 1.54 (s, 6H).

Step 3: Synthesis of 2-methyl-2-(1H-pyrazol-5-yl)propanoic acid (aa14)

A mixture of aa14-3 (500 mg, 2.05 mmol, 1 eq), TFA (23.34 mg, 204.68 μmol, 15.15 μL, 0.1 eq) and 10% Pd/C (100 mg) in EtOH (5 mL) was stirred at 80° C. under 100 Psi of H$_2$ for 16 hr. The reaction was filtered through a pad of Celite, the cake was washed with EtOH (5 mL*3). The filtrate was concentrated in vacuum to give aa14 (300 mg, 1.52 mmol, 74.27% yield, 78.11% purity) as a light yellow oil. LCMS (ESI): RT=1.036 min, m/z calcd. for C$_7$H$_{11}$N$_2$O$_2$ [M+H]$^+$ 155.07, found 155.0. Reverse phase LC-MS was carried out using method A.

$^1$H NMR (400 MHz, METHANOL-d4) δ =7.57-7.50 (m, 1H), 6.26 (d, J=1.8 Hz, 1H), 1.56 (s, 6H).

2.6 the Synthesis of Unnatural Amino Acid [Aa20: (R)-Isomer and Aa21: (S)-Isomer]

Scheme 7 outlines the synthesis of unnatural amino acids (aa20) and (aa21):

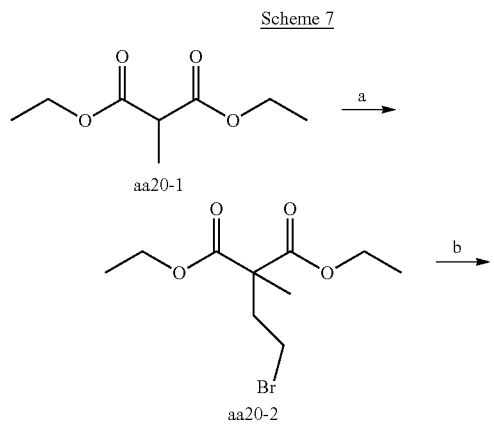

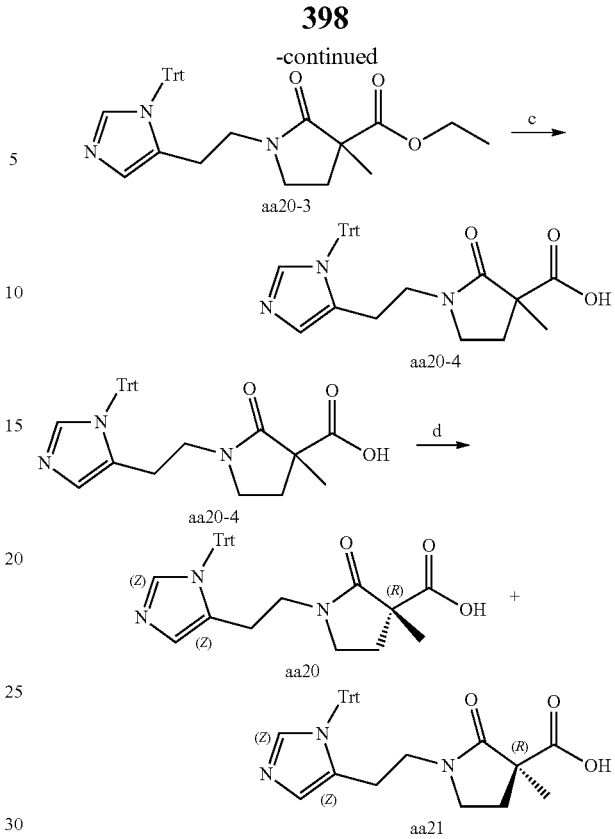

Reagents and conditions: (a) NaH (1.2 eq), dibromoethane (2 eq.), THF (25 ml), 0-100° C., 16h; (b) 2-(1-trityl-1H-imidazol-5-yl) ethanamine (0.9 eq), DMF (5 ml), 60° C., 16h; (c) LiOH (4 eq.), H$_2$O (10 ml), THF (10 ml), 20° C., 16h; (d) SFC separation.

Step 1: Synthesis of diethyl 2-(2-bromoethyl)-2-methylmalonate (aa20-2)

A volume of THF (10 mL) was added to NaH (252.57 mg, 6.31 mmol, 60% purity, 1.1 eq.) under a N$_2$ atmosphere. The THF solution was cooled to 0° C. Compound aa20-1 (1 g, 5.74 mmol, 980.39 μL, 1 eq.) in THF (5 mL) was added over 30 min with stirring. The reaction mixture was allowed to stir for 60 min at 20° C. The generated enolate was dripped into a 1, 2-dibromoethane (2.16 g, 11.48 mmol, 866.23 μL, 2 eq.) in THF (10 mL) over 60 min with stirring under nitrogen atmosphere. The reaction mixture was then heated to 100° C. in solvent for 14 hr. TLC indicated that the reactant was consumed, and one major new spot with lower polarity was detected. The residue was poured into 1N HCl to adjust pH 2-4. Then aqueous phase was extracted with ethyl acetate (30 mL*3). The combined organic phase was washed with brine (50 mL), dried over anhydrous Na$_2$SO$_4$, filtered and concentrated in vacuum. The residue was purified by flash silica gel chromatography (ISCO®; 24 g SepaFlash® Silica Flash Column, Eluent of 0-20% Ethyl acetate/Petroleum ether gradient @ 20 mL/min) for 40 min with 0.8 L solvent. The compound aa20-2 (1.2 g, 4.27 mmol, 74.35% yield) was obtained as a pale yellow liquid.

$^1$H NMR (400 MHz, CHLOROFORM-d) δ 4.18 (q, J=7.20 Hz, 4H), 3.33-3.41 (m, 2H), 2.39-2.47 (m, 2H), 1.43 (s, 3H), 1.22 (s, 6H)

Step 2: Synthesis of ethyl 3-methyl-2-oxo-1-(2-(1-trityl-1H-imidazol-5-yl)ethyl)pyrrolidine-3-carboxylate (aa20-3)

To a solution of 2-(1-trityl-1H-imidazol-5-yl) ethanamine (1 g, 2.83 mmol, 1 eq.) in DMF (10 mL) was added aa20-2 (874.95 mg, 3.11 mmol, 1.1 eq.). The mixture was stirred at 60° C. for 16 hr. LCMS showed the material was consumed completely and the desired product was observed as the major. The residue was poured into water (100 mL). The aqueous phase was extracted with ethyl acetate (50 mL*3). The combined organic phase was washed with brine (100 mL), dried over anhydrous $Na_2SO_4$, filtered and concentrated in vacuum. The crude product was purified by C-18 reverse phase chromatography (ISCO®; 80 g, C-18 Column, Eluent of 0-100% acetonitrile/$H_2O$ gradient @ 40 mL/min, 60 min with total volume 2400 mL) to provide a yellow solid. The compound aa20-3 (650 mg, 903.47 μmol, 31.93% yield, 70.55% purity) was obtained as a yellow solid.

LCMS (ESI): RT=0.861 min, m/z calcd. for $C_{32}H_{34}N_3O_3$ 508.25 [M+H]$^+$, found 508.3. Reverse phase LC-MS was carried out using method A.

Step 3: Synthesis of 3-methyl-2-oxo-1-(2-(1-trityl-1H-imidazol-5-yl)ethyl)pyrrolidine-3-carboxylic acid (aa20-4)

To a mixture of aa20-3 (650 mg, 1.28 mmol, 1 eq.) was added LiOH·$H_2O$ (268.67 mg, 6.40 mmol, 5 eq.) in $H_2O$ (10 mL) and THF (10 mL). The mixture was stirred at 20° C. for 16 hr. LCMS showed the material was consumed completely and the desired product was observed as the major. The residue was poured into $H_2O$ (50 mL), added 5% $KHSO_4$ to adjust pH 2-3. The aqueous phase was extracted with ethyl acetate (50 mL*3). The combined organic phase was washed with brine (50 ml), dried with anhydrous $Na_2SO_4$, filtered and concentrated in vacuum. The crude was purified by prep-HPLC (column: Phenomenex Synergi Max-RP 250*50 mm*10 um; mobile phase: water (0.225% FA)-ACN; B %: 30%-60%, 60 min) to give aa20-4 (180 mg, 375.34 μmol, 29.31% yield) as a white solid.

LCMS (ESI): RT=2.391 min, m/z calcd. for $C_{30}H_{30}N_3O_3$ 480.6, found 480.3 [M+H]$^+$. Reverse phase LC-MS was carried out using a Merck RP-18e 25-2 mm column, with a flow rate of 1.5 mL/min, eluting with a gradient of 10% to 80% acetonitrile containing 0.02% TFA (solvent B) and water containing 0.04% TFA (solvent A)

$^1$H NMR (ES8586-496-P1B1) 1H NMR (400 MHz, METHANOL-d4) δ 7.92 (s, 1H), 7.35-7.42 (m, 9H), 7.12-7.19 (m, 6H), 6.97 (s, 1H), 3.39-3.64 (m, 3H), 3.32 (br d, J=3.75 Hz, 1H), 2.84(br t, J=5.95 Hz, 2H), 2.34-2.42 (m, 1H), 1.86 (td, J=7.99, 12.90 Hz, 1H), 1.25 (s, 3H)

Step 4: Synthesis of (R)-3-methyl-2-oxo-1-(2-(1-trityl-1H-imidazol-5-yl)ethyl)pyrrolidine-3-carboxylic acid (aa20) and (S)-3-methyl-2-oxo-1-(2-(1-trityl-1H-imidazol-5-yl)ethyl)pyrrolidine-3-carboxylic acid (aa21)

The absolute configurations of aa20 (R) and aa21 (S) were not confirmed.

Compound aa20-4 (180 mg, 375.34 μmol) was purified by prep-SFC (column: DAICEL CHIRALPAK IC (250 mm*30 mm, 10 μm; mobile phase: 0.1% $NH_3H_2O$ MEOH; B %: 50%-50%, 80 min). Isomer (R) aa20 (86 mg, 177.18 μmol, 94.41% yield, 98.8% purity) was obtained as a white solid, and isomer (S) aa21 (85 mg, 175.29 μmol, 93.41% yield, 98.9% purity) was also obtained as a white solid.

Isomer aa20 on SFC-HPLC: RT=2.346 min. HPLC conditions: Chiralpak IC-3 100×4.6 mm I.D., 3 μm, flow rate 2.8 mL/min. eluting with a gradient of 40% methanol (0.05% DEA) (solvent B) and $CO_2$ (solvent A).

Isomer aa21 on SFC-HPLC: RT=3.607 min. HPLC conditions: Chiralpak IC-3 100×4.6 mm I.D., 3 μm, flow rate 2.8 mL/min. eluting with a gradient of 40% methanol (0.05% DEA) (solvent B) and $CO_2$ (solvent A).

2.7 the Synthesis of Unnatural Amino Acid [Aa22 (S)-Isomer and Aa23 (R)-Isomer]

Scheme 8 outlines the synthesis of unnatural amino acids (aa22) and (aa23):

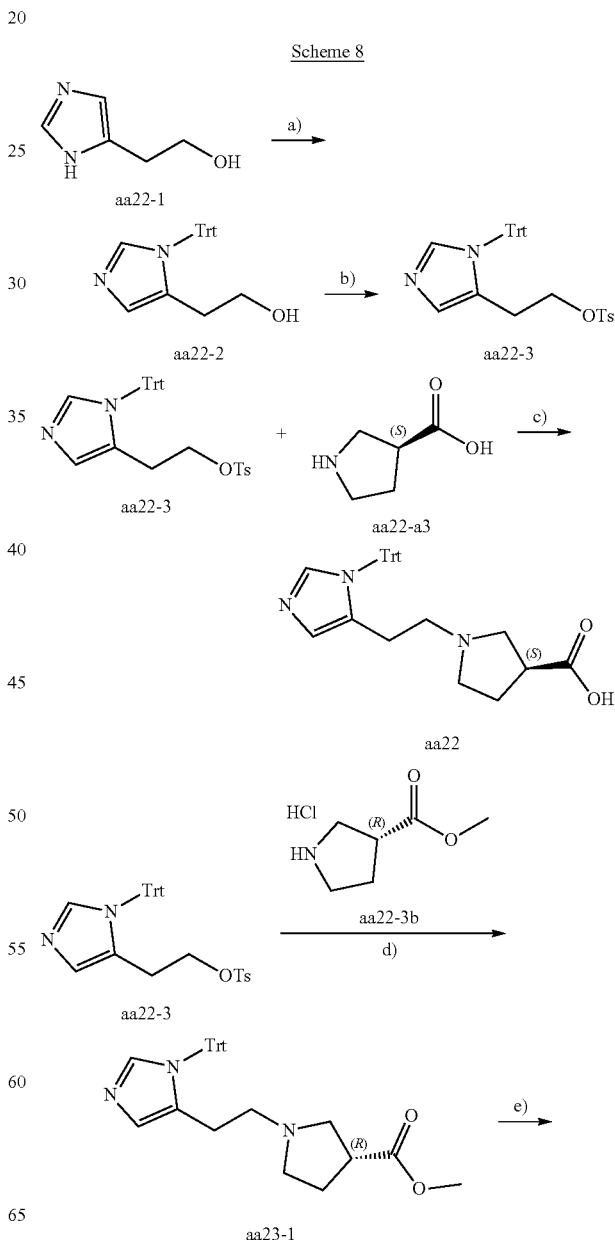

-continued

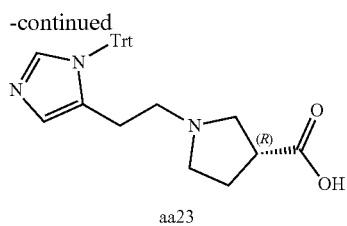

aa23

Reagents and conditions: (a) TrtCl (1.2 eq.), Et₃N (2 eq.), DMF, 20° C., 2 h, 31%; (b) TsCl (1.5 eq.), Et₃N (3 eq.), DMAP (0.5 eq.), DCM, 20° C., 2 h, 66%; (c) aa22-3 (1.0eq.), aa22-3a (1.2 eq.), LiI (1.5 eq.), DIPEA (4 eq.), 60° C., 2 h, 17% yield; (d) aa22-3 (1.0eq.), aa22-3b (1.2 eq.), LiI (1.5 eq.), K₂C03 (4 eq.), 20° C., 3 h, 58% yield; (e) NaOH (2 eq.), MeOH/water, 20° C., 2 h, 87% yield.

Step 1: Synthesis of 2-(1-trityl-1H-imidazol-4-yl)ethanol (aa22-2)

To a solution of aa22-1 (2 g, 17.84 mmol, 1 eq) in DMF (40 mL) were added TEA (3.61 g, 35.67 mmol, 4.97 mL, 2 eq), [chloro(diphenyl)methyl]benzene (5.97 g, 21.40 mmol, 1.2 eq) at 20° C. The reaction mixture was stirred for 2 hr at 20° C. The reaction progress was monitored by TLC (DCM:MeOH=10:1), which indicated that the starting material was consumed and one new spot was observed. The reaction mixture was quenched by NaHCO₃ (sat. aq., 20 mL) and extracted with EtOAc (50 mL*2). The combined organic layers were washed with brine (20 mL), dried over Na₂SO₄, filtered and concentrated under reduced pressure to give a residue. The residue was purified by flash silica gel chromatography (ISCO®; 20 g SepaFlash® Silica Flash Column, Eluent of 0-100% Ethyl acetate/Petroleum ether then 0-10% MeOH (0.5% TEA additive)/DCM gradient @ 30 mL/min) for 25 min with total volume 1.6 L. Compound aa22-2 (2.2 g, 5.59 mmol, 31.32% yield, 90% purity) was obtained as a white solid.

LCMS: (ESI): RT=1.397 min, m/z calcd. for $C_{24}H_{23}N_2O$ 355.2, found 355.2 [M+H]⁺; Reverse phase LC-MS was carried out using method B.

¹H NMR (400 MHz, CHLOROFORM-d) δ =7.39-7.31 (m, 10H), 7.17-7.11 (m, 6H), 6.63-6.57 (m, 1H), 3.89 (t, J=5.6 Hz, 2H), 3.64 (br s, 1H), 2.76 (t, J=5.5 Hz, 2H).

Step 2: Synthesis of 2-(1-trityl-1H-imidazol-4-yl)ethyl 4-methylbenzenesulfonate (aa22-3)

To a solution of aa22-2 (2.2 g, 5.59 mmol, 1 eq) in DCM (20 mL) were added TEA (1.70 g, 16.76 mmol, 2.33 mL, 3 eq), 4-methylbenzenesulfonyl chloride (1.60 g, 8.38 mmol, 1.5 eq) and DMAP (341.23 mg, 2.79 mmol, 0.5 eq) at 20° C. The reaction mixture was stirred for 2 hr at 20° C. The reaction progress was monitored by LC-MS which indicated no starting material remained and formation of desired product. The reaction mixture was quenched by NaHCO₃ (sat. aq., 50 mL) and extracted with EtOAc (50 mL*2). The combined organic layers were washed with brine (20 mL×2), dried over Na₂SO₄, filtered and concentrated under reduced pressure to give a residue. The residue was purified by flash silica gel chromatography (ISCO®; 24 g SepaFlash® Silica Flash Column, Eluent of 0-5% MeOH (4% TEA additive)/DCM gradient @ 20 mL/min) for 35 min with total volume 1.2 L. Compound aa22-3 (2.1 g, 3.72 mmol, 66.52% yield, 90% purity) was obtained as a brown solid. LCMS: (ESI): RT=0.775 min, m/z calcd. for $C_{31}H_{28}N_2O_3SNa$ 531.2 [M+H]⁺, found 531.1. Reverse phase LC-MS was carried out using method D.

¹H NMR (400 MHz, CHLOROFORM-d) δ =7.73 (d, J=8.3 Hz, 2H), 7.38-7.28 (m, 12H), 7.15-7.08 (m, 6H), 6.61 (s, 1H), 4.27 (t, J=7.0 Hz, 2H), 2.91-2.86 (m, 2H), 2.42 (s, 3H).

Step 3: Synthesis of (R)-1-(2-(1-trityl-1H-imidazol-4-yl)ethyl)pyrrolidine-3-carboxylic acid (aa22)

To a solution of aa22-3 (500 mg, 983.03 μmol, 1 eq.) in DMF (2 mL) were added aa22-3a (135.81 mg, 1.18 mmol, 1.2 eq.), LiI (197.36 mg, 1.47 mmol, 56.55 μL, 1.5 eq.), and DIPEA (508.20 mg, 3.93 mmol, 684.91 μL, 4.0 eq.). Then the mixture was heated to 60° C. and stirred at 60° C. for 2 hr. LCMS showed that reactant was consumed completely and the desired MS was detected. The reaction mixture was quenched by addition of water (10 mL), and then diluted with EtOAc (20 mL), then extracted with EtOAc (20 mL*2). The aqueous layers were acidified with 2M HCl to pH 6. Then the aqueous phase was extracted with DCM (20 mL*5). The combined organic layers were concentrated to give the residue. The crude product was purified by reversed-phase HPLC (neutral condition). Product aa22 (80 mg, 168.31 μmol, 17.12% yield, 95% purity) was obtained as an off-white solid. LCMS (ESI): RT=1.986 min mass calcd. for $C_{29}H_{30}N_3O_2$ 452.23, m/z found 452.3 [M+H]⁺. Reverse phase LC-MS was carried out using method A.

Step 4: Synthesis of methyl (3S)-1-[2-(1-tritylimidazol-4-yl)ethyl]pyrrolidine-3-carboxylate (aa23-1)

To a solution of aa22-3 (750 mg, 1.47 mmol, 1 eq.) in DMF (5 mL) was added K₂CO₃ (815.17 mg, 5.90 mmol, 4 eq.), aa22-3b (293.05 mg, 1.77 mmol, 1.2 eq., HCl) and LiI (296.04 mg, 2.21 mmol, 84.83 μL, 1.5 eq.) at 20° C. The reaction mixture was stirred for 3 hr at 20° C. The reaction progress was monitored by LC-MS, which indicated no starting material remained and formation of desired product. The mixture was cooled to 25° C. and poured into water (30 mL) and stirred for 5 min. The aqueous phase was extracted with ethyl acetate (50 mL*2). The combined organic phase was washed with brine (15 mL*2), dried over anhydrous Na₂SO₄, filtered and concentrated in vacuum. The residue was purified by flash silica gel chromatography (ISCO®; 20 g SepaFlash® Silica Flash Column, Eluent of 0-100% Ethyl acetate/Petroleum ether then 0-10% MeOH (0.5% TEA additive)/DCM gradient @ 30 mL/min) for 25 min with total volume 1.6 L. Product aa23-1 (420 mg, 856.99 μmol, 58.12% yield, 95% purity) was obtained as a brown oil.

LCMS: (ESI): RT=0.717 min, m/z calcd. for $C_{30}H_{31}N_3O_2$ 466.2 [M+H]⁺, found 465.9; LC-MS Conditions: Reverse phase LC-MS was carried out using method D.

¹H NMR (400 MHz, CHLOROFORM-d) δ =7.40-7.30 (m, 10H), 7.20-7.09 (m, 6H), 6.58 (s, 1H), 3.75-3.64 (m, 3H), 3.10-2.95 (m, 2H), 2.83-2.74 (m, 5H), 2.72-2.64 (m, 1H), 2.55 (q, J=8.0 Hz, 1H), 2.14-2.07 (m, 2H).

Step 5: Synthesis of methyl (3S)-1-[2-(1-tritylimidazol-4-yl)ethyl]pyrrolidine-3-carboxylate (aa23)

To a solution of aa23-1 (390.00 mg, 837.66 μmol, 1 eq.) in MeOH (3 mL) and Water (3 mL) was added NaOH (67.01 mg, 1.68 mmol, 2 eq.) at 20° C. The reaction mixture was stirred for 2 hr at 20° C. The reaction progress was monitored by LCMS which indicated no starting material remained and formation of desired product. After completion, the reaction mixture was cooled to room temperature. The reaction mixture was concentrated under reduced pressure to remove solvent. The residue was adjusted to pH=6 with 1M HCl and dried by lyophilization. The residue was triturated with DCM/MeOH=10/1 (15 mL*3). The combined organic phase was dried over anhydrous $Na_2SO_4$, filtered and concentrated in vacuum. Product aa23 (350 mg, 736.34 μmol, 87.90% yield, 95% purity) was obtained as a brown solid.

LCMS: (ESI): RT=0.708 min, m/z calcd. for $C_{29}H_{30}N_3O_2$ 452.2 $[M+H]^+$, found 451.9; Reverse phase LC-MS was carried out using method D.

$^1H$ NMR (400 MHz, CHLOROFORM-d) δ =7.38 (s, 1H), 7.36-7.31 (m, 9H), 7.12 (dd, J=3.3, 6.3 Hz, 6H), 6.64 (s, 1H), 3.83 (br s, 1H), 3.56 (br s, 1H), 3.20 (br d, J=18.5 Hz, 2H), 3.05-2.96 (m, 4H), 2.65-2.61 (m, 1H), 2.42-2.30 (m, 1H), 2.18-2.09 (m, 1H).

2.8 the Synthesis of Unnatural Amino Acid (Aa27)

Scheme 9 outlines the synthesis of unnatural amino acid (aa27):

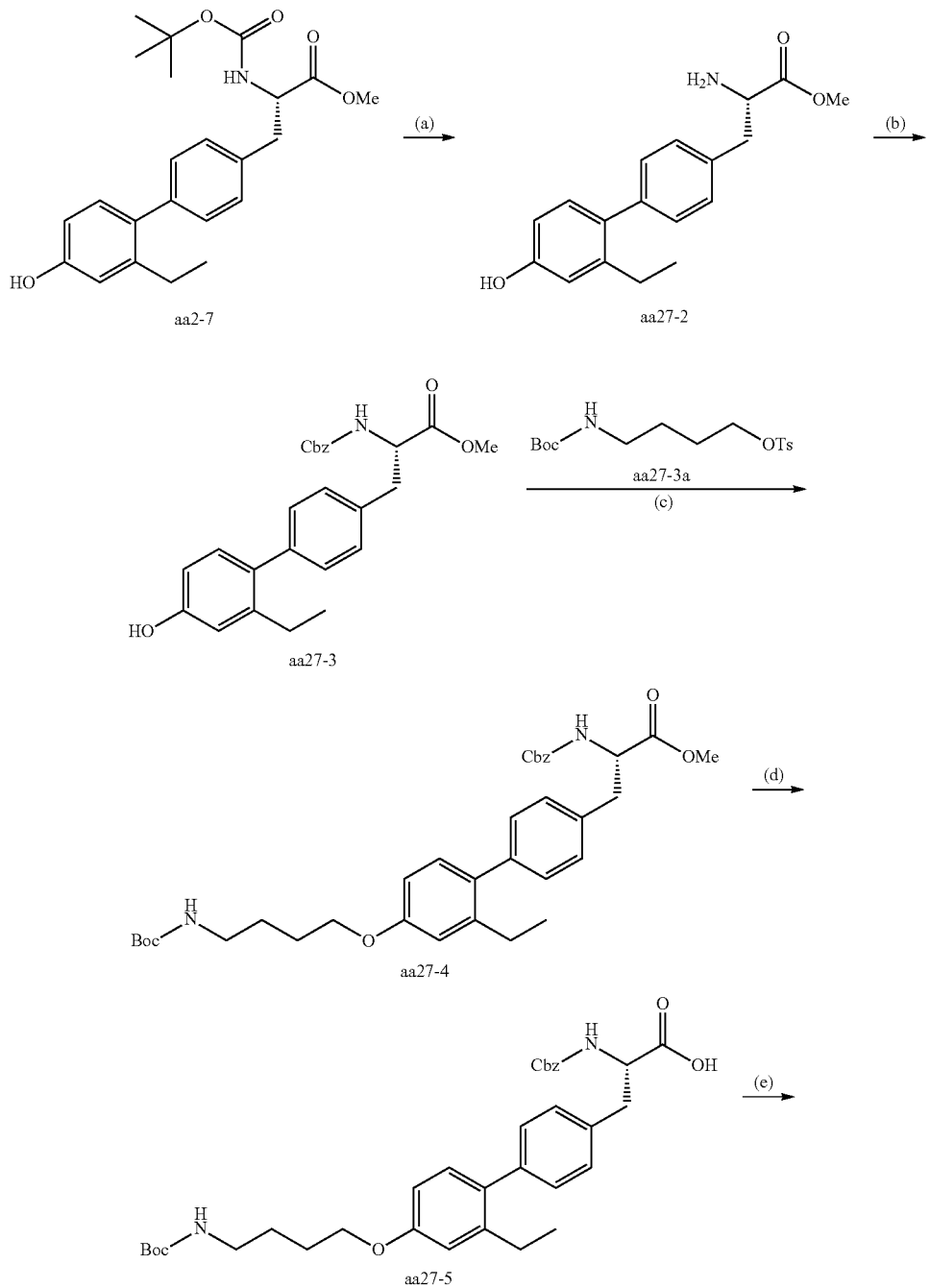

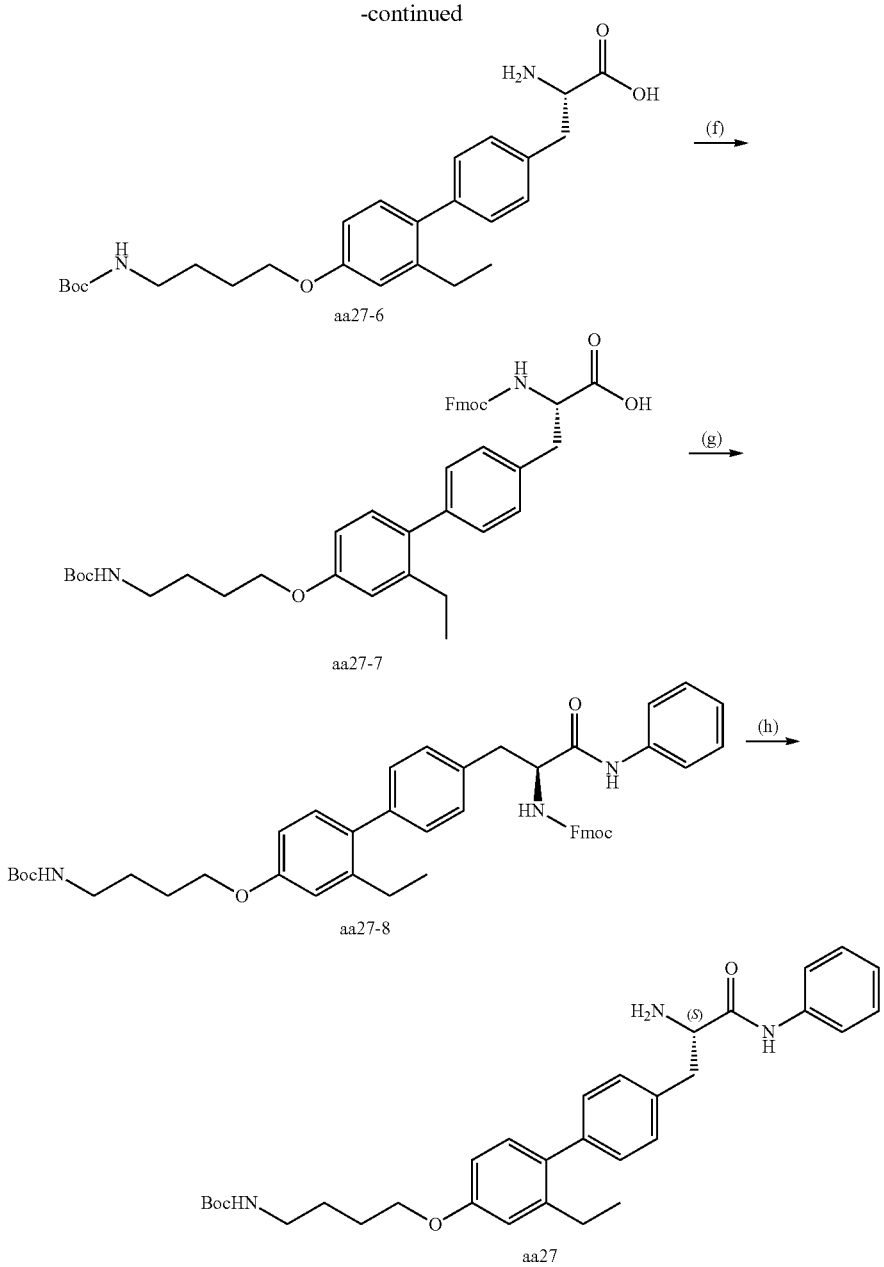

Reagents and conditions: (a) HCl/dioxane, 0-25° C., 2 h, 100%; (b) CbzCl (1.2 eq.), HOSu (1.3 eq.), DIPEA (2 eq.), DCM, 0-20° C., 12 h, 96%; (c) 3a (2 eq.), K$_2$CO$_3$ (2 eq.), 60° C., 12 h, 56%; (d) LiOH (2.0 eq.), THF, H$_2$O, 20° C., 12 h, 94%; (e) H$_2$, Pd(OH)$_2$, AcOH, MeOH, 20° C., 12h; (f) FmocOSu (1.2 eq.), NaHCO$_3$ (2.0 eq.), THF, H$_2$O, 0-20° C., 12 h, 44%; (g) PhNH$_2$ (1.1 eq.), DIC (1.0 eq.), HOBt (1.0 eq.), DCM, 0-20° C., 1 h, 76%; (h) piperidine (5.0 eq.), DMF, 20° C., 1 h, 65%.

Step 1: Synthesis of methyl (2S)-2-amino-3-[4-(2-ethyl-4-hydroxy-phenyl)phenyl]propanoate (aa27-2)

Compound aa27-1 (3.5 g, 8.76 mmol, 1 eq.) was dissolved in HCl/dioxane (4 M, 100 mL, 45.65 eq.) at 0° C. The mixture was stirred at 25° C. for 2 hr. The reaction progress was monitored by LCMS. The reaction mixture was concentrated under reduced pressure to give the crude product. Compound aa27-2 (2.6 g, crude) was obtained as a colorless oil.

LCMS (ESI): RT=0.772 min, mass calcd. for C$_{18}$H$_{22}$NO$_3$, 300.16 [M+H]$^+$, m/z found 300.00 [M+H]$^+$. Reverse phase LC-MS was carried out using method A.

Step 2: Synthesis of methyl (2S)-2-(benzyloxycarbonylamino)-3-[4-(2-ethyl-4-hydroxy-phenyl) phenyl]propanoate (aa27-3)

To a solution of HOSu (1.25 g, 10.86 mmol, 1.3 eq.) in DCM (50 mL) was added DIPEA (3.24 g, 25.05 mmol, 4.36 mL, 3 eq.) and CbzCl (1.57 g, 9.19 mmol, 1.31 mL, 1.1 eq.) at 0° C. After stirred at 25° C. for 2 hr, then Compound aa27-2 (2.5 g, 8.35 mmol, 1 eq.) was added and the mixture was stirred at 20° C. for 10 hr. The reaction progress was monitored by LC-MS and TLC. The mixture was diluted with DCM (30 mL) and washed with $H_2O$ (30 mL*2). The organic layer was dried over $Na_2SO_4$, filtered and concentrated to give a residue, then purified by column chromatography ($SiO_2$, Petroleum ether/Ethyl acetate=2/1). Compound aa27-3 (3.5 g, 8.07 mmol, 96.68% yield) was obtained as a yellow oil.

LCMS (ESI): RT=0.992 min, mass calcd. for C26H27NNaO5+, 456.18 [M+Na]+, m/z found 456.2 [M+Na]+. Reverse phase LC-MS was carried out using method A.

$^1$H NMR (400 MHz, DMSO-d6) b ppm 9.35 (s, 1H) 7.88 (br d, J=8.07 Hz, 1H) 7.21-7.38 (m, 7H) 7.15 (br d, J=8.07 Hz, 2H) 6.93 (d, J=8.31 Hz, 1H) 6.70 (d, J=2.20 Hz, 1H) 6.63 (dd, J=8.07, 2.45 Hz, 1H) 4.99 (br s, 2H) 4.24-4.36 (m, 1H) 3.60-3.65 (m, 3H) 3.07 (br dd, J=13.69, 4.89 Hz, 1H) 2.91 (br dd, J=13.57, 10.39 Hz, 1H) 2.40-2.48 (m, 2H) 0.99 (t, J=7.58 Hz, 3H).

Step 3: Synthesis of (S)-methyl 2-(((benzyloxy)carbonyl)amino)-3-(4'-(4-((tert-butoxycarbonyl)amino)butoxy)-2'-ethyl-[1, 1'-biphenyl]-4-yl)propanoate (aa27-4)

To a solution of aa27-3 (3.3 g, 7.61 mmol, 1 eq.) and aa27-3a (5.23 g, 15.23 mmol, 2 eq.) in DMF (30 mL) was added $K_2CO_3$ (2.10 g, 15.23 mmol, 2 eq.). The mixture was stirred at 60° C. for 12 hr. The reaction progress was monitored by LC-MS and TLC. The reaction mixture was diluted with EtOAc (100 mL) and washed with $H_2O$ (80 mL*3). The organic layer was dried over $Na_2SO_4$, filtered and concentrated to give a residue, then purified by column chromatography ($SiO_2$, Petroleum ether/Ethyl acetate=10/1 to 2/1). Compound aa27-4 (2.9 g, 4.32 mmol, 56.70% yield, 90% purity) was obtained as a yellow oil.

LCMS (ESI): RT=1.140 min, mass calcd. for $C_{35}H_{44}N_2NaO_7$, 627.30 [M+Na]+, m/z found 627.2 [M+Na]+. Reverse phase LC-MS was carried out using method A.

Step 4: Synthesis of (S)-2-(((benzyloxy)carbonyl)amino)-3-(4'-(4-((tert-butoxycarbonyl) amino)butoxy)-2'-ethyl-[1, 1'-biphenyl]-4-yl)propanoic acid (aa27-5)

To a solution of aa27-4 (2.7 g, 4.46 mmol, 1 eq.) in THF (30 mL) were added a solution of LiOH·$H_2O$ (374.72 mg, 8.93 mmol, 2 eq.) in $H_2O$ (15 mL). The mixture was stirred at 20° C. for 2 hr. The reaction progress was monitored by LC-MS. The mixture was adjusted to pH 3-4 with 1M HCl and extracted with EtOAc (20 mL*3). The organic layer was dried over $Na_2SO_4$, filtered and concentrated to give the product. Compound aa27-5 (2.5 g, 4.23 mmol, 94.79% yield) was obtained as a yellow oil.

LCMS (ESI): RT=1.082 min, mass calcd. for $C_{34}H_{42}N_2NaO_7$, 613.29, m/z found 613.2 [M+Na]+. Reverse phase LC-MS was carried out using method A.

$^1$H NMR (400 MHz, CHLOROFORM-d) δ ppm 7.29-7.36 (m, 5H) 7.14-7.21 (m, 4H) 7.07 (br d, J=8.56 Hz, 1H) 6.81 (s, 1H) 6.73 (br d, J=7.83 Hz, 1H) 5.27 (br d, J=7.58 Hz, 1H) 5.05-5.16 (m, 2H) 4.68-4.75 (m, 1H) 4.50-4.68 (m, 2H) 3.99 (br s, 2H) 3.20-3.28 (m, 2H) 2.53 (q, J=7.42 Hz, 2H) 1.62-1.68 (m, 2H) 1.51-1.57 (m, 2H) 1.44 (br s, 9H) 1.07 (t, J=7.46 Hz, 3H).

Step 5: Synthesis of (2S)-2-amino-3-[4-[4-[4-(tert-butoxycarbonylamino)butoxy]-2-ethyl-phenyl]phenyl]propanoic acid (aa27-6)

To a solution of aa27-5 (1.5 g, 2.54 mmol, 1 eq.) in MeOH (30 mL) were added Pd(OH)$_2$/C (300 mg, 213.62 μmol, 10% purity) and AcOH (105.00 mg, 1.75 mmol, 0.1 mL). The mixture was stirred under $H_2$ at 20° C. for 12 hr. The reaction progress was monitored by LC-MS. The mixture was filtered and concentrated to give the crude product. Compound aa27-6 (1.16 g, crude) was obtained as a yellow oil.

LCMS (ESI): RT=0.890 min, mass calcd. for $C_{26}H_{36}N_2NaO_5$, 479.25, m/z found 479.1 [M+Na]+. Reverse phase LC-MS was carried out using method A.

Step 6: Synthesis of (S)-2-((((9H-fluoren-9-yl)methoxy)carbonyl)amino)-3-(4'-(4-((tert-butoxycarbonyl)amino)butoxy)-2'-ethyl-[1, 1'-biphenyl]-4-yl)propanoic acid (aa27-7)

To a solution of aa27-6 (1.16 g, 2.54 mmol, 1 eq.) in THF (15 mL) and $H_2O$ (8 mL) were added NaHCO$_3$ (426.64 mg, 5.08 mmol, 197.52 μL, 2 eq.) and Fmoc-OSu (1.03 g, 3.05 mmol, 1.2 eq.) at 0° C. The mixture was stirred 20° C. for 12 hr. The reaction progress was monitored by LC-MS. The mixture was adjusted to pH 3-4 and extracted with EtOAc (20 mL*2). The organic layer was dried over $Na_2SO_4$, filtered and concentrated to give a residue, then purified by prep-HPLC (AcOH condition; MeCN/$H_2O$, 0-100%). Compound aa27-7 (950 mg, 1.12 mmol, 44.09% yield, 80% purity) was obtained as a colorless oil.

LCMS (ESI): RT=1.142 min, mass calcd. for $C_{41}H_{46}N_2NaO_7$, 701.32, m/z found 701.0 [M+Na]+. Reverse phase LC-MS was carried out using method A.

HPLC: RT=4.33 min, Mobile Phase: 2.75 ML/4L TFA in water (solvent A) and 2.5 ML/4L TFA in acetonitrile (solvent B), using the elution gradient 10%-80% (solvent B) over 6 minutes and holding at 80% for 2 minutes at a flow rate of 1.2 ml/min; Column: Ultimate C18 3.0*50 mm, 3 μm.

SFC: RT=0.598 min, Column: Chiralpak AD-3 50×4.6 mm I.D., 3 μm; Mobile phase: A: CO2 B: ethanol (0.05% DEA) Isocratic: 40% B; Flow rate: 4 mL/min.

$^1$H NMR (400 MHz, CHLOROFORM-d) δ ppm 7.29-7.36 (m, 5H) 7.14-7.21 (m, 4H) 7.07 (br d, J=8.56 Hz, 1H) 6.81 (s, 1H) 6.73 (br d, J=7.83 Hz, 1H) 5.27 (br d, J=7.58 Hz, 1H) 5.05-5.16 (m, 2H) 4.68-4.75 (m, 1H) 4.50-4.68 (m, 2H) 3.99 (br s, 2H) 3.20-3.28 (m, 2H) 2.53 (q, J=7.42 Hz, 2H) 1.62-1.68 (m, 2H) 1.51-1.57 (m, 2H) 1.44 (br s, 9H) 1.07 (t, J=7.46 Hz, 3H).

Step 7: Synthesis of 9H-fluoren-9-ylmethyl N-[(1S)-2-anilino-1-[[4-[4-[4-(tert-butoxycarbonylamino)butoxy]-2-ethyl-phenyl]phenyl]methyl]-2-oxo-ethyl]carbamate (aa27-8)

To a solution of aa27-7 (250 mg, 368.29 μmol, 1 eq.) and HOBt (49.76 mg, 368.29 μmol, 1 eq.) in DCM (1.5 mL) were added aniline (36.01 mg, 386.71 μmol, 35.31 μL, 1.05 eq.) and a solution of DIC (46.48 mg, 368.29 μmol, 57.03 μL, 1 eq.) in DCM (0.5 mL) at 0° C. The mixture was stirred at 20° C. for 1 hr. The reaction progress was monitored by LC-MS. The mixture was diluted with DCM (20 mL) and washed with $H_2O$ (10 mL*2). The organic layer was dried over $Na_2SO_4$, filtered and concentrated to give a residue. The residue was purified by flash silica gel chromatography (ISCO®; 12 g SepaFlash® Silica Flash Column, Eluent of 0-50% Ethyl acetate/Petroleum ether gradient @ 20 mL/min). Compound aa27-8 (220 mg, 283.05 µmol, 76.86% yield, 97% purity) was obtained as a white solid.

LCMS (ESI): RT=1.198 min, mass calcd. for $C_{47}H_{51}N_3NaO_6$ 776.37, m/z found 777.3 [M+Na]$^+$. Reverse phase LC-MS was carried out using method A.

HPLC: RT=8.07 min, Reverse phase HPLC analysis was carried out using method D. SFC: RT=2.186 min; Column: Chiralcel OD-3 50×4.6 mm I.D., 3 µm; Mobile phase: A: CO2 B: ethanol (0.05% DEA); Isocratic: 40% B; Flow rate: 4 mL/min.

$^1$H NMR (400 MHz, CHLOROFORM-d) δ ppm 7.74 (br d, J=7.58 Hz, 2H) 7.51-7.58 (m, 3H) 7.30-7.40 (m, 4H) 7.28 (br d, J=7.58 Hz, 4H) 7.17-7.24 (m, 4H) 7.07-7.11 (m, 1H) 7.02 (d, J=8.31 Hz, 1H) 6.81 (d, J=2.45 Hz, 1H) 6.72 (dd, J=8.31, 2.45 Hz, 1H) 5.57 (br s, 1H) 4.32-4.69 (m, 4H) 4.20 (t, J=6.72 Hz, 1H) 3.99 (t, J=6.24 Hz, 2H) 3.06-3.29 (m, 4H) 2.49 (q, J=7.42 Hz, 2H) 1.77-1.87 (m, 2H) 1.68 (dt, J=14.55, 7.15 Hz, 2H) 1.44 (s, 9H) 1.03 (t, J=7.58 Hz, 3H).

Step 8: Synthesis of tert-butyl N-[4-[4-[4-[(2S)-2-amino-3-anilino-3-oxo-propyl]phenyl]-3-ethyl-phenoxy]butyl]carbamate (aa27)

To a solution of aa27-8 (220 mg, 291.81 µmol, 1 eq.) in DMF (2 mL) was added a solution of piperidine (124.24 mg, 1.46 mmol, 5 eq.). The mixture was stirred at 20° C. for 1 hr. The reaction progress was monitored by LC-MS. The mixture was diluted with EtOAc (30 mL) and washed with H$_2$O (10 mL*3). The organic layer was dried over Na$_2$SO$_4$, filtered and concentrated to give a residue, then purified by column chromatography (SiO$_2$, EtOAc:MeOH=1:0 to 5:1). Compound aa27 (105 mg, 191.56 µmol, 65.65% yield, 97% purity) was obtained as a yellow foam.

LCMS (ESI): RT=0.953 min, mass calcd. for $C_{32}H_{41}N_3NaO_4$ 554.30, m/z found 554.1 [M+Na]$^+$. Reverse phase LC-MS was carried out using method A. HPLC: RT=9.13 min, Reverse phase HPLC analysis was carried out using method C.

SFC: RT=3.185 min, Column: Chiralpak AS-3 100×4.6 mm I.D., 3 µm; Mobile phase: A: CO$_2$ B:ethanol (0.1% ethanolamine) Gradient: from 5% to 40% of B in 4.5 min and hold 40% for 2.5 min, then 5% of B for 1 min; Flow rate: 2.8 mL/min.

$^1$H NMR (400 MHz, CHLOROFORM-d) δ ppm 9.45 (s, 1H) 7.60 (br d, J=7.83 Hz, 2H) 7.33 (t, J=7.83 Hz, 2H) 7.20-7.29 (m, 4H) 7.06-7.13 (m, 2H) 6.84 (d, J=2.20 Hz, 1H) 6.75 (dd, J=8.31, 2.45 Hz, 1H) 4.68 (br s, 1H) 4.01 (t, J=6.11 Hz, 2H) 3.82 (br d, J=5.38 Hz, 1H) 3.41 (br dd, J=13.82, 3.30 Hz, 1H) 3.13-3.27 (m, 2H) 2.84 (br dd, J=13.82, 9.90 Hz, 1H) 2.56 (q, J=7.50 Hz, 2H) 1.79-1.86 (m, 2H) 1.69 (quin, J=7.15 Hz, 2H) 1.45 (s, 9H) 1.09 (t, J=7.58 Hz, 3H)

2.9 the Synthesis of Unnatural Amino Acid (Aa28)

Scheme 10 outlines the synthesis of unnatural amino acid (aa28):

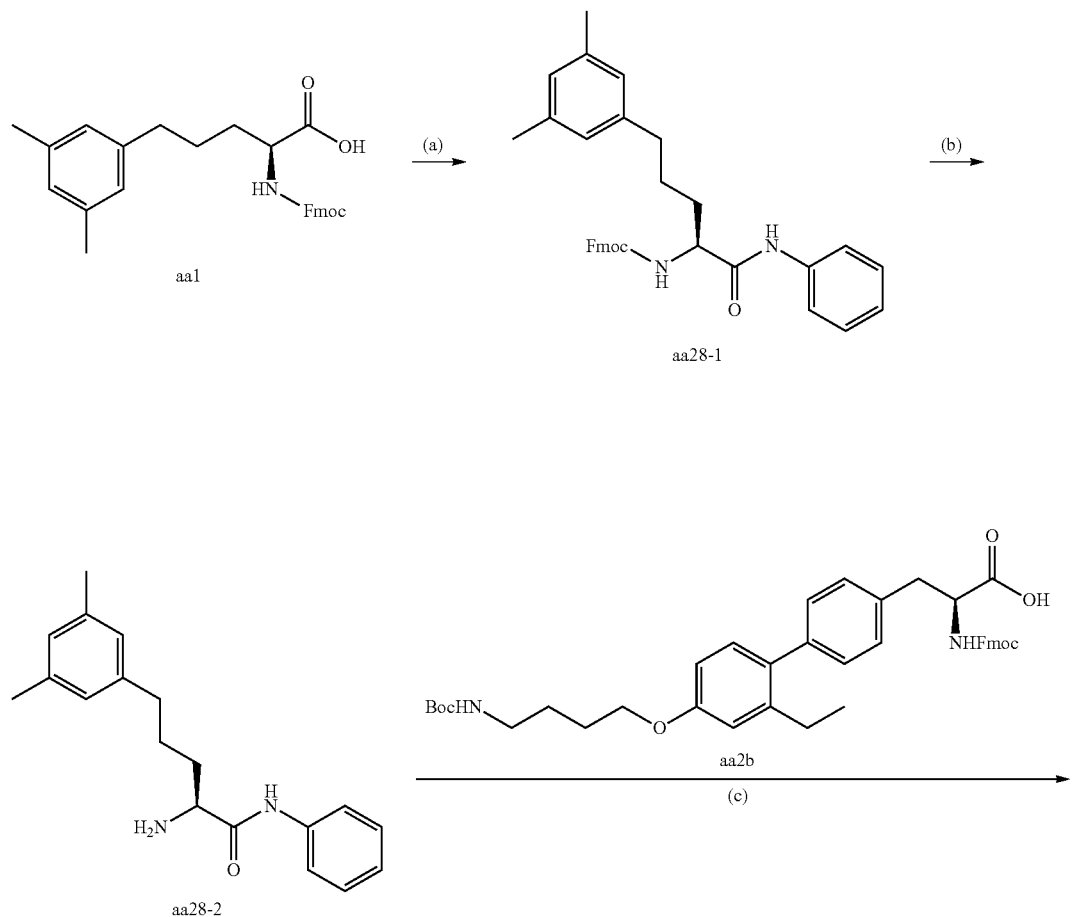

Scheme 10

-continued

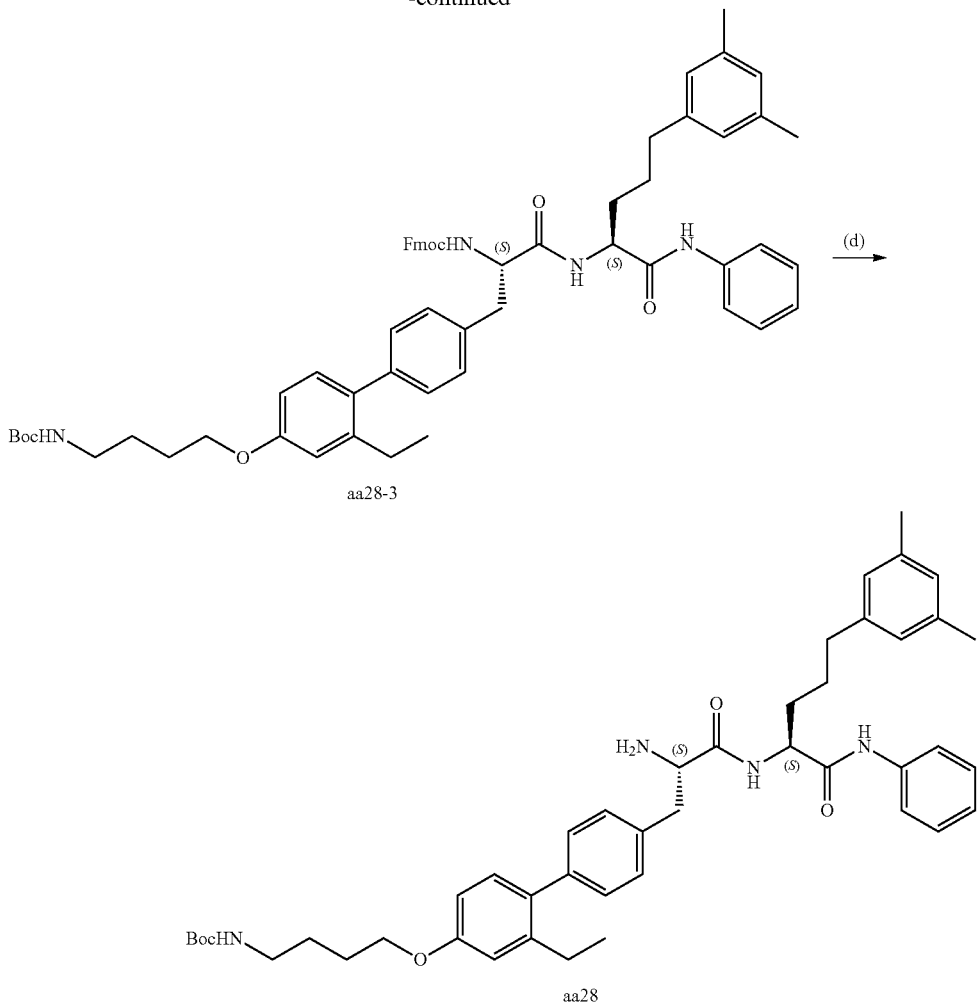

Reagents and conditions: (a) PhNH$_2$ (1.1 eq.), DIC (1.0 eq.), HOBT(1.0 eq.), DCM, 0-20° C., 1h; (b) piperidine (3.0 eq.), DMF, 20° C., 12 h, 52%; (c) 3a (1 eq.), DIC (1.0 eq.), HOBT (1.0 eq.), DCM, 0-20° C., 1 h, 61%; (d) piperidine (15.0 eq.), DMF, 20° C., 0.5 h, 41%.

Step 1: Synthesis of 9H-fluoren-9-ylmethyl N-[(1S)-4-(3,5-dimethylphenyl)-1-(phenylcarbamoyl) butyl]carbamate (aa28-1)

To a solution of aa1 (300 mg, 676.39 μmol, 1 eq.) and HOBt (91.40 mg, 676.39 μmol, 1 eq.) in DCM (1.5 mL) were added aniline (66.14 mg, 710.21 μmol, 64.84 μL, 1.05 eq.) at 0° C. A solution of DIC (85.36 mg, 676.39 μmol, 1 eq.) in DCM (0.5 mL) was added to the mixture. The reaction was stirred at 20° C. for 1 hr. The reaction progress was monitored by LC-MS. The mixture was diluted with DCM (20 mL) and washed with H$_2$O (10 mL*2). The organic layer was dried over Na$_2$SO$_4$, filtered and concentrated to give the crude product. Compound aa28-1 (400 mg, crude) was obtained as a yellow solid.

LCMS (ESI): RT=1.178 min, mass calcd. for C$_{34}$H$_{35}$N$_2$O$_3$+519.26 [M+H]$^+$, m/z found 519.1 [M+H]$^+$. Reverse phase LC-MS was carried out using method A.

Step 2: Synthesis of (2S)-2-amino-5-(3,5-dimethylphenyl)-N-phenyl-pentanamide (aa28-2)

To a solution of aa28-1 (400 mg, 771.24 μmol, 1 eq.) in DMF (2 mL) were added piperidine (197.01 mg, 2.31 mmol, 3 eq) at 20° C. The reaction was stirred at 20° C. for 12 hr. The reaction progress was monitored by LC-MS and TLC. The mixture was diluted with EtOAc (30 mL) and washed with H$_2$O (10 mL*3). The organic layer was dried over Na$_2$SO$_4$, filtered and concentrated to give a residue, then purified by flash silica gel chromatography (ISCO®; 12 g SepaFlash® Silica Flash Column, Eluent of 0-100% Ethyl acetate/Petroleum ethergradient @ 20 mL/min). Compound aa28-2 (150 mg, 399.79 μmol, 51.84% yield, 79% purity) was obtained as a yellow foam. LCMS (ESI): RT=0.861 min, mass calcd. for C$_{19}$H$_{25}$N$_2$O 297.2 [M+H]$^+$, m/z found 297.1 [M+H]$^+$. Reverse phase LC-MS was carried out using method A.

$^1$H NMR (400 MHz, CD3Cl) b ppm 9.46 (br s, 1H), 7.60 (d, J=7.83 Hz, 2H), 7.33 (t, J=7.95 Hz, 2H), 7.07-7.14 (m, 1H), 6.78-6.86 (m, 4H), 3.51 (dd, J=7.95, 4.28 Hz, 1H), 2.57-2.64 (m, 2H), 2.29 (s, 6H), 1.67-1.81 (m, 4H).

Step 3: Synthesis of 9H-fluoren-9-ylmethyl N-[(1S)-1-[[4-[4-[4-(tert-butoxycarbonylamino)butoxy]-2-ethyl-phenyl]phenyl]methyl]-2-[[(1S)-4-(3,5-dimethylphenyl)-1-(phenylcarbamoyl) butyl]amino]-2-oxo-ethyl]carbamate (aa28-3)

To a solution of aa2b (343.52 mg, 506.06 μmol, 1 eq.) and HOBt (68.38 mg, 506.06 μmol, 1 eq) in DCM (2.5 mL) were added aa28-2 (150 mg, 506.06 μmol, 1 eq.) at 0° C. A solution of DIC (63.86 mg, 506.06 μmol, 1 eq.) in DCM (0.5 mL) was added to the mixture. The reaction was stirred at 20° C. for 1 hr. The reaction progress was monitored by TLC. The mixture was diluted with DCM (20 mL) and washed with $H_2O$ (10 mL*2). The organic layer was dried over $Na_2SO_4$, filtered and concentrated to give a residue. The residue was purified by flash silica gel chromatography (ISCO®; 12 g SepaFlash® Silica Flash Column, Eluent of 0-45% Ethylacetate/Petroleum ether gradient @ 20 mL/min). Compound aa28-3 (400 mg, 309.23 μmol, 61.11% yield, 74% purity) was obtained as a yellow solid. LCMS (ESI): RT=6.617 min, mass calcd. for $C_{60}H_{65}N_4NaO_7$ 979.50, m/z found 979.8 $[M+Na]^+$. Reverse phase LC-MS was carried out using method B.

$^1$H NMR (400 MHz, CD3Cl) b ppm 7.72-7.80 (m, 2H), 7.49-7.57 (m, 3H), 7.35-7.41 (m, 2H), 7.20-7.33 (m, 5H), 7.08-7.20 (m, 4H), 6.96-7.08 (m, 2H), 6.76-6.84 (m, 2H), 6.68-6.75 (m, 3H), 5.32-5.47 (m, 1H), 4.64 (br s, 1H), 4.52-4.60 (m, 1H), 4.42-4.51 (m, 2H), 4.37 (br s, 1H), 4.13-4.23 (m, 1H), 4.00 (t, J=6.24 Hz, 2H), 3.05-3.27 (m, 4H), 2.44-2.61 (m, 4H), 2.20-2.25 (m, 6H), 1.82-1.89 (m, 2H), 1.62-1.75 (m, 6H), 1.46 (s, 9H), 1.01-1.09 (m, 3H).

Step 4: Synthesis of tert-butyl N-[4-[4-[4-[(2S)-2-amino-3-[[(1S)-4-(3,5-dimethylphenyl)-1-(phenylcarbamoyl)butyl]amino]-3-oxo-propyl]phenyl]-3-ethyl-phenoxy]butyl]carbamate (aa28)

To a solution of aa28-3 (380 mg, 396.99 μmol, 1 eq.) in DMF (2.5 mL) were added piperidine (507.06 mg, 5.95 mmol, 15 eq.) at 20° C. The reaction was stirred at 20° C. for 0.5 hr. The reaction progress was monitored by LC-MS. The mixture was diluted with ACN (2 mL) and purified by prep-HPLC (HCl condition; column: Agela ASB 150*25 mm*5 μm; mobile phase: [water (0.05% HCl) -ACN]; B %: 55%-85%, 8 min). Compound aa28 (125 mg, 164.97 μmol, 41.56% yield, 97% purity) was obtained as a little yellow foam.

LCMS (ESI): RT=1.061 min, mass calcd. for $C_{45}H_{55}N_4NaO_5$ 757.43, m/z found 757.5 $[M+Na]^+$. Reverse phase LC-MS was carried out using method A. HPLC: RT=10.66 min, Reverse phase HPLC analysis was carried out using method C. SFC: RT=2.161 min, Column: Chiralpak AD-3 50*4.6 mm I.D., 3 μm; Mobile phase: A: $CO_2$ B:iso-propanol (0.05% DEA); Gradient: from 5% to 40% of B in 2 min and hold 40% for 1.2 min, then 5% of B for 0.8 min; Flow rate: 4 mL/min.

$^1$H NMR (400 MHz,CD30D) b ppm 7.55 (br d, J=8.07 Hz, 2H), 7.24-7.31 (m, 4H), 7.14 (d, J=8.07 Hz, 2H), 7.05-7.11 (m, 1H), 6.95 (d, J=8.31 Hz, 1H), 6.81 (d, J=2.45 Hz, 1H), 6.78 (s, 3H), 6.68-6.72 (m, 1H), 4.54 (t, J=6.72 Hz, 1H), 4.20 (t, J=6.85 Hz, 1H), 4.00 (t, J=6.11 Hz, 2H), 3.25-3.30 (m, 1H), 3.12 (br t, J=6.85 Hz, 3H), 2.54-2.63 (m, 2H), 2.51 (q, J=7.50 Hz, 2H), 2.22 (s, 6H), 1.62-1.95 (m, 8H), 1.44 (s, 9H), 1.03 (t, J=7.58 Hz, 3H).

2.10 the Synthesis of Unnatural Amino Acid (Aa29)

Scheme 11 outlines the synthesis of unnatural amino acid (aa29):

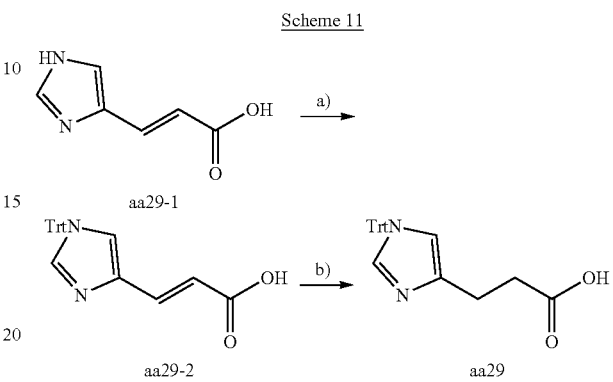

Scheme 11

Reagents and conditions: (a) TrtCl (1.0 eq.), $Et_3N$ (3.0 eq.), DMF, 20° C., 12 h, 29.05%; (b)Pd/C (10 wt %), $H_2$, EtOH, 20° C., 2 h.

Step 1: Synthesis of (E)-3-(1-trityl-1H-imidazol-5-yl) acrylic acid (aa29-2)

Compounds aa29-1 (2 g, 14.48 mmol, 1.0 eq.), TEA (4.40 g, 43.44 mmol, 6.05 mL, 3.0 eq.) and TrtCl (4.04 g, 14.48 mmol, 1.0 eq.) in DMF (34 mL) were stirred at 20° C. for 12 hr. TLC (DCM/MeOH=10/1) showed the reaction was complete. The mixture was diluted with $CH_2Cl_2$, washed with $H_2O$ (3*50 mL) and citric acid solution (3*50 mL). The organic phase was evaporated and purified by column chromatography (eluent: $CH_2Cl_2$/MeOH, 9:1). Compound aa29-2 (1.6 g, 4.21 mmol, 29.05% yield) was obtained as a white solid.

$^1$H NMR (400 MHz, CD30D) δ 7.57 (s, 1H), 7.51 (d, J=15.77 Hz, 1H), 7.38-7.45 (m, 9H), 7.32 (s, 1H), 7.15-7.22 (m, 6H), 6.45 (d, J=15.65 Hz, 1H) ppm.

Step 2: Synthesis of 3-(1-trityl-1H-imidazol-5-yl) propanoic acid (aa29)

To a solution of compound aa29-2 (1.6 g, 4.21 mmol, 1 eq.) in EtOH (20 mL) was added Pd/C (1 g, 10% purity) under $N_2$ atmosphere. The suspension was degassed and purged with $H_2$ for 3 times. The mixture was stirred under $H_2$ (15 Psi.) at 20° C. for 2 h. After completion, the mixture was filtered and the filtrate was concentrated to give the product. Compound aa29 (1.2 g, 3.14 mmol, 74.60% yield) was obtained as a white solid.

LCMS (ESI): RT=0.802 min, mass calcd. for $C_{25}H_{21}N_2O_2$ 381.17$[M-H]^-$, found 381.17 $[M-H]^-$, Reverse phase LCMS was carried out using Waters Xbridge C18 30*2.0 mm, 3.5 μm, with a flow rate of 1.2 ml/min, eluting with a gradient of 5% to 95% acetonitrile containing ACN (solvent B) and water containing 0.05% $NH_3H2O$ in Water (solvent A).

$^1$H NMR (400 MHz, $CD_3OD$) δ 7.34-7.39 (m, 4H), 7.22-7.39 (m, 4H), 7.11-7.14 (m, 3H), 7.06-7.20 (m, 2H), 7.08 (d, J=7.25 Hz, 4H), 2.90 (t, J=7.32 Hz, 2H), 2.80 (t, J=7.38 Hz, 1H), 2.51-2.62 (m, 2H) ppm.

2.11 the Synthesis of Unnatural Amino Acid (Aa30)

Scheme 12 outlines the synthesis of unnatural amino acid (aa30):

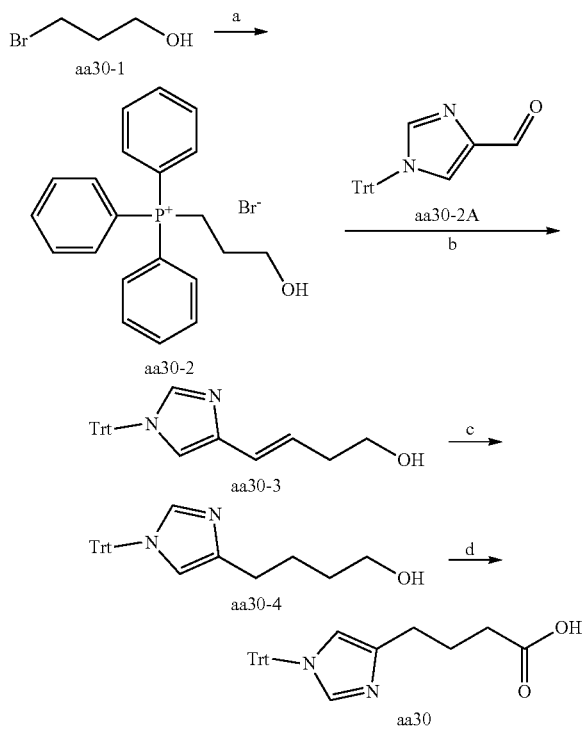

Scheme 12

Reagents and conditions: (a) PPh₃ (1.2 eq.), toluene, 110° C., 12 h; b) aa30-2A (1.5 eq.), LiHMDS (4.0 eq.), THF, -20-25° C., 12 h; c) H₂, Pd/C, MeOH, 25° C., 2 h; d) TEMPO (1.5 eq.), PIDA (2.5 eq.), MeCN/H₂O (3:2), 25° C., 2 h;

Step 1: Synthesis of (3-hydroxypropyl)triphenylphosphonium bromide (aa30-2)

To a solution of 3-bromopropan-1-ol (10 g, 71.95 mmol, 6.49 mL, 1 eq.) in toluene (100 mL) was added PPh₃ (22.65 g, 86.34 mmol, 1.2 eq.). The mixture was stirred at 100° C. under N₂ for 12 h. The reaction progress was monitored by LCMS. After completion, the reaction was cooled to 0° C. and filtered, the filter cake was washed with toluene (10 mL*3), then dried under reduced pressure. Compound aa30-2 (20.7 g, crude) was obtained as a white solid.

LCMS (ESI): RT=0.758 min, mass calcd. for $C_{21}H_{22}OP^+$, 321.14 [M]⁺, found 321.0 [M]⁺. LCMS conditions: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm & 254 nm; Column temperature: 50° C.; MS ionization: ESI.

¹H NMR (400 MHz, CD₃Cl) δ 7.83-7.65 (m, 15H), 4.94 (br s, 1H), 3.87-3.73 (m, 4H), 1.83 (m, 2H) ppm.

Step 2: Synthesis of (E)-4-(1-trityl-1H-imidazol-4-yl)but-3-en-1-ol (aa30-3)

To a solution of aa30-2 (10.67 g, 26.60 mmol, 1.5 eq.) in THF (50 mL) was added LiHMDS (1 M, 70.92 mL, 4 eq.). The mixture was stirred at 0° C. for 0.5 h, then a solution of aa30-2A (1-tritylimidazole-4-carbaldehyde, 6 g, 17.73 mmol, 1.0 eq.) in THF (60 mL) was added to the above mixture and the resulting mixture was stirred at 25° C. for 12 h. The reaction progress was monitored by LCMS. After completion, the mixture was filtered and concentrated under reduced pressure to give a residue, then the residue was re-dissolved in dioxane (50 mL) and the final solution was stirred at 100° C. for 12 h, after that, the solution was concentrated under reduced pressure to give a residue. The residue was purified by flash silica gel chromatography (ISCO®; 80 g SepaFlash® Silica Flash Column, Eluent of 0-80% Ethylacetate/Petroleum ethergradient @60 mL/min). Compound aa30-3 (650 mg, crude) was obtained as a yellow solid.

LCMS (ESI): RT=0.846 min, mass calcd. for $C_{26}H_{24}N_2ONa$, 403.19 [M+Na]⁺, found 403.1 [M+Na]⁺. LCMS conditions: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm & 254 nm; Column temperature: 50° C.; MS ionization: ESI.

¹H NMR (400 MHz, CD₃OD) δ 7.68-7.57 (m, 1H), 7.40-7.37 (m, 9H), 7.18-7.13 (m, 6H), 6.83 (d, J=1.0 Hz, 1H), 6.36-6.14 (m, 2H), 3.62 (t, J=6.7 Hz, 2H), 2.36 (q, J=6.6 Hz, 2H) ppm.

Step 3: Synthesis of 4-(1-trityl-1H-imidazol-4-yl)butan-1-ol (aa30-4)

To a solution of aa30-3 (650 mg, 1.71 mmol, 1 eq.) in MeOH (5 mL) was added Pd/C (50 mg, 489.61 mmol, 10% purity). The mixture was stirred at 25° C. for 2 h under H₂. The reaction progress was monitored by LCMS. After completion, the mixture was filtered and concentrated under reduced pressure to give a residue. The residue was purified by flash silica gel chromatography (ISCO®; 25 g SepaFlash® Silica Flash Column, Eluent of 0-50% Ethyl acetate/Petroleum ether gradient @ 40 mL/min) for 8 min with total volume. Compound aa30-4 (450 mg, 1.18 mmol, 68.87% yield, 100% purity) was obtained as a white solid.

LCMS (ESI): RT=0.850 min, mass calcd. for $C_{26}H_{26}N_2ONa$, 405.20 [M+Na]⁺, found 405.2 [M+Na]⁺. LCMS conditions: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm & 254 nm; Column temperature: 50° C.; MS ionization: ESI.

Step 4: Synthesis of 4-(1-trityl-1H-imidazol-4-yl)butanoic acid (aa30)

To a solution of aa30-4 (450 mg, 1.18 mmol, 1 eq.) in MeCN (5 mL) and H₂O (7 mL) was added TEMPO (277.51 mg, 1.76 mmol, 1.5 eq.) and PIDA (Iodobenzene diacetate (3240-34-4), 947.35 mg, 2.94 mmol, 2.5 eq.). The mixture was stirred at 25° C. for 12 h. The reaction progress was monitored by LCMS. After completion, to the mixture was added citric acid (aq. 15 mL) to adjust pH=4, then extracted with EtOAc (15 mL*2), the organic layers were collected, dried over Na₂SO₄, filtered, and concentrated under reduced pressure to give a residue. Then the residue was triturated by MTBE. Compound aa30 (250 mg, crude) was obtained as a white solid.

LCMS (ESI): RT=2.484 min, mass calcd. for $C_{26}H_{25}N_2O_2$, 397.18 [M+H]$^+$, found 397.2 [M+H]$^+$. LCMS conditions: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min. ESI source, Positive ion mode; Wavelength 220 nm & 254 nm, Oven Temperature 50° C.

$^1$H NMR (400 MHz, CD$_3$OD) δ 8.69 (d, J=1.6 Hz, 1H), 7.53-7.38 (m, 9H), 7.28-7.14 (m, 7H), 2.75 (t, J=7.5 Hz, 2H), 2.34 (t, J=7.1 Hz, 2H), 2.00-1.87 (m, 2H) ppm.

2.12 the Synthesis of Unnatural Amino Acid (Aa31)

Scheme 13 outlines the synthesis of unnatural amino acid (aa31):

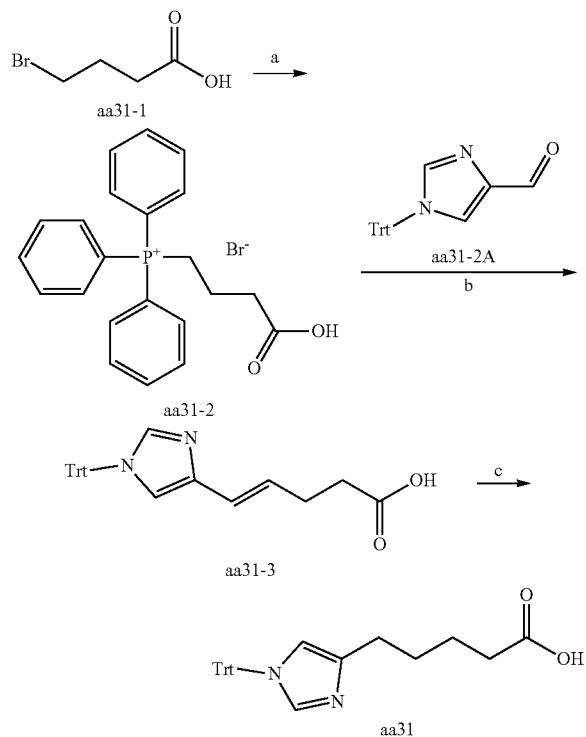

Reagents and conditions: (a) PPh$_3$ (1.2 eq.), toluene, 110° C., 12 h; b) aa31-2A (1.5 eq.), tBuOK (3.0 eq.), THF, 0-25° C., 12 h; c) H$_2$, Pd/C, MeOH, 25° C., 2 h;

Step 1: Synthesis of (3-carboxypropyl)triphenylphosphonium bromide (aa31-2)

To a solution of 4-bromobutanoic acid (5 g, 29.94 mmol, 6.76 mL, 1 eq.) in toluene (70 mL) was added PPh3 (8.64 g, 32.93 mmol, 1.1 eq.). The mixture was stirred at 110° C. under N2 for 12 h. The reaction progress was monitored by TLC and LCMS. Upon completion, the reaction mixture was cooled to 0° C., then filtered and washed with toluene (10 mL*3), the filter cake was collected and dried under reduced pressure. Compound aa31-2 (5.6 g, crude) was obtained as a white solid.

LCMS (ESI): RT=1.076 min, mass calcd. for $C_{22}H_{22}O_2P^+$, 349.14[M]$^+$, found 349.2 [M]$^+$. LCMS conditions: 1.5 ML/4L TFA in water (solvent A) and 0.75 ML/4L TFA in acetonitrile (solvent B), using the elution gradient 10%-80% (solvent B) over 1.35 minutes and holding at 80% for 0.9 minutes at a flow rate of 0.8 ml/min; Column: Xtimate C18 2.1*30 mm, 3 mm; Wavelength: UV 220 nm & 254 nm Column temperature: 50° C.; MS ionization: ESI.

$^1$H NMR (400 MHz, CD$_3$Cl) δ 7.91-7.66 (m, 15H), 3.31-3.22 (m, 2H), 2.55 (t, J=6.3 Hz, 2H), 1.84 (m, 2H) ppm.

Step 2: Synthesis of (E)-5-(1-trityl-1H-imidazol-4-yl)pent-4-enoic acid (aa31-3)

To a solution of aa31-2 (3.81 g, 8.87 mmol, 1.5 eq.) in THF (20 mL) was added tBuOK (1.99 g, 17.73 mmol, 3 eq.) at 0° C. under N$_2$, the mixture was stirred at 0° C. for 30 min, then a solution of aa31-2A (2 g, 5.91 mmol, 1 eq.) in THF (20 mL) was added to the above mixture at 0° C. and the final mixture was stirred at 25° C. for 12 h. The reaction progress was monitored by LCMS. Upon completion, to the mixture was added citric acid to adjust pH=4, then extracted with EtOAc (50 mL*2), the organic layers were collected, dried over Na$_2$SO$_4$, filtered, and concentrated under reduced pressure to give a residue. The residue was purified by flash silica gel chromatography (ISCO®; 80 g SepaFlash® Silica Flash Column, Eluent of 0-10% MeOH/DCM@ 40 mL/min). Compound aa31-3 (4 g, crude) was obtained as a light yellow foam.

LCMS (ESI): RT=1.487 min, mass calcd. for $C_{27}H_{25}N_2O_2$, 409.18 [M+H]$^+$, found 409.3 [M+H]$^+$. LCMS conditions: 1.5 ML/4L TFA in water (solvent A) and acetonitrile (solvent B), using the elution gradient 10%-80% (solvent B) over 1.35 minutes and holding at 80% for 0.9 minutes at a flow rate of 0.8 ml/min; Column: Xtimate C18 2.1*30 mm, 3 mm; Wavelength: UV 220 nm & 254 nm; Column temperature: 50° C.; MS ionization: ESI.

Step 3: Synthesis of 5-(1-trityl-1H-imidazol-4-yl)pentanoic acid (aa31)

To a solution of aa31-3 (3 g, 7.34 mmol, crude purity, 1 eq.) in MeOH (40 mL) was added Pd/C (300 mg, 489.61 mmol, 10% purity). The mixture was stirred at 25° C. for 2 h under H2. The reaction progress was monitored by LCMS. Upon completion, the mixture was filtered and concentrated under reduced pressure to give a residue. The residue was purified by flash silica gel chromatography (ISCO®; 40 g SepaFlash® Silica Flash Column, Eluent of 0-10% MeOH/DCM@ 40 mL/min) for 7 min with total volume. After that, the product was triturated by TBME. Compound aa31 (290 mg, 692.32 mmol, 71.05% yield, 98% purity) was obtained as a white solid.

LCMS (ESI): RT=1.805 min, mass calcd. for $C_{27}H_{27}N_2O_2$, 411.20 [M+H]$^+$, found 411.3 [M+H]$^+$. LCMS conditions: 0.8 mL/4L NH$_3$—H$_2$O in water (solvent A) and acetonitrile (solvent B), using the elution gradient 10%-80% (solvent B) over 6 minutes and holding at 80% for 0.5 minutes at a flow rate of 0.8 ml/min; Column: XBridge C18 3.5 mm 2.1*30 mm; Wavelength: UV 220 nm & 254 nm; Column temperature: 50° C.; MS ionization: ESI.

$^1$H NMR (400 MHz, CD$_3$Cl) δ 7.65 (s, 1H), 7.44-7.34 (m, 9H), 7.16 (dd, J=2.9, 6.8 Hz, 6H), 6.77 (s, 1H), 2.58 (br t, J=6.8 Hz, 2H), 2.28 (t, J=7.1 Hz, 2H), 1.70-1.55 (m, 4H) ppm.

2.13 the Synthesis of Unnatural Amino Acid (Aa32)

Scheme 14 outlines the synthesis of unnatural amino acid (aa32):

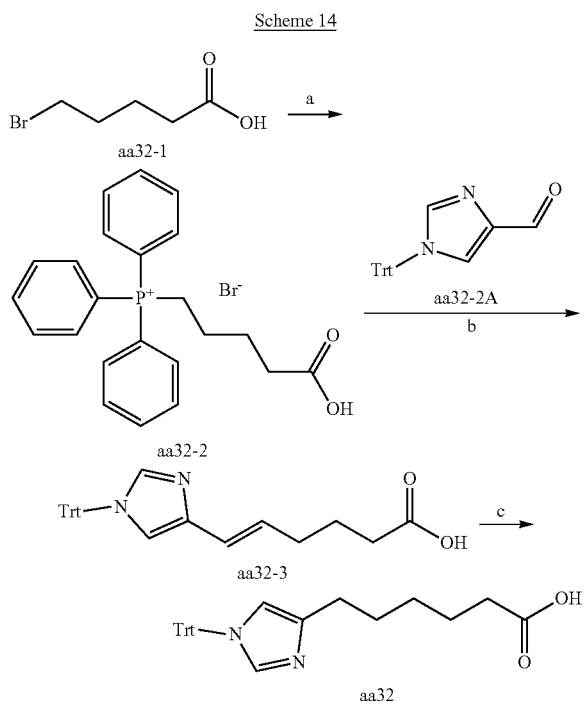

Reagents and conditions: (a) PPh$_3$ (1.2 eq.), toluene, 110° C., 12 h; b) aa32-2A (1.5 eq.), tBuOK (3.0 eq.), THF, 0-25° C., 12 h; c) H$_2$, Pd/C, MeOH, 25° C., 2 h;

Step 1: Synthesis of (4-carboxybutyl)triphenylphosphonium bromide (aa32-2)

To a solution of 5-bromopentanoic acid (10 g, 55.24 mmol, 6.76 mL, 1 eq.) in toluene (100 mL) was added PPh$_3$ (15.94 g, 60.76 mmol, 1.1 eq.). The mixture was stirred at 110° C. for 12 h under N$_2$. The reaction progress was monitored by LCMS. Upon completion, the reaction mixture was cooled to 0° C., then filtered and washed with toluene (10 mL*3), the filter cake was collected and dried under reduced pressure. Compound aa32-2 (16.4 g, 36.99 mmol, 66.97% yield) was obtained as a white solid.

LCMS (ESI): RT=1.076 min, mass calcd. for C$_{22}$H$_{22}$O$_2$P$^+$, 349.14 [M+H]$^+$, found 349.2 [M+H]$^+$. LCMS conditions: 1.5 ML/4L TFA in water (solvent A) and 0.75 ML/4L TFA in acetonitrile (solvent B), using the elution gradient 10%-80% (solvent B) over 1.35 minutes and holding at 80% for 0.9 minutes at a flow rate of 0.8 ml/min; Column: Xtimate C18 2.1*30 mm, 3 mm; Wavelength: UV 220 nm & 254 nm Column temperature: 50° C.;

$^1$H NMR (400 MHz, CD$_3$Cl) δ 7.91-7.66 (m, 15H), 3.31-3.22 (m, 2H), 2.55 (t, J=6.3 Hz, 2H), 1.86-1.82 (m, 4H) ppm.

Step 2: Synthesis of (E)-6-(1-trityl-1H-imidazol-4-yl)hex-5-enoic acid (aa32-3)

To a solution of aa32-2 (7.86 g, 17.73 mmol, 1.5 eq.) in THF (60 mL) was added t-BuOK (3.98 g, 35.46 mmol, 3 eq.) at 0° C. under N$_2$. The mixture was stirred at 0° C. for 30 min. A solution of aa32-2A (4 g, 11.82 mmol, 1 eq.) in THF (40 mL) was added to the above mixture at 0° C. and the resulting mixture was stirred at 25° C. for 12 h. The reaction progress was monitored by LCMS. Upon completion, to the mixture was added citric acid to adjust pH=4, then extracted with EtOAc (50 mL*2), the organic layers were collected, dried over Na$_2$SO$_4$, filtered, and concentrated under reduced pressure to give a residue. The residue was purified by flash silica gel chromatography (ISCO®; 80 g SepaFlash® Silica Flash Column, Eluent of 0-10% MeOH/DCM@ 40 mL/min). Compound aa32-3 (4 g, crude) was obtained as a light yellow foam.

LCMS (ESI): RT=2.739 min, mass calcd. for C$_{28}$H$_{27}$N$_2$O$_2$, 423.20[M+H]$^+$, found 423.2 [M+H]$^+$. LCMS conditions: 1.5 ML/4L TFA in water (solvent A) and acetonitrile (solvent B), using the elution gradient 10%-80% (solvent B) over 1.35 minutes and holding at 80% for 0.9 minutes at a flow rate of 0.8 ml/min; Column: Xtimate C18 2.1*30 mm, 3 mm; Wavelength: UV 220 nm & 254 nm; Column temperature: 50° C.; MS ionization: ESI.

Step 3: Synthesis of 6-(1-trityl-1H-imidazol-4-yl)hexanoic acid (aa32)

To a solution of aa32-3 (4 g, 9.47 mmol, 1 eq.) in MeOH (40 mL) was added Pd/C (300 mg, 489.61 mmol, 10% purity). The mixture was stirred at 25° C. for 2 h under H$_2$. The reaction progress was monitored by LCMS. Upon completion, the mixture was filtered and concentrated under reduced pressure to give a residue. The residue was purified by flash silica gel chromatography (ISCO®; 40 g SepaFlash® Silica Flash Column, Eluent of 0-10% MeOH/DCM@ 40 mL/min). After that, the product was triturated by TBME. Compound aa32 (660 mg, 1.51 mmol, 15.93% yield, 97% purity) was obtained as a white solid.

LCMS (ESI): RT=2.807 min, mass calcd. for C$_{28}$H$_{29}$N$_2$O$_2$, 425.22 [M+H]$^+$, found 425.2 [M+H]$^+$. LCMS conditions: 1.5 ML/4L TFA in water (solvent A) and 0.75 ML/4L TFA in acetonitrile (solvent B), using the elution gradient 10%-80% (solvent B) over 6.0 minutes and holding at 80% for 0.5 minutes at a flow rate of 0.8 ml/min; Column: Xtimate C18 2.1*30 mm, 3 mm; Wavelength: UV 220 nm & 254 nm Column temperature: 50° C.; MS ionization: ESI.

$^1$H NMR (400 MHz, CD$_3$OD) δ 7.43 (d, J=1.3 Hz, 1H), 7.41-7.34 (m, 9H), 7.19-7.11 (m, 6H), 6.65 (s, 1H), 2.52 (t, J=7.4 Hz, 2H), 2.24 (t, J=7.4 Hz, 2H), 1.60 (m, 4H), 1.38-1.27 (m, 2H) ppm.

2.14 The Synthesis of Unnatural Amino Acid (Aa33)

Scheme 15 outlines the synthesis of unnatural amino acid (aa33):

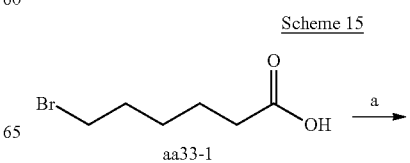

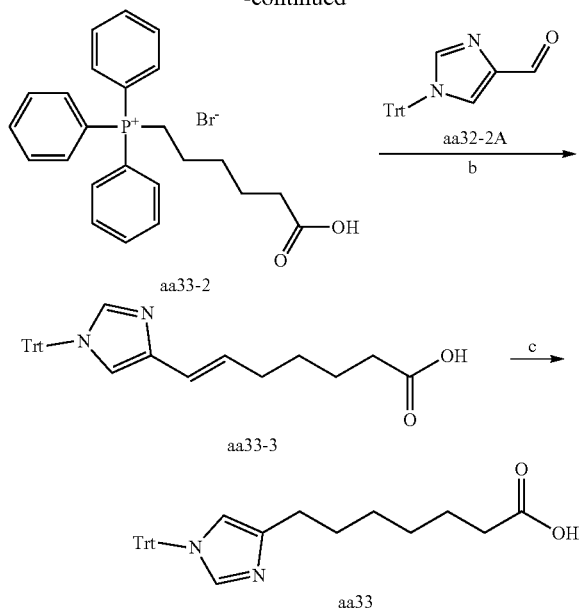

Reagents and conditions: (a) PPh₃ (1.2 eq.), toluene, 110° C., 12 h; b) aa33-2A (1.5 eq.), tBuOK (3.0 eq.), THF, 0-25° C., 12 h; c) H₂, Pd/C, MeOH, 25° C., 2 h;

Step 1: Synthesis of (5-carboxypentyl)triphenylphosphonium bromide (aa33-2)

To a solution of 6-bromohexanoic acid (5 g, 25.63 mmol, 1 eq.) in toluene (50 mL) was added PPh₃ (7.06 g, 26.92 mmol, 1.05 eq.). The resulting solution was stirred at 120° C. over 12 h. After completion, the reaction mixture was cooled to 0° C., then filtered and washed with toluene (10 mL*3), the filter cake was collected and dried under reduced pressure. Compound aa33-2 (6.85 g, 14.47 mmol, 56.44% yield, 96.6% purity) was obtained as a white solid.

LCMS (ESI): RT=0.916 min, m/z calcd. for $C_{24}H_{26}PO_2+$ 377.17, found 377.1 [M-Br]⁺. Reverse phase LCMS was carried out using a Xtimate C18, 2.1*30 mm 3 mm, SN: 3U411301530 column, with a flow rate of 1.5 mL/min, eluting with a gradient of 10% to 80% acetonitrile containing 0.02% TFA (solvent B) and water containing 0.04% TFA (solvent A).

Step 2: Synthesis of (E)-7-(1-trityl-1H-imidazol-4-yl)hept-6-enoic acid (aa33-3)

To a solution of aa33-2 (4.05 g, 8.87 mmol, 2 eq.) in THF (20 mL) was added tBuOK (1 M, 22.16 mL, 5 eq.) at 0° C. under N₂, the mixture was stirred at 0° C. for 30 min, then a solution of aa33-2A (1.5 g, 4.43 mmol, 1 eq.) in THF (20 mL) was added to the above mixture at 0° C. and the final mixture was stirred at 25° C. for 12 h. The reaction progress was monitored by LCMS. After completion, the mixture was added citric acid to adjust pH=4, then extracted with EtOAc (50 mL*2), the organic layers were collected, dried over Na₂SO₄, filtered and concentrated under reduced pressure to give a residue. The crude product was used into the next step without any further purification. Compound aa33-3 (3.8 g, crude) was obtained as a yellow syrup.

LCMS (ESI): RT=2.904 min and 3.068 min, mass calcd. for $C_{29}H_{29}N_2O_2$ 437.22, found 437.3 [M+H]⁺; Reverse phase LCMS was carried out using a Chromolith Flash RP-C18 25-3 mm column, with a flow rate of 1.5 mL/min, eluting with a gradient of 10% to 80% acetonitrile containing 0.02% TFA (solvent B) and water containing 0.04% TFA (solvent A).

Step 3: Synthesis of 7-(1-trityl-1H-imidazol-4-yl)heptanoic acid (aa33)

To a solution of aa33-3 (3 g, 6.87 mmol, 1 eq.) in MeOH (30 mL) was added Pd/C (300 mg, 489.61 mmol, 10% purity). The mixture was stirred at 25° C. for 2 h under H₂. The reaction progress was monitored by LCMS. After completion, the residue was purified by prep-HPLC (column: Boston Prime C18 150*25 mm*5 mm; mobile phase: [water (0.05% ammonia hydroxide v/v)-ACN]; B %: 22%-45%, 7 min). Compound aa33 (200 mg, 456.04 mmol, 6.64% yield, 100% purity) was obtained as a white solid.

LCMS (ESI): RT=2.231 min, mass calcd. for $C_{29}H_{31}N_2O_2$, 439.23 [M+H]⁺, found 439.3 [M+H]⁺. LCMS conditions: Mobile Phase: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min. ESI source, Positive ion mode; Wavelength 220 nm & 254 nm, Oven Temperature 50° C.

¹H NMR (400 MHz, CD₃OD) δ 7.45-7.31 (m, 10H), 7.19-7.11 (m, 6H), 6.64 (s, 1H), 2.52 (t, J=7.3 Hz, 2H), 2.24 (t, J=7.4 Hz, 2H), 1.65-1.52 (m, 4H), 1.38-1.26 (m, 4H) ppm.

2.15 the Synthesis of Unnatural Amino Acid (Aa34)

Scheme 16 outlines the synthesis of unnatural amino acid (aa34):

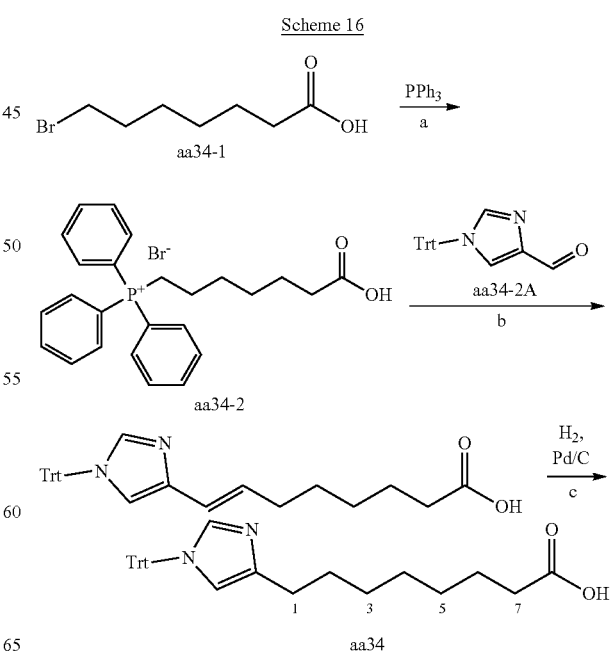

Scheme 16

Reagents and conditions: (a) PPh₃ (1.2 eq.), toluene, 110° C., 12 h; b) aa34-2A (1.5 eq.), tBuOK (3.0 eq.), THF, 0-25° C., 12 h; c) H₂, Pd/C, MeOH, 25° C., 2 h;

Step 1: Synthesis of 7-[BLAH(triphenyl)-λ5-phosphanyl]heptanoic acid (aa34-2)

To a solution of aa34-1 (10 g, 47.83 mmol, 1 eq) in toluene (100 mL) was added PPh₃ (13.80 g, 52.61 mmol, 1.1 eq). The mixture was stirred at 110° C. for 12 hr. After completion, the reaction was filtered under reduced pressure to give a residue. The crude product was used to the next step without further purification. Compound aa34-2 (22.8 g, 43.73 mmol, 91.43% yield, 90.410% purity) was obtained as a yellow oil.

LCMS (ESI): RT=0.792 min, m/z calcd. for $C_{25}H_{28}O_2P^+$ 391.18 [M]⁺, found 391.1 [M]⁺, LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

Step 2: Synthesis of (E)-8-(1-tritylimidazol-4-yl)oct-7-enoic acid (aa34-3)

To a solution of aa34-2 (10.45 g, 22.16 mmol, 1.5 eq.) in THF (150 mL) was added t-BuOK (4.97 g, 44.33 mmol, 3 eq) at 0° C. under N₂, the mixture was stirred at 0° C. then a solution of aa34-2A (5 g, 14.78 mmol, 1 eq) in THF (20 mL) added to the above mixture at 0° C. and the final mixture was stirred at 25° C. for 12 hr. After completion, the mixture was added citric acid to adjust pH=4, then extracted with EtOAc (200 mL*2), the organic layers were collected, dried over Na₂SO₄, filtered and concentrated under reduced pressure to give the target aa34-3 (14.5 g, crude) as a white solid.

LCMS (ESI): RT=0.870 min, m/z calcd. for $C_{30}H_{31}N_2O_2$ 451.23 [M+H]⁺, $C_{30}H_{30}N_2O_2Na$ 473.23 [M+Na]⁺, found 473.1 [M+Na]⁺, LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

Step 3: Synthesis of 8-(1-tritylimidazol-4-yl)octanoic acid (aa34)

To a solution of aa34-3 (14 g, 15.54 mmol, 50% purity, 1 eq) in MeOH (200 mL) was added Pd/C (4 g, 10% purity) and H₂. The mixture was stirred at 25° C. for 3 hr. After completion, the mixture was filtered and concentrated under reduced pressure to give a residue. The crude product was purified by C-18 reverse phase chromatography (ISCO®; 120 g SepaFlash® C-18 Column, Eluent of 60-70% acetonitrile/H₂O gradient @ 80 mL/min, 40 min with total volume 2 L) to give a residue (neutral). Compound aa34 (2.1 g, 4.53 mmol, 29.15% yield, 97.6% purity) was obtained as a white solid.

LCMS (ESI): RT=2.956 min, mass calcd. for $C_{30}H_{33}N_2O_2$ 453.25 [M+H]⁺, found 453.3 [M+H]⁺. LCMS conditions: 1.5 ML/4L TFA in water (solvent A) and 0.75 ML/4L TFA in acetonitrile (solvent B), using the elution gradient 10%-80% (solvent B) over 6.0 minutes and holding at 80% for 0.5 minutes at a flow rate of 0.8 ml/min; Column: Xtimate C18 2.1*30 mm, 3 μm; Wavelength: UV 220 nm & 254 nm Column temperature: 50° C.; MS ionization: ESI.

¹H NMR (400 MHz, CD₃OD) δ 7.47-7.33 (m, 10H), 7.22-7.10 (m, 6H), 6.64 (s, 1H), 2.52 (t, J=7.4 Hz, 2H), 2.26 (t, J=7.4 Hz, 2H), 1.69-1.48 (m, 4H), 1.37-1.26 (m, 6H) ppm.

2.16 the Synthesis of Unnatural Amino Acid (Aa35)

Scheme 17 outlines the synthesis of unnatural amino acid (aa35):

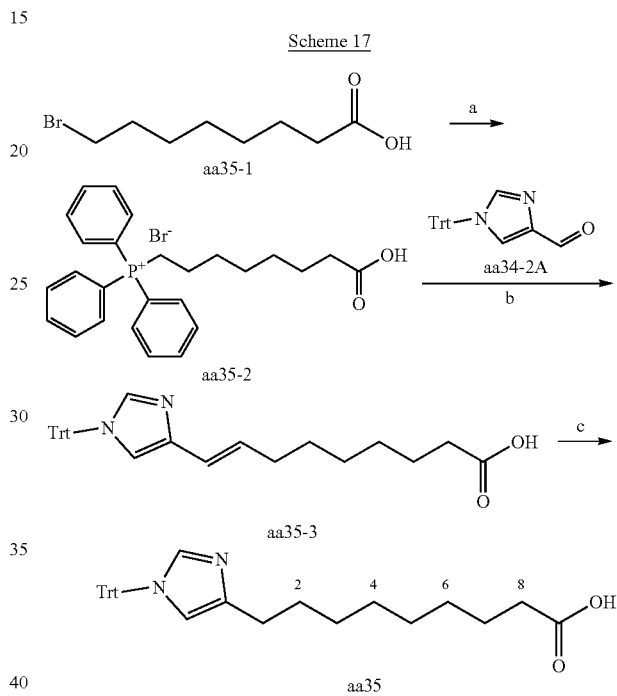

Reagents and conditions: (a) PPh₃ (1.2 eq.), toluene, 110° C., 20 h; b) aa35-2A (1.5 eq.), tBuOK (3.0 eq.), THF, 0-25° C., 20 h; c) H₂, Pd/C, MeOH, 25° C., 10 h;

Step 1: Synthesis of (7-carboxyheptyl)triphenylphosphonium bromide (aa35-2)

To a solution of aa35-1 (15 g, 71.74 mmol, 1 eq.) in toluene (150 mL) was added PPh₃ (20.70 g, 78.92 mmol, 1.1 eq.). The mixture was stirred at 110° C. under N₂ for 20 h. After completion, the reaction mixture was cooled to 0° C., then filtered and washed with toluene (10 mL*3), the filter cake was collected and dried under reduced pressure. The residue was triturated with THF (200 mL). Then the mixture was filtered, and the filter cake was dried to give the product aa35-2 (20 g, 40.31 mmol, 56.18% yield, 95% purity) as a white solid.

LCMS: (ESI): Rt=2.175 min, mass calcd. for $C_{26}H_{30}O_2P^+$ [M+H]⁺ 405.20, found 405.70; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

Step 2: Synthesis of (E)-9-(1-trityl-1H-imidazol-4-yl)non-8-enoic acid (aa35-3)

To a solution of aa35-2 (10.45 g, 22.17 mmol, 1.5 eq.) in THF (150 mL) was added t-BuOK (4.97 g, 44.34 mmol, 3.0 eq.) at 0° C. Then the mixture was stirred at 0° C. for 30 min. A solution of aa35-2A (5 g, 14.78 mmol, 1 eq.) in THF (50 mL) was added. Then the mixture was stirred at 20° C. for 12 h. After completion, the reaction mixture was quenched by addition H2O (100 mL) at 0° C., and then extracted with EtOAc (150 mL*2). The combined organic layers were washed with Sat. NaCl 100 mL (50 mL*2), dried over anhydrous sodium sulfate, filtered, and concentrated under reduced pressure to give a residue. The residue was purified by flash silica gel chromatography (ISCO®; 80 g Special Flash® Silica Flash Column, Eluent of 0-20% Ethyl acetate/ Petroleum ether gradient @ 60 mL/min) to give the product aa35-3 (1.4 g, crude) as a light-yellow oil.

LCMS: (ESI): Rt=3.310 min, mass calcd. for $C_{31}H_{33}N_2O_2$ $[M+H]^+$ 465.25, found 465.20 $[M+H]^+$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

Step 3: Synthesis of 9-(1-tritylimidazol-4-yl)nonanoic acid (aa35)

To a solution of aa35-3 (1.4 g, 3.01 mmol, 1 eq.) in MeOH (40 mL) was added Pd/C (0.2 g, 10% purity). The mixture was stirred at 25° C. under $H_2$ for 3 hr. After completion, the mixture was filtered and concentrated under reduced pressure to give a residue. The crude product was purified by prep-HPLC (column: C18 spherical 20-35 μm, 100A, 12 g; mobile phase: [Water-ACN]; B %: 0%-90%, 15 min) to give the product aa35 (0.12 g, 244.31 μmol, 8.11% yield, 95% purity) was obtained as a white solid.

LCMS: (ESI): Rt=3.257 min, mass calcd. for $C_{31}H_{35}N_2O_2$ $[M+H]^+$ 467.26, found 467.20 $[M+H]^+$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

2.17 the Synthesis of Unnatural Amino Acid (Aa36)

Scheme 18 outlines the synthesis of unnatural amino acid (aa36):

Scheme 18

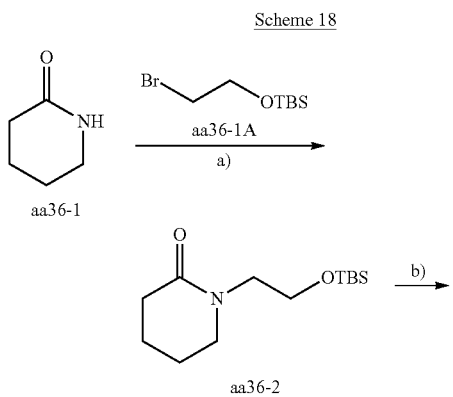

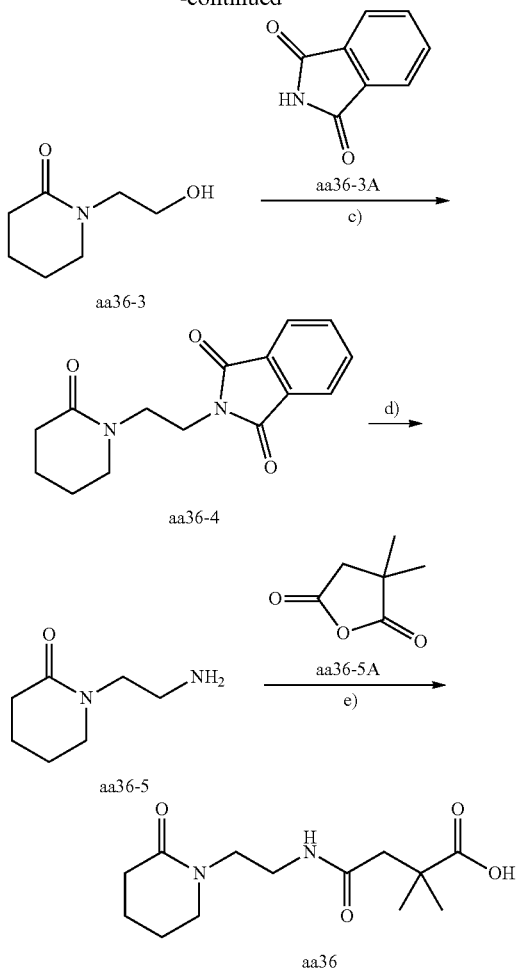

Reagents and conditions: (a) aa36-1A (1 eq.), NaH (1.1 eq.), THF, 0-70° C., 12.5 h; b) HCl/MeOH (2 mL, 30%, v/v), MeOH (3 mL), 0° C., 0.5 h; c) aa36-3A (1.5 eq,), PPh3 (1.5 eq.), DIAD (1.5 eq.), THF (10 mL), 0-20° C., 2 h; d) $NH_2$—$NH_2 \cdot H_2O$ (10 eq.), MeOH, 45° C., 2 h; e) aa36-5A (1.1 eq.), DMF (2 mL), 20° C., 12 h

Step 1: Synthesis of 1-(2-((tert-butyldimethylsilyl)oxy)ethyl)piperidin-2-one (aa36-2)

To a solution of aa36-1 (6 g, 60.53 mmol, 1 eq) in THF (300 mL) was added NaH (2.66 g, 66.58 mmol, 60% purity, 1.1 eq) in portions at 0° C. The mixture was stirred at 20° C. for 0.5 h and aa36-1A (14.48 g, 60.53 mmol, 1 eq) was added. The reaction mixture was heated to 70° C. for 12 h. LCMS showed the desired product was observed. The mixture was cooled to r.t., quenched by water (150 mL) and extracted with EtOAc (150 mL×2). The combined organic layers were dried over anhydrous $Na_2SO_4$, filtered and concentrated in vacuo. The residue was purified by column chromatography ($SiO_2$, Petroleum ether/Ethyl acetate=1/1). Compound aa36-2 (2.7 g, 10.49 mmol, 17.33% yield) was obtained as a colorless oil.

LCMS (ESI): RT=0.974 min, mass calcd. for $C_{13}H_{27}NO_2SiH$ 258.18, found 258.2 $[M+H]^+$; Reverse phase LCMS was carried out using a Chromolith Flash Agilent Pursult 5 C18 20*2.0 mm, with a flow rate of 1.5 mL/min, eluting with a gradient of 5%-95% (solvent B) over 0.7 minutes and holding at 95% for 0.4 minutes.

$^1$H NMR (400 MHz, DMSO-d6) 3.64 (t, J=6.0 Hz, 2H), 3.32-3.29 (m, 4H), 2.16 (t, J=6.0 Hz, 2H), 1.74-1.57 (m, 4H), 0.83 (s, 9H), 0.00 (s, 6H) ppm.

Step 2: Synthesis of 1-(2-hydroxyethyl)piperidin-2-one (aa36-3)

To a solution of aa36-2 (2.7 g, 10.49 mmol, 1 eq) in MeOH (12 mL) was added a solution of HCl/MeOH (v/v=30%, 8 mL) at 0° C. The solution was stirred at 0° C. for 0.5 h. After completion, the solution was concentrated in vacuo. The residue was purified by column chromatography (SiO$_2$, DCM/MeOH=10/1). The crude product aa36-3 (1.4 g, 9.73 mmol, 92.76% yield, 99.5% purity) was obtained as a yellow solid which was used into the next step without further purification.

$^1$H NMR (400 MHz, DMSO-d6) 4.13-4.11 (m, 1H), 3.52-3.44 (m, 2H), 3.34-3.29 (m, 4H), 2.20 (t, J=6.0 Hz, 2H), 1.75-1.61 (m, 4H) ppm.

LCMS (ESI): RT=0.448-0.574 min, mass calcd. for C$_7$H$_{13}$NO$_2$H 144.09, found 144.2 [M+H]$^+$; Reverse phase LCMS was carried out using a Chromolith Flash Agilent Pursult 5 C18 20*2.0 mm, with a flow rate of 1.5 mL/min, eluting with a gradient of 5%-95% (solvent B) over 0.7 minutes and holding at 95% for 0.4 minutes.

Step 3: Synthesis of 2-(2-(2-oxopiperidin-1-yl)ethyl)isoindoline-1,3-dione (aa36-4)

To a solution of aa36-3 (1.5 g, 10.48 mmol, 1 eq) and aa36-3A (1.85 g, 12.57 mmol, 1.2 eq) in THF (40 mL) was added PPh$_3$ (4.12 g, 15.71 mmol, 1.5 eq) and DIAD (3.18 g, 15.71 mmol, 3.06 mL, 1.5 eq) at 0° C. The resulting mixture was stirred at 20° C. for 2 h. LCMS showed the desired product was observed. The mixture was filtered, and the filtrate was concentrated in vacuo. The residue was purified by column chromatography (SiO$_2$, Petroleum ether/Ethyl acetate=1/1). Compound aa36-4 (0.15 g, 550.87 μmol, 5.26% yield) was obtained as a white solid.

LCMS (ESI): RT=0.764 min, mass calcd. for C$_{15}$H$_{16}$N$_2$O$_3$H 273.12, found 273.1 [M+H]$^+$; Reverse phase LCMS was carried out using a Chromolith Flash Agilent Pursult 5 C18 20*2.0 mm, with a flow rate of 1.5 mL/min, eluting with a gradient of 5%-95% (solvent B) over 0.7 minutes and holding at 95% for 0.4 minutes.

$^1$H NMR (400 MHz, DMSO-d6) 7.83-7.65 (m, 4H), 3.68-3.58 (m, 2H), 3.45-3.39 (m, 2H), 3.21 (t, J=6.0 Hz, 2H), 1.89 (t, J=6.4 Hz, 2H), 1.64-1.56 (m, 2H), 1.55-1.47 (m, 2H) ppm.

Step 4: Synthesis of 1-(2-aminoethyl)piperidin-2-one (aa36-5)

To a solution of aa36-4 (0.15 g, 550.87 μmol, 1 eq) in MeOH (10 mL) was added NH$_2$NH$_2$—H$_2$O (275.76 mg, 5.51 mmol, 267.73 μL, 10 eq). The solution was stirred at 45° C. for 2 h. After completion, the solution was cooled to r.t. and concentrated in vacuo. The crude product aa36-5 (0.07 g, crude) was obtained as a colorless oil, which was used into the next step without further purification.

$^1$H NMR (400 MHz, DMSO-d6) 3.27-3.22 (m, 6H), 2.62 (t, J=6.8 Hz, 2H), 2.17 (t, J=6.0 Hz, 2H), 1.76-1.58 (m, 4H) ppm.

Step 5: Synthesis of 2,2-dimethyl-4-oxo-4-((2-(2-oxopiperidin-1-yl)ethyl)amino)butanoic acid (aa36)

To a solution of aa36-5 (0.07 g, 492.27 μmol, 1 eq) in DMF (2 mL) was added aa36-5A (69.38 mg, 541.50 μmol, 60.86 μL, 1.1 eq). The solution was stirred at 20° C. for 12 h. LCMS showed the desired product was observed. The solution was concentrated in vacuo. The residue was purified by prep-HPLC (FA condition; column: Phenomenex Synergi C18 150*30 mm*4 um; mobile phase: [water (0.225% FA)-ACN]; B %: 15%-25%, 11 min). Compound aa36 (20 mg, 73.99 μmol, 15.03% yield) was obtained as a white solid.

LCMS (ESI): RT=0.19 min, mass calcd. for C$_{13}$H$_{22}$N$_2$O$_4$H 271.16, found 271.1 [M+H]$^+$; Reverse phase LCMS was carried out using a Chromolith Flash Agilent Pursult 5 C18 20*2.0 mm, with a flow rate of 1.5 mL/min, eluting with a gradient of 5%-95% (solvent B) over 0.7 minutes and holding at 95% for 0.4 minutes.

$^1$H NMR (400 MHz, METHANOL-d4) 3.51-3.44 (m, 2H), 3.43-3.35 (m, 4H), 2.47 (s, 2H), 2.35 (t, J=6.0 Hz, 2H), 1.91-1.76 (m, 4H), 1.25 (s, 6H) ppm.

2.18 the Synthesis of Unnatural Amino Acid (Aa37)

Scheme 19 outlines the synthesis of unnatural amino acid (aa37):

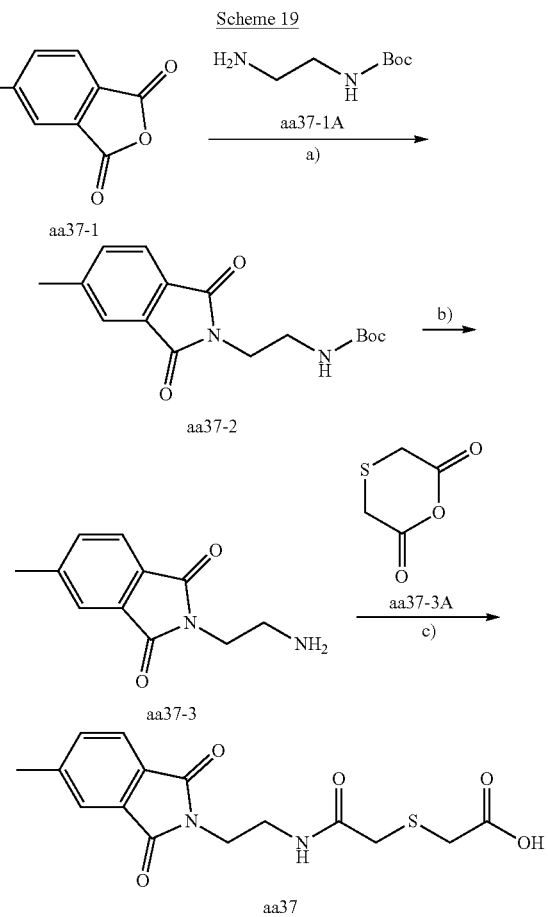

Scheme 19

Reagents and conditions: (a) aa37-1A (1.1 eq.), toluene, 120° C., 12 h, 46% yield; b) HCl/MeOH (4M), 25° C., 12 h; c) aa37-3A (1.5 eq,), DIPEA (2.0 eq.), DMF (10 mL), 25° C., 12 h, 43% yield.

Step 1: Synthesis of tert-butyl N-[2-(5-methyl-1,3-dioxo-isoindolin-2-yl)ethyl]carbamate (aa37-2)

To a solution of aa37-1 (500 mg, 3.08 mmol, 1 eq) in toluene (10 mL) was added aa37-1A (543.46 mg, 3.39 mmol, 532.80 µL, 1.1 eq). The mixture was stirred at 120° C. for 12 hr. After completion, the reaction mixture was concentrated under vacuum to give the crude product, which was triturated with MTBE/PE (1:1) at 25° C. for 1h. Compound aa37-2 (460 mg, 1.44 mmol, 46.56% yield, 95% purity) was obtained as a yellow solid.

LCMS (ESI): RT=0.898 min, m/z calcd. for $C_{16}H_{21}N_2O_4$ 305.14 $[M+H]^+$, $C_{16}H_{21}N_2O_4Na$ 327.14 $[M+Na]^+$, found 327.2 $[M+Na]^+$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

Step 2: Synthesis of 2-(2-aminoethyl)-5-methyl-isoindoline-1,3-dione (aa37-3)

To a solution of aa37-2 (460 mg, 1.51 mmol, 1 eq) was added HCl/MeOH (4 M, 377.87 µL, 1 eq). The mixture was stirred at 25° C. for 12 hr. After completion, the reaction was concentrated in vacuum to give the crude product aa37-3 (300 mg, crude, HCl salt) was obtained as a white solid.

LCMS (ESI): RT=0.638 min, m/z calcd. for $C_{11}H_{13}N_2O_2$ 205.09 $[M+H]^+$, found 205.0 $[M+H]^+$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

$^1$H NMR (400 MHz, CHLOROFORM-d) δ =7.99 (br s, 2H), 7.26-7.21 (m, 1H), 3.56 (br s, 2H), 2.77 (br s, 4H), 2.08 (s, 3H) ppm.

Step 3: Synthesis of 2-[2-[2-(5-methyl-1,3-dioxo-isoindolin-2-yl)ethylamino]-2-oxo-ethyl]sulfanyl-lacetic acid (aa37)

To a solution of aa37-3 (250 mg, 1.22 mmol, 1 eq) and aa37-3A (194.11 mg, 1.47 mmol, 1.2 eq) in DMF (4 mL) was added DIPEA (316.42 mg, 2.45 mmol, 426.45 µL, 2 eq). The mixture was stirred at 25° C. for 12 hr. The reaction mixture was partitioned between EtOAc (50 mL) and water (60 mL). The water layer was acidified to pH=4 by 1 N HCl solution. The organic phase was separated, washed with brine (30 mL×3), and dried over anhydrous $Na_2SO_4$. The resulting solution was concentrated under reduced pressure. The residue was purified by flash silica gel chromatography (ISCO®; 12 g SepaFlash® Silica Flash Column, Eluent of 0-30% Ethyl acetate/Petroleum ether gradient @ 35 mL/min). Compound aa37 (200 mg, 535.14 µmol, 43.72% yield, 90% purity) was obtained as a white solid.

LCMS (ESI): RT=0.757 min, m/z calcd. for $C_{15}H_{16}N_2O_5SNa$ 359.08 $[M+Na]^+$, found 358.9 $[M+Na]^+$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

$^1$H NMR (400 MHz, CHLOROFORM-d) δ =7.69-7.60 (m, 1H), 7.55 (s, 1H), 7.43 (br d, J=7.3 Hz, 1H), 3.82-3.70 (m, 2H), 3.52-3.41 (m, 2H), 2.86 (s, 2H), 2.76 (s, 2H), 2.38 (s, 3H) ppm.

Example 3. Synthesis of GLP1 Peptidomimetics

Figure 13:
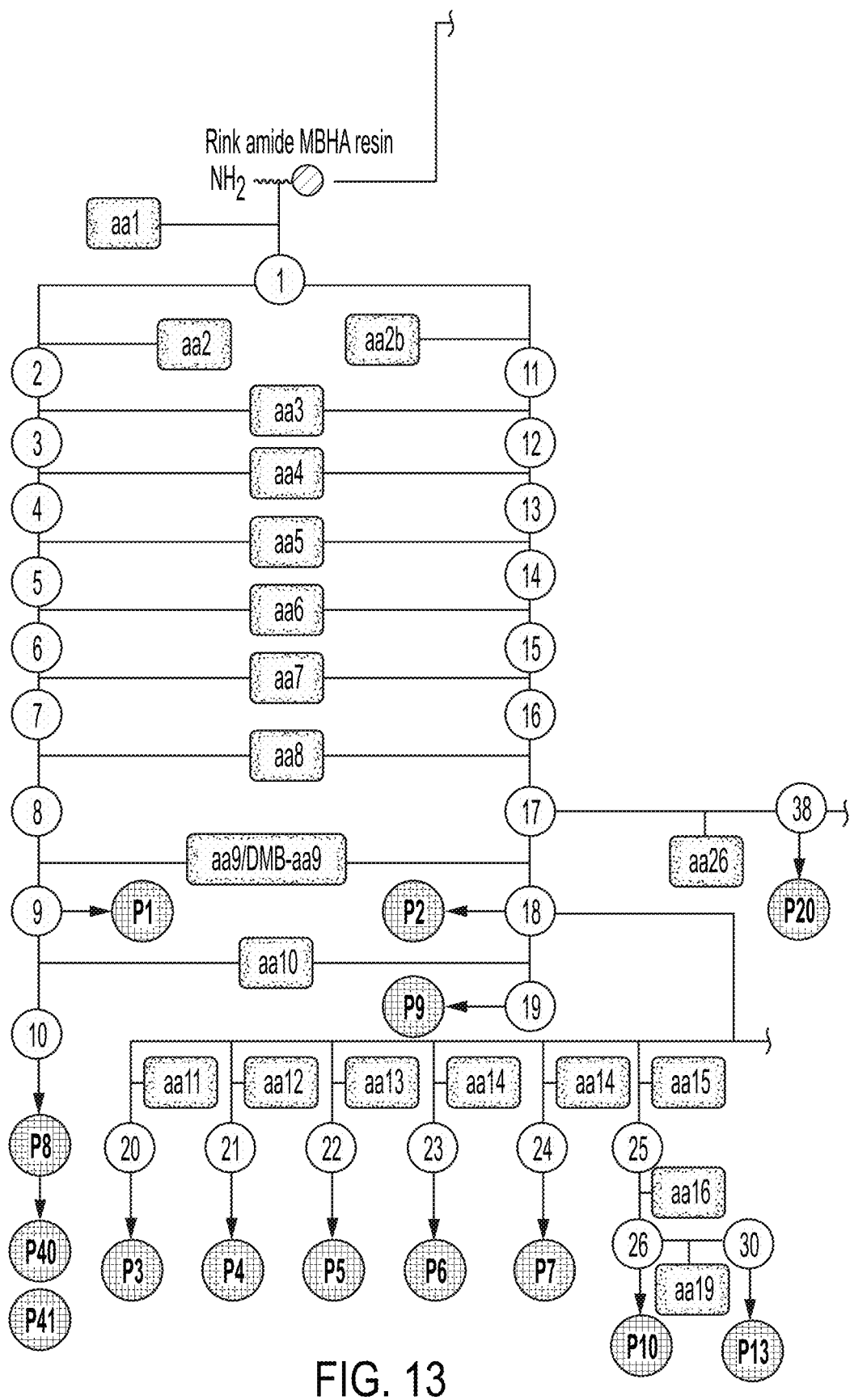
FIG. 13 shows a general synthetic scheme for preparing GLP1 peptidomimetics according to the disclosure.
Figure 13:
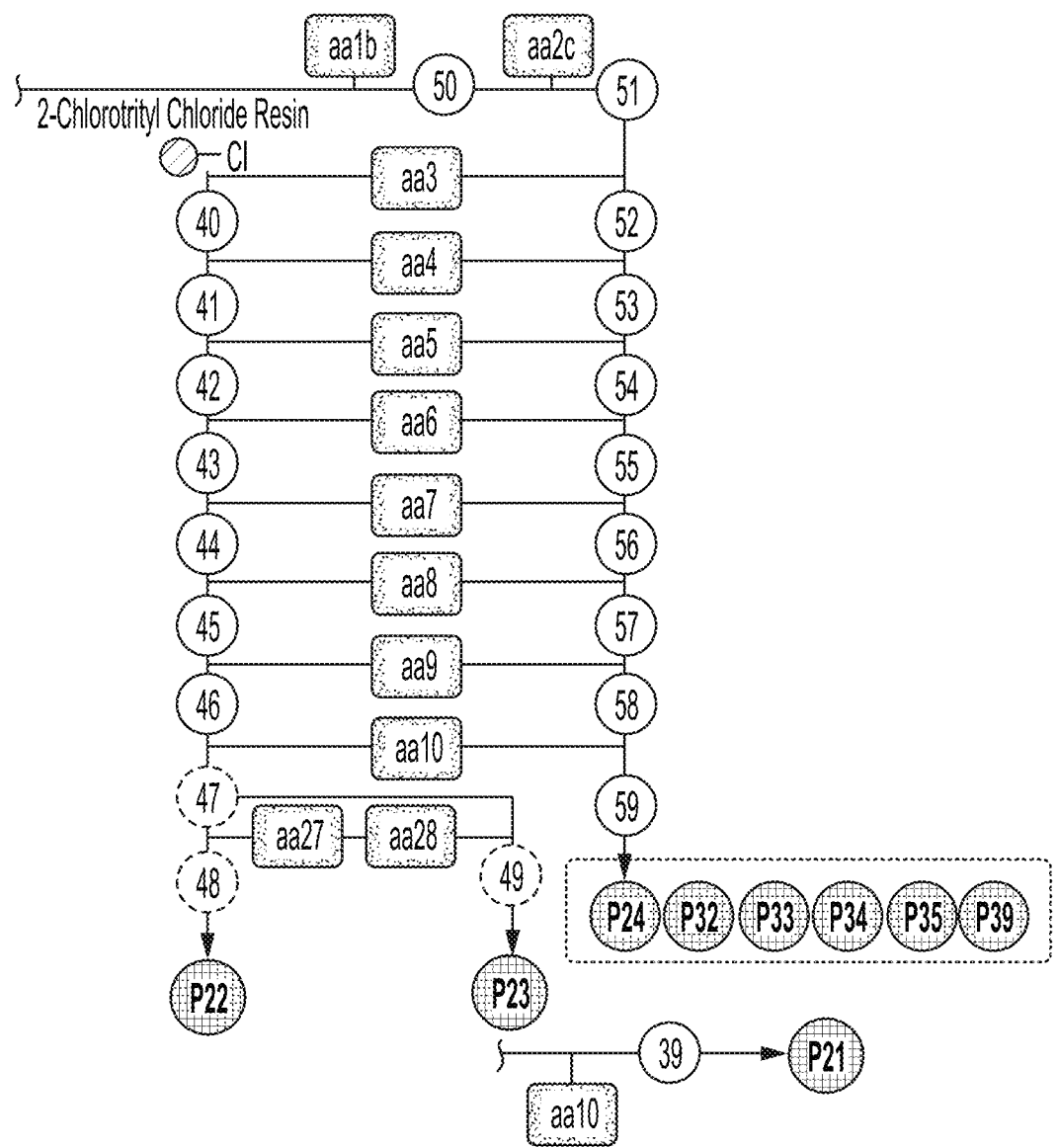
Figure 13:
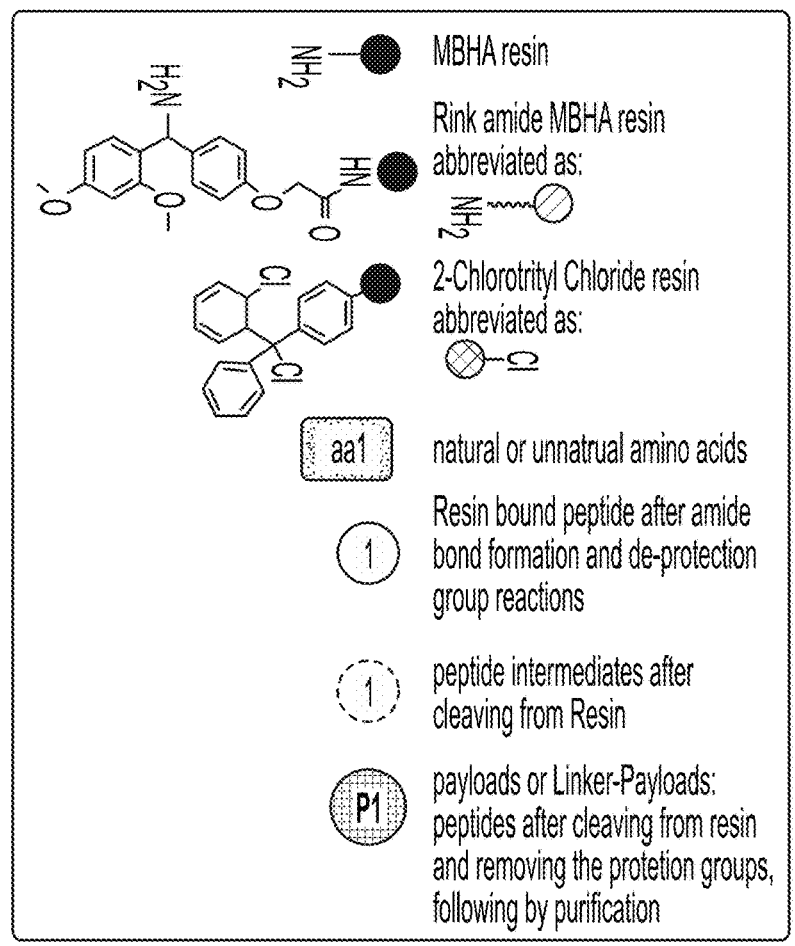
Figure 13:
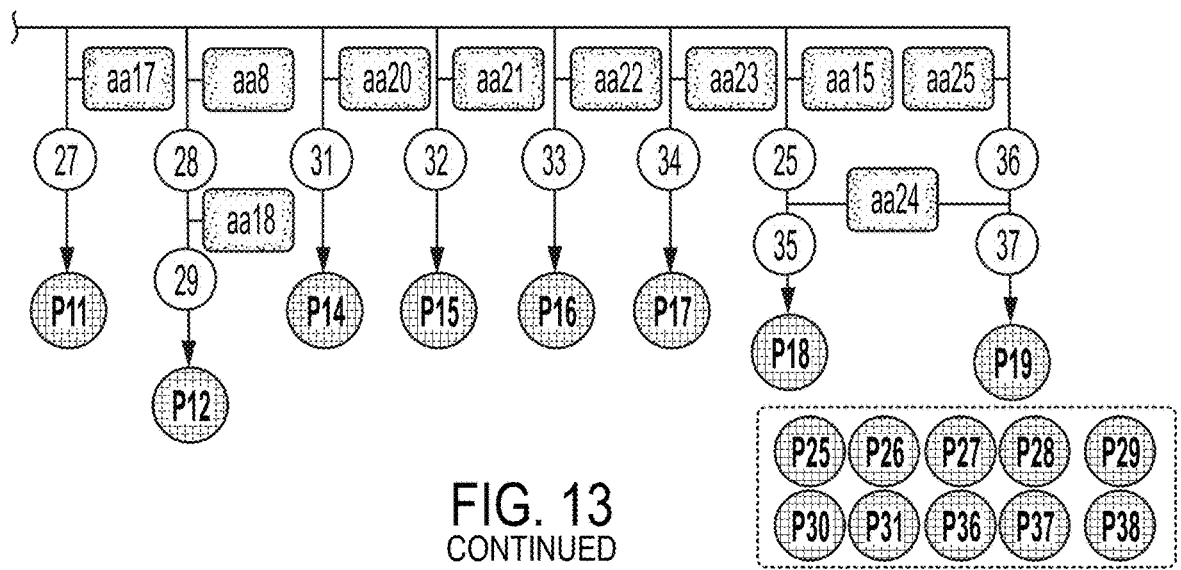

The general synthetic scheme for making GLP1 peptidomimetic payloads according to the present disclosure is shown as FIG. 13. Table 2, shown below, depicts the structures of Rink amide MBHA resin bound peptides and intermediates 1-59.

TABLE 2

| Compound No. | Structure | MF [M − resin − $C_{17}H_{17}NO_4$ + H] | MW (Cal.) |
|---|---|---|---|
| 1 | 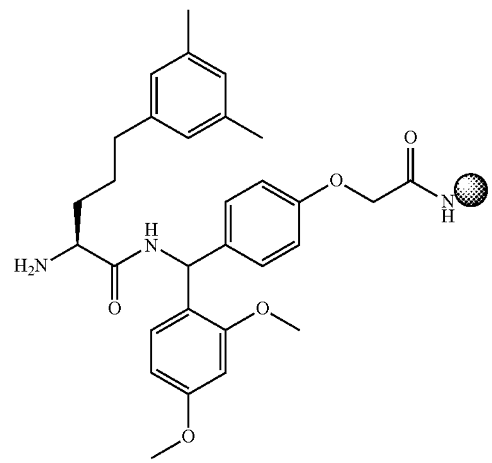 [SMILES: COc1ccc(C(NC(=O)[C@@H](N)CCCc2cc(C)cc(C)c2)c2ccc(OCC(N)=O)cc2)c(OC)c1] | $C_{13}H_{20}N_2O$ | 220.31 |
| 2 | 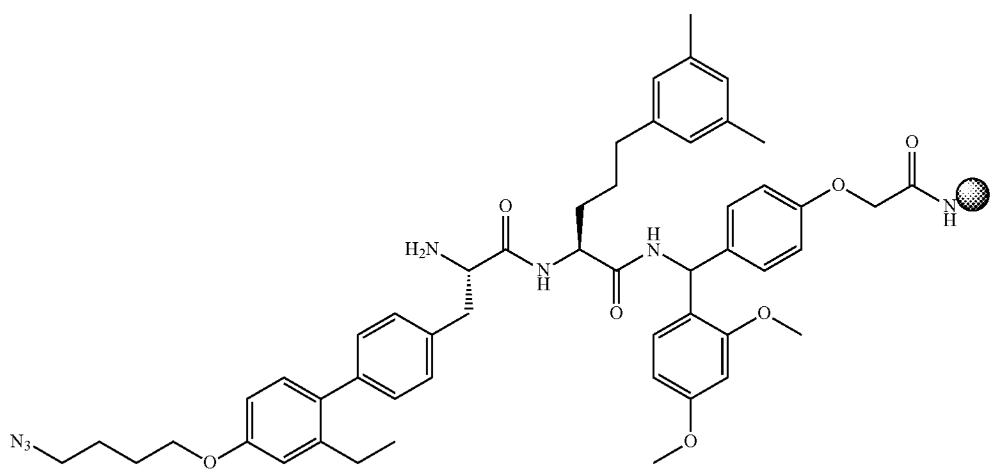 [SMILES: CCc1cc(OCCCCN=[N+]=[N-])ccc1-c1ccc(C[C@H](N)C(=O)N[C@@H](CCCc2cc(C)cc(C)c2)C(=O)NC(c2ccc(OCC(N)=O)cc2)c2ccc(OC)cc2OC)cc1] | $C_{34}H_{44}N_6O_3$ | 584.75 |

TABLE 2-continued

| Compound No. | Structure | MF [M − resin − $C_{17}H_{17}NO_4$ + H] | MW (Cal.) |
|---|---|---|---|
| 3 | 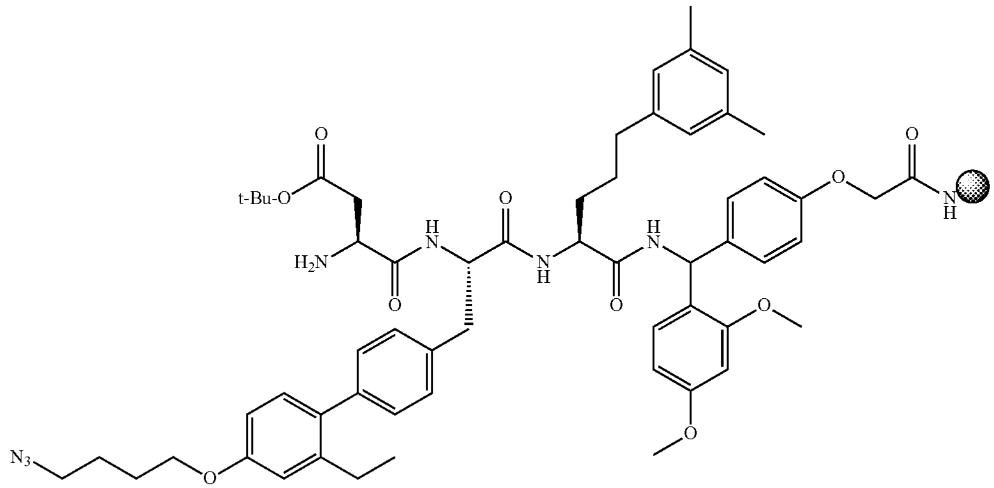 | $C_{42}H_{57}N_7O_6$ | 755.95 |
| 4 | 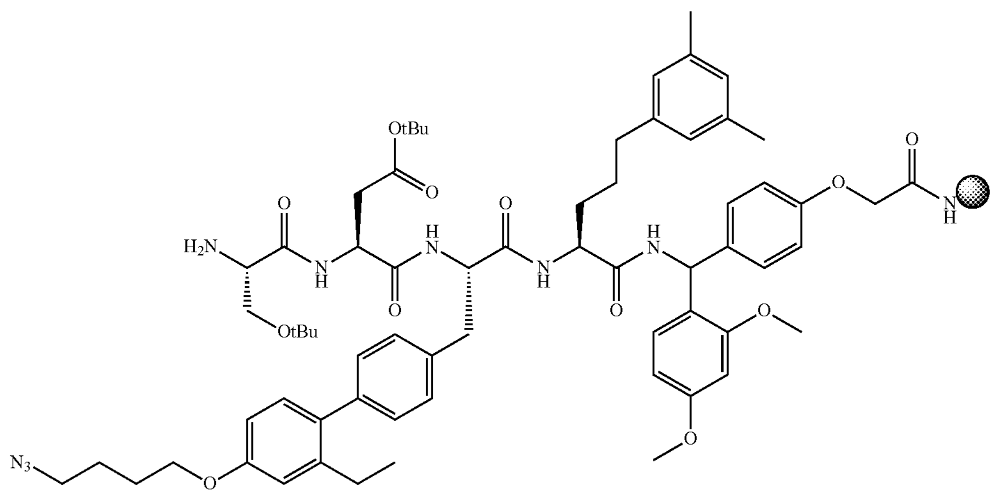 [SMILES: CCc1cc(OCCCCN=[N+]=[N-])ccc1-c1ccc(C[C@H](NC(=O)[C@H](CC(=O)OC(C)(C)C)NC(=O)[C@@H](N)COC(C)(C)C)C(=O)N[C@@H](CCCc2cc(C)cc(C)c2)C(=O)NC(c2ccc(OCC(N)=O)cc2)c2ccc(OC)cc2OC)cc1] | $C_{49}H_{70}N_8O_8$ | 899.13 |

TABLE 2-continued

| Compound No. | Structure | MF [M – resin – $C_{17}H_{17}NO_4$ + H] | MW (Cal.) |
|---|---|---|---|
| 5 | 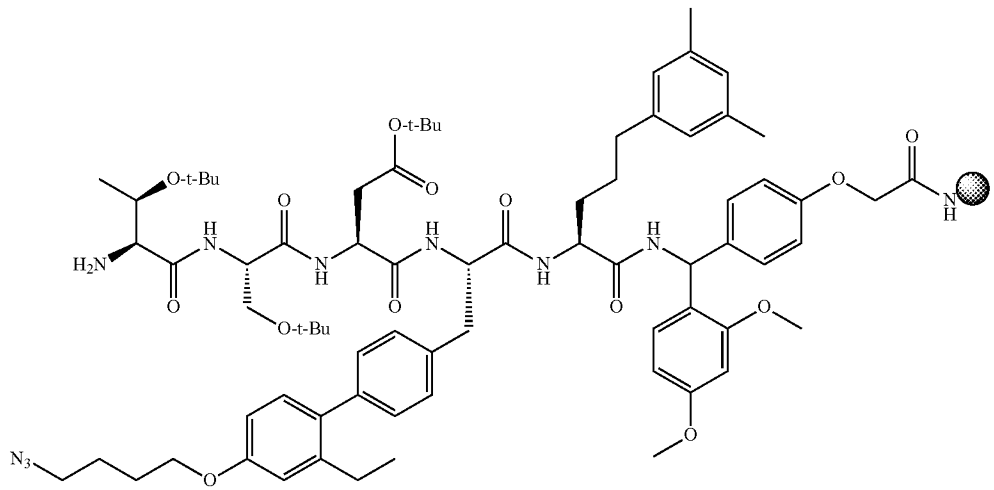 | $C_{57}H_{85}N_9O_{10}$ | 1056.34 |
| 6 | 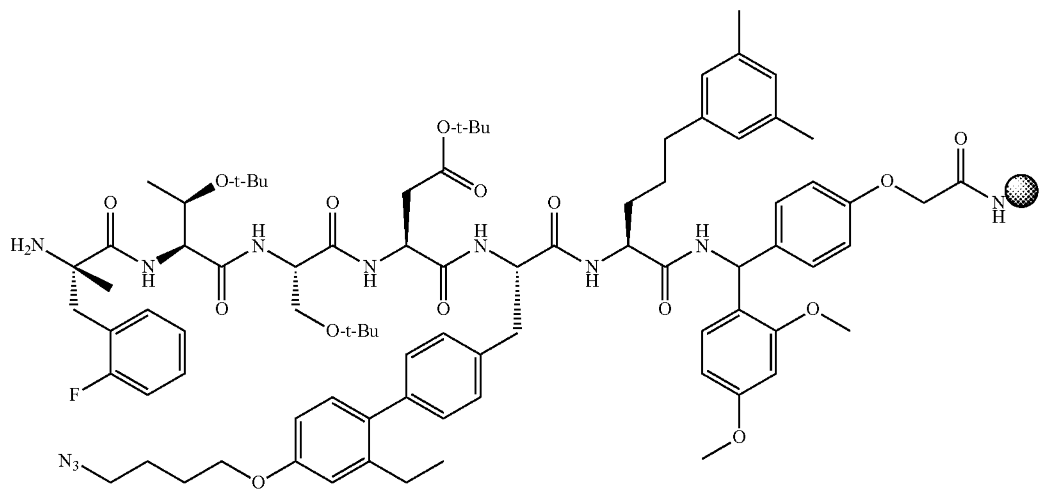 | $C_{67}H_{95}FN_{10}O_{11}$ | 1235.53 |

TABLE 2-continued

| Compound No. | Structure | MF [M − resin − $C_{17}H_{17}NO_4$ + H] | MW (Cal.) |
|---|---|---|---|
| 7 | 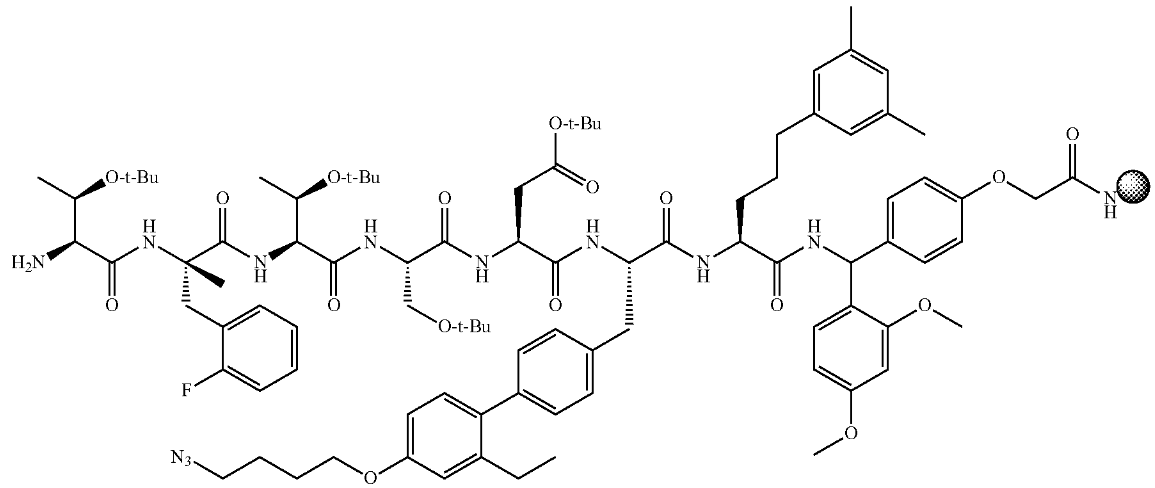 | $C_{75}H_{110}FN_{11}O_{13}$ | 1392.74 |
| 8 | 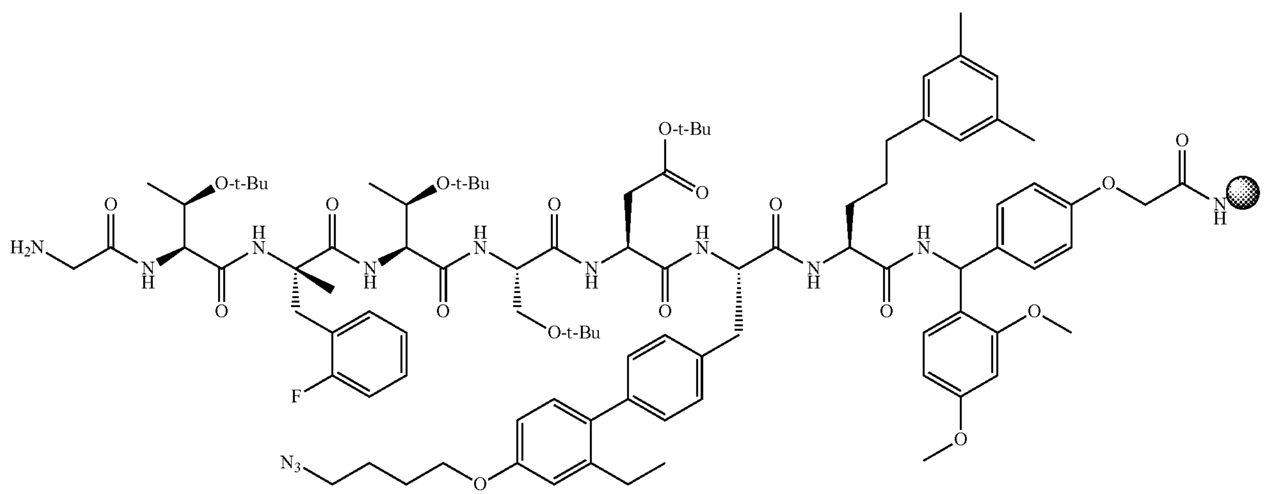 | $C_{77}H_{113}FN_{12}O_{14}$ | 1449.79 |

TABLE 2-continued

| Compound No. | Structure | MF [M − resin − C$_{17}$H$_{17}$NO$_4$ + H] | MW (Cal.) |
|---|---|---|---|
| 9 | 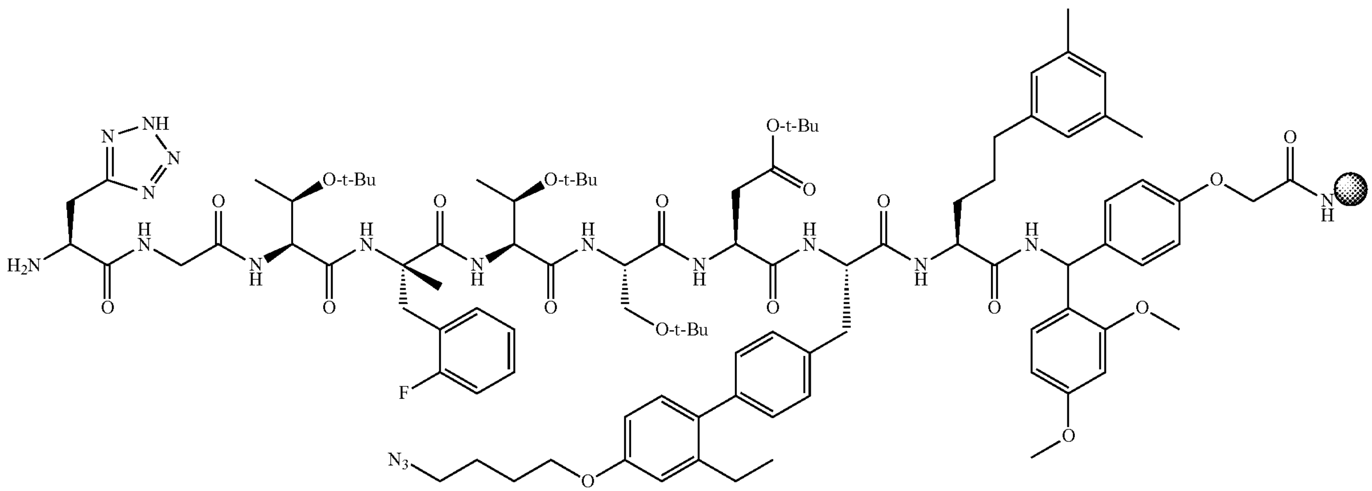 | C$_{81}$H$_{118}$FN$_{17}$O$_{15}$ | 1588.91 |
| 10 | 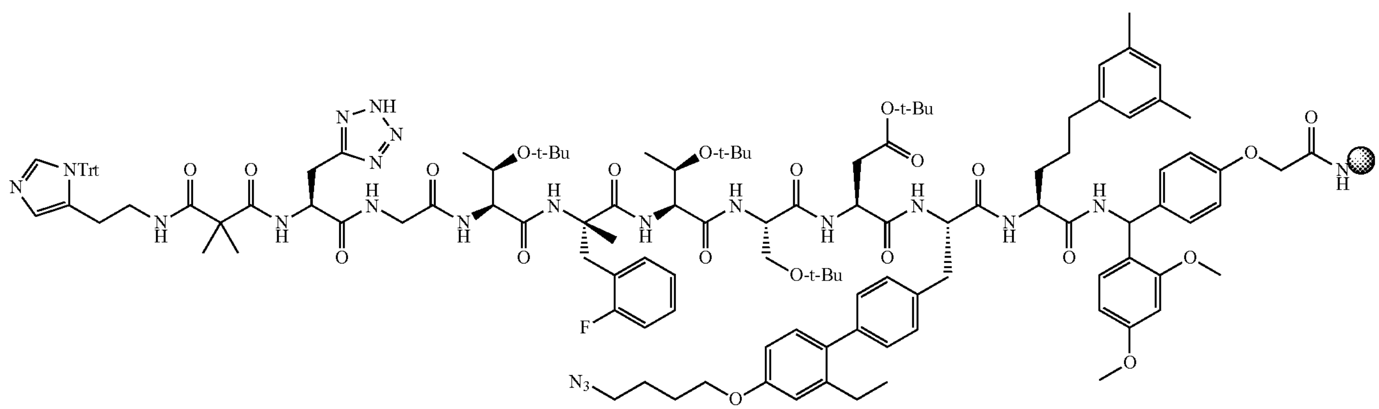 | C$_{110}$H$_{145}$FN$_{20}$O$_{17}$ | 2038.45 |

TABLE 2-continued

| Compound No. | Structure | MF [M − resin − $C_{17}H_{17}NO_4$ + H] | MW (Cal.) |
|---|---|---|---|
| 11 | 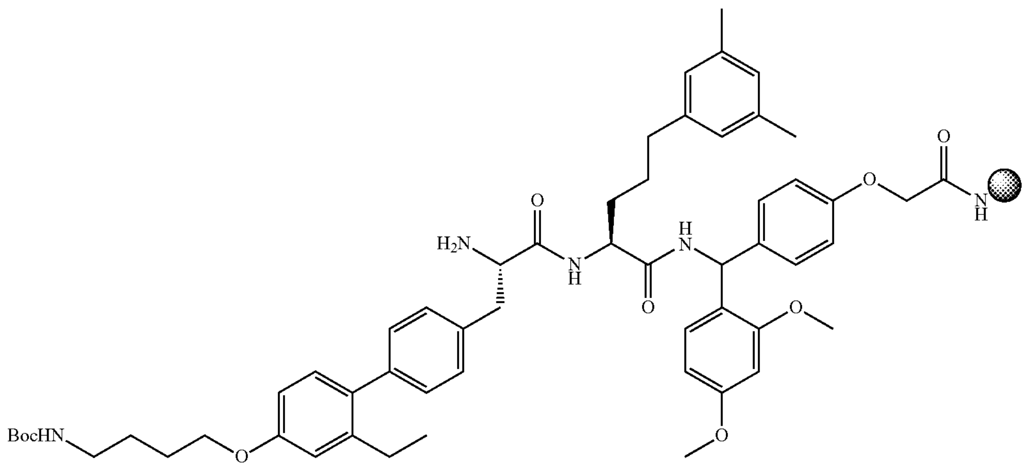 [SMILES: CCc1cc(OCCCCNC(=O)OC(C)(C)C)ccc1-c1ccc(C[C@H](N)C(=O)N[C@@H](CCCc2cc(C)cc(C)c2)C(=O)NC(c2ccc(OCC(N)=O)cc2)c2ccc(OC)cc2OC)cc1] | $C_{39}H_{54}N_4O_5$ | 658.87 |
| 12 | 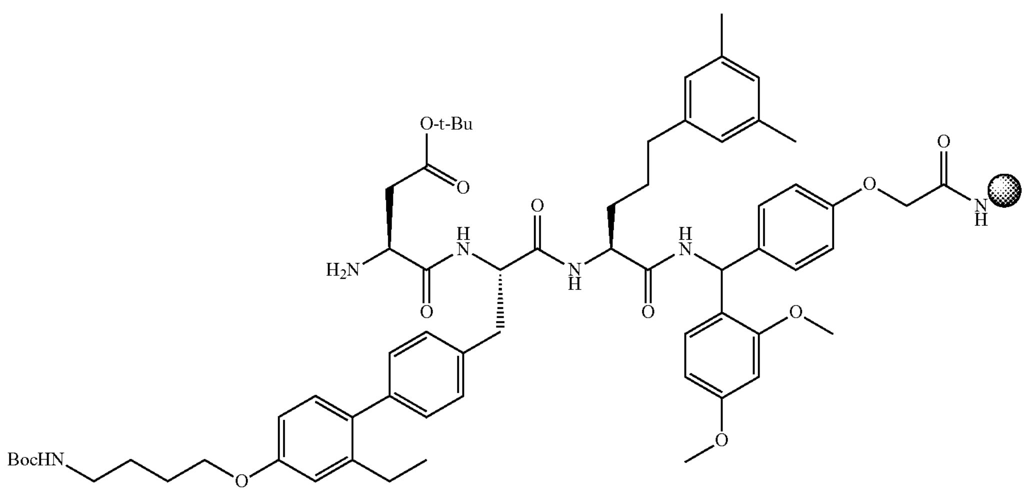 | $C_{47}H_{67}N_5O_8$ | 830.06 |

TABLE 2-continued
| Compound No. | Structure | MF [M − resin − $C_{17}H_{17}NO_4$ + H] | MW (Cal.) |
|---|---|---|---|
| 13 | 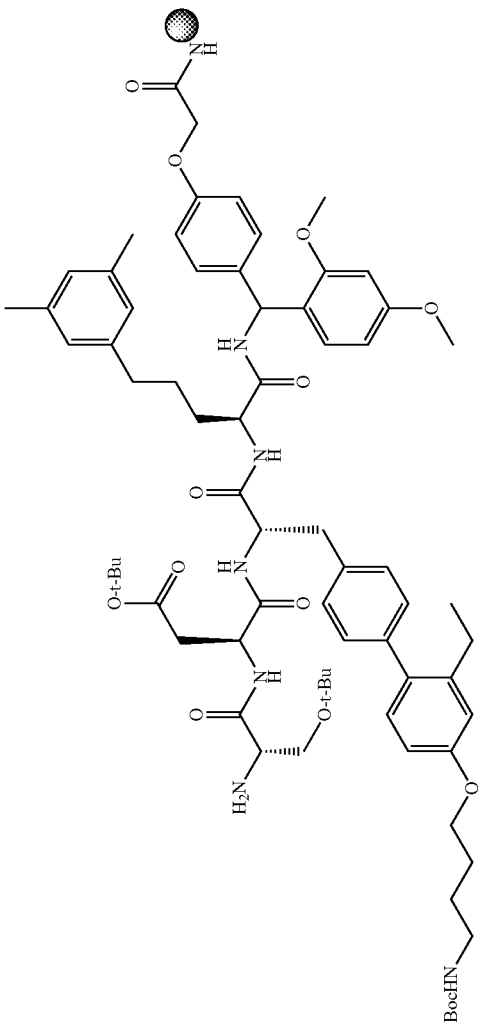 | $C_{43}H_{80}N_6O_{10}$ | 973.24 |
| 14 | 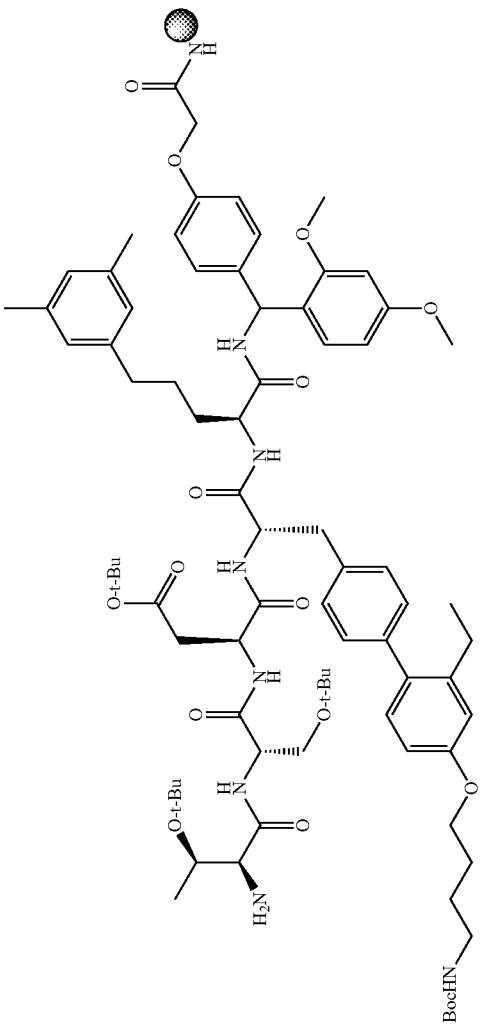 | $C_{62}H_{95}N_7O_{12}$ | 1130.45 |

TABLE 2-continued
| Compound No. | Structure | MF [M – resin – $C_{17}H_{17}NO_4$ + H] | MW (Cal.) |
|---|---|---|---|
| 15 | 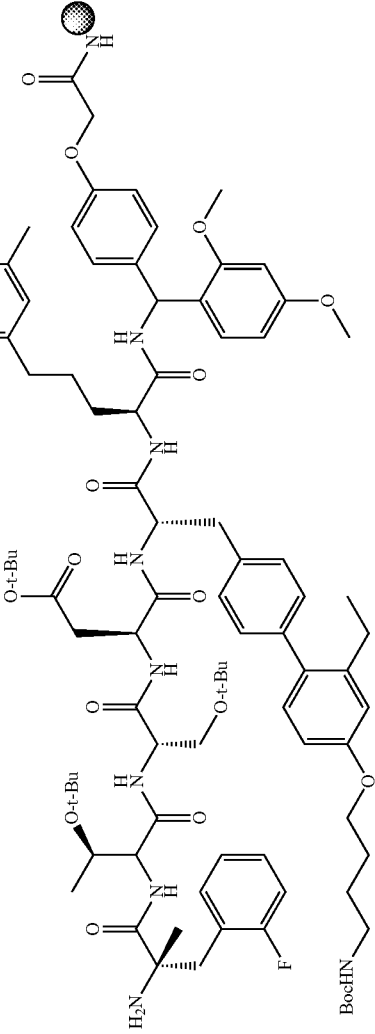 | $C_{72}H_{105}FN_8O_{13}$ | 1309.64 |
| 16 | 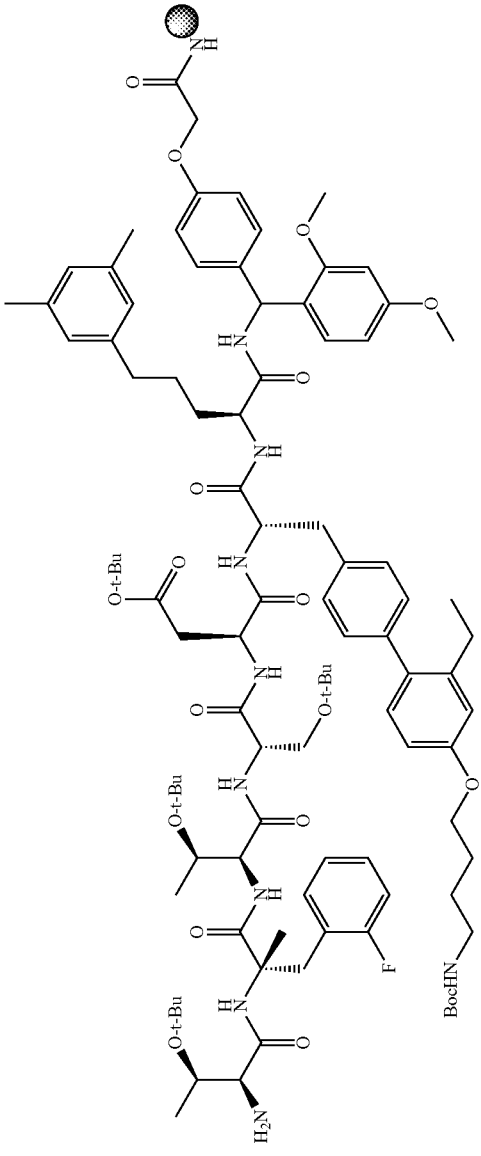 | $C_{80}H_{120}FN_9O_{15}$ | 1466.85 |

TABLE 2-continued
| Compound No. | Structure | MF [M − resin − $C_{17}H_{17}NO_4$ + H] | MW (Cal.) |
|---|---|---|---|
| 17 | 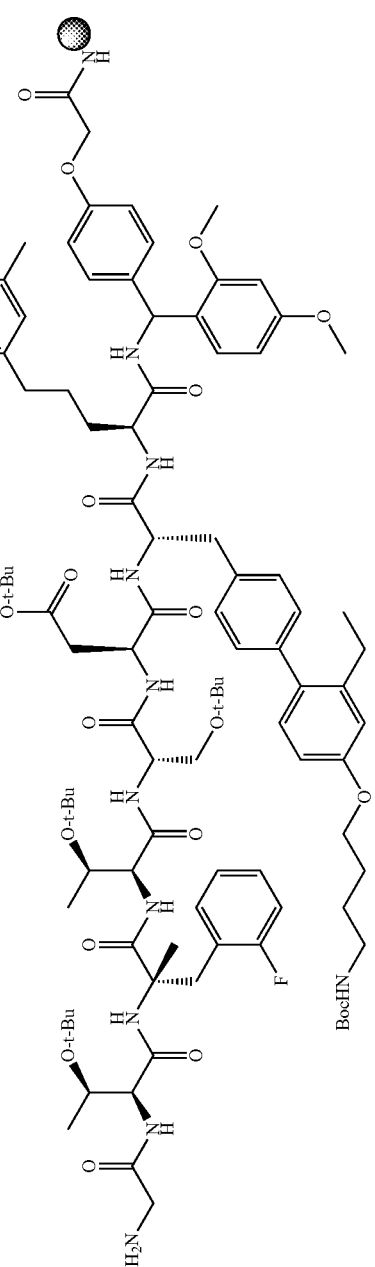 | $C_{82}H_{123}FN_{10}O_{16}$ | 1523.91 |
| 18 | 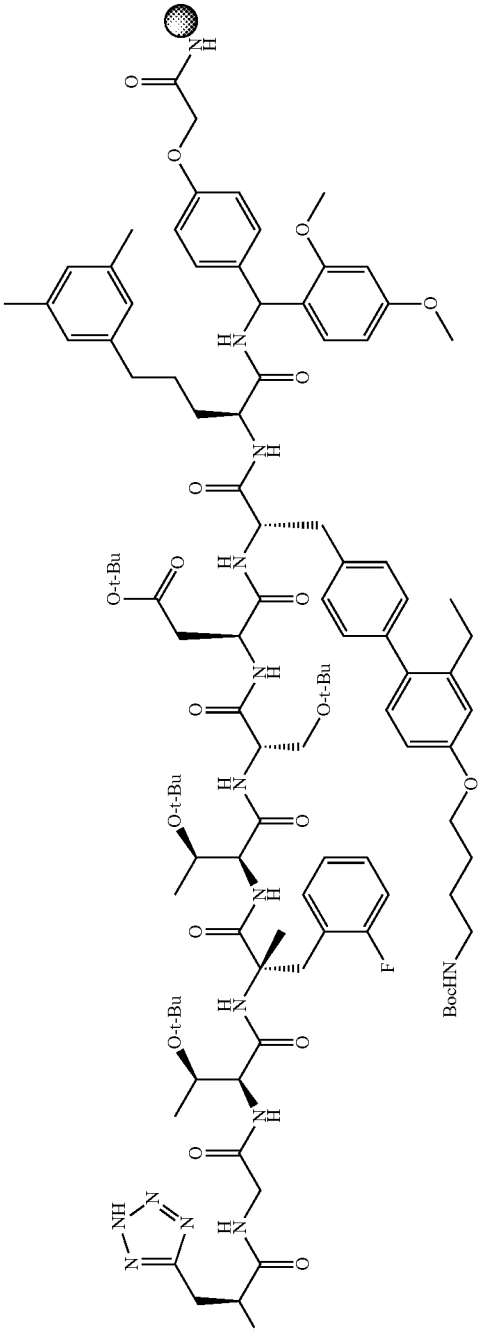 | $C_{86}H_{128}FN_{15}O_{17}$ | 1663.02 |

TABLE 2-continued

| Compound No. | Structure | MF [M − resin − $C_{17}H_{17}NO_4$ + H] | MW (Cal.) |
|---|---|---|---|
| 19 | 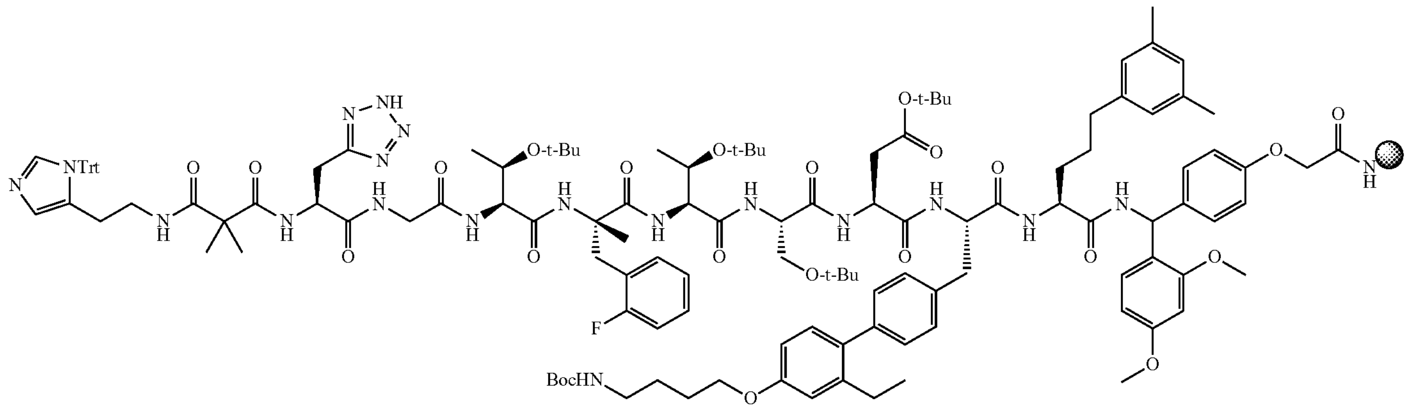 | $C_{115}H_{155}FN_{18}O_{19}$ | 2112.56 |
| 20 | 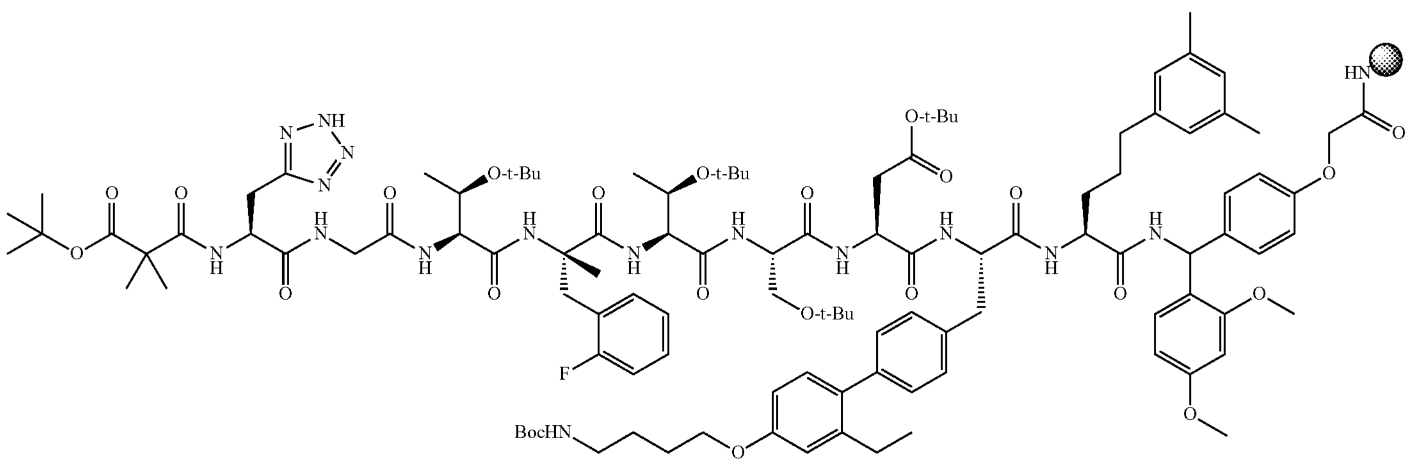 | $C_{95}H_{142}FN_{15}O_{20}$ | 1833.23 |

TABLE 2-continued

| Compound No. | Structure | MF [M − resin − $C_{17}H_{17}NO_4$ + H] | MW (Cal.) |
|---|---|---|---|
| 21 | 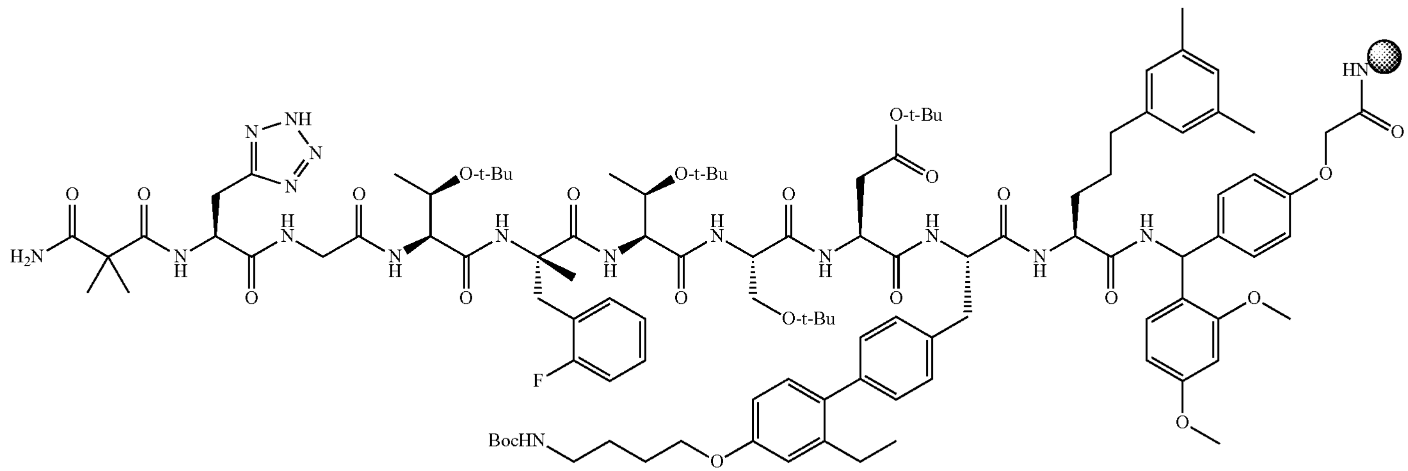 | $C_{91}H_{135}FN_{16}O_{19}$ | 1776.14 |
| 22 | 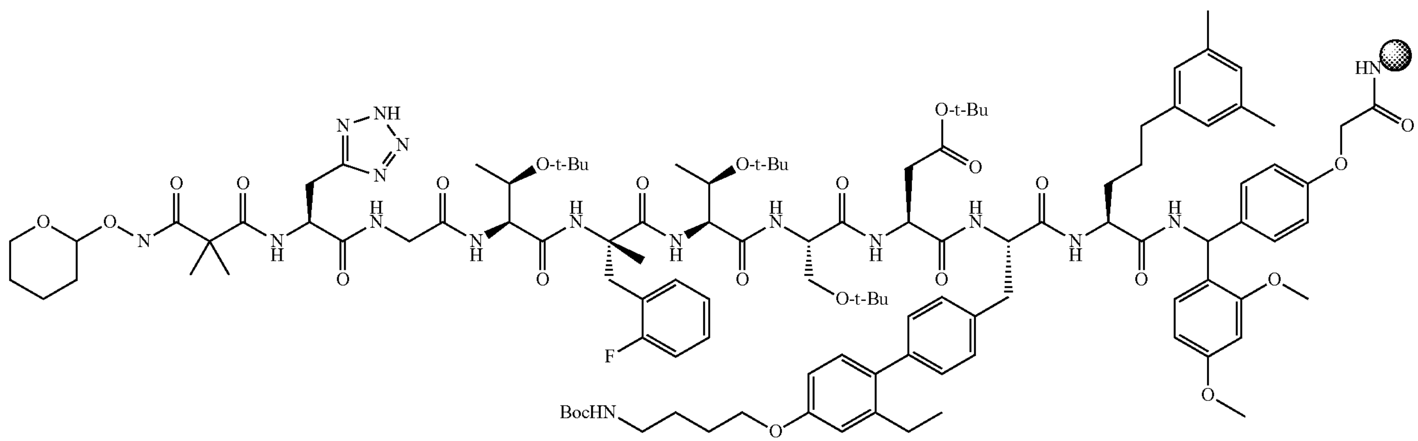 | $C_{96}H_{142}FN_{16}O_{21}$ | 1875.25 |

TABLE 2-continued

| Compound No. | Structure | MF [M − resin − $C_{17}H_{17}NO_4$ + H] | MW (Cal.) |
|---|---|---|---|
| 23 | 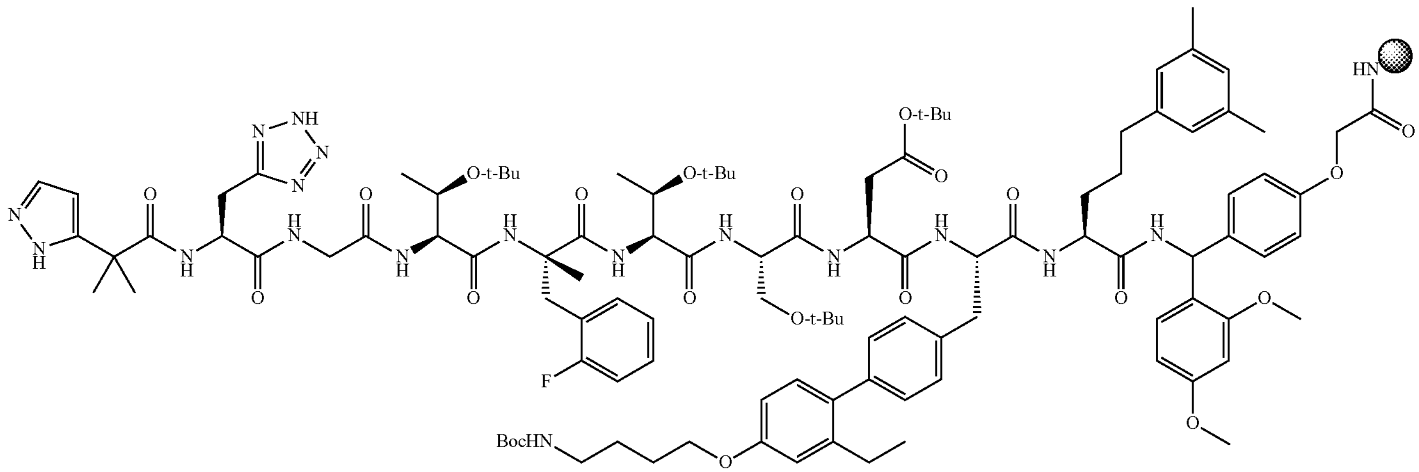 | $C_{93}H_{136}FN_{17}O_{18}$ | 1799.18 |
| 24 | 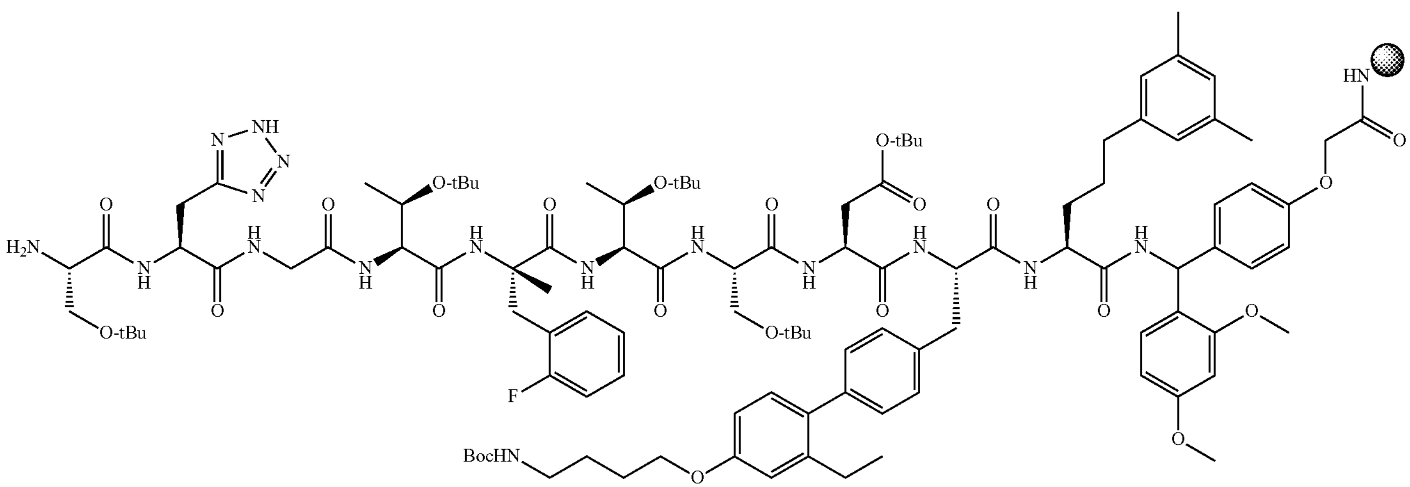 | $C_{93}H_{141}FN_{16}O_{19}$ | 1806.21 |

TABLE 2-continued

| Compound No. | Structure | MF [M – resin – $C_{17}H_{17}NO_4$ + H] | MW (Cal.) |
|---|---|---|---|
| 25 | 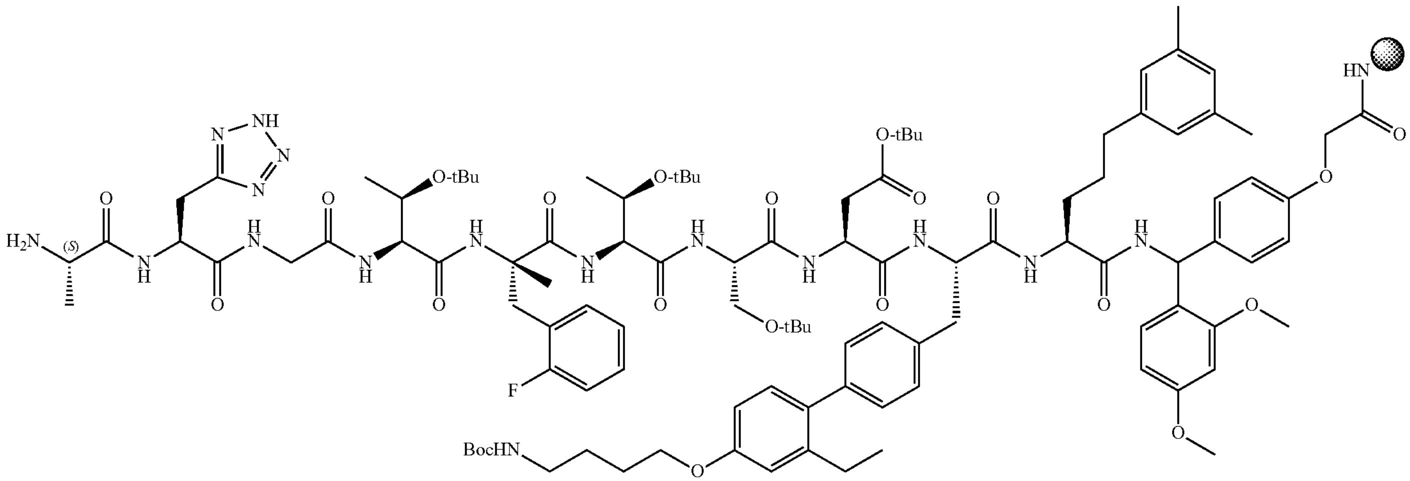 | $C_{89}H_{133}FN_{16}O_{18}$ | 1734.10 |
| 26 | 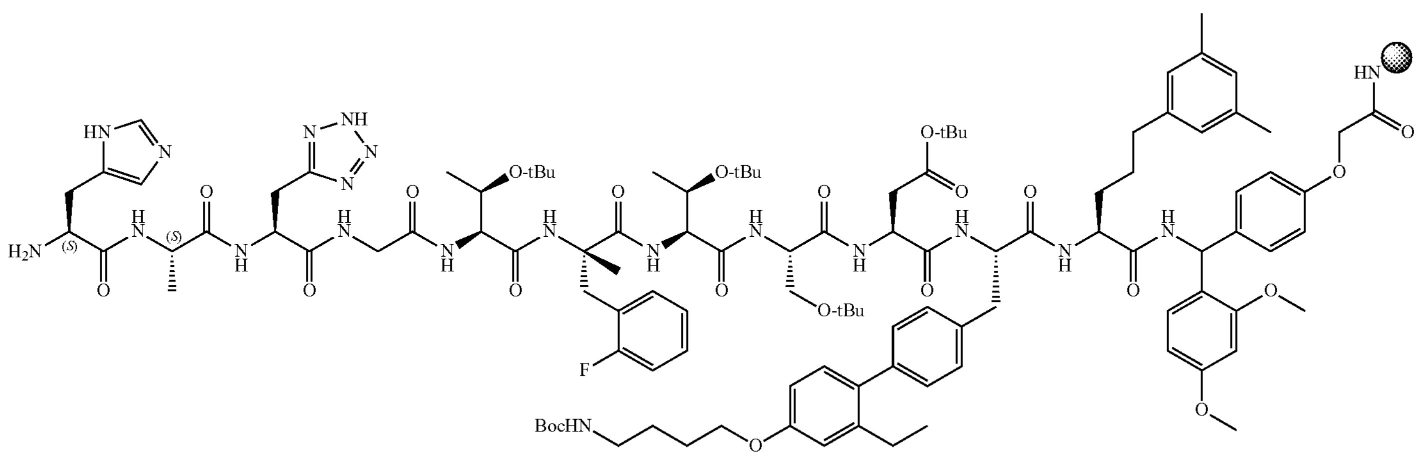 | $C_{95}H_{140}FN_{19}O_{19}$ | 1871.24 |

TABLE 2-continued

| Compound No. | Structure | MF [M − resin − C$_{17}$H$_{17}$NO$_4$ + H] | MW (Cal.) |
|---|---|---|---|
| 27 | 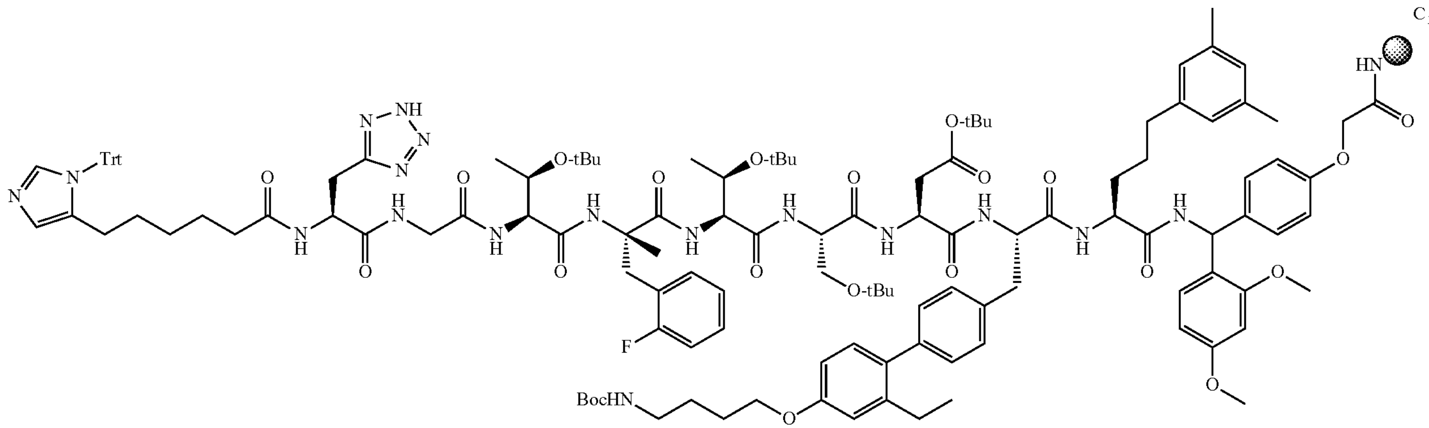 | C$_{114}$H$_{154}$FN$_{17}$O$_{18}$ | 2069.54 |
| 28 | 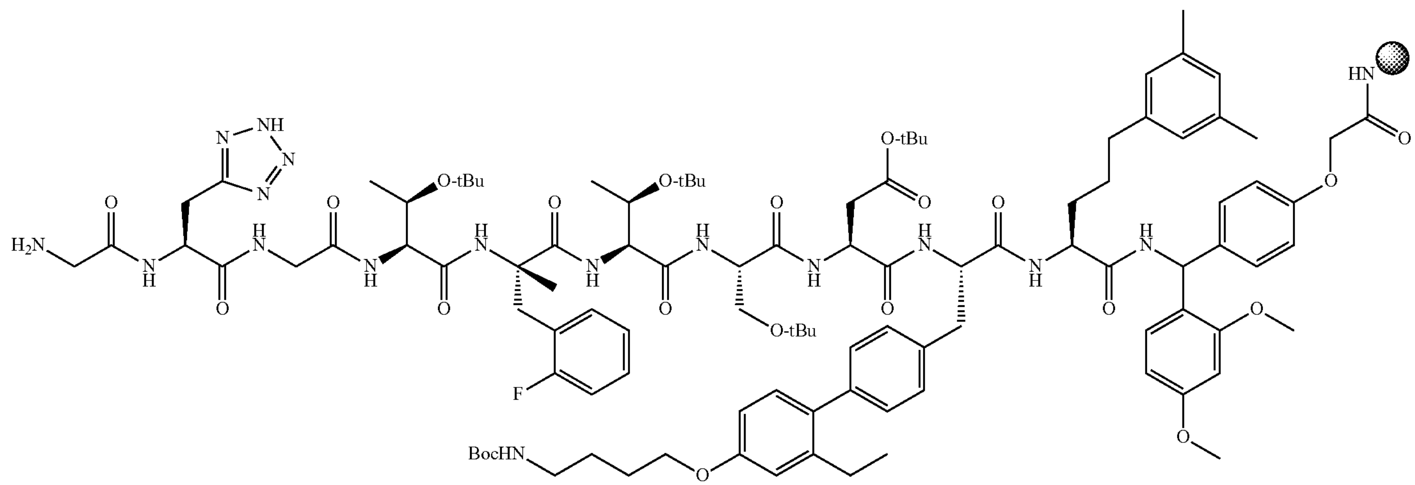 | C$_{88}$H$_{131}$FN$_{16}$O$_{18}$ | 1720.08 |

TABLE 2-continued

| Compound No. | Structure | MF [M – resin – $C_{17}H_{17}NO_4$ + H] | MW (Cal.) |
|---|---|---|---|
| 29 | 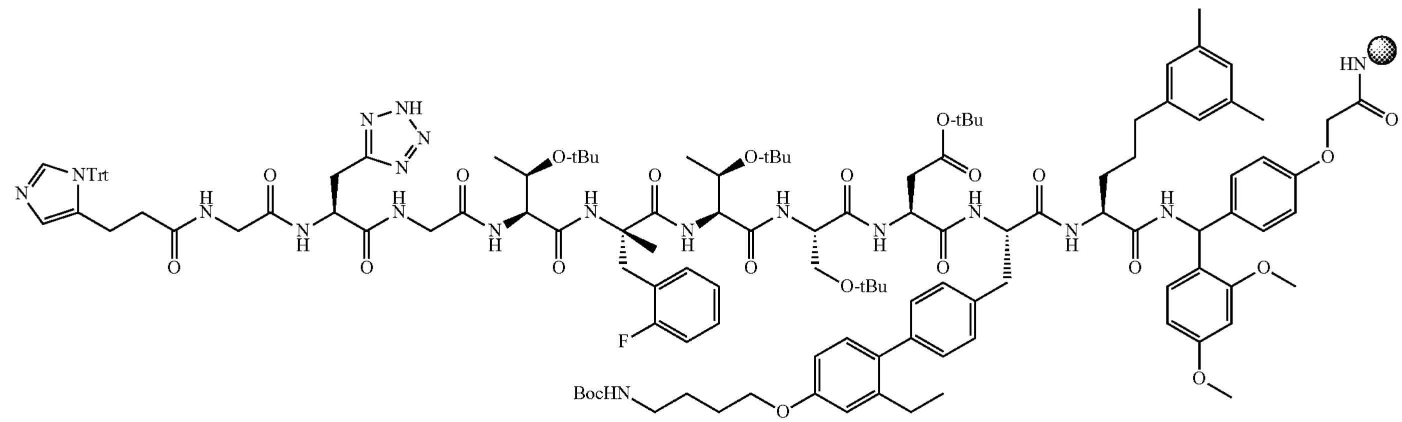 | $C_{113}H_{151}FN_{18}O_{19}$ | 2084.52 |
| 30 | 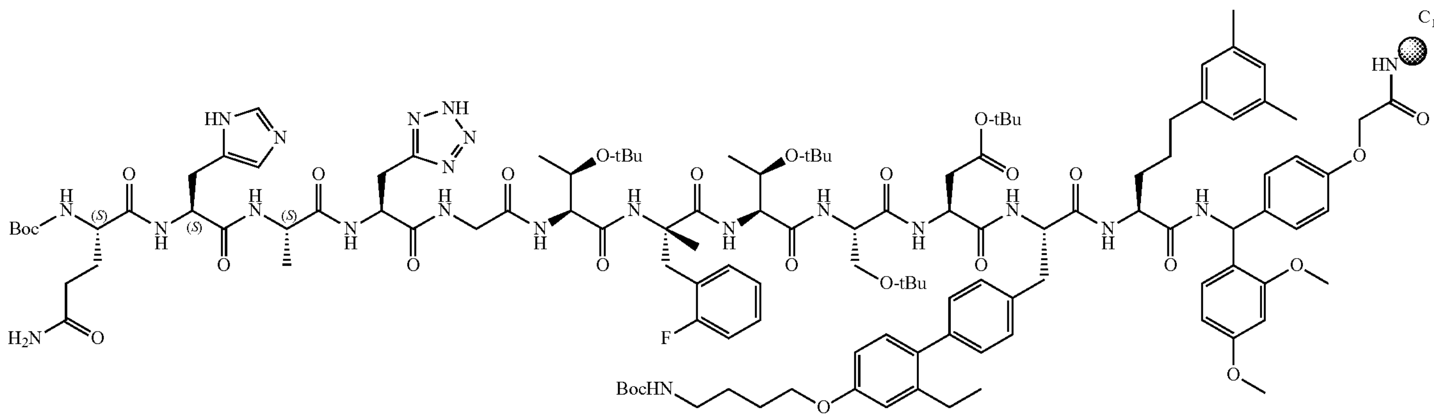 | $C_{105}H_{156}FN_{21}O_{23}$ | 2099.49 |

TABLE 2-continued

| Compound No. | Structure | MF [M − resin − $C_{17}H_{17}NO_4$ + H] | MW (Cal.) |
|---|---|---|---|
| 31 | 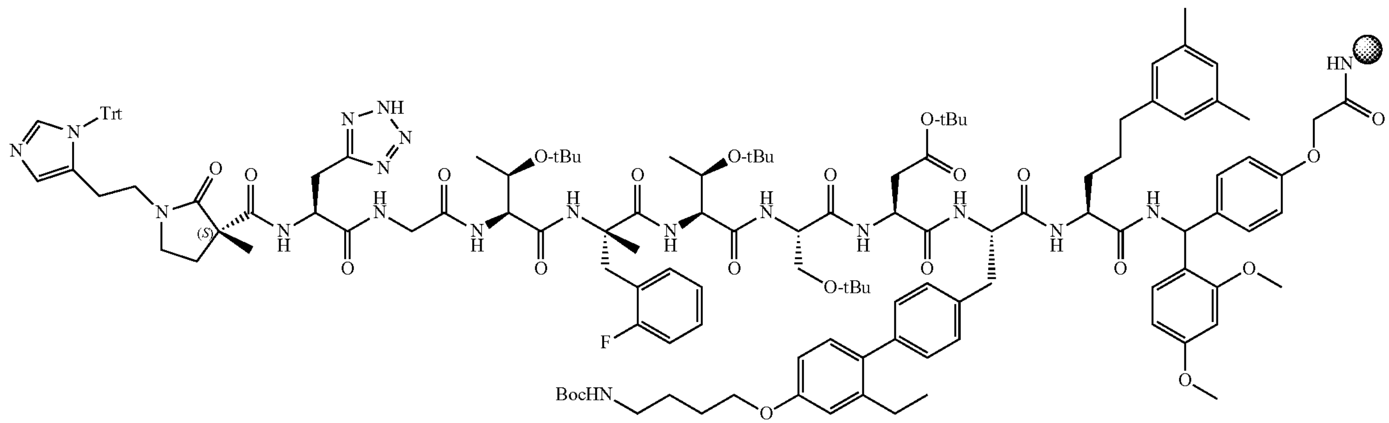 | $C_{116}H_{155}FN_{18}O_{19}$ | 2124.58 |
| 32 | 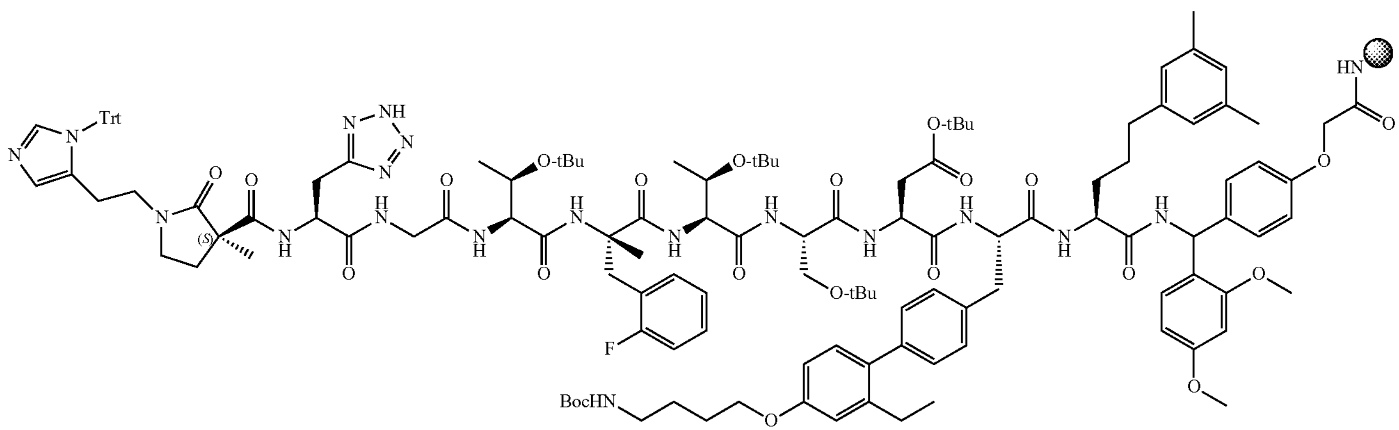 | $C_{116}H_{155}FN_{18}O_{19}$ | 2124.58 |

TABLE 2-continued

| Compound No. | Structure | MF [M − resin − C17H17NO4 + H] | MW (Cal.) |
|---|---|---|---|
| 33 | 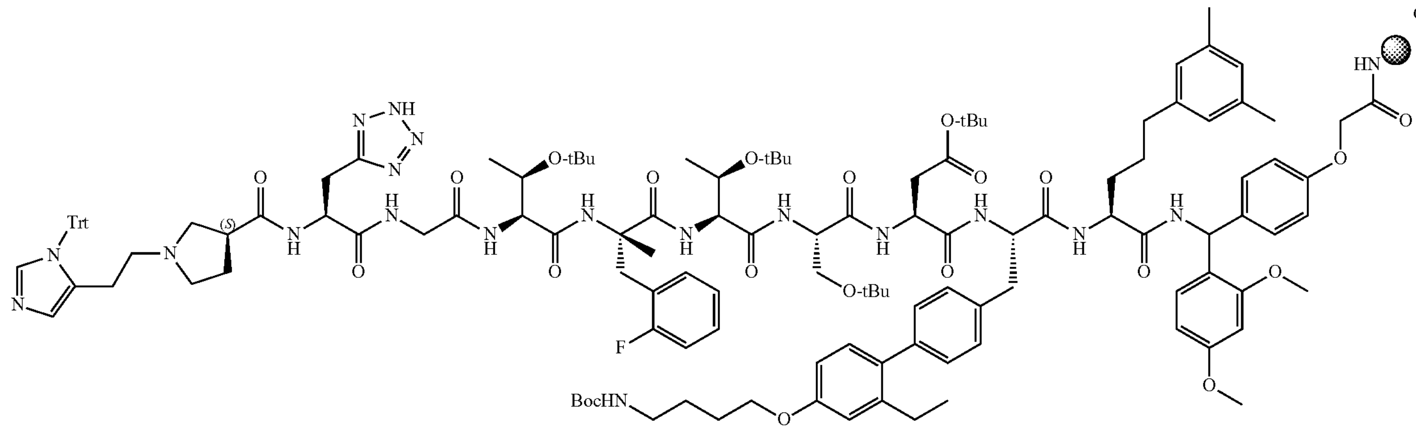 | C115H155FN18O18 | 2096.57 |
| 34 | 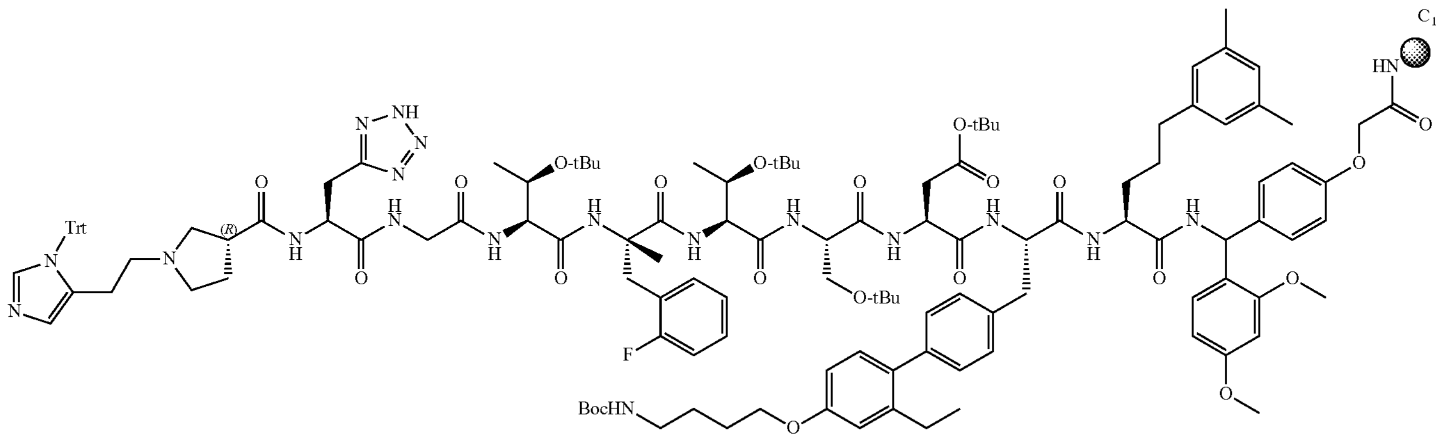 | C115H155FN18O18 | 2096.57 |

TABLE 2-continued

| Compound No. | Structure | MF [M – resin – $C_{17}H_{17}NO_4$ + H] | MW (Cal.) |
|---|---|---|---|
| 35 | 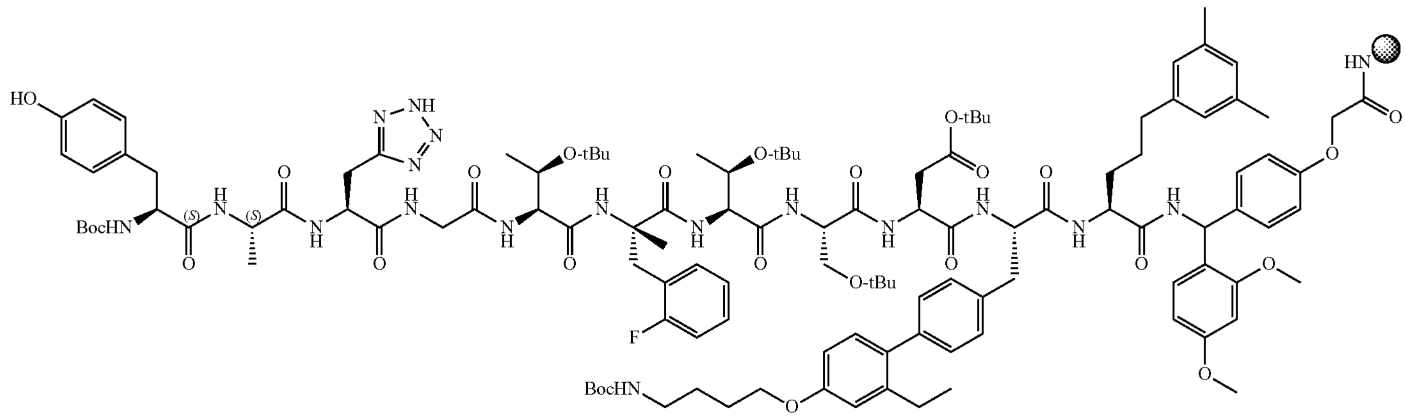 | $C_{103}H_{150}FN_{17}O_{22}$ | 1997.39 |
| 36 | 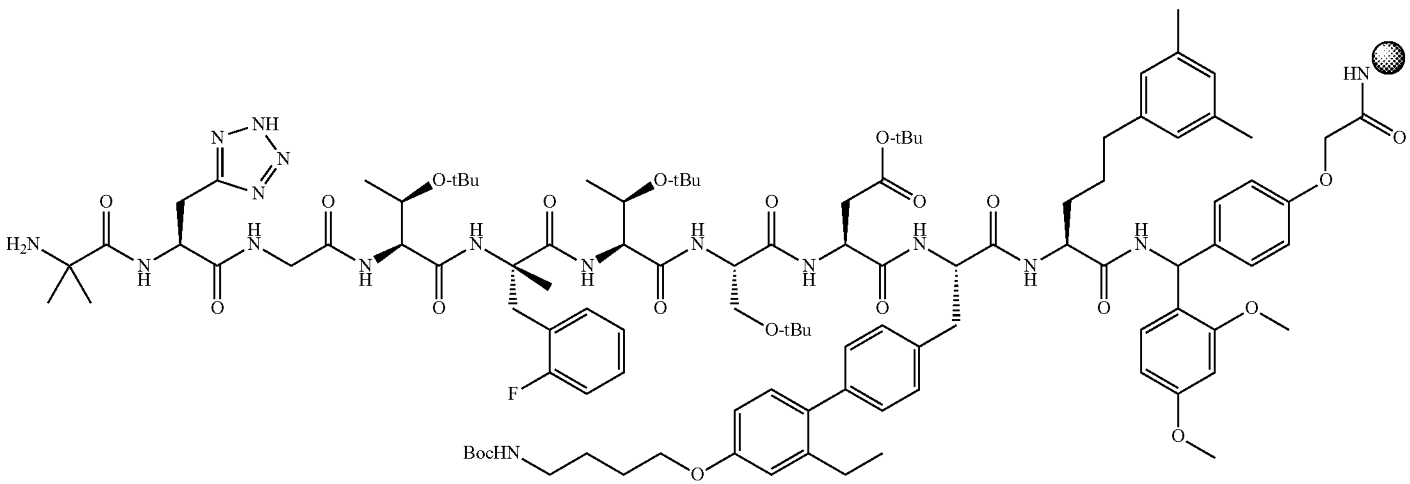 | $C_{90}H_{135}FN_{16}O_{18}$ | 1748.13 |

TABLE 2-continued

| Compound No. | Structure | MF [M − resin − C$_{17}$H$_{17}$NO$_4$ + H] | MW (Cal.) |
|---|---|---|---|
| 37 | 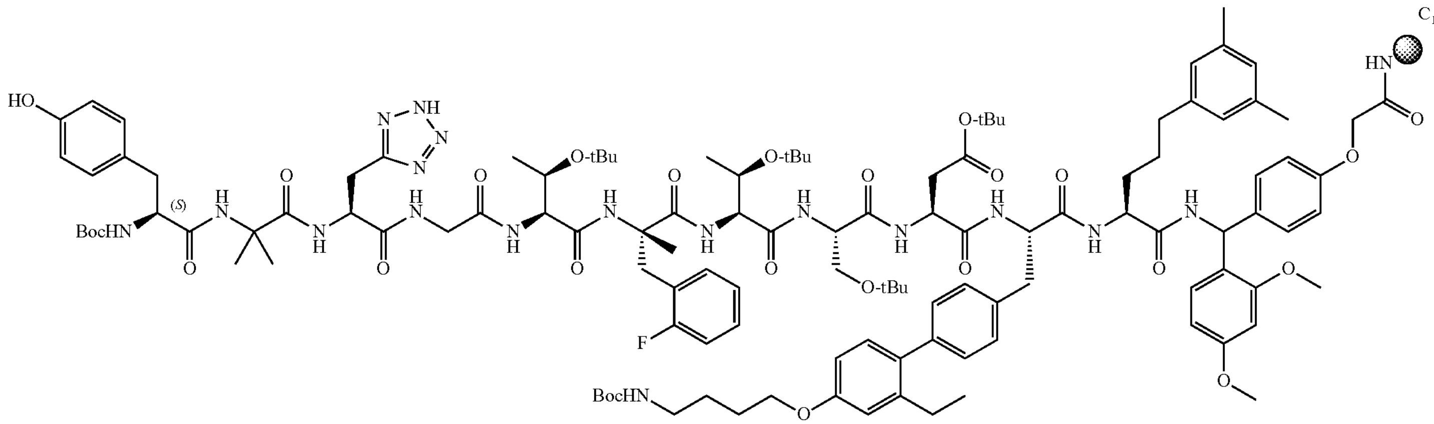 | C$_{104}$H$_{152}$FN$_{17}$O$_{22}$ | 2011.42 |
| 38 | 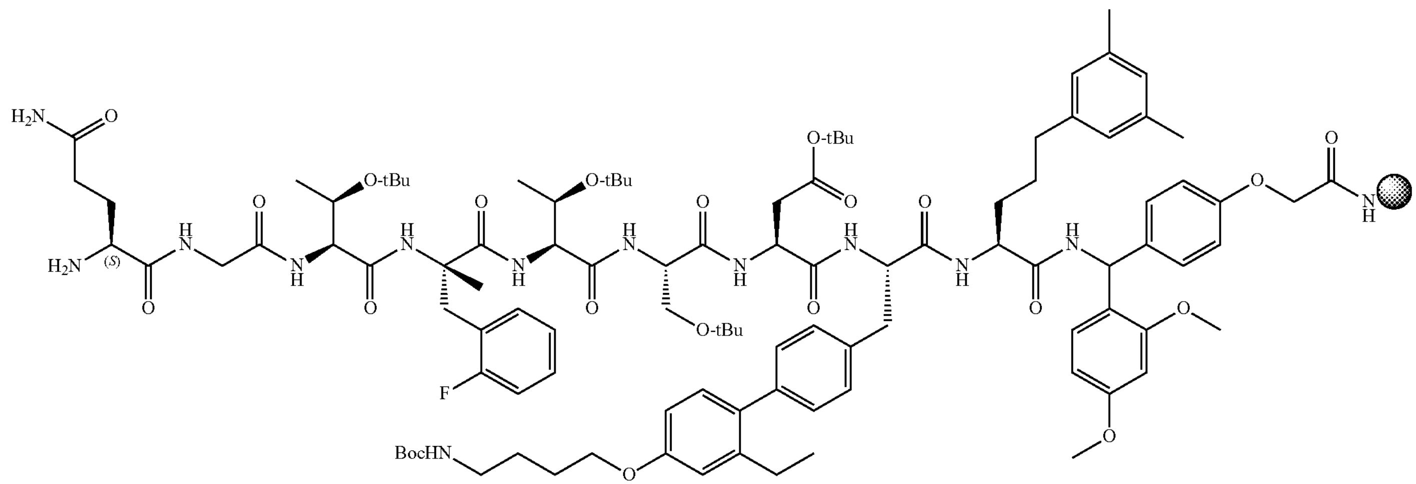 | C$_{87}$H$_{131}$FN$_{12}$O$_{18}$ | 1652.04 |

TABLE 2-continued

| Compound No. | Structure | MF [M − resin − C$_{17}$H$_{17}$NO$_4$ + H] | MW (Cal.) |
|---|---|---|---|
| 39 | 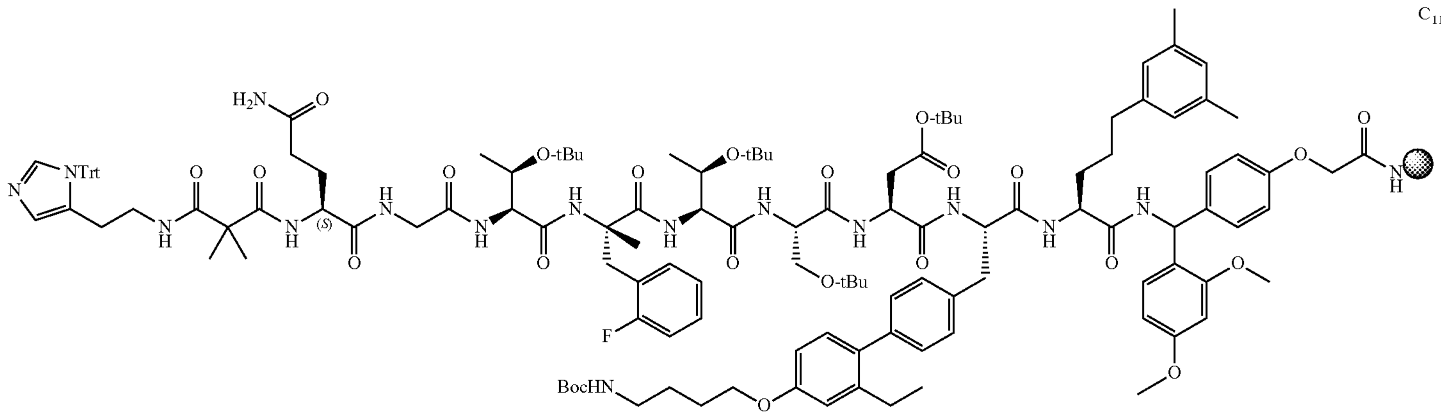 | C$_{116}$H$_{158}$FN$_{15}$O$_{20}$ | 2101.58 |
| 40 | 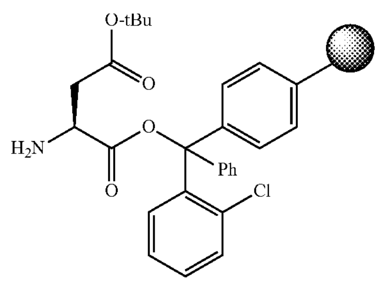 | [M − resin − ClTrt + H] C$_8$H$_{15}$NO$_4$ | 189.21 |
| 41 | 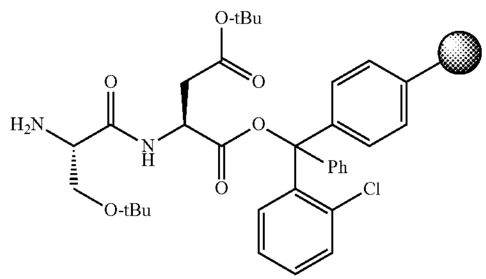 | [M − resin − ClTrt + H] C$_{15}$H$_{28}$N$_2$O$_6$ | 332.39 |

TABLE 2-continued

| Compound No. | Structure | MF [M − resin − ClTrt + H] | MW (Cal.) |
|---|---|---|---|
| 42 | 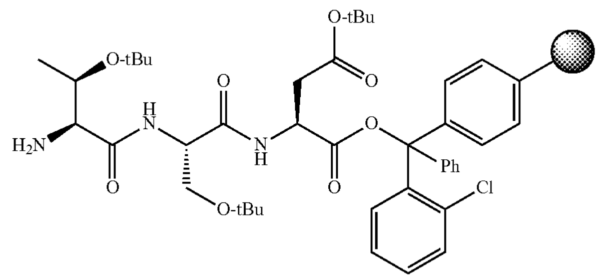 | [M − resin − ClTrt + H] $C_{23}H_{43}N_3O_8$ | 489.60 |
| 43 | 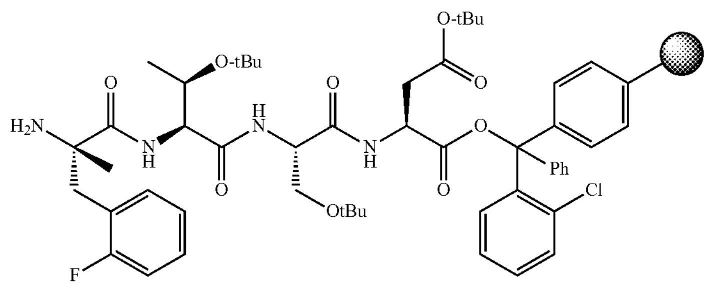 | [M − resin − ClTrt + H] $C_{33}H_{53}FN_4O_9$ | 668.79 |
| 44 | 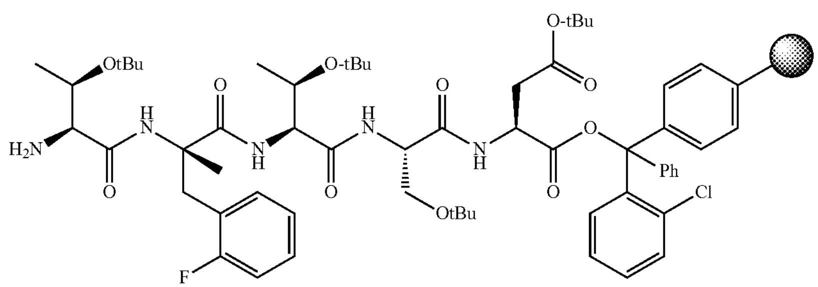 | [M − resin − ClTrt + H] $C_{41}H_{68}FN_5O_{11}$ | 826.00 |

TABLE 2-continued

| Compound No. | Structure | MF [M − resin − ClTrt + H] | MW (Cal.) |
|---|---|---|---|
| 45 | 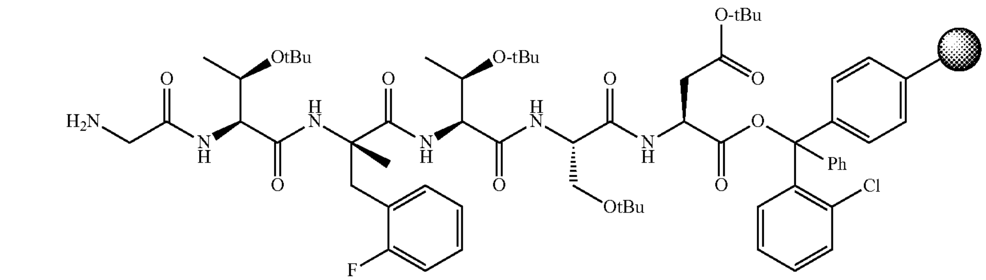 | [M − resin − C17H17NO4 + H] C43H71FN6O12 | 883.06 |
| 46 | 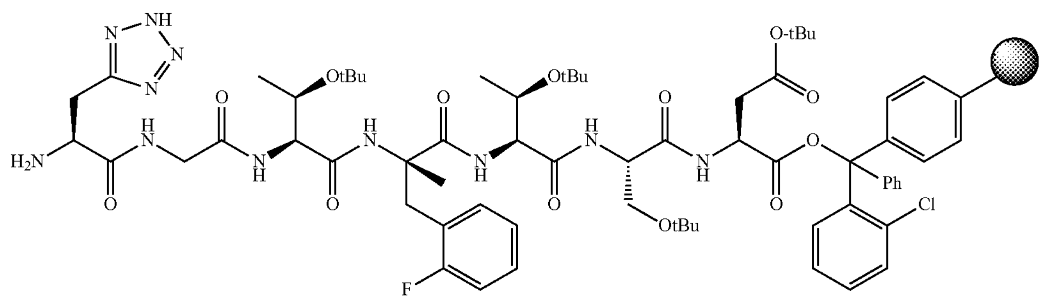 | [M − resin − ClTrt + H] C47H76FN11O13 | 1022.17 |
| 47 | 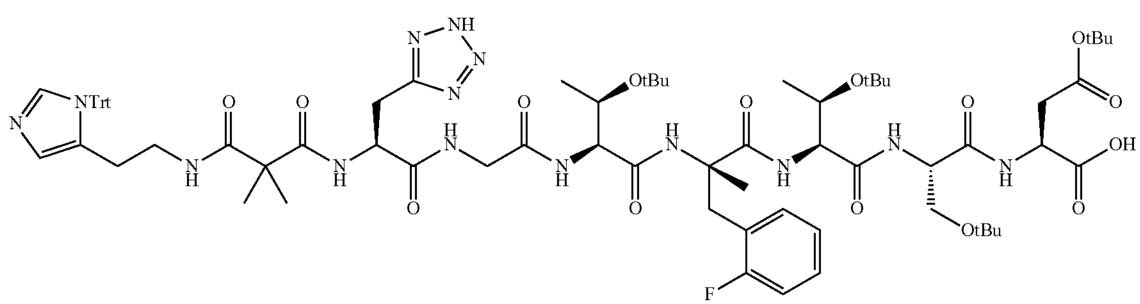 | C76H103FN14O15 | 1471.71 |

TABLE 2-continued
| Compound No. | Structure | MF [M – resin – $C_{17}H_{17}NO_4$ + H] | MW (Cal.) |
|---|---|---|---|
| 48 | 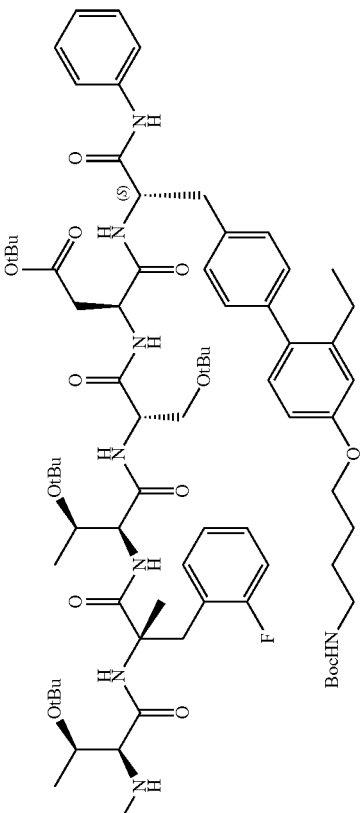 | $C_{108}H_{142}FN_{17}O_{18}$ | 1985.38 |
| 49 | 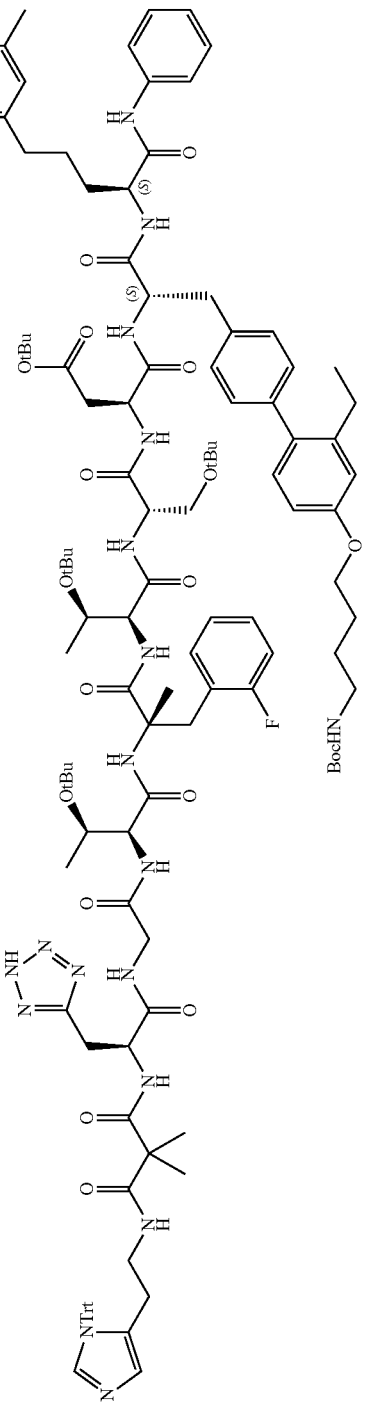 | $C_{121}H_{159}FN_{18}O_{19}$ | 2188.66 |

TABLE 2-continued

| Compound No. | Structure | MF [M – resin – $C_{17}H_{17}NO_4$ + H] | MW (Cal.) |
|---|---|---|---|
| 50 | 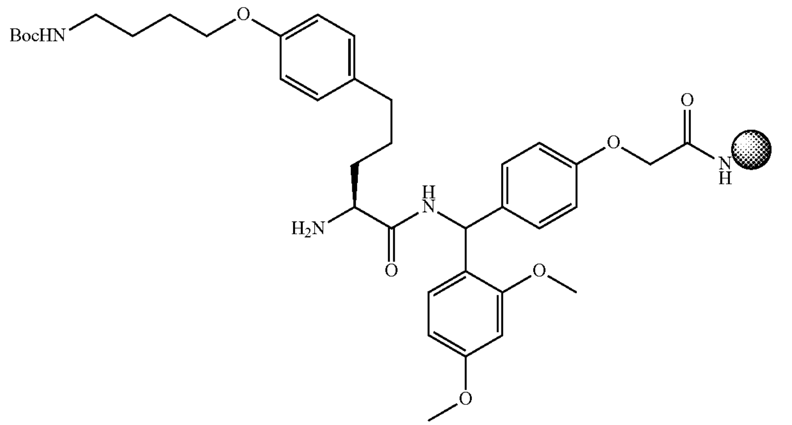 [SMILES: COc1ccc(C(NC(=O)[C@@H](N)CCCc2ccc(OCCCCNC(=O)OC(C)(C)C)cc2)c2ccc(OCC(N)=O)cc2)c(OC)c1] | $C_{20}H_{33}N_3O_4$ | 379.49 |
| 51 | 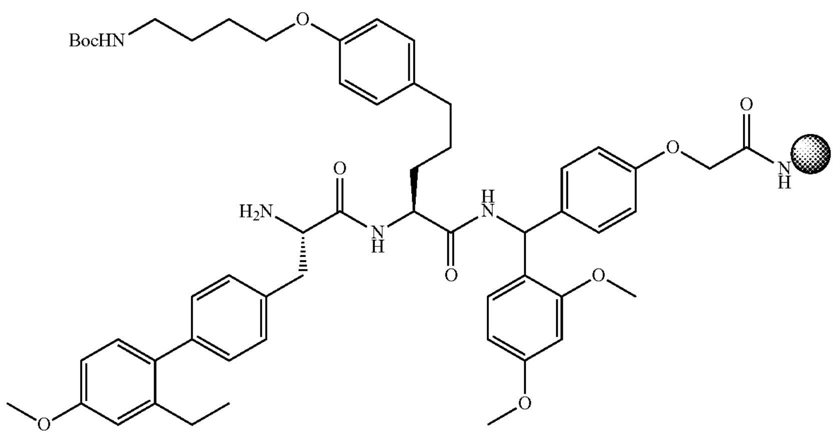 [SMILES: CCc1cc(OC)ccc1-c1ccc(C[C@H](N)C(=O)N[C@@H](CCCc2ccc(OCCCCNC(=O)OC(C)(C)C)cc2)C(=O)NC(c2ccc(OCC(N)=O)cc2)c2ccc(OC)cc2OC)cc1] | $C_{38}H_{52}N_4O_6$ | 660.3887 |

TABLE 2-continued

| Compound No. | Structure | MF [M – resin – $C_{17}H_{17}NO_4$ + H] | MW (Cal.) |
|---|---|---|---|
| 52 | 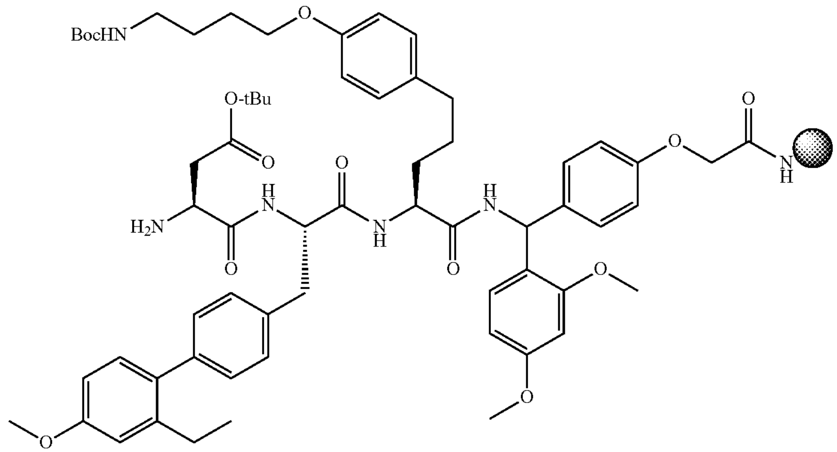 | $C_{46}H_{65}N_5O_9$ | 831.4782 |
| 53 | 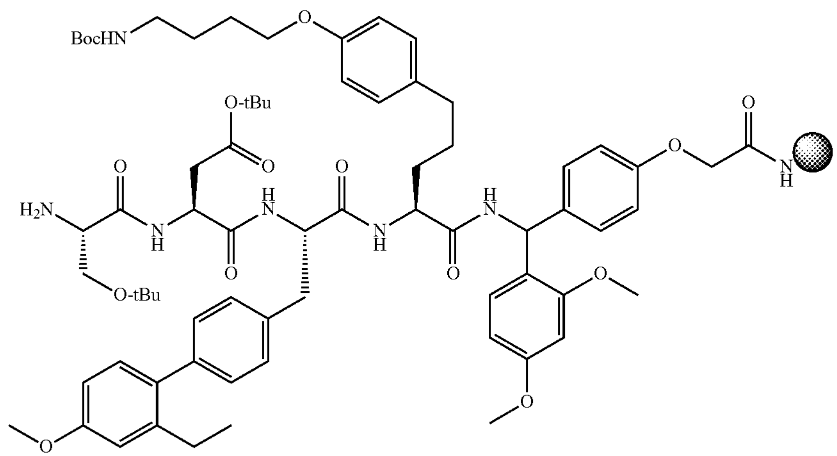 | $C_{53}H_{78}N_6O_{11}$ | 974.5729 |

TABLE 2-continued

| Compound No. | Structure | MF [M − resin − $C_{17}H_{17}NO_4$ + H] | MW (Cal.) |
|---|---|---|---|
| 54 | 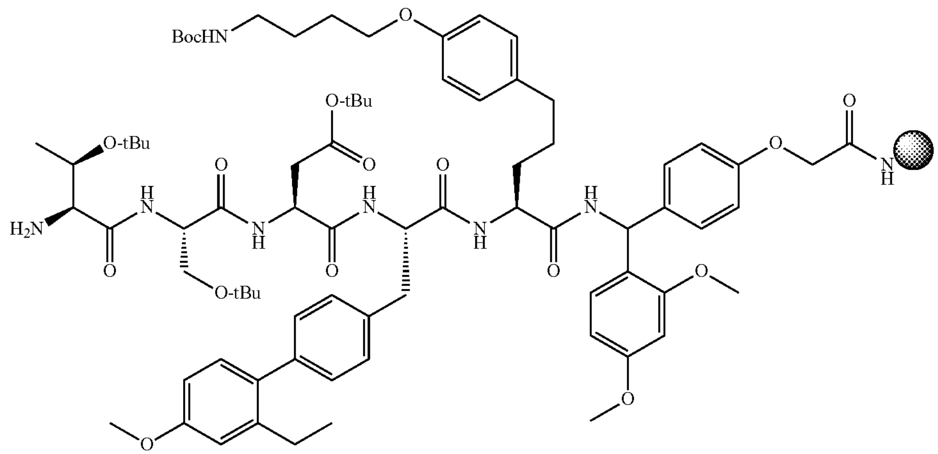 | $C_{61}H_{93}N_7O_{13}$ | 1131.68 |
| 55 | 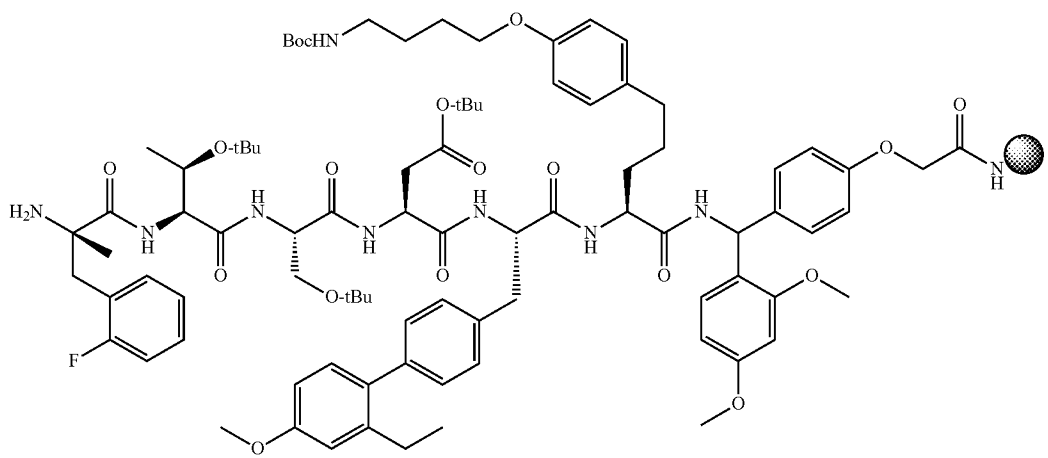 | $C_{71}H_{103}FN_8O_{14}$ | 1310.76 |

TABLE 2-continued

| Compound No. | Structure | MF [M − resin − $C_{17}H_{17}NO_4$ + H] | MW (Cal.) |
|---|---|---|---|
| 56 | 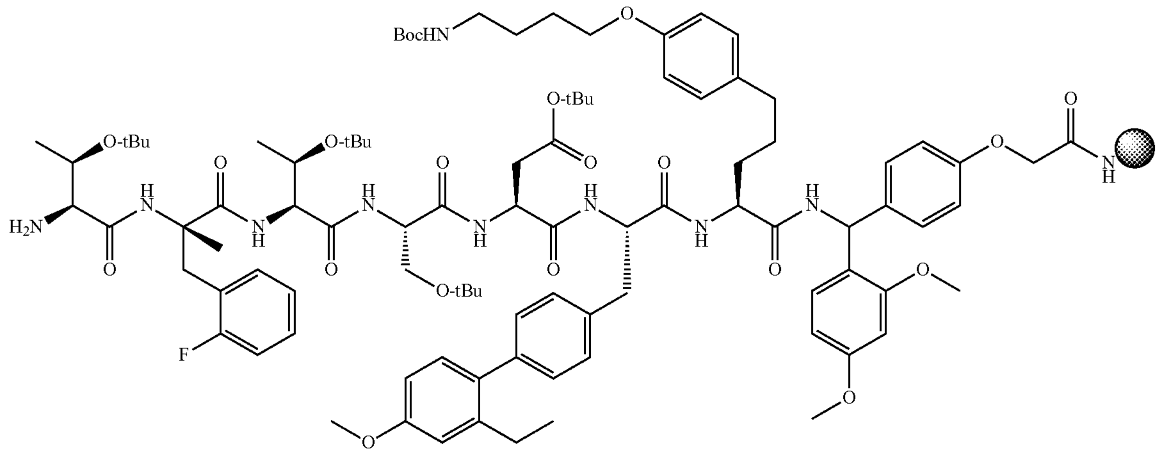 | $C_{79}H_{118}FN_9O_{16}$ | 1467.868 |
| 57 | 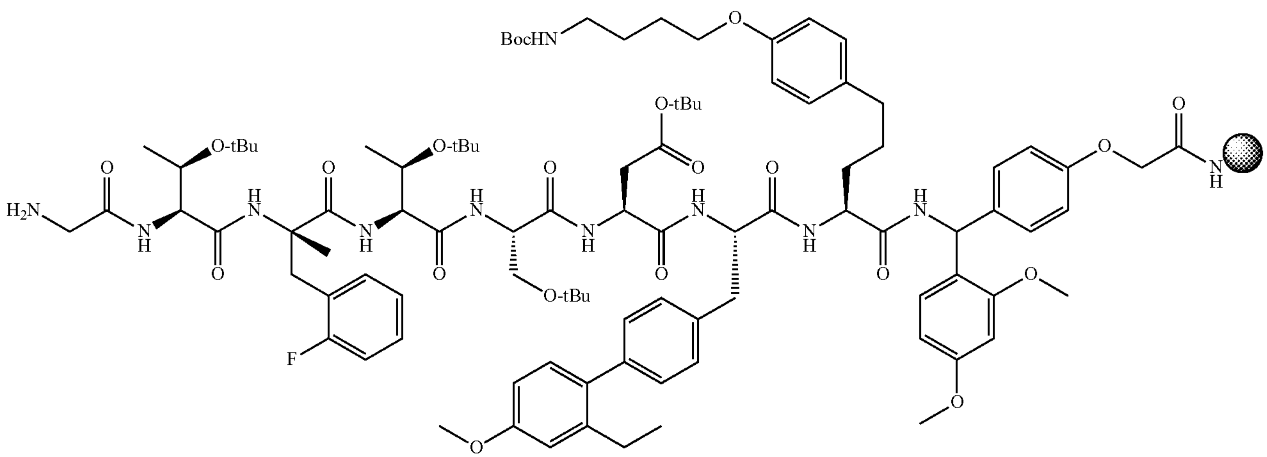 | $C_{81}H_{121}FN_{10}O_{17}$ | 1524.8895 |

TABLE 2-continued

| Compound No. | Structure | MF [M − resin − $C_{17}H_{17}NO_4$ + H] | MW (Cal.) |
|---|---|---|---|
| 58 | 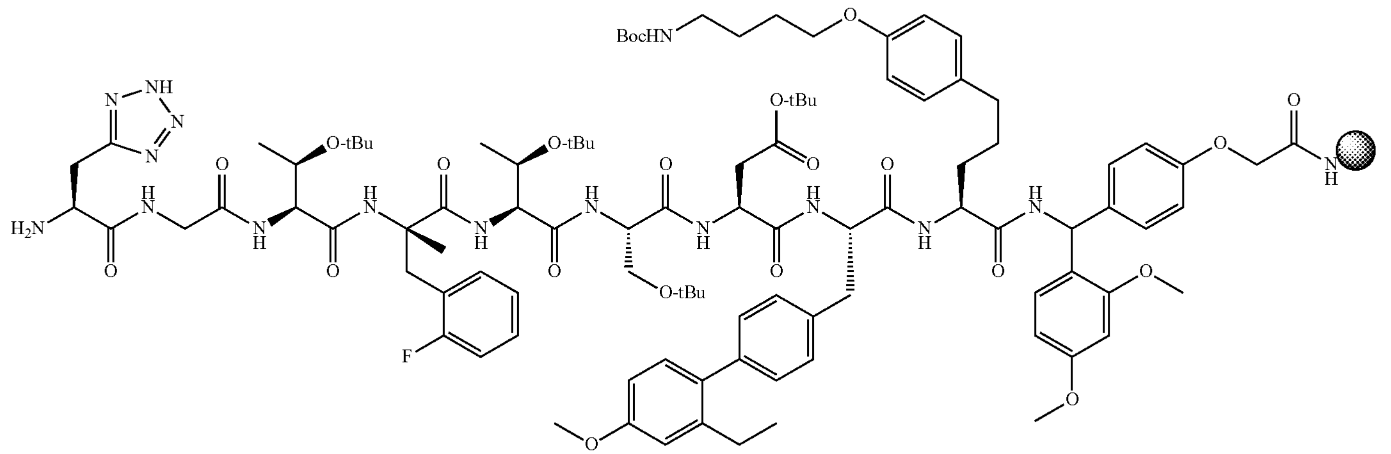 | $C_{85}H_{126}FN_{15}O_{18}$ | 1663.9389 |
| 59 | 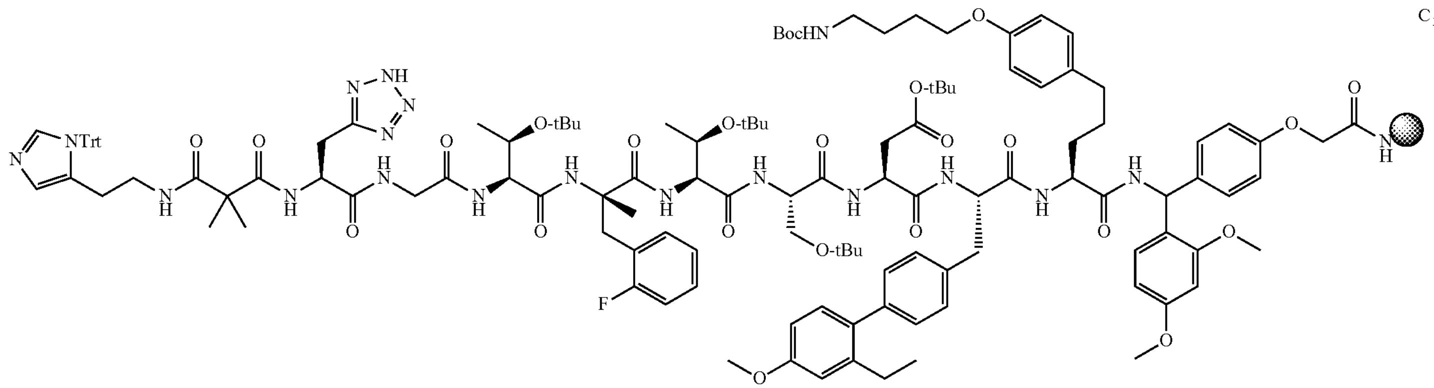 | $C_{114}H_{153}FN_{18}O_{20}$ | 2113.149 |

The Rink amide MBHA resin bound peptides and intermediates (1~59) were analyzed by LC-MS after cleavage from the Resin. Table 21B, below, summarizes these intermediates.

TABLE 2B
Intermediates Cleaved from MBHA Resin
| No. | Structure | MF | MW (Cal.) | MS (m/z) |
|---|---|---|---|---|
| 1 | 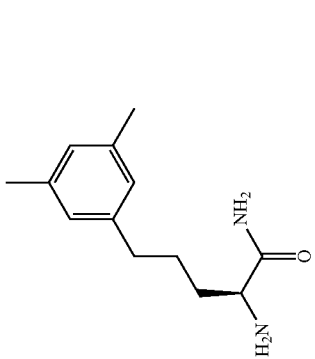 | $C_{13}H_{20}N_2O$ | 220.3 | 221.4 [M + H]$^+$ |
| 2 | 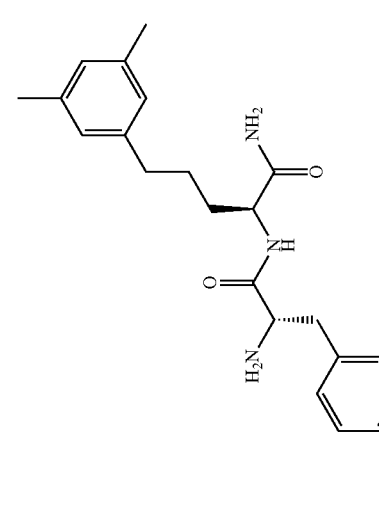 | $C_{34}H_{44}N_6O_3$ | 584.8 | 585.3 [M + H]$^+$ 607.30 [M + Na]$^+$ |

TABLE 2B-continued

Intermediates Cleaved from MBHA Resin

| No. | Structure | MF | MW (Cal.) | MS (m/z) |
|---|---|---|---|---|
| 3 | 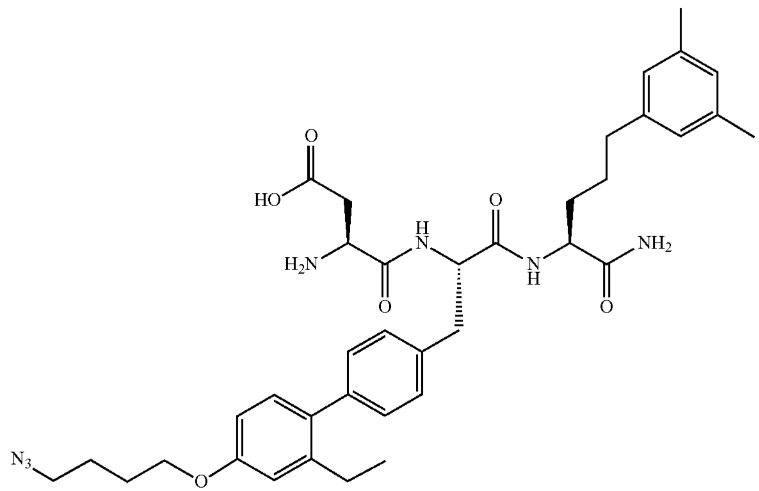 [SMILES: CCc1cc(OCCCCN=[N+]=[N-])ccc1-c1ccc(C[C@H](NC(=O)[C@@H](N)CC(=O)O)C(=O)N[C@@H](CCCc2cc(C)cc(C)c2)C(N)=O)cc1] | $C_{38}H_{49}N_7O_6$ | 699.4 | 700.4 [M + H]$^+$ |
| 4 | 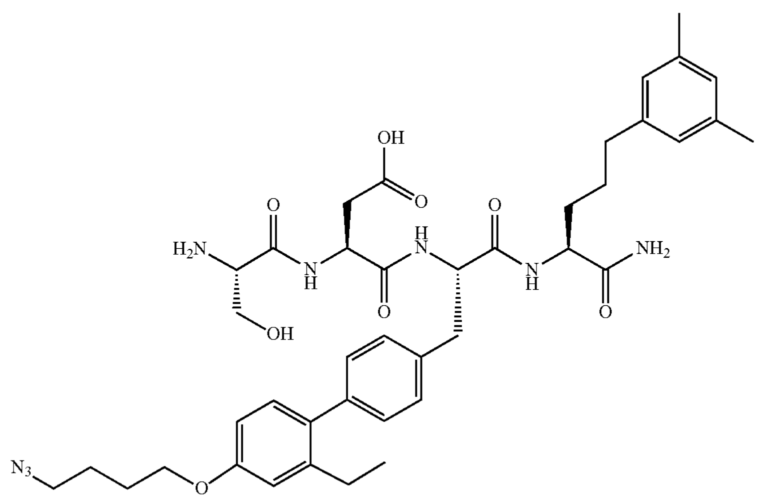 [SMILES: CCc1cc(OCCCCN=[N+]=[N-])ccc1-c1ccc(C[C@H](NC(=O)[C@H](CC(=O)O)NC(=O)[C@@H](N)CO)C(=O)N[C@@H](CCCc2cc(C)cc(C)c2)C(N)=O)cc1] | $C_{41}H_{54}N_8O_8$ | 786.4 | 787.4 [M + H]$^+$ |

TABLE 2B-continued
Intermediates Cleaved from MBHA Resin
| No. | Structure | MF | MW (Cal.) | MS (m/z) |
|---|---|---|---|---|
| 5 | 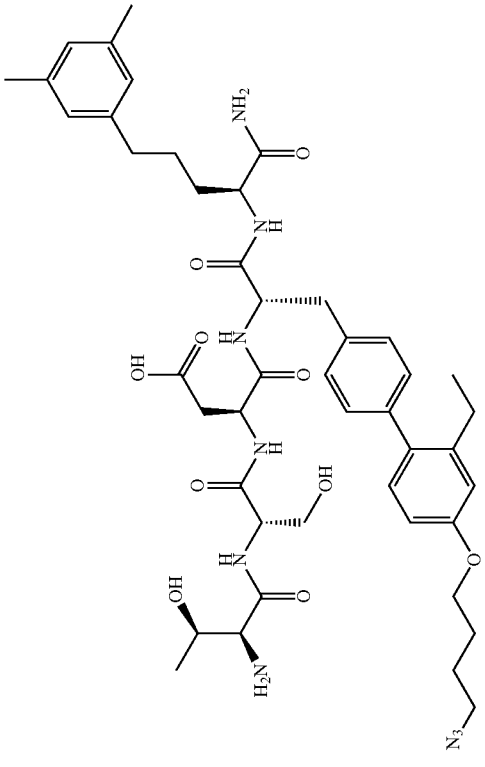 | $C_{45}H_{61}N_9O_{10}$ | 887.5 | 888.5 $[M + H]^+$ |
| 6 | 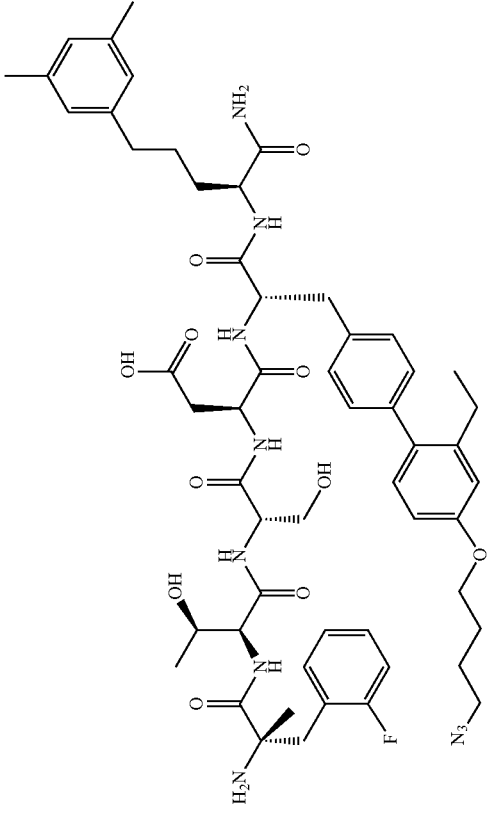 | $C_{55}H_{71}FN_{10}O_{11}$ | 1066.7 | 1067.7 $[M + H]^+$ |

TABLE 2B-continued

Intermediates Cleaved from MBHA Resin

| No. | Structure | MF | MW (Cal.) | MS (m/z) |
|---|---|---|---|---|
| 7 (SEQ ID NO: 130) | 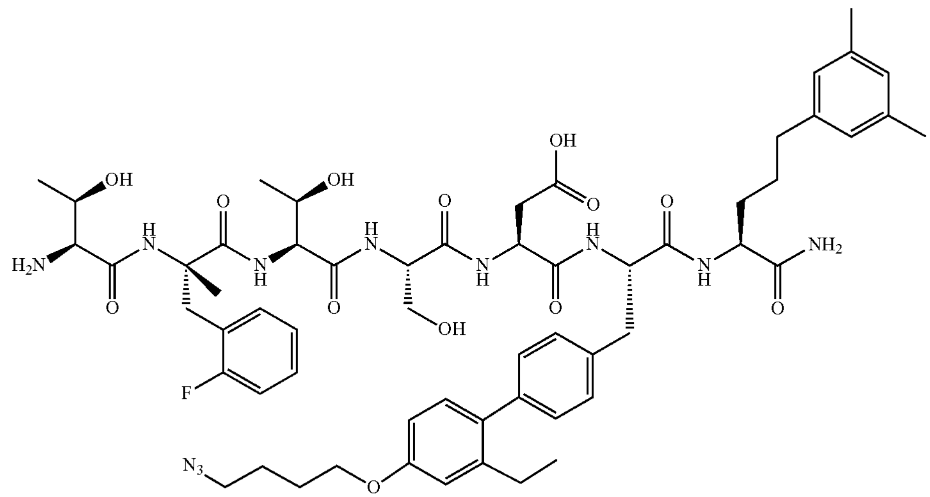 [SMILES: CCc1cc(OCCCCN=[N+]=[N-])ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](N)[C@@H](C)O)[C@@H](C)O)C(=O)N[C@@H](CCCc2cc(C)cc(C)c2)C(N)=O)cc1] | $C_{59}H_{78}FN_{11}O_{13}$ | 1167.6 | 1168.2 $[M + H]^+$ |
| 8 (SEQ ID NO: 131) | 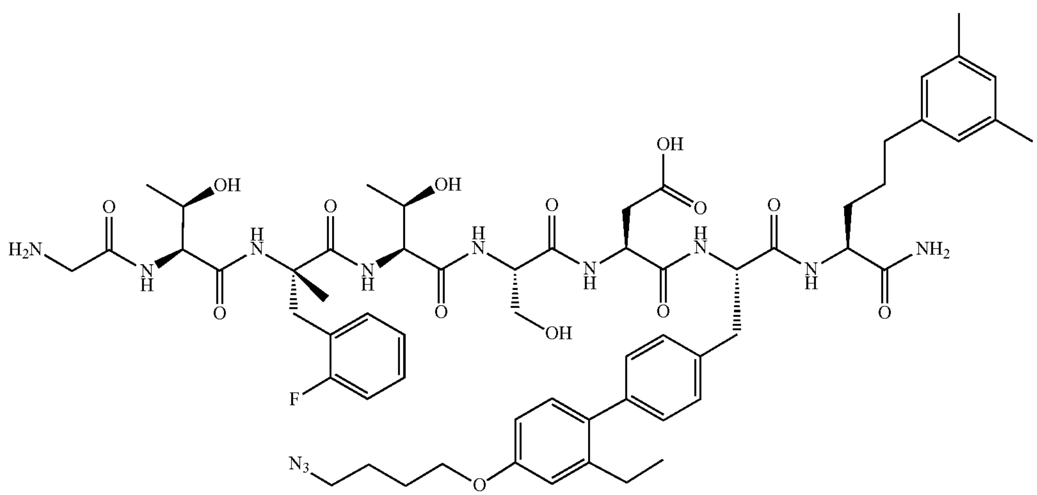 [SMILES: CCc1cc(OCCCCN=[N+]=[N-])ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CN)[C@@H](C)O)[C@@H](C)O)C(=O)N[C@@H](CCCc2cc(C)cc(C)c2)C(N)=O)cc1] | $C_{61}H_{81}FN_{12}O_{14}$ | 1224.6 | 1225.9 $[M + H]^+$ |

TABLE 2B-continued
Intermediates Cleaved from MBHA Resin
| No. | Structure | MF | MW (Cal.) | MS (m/z) |
|---|---|---|---|---|
| 9 (SEQ ID NO: 141) | 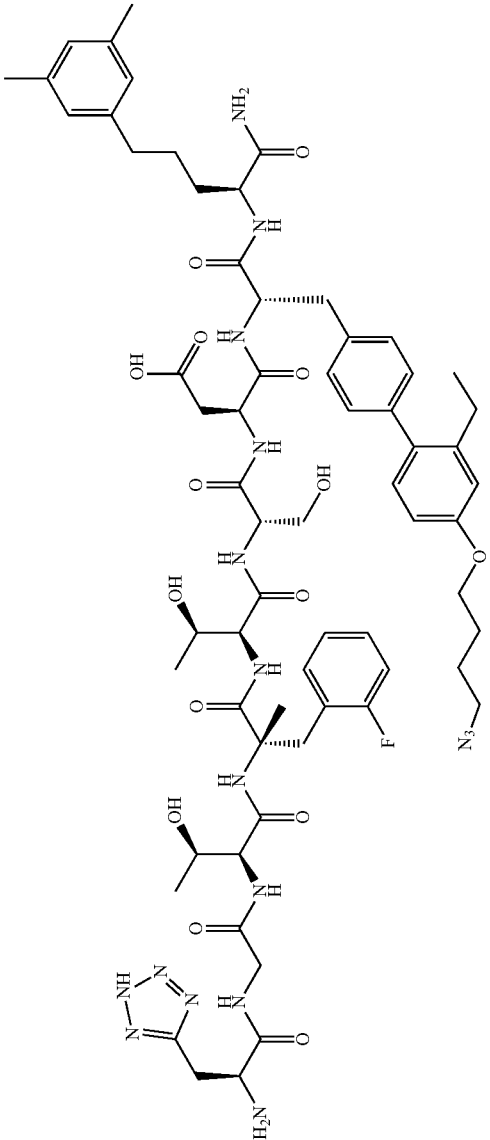 | $C_{65}H_{86}FN_{17}O_{15}$ | 1363.6 | 1364.9 [M + H]$^+$ |
| 10 (SEQ ID NO: 48) | 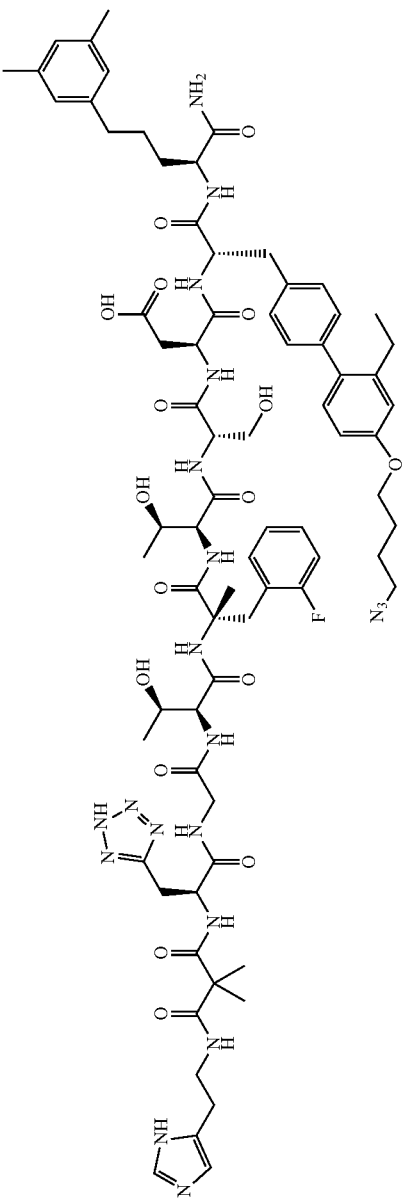 | $C_{75}H_{99}FN_{20}O_{17}$ | 1570.7 | 787.1 [M + 2H]$^{2+}$ |

TABLE 2B-continued

Intermediates Cleaved from MBHA Resin

| No. | Structure | MF | MW (Cal.) | MS (m/z) |
|---|---|---|---|---|
| 11 | 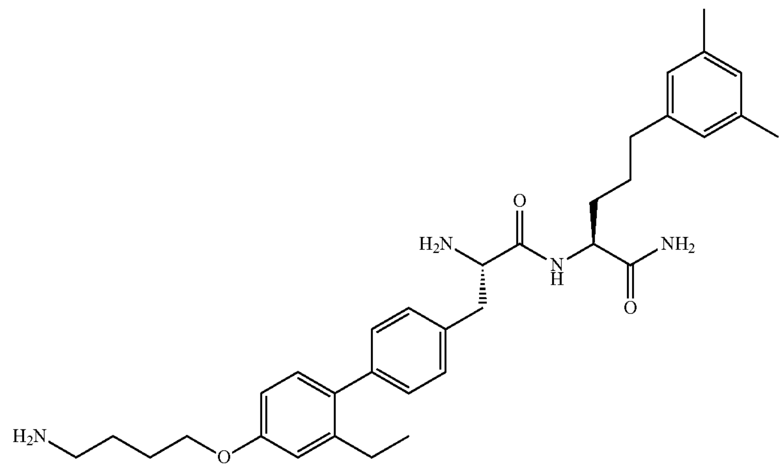 [SMILES: CCc1cc(OCCCCN)ccc1-c1ccc(C[C@H](N)C(=O)N[C@@H](CCCc2cc(C)cc(C)c2)C(N)=O)cc1] | $C_{34}H_{46}N_4O_3$ | 558.4 | 559.4 $[M+H]^+$ |
| 12 | 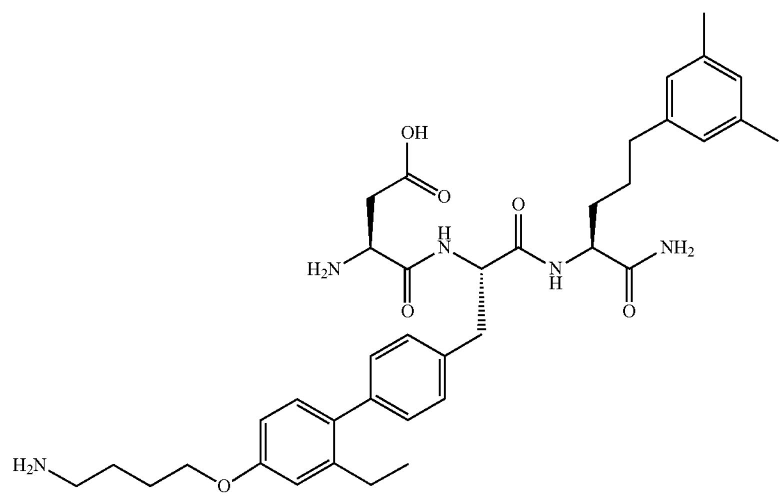 [SMILES: CCc1cc(OCCCCN)ccc1-c1ccc(C[C@H](NC(=O)[C@@H](N)CC(=O)O)C(=O)N[C@@H](CCCc2cc(C)cc(C)c2)C(N)=O)cc1] | $C_{38}H_{51}N_5O_6$ | 673.4 | 674.2 $[M+H]^+$ |

TABLE 2B-continued
Intermediates Cleaved from MBHA Resin
| No. | Structure | MF | MW (Cal.) | MS (m/z) |
|---|---|---|---|---|
| 13 | 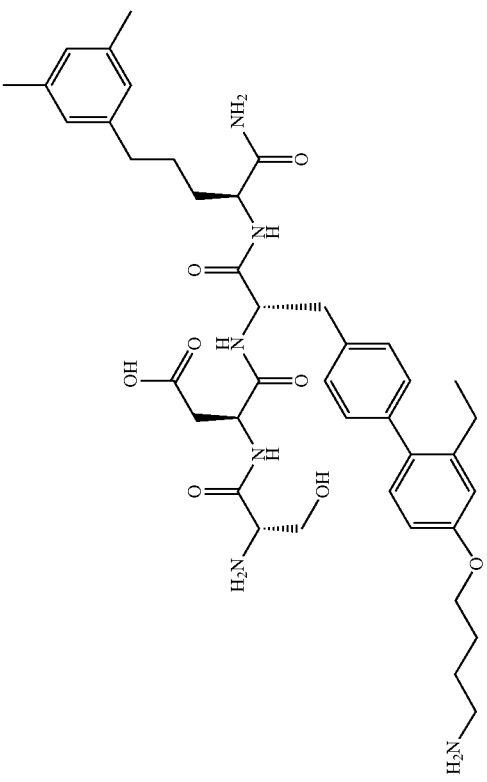 | $C_{41}H_{56}N_6O_8$ | 760.4 | 761.4 [M + H]$^+$ 381.3 [M + 2H]$^{2+}$ |
| 14 | 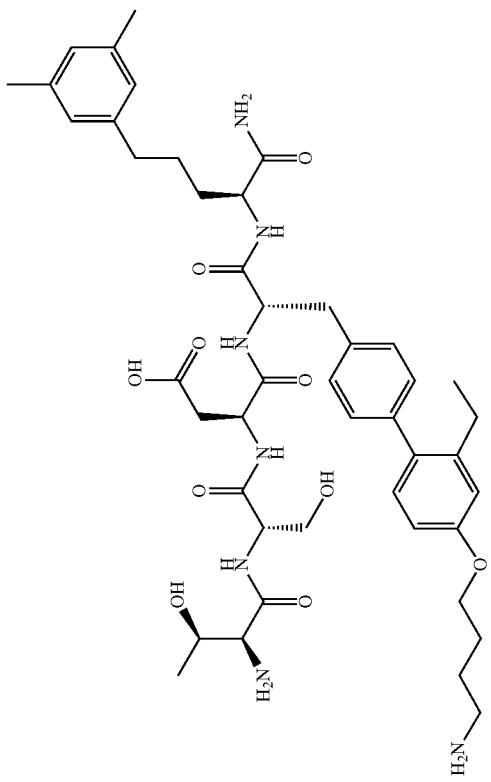 | $C_{45}H_{63}N_7O_{10}$ | 861.5 | 862.9 [M + H]$^+$ 431.9 [M + 2H]$^{2+}$ |

TABLE 2B-continued
Intermediates Cleaved from MBHA Resin
| No. | Structure | MF | MW (Cal.) | MS (m/z) |
|---|---|---|---|---|
| 15 | 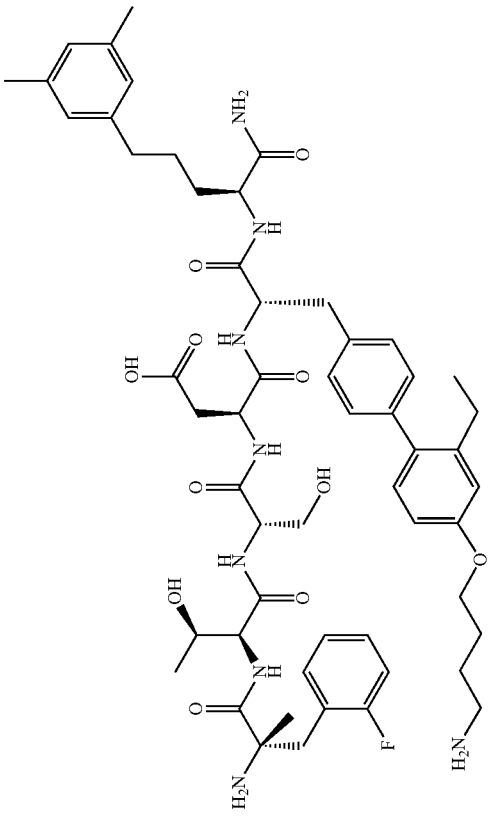 | $C_{55}H_{73}FN_8O_{11}$ | 1040.5 | 521.6 $[M + 2H]^{2+}$ |
| 16 (SEQ ID NO: 132) | 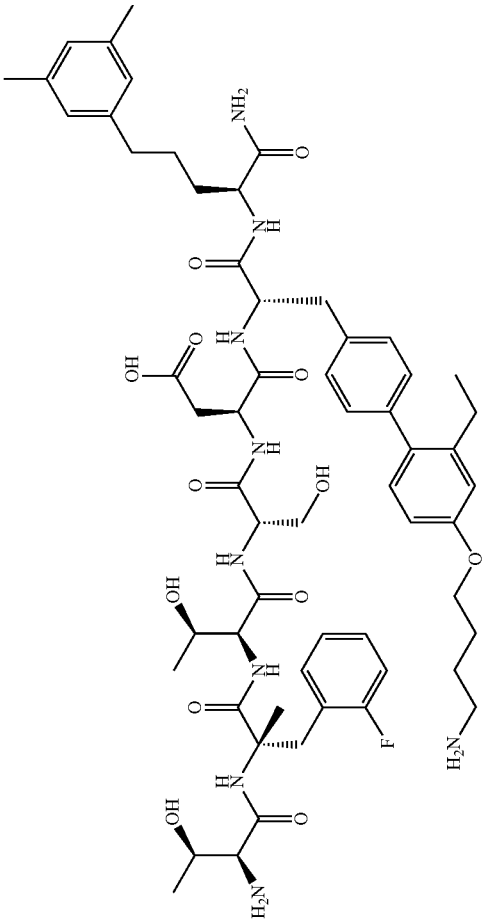 | $C_{59}H_{80}FN_9O_{13}$ | 1141.6 | 572.0 $[M + 2H]^{2+}$ |

TABLE 2B-continued
Intermediates Cleaved from MBHA Resin
| No. | Structure | MF | MW (Cal.) | MS (m/z) |
|---|---|---|---|---|
| 17 (SEQ ID NO: 133) | 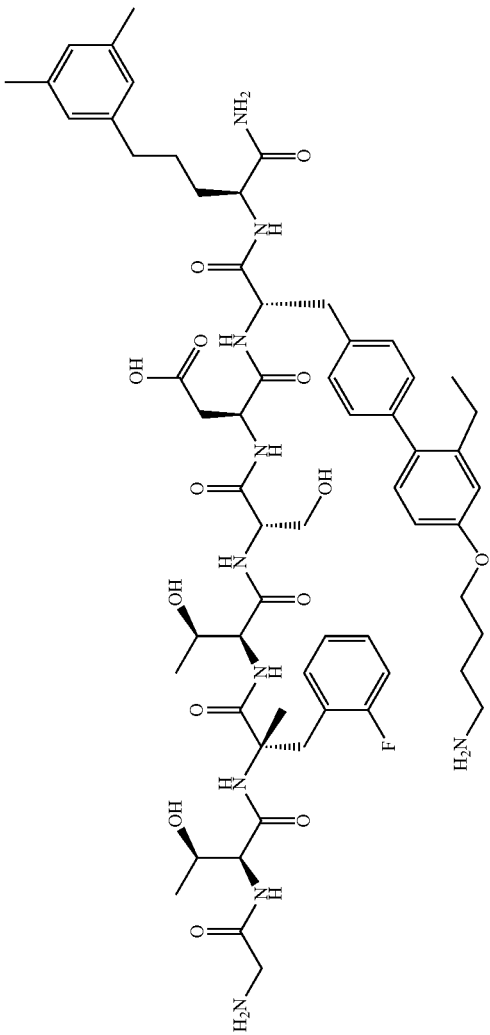 | $C_{61}H_{83}FN_{10}O_{14}$ | 1198.6 | 600.6 $[M + 2H]^{2+}$ |
| 18 (SEQ ID NO: 42) | 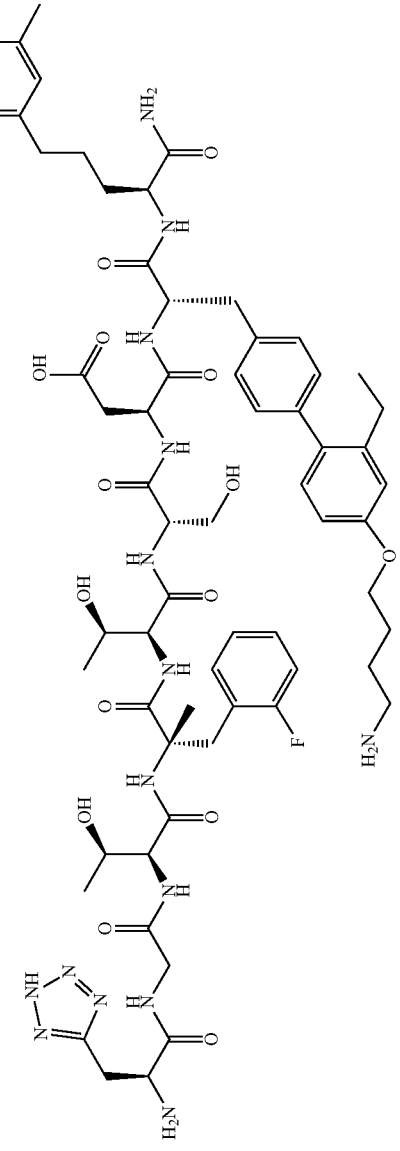 | $C_{65}H_{88}FN_{15}O_{15}$ | 1337.7 | 670.1 $[M + 2H]^{2+}$ |

TABLE 2B-continued
Intermediates Cleaved from MBHA Resin
| No. | Structure | MF | MW (Cal.) | MS (m/z) |
|---|---|---|---|---|
| 19 (SEQ ID NO: 49) | 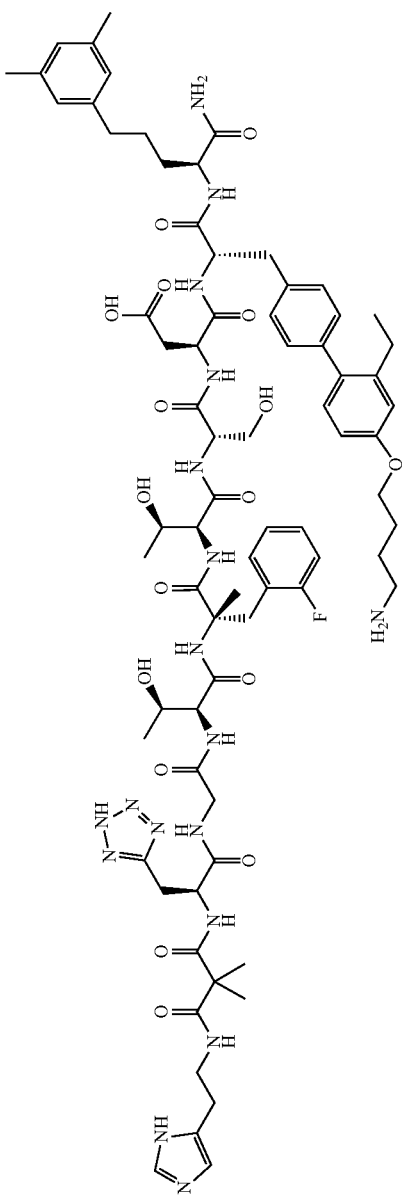 | $C_{75}H_{101}FN_{18}O_{17}$ | 1544.8 | 773.7 $[M+2H]^{2+}$ |
| 20 (SEQ ID NO: 134) | 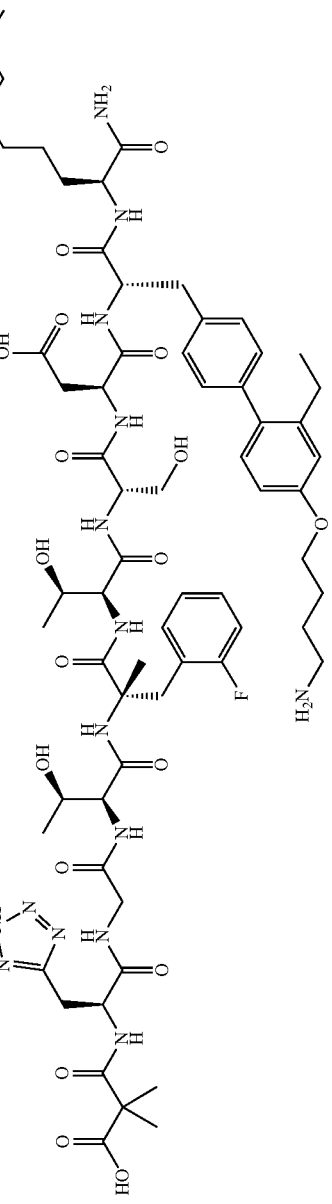 | $C_{70}H_{94}FN_{15}O_{18}$ | 1451.7 | 726.9 $[M+2H]^{2+}$ |

TABLE 2B-continued
Intermediates Cleaved from MBHA Resin
| No. | Structure | MF | MW (Cal.) | MS (m/z) |
|---|---|---|---|---|
| 21 (SEQ ID NO: 135) | 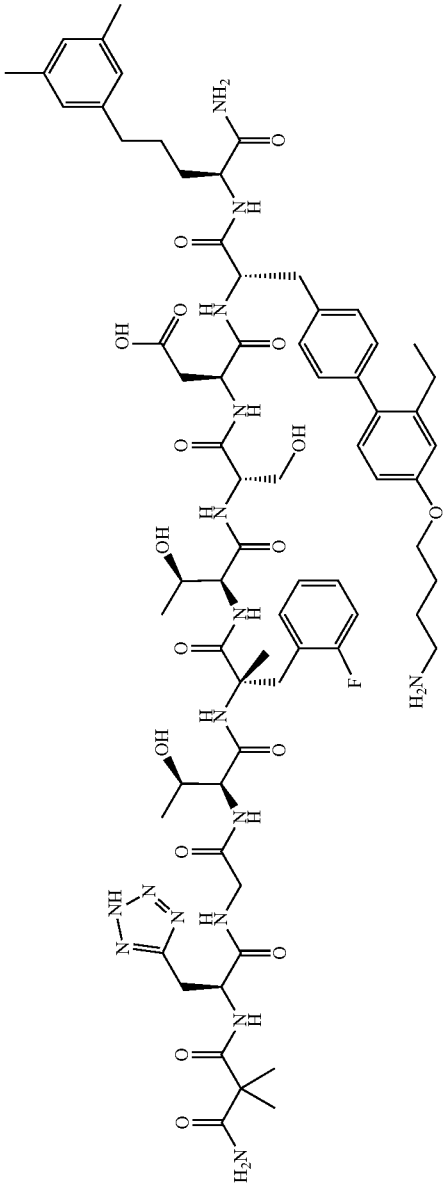 | $C_{70}H_{95}FN_{16}O_{17}$ | 1450.7 | 1452.1 $[M + H]^+$ |
| 22 (SEQ ID NO: 136) | 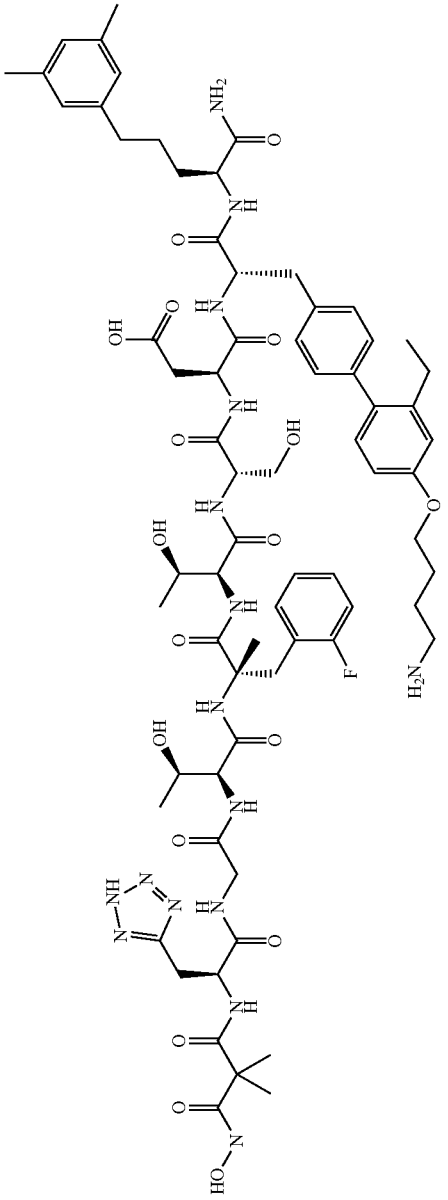 | $C_{70}H_{94}FN_{16}O_{18}$ | 1465.7 | 734.4 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 23 (SEQ ID NO: 137) | 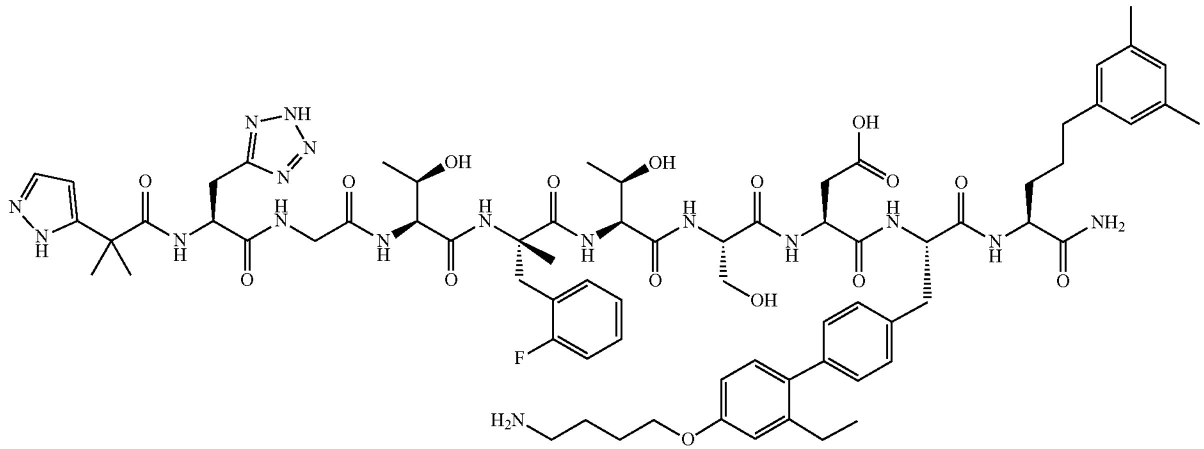 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)c2ccn[nH]2)[C@@H](C)O)[C@@H](C)O)C(=O)N[C@@H](CCCc2cc(C)cc(C)c2)C(N)=O)cc1] | $C_{72}H_{96}FN_{17}O_{16}$ | 1473.7 | 738.2 $[M + 2H]^{2+}$ |
| 24 (SEQ ID NO: 138) | 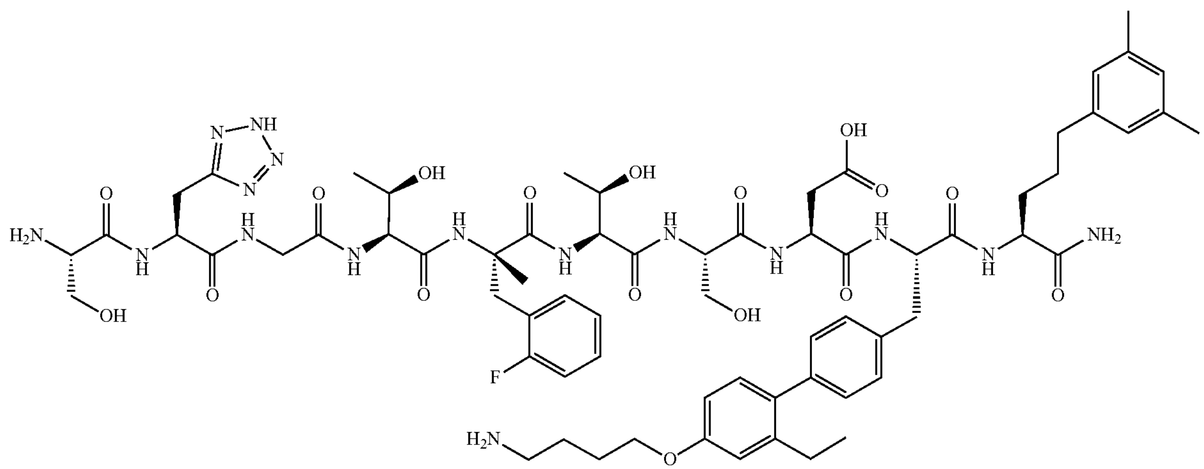 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)[C@@H](N)CO)[C@@H](C)O)[C@@H](C)O)C(=O)N[C@@H](CCCc2cc(C)cc(C)c2)C(N)=O)cc1] | $C_{68}H_{93}FN_{16}O_{17}$ | 1424.7 | 713.8 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 25 (SEQ ID NO: 139) | 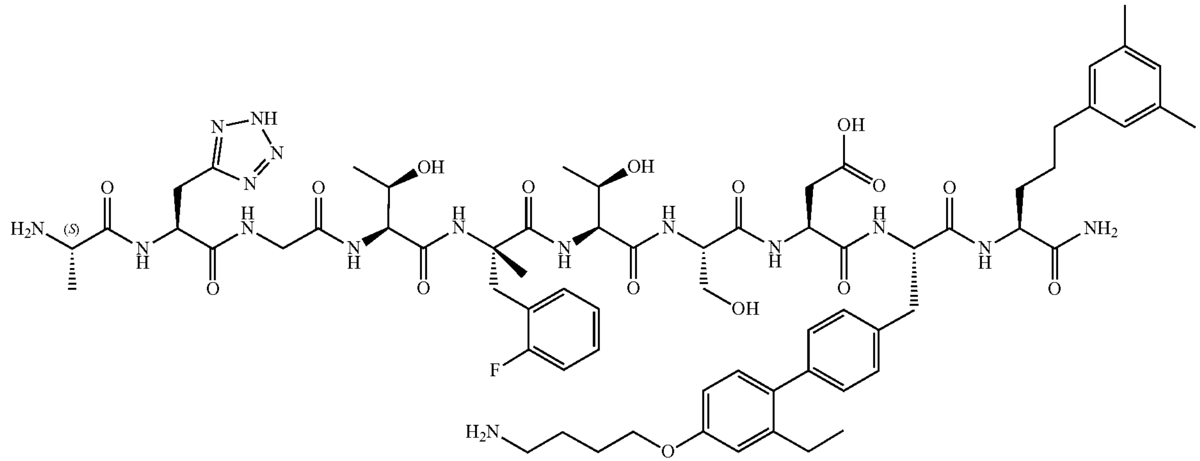 | $C_{68}H_{93}FN_{16}O_{16}$ | 1408.7 | 705.8 $[M + 2H]^{2+}$ |
| 26 (SEQ ID NO: 50) | 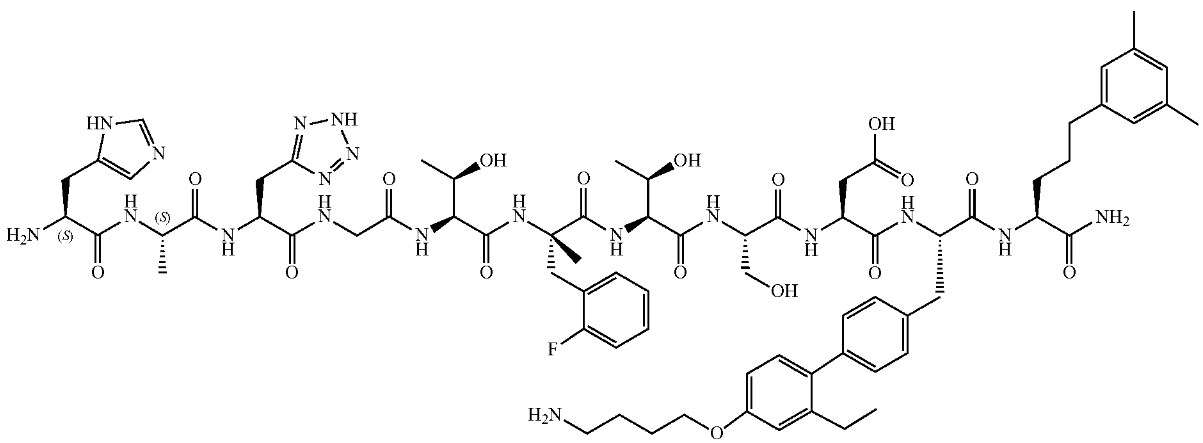 | $C_{74}H_{100}FN_{19}O_{17}$ | 1545.8 | 773.9 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 27 (SEQ ID NO: 51) | 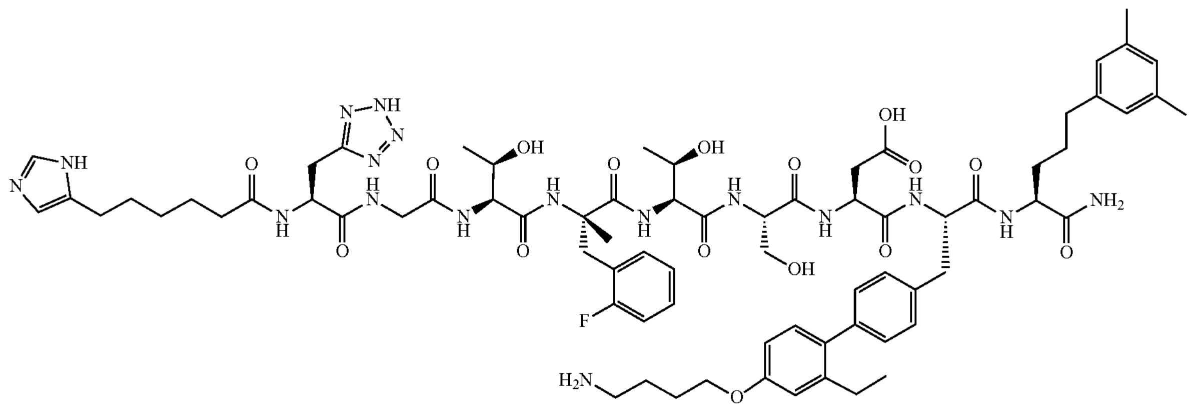 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)CCCCCc2cnc[nH]2)[C@@H](C)O)[C@@H](C)O)C(=O)N[C@@H](CCCc2cc(C)cc(C)c2)C(N)=O)cc1] | $C_{74}H_{100}FN_{17}O_{16}$ | 1501.8 | 752.0 $[M + 2H]^{2+}$ |
| 28 (SEQ ID NO: 140) | 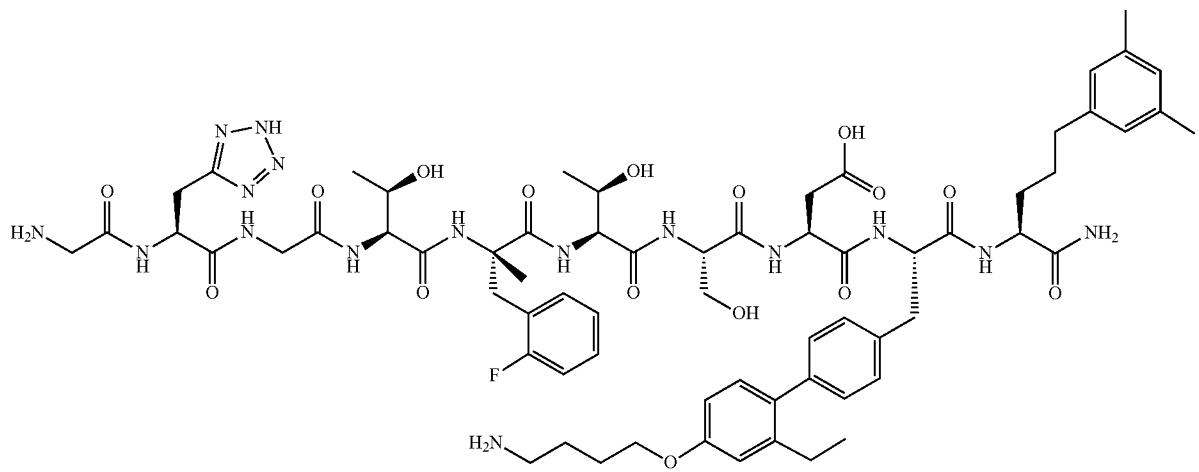 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)CN)[C@@H](C)O)[C@@H](C)O)C(=O)N[C@@H](CCCc2cc(C)cc(C)c2)C(N)=O)cc1] | $C_{67}H_{91}FN_{16}O_{16}$ | 1394.7 | 698.6 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 29 (SEQ ID NO: 52) | 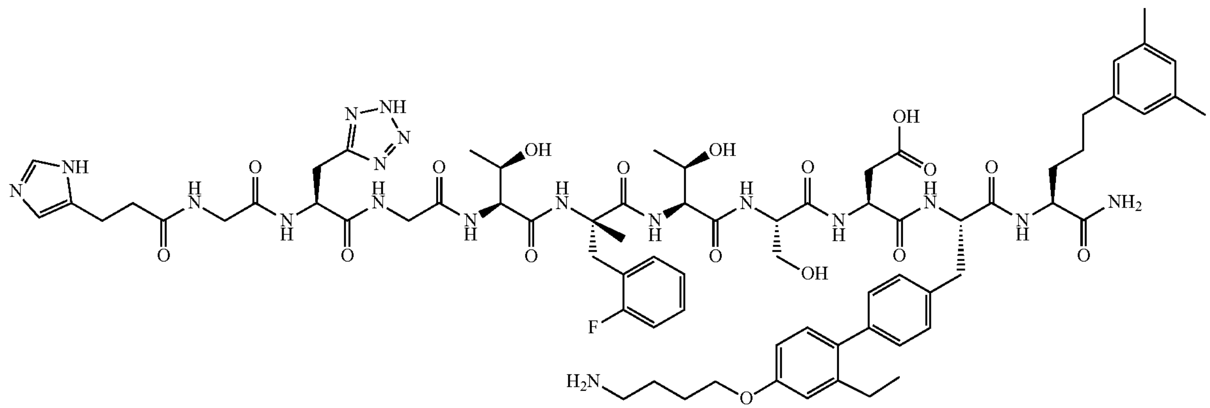 [SMILES: CCc1cc(OCCCCN)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)CNC(=O)CCc2cnc[nH]2)[C@@H](C)O)[C@@H](C)O)C(=O)N[C@@H](CCCc2cc(C)cc(C)c2)C(N)=O)cc1] | $C_{37}H_{97}FN_{18}O_{17}$ | 1516.7 | 759.7 $[M + 2H]^{2+}$ |
| 30 (SEQ ID NO: 53) | 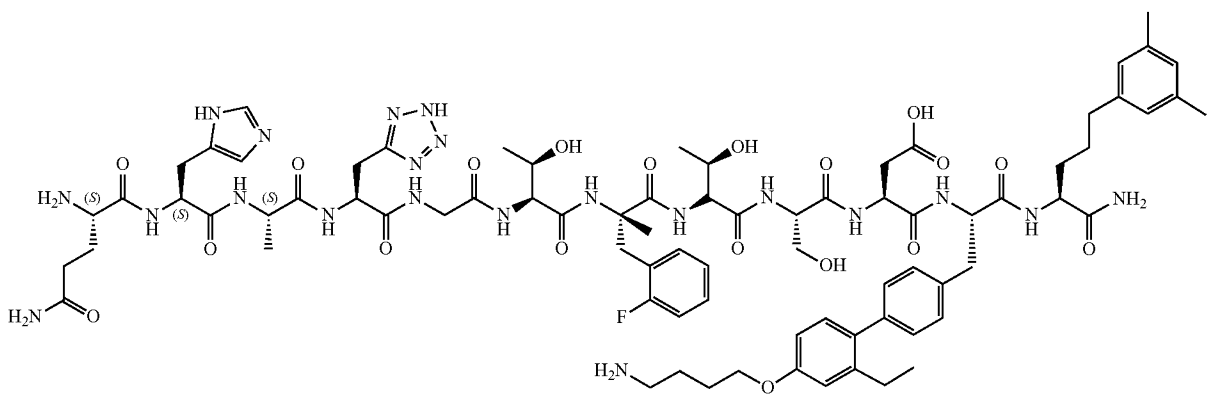 | $C_{79}H_{108}FN_{21}O_{19}$ | 1673.8 | 838.2 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 31 (SEQ ID NO: 54) | 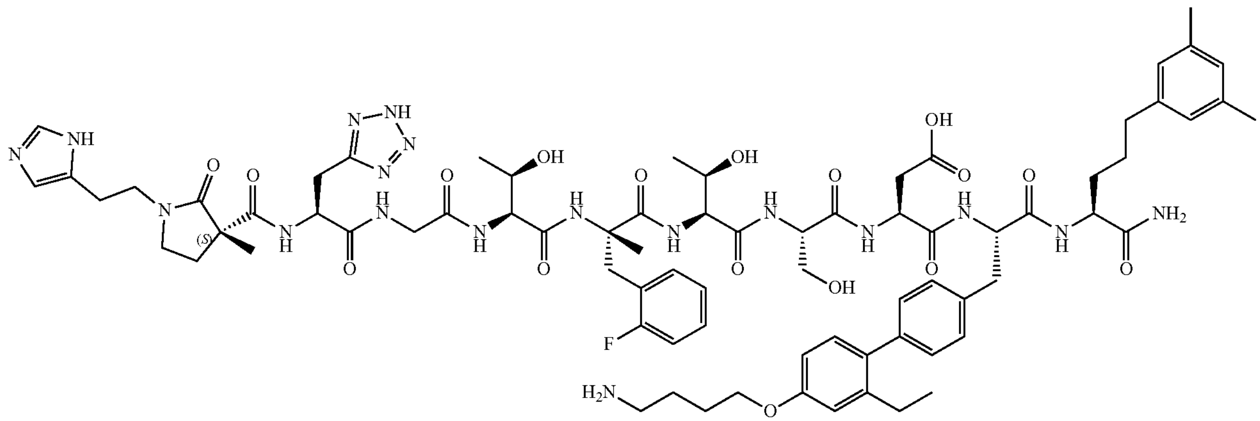 | $C_{76}H_{101}FN_{18}O_{17}$ | 1556.8 | 779.7 $[M + 2H]^{2+}$ |
| 32 (SEQ ID NO: 55) | 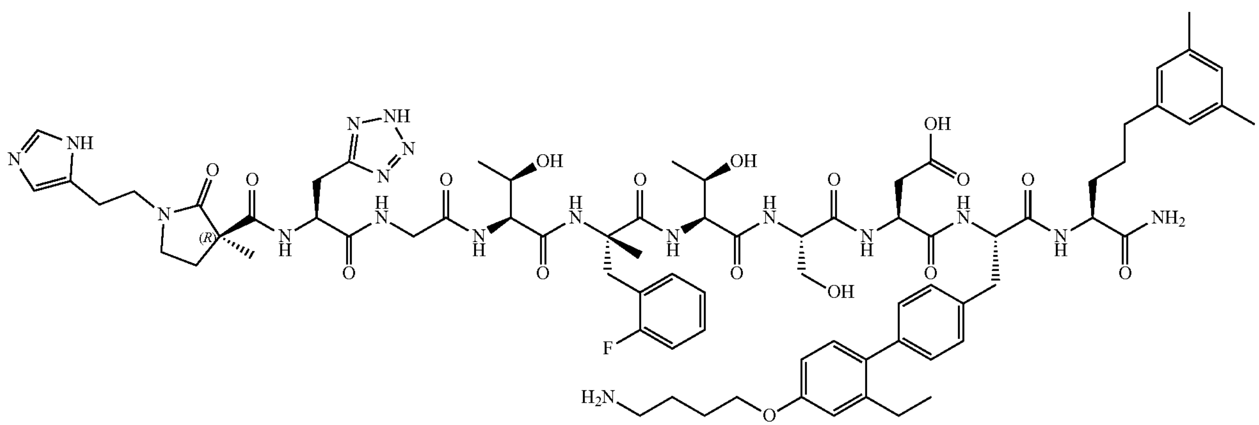 | $C_{76}H_{101}FN_{18}O_{17}$ | 1556.8 | 779.8 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 33 (SEQ ID NO: 56) | 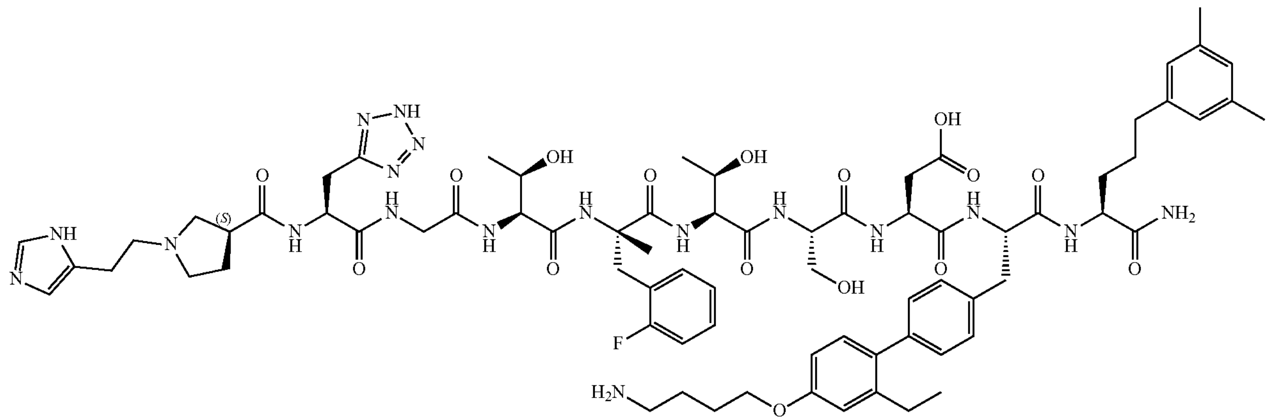 | $C_{75}H_{101}FN_{18}O_{16}$ | 1528.8 | 765.8 $[M + 2H]^{2+}$ |
| 34 (SEQ ID NO: 57) | 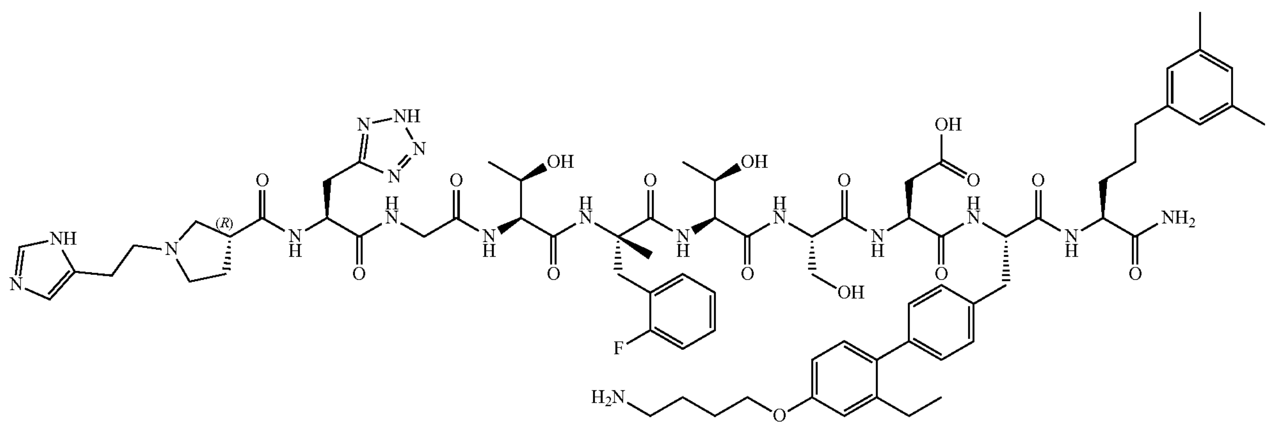 | $C_{75}H_{101}FN_{18}O_{16}$ | 1528.8 | 765.8 $[M + 2H]^{2+}$ |

TABLE 2B-continued
Intermediates Cleaved from MBHA Resin
| No. | Structure | MF | MW (Cal.) | MS (m/z) |
|---|---|---|---|---|
| 35 (SEQ ID NO: 141) | 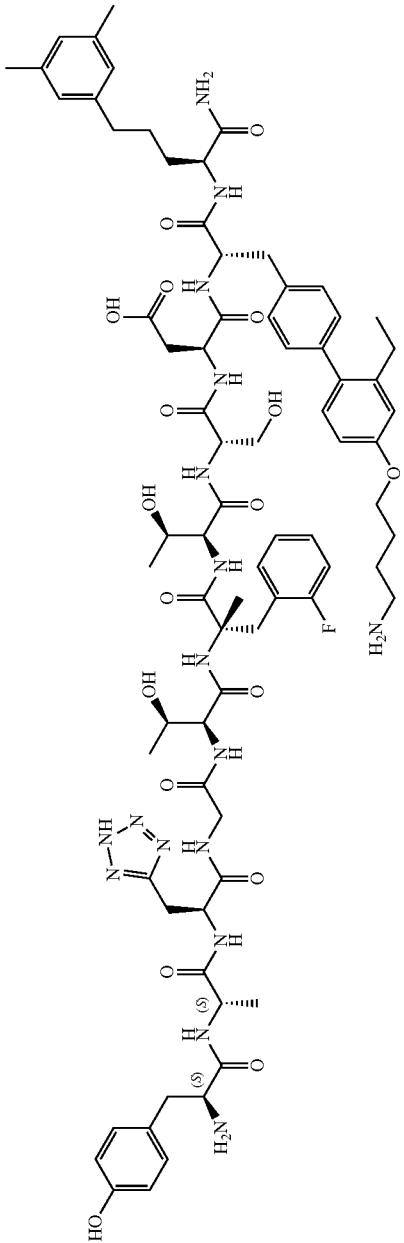 | $C_{77}H_{102}FN_{17}O_{18}$ | 1571.8 | 787.4 $[M + 2H]^{2+}$ |
| 36 (SEQ ID NO: 142) | 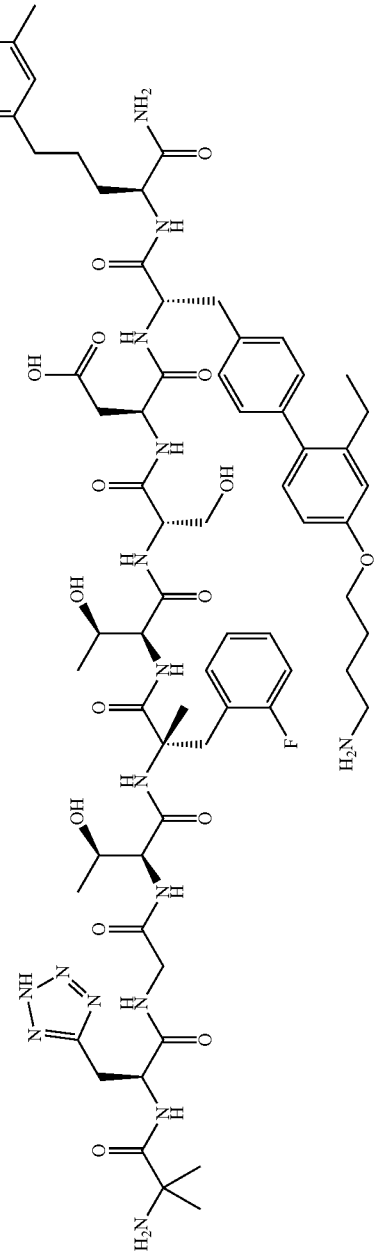 | $C_{69}H_{95}FN_{16}O_{16}$ | 1422.7 | 712.7 $[M + 2H]^{2+}$ |

TABLE 2B-continued
Intermediates Cleaved from MBHA Resin
| No. | Structure | MF | MW (Cal.) | MS (m/z) |
|---|---|---|---|---|
| 36A (SEQ ID NO: 143) | 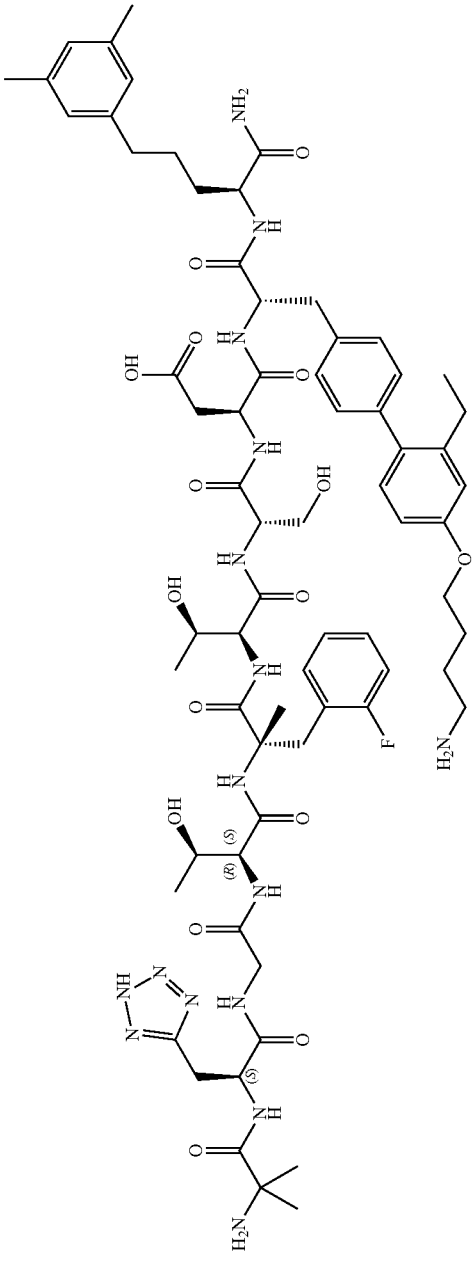 | $C_{69}H_{93}FN_{18}O_{16}$ | 1448.7 | 1450.4 [M + H]+ |
| 37 (SEQ ID NO: 59) | 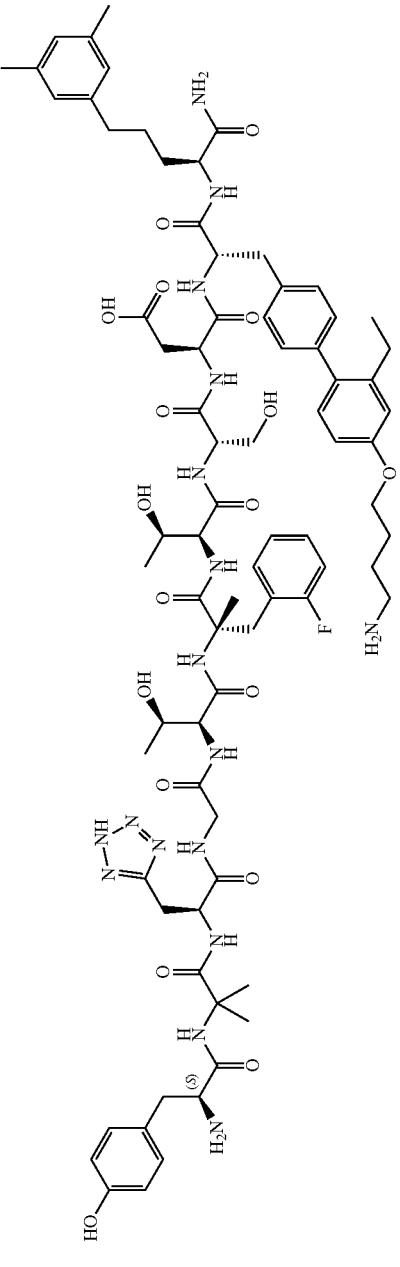 | $C_{78}H_{104}FN_{17}O_{18}$ | 1585.8 | 794.3 [M + 2H]2+ |

TABLE 2B-continued
Intermediates Cleaved from MBHA Resin
| No. | Structure | MF | MW (Cal.) | MS (m/z) |
|---|---|---|---|---|
| 38 (SEQ ID NO: 60) | 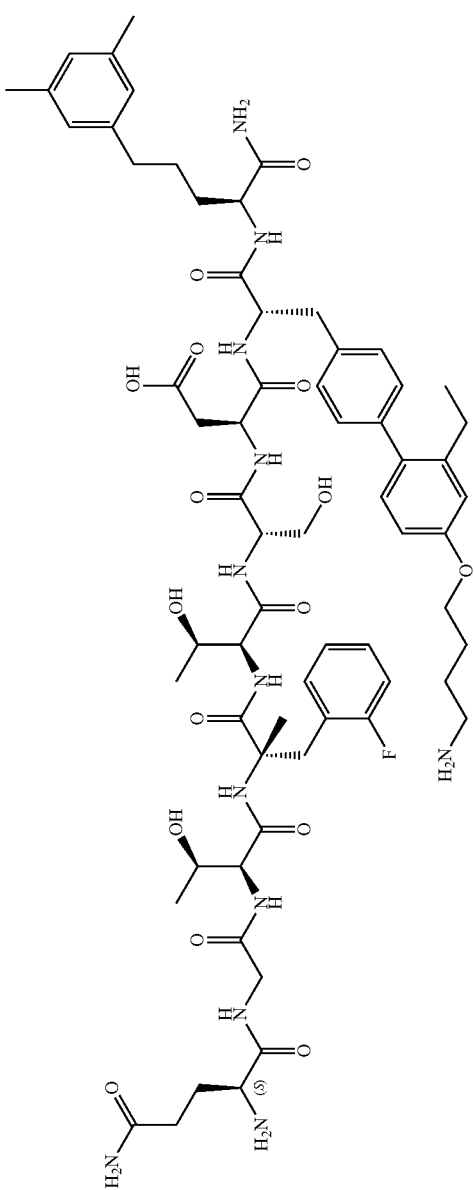 | $C_{66}H_{91}FN_{12}O_{16}$ | 1326.7 | 664.6 $[M + 2H]^{2+}$ |
| 39 (SEQ ID NO: 61) | 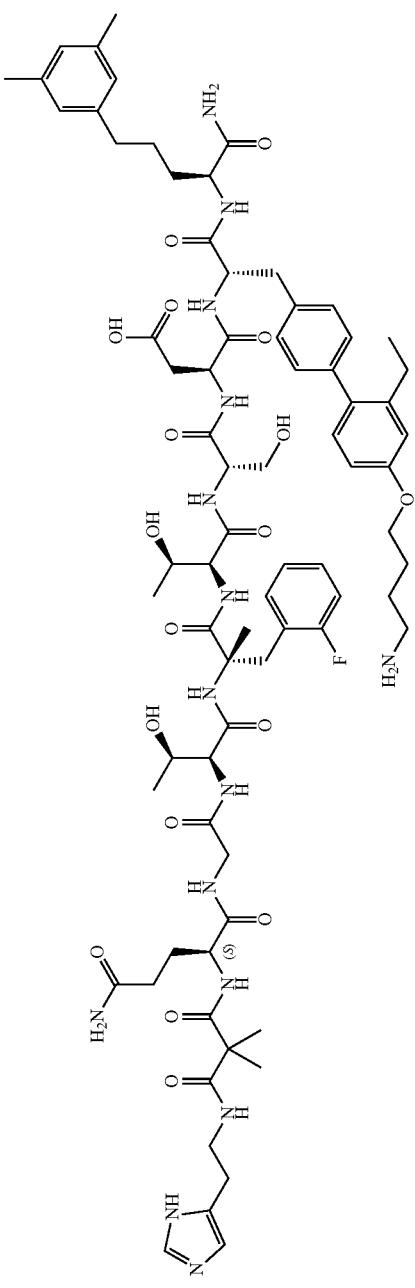 | $C_{76}H_{104}FN_{15}O$ | 1533.8 | 768.3 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 40 | 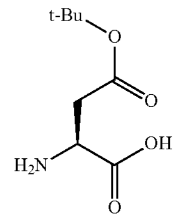 | C₆H₁₅NO₄ | 189.2 | / |
| 41 | 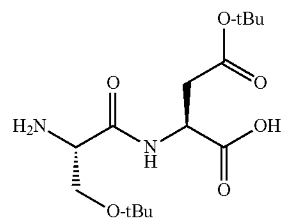 | C₁₅H₂₈N₂O₆ | 332.2 | 333.0 [M + H]⁺ |
| 42 | 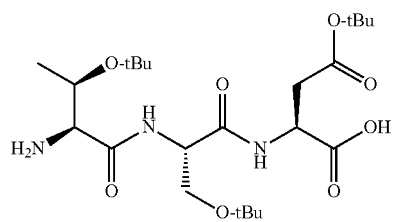 | C₂₃H₄₃N₃O₈ | 489.3 | 490.2 [M + H]⁺ |
| 43 | 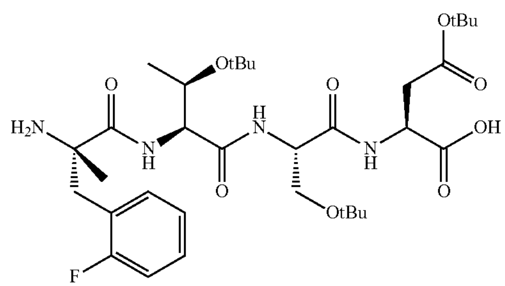 [SMILES: C[C@@H](OC(C)(C)C)[C@H](NC(=O)[C@@](C)(N)Cc1ccccc1F)C(=O)N[C@@H](COC(C)(C)C)C(=O)N[C@@H](CC(=O)OC(C)(C)C)C(=O)O] | C₃₃H₅₃FN₄O₉ | 668.4 | 669.3 [M + H]⁺ |

TABLE 2B-continued

Intermediates Cleaved from MBHA Resin

| No. | Structure | MF | MW (Cal.) | MS (m/z) |
|---|---|---|---|---|
| 44 | 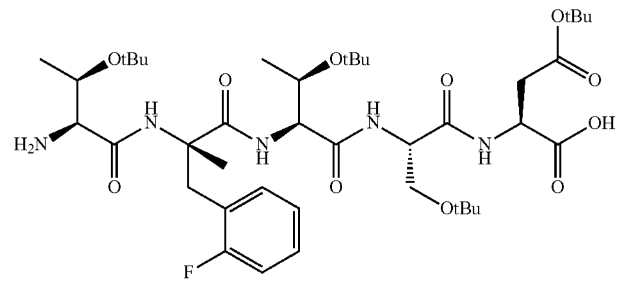 [SMILES: C[C@@H](OC(C)(C)C)[C@H](N)C(=O)N[C@@](C)(Cc1ccccc1F)C(=O)N[C@H](C(=O)N[C@@H](COC(C)(C)C)C(=O)N[C@@H](CC(=O)OC(C)(C)C)C(=O)O)[C@@H](C)OC(C)(C)C] | $C_{41}H_{68}FN_5O_{11}$ | 825.5 | 826.5 $[M + H]^+$ |
| 45 | 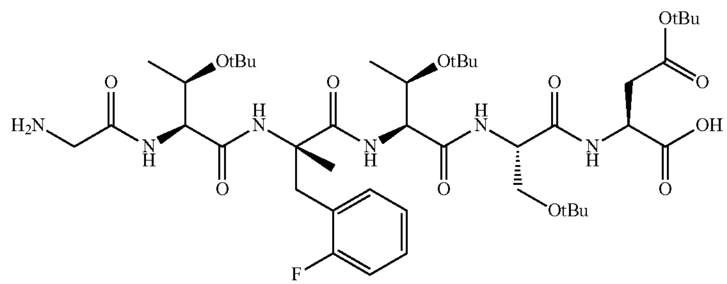 [SMILES: C[C@@H](OC(C)(C)C)[C@H](NC(=O)CN)C(=O)N[C@@](C)(Cc1ccccc1F)C(=O)N[C@H](C(=O)N[C@@H](COC(C)(C)C)C(=O)N[C@@H](CC(=O)OC(C)(C)C)C(=O)O)[C@@H](C)OC(C)(C)C] | $C_{43}H_{71}FN_6O_{12}$ | 882.5 | 883.4 $[M + H]^+$ |
| 46 | 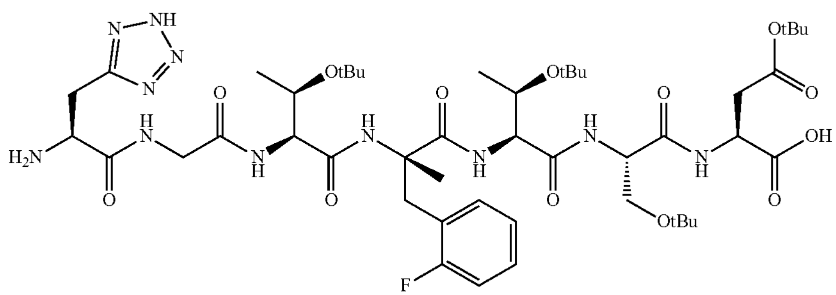 [SMILES: C[C@@H](OC(C)(C)C)[C@H](NC(=O)CNC(=O)[C@@H](N)Cc1nn[nH]n1)C(=O)N[C@@](C)(Cc1ccccc1F)C(=O)N[C@H](C(=O)N[C@@H](COC(C)(C)C)C(=O)N[C@@H](CC(=O)OC(C)(C)C)C(=O)O)[C@@H](C)OC(C)(C)C] | $C_{47}H_{76}FN_{11}O_{13}$ | 1021.6 | 1022.5 $[M + H]^+$ |

TABLE 2B-continued

Intermediates Cleaved from MBHA Resin

| No. | Structure | MF | MW (Cal.) | MS (m/z) |
|---|---|---|---|---|
| 47 | 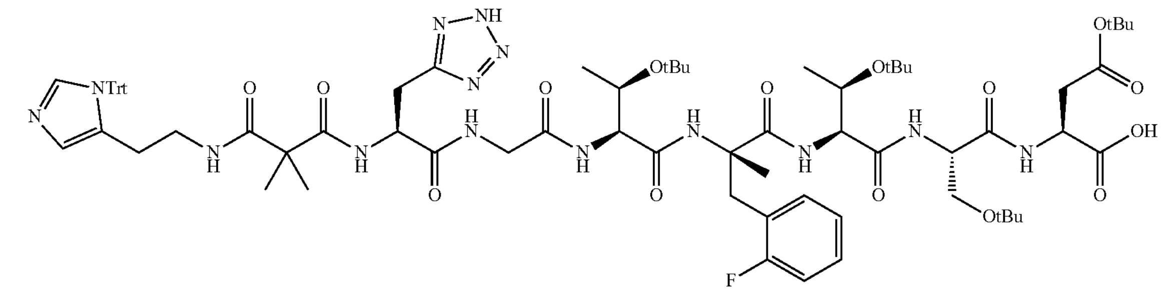 | $C_{76}H_{103}FN_{14}O_{15}$ | 1470.8 | 1471.8 $[M + H]^+$ |
| 48 | 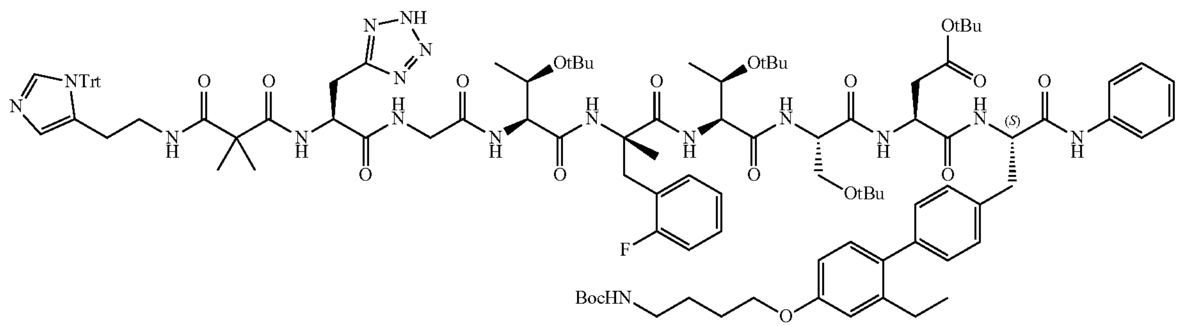 | $C_{108}H_{142}FN_{17}O_{18}$ | 1984.1 | 993.8 $[M + 2H]^{2+}$ |
| 49 | 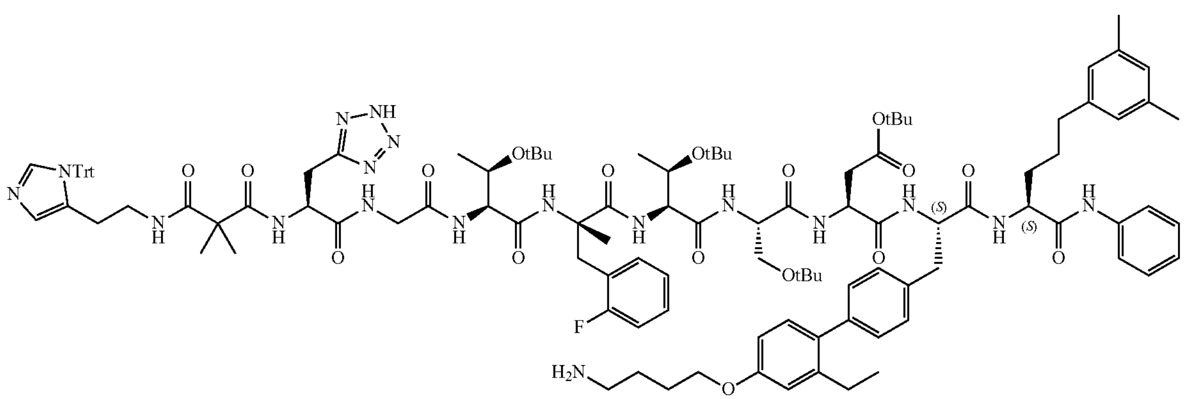 | $C_{116}H_{151}FN_{18}O_{17}$ | 2087.1 | 1044.8 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 50 | 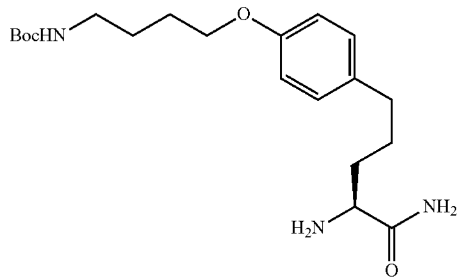 [SMILES: CC(C)(C)OC(=O)NCCCCOc1ccc(CCC[C@H](N)C(N)=O)cc1] | $C_{20}H_{33}N_3O_4$ | 379.5 | / |
| 51 | 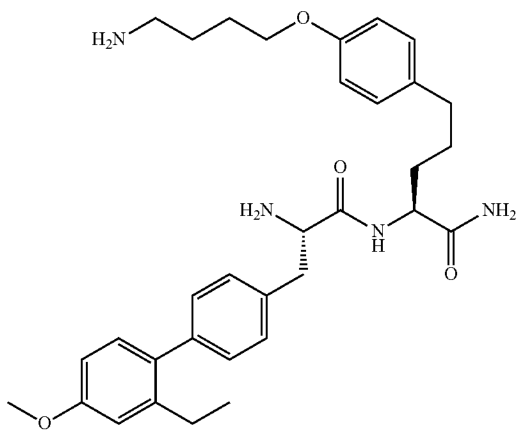 [SMILES: CCc1cc(OC)ccc1-c1ccc(C[C@H](N)C(=O)N[C@@H](CCCc2ccc(OCCCCN)cc2)C(N)=O)cc1] | $C_{33}H_{44}N_4O_4$ | 560.3 | 583.3 [M + Na]$^+$ |

TABLE 2B-continued

Intermediates Cleaved from MBHA Resin

| No. | Structure | MF | MW (Cal.) | MS (m/z) |
|---|---|---|---|---|
| 52 | 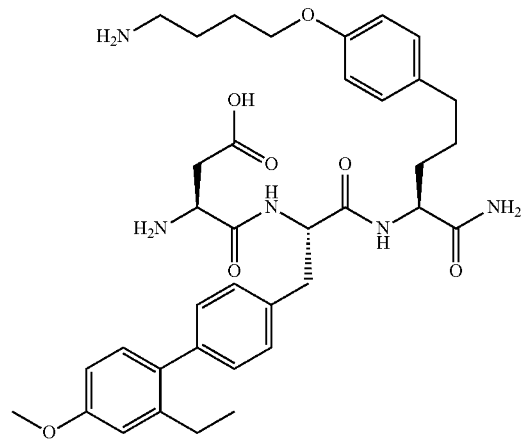 [SMILES: CCc1cc(OC)ccc1-c1ccc(C[C@H](NC(=O)[C@@H](N)CC(=O)O)C(=O)N[C@@H](CCCc2ccc(OCCCCN)cc2)C(N)=O)cc1] | $C_{37}H_{49}N_5O_7$ | 675.4 | 676.1 [M + H]$^+$ |
| 53 | 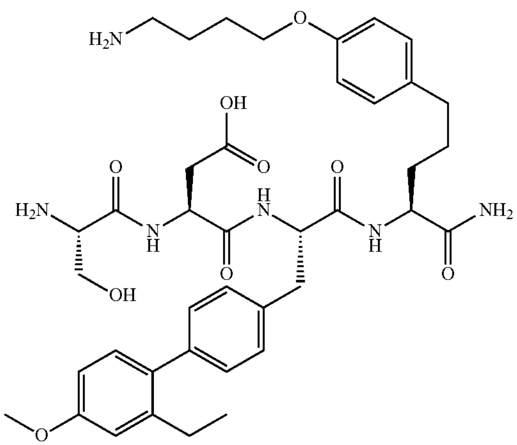 [SMILES: CCc1cc(OC)ccc1-c1ccc(C[C@H](NC(=O)[C@H](CC(=O)O)NC(=O)[C@@H](N)CO)C(=O)N[C@@H](CCCc2ccc(OCCCCN)cc2)C(N)=O)cc1] | $C_{40}H_{54}N_6O_9$ | 762.4 | 763.4 [M + H]$^+$ |

TABLE 2B-continued
Intermediates Cleaved from MBHA Resin
| No. | Structure | MF | MW (Cal.) | MS (m/z) |
|---|---|---|---|---|
| 54 | 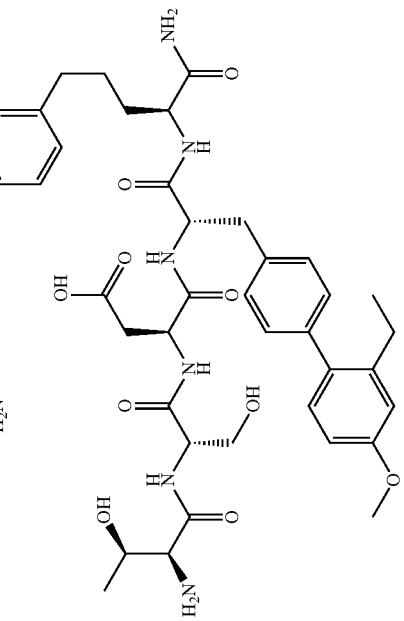 | $C_{44}H_{61}N_7O_{11}$ | 863.4 | 864.4 $[M + H]^+$ |
| 55 | 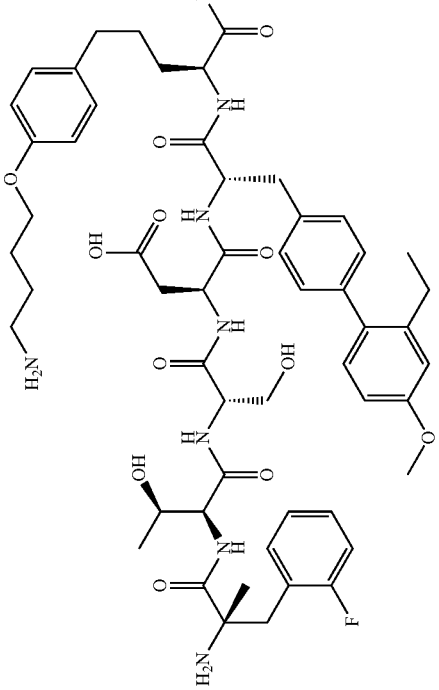 | $C_{54}H_{71}FN_8O_{12}$ | 1042.5 | 522.5 $[M + 2H]^{2+}$ |

TABLE 2B-continued
Intermediates Cleaved from MBHA Resin
| No. | Structure | MF | MW (Cal.) | MS (m/z) |
|---|---|---|---|---|
| 56 | 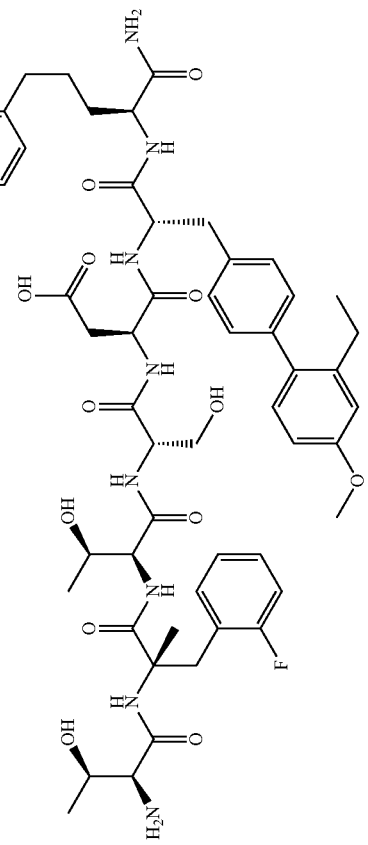 | $C_{58}H_{78}FN_9O_{14}$ | 1143.6 | 573.0 $[M + 2H]^{2+}$ |
| 57 (SEQ ID NO: 144) | 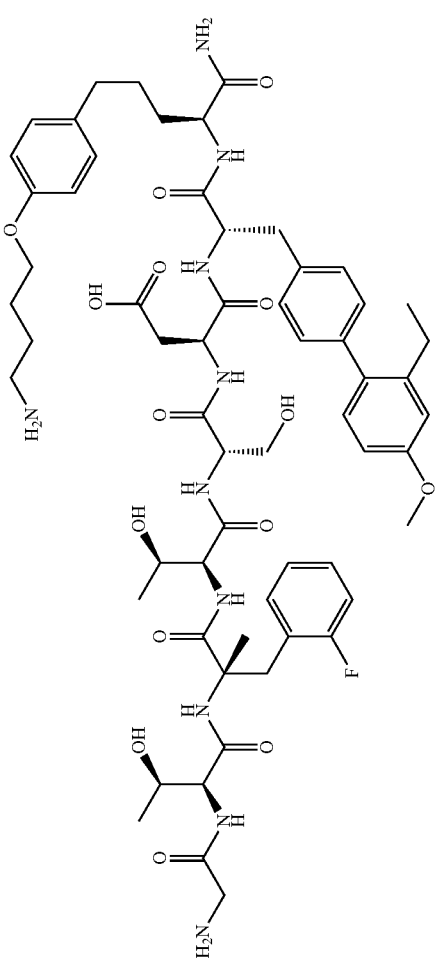 | $C_{60}H_{81}FN_{10}O_{15}$ | 1200.6 | 601.5 $[M + 2H]^{2+}$ |

TABLE 2B-continued

Intermediates Cleaved from MBHA Resin

| No. | Structure | MF | MW (Cal.) | MS (m/z) |
|---|---|---|---|---|
| 58 (SEQ ID NO: 145) | 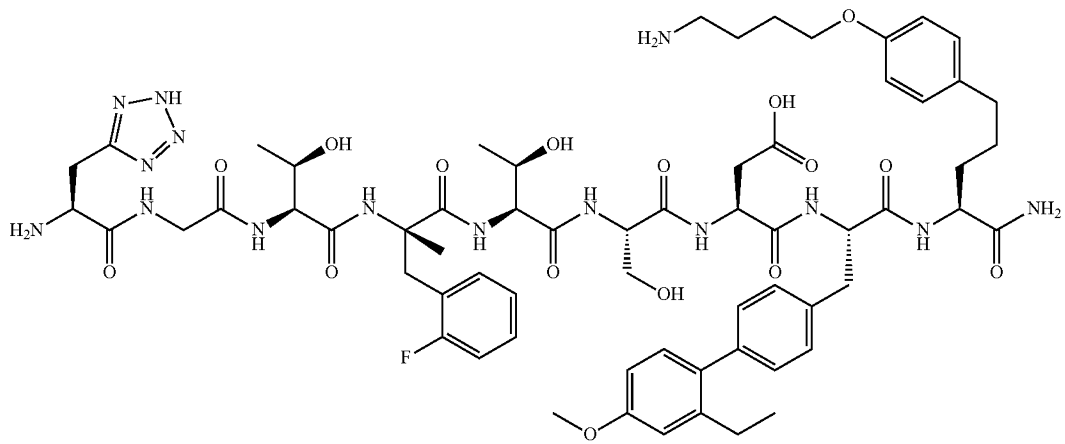 [SMILES: CCc1cc(OC)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@@H](N)Cc2nn[nH]n2)[C@@H](C)O)[C@@H](C)O)C(=O)N[C@@H](CCCc2ccc(OCCCCN)cc2)C(N)=O)cc1] | $C_{64}H_{86}FN_{15}O_{16}$ | 1339.6 | 671.0 $[M + 2H]^{2+}$ |
| 59 (SEQ ID NO: 64) | 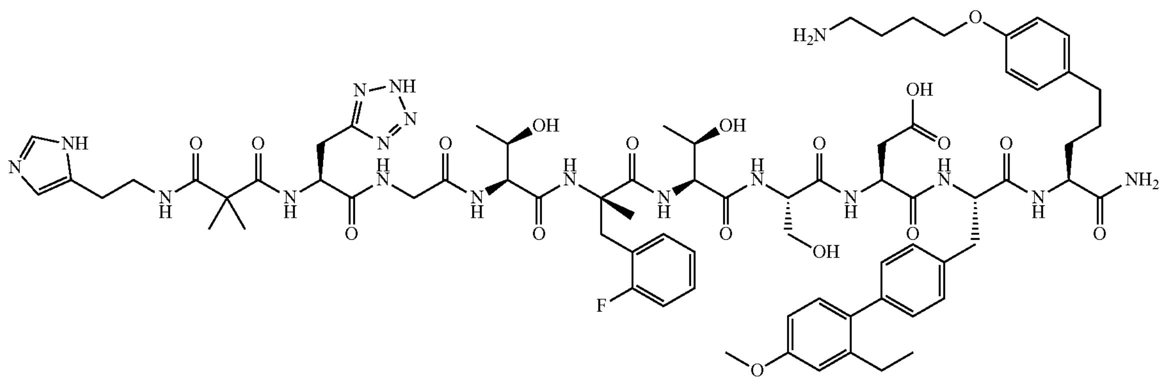 [SMILES: CCc1cc(OC)ccc1-c1ccc(C[C@H](NC(=O)[C@H](CC(=O)O)NC(=O)[C@H](CO)NC(=O)[C@@H](NC(=O)[C@](C)(Cc2ccccc2F)NC(=O)[C@@H](NC(=O)CNC(=O)[C@H](Cc2nn[nH]n2)NC(=O)C(C)(C)C(=O)NCCc2cnc[nH]2)[C@@H](C)O)[C@@H](C)O)C(=O)N[C@@H](CCCc2ccc(OCCCCN)cc2)C(N)=O)cc1] | $C_{74}H_{99}FN_{18}O_{18}$ | 1546.7 | 774.6 $[M + 2H]^{2+}$ |

Figure 14:
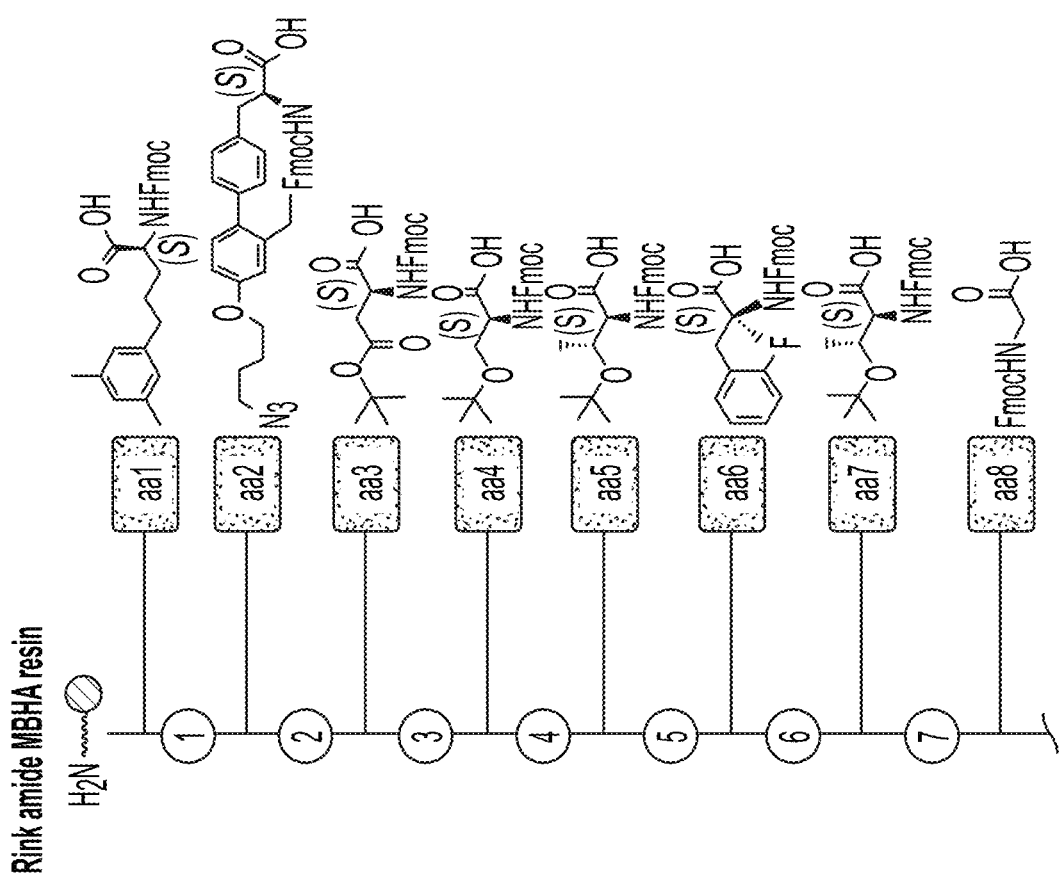
FIG. 14 shows a sequence for solid-supported synthesis of GLP1 peptidomimetic payloads P1 and P8 according to the disclosure.
Figure 14:
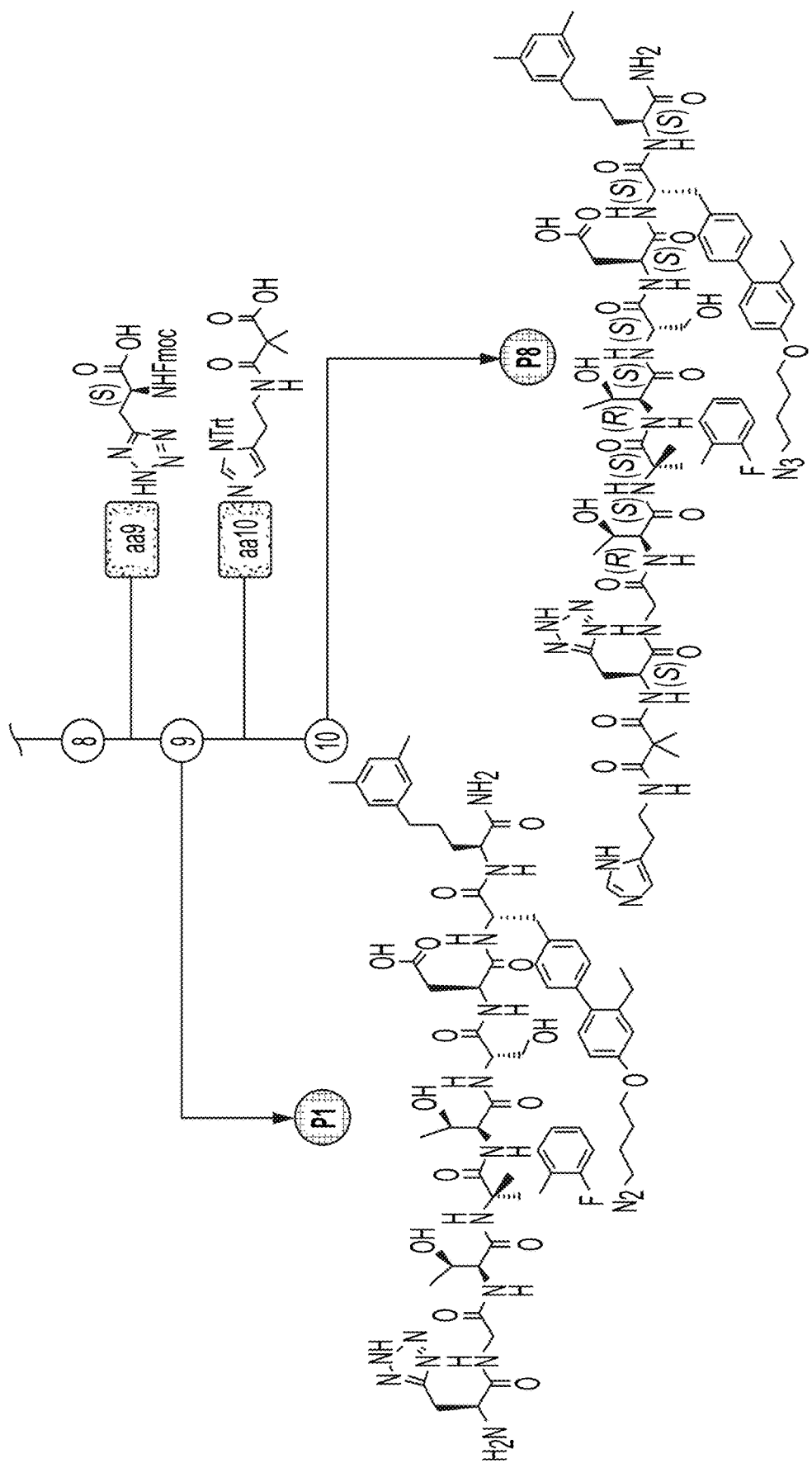

FIG. 14 depicts the sequence of steps for solid support synthesis of GLP1 peptidomimetic payloads P1 and P8 according to the disclosure.

3.1 Preparation of (3S,6S,9R,12S,15S,21S)-21-amino-3-(((S)-1-(((S)-1-amino-5-(3,5-dimethylphenyl)-1-oxopentan-2-yl)amino)-3-(4'-(4-aminobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-12-methyl-5,8,11,14,17,20-hexaoxo-22-(2H-tetrazol-5-yl)-4,7,10,13,16,19-hexaazadocosan-1-oic acid (P1)

The corresponding Fmoc-protected aa9-aa8-aa7-aa6-aa5-aa4-aa3-aa2-aa1 peptidyl Rink Amide MBHA Resin (9, 16.59 μmol) was prepared as described in the general procedure of SPPS. The resin-bound peptide 9 was cleaved following the general procedure to give the crude product as a white solid. This crude product was dissolved in DMF (1 mL), and piperidine (14.13 mg, 165.94 μmol, 16.39 μL, 10.0 eq.) was added in one portion at 20° C. under nitrogen. The mixture was stirred at 20° C. for 2 hours. The mixture was concentrated in vacuum to give the residue. The residue was purified by prep-HPLC (column: mobile phase: [water (0.1% TFA)-ACN]; B %: 30%-60%, 60 min) to afford pure product. The product was suspended in water (10 mL), the mixture frozen in a dry-ice/ethanol bath, and then lyophilized to dryness to afford the desired product P1 (1.02 mg, 7.48e-1 μmol, 4.50% yield, 100% purity) as a white solid. HRMS (ESI): mass calcd. for $C_{65}H_{87}FN_{17}O_{15}$ 1364.6552, m/z found 1364.4887 $[M+H]^+$.

HPLC: RT=10.15 min, Reverse phase HPLC was carried out using a MERCK, RP-18e 25-2 mm column, with a flow rate of 1.2 mL/min, eluting with a gradient of 10% to 80% acetonitrile containing 0.02% TFA (solvent B) and water containing 0.04% TFA (solvent A). 3.2 Preparation of (8S,14S,17S,20S,23S,26S)-8-((2H-tetrazol-5-yl)methyl)-26-(((S)-1-(((S)-1-amino-5-(3,5-dimethylphenyl)-1-oxopentan-2-yl)amino)-3-(4'-(4-aminobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13,16,19,22,25-octaazaoctacosan-28-oic acid (P8)

The corresponding aa10-aa9-aa8-aa7-aa6-aa5-aa4-aa3-aa2-aa1 peptidyl Rink Amide MBHA Resin (10, 100.99 μmol) was assembled as described in the general procedure of SPPS. The resin-bound peptide 10 was cleaved following the general procedure to give the crude product as a white solid. The crude was purified by preparative HPLC using column: Luna 200*25 mm, C18, 10 μm; mobile phase: [water (0.1% TFA)-ACN]; B %: 30%-60%, 60 min to afford pure product. The product was suspended in water (10 mL), the mixture frozen in a dry-ice/acetone bath, and then lyophilized to dryness to afford the desired product P8 (25.00 mg, 17.49 μmol, 17.32% yield, 100% purity) as a white solid.

HRMS (ESI): mass calcd for $C_{75}H_{100}FN_{20}O_{17}$ 1571.7559, m/z found 1571.7589 $[M+H]^+$.

HPLC: RT=10.14 min. Reverse phase HPLC was carried out using a YMC-Pack ODS-A 150*4.6 mm, 5 μm column, with a flow rate of 1.5 mL/min, eluting with a gradient of 10% to 80% acetonitrile containing 0.062% TFA (solvent B) and water containing 0.068% TFA (solvent A).

Figure 15:
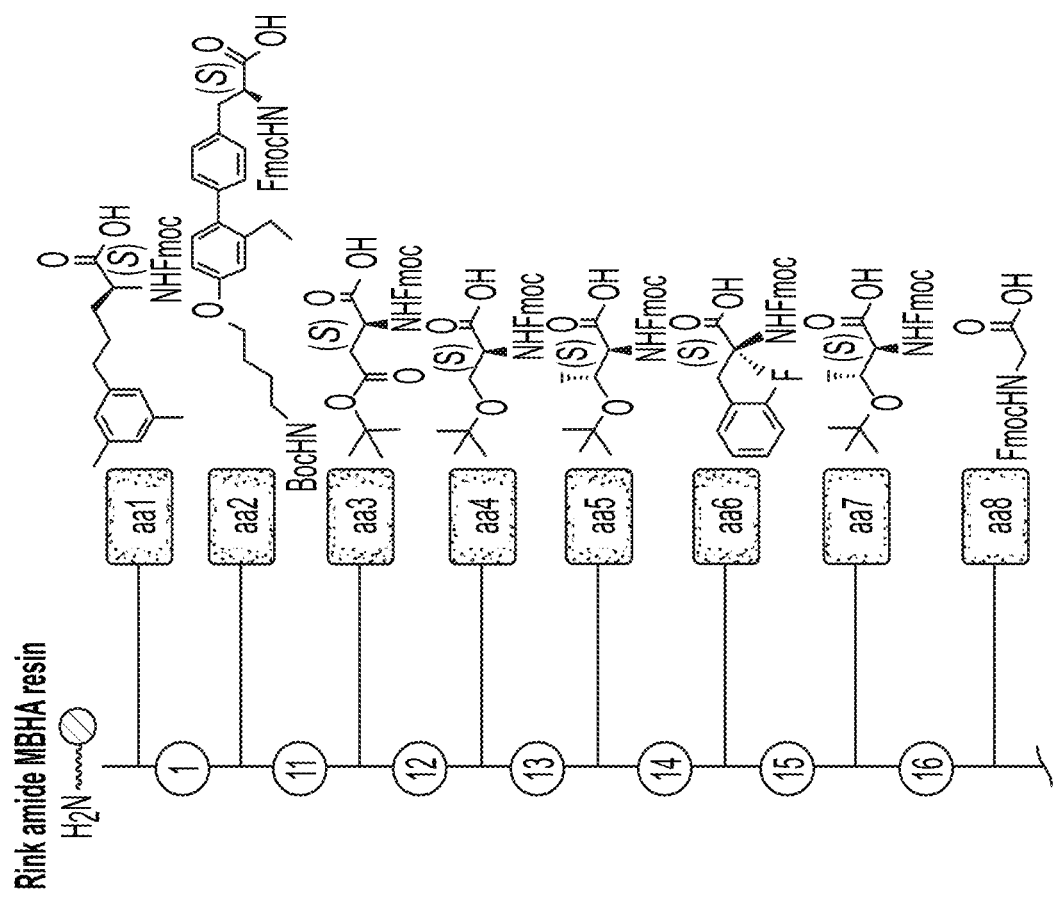
FIG. 15 shows a sequence for solid-supported synthesis of GLP1 peptidomimetic payloads P2 and P9 according to the disclosure.
Figure 15:
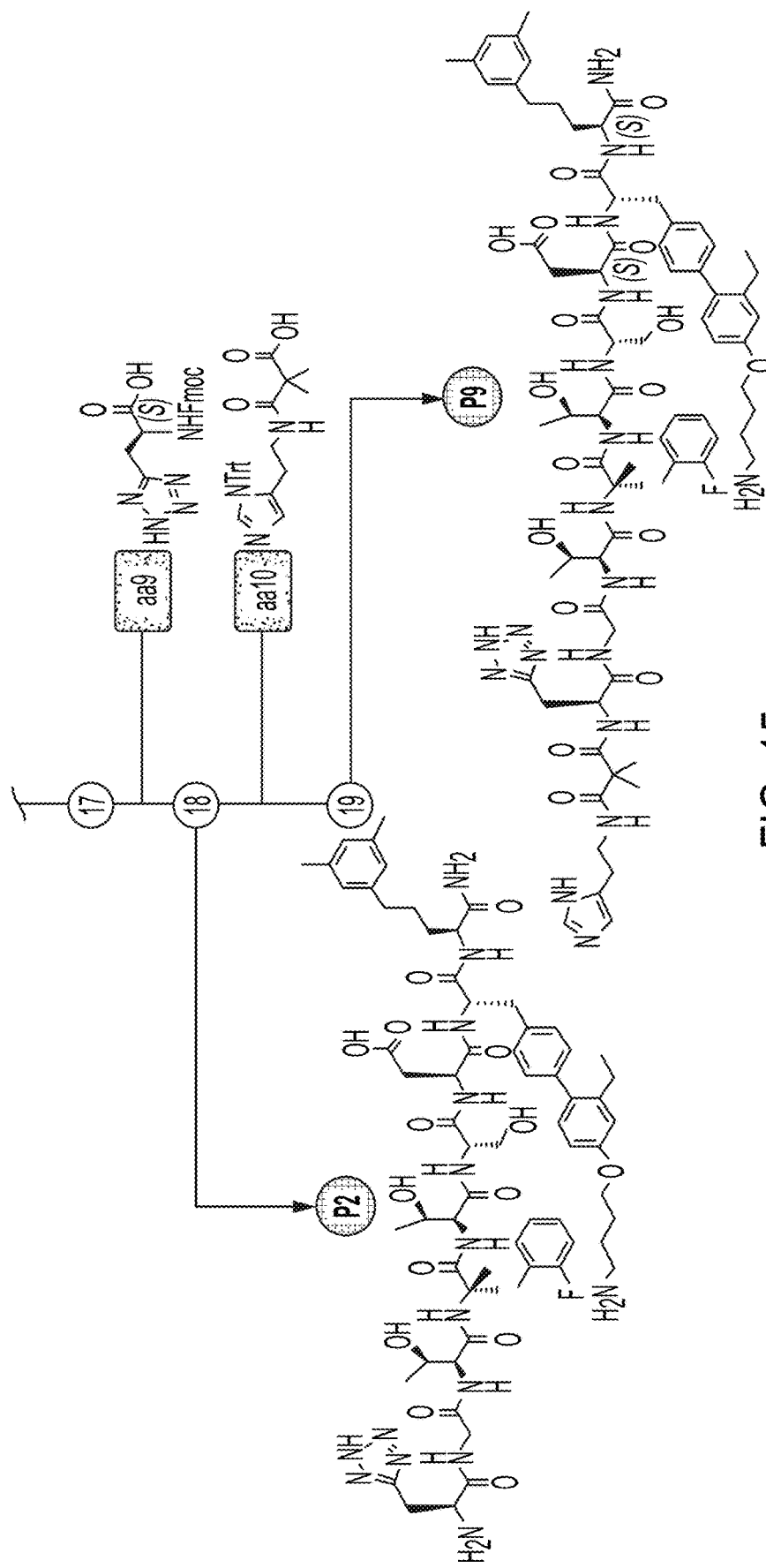

FIG. 15 depicts the sequence of steps for solid support synthesis of GLP1 peptidomimetic payloads P2 and P9 according to the disclosure.

3.3 Preparation of (8S,14S,17S,20S,23S,26S)-8-((2H-tetrazol-5-yl)methyl)-26-(((S)-1-(((S)-1-amino-5-(3,5-dimethylphenyl)-1-oxopentan-2-yl)amino)-3-(4'-(4-aminobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13, 16,19,22,25-octaazaoctacosan-28-oic acid (P2)

The corresponding aa9-aa8-aa7-aa6-aa5-aa4-aa3-aa2b-aa1 peptidyl Rink Amide MBHA Resin (18, 74.75 μmol) was prepared as described in the general procedure of SPPS. The resin-bound peptide 18 was cleaved following the general procedure to give the crude product as a white solid. The crude product was sent to prep-HPLC (column: mobile phase: [water (0.1% TFA)-ACN];B %: 20%-50%, 60 min) to afford pure product. The product was suspended in water (100 mL), the mixture frozen in a dry-ice/acetone bath, and then lyophilized to dryness to afford the desired product P2 (11.56 mg, 8.45 μmol, 11.27% yield, 97.84% purity) was obtained as a white solid.

LCMS (ESI): RT=0.830 min, mass calcd. for $C_{65}H_{88}FN_{15}O_{15}$ 1337.66 $[M-4tBu-Boc+6H]+669.83$ $[M-4tBu-Boc+7H]2+$, found 670.0 $[M-4tBu-Boc+7H]2+$. Reverse phase LC-MS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

HPLC: RT=7.77 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 μm; Wavelength: UV 220 nm&215 nm&254 nm; Column temperature: 40° C.

3.4 Preparation of (8S,14S,17S,20S,23S,26S)-8-((2H-tetrazol-5-yl)methyl)-26-(((S)-1-(((S)-1-amino-5-(3,5-dimethylphenyl)-1-oxopentan-2-yl)amino)-3-(4'-(4-aminobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13, 16,19,22,25-octaazaoctacosan-28-oic acid (P9)

The corresponding aa10-aa9-aa8-aa7-aa6-aa5-aa4-aa3-aa2b-aa1 peptidyl Rink Amide MBHA Resin (19) was prepared as described in the general procedure of SPPS. The resin-bound peptide 19 was cleaved following the general procedure to give the crude product as a white solid. The crude product was sent to prep-HPLC (TFA: mobile phase: [water (0.075% TFA)-ACN]; B %: 15%-45%, 55 min) to afford pure product. The product was suspended in water (20 mL), the mixture frozen in a dry-ice/acetone bath, and then lyophilized to dryness to afford the desired product P9 (125 mg, 79.82 μmol, 7.70% yield, 98.7% purity) was obtained as a white solid.

LCMS (ESI): RT=0.843 min, mass calcd. for $C_{75}H_{102}FN_{18}O17$ 1545.77 $[M-4tBu-Boc+6H]^+773.385$ $[M-4tBu-Boc+7H]2+$, found 773.9 $[M-4tBu-Boc+7H]2+$.

Reverse phase LC-MS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

Figure 16:
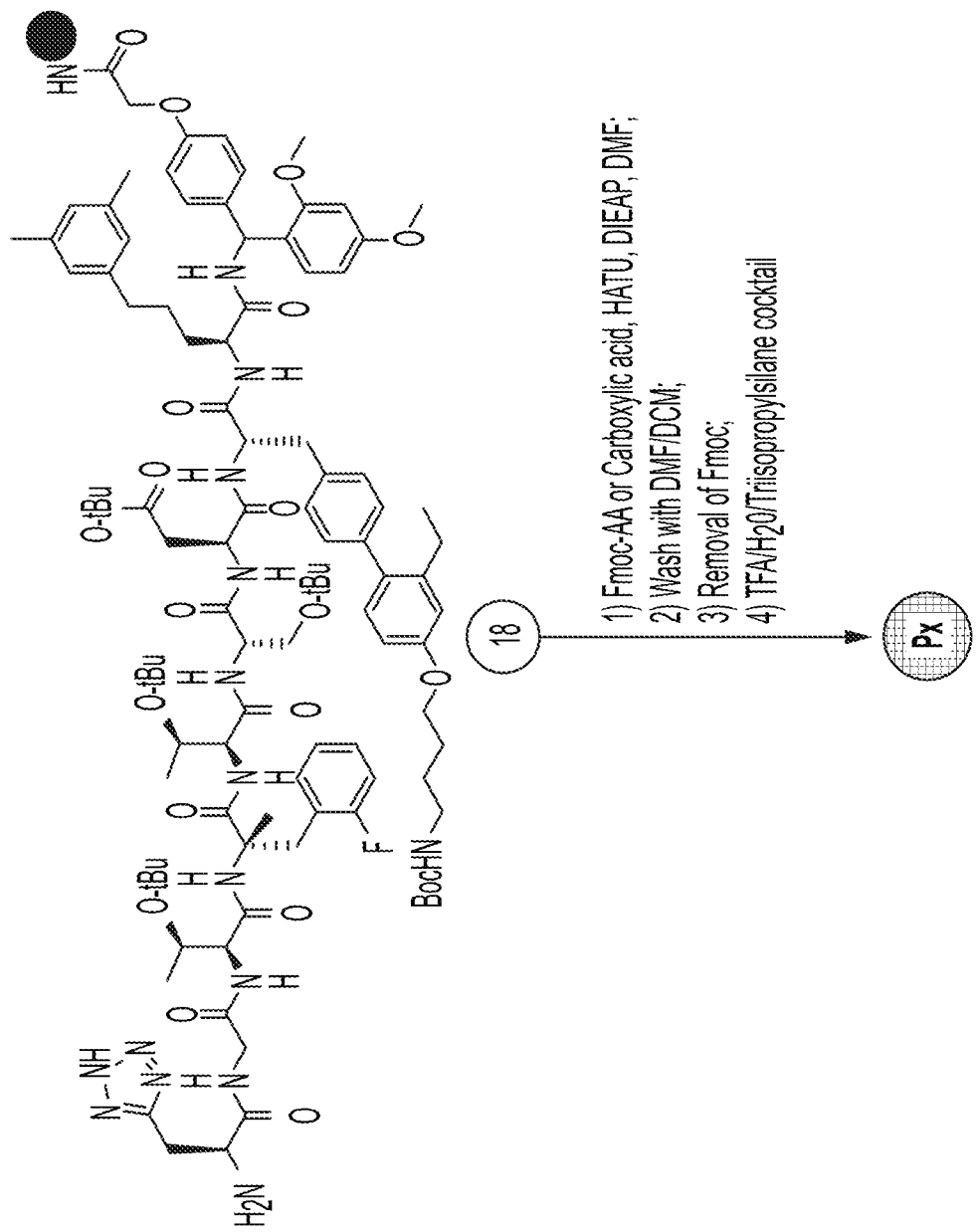
FIG. 16 shows a sequence for solid-supported synthesis of GLP1 peptidomimetic payloads P3, P4, P5, P6, P7, P11, P13, P14, P15, P16 and P17 according to the disclosure.
Figure 16:
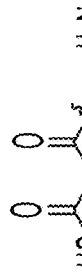

FIG. 16 depicts the sequence of steps for solid support synthesis of GLP1 peptidomimetic payloads P3, P4, P5, P6, P7, P11, P13, P14, P15, P16 and P17 according to the disclosure.

3.5 Preparation of 3-[[(1S)-2-[[2-[[[(1S,2R)-1-[[(1S)-2-[[(1S,2R)-1-[[(1S)-2-[[(1S)-2-[[(1S)-1-[[4-[4-(4-aminobutoxy)-2-ethyl-phenyl]phenyl]methyl-2-[[(1S)-1-carbamoyl-4-(3,5-dimethylphenyl) butyl]amino]-2-oxo-ethyl]amino]-1-(carboxymethyl)-2-oxo-ethyl]amino]-1-(hydroxymethyl)-2-oxo-ethyl]carbamoyl]-2-hydroxy-propyl]amino]-1-[(2-fluorophenyl)methyl]-1-methyl-2-oxo-ethyl]carbamoyl]-2-hydroxy-propyl]amino]-2-oxo-ethyl]amino]-2-oxo-1-(2H-tetrazol-5-ylmethyl])ethyl]amino]-2,2-dimethyl-3-oxo-propanoic acid (P3)

Starting from the corresponding aa9-aa8-aa7-aa6-aa5-aa4-aa3-aa2b-aa1 peptidyl Rink Amide MBHA Resin (18, 152.96 µmol) and aa11 (57.58 mg, 305.91 µmol, 2.0 eq.), the corresponding aa11-aa10-aa9-aa8-aa7-aa6-aa5-aa4-aa3-aa2b-aa1 peptidyl Rink Amide MBHA Resin (20, 119 µmol) was prepared as described in the general procedure of SPPS.

The corresponding resin-bound peptide 20 (119 µmol) was further cleaved following the general procedure to give the crude product as a white solid. The crude was purified by prep-HPLC (column: YMC-Exphere C18 10 µm 300*50 mm, 12 nm; mobile phase: [water(0.1% TFA)-ACN];B %: 15%-45%, 55 min) to provide P3 (8 mg, 5.47 µmol, 3.58% yield, 99.37% purity) as a light yellow solid.

HPLC: RT=8.10 min. HPLC conditions: YMC-Pack ODS-A 150*4.6 mm, 5 µm column, flow rate of 1.5 mL/min, eluting with a gradient of 10% to 80% acetonitrile containing 0.12% TFA (solvent B) and water containing 0.1% TFA (solvent A).

LCMS: (ESI): RT=0.841 min, m/z calcd. for C18H21NO2 1452.69 [M+H]$^+$, found 727.3 [M+2H]2+; LCMS conditions: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

3.6 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[2-[[(2S)-2-[(3-amino-2,2-dimethyl-3-oxo-propanoyl)amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl]amino]-4-oxo-butanoic acid Starting from the corresponding aa9-aa8-aa7-aa6-aa5-aa4-aa3-aa2b-aa1 peptidyl RinkAmide MBHA Resin compound 18 (192.73 µmol) and aa12 (75.82 mg, 578.18 µmol, 3 eq.), the corresponding aa12-aa10-aa9-aa8-aa7-aa6-aa5-aa4-aa3-aa2b-aa1 peptidyl Rink Amide MBHA Resin (21, 192.73 µmol) was obtained as described in the general procedure of SPPS.

The corresponding resin-bound peptide 21 (192.73 µmol) was further cleaved following the general procedure to give the crude product as a white solid. The crude was purified by prep-HPLC (column: YMC-Exphere C18 10 µm 300*50 mm, 12 nm; mobile phase: [water(0.1% TFA)-ACN];B %: 15%-45%, 55 min) to provide P4 (35 mg, 24.03 µmol, 8.73% yield, 99.66% purity) as a light yellow solid.

LCMS: (ESI): RT=0.861 min, mass calcd. for C76H103FN18O17 726.36 m/z [M+2H]2+; found 726.7 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.854 min, mass calcd. for C76H103FN18O17 726.36 m/z [M+2H]2+; found 726.7 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.90 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm; Wavelength: UV 220 nm&215 nm&254 nm; Column temperature: 40° C.

3.7 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-(hydroxyamino)-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (P5)

Starting from the corresponding aa9-aa8-aa7-aa6-aa5-aa4-aa3-aa2b-aa1 peptidyl Rink Amide MBHA Resin compound 18 (152.96 µmol) and aa13 (60 mg, 259.47 µmol, 1.7 eq.), the corresponding aa13-aa10-aa9-aa8-aa7-aa6-aa5-aa4-aa3-aa2b-aa1 peptidyl Rink Amide MBHA Resin (22, 152.67 µmol) was obtained as described in the general procedure of SPPS.

The corresponding resin-bound peptide 22 was cleaved following the general procedure to give the crude product as a white solid. The crude was purified by prep-HPLC (column: YMC-Exphere C18 10 µm 300*50 mm, 12 nm; mobile phase: [water(0.1% TFA)-ACN]; B %: 15%-45%, 55 min) to provide P5 (4 mg, 2.66 µmol, 42.12% yield, 97.7% purity) as a light yellow solid.

LCMS: (ESI): RT=0.705 min, mass calcd. for $C_{70}H_{96}FN_{16}O_{18}$ 733.85 m/z [M+2H]$^{2+}$; found 718.2 m/z [M−2OH+4H]$^{2+}$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.847 min, mass calcd. for $C_{70}H_{96}FN_{16}O_{18}$ 733.85 m/z [M+2H]$^{2+}$; found 735.2 m/z [M+2H]$^{2+}$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=8.00 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 μm; Wavelength: UV 220 nm&215 nm&254 nm; Column temperature: 40° C. 3.8 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[2-methyl-2-(1H-pyrazol-5-yl) propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (P6)

Starting from the corresponding aa9-aa8-aa7-aa6-aa5-aa4-aa3-aa2b-aa1 peptidyl Rink Amide MBHA Resin compound 18 (82.60 μmol) and aa14 (25.47 mg, 165.19 μmol, 2 eq.), the corresponding aa14-aa10-aa9-aa8-aa7-aa6-aa5-aa4-aa3-aa2b-aa1 peptidyl Rink Amide MBHA Resin (23, 82.60 μmol) was obtained as described in the general procedure of SPPS.

The corresponding resin-bound peptide 23 (82.60 μmol) was cleaved following the general procedure to give the crude product as a white solid. The crude was purified by prep-HPLC (column: YMC-Exphere C18 10 μm 300*50 mm, 12 nm; mobile phase: [water (0.1% TFA)-ACN]; B %: 15%-45%, 55 min) to provide P6 (9 mg, 6.10 μmol, 7.40% yield, 97.34% purity) as a light yellow solid.

LCMS: (ESI): RT=0.856 min, mass calcd. for C72H98FN17O16 737.87 m/z [M−4tBu-Boc-C17H17NO4+8H]2+, rink amide (C17H17NO4, exact mass=299.12); found 738.2 m/z [M−4tBu-Boc-C17H17NO4+8H]2+, rink amide (C17H17NO4, exact mass=299.12); LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.856 min, mass calcd. for C72H98FN17O16 737.87 m/z [M−4tBu-Boc-C17H17NO4+8H]2+, rink amide (C17H17NO4, exact mass=299.12); found 738.2 m/z [M−4tBu-Boc-C17H17NO4+8H]2+, rink amide (C17H17NO4, exact mass=299.12); LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=8.16 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 μm; Wavelength: UV 220 nm&215 nm&254 nm; Column temperature: 40° C.

3.9 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[f2-[[(2S)-2-[[(2S)-2-amino-3-hydroxy-propanoyl]amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl]amino]-4-oxo-butanoic acid Starting from the corresponding aa9-aa8-aa7-aa6-aa5-aa4-aa3-aa2b-aa1 peptidyl Rink Amide MBHA Resin (18, 76.48 μmol) and aa4 (87.98 mg, 229.44 μmol, 3 eq.). The corresponding aa4-aa10-aa9-aa8-aa7-aa6-aa5-aa4-aa3-aa2b-aa1 peptidyl Rink Amide MBHA Resin (24, 76.48 μmol) was obtained as described in the general procedure of SPPS.

The corresponding resin-bound peptide 24 (76.48 μmol) was cleaved following the general procedure to give the crude product as a white solid. The crude was purified by prep-HPLC (column: Waters Xbridge Prep OBD C18 150*40 mm*10 μm; mobile phase: [water(0.1% TFA)-ACN];B %: 28%-58%,30 min) to provide P7 (17 mg, 11.16 μmol,14.59% yield, 93.57% purity) as a white solid.

LCMS: (ESI): RT=2.675 min, m/z calcd. for C68H95FN16O17, 713.35 [M+2H]2+, m/z found 713.8 [M+2H]2+; Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min;

LCMS: (ESI): RT=0.757 min, m/z calcd. for C68H95FN16O17, 713.35 [M+2H]2+, m/z found 713.8 [M+2H]2+; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A);

HPLC (Rt=7.58 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min. 3.10 Preparation of (3S)-4-[[(1S)-1-[[4-[4-(4-aminobutoxy)-2-ethyl-Phenyl]Phenyl]methyl]-2-[[1 S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[6-(1H-imidazol-5-yl) hexanoylamino]-3-(2H-tetrazol-5-yl) propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (P11)

Starting from the corresponding aa9-aa8-aa7-aa6-aa5-aa4-aa3-aa2b-aa1 peptidyl Rink Amide MBHA Resin (18, 74.75 μmol) and aa17 (70.13 mg, 165.19 μmol, 2 eq.), the corresponding aa17-aa10-aa9-aa8-aa7-aa6-aa5-aa4-aa3-aa2b-aa1 peptidyl Rink Amide MBHA Resin (27, 74.75 μmol) was obtained as described in the general procedure of SPPS.

The corresponding resin-bound peptide compound 27 (74.75 μmol) was cleaved following the general procedure to give the crude product as a white solid. The crude was purified by prep-HPLC (column: YMC-Exphere C18 10 μm 300*50 mm, 12 nm; mobile phase: [water (0.1% TFA)-ACN]; B %: 15%-45%, 55 min) to provide P7 (9 mg, 5.80 μmol, 7.05% yield, 96.92% purity) as a white solid.

HPLC: RT=7.72 min. HPLC conditions: YMC-Pack ODS-A 150*4.6 mm, 5 μm column, flow rate of 1.5 mL/min, eluting with a gradient of 10% to 80% acetonitrile containing 0.12% TFA (solvent B) and water containing 0.1% TFA (solvent A).

LCMS: (ESI): RT=0.828 min, m/z calcd. for C18H21NO2 1502.75 [M+H]+, found 752.3 [M+2H]2+; LCMS conditions: MERCK, RP-18e 25-2 mm column, flow rate 1.5 mL/min, eluting with a gradient of 5% to 95% acetonitrile containing 0.02% TFA (solvent B) and water containing 0.04% TFA (solvent A). 3.11 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[2-[[(2S)-2-[[(2S)-2-[[(2S)-2,5-diamino-5-oxo-pentanoyl]amino]-3-(1H-imidazol-4-yl)propanoyl]amino]propanoyl]amino]-3-(2H- tetrazol-5-yl)propanoyl]amino]acetyl]amino]-3-hydroxy-butanoyl]amino]-3-(2-fluorophenyl)-2-methyl-propanoyl]amino]-3-hydroxybutanoyl]amino]-3-hydroxy-propanoyl]amino]-4-oxo-butanoic acid (P13)

Starting from the corresponding aa9-aa8-aa7-aa6-aa5-aa4-aa3-aa2b-aa1 peptidyl RinkAmide MBHA Resin compound 18 (82.60 µmol), aa15 (77.14 mg, 247.79 µmol, 3 eq.), aa16 (93.40 mg, 247.49 µmol, 3 eq.), and aa19 (40.63 mg, 165.00 µmol, 2 eq.), the corresponding aa19-aa16-aa15-aa9-aa8-aa7-aa6-aa5-aa4-aa3-aa2b-aa1 peptidyl RinkAmide MBHA Resin (30, 82.50 µmol) was prepared as described in the general procedure of SPPS.

The corresponding resin-bound peptide 30 (82.50 µmol) was cleaved following the general procedure to give the crude product as a white solid. The crude was purified by prep-HPLC (column: YMC-Exphere C18 10 µm 300*50 mm, 12 nm; mobile phase: [water (0.1% TFA)-ACN]; B %: 15%-45%, 55 min) to provide P13 (10 mg, 5.69 µmol, 6.90% yield, 95.28% purity) as a white solid.

LCMS: (ESI): RT=0.807 min, mass calcd. for C79H110FN21O19 837.9 m/z [M−4tBu−2Boc−C17H17NO4+9H]2+, rink amide (C17H17NO4, exact mass=299.12); found 838.4 m/z [M−4tBu−Boc−C17H17NO4+9H]2+, rink amide (C17H17NO4, exact mass=299.12); LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.820 min, mass calcd. for C79H110FN21O19 837.9 m/z [M−4tBu−2Boc−C17H17NO4+9H]2+, rink amide (C17H17NO4, exact mass=299.12); found 838.3 m/z [M−4tBu−Boc−C17H17NO4+9H]2+, rink amide (C17H17NO4, exact mass=299.12); LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.37 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm; Wavelength: UV 220 nm&215 nm&254 nm; Column temperature: 40° C.

3.12 Preparation of (3S)-4-[[(1S)-1-[[4-[4-(4-aminobutoxy)-2-ethyl-Phenyl]Phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[(3R)-1-[2-(1H-imidazol-5-yl) ethyl]-3-methyl-2-oxo-pyrrolidine-3-carbonyl]amino]-3-(2H-tetrazol-5-yl) propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (P14)

Starting from the corresponding aa9-aa8-aa7-aa6-aa5-aa4-aa3-aa2b-aa1 peptidyl Rink Amide MBHA Resin (18, 82.60 µmol) and aa20 (79.22 mg, 165.19 µmol, 2 eq.), the corresponding aa20-aa9-aa8-aa7-aa6-aa5-aa4-aa3-aa2b-aa1 peptidyl Rink Amide MBHA Resin (31, 82.60 µmol) was prepared as described in the general procedure of SPPS.

The corresponding resin-bound peptide 31 (82.60 µmol) was further cleaved following the general procedure to give the crude product as a white solid. The crude was purified by prep-HPLC (column: YMC-Exphere C18 10 µm 300*50 mm, 12 nm; mobile phase: [water (0.1% TFA)-ACN]; B %: 15%-45%, 55 min) to provide P14 (8 mg, 3.85 µmol, 6.2% yield, 93.37% purity) as a white solid.

LCMS: (ESI): RT=0.840 min, mass calcd. for C76H103FN18O17 779.39 m/z [M+2H]2+; found 779.9 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.864 min, mass calcd. for C76H103FN18O17 779.39 m/z [M+2H]2+; found 779.9 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.60 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm; Wavelength: UV 220 nm&215 nm&254 nm; Column temperature: 40° C.

3.13 Preparation of (3S)-4-[[(1S)-1-[[4-[4-(4-aminobutoxy)-2-ethyl-Phenyl]Phenyl]methyl]-2-[[1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[(3R)-1-[2-(1H-imidazol-5-yl) ethyl]-3-methyl-2-oxo-pyrrolidine-3-carbonyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (P15)

Starting from the corresponding aa9-aa8-aa7-aa6-aa5-aa4-aa3-aa2b-aa1 peptidyl Rink Amide MBHA Resin (18, 82.60 µmol) and aa21 (79.22 mg, 165.19 µmol, 2 eq.), the corresponding aa21-aa9-aa8-aa7-aa6-aa5-aa4-aa3-aa2b-aa1 peptidyl RinkAmide MBHA Resin (32, 82.60 µmol) was prepared as described in the general procedure of SPPS.

The corresponding resin-bound peptide 32 (82.60 µmol) was further cleaved following the general procedure to give the crude product as a white solid. The crude was purified by prep-HPLC (column: YMC-Exphere C18 10 µm 300*50 mm, 12 nm; mobile phase: [water (0.1% TFA)-ACN]; B %: 15%-45%, 55 min) to provide P15 (10.5 mg, 6.54 µmol, 7.91% yield, 96.96% purity) as a white solid.

LCMS: (ESI): RT=0.828 min, mass calcd. for C76H103FN18O17 779.39 m/z [M+2H]2+; found 779.8 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.830 min, mass calcd. for C76H103FN18O17 779.39 m/z [M+2H]2+; found 779.8 m/z [M+2H]2+; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.62 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 μm; Wavelength: UV 220 nm&215 nm&254 nm; Column temperature: 40° C.

3.14 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[(3S)-1-[2-(1H-imidazol-5-yl) ethyl] pyrrolidine-3-carbonyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (P16)

Starting from the corresponding aa9-aa8-aa7-aa6-aa5-aa4-aa3-aa2b-aa1 peptidyl Rink Amide MBHA Resin (18 (141.13 μmol) and aa22 (127.46 mg, 282.27 μmol, 2.0 eq.), the corresponding aa22-aa9-aa8-aa7-aa6-aa5-aa4-aa3-aa2b-aa1 peptidyl Rink Amide MBHA Resin (33, 141.13 μmol) was prepared as described in the general procedure of SPPS.

The corresponding resin-bound peptide 33 (141.13 μmol) was further cleaved following the general procedure to give the crude product as a white solid. The crude was purified by prep-HPLC (column: YMC-Exphere C18 10 μm 300*50 mm, 12 nm; mobile phase: [water(0.1% TFA)-ACN]; B %: 15%-45%, 55 min) to provide P16 (15 mg, 9.71 μmol, 6.88% yield, and 99% purity) as a white solid.

LCMS (ESI): RT=2.361 min, m/z calcd. for C75H103FN18O16, 1530.76 M-Boc-4tBu+2H]2+, m/z found 765.8, Mobile Phase: 1.5 ML/4L TFA in water (solvent A) and 0.75 ML/4L TFA in acetonitrile (solvent B), using the gradient 10% -80% (solvent B) over 2.5 minutes and holding at 80% for 0.5 minutes at a flow rate of 0.8 ml/min.ESI source, Positive ion mode; Wavelength 220 nm&254 nm,OvenTemperature 50° C.

LCMS (ESI): RT=0.755 min, m/z calcd. for C75H103FN18O16, 1530.76 M-Boc-4tBu+2H]2+, m/z found 765.8, Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm;Column temperature: 50° C.;MS ionization: ESI HPLC: RT=7.18 min Mobile Phase: 2.75 ML/4LTFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm Wavelength: UV 220 nm, 215 nm& 254 nm Column temperature: 40° C.

3.15 Preparation of (3S,9S,12S,15S,18S,21S)-tert-butyl1-((R)-1-(2-(1H-imidazol-5-yl)ethyl) pyrrolidin-3-yl)-3-((2H-tetrazol-5-yl)methyl)-21-(((S)-1-(((S)-1-amino-5-(3,5-dimethylphenyl)-1-oxopentan-2-yl)amino)-3-(4'-(4-aminobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-18-(hydroxymethyl)-12-methyl-1,4,7,10,13, 16,19-heptaoxo-2,5,8,11,14,17,20-heptaazatricosan-23-oate (P17)

Starting from the corresponding aa9-aa8-aa7-aa6-aa5-aa4-aa3-aa2b-aa1 peptidyl Rink Amide MBHA Resin compound 18 (101.97 μmol) and aa23 (80 mg, 177.16 μmol, 1.74 eq.), the corresponding aa23-aa9-aa8-aa7-aa6-aa5-aa4-aa3-aa2b-aa1 peptidyl Rink Amide MBHA Resin (34, 101.88 μmol) was prepared as described in the general procedure of SPPS.

The corresponding resin-bound peptide 34 (101.88 μmol) was further cleaved following the general procedure to give the crude product as a white solid. The crude was purified by prep-HPLC (column: YMC-Exphere C18 10 μm 300*50 mm, 12 nm; mobile phase: [water (0.1% TFA)-ACN]; B %: 15%-45%, 55 min) to provide P17 (18 mg, 11.65 μmol, 11.43% yield, 99% purity) as a white solid.

LCMS (ESI): RT=0.828 min, m/z calcd. for C75H103FN18O16, 1530.76 M-Boc-4tBu+2H]2+, m/z found 765.8, Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm; Column temperature: 50° C.; MS ionization: ESI HPLC: RT=7.36 min Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm Wavelength: UV 220 nm, 215 nm& 254 nm Column temperature: 40° C.

Figure 17A:
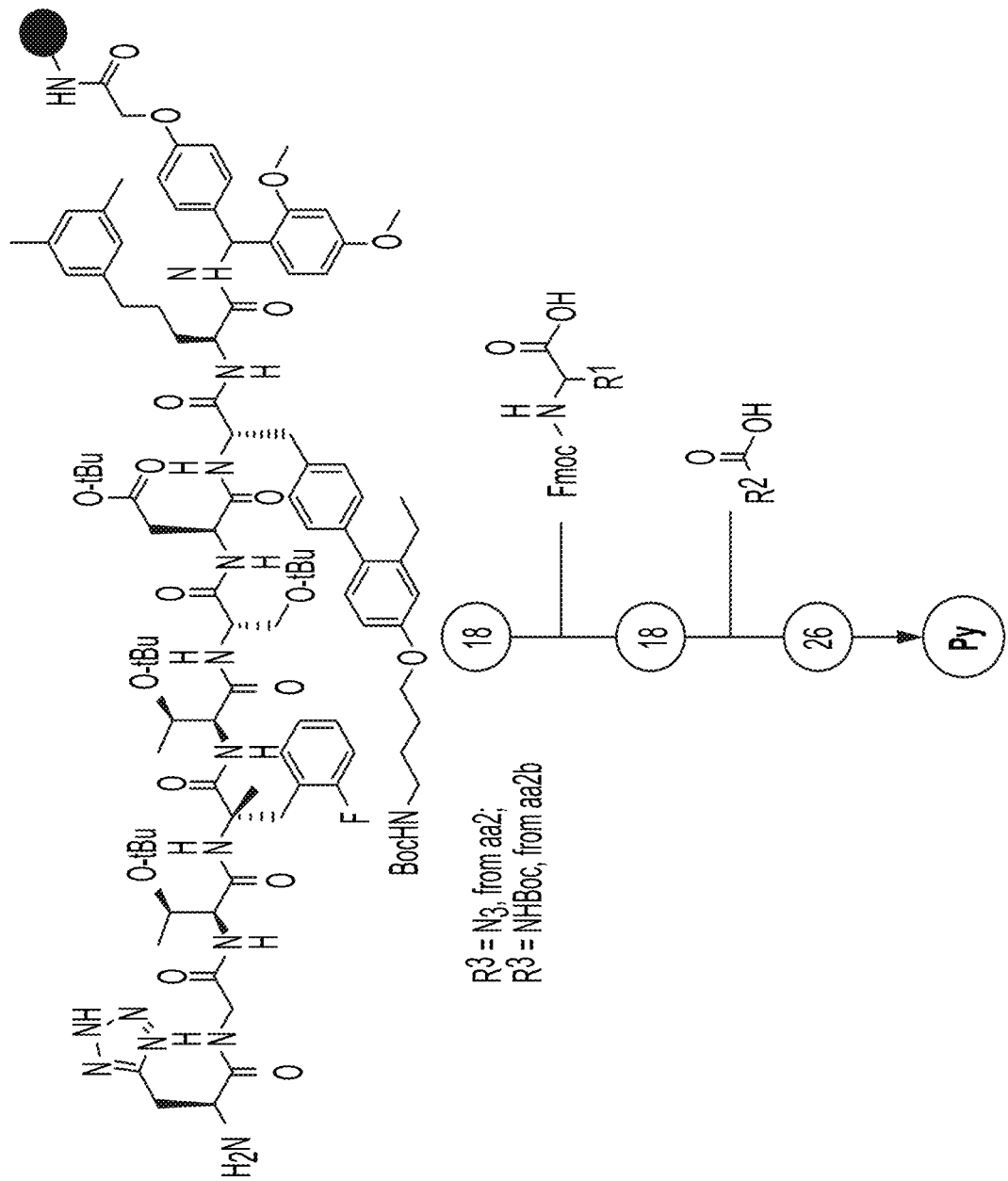
Figure 17A:
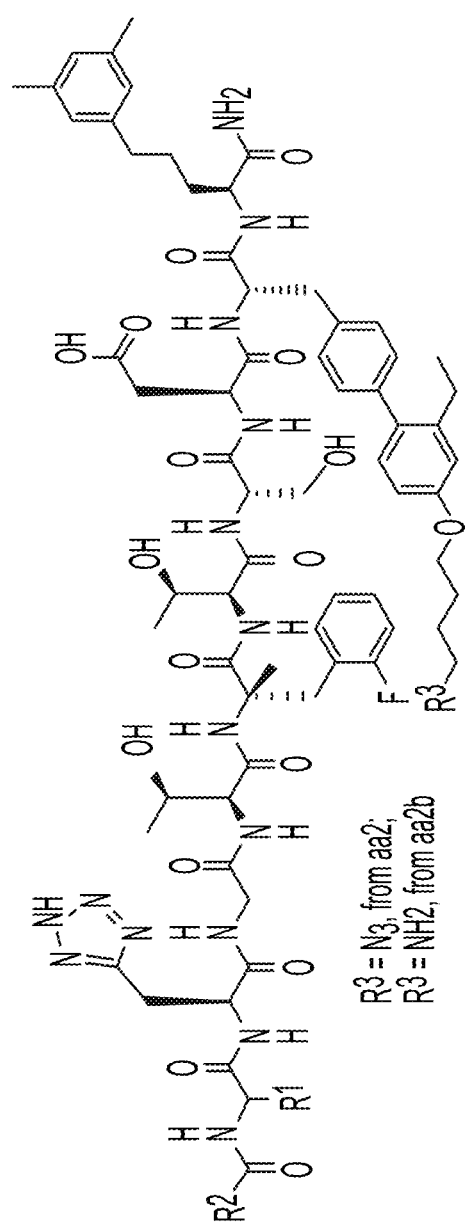
Figure 17B:
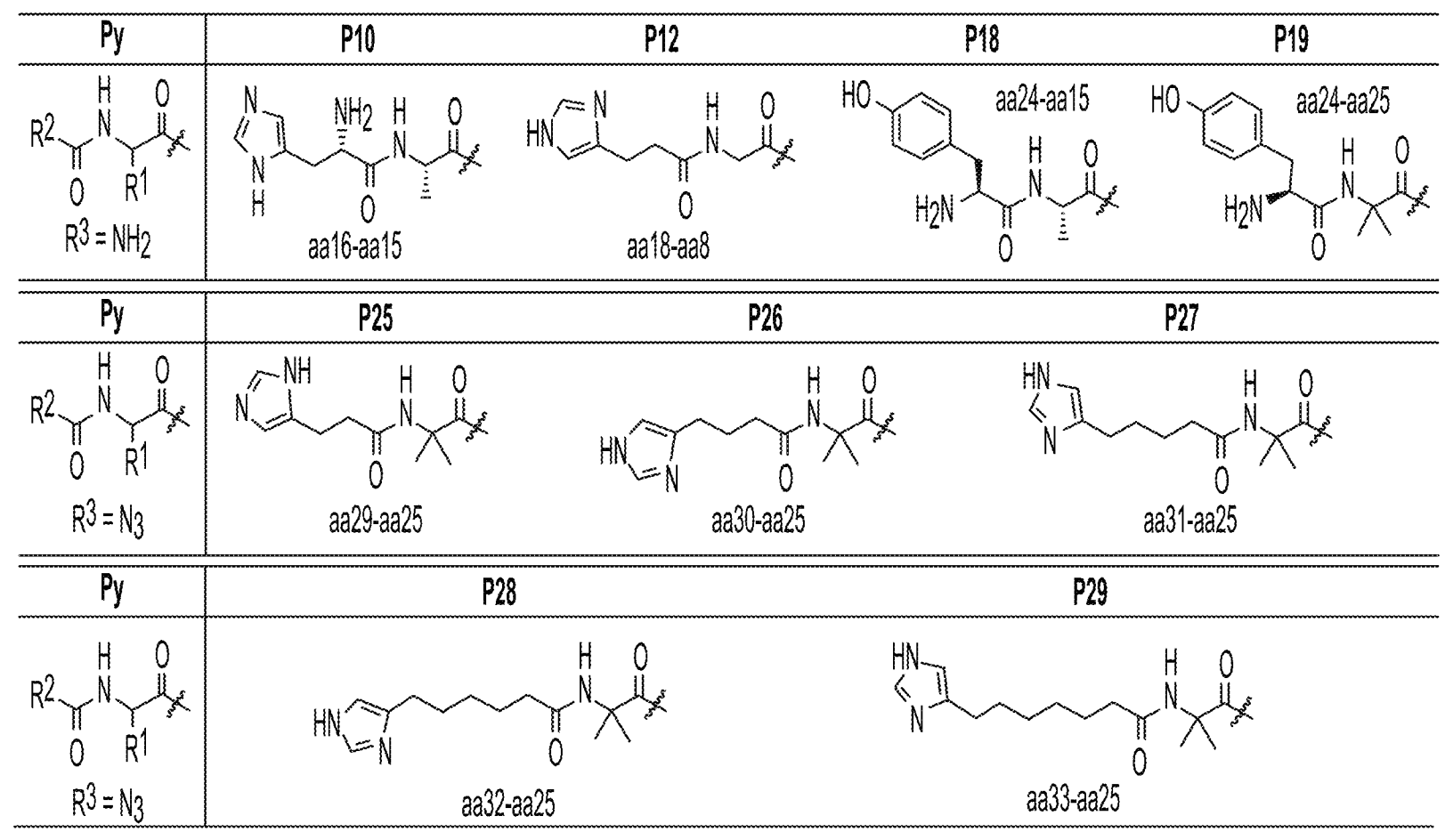
Figure 17B:
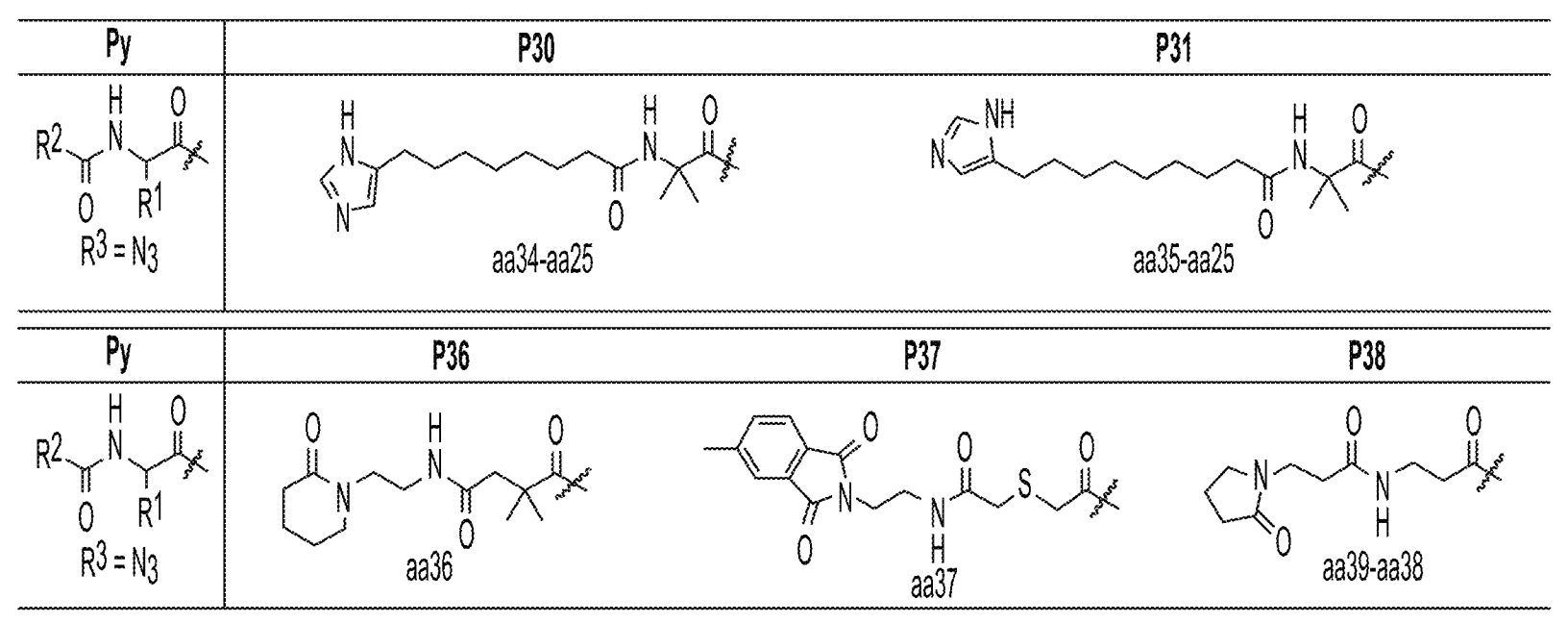

FIGS. 17A and 17B depict the sequence of steps for solid support synthesis of GLP1 peptidomimetic payloads P10, P12, P18, P19, P25, P26, P27, P28, P29, P30, P31, P36, P37, and P38 according to the disclosure.

3.16 Preparation of [[(2S)-2-[[(2S)-2-amino-3-(1H-imidazol-5-yl)propanoyl]amino]propanoyl]amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl] amino]-3-hydroxy-propanoyl]amino]-4-oxo-butanoic acid (P10)

Starting from the corresponding aa9-aa8-aa7-aa6-aa5-aa4-aa3-aa2b-aa1 peptidyl RinkAmide MBHA Resin (18, 137.66 μmol), the corresponding aa16-aa15-aa9-aa8-aa7-aa6-aa5-aa4-aa3-aa2b-aa1 peptidyl Rink Amide MBHA Resin (26, 137.28 μmol) was prepared as described in the general procedure of SPPS by elongating the peptide with aa15 (128.58 mg, 412.99 μmol, 3 eq.) and then aa16 (155.42 mg, 411.83 μmol, 3 eq.).

The corresponding resin-bound peptide 26 (137.28 μmol) was further cleaved following the general procedure to give the crude product as a white solid. The crude was purified by prep-HPLC (column: YMC-Exphere C18 10 μm 300*50 mm, 12 nm; mobile phase: [water (0.1% TFA)-ACN]; B %: 15%-45%, 55 min) to provide P10 (16 mg, 10.33 μmol, 7.55% yield, 99.85% purity) as a white solid.

LCMS (ESI): RT=0.808 min, mass calcd. for C74H100FN19O17 1545.75 [M-4tBu-Boc+6H]$^+$773.88 [M−4tBu-Boc+7H]2+, found 774.2 [M−4tBu-Boc+7H]2+. Reverse phase LC-MS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

HPLC: RT=7.46 min. Mobile Phase: 2.75 ML/4L TFA in water (solvent A) and 2.5 ML/4L TFA in acetonitrile (solvent B), using the elution gradient 10%-80% (solvent B)

over 10 minutes and holding at 80% for 5 minutes at a flow rate of 1.5 ml/min; Column: YMC-Pack ODS-A 150*4.6 mm,5 µm; Wavelength: UV 220 nm&215 nm&254 nm; Column temperature: 40° C. 3.17 Preparation of (3S)-4-[[(1S)-1-[[4-[4-(4-aminobutoxy)-2-ethyl-phenyl]phenyl]methyl]-2-[[(1S)-1-carbamoyl-4-(3-hydroxy-5-methyl-phenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[2-[3-(1H-imidazol-4-yl)propanoylamino]acetyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (P12)

Starting from the corresponding aa9-aa8-aa7-aa6-aa5-aa4-aa3-aa2b-aa1 peptidyl Rink Amide MBHA Resin (18, 82.60 µmol), the corresponding aa18-aa8-aa9-aa8-aa7-aa6-aa5-aa4-aa3-aa2b-aa1 peptidyl RinkAmide MBHA Resin (29, 82.60 µmol) was prepared as described in the general procedure of SPPS by elongating the peptide with aa8 (73.67 mg, 247.79 µmol, 3 eq.) and then aa18 (63.18 mg, 165.19 µmol, 2 eq.).

The corresponding resin-bound peptide 29 (82.60 µmol) was further cleaved following the general procedure to give the crude product as a white solid. The crude was purified by prep-HPLC (column: YMC-Exphere C18 10 µm 300*50 mm, 12 nm; mobile phase: [water (0.1% TFA)-ACN]; B %: 15%-45%, 55 min) to provide P12 (11 mg, 7.09 µmol, 8.59% yield, 97.99% purity) as a white solid.

LCMS: (ESI): RT=0.828 min, mass calcd. for $C_{72}H_{96}FN_{18}O_{18}$ 759.86 m/z $[M+2H]2+$; found 759.7 m/z $[M+2H]2+$; $[M+2H]2+$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=0.828 min, mass calcd. for $C_{72}H_{96}FN_{18}O_{18}$ 759.86 m/z $[M+2H]2+$; found 759.8 m/z $[M+2H]2+$; $[M+2H]2+$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.65 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm; Wavelength: UV 220 nm&215 nm&254 nm; Column temperature: 40° C.

3.18 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[2-[[(2S)-2-[[(2S)-2-amino-3-hydroxy-propanoyl]amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl]amino]-4-oxo-butanoic acid (P18)

Starting from the corresponding aa9-aa8-aa7-aa6-aa5-aa4-aa3-aa2b-aa1 peptidyl RinkAmide MBHA Resin compound 18 (76.48 µmol), the corresponding aa24-aa15-aa9-aa8-aa7-aa6-aa5-aa4-aa3-aa2b-aa1 peptidyl Rink Amide MBHA Resin compound 35 (76.48 µmol) was prepared as described in the general procedure of SPPS by elongating the peptide with aa15 (71.43 mg, 229.44 µmol, 3 eq.) and then aa24 (64.54 mg, 229.44 µmol, 3 eq.).

The corresponding resin-bound peptide 35 (76.48 µmol) was further cleaved following the general procedure to give the crude product as a white solid. The crude was purified by prep-HPLC (column: YMC-Exphere C18 10 µm 300*50 mm, 12 nm; mobile phase: [water (0.1% TFA)-ACN]; B %: 15%-45%, 55 min) to provide P18 (16 mg, 10.15 µmol, 11.76% yield, 99.77% purity) as a white solid.

LCMS: (ESI): RT=0.762 min, m/z calcd. for $C_{77}H_{104}FN_{17}O_{18}$, 786.89 $[M+2H]2+$, m/z found 787.3 $[M+2H]2+$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC (Rt=7.68 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 mL/min.

3.19 Preparation of (3S)-4-[[(1S)-1-[[4-[4-(4-aminobutoxy)-2-ethyl-Phenyl]Phenyl]methyl]-2-[[1 S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[2-[[(2S)-2-[[(2S)-2-amino-3-(4-hydroxyphenyl) propanoyl]amino]-2-methyl-propanoyl]amino]-3-(2H-tetrazol-5-yl) propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxypropanoyl]amino]-4-oxo-butanoic acid (P19)

Starting from the corresponding aa9-aa8-aa7-aa6-aa5-aa4-aa3-aa2b-aa1 peptidyl RinkAmide MBHA Resin compound 18 (81.07 µmol), the corresponding aa24-aa25-aa9-aa8-aa7-aa6-aa5-aa4-aa3-aa2b-aa1 peptidyl Rink Amide MBHA Resin compound 37 (81.07 µmol) was prepared as described in the general procedure of SPPS by elongating the peptide with aa25 (79.13 mg, 243.20 µmol, 3 eq.) and then aa24 (68.41 mg, 243.20 µmol, 3 eq.).

The corresponding resin-bound peptide 37 was further cleaved following the general procedure to give the crude product as a white solid. The crude was purified by prep-HPLC (column: Phenomenex Gemini-NX 150*30 mm*5 µm; mobile phase: [water (0.04% $NH_3H_2O$+10 mM $NH_4HCO_3$)-ACN]; B %: 10%-50%, 15 min) to provide P19 (9 mg, 5.62 µmol, 7.03% yield, 99% purity) as a white solid.

LCMS: (ESI): RT=0.841 min, m/z calcd. for $C_{78}H_{106}FN_{17}O_{18}$, 793.90 $[M+2H]^{2+}$, m/z found 794.2 $[M+2H]^{2+}$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

Crude HPLC: (Rt=7.81 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

LCMS: (ESI): RT=0.813 min, m/z calcd. for $C_{78}H_{106}FN_{17}O_{18}$, 793.90 $[M+2H]^{2+}$, m/z found 794.4 $[M+2H]^{2+}$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: Rt=7.81 min. Mobile Phase: 2.75 ML/4LTFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min. 3.20 Preparation of (3S,6S,9S,12S,15S, 21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-28-(1H-imidazol-5-yl)-12,24,24-trimethyl-5,8,11,14,17,20,23,26-octaoxo-4,7,10,13,16,19,22,25-octaazaoctacosan-1-oic acid (P25)

Starting from the corresponding aa9-aa8-aa7-aa6-aa5-aa4-aa3-aa2b-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (0.1 g, 50.70 µmol, 1.0 eq.) in DMF (20 mL) was added a solution of compound aa29 (58.17 mg, 152.11 µmol, 3.0 eq.), PyBOP (73.88 mg, 141.96 µmol, 2.8 eq.) and DIPEA (39.32 mg, 304.21 µmol, 52.99 µl, 6.0 eq) in DMF (20 mL) in one portion at 20° C. The mixture was bubbled with N2 at 20° C. for 2 hours. The mixture was filtered, and the collected resin was washed with DMF (50 mL*3), DCM (50 mL*3) to give the crude product on solid phase, which was subjected to acidic cleavage by using TFA cocktail (6 mL of TFA, 0.4 mL of water, 0.3 mL of triisopropylsilane, 120 mg of phenol). The mixture was filtered and the filtrate was diluted with t-BuOMe (1000 mL) to give a precipitate, which was centrifuged (5000 R) for 10 min. The residue was purified by prep-HPLC (column: Phenomenex Gemini-NX C18 80*3 0 mm*5 µm; mobile phase: [water (0.1% TFA)-ACN]; B %: 10%-60%, 20 min) to give the product P25 (2.3 mg, 1.33 µmol, 2.63% yield, 91% purity) as a white solid LCMS (ESI): RT=4.006 min, m/z calcd. for $C_{75}H_{100}FN_{20}O_{17}$ 1571.76 [M+H]$^+$, found 786.20 [M+2H]$^{2+}$, Mobile Phase: 1.5 ML/4L TFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm&254 nm, Oven Temperature 50° C.

HPLC: RT=9.54 min, 98.48% purity. HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.21 Preparation of (3S,6S,9S,12S,15S,21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-29-(1H-imidazol-5-yl)-12,24,24-trimethyl-5,8,11,14,17,20,23,26-octaoxo-4,7,10,13,16,19,22,25-octaazanonacosan-1-oic acid (P26)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

The Resin bound compound 36A (50 mg, 25.35 µmol, 1 eq.) was subjected to acidic cleavage by using TFA cocktail (5 mL, TFA/TIPS/H$_2$O=95:2.5:2.5). The mixture was filtered, and the filtrate was diluted with t-BuOMe (50 mL) and then centrifuged (5000 R) for 10 min to give a crude product aa25-aa9-aa8-aa7-aa6-aa5-aa4-aa3-aa2-aa1 (50 mg, crude) as a white solid.

LCMS (ESI): RT=3.968 min, m/z calcd. for C69H95FN18O16 1449.70, found 1449.7 [M+H]$^+$, Mobile Phase: 1.5 ML/4L TFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm, 254 nm, Oven Temperature 50° C.

To a solution of aa30 (34.19 mg, 86.23 µmol, 2.5 eq.) in DMF (4 mL) was added PyBOP (39.49 mg, 75.88 µmol, 2.2 eq.) and DIPEA (26.75 mg, 206.96 µmol, 36.05 µL, 6 eq.), the mixture was stirred at 25° C. for 10 min, then aa25-aa9-aa8-aa7-aa6-aa5-aa4-aa3-aa2-aa1 (50 mg, 34.49 µmol, 1 eq.) was added, and the final mixture was stirred for 2 h at 25° C. The reaction progress was monitored by LCMS. After completion, the mixture was triturated by TBME (25 mL) to give a crude product, which was added into a solution of H$_2$O (0.1 mL), triisopropylsilane (77.10 mg, 486.88 µmol, 0.1 mL, 14.83 eq.) and TFA (2.77 g, 24.31 mmol, 1.8 mL, 740.69 eq.). The mixture was stirred at 25° C. for 1 h. The reaction progress was monitored by LCMS. After completion, the mixture was filtered and then triturated by TBME (50 mL) to give a crude product, which was purified by prep-HPLC (column: Gemini NX C18 5 µm*10*150 mm; mobile phase: [water (0.1% TFA)-ACN]; B %: 10%-60%, 30 min) to give P26 (7.72 mg, 4.77 µmol, 14.54% yield, 98% purity) as a white solid.

LCMS (ESI): RT=3.991 min, mass calcd. for $C_{76}H_{103}FN_{20}O_{17}$, 793.38 [M+H]$^+$, found 793.7 [M+H]$^+$. LCMS conditions: 1.5 ML/4L TFA in water (solvent A) and 0.75 ML/4L TFA in acetonitrile (solvent B), using the elution gradient 10%-80% (solvent B) over 6.0 minutes and holding at 80% for 0.5 minutes at a flow rate of 0.8 ml/min; Column: X timate C18 2.1*30 mm, 3 µm; Wavelength: UV 220 nm & 254 nm Column temperature: 50° C.; MS ionization: ESI.

HPLC: RT=9.55 min, HPLC conditions: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: WELCH Ultimate LP-C18 150*4.6 mm 5 µm; Wavelength: UV 220 nm, 215 nm, 254 nm; Column temperature: 40° C.

3.22 Preparation of (3S,6S,9S,12S,15S,21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-30-(1H-imidazol-5-yl)-12,24,24-trimethyl-5,8,11,14,17,20,23,26-octaoxo-4,7,10,13,16,19,22,25-octaazatriacontan-1-oic acid (P27)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (120 mg, 60.84 µmol, 1 eq.) in DMF (4 mL) was added a solution of aa31 (62.44 mg, 152.11 µmol, 2.5 eq.), PyBOP (69.66 mg, 133.85 µmol, 2.2 eq.) and DIPEA (47.18 mg, 365.05 µmol, 63.59 µL, 6 eq.) in DMF (10 mL) in one portion at 20° C., and the final mixture was bubbled with N2 at 20° C. for 2 h and repeat this progress for twice. The reaction progress was monitored by LCMS. After completion, the mixture was filtered and washed with DMF (10 mL*4) and DCM (10 mL*4) to give the crude product on solid phase, which was subjected to acidic cleavage by using TFA cocktail (5 mL, TFA/TIPS/ $H_2O$=95:2.5:2.5). The mixture was filtered, and the filtrate was diluted with t-BuOMe (50 mL) to give a precipitate, which was centrifuged (5000 R) for 10 min. The residue was purified by prep-HPLC (column: Phenomenex Gemini NX C18 150*40 mm*5 µm; mobile phase: [water (0.1% TFA)-ACN]; B %: 0%-45%, 30 min) to give the product P27 (2.4 mg, 1.47 µmol, 2.48% yield, 98% purity) as a white solid LCMS (ESI): RT=4.071 min, m/z calcd. for $C_{77}H_{105}FN_{20}O_{17}$ 800.39 $[M+2H]^{2+}$, found 800.8, Mobile Phase: 1.5 ML/4L TFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm & 254 nm, Oven Temperature 50° C.

HPLC: RT=9.58 min, HPLC conditions: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: WELCH Ultimate LP-C18 150*4.6 mm 5 µm; Wavelength: UV 220 nm, 215 nm, 254 nm; Column temperature: 40° C.

3.23 Preparation of (3S,6S,9S,12S,15S,21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-31-(1H-imidazol-4-yl)-12,24,24-trimethyl-5,8,11,14,17,20,23,26-octaoxo-4,7,10,13,16,19,22,25-octaazahentriacontan-1-oic acid (P28)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (120 mg, 60.84 µmol, 1 eq.) in DMF (4 mL) was added a solution of aa32 (64.57 mg, 152.10 µmol, 2.5 eq.), PyBOP (69.65 mg, 133.85 µmol, 2.2 eq.) and DIPEA (39.32 mg, 304.20 µmol, 52.99 µL, 5 eq.) in DMF (10 mL) in one portion at 20° C., and the final mixture was bubbled with N2 at 20° C. for 2 h and repeat this progress for twice. The reaction progress was monitored by LCMS. After completion, the mixture was filtered and washed with DMF (10 mL*4) and DCM (10 mL*4) to give the crude product on solid phase, which was subjected to acidic cleavage by using TFA cocktail (5 mL, TFA/TIPS/ $H_2O$=95:2.5:2.5). The mixture was filtered, and the filtrate was diluted with t-BuOMe (50 mL) to give a precipitate, which was centrifuged (5000 R) for 10 min. The residue was purified by prep-HPLC (column: Phenomenex Gemini-NX 150*30 mm*5 µm; mobile phase: [water (0.05% ammonia hydroxide v/v)-ACN]; B %: 0%-45%, 30 min) to give the product P28 (8.5 mg, 5.21 µmol, 10.34% yield, 99% purity) as a white solid LCMS (ESI): RT=4.035 min, m/z calcd. for $C_{78}H_{107}FN_{20}O_{17}$ 807.40 $[M+2H]^{2+}$, found 807.8, Mobile Phase: 1.5 ML/4L TFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm & 254 nm, Oven Temperature 50° C.

HPLC: RT=9.60 min, HPLC conditions: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: WELCH Ultimate LP-C18 150*4.6 mm 5 µm; Wavelength: UV 220 nm, 215 nm, 254 nm; Column temperature: 40° C.

3.24 Preparation of (3S,6S,9S,12S,15S,21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-32-(1H-imidazol-4-yl)-12,24,24-trimethyl-5,8,11,14,17,20,23,26-octaoxo-4,7,10,13,16,19,22,25-octaazadotriacontan-1-oic acid (P29)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (120 mg, 60.84 µmol, 1 eq.) in DMF (4 mL) was added a solution of aa33 (64.04 mg, 146.02 µmol, 2.4 eq.), PyBOP (63.32 mg, 121.68 µmol, 2 eq.) and DIPEA (39.32 mg, 304.21 µmol, 52.99 µL, 5 eq.) in DMF (10 mL) in one portion at 20° C., and the final mixture was bubbled with N2 at 20° C. for 2 h and repeat this progress for twice. The reaction progress was monitored by LCMS. After completion, the mixture was filtered and washed with DMF (10 mL*4) and DCM (10 mL*4) to give the crude product on solid phase, which was subjected to acidic cleavage by using TFA cocktail (5 mL, TFA/TIPS/ $H_2O$=95:2.5:2.5). The mixture was filtered, and the filtrate was diluted with t-BuOMe (50 mL) to give a precipitate, which was centrifuged (5000 R) for 10 min. The residue was purified by prep-HPLC (column: Phenomenex Gemini-NX 150 * 30 mm*5 µm; mobile phase: [water (0.1% TFA)-ACN]; B %: 15%-55%, 20 min) to give the product P29 (5 mg, 3.05 µmol, 5.22% yield, 99.4% purity) as a white solid LCMS (ESI): RT=3.997 min, m/z calcd. for $C_{77}H_{103}FN_{20}O_{17}$, 814.40 $[M+2H]^{2+}$, found 814.9, Mobile Phase: 1.5 ML/4L TFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm & 254 nm, Oven Temperature 50° C.

HPLC: RT=9.61 min, HPLC conditions: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: WELCH Ultimate LP-C18

150*4.6 mm 5 μm; Wavelength: UV 220 nm, 215 nm, 254 nm; Column temperature: 40° C.

3.25 Preparation of (3S)-4-[[(1S)-1-[[4-[4-(4-azidobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[2-[8-(1H-imidazol-5-yl) octanoylamino]-2-methyl-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (P30)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (500 mg, 126.75 μmol, 50% purity, 1 eq) in DMF (4 mL) was added a solution of aa34 (286.84 mg, 633.77 μmol, 5 eq), HATU (86.75 mg, 228.16 μmol, 1.8 eq) and DIPEA (65.53 mg, 507.02 μmol, 88.31 μL, 4 eq) in DMF (20 mL) in one portion at 20° C., and the final mixture was bubbled with N₂ at 20° C. for 2 h. The reaction progress was monitored by LCMS. After completion, the mixture was filtered and washed with DMF (10 mL*4) and DCM (10 mL*4) to give the crude product on solid phase, which was subjected to acidic cleavage by using TFA cocktail (10 mL, TFA/TIPS/H₂O=95:2.5:2.5). The mixture was filtered, and the filtrate was diluted with t-BuOMe (100 mL) to give a precipitate, which was centrifuged (5000 R) for 10 min. The residue was purified by prep-HPLC (column: Boston Green ODS 150*30 mm*5 μm; mobile phase: [water (0.1% TFA)-ACN];B %: 22%-62%, 9 min) to give the product P30 (7.68 mg, 4.62 μmol, 4.45% yield, 98.82% purity) as a white solid LCMS (ESI): RT=3.998 min, m/z calcd. for $C_{30}H_{110}FN_{20}O_{17}$ 1641.83 [M+H]⁺, $C_{30}H_{111}FN_{20}O_{17}$ 821.4 [M+2H]²⁺, found 821.8 [M+2H]2+. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=9.63 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 μm.

3.26 Preparation of (3S)-4-[[(1S)-1-[[4-[4-(4-azidobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[2-[9-(1H-imidazol-5-yl) nonanoylamino]-2-methyl-propanoyl]amino]-3-(2H-tetrazol-5-yl) Propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (P31)

Starting from the corresponding aa9-aa8-aa7-aa6-aa5-aa4-aa3-aa2-aa1 peptidyl Rink Amide MBHA Resin (1.03 mmol), aa25 (669 mg, 206 mmol, 2.0 eq.), the corresponding aa25-aa9-aa8-aa7-aa6-aa5-aa4-aa3-aa2-aa1 peptidyl Rink Amide MBHA Resin compound 36A (1.03 mmol) was prepared as described in the general procedure of SPPS.

To a mixture of Compound 36A (125 mg, 63.38 μmol, 1 eq.) in DMF (4 mL) was added a solution of aa35 (57.37 mg, 126.75 μmol, 2.0 eq.), HATU (43.38 mg, 114.08 μmol, 1.8 eq.) and DIPEA (32.76 mg, 253.51 μmol, 44.16 μl, 4.0 eq.) in DMF (10 mL) in one portion at 20° C., and the final mixture was bubbled with N₂ at 20° C. for 2 h. The reaction progress was monitored by LCMS. After completion, the mixture was filtered and washed with DMF (10 mL*4) and DCM (10 mL*4) to give the crude product on solid phase, which was subjected to acidic cleavage by using TFA cocktail (5 mL, TFA/TIPS/H₂O=95:2.5:2.5). The mixture was filtered, and the filtrate was diluted with t-BuOMe (50 mL) to give a precipitate, which was centrifuged (5000 R) for 10 min. The residue was purified by prep-HPLC (column: Boston Green ODS 150*30 mm*5 μm; mobile phase: [water (0.1% TFA)-ACN]; B %: 25%-65%, 9 min) to give the product P31 (7.0 mg, 4.23 μmol, 6.69% yield, 100% purity) as a white solid.

LCMS (ESI): RT=4.023 min, m/z calcd. for $C_{75}H_{100}FN_{20}O_{17}$ 1571.76 [M+H]⁺, 786.38 [M+2H]²⁺, found 786.20 [M+2H]²⁺, Mobile Phase:1.5 ML/4LTFA in water (solvent A) and 0.75 ML/4L TFA in acetonitrile (solvent B), using the gradient 10%-80% (solvent B) over 2.5 minutes and holding at 80% for 0.5 minutes at a flow rate of 0.8 ml/min. ESI source, Positive ion mode; Wavelength 220 nm, 254 nm, OvenTemperature 50° C.

HPLC: RT=9.80 min, 100% purity. HPLC method A: Column: YMC-Pack ODS-A 150*4.6 mm, 5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.27 Preparation of (9S,15S,18S,21S,24S,27S)-9-((2H-tetrazol-5-yl)methyl)-27-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-18-(2-fluorobenzyl)-15,21-bis((R)-1-hydroxyethyl)-24-(hydroxymethyl)-6,6,18-trimethyl-4,7,10,13,16,19,22,25-octaoxo-1-(2-oxopiperidin-1-yl)-3,8,11,14,17,20,23,26-octaazanonacosan-29-oic acid (P36)

To a mixture of aa9-aa8-aa7-aa6-aa5-aa4-aa3-aa2-aa1 peptidyl Rink Amide MBHA Resin (75 mg, 19.87 μmol, 50% purity, 1 eq) in DMF (2 mL) was added a solution of aa36 (20 mg, 73.99 μmol, 3.72 eq), HATU (15.11 mg, 39.74 μmol, 2 eq) and DIPEA (25.68 mg, 198.71 μmol, 34.61 μL, 10 eq) in DMF (10 mL) in one portion at 20° C., and the final mixture was bubbled with N2 at 20° C. for 2 h. The reaction progress was monitored by LCMS. After completion, the mixture was filtered and washed with DMF (10 mL×4) and DCM (10 mL×4) to give the crude product on solid phase, which was subjected to acidic cleavage by using TFA cocktail (5 mL, TFA/TIPS/H₂O=95:2.5:2.5). The mixture was filtered, and the filtrate was diluted with t-BuOMe (50 mL) to give a precipitate, which was centrifuged (5000 R) for 10 min. The residue was purified by prep-HPLC (column: Welch Xtimate C18 100*40 mm*3 μm; mobile phase: [water(0.075% TFA)-ACN];B %: 50%-80%, 10 min) to give the product P36 (2.4 mg, 1.48 μmol, 7.47% yield, 100% purity) as a white solid.

LCMS (ESI): RT=4.416 min, mass calcd. for $C_{95}H_{122}N_{20}O_{22}FH$ 1917.11 [M+H]$^+$, $C_{95}H_{122}N_{20}O_{22}F$ 809.1 [M+2H]$^{2+}$, found 809.3 [M+2H]2+; Reverse phase LCMS was carried out using a Chromolith Flash column 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 µm, C18, 2.1*30 mm.

HPLC: RT=5.24 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: Ultimate XB-C18, 3 µm,3.0*50 mm. 3.28 Preparation of (3S)-4-[[(1S)-1-[[4-[4-(4-azidobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[2-[2-[2-(5-methyl-1,3-dioxo-isoindolin-2-yl)ethylamino]-2-oxo-ethyl]sulfanylacetyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (P37)

To a mixture of aa9-aa8-aa7-aa6-aa5-aa4-aa3-aa2-aa1 peptidyl Rink Amide MBHA Resin (100 mg, 26.49 µmol, 1 eq) in DMF (2 mL) was added a solution of aa36 (44.56 mg, 132.47 µmol, 5 eq), HATU (18.13 mg, 47.69 µmol, 1.8 eq) and DIPEA (13.70 mg, 105.98 µmol, 18.46 µL, 4 eq) in DMF (10 mL) in one portion at 20° C., and the final mixture was bubbled with N$_2$ at 20° C. for 2 h. The reaction progress was monitored by LCMS. After completion, the mixture was filtered and washed with DMF (10 mL×4) and DCM (10 mL×4) to give the crude product on solid phase, which was subjected to acidic cleavage by using TFA cocktail (5 mL, TFA/TIPS/H$_2$O=95:2.5:2.5). The mixture was filtered, and the filtrate was diluted with t-BuOMe (50 mL) to give a precipitate, which was centrifuged (5000 R) for 10 min. The residue was purified by prep-HPLC (column: Waters Xbridge BEH C18 100*25 mm*5 µm; mobile phase: [water (0.1% TFA)-ACN];B %: 20%-80%,15 min) to give the product P37 (4.81 mg, 2.86 µmol, 10.86% yield, 100% purity) as a white solid.

LCMS (ESI): RT=4.602 min, m/z calcd. for $C_{30}H_{101}FN_{19}O_{19}S$ 1682.71 [M+H]$^+$, $C_{30}H_{100}FN_{19}O_{19}S$ 841.85 [M+2H]$^{2+}$, found 842.3 [M+2H]$^{2+}$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=4.844 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm.

3.29 Preparation of (3S,6S,9S,12S,15S,21S)-21-((2H-tetrazol-5-yl)methyl)-3-(((S)-1-(((S)-1-amino-5-(3,5-dimethylphenyl)-1-oxopentan-2-yl)amino)-3-(4'-(4-azidobutoxy)-2'-ethyl-[1,1'-biphenyl]-4-yl)-1-oxopropan-2-yl)carbamoyl)-12-(2-fluorobenzyl)-9,15-bis((R)-1-hydroxyethyl)-6-(hydroxymethyl)-12-methyl-5,8,11,14,17,20,23,27-octaoxo-29-(2-oxopyrrolidin-1-yl)-4,7,10,13,16,19,22,26-octaazanonacosan-1-oic acid (P38)

To a mixture of aa9-aa8-aa7-aa6-aa5-aa4-aa3-aa2-aa1 peptidyl Rink Amide MBHA Resin (0.2 g, 52.99 µmol, 50% purity, 1.0 eq.) in DMF (2 mL) was added a solution of aa38 (82.48 mg, 264.94 µmol, 5.0 eq.), HATU (90.66 mg, 238.45 µmol, 4.5 eq.) and DIPEA (68.48 mg, 529.88 µmol, 92.29 µL, 10.0 eq.) in DMF (10 mL) in one portion at 20° C., and the final mixture was bubbled with N2 at 20° C. for 2 h. The reaction progress was monitored by LCMS. After completion, the mixture was filtered and washed with DMF (10 mL×4) and DCM (10 mL×4) to give the crude product on solid phase, which was swelled again with 20% piperidine/DMF (20 mL) and bubbled with N2 at 20° C. for 2 hr. After completion, the mixture was filtered, and the collected resin was washed with DMF (100 mL×3), DCM (100 mL×3) to give the crude product aa38-aa9-aa8-aa7-aa6-aa5-aa4-aa3-aa2-aa1 on solid phase (52.99 µmol).

To a mixture of aa38-aa9-aa8-aa7-aa6-aa5-aa4-aa3-aa2-aa1 peptidyl Rink Amide MBHA Resin (52.60 µmol, 1 eq.) in DMF (2 mL) was added a solution of aa39 (41.33 mg, 262.98 µmol, 5.0 eq.), HATU (90.00 mg, 236.69 µmol, 4.5 eq.) and DIPEA (67.98 mg, 525.97 µmol, 91.61 µL, 10.0 eq.) in DMF (10 mL) in one portion at 20° C., and the final mixture was bubbled with N$_2$ at 20° C. for 2 h. The reaction progress was monitored by LCMS. After completion, the mixture was filtered and washed with DMF (10 mL×4) and DCM (10 mL×4) to give the crude product on solid phase, which was subjected to acidic cleavage by using TFA cocktail (10 mL, TFA/TIPS/H$_2$O=95:2.5:2.5). The mixture was filtered, and the filtrate was diluted with t-BuOMe (100 mL) to give a precipitate, which was centrifuged (5000 R) for 10 min. The residue was purified by prep-HPLC (column: Boston Green ODS 150*30 mm*5 µm; mobile phase: [water (0.1% TFA)-ACN]; B %: 36%-76%, 9 min) and prep-HPLC (column: Waters X-bridge BEH C18 100*25 mm*5 µm; mobile phase: [water (0.05% NH$_3$H$_2$O)-ACN]; B %: 5%-49%, 11 min) to give the product P38 (3.0 mg, 1.71 µmol, 3.26% yield, 90% purity) as a white solid. LCMS (ESI): RT=4.313 min, m/z calcd. for $C_{75}H_{102}FN_{19}O_{18}$ 1575.76 [M+H]$^+$, 788.38 [M+2H]$^{2+}$, found 788.20 [M+2H]$^{2+}$. LCMS conditions: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 µm, C18,2.1*30 mm; HPLC: RT=9.93 min, 90% purity. HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Figure 18:
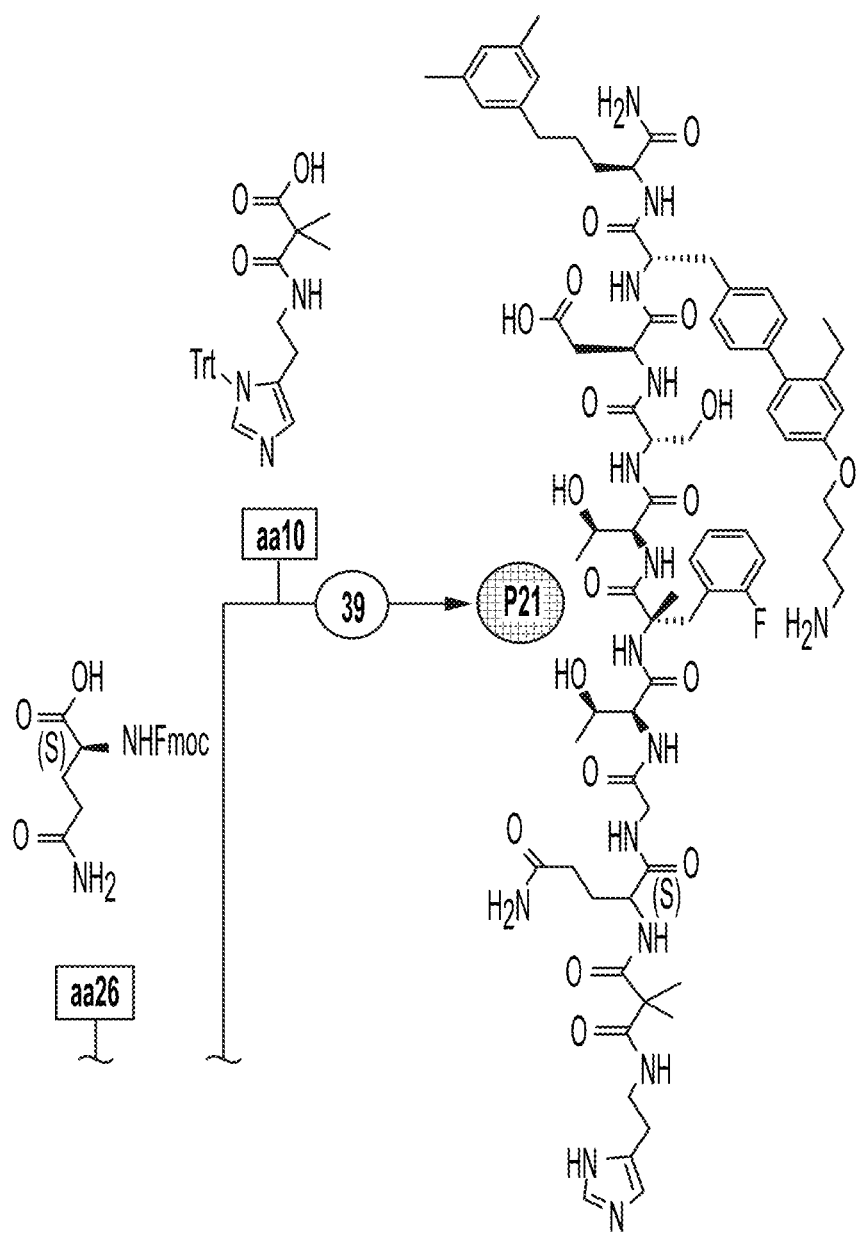
FIG. 18 shows a sequence for solid-supported synthesis of GLP1 peptidomimetic payloads P20 and P21 according to the disclosure.
Figure 18:
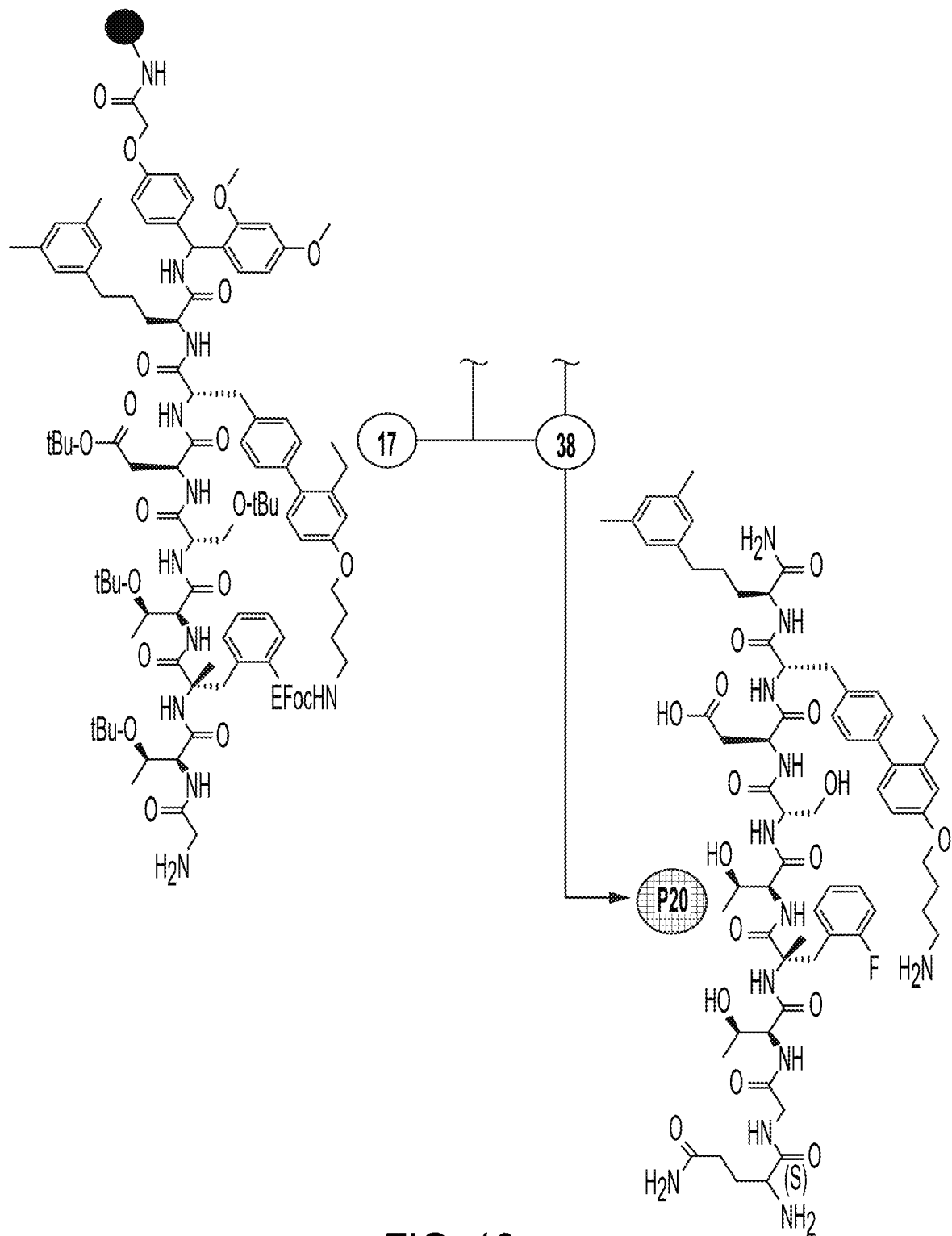

FIG. 18 depicts the sequence of steps for solid support synthesis of GLP1 peptidomimetic payloads P20 and P21 according to the disclosure.

3.30 Preparation of (3S)-4-[[(1S)-1-[[4-[4-(4-aminobutoxy)-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-2-[[(2S,3R)-2-[[2-[[(2S)-2,5-diamino-5-oxopentanoyl]amino]acetyl]amino]-3-hydroxy-butanoyl]amino]-3-(2-fluorophenyl)-2-methyl-propanoyl]amino]-3-hydroxybutanoyl]amino]-3-hydroxy-propanoyl]amino]-4-oxo-butanoic acid (P20)

Starting from the corresponding aa8-aa7-aa6-aa5-aa4-aa3-aa2b-aa1 peptidyl Rink Amide MBHA Resin (17, 175.17 µmol) and aa26 (193.59 mg, 525.51 µmol, 3 eq.), the corresponding aa26-aa8-aa7-aa6-aa5-aa4-aa3-aa2b-aa1 peptidyl Rink Amide MBHA Resin (38, 175.17 µmol) was prepared as described in the general procedure of SPPS.

The corresponding resin-bound peptide 38 (175.17 µmol) was further cleaved following the general procedure to give the crude product as a white solid. The crude was purified by prep-HPLC (column: Waters Xbridge Prep OBD C18 150*40 mm*10 µm; mobile phase: [water (10 mM NH$_4$HCO$_3$)-ACN]; B %: 0%-90%,25 min) to provide P20 (4.65 mg, 3.35 µmol, 95.77% purity) as a white solid.

LCMS: (ESI): RT=0.789 min, mass calcd. for C$_{66}$H$_{93}$FN$_{12}$O$_{16}$ 664.34 m/z [M+2H]$^{2+}$; found 665.0 m/z [M+2H]$^{2+}$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

LCMS: (ESI): RT=1.362 min, mass calcd. for C$_{66}$H$_{92}$FN$_{12}$O$_{16}$ 1327.67 m/z [M+H]$^+$; found 1327.7 m/z [M+H]$^+$; LC-MS: Mobile Phase:1.5 ML/4L TFA in water (solvent A) and 0.75 ML/4L TFA in acetonitrile (solvent B), using the gradient 10%-80% (solvent B) over 2 minutes and holding at 80% for 0.48 minutes at a flow rate of 0.8 ml/min.

HPLC: RT=7.40 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm,5 µm; Wavelength: UV 220 nm&215 nm&254 nm; Column temperature: 40° C.

3.31 Preparation of (3S)-4-[[(1S)-1-[[4-[4-(4-aminobutoxy)-2-ethyl-Phenyl]Phenyl]methyl]-2-[[1 S)-1-carbamoyl-4-(3,5-dimethylphenyl)butyl] amino]-2-oxo-ethyl]amino]-3-[[(2S)-2-[[(2S,3R)-2-[[(2S)-2-[[(2S,3R)-2-[[2-[[(2S)-5-amino-2-[[3-[2-(1H-imidazol-5-yl)ethylamino]-2,2-dimethyl-3-oxo-propanoyl]amino]-5-oxo-pentanoyl]amino]acetyl] amino]-3-hydroxy-butanoyl]amino]-3-(2-fluorophenyl)-2-methyl-propanoyl]amino]-3-hydroxy-butanoyl]amino]-3-hydroxy-propanoyl] amino]-4-oxo-butanoic acid (P21)

Starting from the corresponding aa26-aa8-aa7-aa6-aa5-aa4-aa3-aa2b-aa1 peptidyl Rink Amide MBHA Resin compound 38 (175.17 µmol) and aa10 (163.80 mg, 350.34 µmol, 2 eq.), the corresponding aa10-aa26-aa8-aa7-aa6-aa5-aa4-aa3-aa2b-aa1 peptidyl Rink Amide MBHA Resin (39, 175.17 µmol) was prepared as described in the general procedure of SPPS.

The corresponding resin-bound peptide 39 (175.17 µmol) was further cleaved following the general procedure to give the crude product as a white solid. The crude was purified by prep-HPLC (column: Waters Xbridge Prep OBD C18 150*40 mm*10 µm; mobile phase: [water (0.1% TFA)-ACN]; B %: 15%-45%, 20 min) to provide P21 (20 mg, 12.94 µmol, 7.39% yield, 99.31% purity) as a white solid.

LCMS: (ESI): RT=0.833 min, mass calcd. for C$_{76}$H$_{106}$FN$_{15}$O$_{18}$ 767.89 m/z [M+2H]$^{2+}$; found 768.3 m/z [M+2H]$^{2+}$; LC-MS: MERCK, RP-18e 25-2 mm column, flow rate 1.5 mL/min, eluting with a gradient of 5% to 95% acetonitrile containing 0.02% TFA (solvent B) and water containing 0.04% TFA (solvent A).

HPLC: RT=7.44 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm,5 µm; Wavelength: UV 220 nm&215 nm&254 nm; Column temperature: 40° C.

Figure 19:
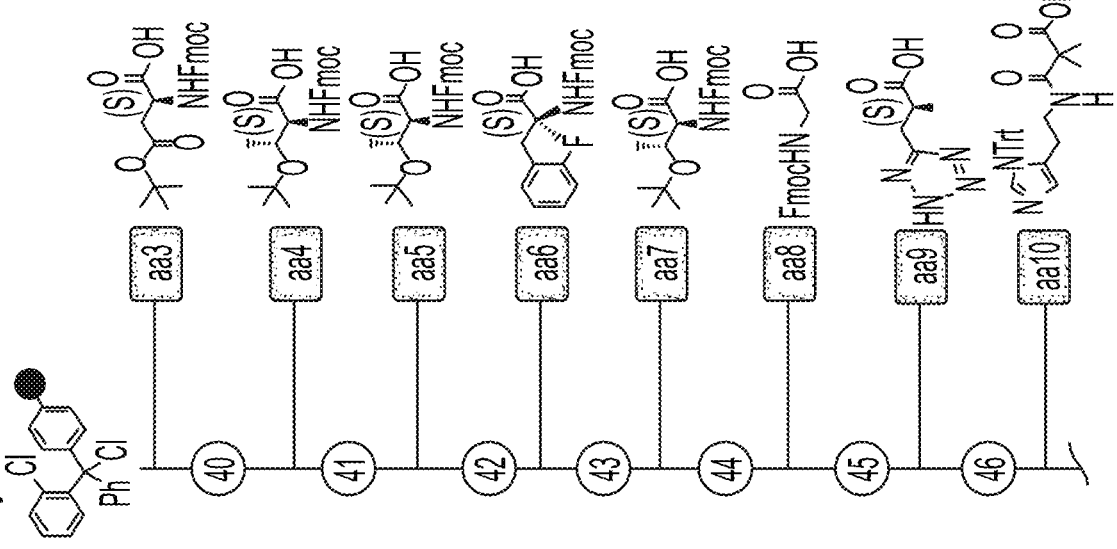
FIG. 19 shows a sequence for solid-supported synthesis of GLP1 peptidomimetic payloads P22 and P23 according to the disclosure.
Figure 19:
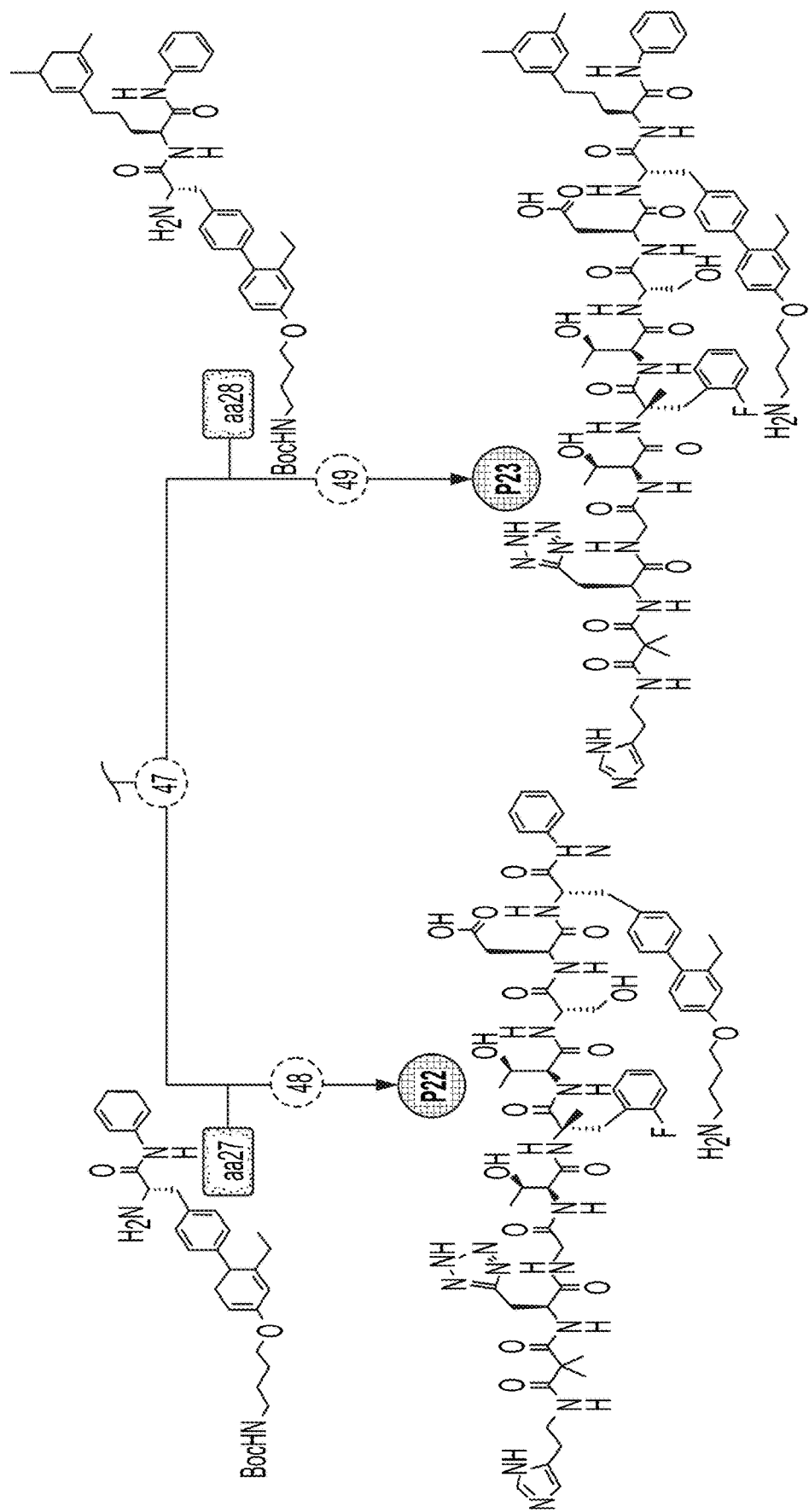

FIG. 19 depicts the sequence of steps for solid support synthesis of GLP1 peptidomimetic payloads P22 and P23 according to the disclosure.

3.32 Preparation of (3S)-4-[[(1S)-1-[[4-[4-(4-aminobutoxy)-2-ethyl-phenyl]phenyl]methyl]-2-anilino-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (P22)

The corresponding aa10-aa9-aa8-aa7-aa6-aa5-aa4-aa3 peptidyl 2-Chlorotrityl Chloride Resin bound 47 was prepared as described in the general procedure of SPPS.

To a mixture of the corresponding resin-bound peptide (47, 553.98 µmol) was added TFE (2.61 g, 26.09 mmol, 1.88 mL, 47.09 eq.) and AcOH (1.97 g, 32.83 mmol, 1.88 mL, 59.26 eq.) in DCM (8 mL) in one portion at 25° C. under N$_2$. The mixture was shaked at 25° C. for 2 hours. LCMS trace showed that the reaction was complete. The mixture was filtered, and the cake was washed with DCM (5 mL×3). The filtrate was concentrated in vacuum to give a yellow oil, which was diluted with water (5 mL). The mixture was adjusted to pH=8 with aq. sat. NaHCO$_3$, yellow solids were precipitated. The mixture was filtered, and the cake was washed with water (5 mL×2), dried in vacuum to give crude product (550 mg, crude) as a yellow solid. The crude was purified by prep-HPLC (column: Xtimate C18 150*25 mm*5 µm; mobile phase: [water (0.225% FA)-ACN]; B %: 48%-58%, 11 min) to give compound 47 (220 mg, 122.65 µmol, 36.10% yield, 82.05% purity) as an off-white solid.

LCMS (ESI): RT=1.073 min, mass calcd. for C$_{76}$H$_{104}$FN$_{14}$O$_{15}$ 1471.78 m/z [M-C$_{19}$H$_{13}$Cl+2H]$^+$, m/z found 1471.65; [M-C$_{19}$H$_{13}$Cl+2H]$^+$, rink 2-[chloro(diphenyl)methyl]benzene (C$_{19}$H$_{13}$Cl, exact mass=276.1); Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

LCMS (ESI): RT=1.079 min, mass calcd. for C$_{76}$H$_{104}$FN$_{14}$O$_{15}$ 1471.78 m/z [M-C$_{19}$H$_{13}$Cl+2H]$^+$, m/z found 1471.8; [M-C$_{19}$H$_{13}$Cl+2H]$^+$, rink 2-[chloro(diphenyl)methyl]benzene (C$_{19}$H$_{13}$Cl, exact mass=276.1); Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: RT=10.96 min. HPLC: Column: YMC-Pack ODS-A 150*4.6 mm,5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min To a solution of compound 47 (37.37 µmol) and HOBt (5.05 mg, 37.37 µmol, 1 eq.) in CHCl$_3$ (0.225 mL) and DMF (0.025 mL) was added aa27 (19.87 mg, 37.37 µmol, 1 eq.) at 20° C. A solution of DIC (4.72 mg, 37.37 µmol, 5.79 µL, 1 eq.) in CHCl$_3$ (0.225 mL) and DMF (0.025 mL) were added to the mixture. The reaction was stirred at 20° C. for 16 hours. LCMS trace showed that the reaction was complete. The reaction was concentrated in vacuum to give crude product 48 (74.2 mg, 37.37 µmol) as a brown oil, which was used to the next step without further purification.

LCMS (ESI): RT=1.215 min, mass calcd. for $C_{103}H_{144}FN_{17}O_{13}$ 993.05 m/z $[M+2H]^{2+}$, m/z found 993.8 m/z $[M+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

To a mixture of compound 48 (74.2 mg, 37.37 µmol, 1 eq.) was added triisopropylsilane (137.30 mg, 867.01 µmol, 178.08 µL, 23.20 eq.) in TFA (2 mL) and $H_2O$ (0.06 mL) in one portion at 25° C. under $N_2$. The mixture was standing at 15° C. for 2.5 hours. LCMS trace showed that the reaction was complete. The mixture was concentrated in vacuum to give crude as a yellow oil. The crude was purified by prep-HPLC (column: Waters Xbridge Prep OBD C18 150*30 mm, 10 µm; mobile phase: [water (10 mM $NH_4HCO_3$)-ACN]; B %: 28%-58%, 11 min) to give compound P22 (7.5 mg, 5.18 µmol, 13.86% yield, 97.96% purity) as a white solid.

LCMS (ESI): RT=0.811 min, mass calcd. for $C_{68}H_{90}FN_{17}O_{16}$ 709.84 m/z $[M+2H]^{2+}$, m/z found 710.2 m/z $[M+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: RT=7.06 min. HPLC: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min.

3.33 Preparation of (3S)-4-[[(1S)-1-[[4-[4-(4-aminobutoxy)-2-ethyl-phenyl]phenyl]methyl]-2-[[(1S)-4-(3,5-dimethylphenyl)-1-(phenylcarbamoyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (P23)

To a solution of 47 (27.18 µmol) and HOBt (3.67 mg, 27.18 µmol, 1 eq.) in $CHCl_3$ (0.225 mL) and DMF (0.025 mL) was added aa28 (19.98 mg, 27.18 µmol, 1 eq.) at 20° C. A solution of DIC (3.43 mg, 27.18 µmol, 4.21 µL, 1 eq.) in $CHCl_3$ (0.225 mL) and DMF (0.025 mL) were added to the mixture. The reaction was stirred at 20° C. for 16 hours. LCMS trace showed that the reaction was complete. The reaction was concentrated in vacuum to give crude product 49 (59.49 mg, 27.18 µmol) as a brown oil, which was used to the next step without further purification.

LCMS (ESI): RT=1.223 min, mass calcd. for $C_{116}H_{154}FN_{18}O_{17}$ 1045.09 m/z $[M-Boc+3H]^{2+}$, m/z found 1044.8 m/z $[M-Boc+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

To a mixture of compound 49 (59.49 mg, 27.18 µmol, 1 eq.) was added triisopropylsilane (131.07 mg, 827.67 µmol, 0.17 mL, 30.45 eq.) in TFA (6 mL) and $H_2O$ (0.17 mL) in one portion at 15° C. under $N_2$. The mixture was standing at 15° C. for 2.5 hours. LCMS trace showed that the reaction was complete. The mixture was concentrated in vacuum to give crude as yellow oil. The crude was purified by prep-HPLC (column: Xtimate C18 10 µm, 250 mm*50 mm; mobile phase: [water (0.04% $NH_3H_2O$+10 mM $NH4HCO3$)-ACN]; B %: 25%-55%, 8 min) to give compound P23 (7.5 mg, 4.60 µmol, 16.91% yield, 99.38% purity) as a white solid.

LCMS (ESI): RT=0.875 min, mass calcd. for $C_{31}H_{107}FN_{18}O_{17}$ 811.4 m/z $[M+2H]^{2+}$, m/z found 811.9 m/z $[M+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

LCMS (ESI): RT=0.882 min, mass calcd. for $C_{31}H_{107}FN_{18}O_{17}$ 811.4 m/z $[M+2H]^{2+}$, m/z found 811.8 m/z $[M+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: RT=8.30 min. HPLC: Column: YMC-Pack ODS-A 150*4.6 mm,5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Figure 20:
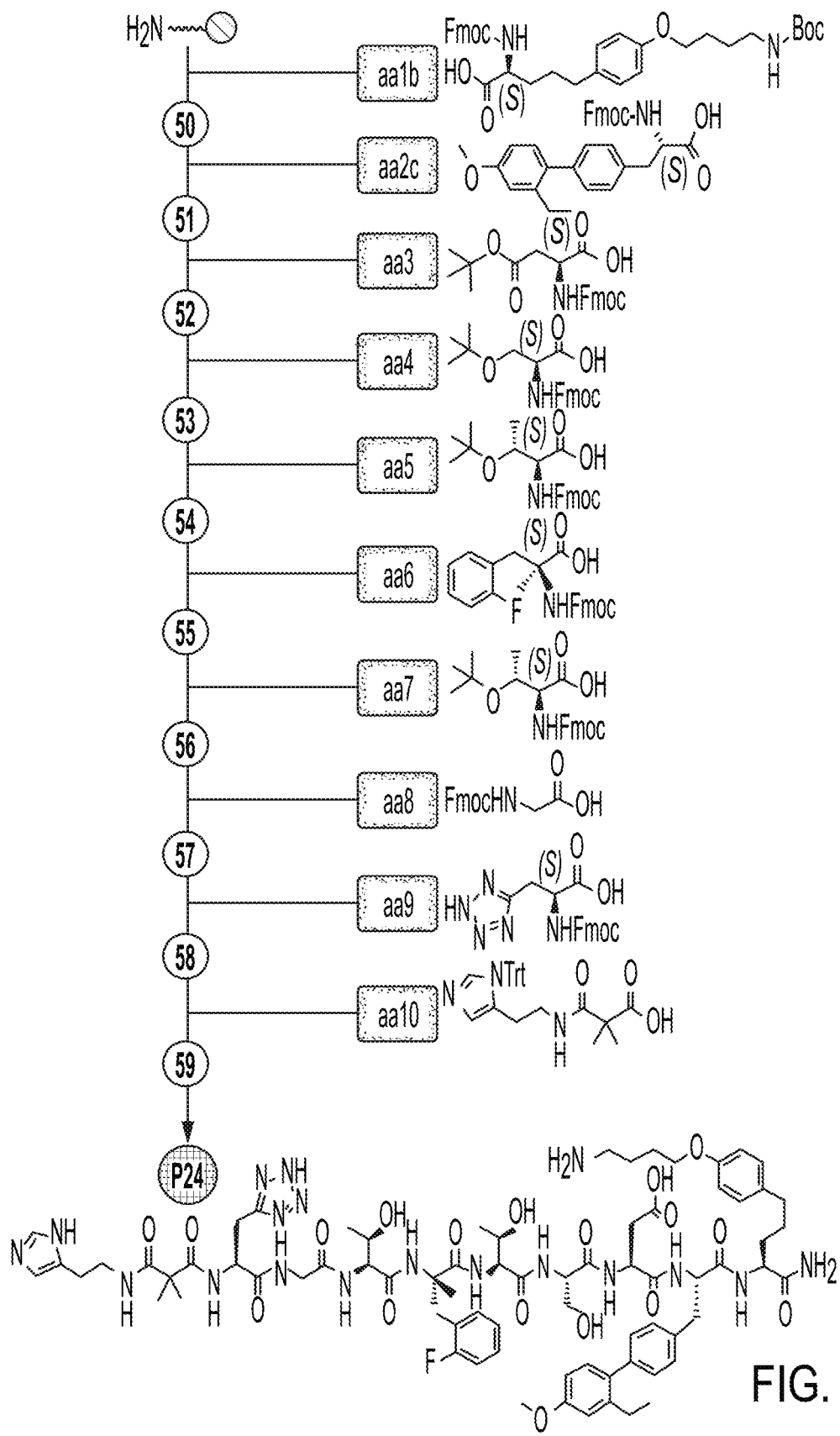
FIG. 20 shows a sequence for solid-supported synthesis of GLP1 peptidomimetic payload P24 according to the disclosure.

FIG. 20 depicts the sequence of steps for solid support synthesis of GLP1 peptidomimetic payload P24 according to the disclosure.

3.34 Preparation of (3S)-4-[[(1S)-2-[[(1S)-4-[4-(4-aminobutoxy)phenyl]-1-carbamoyl-butyl]amino]-1-[[4-(2-ethyl-4-methoxy-phenyl)phenyl]methyl]-2-oxo-ethyl]amino]-3-[[(2S)-2-[[(2R,3R)-2-[[(2S)-3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (P24)

The corresponding aa10-aa9-aa8-aa7-aa6-aa5-aa4-aa3-aa2c-aa1b peptidyl Rink Amide MBHA Resin (59) was prepared as described in the general procedure of SPPS.

The corresponding resin-bound peptide 59 was further cleaved following the general procedure to give the crude product as a white solid. The crude product was purified by prep-HPLC (column: mobile phase: [water (10 mM $NH_4HCO_3$)-ACN]; B %: 15%-45%, 55 min) to afford pure product. The product was suspended in water (20 mL), the mixture frozen in a dry-ice/acetone bath, and then lyophilized to dryness to afford the desired product. Compound P24 (50 mg, 29.69 µmol, 6.76% yield, 98.686% purity, TFA salt) was obtained as a white solid.

LCMS (ESI): RT=0.821 min, mass calcd. for $C_{74}H_{99}FN_{18}O_{18}$ 1546.74 $[M+H]^+$, 773.4 $[M+H]^{2+}$, m/z found 774.8 $[M+H]^{2+}$. Reverse phase LC-MS was carried out using a Chromolith Flash RP-18e 25-2 mm column, with a flow rate of 1.5 mL/min, eluting with a gradient of 5% to 95% acetonitrile containing 0.02% TFA (solvent B) and water containing 0.04% TFA (solvent A).

Figure 21:
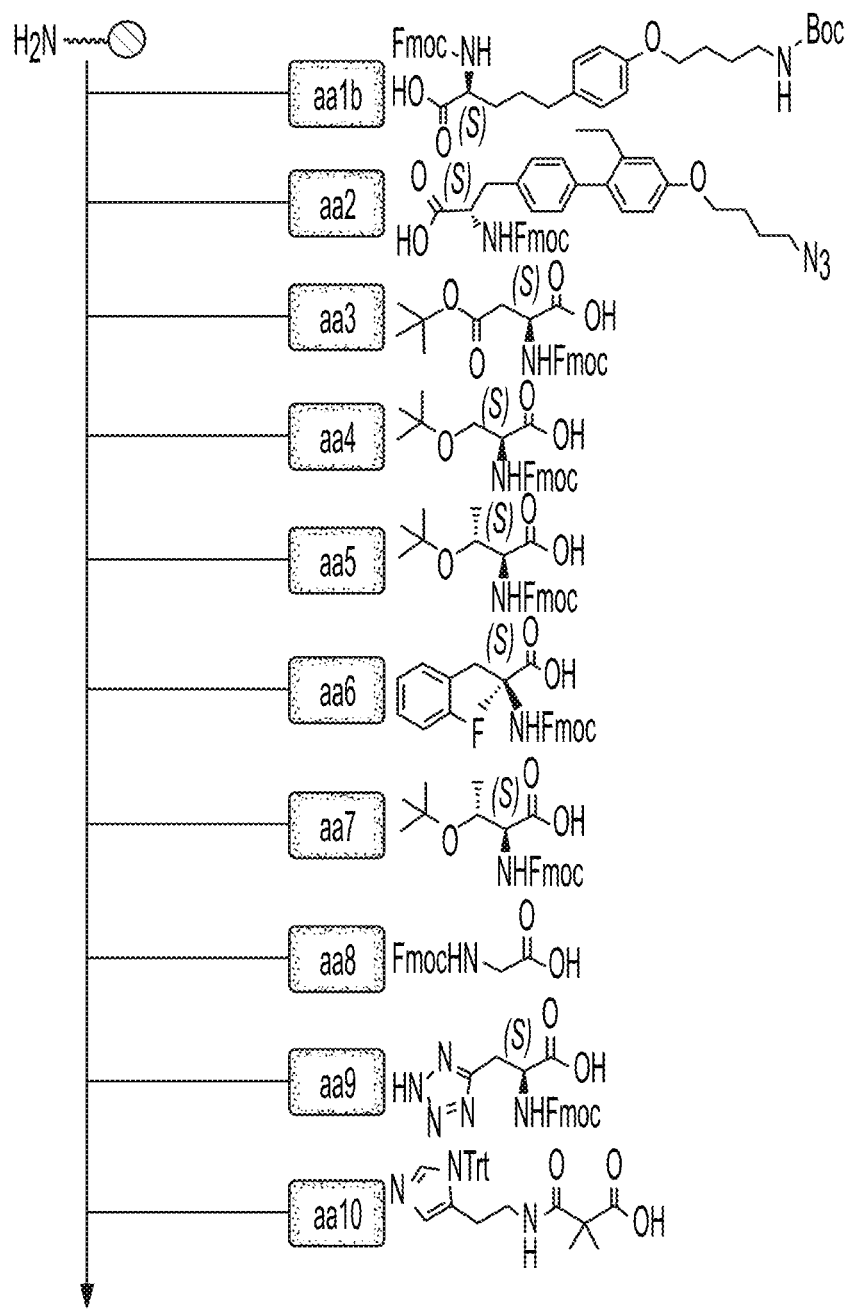
FIG. 21 shows a sequence for solid-supported synthesis of GLP1 peptidomimetic payloads P32, P33, P34 and P35 according to the disclosure.
Figure 21:
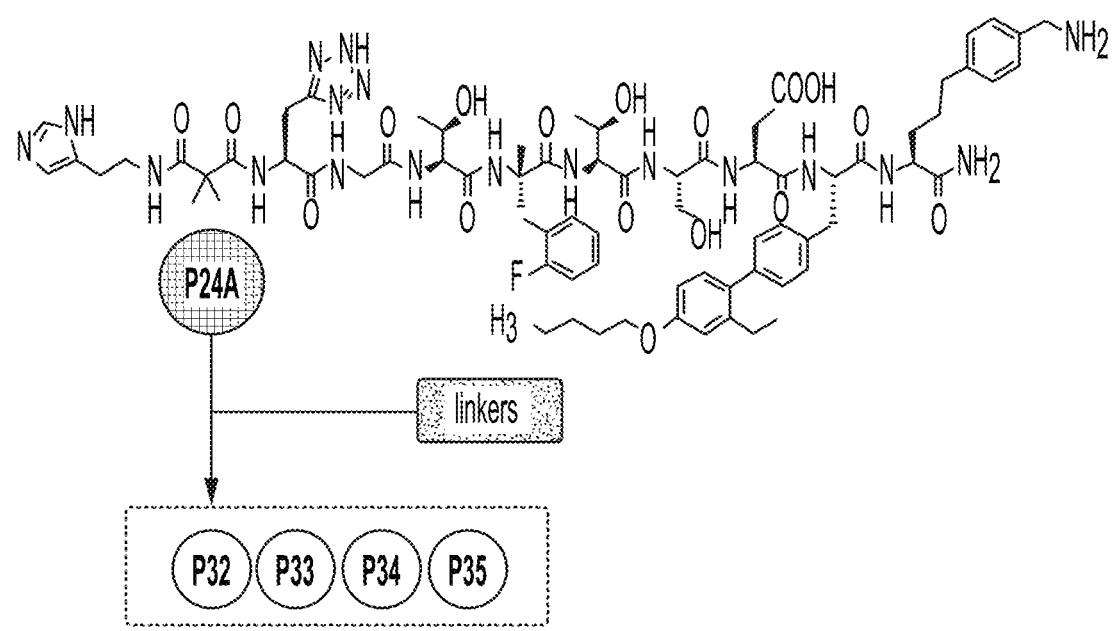

FIG. 21 depicts the sequence of steps for solid support synthesis of GLP1 peptidomimetic payloads P32, P33, P34, and P35 according to the disclosure.

3.35 Preparation of (8S,14S,17S,20S,23S,26S)-8-((2H-tetrazol-5-yl)methyl)-26-(((S)-1-(((S)-1-amino-5-(4-(aminomethyl)phenyl)-1-oxopentan-2-yl) amino)-3-(4'-(4-azidobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13,16,19,22,25-octaazaoctacosan-28-oic acid (P24A (SEQ ID NO: 146))

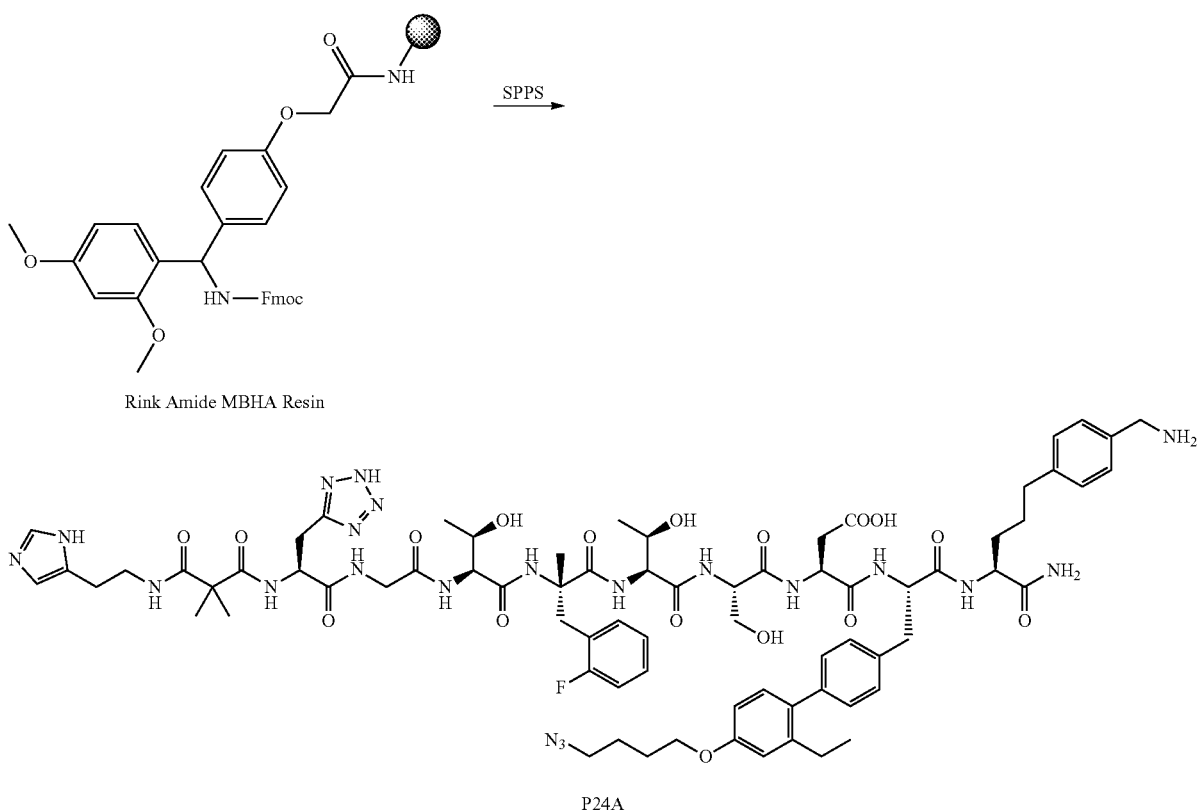

P24A

The peptide elongation was performed on a 0.5 mmol scale using Liberty Lite Automated Microwave Peptide Synthesizer. To a polypropylene solid-phase reaction vessel was added Rink Amide MBHA Resin (0.5 mmol, 1 eq.). The resin was washed (swelled) two times as follows: to the reaction vessel was added DMF (10 mL) through the top of the vessel upon which the mixture was agitated for 5 minutes before the solvent was drained through the frit.

The general coupling reaction of each amino acid was carried out after general removal of Fmoc group procedure. A) General removal of Fmoc group procedure: To the reaction vessel containing the resin from the previous step was added piperidine:DMF (1:4 v/v, 5 mL). The mixture was agitated under microwave at 90° C. for 2 min and then the solution was drained through the frit. The resin was washed five times as follows: for each wash, DMF (5 mL) was added through the top of the vessel and the resulting mixture was periodically agitated for 0.5 minutes before the solution was drained through the frit. B) General coupling reaction procedure:

To the reaction vessel was added the amino acid (0.2 M in DMF, 12.5 mL, 5 eq.), then DIC (0.5 M in DMF, 4 mL, 4 eq.) and oxyma (0.5 M in DMF, 2 mL, 2 eq.). The mixture was agitated under microwave at 90° C. for 10 min, then the reaction solution was drained through the frit. The resin was washed four times as follows: for each wash, DMF (8 mL) was added through the top of the vessel and the resulting mixture was periodically agitated for 0.5 minutes before the solution was drained through the frit. After completion of synthesis, resin was thoroughly rinsed with DMF (6×6 mL) then $CH_2Cl_2$ (6×6 mL). The resulting resin was subjected to acidic cleavage by using TFA cocktail (TFA/TIPS/$H_2O$=95:2.5:2.5) for 2 hours, then filtered and the filtrate was diluted with t-BuOMe to give a precipitate, which was centrifuged (5000 R) for 10 min and decanted to give a crude product.

The corresponding aa10-aa9-aa8-aa7-aa6-aa5-aa4-aa3-aa2-aa1b peptidyl Rink Amide MBHA Resin was prepared as described in the general procedure of SPPS. The crude product was purified by prep-HPLC (column: Phenomenex Gemini-NX C18 80*30 mm*5 μm; mobile phase: [water (0.1% TFA)-ACN]; B %: 5%-55%, 8 min) to afford pure product P24A (50 mg, 31.79 μmol, 41.80% yield) as a white solid.

LCMS (ESI): RT=2.913 min, m/z calcd. $C_{75}H_{101}FN_{20}O_{17}$ 786.37, found 786.9 $[M+2H]^{2+}$. LCMS conditions: 1.5 ML/4LTFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 μm, C18, 2.1*30 mm.

HPLC: RT=7.44 min, 99.18% purity. HPLC method A: Column: YMC-Pack ODS-A 150*4.6 mm, 5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.36 Preparation of (8S,14S,17S,20S,23S,26S)-8-((2H-tetrazol-5-yl)methyl)-26-(((S)-1-(((S)-1-amino-5-(4-(13-amino-3,6,9,12-tetraoxo-2,5,8,11-tetraazatridecyl)phenyl)-1-oxopentan-2-yl)amino)-3-(4'-(4-azidobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-y)-5,5,17-trimethyl-4,6,9,12,15,18,21,24-octaoxo-3,7,10,13,16,19,22,25-octaazaoctacosan-28-oic acid (P32)

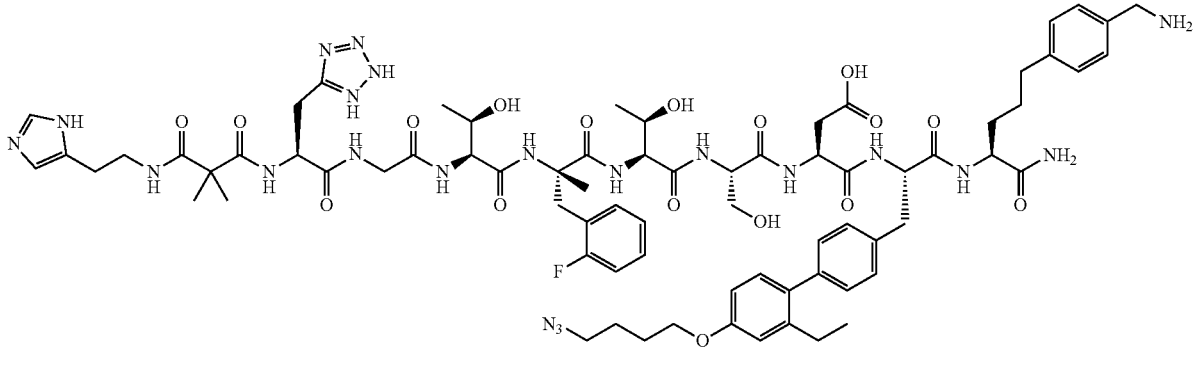

P24A

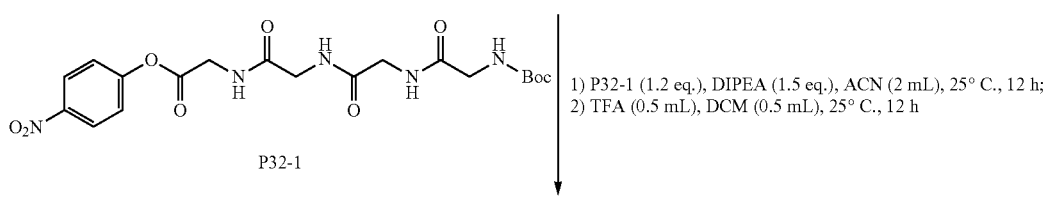

P32-1

1) P32-1 (1.2 eq.), DIPEA (1.5 eq.), ACN (2 mL), 25° C., 12 h;
2) TFA (0.5 mL), DCM (0.5 mL), 25° C., 12 h

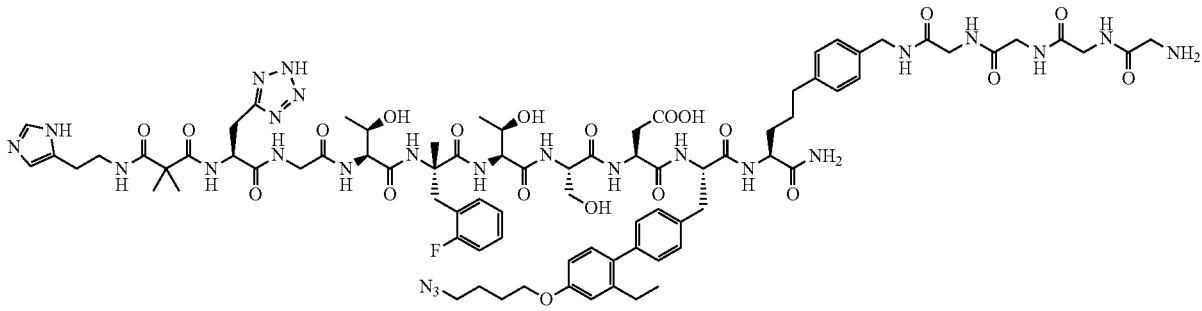

P32

To a solution of P24A (SEQ ID NO: 146) (20 mg, 12.72 µmol, 1 eq.) in DMF (2 mL) were added P32-1 (7.13 mg, 15.26 µmol, 1.2 eq.) and DIPEA (3.29 mg, 25.43 µmol, 4.43 µL, 2.0 eq.). Then the solution was stirred at 20° C. for 2 hr. After completion, water (6 mL) was added and the mixture was lyophilized to give a white solid (25 mg, crude), which was added in DCM (2.5 mL), followed by the addition of TFA (3.85 g, 33.77 mmol, 2.5 mL, 2567.52 eq.). Then the solution was stirred at 20° C. for 2 hr. After completion, the solvent of the solution was removed under reduced pressure to give the crude. It was purified by prep-HPLC (column: Phenomenex Gemini-NX 80*40 mm*3 µm; mobile phase: [water (0.1% TFA)-ACN]; B %: 5%-45%, 30 min). P32 (SEQ ID NOS 147 and 176, respectively, in order of appearance) (7.2 mg, 3.60 µmol, 27.36% yield, 90% purity) was obtained as a white solid.

LCMS: (ESI): Rt=2.880 min, mass calcd. for $C_{82}H_{112}FN_{25}O_{21}$ 901.20, found 900.91 $[M+2H]^{2+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC: RT=7.23 min, 100% purity. HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.37 Preparation of (8S,14S,17S,20S,23S,26S)-8-((2H-tetrazol-5-yl)methyl)-26-(((S)-1-(((S)-1-amino-5-(4-(17-hydroxy-3-oxo-6,9,12,15-tetraoxa-2-aza-heptadecyl)phenyl)-1-oxopentan-2-yl)amino)-3-(4'-(4-azidobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13,16,19,22,25-octaazaoctacosan-28-oic acid (P33)

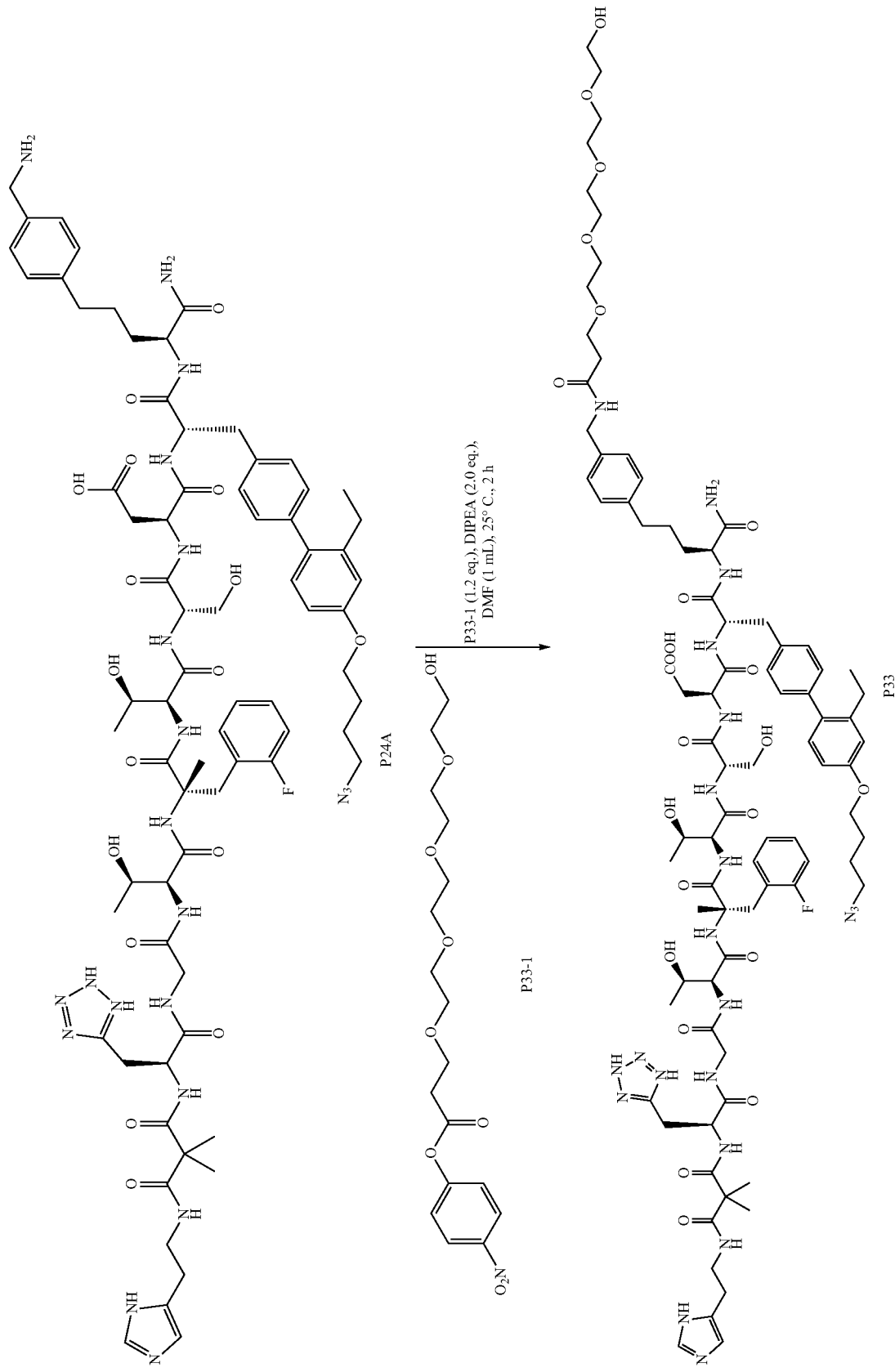

To a solution of P24A (SEQ ID NO: 146) (10 mg, 6.36 µmol, 1 eq.) in DMF (0.3 mL) were added P33-1 (2.96 mg, 7.63 µmol, 1.2 eq.) and DIPEA (1.64 mg, 12.72 µmol, 2.22 µL, 2.0 eq). Then the solution was stirred at 20° C. for 2 hr. After completion, the reaction mixture was purified by prep-HPLC (TFA condition, column: Boston Green ODS 150*30 mm*5 µm; mobile phase: [water (0.1% TFA)-ACN]; B %: 14%-54%,9 min) to afford P33 (SEQ ID NO: 148) (2.0 mg, 1.13 µmol, 17.69% yield, 95% purity) as a white solid.

LCMS: (ESI): Rt=3.383 min, mass calcd. for $C_{55}H_{120}FN_{21}O_{23}$ 911.40, found 911.40 $[M+2H]^{2+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC: RT=7.96 min, 95.47% purity. HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.38 Preparation of (8S,14S,17S,20S,23S,26S)-8-((2H-tetrazol-5-yl)methyl)-26-(((S)-1-(((S)-1-amino-5-(4-(29,29-dimethyl-3,6,9,12,15,18,21,24,27-non-aoxo-28-oxa-2,5,8,11,14,17,20,23,26-nonaazatriacontyl)phenyl)-1-oxopentan-2-yl)amino)-3-(4'-(4-azidobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3, 7, 10, 13, 16, 19,22,25-octaazaoctacosan-28-oic acid (P34)

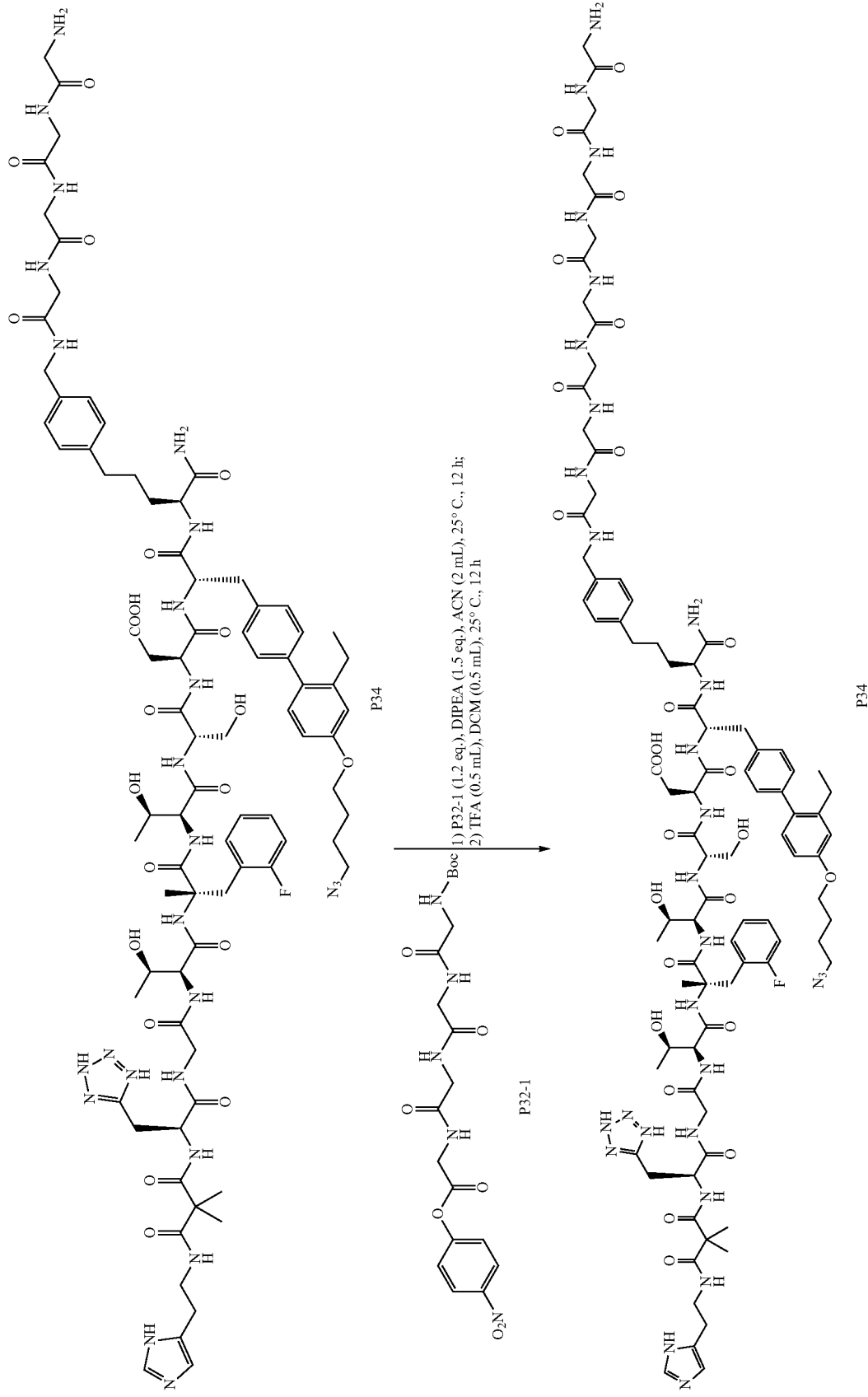

To a solution of P32 (SEQ ID NOS 147 and 176, respectively, in order of appearance) (5 mg, 2.78 μmol, 1 eq) in DMF (1 mL) were added P32-1 (1.56 mg, 3.33 μmol, 1.2 eq) and DIPEA (717.64 μg, 5.55 μmol, 9.67e-1 μL, 2.0 eq.). Then the solution was stirred at 20° C. for 2 hr. After completion, water (6 mL) was added and the mixture was lyophilized to give a white solid (25 mg, crude), which was added in DCM (0.2 mL), followed by the addition of TFA (256.67 mg, 2.25 mmol, 166.67 μL, 958.60 eq.). Then the solution was stirred at 20° C. for 2 hr. After completion, the solvent of the solution was removed under reduced pressure to give the crude. It was purified by prep-HPLC (column: Waters Xbridge BEH C18 100*25 mm*5 μm; mobile phase: [water (0.1% TFA)-ACN]; B %: 10%). P34 (SEQ ID NOS 149 and 177, respectively, in order of appearance) (1.72 mg, 7.63e-1 μmol, 32.49% yield, 90% purity) was obtained as a white solid.

LCMS: (ESI): Rt=2.760 min, mass calcd. for $C_{90}H_{124}FN_{29}O_{25}$ 1014.98, found 1015.20 $[M+2H]^{2+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC: RT=7.15 min, 100% purity. HPLC method A: Column: YMC-Pack ODS-A 150*4.6 mm, 5 μm; 2.75 ML/4 LTFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

3.39 Preparation of (8S,14S,17S,20S,23S,26S)-8-((2H-tetrazol-5-yl)methyl)-26-(((S)-1-(((S)-1-amino-5-(4-(17-hydroxy-3-oxo-6,9,12,15-tetraoxa-2-azaheptadecyl)phenyl)-1-oxopentan-2-yl)amino)-3-(4'-(4-azidobutoxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6, 9,12,15,18, 21,24-octaoxo-3,7,10,13,16,19,22,25-octaazaoctacosan-28-oic acid (P35)

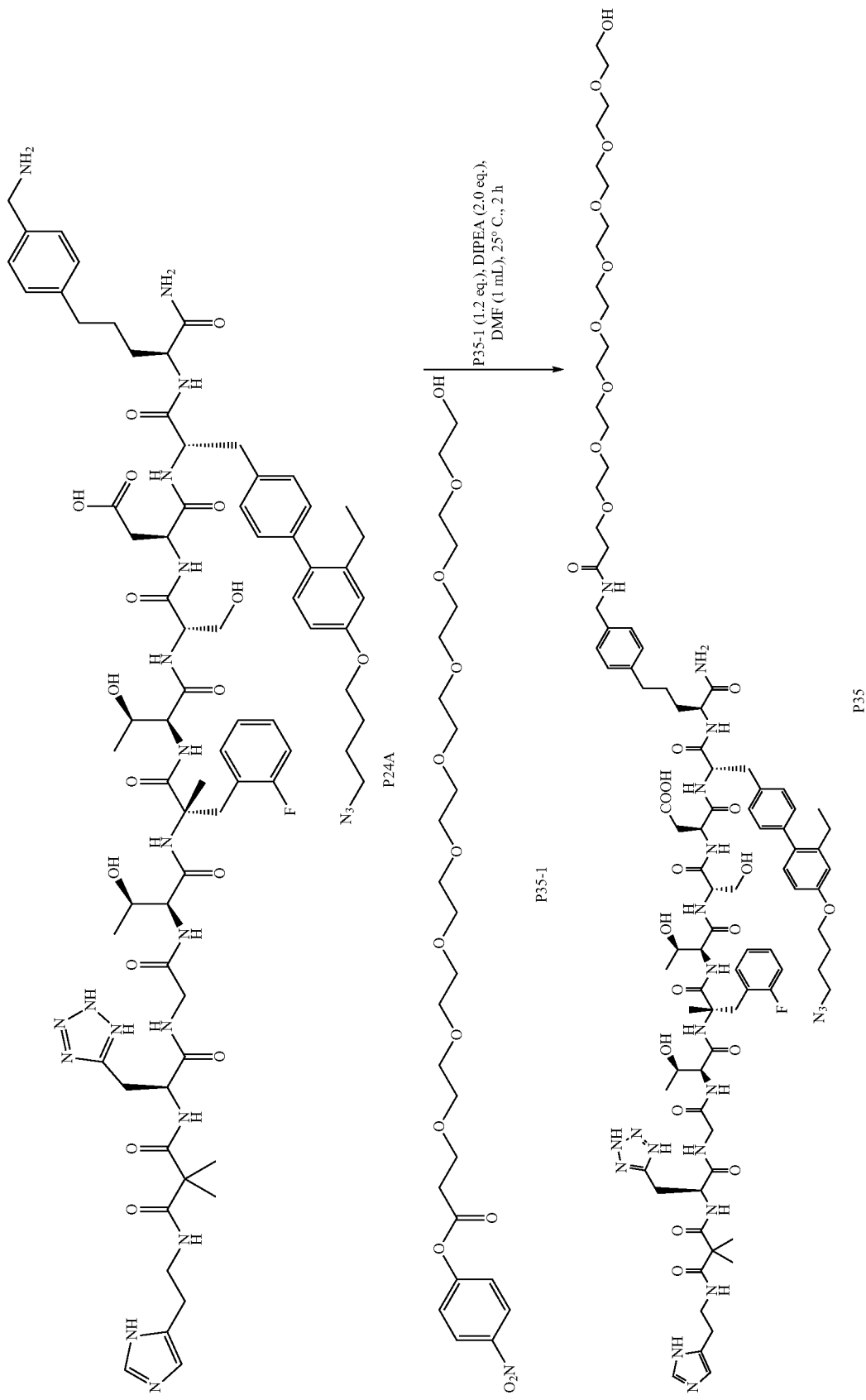

To a solution of P24A (SEQ ID NO: 146) (20 mg, 12.72 µmol, 1 eq.) in DMF (0.3 mL) were added P35-1 (10.75 mg, 19.08 µmol, 1.5 eq.) and DIPEA (3.29 mg, 25.43 µmol, 4.43 µL, 2.0 eq.). Then the solution was stirred at 20° C. for 2 hr. After completion, the reaction mixture was purified by prep-HPLC (column: Boston Green ODS 150*30 mm*5 µm; mobile phase: [water (0.1% TFA)-ACN]; B %: 14%-54%,9 min) to afford P33 (SEQ ID NO: 75) (20 mg, 10.01 µmol, 78.75% yield, 100% purity) as a white solid.

LCMS: (ESI): Rt=3.325 min, mass calcd. for $C_{93}H_{136}FN_{21}O_{27}$ 998.98, found 999.40 $[M+2H]^{2+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC: RT=7.88 min, 100% purity. HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Figure 22:
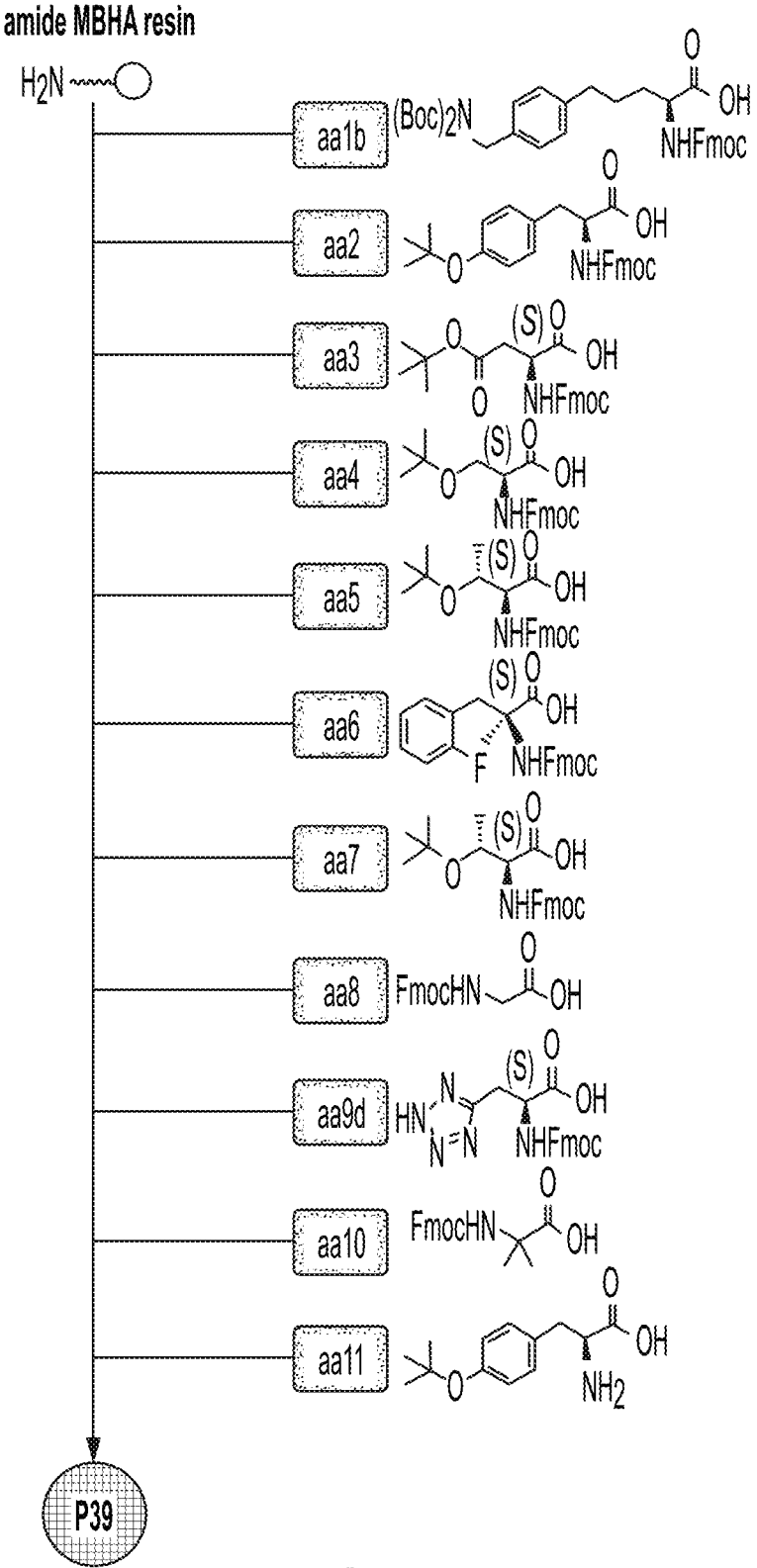
FIG. 22 shows a sequence for solid-supported synthesis of GLP1 peptidomimetic payload P39 according to the disclosure.
Figure 22:
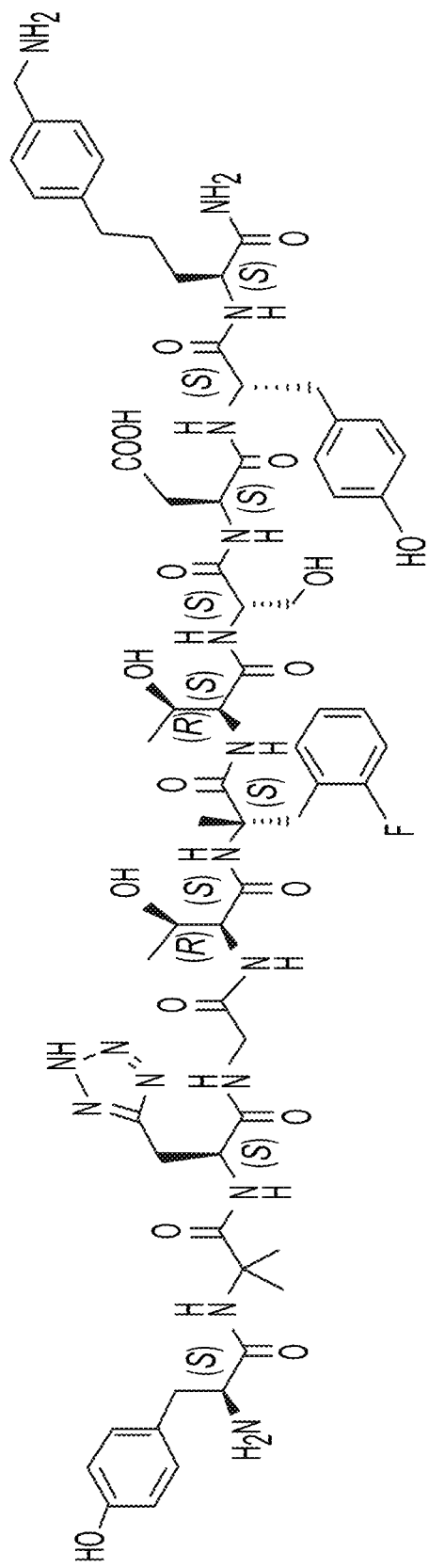
Figure 23:
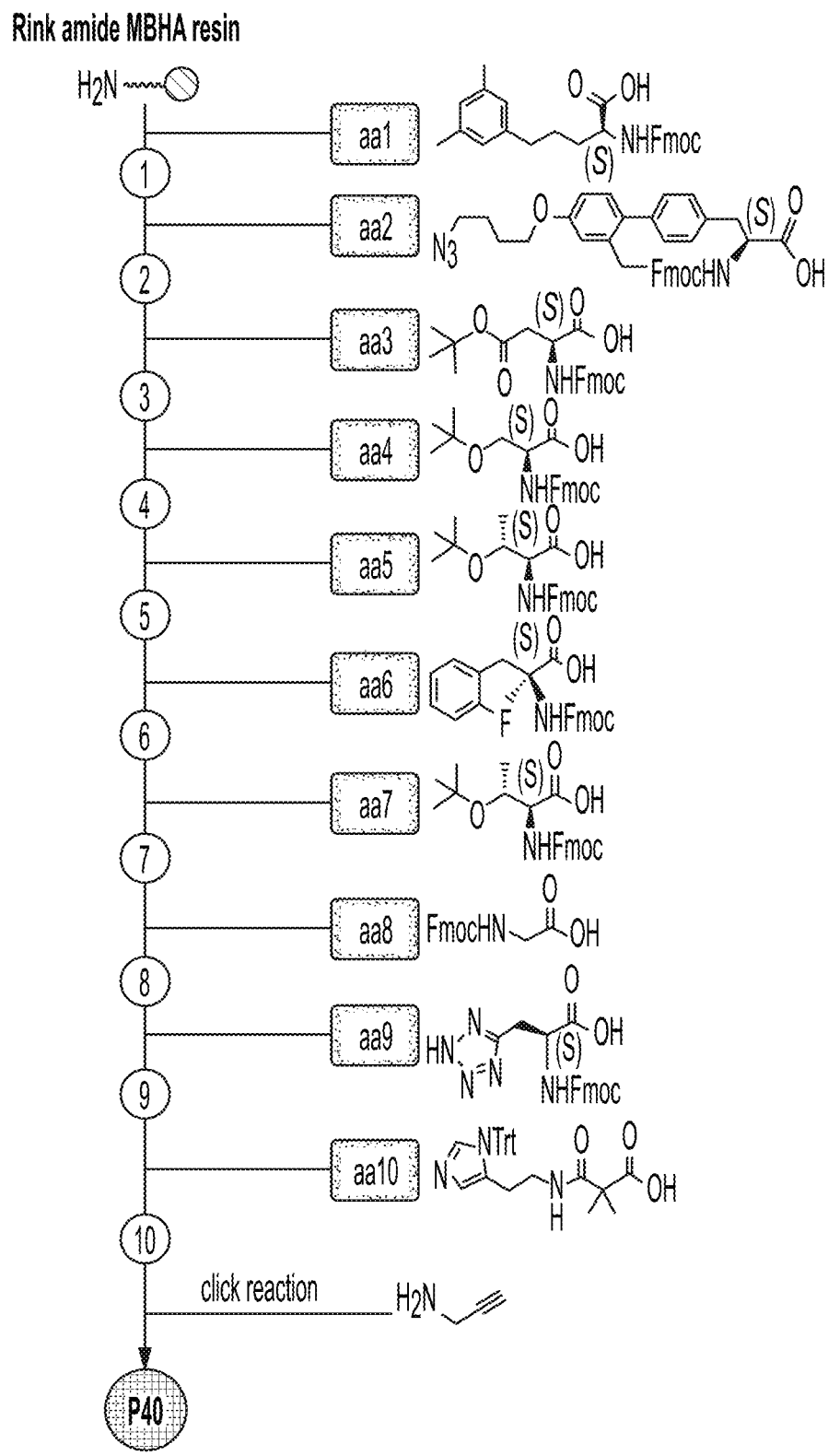
FIG. 23 shows a sequence for solid-supported synthesis of GLP1 peptidomimetic payload P40 according to the disclosure.
Figure 23:
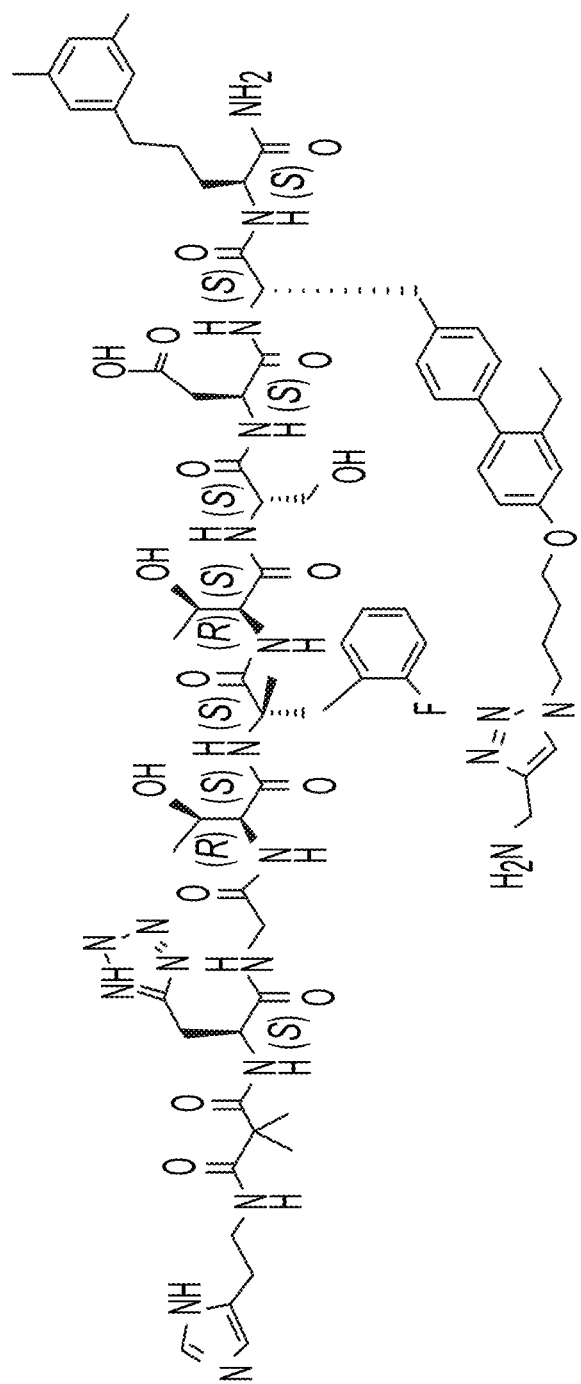
Figure 24:
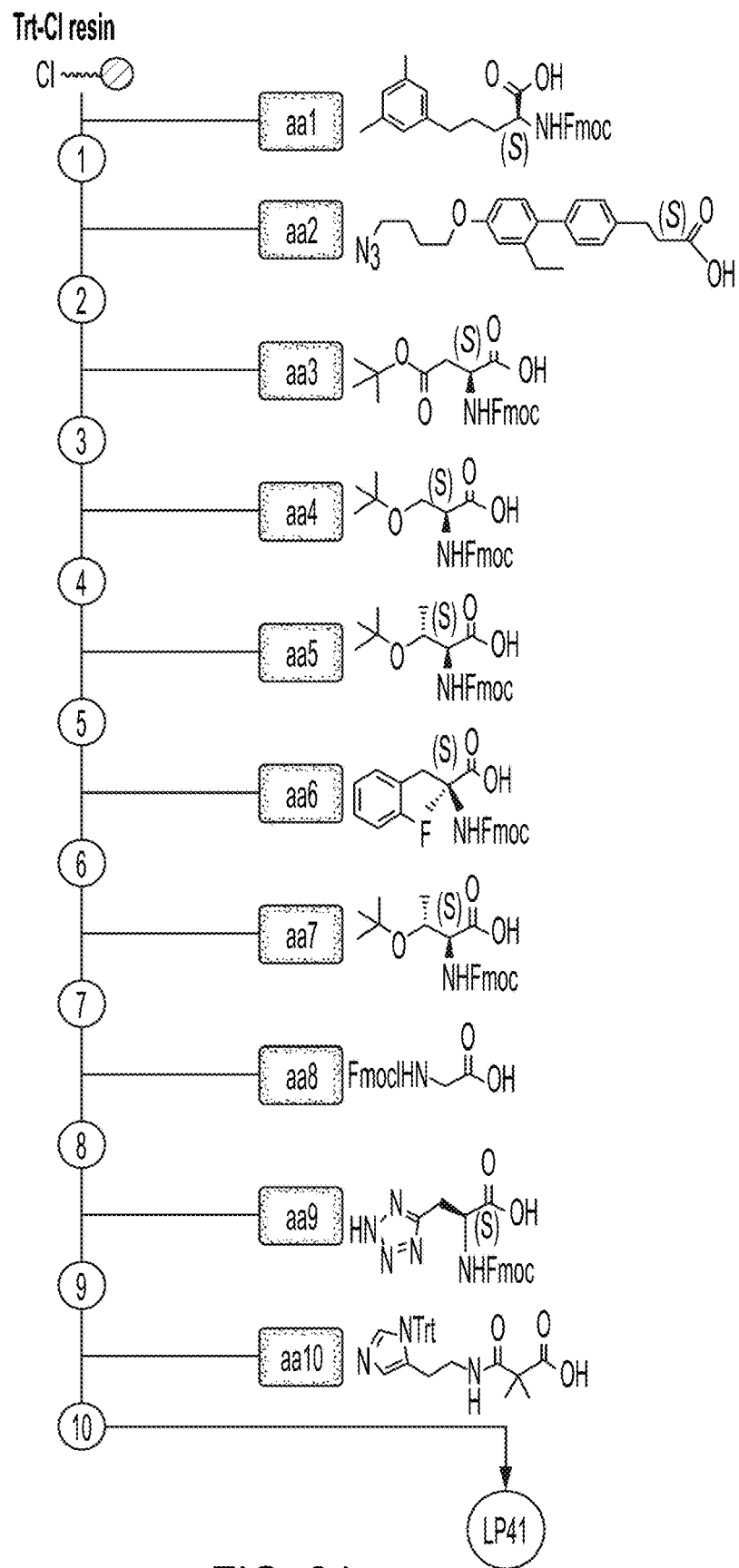
FIG. 24 shows a sequence for solid-supported synthesis of GLP1 peptidomimetic payload P41 according to the disclosure.
Figure 24:
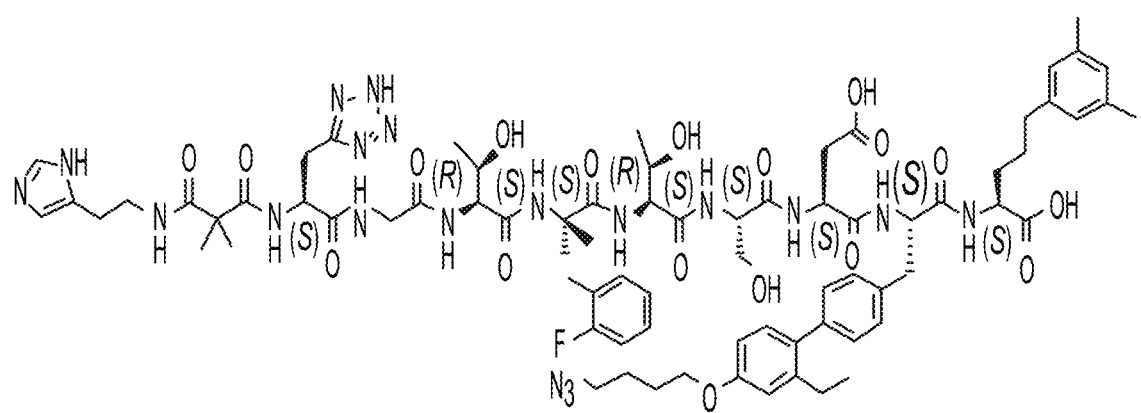
Figure 25:
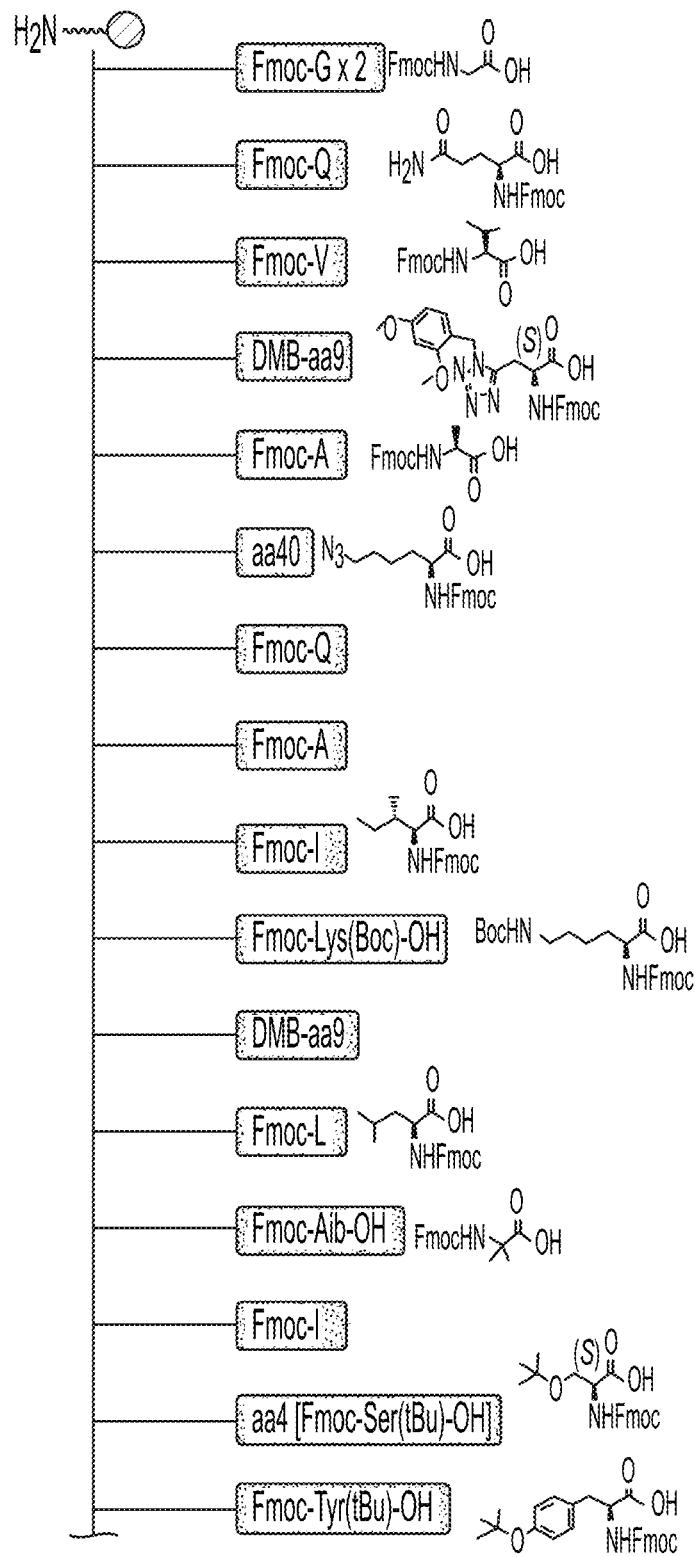
FIG. 25 shows a sequence for solid-supported synthesis of GLP1 peptidomimetic payload P42 according to the disclosure.
Figure 25:
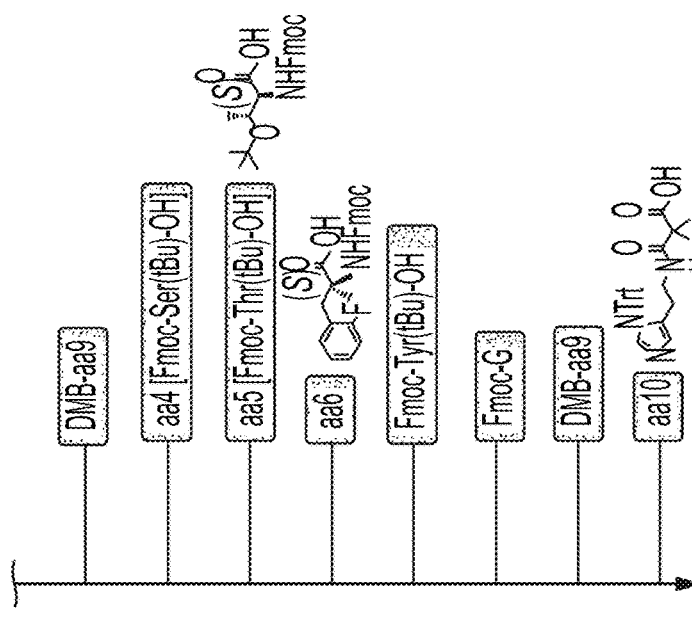
Figure 25:
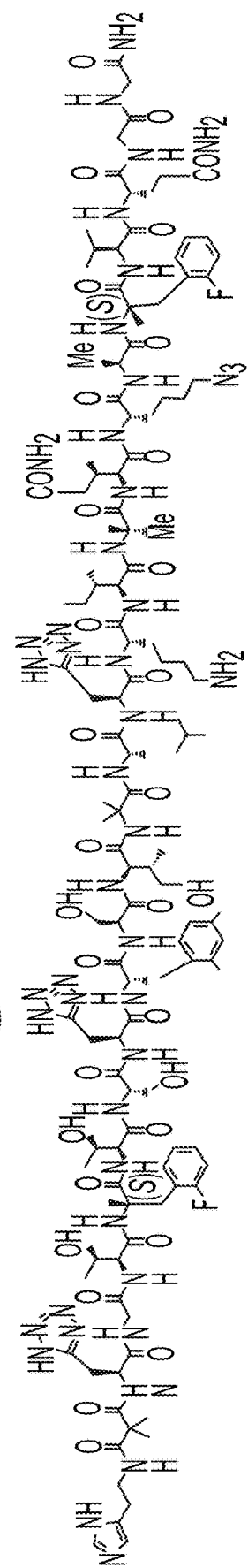

FIG. 22 depicts the sequence for synthesis of P39.

Preparation of (3S,6S,9S,12S,15S,21S,27S)-21-((2H-tetrazol-5-yl)methyl)-27-amino-3-(((S)-1-(((S)-1-amino-5-(4-(aminomethyl)phenyl)-1-oxopentan-2-yl)amino)-3-(4-hydroxyphenyl)-1-oxopropan-2-yl)carbamoyl)-12-(2-fluorobenzyl)-9,15-bis((R)-1-hydroxyethyl)-6-(hydroxymethyl)-28-(4-hydroxyphenyl)-12,24,24-trimethyl-5,8,11,14,17,20,23,26-octaoxo-4, 7,10,13,16,19,22,25-octaazaoctacosan-1-oic acid (P39 (SEQ ID NO: 79))

synthesizer: a) De-protection: a solution of 20% piperidine/DMF (5 mL) was added to the resin vessel, agitated with $N_2$ for 2 min at 90° C. Then drained the vessel and washed with DMF (3 mL×3) at 20° C. b) Coupling (each amino acid reacted for triple with 5.0 eq.): a solution of amino acid (2.5 mmol, 5 eq.) in DMF (5 mL), DIC (2 mL) and oxyma (1 mL) were added to the vessel and agitated with $N_2$ for 10 min at 90° C. Repeat a) and b) for all amino acids. The resin was subjected to acidic cleavage by using TFA cocktail (TFA/TIPS/$H_2O$=95:2.5:2.5), then filtered and the filtrate was diluted with t-BuOMe to give a precipitate, which was centrifuged (5000 R) for 10 min to give the crude product.

The corresponding aa24-aa25-aa9-aa8-aa7-aa6-aa5-aa4-aa3-Y-aa1b peptidyl Rink Amide MBHA Resin was prepared as described in the general procedure of SPPS. The crude product was purified by prep-HPLC (column: Boston Prime C18 150*30 mm*5 µm; mobile phase: [water (0.05% ammonia hydroxide v/v)-ACN]; B %: 0%-35%, 9 min) to afford pure product P39 (15 mg, 9.35 µmol, 9.35% yield, 88% purity) as a white solid. The product was further purified by prep-HPLC (column: Welch Xtimate C18 100*40 mm*3 µm; mobile phase: [water (0.075% TFA)-ACN]; B %: 5%-45%, 12 min) to give the product (10 mg, 6.96 µmol, 65.51% yield, 98.26% purity) was obtained as a white solid.

LCMS (ESI): RT=1.573 min, m/z calcd. for C65H87FN17O18 $[M+H]^+$ 1412.63, C65H88FN17O18 $[M+2H]^{2+}$ 707.81, found $C_{65}H_{87}FN_{17}O_{18}$ $[M+H]^+$ 1412.70, $C_{65}H_{88}FN_{17}O_{18}$ $[M+2H]^{2+}$707.30 found. LCMS conditions: Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

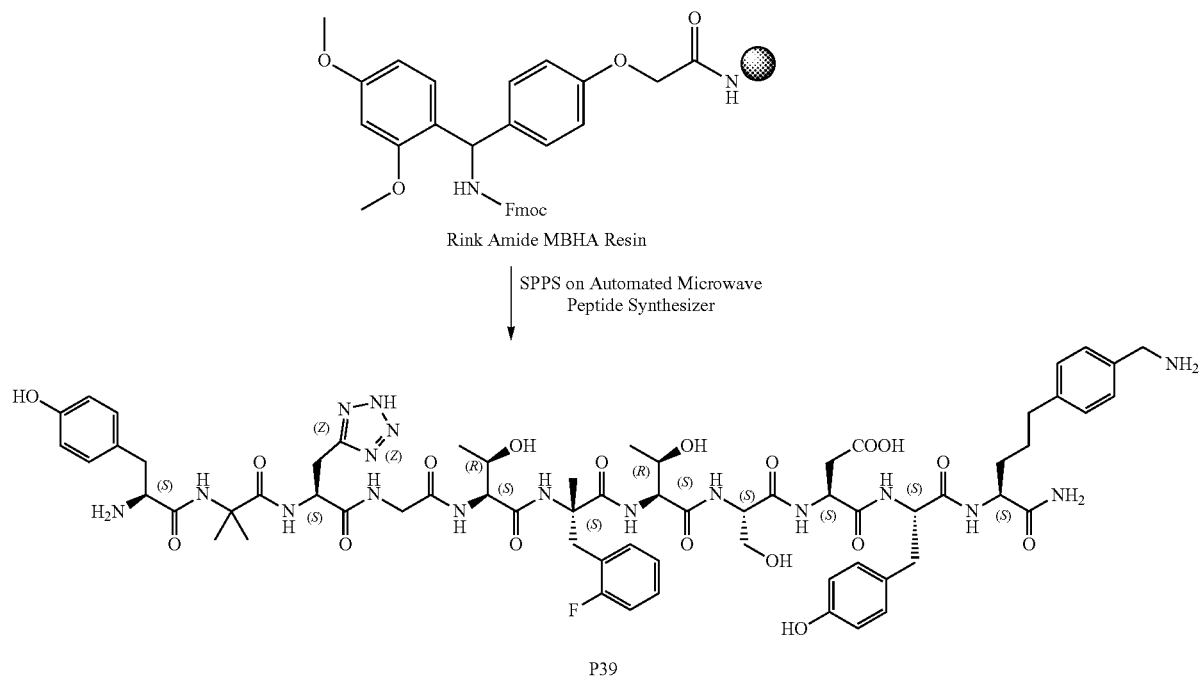

P39

The peptide elongation was performed on a 0.5 mmol scale using Liberty Lite Automated Microwave Peptide Synthesizer. Following the standard operation on peptide HPLC: RT=4.72 min, 98.26% purity LC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Example 4. Synthesis of Linkers 4.1 Preparation of PEG Linkers

Scheme 20, below, depicts synthesis of PEGn linkers (n=4, 8, 12 and 24):

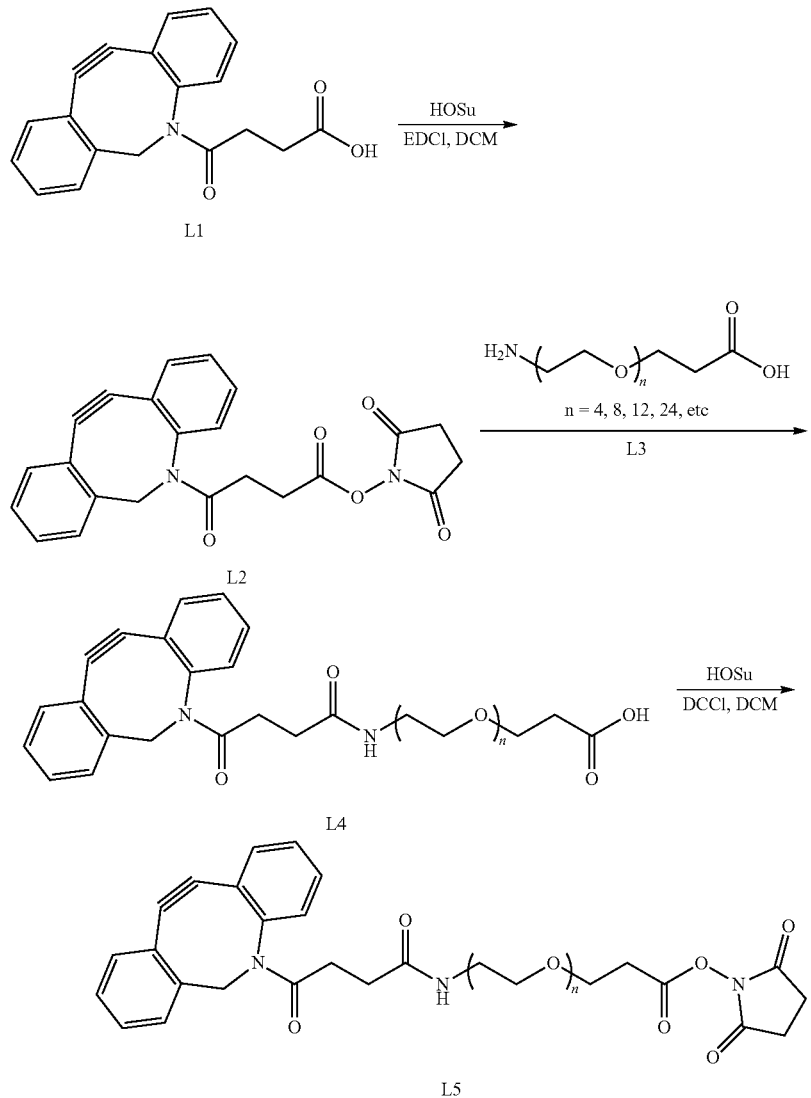

Synthesis of PEGn linker with n=8 is provided as an example; linkers of other lengths were prepared in the same fashion. Synthesis of L1 ((11,12-Didehydrodibenzo[b,f]azocin-5(6H)-yl)-4-oxobutanoic acid) was performed according to L. S. Campbell-Verduyn, L. Mirfeizi, A. K. Schoonen, R. A. Dierckx, P. H. Elsinga, and B. L. Feringa, *Strain-Promoted Copper-Free "Click" Chemistry for $^{18}F$ Radiolabeling of Bombesin*. Angew. Chem. Int. Ed., Vol. 50, No. 47, 2011, 11117-11120.

Step 1: Synthesis of 2,5-dioxopyrrolidin-1-yl 4-(didehydrodibenzo[b,f]azocin-5(6H)-yl)-4-oxobutanoate (L2)

To a solution of L1 (0.35 g, 1.15 mmol, 1 eq.) in DCM (4 mL) were added HOSu (158.31 mg, 1.38 mmol, 1.2 eq.) and EDCl (263.70 mg, 1.38 mmol, 1.2 eq.). The mixture was stirred at 20° C. for 1 hr. TLC (PE:EtOAc=1:1) indicated that the complete consumption of reactant. The mixture was filtered and concentrated to give a residue. The residue was purified by column chromatography (SiO$_2$, Petroleum ether/

Ethyl acetate=3/1 to 1/1). The desired compound L2 (450 mg, 1.12 mmol, 97.56% yield) was obtained as a white solid.

Step 2: Synthesis of 3-[2-[2-[2-[2-[2-[2-[2-[2-[[4-(39-azatricyclohexadeca-(4),1(5),2(6),3(7),31,33-hexaen-9-yn-39-yl)-4-oxo-butanoyl] amino] ethoxy] ethoxy] ethoxy] ethoxy] ethoxy] ethoxy]ethoxy] ethoxy] propanoic acid (L4)

To a solution of L2 (54.68 mg, 135.90 μmol, 1.5 eq.) in DMF (0.5 mL) was added L3 (n=8, 40 mg, 90.60 μmol, 1 eq.) and DIPEA (58.54 mg, 452.99 μmol, 78.90 μL, 5 eq.). The mixture was stirred at 25° C. for 1 hr. LCMS trace indicated that the complete consumption of reactant and the formation of the desired mass. The mixture was filtered and purified by prep-HPLC (AcOH 0.3%, MeCN/H$_2$O, 0-43%, 25 mL/min, 15 min). The desired L4 (60 mg, 74.09 μmol, 81.78% yield, 90% purity) was obtained as a pale-yellow oil.

LCMS (ESI): RT=0.900 min, mass calcd. for $C_{38}H_{53}N_2O_{12}$ 729.36, m/z found 729.3 [M+H]$^+$. Reverse phase LC-MS was carried out using a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

Step 3: Synthesis of (2,5-dioxopyrrolidin-1-yl) 3-[2-[2-[2-[2-[2-[2-[2-[2-[[4-(43-azatricyclohexadeca-(4),1(5),2(6),3(7),33,35-hexaen-11-yn-43-yl)-4-oxo-butanoyl] amino]ethoxy] ethoxy] ethoxy] ethoxy] ethoxy]ethoxy]ethoxy]ethoxy]propanoate (L5)

To a solution of L4 (20 mg, 27.44 μmol, 1 eq.) in DCM (0.5 mL) was added HOSu (6.32 mg, 54.88 μmol, 2 eq.) and DCC (8.49 mg, 41.16 μmol, 8.33 μL, 1.5 eq.). The mixture was stirred at 25° C. for 1 hr. LCMS trace indicated that the complete consumption of reactant and the formation of the desired mass. The mixture was filtered and purified by prep-HPLC (AcOH 0.3%, MeCN/H$_2$O, 0-65%, 18 mL/min, 15 min). The desired compound L5 (18 mg, 17.87 μmol, 65.13% yield, 82% purity) was obtained as a pale-yellow oil.

LCMS (ESI): RT=0.920 min, mass calcd. for $C_{42}H_{55}N_3O_{14}$ 825.37, m/z found 848.2 [M+Na]$^+$. Reverse phase LC-MS was carried out using a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

4.2 Preparation of Peptide Linker L8

Scheme 21, below, depicts synthesis of SG4-SH peptide linker L8:

Scheme 21

(SEQ ID NO: 150)

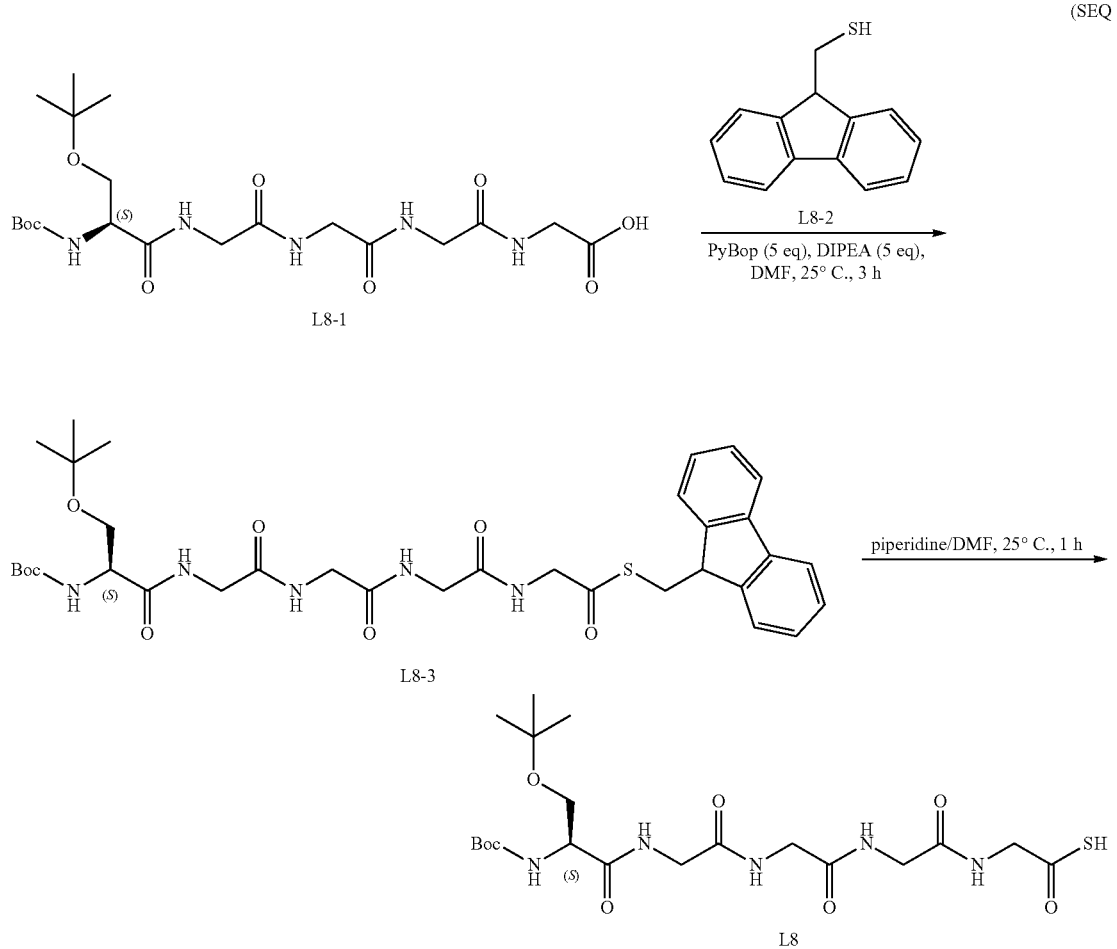

See the following references D. Crich, K. Sana, and S. Guo, *Amino Acid and Peptide Synthesis and Functionalization by the Reaction of Thioacids with 2,4-Dinitrobenzenesulfonamides*. Org. Lett., Vol. 9, No. 22, 2007, 4423-4426 and X. Y. Wu, J. L. Stockdill, P. K. Park, J. Samuel, and S. J. Danishefsky, *Expanding the Limits of Isonitrile-Mediated Amidations: On the Remarkable Stereosubtleties of Macrolactam Formation from Synthetic Seco-Cyclosporins*. J. Am. Chem. Soc., Vol. 134, No. 4, 2012, 2378-2384.

Step 1: (S)-S-((9H-fluoren-9-yl)methyl) 6-(tert-butoxymethyl)-2,2-dimethyl-4,7,10,13,16-pentaoxo-3-oxa-5,8,11,14,17-pentaazanonadecane-19-thioate (L8-3)

To a solution of L8-1 (700 mg, 1.43 mmol, 1 eq.) in DMF (7 mL) were added 4A MOLECULAR SIEVE (1 g) and L8-2 (455.40 mg, 2.14 mmol, 1.5 eq.) and the mixture was stirred at −20° C. After 15 min, PyBOP (1.12 g, 2.14 mmol, 1.5 eq.) and DIPEA (369.63 mg, 2.86 mmol, 498.15 µL, 2 eq.) were added and the reaction mixture was stirred at −20° C. for 1.5h. LCMS trace showed that the reaction converted completely. The reaction was diluted with EtOAc (30 mL) and filtered, the cake was washed with EtOAc (10 mL*2). The filtrate was washed with aq·NH$_4$Cl (20 mL), water (20 mL), brine (20 mL), dried over anhydrous Na$_2$SO$_4$, filtered and concentrated in vacuum to give crude as yellow oil. The residue was purified by flash silica gel chromatography (ISCO®; 40 g SepaFlash® Silica Flash Column, Eluent of 0-20% MeOH/DCM gradient @ 30 mL/min) to give L8-3 (700 mg, 814.78 µmol, 56.98% yield, 79.594% purity) as a light-yellow oil.

LCMS: (ESI): RT=0.882 min, m/z calcd. for C$_{29}$H$_{38}$N$_5$O$_6$S, 584.25 [M-Boc+2H]$^{2+}$, m/z found 584.3 [M-Boc+2H]$^{2+}$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

$^1$H NMR (400 MHz, METHANOL-d4) δ=7.78 (d, J=7.3 Hz, 2H), 7.66 (d, J=7.2 Hz, 2H), 7.42-7.29 (m, 4H), 4.15 (d, J=5.0 Hz, 2H), 4.04 (s, 2H), 3.92 (d, J=4.3 Hz, 6H), 3.68-3.57 (m, 4H), 3.38-3.35 (m, 3H), 1.46 (s, 9H), 1.19 (s, 10H).

Step 2: (S)-6-(tert-butoxymethyl)-2,2-dimethyl-4,7,10,13,16-pentaoxo-3-oxa-5,8,11,14,17-pentaazanonadecane-19-thioic S-acid (L8)

To a solution of L8-3 (560 mg, 818.94 µmol, 1 eq.) in THF (7 mL) was added piperidine (139.46 mg, 1.64 mmol, 161.75 µL, 2 eq.) at 20° C. The reaction was stirred at 20° C. for 2 h. LCMS trace showed that the reaction converted completely. The reaction was added MTBE (50 mL), white solids were precipitated. The mixture was filtered to give a crude as an off-white solid. The crude was purified by prep-HPLC (reversed-phase column, 40 g, 0%-35% 0.4% AcOH in water/ACN, 15 min) to give L8 (180 mg, 252.88 µmol, 30.88% yield, 71.028% purity) as an off-white solid.

LCMS: (ESI): RT=0.709 min, m/z calcd. for C$_{15}$H$_{28}$N$_5$O$_6$S, 406.18 [M-Boc+2H]$^+$, m/z found 406.2 [M-Boc+2H]$^+$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

4.3 Preparation of Peptide Linker L9

Scheme 22, below, depicts synthesis of SG4-SH peptide linker L8:

(SEQ ID NO: 151)

Scheme 22

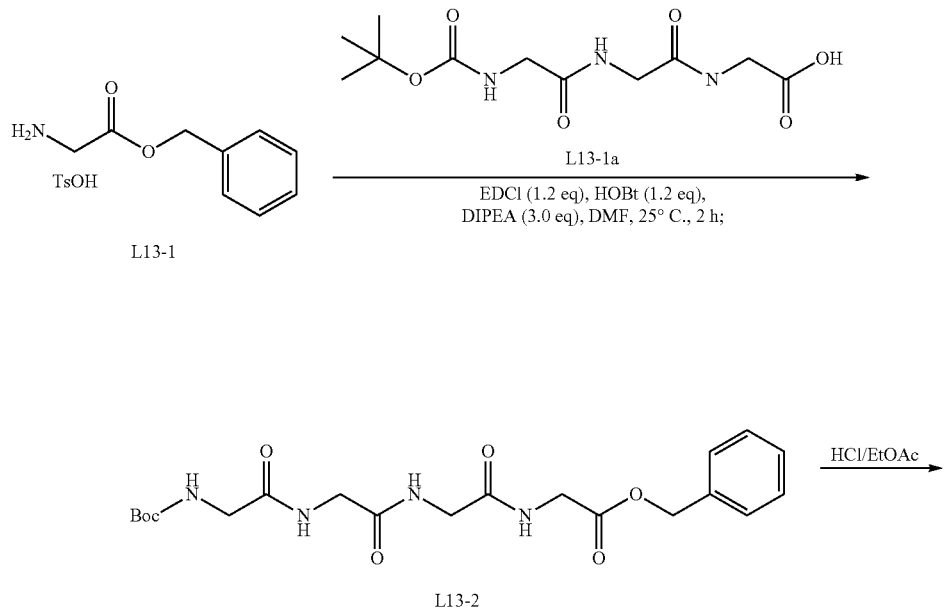

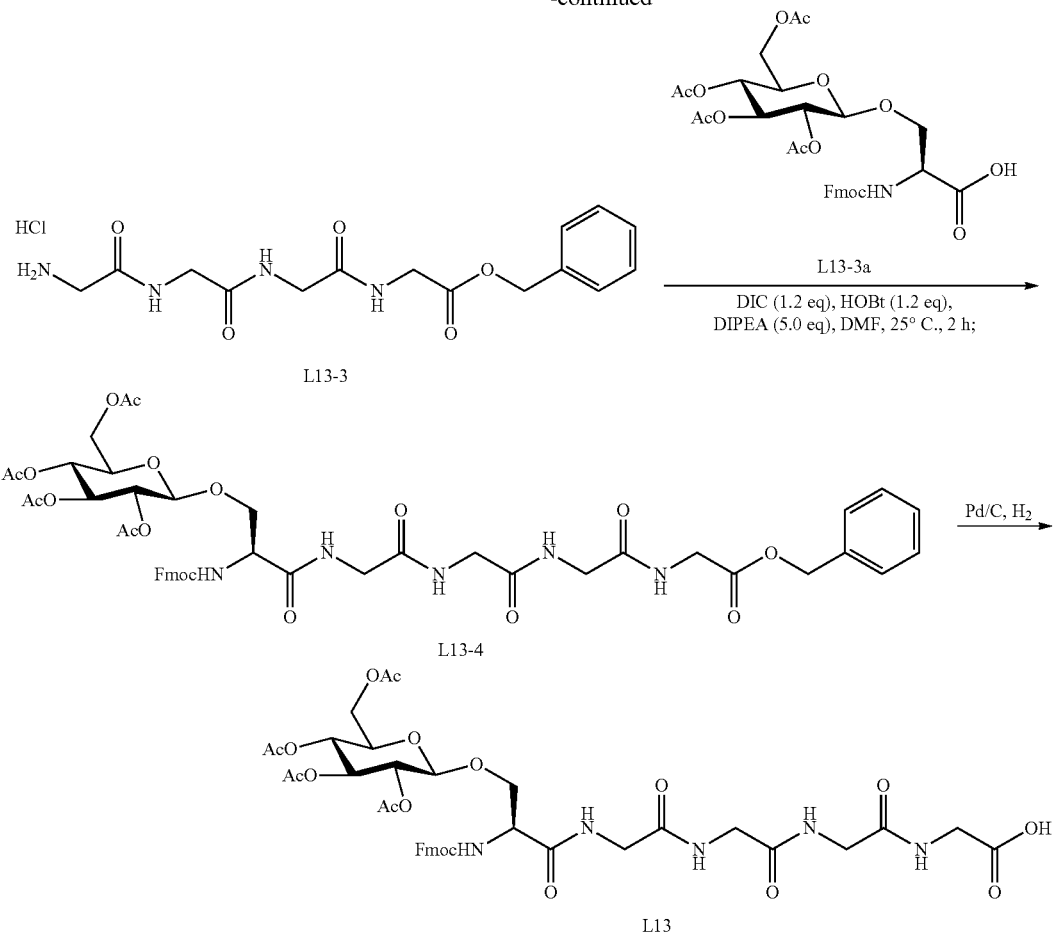

Glycopeptide L13-3a, was synthesized according to J. J. Du, X. F. Gao, L. M. Xin, Z. Lei, Z. Liu, and J. Guo, *Convergent Synthesis of N-Linked Glycopeptides via Aminolysis of ω-Asp p-Nitrophenyl Thioesters in Solution*. Org. Lett., Vol. 18, No. 19, 2016, 4828-4831. Synthesis of L13-1awas performed according to Y. A. Naumovich, I. S. Golovanov, A. Y. Sukhorukov, and S. L. Ioffe, *Addition of HO-Acids to N,N-Bis(oxy)enamines: Mechanism, Scope and Application to the Synthesis of Pharmaceuticals*. Eur. J. Org. Chem., Vol. 2017, No. 4, 2017, 6209-6227.

Step 1: Synthesis of benzyl 2,2-dimethyl-4,7,10,13-tetraoxo-3-oxa-5,8,11,14-tetraazahexadecan-16-oate (L13-2)

To a solution of L13-1a (10 g, 34.57 mmol, 1 eq.) in DMF (60 mL) was added HOBt (5.61 g, 41.48 mmol, 1.2 eq.), DIPEA (22.34 g, 172.84 mmol, 30.10 mL, 5 eq.) and EDCl (7.95 g, 41.48 mmol, 1.2 eq.) at 20° C. The mixture was stirred at 20° C. for 15 min, L13-1 (11.08 g, 32.84 mmol, 0.95 eq.) was added and the reaction mixture was stirred at 20° C. for 2 h. The reaction progress was monitored by LC-MS, which indicated no starting material was remained and formation of desired product. The mixture was quenched with a saturated solution of NaHCO$_3$ (20 mL) and brine (20 mL×3), the solid precipitation was collected and washed with PE (20 mL×2), concentrated under reduced pressure to give L13-2 (13.5 g, 29.38 mmol, 85.00% yield, 95% purity) as a white solid.

LCMS: (ESI): RT=0.714 min, m/z calcd. for $C_{20}H_{23}N_4O_7Na$ 459.2 [M+Na]$^+$, found 459.1; LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursuit 5 C18 20*2.0 mm.

$^1$H NMR (400 MHz, DMSO-d6) δ =8.31 (br t, J=5.7 Hz, 1H), 8.19 (br t, J=5.8 Hz, 1H), 8.05 (br t, J=5.3 Hz, 1H), 7.43-7.29 (m, 5H), 7.04-6.95 (m, 1H), 5.13 (s, 2H), 3.90 (d, J=5.9 Hz, 2H), 3.75 (d, J=5.6 Hz, 4H), 3.58 (br d, J=6.0 Hz, 2H), 1.38 (s, 9H).

Step 2: Synthesis of benzyl 2-(2-(2-(2-aminoacetamido)acetamido)acetamido)acetate hydrochloride (L13-3)

A solution of HCl/EtOAc (4 M, 14.80 mL, 4 eq.) was added to L13-2 (7 g, 14.80 mmol, 1 eq, HCl) dropwise at 20° C. The mixture was stirred at 20° C. for 10 min. The reaction progress was monitored by LC-MS, which indicated no starting material was remained and formation of desired product. The mixture was concentrated in vacuum and lyophilization to provide the L13-3 (5.5 g, 10.33 mmol, 69.77% yield, 70% purity, HCl) as a white solid.

LCMS: (ESI): RT=0.479 min, m/z calcd. for $C_{15}H_{21}N_4O_5$ 337.1 [M+H]$^+$, found 337.1; LC-MS Conditions: Mobile Phase: 1.5 ML/4LTFA in water (solvent A) and 0.75

ML/4LTFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

Step 3: Synthesis of (2R,3R,4S,5R,6R)-2-(((S)-16-((((9H-fluoren-9-yl)methoxy)carbonyl)amino)-3,6,9,12,15-pentaoxo-1-phenyl-2-oxa-5,8,11,14-tetraaza-heptadecan-17-yl)oxy)-6-(acetoxymethyl)tetrahydro-2H-pyran-3,4,5-triyl triacetate (L13-4)

To a solution of L13-3a (2.9 g, 4.41 mmol, 1 eq.) in DMF (20 mL) was added HOBt (715.03 mg, 5.29 mmol, 1.2 eq.), DIPEA (3.42 g, 26.46 mmol, 4.61 mL, 6 eq.) and DIC (667.82 mg, 5.29 mmol, 819.42 µL, 1.2 eq.) at 20° C. The mixture was stirred at 20° C. for 15 min, L13-3 (3.29 g, 6.61 mmol, 1.5 eq, HCl) was added and the reaction mixture was stirred at 20° C. for 12 h. The reaction progress was monitored by LC-MS, which indicated no starting material was remained and formation of desired product. The mixture was quenched with water (40 mL), and extracted with ethyl acetate (40 mL×2). The organic layer was washed with water and brine (30 mL×3), dried over anhydrous $Na_2SO_4$, filtered, and concentrated in vacuum. The residue was purified by flash silica gel chromatography (ISCO®; 40 g SepaFlash® Silica Flash Column, Eluent of 0-5% MeOH/DCM) for 25 min with total volume 1.6 L to provide L13-4 (2.1 g, 1.72 mmol, 39.04% yield, 80% purity) as a white solid.

LCMS: (ESI): RT=1.937 min, m/z calcd. for $C_{47}H_{54}N_5O_{18}$ 976.3 [M+H]$^+$, found 976.3; LC-MS Conditions: Mobile Phase: 1.5 ML/4L TFA in water (solvent A) and 0.75 ML/4L TFA in acetonitrile (solvent B), using the elution gradient 10%-80% (solvent B) over 2.0 minutes and holding at 80% for 0.48 minutes at a flow rate of 0.8 ml/min; Column: Xtimate 3 µm, C18,2.1*30 mm.

$^1$H NMR (400 MHz, CHLOROFORM-d) δ =7.83-7.73 (m, 2H), 7.59 (br d, J=7.5 Hz, 2H), 7.47-7.28 (m, 10H), 7.21-7.03 (m, 2H), 5.87 (br d, J=5.5 Hz, 1H), 5.27-4.89 (m, 5H), 4.61-4.38 (m, 4H), 4.29-3.81 (m, 13H), 2.10-1.98 (m, 12H).

Step 4: Synthesis of (S)-1-(9H-fluoren-9-yl)-3,6,9,12,15-pentaoxo-5-((((2R,3R,4S,5R,6R)-3,4,5-triacetoxy-6-(acetoxymethyl)tetrahydro-2H-pyran-2-yl)oxy)methyl)-2-oxa-4,7,10,13,16-pentaazaoctadecan-18-oic acid (L13)

To a solution of L13-4 (2.1 g, 2.15 mmol, 1 eq.) in EtOAc (16 mL) and MeOH (2 mL) was added Pd/C (300 mg, 430.35 µmol, 10.35 µL, 10% purity, 0.20 eq.) at 20° C. and the mixture was stirred at 20° C. for 4 hr under $H_2$ (4.35 mg, 2.15 mmol, 1 eq.) (15 psi). The reaction progress was monitored by LC-MS, which indicated no starting material was remained and formation of desired product. The mixture was filtered and the filtered cake was washed with MeOH (10 mL×3), concentrated in vacuum to provide L13 (1.2 g, 1.29 mmol, 59.81% yield, 95% purity) as a white solid.

LCMS: (ESI): RT=0.788 min, m/z calcd. for $C_{40}H_{48}N_5O_{18}$ 886.3 [M+H]$^+$, found 886.3; LC-MS Conditions: Mobile Phase: 1.5 ML/4LTFA in water (solvent A) and 0.75 ML/4LTFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

$^1$H NMR (400 MHz, METHANOL-d4) δ =7.81 (br d, J=7.4 Hz, 2H), 7.73-7.63 (m, 2H), 7.44-7.37 (m, 2H), 7.36-7.29 (m, 2H), 5.31-5.18 (m, 1H), 5.03 (t, J=9.8 Hz, 1H), 4.94-4.89 (m, 2H), 4.51-4.20 (m, 5H), 4.16-4.08 (m, 1H), 4.06-3.75 (m, 11H), 2.05-1.98 (m, 12H).

Example 5. Synthesis of GLP1 Peptidomimetic Linker-Payloads

Figure 26:
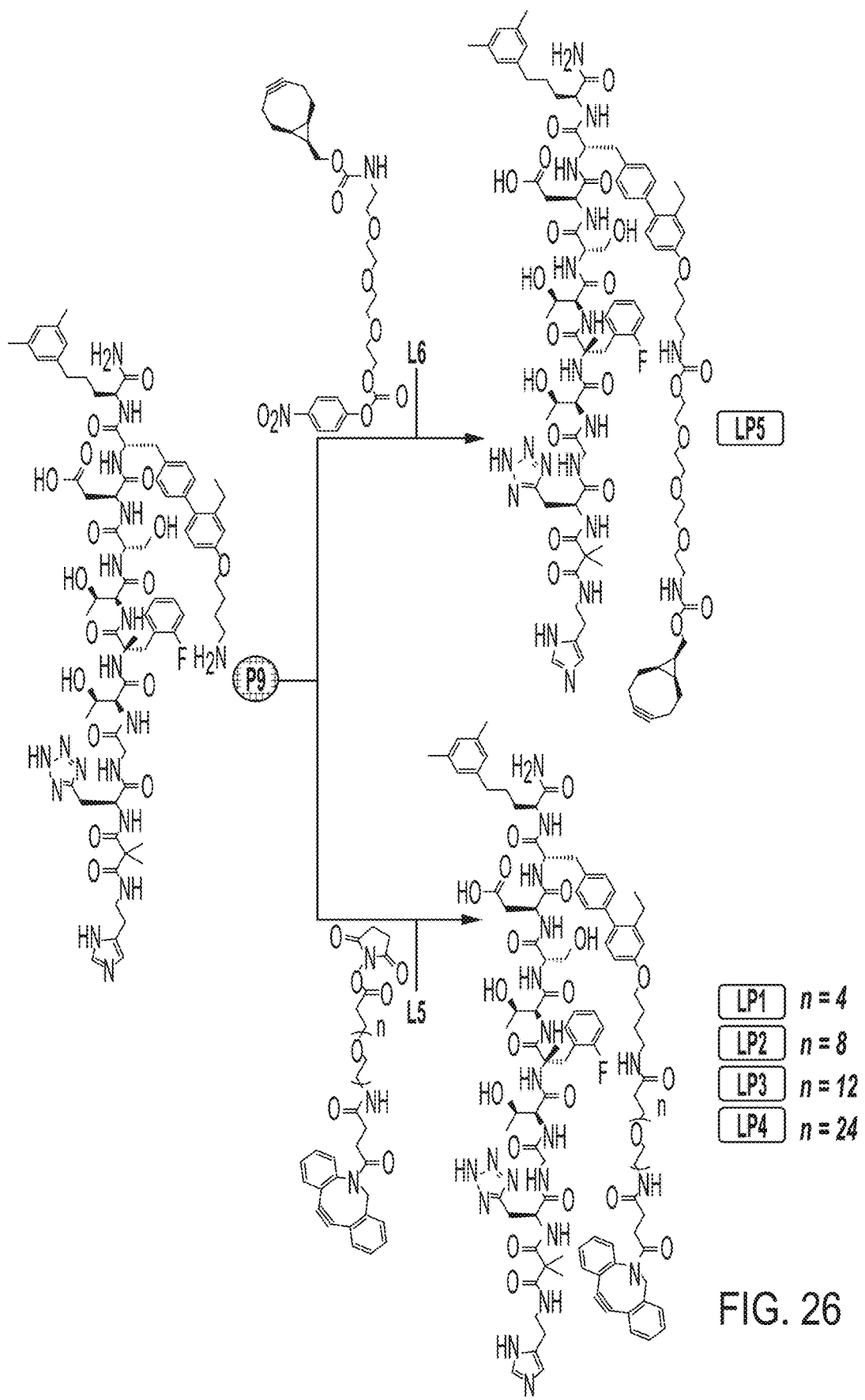
FIG. 26 shows a synthetic route for preparation of Linker-Payloads LP1, LP2, LP3, LP4 and LP5 according to the disclosure.

FIG. 26 depicts synthesis of linker-payloads LP1, LP2, LP3, LP4, and LP5 according to the disclosure.

5.1 Preparation of (3S)-4-[[(1S)-1-[[4-[4-[4-[3-[2-[2-[2-[2-[[4-(124-azatricyclohexadeca-8(14), 9(15), 10(16),12(18),68,70(73)-hexaen-33-yn-124-yl)-4-oxo-butanoyl]amino] ethoxy] ethoxy] ethoxy]propanoyl]amino]butoxy]-2-ethyl-72-phenyl] phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino] butanoyl]amino]-2-methyl-propanoyl]amino]-3-hydroxy-butanoyl]amino]-3-hydroxypropanoyl] amino]-4-oxo-butanoic acid (LP1)

To a solution of P9 (9.46 mg, 14.56 µmol, 1.5 eq.) in DMF (0.5 mL) was added L5 (n=4, 15 mg, 9.70 µmol, 1 eq.) and DIPEA (6.27 mg, 48.52 µmol, 8.45 µL, 5 eq.). The mixture was stirred at 25° C. for 1 hr. LCMS trace indicated that the complete consumption of reactant and the formation of the desired mass. The mixture was filtered and purified by prep-HPLC (TFA condition; column: Phenomenex Gemini-NX 150*30 mm*5 µm; mobile phase: [water (10 mM $NH_4HCO_3$)-ACN]; B %: 30%-60%, 11 min) to give LP1 (4.84 mg, 2.23 µmol, 23.02% yield, 96% purity) as a white solid.

LCMS (ESI): RT=0.944 min, mass calcd. for $C_{105}H_{135}FN_{20}O_{24}$ 2078.99, m/z found 1041.0 [M+2H]$^{2+}$. Reverse phase LC-MS was carried out using a Merck RP-18e 25-2 mm column, with a flow rate of 1.5 mL/min, eluting with a gradient of 5% to 95% acetonitrile containing 0.04% TFA (solvent B) and water containing 0.06% TFA (solvent A).

5.2 Preparation of 3S)-4-[[(1S)-1-[[4-[4-[4-[3-[2-[2-[2-[2-[2-[2-[2-[[4-(132-azatricyclohexadeca-8 (14),9(15),10(16),12(18),76,78(81)-hexaen-33-yn-132-yl)-4-oxo-butanoyl]amino]ethoxy] ethoxy] ethoxy] ethoxy] ethoxy] ethoxy] ethoxy] propanoylamino]butoxy]-2-ethyl-80-phenyl]phenyl] methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl) propanoyl]amino]acetyl]amino] butanoyl]amino]-2-methyl-propanoyl]amino]-3-hydroxy-butanoyl]amino]-3-hydroxy-propanoyl] amino]-4-oxo-butanoic acid (LP2)

Starting from P9 (18 mg, 21.79 µmol, 2.25 eq.) and using the same procedure as described in Example 1, the desired LP2 (3.41 mg, 1.41 µmol, 14.63% yield, 94% purity) was obtained as a white solid. Water solubility of LP2 was assessed and determined to be equal to or greater than 60 nM.

LCMS (ESI): RT=0.949 min, mass calcd. for $C_{113}H_{151}FN_{20}O_{23}$ 2255.10, m/z found 1128.9 [M+2H]$^{2+}$.

Reverse phase LC-MS was carried out using a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=15.273 min. Reverse phase HPLC was carried out using a Gemini-NX 5 μm 150*4.6 mm, C18, 110A column, with a flow rate of 1.0 mL/min, eluting with a gradient of 10% to 80% acetonitrile containing 0.12% TFA (solvent B) and water containing 0.12% TFA (solvent A). 5.3 Preparation of (3S)-4-[[(1S)-1-[[4-[4-[4-[3-[2-[2-[2-[2-[2-[2-[2-[2-[2-[2-[2-[[4-(140-azatricyclohexadeca-8(14),9(15),10(16),12(18),84,86(89)-hexaen-33-yn-140-yl)-4-oxo-butanoyl]amino]ethoxy]ethoxy]ethoxy]ethoxy]ethoxy]ethoxy]ethoxy]ethoxy]ethoxy]ethoxy]ethoxy]propanoyl]amino]butoxy]-2-ethyl-88-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP3)

Starting from P9 (14.59 mg, 14.56 μmol, 1.5 eq.) and using the same procedure as described in Example 1, the desired product LP3 (4.68 mg, 1.68 μmol, 17.27% yield, 87.1% purity) was obtained as a white solid.

HPLC condition: RT=15.120 min, Reverse phase HPLC was carried out using a Gemini-NX 5u C18 110A 150*4.6 mm column, with a flow rate of 1.0 mL/min, eluting with a gradient of 10% to 80% acetonitrile containing 0.1% TFA (solvent B) and water containing 0.1% TFA (solvent A). 5.4 Preparation of (3S)-4-[[(1S)-1-[[4-[4-[4-[3-[2-[2-[2-[2-[2-[2-[2-[2-[2-[2-[2-[2-[2-[2-[2-[2-[2-[2-[[4-(164-azatricyclohexadeca-8,10(16),12(18),14(108),15(109),110(113)-hexaen-33-yn-164-yl)-4-oxo-butanoyl]amino]ethoxy]ethoxy]ethoxy]ethoxy]ethoxy]ethoxy]ethoxy]ethoxy]ethoxy]ethoxy]ethoxy]ethoxy]propanoylamino]butoxy]-2-ethyl-112-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP4)

Starting from P9 (20 mg, 12.94 μmol, 1.0 eq.) and using the same procedure as described in Example 1, the desired product LP4 (5.58 mg, 1.76 μmol, 13.59% yield, 93.29% purity) was obtained as a white solid.

LCMS (ESI): RT=0.912 min, mass calcd. for $C_{145}H_{215}FN_{20}O_{44}$ 2961.36 $[M+H]^+$, 987.514 $[M+3H]^{3+}$, m/z found 988.3 $[M+3H]^{3+}$. Reverse phase LC-MS was carried out using a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HRMS (ESI): mass calcd for $C_{145}H_{216}FN_{20}O_{44}$ 2960.5263 $[M+H]^+$, 1480.7632 $[M+2H]^{2+}$, 987.5088 $[M+3H]^{3+}$, m/z found 2960.53 $[M+H]^+$, 1481.26 $[M+2H]^{2+}$, 987.8517 $[M+3H]^{3+}$.

5.5 Preparation of 8S,14S,17S,20S,23S,26S)-8-((2H-tetrazol-5-yl)methyl)-26-(((S)-1-(((S)-1-amino-5-(3,5-dimethylphenyl)-1-oxopentan-2-yl)amino)-3-(4'-((1-((1R,8S,9s)-bicyclo[6.1.0] non-4-yn-9-yl)-3,17-dioxo-2,7,10,13,16-pentaoxa-4,18-diazadocosan-22-yl)oxy)-2'-ethyl-[1,1'-biphenyl]-4-yl)-1-oxopropan-2-yl)carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13, 16,19,22,25-octaazaoctacosan-28-oic acid (LP5)

To a solution of P9 (12 mg, 7.76 μmol, 1 eq.) in DMF (0.5 mL) were added L6 (8.30 mg, 15.53 μmol, 2.0 eq.) and TEA (1.57 mg, 15.53 μmol, 2.16 μL, 2.0 eq.). Then the mixture was stirred at 20° C. for 12 h. LCMS trace showed that most of reactant was consumed completely and the desired MS was detected. It was purified by prep-HPLC (column: Phenomenex Gemini-NX 150*30 mm*5 μm; mobile phase: [water (0.225% FA)-ACN]; B %: 0%-55%, 45 min). Compound LP5 (4 mg, 2.00 μmol, 25.75% yield, 97% purity) was obtained as a white solid.

LCMS: (ESI): Rt=4.087 min, mass calcd. for $C_{95}H_{132}FN_{19}O_{24}$ $[M+2H]^2+971.5$, m/z found 971.5 $[M+2H]^{2+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC: (ESI): Rt=10.12 min, Reverse phase LCMS was carried out using Column: YMC-Pack ODS-A 150*4.6 mm, with a flow rate of 1.5 ml/min, eluting with a gradient of 10% to 80% acetonitrile containing 0.02% TFA (solvent B) and water containing 0.04% TFA (solvent A).

Figure 27:
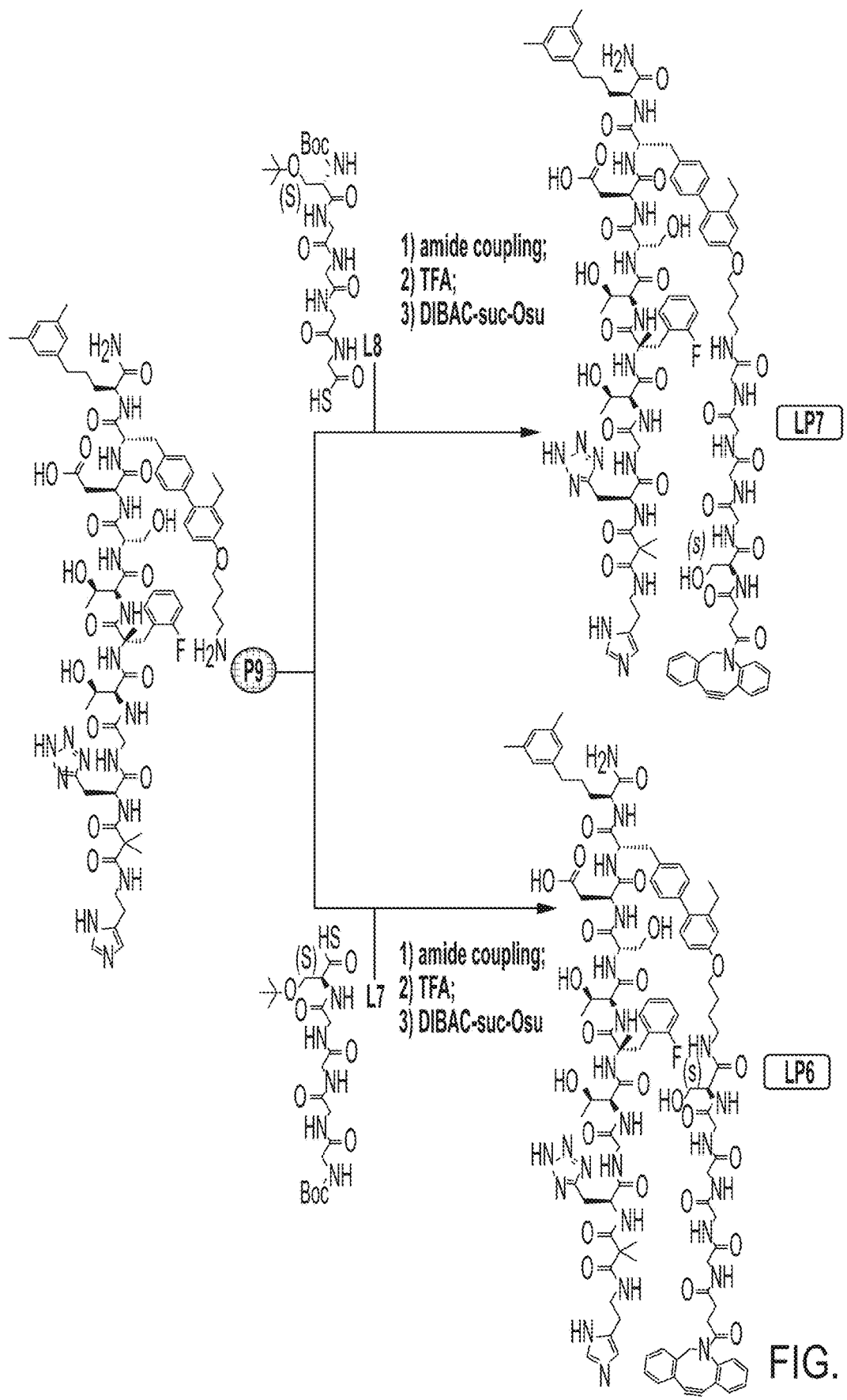
FIG. 27 shows a synthetic route for preparation of Linker-Payloads LP6 and LP7 according to the disclosure.

FIG. 27 depicts synthesis of linker-payloads LP6 and LP7 according to the disclosure.

5.6 Preparation of (3S)-4-[[(1S)-1-[[4-[4-[4-[[(2S)-2-[[2-[[2-[[2-[[2-[[4-(128- azatricyclohexadeca-8(14),9(15),10(16),12(18),63,65(68)-hexaen-33-yn-128-yl)-4-oxo-butanoyl]amino]acetyl]amino]acetyl]amino]acetyl]amino]acetyl]amino]-3-hydroxy-propanoyl]amino]butoxy]-2-ethyl-67-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP6)

To an oven-dried vial were charged L7 (163.54 mg, 323.48 μmol, 2.5 eq.) and P9 (200 mg, 129.39 μmol, 1 eq.). A stock solution of HOBt (69.93 mg, 517.56 μmol, 4 eq.), DIPEA (50.17 mg, 388.17 μmol, 3 eq.) in DMF (1 mL) and 12 (39.41 mg, 155.27 μmol, 1.2 eq.) in DMF (1 mL) was added to the vial. The reaction mixture was stirred at 15° C. for 12 h. The reaction progress was monitored by LCMS trace. The mixture was filtered, then precipitated by added EtOAc (20 mL). After filtration, the crude product protected G4S-P9 (261 mg, 116.45 µmol, 90.00% yield, 90% purity) was obtained as a pale-yellow foam.

LCMS (ESI): RT=3.283 min, mass calcd. for $C_{95}H_{136}FN_{23}O_{25}{}^{2+}$ 1009.005 $[M+2H-Boc]^{2+}$, m/z found 1009.5 $[M+2H]^{2+}$. LCMS conditions: Flash RP-18e 25-2 mm, with a flow rate of 0.8 mL/min, eluting with a gradient of 10% to 80% acetonitrile containing 0.02% TFA (solvent B) and water containing 0.04% TFA (solvent A).

To an oven-dried vial was charged protected G4S-P9 (261 mg, 129.39 µmol, 1 eq.) and DCM (5 mL). TFA (6.70 g, 58.75 mmol, 4.35 mL, 454.08 eq.) was added to the vial. The reaction mixture was stirred at 20° C. for 2 h. The reaction progress was monitored by LCMS. The reaction mixture was concentrated and purified by prep-HPLC (TFA condition; column: Waters Xbridge Prep OBD C18 150*40 mm*10 µm; mobile phase: [water (0.1% TFA)-ACN]; B %: 0%-70%, 30 min). G4S-P9 (206 mg, 98.61 µmol, 76.21% yield, 100% purity, 2 TFA) was obtained as a white foam.

LCMS (ESI): RT=2.497 min, mass calcd. for $C_{95}H_{136}FN_{23}O_{25}{}^{2+}$ 930.945 $[M+2H]^{2+}$, m/z found 931.0 $[M+2H]^{2+}$. LCMS conditions: Chromolith Flash RP-C18 25-3 mm, with a flow rate of 1.5 mL/min, eluting with a gradient of 10% to 80% acetonitrile containing 0.02% TFA (solvent B) and water containing 0.04% TFA (solvent A).

To an oven-dried vial were charged DIBAC-suc-OSu (39.68 mg, 98.61 µmol, 1 eq.) and G4S-P9 (206 mg, 98.61 µmol, 1 eq., 2 TFA). DMF (2 mL) and DIPEA (38.23 mg, 295.83 µmol, 3 eq.) were added to the vial. The reaction mixture was stirred at 20° C. for 1 h. The reaction progress was monitored by LC-MS. The reaction was filtered and purified by prep-HPLC (neutral condition; column: Waters Xbridge Prep OBD C18 150*40 mm*10 µm; mobile phase: [water (10 mM NH$_4$HCO$_3$)-ACN]; B %: 0%-50%, 30 min.). LP6 (112 mg, 52.13 µmol, 52.87% yield, 100% purity) was obtained as a white foam.

LCMS (ESI): RT=2.419 min, mass calcd. for $C_{105}H_{133}FN_{24}O_{25}{}^{2+}$ 1074.49 $[M+2H]^{2+}$, m/z found 1074.8 $[M+2H]^{2+}$. LCMS conditions: Waters Xbridge C18 30*2.0 mm, 3.5 µm Mobile phase: A) 0.05% NH$_3$H$_2$O in Water; B) ACN. Gradient: 0% B increase to 95% B within 5.8 min; hold at 95% B for 1.1 min; then back to 0% B at 6.91 min and hold for 0.09 min. Flow rate 1.0 mL/min.

HPLC: RT=3.58 min. HPLC conditions: Mobile Phase: 0.2 ML/1 L NH$_3$·H$_2$O in water (solvent A) and acetonitrile (solvent B), using the elution gradient 0%-60% (solvent B) over 5 minutes and holding at 60% for 2 minutes at a flow rate of 1.2 ml/min; Column: Xbridge Shield RP-18, 5 µm,2.1*50 mm.

$^1$H NMR (400 MHz, ACETONITRILE-d$_3$) δ ppm 8.40 (s, 1H) 7.52 (brt, J=6.82 Hz, 2H) 7.35-7.46 (m, 3H) 7.27-7.34 (m, 2H) 7.19-7.25 (m, 1H) 7.05-7.15 (m, 4H) 6.95 (br d, J=5.75 Hz, 4H) 6.86-6.91 (m, 1H) 6.74-6.82 (m, 5H) 6.70 (br d, J=8.13 Hz, 1H) 4.98 (br d, J=14.51 Hz, 1H) 4.61 (br s, 1H) 4.38-4.46 (m, 2H) 4.29 (br s, 2H) 4.16-4.21 (m, 1H) 4.09-4.12 (m, 2H) 3.89-4.01 (m, 6H) 3.79-3.88 (m, 10H) 3.57-3.77 (m, 7H) 3.28-3.36 (m, 3H) 3.16 (br s, 4H) 3.09 (br s, 1H) 2.82-2.89 (m, 1H) 2.76 (br d, J=3.75 Hz, 2H) 2.61-2.70 (m, 1H) 2.37-2.48 (m, 6H) 2.16 (s, 6H) 1.53-1.81 (m, 8H) 1.28 (br d, J=3.38 Hz, 3H) 1.17-1.22 (m, 6H) 1.11 (br d, J=6.00 Hz, 6H) 0.92 (br t, J=7.44 Hz, 3H).

5.7 Preparation of (3S)-4-[[(1S)-1-[[4-[4-[4-[[2-[[2-[[2-[[2-[[(2S)-2-[[4-(128- azatricyclohexadeca-8(14),9(15),10(16),12(18),63,65(68)-hexaen-33-yn-128-yl)-4-oxo-butanoyl]amino]-3-hydroxypropanoyl]amino]acetyl]amino]acetyl]amino]acetyl]amino]acetyl]amino]butoxy]-2-ethyl-67-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[f2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (LP7)

Starting from L8 (50 mg, 32.35 µmol, 1 eq.) and P9 (32.71 mg, 64.70 µmol, 2 eq.), LP7 (15 mg, 6.74 µmol, 53.21% yield, 96.47% purity) was obtained as a white solid using the same procedure as described in Example 6.

LCMS: (ESI): RT=0.845 min, m/z calcd. for $C_{105}H_{133}FN_{24}O_{25}$, 1075.5 $[M+2H]^{2+}$, m/z found 1074.6 $[M+2H]^{2+}$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=3.55 min. Mobile Phase: Mobile Phase: 0.5 ML/1L NH3H$_2$O in water (solvent A) and acetonitrile (solvent B), using the elution gradient 0%-60% (solvent B) over 5 minutes and holding at 60% for 2 minutes at a flow rate of 1.2 ml/min.

Figure 28:
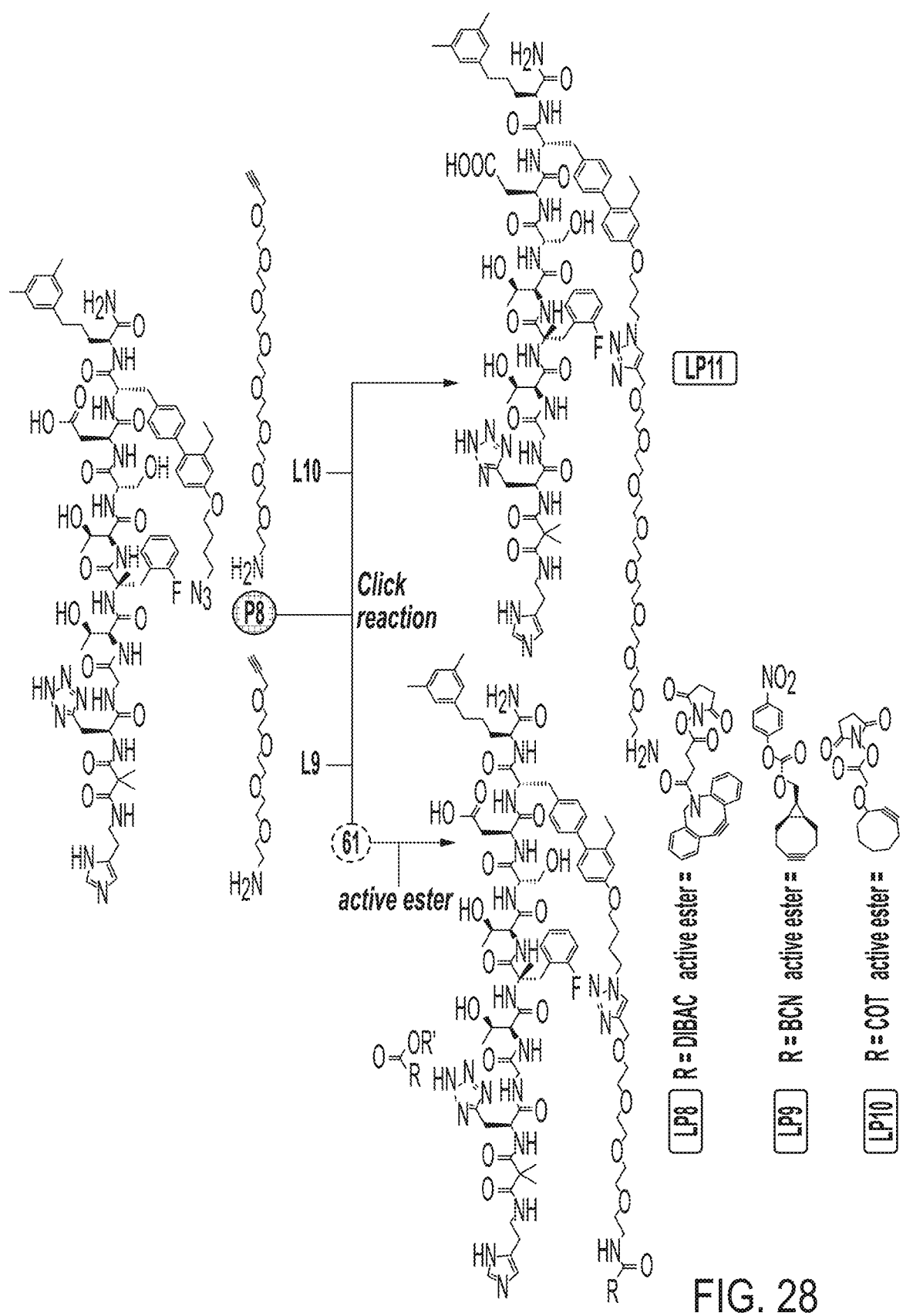
FIG. 28 shows a synthetic route for preparation of Linker-Payloads LP8, LP9, LP10 and LP11 according to the disclosure.

FIG. 28 depicts synthesis of linker-payloads LP8, LP9, LP10 and LP11 according to the disclosure.

5.8 Preparation of (3S)-4-[[(1S)-1-[[4-[4-[4-[2-[2-[2-[2-[[4-(2-azatricyclo[10.4.0.04,9]hexadeca-1(12),4(9),5,7,13,15-hexaen-10-yn-2-yl)-4-oxobutanoyl]amino]ethoxy]ethoxy]ethoxy]ethoxymethyl]triazol-1-yl]butoxy]-2-ethyl-phenyl]phenyl]methyl]-2-[[(1S)-carbamoyl-4-(3,5-dimethylphenyl)butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (LP8)

To a solution of P8 (20 mg, 12.73 µmol, 1 eq.) and L9 (8.83 mg, 38.18 µmol, 3.0 eq.) in H$_2$O (0.25 mL) and t-BuOH (0.5 mL) were added CuSO$_4$·5H$_2$O (635.45 µg, 2.55 µmol, 0.2 eq.) and sodium;(2R)-2-[(1S)-1,2-dihydroxyethyl]-4-hydroxy-5-oxo-2H-furan-3-olate (1.01 mg, 5.09 µmol, 0.4 eq). The mixture was stirred at 20° C. for 1.5 h. LCMS trace showed the material was disappeared and the desired product was observed as the major. The green solution was filtered to give the crude product. The crude product was purified by reversed phase HPLC (ISCO®; 20 g C18@ Silica Flash Column, Eluent of 0-60.1% CH$_3$CN/H$_2$O (0.4% AcOH) gradient @ 18 mL/min). The desired fluent was lyophilized in freeze dryer to give compound 61 (15 mg, 8.24 µmol, 64.78% yield, 99.090% purity) as a white solid.

LCMS (ESI): RT=0.764 min, mass calcd. for $C_{23}H_{43}N_{11}O_6$ 901.95, m/z found 902.3 [M+H]$^+$. LC-MS method A: a Xtimate C18 2.1*30 mm, 3 μm column, with a flow rate of 1.2 mL/min, eluting with a gradient of 5% to 95% acetonitrile containing 0.75 ML/4L TFA (solvent B) and 1.5 ML/4L TFA in water (solvent A).

To a solution of 61 (17 mg, 9.43 μmol, 1 eq.) and DIBAC-suc-OSu (5.05 mg, 12.55 μmol, 1.33 eq.) in DMF (2 mL) was added DIPEA (2.44 mg, 18.86 μmol, 3.28 μL, 2.0 eq.). The solution was stirred at 15° C. for 1 h. LCMS showed the reaction was converted completely and the desired product was observed. The solution was filtered and purified by prep-HPLC (neutral condition: Column: Durashell C18(L) 100*10 mm*5 μm; Mobile phase: [water (10 mM NH4HCO3)-ACN]; B %: 12%-52%, 12 min). The desired fluent was lyophilized in freeze dryer to give LP8 (7.0 mg, 3.21 μmol, 30.42% yield, 95.745% purity) as a white solid.

LCMS (ESI): RT=1.337 min, m/z calcd. for $C_{105}H_{135}FN_{22}O_{23}$ [M+2H]$^2$+1045.50, found 1046.1. LCMS conditions: 0.8 mL/4L $NH_3H_2O$ in water (solvent A) and acetonitrile (solvent B), using the gradient 10%-80% (solvent B) over 2 minutes and holding at 80% for 0.48 minutes at a flow rate of 1 ml/min; Column: XBridge C18 3.5 μm 2.1*30 mm; Wavelength: UV 220 nm&254 nm; Column temperature: 50° C.;

HPLC: RT=2.868 min, Mobile Phase: 0.2 mL/1L $NH_3 \cdot H_2O$ in water (solvent A) and acetonitrile (solvent B), using the elution gradient 10%-80% (solvent B) over 6 minutes and holding at 80% for 2 minutes at a flow rate of 0.8 ml/min; Column: Xbridge Shield C18, 5 μm, 2.1*50 mm;

5.9 Preparation of (3S)-4-[[(1S)-1-[[4-[4-[4-[4-[2-[2-[2-[2-[[(1S,8R)-9-bicyclo[6.1.0]non-4-ynyl] methoxycarbonylamino]ethoxy]ethoxy]ethoxy] ethoxymethyl]triazol-1-yl]butoxy]-2-ethyl-phenyl] phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl] amino]-3-(2H-tetrazol-5-yl) propanoyl]amino] acetyl]amino]butanoyl]amino]-2-methyl-propanoyl] amino]-3-hydroxy-butanoyl]amino]-3-hydroxy-propanoyl]amino]-4-oxo-butanoic acid (LP9)

To a solution of compound 61 (14.55 mg, 8.07 μmol, 1 eq.) in DMF (2.0 mL) were added (1R,8S,9s)-bicyclo[6.1.0]non-4-yn-9-ylmethyl (4-nitrophenyl) carbonate (BCN—CO—PNP) (5.81 mg, 18.41 μmol, 2.28 eq.) and DIPEA (2.09 mg, 16.14 μmol, 2.81 μL, 2.0 eq.). The solution was purified by prep-HPLC (FA condition) (Column: Phenomenex Gemini-NX 150*30 mm*5 μm; mobile phase: [water (0.225% FA)-ACN]; B %: 0%-55%, 45 min) to give LP9 (3.6 mg, 1.79 μmol, 22.21% yield, 98.54% purity) was obtained as a white solid.

LCMS (ESI): RT=4.040 min, mass calcd. for $C_{97}H_{134}FN_{21}O_{23}$ [M+2H]$^2$+989.89, found 990.6. LCMS conditions: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 μm, C18,2.1*30 mm;

HPLC: RT=9.89 min, Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm,5 μm.

5.10 Preparation of (3S)-4-[[(1S)-2-[[(1S)-1-carbamoyl-4-(3,5-dimethylphenyl)butyl]amino]-1-[[4-[4-[4-[2-[2-[2-[2-[(2-cyclooct-2-yn-1-yloxy-acetyl)amino]ethoxy]ethoxy]ethoxy]ethoxymethyl] triazol-1-yl]butoxy]-2-ethyl-phenyl]phenyl]methyl]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP10)

To a solution of 61 (14 mg, 7.76 μmol, 1 eq) in DMF (0.5 mL) were added 2,5-dioxopyrrolidin-1-yl 2-(cyclooct-2-yn-1-yloxy)acetate (5.18 mg, 18.53 μmol, 2.39 eq) and DIPEA (2.01 mg, 15.53 μmol, 2.70 μL, 2.0 eq). The solution was stirred at 20° C. for 1 hr. LCMS showed the reaction was converted completely and the desired product was observed. The mixture was diluted with CH3CN, and the crude product was purified by prep-HPLC (FA condition: Column: Phenomenex Gemini-NX 150*30 mm*5 μm; Mobile phase: [water (0.225% FA)-ACN]; B %: 5%-55%, 35 min). The desired fluent was lyophilized in freeze dryer to give LP10 (2.6 mg, 1.26 μmol, 13.08% yield, 95.26% purity) as a white solid.

LCMS (ESI): RT=3.805 min, m/z calcd. for $C_{96}H_{134}FN_{21}O_{23}$ [M+2H]$^2$+983.99, found 984.7. LCMS conditions: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 μm, C18,2.1*30 mm.

HPLC: RT=9.74 min, Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm,5 μm; HPLC: RT=9.89 min, Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 μm.

5.11 Preparation of (3S)-4-[[(1S)-1-[[4-[4-[4-[2-[2-[2-[2-[2-[2-(2-aminoethoxy)ethoxy]ethoxy] ethoxy]ethoxy]ethoxy]ethoxymethyl]triazol-1-yl]butoxy]-2-ethyl-phenyl]phenyl]methyl]-2-[[(1S)-1-carbamoyl-4-(3,5-dimethylphenyl)butyl] amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl] amino]-3-hydroxypropanoyl]amino]-4-oxo-butanoic acid (LP11)

A mixture of P8 (10 mg, 6.36 μmol, 1 eq.), sodium ascorbate (504.18 μg, 2.54 μmol, 0.4 eq.) and $CuSO_4 \cdot 5H_2O$ (317.72 μg, 1.27 μmol, 0.2 eq.) in t-BuOH (0.8 mL) and $H_2O$ (0.4 mL) were stirred at 20° C. for 2h. LCMS showed P8 was consumed completely. The reaction was filtered to give a residue. The residue was purified by prep-HPLC (column: Phenomenex Genimi NX C18 150*40 mm*5 µm; mobile phase: [water (0.1% TFA)-ACN]; B %: 0%-60%, 25 min) to give LP11 (4.32 mg, 2.18 µmol, 34.31% yield) was obtained as a white solid.

LCMS: (ESI): RT=3.121 min, m/z calcd. for $C_{94}H_{13}FN_{21}O_{25}$, 990.01 $[M+2H]^{2+}$, m/z found 990.6 $[M+2H]^{2+}$; Mobile Phase: Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min.

HPLC (ES8584-1120-P1C1) was attached. RT=3.75 min, 99.72% purity. HPLC method: Column: Ultimate XB-C18.3 µm,3.0*50 mm; 2.75 ML/4L TFA in water (solvent A) and 2.5 ML/4L TFA in acetonitrile (solvent B), using the elution gradient 10%-80% (solvent B) over 7 minutes and holding at 80% for 0.5 minutes at a flow rate of 1.5 ml/min.

Figure 29:
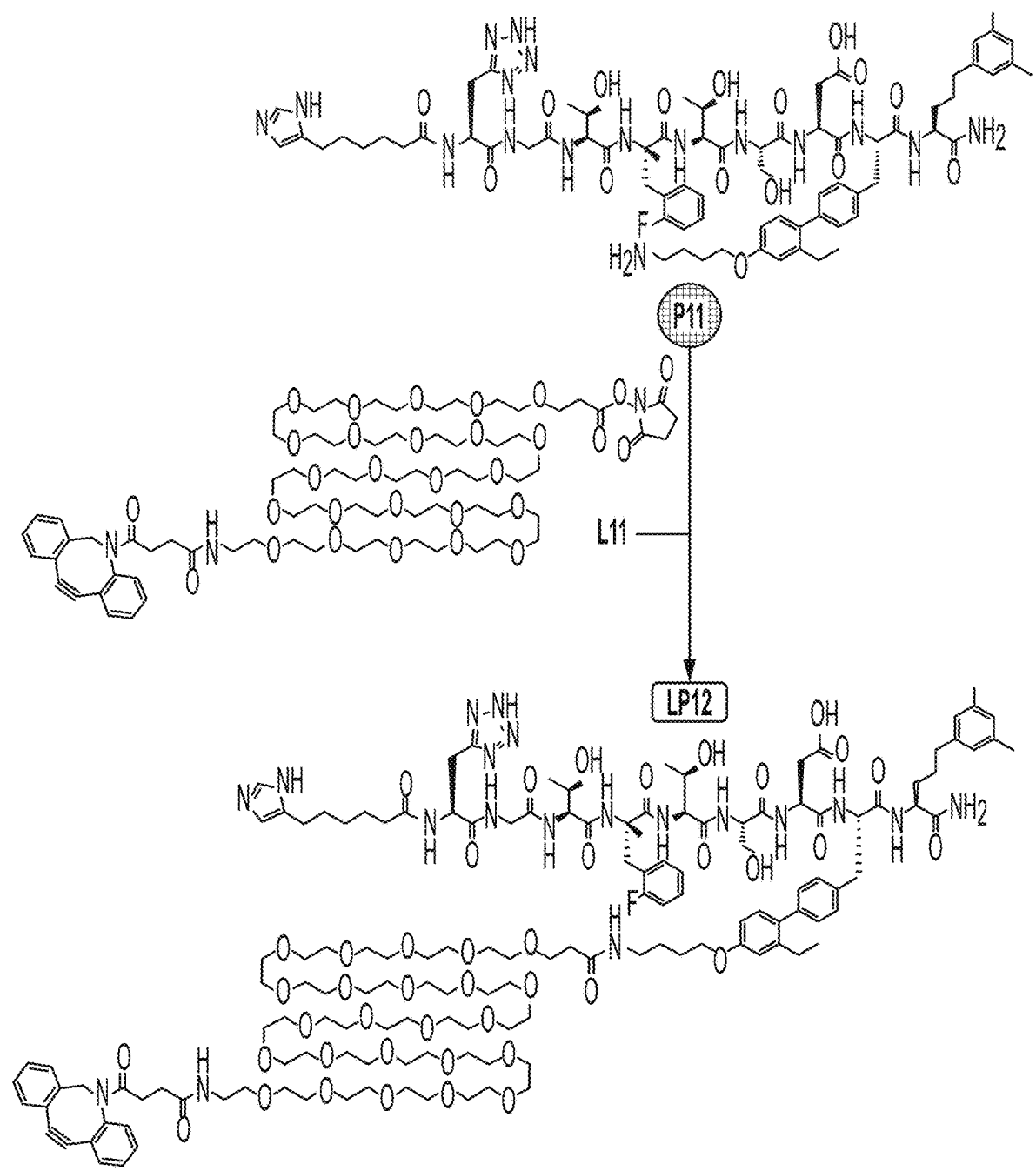
FIG. 29 shows a synthetic route for preparation of Linker-Payload LP12 according to the disclosure.

FIG. 29 depicts synthesis of linker-payload LP12 according to the disclosure.

5.12 Preparation of (3S)-4-[[(1S)-1-[[4-[4-[4-[3-[2-[2-[2-[2-[2-[2-[2-[2-[2-[2-[2-[2-[2-[2-[2-[2-[2-[2-[2-[2-[2-[[4-(162-azatricyclohexadeca-6(12),7(13),8(14),10(16),109,111(114)-hexaen-31-yn-162-yl)-4-oxo-butanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]e thoxy]ethoxy]ethoxy]propanoylamino]butoxy]-2-ethyl-113-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[6-(1H-imidazol-5-yl) hexanoylamino]-3-(2H-tetrazol-5-yl)propanoyl]amino]acetyl]amino] butanoyl]amino]-2-methyl-propanoyl]amino]-3-hydroxy-butanoyl]amino]-3-hydroxy-propanoyl] amino]-4-oxo-butanoic acid (LP12)

To a solution of P11 (30 mg, 14.65 µmol, 1 eq., TFA) and L11 (22.43 mg, 14.65 µmol, 1 eq.) in DMF (1.5 mL) was added DIPEA (9.47 mg, 73.25 µmol, 12.76 µL, 5 eq.) at 15° C. The mixture was stirred at 15° C. for 1h. LCMS trace showed that the reaction was complete. The mixture was filtered to give crude as yellow oil, and the residue was purified by prep-HPLC (column: Waters Xbridge Prep OBD C18 150*40 mm*10 µm; mobile phase: [water (10 mM NH$_4$HCO$_3$)-ACN]; B %: 0%-80%, 30 min) to give LP12 (25 mg, 8.18 µmol, 47.72% yield, 95.49% purity) as a white solid.

LCMS: (ESI): RT=0.970 min, m/z calcd. for $C_{144}H_{217}FN_{19}O_{43}$, 973.18 $[M+3H]^{3+}$, m/z found 974.0 $[M+3H]^{3+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: Rt=2.53; Mobile Phase: 0.2 ML/1L NH$_3$H$_2$O in water (solvent A) and acetonitrile (solvent B), using the elution gradient 10%-80% (solvent B) over 5 minutes and holding at 80% for 2 minutes at a flow rate of 1.2 ml/min Column: Xbridge Shield RP-18.5 µm, 2.1*50 mm.

Figure 30:
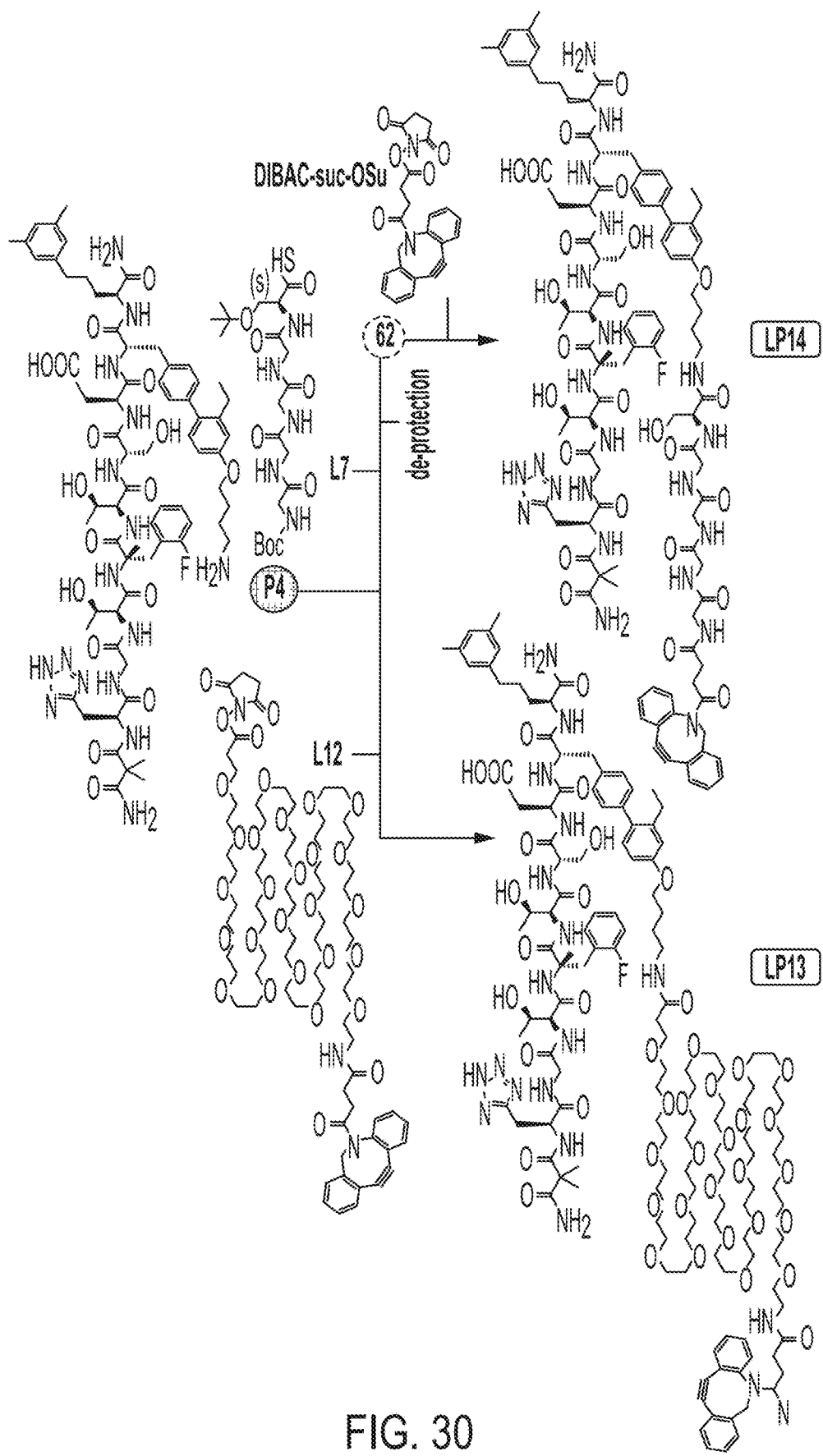
FIG. 30 shows a synthetic route for preparation of Linker-Payloads LP13 and LP14 according to the disclosure.

FIG. 30 depicts synthesis of linker-payloads LP13 and LP14 according to the disclosure. 5.13 Preparation of (3S)-3-[[(2S)-2-[[(2S,3R)-2-[[(2S)-2-[[(2S,3R)-2-[[2-[[(2S)-2-[(3-amino-2,2-dimethyl-3-oxo-propanoyl)amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl] amino]-4-[[(1 S)-1-[[4-[4-[4-[3-[2-[2-[2-[2-[2-[2-[2-[2-[2-[2-[2-[2-[2-[2-[2-[2-[2-[[4-(157-azatricyclohexadeca-8(14),9(15),10(16),12(18),104, 106(109)-hexaen-31-yn-157-yl)-4-oxobutanoyl]amino]ethoxy] ethoxy]ethoxy]ethoxy]ethoxyl ethoxy]ethoxy]ethoxy] ethoxy]ethoxy]ethoxy]ethoxy]ethoxy]ethoxy]ethoxy] ethoxy]ethoxy]ethoxy]e thoxy]ethoxy]ethoxy]ethoxy] ethoxy]ethoxy]propanoy]amino]butoxy]-2-ethyl-108-phenyl]phenyl]methyl]-2-[[(1S)-1-carbamoyl-4-(3,5-dimethylphenyl)butyl]amino]-2-oxo-ethyl]amino]-4-oxo-butanoic acid (LP13)

To a solution of P4 (10 mg, 6.89 µmol, 1 eq.) and L12 (10.55 mg, 6.89 µmol, 1 eq.) in DMF (0.5 mL) was added DIPEA (4.45 mg, 34.44 µmol, 6.00 µL, 5 eq.) at 15° C. The mixture was stirred at 15° C. for 1h. LCMS showed that the reaction was converted completely. The mixture was filtered to give crude as a yellow oil, which was purified by prep-HPLC (column: Waters Xbridge Prep OBD C18 150*30 mm, 10 µm; mobile phase: [water(10 mM NH$_4$HCO$_3$)-ACN]; B %: 10%-50%, 55 min) to give LP13 (11 mg, 3.84 µmol, 36.67% yield) as a white solid.

LCMS: (ESI): RT=0.965 min, m/z calcd. for $C_{140}H_{213}FN_{18}O_{44}$, 717.38 $[M+4H]^{2+}$, m/z found 717.8 $[M+4H]^{4}$—; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: RT=3.97; Mobile Phase: 0.2 ML/1L NH$_3$H$_2$O in water (solvent A) and acetonitrile (solvent B), using the elution gradient 0%-60% (solvent B) over 5 minutes and holding at 60% for 2 minutes at a flow rate of 1.2 ml/min-Column: Xbridge Shield RP-18.5 µm,2.1*50 mm Wavelength: 220 nm&215 nm&254 nm.

5.14 Preparation of (3S)-3-[[(2S)-2-[[(2S,3R)-2-[[(2S)-2-[[(2S,3R)-2-[[2-[[(2S)-2-[(3-amino-2,2-dimethyl-3-oxo-propanoyl)amino]-3-(2H-tetrazol-5-yl)propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl]amino]-4-[[(1 S)-1-[[4-[4-[4-[[(2S)-2-[[2-[[2-[[2-[[4-(121-azatricyclohexadeca-8(14),9(15),10(16),12(18),59, 61(64)-hexaen-31-yn-121-yl)-4-oxo-butanoyl] amino]acetyl]amino]acetyl]amino]acetyl]amino] acetyl]amino]-3-hydroxy-propanoyl]amino]butoxyl-2-ethyl-63-phenyl]phenyl]methyl]-2-[[(1S)-1-carbamoyl-4-(3,5-dimethylphenyl)butyl]amino]-2-oxo-ethyl]amino]-4-oxo-butanoic acid (LP14)

To a solution of P4 (40 mg, 27.56 µmol, 1 eq.) in DMF (0.5 mL) were added HOBt (14.89 mg, 110.22 µmol, 4 eq.), DIPEA (10.68 mg, 82.67 µmol, 14.40 µL, 3 eq.) and L7 (34.83 mg, 68.89 µmol, 2.5 eq.); then I$_2$ (8.39 mg, 33.07 µmol, 6.66 µL, 1.2 eq.) in DMF (0.5 mL) was added. The reaction mixture was stirred at 20° C. for 16 hr. To the reaction was added EtOAc (15 mL) and white solids were precipitated. The mixture was centrifuged for 3 min (5000 R) to get the solid. Then the solid was dissolved in H$_2$O (10 mL) and CAN (2 mL). The solution was lyophilized to give the crude protected compound 62 (59 mg, 23.01 µmol, 83.50% yield, 75% purity) as a white solid.

LCMS (ESI): RT=3.882 min, mass calcd. for $C_{90}H_{130}FN_{21}O_{25}$ 1923.94 961.9[M+2H]$^{2+}$, m/z found 962.5 [M+2H]$^{2+}$; Mobile Phase: 1.5 ML/4L TFA in water (solvent A) and 0.75 ML/4L TFA in acetonitrile (solvent B), using the elution gradient 10%-80% (solvent B) over 3 minutes and holding at 80% for 0.5 minutes at a flow rate of 0.8 ml/min; Column: Xtimate C18 2.1*30 mm, 3 µm; Wavelength: UV 220 nm; Column temperature: 50° C.; MS ionization: ESI To a solution of protected compound 62 (59 mg, 30.68 µmol, 1 eq.) in DCM (0.5 mL) was added TFA (0.5 mL) at 0° C. Then the mixture was warmed to 20° C. and stirred at 20° C. for 2 hr. LCMS trace showed the reactant was consumed completely and the desire MS was detected. The solvent was removed under reduced pressure at 30° C. to give the crude. The residue was purified by prep-HPLC (column: Phenomenex Gemini-NX C18 75*30 mm*3 µm; mobile phase: [water (0.075% TFA)-ACN]; B %: 0%-60%, 35 min.) to give compound 62 (11 mg, 5.91 µmol, 19.28% yield, 95% purity) as a white solid.

LCMS (ESI): RT=2.936 min, mass calcd. for $C_{81}H_{114}FN_{21}O_{23}$ 1767.82 884.2 [M+2H]$^{2+}$, m/z found 884.2 [M+2H]$^{2+}$; Mobile Phase: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min. ESI source, Positive ion mode; Wavelength 220 nm&254 nm, OvenTemperature 50° C.

HPLC: RT=6.05 min Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm; Wavelength: UV 220 nm&215 nm&254 nm; Column temperature To a solution of compound 62 (11 mg, 6.23 µmol, 1 eq.) and DIBAC-suc-OSu (2.76 mg, 6.85 µmol, 1.1 eq.) in DMF (0.5 mL) was added DIPEA (4.02 mg, 31.13 µmol, 5.42 µL, 5.0 eq.) at 20° C. Then the mixture was stirred at 20° C. for 2 hr. LCMS trace showed the reactant was consumed completely and the desired MS was detected. It was purified by prep-HPLC (column: Phenomenex Gemini-NX C18 75*30 mm*3 µm; mobile phase: [water (10 mM $NH_4HCO_3$)-ACN]; B %: 0%-60%, 35 min). LP14 (10 mg, 4.62 µmol, 74.28% yield, 95% purity) was obtained as a white solid.

LCMS (ESI): RT=0.939 min, mass calcd. for $C_{100}H_{127}FN_{22}O_{25}$ 2054.92, m/z found 1028.0 [M+2H]$^{2+}$ Mobile Phase: 1.5 mL/4L TFA in water (solvent A) and 0.75 mL/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm Wavelength: UV 220 nm; Column temperature: 50° C.

HPLC: RT=3.75 min Mobile Phase: water (solvent A) and acetonitrile (solvent B), using the elution gradient 0%-60% (solvent B) over 5 minutes and holding at 60% for 2 minutes at a flow rate of 1.2 ml/min; Column: Xbridge Shield RP-18, 5 µm, 2.1*50 mm; Wavelength: UV 220 nm, 215 nm&254 nm; Column temperature: 40° C.

Figure 31:
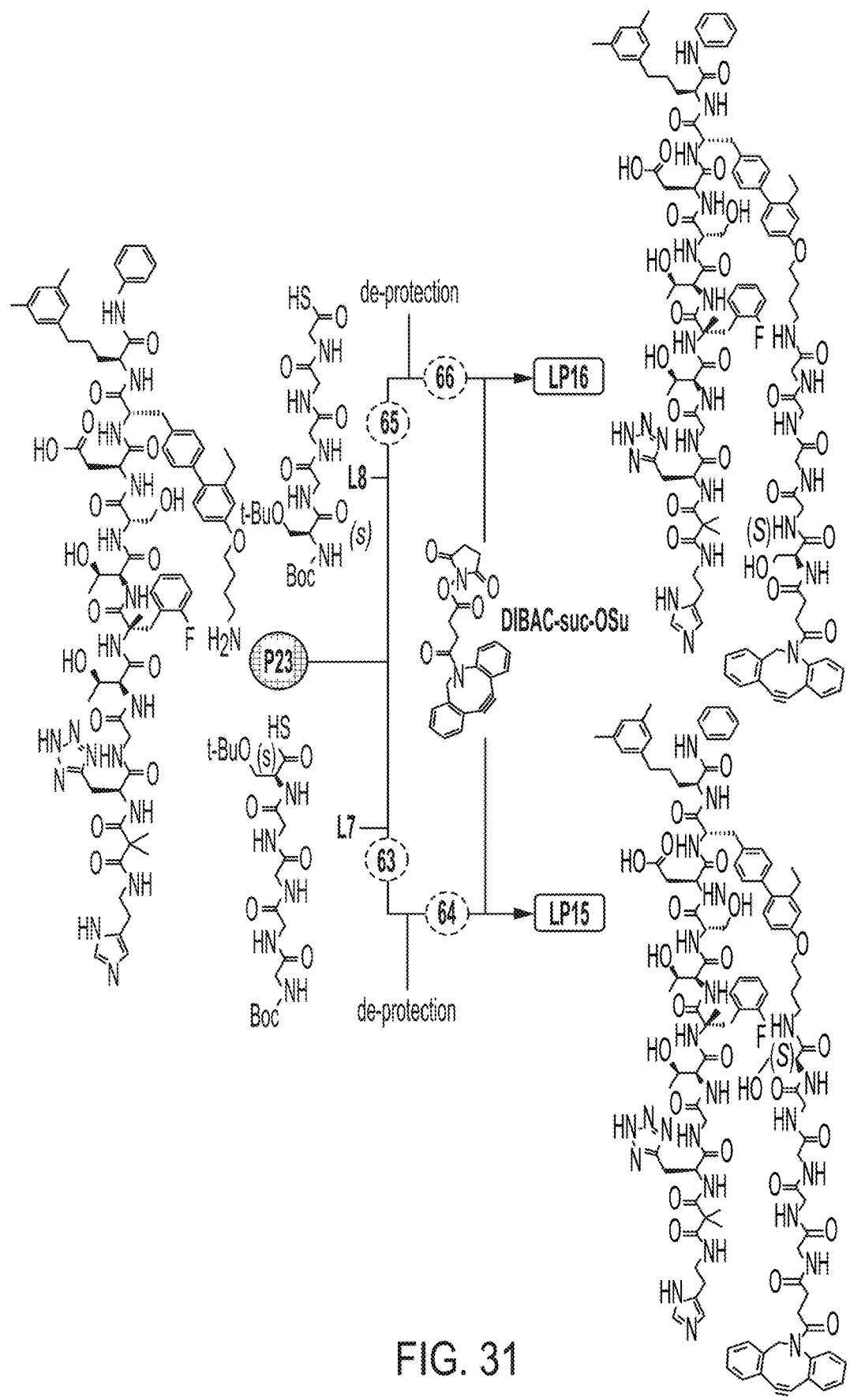
FIG. 31 shows a synthetic route for preparation of Linker-Payloads LP15 and LP18 according to the disclosure.

FIG. 31 depicts synthesis of linker-payloads LP15 and LP16 according to the disclosure.

5.15 Preparation of (3S)-4-[[(1S)-1-[[4-[4-[4-[[(2S)-2-[[2-[[2-[[2-[[4-(134- azatricyclohexadeca-11 (19),12(20),13(21),15(23),69,71(74)-hexaen-38-yn-134-yl)-4-oxobutanoyl]amino]acetyl]amino]acetyl] amino]acetyl]amino]acetyl]amino]-3-hydroxy-propanoyl]amino]butoxy]-2-ethyl-73-phenyl]phenyl] methyl]-2-[[(1S)-4-(3,5-dimethylphenyl)-1-(phenylcarbamoyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl] amino]acetyl]amino]butanoyl]amino]-2-methylpropanoyl]amino]-3-hydroxy-butanoyl] amino]-3-hydroxy-propanoyl]amino]-4-oxo-butanoic acid (LP15)

To an oven-dried vial were charged L7 (47.33 mg, 93.62 µmol, 2.5 eq.) and P23 (65 mg, 37.45 µmol, 1 eq., TFA). A stock solution of HOBt (20.24 mg, 149.78 µmol, 4 eq.), DIPEA (14.52 mg, 112.34 µmol, 19.57 µL, 3 eq.) in DMF (0.5 mL) and 12 (11.40 mg, 44.94 µmol, 9.05 µL, 1.2 eq.) in DMF (2 mL) was added to the vial. The reaction mixture was stirred at 20° C. for 16 h. LCMS trace showed that the reaction was complete. The reaction was added EtOAc (15 mL) and white solids were precipitated. The mixture was centrifuged for 3 min (5000 R) to give the crude product 63 (60 mg, 27.82 µmol, 74.29% yield, and 97.06% purity) as a white solid.

LCMS (ESI): RT=0.940 min, mass calcd. for $C_{96}H_{132}FN_{23}O_{23}$ 997 m/z [M-Boc+3H]2+, m/z found 997.5 m/z [M-Boc+3H]2+; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

A solution of 63 (60 mg, 28.66 µmol, 1 eq.) in TFA (1 mL) and DCM (1 mL) were stirred at 20° C. for 2h. LCMS trace showed that the reaction was complete. The reaction was concentrated in vacuum to give crude as yellow oil. The crude was purified by prep-HPLC (column: Waters Xbridge Prep OBD C18 150*40 mm*10 µm; mobile phase: [water (0.1% TFA)-ACN]; B %: 0%-60%, 30 min.) to give 64 (45 mg, 22.72 µmol, 79.27% yield, 97.81% purity) as a white solid.

LCMS (ESI): RT=0.890 min, mass calcd. for $C_{92}H_{124}FN_{23}O_{23}$ 968.96 m/z [M+2H]2+, m/z found 969.5 m/z [M+2H]2+; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC (ES8584-719-P1C1) was attached. RT=4.18 min., 97.81% purity. HPLC method A: Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; back to 1.0% CAN in water (0.1% TFA) at 8.01 min, and hold two minutes.Flow rate: 1.2 ml/min.

To a solution of 64 (40 mg, 19.50 µmol, 1 eq., TFA) and DIBAC-suc-OSu (7.85 mg, 19.50 µmol, 1 eq.) in DMF (1.5 mL) was added DIPEA (12.60 mg, 97.51 µmol, 16.98 µL, 5 eq.) at 18° C. The reaction was stirred at 18° C. for 2h. LCMS trace showed that the reaction was complete. The crude was purified by prep-HPLC (column: Waters Xbridge Prep OBD C18 150*40 mm*10 µm; mobile phase: [water (10 mM NH4HCO3)-ACN]; B %: 0%-50%, 35 min.) to give LP15 (27 mg, 12.07 µmol, 55.75% yield, 99.42% purity) as a white solid.

LCMS (ESI): RT=0.948 min, mass calcd. for $CH_{111}_{137}FN_{24}O_{25}$ 1112.51 m/z $[M+2H]^{2+}$, m/z found 1113.1 m/z $[M+2H]^{2+}$; Reverse phase LC-MS was carried out using a Chromolith Flash RP-18e 25-3 mm column, with a flow rate of 1.5 mL/min, eluting with a gradient of 5% to 95% acetonitrile containing 0.02% TFA (solvent B) and water containing 0.04% TFA (solvent A).

HPLC: Reverse phase 0.2 ML/1L $NH_3$—$H_2O$ in water (solvent A) and acetonitrile (solvent B), using the elution gradient 10%-80% (solvent B) over 5 minutes and holding at 80% for 2 minutes at a flow rate of 1.2 ml/min Column: Xbridge Shield RP-18, 5 µm, 2.1*50 mm Wavelength: 220 nm&215 nm&254 nm, Column temperature: 40° C.

5.16 Preparation of (3S)-4-[[(1S)-1-[[4-[4-[4-[[2-[[2-[[2-[[2-[[(2S)-2-[[4-(134- azatricyclohexadeca-11(19),12(20),13(21),15(23),69,71(74)-hexaen-38-yn-134-yl)-4-oxo-butanoyl]amino]-3-hydroxypropanoyl]amino]acetyl]amino]acetyl]amino]acetyl]amino]acetyl]amino]butoxy]-2-ethyl-73-phenyl]phenyl]methyl]-2-[[(1S)-4-(3,5-dimethylphenyl)-1-(phenylcarbamoyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxypropanoyl]amino]-4-oxo-butanoic acid (LP16)

Starting from P23 (70 mg, 43.16 µmol, 1 eq), L8 (43.64 mg, 86.32 µmol, 2 eq) and DIBAC-suc-OSu (3.92 mg, 9.75 µmol, 1 eq), LP16 (10 mg, 4.25 µmol, 34.87% yield, 94.53% purity) as a white solid was prepared using the same procedure as described in Example 15.

LCMS: (ESI): RT=0.845 min, mass calcd. for $C_{111}H_{137}FN_{24}O_{25}$ 1112.51 $[M+2H]^{2+}$, m/z found 1112.9 $[M+2H]^{2+}$; Mobile Phase: 0.8 mL/4L $NH_3·H_2O$ in water (solvent A) and acetonitrile (solvent B), using the elution gradient 10%-80% (solvent B) over 2 minutes and holding at 80% for 0.48 minutes at a flow rate of 1 ml/min;

HPLC: RT=3.73 min, 94.53% purity. Mobile Phase: 2.0 ML/4L $NH_3H_2O$ in water (solvent A) and Aetonitrile (solvent B), using the elution gradient 0%-60% (solvent B) over 4 minutes and holding at 60% for 2 minutes at a flow rate of 1.2 ml/min.

Figure 32:
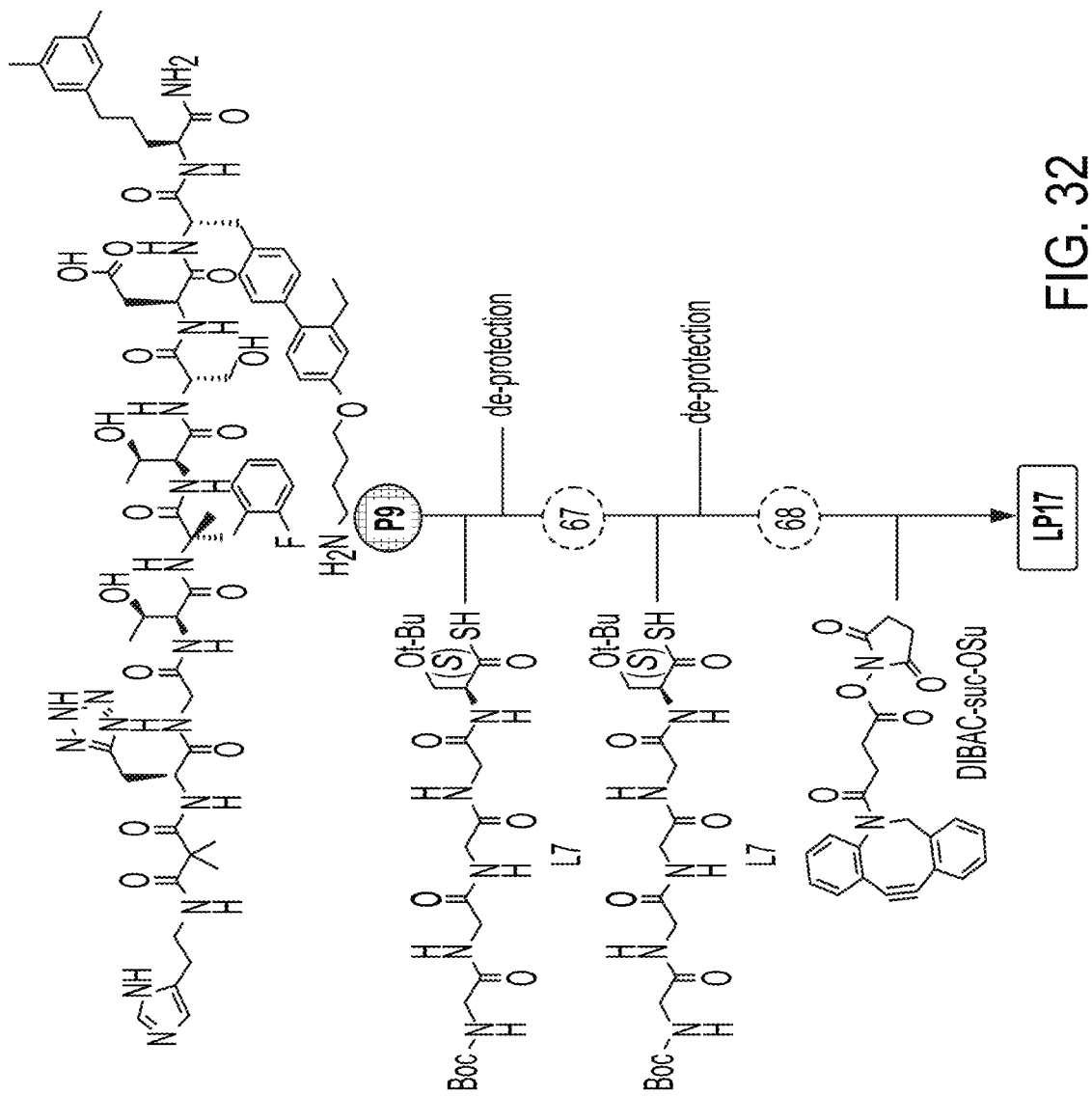
FIG. 32 shows a synthetic route for preparation of Linker-Payload LP17 according to the disclosure.
Figure 32:
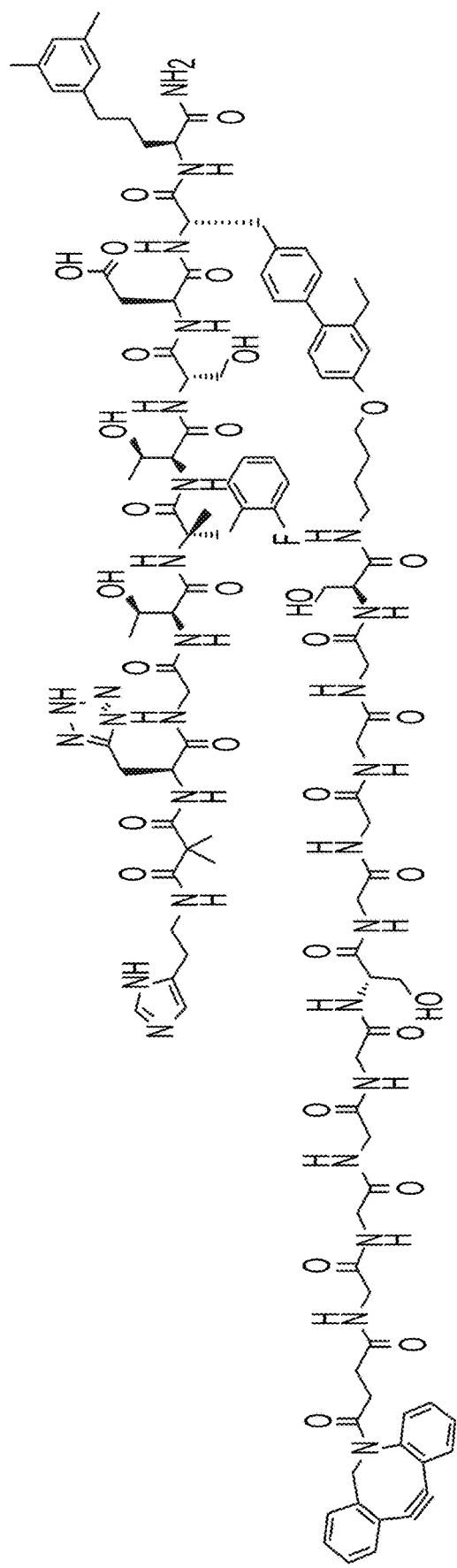

FIG. 32 depicts synthesis of linker-payload LP17 according to the disclosure. 5.17 Preparation of (3S)-4-[[(1S)-1-[[4-[4-[4-[[(2S)-2-[[2-[[2-[[2-[[2-[[(2S)-2-[[2-[[2-[[2-[[4-(144-azatricyclohexadeca-8(14),9(15),10(16),12(18),68,70(73)-hexaen-33-yn-144-yl)-4-oxo-butanoyl]amino]acetyl]amino]acetyl]amino]acetyl]amino]acetyl]amino]-3-hydroxy-propanoyl]amino]acetyl]amino]acetyl]amino]acetyl]amino]acetyl]amino]-3-hydroxy-propanoyl]amino]butoxy]-2-ethyl-72-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP17)

To an oven-dried vial were charged L7 (26.17 mg, 51.76 µmol, 2 eq.), P9 (40.00 mg, 25.88 µmol, 1 eq.) and 4A MS (5 mg). A stock solution of HOBt (6.99 mg, 51.76 µmol, 2 eq.), DIPEA (5.02 mg, 38.82 µmol, 6.76 µL, 1.5 eq.) in DMF (0.1 mL) and 12 (3.94 mg, 15.53 µmol, 3.13 µL, 0.6 eq.) in DMF (0.1 mL) was added to the vial. The reaction mixture was stirred at 15° C. for 48 h. The reaction progress was monitored by LC-MS. The mixture was filtered, then precipitated by added EtOAc (3 mL). After filtration, protected G4S-P9 (50 mg, 22.31 µmol, 86.20% yield, 90% purity) was obtained as a white foam.

LCMS (ESI): RT=0.907 min, mass calcd. for $C_{95}H_{136}FN_{23}O_{25}^{2+}$ 1009.005 $[M+2H]^{2+}$, m/z found 1010.4 $[M+2H]^{2+}$. LCMS conditions: a Merck, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=8.87 min. HPLC conditions: YMC-Pack ODS-A 150*4.6 mm, 5 mm column, flow rate 1.5 mL/min, eluting with a gradient of 10% to 80% acetonitrile containing 0.12% TFA (solvent B) and water containing 0.1% TFA (solvent A).

To an oven-dried vial were charged protected G4S-P9 (35 mg, 17.35 µmol, 1 eq.) and DCM (1 mL). TFA (1.54 g, 13.51 mmol, 1 mL, 778.42 eq.) was added to the vial. The reaction mixture was stirred at 20° C. for 3 h. The reaction progress was monitored by LC-MS. LCMS (ESI): RT=0.832 min, mass calcd. for $C_{95}H_{136}FN_{23}O_{25}^{2+}$ 930.945 $[M+2H]^{2+}$, m/z found 931.3 $[M+2H]^{2+}$. LCMS conditions: a Merck, RP-18e 25-2 mm column, with a flow rate of 1.5 mL/min, eluting with a gradient of 5% to 95% acetonitrile containing 0.02% TFA (solvent B) and water containing 0.04% TFA (solvent A). The reaction mixture was concentrated to give the crude product 67 (35 mg, crude) as a yellow solid.

To an oven-dried vial were charged L7 (19.02 mg, 37.61 µmol, 2 eq.) and compound 67 (35 mg, 18.81 µmol, 1 eq.). A stock solution of HOBt (10.16 mg, 75.23 µmol, 4 eq.) and DIPEA (7.29 mg, 56.42 µmol, 9.83 µL, 3 eq.) in DMF (0.5 mL) and 12 (5.73 mg, 22.57 µmol, 4.55 µL, 1.2 eq.) in DMF (0.5 mL) was added to the vial. The reaction mixture was stirred at 15° C. for 24 h. The reaction progress was monitored by LC-MS. The mixture was filtered, then precipitated by added EtOAc (6 mL). After filtration, the crude product protected G4S-G4S-P9 (40 mg, 13.38 µmol, 71.12% yield, 78% purity) was obtained as a pale yellow foam.

LCMS (ESI): RT=3.400 min, mass calcd. for $C_{106}H_{153}FN_{28}O_{31}^{2+}$ 1166.56, m/z found 1166.9 $[M+2H]^{2+}$. LCMS conditions: a Merck, RP-18e 25-2 mm column, with a flow rate of 0.8 mL/min, eluting with a gradient of 10% to 80% acetonitrile containing 0.02% TFA (solvent B) and water containing 0.04% TFA (solvent A).

HPLC: RT=8.10 min. HPLC conditions: YMC-Pack ODS-A 150*4.6 mm, 5 mm column, flow rate 1.5 mL/min, eluting with a gradient of 10% to 80% acetonitrile containing 0.12% TFA (solvent B) and water containing 0.1% TFA (solvent A).

To an oven-dried vial were charged protected G4S-G4S-P9 (40 mg, 17.15 µmol, 1 eq.) and DCM (2 mL). TFA (3.08 g, 27.01 mmol, 2 mL) was added to the vial. The reaction mixture was stirred at 20° C. for 2 h. The reaction progress was monitored by LC-MS. The reaction was concentrated to give a residue, then purified by prep-HPLC (TFA condition; column: Waters Xbridge Prep OBD C18 150*30 mm, 10 μm; mobile phase: [water(0.1% TFA)-ACN];B %: 0%-60%, 16 min). Compound 68 (15 mg, 6.62 μmol, 38.58% yield, 96% purity) was obtained as a white foam.

LCMS (ESI): RT=0.744 min, mass calcd. for $C_{97}H_{137}FN_{28}O_{29}{}^{2+}$ 1088.505 [M+2H]$^{2+}$, m/z found 1089.2 [M+2H]$^{2+}$. LCMS conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

HPLC: RT=3.89 min. HPLC conditions: Mobile phase: 1.0% ACN in water (0.1% TFA) to 5% ACN in water (0.1% TFA) in 1 min;then from 5% ACN in water (0.1% TFA) to 100% ACN (0.1% TFA) in 5 minutes; hold at 100% ACN (0.1% TFA) for 2 minutes; back to 1.0% ACN in water (0.1% TFA) at 8.01 min, and hold two minutes.Flow rate:1.2 ml/min.

To a solution of DIBAC-suc-OSu (3.37 mg, 8.36 μmol, 1.3 eq.) in DMF (0.3 mL) was added compound 68 (14 mg, 6.43 μmol, 1 eq.) and DIPEA (4.16 mg, 32.17 μmol, 5.60 μL, 5 eq.). The mixture was stirred at 20° C. for 2 hr. The reaction progress was monitored by LC-MS. The reaction mixture was diluted with DMSO (2 mL) and purified by prep-HPLC (neutral condition, column: Waters Xbridge Prep OBD C18 150*40 mm*10 μm; mobile phase: [water (10 mM NH4HCO3)-ACN];B %: 0%-60%,55 min). LP17 (1.73 mg, 0.65 μmol, 10.15% yield, 93% purity) was obtained as a white foam.

LCMS (ESI): RT=2.531 min, mass calcd. for $C_{116}H_{150}FN_{29}O_{31}{}^{2+}$ 1232.05 [M+2H]$^{2+}$, m/z found 1232.4 [M+2H]$^{2+}$. LCMS conditions: Mobile Phase: A) 0.05% NH$_3$H$_2$O in Water; B) ACN. Gradient: 0% B increase to 95% B within 5.8 min; hold at 95% B for 1.1 min; then back to 0% B at 6.91 min and hold for 0.09 min. Flow rate 1.0 mL/min; Column: Waters Xbridge C18 30*2.0 mm,3.5 μm.

HPLC: RT=2.17 min. HPLC conditions: Mobile Phase: 0.2 ML/1L NH$_3$H$_2$O in water (solvent A) and acetonitrile (solvent B), using the elution gradient 10%-80% (solvent B) over 5 minutes and holding at 80% for 2 minutes at a flow rate of 1.2 ml/min; Column: Xbridge Shield RP-18.5 μm,2.1*50 mm.

Figure 33:
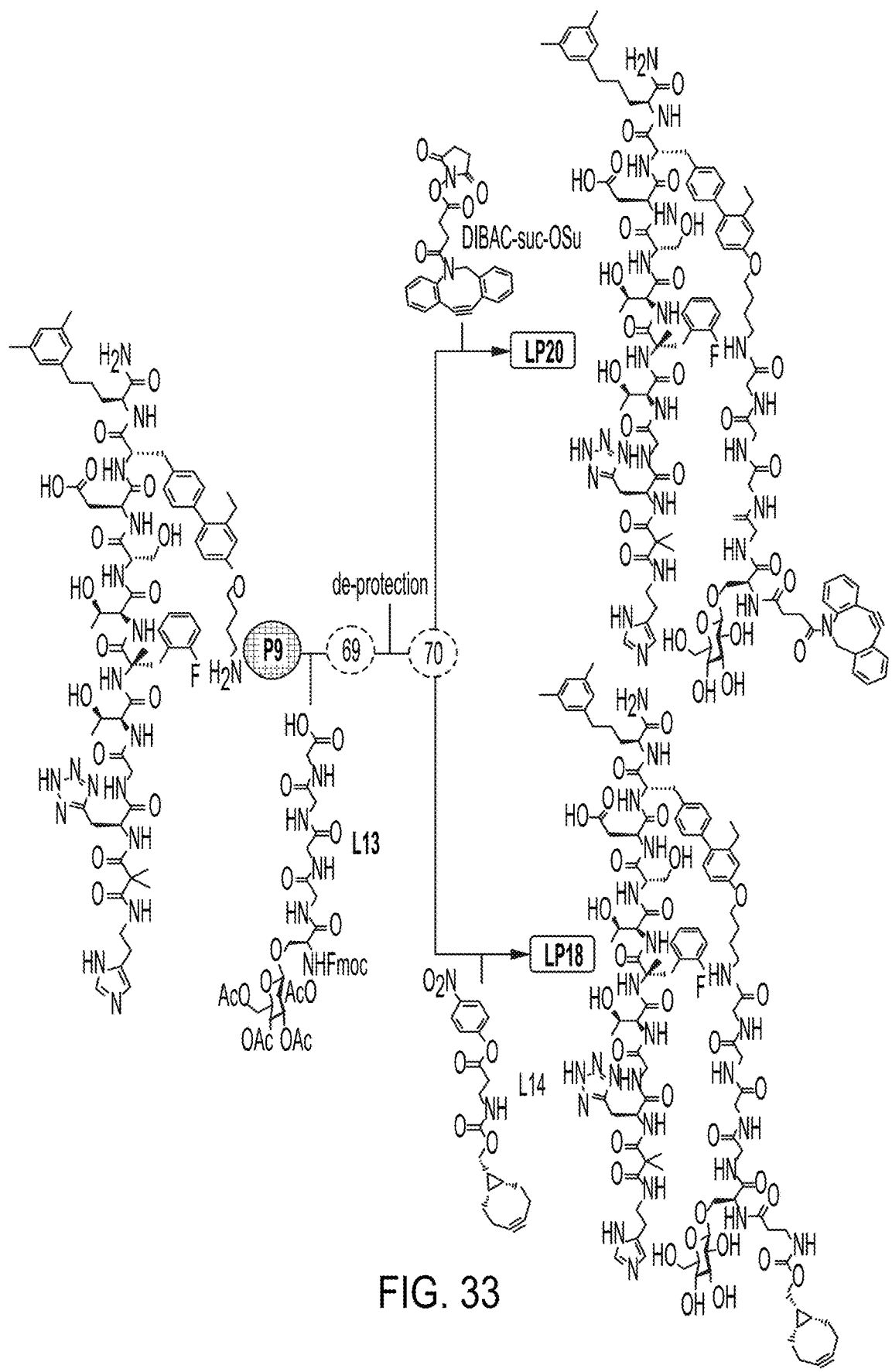
FIG. 33 shows a synthetic route for preparation of Linker-Payloads LP18 and LP20 according to the disclosure.

FIG. 33 depicts synthesis of linker-payloads LP18 and LP20 according to the disclosure.

5.18 Preparation of (3S)-4-[[(1S)-1-[[4-[4-[4-[[2-[[2-[[2-[[2-[[(2S)-2-[3-[[(1S,8R)- 9-bicyclo[6.1.0]non-4-ynyl]methoxycarbonylamino]propanoylamino]-3-[(2R,4S,5S)-3,4,5-trihydroxy-6-(hydroxymethyl)tetrahydropyran-2-yl]oxypropanoyl]amino]acetyl]amino]acetyl]amino]acetyl]amino]acetyl]amino]butoxyl-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[f2-[[(2S)-2-[[3-2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]asminol-3-hydroxypropanoyl]amino]-4-oxo-butanoic acid (LP18)

To a solution of L13 (22.92 mg,25.88 μmol, 2 eq.), PyBOP (13.47 mg, 25.88 μmol, 2 eq.) and DIPEA (6.69 mg, 51.76 μmol, 9.01 μL, 4 eq.) in DMF (0.1 mL) was stirred at 25° C. for 5 min. A solution of P9 (20 mg, 12.94 μmol, 1 eq.) in DMF (0.1 mL) was added to the mixture, the reaction was stirred at 25° C. for 5 min. The mixture was diluted with EtOAc (15 mL) to give precipitate, which was centrifuged for 3 min (5000 R) to give the crude product as a white solid. The residue was diluted with water (2 mL) and ACN (2 mL). The solution was dried by lyophilization to give compound 69 (25 mg, 8.53 μmol, 65.95% yield, 82.384% purity) as a white solid.

LCMS: (ESI): RT=2.376 min, m/z calcd. for $C_{115}H_{148}FN_{23}O_{34}$, 1207.03 [M+2H]$^{2+}$, m/z found 1207.4 [M+2H]$^{2+}$; Mobile Phase: 1.5 ML/4L TFA in water (solvent A) and 0.75 ML/4L TFA in acetonitrile (solvent B), using the elution gradient 10%-80% (solvent B) over 3 minutes and holding at 80% for 0.5 minutes at a flow rate of 0.8 ml/min.

To a solution of compound 69 (20 mg, 8.29 μmol, 1 eq.) in DMF (2 mL) was added NH$_2$NH$_2$·H$_2$O (488.04 μg, 8.29 μmol, 0.2 mL, 85% purity, 1 eq.) at 25° C. The reaction was stirred at 25° C. for 1h. LCMS showed that the reaction converted completely. The mixture was filtered to give a residue, which was purified by prep.-HPLC (column: Phenomenex Gemini-NX 150*30 mm*5 μm; mobile phase: [water(0.075% TFA)-ACN];B %: 0%-60%,30 min) to give compound 70 (15 mg, 7.38 μmol, 71.28% yield, 99.58% purity) as a white solid.

LCMS: (ESI): RT=0.791 min, m/z calcd. for $C_{92}H_{130}FN_{23}O_{28}$, 1011.97 [M+2H]$^{2+}$, m/z found 1012.2 [M+2H]$^{2+}$; Reverse phase LCMS was carried out using a Merck RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: Rt=3.47 min. Mobile phase: 1.0% ACN in water (0.1% TFA) to 5% ACN in water (0.1% TFA) in 1 min;then from 5% ACN in water(0.1% TFA) to 100% ACN (0.1% TFA) in 5 minutes; hold at 100% ACN (0.1% TFA) for 2 minutes; back to 1.0% ACNin water (0.1% TFA) at 8.01 min, and hold two minutes. Flow rate: 1.2 ml/min.

A solution of compound 70 (18 mg, 8.90 μmol, 1 eq.) and L14 (6.88 mg, 17.79 μmol, 2 eq.) in PBS buffer (0.45 mL, pH=8.2) and DMF (0.9 mL) was stirred at 25° C. for 6h. LCMS showed the reaction was complete. The reaction was filtered to give a residue. The residue was purified by prep-HPLC (column: Phenomenex Gemini-NX 150*30 mm*5 μm; mobile phase: [water (0.225% FA)-ACN]; B %: 0%-60%, 35 min) to give LP18 (7.5 mg, 3.24 μmol, 36.45% yield, 98.18% purity) as a white solid.

LCMS: (ESI): RT=1.595 min, m/z calcd. for $C_{106}H_{147}FN_{24}O_{31}$, 1135.53 [M+2H]$^{2+}$, m/z found 1136.0 [M+2H]$^{2+}$; Mobile Phase: 1.5 ML/4L TFA in water (solvent A) and 0.75 ML/4L TFA in acetonitrile (solvent B), using the elution gradient 10%-80% (solvent B) over 2 minutes and holding at 80% for 0.48 minutes at a flow rate of 0.8 ml/min; Chromolith Flash RP-C18 2.1-30 mm HPLC: RT=8.17 min, 98.18% purity. HPLC method A: Column: YMC-Pack ODS-A150*4.6 mm,5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min.

5.19 Preparation of (3S)-4-[[(1S)-1-[[4-[4-[4-[[2-[[2-[[2-[[2-[[(2S)-2-[[4-(153- azatricyclohexadeca-8 (18),10(20),12(22),15(25),77(79),81(85)-hexaen-42 (44)-yn-153-yl)-4-oxo-butanoyl]amino]-3-[6-[[4-(153-azatricyclohexadeca-8(18),10(20),12(22),15 (25),77(79),81(85)-hexaen-42(44)-yn-153-yl)-4-oxo-butanoyl]oxymethyl]-3,4,5-trihydroxytetrahydropyran-2-yl]oxy-propanoyl] amino]acetyl]amino]acetyl]amino]acetyl]amino] acetyl]amino]butoxy]-2-ethyl-84-phenyl]phenyl] methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxopropanoyl]amino]-3-(2H-tetrazol-5-yl) propanoyl]amino]acetyl]amino]butanoyl]amino]-2-methyl-propanoyl]amino]-3-hydroxybutanoyl] amino]-3-hydroxy-propanoyl]amino]-4-oxo-butanoic acid (LP20)

To a solution of 70 (7.90 mg, 18.54 µmol, 2.5 eq) was added DIPEA (4.79 mg, 37.07 µmol, 6.46 µL, 5 eq) in DMF (0.5 mL) at 25° C. The reaction was stirred at 25° C. for 16 h. Then H$_2$O (2.5 mL) was added and it was stirred at 25° C. for 2h. LCMS showed the reaction was complete. The reaction was filtered to give a residue as a yellow solution. The residue was purified by prep-HPLC (column: Phenomenex Gemini-NX 150*30 mm*5 µm; mobile phase: [water (0.04% NH$_3$H$_2$O+10 mM NH$_4$HCO$_3$)-ACN]; B %: 17%-47%, 8 min) to give LP20 (3.7 mg, 1.52 µmol, 20.82% yield, 95.093% purity) as a white solid.

LCMS: (ESI): RT=1.328 min, m/z calcd. for C$_{111}$H$_{143}$FN$_{24}$O$_{30}$, 1155.52 [M+2H]$^{2+}$, m/z found 1156.0 [M+2H]$^{2+}$; Mobile Phase: 0.8 mL/4L NH$_3$·H$_2$O in water (solvent A) and acetonitrile (solvent B), using the elution gradient 10%-80% (solvent B) over 2 minutes and holding at 80% for 0.48 minutes at a flow rate of 1 ml/min; Column: XBridge C18 3.5 µm 2.1*30 mm; Wavelength:UV 220 nm & 254 nm; Column temperature: 50° C.

HPLC: RT=1.328 min, 92.31% purity. HPLC method A: Mobile Phase: 0.8 mL/4L NH3·H$_2$O in water (solvent A) and acetonitrile (solvent B), using the elution gradient 0%-60% (solvent B) over 5 minutes and holding at 60% for 0.48 minutes at a flow rate of 1 ml/min; Column: Xbridge Shield RP18 5 µm 2.1*50 mm; Wavelength: UV 220 nm & 254 nm.

Figure 34:
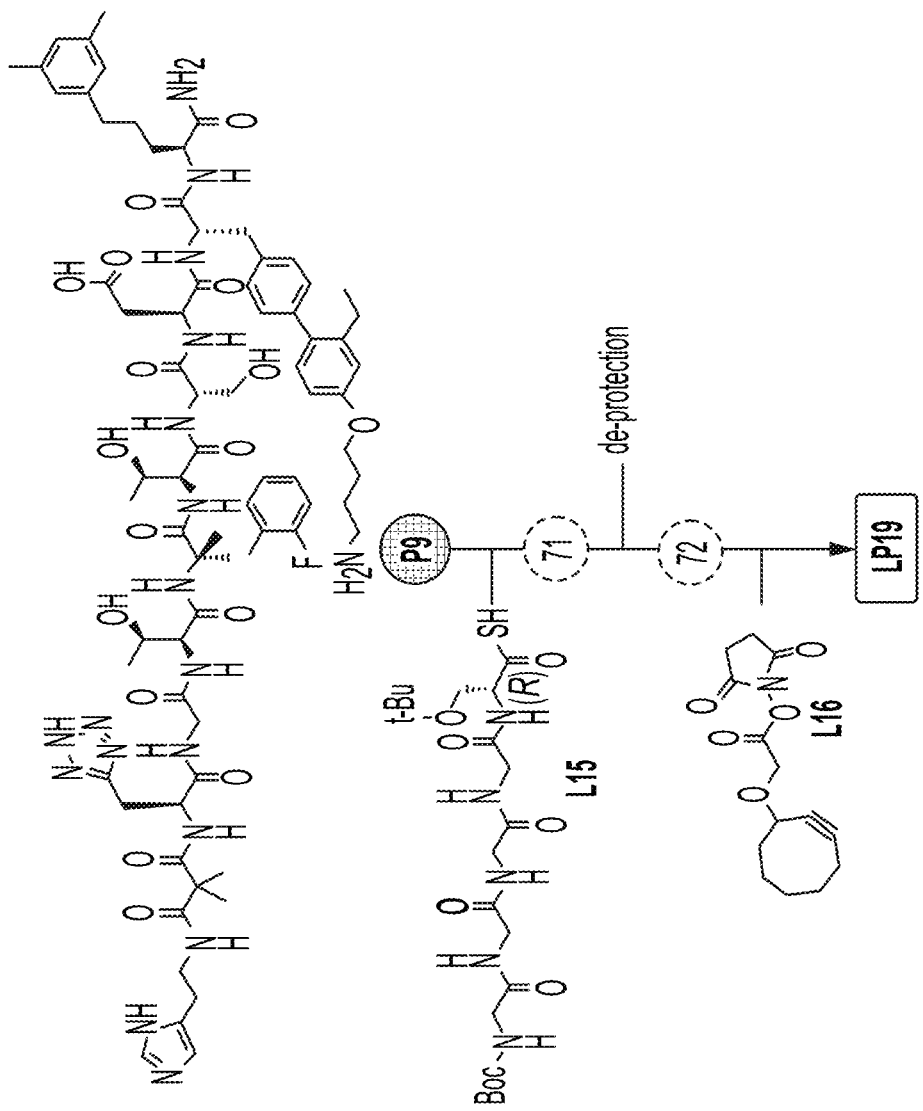
FIG. 34 shows a synthetic route for preparation of Linker-Payload LP19 according to the disclosure.
Figure 34:
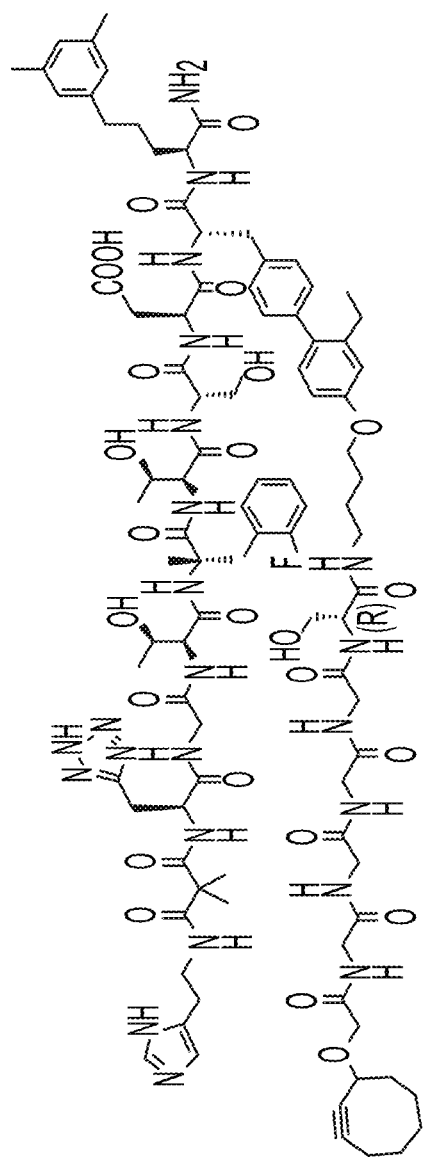

FIG. 34 depicts synthesis of linker-payload LP19 according to the disclosure. 5.20 Preparation of (3S)-4-[[(1S)-2-[[(1S)-1-carbamoyl-4-(3,5-dimethylphenyl)butyl]amino]-1-[[4-[4-[4-[[(2R)-2-[[2-[[2-[[2-[[2-(2-cyclooct-2-yn-1-yloxoacetyl)amino]acetyl]amino]acetyl]amino]acetyl] amino]acetyl]amino]-3-hydroxypropanoyl]amino]butoxy]-2-ethyl-phenyl]phenyl]methyl]-2-oxo-ethyl]amino]-3-[[(2S)-2-[[(2S,3R)-2-[[f3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino]butanoyl] amino]-2-methyl-propanoyl]amino]-3-hydroxy-butanoyl] amino]-3-hydroxypropanoyl]amino]-4-oxo-butanoic acid (LP19)

To a colorless solution of P9 (25 mg, 16.17 µmol, 1 eq), L15 (16.35 mg, 32.35 µmol, 2.0 eq) and HOBt (4.37 mg, 32.35 µmol, 2.0 eq), DIPEA (3.14 mg, 24.26 µmol, 4.23 µL, 1.5 eq) in DMF (0.3 mL) was added a solution of 12 (2.87 mg, 11.32 µmol, 2.28 µL, 0.7 eq) in DMF (0.25 mL). The solution was stirred at 20° C. for 1 hr. LCMS trace showed the reaction was converted completely and the desired product was observed. The solution was treated with EtOAc (25 mL), the formed precipitate was collected by centrifuged for 5 min (5000 R). The collected white solid was lyophilized in freeze dryer to give compound 71 (45 mg, 21.11 µmol, 93.25% yield, 94.65% purity) as a white solid.

LCMS (ESI): RT=0.880 min, m/z calcd. for C$_{95}$H$_{126}$FN$_{23}$O$_{23}$ [M-Boc+2H]$^2$+958.97, found 959.0. LC-MS method A: a Xtimate C18 2.1*30 mm, 3 µm column, with a flow rate of 1.2 mL/min, eluting with a gradient of 5% to 95% acetonitrile containing 0.75 ML/4L TFA (solvent B) and 1.5 ML/4L TFA in water (solvent A).

HPLC: RT=4.43 min. Mobile phase: 1.0% ACN in water (0.1% TFA) to 5% ACN in water (0.1% TFA) in 1 min; then from 5% ACN in water (0.1% TFA) to 100% ACN (0.1% TFA) in 5 minutes; hold at 100% ACN (0.1% TFA) for 2 minutes; back to 1.0% ACN in water (0.1% TFA) at 8.01 min, and hold two minutes. Flow rate: 1.2 ml/min To a solution of 71 (35 mg, 17.35 µmol, 1 eq) in DCM (1 mL) was added TFA (1.54 g, 13.51 mmol, 1 mL, 778.42 eq). The solution was stirred at 20° C. for 1 hr. LCMS trace showed the reaction was converted completely and the desired product was observed. The solution was concentrated in vacuum to give a residue. The residue was purified by reversed phase HPLC (0.4% AcOH) (20 g column, Eluent of 0-44% CH$_3$CN/H$_2$O, gradient @ 25 mL/min). The desired fluent was lyophilized in freeze dryer to give 72 (18 mg, 8.91 µmol, 51.35% yield, 92.108% purity) as a white solid.

LCMS (ESI): RT=0.815 min, m/z calcd. for C$_{86}$H$_{120}$FN$_{23}$O$_{23}$ [M+2H]2+930.94, found 931.2. LC-MS method A: a Xtimate C18 2.1*30 mm, 3 µm column, with a flow rate of 1.2 mL/min, eluting with a gradient of 5% to 95% acetonitrile containing 0.75 ML/4L TFA (solvent B) and 1.5 ML/4L TFA in water (solvent A).

To a solution of 72 (17 mg, 9.13 µmol, 1 eq) and L16 (5.10 mg, 18.27 µmol, 2.0 eq) in DMF (0.5 mL) was added DIPEA (2.36 mg, 18.27 µmol, 3.18 µL, 2.0 eq). The solution was stirred at 20° C. for 1 hr. LCMS trace showed the reaction was converted completely and the desired product was observed. The solution was purified by prep-HPLC (FA condition: Column: Phenomenex Gemini-NX 150*30 mm*5 µm; mobile phase: [water (0.1% TFA)-ACN]; B %: 0%-50%, 35 min). The desired fluent was lyophilized in freeze dryer to give LP19 (8.36 mg, 4.12 µmol, 36.34% yield, 99.72% purity) as a white solid.

LCMS (ESI): RT=3.379 min, m/z calcd. for C$_{96}$H$_{132}$FN$_{23}$O$_{25}$ [M+2H]$^2$+1012.98, found 1013.7. LCMS conditions: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate 3 µm,C18,2.1*30 mm;

HPLC: RT=8.70 min, Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: YMC-Pack ODS-A 150*4.6 mm, 5 µm.

Figure 35:
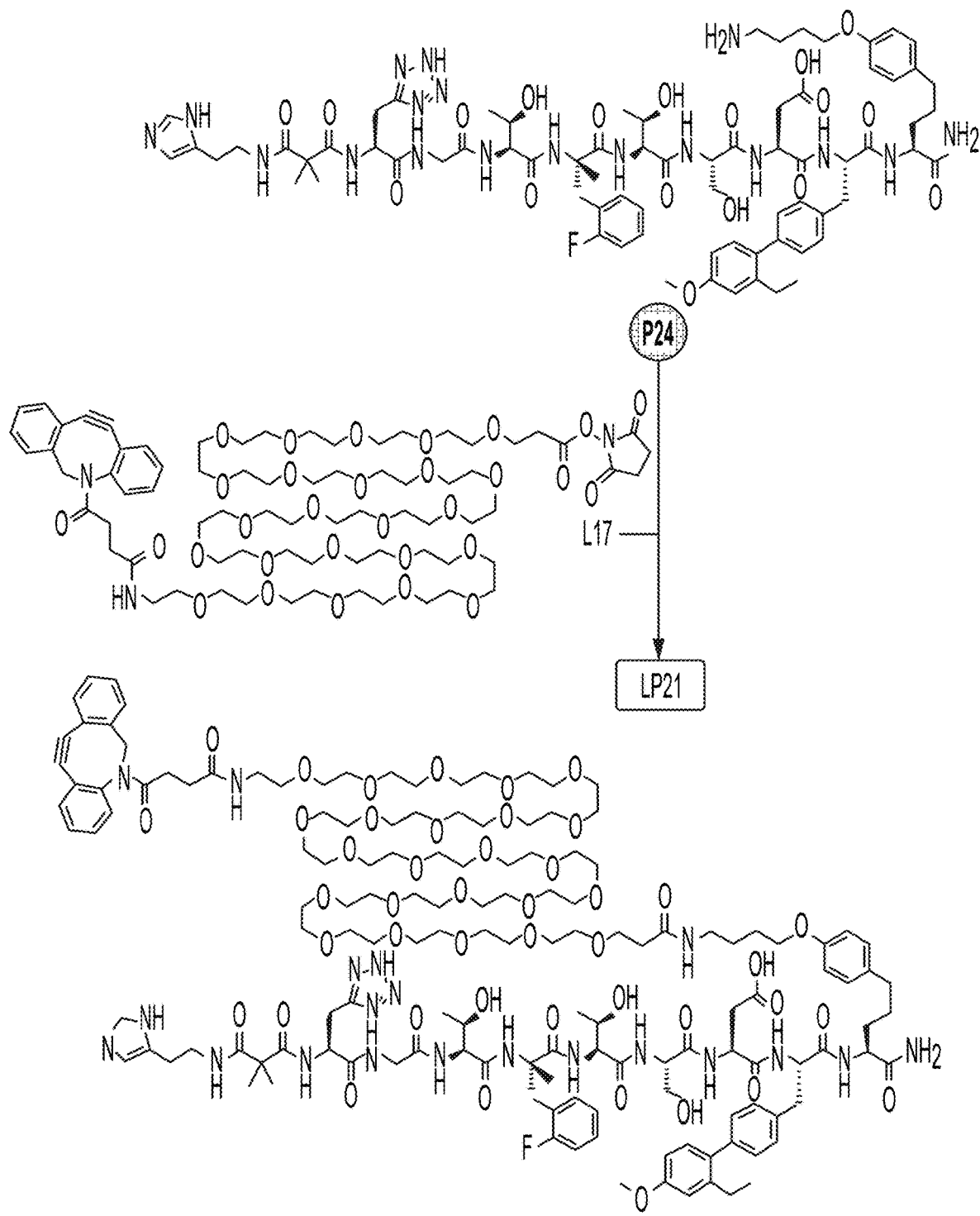
FIG. 35 shows a synthetic route for preparation of Linker-Payload LP21 according to the disclosure.

FIG. 35 depicts synthesis of linker-payload LP21 according to the disclosure.

5.21 Preparation of (3S)-4-[[(1S)-2-[[(1S)-4-[4-[4-[3-[2-[2-[2-[2-[2-[2-[2-[2-[2-[2-[2-[2-[2-[2-[2-[2-[2-[2-[2-[2-[2-[2-[[4-(163-azatricyclohexadeca-7(13),8(14),9(15),11(17),108,110(113)-hexaen-33-yn-163-yl)-4-oxo-butanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxyl ethoxy]ethoxy]ethoxy]ethoxy]ethoxy]propanoy]amino]butoxy]phenyl]-1-carbamoyl-butyl]amino]-1-[[4-(2-ethyl-4-methoxy-phenyl)phenyl]methyl]-2-oxo-ethyl]amino]-3-[[(2S)-2-[[(2R,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP21)

To a mixture of P24 (15 mg, 9.69 µmol, 1 eq.) and L17 (22.25 mg, 14.54 µmol, 1.5 eq.) in DMF (1 mL) was added DIPEA (6.26 mg, 48.46 µmol, 8.44 µL, 5 eq.) in one portion at 25° C. under nitrogen. The mixture was stirred at 25° C. for 2 h. LCMS trace showed that the reaction was converted completely. The reaction mixture was concentrated in vacuum to give residue. The residue was purified by prep-HPLC (column: mobile phase: [water(10 mM NH4HCO3)-ACN]; B %: 20%-50%, 55 min) to give pure product. The product was suspended in water (10 mL), the mixture frozen in a dry-ice/ethanol bath, and then lyophilized to dryness to afford the desired product LP21 (8.2 mg, 2.70 µmol, 27.86% yield, 97.5798% purity) as a white solid.

LCMS (ESI): RT=0.924 min, mass calcd. for $C_{144}H_{213}FN_{20}O_{45}$ 2961.50 [M+H]$^+$, 987.167 [M+3H]$^{3+}$, m/z found 988.8 [M+3H]$^{3+}$. Reverse phase LCMS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

HPLC condition: RT=14.496 min, Reverse phase HPLC was carried out using a Gemini-NX 5u C18 110A 150*4.6 mm column, with a flow rate of 1.0 mL/min, eluting with a gradient of 10% to 80% acetonitrile containing 0.1% TFA (solvent B) and water containing 0.1% TFA (solvent A).

Figure 36:
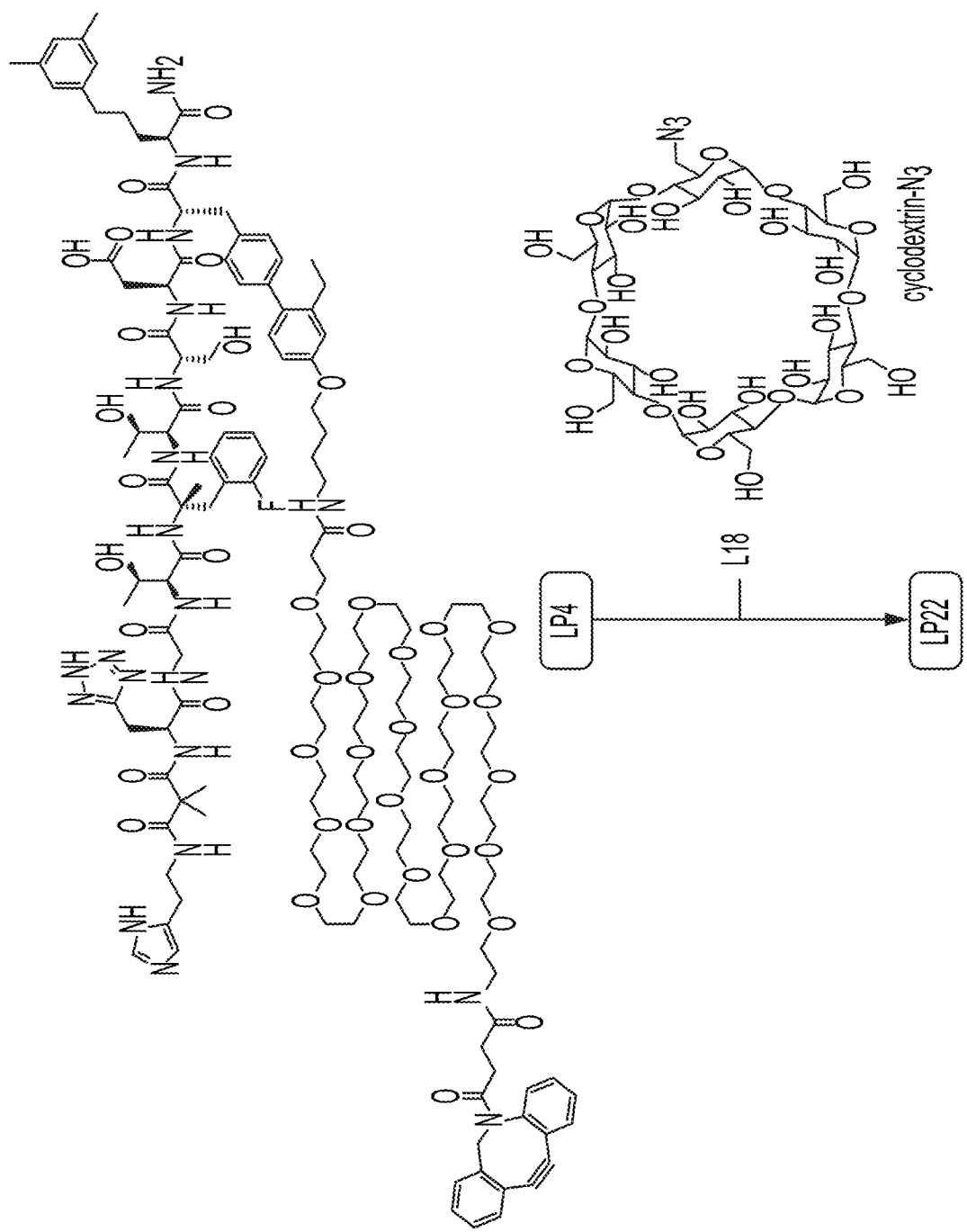
FIG. 36 shows a synthetic route for preparation of Linker-Payload LP22 according to the disclosure.
Figure 36:
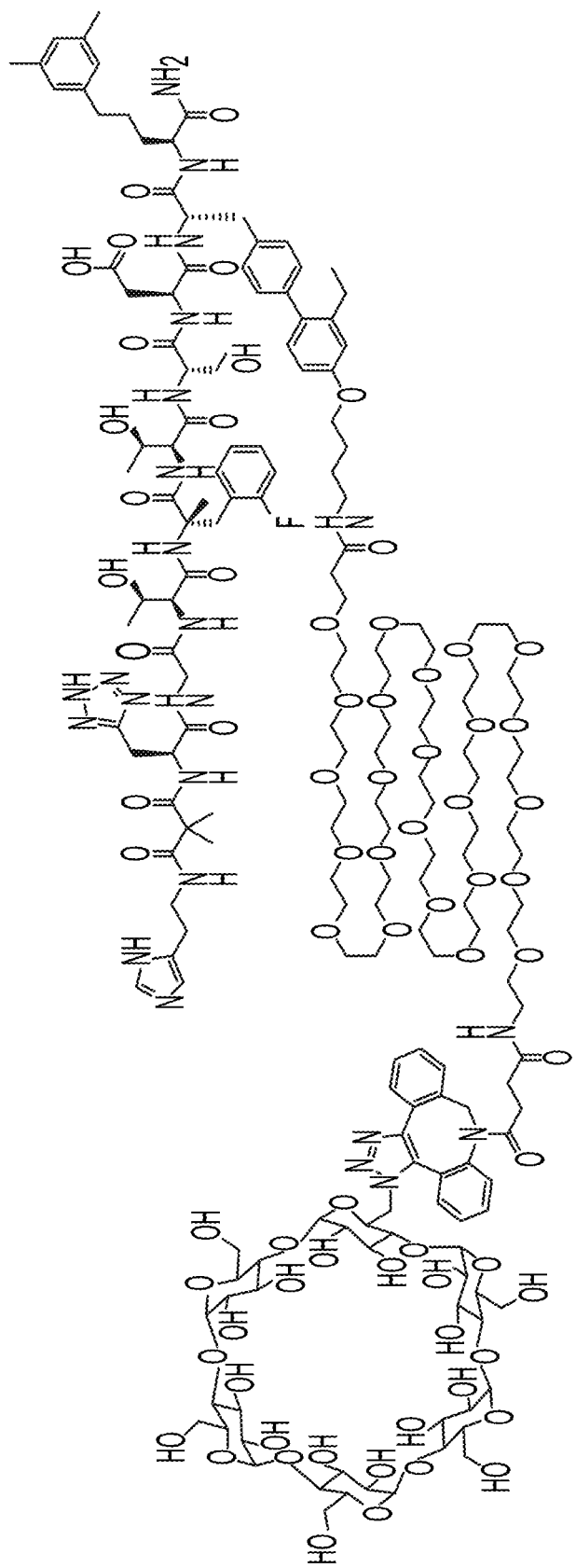

FIG. 36 depicts synthesis of linker-payload LP22 according to the disclosure.

5.22 Preparation of (3S)-4-[[(1S)-2-[[(1S)-1-carbamoyl-4-(3,5-dimethylphenyl)butyl]amino]-1-[[4-[4-[4-[3-[2-[2-[2-[2-[2-[2-[2-[2-[2-[2-[2-[2-[2-[2-[2-[2-[2- [2-[2-[2-[2-[2-[[4-[202-[[131,132,133,134,135,136,137,138,139,140,141,142-dodecahydroxy-126,127,128,129,130-pentakis (hydroxymethyl)-240,241,242,243,244,245,246,247,248,249,250,251-dodecaoxahepta cyclodotetracontan-125-yl]methyl]-187,189,202,203-tetrazatetracyclononadeca-8(14),10(16),11(17),12(18),112(114),115(117),123,187(189)-octaen-203-yl]-4-oxo-butanoyl]amino]ethoxy]ethoxy]ethoxy]ethoxy]ethoxy]ethoxy]ethoxy]ethoxyl ethoxy]ethoxy]ethoxy]ethoxy]ethoxy]ethoxy]ethoxy]ethoxy]ethoxy]ethoxy]ethoxy]ethoxy]ethoxy]e thoxy]ethoxy]ethoxy]propanoy]amino]butoxy]-2-ethyl-116-phenyl]phenyl]methyl]-2-oxo-ethyl]amino]-3-[[(2S)-2-[[(2R,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP22)

To a mixture of compound LP4 (5 mg, 1.69 µmol, 1 eq.) in DMF (0.3 mL) was added and compound L18 (cyclodextrin-N$_3$, 4.38 mg, 4.39 µmol, 2.6 eq.) in one portion at 25° C. under N$_2$. The mixture was stirred at 25° C. for 12 hours. LCMS and HPLC trace showed the reaction were complete. The residue was purified by prep-HPLC (neutral: column: Waters Xbridge 150*25 5u; mobile phase: [water (10 mM NH$_4$HCO$_3$)-ACN]; B %: 20%-50%, 7 min) to give LP22 (1.66 mg, 4.03e-1 µmol, 23.88% yield, 96.149% purity) as a white solid.

HPLC: RT=11.976 min, Reverse phase HPLC was carried out using a Gemini-NX 5u C18 110A 150*4.6 mm column, with a flow rate of 1.0 mL/min, eluting with a gradient of 10% to 80% acetonitrile containing 0.1% TFA (solvent B) and water containing 0.1% TFA (solvent A).

LCMS (ESI): RT=0.877 min, mass calcd. for $C_{74}H_{120}N_3O_{30}$ 3956.84 [M+H]$^+$, 1318.95 [M+3H]3+, found 1320.2 [M+3H]3+. Reverse phase LC-MS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

Figure 37:
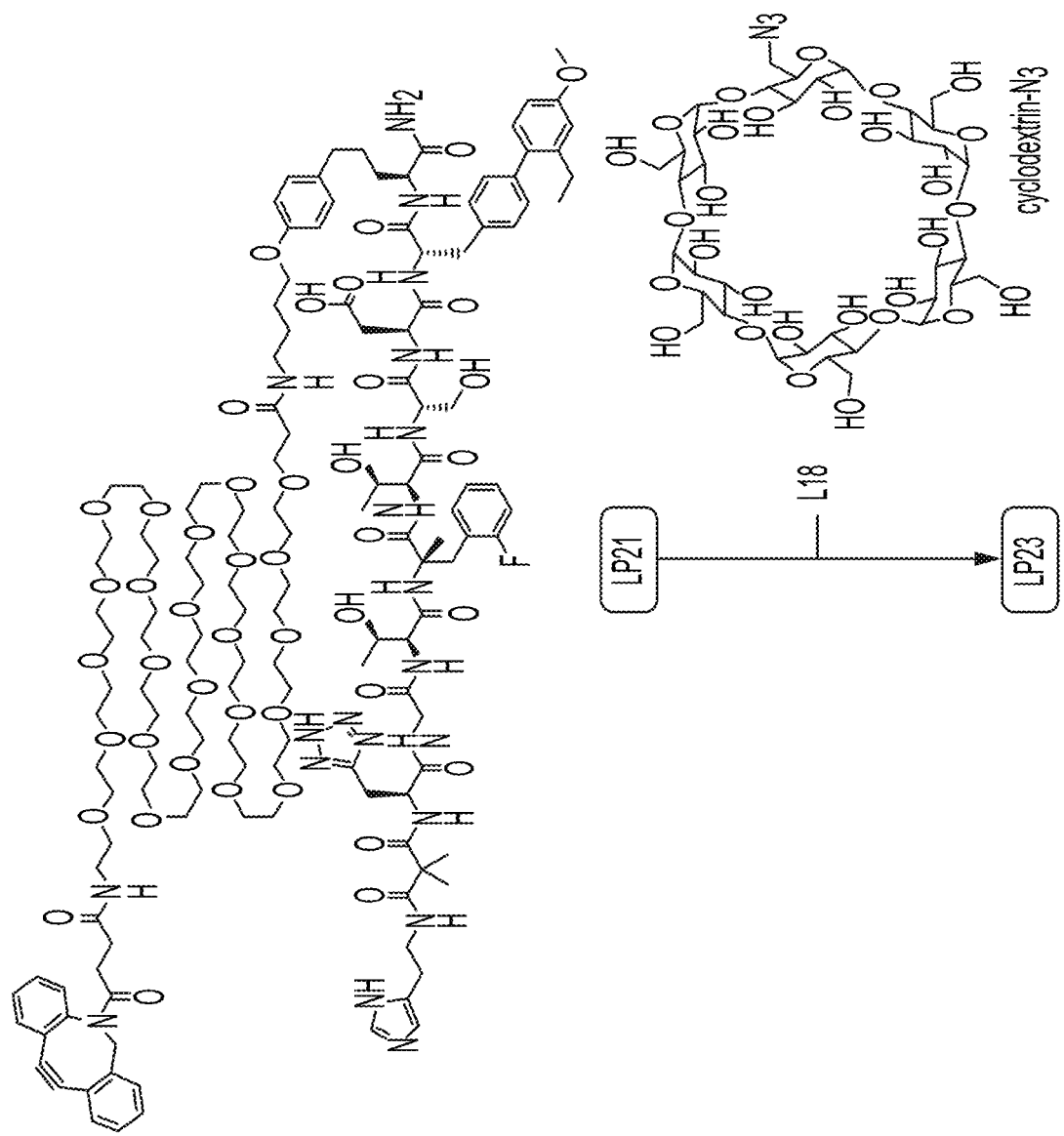
FIG. 37 shows a synthetic route for preparation of Linker-Payload LP23 according to the disclosure.
Figure 37:
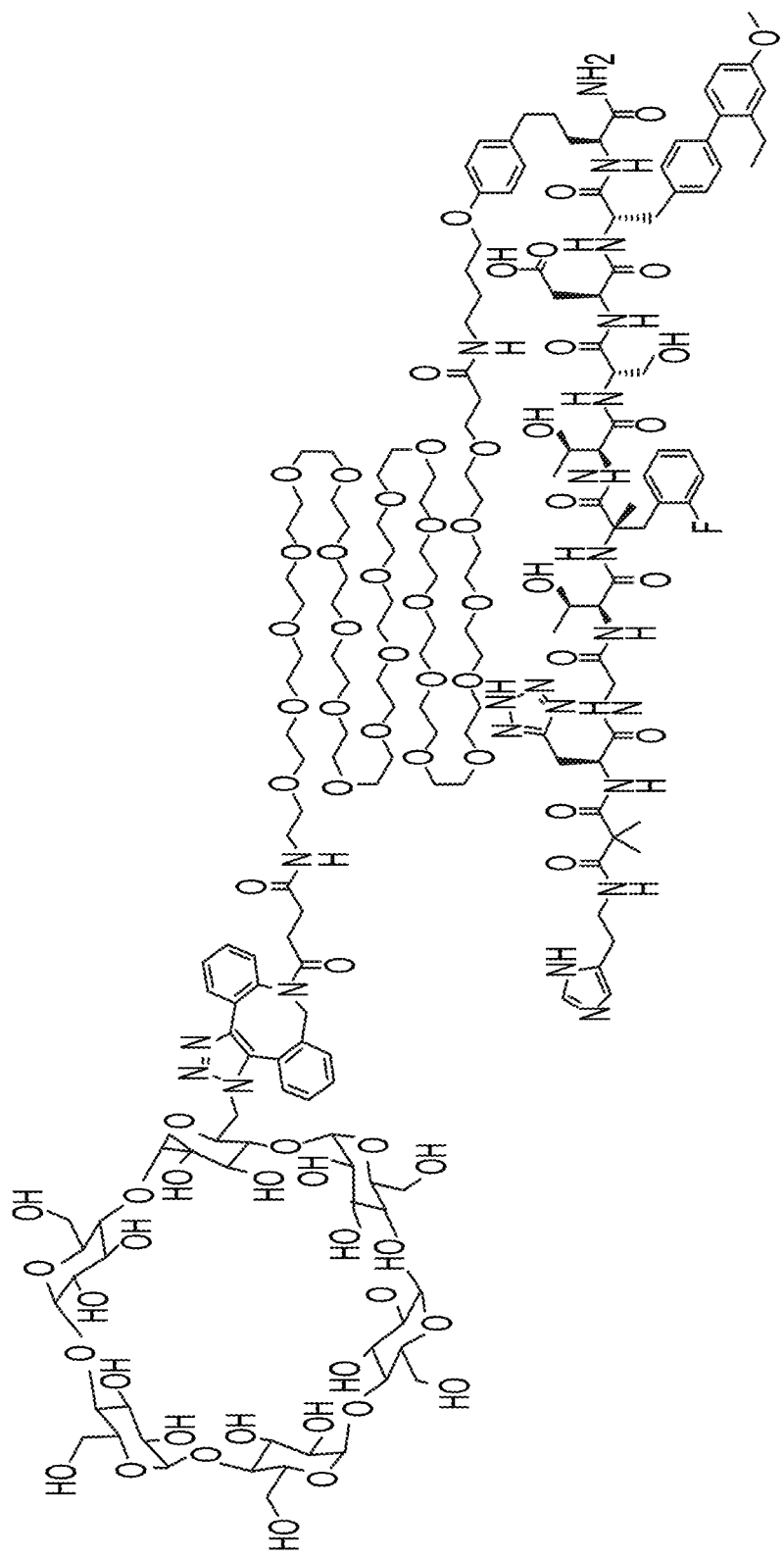

FIG. 37 depicts synthesis of linker-payload LP23 according to the disclosure.

5.23 Preparation of (3S)-4-[[(1S)-2-[[(1S)-1-carbamoyl-4-[4-[4-[3-[2-[2-[2-[2-[2-[2-[2-[2-[2-[2-[2-[2-[2-[2-[2-[2-[2-[2-[2-[2-[2-[2-[2-[[4-201-[[130, 131,132,133,134,135,136,137,138,139,140, 141-dodecahydroxy-125,126,127,128,129-pentakis (hydroxymethyl)-239,240,241,242,243, 244, 245, 246,247,248,249,250-dodecaoxaheptacyclodotetracontan-124-yl]methyl]-186,188,201, 202-tetrazatetracyclononadeca-7(13),9 (15),10(16),11(17), 112(114),115(117),122, 186 (188)-octaen-202-yl]-4-oxo-butanoyl]amino]ethoxy] ethoxy]ethoxy]ethoxy]ethoxy]ethoxy] ethoxy]ethoxy]ethoxy]ethoxy]ethoxy]ethoxy] ethoxy]ethoxy]ethoxy]ethoxy]ethoxy]ethoxy] ethoxy]e thoxy]ethoxy]ethoxy]ethoxy]propanoyl] amino]butoxy]phenyl]butyl]amino]-1-[[4-(2-ethyl-4-methoxy-phenyl)phenyl]methyl]-2-oxo-ethyl] amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP23)

Starting from LP21 (9.3 mg, 3.10 μmol, 1 eq.) and L18 (cyclodextrin-$N_3$, 3.7 mg, 3.7 μmol, 1.2 eq.) LP23 (3.5 mg, 8.84e-1 μmol, 50.00% yield, 100% purity) was obtained as a white solid following the same procedure in Example 22.

HPLC condition: RT=8.14 min, Reverse phase HPLC was carried out using a YMC-Pack ODS-A 150*4.6 mm, 5 μm, with a flow rate of 1.5 mL/min, eluting with a gradient of 10% to 80% acetonitrile containing 0.1% TFA (solvent B) and water containing 0.1% TFA (solvent A).

LCMS (ESI): RT=0.868 min, mass calcd. for $C_{75}H_{102}FN_{18}O_{17}$ 3958.82 [M+H]$^+$ 1319.61 [M+H]3+, found 1321.5 [M+H]3+. Reverse phase LC-MS was carried out using a Chromolith Flash RP-18e 25-3 mm column, with a flow rate of 1.5 mL/min, eluting with a gradient of 5% to 95% acetonitrile containing 0.04% TFA (solvent B) and water containing 0.06% TFA (solvent A).

Figure 38:
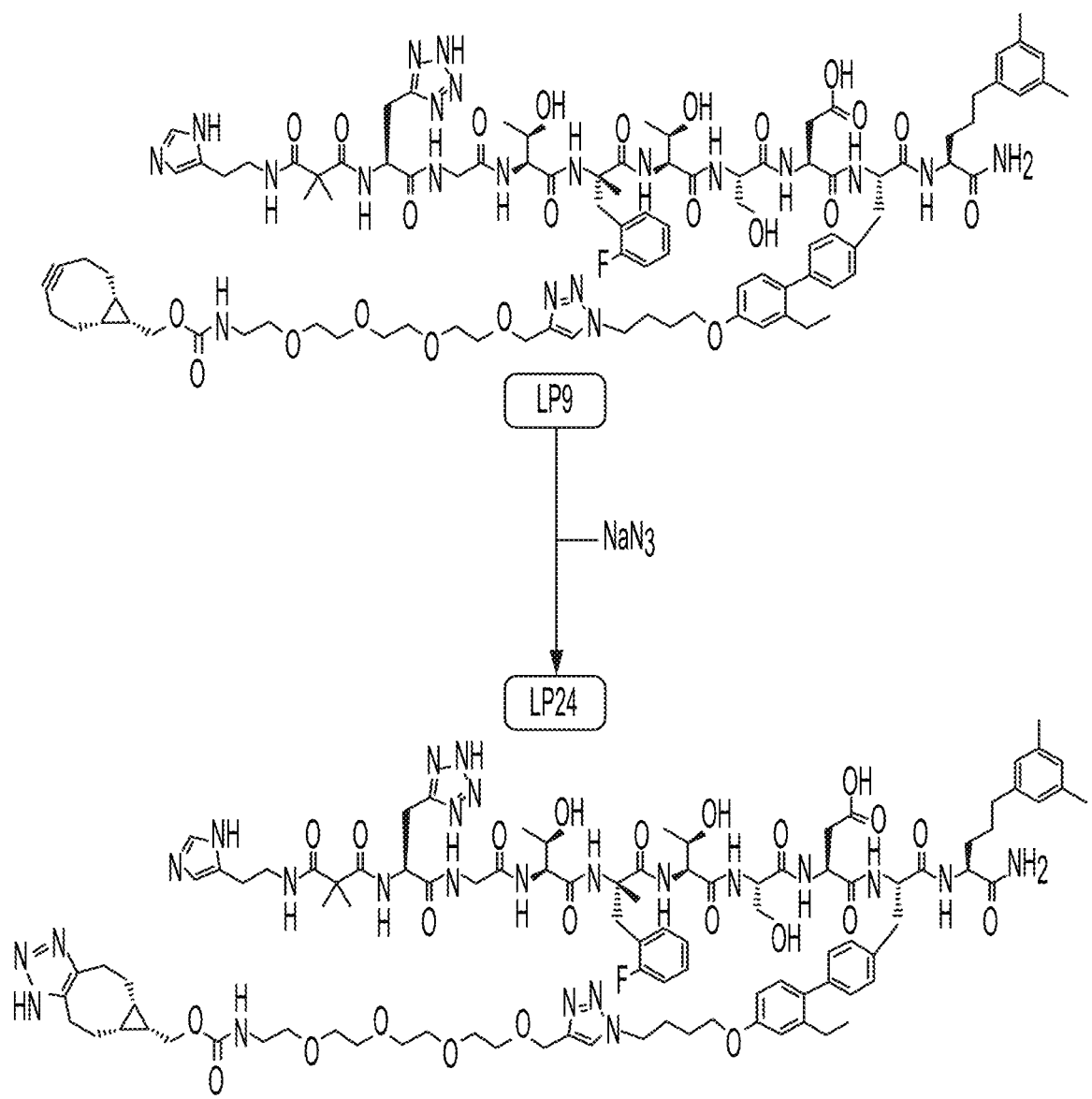
FIG. 38 shows a synthetic route for preparation of Linker-Payload LP24 according to the disclosure.

FIG. 38 depicts synthesis of linker-payload LP24 according to the disclosure.

5.24 Preparation of (3S)-4-[[(1S)-2-[[(1S)-1-carbamoyl-4-(3,5-dimethylphenyl)butyl]amino]-1-[[4-[2-ethyl-4-[4-[2-[2-[2-[2-[[(68S,69R,71S)-106, 107,108-triazatricyclododeca-72(107),106(108)-dien-71-yl]methoxycarbonylamino]ethoxy]ethoxy] ethoxy]ethoxymethyl]triazol-120-yl]butoxy]-61-phenyl]phenyl]methyl]-2-oxoethyl]amino]-3-[[(2S)-2-[[(28,3R)-2-[[3-(2-fluorophenyl)-2-[[(28,3R)-3-hydroxy-2-[[2-[[(2S)-2-[[3-[2-(1H-imidazol-5-yl) ethylamino]-2,2-dimethyl-3-oxo-propanoyl]amino]-3-(2H-tetrazol-5-yl)propanoyl]amino]acetyl]amino] butanoyl]amino]-2-methyl-propanoyl]amino]-3-hydroxy-butanoyl]amino]-3-hydroxy-propanoyl] amino]-4-oxo-butanoic acid (LP24)

A mixture of LP9 (1.13 mg, 0.571 μmol, 1 eq.) and NaN$_3$ (44.54 μg, 0.685 μmol, 1.2 eq.) in DMSO (0.1 mL) was stirred at 37° C. for 16 h. LCMS showed the reaction was complete. The crude product LP24 (1.15 mg, 0.569 μmol, 100.00% yield) was sent for the bio-assay directly without any further purification.

LCMS: (ESI): RT=3.561 min, m/z calcd. for $C_{97}H_{135}FN_{24}O_{23}$, 1011.51 [M+2H]$^{2+}$, found 1012.0 [M+2H]$^{2+}$; Reverse phase LC-MS was carried out using method B.

Figure 39:
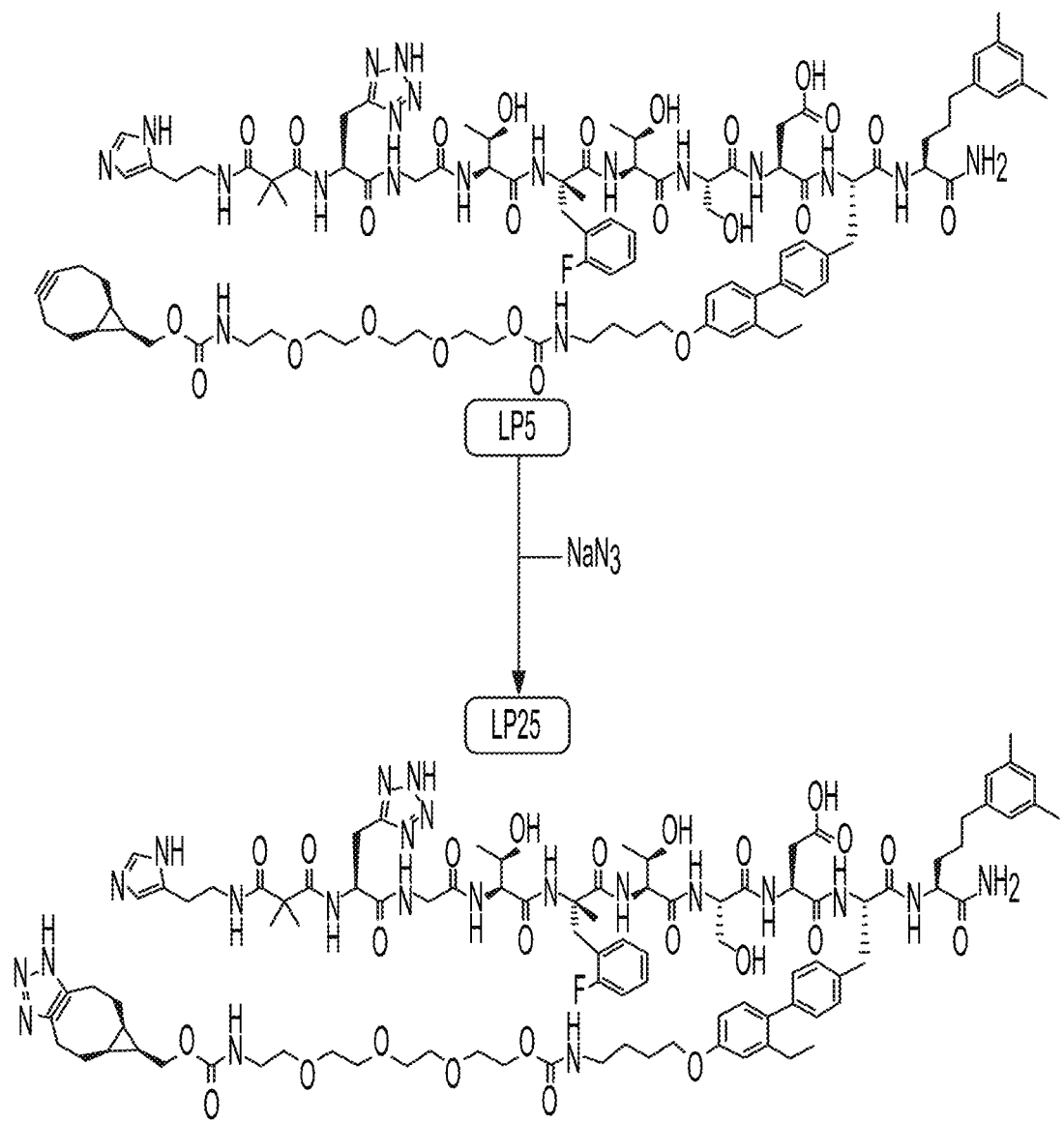
FIG. 39 shows a synthetic route for preparation of Linker-Payload LP25 according to the disclosure.

FIG. 39 depicts synthetic route of GLP-1R agonist Linker-payloads (LP25)

5.25 Preparation of (3S)-4-[[(1S)-2-[[(1S)-1-carbamoyl-4-(3,5-dimethylphenyl)butyl]amino]-1-[[4-[2-ethyl-4-[4-[2-[2-[2-[2-[[(65R,66S,68R)-102,103, 104-triazatricyclododeca-69(103),102(104)-dien-68-yl]methoxycarbonylamino]ethoxy]ethoxy]ethoxy] ethoxycarbonylamino]butoxy]-59-phenyl]phenyl] methyl]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methylpropanoyl]amino]-3-hydroxy-butanoyl] amino]-3-hydroxy-propanoyl]amino]-4-oxo-butanoic acid (LP25)

A mixture of LP5 (1.12 mg, 0.577 μmol, 1 eq.) and NaN$_3$ (45.01 μg, 0.692 μmol, 1.2 eq.) in DMSO (0.1 mL) was stirred at 37° C. for 16h. LCMS showed the reaction was complete. The crude product LP25 (1.14 mg, 4.42e-1 μmol, 76.68% yield, 77% purity) was sent for the bio-assay directly without any further purification.

LCMS: (ESI): RT=3.571 min, m/z calcd. for $C_{105}H_{134}FN_{27}O_{25}$, 992.49 [M+2H]$^{2+}$, found 993.0 [M+2H]$^{2+}$; Reverse phase LC-MS was carried out using method B.

Figure 40:
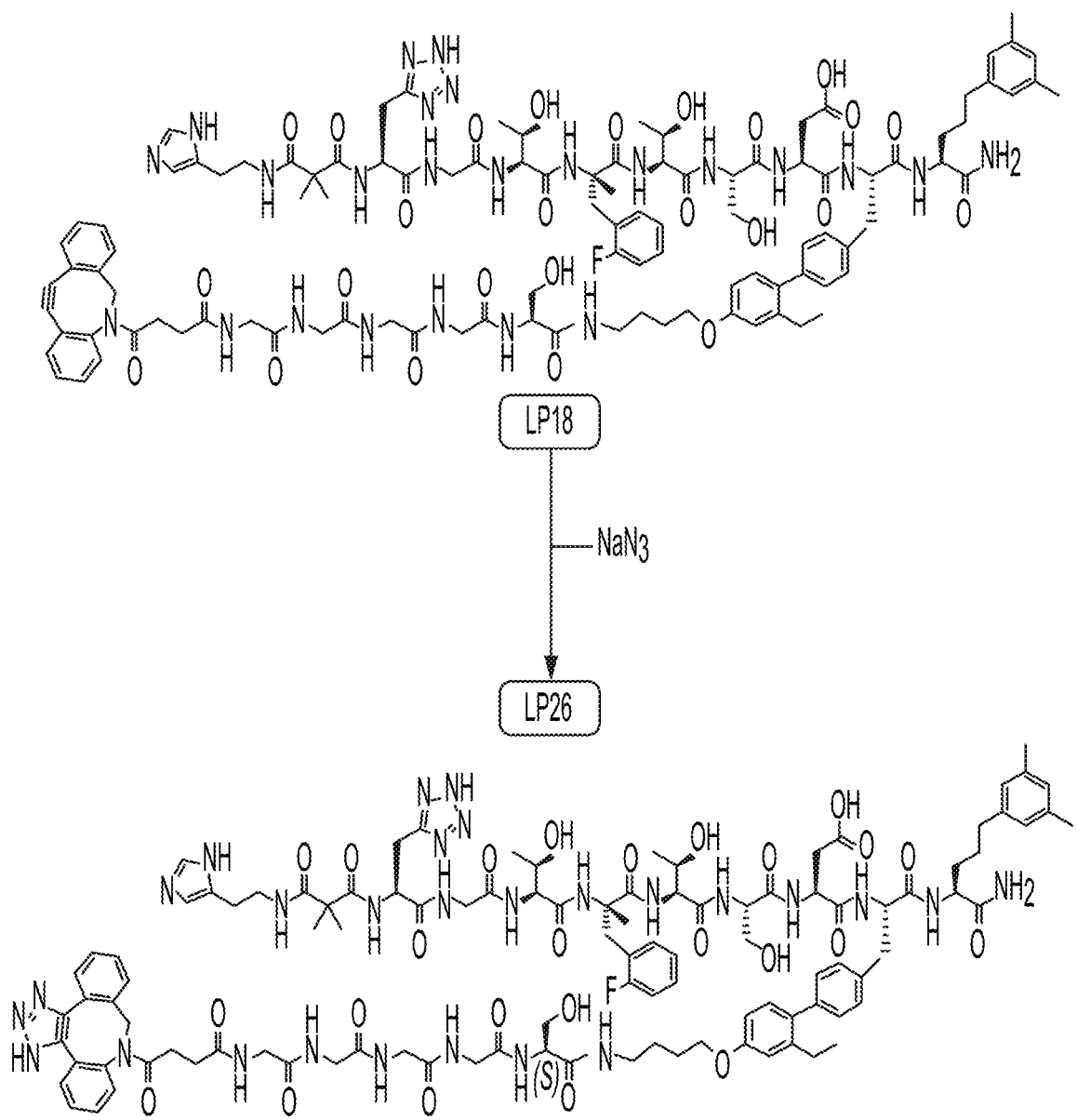
FIG. 40 shows a synthetic route for preparation of Linker-Payload LP26 according to the disclosure.

FIG. 40 depicts synthetic route of GLP-1R agonist Linker-payloads (LP26)

5.26 Preparation of (3S)-4-[[(1S)-2-[[(1S)-1-carbamoyl-4-(3,5-dimethylphenyl)butyl]amino]-1-[[4-[2-ethyl-4-[4-[[(2S)-3-hydroxy-2-[[2-[[2-[[2-[[4-oxo-4-(112,113,114,131-tetrazatetracyclononadeca-8 (14),10(16),11(17),12(18),61(64),65,73(113),112 (114)-octaen-131-yl)butanoyl]amino]acetyl]amino] acetyl]amino]acetyl]amino]acetyl]amino]propanoyl] amino]butoxy]-63-phenyl]phenyl]methyl]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP26)

A mixture of LP18 (1 mg, 4.65e-1 μmol, 1 eq.) and NaN$_3$ (36.31 μg, 0.559 μmol, 1.2 eq.) in DMSO (0.1 mL) was stirred at 37° C. for 16h. LCMS showed the reaction was complete. The crude product LP26 (1.02 mg, 0.465 μmol, 100.00% yield) was sent for the bio-assay directly without any further purification.

LCMS: (ESI): RT=3.259 min, m/z calcd. for $C_{105}H_{134}FN_{27}O_{25}$, 1096.0, found 1096.7 [M+2H]$^{2+}$; Reverse phase LC-MS was carried out using method F.

Figure 41:
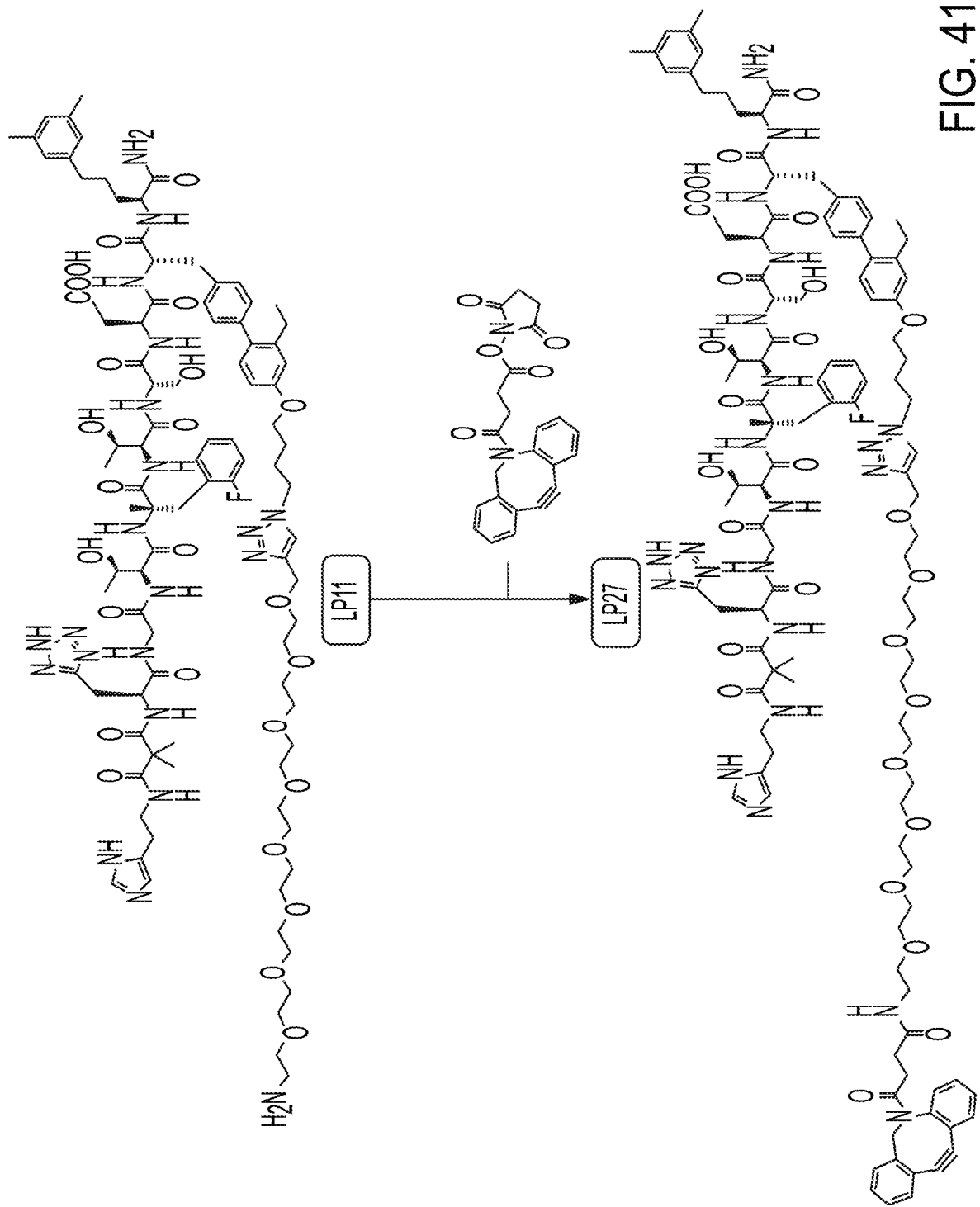
FIG. 41 shows a synthetic route for preparation of Linker-Payloads LP27 and LP28 according to the disclosure.
Figure 41:
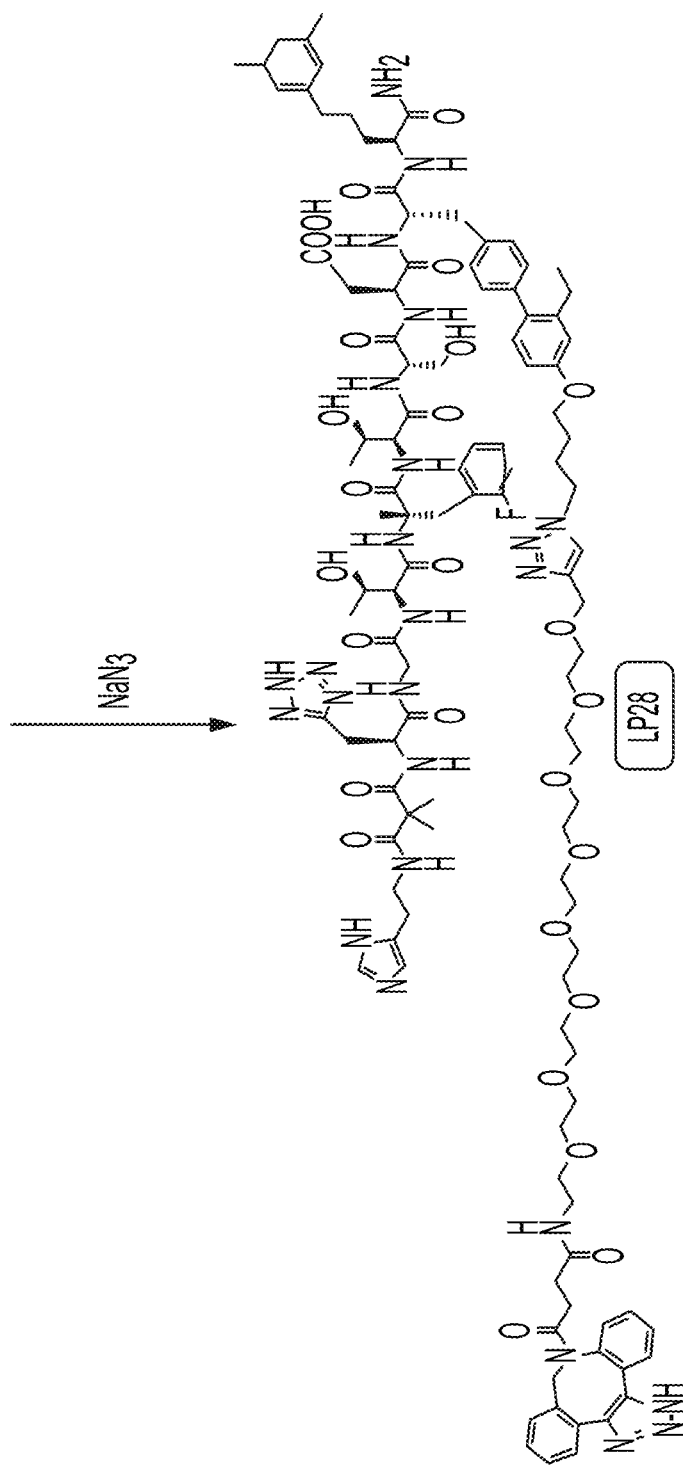

FIG. 41 depicts synthetic route of GLP-1R agonist Linker-payloads (LP27 and LP28)

5.27 Preparation of (3S)-4-[[(1S)-1-[[4-[4-[4-[4-[2-[2-[2-[2-[2-[2-[2-[2-[[4-(2-azatricyclo[10.4.0.04,91 hexadeca-1(12),4(9),5,7,13,15-hexaen-10-yn-2-yl)-4-oxo-butanoyl]amino]ethoxy]ethoxy] ethoxy] ethoxy]ethoxy]ethoxy]ethoxy]ethoxymethyl]triazol-1-yl]butoxy]-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP27)

To a solution of LP11 (70 mg, 35.37 µmol, 1 eq) and DIBAC-suc-OSu (19.92 mg, 49.51 µmol, 1.4 eq) in DMF (0.5 mL) was added DIPEA (9.14 mg, 70.74 µmol, 12.32 µL, 2 eq). The mixture was stirred at 25° C. for 1 hr. LCMS showed the reaction was converted completely and the desired product was observed. The solution was filtered and purified by prep-HPLC (neutral condition. column: Phenomenex Gemini-NX 80*30 mm*3 µm; mobile phase: [water (10 mM NH4HCO3)-ACN];B %: 25%-55%,9 min). The desired fluent was lyophilized in freeze dryer to give LP27 (24.87 mg, 10.56 µmol, 29.86% yield, 96.235% purity) as a white solid.

LCMS (ESI): RT=2.316 min, m/z calcd. for $C_{113}H_{150}FN_{22}O_{27}$ 2266.09 [M+H]$^+$, 756.03 [M+3H]$^{3+}$, found 756.3 [M+3H]$^{3+}$, LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

HPLC: RT=9.17 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 µm.

5.28 Preparation of (3S)-4-[[(1S)-2-[[(1S)-1-carbamoyl-4-(3,5-dimethylphenyl)butyl]amino]-1-[[4-[2-ethyl-4-[4-[2-[2-[2-[2-[2-[2-[2-[[4-oxo-4-(3,4,5,13-tetrazatetracyclo[13.4.0.02,6.07,121nonadeca-1(15),2(6),3,7(12),8,10,16,18-octaen-13-yl) butanoyl]amino]ethoxy] ethoxy]ethoxy] ethoxy]ethoxy] ethoxy]ethoxy]ethoxymethyl]triazol-1-yl]butoxy]phenyl]phenyl]methyl]-2-oxo-ethyl] amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl] amino]acetyl]amino]butanoyl]amino]-2-methyl-propanoyl]amino]-3-hydroxy-butanoyl]amino]-3-hydroxy-propanoyl]amino]-4-oxo-butanoic acid (LP28)

To a solution of LP27 (3 mg, 1.32 µmol, 1 eq) in DMSO (0.5 mL) was added NaN3 (258.14 µg, 3.97 µmol, 3 eq). The mixture was stirred at 25° C. for 1 hr. LC-MS showed LP27 was consumed completely and one main peak with desired mass was detected. The reaction was added NH4Cl solution (5 mL). The aqueous layer was separated and extracted with EtOAc (5 mL*2). The organic layers were combined and washed with water/brine=1/1 (400 mL*2), dried over anhydrous Na2SO4, filtered and concentrated in vacuum to give product as brown oil. The residue was purified by prep-HPLC (TFA condition; column: Waters Xbridge BEH C18 100*25 mm*5 µm; mobile phase: [water(0.075% TFA)-ACN];B %: 15%-55%,16 min) to give LP28 (1.02 mg, 4.23e-1 µmol, 31.99% yield, 95.869% purity) was obtained as a white solid.

LCMS (ESI): RT=3.512 min, m/z calcd. for $C_{113}H_{151}FN_{25}O_{27}$ 2309.11 [M+H]$^+$, $C_{113}H_{152}FN_{25}O_{27}$ 1155.56 [M+2H]$^{2+}$, found 1155.5 [M+2H]$^{2+}$. LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

HPLC: RT=4.024 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 µm.

Figure 42:
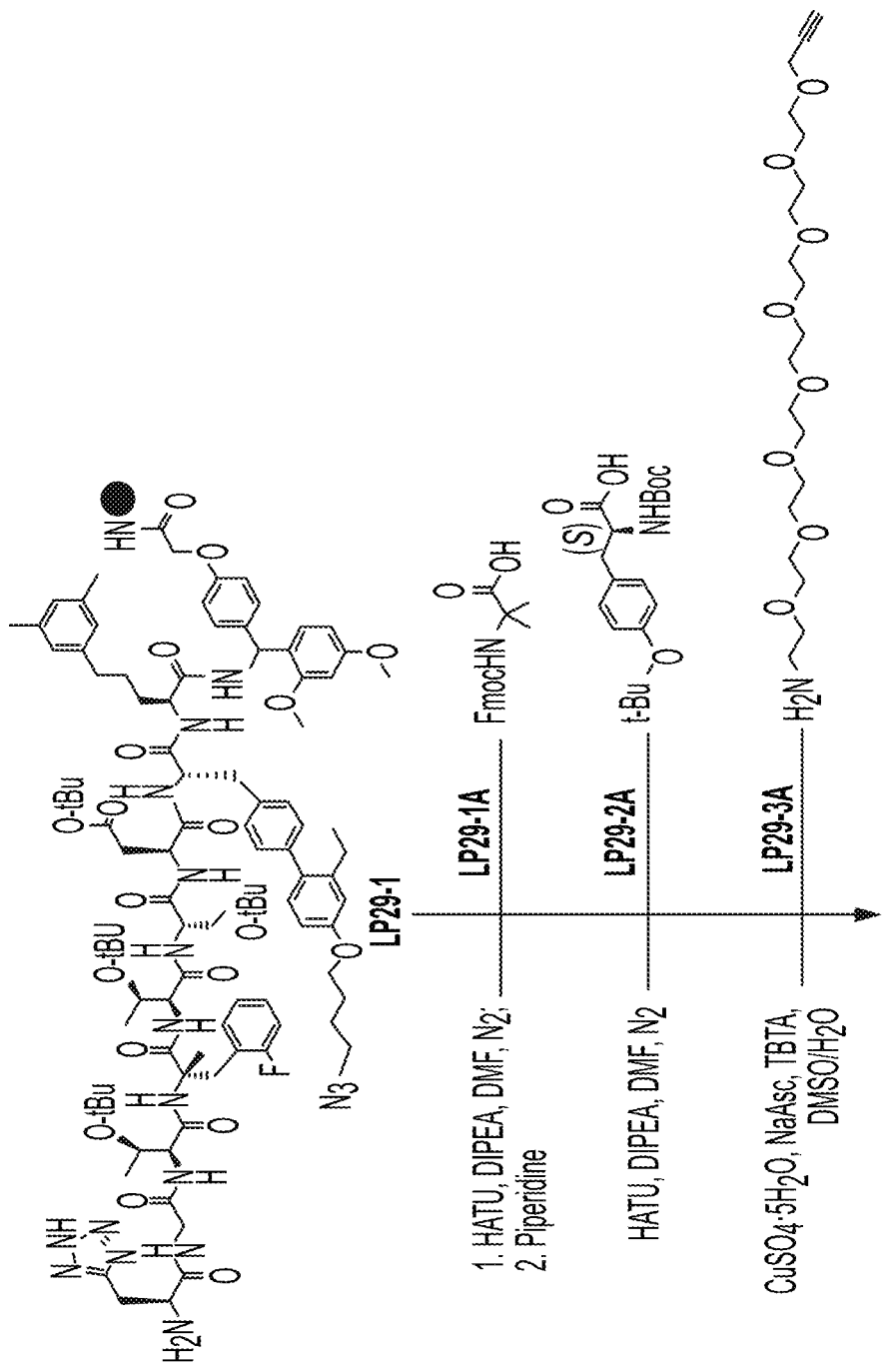
FIG. 42 shows a synthetic route for preparation of Linker-Payload LP29 according to the disclosure.
Figure 42:
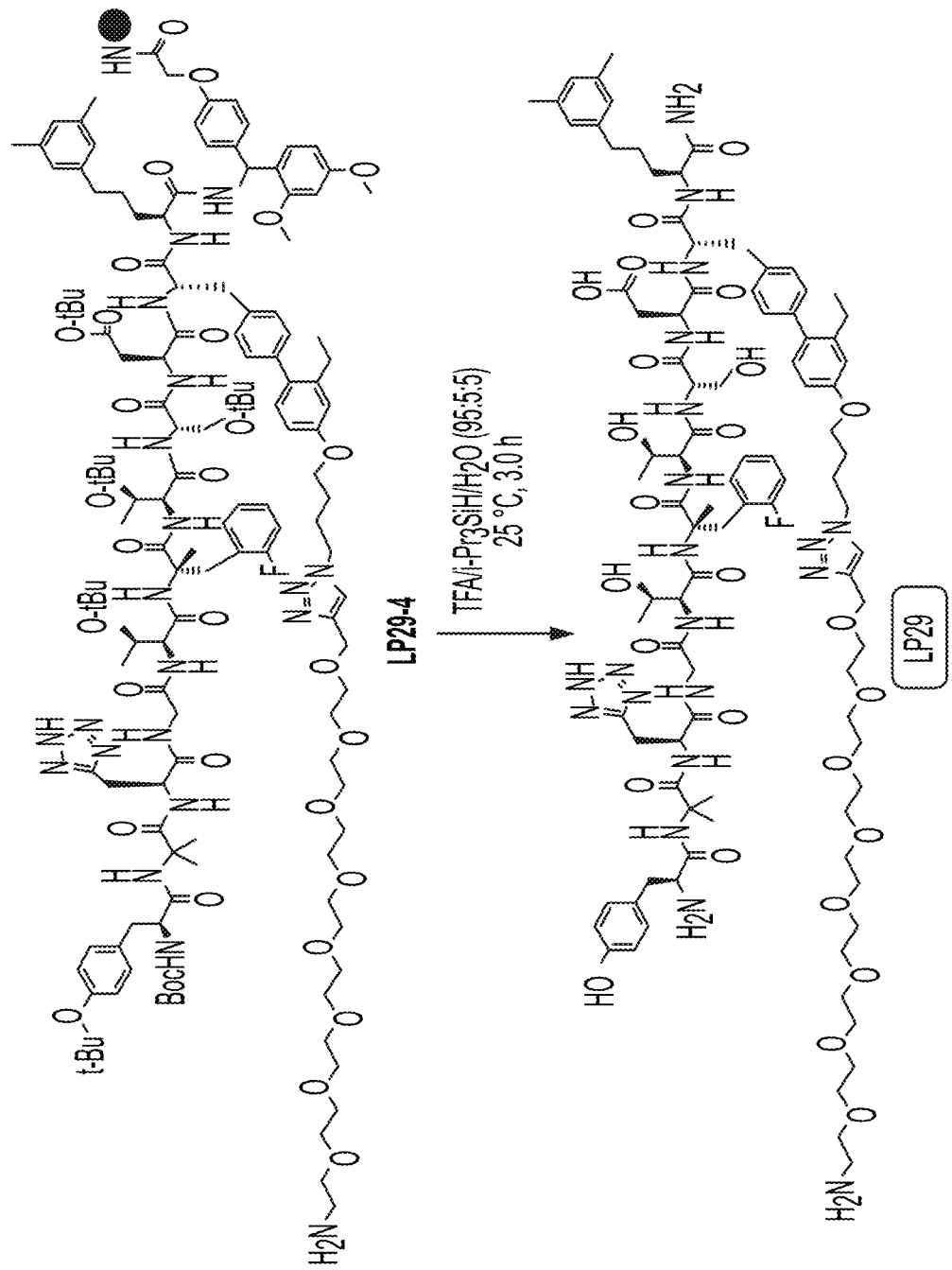

FIG. 42 depicts synthetic route of GLP-1R agonist Linker-payloads (LP29)

Step 1: Preparation of tert-butyl (3S)-4-[[(1S)-2-[[(1S)-1-[[[4-(2-amino-2-oxo-ethoxy)phenyl]-(2,4-dimethoxyphenyl)methyl]carbamoyl]-4-(3,5-dimethylphenyl)butyl]amino]-1-[[4-[4-(4-azidobutoxy)-2-ethyl-phenyl]phenyl]methyl]-2-oxo-ethyl]amino]-3-[[(2S)-3-tert-butoxy-2-[[(2S,3R)-3-tert-butoxy-2-[[(2S)-2-[[(2S,3R)-3-tert-butoxy-2-[[2-[[(2S)-2-[[2-(9H-fluoren-9-ylmethoxycarbonylamino)-2-methyl-propanoyl]amino]-3-(2H-tetrazol-5-yl)propanoyl] amino]acetyl]amino]butanoyl]amino]-3-(2-fluorophenyl)-2-methyl-propanoyl]amino]butanoyl] amino]propanoyl]amino]-4-oxo-butanoate (LP29-2)

To a solution of LP29-1A (86.20 mg, 264.94 µmol, 1 eq) in DMF (10 mL) was added HATU (181.33 mg, 476.89 µmol, 1.8 eq) and DIPEA (136.96 mg, 1.06 mmol, 184.59 µL, 4 eq) at 25° C. over 10 min. Then the solution was added into LP29-1 (1 g, 264.94 µmol, 50% purity, 1 eq), and the mixture was bubbled with N2 at 20° C. for 2 h. After completion, the mixture was filtered, and the collected resin was washed with DMF (30 mL*3), DCM (30 mL*3) to give the crude product on solid phase, which was swelled in 20% piperidine/DMF (10 mL), and the mixture was bubbled with N2 at 25° C. for 2 hr. After completion, the mixture was filtered, and the collected resin was washed with DMF (100 mL*3), DCM (100 mL*3) to give the crude product bound on resin LP29-2 (264.94 µmol, crude) as a white solid.

LCMS (ESI): RT=3.923 min, m/z calcd. for $C_{102}H_{141}FN_{19}O_{20}$ 1448.70, found 1450.40 [M−4*tBu-$C_{17}H_{17}NO_4$+7H]$^+$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

Step 2: Synthesis of tert-butyl (3S)-4-[[(1S)-2-[[(1S)-1-[[[4-(2-amino-2-oxo-ethoxy)phenyl]-(2,4-dimethoxyphenyl)methyl]carbamoyl]-4-(3,5-dimethylphenyl)butyl]amino]-1-[[4-[4-(4-azidobutoxy)-2-ethyl-phenyl]phenyl]methyl]-2-oxo-ethyl]amino]-3-[[(2S)-3-tert-butoxy-2-[[(2S,3R)-3-tert-butoxy-2-[[(2S)-2-[[(2S,3R)-3-tert-butoxy-2-[[2-[[(2S)-2-[[2-[[(2S)-2-(tert- butoxycarbonylamino)-3-(4-tert-butoxyphenyl)propanoyl]amino]-2-methyl-propanoyl]amino]-3-(2H-tetrazol-5-yl)propanoyl]amino]acetyl]amino]butanoyl]amino]-3-(2-fluorophenyl)-2-methyl-propanoyl]amino]butanoyl]amino]propanoyl]amino]-4-oxo-butanoate (LP29-3)

To a solution of LP29-2A (222.39 mg, 659.12 µmol, 5 eq) in DMF (5 mL) was added HATU (90.22 mg, 237.28 µmol, 1.8 eq) and DIPEA (68.15 mg, 527.30 µmol, 91.85 µL, 4 eq) at 25° over 10 min. Then the solution was added into LP29-2 (131.82 µmol, 1 eq), and the mixture was bubbled with $N_2$ at 25° C. for 1 h. After completion, the mixture was filtered, and the collected resin was washed with DMF (50 mL*3), DCM (50 mL*3) to give the crude product bound on resin LP29-3 (131.82 µmol, crude) as a yellow solid.

LCMS (ESI): RT=3.990 min, m/z calcd. for $C_{78}H_{102}FN_{19}O_{18}$ 806.88, found 807.3 [M−5tBu-Boc-$C_{17}H_{17}NO_4$]$^{2+}$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

Step 3: Synthesis of tert-butyl (3S)-4-[[(1S)-1-[[4-[4-[4-[4-[2-[2-[2-[2-[2-[2-(2-aminoethoxy)ethoxy]ethoxy]ethoxy]ethoxy]ethoxy]ethoxymethyl]triazol-1-yl]butoxy]-2-ethyl-phenyl]phenyl]methyl]-2-[[(1S)-1-[[[4-(2-amino-2-oxo-ethoxy)phenyl]-(2,4-dimethoxyphenyl)methyl]carbamoyl]-4-(3,5-dimethylphenyl)butyl]amino]-2-oxo-ethyl]amino]-3-[[(2S)-3-tert-butoxy-2-[[(2S,3R)-3-tert-butoxy-2-[[(2S)-2-[[(2S,3R)-3-tert-butoxy-2-[[2-[[(2S)-2-[[2- [[(2S)-2-(tert-butoxycarbonylamino)-3-(4-tert-butoxyphenyl)propanoyl]amino]-2-methyl-propanoyl]amino]-3-(2H-tetrazol-5-yl)propanoyl]amino]acetyl]amino]butanoyl]amino]-3-(2-fluorophenyl)-2-methyl-propanoyl]amino]butanoyl]amino]propanoyl]amino]-4-oxo-butanoate (LP29-4)

To a solution of LP29-3 (22.23 µmol, 1 eq) and LP29-3A (17.78 mg, 43.64 µmol, 2 eq) in DMF (5 mL) was added SODIUM ASCORBATE (21.61 mg, 109.09 µmol, 5 eq), TBTA (11.58 mg, 21.82 µmol, 1 eq) and CuI (20.78 mg, 109.09 µmol, 5 eq). The mixture was stirred at 25° C. for 2 hr. After completion, the mixture was filtered, and the collected resin was washed with DMF (50 mL*3), DCM (50 mL*3) to give the crude product bound on resin LP29-4 (22.23 µmol, crude) as a green solid.

LCMS (ESI): RT=3.085 min, m/z calcd. for $C_{97}H_{139}FN_{20}O_{26}$ 1010.51, found 1011.0 [M+2H]$^{2+}$, LC-MS Conditions: Mobile Phase: 1.5 ML/4L TFA in water (solvent A) and 0.75 ML/4L TFA in acetonitrile (solvent B), using the elution gradient 5%-95% (solvent B) over 0.7 minutes and holding at 95% for 0.4 minutes at a flow rate of 1.5 mL/min; Column: Agilent Pursult 5 C18 20*2.0 mm.

Step 4: Synthesis of (3S)-4-[[(1S)-1-[[4-[4-[4-[4-[2-[2-[2-[2-[2-[2-(2-aminoethoxy)ethoxy] ethoxy]ethoxy]ethoxy]ethoxy]ethoxymethyl]triazo-1-yl]butoxy]-2-ethyl-phenyl]phenyl]methyl]-2-[[(1S)-1-carbamoyl-4-(3,5-dimethylphenyl)butyl] amino]-2-oxo-ethyl]amino]-3-[[(2S)-2-[[(2S,3R)-2-[[(2S)-2-[[(2S,3R)-2-[[f2-[[(2S)-2-[[f2-[[(2S)-2-amino-3-(4-hyd roxyphenyl) propanoyl]amino]-2-methyl-propanoyl]amino]-3-(2H-tetrazol-5-yl) propanoyl]amino]acetyl]amino]-3-hydroxy-butanoyl]amino]-3-(2-fluorophenyl)-2-methyl-propanoyl]amino]-3-hydroxy-butanoyl]amino]-3-hydroxy-propanoyl]amino]-4-oxo-butanoic acid (LP29)

The resin bound compound LP29-4 (22.23 µmol, 1 eq) was subjected to acidic cleavage by using a TFA cocktail (TFA/TIPS/$H_2O$=95:2.5:2.5, 10 mL), the mixture was shaken at 25° C. for 2 hours. The mixture was filtered and the filtrate was diluted with t-BuOMe (100 mL) at 0° C. to give a precipitate, which was centrifuged (5000 R) for 10 min. The residue was purified by prep-HPLC (column: Boston Green ODS 150*30 mm*5 µm;mobile phase: [water (0.1% TFA)-ACN];B %: 17%-57%,9 min) to give the product LP29 (7.55 mg, 3.69 µmol, 16.58% yield, 98.63% purity) as a white solid.

LCMS (ESI): RT=3.133 min, m/z calcd. for $C_{97}H_{139}FN_{20}O_{26}$ 1010.51, found 1011.0 [M+2H]$^{2+}$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvents A).

HPLC: RT=3.77 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 µm.

Figure 43:
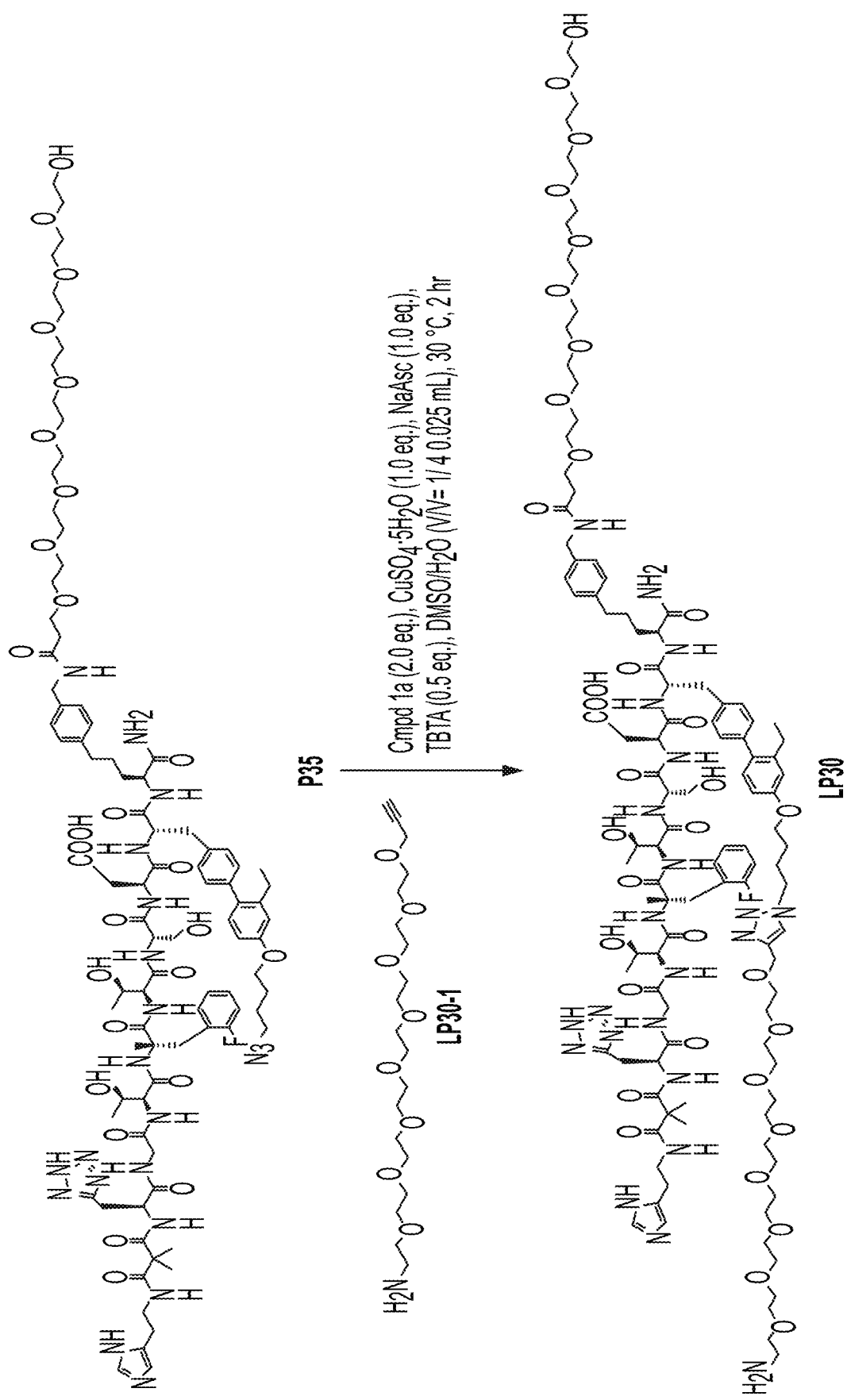
FIG. 43 shows a synthetic route for preparation of Linker-Payload LP30 according to the disclosure.

FIG. 43 depicts synthetic route of GLP-1R agonist Linker-payloads (LP30)

5.30 Preparation of (8S,14S,17S,20S,23S,26S)-8-((2H-tetrazol-5-yl)methyl)-26-(((S)-3-(4'-(4-(4-(25-amino-2,5,8,11,14,17,20,23-octaoxapentacosyl)-1H-1,2,3-triazol-1-yl)butoxy)-2'-ethyl-[1,1'-biphenyl]-4-yl)-1-(((S)-1-amino-5-(4-(23-hydroxy-3-oxo-6,9,12,15,18,21-hexaoxa-2-azatricosyl) phenyl)-1-oxopentan-2-yl)amino)-1-oxopropan-2-yl) carbamoyl)-17-(2-fluorobenzyl)-14,20-bis((R)-1-hydroxyethyl)-23-(hydroxymethyl)-1-(1H-imidazol-5-yl)-5,5,17-trimethyl-4,6,9,12,15,18,21,24-octaoxo-3,7,10,13,16,19,22,25-octaazaoctacosan-28-oic acid (LP30)

To a solution of P35 (15 mg, 7.51 µmol, 1 eq.) in $H_2O$ (0.09 mL) was added a solution of $CuSO_4.5H_2O$ (1.88 mg, 7.51 µmol, 1.0 eq.), sodium;(2R)-2-[(1S)-1,2-dihydroxyethyl]-4-hydroxy-5-oxo-2H-furan-3-olate (1.49 mg, 7.51 µmol, 1.0 eq.) in DMSO (0.03 mL), and followed by TBTA (1.99 mg, 3.76 µmol, 0.5 eq.) in $H_2O$ (0.03 mL) and a solution of LP30-1 (6.12 mg, 15.02 µmol, 2.0 eq.) in DMSO (0.03 mL). The mixture was stirred at 30° C. for 2.5 hr. LCMS showed the desired MS was detected. The reaction mixture was purified by prep-HPLC (column: Waters X bridge BEH C18 100*25 mm*5 µm; mobile phase: [water (0.1% TFA)-ACN]; B %: 5%-42.5%, 12 min) to afford LP30 (2 mg, 8.15e-1 μmol, 10.85% yield, 98% purity) as a white solid.

LCMS (ESI): RT=2.628 min, mass calcd. for $C_{112}H_{174}FN_{22}O_{35}$ 2406.23 $[M+H]^+$, 802.74 $[M+3H]^{3+}$, found 802.20 $[M+3H]^{3+}$. LC-MS Conditions: Mobile Phase: 1.5 ML/4L TFA in water (solvent A) and 0.75 ML/4L TFA in acetonitrile (solvent B), using the elution gradient 10%-80% (solvent B) over 6.0 minutes and holding at 80% for 0.5 minutes at a flow rate of 0.8 ml/min; Column: Xtimate3 μm, C18,2.1*30 mm. Wave length: UV 220 nm&254 nm; Column temperature: 50° C.

HPLC: RT=6.32 min, 98% purity. HPLC method A: Column: YMC-Pack ODS-A 150*4.6 mm, 5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Figure 44:
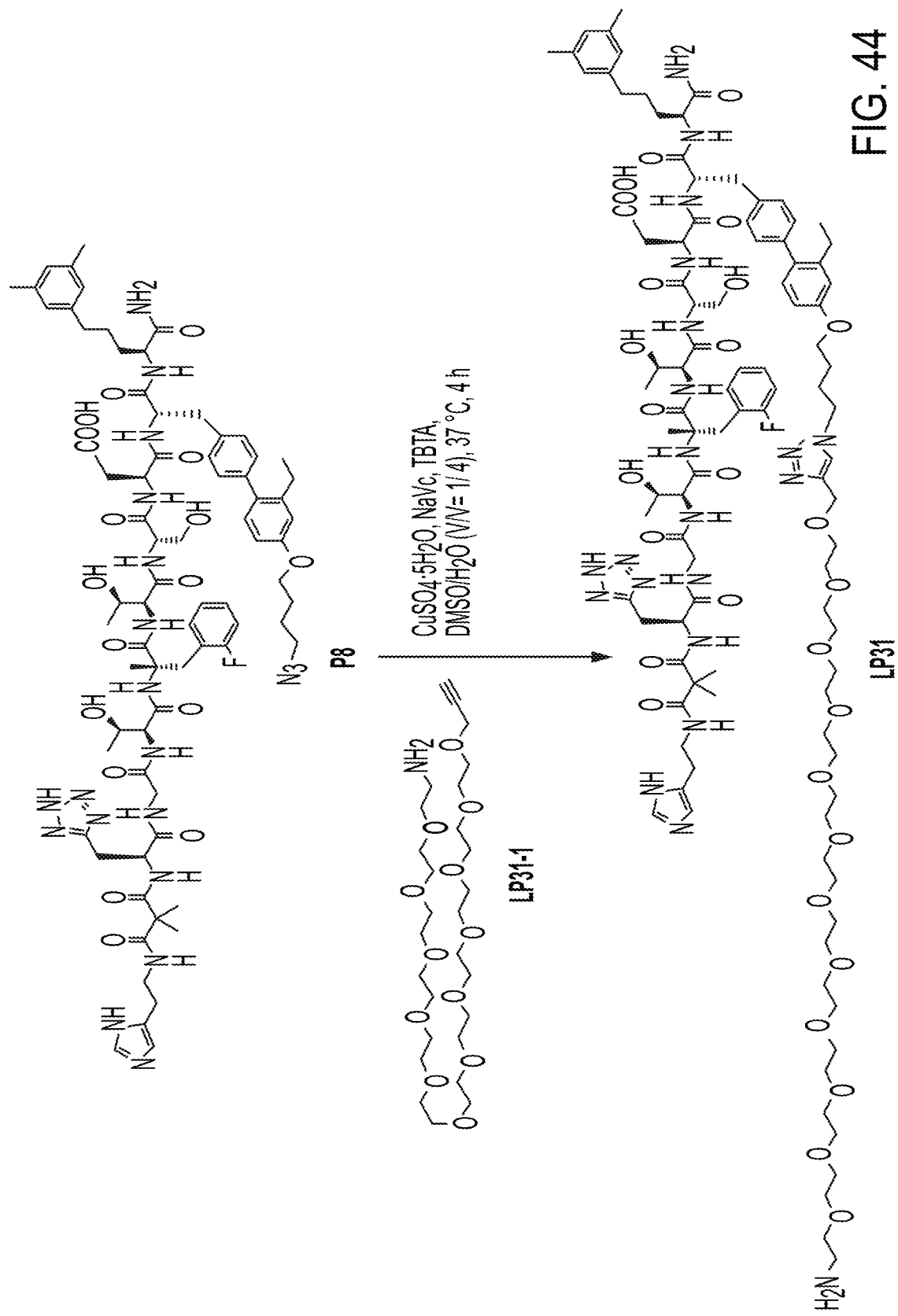
FIG. 44 shows a synthetic route for preparation of Linker-Payload LP31 according to the disclosure.

FIG. 44 depicts synthetic route of GLP-1R agonist Linker-payloads (LP31)

5.31 Preparation of (3S)-4-[[(1S)-1-[[4-[4-[4-[4-[2-[2-[2-[2-[2-[2-[2-[2-[2-[2-(2-aminoeth-oxy) ethoxy]ethoxy]ethoxy]ethoxy]ethoxy] ethoxy]ethoxy]ethoxy]ethoxy]ethoxymethyl]triazol-1-yl]butoxy]-2-ethyl-phenyl]phenyl]methyl]-2-[[(1S)-1-carbamoyl-4-(3,5-dimethylphenyl) butyl] amino]-2-oxo-ethyl]amino]-3-[[(2S)-2-[[(2S,3R)-2-[[f3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP31)

To a solution of P8 (40 mg, 25.45 μmol, 1 eq) and LP31-1 (29.71 mg, 50.90 μmol, 2 eq) in DMSO (0.1 mL) and H₂O (0.4 mL) was added TBTA (6.75 mg, 12.72 μmol, 0.5 eq), CuSO₄.5H₂O (6.35 mg, 25.45 μmol, 1 eq) and SODIUM ASCORBATE (5.04 mg, 25.45 μmol, 1 eq). The mixture was stirred at 37° C. for 4 hr. LC-MS showed the desired mass was detected. The green solution was filtered to give the crude product. The residue was purified by prep-HPLC (TFA condition. column: Welch Xtimate C18 100*40 mm*3 μm; mobile phase: [water (0.075% TFA)-ACN]; B %: 23%-53%, 10 min) to afford LP31 (batch 1: 11.59 mg, 5.21 μmol, 20.48% yield, 96.94% purity) and (batch 2: 11.13 mg, 4.95 μmol, 19.45% yield, 95.86% purity) as yellow gum.

Batch 1: LCMS (ESI): RT=3.160 min, m/z calcd. for $C_{102}H_{153}FN_{21}O_{29}$ 2155.10 $[M+H]^+$, $C_{102}H_{154}FN_{21}O_{29}$ 1078.05 $[M+2H]^{2+}$, found 1078.6 $[M+2H]^{2+}$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=7.48 min. HPLC Conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 μm.

Batch 2: LCMS (ESI): RT=3.147 min, m/z calcd. for $C_{102}H_{153}FN_{21}O_{29}$ 2155.10 $[M+H]^+$, $C_{102}H_{154}FN_{21}O_{29}$ 1078.05 $[M+2H]^{2+}$, found 1078.6 $[M+2H]^{2+}$. LC-MS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

HPLC: RT=7.48 min. HPLC Conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: YMC-Pack ODS-A 150*4.6 mm, 5 μm.

Figure 45:
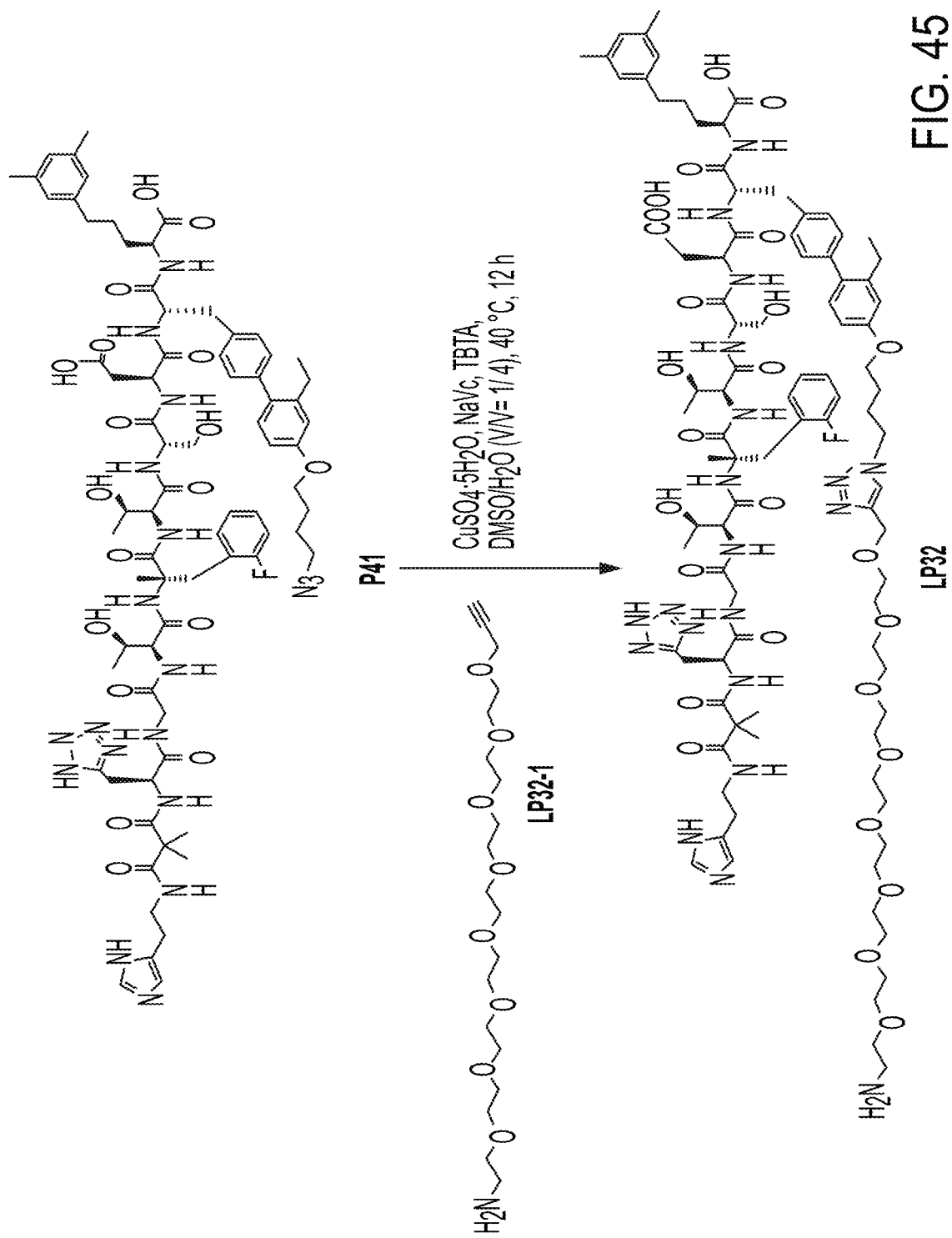
FIG. 45 shows a synthetic route for preparation of Linker-Payload LP32 according to the disclosure.

FIG. 45 depicts synthetic route of GLP-1R agonist Linker-payloads (LP32)

5.32 Preparation of (2S)-2-[[(2S)-3-[4-[4-[4-[2-[2-[2-[2-[2-[2-(2-aminoethoxy)ethoxy]ethoxy] ethoxy]ethoxy]ethoxy]ethoxy]ethoxymethyl]triazol-1-yl]butoxy]-2-ethyl-phenyl]phenyl]-2-[[(2S)-3-carboxy-2-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]propanoyl] amino]propanoyl]amino]-5-(3,5-dimethylphenyl) pentanoic acid (LP32)

To a solution of LP31-1 (35 mg, 22.25 μmol, 1 eq) in H₂O (1 mL) was added a solution of CuSO₄·5H₂O (5.56 mg, 22.25 μmol, 1 eq) and NaVc (4.41 mg, 22.25 μmol, 1 eq), a solution of TBTA (5.90 mg, 11.13 μmol, 0.5 eq) and a solution of P41 (18.14 mg, 44.51 μmol, 2 eq) in DMSO (0.25 mL). The mixture was stirred at 40° C. for 12 hr. The reaction mixture was diluted with H₂O (3 mL) and ACN (2 mL), then the mixture was filtered. The filtrate was purified by prep-HPLC (column: Welch Xtimate C18 100*40 mm*3 μm; mobile phase: [water (TFA)-ACN]; B %: 20%-60%,10 min) to give the LP31 (1 mg, 0.46 μmol, 10.11% yield, 91% purity).

LCMS (ESI): RT=2.910 min, m/z calcd. for C94H136FN20O26 991.05[M+H]⁺, found 990.9 [M+H]⁺.LC-MS method A: a MERCK, RP-18e 25-2 mm column, with a flow rate of 1.5 mL/min, eluting with a gradient of 10% to 80% acetonitrile containing 0.02% TFA (solvent B) and water containing 0.04% TFA (solvent A).

HPLC: RT=7.56 min; Mobile Phase: 2.75 ML/4L TFA in water (solvent A) and 2.5 ML/4L TFA in acetonitrile (solvent B), using the elution gradient 10%-80% (solvent B) over 10 minutes and holding at 100% for 5 minutes at a flow rate of 1.5 ml/min; Column: YMC-Pack ODS-A150*4.6 mm, 5 μm.

Figure 46:
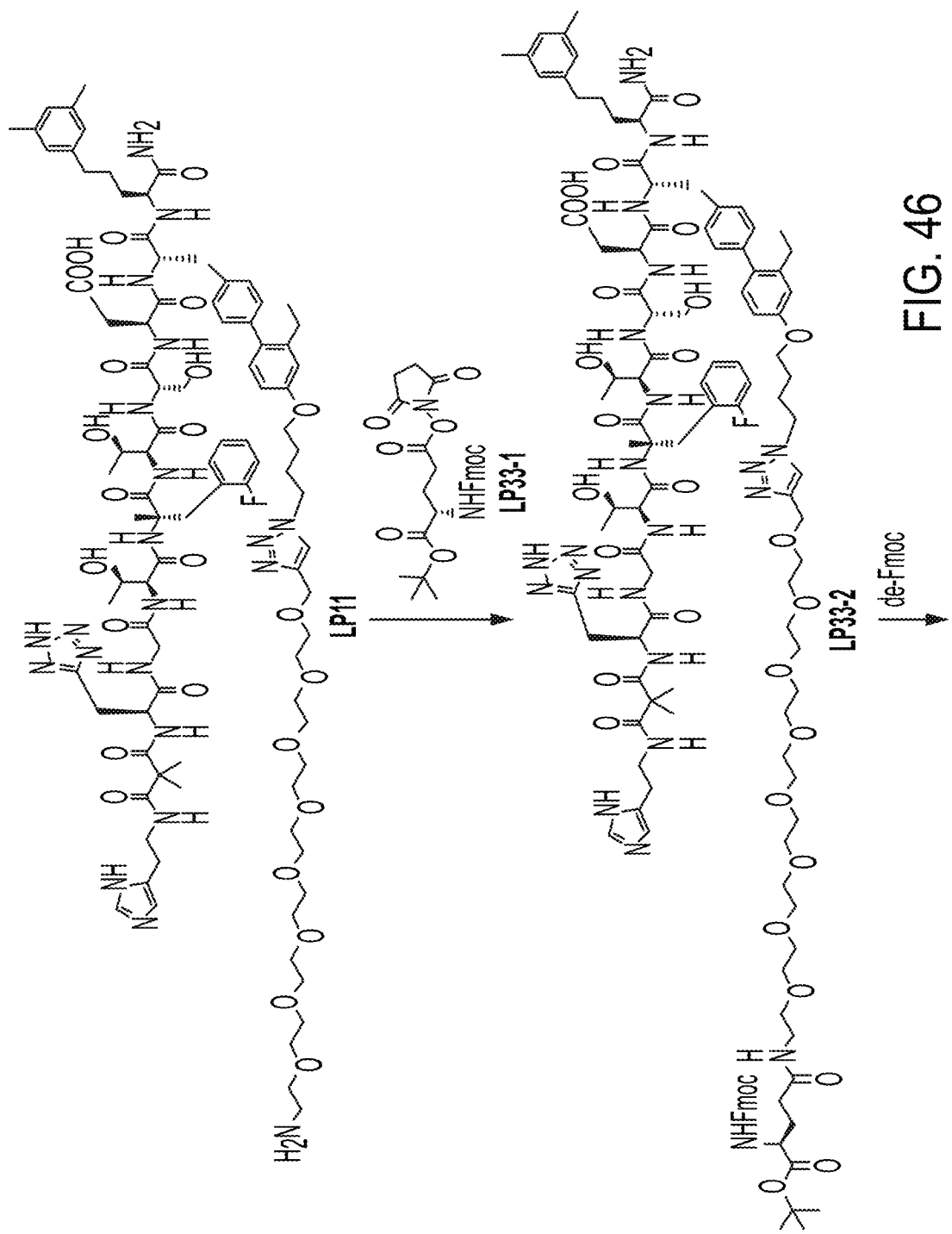
FIG. 46 shows a synthetic route for preparation of Linker-Payload LP33 according to the disclosure.
Figure 46:
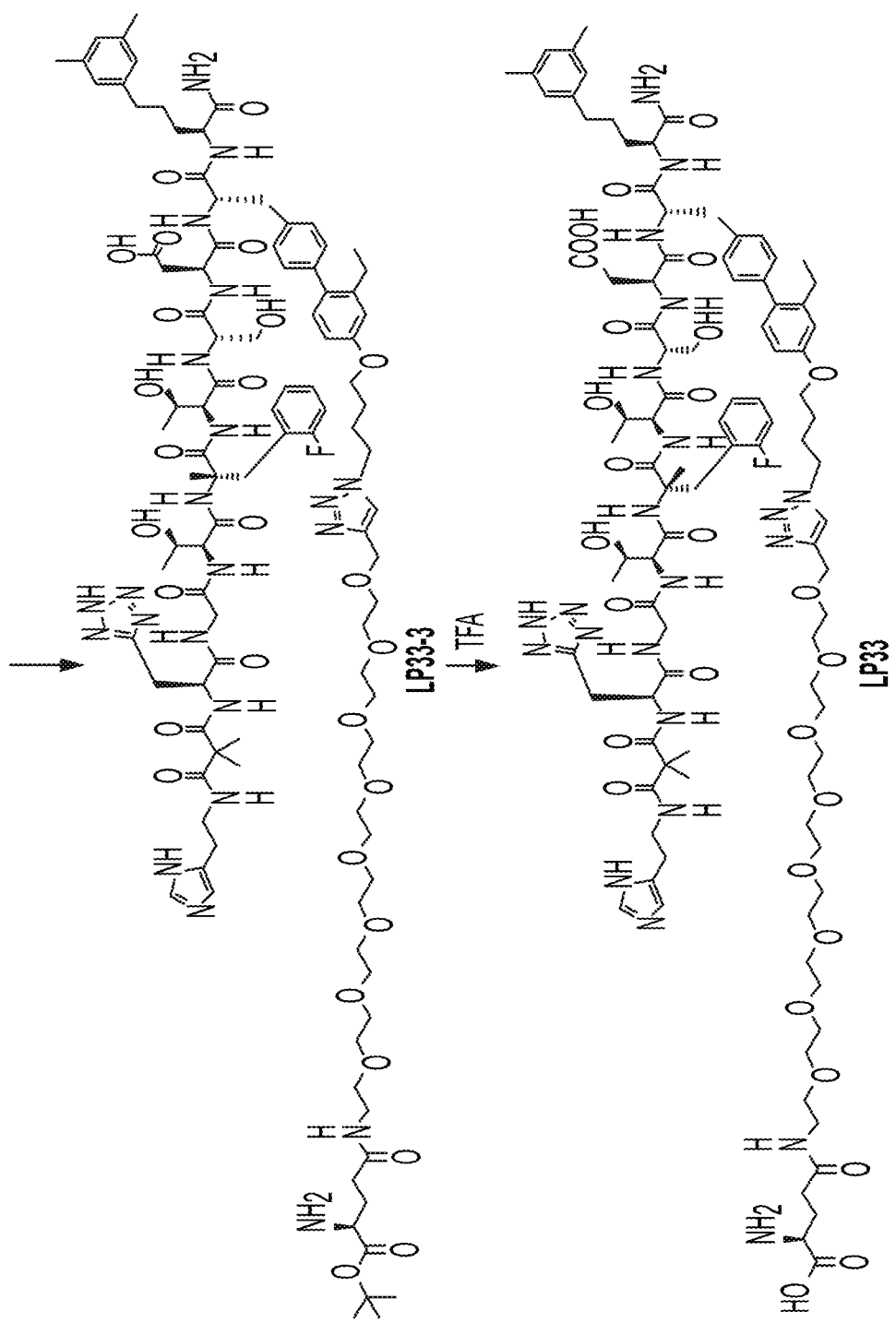

FIG. 46 depicts synthetic route of GLP-1R agonist Linker-payloads (LP33)

Step 1: Synthesis of (3S)-4-[[(1S)-1-[[4-[4-[4-[2-[2-[2-[2-[2-[2-[2-[[(4S)-5-tert-butoxy-4-(9H-fluoren-9-ylmethoxycarbonylamino)-5-oxo-pentanoyl] amino]ethoxy]ethoxy]ethoxy]ethoxy]ethoxy]ethoxy] ethoxy]ethoxymethyl]triazol-1-yl]butoxy]-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl] amino]-3-(2H-tetrazol-5-yl)propanoyl]amino]acetyl] amino]butanoyl]amino]-2-methyl-propanoyl]amino]-3-hydroxy-butanoyl]amino]-3-hydroxy-propanoyl] amino]-4-oxo-butanoic acid (LP33-2)

To a solution of LP11 (10 mg, 5.05 μmol, 1 eq.) and LP33-1 (2.9 mg, 5.5 μmol, 1 eq) in DMF (2 mL) was added DIPEA (1.96 mg, 15.16 μmol, 2.64 μl, 3 eq.). The mixture was stirred at 20° C. for 12 hr. LC-MS showed LP11 was consumed completely and one main peak with desired mass was detected. LCMS (ESI): RT=4.030 min, m/z calcd. for $C_{118}H_{163}O_{30}N_{22}F$ 796.6[M+3H]$^{3+}$, found 796.5. Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min; Column: Xtimate C18 2.1*30 mm, 3 μm; Wavelength: UV 220 nm, 254 nm; Column temperature: 50° C.; MS ionization: ESI. The reaction was purified by prep-HPLC (column: 0-phenomenex clarity RP 150*10 mm*5 μm; mobile phase: [water (0.075% TFA)-ACN]; B %: 20%-70%, 20 min) to give the product LP33-2 (8 mg, 3.12 μmol, 61.70% yield, 93% purity).

LCMS (ESI): RT=4.003 min, m/z calcd. for C118H163O30N22F 1194.17[M+2H]+/2, found 1194.3. Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min; Column: Xtimate C18 2.1*30 mm, 3 μm; Wavelength: UV 220 nm, 254 nm; Column temperature: 50° C.; MS ionization: ESI.

Step 2: (3S)-4-[[(1S)-1-[[4-[4-[4-[4-[2-[2-[2-[2-[2-[2-[2-[2-[[(4S)-4-amino- 5-tert-butoxy-5-oxopentanoyl]amino]ethoxy]ethoxy]ethoxy]ethoxy]ethoxy]ethoxy]ethoxymethyl]triazol-1-yl]butoxy]-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP33-3)

To a solution of LP32-2 (8 mg, 3.35 μmol, 1 eq.) in THF (0.5 mL) was added N-ethylethanamine (2.45 mg, 33.52 μmol, 3.45 μl, 10 eq.). The mixture was stirred at 20° C. for 3 hr. LC-MS showed LP32-3 was consumed completely and one main peak with desired mass was detected. LCMS (ESI): RT=3.070 min, m/z calcd. for $C_{118}H_{153}O_{28}N_{22}F$ 1082.5[M+2H]$^{2+}$, found 1082.9. Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min; Column: Xtimate C18 2.1*30 mm, 3 μm; Wavelength: UV 220 nm, 254 nm; Column temperature: 50° C.; MS ionization: ESI. The reaction mixture was concentrated under reduced pressure to give LP33-3 (7 mg, crude) as a colourless oil.

Step 3: (2S)-2-amino-5-[2-[2-[2-[2-[2-[2-[2-[2-[[1-[4-[4-[4-[(2S)-3-[[(1S)-1-carbamoyl-4-(3,5-dimethylphenyl)butyl]amino]-2-[[(2S)-3-carboxy-2-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]propanoyl]amino]-3-oxo-propyl]phenyl]-3-ethyl-phenoxy]butyl]triazol-4-yl]methoxy]ethoxy]ethoxy]ethoxy]ethoxy]ethoxy]ethoxy]ethylamino]-5-oxo-pentanoic acid (LP33)

To a solution of LP33-3 (7 mg, 3.23 μmol, 1 eq.) in DCM (0.5 mL) was added TFA (770.00 mg, 6.75 mmol, 500.00 μl, 2088.06 eq.). The mixture was stirred at 20° C. for 1 hr. LC-MS showed LP32-4 was consumed completely and one main peak with desired mass was detected. LCMS (ESI): RT=2.977 min, m/z calcd. for $C_{99}H_{145}O_{28}N_{22}F$ 1054.52[M+2H]$^{2+}$, found 1054.9. Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min; Column: Xtimate C18 2.1*30 mm, 3 μm; Wavelength: UV 220 nm, 254 nm; Column temperature: 50° C.; MS ionization: ESI. The reaction mixture was filtered to give a residue. The residue was purified by prep-HPLC (column: 0-phenomenex clarity RP 150*10 mm*5 μm; mobile phase: [water (0.075% TFA)-ACN]; B %: 15%-65%, 25 min) give the product LP33 (2.1 mg, 9.66e-1 μmol, 29.87% yield, 97% purity) as a white solid.

LCMS (ESI): RT=2.950 min, m/z calcd. for $C_{99}H_{145}O_{28}N_{22}F$ 1054.52[M+2H]$^{+}$/2, found 1054.9. Mobile Phase: 1.5 ML/4L TFA in water (solvent A) and 0.75 ML/4L TFA in acetonitrile (solvent B), using the elution gradient 10%-80% (solvent B) over 6 minutes and holding at 80% for 0.5 minutes at a flow rate of 0.8 ml/min; Column: Xtimate C18 2.1*30 mm, 3 μm; Wavelength: UV 220 nm, 254 nm; Column temperature: 50° C.; MS ionization: ESI.

UPLC RT=3.277 min Mobile Phase: 0.05% TFA in water (solvent A) and 0.05% TFA in acetonitrile (solvent B), using the elution gradient 5%-95% (solvent B) over 5 minutes, later holding at 95% for 3 minutes at a flow rate of 0.6 ml/minutes; Column: Waters ACQUITY UPLC HSS T3 1.8 μm, 2.1×100 mm.

Figure 47:
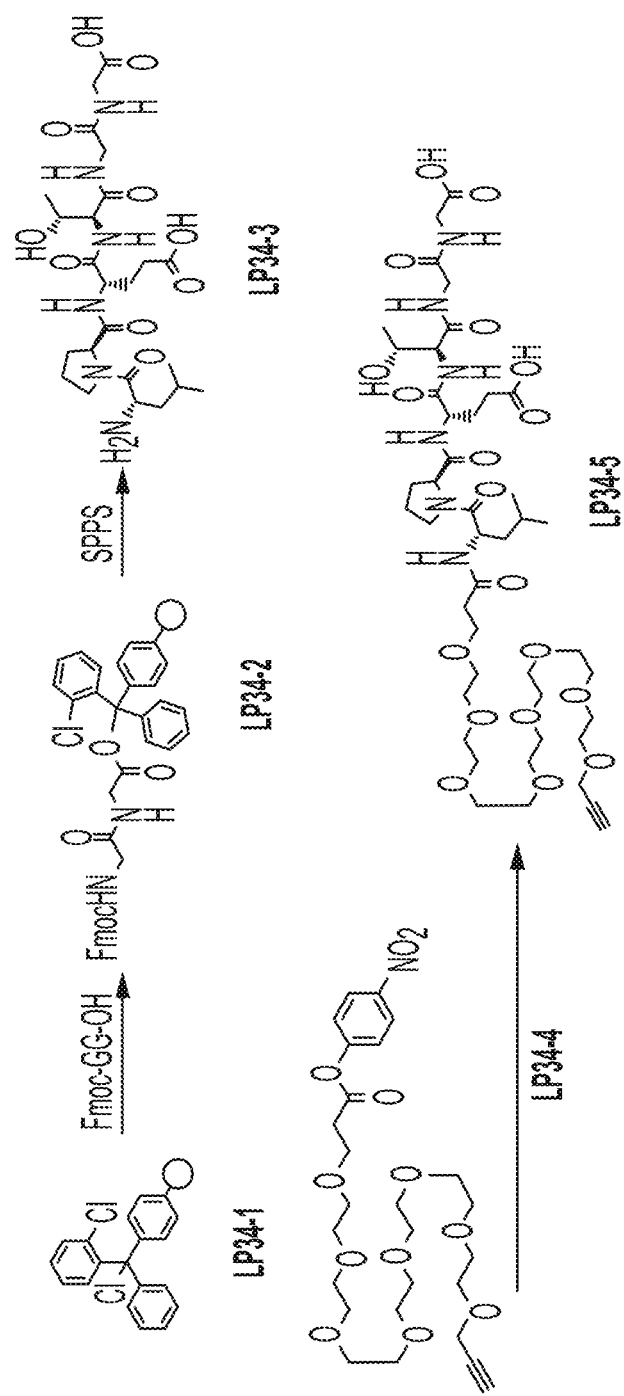
FIG. 47 shows a synthetic route for preparation of Linker-Payload LP34 according to the disclosure.
Figure 47:
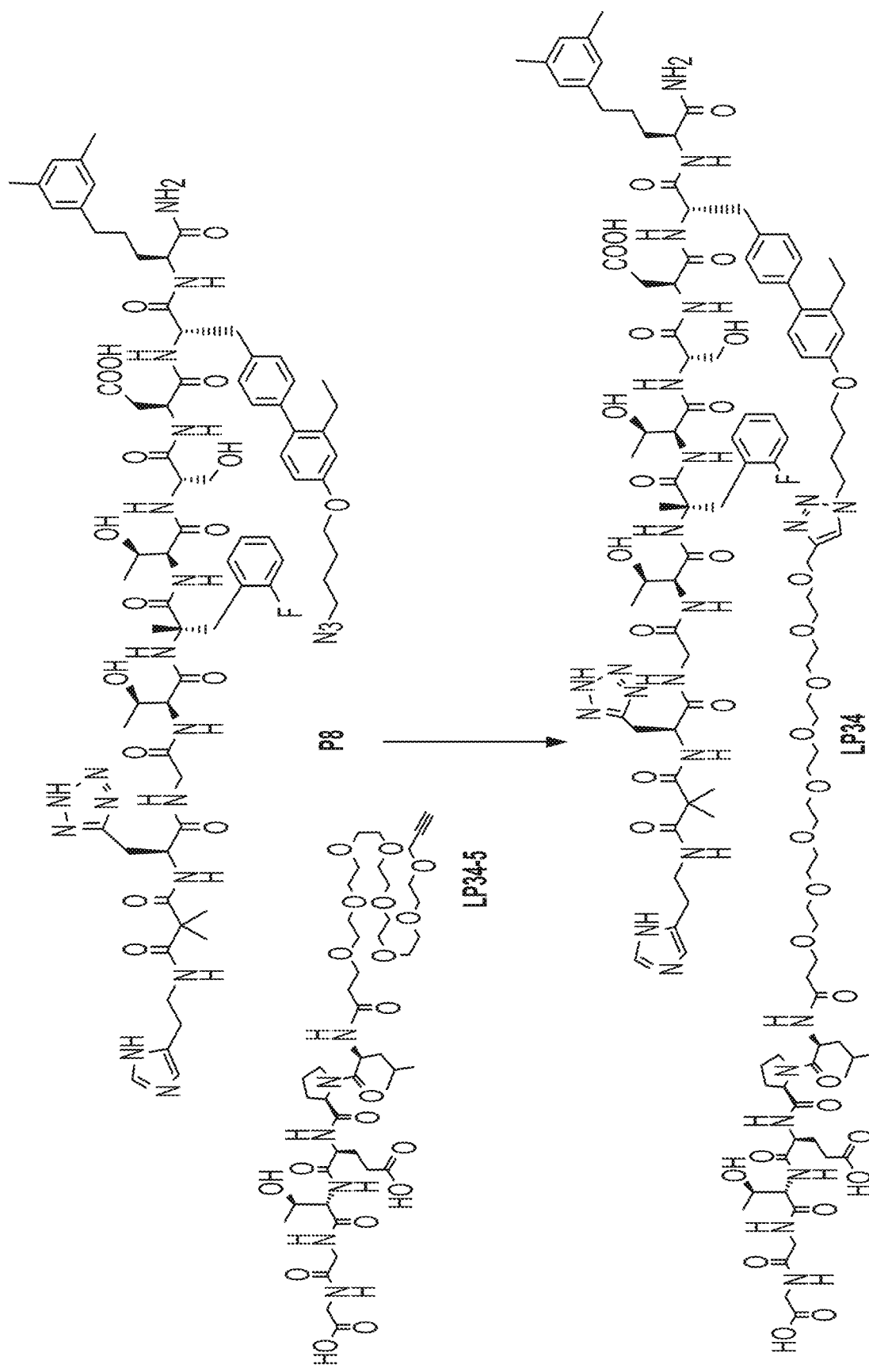

FIG. 47 depicts synthetic route of GLP-1R agonist Linker-payloads (LP34)

Step 1: Preparation of [(2-chlorophenyl)-diphenyl-methyl]2-[[2-(9H-fluoren-9-ylmethoxycarbonylamino)acetyl]amino]acetate (LP34-2)

To a mixture LP34-1 (20 g, 21.01 mmol, 32.8% purity, 1 eq.) in DMF (200 mL) was shaked for 30 min and a solution of 2-[[2-(9H-fluoren-9-ylmethoxycarbonylamino)acetyl]amino]acetic acid (37.23 g, 105.06 mmol, 5 eq.) and DIPEA (27.16 g, 210.11 mmol, 36.60 mL, 10 eq.) in DMF (200 mL) was added. The resulting mixture was shaked for 12 h at 20° C. The resulting mixture was shaked for 12 h at 20° C. The mixture was added MeOH (100 mL) and shaked for another 2 h. The crude product WUXI-262-2 (26.68 g, crude) was used into the next step without further purification as a yellow solid.

Step 2: Preparation of (4S)-4-[[(2S)-1-[(2S)-2-amino-4-methyl-pentanoyl]pyrrolidine-2-carbonyl]amino]-5-[[(1S,2R)-1-[[2-(carboxymethylamino)-2-oxo-ethyl]carbamoyl]-2-hydroxy-propyl]amino]-5-oxo-pentanoic acid (LP34-3)

The solid-phase peptide synthesis was carried on Liberty Lite—Automated Microwave Peptide Synthesizer. The LP34-2 Resin (0.43 mmol, 1 eq.) was swollen with DMF (10 mL) for 300S on standard. Following the standard operation on peptide synthesizer: a) De-protection: a solution of 20% piperidine/DMF (5 mL) was added to the resin vessel, agitated with $N_2$ for 2 min at 90° C. Then drained the vessel and washed with DMF (3 mL×3) at 20° C. b) Coupling (each amino acid reacted for triple with 5.0 eq.): a solution of amino acid (2.5 mmol, 5 eq.) in DMF (5 mL), DIC (2 mL) and oxyma (1 mL) were added to the vessel and agitated with $N_2$ for 10 min at 90° C. Repeat a) and b) for all amino acids. The resin was subjected to acidic cleavage by using TFA cocktail (TFA/TIPS/$H_2O$=95:2.5:2.5), then filtered and the filtrate was diluted with t-BuOMe to give a precipitate, which was centrifuged (5000 R) for 10 min to afford product P34-3 (0.6 g, crude, TFA) as a white solid. $^1$H NMR (400 MHz, DMSO-d6) 13.13-11.71 (m, 2H), 8.52-7.97 (m, 7H), 7.85-7.59 (m, 1H), 5.06 (br s, 1H), 4.48-4.28 (m, 2H), 4.26-4.16 (m, 1H), 4.12 (br s, 1H), 4.04-3.94 (m, 1H), 3.90-3.68 (m, 5H), 2.35-1.72 (m, 9H), 1.64-1.44 (m, 2H), 1.03 (d, J=6.3 Hz, 3H), 0.96-0.87 (m, 6H).

Step 3: Preparation of (4S)-5-[[(1S,2R)-1-[[2-(carboxymethylamino)-2-oxo-ethyl]carbamoyl]-2-hydroxy-propyl]amino]-4-[[(2S)-1-[(2S)-4-methyl-2-[3-[2-[2-[2-[2-[2-(2-prop-2-ynoxyethoxy)ethoxy]ethoxy]ethoxy]ethoxy]ethoxy]propanoylamino]pentanoyl]pyrrolidine-2-carbonyl]amino]-5-oxo-pentanoic acid (LP34-5 (SEQ ID NO: 153))

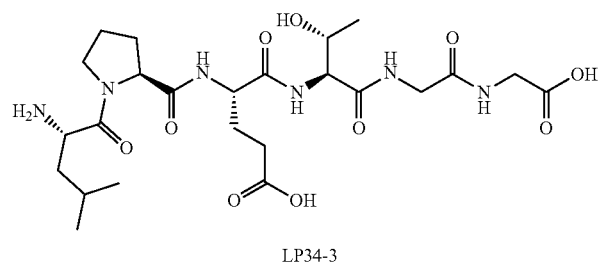

LP34-3

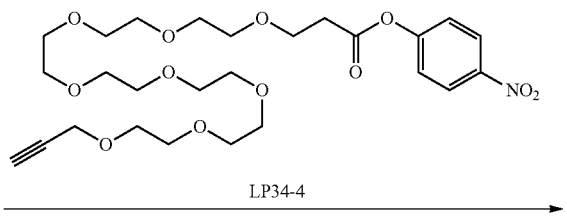

LP34-4

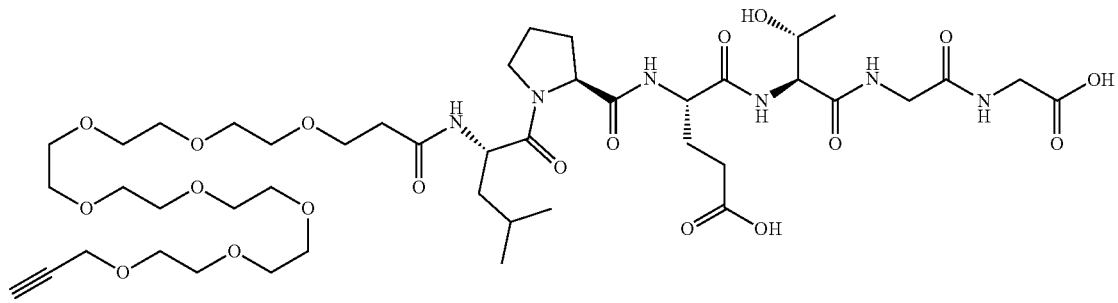

LP34-5

To a solution of LP34-3 (SEQ ID NO: 152) (45 mg, 65.54 μmol, 1 eq., TFA) and LP34-4 (36.54 mg, 65.54 μmol, 1 eq.) in DMF (2 mL) was added DIPEA (16.94 mg, 131.07 μmol, 22.83 μl, 2 eq.). The solution was stirred at 20° C. for 1 h. LCMS showed the desired product was observed. (ESI): RT=2.455 min, mass calcd. for $C_{47}H_{77}N_{19}O_{19}N_6$ 992.08 [M+H]$^+$, found 991.6 [M+H]$^+$. Reverse phase LCMS was carried out using a Chromolith Flash 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate3 μm,C18,2.1*30 mm; The mixture was diluted with CH3CN (2 mL). The residue was purified by prep-HPLC (TFA condition; column: Welch Xtimate C18 100*40 mm*3 μm; mobile phase: [water (0.075% TFA)-ACN]; B %: 15%-45%, 10 min). LP34-5 (50 mg, 49.54 μmol, 75.59% yield, 98.2% purity) was obtained as colorless oil confirmed by LCMS: ES17478-97-P1 D2, HPLC: ES17478-97-p1C1 and HNMR: ES17478-97-P1B1.

(ESI): RT=3.158 min, mass calcd. for $C_{47}H_{77}N_{19}O_{19}N_6$ 992.08 [M+H]$^+$, found 991.6 [M+H]$^+$ Reverse phase LCMS was carried out using a Chromolith Flash 1.5 ML/4L TFA in water (solvent A) and 0.75 ML/4L TFA in acetonitrile (solvent B), using the gradient 0%-60% (solvent B) over 6 minutes and holding at 60% for 0.5 minutes at a flow rate of 0.8 ml/min; Column: Xtimate3 μm,C18,2.1*30 mm;

HPLC: RT=3.69 min. HPLC conditions: Mobile Phase: 2.75 ML/4L TFA in water (solvent A) and 2.5 ML/4L TFA in acetonitrile (solvent B), using the elution gradient 1%-100% (solvent B) over 10 minutes and holding at 100% for 5 minutes at a flow rate of 1.5 ML/min; Column: Ultimate XB-C18.3 μm,3.0*50 mm.

$^1$H NMR (400 MHz, DMSO-d6) 8.20-8.06 (m, 4H), 7.61 (d, J=8.0 Hz, 1H), 4.62-4.50 (m, 1H), 4.34 (br dd, J=4.4, 8.0 Hz, 1H), 4.31-4.24 (m, 1H), 4.19 (dd, J=4.0, 8.0 Hz, 1H), 4.14 (d, J=2.4 Hz, 2H), 4.04-3.96 (m, 1H), 3.82-3.73 (m, 4H), 3.60-3.47 (m, 34H), 2.41-2.25 (m, 4H), 1.99-1.82 (m,

4H), 1.80-1.69 (m, 1H), 1.67-1.56 (m, 1H), 1.50-1.35 (m, 2H), 1.32-1.22 (m, 1H), 1.03 (d, J=6.4 Hz, 3H), 0.88 (t, J=7.2 Hz, 6H).

Step 4: Preparation of (4S)-4-[[[(2R)-1-[(2S)-2-[3-[2-[2-[2-[2-[2-[2-[2-[[1-[5-[4-[4-[(2S)-3-[[(1S)-1-carbamoyl-4-(3,5-dimethylphenyl)butyl]amino]-2-[[(2S)-3-carboxy-2-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]propanoyl]amino]-3-oxo-propyl]phenyl]-3-ethyl-phenoxy]pentyl]triazol-4-yl]methoxy]ethoxy]ethoxy]ethoxy]ethoxy]ethoxy]ethoxy]propanoylamino]-4-methyl-pentanoyl]pyrrolidine-2-carbonyl]amino]-5-[[(1S,2R)-1-[[2-(carboxymethylamino)-2-oxo-ethyl]carbamoyl]-2-hydroxy-propyl]amino]-5-oxo-pentanoic acid (LP34)

To a solution of P8 (15 mg, 9.54 µmol, 1 eq.), LP34-5 (19.00 mg, 19.17 µmol, 2.01 eq.) in DMSO (0.8 mL) and H$_2$O (0.8 mL) were added CuSO$_4$·5H$_2$O (2.38 mg, 9.54 µmol, 1 eq.), SODIUM ASCORBATE (1.89 mg, 9.54 µmol, 1 eq.) and 1-(1-benzyltriazol-4-yl)-N,N-bis[(1-benzyltriazol-4-yl)methyl]methanamine (2.5 mg, 4.77 µmol, 0.5 eq.). The resulting mixture was stirred at 25° C. for 3 h. LCMS showed the desired product was observed. (ESI): RT=3.677 min, mass calcd. for C$_{120}$H$_{175}$N$_{26}$O$_{36}$FH 2562.25[M+H]$^+$, 1282.6 [M+2H]$^{2+}$, found 1282.2 [M+2H]$^{2+}$. Reverse phase LCMS was carried out using a Chromolith Flash 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate3 µm,C18,2.1*30 mm; The mixture was diluted with MeOH (2 mL), filtered and the filtrate was sent to Prep-HPLC. The residue was purified by prep-HPLC (TFA condition). Column: Welch Xtimate C18 100*40 mm*3 µm; mobile phase: [water (0.075% TFA)-ACN]; B %: 28%-58%, 8 min. LP34 (8.9 mg, 3.33 µmol, 34.85% yield, 96.3% purity) was obtained as a white solid.

LCMS RT=3.682 min, mass calcd. for C$_{120}$H$_{175}$N$_{26}$O$_{36}$FH 2562.25[M+H]$^+$, 1282.6 [M+2H]$^{2+}$, found 1282.2 [M+2H]$^{2+}$. Reverse phase LCMS was carried out using a Chromolith Flash 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min; Column: Xtimate3 µm,C18,2.1*30 mm.

HPLC: RT=4.34 min. HPLC conditions: Mobile Phase: 2.75 ML/4L TFA in water (solvent A) and 2.5 ML/4L TFA in acetonitrile (solvent B), using the elution gradient 1%-100% (solvent B) over 10 minutes and holding at 100% for 5 minutes at a flow rate of 1.5 ML/min; Column: Ultimate XB-C18.3 µm,3.0*50 mm.

Figure 48:
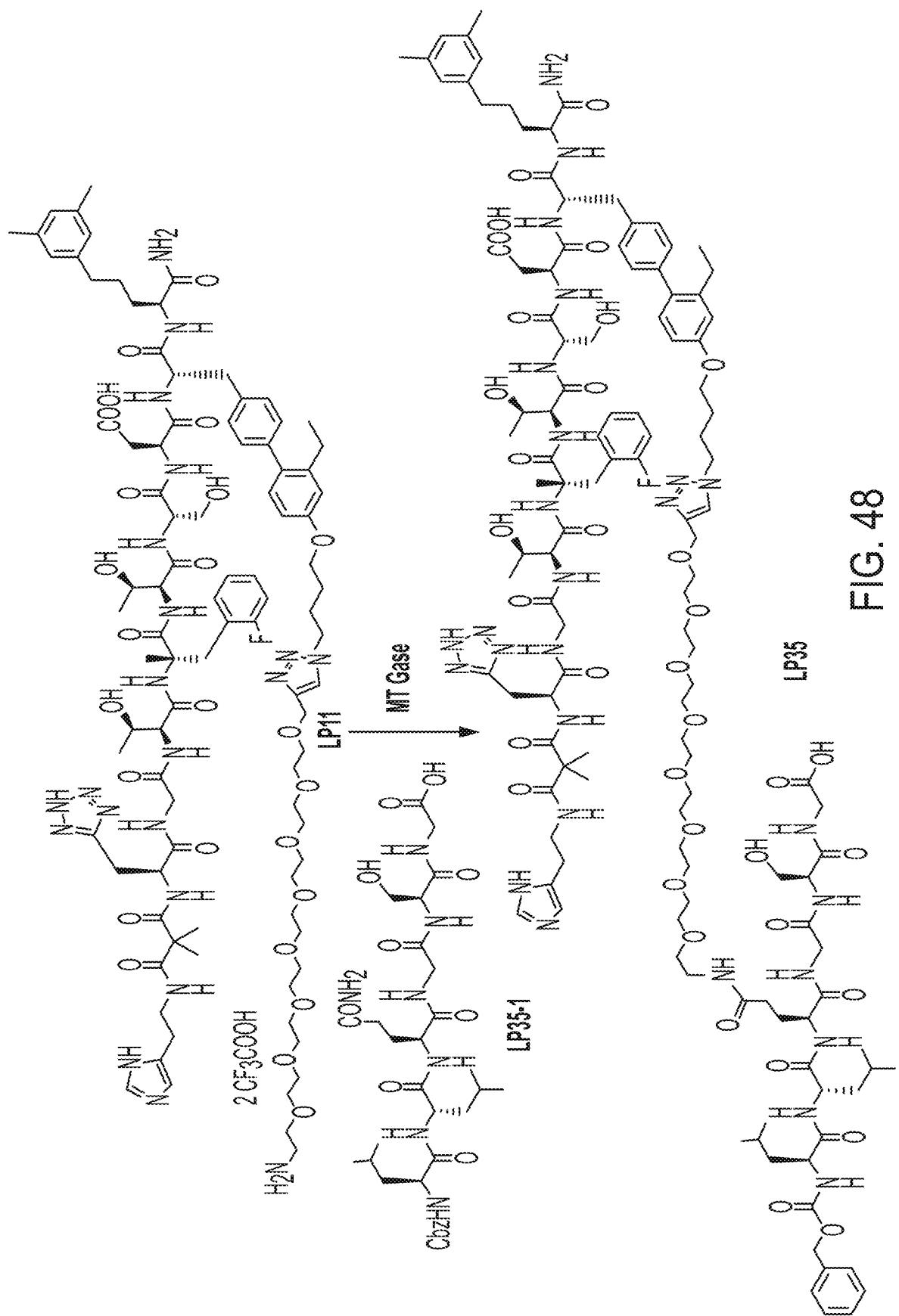
FIG. 48 shows a synthetic route for preparation of Linker-Payload LP35 according to the disclosure.

FIG. 48 depicts synthetic route of GLP-1R agonist Linker-payloads (LP35)

Preparation of (3S)-4-[[(1S)-1-[[4-[4-[4-[2-[2-[2-[2-[2-[2-[2-[2-[[(4S)-4-[[(2S)-2-[[(2S)-2-(benzyloxycarbonylamino)-4-methyl-pentanoyl]amino]-4-methyl-pentanoyl]amino]-5-[[2-[[(1S)-2-(carboxymethylamino)-1-(hydroxymethyl)-2-oxo-ethyl]amino]-2-oxo-ethyl]amino]-5-oxo-pentanoyl]amino]ethoxy]ethoxy]ethoxy]ethoxy]ethoxy]ethoxy]ethoxymethyl]triazol-1-yl]butoxy]-2-ethyl-phenyl]phenyl]methyl]-2-[[(1S)-1-carbamoyl-4-(3,5-dimethylphenyl) butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP35)

A solution of LP11 (6.0 mg, 2.72 µmol, 1.0 eq., 2TFA) and PBS buffer (K-free, 100 mM, pH=7.20) (7.2 mL) was measured pH as 7.2. LP35-1 (9.62 mg, 13.59 µmol, 5.0 eq.) and MTGase (Ajinomoto-TI, 51.6 mg) were added. The resulting mixture was stirred at 37° C. for 16 h. The reaction progress was monitored by LCMS. Upon completion, the reaction mixture was quenched with aqueous AcOH solution (1% v/v, 7.2 mL). The obtained solid was rinsed with DMF/H$_2$O (3 mL, 1/1), and then the filtrate was purified by prep-HPLC (column: O-Xbridge C18 150*10 mm*5 µm; mobile phase: [water (0.075% TFA)-ACN]; B %: 10%-65%, 20 min) to afford LP35 (2.62 mg, 0.926 µmol, 34.1% yield, 98.3% purity, TFA salt) as a white solid.

LCMS: (ESI): RT=3.62 min, m/z calcd. for C$_{126}$H$_{184}$FN$_{27}$O$_{36}$ 1335.17 [M+2H]$^{2+}$, found 1335.6; 100% purity at 220 nm. LCMS conditions: Xtimate C18 2.1*30 mm, 3 µm; 1.5 mL/4 L TFA in water (solvent A) and 0.75 mL/4 L TFA in acetonitrile (solvent B), using the elution gradient 10%-80% (solvent B) over 6 minutes and holding at 80% for 0.5 minutes at a flow rate of 0.8 mL/min.

UPLC: RT=7.15 min, 98.38% purity at 220 nm. UPLC method: Waters ACQUITY UPLC BEH C18 1.7 µm, 2.1*100 mm; 0.05% TFA in 1L water (solvent A) and 0.05% TFA in 1L acetonitrile (solvent B), using the elution gradient 3%-100% (solvent B) over 11 minutes and holding at 100% for 4 minutes at a flow rate of 0.4 mL/minute.

Figure 49:
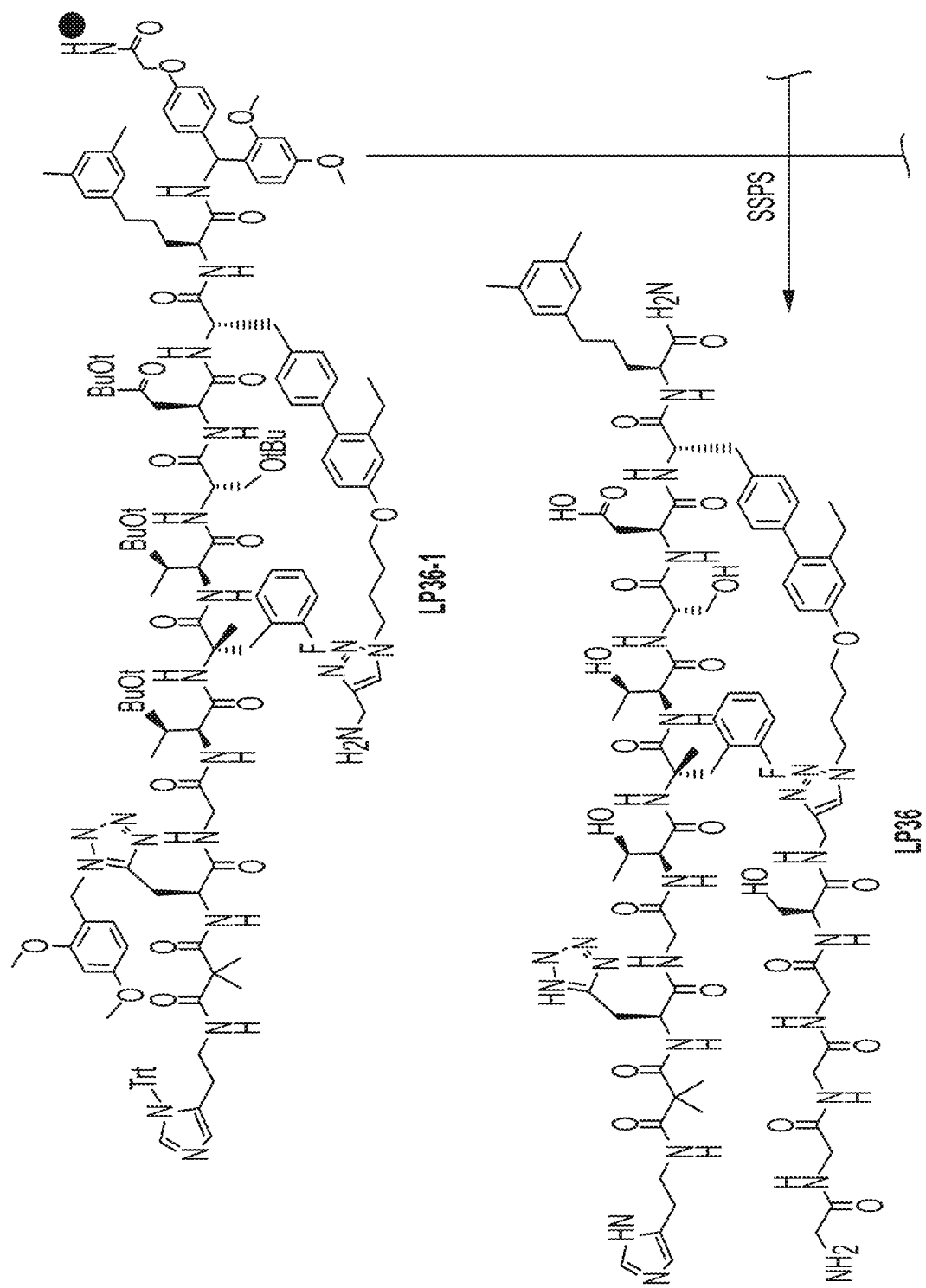
FIG. 49 shows a synthetic route for preparation of Linker-Payloads LP36, LP37, LP38, LP39, LP40, and LP41 according to the disclosure.
Figure 49:
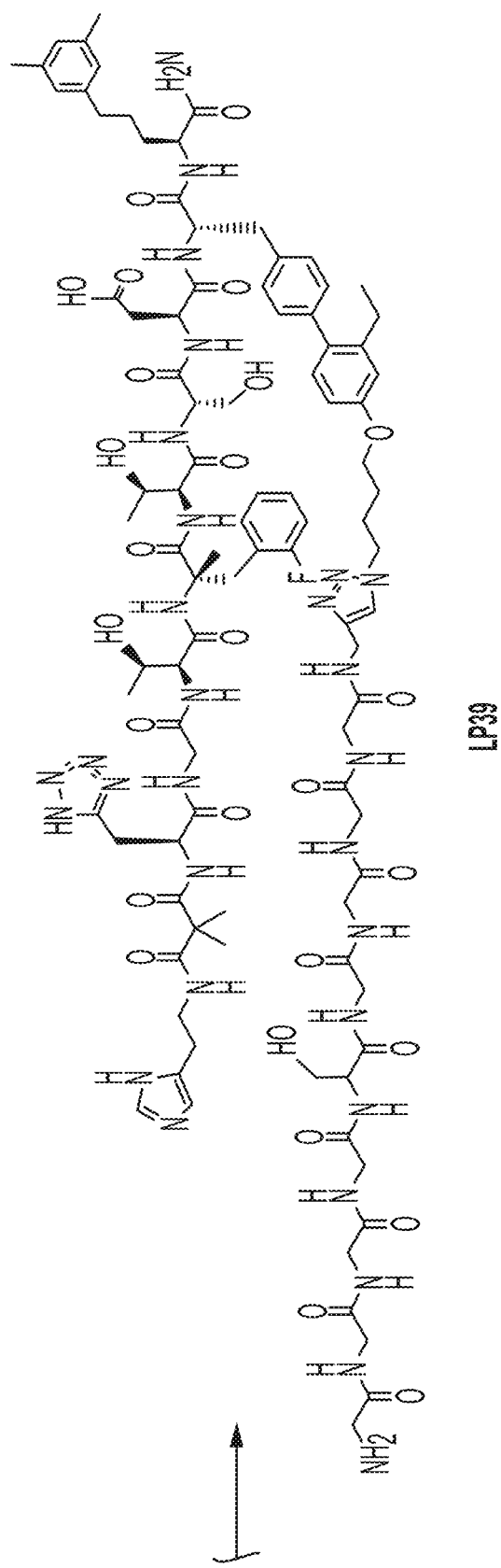
Figure 49:
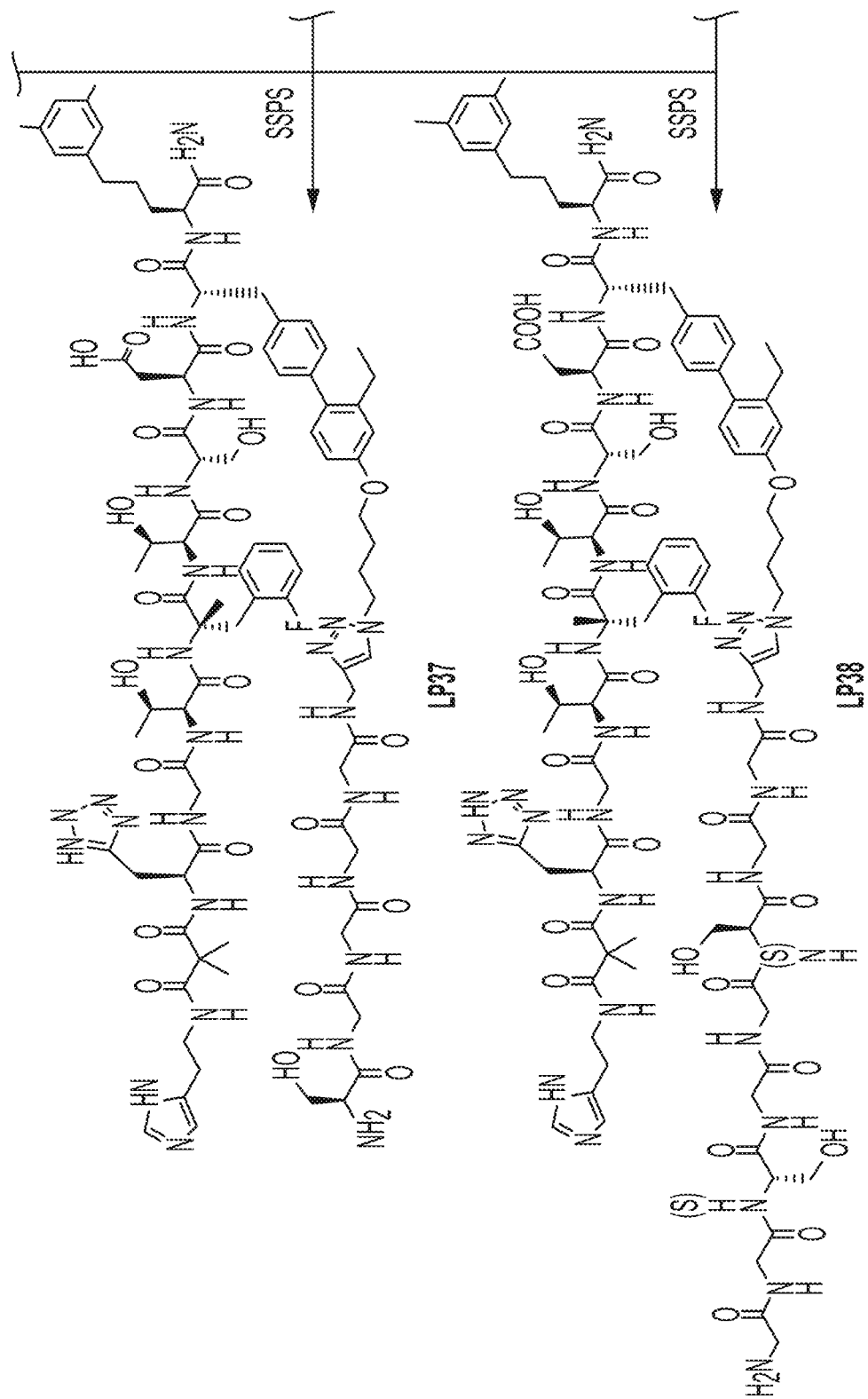
Figure 49:
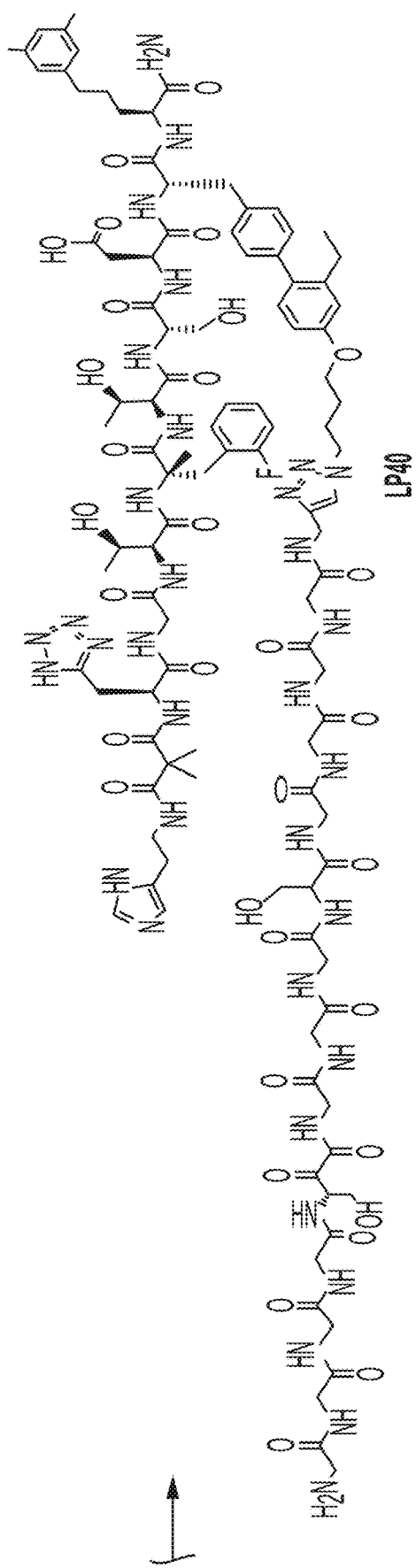
Figure 49:
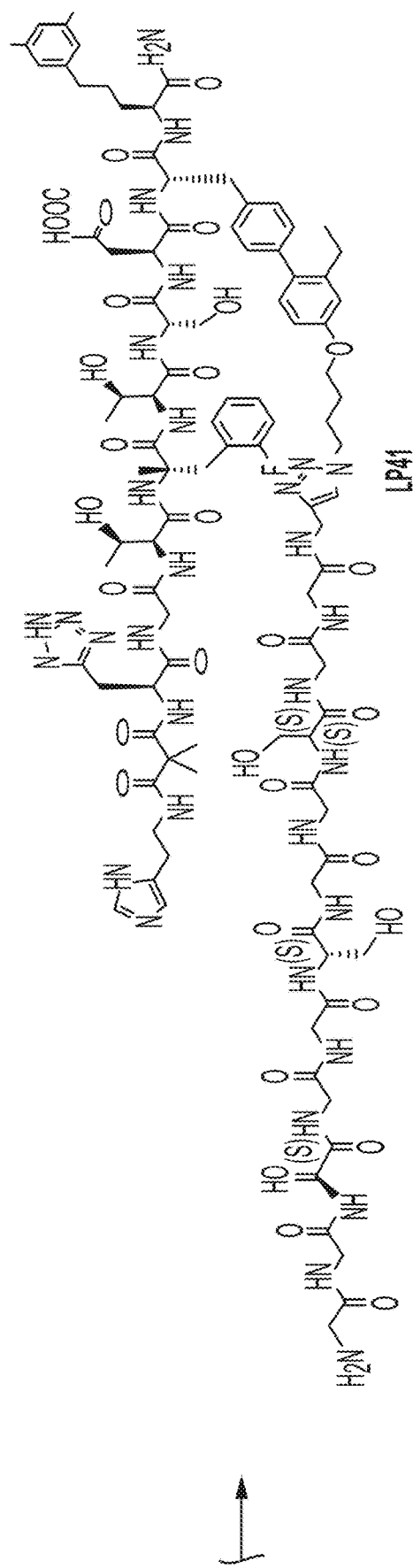

FIG. 49 depicts synthetic route of GLP-1R agonist Linker-payloads (LP36, LP37, LP38, LP39, LP40, LP41)

5.36 Preparation of (3S)-4-[[(1S)-1-[[4-[4-[4-[4-[[[(2S)-2-[[2-[[2-[(2-aminoacetyl)amino]acetyl]amino]acetyl]amino]acetyl]amino]-3-hydroxy-propanoyl]amino]methyl]triazol-1-yl]butoxy]-2-ethyl-phenyl]phenyl]methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(1H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]-4-oxo-butanoic acid (LP36)

The solid-phase peptide synthesis was carried out on the Liberty Lite—Automated Microwave Peptide Synthesizer. The LP36-1 (0.43 mmol, 1 eq.) was swollen with DMF (10 mL) for 300S on standard. Following the standard operation on peptide synthesizer: a) De-protection: a solution of 20% piperidine/DMF (5 mL) was added to the resin vessel, agitated with $N_2$ for 2 min at 90° C. Then drained the vessel and washed with DMF (3 mL×3) at 20° C. b) Coupling (each amino acid reacted for triple with 5.0 eq.): a solution of amino acid (2.5 mmol, 5 eq.) in DMF (5 mL), DIC (2 mL) and oxyma (1 mL) were added to the vessel and agitated with $N_2$ for 10 min at 90° C. Repeat a) and b) for all amino acids. The resin was subjected to acidic cleavage by using TFA cocktail (TFA/TIPS/$H_2O$=95:2.5:2.5), then filtered and the filtrate was diluted with t-BuOMe to give a precipitate, which was centrifuged (5000 R) for 10 min to give the crude product.

LP36 was prepared as described in the general procedure of SPPS. The crude product was purified by prep-HPLC (column: Welch Xtimate C18 100*40 mm*3 μm; mobile phase: [water (0.075% TFA)-ACN];B %: 0%-40%,15 min) to afford pure product LP36 (13.9 mg, 6.25 μmol, 1.44% yield, 97.58% purity, 2TFA) as a white solid.

LCMS: (ESI): Rt=2.715 min, m/z calcd. For $C_{89}H_{123}FN_{26}O_{23}$, 971.46, $[M+2H]^{2+}$; found 971.9 $[M+2H]^{2+}$; Reverse phase LCMS was carried out using Chromolith Flash RPC1825-3 mm, with a flow rate of 0.8 ml/min, eluting with a gradient of 10% to 80% acetonitrile containing 0.02% TFA (solvent B) and water containing 0.04% TFA (solvent A).

HPLC: RT=6.62 min. HPLC Conditions: Mobile phase: 1.0% ACN in water (0.1% TFA) to 5% ACN in water (0.1% TFA) in 1 minutes; then from 5% ACN in water(0.1% TFA) to 100% ACN (0.1% TFA) in 5 minutes; hold at 100% ACN (0.1% TFA) for 2 minutes;back to 1.0% ACN in water (0.1% TFA) at 8.01 minutes, and hold two minutes.Flow rate:1.2 ml/minColumn: Ultimate XB-C18.3 μm,3.0*50 mm HRMS (ESI): m/z calcd for $C_{89}H_{121}FN_{26}O_{23}$ 1941.91 $[M+H]^+$, 971.46 $[M+2H]^{2+}$, found 1942.9299 $[M+H]^+$, 971.9736 $[M+2H]^{2+}$.

UPLC: RT=5.824 min. conditions: Mobile Phase: 0.05% TFA in 1 L water (solvent A) and 0.05% TFA in 1 L acetonitrile (solvent B), using the elution gradient 30%-80% (solvent B) over 10 minutes and holding at 80% for 5 minutes at a flow rate of 0.4 mL/minute; Column: Waters ACQUITY UPLC HSS T3 1.8 μm, 2.1*100 mm;

5.37 LP37 was obtained as the same with LP36. The crude product was purified by prep-HPLC (column: Welch Xtimate C18 100*40 mm*3 μm; mobile phase: [water (0.075% TFA)-ACN];B %: 0%-40%,15 min) to afford pure product LP37 (5 mg, 2.50 μmol, 1.25% yield, 97% purity) as a white solid.

LCMS: (ESI): Rt=2.800 min, mass calcd. for $C_{89}H_{121}FN_{26}O_{23}$; found 971.45 $[M/2+H]^+$ found 971.0; Reverse phase LCMS was carried out using Chromolith Flash RPC1825-3 mm, with a flow rate of 0.8 ml/min, eluting with a gradient of 10% to 80% acetonitrile containing 0.02% TFA (solvent B) and water containing 0.04% TFA (solvent A).

HPLC: RT=6.61 min. Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min; Column: WELCH Ultimate LP-C18 150*4.6 mm 5 μm; Wavelength: UV 220 nm&215 nm&254 nm; Column temperature: 40° C.

HRMS-TOF: $C_{89}H_{122}N_{26}O_{23}F$ $[M+H]$=1942.9573. The mobile phase: 0.1% FA in water (solvent A) and 0.05% FA in ACN (solvent B);Elution Gradient: 5%-95% (solvent B) over 1.3 minutes and holding at 95% for 0.7 minutes at a flow rate of 1.2 ml/minute; Column: Agilent Poroshell HPH-C182.7 μm, 2.1*50 mm; Ion Source: AJS ESI source; Ion Mode: Positive; Nebulization Gas: Nitrogen; Drying Gas ($N_2$) Flow: 8 L/min; Nebulizer Pressure: 35 psi;Gas Temperature: 325oC;Sheath gas Temperature: 350oC; Sheath gas flow: 11 L/min; Capillary Voltage: 3.5 KV; Fragmentor Voltage: 300 V.

UPLC: RT=4.595 min, mass calcd. Mobile Phase: 0.05% TFA in 1L water (solvent A) and 0.05% TFA in 1L acetonitrile (solvent B), using the elution gradient 0%-95% (solvent B) over 6 minutes and holding at 95% for 4 minutes at a flow rate of 0.6 mL/minute; Column: Waters ACQUITY UPLC HSS T3 2.1*50 mm,1.8 μm; Column temp:40° C.

5.38 LP38 was obtained as the same with LP36. The crude product was purified by prep-HPLC (column: Welch Xtimate C18 100*40 mm*3 μm; mobile phase: [water (0.075% TFA)-ACN]; B %: 15%-45%, 15 min) to afford pure product LP38 (52.17 mg, 8.87 μmol, 2.53% yield, 95% purity) as a white solid.

LCMS: (ESI): Rt=2.723 min, mass calcd. for $C_{96}H_{134}FN_{29}O_{27}$ $[M+2H]^2$+1071.99, $C_{96}H_{135}FN_{29}O_{27}$ $[M+3H]^3$+714.99; found 1072.40 $[M+2H]^{2+}$ found 715.30 $[M+3H]^{3+}$; Reverse phase LCMS was carried out using Chromolith Flash RP-C18 25-3 mm, with a flow rate of 0.8 ml/min, eluting with a gradient of 10% to 80% acetonitrile containing 0.02% TFA (solvent B) and water containing 0.04% TFA (solvent A).

HPLC RT=9.00 min, 95% purity. HPLC method A: Column: YMC-Pack ODS-A 150*4.6 mm, 5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min;

5.39 LP39 was obtained as the same with LP36. The crude product was purified by prep-HPLC (column: Welch Xtimate C18 100*40 mm*3 μm; mobile phase: [column: Waters X bridge BEH C18 100*25 mm*5 μm; mobile phase: [water (0.05% $NH_3H_2O$)-ACN]; B %: 5%-32%, 11 min) o afford pure product LP39 (20 mg, 8.75 μmol, 2.50% yield, 95% purity) as a white solid.

LCMS: (ESI): Rt=2.711 min, mass calcd. for $C_{97}H_{135}FN_{30}O_{27}$ $[M+2H]^{2+}$ 1085.49, $C_{97}H_{136}FN_{30}O_{27}$ $[M+3H]^{3+}$ 724.30; found 1085.90 $[M+2H]^{2+}$ found 725.30 $[M+3H]3+$; Reverse phase LCMS was carried out using Chromolith Flash RP-C1825-3 mm, with a flow rate of 0.8 ml/min, eluting with a gradient of 10% to 80% acetonitrile containing 0.02% TFA (solvent B) and water containing 0.04% TFA (solvent A).

HPLC RT=8.99 min, 95% purity. HPLC method A: Column: YMC-Pack ODS-A 150*4.6 mm, 5 μm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min;

5.40 LP40 was obtained as the same with LP36. The crude product was purified by prep-HPLC (column: Welch Xtimate C18 100*40 mm*3 μm; mobile phase: [water (0.075% TFA)-ACN]; B %: 6%-46%, 20 min) to afford pure product LP40 (3.5 mg, 1.38 μmol, 3.94e-1% yield, 97.99% purity) as a white solid.

LCMS: (ESI): Rt=2.740 min, mass calcd. for $C_{108}H_{152}FN_{35}O_{33}$ $[M+2H]^2$+1243.05, $C_{108}H_{153}FN_{35}O_{33}$ $[M+3H]^3$+829.03; found 829.4$[M+2H]^{2+}$ found 1243.30 $[M+3H]^{3+}$; Reverse phase LCMS was carried out using X Bridge C18 3.5 μm 2.1*30 mm, with a flow rate of 0.8 ml/min, eluting with a gradient of 10% to 80% acetonitrile (solvent B) and $NH3-H_2O$ in water (solvent A).

HPLC RT=6.50 min, 97.99% purity; HPLC method A: Column: YMC-Pack ODS-A 150*4.6 mm, 5 μm; 2.75

ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min;

5.41 LP41 was obtained as the same with LP36. The crude product was purified by prep-HPLC (column: Welch Xtimate C18 100*40 mm*3 µm; mobile phase: [water (0.075% TFA)-ACN]; B %: 6%-46%, 20 min) to afford pure product LP41 (4.5 mg, 1.89 µmol, 0.54% yield, 98.52% purity) as a white solid.

LCMS: (ESI): Rt=2.590 min, mass calcd. for $C_{103}H_{145}FN_{32}O_{31}$ $[M+2H]^2+1173.21$, $C_{103}H_{146}FN_{32}O_{31}$ $[M+3H]^3+782.47$; found 1172.90 $[M+2H]^{2+}$ found 782.30 $[M+3H]^{3+}$; Reverse phase LCMS was carried out using X Bridge C18 3.5 µm 2.1*30 mm, with a flow rate of 0.8 ml/min, eluting with a gradient of 10% to 80% acetonitrile (solvent B) and NH3-H2O in water (solvent A).

HPLC RT=6.54 min, 98.52% purity; HPLC method A: Column: YMC-Pack ODS-A 150*4.6 mm, 5 µm; 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ml/min.

Figure 50:
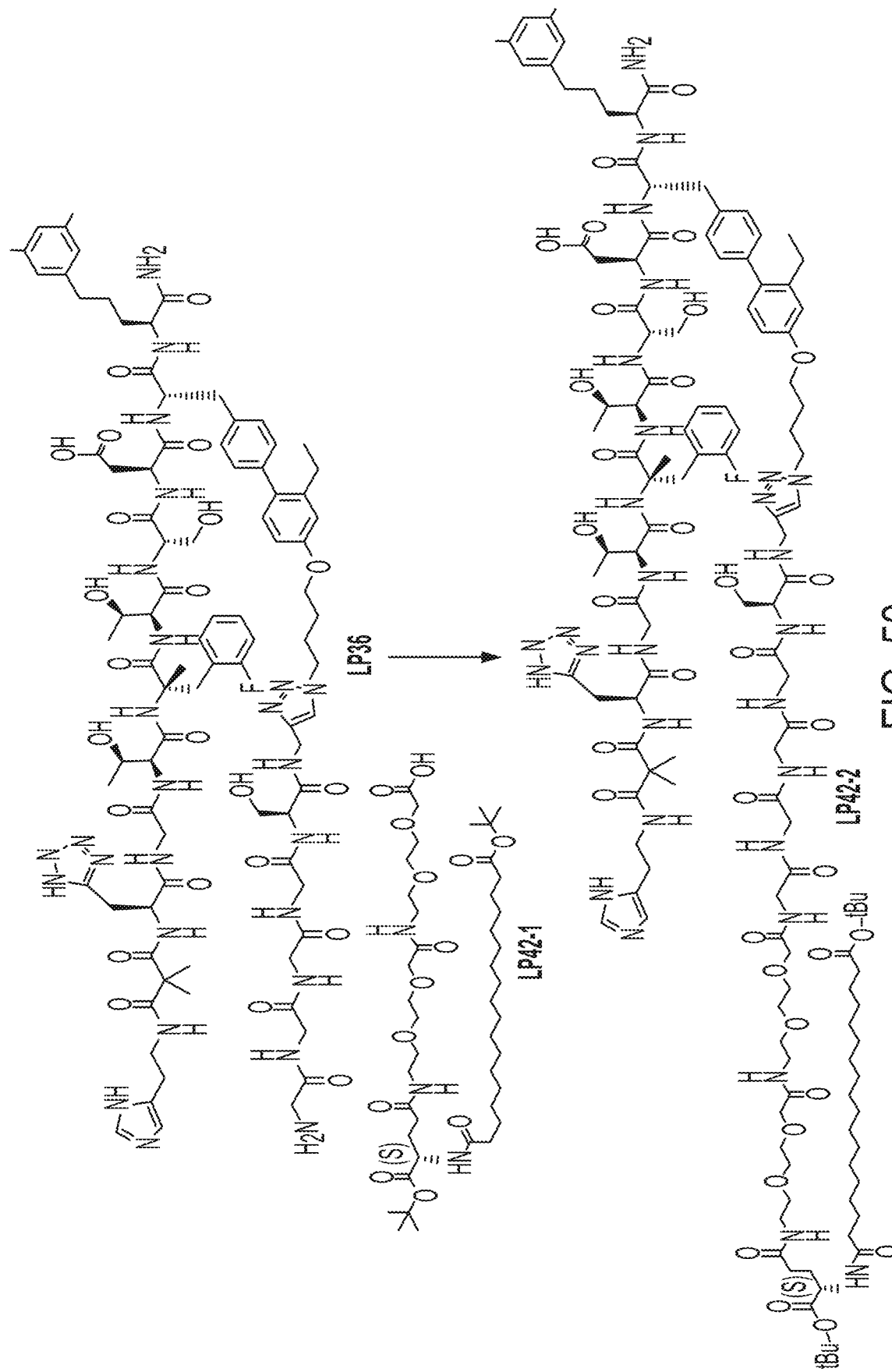
FIG. 50 shows a synthetic route for preparation of Linker-Payload LP42 according to the disclosure.
Figure 50:
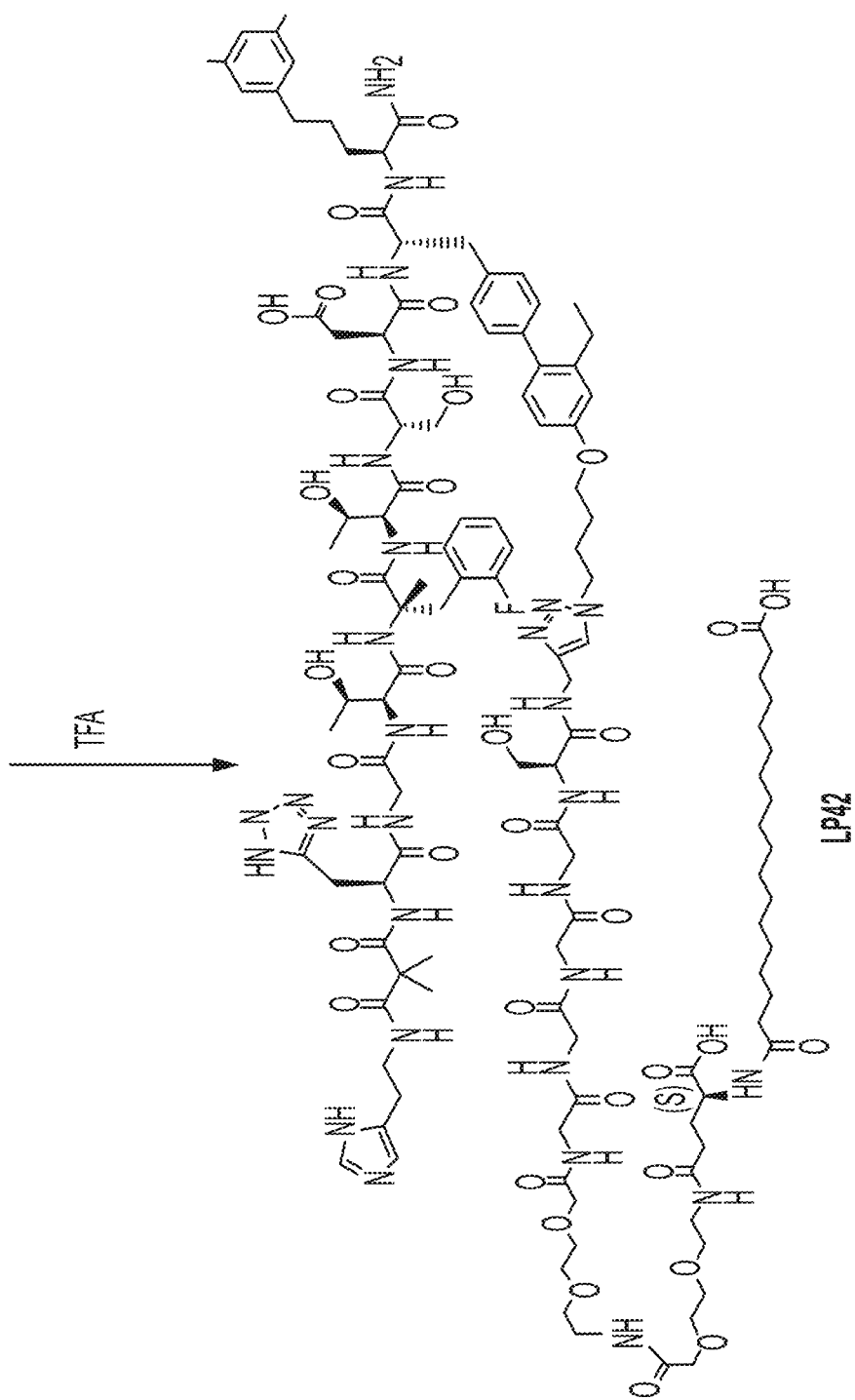

FIG. 50 depicts synthetic route of GLP-1R agonist Linker-payloads (LP42)

Step 1: Preparation of (3S)-4-[[(1S)-1-[[4-[4-[4-[4-[[[(2S)-2-[[2-[[2-[[2-[[2-[[2-[2-[2-[[2-[2-[2-[[(4S)-5-tert-butoxy-4-[(18-tert-butoxy-18-oxo-octadecanoyl) amino]-5-oxo-pentanoyl]amino]ethoxy]ethoxy] acetyl]amino]ethoxy]ethoxy]acetyl]amino]acetyl] amino]acetyl]amino]acetyl]amino]acetyl]amino]-3-hydroxy-propanoyl]amino]methyl]triazol-1-yl] butoxyl-2-ethyl-phenyl]phenyl]methyl]-2-[[(15S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(1H-tetrazol-5-yl)propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP42-2)

To a solution of LP42-1 (45.75 mg, 54.07 µmol, 1.5 eq.) and HATU (16.45 mg, 43.25 µmol, 1.2 eq.) in DMF (2 mL) was added DIPEA (13.98 mg, 108.13 µmol, 18.83 µL, 3 eq). The mixture was stirred at 20° C. for 0.1 hr. LP36 (70 mg, 36.04 µmol, 1 eq.) was added and the mixture was stirred at 20° C. for 1 hr. LCMS showed the reaction converted completely. The reaction mixture was added into MTBE (40 mL) dropwise. The precipitated yellow solid was collected by centrifuged. LP42-2 (110 mg, 25.49 µmol, 70.71% yield, 64.18% purity) was obtained as a light-yellow solid.

LCMS (ESI): RT=4.670 min, m/z calcd. For $C_{132}H_{199}FN_{29}O_{35}$ 1385.23 [M+2H]2+; m/z found 1385.8;

LCMS Conditions: Mobile Phase:1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min. Column: Xtimate C18 2.1*30 mm, 3 µm.

Step 2: Preparation of 18-[[(1S)-4-[2-[2-[2-[2-[2-[2-[[2-[[2-[[2-[[2-[[(1S)-2-[[1-[4-[4-[4-[(2S)-3-[[(1S)-1-carbamoyl-4-(3,5-dimethylphenyl)butyl]amino]-2-[[(2S)-3-carboxy-2-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(1H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]propanoyl]amino]-3-oxo-propyl]phenyl]-3-ethyl-phenoxy]butyl]triazol-4-yl]methylamino]-1-(hydroxymethyl)-2-oxo-ethyl]amino]-2-oxo-ethyl]amino]-2-oxo-ethyl]amino]-2-oxo-ethyl]amino]-2-oxo-ethyl]amino]-2-oxo-ethoxyl ethoxy]ethylamino]-2-oxo-ethoxy] ethoxy]ethylamino]-1-carboxy-4-oxo-butyl]amino]-18-oxo-octadecanoic acid (LP42)

To a solution of LP42-2 (110 mg, 25.49 µmol, 64.18% purity, 1 eq.) in DCM (1 mL) was added TFA (1.54 g, 13.51 mmol, 1 mL, 529.95 eq.). The mixture was stirred at 20° C. for 1 hr. LCMS showed the reaction converted completely. The reaction mixture was purified by prep-HPLC (column: Welch Xtimate C18 100*40 mm*3 µm; mobile phase: [water (0.075% TFA)-ACN]; B %: 10%-50%, 40 min) to give the dedired compound LP42 (24 mg, 8.68 µmol, 17.03% yield, 96.11% purity) as a white solid.

LCMS: (ESI): Rt=3.943 min, m/z calcd. For $C_{124}H_{184}FN_{29}O_{35}$ 1329.17 $[M+2H]^{2+}$; m/z found 1329.6; Reverse phase LCMS was carried out using Chromolith Flash RPC1825-3 mm, with a flow rate of 0.8 ml/min, eluting with a gradient of 10% to 80% acetonitrile containing 0.02% TFA (solvent B) and water containing 0.04% TFA (solvent A).

HPLC: RT=8.52 min. HPLC conditions: Mobile phase: 1.0% ACN in water (0.1% TFA) to 5% ACN in water (0.1% TFA) in 1 minutes; then from 5% ACN in water (0.1% TFA) to 100% ACN (0.1% TFA) in 5 minutes; hold at 100% ACN (0.1% TFA) for 2 minutes; back to 1.0% ACN in water (0.1% TFA) at 8.01 minutes, and hold two minutes. Flow rate: 1.2 ml/min. Column: Ultimate XB-C18, 3 µm, 3.0*50 mm HRMS (ESI): m/z calcd for $C_{124}H_{183}FN_{29}O_{35}$ 2657.33 $[M+H]^+$, 1329.665 $[M+2H]^{2+}$, found 2657.33 $[M+H]^+$, 1329.6703 $[M+2H]^{2+}$.

UPLC: RT=5.411 min. conditions: Mobile Phase: 0.05% TFA in 1 L water (solvent A) and 0.05% TFA in 1L acetonitrile (solvent B), using the elution gradient 0%-95% (solvent B) over 6 minutes and holding at 95% for 4 minutes at a flow rate of 0.4 mL/minute; Column: Waters ACQUITY UPLC HSS T3 1.8 µm, 2.1*100 mm.

Figure 51:
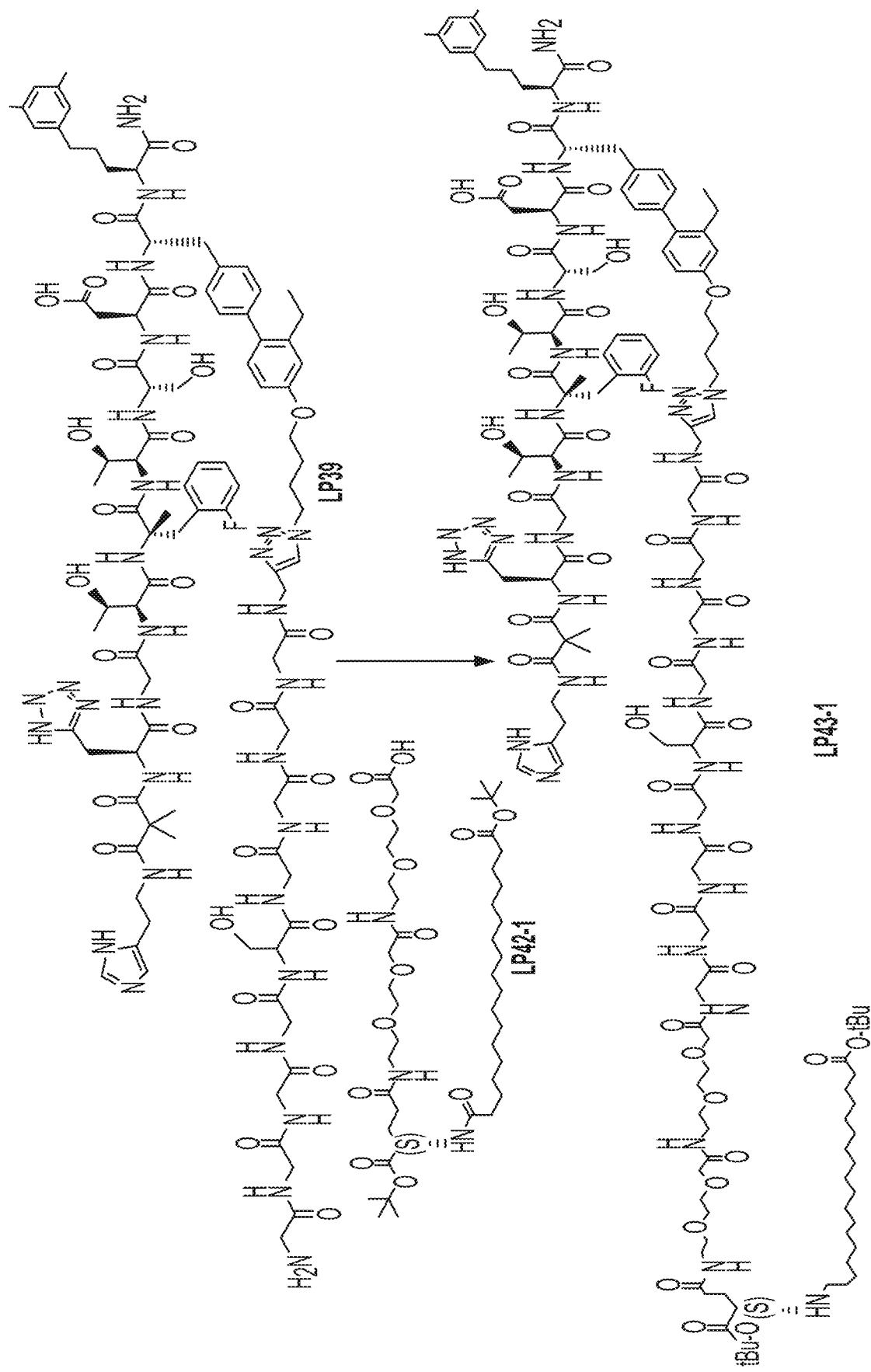
FIG. 51 shows a synthetic route for preparation of Linker-Payload LP43 according to the disclosure.
Figure 51:
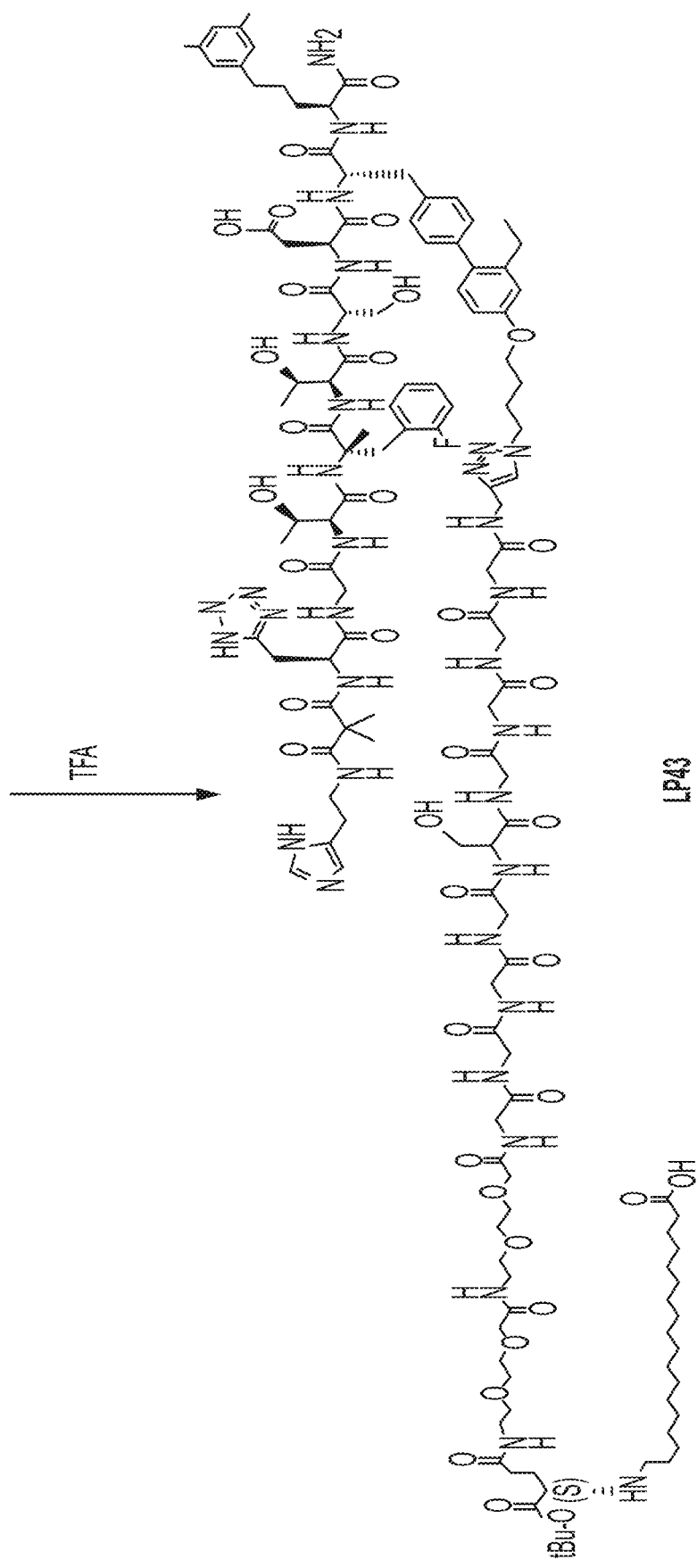

FIG. 51 depicts synthetic route of GLP-1R agonist Linker-payloads (LP43)

Step 1: Preparation of (3S)-4-[[(1S)-1-[[4-[4-[4-[4-[[2-[[2-[[2-[[2-[[(2S)-2-[[2-[[2-[[2-[[2-[[2-[2-[[2-[2-[2-[[(4S)-5-tert-butoxy-4-[(18-tert-butoxy-18-oxo-octadecanoyl)amino]-5-oxo-pentanoyl]amino] ethoxy] ethoxy]acetyl]amino]ethoxy]ethoxy]acetyl] amino]acetyl]amino]acetyl]amino]acetyl]amino] acetyl]amino]-3-hydroxy-propanoyl]amino]acetyl] amino]acetyl]amino]acetyl]amino]acetyl]amino] methyl]triazol-1-yl]butoxy]-2-ethyl-phenyl]phenyl] methyl]-2-[[(1S)-1-carbamoyl-4-(3,5-dimethylphenyl)butyl]amino]-2-oxo-ethyl]amino]-3-[[(2S)-2-[[(2S,3R)-2-[[(2S)-3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(1H-tetrazol-5-yl) propanoyl] amino]acetyl]amino]butanoyl]amino]-2-methyl-propanoyl]amino]-3-hydroxy-butanoyl]amino]-3-hydroxy-propanoyl]amino]-4-oxo-butanoic acid (LP43-1)

To a solution of LP42-1 (41 mg, 18.89 μmol, 1 eq.) and HATU (8.62 mg, 22.67 μmol, 1.2 eq.) in DMF (0.3 mL) was added DIPEA (7.32 mg, 56.67 μmol, 9.87 μL, 3 eq). The mixture was stirred at 20° C. for 0.1 hr. LP39 (23.98 mg, 28.34 μmol, 1.5 eq.) was added and the mixture was stirred at 20° C. for 1 hr. LCMS showed the reaction converted completely. The reaction mixture was added into MTBE (40 mL) dropwise. The precipitated yellow solid was collected by centrifuged. LP43-1 (80 mg, 12.56 μmol, 66.49% yield, 47.08% purity) as a light yellow solid.

LCMS (ESI): RT=4.603 min, m/z calcd. For $C_{140}H_{213}FN_{33}O_{39}$ 999.85 $[M+3H]^{3+}$; m/z found 1000.3; LCMS Conditions: Mobile Phase: 1.5 ML/4L TFA in water (solvent A) and 0.75 ML/4L TFA in acetonitrile (solvent B), using the gradient 10%-80% (solvent B) over 6 minutes and holding at 80% for 0.5 minutes at a flow rate of 0.8 ml/min. Column: Xtimate C18 2.1*30 mm, 3 μm.

Step 3: Preparation of 18-[[[(1S)-4-[2-[2-[2-[2-[2-[2-[[2-[[2-[[2-[[2-[[(1S)-2-[[2- [[2-[[2-[[2-[[1-[4-[4-[4-[(2S)-3-[[(1S)-1-carbamoyl-4-(3,5-dimethylphenyl) butyl]amino]-2-[[(2S)-3-carboxy-2-[[(2S)-2-[[(2S, 3R)-2-[[(2S)-3-(2-fluorophenyl)-2-[[(2S,3R)-3-hydroxy-2-[[2-[[(2S)-2-[[3-[2-(1H-imidazol-5-yl) ethylamino]-2,2-dimethyl-3-oxo-propanoyl]amino]-3-(1H-tetrazol-5-yl)propanoyl]amino]acetyl]amino] butanoyl]amino]-2-methyl-propanoyl]amino]-3-hydroxy-butanoyl]amino]-3-hydroxy-propanoyl] amino] propanoyl]amino]-3-oxo-propyl]phenyl]-3-ethyl-phenoxy]butyl]triazol-4-yl]methylamino]-2-oxo-ethyl]amino]-2-oxo-ethyl]amino]-2-oxo-ethyl] amino]-2-oxo-ethyl]amino]-1-(hydroxymethyl)-2-oxo-ethyl]amino]-2-oxo-ethyl]amino]-2-oxo-ethyl] amino]-2-oxo-ethyl]amino]-2-oxo-ethyl]amino]-2-oxo-ethoxy] ethoxy]ethylamino]-2-oxo-ethoxy] ethoxy]ethylamino]-1-carboxy-4-oxo-butyl]amino]-18-oxo-octadecanoic acid (LP43)

To a solution of LP43-1 (80 mg, 12.56 μmol, 47.08% purity, 1 eq.) in DCM (0.7 mL) was added TFA (2.31 g, 20.26 mmol, 1.5 mL, 1612.83 eq). The mixture was stirred at 20° C. for 3 hr. LCMS showed the reaction converted completely. The residue was purified by prep-HPLC (column: 0-phenomenex clarity RP 150*10 mm*5 μm; mobile phase: [water (0.075% TFA)-ACN]; B %: 30%-52%, 20 min) to provide the desired compound LP43 (1.8 mg, 0.571 μmol, 4.55% yield, 91.60% purity) as a white solid.

LCMS: (ESI): RT=3.883 min, m/z calcd. For $C_{132}H_{196}FN_{33}O_{39}$ 1443.21 $[M+2H]^{2+}$; m/z found 1443.8; Reverse phase LCMS was carried out using Chromolith Flash RPC1825-3 mm, with a flow rate of 0.8 ml/min, eluting with a gradient of 10% to 80% acetonitrile containing 0.02% TFA (solvent B) and water containing 0.04% TFA (solvent A).

HPLC: RT=8.30 min. HPLC conditions: Mobile phase: 1.0% ACN in water (0.1% TFA) to 5% ACN in water (0.1% TFA) in 1 minutes; then from 5% ACN in water (0.1% TFA) to 100% ACN (0.1% TFA) in 5 minutes; hold at 100% ACN (0.1% TFA) for 2 minutes; back to 1.0% ACN in water (0.1% TFA) at 8.01 minutes, and hold two minutes. Flow rate: 1.2 ml/min Column: Ultimate XB-C18, 3 μm, 3.0*50 mm.

HRMS (ESI): m/z calcd for $C_{132}H_{195}FN_{33}O_{39}$ 2885.42 $[M+H]^+$, 1442.21 $[M+2H]^{2+}$, found 1442.21 $[M+H]^+$, 1443.7161 $[M+2H]^{2+}$.

UPLC: RT=5.316 min. conditions: Mobile Phase: 0.05% TFA in 1 L water (solvent A) and 0.05% TFA in 1L acetonitrile (solvent B), using the elution gradient 0%-95% (solvent B) over 10 minutes and holding at 80% for 5 minutes at a flow rate of 0.4 mL/minute; Column: Waters ACQUITY UPLC HSS T3 1.8 μm, 2.1*100 mm.

Figure 52:
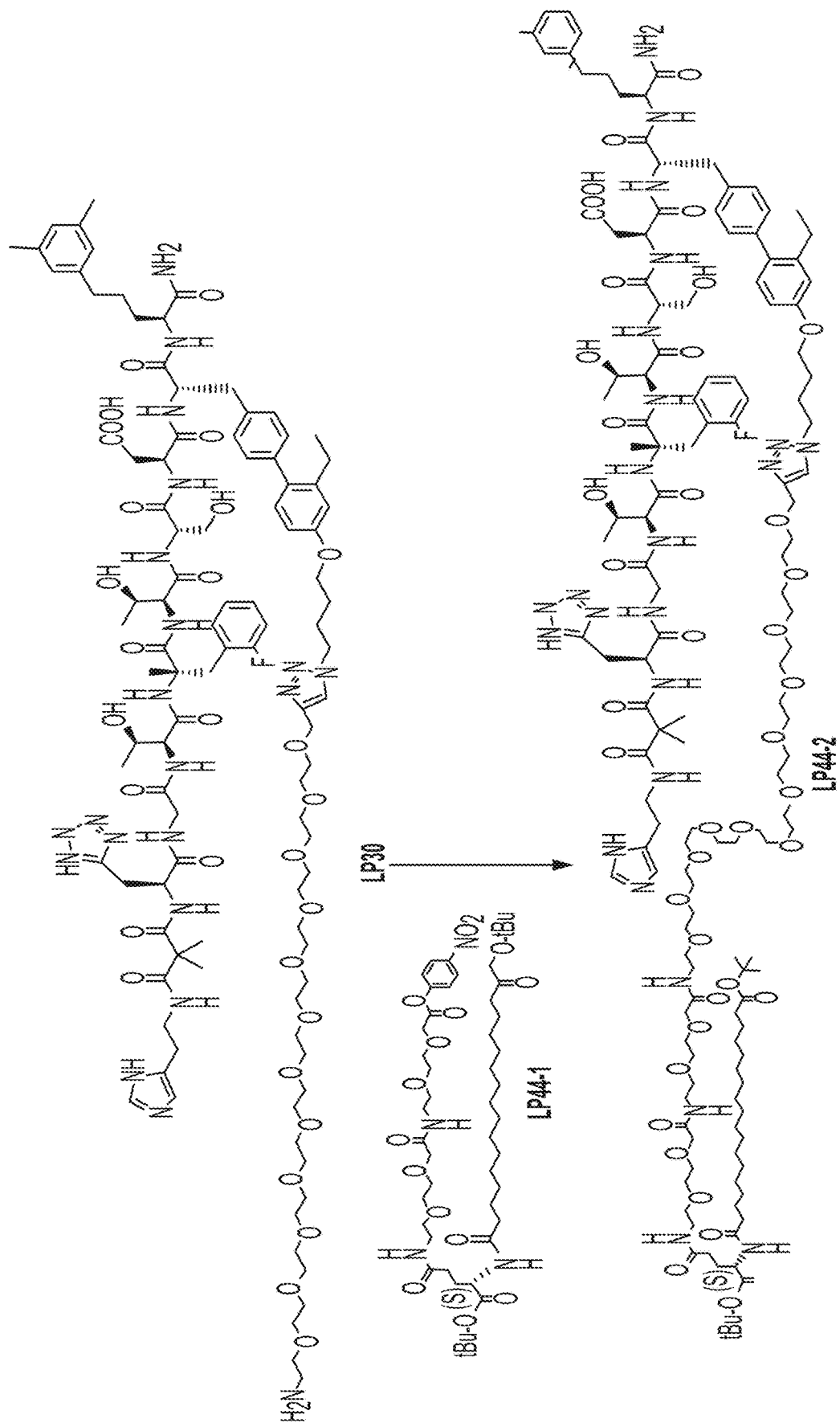
FIG. 52 shows a synthetic route for preparation of Linker-Payload LP44 according to the disclosure.
Figure 52:
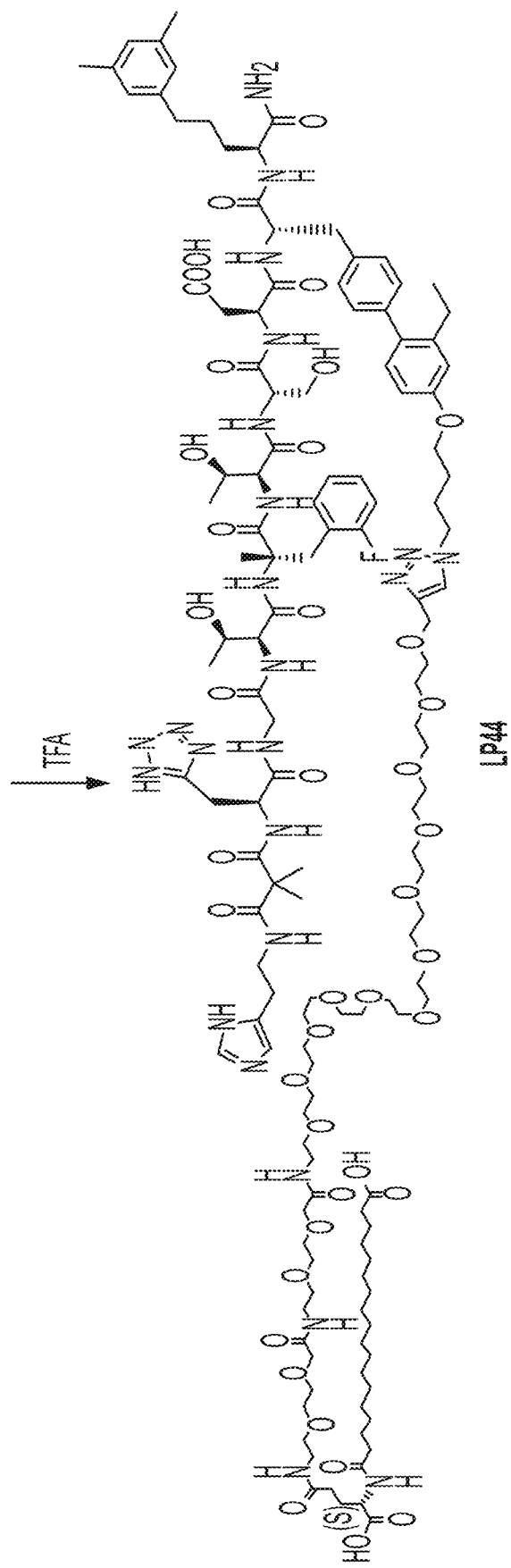

FIG. 52 depicts synthetic route of GLP-1R agonist Linker-payloads (LP44)

Step 1: Preparation of (8S,14S,17S,20S,23S,26S)-8-((1H-tetrazol-5-yl)methyl)-26-(((S)-1-(((S)-1-amino-5-(3,5-dimethylphenyl)-1-oxopentan-2-yl)amino)-3-(4'-(4-(4-((S)-60-(tert-butoxycarbonyl)-81,81-dimethyl-39,48,57,62,79-pentaoxo-2,5,8,11,14,17, 20,23,26,29,32,35, 41,44,50,53,80-heptadecaoxa-38, 47,56,61-tetraazadooctacontyl)-1H-1,2,3-triazol-1-yl)butoxy)-2'-ethyl-[1,1'-biphenyl]-4-yl)-1-oxopropan-2-yl)carbamoyl)-17-(2-fluorobenzyl)-14, 20-bis((R)-1-hydroxyethyl)-23-(hydroxymethyl)-1-(1H-imidazol-5-yl)-5,5,17-trimethyl-4,6,9,12,15,18, 21, 24-octaoxo-3,7,10,13,16,19,22,25-octaazaoctacosan-28-oic acid (LP44-2)

To a solution of LP30 (40 mg, 18.56 μmol, 1 eq.) in DMF (1 mL) were added DIPEA (7.2 mg, 55.68 μmol, 10 μL, 3 eq.) and LP44-1 (22 mg, 22.27 μmol, 1.2 eq.). The resulting mixture was stirred at 20° C. for 0.5 h. LCMS showed the reaction was complete and the desired product was observed. The mixture was poured into ice-cooled MTBE, then filtered and the filter-cake was dried in vacuum. LP44-2 (55 mg, crude) was obtained as a colorless oil.

LCMS (ESI): RT=6.396 min, mass calcd. for $C_{145}H_{230}FN_{24}O_{41}$ 2982.66 $[M+H]^+$, 746.44 $[M+4H]^{4+}$, found 747.2 $[M+4H]^{4+}$. Reverse phase LCMS was carried out using a Chromolith Flash 1.5 ML/4L TFA in water (solvent A) and 0.75 ML/4L TFA in acetonitrile (solvent B), using the gradient 10-80% (solvent B) over 6 minutes and holding at 80% for 0.5 minutes at a flow rate of 0.8 ml/min; Column: Xtimate3 μm, C18,2.1*30 mm.

Step 2: Preparation of 18-[[(1S)-4-[2-[2-[2-[2-[2-[2-[2-[2-[2-[2-[2-[2-[2-[2-[2-[2-[2-[[1-[4-[4-[4-[(2S)-3-[[(1 S)-1-carbamoyl-4-(3,5-dimethylphenyl) butyl]amino]-2-[[(2S)-3-carboxy-2-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(1H-tetrazol-5-yl)propanoyl]amino]acetyl]amino]butanoyl]amino]-2-methyl-propanoyl]amino]-3-hydroxy-butanoyl]amino]-3-hydroxy-propanoyl]amino]propanoyl]amino]-3-oxo-propyl]Phenyl]-3-ethyl-phenoxy]butyl]triazol-4-yl]methoxy]ethoxy]ethoxy]ethoxy]ethoxy]ethoxy]ethoxy]ethoxy]ethoxy]ethoxy]ethoxy]ethoxy]ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid (LP44-2)

A solution of LP44-2 (55 mg, 18.26 µmol, 1 eq.) in TFA (0.5 mL) and DCM (0.5 mL) was stirred at 20° C. for 1 h. LCMS showed the reaction completed and the desired product was observed. (ESI): RT=4.219 min, mass calcd. for $C_{137}H_{214}FN_{24}O_{41}$ 2870.53[M+H]$^+$, 1436.27[M+2H]$^{2+}$, found 1436.2 [M+2H]$^{2+}$. Reverse phase LCMS was carried out using a Chromolith Flash 1.5 ML/4L TFA in water (solvent A) and 0.75 ML/4L TFA in acetonitrile (solvent B), using the gradient 10-80% (solvent B) over 6 minutes and holding at 80% for 0.5 minutes at a flow rate of 0.8 ml/min; Column: Xtimate 3 µm, C18, 2.1*30 mm. The reaction solution was concentrated in vacuum. The residue was purified by prep-HPLC (TFA condition; column: 0-phenomenex clarity RP 150*10 mm*5 µm; mobile phase: [water (0.075% TFA)-ACN]; B %: 40%). The desired compound LP44 (12 mg, 4.05 µmol, 22.19% yield, 96.97% purity) was obtained as a white solid.

LCMS (ESI): RT=4.243 min, mass calcd. for $C_{137}H_{214}FN_{24}O_{41}$ 2870.53 [M+H]$^+$, 1436.27 [M+2H]$^{2+}$, found 1436.4 [M+2H]$^{2+}$. Reverse phase LCMS was carried out using a Chromolith Flash 1.5 ML/4L TFA in water (solvent A) and 0.75 ML/4L TFA in acetonitrile (solvent B), using the gradient 10-80% (solvent B) over 6 minutes and holding at 80% for 0.5 minutes at a flow rate of 0.8 ml/min; Column: Xtimate3 µm, C18, 2.1*30 mm.

HPLC RT=9.13 min. HPLC conditions: Mobile Phase: 2.75 ML/4L TFA in water (solvent A) and 2.5 ML/4L TFA in acetonitrile (solvent B), using the elution gradient 10%-80% (solvent B) over 10 minutes and holding at 80% for 5 minutes at a flow rate of 1.5 ML/min; Column: Ultimate XB-C18.3 µm,3.0*50 mm.

Figure 53:
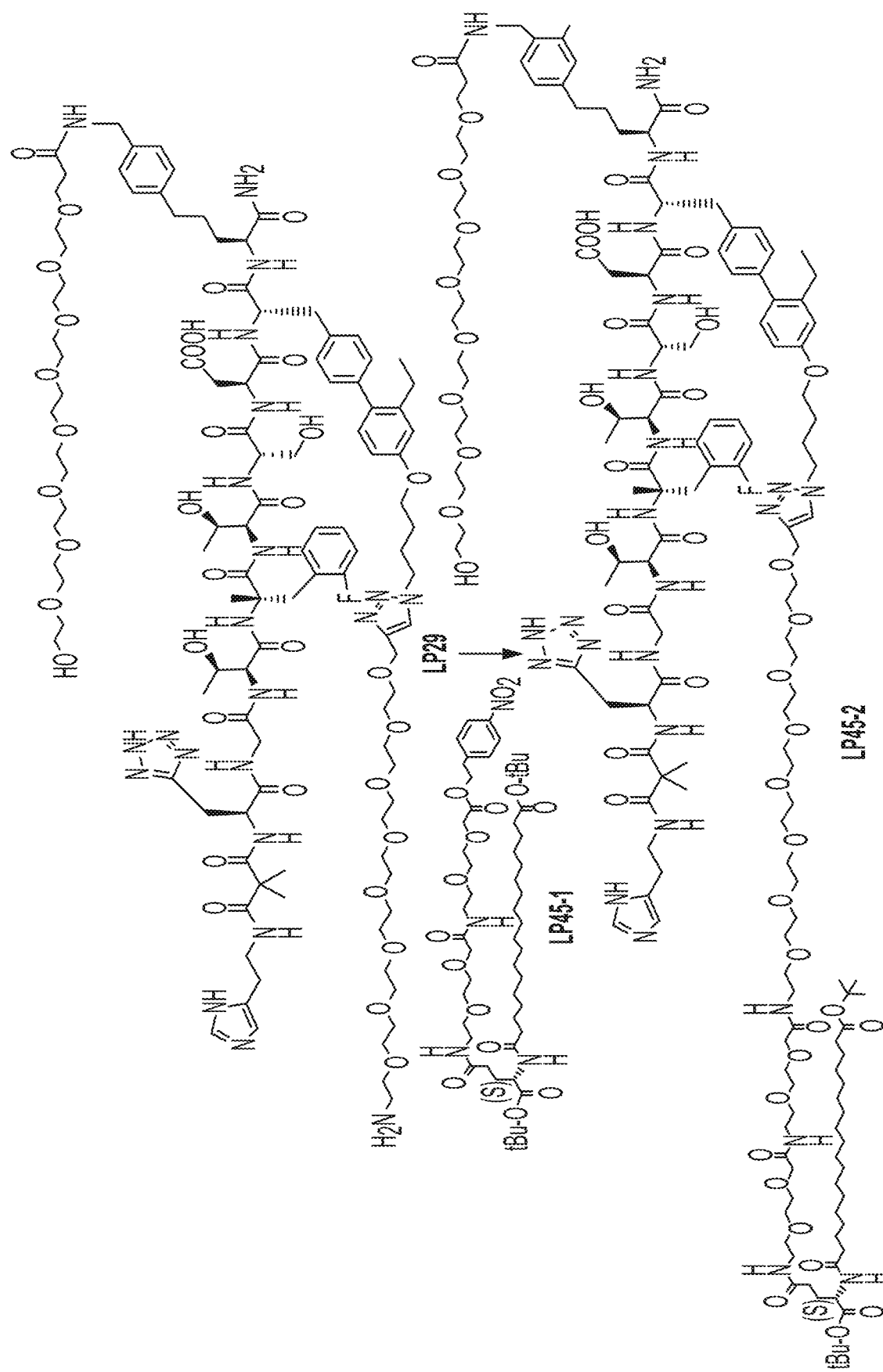
FIG. 53 shows a synthetic route for preparation of Linker-Payload LP45 according to the disclosure.
Figure 53:
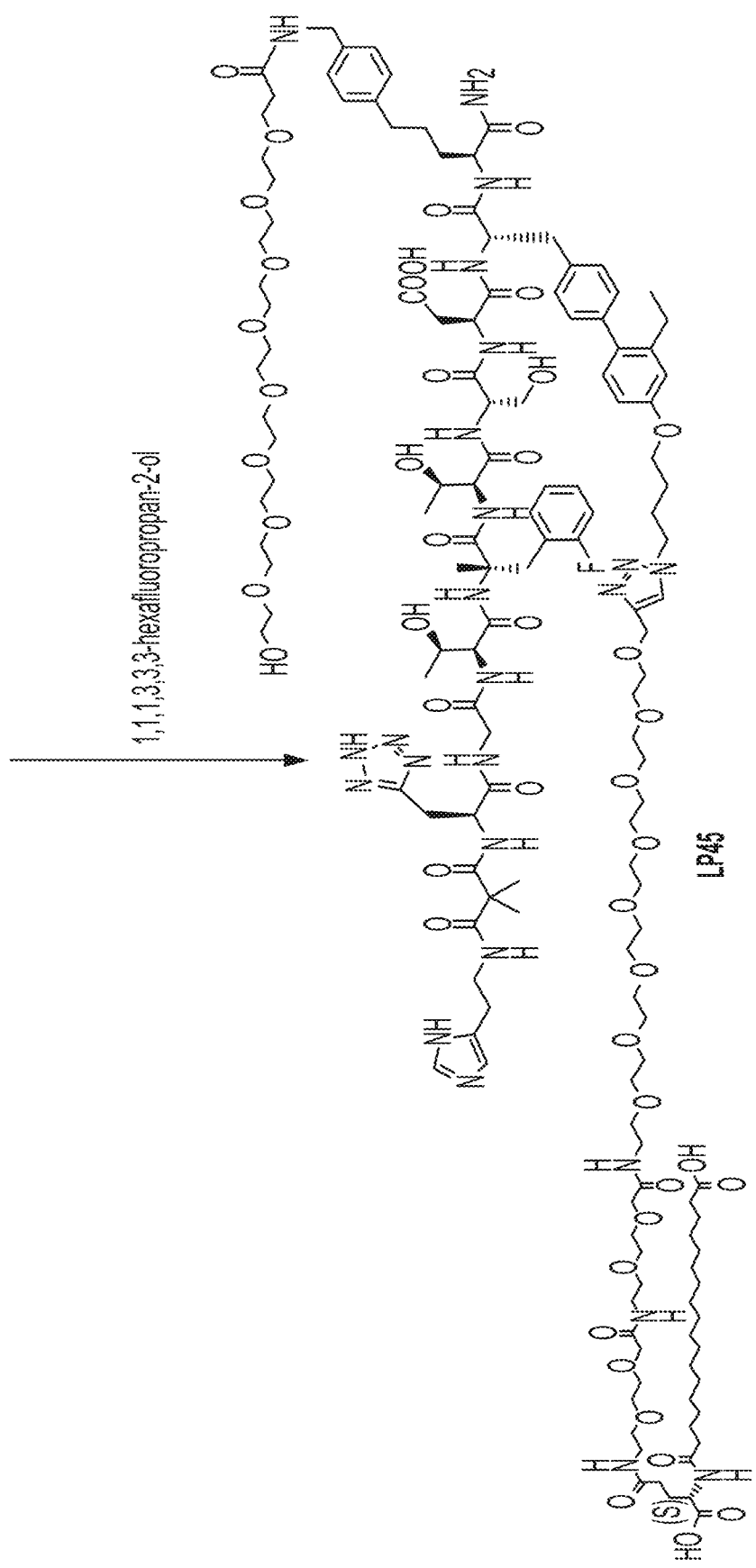

FIG. 53 depicts synthetic route of GLP-1R agonist Linker-payloads (LP45)

Step 1: Preparation of (3S)-4-[[(1S)-1-[[4-[4-[4-[4-[2-[2-[2-[2-[2-[2-[2-[2-[[2-[2-[2-[[2-[2-[2-[[(4S)-5-tert-butoxy-4-[(18-tert-butoxy-18-oxo-octadecanoyl)amino]-5-oxo-pentanoyl]amino]ethoxy]ethoxy]acetyl]amino]ethoxy]ethoxy]acetyl]amino]ethoxy]ethoxy]ethoxy]ethoxy]ethoxy]eth oxy]ethoxy]ethoxymethyl]triazo-1-yl]butoxy]-2-ethyl-Phenyl] Phenyl]methyl]-2-[[(1S)-1-carbamoyl-4-[4-[[3-[2-[2-[2-[2-[2-[2-[2-(2-hydroxyethoxy)ethoxy]ethoxy]ethoxy]ethoxy] ethoxy]ethoxy]ethoxy]ethoxy] propanoylamino]methyl]phenyl]butyl]amino]-2-oxo-ethyl]amino]-3-[[(2S)-2-[[(2S,3R)-2-[[3-(2-fluorophenyl)-2-[[(2S,3R)-3-hydroxy-2-[[2-[[(2S)-2-[[3-[2-(1H-imidazol-5-yl)ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl] amino]-3-hydroxy-propanoyl]amino]-4-oxo-butanoic acid (LP45-2)

To a solution of LP29 (210 mg, 87.33 µmol, 1 eq.) in DMF (0.5 mL) were added DIPEA (22.57 mg, 174.66 µmol, 30.42 µL, 2 eq) and LP45-1 (168.93 mg, 174.66 µmol, 2 eq). The mixture was stirred at 25° C. for 1 hr. LCMS showed LP29 was consumed completely and one main peak with the desired mass was detected. The reaction mixture was partitioned in H$_2$O (20 mL) and extracted with EtOAc (10 mL×3). The organic phase was separated, washed with brine (10 mL), dried over Na$_2$SO$_4$, filtered and concentrated under reduced pressure to give a residue. The desired compound LP45-2 (200 mg, crude) was obtained as a yellow oil.

LCMS (ESI): RT=5.154 min, mass calcd. for $C_{155}H_{248}FN_{25}O_{47}$ 3231.78 [M+H]$^+$, $C_{155}H_{251}FN_{25}O_{47}$ 1077.9 [M+3H]$^{3+}$, found 1078.45 [M+3H]$^{3+}$. LCMS method A: a MERCK, RP-18e 25-2 mm column, with a flow rate of 1.5 mL/min, eluting with a gradient of 5% to 95% acetonitrile containing 0.02% TFA (solvent B) and water containing 0.04% TFA (solvent A).

Step 2: Preparation of 18-[[(1S)-4-[2-[2-[2-[2-[2-[2-[2-[2-[2-[2-[2-[2-[2-[2-[[1-[4-[4-[4-[(2S)-3-[[(1S)-1-carbamoyl-4-[4-[[3-[2-[2-[2-[2-[2-[2-[2-(2-hydroxy-ethoxy)ethoxy]ethoxy]ethoxy]ethoxy]ethoxy]ethoxy]ethoxy]propanoylamino]methyl]phenyl] butyl]amino]-2-[[(2S)-3-carboxy-2-[[(2S)-2-[[(2S,3R)-2-[[3-(2-fluorophenyl)-2-[[(2S,3R)-3-hydroxy-2-[[2-[[(2S)-2-[[3-[2-(1H- imidazol-5-yl) ethylamino]-2,2-dimethyl-3-oxo-propanoyl]amino]-3-(2H-tetrazol-5-yl) propanoyl]amino]acetyl]amino]butanoyl]amino]-2-methyl-propanoyl]amino]-3-hydroxy-butanoyl]amino]-3-hydroxy-propanoyl]amino]propanoyl]amino]-3-oxo-propyl]phenyl]-3-ethyl-phenoxy]butyl]triazol-4-yl]methoxy]ethoxy] ethoxy]ethoxy]ethoxy]ethoxy]ethoxy]ethoxyl ethylamino]-2-oxo-ethoxy]ethoxy]ethylamino]-2-oxo-ethoxy]ethoxy]ethylamino]-1-carboxy-4-oxo-butyl]amino]-18-oxo-octadecanoic acid (LP45)

To a solution of LP45-2 (200 mg, 61.87 µmol, 1 eq) in 1,1,1,3,3,3-HEXAFLUORO-2-PROPANOL (2 mL). The mixture was stirred at 90° C. for 2 hr under microwave. LCMS showed LP45-2 was consumed completely and one main peak with desired mass was detected. LCMS (ESI): RT=3.575 min, mass calcd. for $C_{147}H_{233}FN_{25}O_{47}$ 3119.65 [M+H]$^+$, $C_{147}H_{235}FN_{25}O_{47}$ 780.7 [M+4H]$^{4+}$, found 781.0 [M+4H]$^{4+}$. LCMS method A: a MERCK, RP-18e 25-2 mm column, with a flow rate of 1.5 mL/min, eluting with a gradient of 10% to 80% acetonitrile containing 0.02% TFA (solvent B) and water containing 0.04% TFA (solvent A). The reaction mixture was concentrated under vacuum to give crude. The residue was purified by prep-HPLC (column: YMC-Actus Triart C18 150*30 mm*5 µm; mobile phase: [water (0.1% TFA)-ACN]; B %: 36%-56%, 10.5 min) to obtain LP45 (18.03 mg, 5.75 µmol, 9.29% yield, 99.51% purity) as a white solid.

LCMS (ESI): RT=3.550 min, m/z calcd. for $C_{147}H_{233}FN_{25}O_{47}$ 3119.65 $[M+H]^+$, $C_{147}H_{235}FN_{25}O_{47}$ 780.7 $[M+4H]^{4+}$, found 781.0 $[M+4H]^{4+}$. LC-MS method A: a MERCK, RP-18e 25-2 mm column, with a flow rate of 1.5 mL/min, eluting with a gradient of 10% to 80% acetonitrile containing 0.02% TFA (solvent B) and water containing 0.04% TFA (solvent A).

Example 6. Preparative HPLC Purification of the Crude Peptidomimtics

The preparative HPLC was carried out on a Shimadzu LC-8a Liquid chromatograph. A solution of crude peptide dissolved in DMF or water was injected into a column and eluted with a linear gradient of ACN in water. Different methods were used. (See General Information). The desired product eluted were in fractions and the pure peptidomimetics were obtained as amorphous with powders by lyophilization of respective HPLC fractions. In general, after the prep-HPLC purification, the overall recovery was found to be in the range of 40-50% yield.

Preparative HPLC method A: using FA condition (column: Xtimate C18 150*25 mm*5 µm; mobile phase: [water (0.225% FA)-ACN]; B %: 40%-70%, 7 min) to afford a pure product.

Preparative HPLC method B: using TFA condition (column: YMC-Exphere C18 10 µm 300*50 mm 12 nm; mobile phase: [water (0.1% TFA)-ACN]; B %: 15%-45%, 55 min) to afford a pure product.

Preparative HPLC method C: using neutral condition (column: Phenomenex Gemini-NX 150*30 mm*5 µm; mobile phase: [water (10 mM $NH_4HCO_3$)-ACN]; B %: 21%-51%, 11 min) to afford a pure product.

Preparative HPLC method D: using neutral condition (column: Waters Xbridge 150*255u; mobile phase: [water (10 mM $NH_4HCO_3$)-ACN]; B %: 20%-50%, 7 min) to afford a pure product.

Preparative HPLC method E: using FA condition (column: Phenomenex Luna C18 250*50 mm*10 µm; mobile phase: [water (0.225% FA)-ACN]; B %: 55%-86%, 21 min) to afford a pure product.

Example 7. Preparation of Antibody-Drug Conjugates

7.1 General Site-Specific Conjugation

This example demonstrates two methods for site-specific ATDC conjugation, generally, of a payload to an antibody comprising a Q-tag thereof. ATDCs 1-30 were prepared with LP1-LP11 and anti-GLP1R antibodies mAb1-mAb13 or control antibodies mAb1-mAb6 as summarized in Table 3 below. The ES-MS results and DAR values of the ADCs according to the disclosure are summarized in Table 3.

TABLE 3

Site-specific GLP1 Antibody-Drug Conjugates

| Target Ab | Ab # | LP # | Yield | LCMS DAR | MS (DAR2) | ATDC # |
|---|---|---|---|---|---|---|
| GLP1R | COMP mAb 1 | LP1 | 20% | 1.4 | 103081 F(ab')2 | 1 |
| non-target molecule (Cont 1) | Isotype control mAb 3 | LP1 | 50% | 2.0 | 150044 | 2 |
| GLP1R | COMP mAb 1 | LP2 | 35% | 1.5 | 103435 F(ab')2 | 3 |
| non-target molecule (Cont 1) | Isotype control mAb 3 | LP2 | 70% | 2.0 | 150396 | 4 |
| GLP1R | COMP mAb 1 | LP3 | 40% | 1.4 | 151304 | 5 |
| non-target molecule (Cont 1) | Isotype control mAb 3 | LP3 | 30% | 2.0 | 150748 | 6 |
| GLP1R | COMP mAb 1 | LP4 | 93% | 2.0 | 155254 | 7 |
| GLP1R | mAb 7 | LP4 | 91% | 2.0 | 149325 | 8 |
| GLP1R | mAb 8 | LP4 | 50% | 4.2 | 156816 (DAR4) | 9 |
| GLP1R | mAb 9 | LP4 | 97% | 3.3 | 154870 | 10 |
| GLP1R | mAb 2 | LP4 | 99% | 2.4 | 155367 | 11 |
| non-target molecule (Cont 2) | control mAb 4 | LP4 | 40% | 2.0 | 151752 | 12 |
| non-target molecule (Cont 3) | control mAb 5 | LP4 | 95% | 2.0 | 155027 | 13 |
| non-target molecule (Cont 4) | control mAb 6 | LP4 | 95% | 2.2 | 155060 | 14 |
| non-target molecule (Cont 1) | Isotype control mAb 3 | LP4 | 55% | 2.0 | 151789 | 15 |
| GLP1R | COMP mAb 1 | LP6 | 30% | 1.1 | 150757 | 16 |
| GLP1R | mAb 10 | LP6 | 8% | 2.9 | 153054 | 17 |

TABLE 3-continued

Site-specific GLP1 Antibody-Drug Conjugates

| Target Ab | Ab # | LP # | Yield | LCMS DAR | MS (DAR2) | ATDC # |
|---|---|---|---|---|---|---|
| GLP1R | mAb 2 | LP6 | 77% | 2.5 | 153738 | 18 |
| non-target molecule (Cont 3) | control mAb 5 | LP6 | 28% | 2.0 | 153389 | 19 |
| GLP1R | mAb 2 | LP9 | 44% | 2.2 | 153413 | 20 |
| GLP1R | mAb 2 | LP11 | 72% | 1.2 | 152981 | 21 |
| GLP1R | mAb 6 | LP11 | 69% | 1.6 | 152994 | 22 |
| GLP1R | mAb 11 | LP11 | 64% | 1.5 | 151878 | 23 |
| GLP1R | mAb 3 | LP11 | 68% | 1.5 | 151876 | 24 |
| GLP1R | mAb 12 | LP11 | 55% | 1.6 | 153132 | 25 |
| GLP1R | mAb 5 | LP11 | 49% | 1.4 | 152661 | 26 |
| GLP1R | mAb 13 | LP11 | 46% | 1.7 | 152769 | 27 |
| GLP1R | mAb 4 | LP11 | 41% | 1.5 | 152735 | 28 |
| GLP1R | Isotype control mAb 3 | LP4 | 61% | 1.7 | 155264 | 31 |
| GLP1R | mAb 14 | LP11 | 25% | 1.4 | 153549 | 32 |
| GLP1R | mAb 15 | LP11 | 53% | 1.3 | 153514 | 33 |
| GLP1R | mAb 16 | LP11 | 66% | 1.1 | 153096 | 34 |
| GLP1R | mAb 17 | LP11 | 47% | 1.3 | 152660 | 35 |
| GLP1R | mAb 18 | LP11 | 25% | 1.1 | 154279 | 36 |
| GLP1R | mAb 19 | LP11 | 62% | 0.9 | 154246 | 37 |
| GLP1R | mAb 20 | LP11 | 27% | 1.3 | 154623 | 38 |
| GLP1R | mAb 21 | LP11 | 12% | 1.0 | 154614 | 39 |
| GLP1R | mAb 6 | LP11 | 67% | 1.6 | 152994 | 40 |
| GLP1R | mAb 2 | LP11 | 82% | 1.4 | 152989 | 41 |
| GLP1R | mAb 3 | LP11 | 60% | 1.6 | 151882 | 42 |
| GLP1R | mAb 4 | LP11 | 60% | 1.7 | 152731 | 43 |
| GLP1R | mAb 5 | LP11 | 69% | 1.7 | 152660 | 44 |
| GLP1R | mAb 3 | LP11 | 73% | 1.7 | 25811 (LC-DAR1) | 45 |
| GLP1R | mAb 15 | LP11 | 69% | 1.5 | 25759 (LC-DAR1) | 46 |
| GLP1R | mAb 16 | LP11 | 86% | 1.3 | 26660 (LC-DAR1) | 47 |
| GLP1R | mAb 17 | LP11 | 81% | 1.5 | 26007 (LC-DAR1) | 48 |
| GLP1R | mAb 19 | LP11 | 86% | 1.0 | 26146 (LC-DAR1) | 49 |
| GLP1R | mAb 3 | LP11 | 78% | 1.7 | 151865 | 50 |
| GLP1R | mAb 17 | LP11 | 63% | 1.7 | 152637 | 51 |
| GLP1R | mAb 3 | LP11 | n/a | 2.1 | 148977 | 52 |
| GLP1R | mAb 17 | LP11 | n/a | 2.1 | 149754 | 53 |
| GLP1R | mAb 3 | LP11 | 81% | 2.2 | 148971 | 54 |
| GLP1R | mAb 17 | LP11 | 60% | 2.1 | 149752 | 55 |
| GLP1R | mAb 3 | LP11 | 78% | 2.2 | 148978 | 56 |
| GLP1R | mAb 17 | LP11 | 80% | 2.1 | 149753 | 57 |
| non-target molecule (Cont 5) | Isotype control mAb 1 | LP11 | 65% | 1.7 | 151998 | 29 |
| non-target molecule (Cont 6) | Isotype control mAb 2 | LP11 | 62% | 1.5 | 151995 | 30 |
| non-target molecule (Cont 6) | Isotype control mAb 2 | LP11 | 80% | 1.7 | 151996 | 58 |
| non-target molecule (Cont 6) | Isotype control mAb 2 | LP11 | 91% | 1.6 | 26410 (LC-DAR1) | 59 |
| C.Difficile (Cont 7) | Isotype control mAb 7 | LP11 | 64% | 1.1 | n/a | 60 |
| hANGPTL4 (Cont 8) | Isotype control mAb 8 | LP11 | 52% | 1.3 | n/a | 61 |
| EGFRvIII (Cont 9) | Isotype control mAb 9 | LP11 | 51% | 1.6 | n/a | 62 |

7.2 General Two-Step Conjugation Protocol

Figure 54:
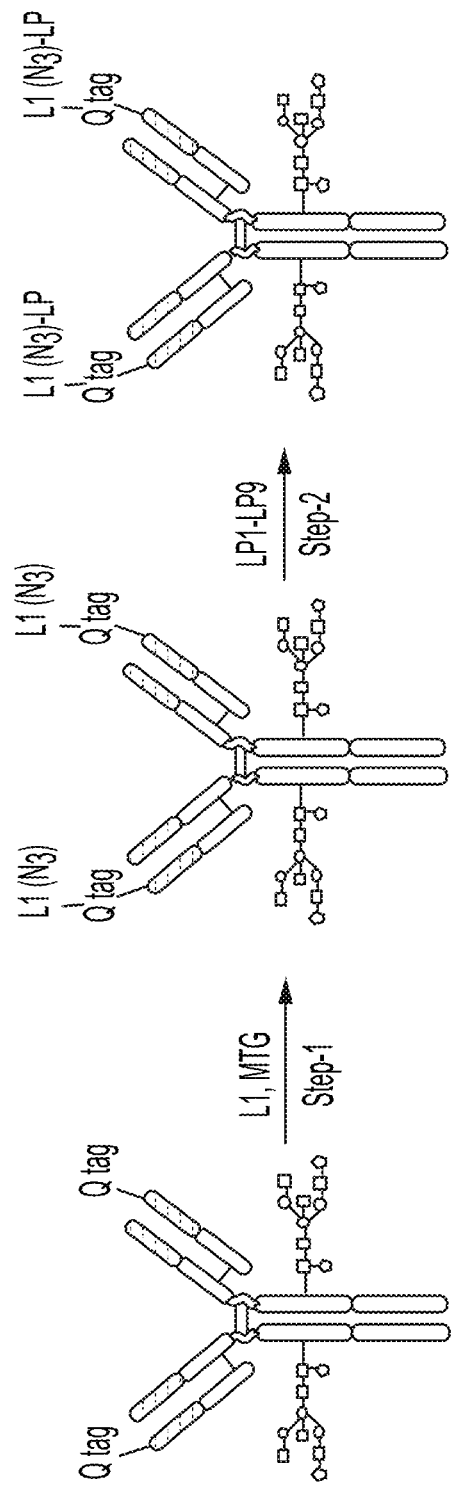
FIG. 54 shows a schematic of a general two-step conjugation procedure for the preparation of site-specific antibody-drug conjugates.

This method includes two step process shown in FIG. 54. The first step is microbial transglutaminase (MTG) mediated attachment of a First Linker (La), e.g., a small molecular amine, e.g., an azide-PEG3-amine, to the antibody, wherein an excess of the amine reagent is used to avoid potential cross-linking of antibody chains. The second step attaches the alkyne-linked payload linker payload (LP) to the Azido-tagged conjugate via a strain-promoted azide-alkyne cycloaddition (SPAAC).

The generic procedures are following.

Step 1: Making a Site-Specific Azido-Functionalized Antibody Drug Conjugate Containing Two Azido Groups Anti-GLP1R human IgG antibody or isotype control antibody containing Q-tag was mixed with 100-200 molar equivalent of azido-PEG3-amine (L1, MW 218.26 g/mol). The resulting solution was mixed with transglutaminase (Zedira, Darmstadt, Germany, 1 U MTG per mg of antibody)

resulting in a final concentration of the antibody at 1-10 mg/mL. The reaction mixture was incubated at 25-37° C. for 4-72 hours with gently shaking while reaction was monitored by ESI-MS. Upon the completion, the excess amine and MTG were removed by size exclusion chromatography (SEC) or protein A column chromatography. The conjugate was characterized by UV-Vis, SEC and ESI-MS. The azido linkers attached antibody (Ab-N$_3$) resulting in a 402 Da mass increase for the DAR2 conjugate. Conjugate's monomer purity was >95%.

Step 2: Making Site-Specific Conjugates in Table 1 Via [2+3] Click Reactions Between Azido-Functionalized Antibodies (Ab-N$_3$) and an Alkyne Containing Linker-Payload A site-specific antibody drug conjugate was prepared by incubating azido-functionalized antibody (Ab-N$_3$, 1-20 mg/mL) in PBS (pH7.4) with >3 molar equivalents of a linker-payload dissolved in an organic solvent, such as DMSO or DMA (10-20 mg/mL) to have the reaction mixture containing 5-15% organic solvent (v/v), at 25-37° C. for 1-48 hours while gently shaking. The reaction was monitored by ESI-MS. Upon completion, the excess amount of linker-payload and protein aggregates were removed by size exclusion chromatography (SEC). The purified conjugate was concentrated, sterile filtered and characterized by UV-Vis, SEC, HIC and ESI-MS. Conjugates monomer purity was >95%.

In a specific example, 36 mg anti-GLP1R mouse IgG antibody COMP mAb 1 containing a heavy chain N-term Q-tag was mixed with 150 molar equivalents of azido-PEG3-amine (L1, MW 218.26 g/mol). The resulting solution was mixed with microbial transglutaminase (1 U mTG per mg of antibody, Zedira, Darmstadt, Germany) resulting in a final concentration of the antibody at 4.0 mg/mL. The reaction mixture was incubated at 37° C. for 18 hours while gently shaking while monitored by ESI-MS. Upon the completion, the excess amine and mTG were removed by size exclusion chromatography (SEC). The concentrated site-specific antibody azido conjugate (2.9 mg/mL) in PBS (pH7.4) was mixed with 5 molar equivalents of linker-payload (LP4) in 10 mg/mL of DMSO. Additional DMSO was added to 10% total DMSO (v/v), and the solution was set at 25° C. for 22 hours with gently shaking. The reaction was monitored by ESI-MS. Upon completion, the excess amount of linker-payload and protein aggregates were removed by size exclusion chromatography (SEC). The purified conjugate was concentrated, sterile filtered and characterized by UV-Vis, SEC, HIC and ESI-MS. Conjugate monomer purity was 99.7%. The drug attached antibody resulting in a 5931 Da mass increase for the DAR2 conjugate.

S7.3 General One-Step Conjugation Protocol

Figure 55:
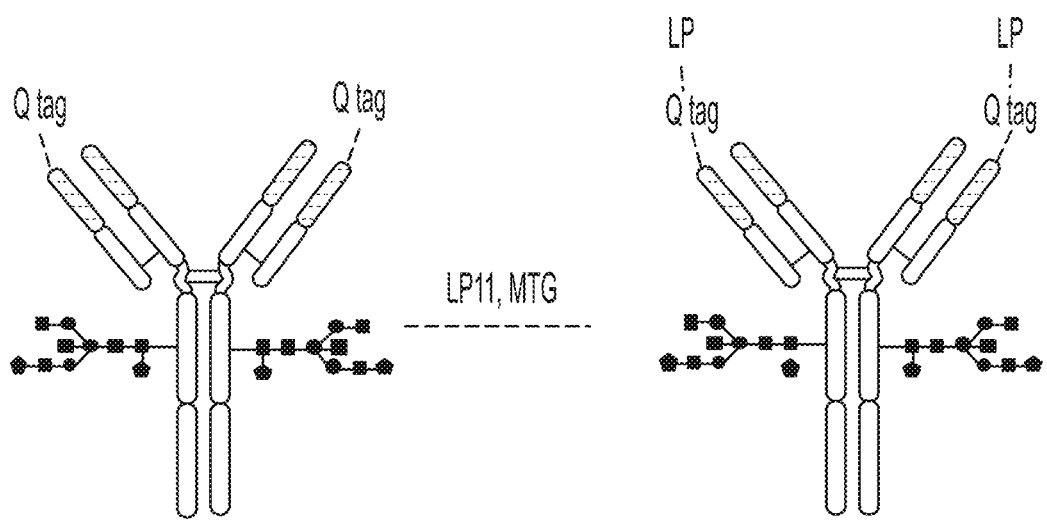
FIG. 55 shows a schematic of a general one-step conjugation procedure for the preparation of site-specific antibody-drug conjugates.

This method includes microbial transglutaminase (MTG) mediated attachment of Linker payload (LP) to the antibody, shown in FIG. 55.

The generic procedure is following.

Anti-GLP1R human IgG antibody or isotype control antibody containing Q-tag was mixed with 10-20 molar equivalent of linker payload (LP11, MW 1979.24 g/mol); Tris-HCl was added to elevate pH to around pH7.4. The resulting solution was mixed with transglutaminase (Zedira, Darmstadt, Germany, 1 U MTG per mg of antibody) resulting in a final concentration of the antibody at 1-10 mg/mL. The reaction mixture was incubated at 25-37° C. for 4-72 hours with gently shaking while reaction was monitored by ESI-MS. Upon the completion, the excess amount of linker-payload, protein aggregates and MTG were removed by size exclusion chromatography (SEC). The purified conjugate was sterile filtered and characterized by UV-Vis, SEC, HIC and ESI-MS. Conjugates monomer purity was >95%.

In a specific example, 1.5 mg anti-GLP1R human IgG antibody mAb 6 containing a heavy chain N-term Q-tag was mixed with 15 molar equivalents of linker-payload (LP11) in 10 mg/mL of DMSO. Additional DMSO was added to a 10% total DMSO (v/v), followed by 1M Tris-HCl pH8 to bring the Tris concentration to 25 mM (pH ~8). The resulting solution was mixed with transglutaminase (Zedira, Darmstadt, Germany, 1 U MTG per mg of antibody) resulting in a final concentration of the antibody at 3.0 mg/mL. The solution was set at 37° C. for 23 hours with gently shaking. The reaction was monitored by ESI-MS. Upon completion, the excess amount of linker-payload, protein aggregates and MTG were removed by size exclusion chromatography (SEC). The purified conjugate was concentrated, sterile filtered and characterized by UV-Vis, SEC, HIC and ESI-MS. The drug attached antibody resulting in a 3924 Da mass increase for the DAR2 conjugate.

Example 8. In Vitro Characterization of Payloads and Linker-Payloads 8.1 Human GLP1R cAMP Accumulation Assay (Cyclic AMP Determination)

The functional activity of the test compounds for agonizing GLP1R were evaluated using a cell-based assay. For the assay, HEK293 cells over-expressing full length human GLP-1R were utilized and the downstream cAMP accumulation was assessed as a measure of human GLP-1R stimulation. For the assay, compounds were 5-fold serially diluted in DMSO with a starting concentration of 1 µM in PP-384 microplates using an automated Bravo liquid handling platform. Diluted compounds were transferred to OptiPlates (100 nL/well) using an Echo liquid handler. HEK293/hGLP1R cells were thawed in 37° C. water-bath, washed 2 times with HBSS and re-suspended in assay buffer (HBSS+5 mM HEPES+500 µM IBMX+0.1% BSA). After the compounds were added, HEK293 cells were then seeded at 1×10$^5$ cells/well (10 µL) into the 384 OptiPlates containing diluted compounds. After centrifugation, the assay plate was incubated at 23° C. for 30 min. The reaction was terminated by adding 10 µL of lysis buffer containing D2-cAMP and a cAMP-antibody from the cyclic AMP immunoassay kit (Cisbio, Cat #62AM4PEJ). Following a one-hour incubation, assay plates were read on an EnVision plate reader at 665/615 nm. The levels of cAMP per well were calculated using a standard curve generated by GraphPad Prism. Percent activity was calculated according to the formula (% Activity=100%* (cAMP level-LC)/(HC-LC)). EC$_{50}$ values were fitted from a four-parameter logistic equation over a 10-point response curve (GraphPad Prism).

As shown in Table 4, the test payloads and linker-payloads demonstrated cAMP activation with EC$_{50}$ values ranging from 39 µM to >11 nM, with most agonizing GLP1R with EC$_{50}$ values of <1 nM. The reference compound, GLP1, demonstrated cAMP activation with an EC$_{50}$ value of 28 µM.

TABLE 4

Activity of Payloads and Linker-Payloads in the cAMP Accumulation Assay

| P# | cAMP EC$_{50}$ (nM) |
|---|---|
| GLP1 | 0.028 |
| P3 | 1.433 |
| P4 | 0.156 |
| P5 | 0.115 |
| P6 | 0.853 |
| P7 | 2.055 |
| P8 | 0.497 |
| P9 | 0.050 |
| P10 | 0.047 |
| P11 | 1.028 |
| P12 | 0.039 |
| P13 | 0.914 |
| P14-S | 0.727 |
| P15-R | 0.117 |
| P16-S | 0.544 |
| P17-R | 11.240 |
| P18 | 0.370 |
| P19 | 0.156 |
| P20 | 0.370 |
| P21 | 0.427 |
| P22 | 0.603 |
| P23 | 0.198 |
| P24 | 0.136 |
| LP5 | 0.044 |
| LP6 | 0.436 |
| LP7 | 0.378 |
| LP8 | 0.412 |
| LP9 | 0.078 |
| LP10 | 0.982 |
| LP15 | 0.649 |
| LP16 | 1.038 |
| LP11 | 0.318 |
| LP18 | 0.458 |
| LP19 | 0.558 |
| LP20 | 0.314 |
| LP22 | 2.706 |
| LP23 | 0.534 |

8.2 Plasma Stability

The plasma stability of payloads and linker payloads of the disclosure were measured. For the assay, pooled frozen plasma (human, mouse or monkey) was thawed in cold water or a 37° C. water bath prior to experiment. Plasma was centrifuged at 4000 rpm for 5 min if any clots were observed, they were subsequently removed. If required, the pH was adjusted to 7.4±0.1. For the preparation of compounds and positive controls, a 1 mM intermediate solution was prepared by diluting 10 µL of their stock solution with 90 µL DMSO; a 1 mM intermediate solution of the positive control (Propantheline) was prepared by diluting 10 µL of its stock solution with 90 µL ultrapure water. Subsequently, 100 µM dosing solution for each compound was prepared by diluting 20 µL of the intermediate solution (1 mM) with 180 µL 45% MeOH/H$_2$O. 98 µL of plasma was spiked with 2 µL of dosing solution (100 µM) to achieve the final concentration of 2 µM in duplicate. Samples were then incubated at 37° C. in a water bath. Four sets of time points were collected: (A) for the 2 hours test, the samples were collected at 0, 10, 30, 60 and 120 min; (B) for the 24 hours test the samples were collected at 0, 10, 60, 240 and 1440 min; (C) for the for 3 days test, the samples were collected at 0, 24, 48 and 72 hours (D) for the for 7 days test, the samples were collected at 0, 24, 48, 72, 96, 120, 144 and 168 hours. At each time point, 400 µL of stop solution (200 ng/mL tolbutamide plus 200 ng/mL labetalol in 50% ACN/MeOH) was added to precipitate protein and mixed thoroughly. Sample plates were then centrifuged at 4,000 rpm for 10 min. An aliquot of supernatant (50 µL) was transferred from each well and mixed with 100 µL ultra-pure water. The samples were then shaken at 800 rpm for approximately 10 min before submitting for LC-MS/MS analysis.

As shown in Table 5A, most of the test payloads and linker-payloads were highly stable in human plasma, having T$_{1/2}$ values of >48 hours in a one-day plasma assay and >14 days in a 7-day plasma assay; the reference compound, GLP1, is unstable in human plasma and demonstrated a T$_1$/2 value of <10 minutes. As shown in Table 5B, The one linker payload of the disclosure (LP11) tested in monkey plasma had a T$_{1/2}$ value of >49.4 hours. Two linker payloads of the disclosure (LP11 and LP23) that were tested in mouse plasma stability had T$_{1/2}$ values of either >6 days in the 3 day assay or >4 hours in the 2 hour assay.

TABLE 5A

Human plasma stability of Payloads and Linker-Payloads

| P# | Human plasma stability assay T½ (hr) | Tested time* |
|---|---|---|
| P2 | 10.74 | B |
| P3 | >57.81 | A |
| P4 | >57.81 | A |
| P6 | >57.81 | A |
| P8 | >57.81 | A |
| P9 | >57.81 | A |
| P10 | 1.83 | B |
| P11 | >57.81 | A |
| P12 | >57.81 | A |
| P13 | 16.9 | A |
| P19 | >57.81 | A |
| P21 | >173.4 | C |
| P23 | 10.74 | B |
| P41 | >57.81 | A |
| LP11 | >173.4 (human) | C |
| LP11 | >49.4 (monkey) | C |
| LP11 | >173.4 (mouse) | C |
| LP23 | >4.8 hr (mouse) | B |
|  | >4.8 hr (human) |  |
| LP24 | >404.7 hr | D |
| LP25 | 284.8 hr | D |
| LP26 | >404.7 hr | D |
| LP28 | >173.4 | C |
| LP29 | >173.4 | C |
| LP34 | >173.4 | C |

*Tested for 1 day in A;
2 hrs in B;
3 days in C;
7 days in D.

TABLE 5B

Monkey and Mouse plasma stability of Linker-Payloads

| Species | P# | plasma stability T½ | Assay time |
|---|---|---|---|
| Monkey | LP11 | >49.4 hr | 3 days |
| Mouse | LP11 | >6 days | 3 days |
|  | LP23 | >4 hr | 2 hr |

Table 5C, below, summarizes tested parameters for Linker-Payload LP11 having the structure shown below.

(LP11 (SEQ ID NO: 91))

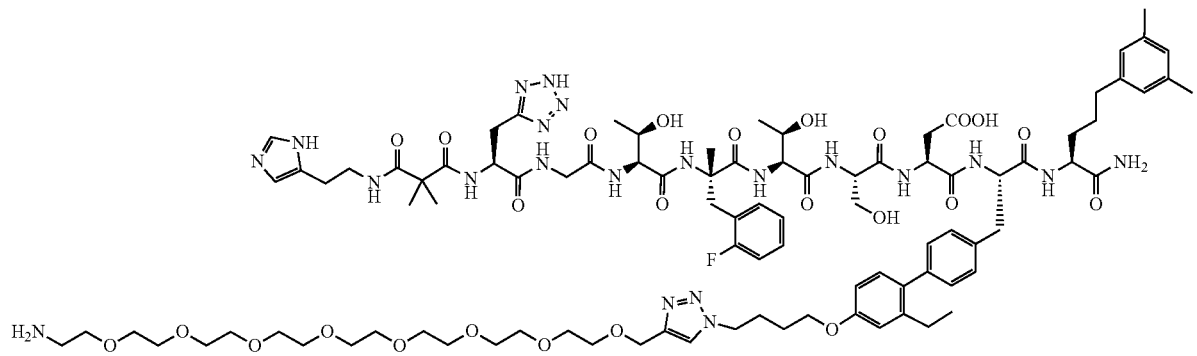

TABLE 5C

LP11 Characterization

| Assay | | Linker-Payload LP11 |
|---|---|---|
| GLP1R LUC EC$_{50}$ (nM) | | 0.016 nM |
| GLP2R, GIPR, or GCGR EC$_{50}$ (nM) | | Completely inactive |
| c-AMP EC$_{50}$ | | 0.318 nM |
| Plasma Stability | Mouse T½ | >7 days |
| | Monkey T$_{1/2}$ | >2 days |
| | Human T½ | >7 days |
| Human Liver | T$_{1/2}$ | >145 min |
| microsome | CL$_{int(mic)}$ | <9.6 µL/min/mg |
| | CL$_{int(liver)}$ | <8.6 mL/min/kg |
| Water solubility | | 60 mM |
| Protein binding | | 97.97% |
| hERG IC$_{50}$ | | >100 uM |
| Ames (TA98 and TA100) in the presence and absence of S9 | | Negative for mutagenicity |

8.3 hERG Assay

Figure 56:
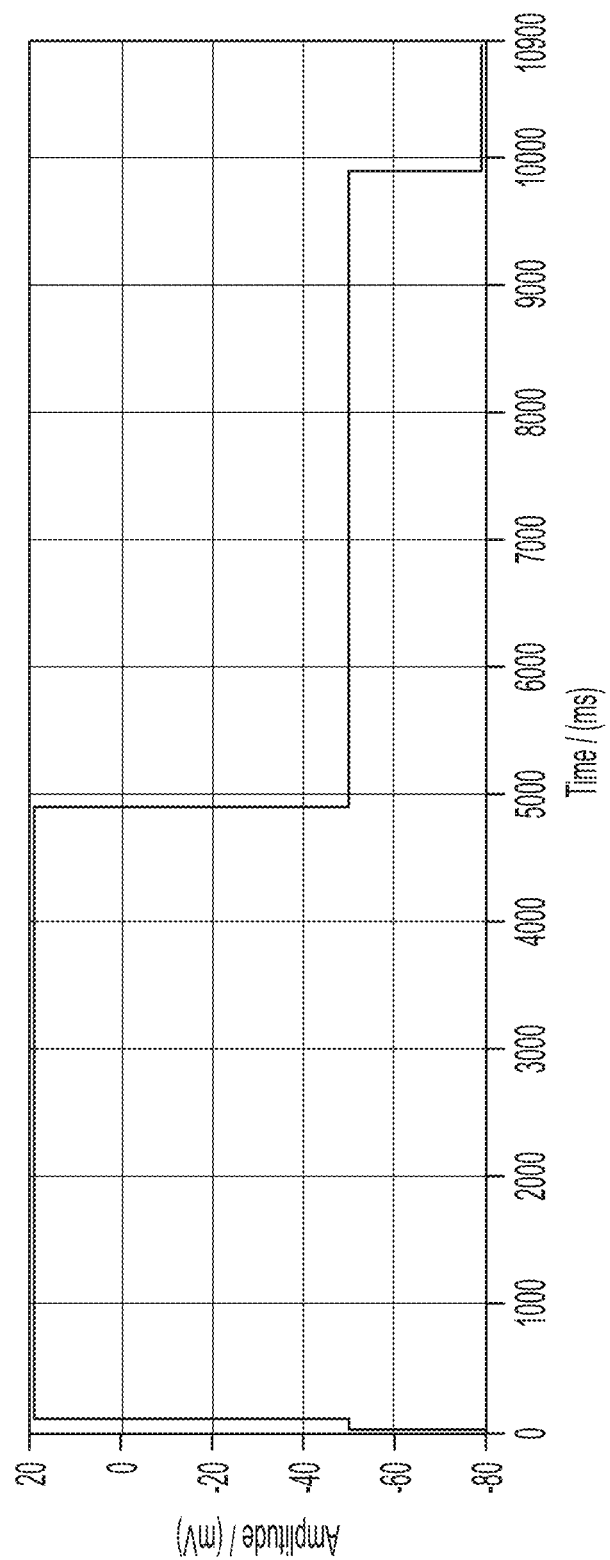
FIG. 56 shows the commander voltage protocol for electrophysiological study. From a holding potential of −80 mV, the voltage was first stepped to −50 mV for 80 ms for leak subtraction, and then stepped to +20 mV for 4800 ms to open hERG channels. After that, the voltage was stepped back down to −50 mV for 5000 ms, causing a "rebound" or tail current, which was measured and collected for data analysis. Finally, the voltage was stepped back to the holding potential (−80 mV, 1000 ms). Voltage command protocol was repeated every 20 sec and performed continuously during the test (vehicle control and test compound).

To determine if compounds of the disclosure had impacts on hERG potassium channels activity, cell based assay was performed. For the assay, CHO cells stably expressing hERG potassium channels were plated and cultured for at least 2 days in a humidified and air-controlled (5% CO$_2$) incubator at 37° C. prior to use in electrophysiological experiments. Cells were then harvested using TrypLE and resuspended in physiological solution (10 mM HEPES, 80 mM NaCl, 4 mM KCl, 2 mM CaCl$_2$, 1 mM MgCl$_2$, 5 mM Glucose, 60 mM NMDG, pH 7.4). Test compounds were dissolved in water to obtain stock solutions for different test concentrations. Stock solutions were further diluted into external electrophysiological recording solution (10 mM HEPES, 140 mM NaCl, 4 mM KCl, 2 mM CaCl$_2$, 1 mM MgCl$_2$, 5 mM Glucose, pH 7.4) to achieve final concentrations for testing. Recordings were performed at room temperature using a Nanion SyncroPatch 384PE, a 384-well automated patch-clamp platform (Internal recording solution: 10 mM HEPES, 10 mM NaCl, 10 mM KCl, 110 mM KF, 10 mM EGTA, pH 7.2). A schematic of the voltage command protocol used for electrophysiological recordings is shown in FIG. 56. One 40 µL addition of the vehicle was applied, followed by a 300 s baseline recording period. Then 40 µL doses of compounds were added at each concentration with an exposure time of no less than 300 s. Recordings were required to pass quality control over the duration of the recording or the well was abandoned, and the compound was retested, all automatically set by PatchControl. Five concentrations (0.3 µM, 3 µM, 10.00 µM, 30.00 µM and 100.00 µM) were tested for each compound as well as a positive control (Amitriptyline). A minimum of 2 replicates per concentration were obtained. Data analysis was carried out using DataControl, Excel 2013 (Microsoft) and GraphPad Prism 5.0. Curve-fitting and IC$_{50}$ value calculations were performed by GraphPad Prism 5.0. If the inhibition obtained at the lowest concentration tested was over 50%, or at the highest concentration tested was less than 50%, the IC$_{50}$ value was reported as less than lowest concentration, or higher than highest concentration, respectively. The IC$_{50}$ values of the test compounds on whole cell hERG currents were summarized in Table 6.

TABLE 6

IC$_{50}$ of the test compounds on whole cell hERG currents

| Compound ID | IC$_{50}$ (µM) | HillSlope | N |
|---|---|---|---|
| Amitriptyline | 2.90 | 1.25 | 3 |
| LP10 | >100.00 | — | 2 |
| LP11 | >100.00 | — | 2 |

8.4 Ames Assay

The objective of this Mini-Ames study was to evaluate the test article LP11, for its ability to induce reverse mutations in the genome of strains of *Salmonella typhimurium* TA98 and TA100 in the presence and absence of metabolic activation (S9 mixture).

The Mini-Ames assay was conducted for the test article in the presence and absence of the S9 mixture, concurrently with the negative/solvent control (DMSO) using six wells and positive controls (2 µg/well TA98 alone, 0.2 µg/well TA100 alone or 0.4 µg/well TA98+TA100 in the presence of S9) using three wells. The tested dose levels for the test article, in the presence and absence of S9 mix, were 1000, 400, 160, 64, 25, 10, 4, and 1.5 µg per well, with each dose tested in triplicate. The study was conducted using fresh cultures of the bacterial strains and fresh test article formulations.

For test article LP11, no obvious cytotoxicity was observed at any dose level with or without S9 mix in any tester strain. No obvious precipitates (by naked eye after the incubation period) were observed at any dose level with or without S9 mix in any tester strain.

LP11 did not induce more than 2.0-fold increase in the two strains TA98 or TA100 in the mean number of revertant colonies at any dose level relative to the concurrent negative/solvent control, either in the presence or absence of S9 mix. No dose response was observed either.

For both tester strains used in this study, the mean number of revertant colonies observed for the negative/solvent control was comparable to the laboratory historical negative control data. All positive controls induced the expected increase of greater than three-fold in the mean number of revertant colonies, in the presence and absence of S9 mix, when compared to the concurrent negative/solvent control, thereby confirming the responsiveness of the strains.

The genotypes of all the tester strains used in this assay were confirmed. It was concluded that this Mini-Ames study was valid and LP11 was negative for mutagenicity under the conditions of this study.

8.5 In Vitro ADME

To assess the in vitro ADME properties of the LP, microsomal stability assay was performed to determine intrinsic clearance, and plasma protein binding assay was performed to understand the distribution potential. The results are listed in Tables 7 and 8 below.

TABLE 7

Liver Microsome Stability

| Sample Name | $T_{1/2}$ (min) | $CL_{int(mic)}$ (µL/min/mg) | $CL_{int(liver)}$ (mL/min/kg) |
|---|---|---|---|
| LP11 | >145 | <9.6 | <8.6 |
| Testosterone | 16.2 | 85.7 | 77.2 |

An assay was performed to determine the plasma protein binding of compounds of the disclosure. For the assay, on the day of experiment, the plasma was thawed in cold water and centrifuged at 3220 rpm for 5 minutes to remove any clots. The pH value of the resulting plasma was checked The 96-well equilibrium dialysis device (Cat #1006) and HTD 96 a/b cellulose membrane strips with molecular mass cutoff of 12-14 kDa (Cat #1101) were obtained from HTDialysis LLC, Gales Ferry, CT) and the dialysis device was assembled following the manufacturer's instructions. (<http://www.htdialysis.com/>).

For the dialysis, the test compound and control compound were dissolved in DMSO to achieve 10 mM stock solutions. DMSO working solutions were prepared at 400 µM. To prepare the loading matrix, compound working solutions (5 µL) were added in a 1:200 ratio to blank matrix (995 µL) and mixed thoroughly. To prepare the time zero (TO) samples to be used for recovery determination, 50 µL aliquots of loading matrix were transferred in triplicate to the sample collection plate. The samples were immediately matched with opposite blank buffer to obtain a final volume of 100 µL of 1:1 matrix/dialysis buffer (v/v) in each well. 500 µL of stop solution were added to these TO samples. This was then stored at 2-8° C. pending further processes along with other post-dialysis samples. To load the dialysis device, an aliquot of 150 µL of the loading matrix was transferred to the donor side of each dialysis well in triplicate, and 150 µL of the dialysis buffer was loaded to the receiver side of the well. The dialysis plate was placed in a humidified incubator at 37° C. with 5% $CO_2$ on a shaking platform that rotated slowly (about 100 rpm) for 4 hours. At the end of the dialysis, aliquots of 50 µL of samples were taken from both the buffer side and the matrix side of the dialysis device. These samples were transferred into new 96-well plates. Each sample was mixed with an equal volume of opposite blank matrix (buffer or matrix) to reach a final volume of 100 µL of 1:1 matrix/dialysis buffer (v/v) in each well. All samples were further processed by adding 500 µL of stop solution containing internal standards. The mixture was vortexed and centrifuged at 4000 rpm for about 20 minutes. An aliquot of 100 µL of supernatant of all the samples was then removed for LC-MS/MS analysis. The single blank samples were prepared by transferring 50 µL of blank matrix to a 96 well plate and adding 50 µL of blank PBS buffer to each well. The blank plasma must match the species of plasma used in the plasma side of the well. Then the matrix-matched samples were further processed by adding 500 µL of stop solution containing internal standards, following the same sample processing method as the dialysis samples.

The percent unbound, percent bound, and percent recovery values were calculated using the following equations:

$$\% \text{ Ubound} = 100 \times \frac{[F]}{[T]}$$

$$\% \text{ Bound} = 100 \times \left(1 - \frac{[F]}{[T]}\right)$$

$$\% \text{ Recovery} = 100 \times \left(\frac{[F] + [T]}{[T_0]}\right),$$

where [F] is the analyte concentration or peak area ratio of analyte/internal standard on the buffer (receiver) side of the membrane, [T] is the analyte concentration or peak area ratio of analyte/internal standard on the matrix (donor) side of the membrane, and [TO] is the analyte concentration or the peak area ratio of analyte/internal standard in the loading matrix sample at time zero. Table 8, below, summarizes the plasma protein binding assay results.

TABLE 8

Plasma Protein Binding Assay Results

| Compound ID | Species/ Matrix | % Unbound | % Unbound SD | % Bound | % Recovery | % Recovery SD |
|---|---|---|---|---|---|---|
| Warfarin | Human Plasma | 1.25 | 0.2 | 98.75 | 98.3 | 3.0 |
| LP11 | Human Plasma | 2.03 | 0.4 | 97.97 | 89.2 | 1.7 |

Example 9. Activities of GLP1R Peptidomimetic Payloads and Linker-Payloads Against GPCR Family Members To test the activity of GLP1R agonist payloads and GLP1R agonist linker-payloads (LPs) in vitro, a cell-based cAMP responsive luciferase reporter assay was developed. Human embryonic kidney cells (HEK293) expressing a cyclic AMP response element (CRE)-luciferase reporter were generated that express either Myc-tagged full length human GLP1R (amino acids 1 to 463 of accession number NP_002053); referred to as HEK293/Myc-hGLP1R/Cre--

Luc cell line), full length human gastric inhibitory polypeptide receptor (GIPR) (amino acids 1 to 466 of accession number NP_000155.1; referred to as HEK293/Myc-hGIPR/Cre-Luc cell line), full length human glucagon-like peptide 2 receptor (GLP2R) (amino acids 1 to 553 of accession number NP_004237; referred to as HEK293/Myc-hGLP2R/Cre-Luc cell line) or full length human glucagon receptor (GCGR) (amino acids 1 to 477 of accession number NP_000151.1; referred to as HEK293/Myc-hGCGR/Cre-Luc cell line) using standard methods for the generation of stable cell lines. Cell surface expression of the receptors was confirmed by flow cytometry, using an antibody recognizing the Myc tag.

For the bioassay, cells were plated at a density of 20,000 cells/well in 80 µL of Opti-MEM supplemented with 0.1% FBS in a 96-well clear bottom white plates (Corning, #356693). Cells were incubated overnight at 37° C. in 5% $CO_2$. Test reagents, including payload, a linker payload, and positive control ligands [human GLP1 (R&D Systems, #5374), human GIP (R&D Systems, #2084), human GCG (R&D Systems, #6927), or human GLP2 (R&D Systems, #2258)], were serially diluted in Opti-MEM with 0.1% FBS and were then added to the cells at 10 µL/well for each concentration tested. Plates were incubated for 5.5h at 37° C. in 5% $CO_2$. For end-point measurement, 100 µL/well of One-Glo reagent (Promega, #E6051) was added and plates were kept at room temperature for 5-10 minutes. Luciferase activity was measured on Envision Multilabel Plate Reader (Perkin Elmer) in Luminescent mode. The relative light units (RLU) values were obtained and the results were analyzed using nonlinear regression with GraphPad Prism software (GraphPad).

As shown in Table 9 and FIGS. 6A-6D, the payloads and linker-payload demonstrated activation in the HEK293/Myc-hGLP1R/Cre-Luc cell line with $EC_{50}$ values ranging from 3.32 µM to 71.5 µM. The payloads and linker payload did not demonstrate an measurable activity in the other cell lines evaluated. All of the positive control reference ligands (human GLP1, GIP, GLP2, and GCG) activated individual cell lines as expected.

TABLE 9

CRE-Dependent Reporter Activity by GLP1R payload and linker-payload Agonists in GLP1R, GIPR, GLP2R and GCGR cell lines

| Compound | HEK293/Myc-hGLP1R/Cre-Luc $EC_{50}$ (M) | HEK293/Myc-hGIPR/Cre-Luc $EC_{50}$ (M) | HEK293/Myc-hGLP2R/Cre-Luc $EC_{50}$ (M) | HEK293/Myc-hGCGR/Cre-Luc $EC_{50}$ (M) |
|---|---|---|---|---|
| P9 | 3.32E−12 | N/A | N/A | N/A |
| P8 | 7.60E−12 | N/A | N/A | N/A |
| LP4 | 7.15E−11 | N/A | N/A | N/A |
| LP11 | 1.6E−11 | N/A | N/A | N/A |
| Reference* | 1.46E−12 | 1.29E−12 | 1.23E−11 | 1.03E−9 |

N/A = Not Active
Reference for GLP1R assay = GLP1
Reference for GIPR assay = GIP
Reference for GLP2R assay = GLP2
Reference for GCGR assay = GCG Example 10. In Vitro Plasma Stability To determine the plasma stability of ATDC anti-GLP1R mAB2-LP11 bearing GLP1R agonist P8, the ATDCs was incubated in vitro with the plasma from different species and the drug to antibody ratio (DAR) was evaluated. Anti-GLP1R mAB2 is a biotinylated anti-Fc antibody.

The ATDC solution was spiked into pooled C57BL/6 mouse, cynomolgus monkey (Cyno), or IgG depleted human plasma (BioIVT) to a final concentration of 50 µg/mL, and subsequently incubated at 37° C. on ThermoMixer C (Eppendorf, Cat #2231000574). A 100-µL aliquot was removed at times 0, 1, 2, 3 and 7 days and then immediately stored frozen at −80° C. until analysis.

For DAR analysis, the ATDC was purified from plasma samples by immunoaffinity capture using a DynaMag-2 magnetic rack (Life Technologies, Cat #12321D). First, biotinylated anti-human Fc antibody (Regeneron generated reagent) was immobilized on Dynabeads M280 streptavidin beads (Invitrogen, Cat #60210). Each plasma sample containing the ATDC was mixed at 950 rpm with 0.5 mg of the beads at room temperature for 2 hours with gentle shaking. The beads were then washed three times with 500 µL of HBS-EP pH 7.4 buffer (GE Healthcare, Cat #BR100188), once with 500 µL water and once with 500 µL of 10% acetonitrile (VWR Chemicals, Cat #BDH83640.100E) in water. Following the washes, the ATDC was eluted by incubating the beads with 70 µL of 1% formic acid in 30:70 acetonitrile:water (v/v) for 15 minutes at room temperature. Fifty µL eluted samples were further reduced by adding 50 µL 10 mM TCEP (Sigma, Cat 646547-10×₁ ML) and incubated at 37° C. for 20 min in ThermoMixer C.

The reduced ATDC samples were then injected onto a 0.3×50 mm 1.7 µm BEH300 C4 column (Waters, Cat #186009260) for separation and detected by Synapt G2-Si Mass Spectrometer (Waters). The flow rate used was 10 µL/min (mobile phase A: 0.1% formic acid in water; mobile phase B: 0.1% formic acid in acetonitrile). The HPLC gradient eluted ATDC between 3.5-6.5 minutes corresponding to 25-40% of mobile phase B. The acquired spectra were deconvoluted using MaxEnt1 software (Waters) with the following parameters: Mass range: 20-60 kDa; m/z range: 800-2500 Da; Resolution: 1.0 Da/channel; Width at half height: 0.8 Da; Minimum intensity ratios: 33%; Iteration max: 15. DAR was calculated based on peak intensity corresponding to individual DAR species in the deconvoluted spectra.

Figure 57:
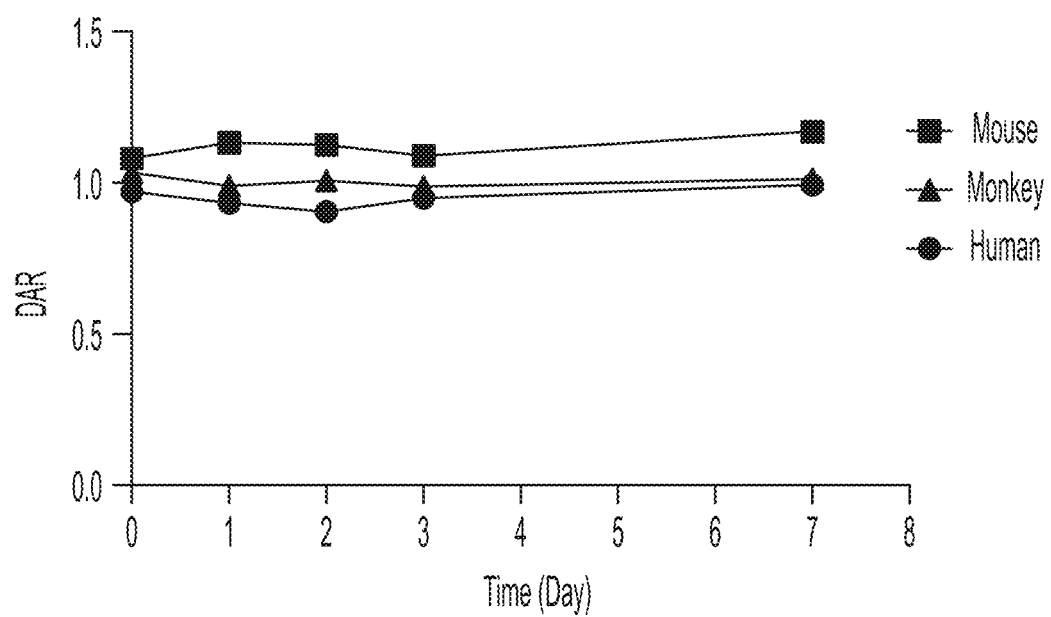
FIG. 57 shows in vitro stability of anti-GLP1R mAB2-LP11 over a 7-day, 37° C. incubation in mouse, monkey and human plasma.
Figure 58:
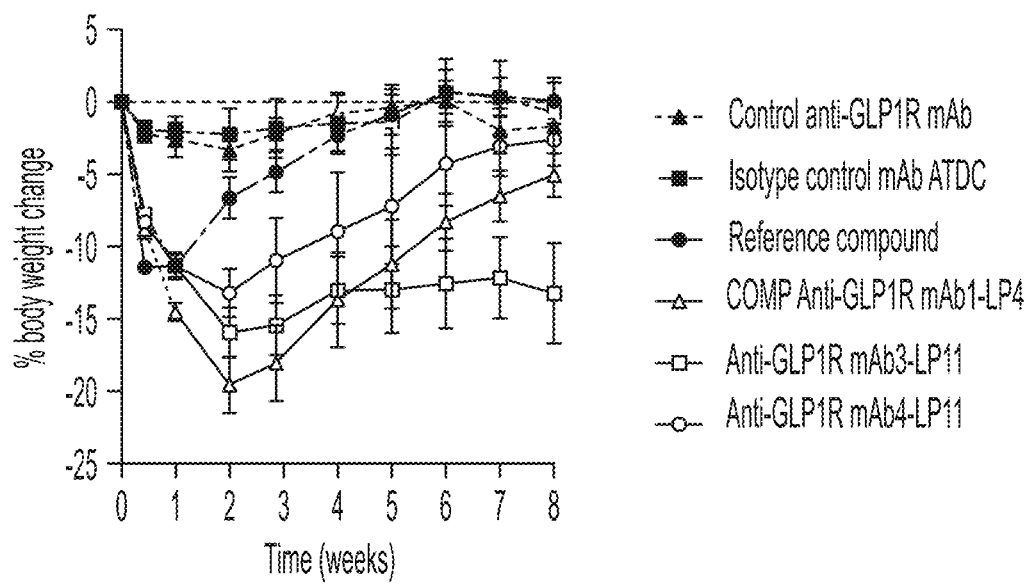
FIG. 58 shows the effects of GLP1R ATDCs on percent body weight changes in obese GLP1R humanized mice.
Figure 59:
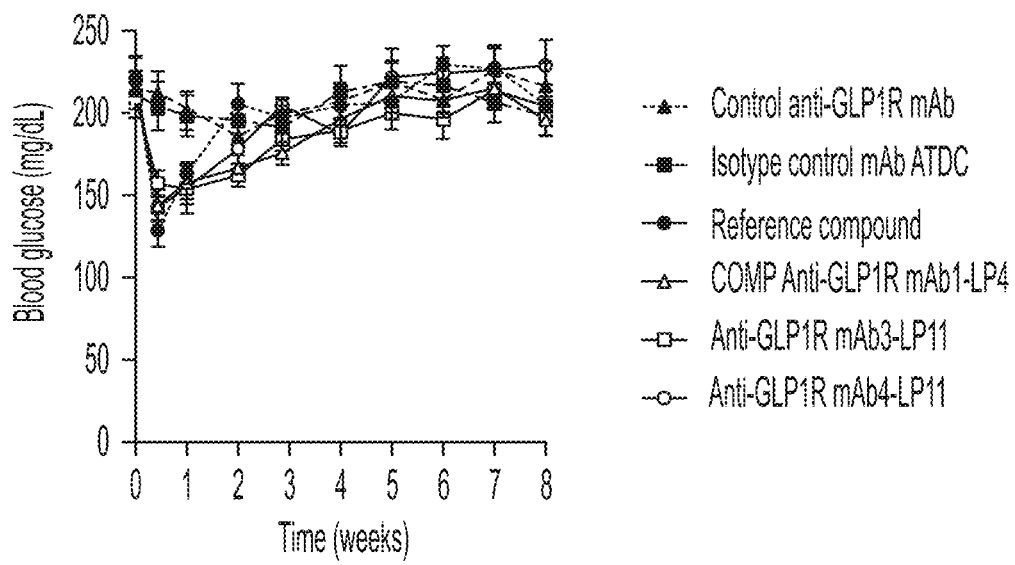
FIG. 59 shows the effects of GLP1R ATDCs on blood glucose levels in obese GLP1R humanized mice.
Figure 60:
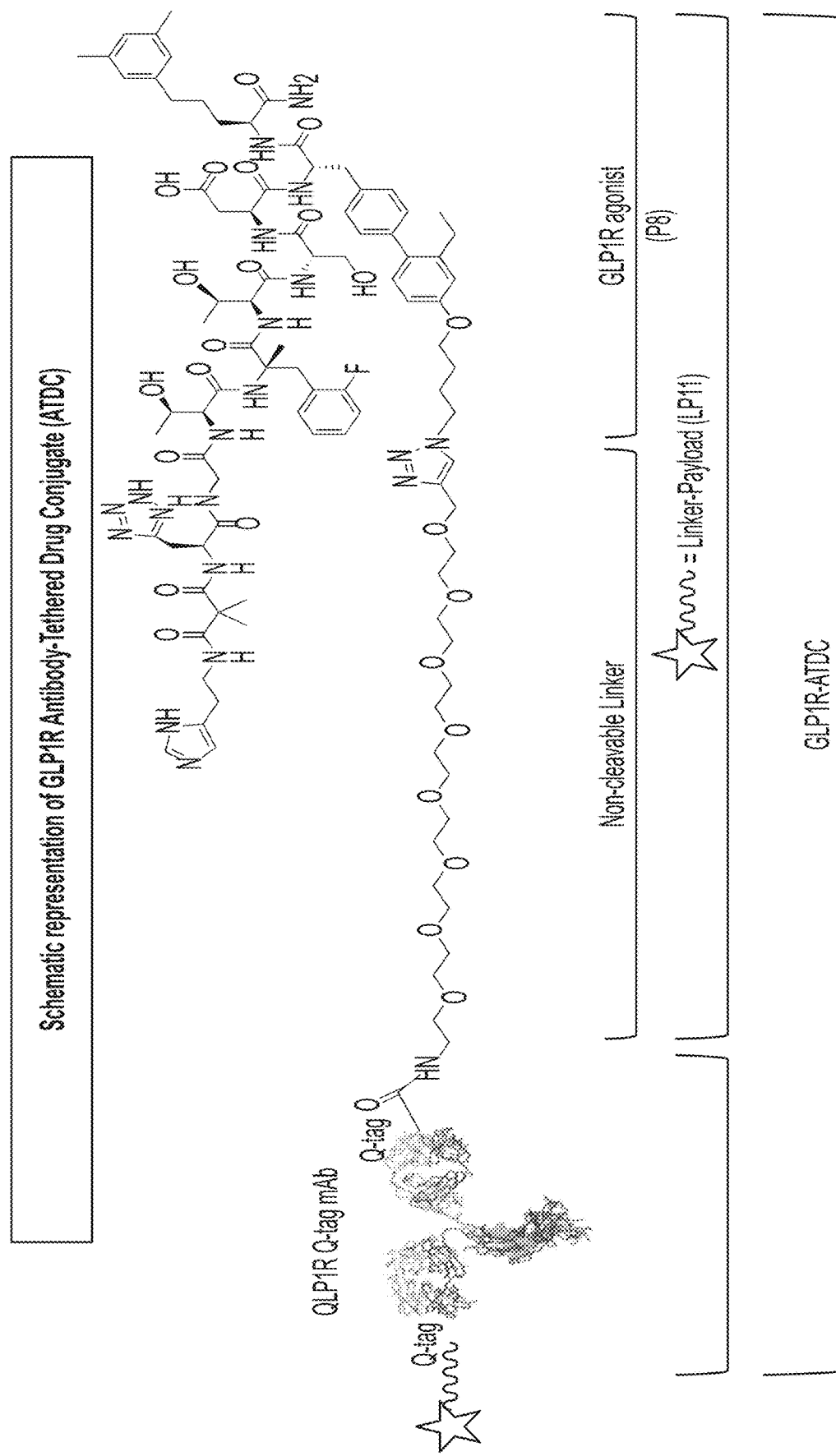
FIG. 60 is a schematic representation of a GLP1R ATDC according to an exemplary embodiment of the disclosure.

No significant change in DAR was observed for anti-GLP1R mAb2-LP11 after a 7-day incubation in mouse, cynomolgus monkey or IgG depleted human plasma. The results are presented in Table 10 and FIG. 57.

TABLE 10

In vitro stability of anti-GLP1R mAB2-LP11 over a 7-day, 37° C. incubation in mouse, monkey and human plasma

| Time (Days) | DAR in Mouse Plasma | DAR in Monkey Plasma | DAR in Human Plasma |
|---|---|---|---|
| 0 | 1.1 | 1.0 | 0.97 |
| 1 | 1.1 | 0.99 | 0.93 |
| 2 | 1.1 | 1.0 | 0.90 |
| 3 | 1.1 | 0.99 | 0.95 |
| 7 | 1.2 | 1.0 | 0.99 |

Example 11. Luciferase Reporter Assay

To test the activity of GLP1R agonist payloads, GLP1R agonist linker-payloads (LPs), and anti-GLP1R antibody tethered drug conjugates (ATDCs) of the disclosure, a cell-based cAMP responsive luciferase reporter assay was developed. To generate the assay cell line, the firefly luciferase gene was placed under the control of a cAMP response element (CRE) located upstream of a minimal promoter and transfected into HEK293 cells and referred to herein as HEK293/CRE-Luc cells. HEK293/CRE-Luc cells were then engineered to express full-length human GLP1R (amino acids 1 to 463 of accession number NP_002053) and are referred to herein as HEK293/CRE-Luc/hGLP1R cells.

For the assays, cells were seeded into 96 well plates at 10,000 or 20,000 cells/well in assay media (Optimem, 0.1% BSA, 100 units/ml Penicillin, 100 μg/ml Streptomycin, 292 μg/ml L-glutamine) and incubated overnight. Three-fold serial dilutions of free payloads or LPs were prepared in 100% DMSO, transferred to fresh assay media, and added to the cells at a final constant DMSO concentration of 0.2%. The last well in the plate served as a blank control containing only the assay media and 0.2% DMSO (untreated well) and was plotted as a continuation of the 3-fold serial dilution. Four to six hours later, luciferase activity was determined after the addition of One-Glo™ reagent (Promega, Cat #E6130) to each well. Relative light units (RLUs) were measured on an Envision luminometer (PerkinElmer) and $EC_{50}$ values were determined using a four-parameter logistic equation over a 12-point dose response curve (GraphPad Prism). The signal to noise (S/N) was determined by taking the ratio of the highest RLU on the dose response curve to the RLU in the untreated wells. $EC_{50}$ and S/N values are summarized in Table 11. Data was generated across several experiments (A, B, and D) with P8 serving as a reference standard in each experiment to calculate the payload relative potency [(P8 $EC_{50}$/payload $EC_{50}$)*100] and relative S/N [(payload SN/P8 SN)*100].

As shown in Table 11, payload and linker-payload $EC_{50}$ values ranged from 3.97 μM to 1.95 nM and relative potency (% P8) ranged from 0.3% to 133.8% in HEK293/CRE-Luc/hGLP1R cells. Most tested payloads reached similar max activity with relative S/N values (% P8) ranging from 68.6% to 116.27%. The GLP1 ligand was also included for reference and increased CRE-dependent luciferase activity in HEK293/CRE-Luc/hGLP1R cells with an $EC_{50}$ of 14.3 μM, relative potency of 37.2%, and relative S/N of 96.8%. All tested agonists had minimal impact on luciferase activity in the absence of hGLP1R expression (HEK293/CRE-Luc cells), with S/N values <1.7 and $EC_{50}$ values >200.0 nM.

TABLE 11

CRE-Dependent Reporter Activity by GLP1R payload and linker-payload Agonists in HEK293/CRE-Luc/hGLP1R cells

| | HEK293/CRE-LUC/hGLP1R | | | | HEK293/CRE-LUC | | |
|---|---|---|---|---|---|---|---|
| Molecule | $EC_{50}$ | Relative Potency (% P8 $EC_{50}$) | S/N | Relative Signal:Noise (% P8) | $EC_{50}$ | S/N | Experiment |
| P9 | 3.97E−12 | 133.8 | 75.2 | 114.3 | >2E−07 | 1.3 | A |
| P23 | 5.15E−12 | 103.0 | 57.1 | 86.9 | >2E−07 | 1.6 | A |
| P8 | 5.31E−12 | 100.0 | 65.8 | 100.0 | >2E−07 | 1.5 | A |
| P12 | 1.14E−11 | 46.5 | 76.4 | 116.2 | >2E−07 | 1.2 | A |
| P15-R | 1.32E−11 | 40.3 | 67.8 | 103.1 | >2E−07 | 1.1 | A |
| P10 | 1.40E−11 | 38.0 | 45.1 | 68.6 | >2E−07 | 1.2 | A |
| GLP1 | 1.43E−11 | 37.2 | 63.6 | 96.8 | >2E−07 | 1.3 | A |
| LP11 | 1.61E−11 | 33.1 | 74.5 | 113.3 | >2E−07 | 1.3 | A |
| P8 | 2.0E−11 | 100.0 | 327.9 | 100.0 | NT | NT | B |
| P8 | 2.73E−11 | 100.0 | 235.9 | 100.0 | NT | NT | D |
| P4 | 8.37E−11 | 6.3 | 66.9 | 101.8 | >2E−07 | 1.6 | A |
| LP4 | 1.27E−10 | 4.2 | 63.8 | 97.1 | >2E−07 | 1.7 | A |
| P13 | 3.57E−10 | 1.5 | 69.5 | 105.6 | >2E−07 | 1.2 | A |
| P6 | 6.02E−10 | 0.9 | 60.7 | 92.3 | >2E−07 | 1.0 | A |
| P11 | 6.85E−10 | 0.8 | 54.8 | 83.4 | >2E−07 | 1.1 | A |
| P21 | 7.38E−10 | 0.7 | 58.8 | 89.5 | >2E−07 | 1.3 | A |
| P3 | 1.95E−09 | 0.3 | 46.3 | 70.3 | >2E−07 | 1.2 | A |

NT = not tested

Figure 10:
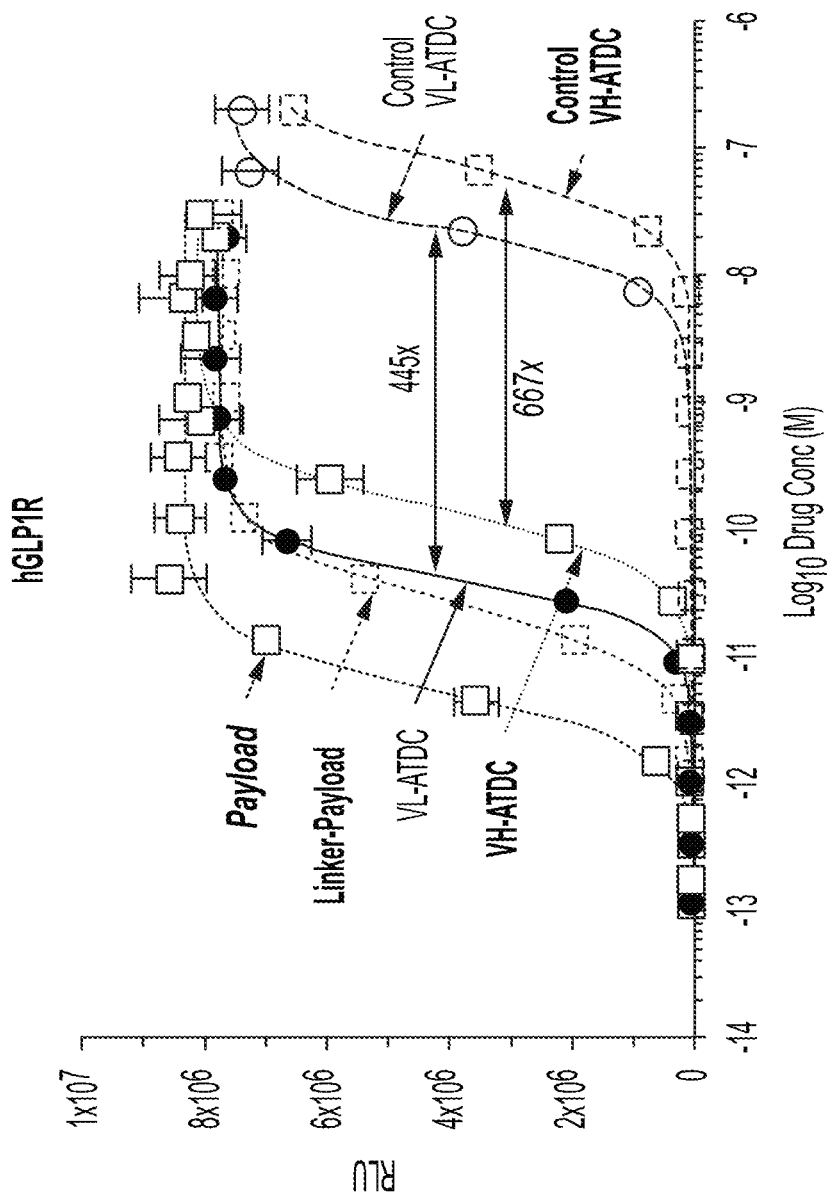
FIG. 10 shows CRE-dependent luciferase reporter activity by anti-GLP1R ATDCs. Anti-GLP1R ATDCs showed better in vitro potency than isotype control ATDCs. Unconjugated mAbs did not activate hGLP1R cells (not shown). ATDCs did not activate Glucagon-like peptide-2 receptor (GLP2R), glucagon receptor (GCGR), or gastric inhibitory polypeptide receptor (GIPR) (not shown).
Figure 11A:
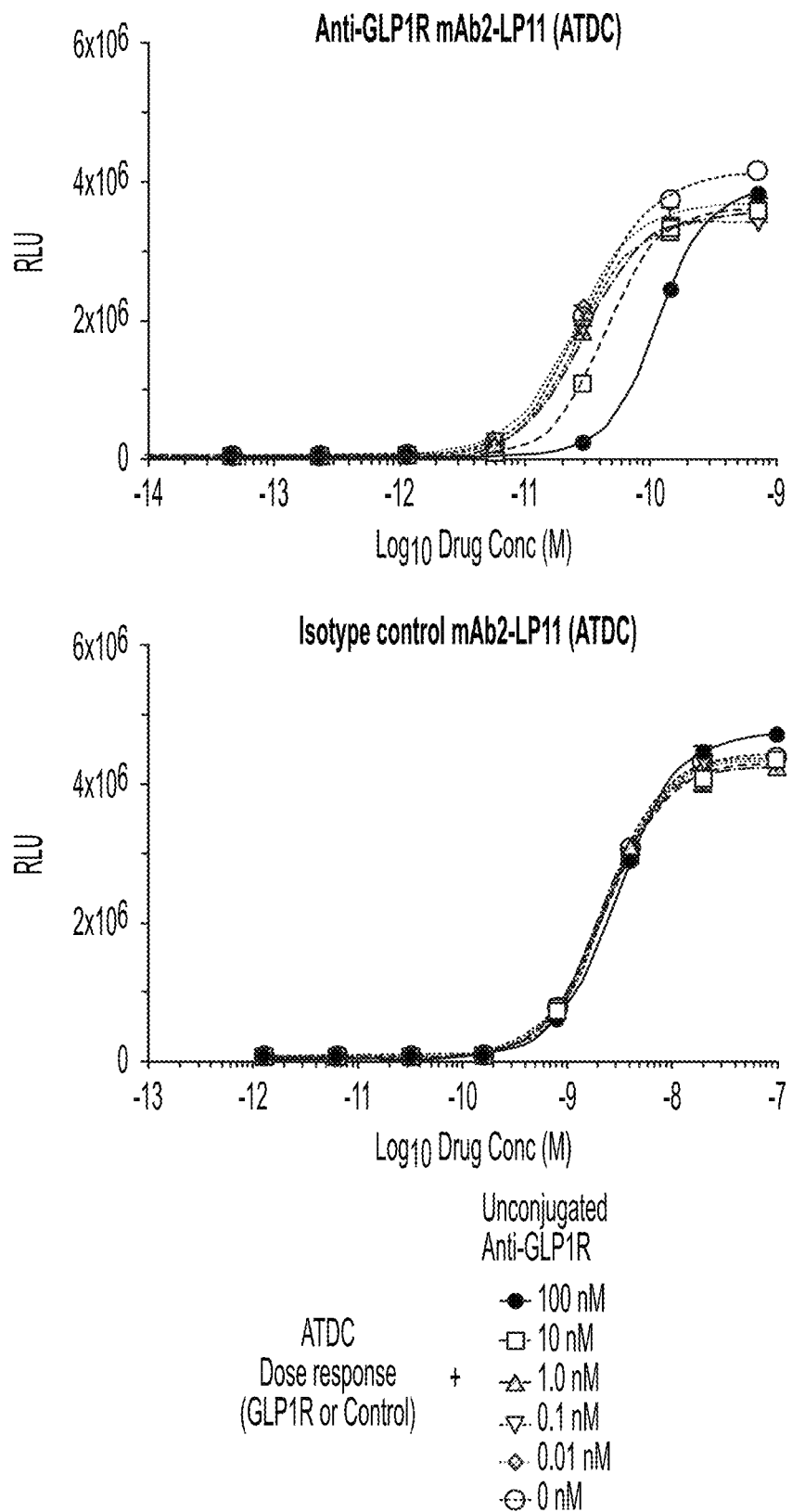
FIG. 11A shows cyclic AMP response element (CRE)-dependent luciferase reporter activity by anti-GLP1R ATDCs in the presence of unconjugated anti-GLP1R antibodies. It shows that the unconjugated anti-GLP1R mAb concentrations <10 nM had no impact on anti-GLP1R ATDC activity. 100 nM unconjugated anti-GLP1R mAb reduced anti-GLP1R ATDC potency by 3.8-fold. The assay was performed by adding unconjugated anti-GLP1R mAb first, then immediately adding anti-GLP1R ATDC, and incubating for 4 hours.
Figure 12:
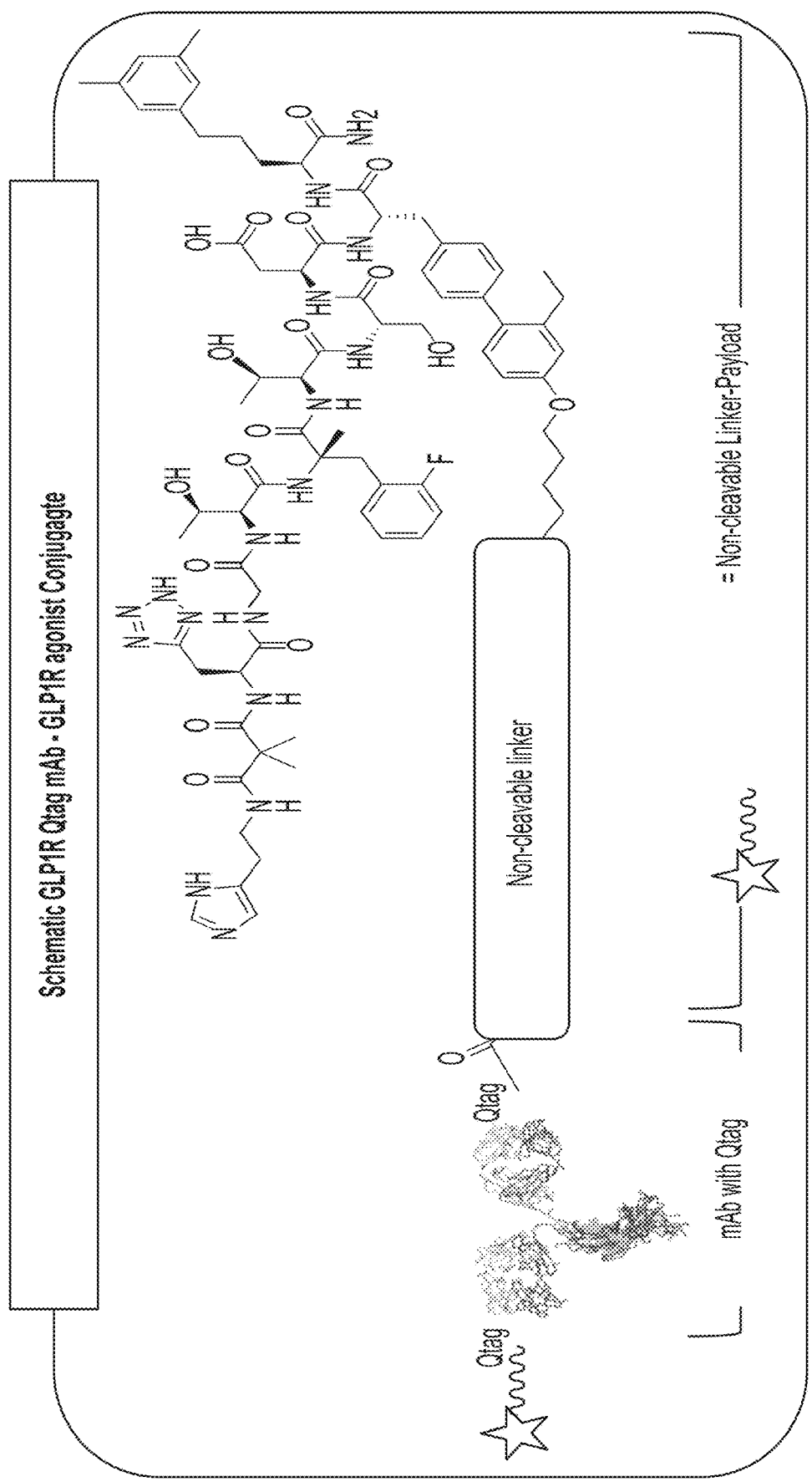
FIG. 12 shows a schematic representation of an exemplary GLP1R Q-tag mAb-GLP1R agonist conjugate of the present disclosure.

>= $EC_{50}$ values could not be determined with accuracy because the binding did not reach saturation within the tested antibody concentration range. $EC_{50}$ is reported as greater than the highest tested concentration GLP1R agonist linker payloads were conjugated to anti-hGLP1R antibodies via N-terminal heavy or light chain Q tags. Several resulting anti-GLP1R antibody tethered drug conjugates (ATDCs) were tested for activity in the HEK293/CRE-Luc/hGLP1R reporter assay as described above for the free GLP1R payload and linker-payload agonists. As shown in Table 12, anti-GLP1R ATDCs increased CRE-dependent luciferase reporter activity in HEK293/CRE-Luc/hGLP1R cells with $EC_{50}$ values ranging from 21.7 μM to 112 μM and relative potency values (% P8) ranging from 14.5% to 126%. Most tested ATDCs reached similar max activity with relative S/N values (% P8) ranging from 87.4% to 158.4%. The anti-GLP1R ATDCs were inactive in reporter cells that did not express hGLP1R (HEK293/CRE-Luc). Non-binding ATDCs tended to be less active than the anti-GLP1R ATDCs with $EC_{50}$ values ranging from 1.92 nM to 74.6 nM and relative potency values (% P8) ranging from <0.1% to 1.4%. A selected set of results are presented in FIG. 10.

TABLE 12

CRE-Dependent Reporter Activity by anti-GLP1R ATDCs in HEK293/CRE-Luc/hGLP1R cells

| Test Article | mAb Q tag | LP | EC$_{50}$ | Relative Potency (% P8 EC$_{50}$) | S/N | Relative Signal:Noise (% P8) | Experiment | HEK293/ CRE-Luc EC$_{50}$ | S/N |
|---|---|---|---|---|---|---|---|---|---|
| Anti-GLP1R mAB2 | VL N-term | LP11 | 2.73E−11 | 59.5 | 101.9 | 158.4 | A | >2.0E−08 | 1.2 |
| Anti-GLP1R mAB6 | VH N-term | LP11 | 1.12E−10 | 14.5 | 62.5 | 97.1 | A | >2.0E−08 | 0.9 |
| GLP1 | None | None | 2.75E−11 | 58.9 | 88.7 | 137.9 | A | >2.0E−08 | 1.4 |
| P8 | None | None | 1.62E−11 | 100.0 | 64.3 | 100.0 | A | >2.0E−08 | 1.3 |
| Isotype Control mAb1 | VH N-term | LP11 | 7.46E−08 | <0.1% | 69.9 | 108.7 | A | >2.0E−08 | 1.6 |
| Isotype Control mAb2 | VL N-term | LP11 | 1.24E−08 | 0.1 | 69.4 | 107.8 | A | >2.0E−08 | 1.2 |
| COMP Anti-GLP1R mAb1 | VH N-term | LP4 | 6.29E−11 | 55.3 | 284.1 | 87.4 | D | >2.0E−8 | 1.6 |
| COMP Anti-GLP1R mAb1 | VH N-term | LP3 | 4.40E−11 | 62.1 | 271.7 | 115.2 | D | NT | NT |
| COMP Anti-GLP1R mAb1 | VH N-term | LP1 | 2.82E−11 | 96.7 | 213.0 | 90.3 | D | NT | NT |
| COMP Anti-GLP1R mAb1 | VH N-term | LP2 | 2.17E−11 | 126.0 | 227.3 | 96.4 | D | NT | NT |
| P8 | None | None | 2.73E−11 | 100.0 | 235.9 | 100.0 | D | NT | NT |
| Isotype Control mAb3 | VH N-term | LP4 | 1.92E−09 | 1.4 | 252.0 | 106.8 | D | NT | NT |
| Isotype Control mAb3 | VH N-term | LP3 | 2.31E−09 | 1.2 | 218.8 | 92.8 | D | NT | NT |
| Isotype Control mAb3 | VH N-term | LP1 | 2.54E−09 | 1.1 | 235.0 | 99.6 | D | NT | NT |
| Isotype Control mAb3 | VH N-term | LP2 | 2.94E−09 | 0.9 | 285.0 | 120.8 | D | NT | NT |

NT = not tested
>= EC$_{50}$ values could not be determined with accuracy because the binding did not reach saturation within the tested antibody concentration range. EC$_{50}$ is reported as greater than the highest tested concentration In a separate experiment, the ability of unconjugated anti-GLP1R antibodies to compete for anti-GLP1R ATDC activity was assessed in the HEK293/CRE-Luc/hGLP1R reporter assay. In this experiment, reporter cells were incubated with a dose titration of the anti-GLP1R ATDC in the absence or presence of a constant amount (0.01, 0.1, 1.0, 10, or 100 nM) of the unconjugated anti-GLP1R antibody. The EC$_{50}$ values are reported in Table 13, and the fold-change in the EC$_{50}$ value relative to the ATDC alone condition (EC$_{50}$ fold-change) was calculated as follows: EC$_{50}$ of ATDC+ unconjugated mAb/EC$_{50}$ of ATDC alone. As shown in Table 13, unconjugated mAb concentrations up to 10 nM had minimal impact on anti-GLP1R ATDC activity with the EC$_{50}$ fold-change values less than or equal to 1.5. The highest tested unconjugated antibody concentration of 100 nM reduced the EC$_{50}$ value by 4.0-fold. A non-binding control ATDC was not impacted by the presence of unconjugated anti-GLP1R antibody.

TABLE 13

CRE-Dependent Reporter Activity by anti-GLP1R ATDCs in the presence of unconjugated anti-GLP1R antibodies

| ATDC | Unconjugated mAb constant concentration | ATDC EC$_{50}$ (M) | EC$_{50}$ fold-change |
|---|---|---|---|
| Anti-GLP1R mAb2 | +100 nM mAb | 1.2E−10 | 4.0 |
| | +10 nM mAb | 4.4E−11 | 1.5 |
| | +1 nM mAb | 2.9E−11 | 1.0 |
| | +0.1 nM mAb | 2.7E−11 | 0.9 |

TABLE 13-continued

CRE-Dependent Reporter Activity by anti-GLP1R ATDCs in the presence of unconjugated anti-GLP1R antibodies

| ATDC | Unconjugated mAb constant concentration | ATDC EC$_{50}$ (M) | EC$_{50}$ fold-change |
|---|---|---|---|
| | +0.01 nM mAb | 2.4E−11 | 0.8 |
| | 0 nM mAb | 3.0E−11 | 1.0 |
| Isotype Control mAb2 | +100 nM mAb | 3.0E−09 | 1.3 |
| | +10 nM mAb | 2.4E−09 | 1.0 |
| | +1 nM mAb | 2.2E−09 | 0.9 |
| | +0.1 nM mAb | 2.50−09 | 1.1 |
| | +0.01 nM mAb | 2.30E−09 | 1 |
| | 0 nM mAb | 2.30E−09 | 1 |

Example 12. Effects of Anti-GLP1R mAb ATDCs on Body Weight and Blood Glucose in Diet-Induced Obese GLP1R Humanized Mice To determine body weight and blood glucose lowering effects of three anti-GLP1R antibody-tethered-drug conjugates (ATDCs) in obese animals, mice homozygous for the expression of human GLP1R in place of mouse GLP1R (referred to as GLP1R humanized mice) were placed on high-fat diet (60% kcal % fat) for 6 months. Forty-four, 9-month-old male, GLP1R humanized mice were stratified into six groups of five to eight mice, based on their day 0 body weights. After the stratification, each group was subcutaneously administered with 25 mg/kg of COMP anti-GLP1R mAb1-LP4 (n=8), anti-GLP1R mAb3-LP11 (n=8), anti-GLP1R mAb4-LP11 (n=5), control anti-GLP1R mAb (n=7), isotype control mAb ATDC (n=8) or reference compound (n=8) on day 0.

The control anti-GLP1R mAb used in this study is a high-affinity anti-GLP1R antibody, which does not activate or inactivate GLP1R, without any drug conjugation. The control anti-GLP1R mAb is antibody 5A10 described in US Publication No. US20060275288A1, which is incorporated herein by reference in its entirety. The control anti-GLP1R mAb does not have a Q-tag. COMP anti-GLP1R mAb1-LP4 comprises the same control anti-GLP1R mAb with a N-terminal heavy chain Q-tag. The isotype control mAb ATDC is a GLP1 peptide mimetic described herein, conjugated to an antibody that does not bind to any protein in GLP1R humanized mice. The reference compound has identical amino acid sequences to dulaglutide in GLP1 analogue and linker segments, but was made with a hFc with three mutations (P16E; V17A; G19 insert).

On days three and seven post administration and weekly from day fourteen to day fifty-six, body weights of the animals were recorded, and their blood glucose levels were measured with a handheld glucometer. Mean±SEM of percent changes in body weight from day 0 at each time point was calculated for each group and are shown in Table 14. Mean±SEM of blood glucose levels at each time point was calculated for each group and are shown in Table 15. Statistical analyses were performed by two-way ANOVA followed by Bonferroni post-hoc tests, comparing the control antibody group to the other five groups. The results are also presented in FIGS. 39 and 40.

Body weights and blood glucose levels were stable in animals administered with the control anti-GLP1R mAb, with nominal handling (i.e., bleeding, cage changes) related fluctuations. Compared to animals in the control anti-GLP1R mAb group, animals administered with the isotype control mAb ATDC showed no significant differences in percent body weight change or blood glucose levels. In animals administered with the reference compound, weight reductions were observed on days 3 and 7, whereas glucose was reduced only on day 3. In animals administered anti-GLP1R mAb ATDCs, weight reductions lasted for 42, 56, and 28 days, depending on which GLP1R ATDC was dosed, respectively, while glucose was lowered for 7 days for all GLP1R ATDCs tested.

In conclusion, single administration of the three anti-GLP1R mAb ATDCs tested leads to long-term weight loss in obese animals.

TABLE 14

Effects of GLP1R ATDCs on percent body weight changes in obese GLP1R humanized mice

| Time (day) | Control anti-GLP1R mAb Mean | SEM | Isotype control mAb ATDC Mean | SEM | Reference compound Mean | SEM | COMP anti-GLP1R mAb mAb1-LP4 Mean | SEM | Anti-GLP1R mAb mAb3-LP11 Mean | SEM | Anti-GLP1R mAb mAb4-LP11 Mean | SEM |
|---|---|---|---|---|---|---|---|---|---|---|---|---|
| 0 | 0 | 0 | 0 | 0 | 0 | 0 | 0 | 0 | 0 | 0 | 0 | 0 |
| 3 | −2.2 | 0.6 | −1.9 | 0.6 | −11.4** | 0.3 | −8.8 | 0.7 | −7.8 | 0.2 | −8.3 | 0.4 |
| 7 | −2.6 | 1.2 | −2.0 | 1.1 | −11.4** | 0.9 | −14.5**** | 0.6 | −11.3** | 0.9 | −11.3* | 0.8 |
| 14 | −3.3 | 1.5 | −2.2 | 1.8 | −6.6 | 1.4 | −19.6**** | 2.0 | −15.9**** | 1.7 | −13.2** | 1.7 |
| 20 | −2.2 | 1.1 | −1.8 | 2.0 | −4.8 | 1.4 | −18.0**** | 2.6 | −15.4**** | 2.0 | −10.9* | 3.0 |
| 28 | −0.7 | 1.3 | −1.5 | 2.1 | −2.3 | 1.1 | −13.7**** | 3.3 | −13.0**** | 2.3 | −8.9* | 4.1 |
| 35 | −0.3 | 1.5 | −1.4 | 2.3 | −0.9 | 1.4 | −11.2*** | 3.1 | −13.0**** | 3.0 | −7.2 | 4.0 |
| 42 | 0.1 | 1.4 | 0.7 | 2.3 | 0.7 | 1.5 | −8.3** | 2.0 | −12.6**** | 3.1 | −4.3 | 2.9 |
| 49 | −2.0 | 1.6 | 0.3 | 2.6 | 0.3 | 1.3 | −6.5 | 1.8 | −12.1*** | 2.8 | −3.1 | 2.0 |
| 56 | −1.7 | 1.1 | −0.7 | 2.1 | 0.1 | 1.6 | −5.0 | 1.5 | −13.2**** | 3.5 | −2.6 | 1.8 |

*P < 0.05, P < 0.01, *P < 0.001, ****P < 0.0001, compared to the control anti-GLP1R mAb group.

TABLE 15

Effects of GLP1R ATDCs on blood glucose levels in obese GLP1R humanized mice

| Time (day) | Control anti-GLP1R mAb Mean | SEM | Isotype control mAb ATDC Mean | SEM | Reference compound Mean | SEM | COMP anti-GLP1R mAb mAb1-LP4 Mean | SEM | Anti-GLP1R mAb mAb3-LP11 Mean | SEM | Anti-GLP1R mAb mAb4-LP11 Mean | SEM |
|---|---|---|---|---|---|---|---|---|---|---|---|---|
| 0 | 215 | 6 | 211 | 14 | 220 | 14 | 214 | 12 | 209 | 12 | 221 | 14 |
| 3 | 212 | 13 | 205 | 15 | 129**** | 10 | 144**** | 10 | 157** | 8 | 143*** | 8 |
| 7 | 202 | 12 | 198 | 13 | 163 | 6 | 158* | 10 | 154* | 9 | 155* | 16 |
| 14 | 186 | 5 | 196 | 9 | 206 | 12 | 167 | 8 | 162 | 7 | 178 | 9 |
| 20 | 200 | 10 | 191 | 10 | 198 | 8 | 176 | 7 | 184 | 7 | 205 | 4 |
| 28 | 207 | 11 | 213 | 16 | 204 | 13 | 197 | 9 | 190 | 8 | 188 | 8 |
| 35 | 219 | 12 | 220 | 12 | 207 | 11 | 211 | 10 | 200 | 10 | 222 | 17 |
| 42 | 208 | 11 | 217 | 17 | 229 | 12 | 208 | 7 | 196 | 12 | 224 | 10 |
| 49 | 226 | 15 | 207 | 12 | 228 | 13 | 215 | 10 | 214 | 12 | 226 | 13 |
| 56 | 217 | 14 | 198 | 12 | 205 | 12 | 196 | 10 | 204 | 4 | 229 | 16 |

*P < 0.05, P < 0.01, *P < 0.001, ****P < 0.0001, compared to the control anti-GLP1R mAb group.

REFERENCES

1. Zhang et al. Nature volume 546, pages 248-253(2017)
2. Chepurny et al. J Biol Chem. 2019 Mar. 8; 294(10):3514-3531.
3. De Graaf et al. Pharmacological Reviews October 2016, 68 (4) 954-1013.
4. Manandhar and Ahn. J. Med. Chem. 2015, 58, 3, 1020-1037
5. Jazayeri A, et al. Nature volume 546, pages 254-258 (2017)
6. Donnelly D, British Journal of Pharmacology, 2011: 166:27-41, PMID 21950636
7. GB2551945a
8. Jazayeri, A.; Rappas, M.; Brown, A. H.; Kean J.; Errey, J. C.; Robertson, N. J.; Fiez-Vandal, C.; Andrews, S. P.; Congreve, M.; Bortolato, A.; Mason, J. S.; Baig, A. H.; Teobald, I.; Dore, A. S.; Weir, M.; Cooke, R. M.; Marshall, F. H. Crystal structure of the GLP-1 receptor bound to a peptide agonist. Nature. 2017, 546, 254-258.
9. US2006/4222
10. Sureshbabu, V. V.; Venkataramanarao, R.; Naik, S. A.; G. Synthesis of tetrazole analogues of amino acids using Fmoc chemistry: isolation of amino free tetrazoles and their incorporation into peptides. Tetrahedron Letters 2007, 48, 7038-7041.
11. Ceretti, S.; Luppi, G.; Pol, S. D.; Formaggio, F.; Crisma, M.; Toniolo, C.; Tomasini, C. Total Synthesis of Sequential Retro-Peptide Oligomers. Eur. J. Org. Chem. 2004, 4188-4196.
12. WO2010/052253
13. US2003/114668
14. Colobert, F.; Mazery, R. D.; Solladie, G.; Carreño, M. C.; First Enantioselective Total Synthesis of (-)-Centrolobine. Org. Lett. 2002, 4, 1723-1725.
15. Dondoni, A.; Massi, A.; Aldhoun, M. Hantzsch-Type Three-Component Approach to a New Family of Carbon-Linked Glycosyl Amino Acids. Synthesis of C-Glycosylmethyl Pyridylalanines. J. Org. Chem. 2007, 72, 7677-7687.
16. Berezowska, I.; Chung, N. N.; Lemieux, C.; Wilkes, B. C.; Schiller, P. W. Agonist vs Antagonist Behavior of δ Opioid Peptides Containing Novel Phenylalanine Analogues in Place of Tyr. J. Med. Chem. 2009, 52, 6941-6945.
17. US2015/380666
18. Campbell-Verduyn,L. S.; Mirfeizi, L.; Schoonen, A. K.; Rudi A. Dierckx, R. A.; Elsinga, P. H.; Feringa, B. L. Strain-Promoted Copper-Free "Click" Chemistry for 18F Radiolabeling of Bombesin. Angew. Chem. Int. Ed. 2011, 50, 11117-11120.
19. Crich, D.; Sana, K.; Guo, S. Amino Acid and Peptide Synthesis and Functionalization by the Reaction of Thioacids with 2,4-Dinitrobenzenesulfonamides. Org. Lett. 2007, 9, 4423-4426.
20. Wu, X. Y.; Stockdill, J. L.; Park, P. K.; Samuel J. Danishefsky, S. J. Expanding the Limits of Isonitrile-Mediated Amidations: On the Remarkable Stereosubtleties of Macrolactam Formation from Synthetic Seco-Cyclosporins. J. Am. Chem. Soc. 2012, 134, 2378-2384.
21. Du, J. J.; Gao, X. F.; Xin, L. M.; Lei, Z.; Liu, Z.; and Guo, J. Convergent Synthesis of N-Linked Glycopeptides via Aminolysis of w-Asp p-Nitrophenyl Thioesters in Solution. Org. Lett. 2016, 18, 4828-4831.
22. Naumovich, Y. A.; Golovanov, I. S.; Sukhorukov, A. Y.; Loffe, S. L. Addition of HO-Acids to N,N-Bis(oxy) enamines: Mechanism, Scope and Application to the Synthesis of Pharmaceuticals. Eur. J. Org. Chem. 2017, 41, 6209-6227.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A compound of Formula (A):

$$BA\text{-}(L\text{-}P)_m \qquad (A),$$

wherein:

BA is an antibody or an antigen-binding fragment thereof,

L is a linker comprising one or more of a carbamate group: a cyclodextrin; a polyethylene glycol (PEG) segment having 1 to 36 —CH$_2$CH$_2$O— (EG) units; a —(CH$_2$)$_{2\text{-}24}$— chain: a triazole: one or more amino acids selected from glycine, serine, glutamic acid, alanine, valine, and proline, and combinations thereof;

P is a payload selected from the group consisting of:

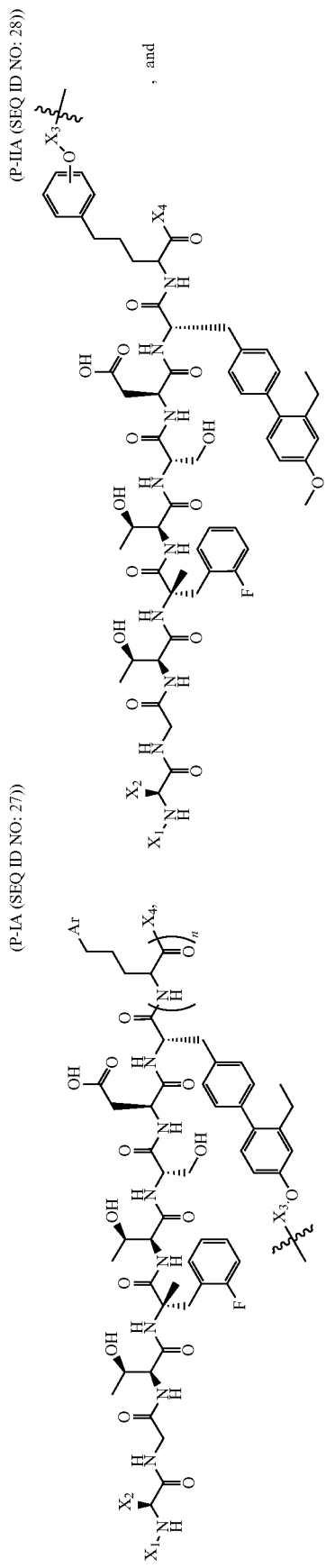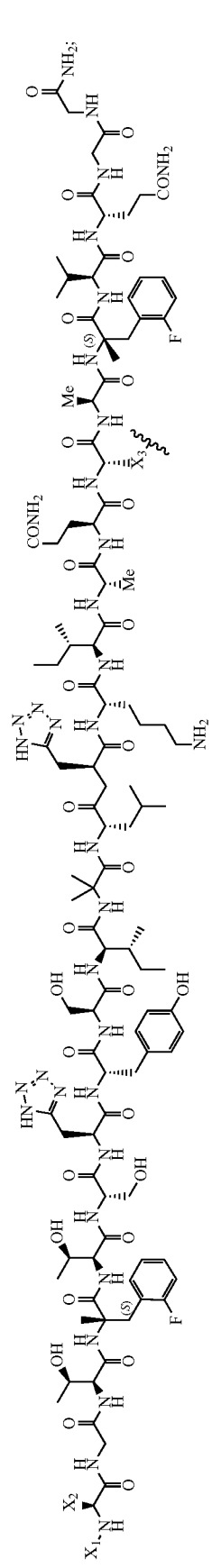

wherein

is the point of attachment of the payload to L;
X₁ is selected from H

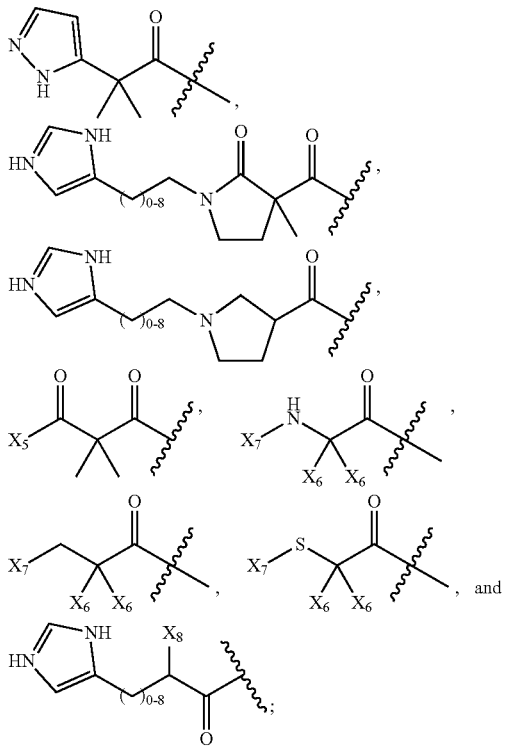

X₂ is selected from

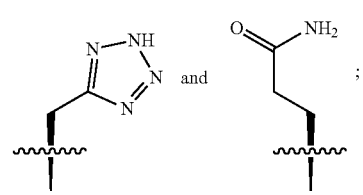

X₃ is selected from a bond, —(CH₂)₂₋₆—NH—, —(CH₂)₂₋₆—Tr-, and —(CH₂)₂₋₆—Tr-(CH₂)₁₋₆—NH, wherein Tr is a triazole moiety;
n is 0 or 1;
X₄ is selected from —NH₂, —OH and —N(H)(phenyl);
X₅ is selected from —OH, —NH2, —NH—OH, and

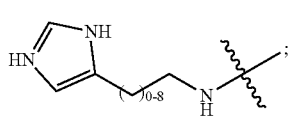

X₆ is independently at each occurrence selected from H, —OH, —CH₃, and —CH₂OH;
X₇ is selected from H

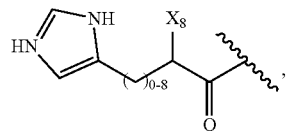

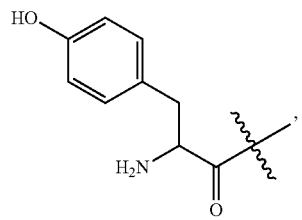

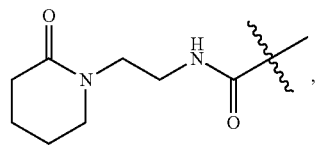

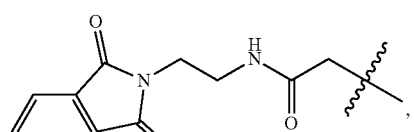, and

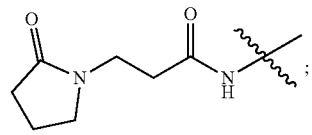

X₈ is selected from H, —OH, —NH₂, and

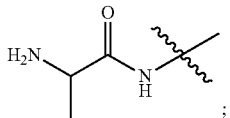

Ar is selected from

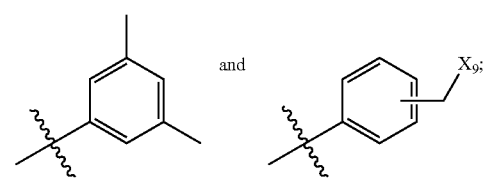

$X_9$ is selected from —NH$_2$

[chemical structure showing —NH—C(=O)—CH$_2$— repeating 1-8 times with terminal NH$_2$], and

[chemical structure showing —NH—C(=O)—(CH$_2$)$_n$—(O—CH$_2$CH$_2$)$_{1-12}$—OH];

and m is an integer from 1 to 4, or a pharmaceutically acceptable salt thereof.

2. The compound of claim 1, wherein the BA is a glucagon like peptide-1 receptor (GLP1R)-targeting antibody or an antigen-binding fragment thereof.

3. The compound of claim 2, wherein the GLP1R-targeting antibody is a GLP1R agonist antibody selected from the group consisting of 5A10, 9A10, h38C2, and glutazumab.

4. The compound of claim 1, wherein the linker L is attached to one or both heavy chains of the BA or to one or both light chains of the BA.

5. The compound of claim 4, wherein the linker L is attached to one or both heavy chain variable domains of the BA or to one or both light chain variable domains of the BA.

6. The compound of claim 1, wherein the linker L is attached to the BA via a glutamine residue or a lysine residue.

7. The compound of claim 1, wherein m is 1 or 2.

8. The compound of claim 1, wherein the linker L has-comprises the structure of formula (L'):

—La—Y-Lp—  (L'), wherein La is a first linker covalently attached to the BA;
Y is a group comprising a triazole moiety; and
Lp is absent or a second linker covalently attached to the P, and wherein when Lp is absent,
Y is also absent.

9. The compound of claim 8, wherein the Y-Lp is absent.

10. The compound of claim 8, wherein the La comprises a structure selected from the group consisting of:

[chemical structure: HN–CH$_2$CH$_2$–(O–CH$_2$CH$_2$)$_7$–O–] and

[chemical structure: HN–CH$_2$CH$_2$–(O–CH$_2$CH$_2$)$_{11}$–O–].

11. The compound of claim 1, wherein P is P-IA (SEQ ID NO: 27).

12. The compound of claim 1, wherein the compound has a plasma half life of longer than 7 days.

13. The compound of claim 1, wherein the compound does not bind to G protein-coupled receptors (GPCRs) other than GLP1R.

14. A pharmaceutical composition comprising the compound of claim 1.

15. A pharmaceutical dosage form comprising the compound of claim 1.

16. A method of selectively targeting GLP1R on a surface of a cell, wherein the method comprises contacting the cell with the compound of claim 1.

17. A method of enhancing GLP1R activity in an individual in need thereof comprising administering to the individual an effective amount of the compound of claim 1.

18. A method of lowering blood glucose levels in an individual in need thereof comprising administering to the individual an effective amount of the compound of claim 1.

19. A method of lowering body weight in an individual in need thereof comprising administering to the individual an effective amount of the compound of claim 1.

20. A method of producing the compound of Formula (A):

BA-(L-P)$_m$  (A), wherein the method comprises the steps of:
a) contacting, in the presence of a transglutaminase, the BA comprising at least m glutamine residues with at least equivalent number of the compound L-P, and
b) isolating the produced compound of Formula (A); and
wherein the BA, L, P, and m are as defined in claim 1.

21. A compound of Formula (I):

BA-L-P  (I), wherein:
BA is an antibody or an antigen-binding fragment thereof,
L is a linker comprising one or more of

[chemical structure showing succinamide-type linker];

a carbamate group; a cyclodextrin; a polyethylene glycol (PEG) segment having 1 to 36 —CH$_2$CH$_2$O— (EG) units; a —(CH$_2$)$_{2\text{-}24}$— chain: a triazole: one or more amino acids selected from glycine, serine, glutamic acid, alanine, valine, and proline, and combinations thereof;

P is a payload selected from the group consisting of:
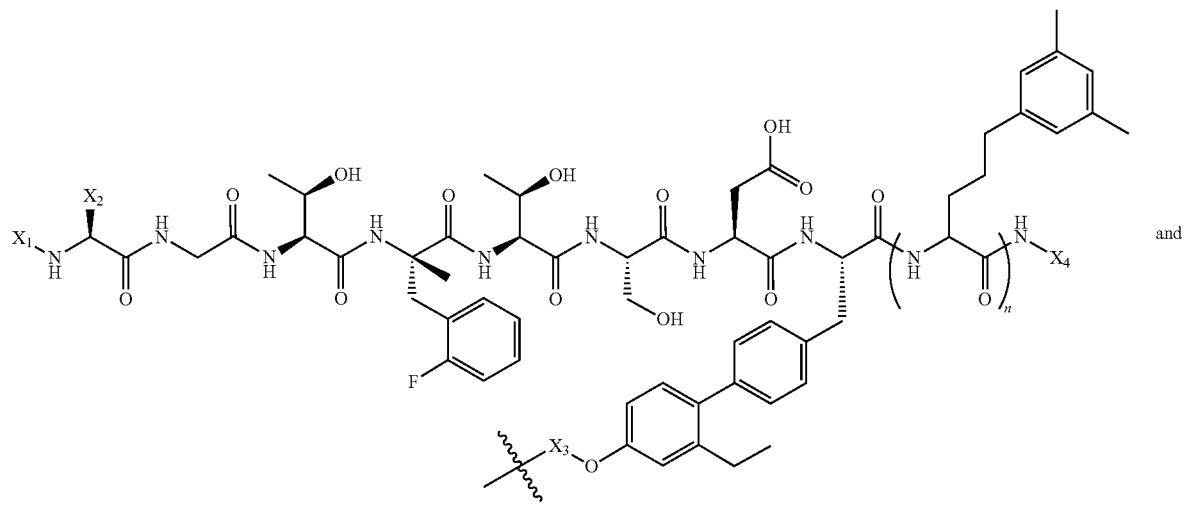
(P-I (SEQ ID NO: 30))
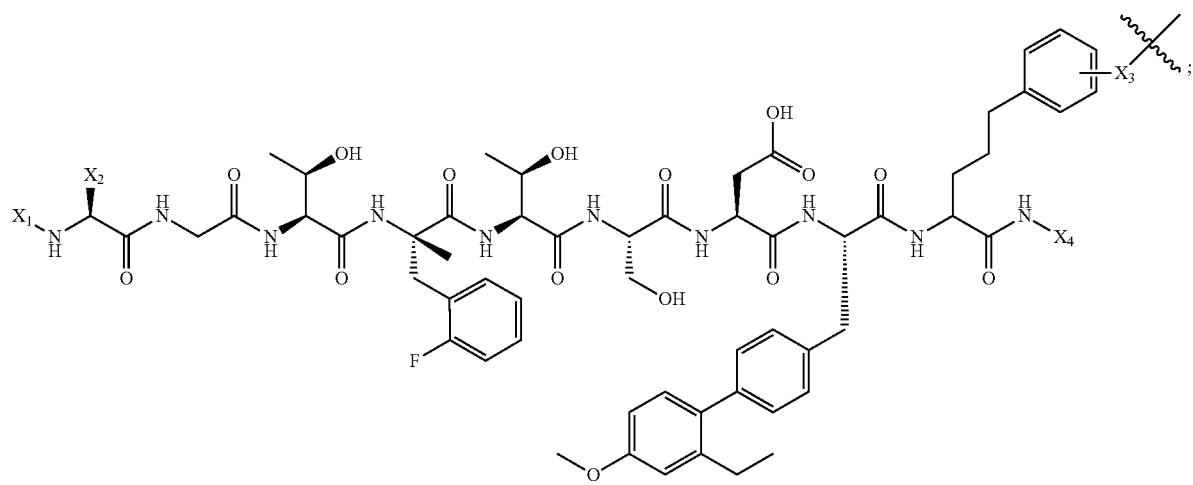
(P-II (SEQ ID NO: 28));
wherein
is the point of attachment of the payload to L;
$X_1$ is selected from H
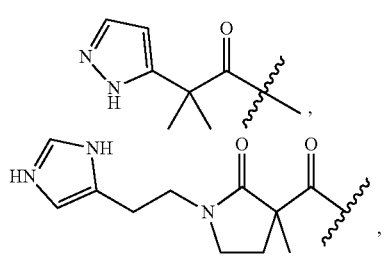
-continued
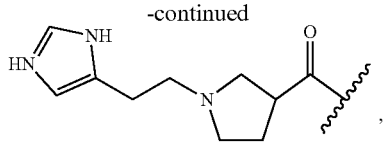
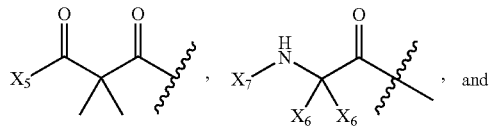
, and
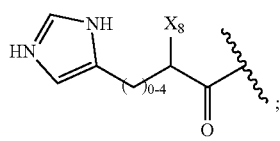
;

$X_2$ is selected from

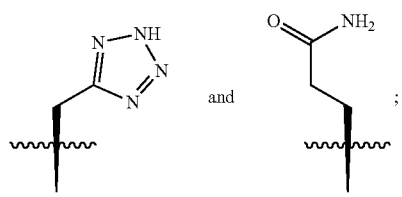

$X_3$ is selected from —$(CH_2)_{2-6}$—NH— and —$(CH_2)_{2-6}$—Tr-, wherein Tr is a triazole moiety;
n is 0 or 1;
$X_4$ is selected from H and phenyl;
$X_5$ is selected from —OH, —$NH_2$, —NH—OH,

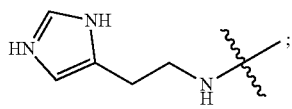 [SMILES: *NCCc1cnc[nH]1]

$X_6$ is independently at each occurrence selected from H, —OH, —$CH_3$, and —$CH_2OH$;
$X_7$ is selected from H

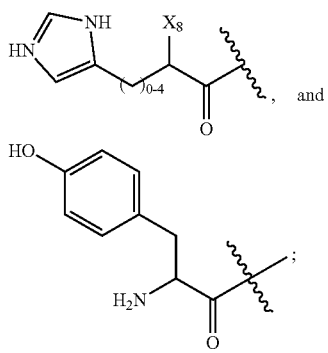

$X_8$ is selected from H, —OH, —$NH_2$, and

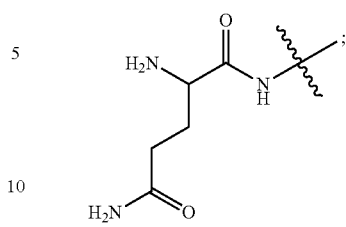

or a pharmaceutically acceptable salt thereof.

22. A compound of Formula (A):

$$BA\text{-}(L\text{-}P)m \qquad (A),$$

or a pharmaceutically acceptable salt thereof, wherein:
BA is an antibody or an antigen-binding fragment thereof;
L is a linker comprising one or more of

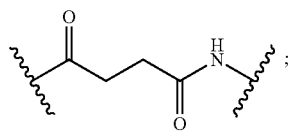 [SMILES: *NC(=O)CCC(*)=O ; ";"]

a carbamate group; a cyclodextrin: a polyethylene glycol (PEG) segment having 1 to 36 —$CH_2CH_2O$— (EG) units; a —$(CH_2)_{2-24}$— chain: a triazole: one or more amino acids selected from glycine, serine, glutamic acid, alanine, valine, and proline, and combinations thereof;
m is an integer from 1 to 4; and
P is selected from the group consisting of:

(SEQ ID NO: 41)

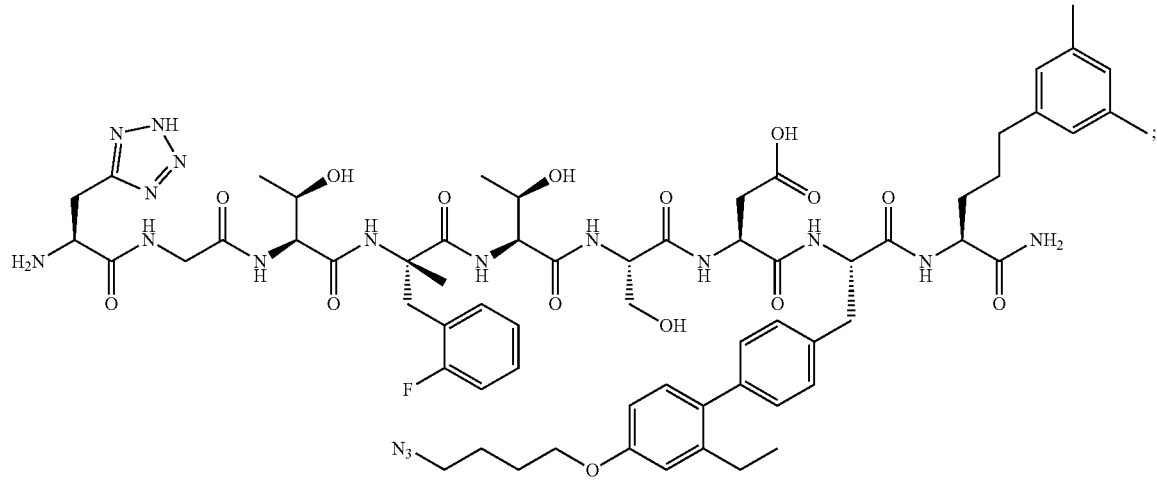

(SEQ ID NO: 42)
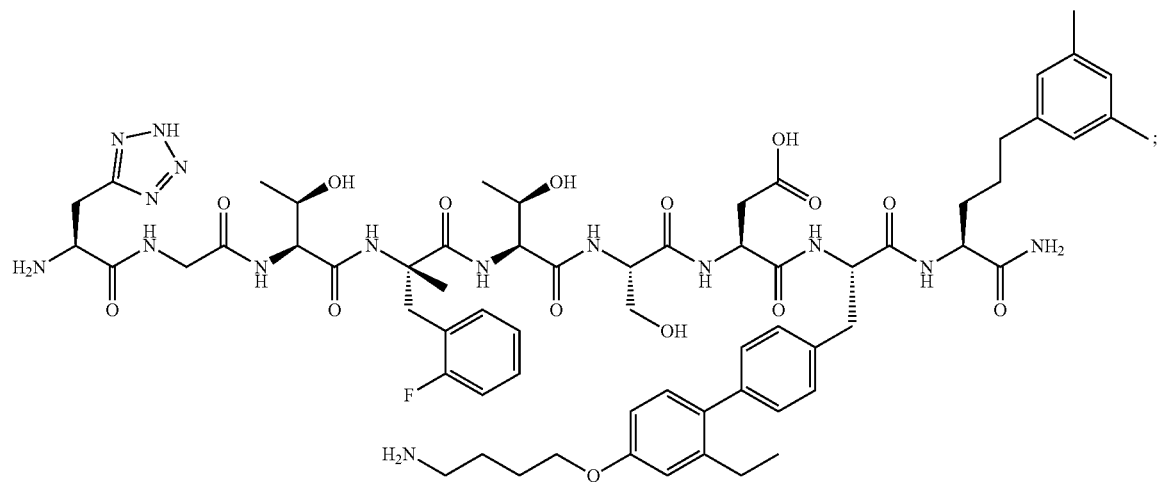
(SEQ ID NO: 43)
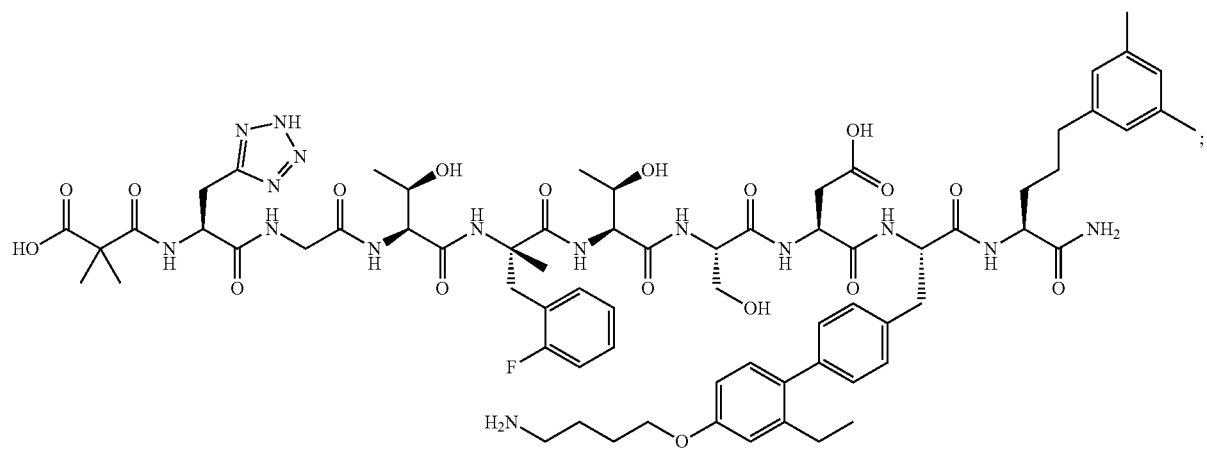
(SEQ ID NO: 44)
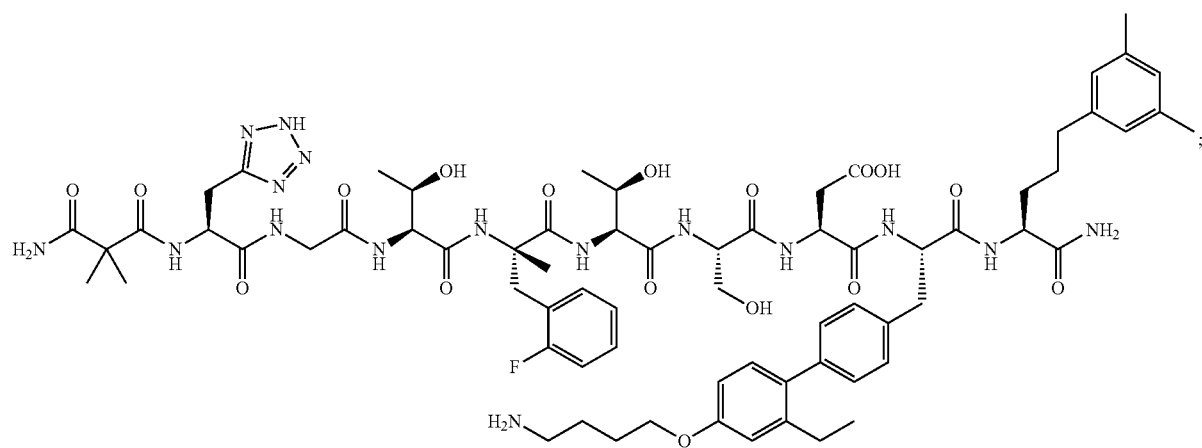

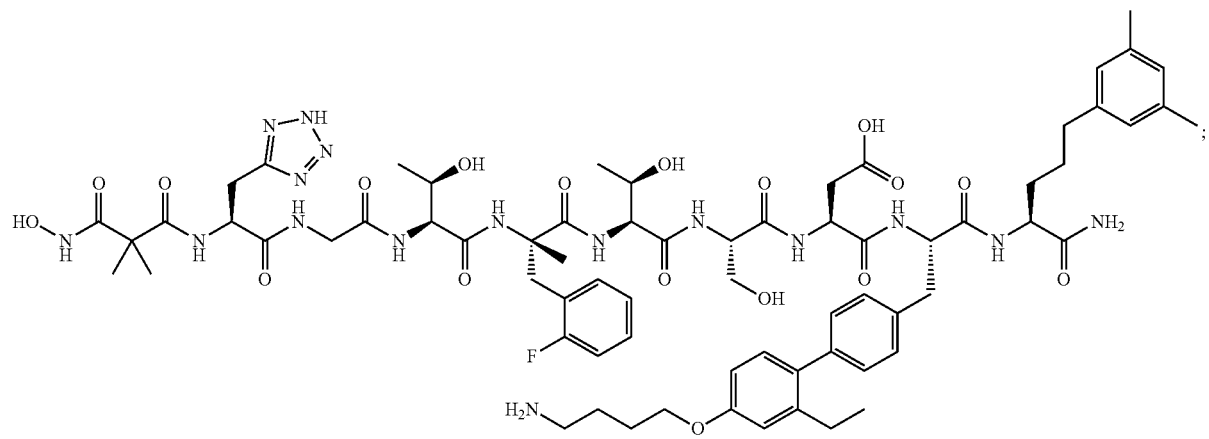
(SEQ ID NO: 45)
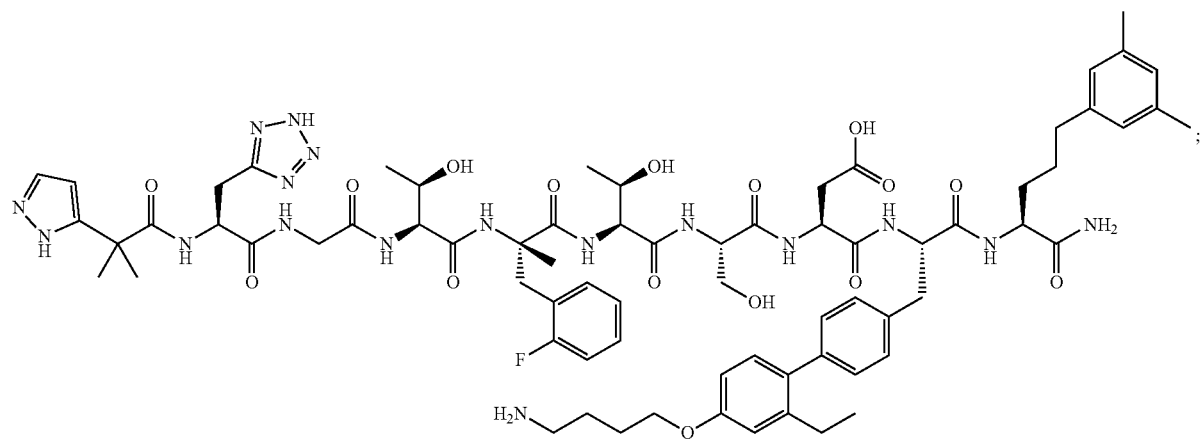
(SEQ ID NO: 46)
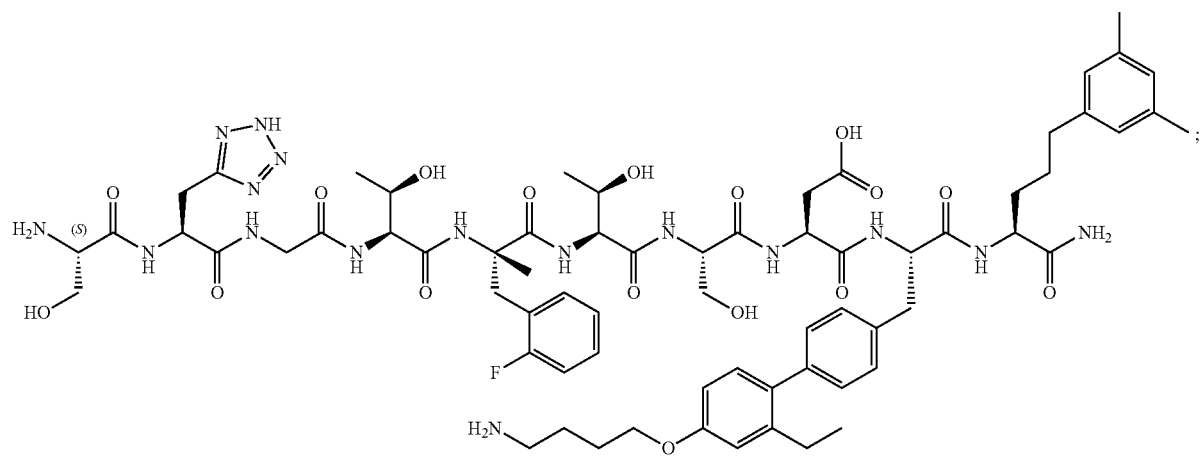
(SEQ ID NO: 47)

(SEQ ID NO: 48)
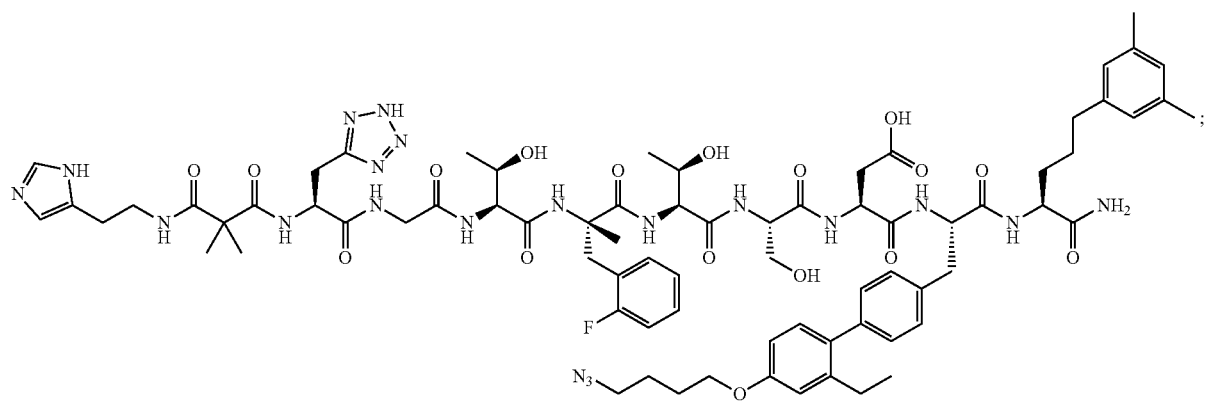
(SEQ ID NO: 49)
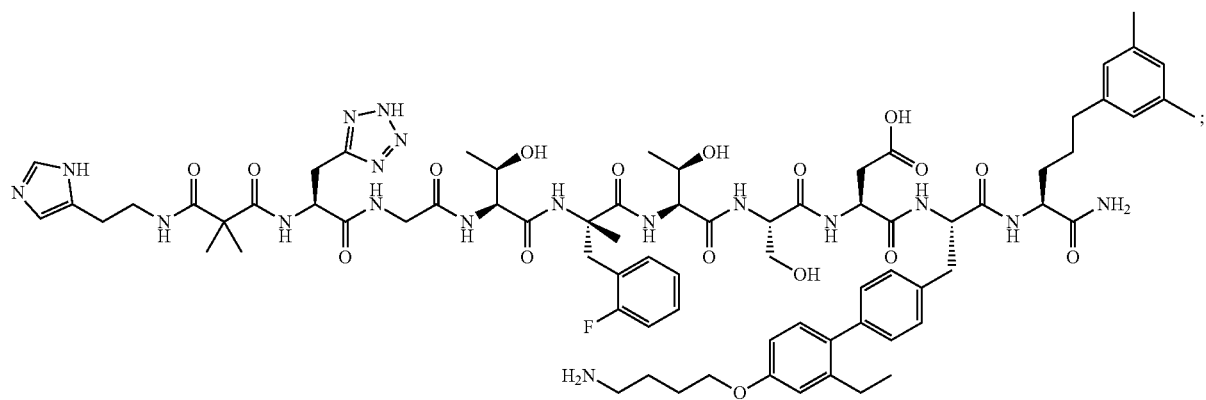
(SEQ ID NO: 50)
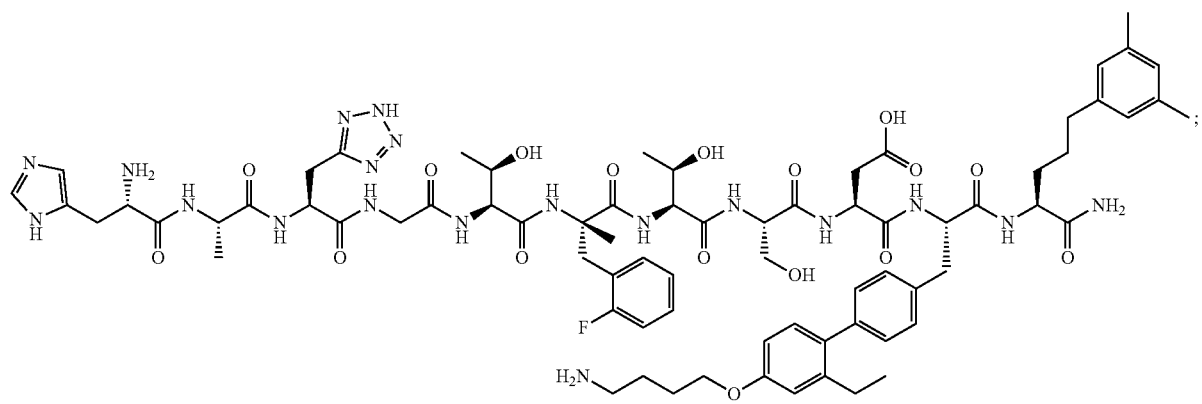

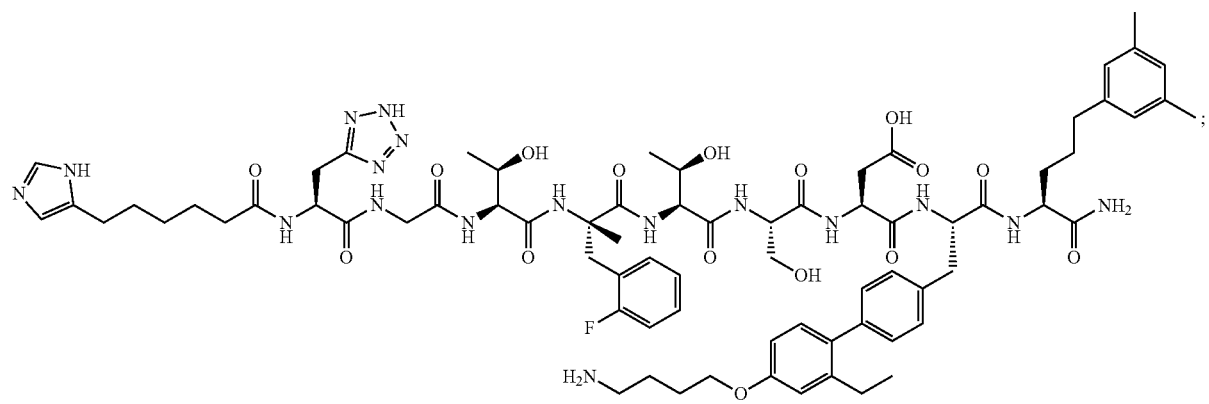
(SEQ ID NO: 51)
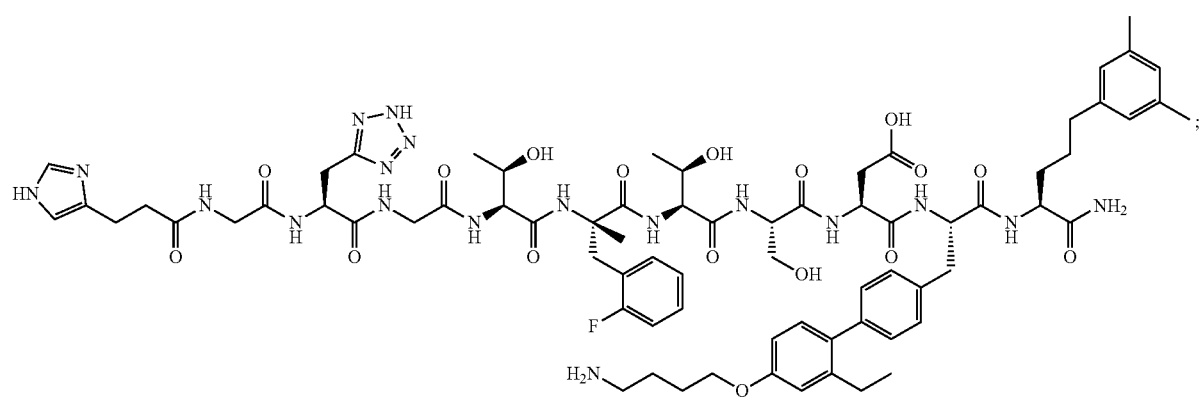
(SEQ ID NO: 52)
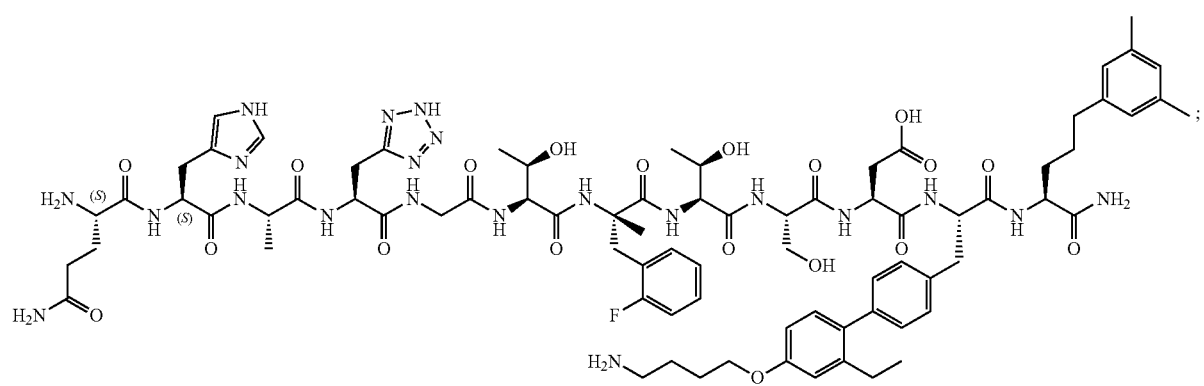
(SEQ ID NO: 53)
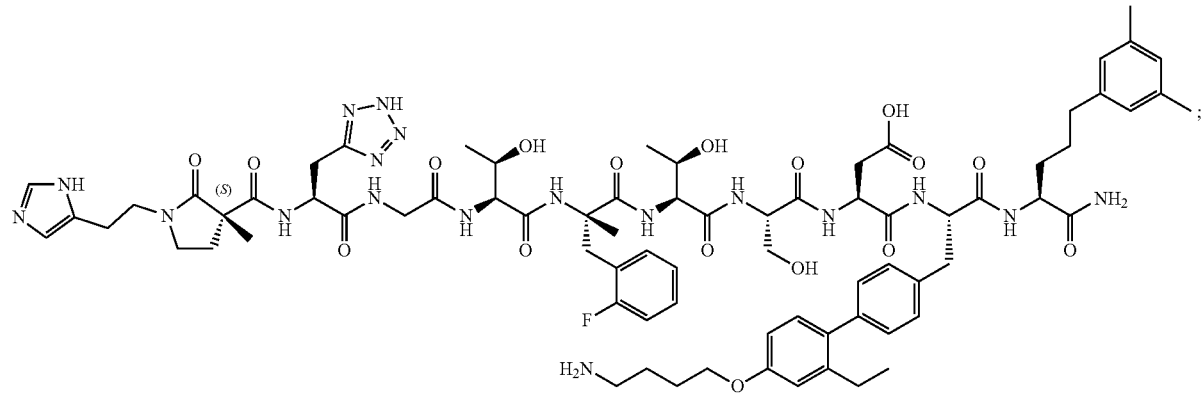
(SEQ ID NO: 54)

-continued
(SEQ ID NO: 55)
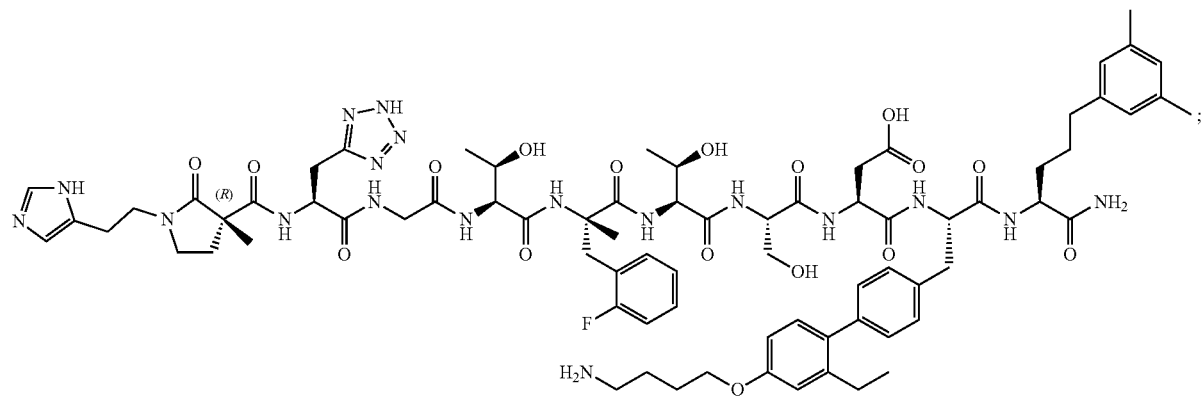
(SEQ ID NO: 56)
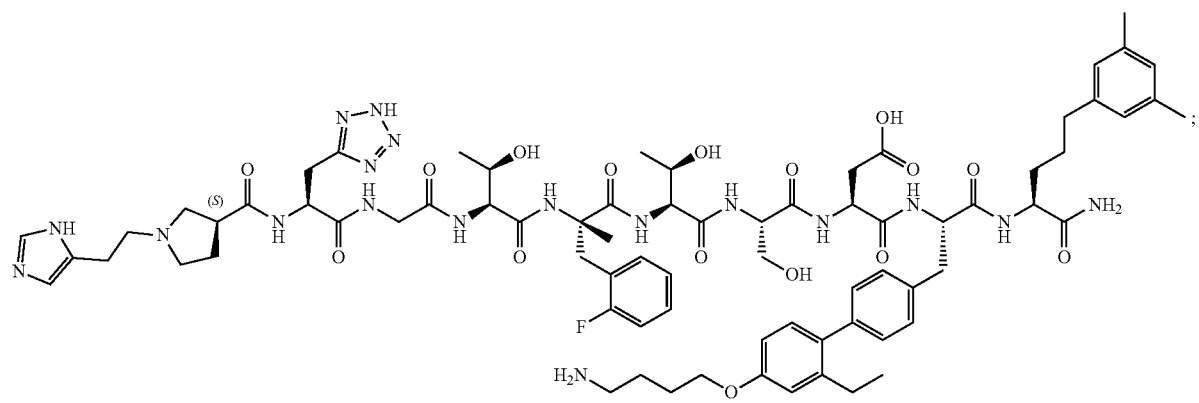
(SEQ ID NO: 57)
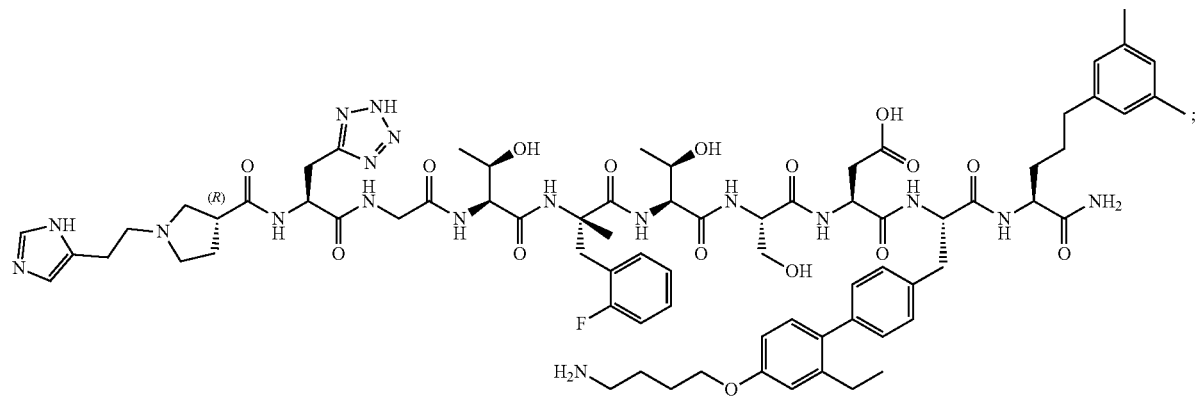

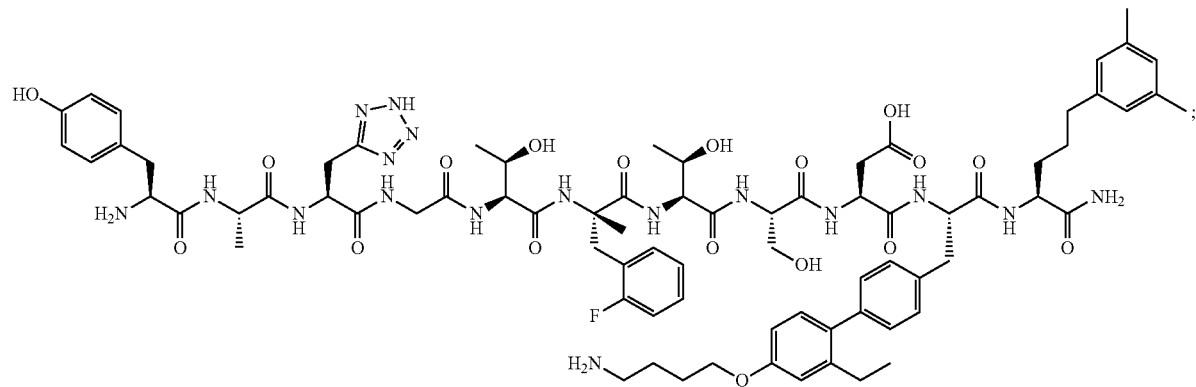
(SEQ ID NO: 58)
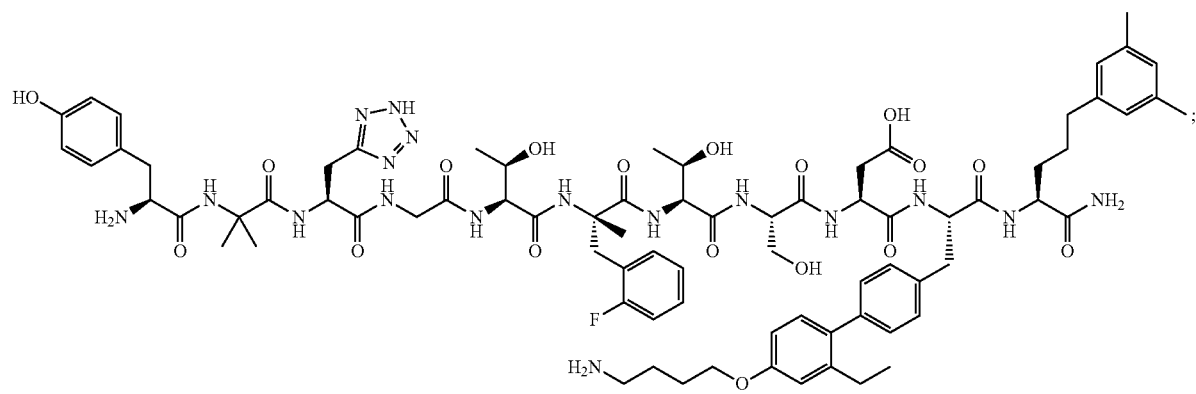
(SEQ ID NO: 59)
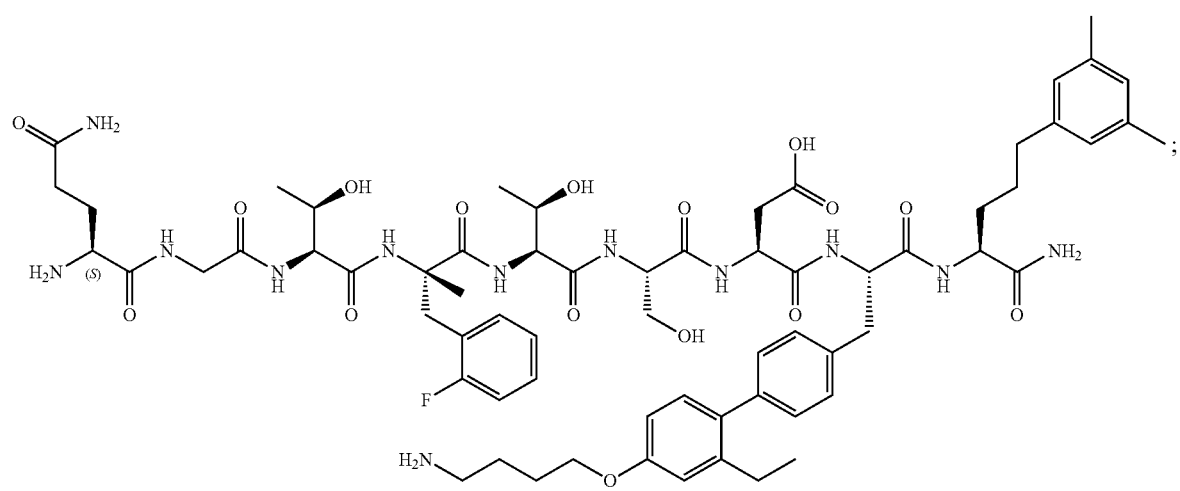
(SEQ ID NO: 60)

(SEQ ID NO: 61)
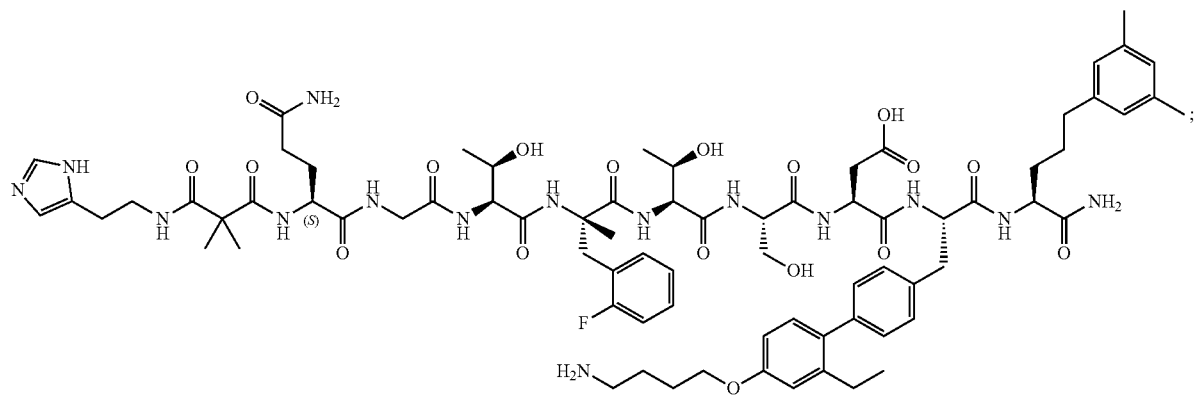
(SEQ ID NO: 62)
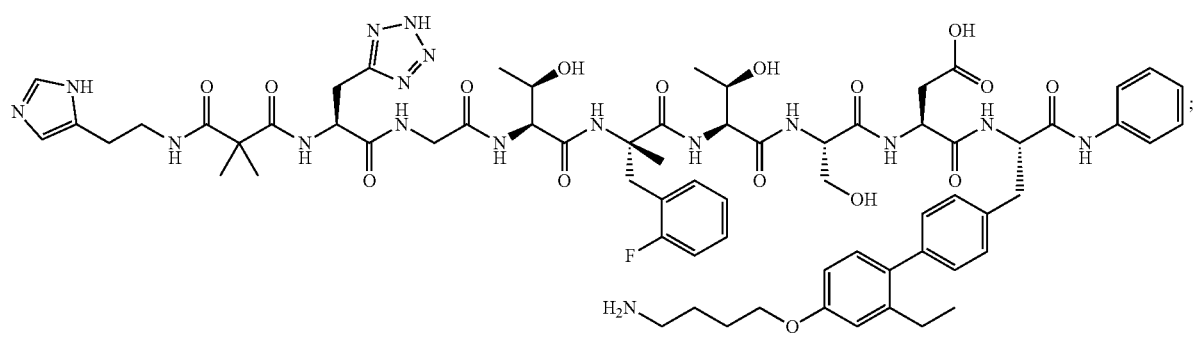
(SEQ ID NO: 63)
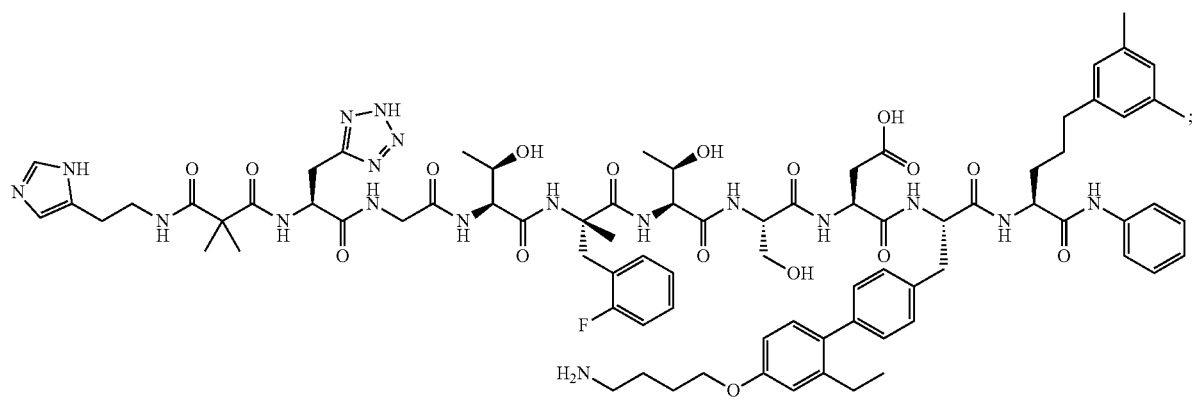
(SEQ ID NO: 64)
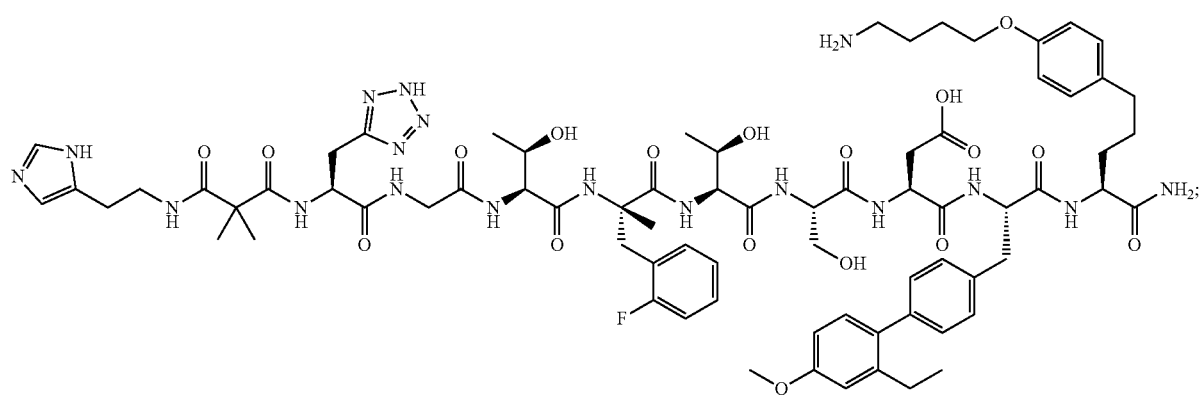

-continued
(SEQ ID NO: 65)
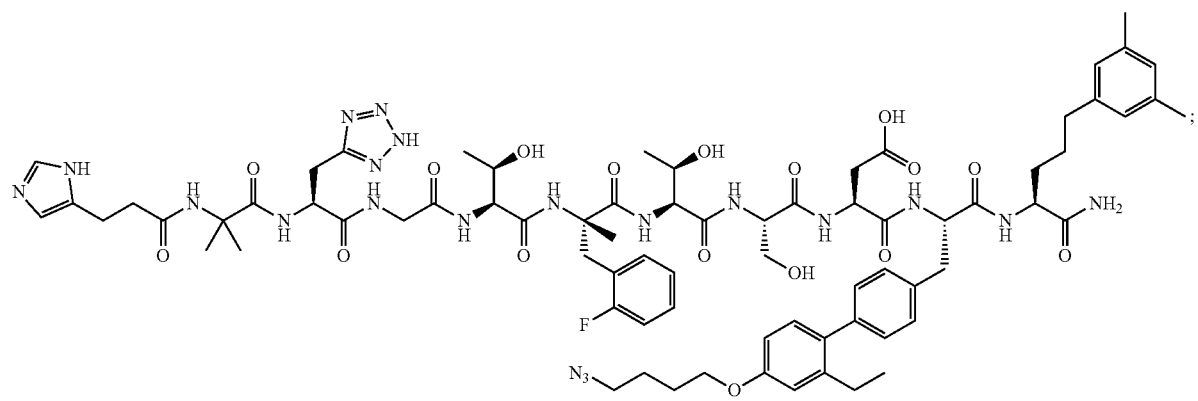
(SEQ ID NO: 66)
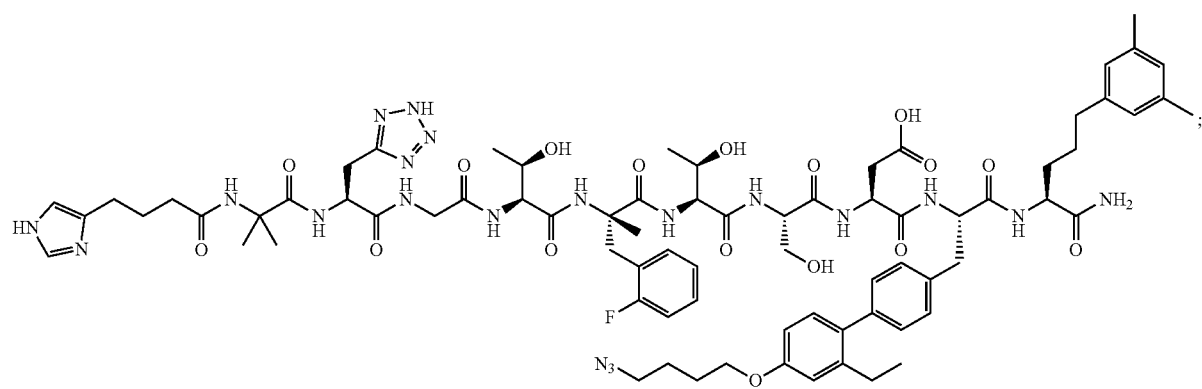
(SEQ ID NO: 67)
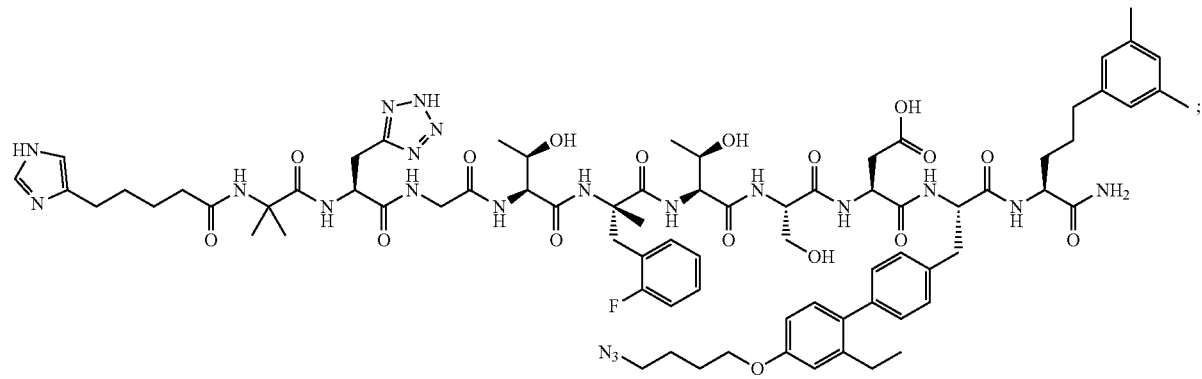
(SEQ ID NO: 68)
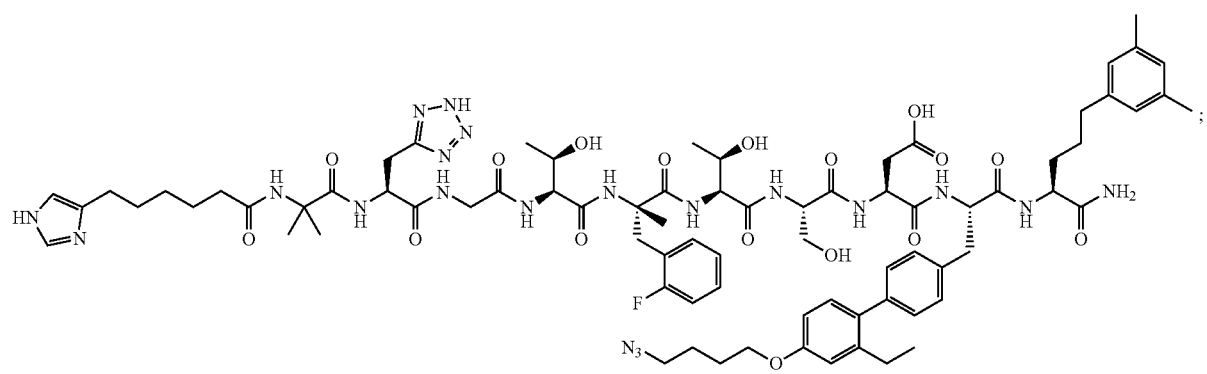

(SEQ ID NO: 69)
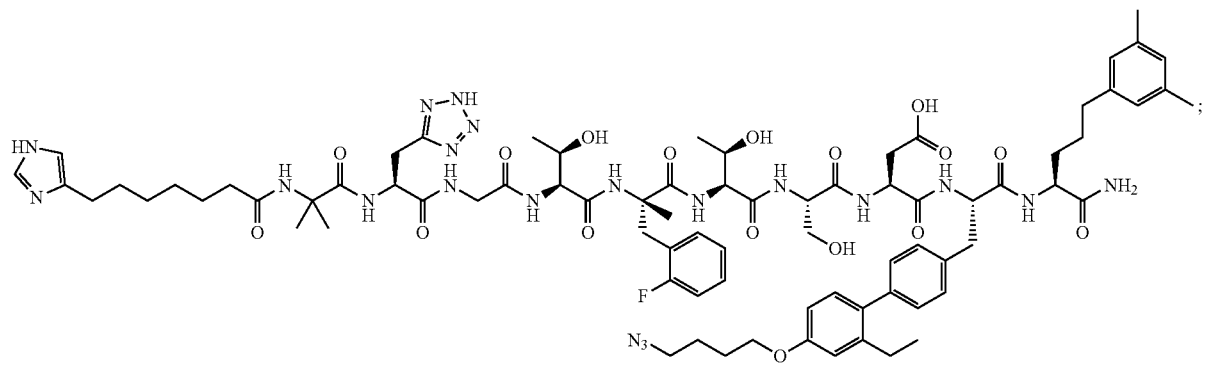
(SEQ ID NO: 70)
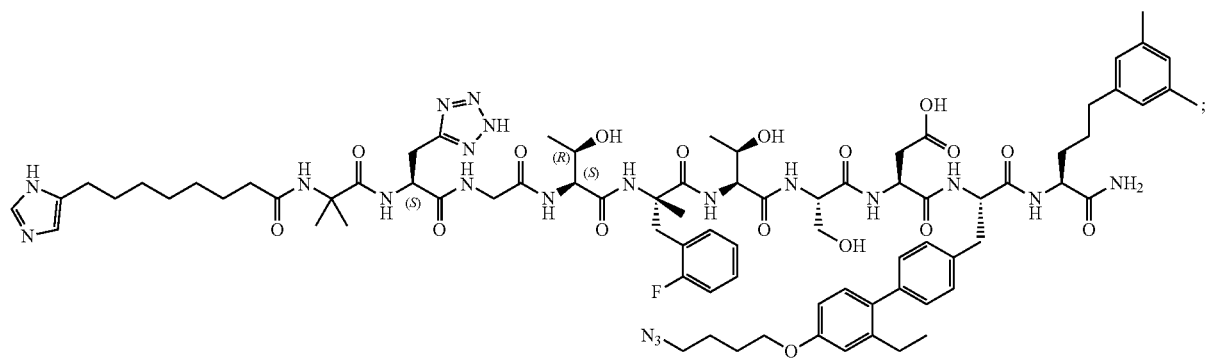
(SEQ ID NO: 71)
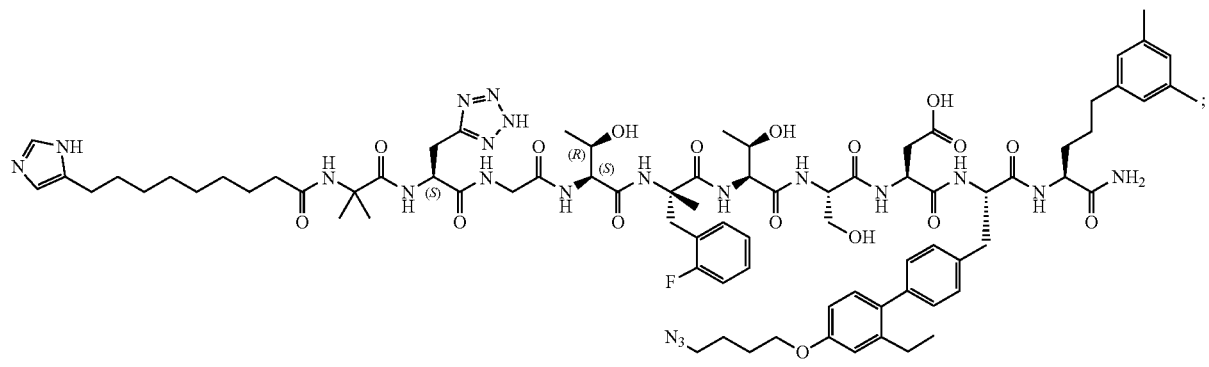
(Main Structure: SEQ ID NO: 72; Branched Sequence: SEQ ID NO: 154)
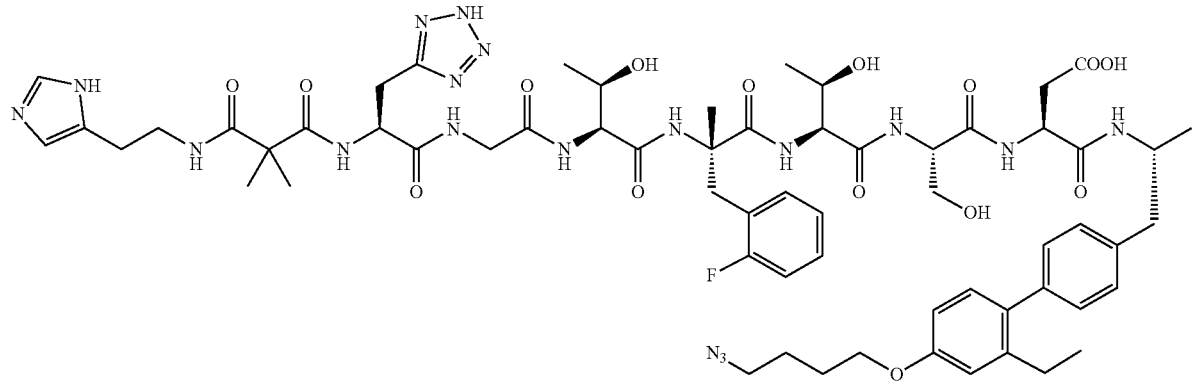

-continued
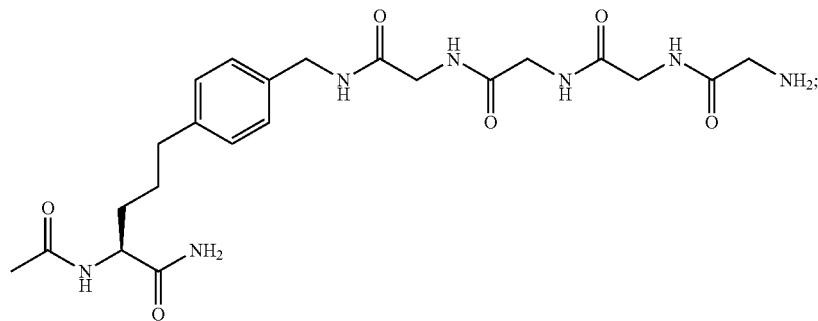
(SEQ ID NO: 73)
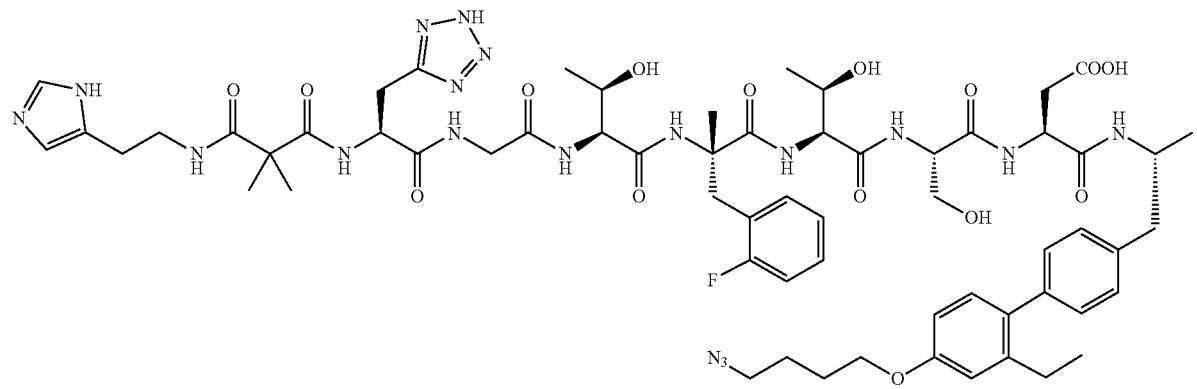
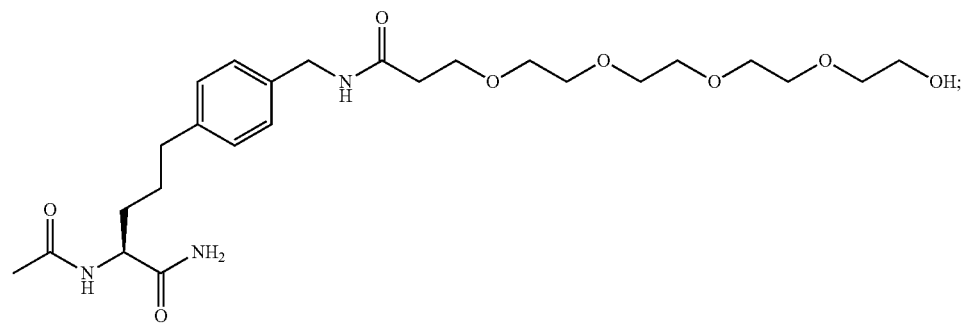
(Main Structure: SEQ ID NO: 74; Branched Sequence: SEQ ID NO: 155)
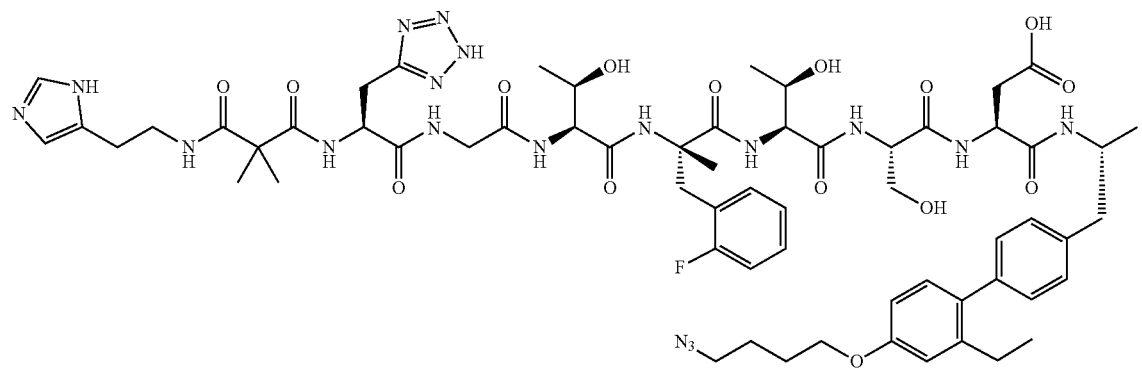

833
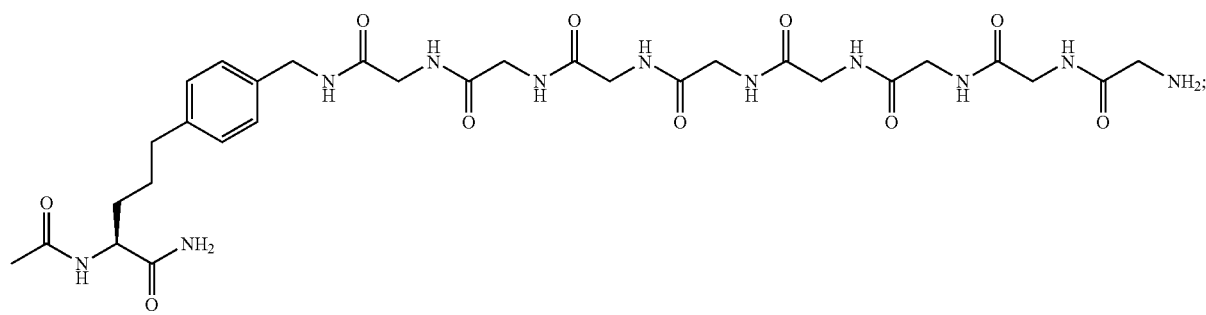
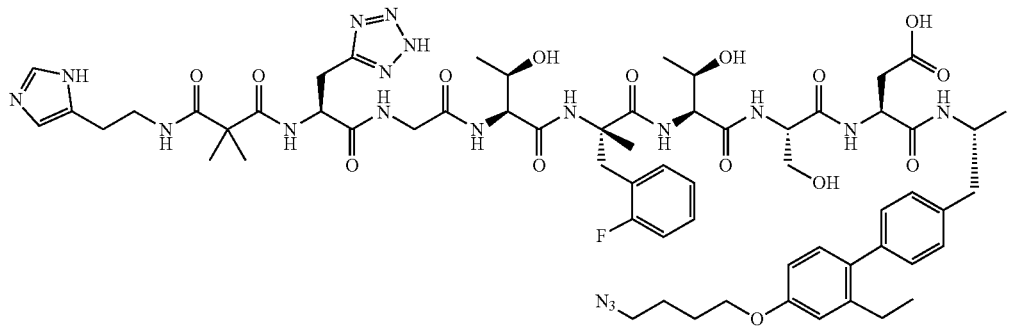
(SEQ ID NO: 75)
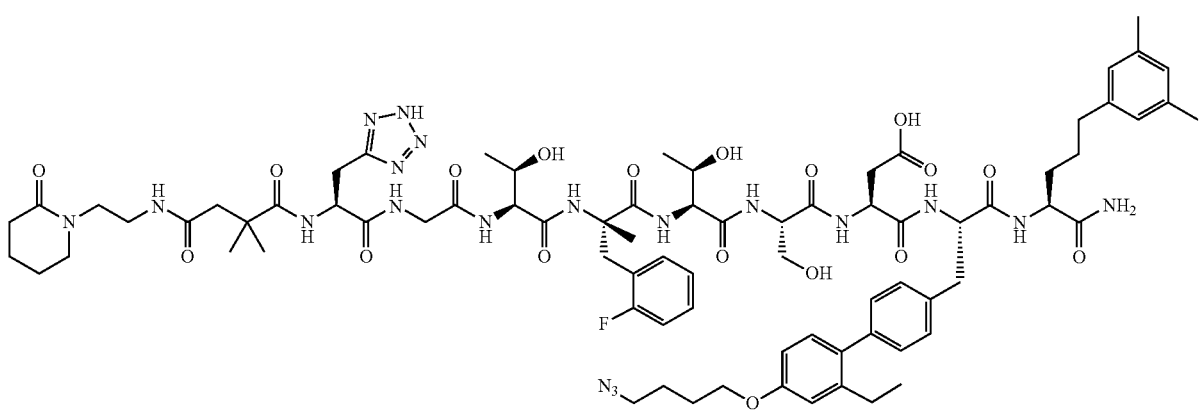
(SEQ ID NO: 76)
834

(SEQ ID NO: 77)
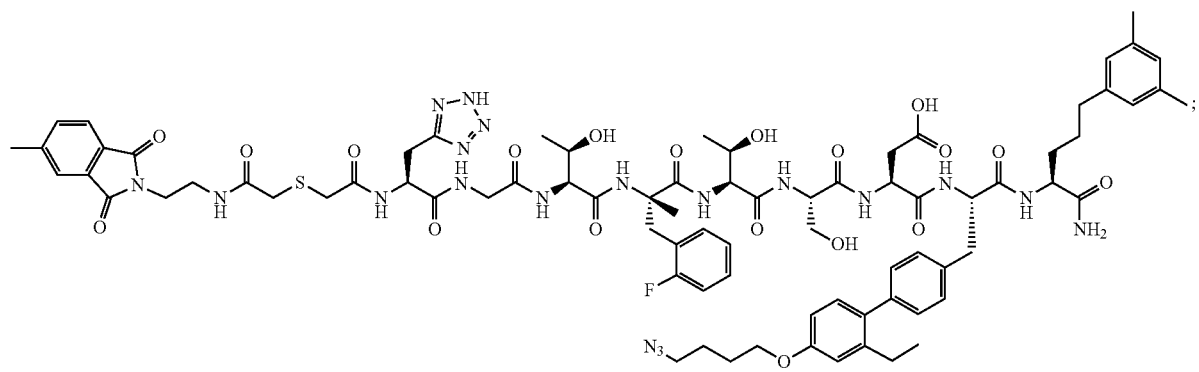
(SEQ ID NO: 78)
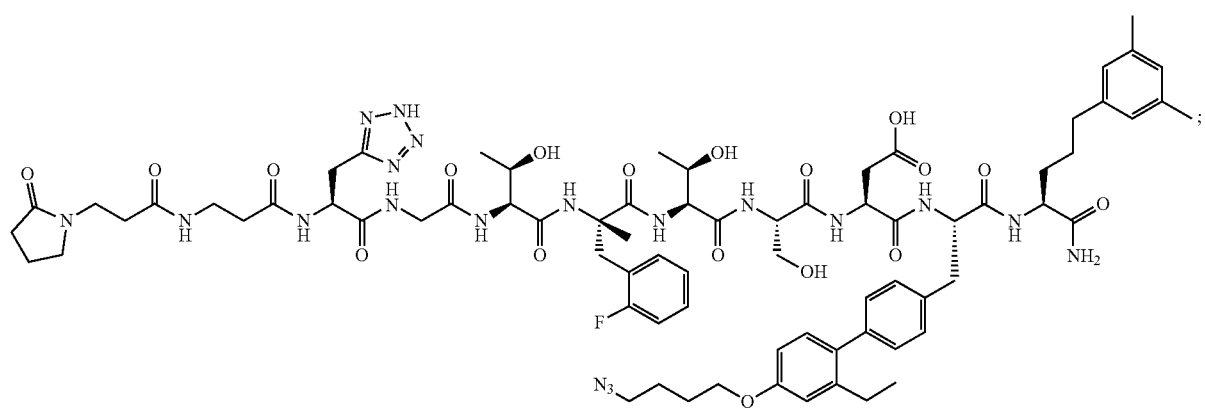
(SEQ ID NO: 80)
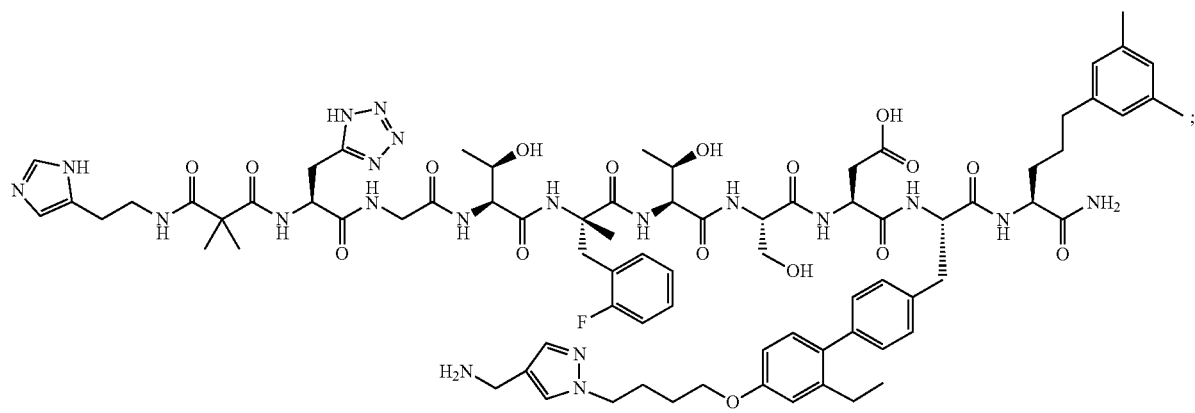
(SEQ ID NO: 81)
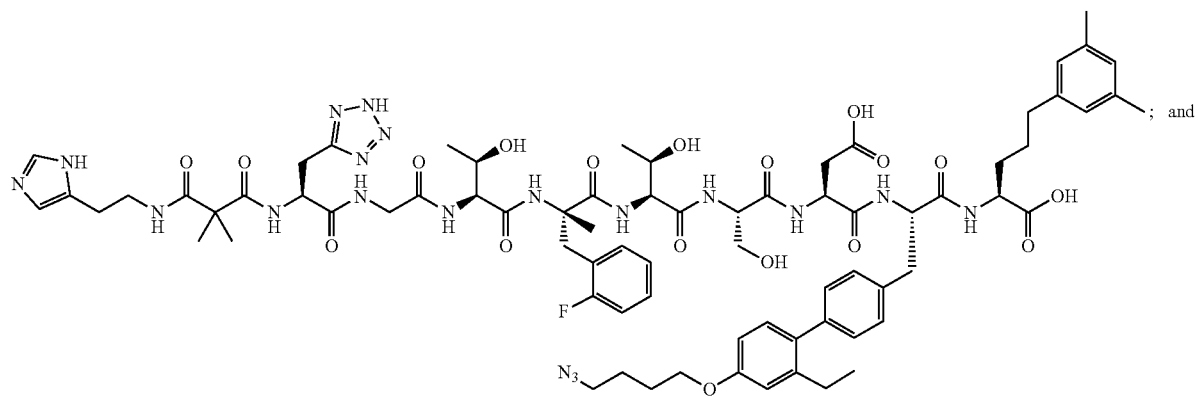
; and (SEQ ID NO: 82)
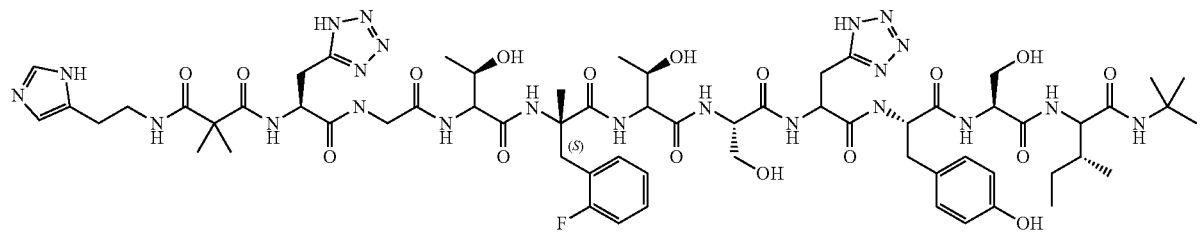
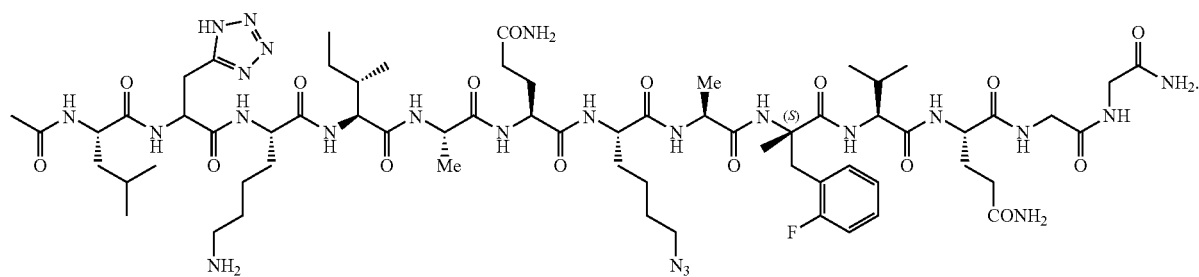
23. A compound selected from the group consisting of Formula (P-IB), Formula (P-IIB), and Formula (P-IIIB):
(P-IB (SEQ ID NO: 83))
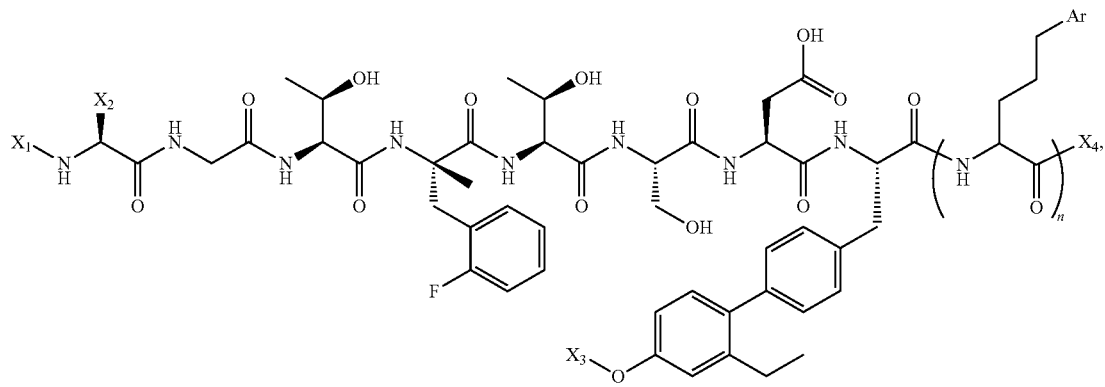
(P-IIB (SEQ ID NO: 84)) and
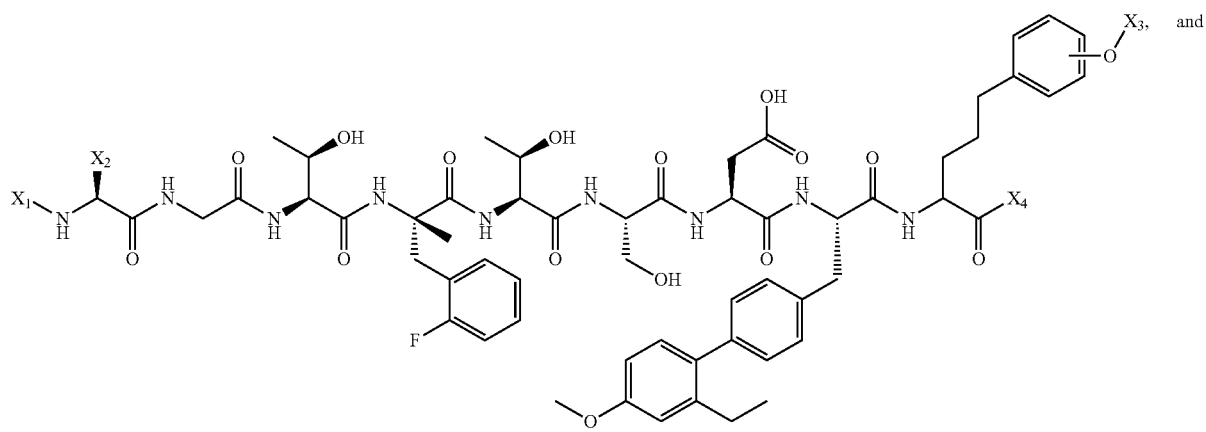

(P-IIIB (SEQ ID NO: 84))
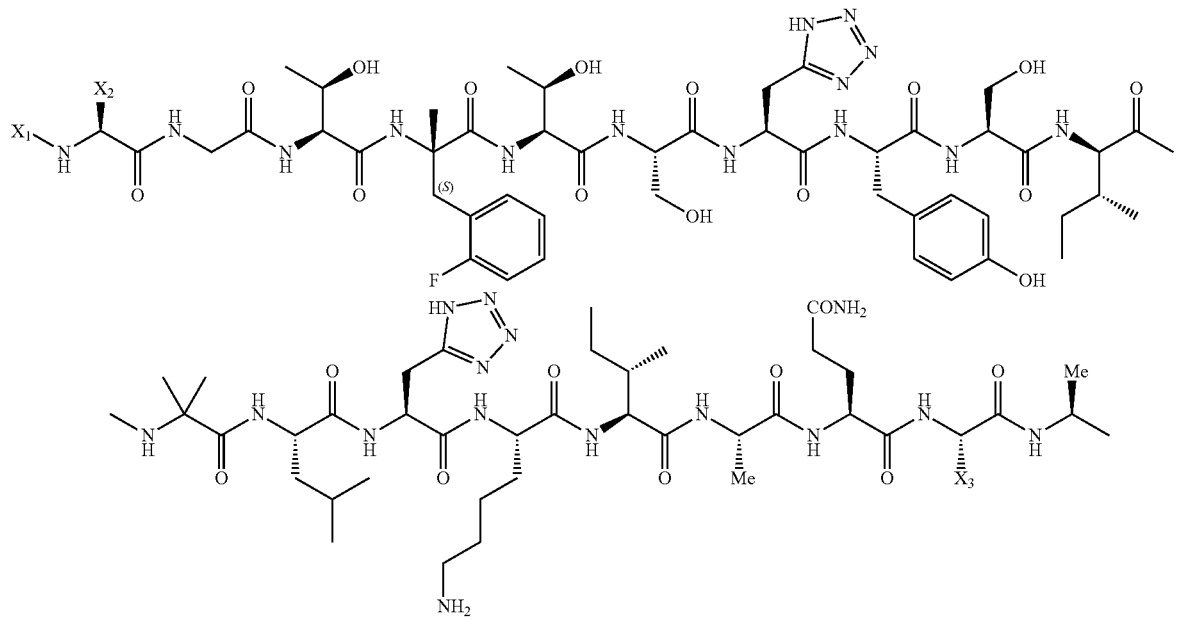
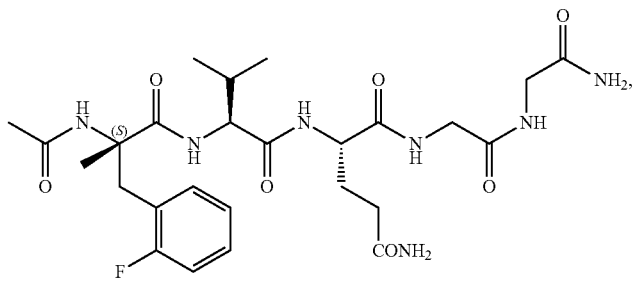
wherein:
X₁ is selected from H
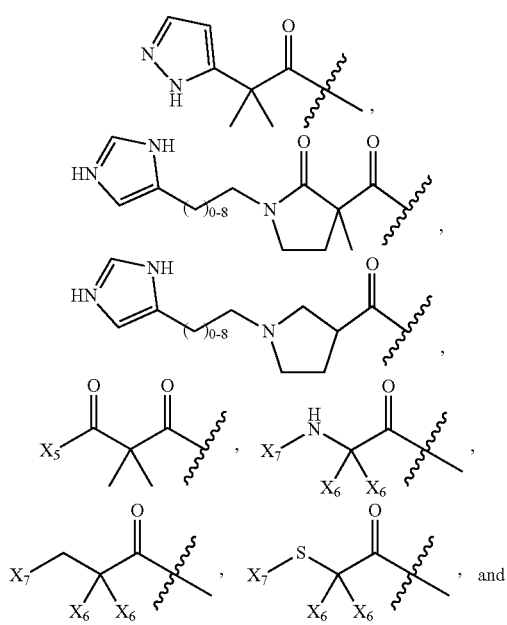
X₂ is selected from
[structures shown: tetrazole-CH₂- and H₂N-CO-CH₂CH₂-]
and
X₃ is selected from —(CH₂)₂₋₆—NH₂, —(CH₂)₂₋₆—N₃, and —(CH₂)₂₋₆—Tr-(CH₂)₁₋₆—NH₂,
wherein Tr is a triazole moiety;
n is 0 or 1;
X₄ is selected from —NH₂, —OH and —N(H)(phenyl);
X₅ is selected from —OH, —NH₂, —NH—OH, and 841
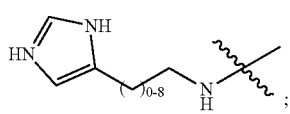;
$X_6$ is independently at each occurrence selected from H, —OH, —CH$_3$, and —CH$_2$OH;
$X_7$ is selected from H,
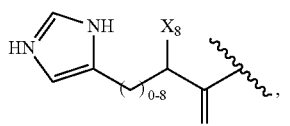,
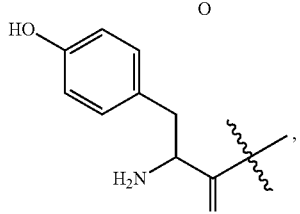,
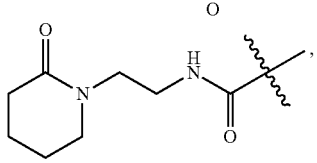,
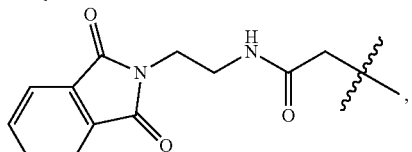, and
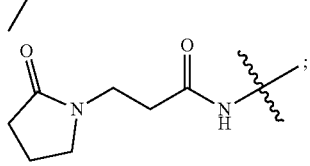;
842
$X_8$ is selected from H, —OH, —NH$_2$, and
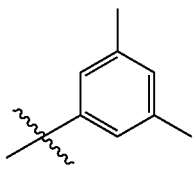;
Ar is selected from
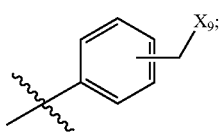;
$X_9$ is selected from —NH$_2$,
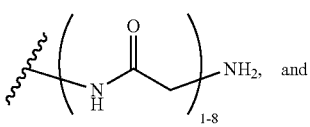, and
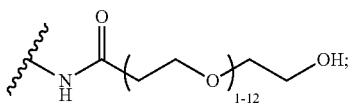;
or a pharmaceutically acceptable salt thereof.
24. A compound of Formula (II):
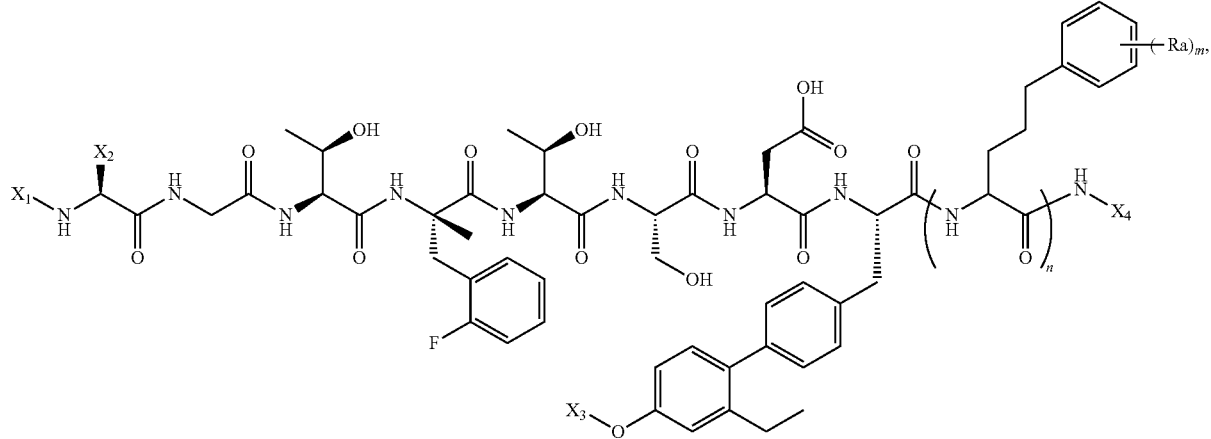
(II (SEQ ID NO: 85))

wherein:

$X_1$ is selected from H,

[structure: pyrazole-C(CH3)2-C(=O)-],

[structure: imidazole-CH2CH2-N(pyrrolidinone with methyl)-C(=O)-],

[structure: imidazole-CH2CH2-N(pyrrolidine)-C(=O)-],

[structure: $X_5$-C(=O)-C(CH3)2-C(=O)-]; [structure: $X_7$-NH-C($X_6$)($X_6$)-C(=O)-], and

[structure: imidazole-(CH2)0-4-CH($X_8$)-C(=O)-];

$X_2$ is selected from

[structure: tetrazole-CH2-] and [structure: -CH2CH2-C(=O)-NH2];

$X_3$ is selected from —(CH$_2$)$_{2-6}$—NH$_2$, —(CH$_2$)$_{2-6}$—N$_3$, and —CH$_3$, with the proviso that when $X_3$ is —CH$_3$, n is 1 and Ra in at least one occurrence is selected from —(CH$_2$)$_{2-6}$—NH$_2$ and —(CH$_2$)$_{2-6}$—N$_3$;

n is 0 or 1;

m is an integer from 0 to 3;

Ra is independently at each occurrence selected from —CH$_3$, —(CH$_2$)$_{2-6}$—NH$_2$, and —(CH$_2$)$_{2-6}$—N$_3$;

$X_4$ is selected from H and phenyl;

$X_5$ is selected from —OH, —NH$_2$, —NH—OH, and

[structure: imidazole-CH2CH2-NH-C(CH3)2-];

$X_6$ is independently at each occurrence selected from H, —OH, —CH$_3$, and —CH$_2$OH;

$X_7$ is selected from H,

[structure: imidazole-(CH2)0-4-CH($X_8$)-C(=O)-], and

[structure: HO-phenyl-CH2-CH(NH2)-C(=O)-];

$X_8$ is selected from H, —OH, —NH$_2$, and

[structure: H2N-CH(CH2CH2-C(=O)-NH2)-C(=O)-NH-C(CH3)2-], or a pharmaceutically acceptable salt thereof.

25. A compound selected from the group consisting of:
(SEQ ID NO: 41)
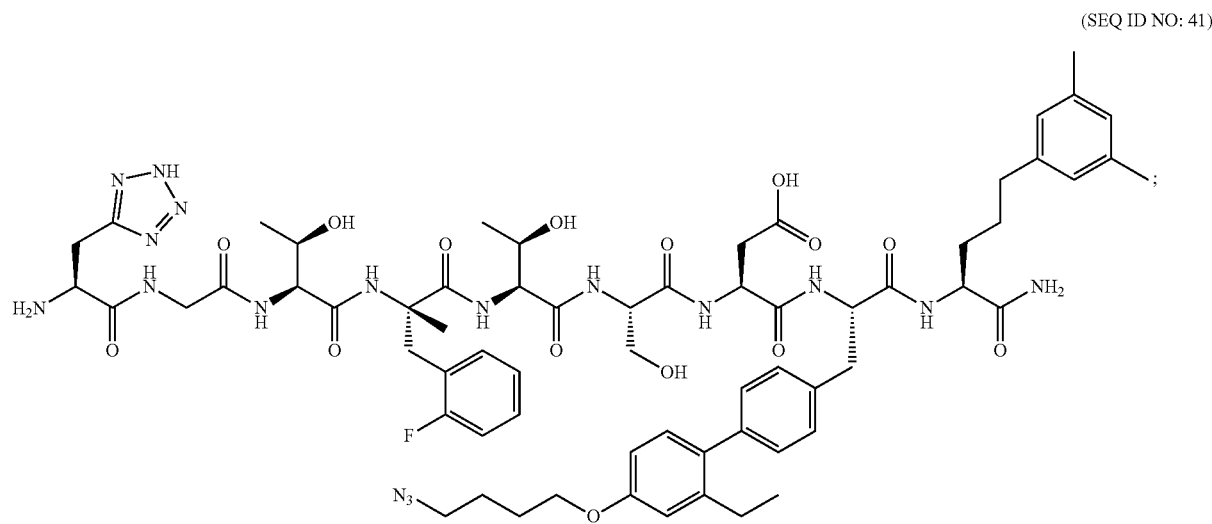
(SEQ ID NO: 42)
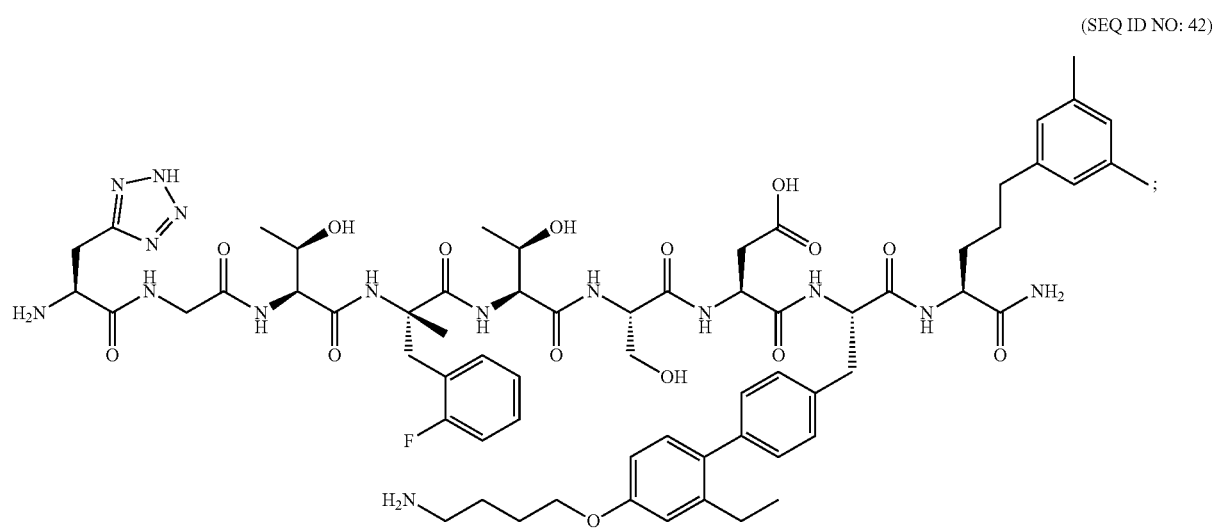
(SEQ ID NO: 43)
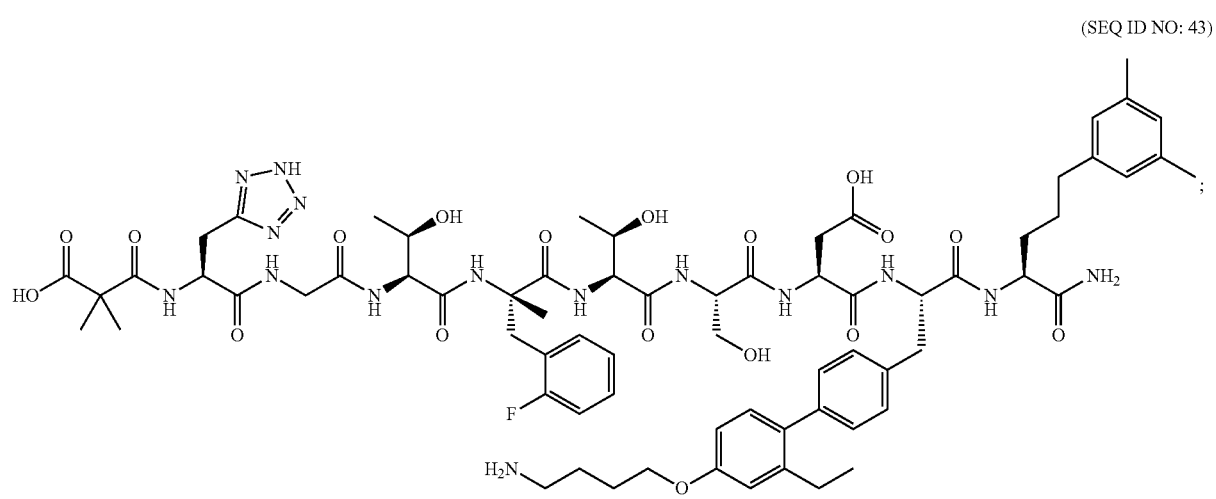

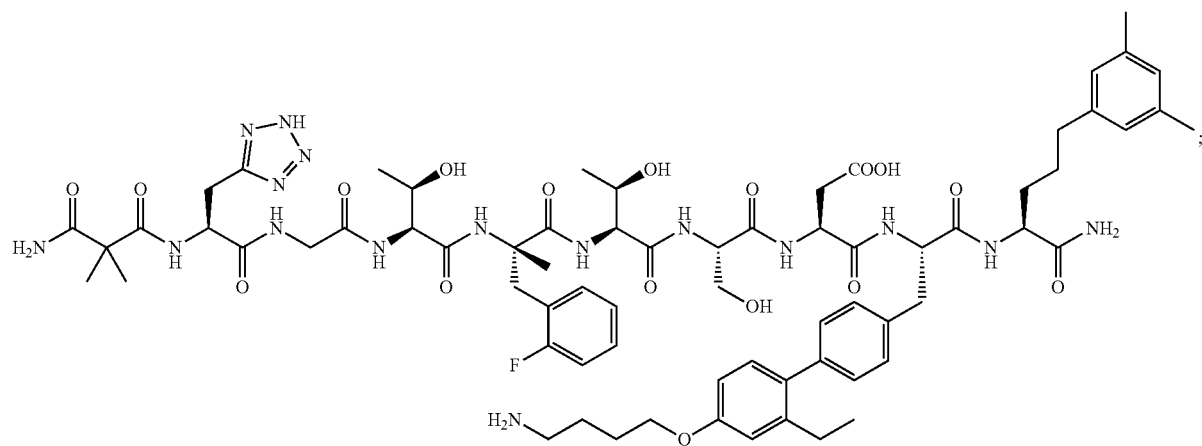
(SEQ ID NO: 44)
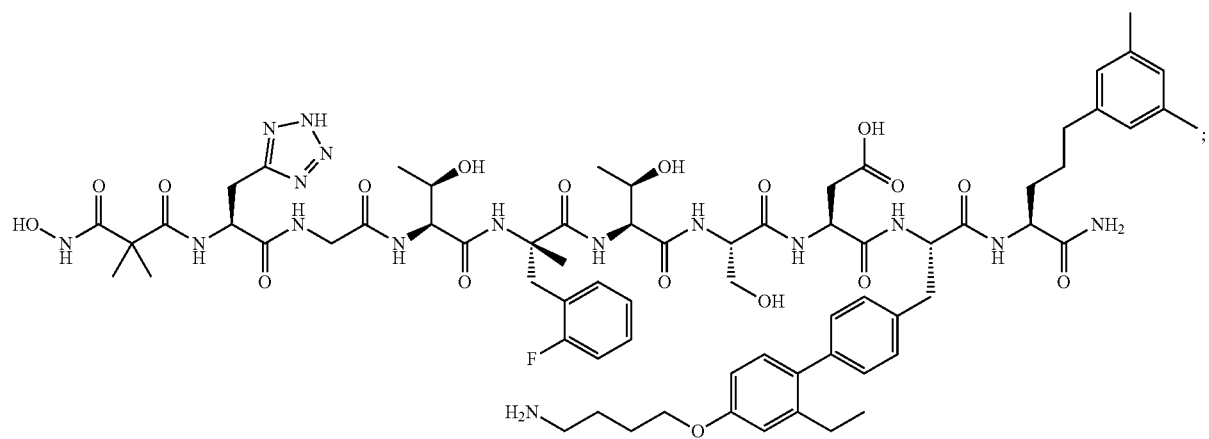
(SEQ ID NO: 45)
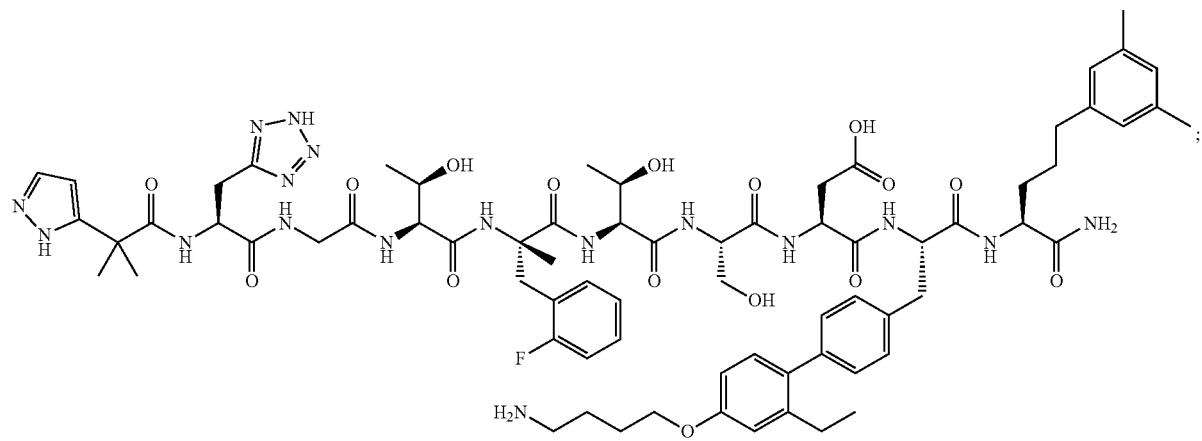
(SEQ ID NO: 46)

-continued
(SEQ ID NO: 47)
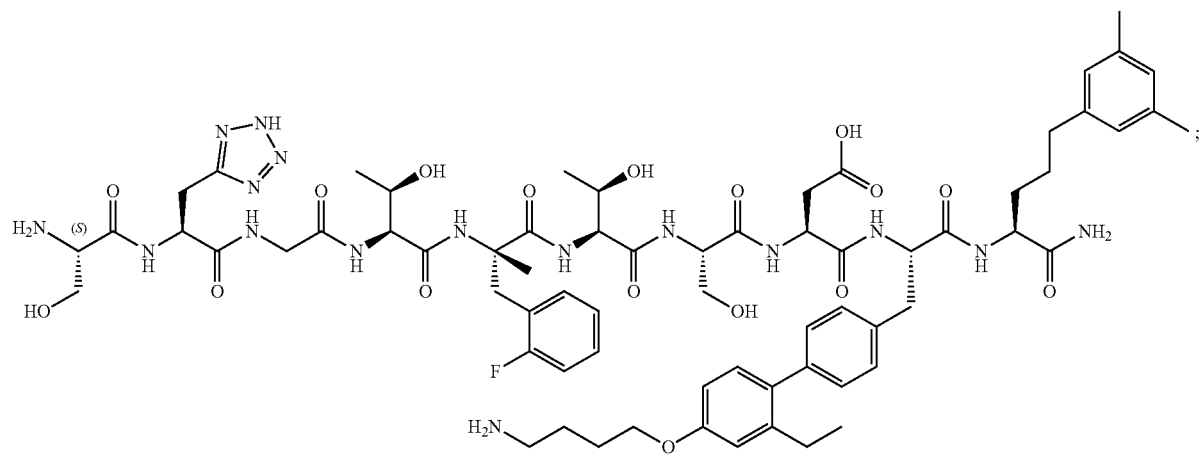
(SEQ ID NO: 48)
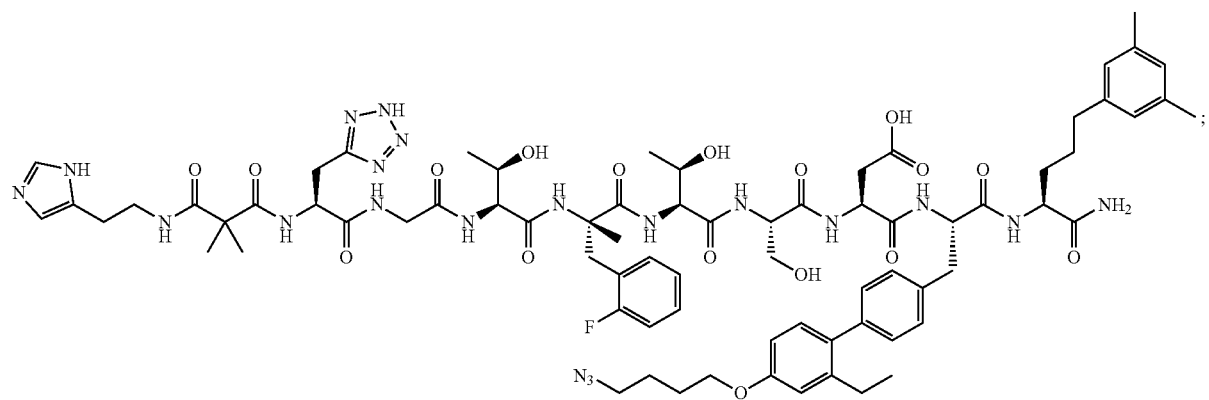
(SEQ ID NO: 49)
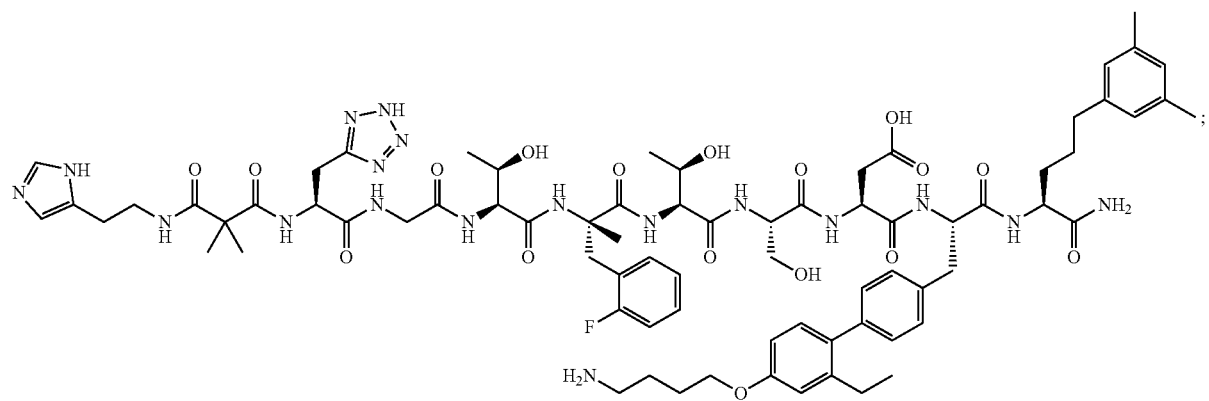

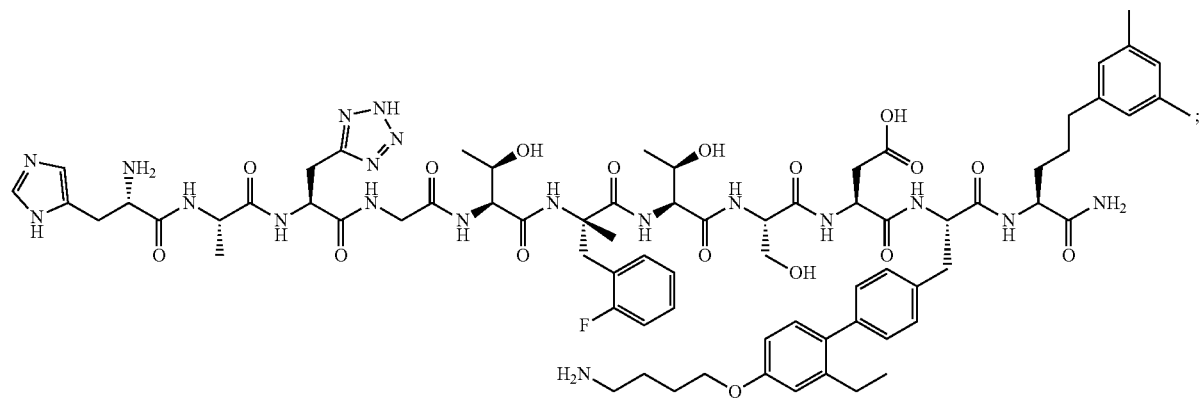
(SEQ ID NO: 50)
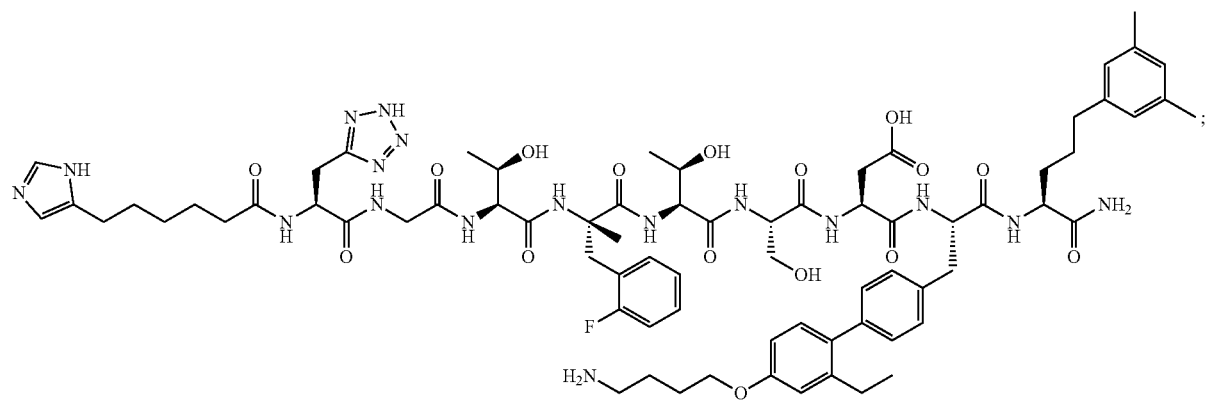
(SEQ ID NO: 51)
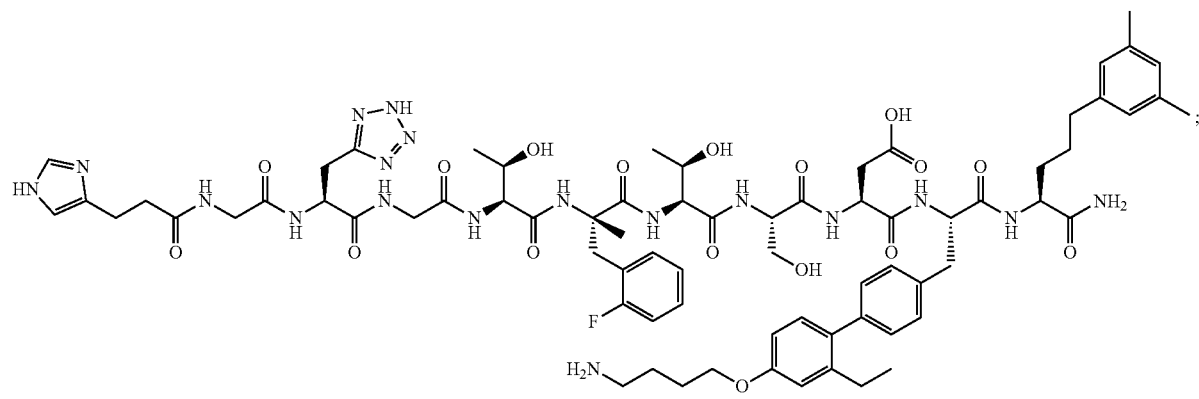
(SEQ ID NO: 52)
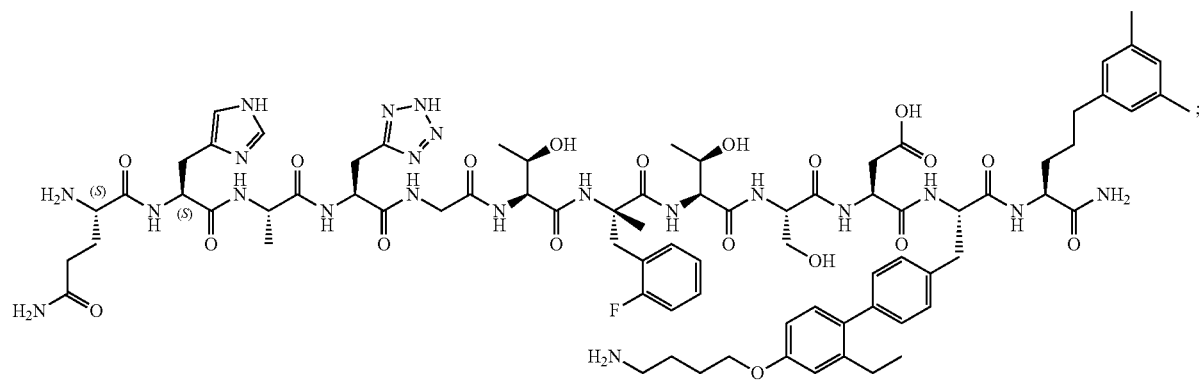
(SEQ ID NO: 53)

(SEQ ID NO: 54)
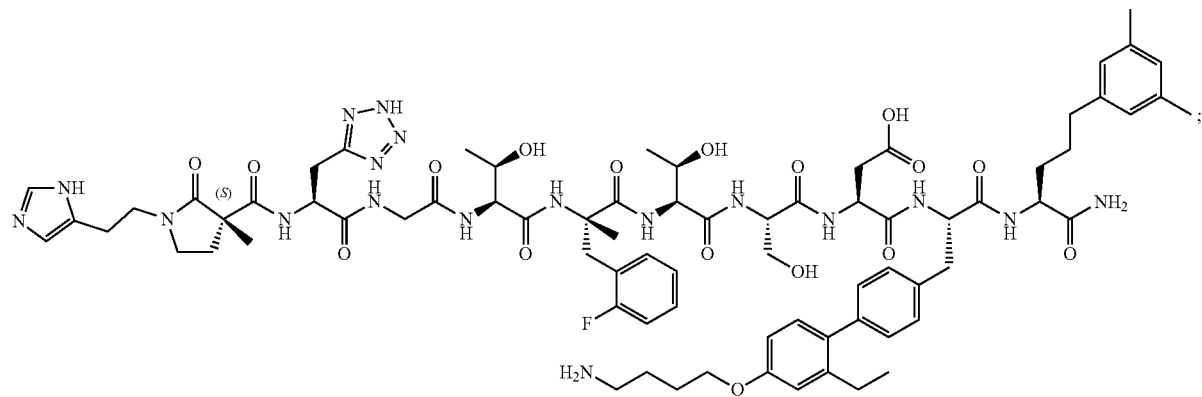
(SEQ ID NO: 55)
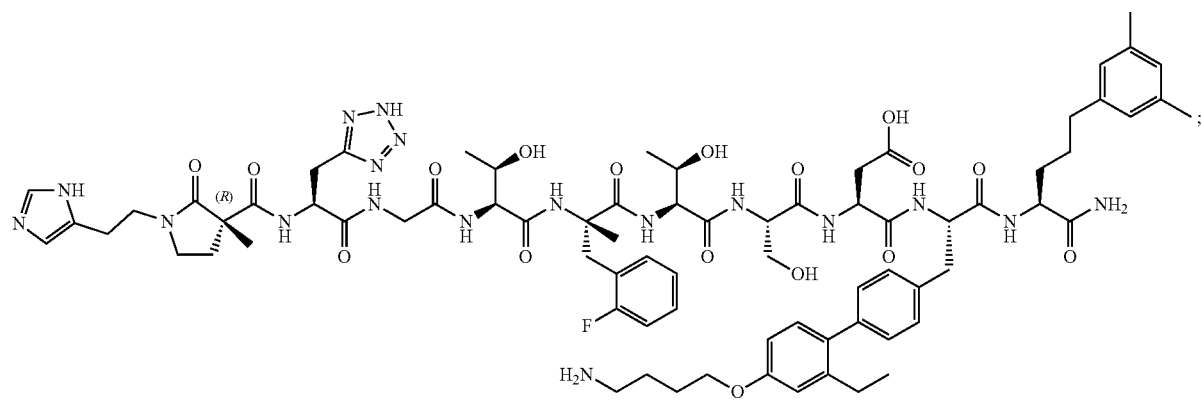
(SEQ ID NO: 56)
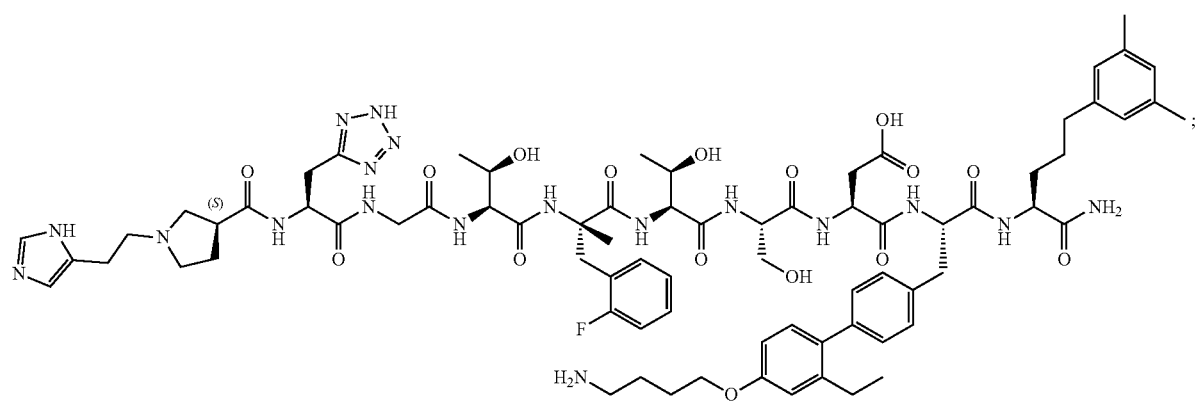

(SEQ ID NO: 57)
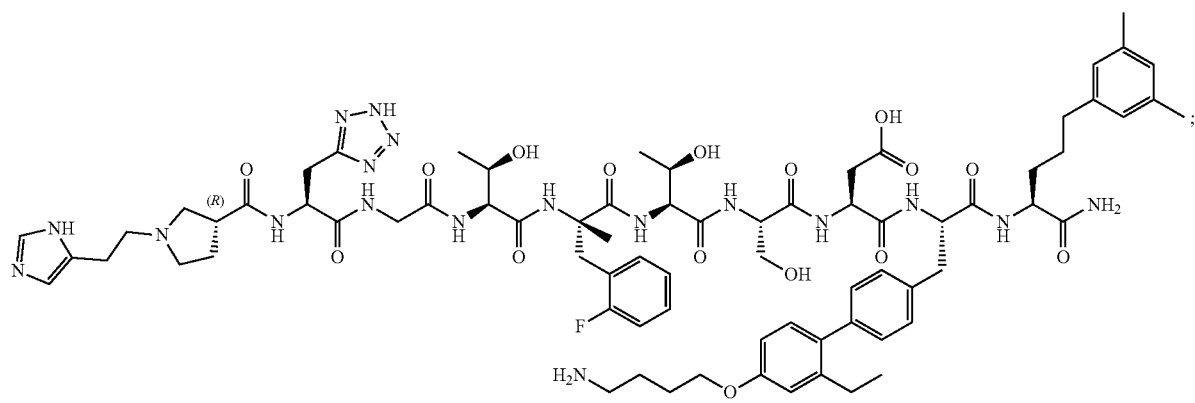
(SEQ ID NO: 58)
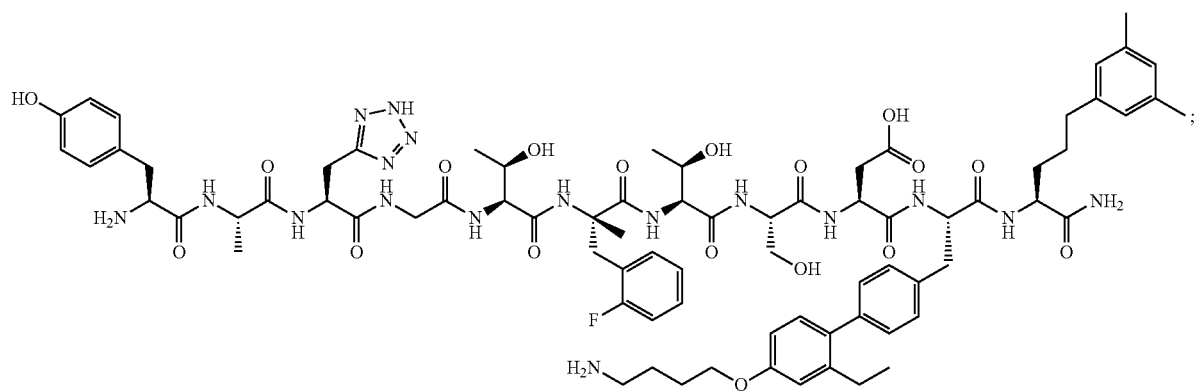
(SEQ ID NO: 59)
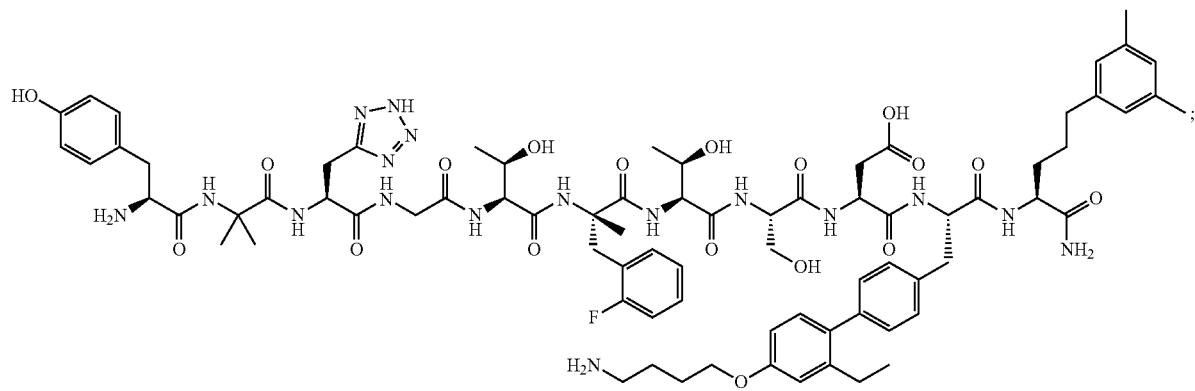

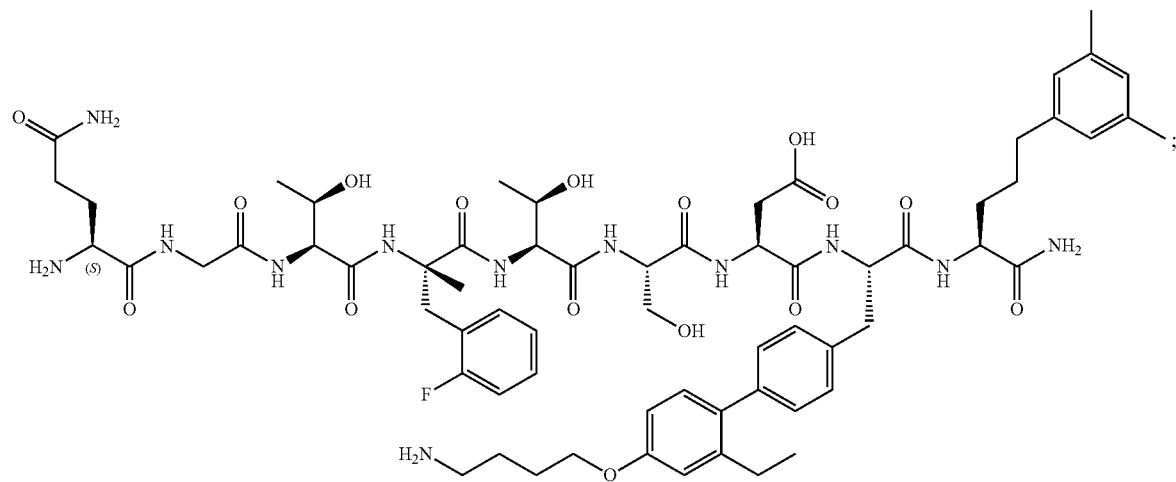
(SEQ ID NO: 60)
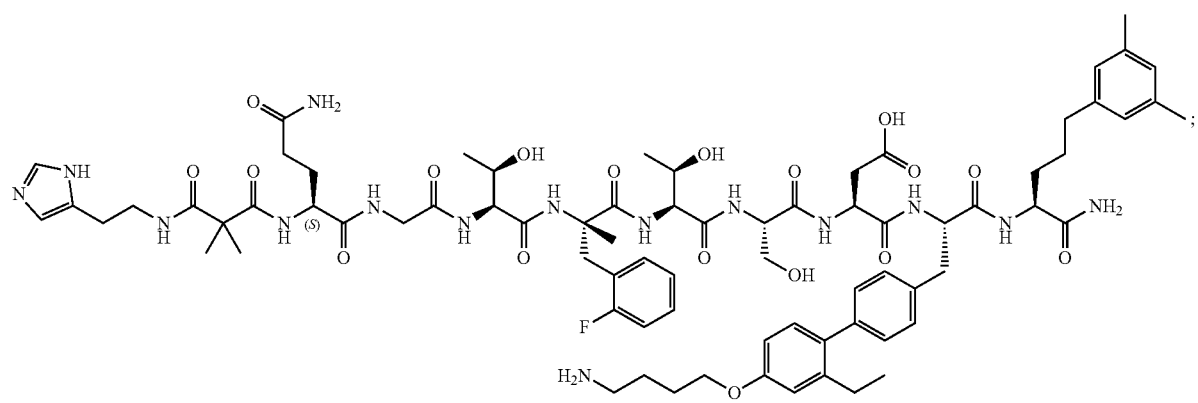
(SEQ ID NO: 61)
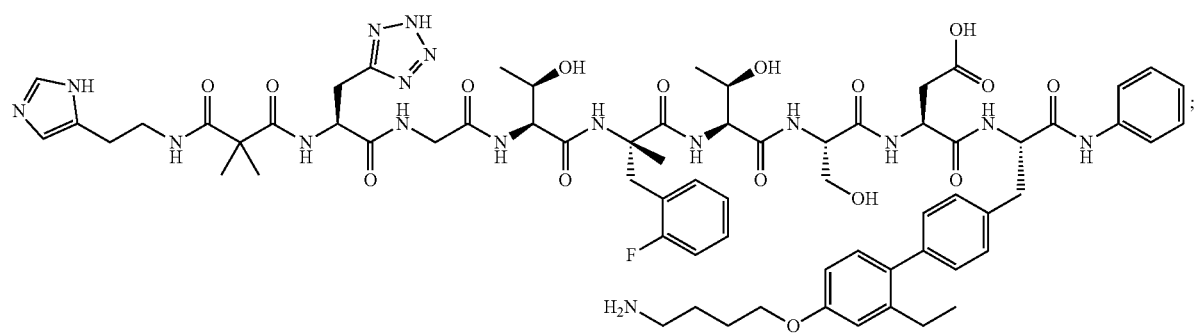
(SEQ ID NO: 62)

(SEQ ID NO: 63)
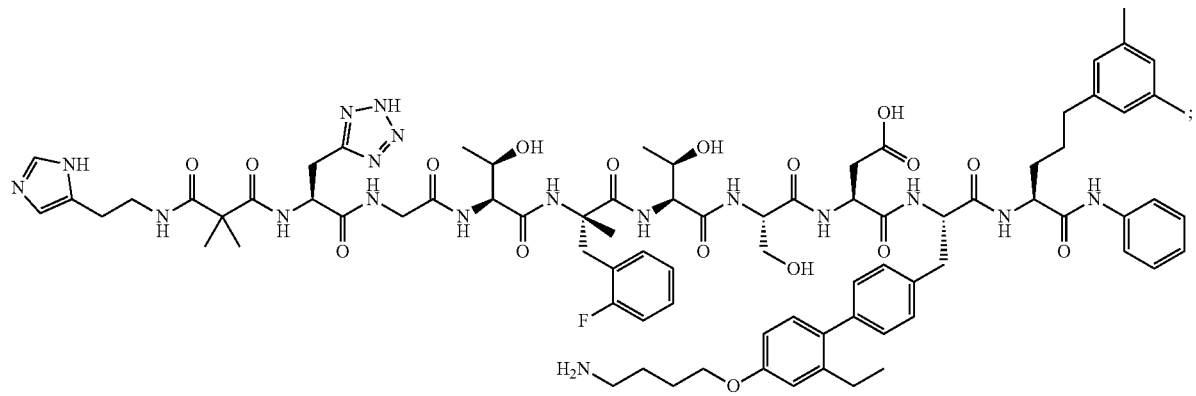
(SEQ ID NO: 64)
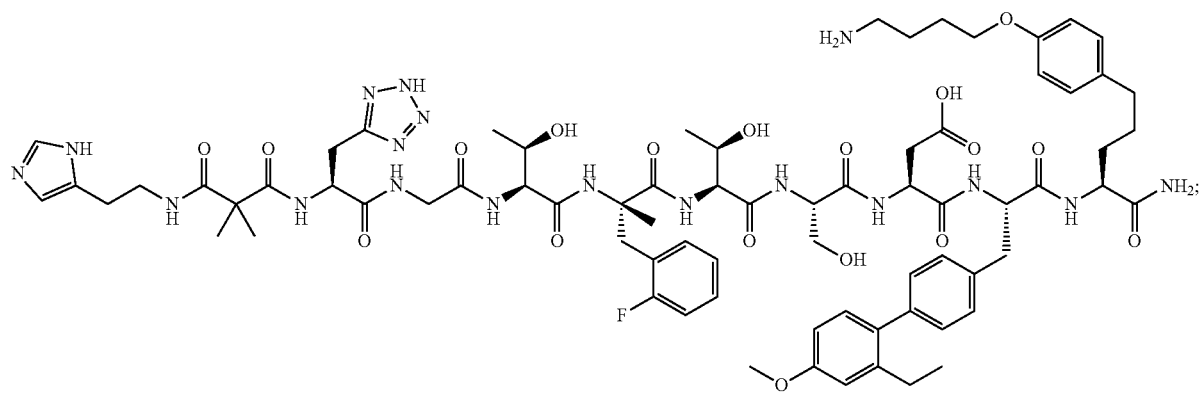
(SEQ ID NO: 65)
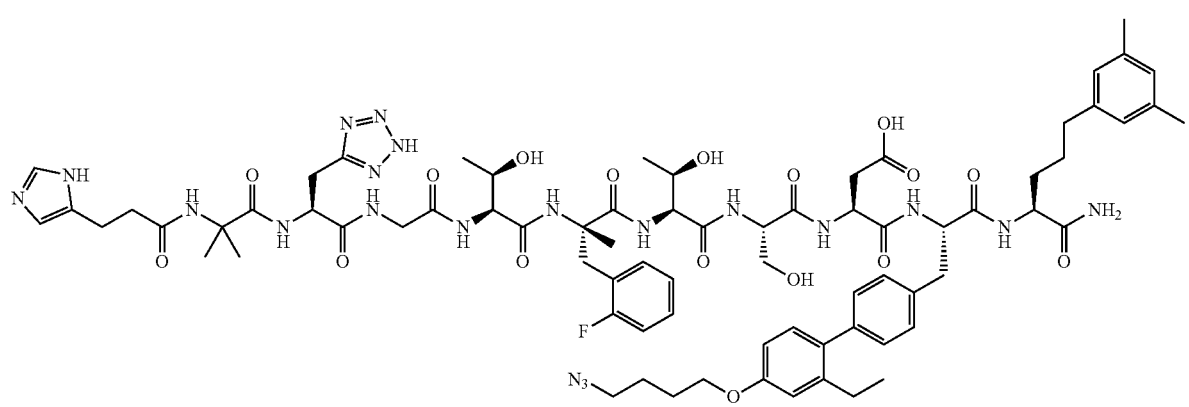
(SEQ ID NO: 66)
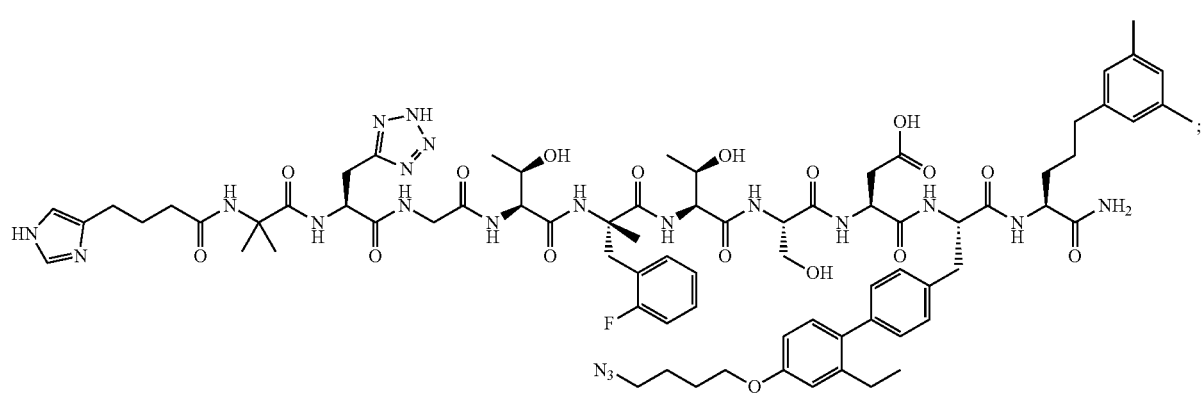

(SEQ ID NO: 67)
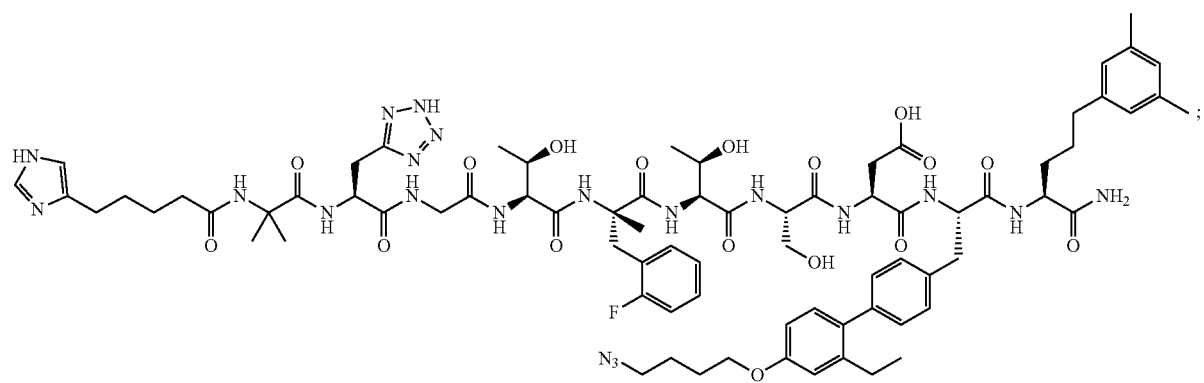
(SEQ ID NO: 68)
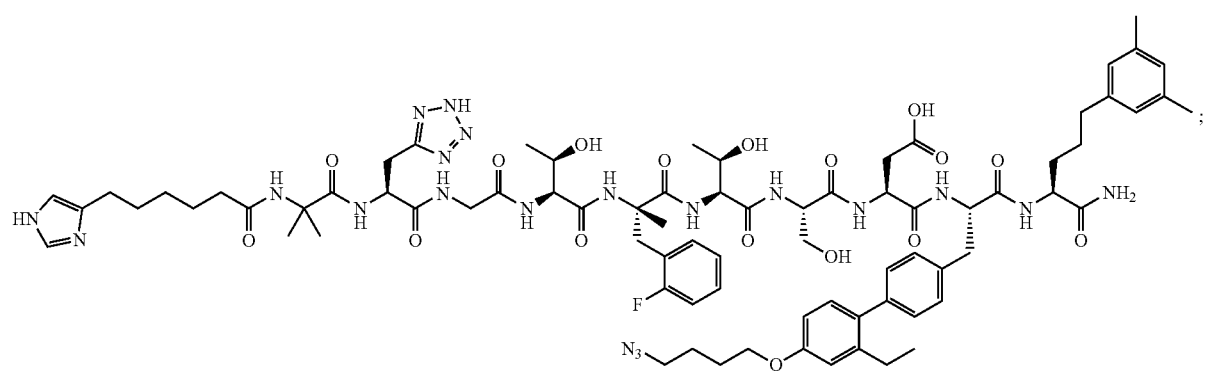
(SEQ ID NO: 69)
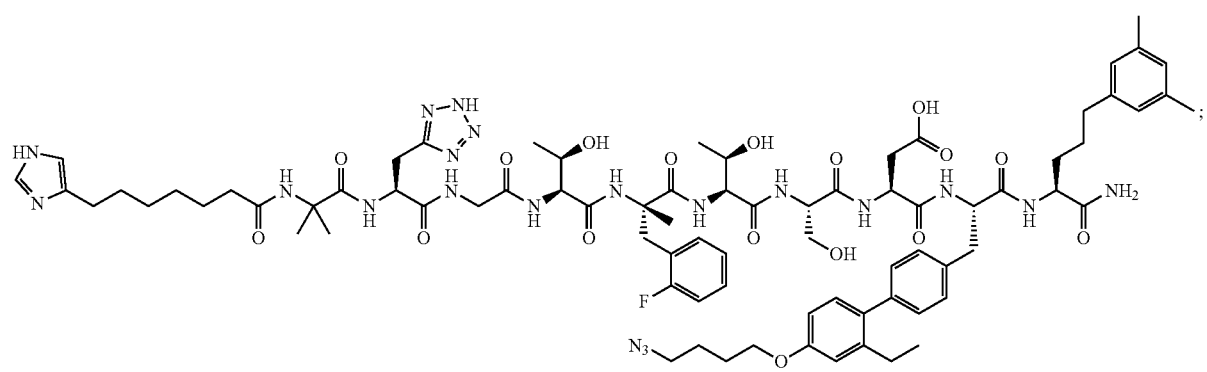
(SEQ ID NO: 70)
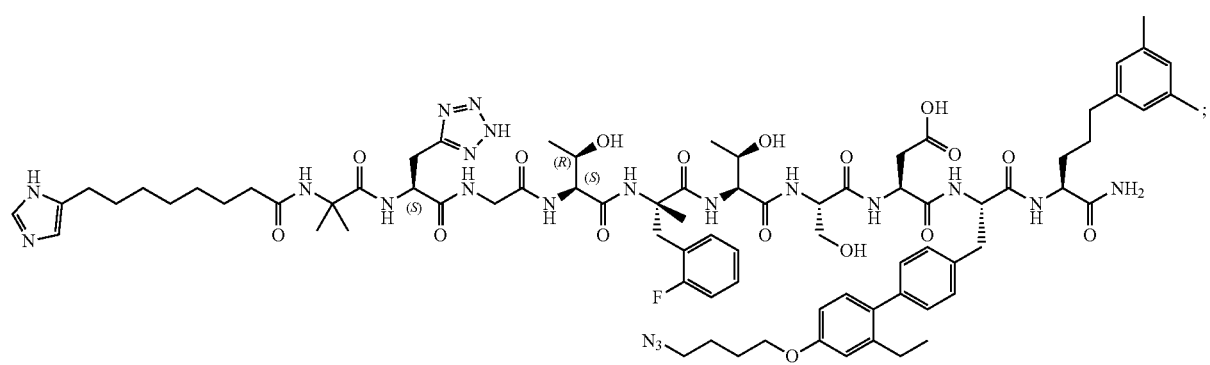

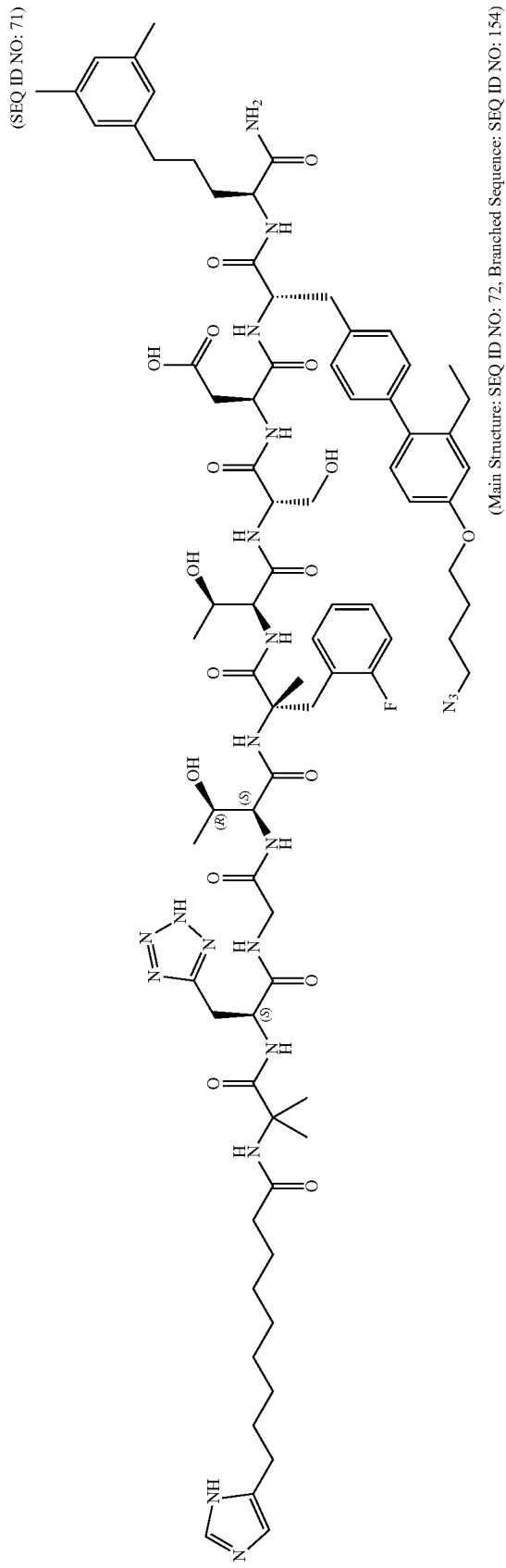
863 (SEQ ID NO: 71)
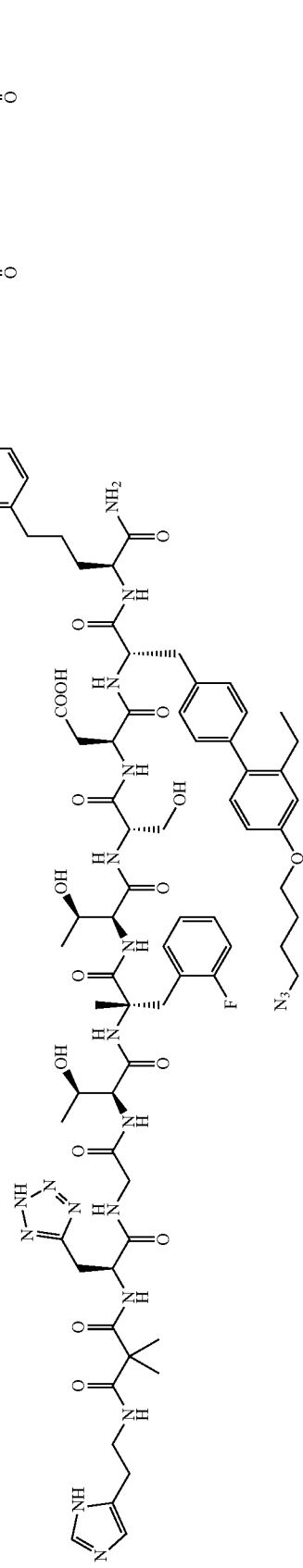
864 (Main Structure: SEQ ID NO: 72, Branched Sequence: SEQ ID NO: 154)

-continued
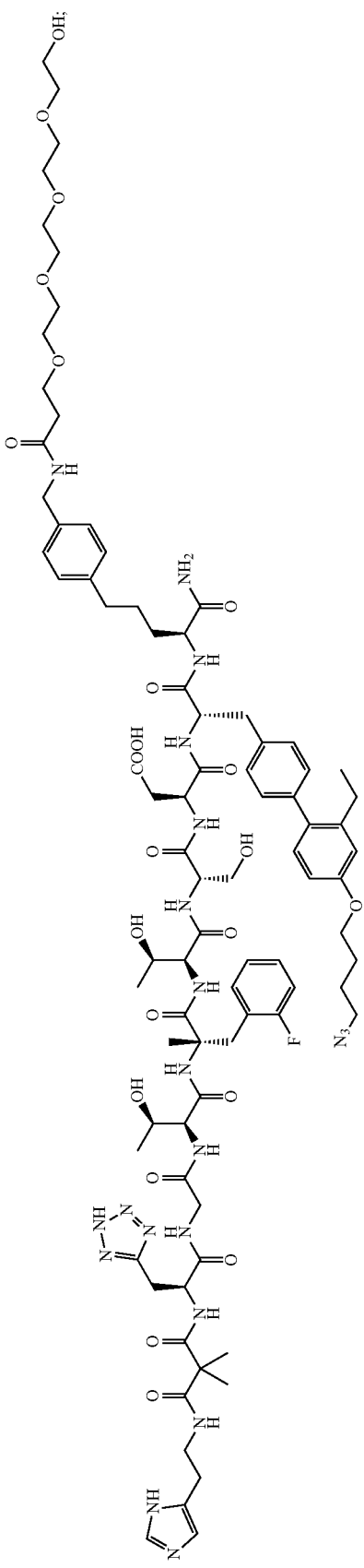
(SEQ ID NO: 73)
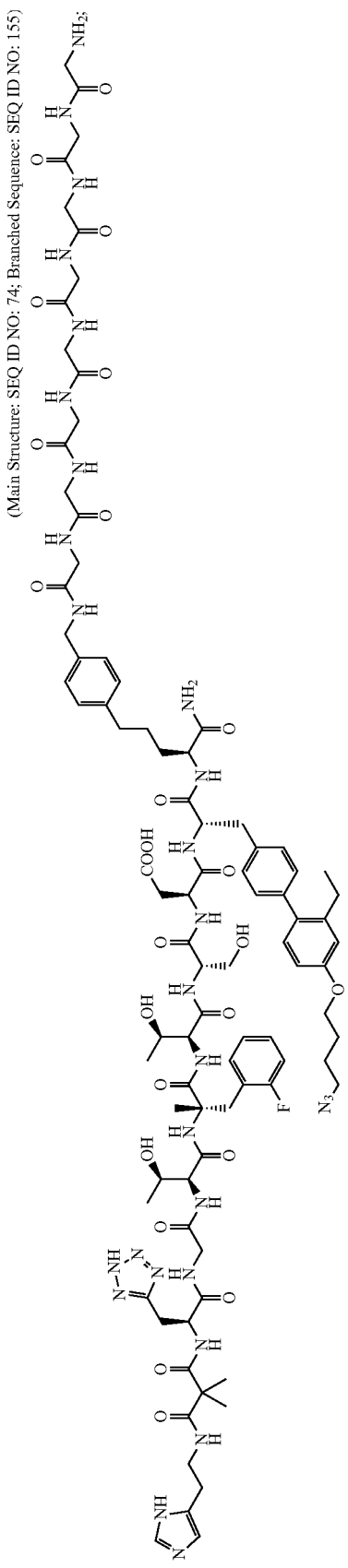
(Main Structure: SEQ ID NO: 74; Branched Sequence: SEQ ID NO: 155)

-continued
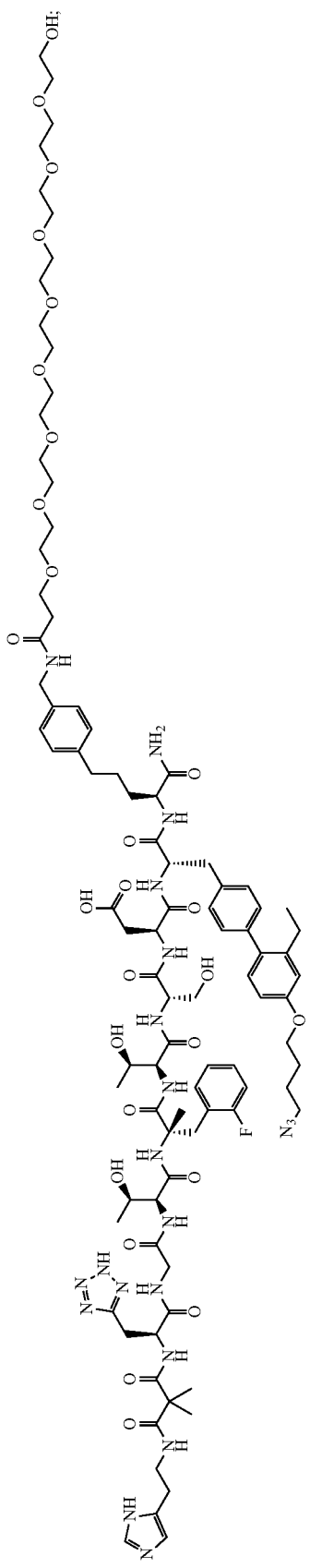
(SEQ ID NO: 75)
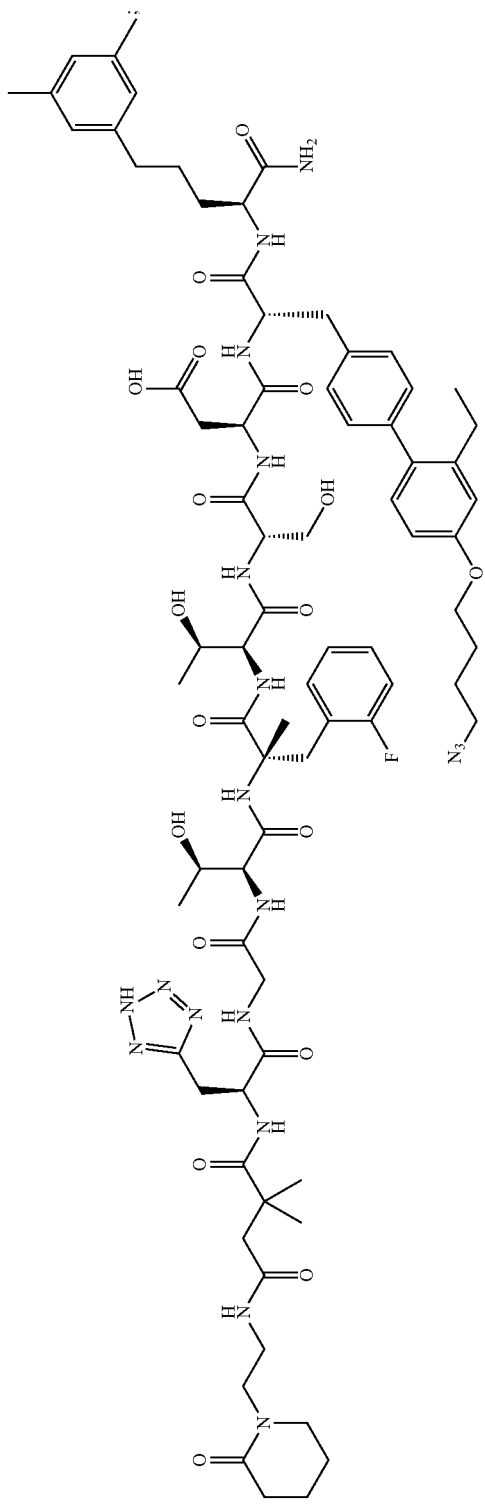
(SEQ ID NO: 76)

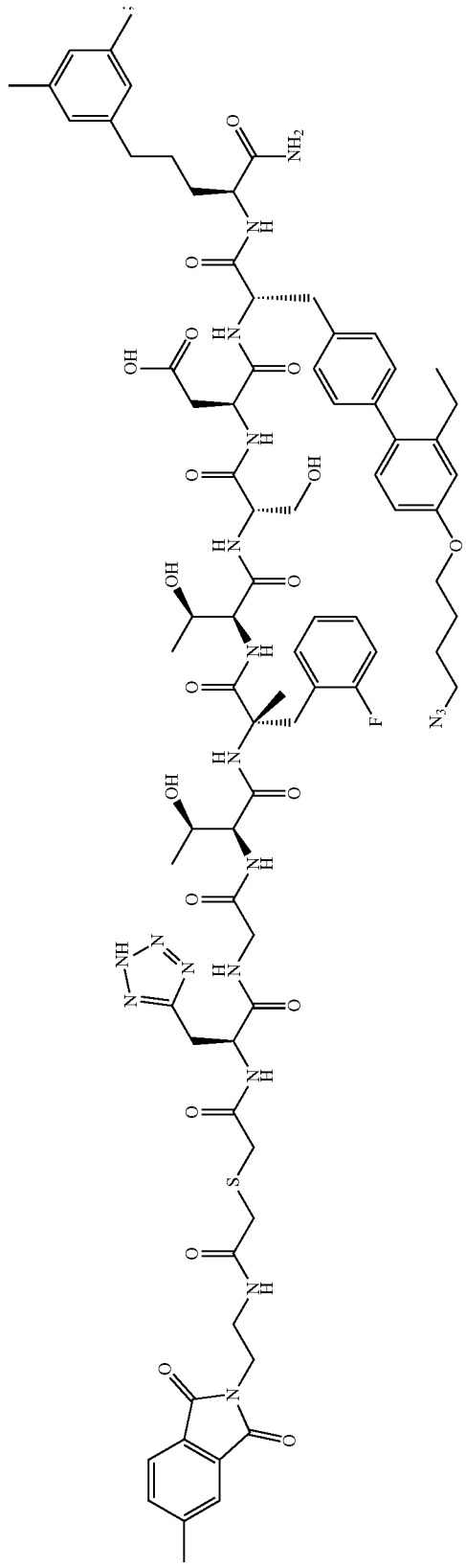
(SEQ ID NO: 77)
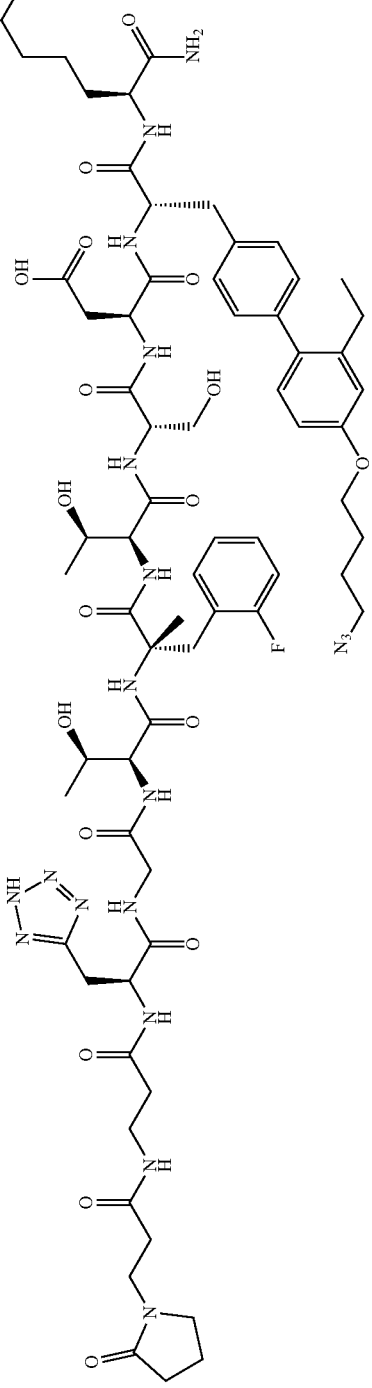
(SEQ ID NO: 78)

871 (SEQ ID NO: 80)
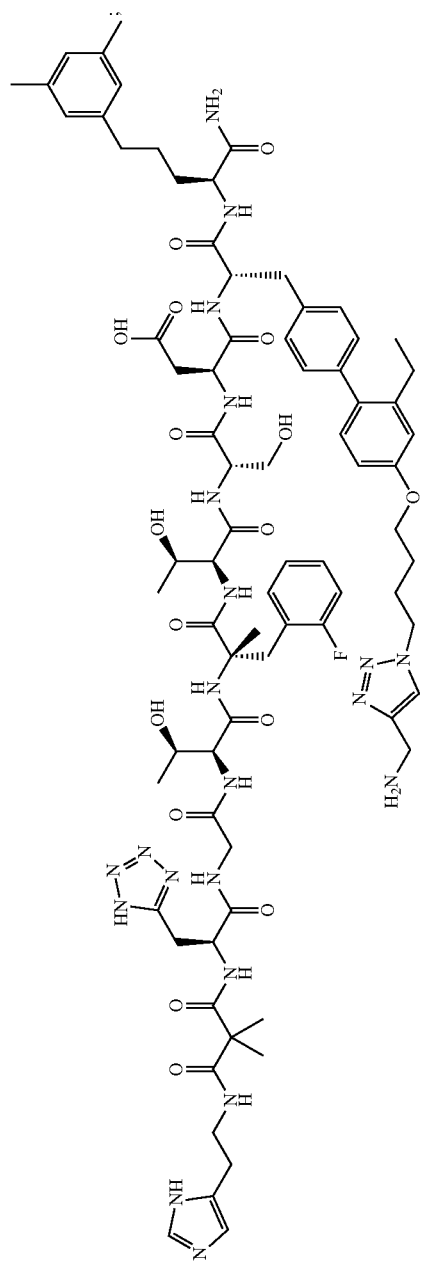
872 (SEQ ID NO: 81)
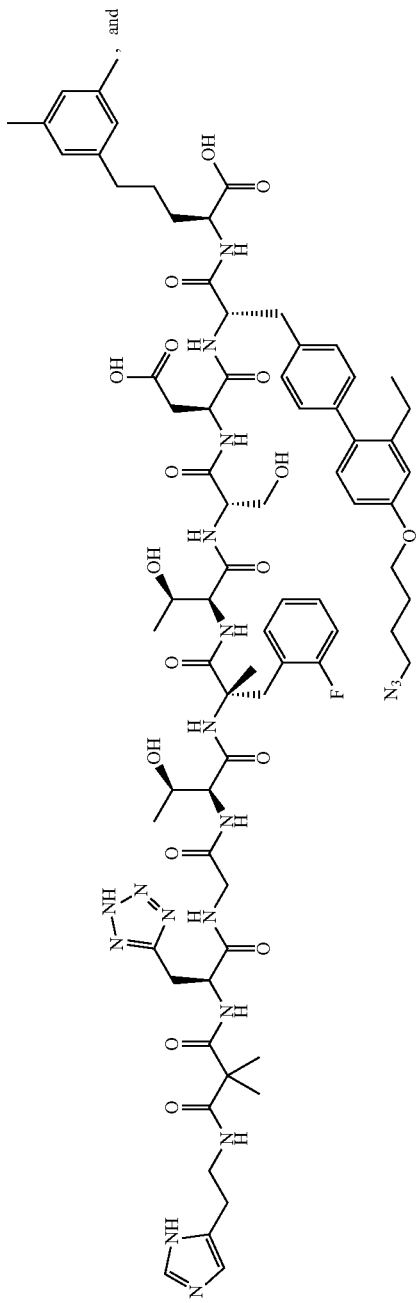
, and
(SEQ ID NO: 82)
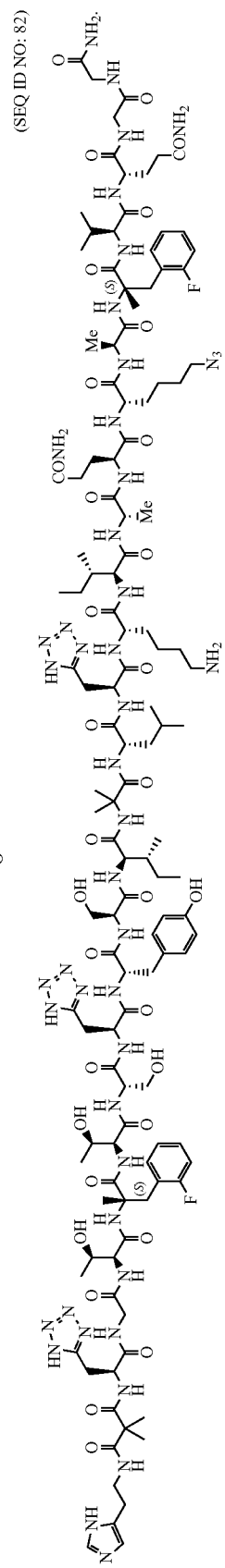

26. A compound of Formula (C):

(C (SEQ ID NO: 27))

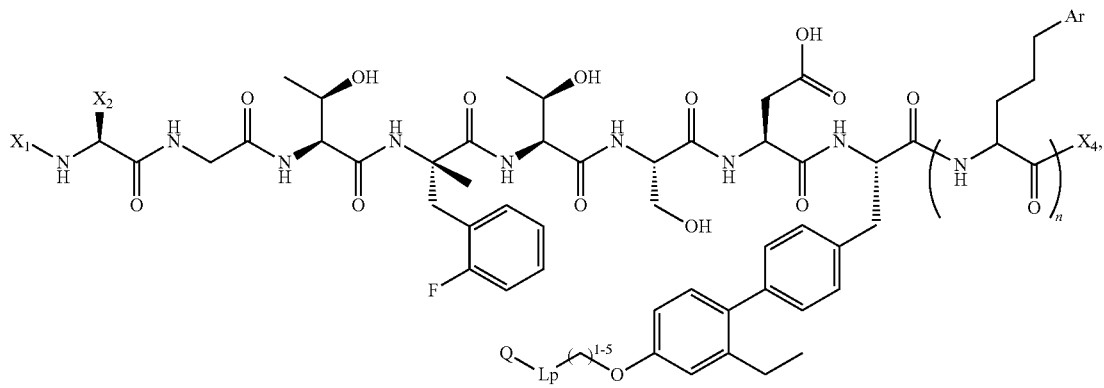

wherein:

$L_p$ is absent or a linker comprising one or more of

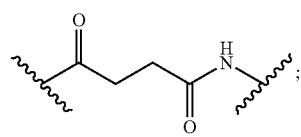 [SMILES: *NC(=O)CCC(*)=O]

a carbamate group; a cyclodextrin; a polyethylene glycol (PEG) segment having 1 to 36 —CH$_2$CH$_2$O— (EG) units; a —(CH$_2$)$_{2-24}$— chain; a triazole; one or more amino acids selected from glycine, serine, glutamic acid, alanine, valine, and proline, and combinations thereof;

Q is a moiety selected from —NH$_2$, —N$_3$,

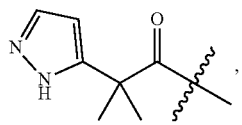

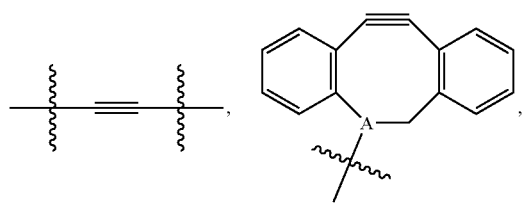

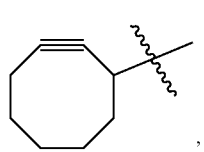

wherein A is C or N;

$X_1$ is selected from H

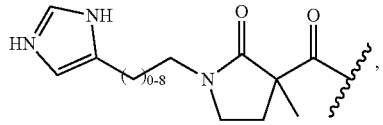

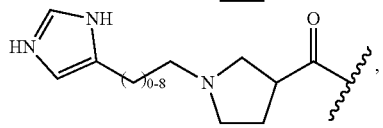

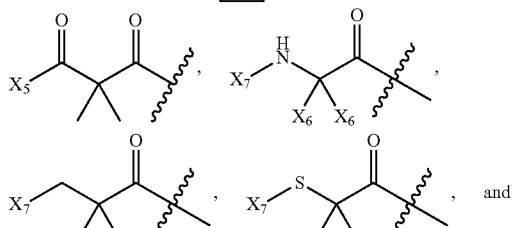

$X_2$ is selected from

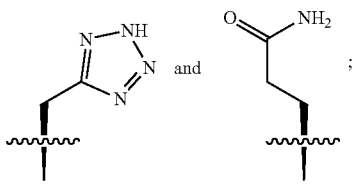

n is 0 or 1;
$X_4$ is selected from —$NH_2$, —OH and —N(H)(phenyl);
$X_5$ is selected from —OH, —$NH_2$, —NH—OH, and
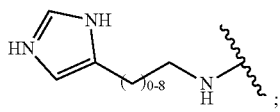
$X_6$ is independently at each occurrence selected from H, —OH, —$CH_3$, and —$CH_2OH$;
$X_7$ is selected from H,
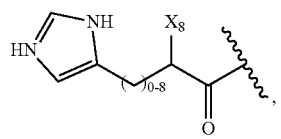
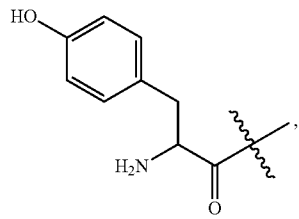
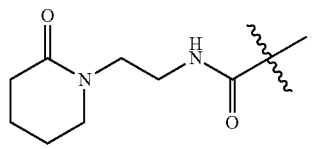
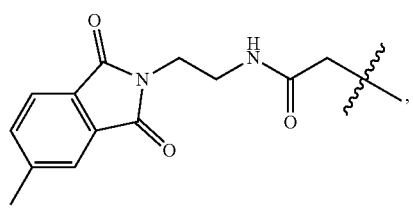
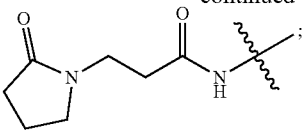
$X_8$ is selected from H, —OH, —$NH_2$, and
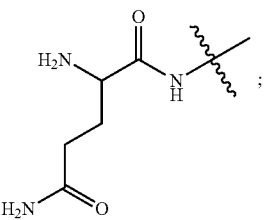
Ar is selected from
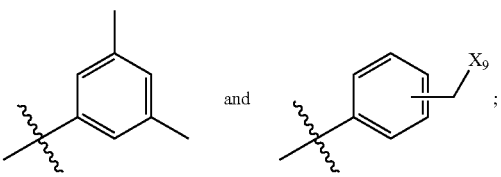
$X_9$ is selected from —$NH_2$
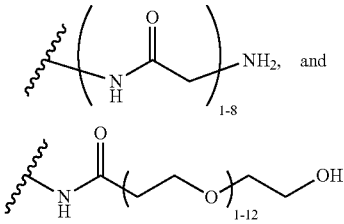
or a pharmaceutically acceptable salt thereof.
27. A compound of Formula (III):
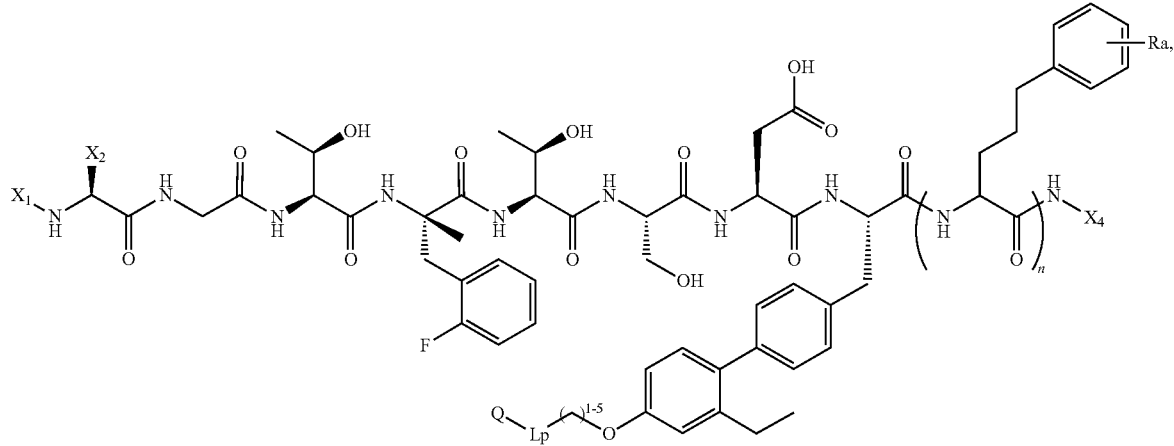
(III (SEQ ID NO: 86))

wherein:

$L_p$ is absent or a linker comprising one or more of

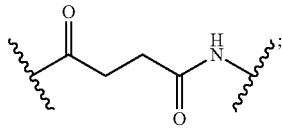 [SMILES: *NC(=O)CCC(*)=O]

a carbamate group; a cyclodextrin; a polyethylene glycol (PEG) segment having 1 to 36 —CH$_2$CH$_2$O— (EG) units; one or more amino acids selected from glycine, serine, glutamic acid, alanine, valine, and proline, and combinations thereof;

Q is a moiety selected from —N$_3$,

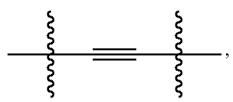

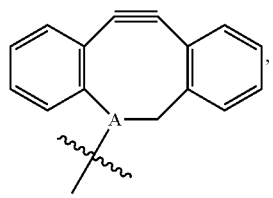

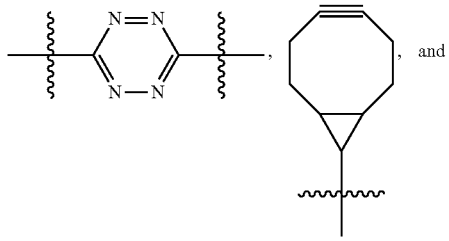, and

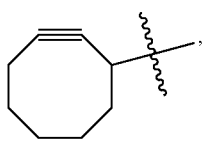

wherein A is C or N;

$X_1$ is selected from H

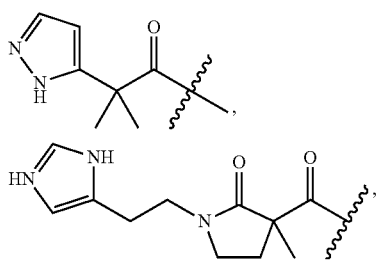

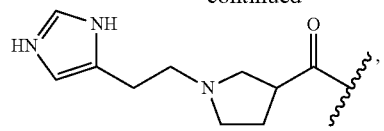

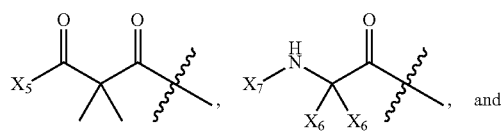, and

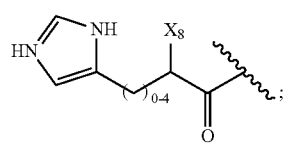

$X_2$ is selected from

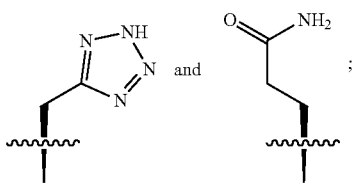

n is 0 or 1;

Ra is selected from H, —CH$_3$, —(CH$_2$)$_{2-6}$—NH$_2$, and —(CH$_2$)$_{2-6}$—N$_3$;

$X_4$ is selected from H and phenyl;

$X_5$ is selected from —OH, —NH$_2$, —NH—OH, and

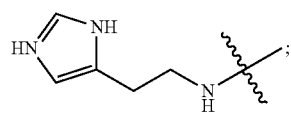 [SMILES: *NCCc1cnc[nH]1]

$X_6$ is independently at each occurrence selected from H, —OH, —CH$_3$, and —CH$_2$OH;

$X_7$ is selected from H,

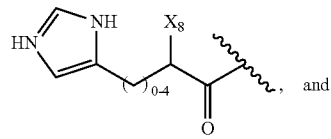, and

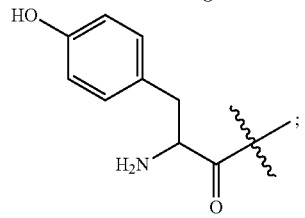

$X_8$ is selected from H, —OH, —NH$_2$, and
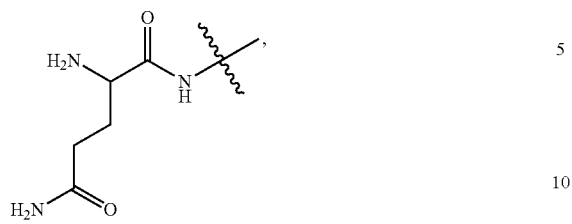
or a pharmaceutically acceptable salt thereof.
28. A compound selected from the group consisting of:
Structure
(SEQ ID NO: 179)
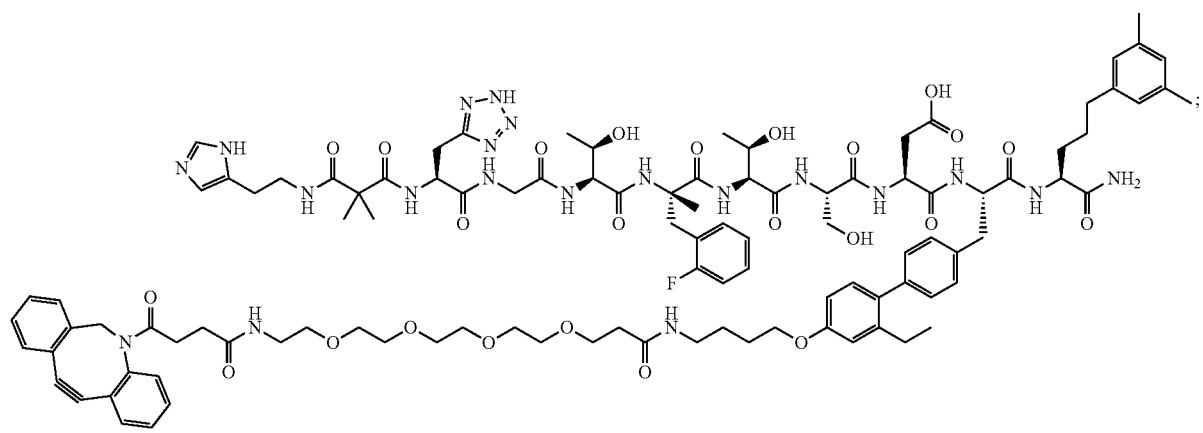
(SEQ ID NO: 180)
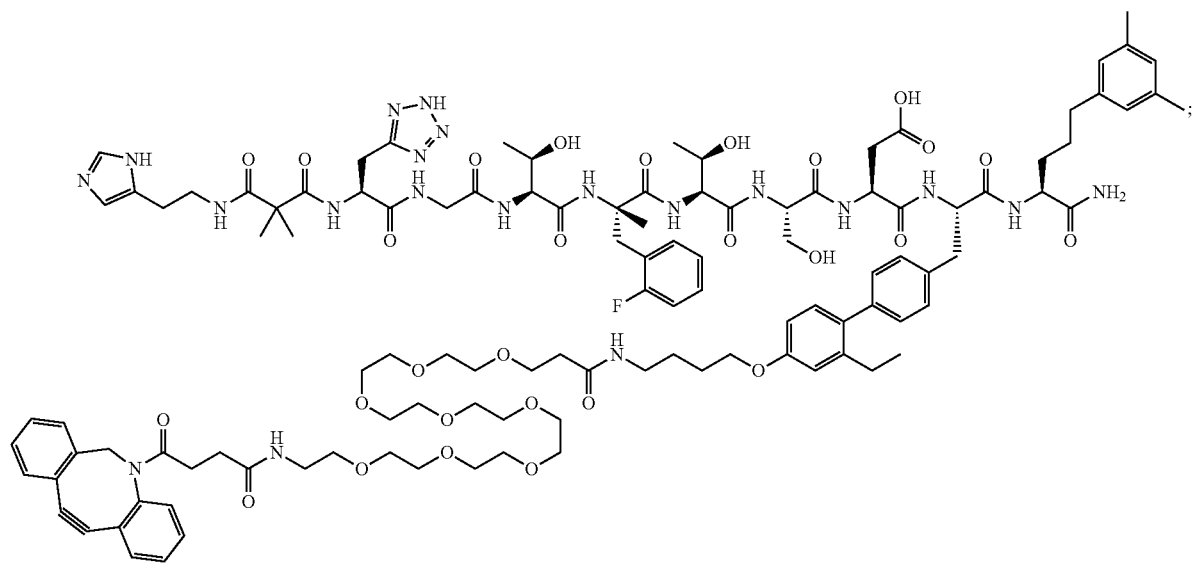

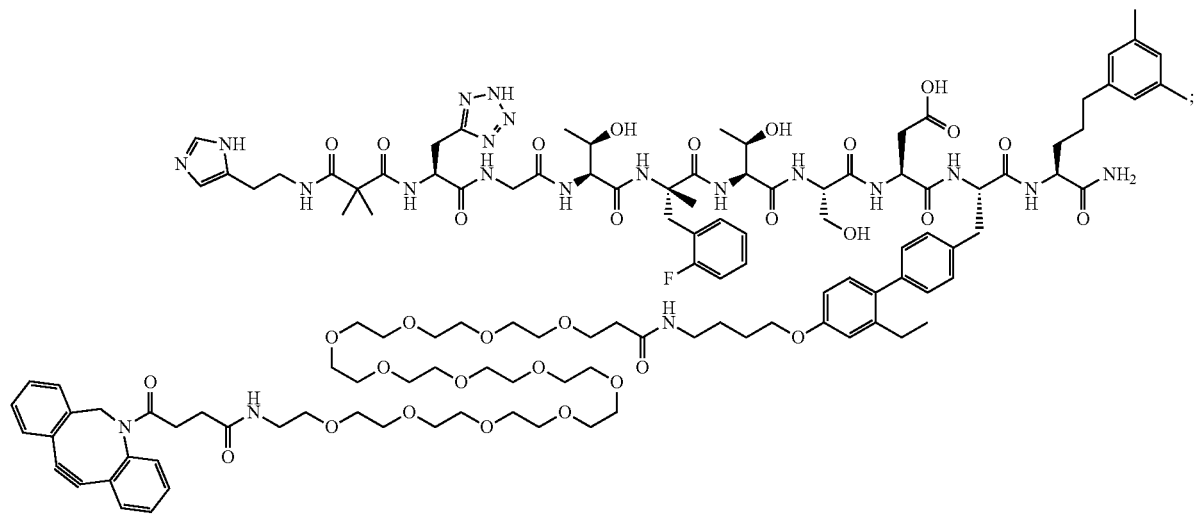
(SEQ ID NO: 181)
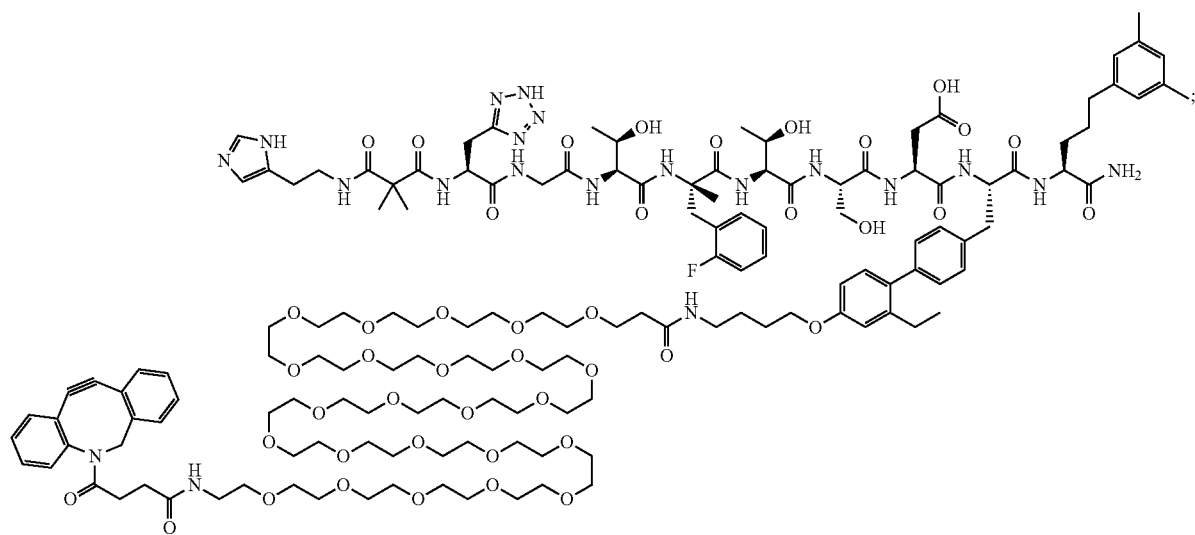
(SEQ ID NO: 182)
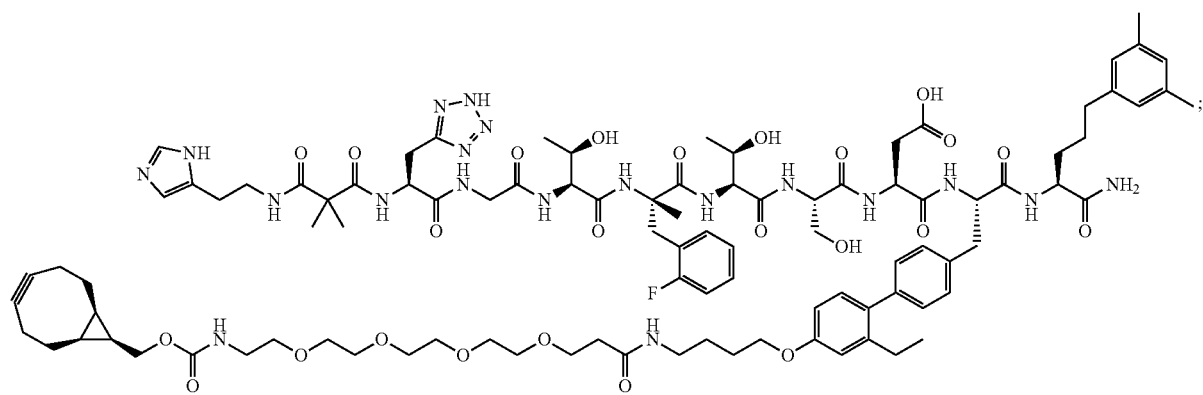
(SEQ ID NO: 183)

-continued
(Main Structure: SEQ ID NO: 88; Branched Sequence: SEQ ID NO: 156)
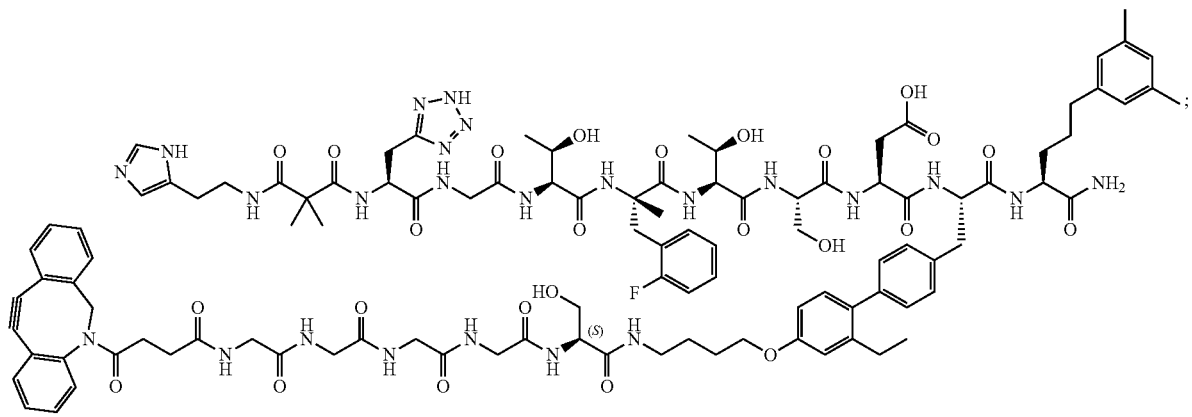
(Main Structure: SEQ ID NO: 89; Branched Sequence: SEQ ID NO: 157)
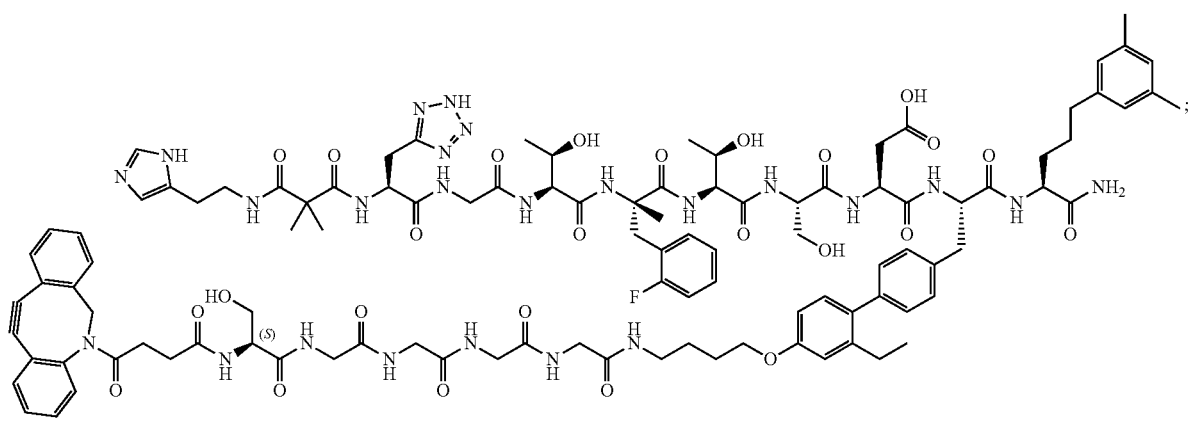
(SEQ ID NO: 184)
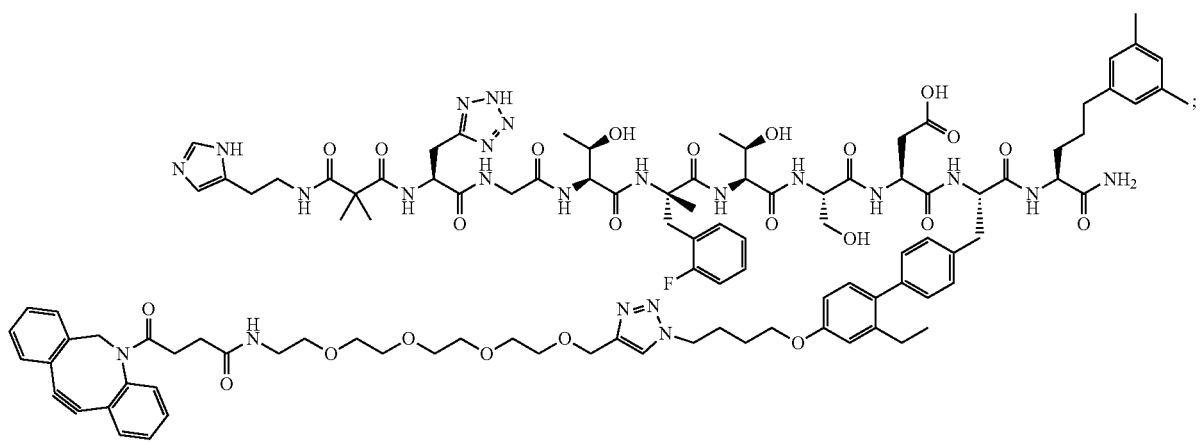

(SEQ ID NO: 185)
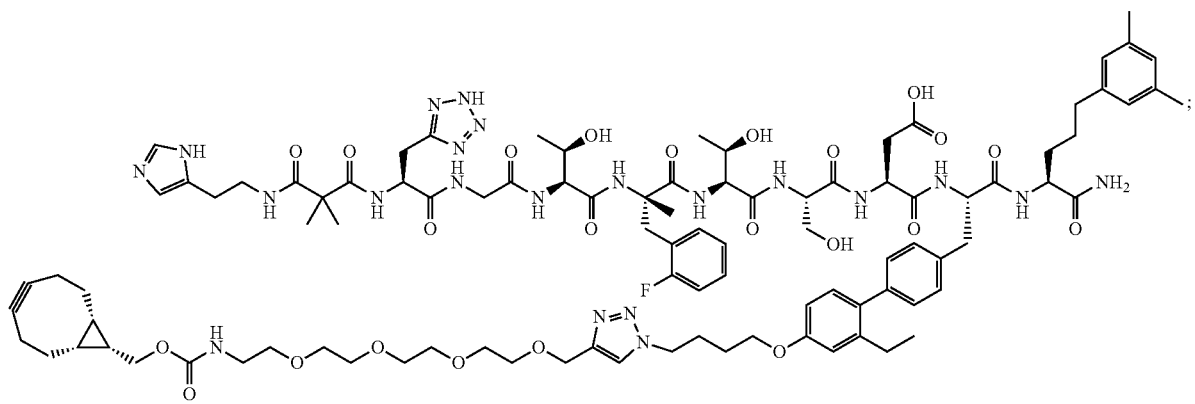
(SEQ ID NO: 186)
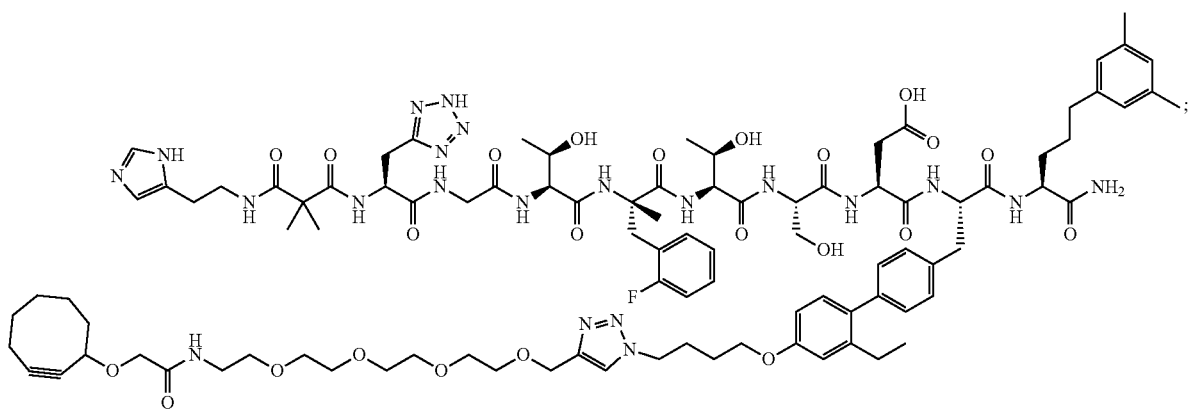
(SEQ ID NO: 91)
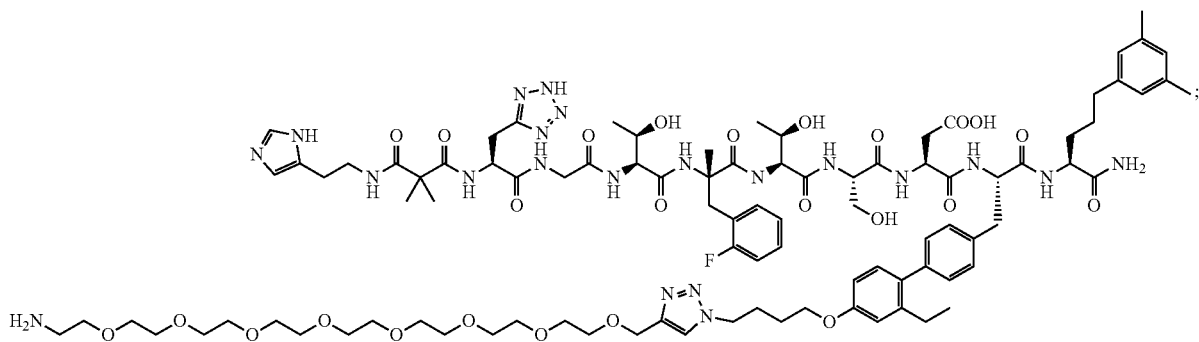

(SEQ ID NO: 92)
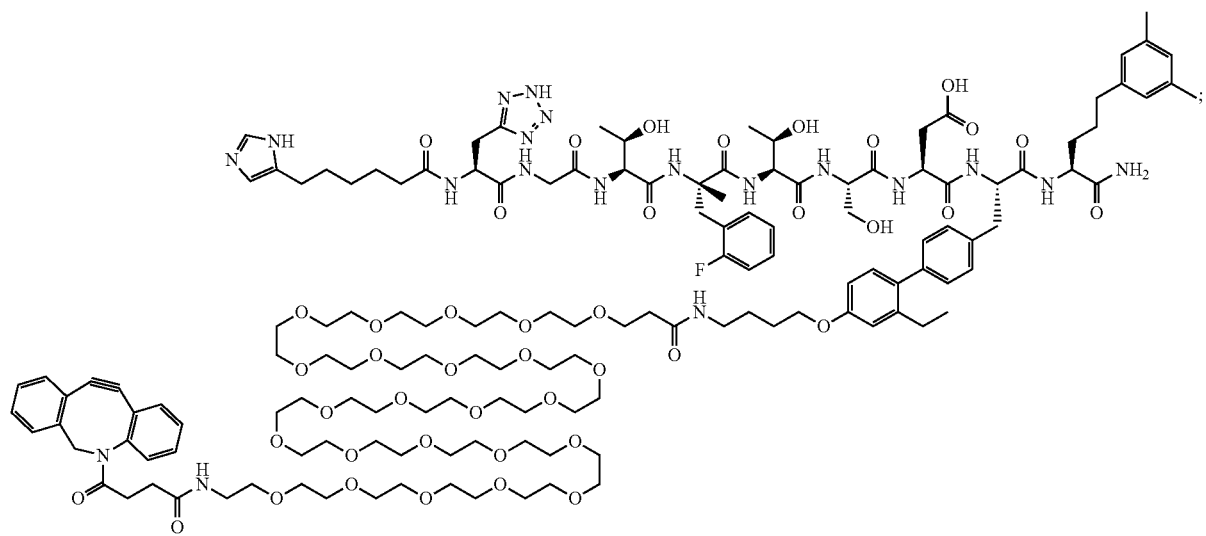
(SEQ ID NO: 93)
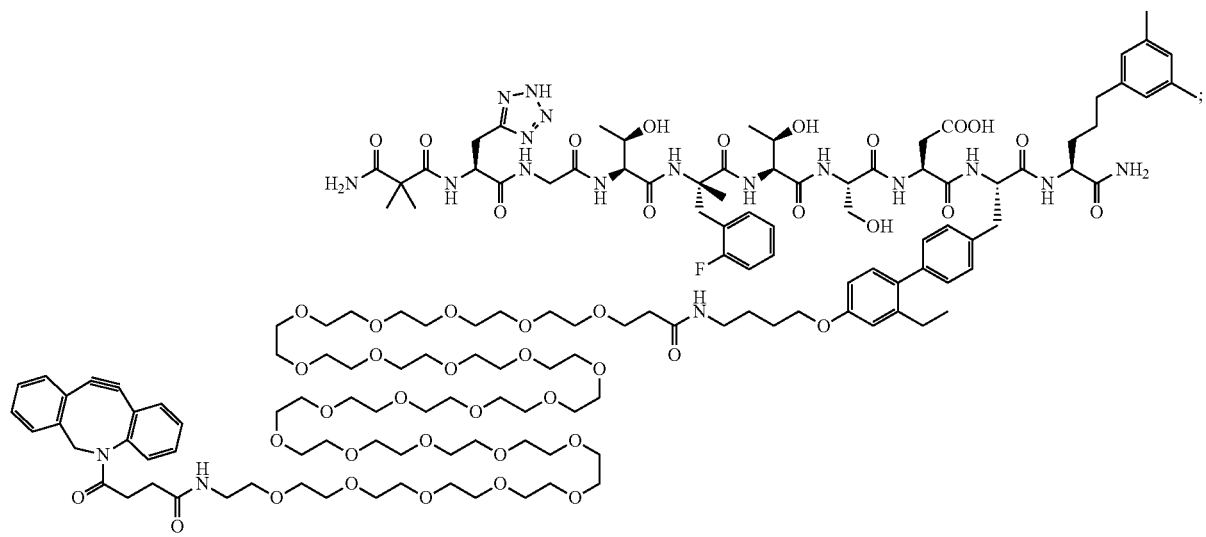
(Main Structure: SEQ ID NO: 94; Branched Sequence: SEQ ID NO: 158)
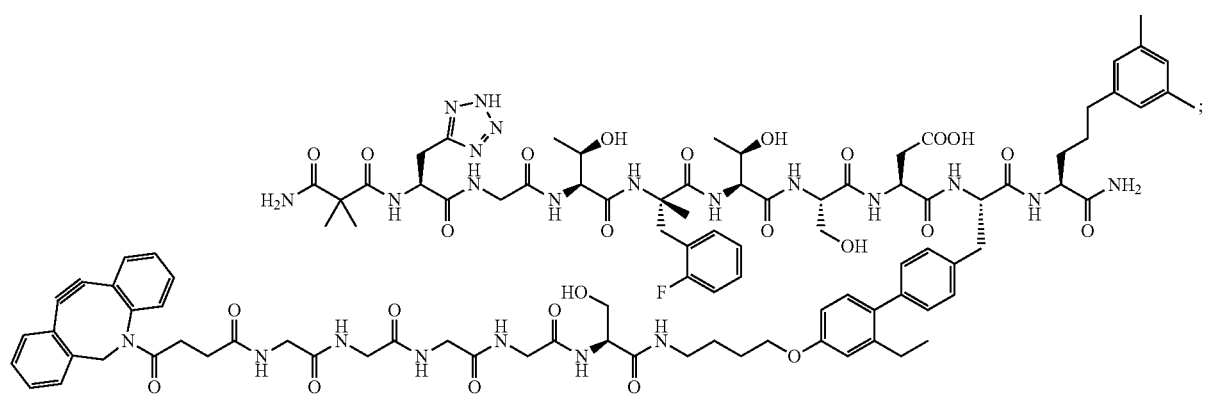

(Main Structure: SEQ ID NO: 95; Branched Sequence: SEQ ID NO: 159)
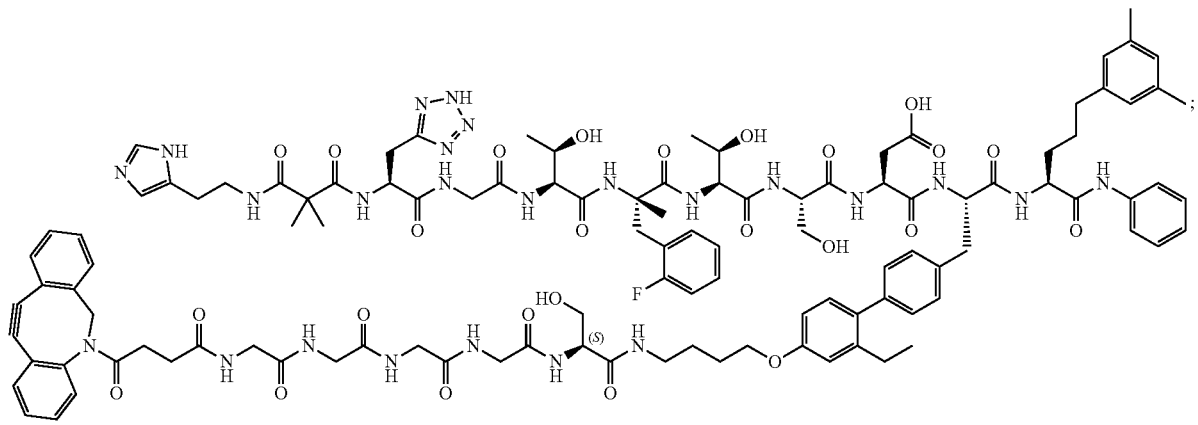
(Main Structure: SEQ ID NO: 96; Branched Sequence: SEQ ID NO: 160)
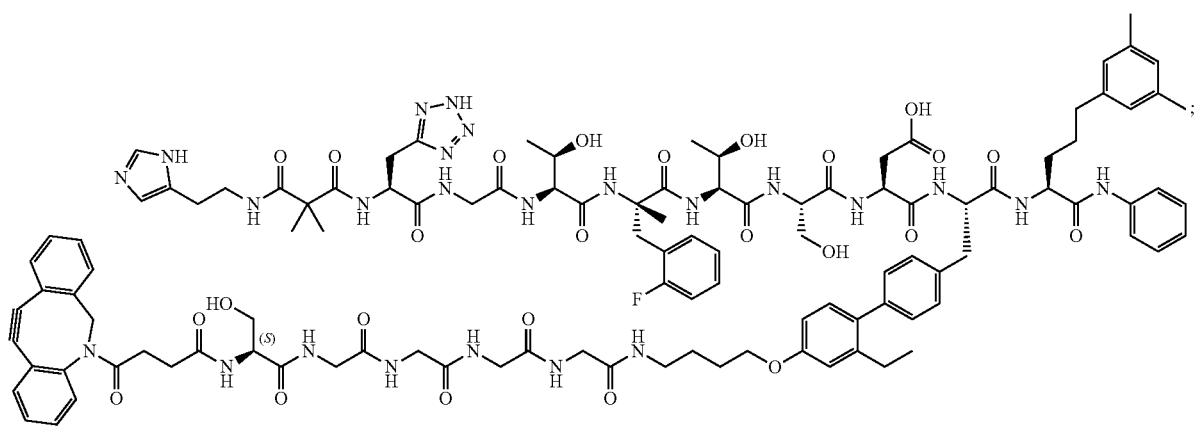
(Main Structure: SEQ ID NO: 97; Branched Sequence: SEQ ID NO: 161)
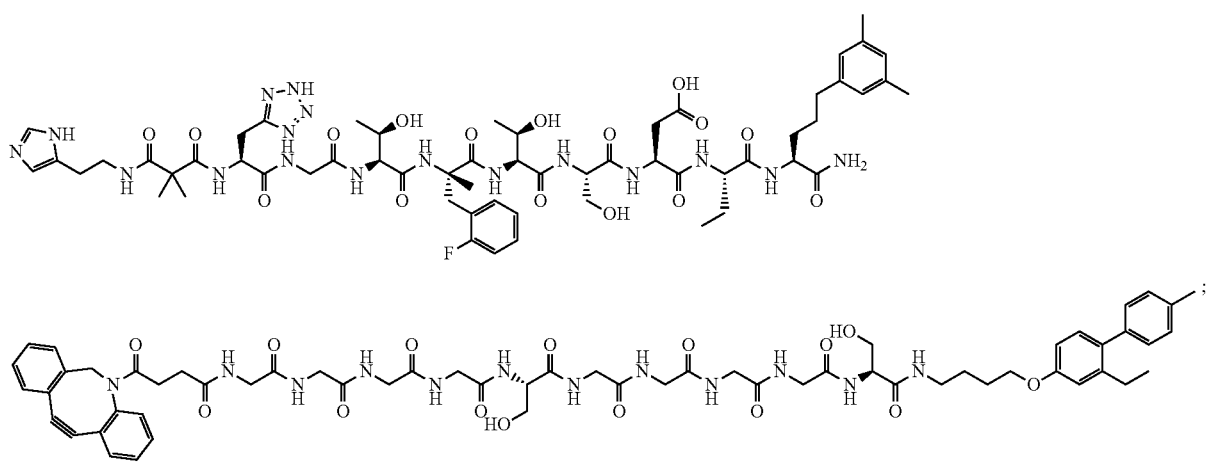

-continued
(Main Structure: SEQ ID NO: 98; Branched Sequence: SEQ ID NO: 162)
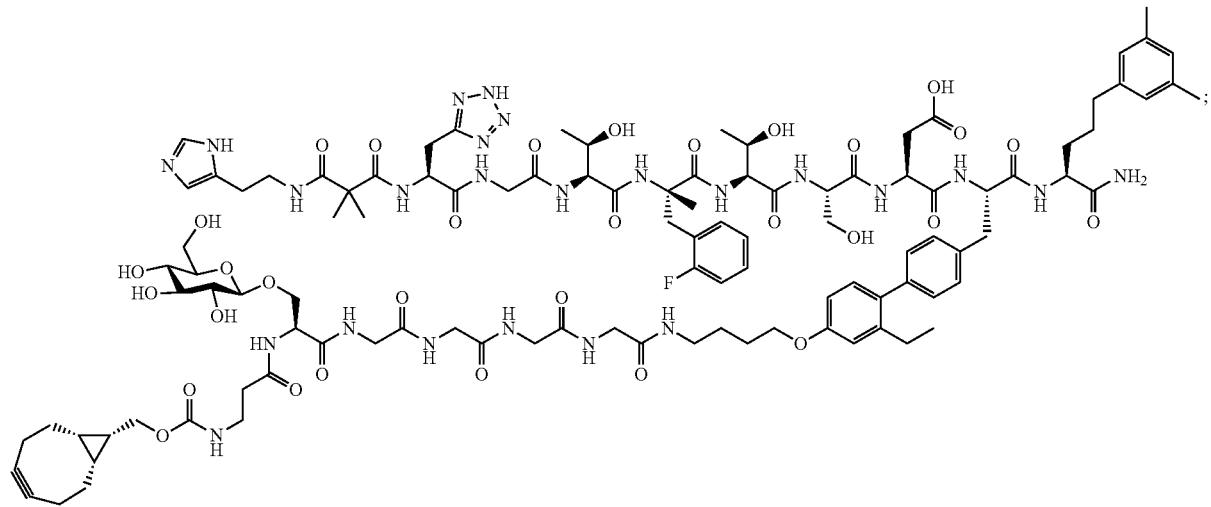

893
(Main Structure: SEQ ID NO: 99; Branched Sequence: SEQ ID NO: 163)
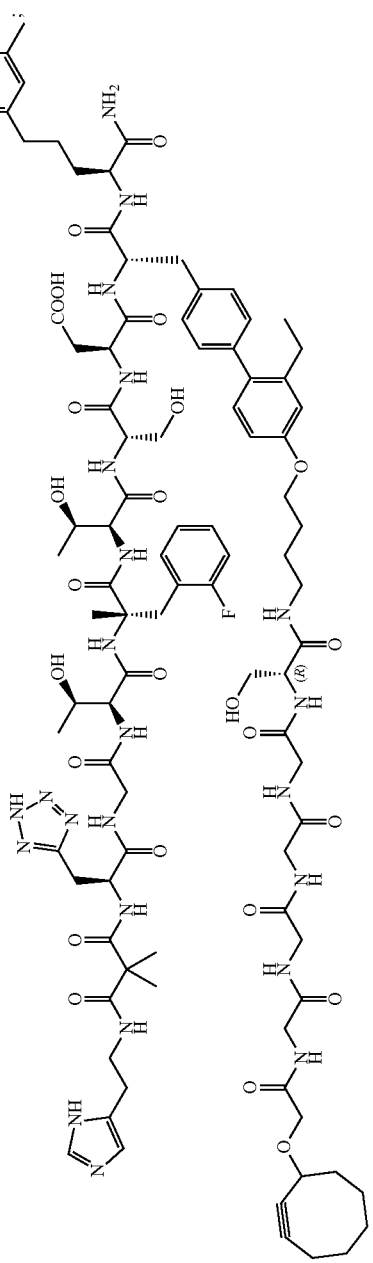
894
(Main Structure: SEQ ID NO: 100; Branched Sequence: SEQ ID NO: 164)
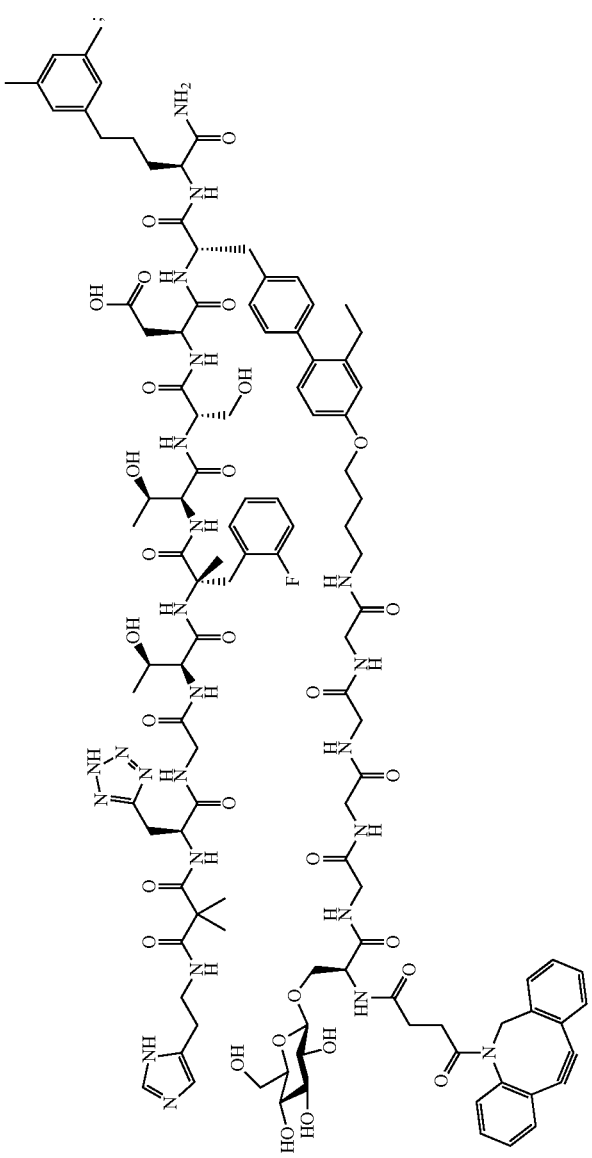

(SEQ ID NO: 101)
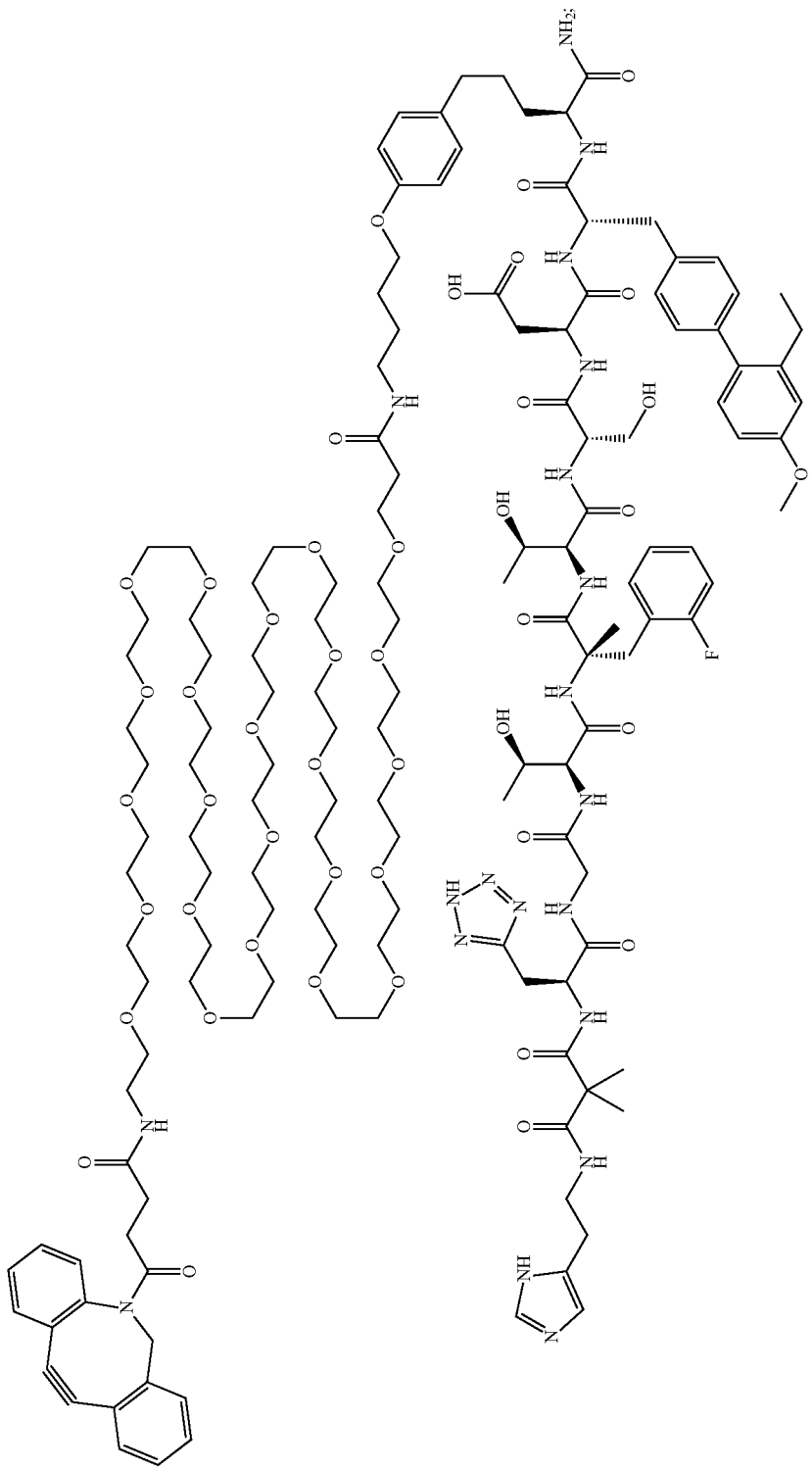

-continued
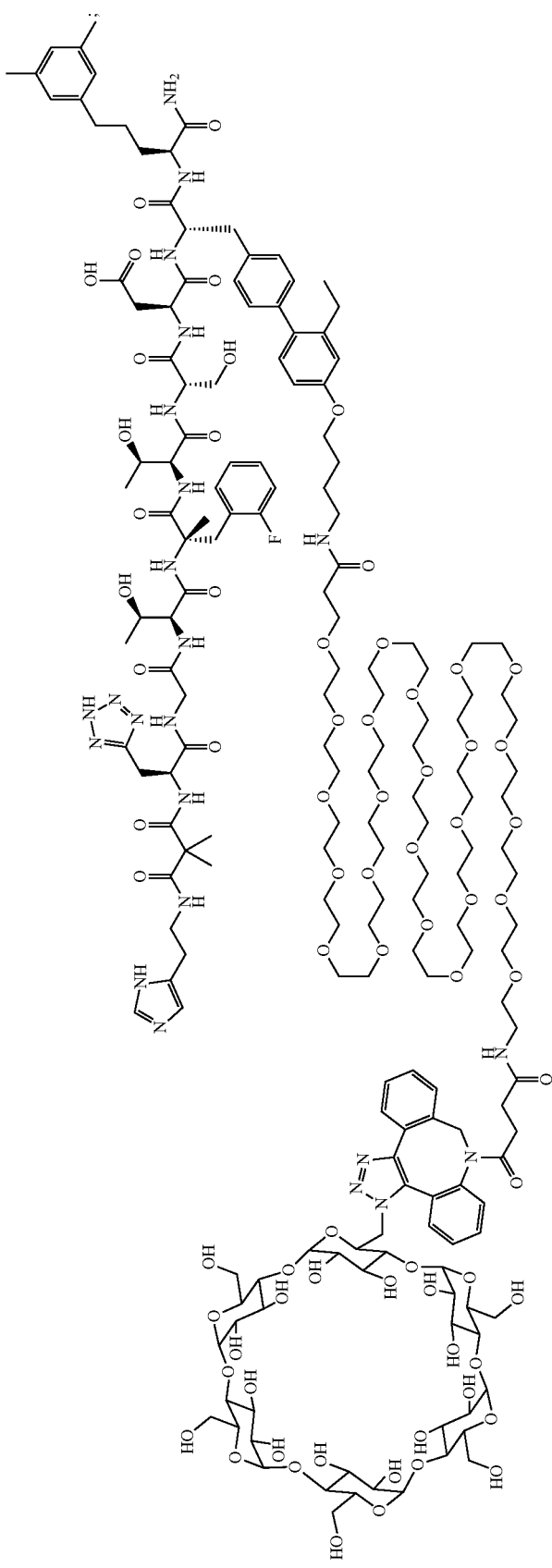
(SEQ ID NO: 102)

(SEQ ID NO: 103)
-continued
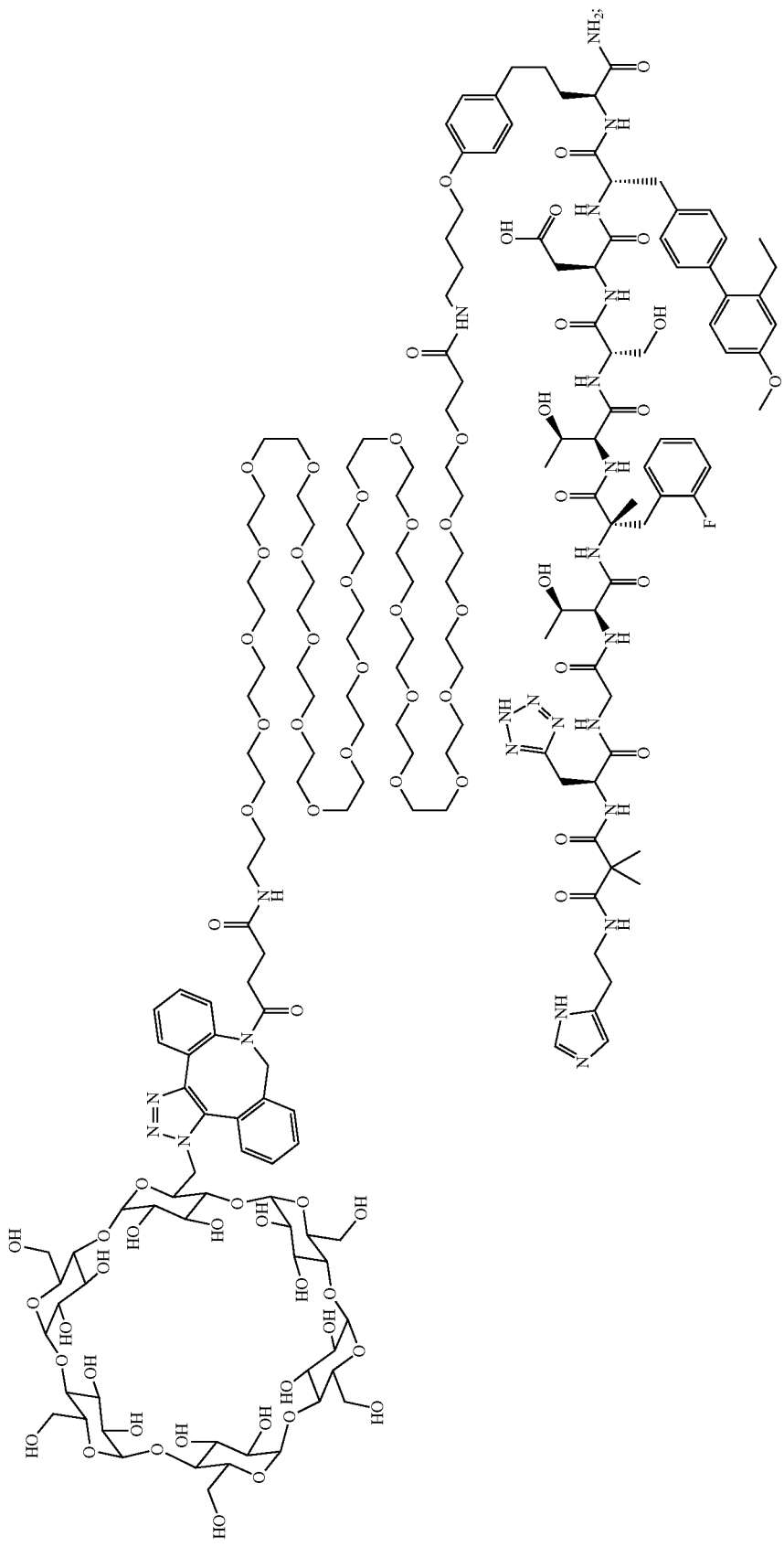

901 (SEQ ID NO: 104) 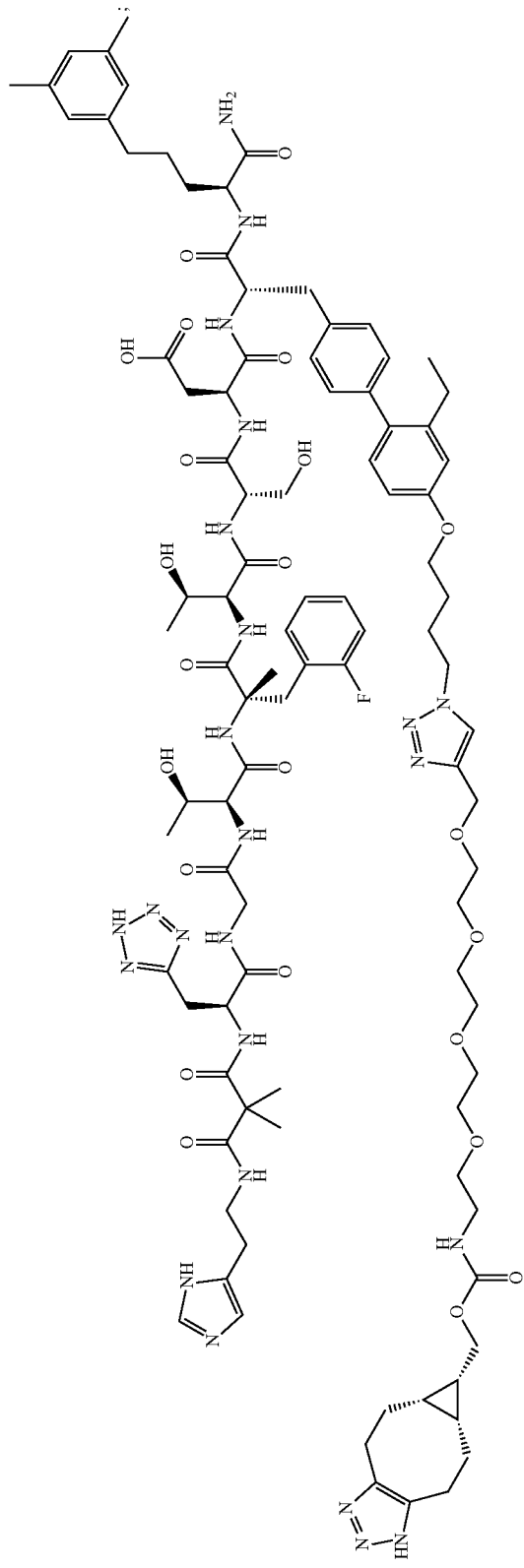
902 (SEQ ID NO: 105) 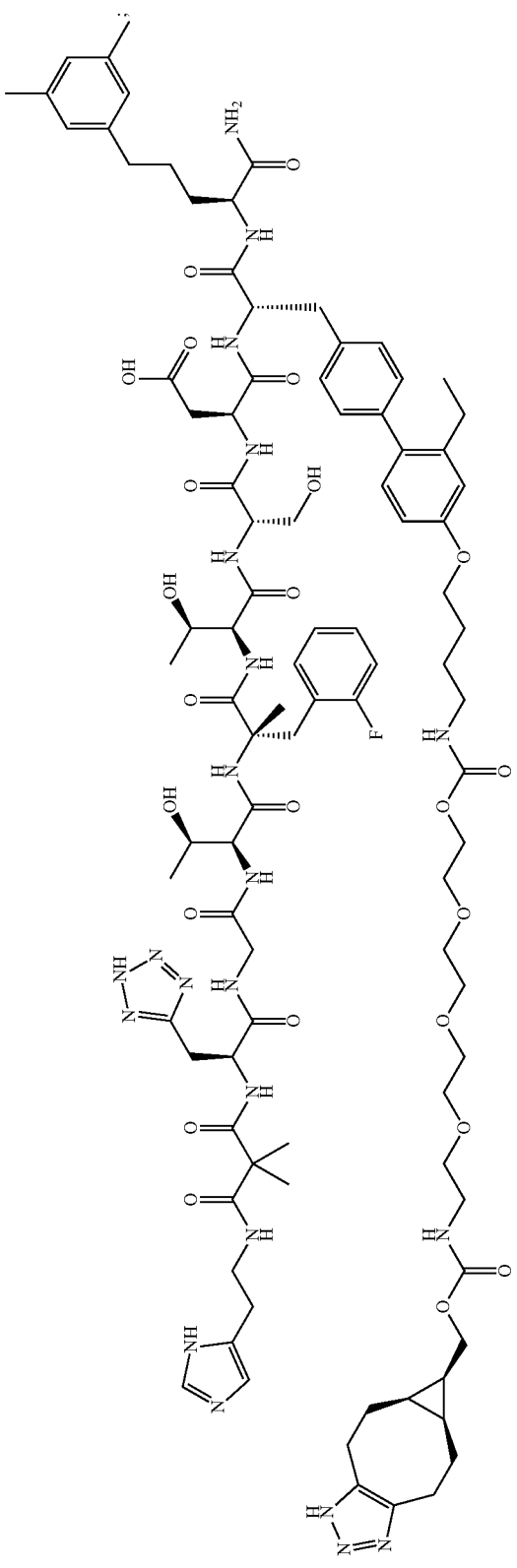

903
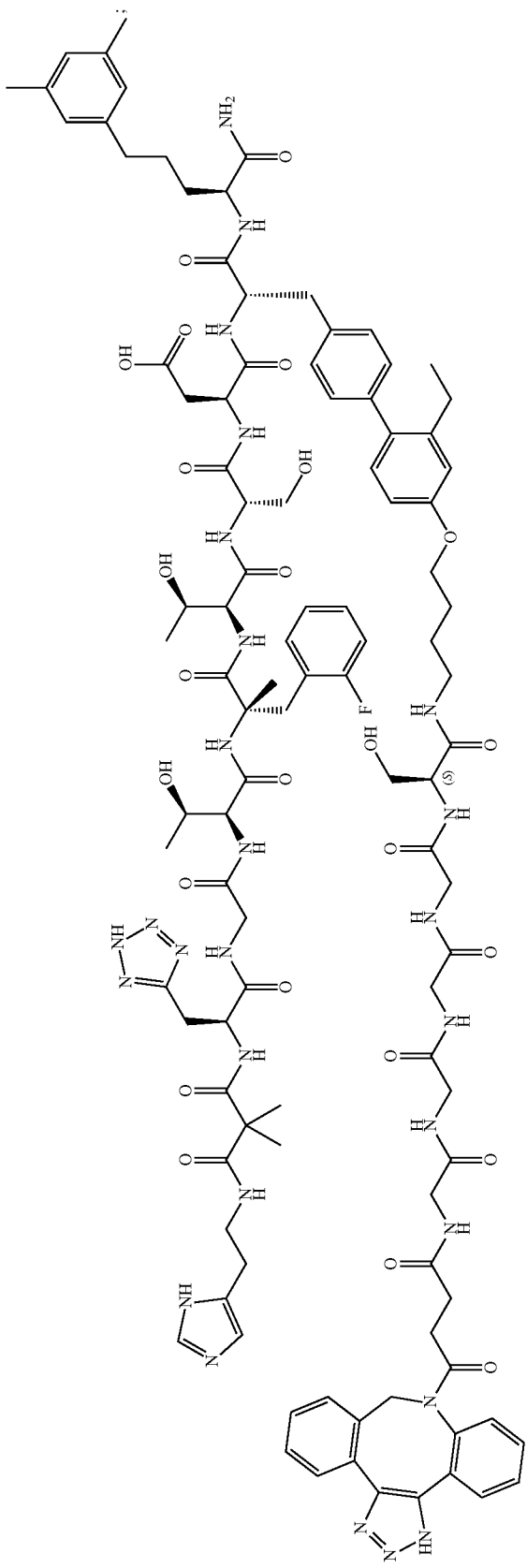
(Main Structure: SEQ ID NO: 106; Branched Sequence: SEQ ID NO: 165)
904
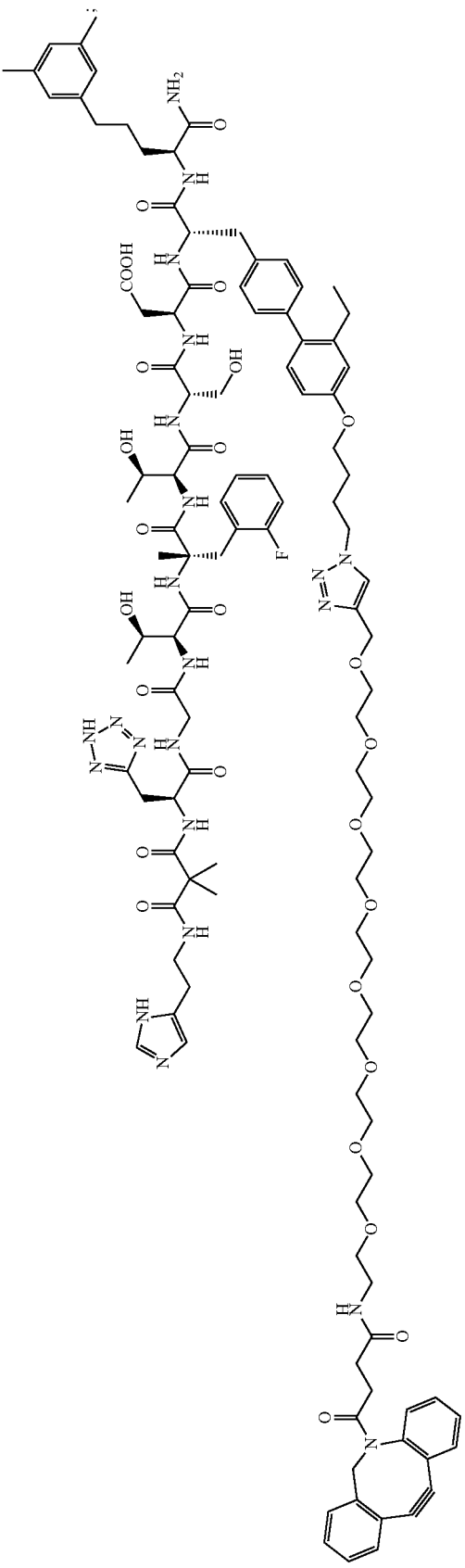
(SEQ ID NO: 187)

905
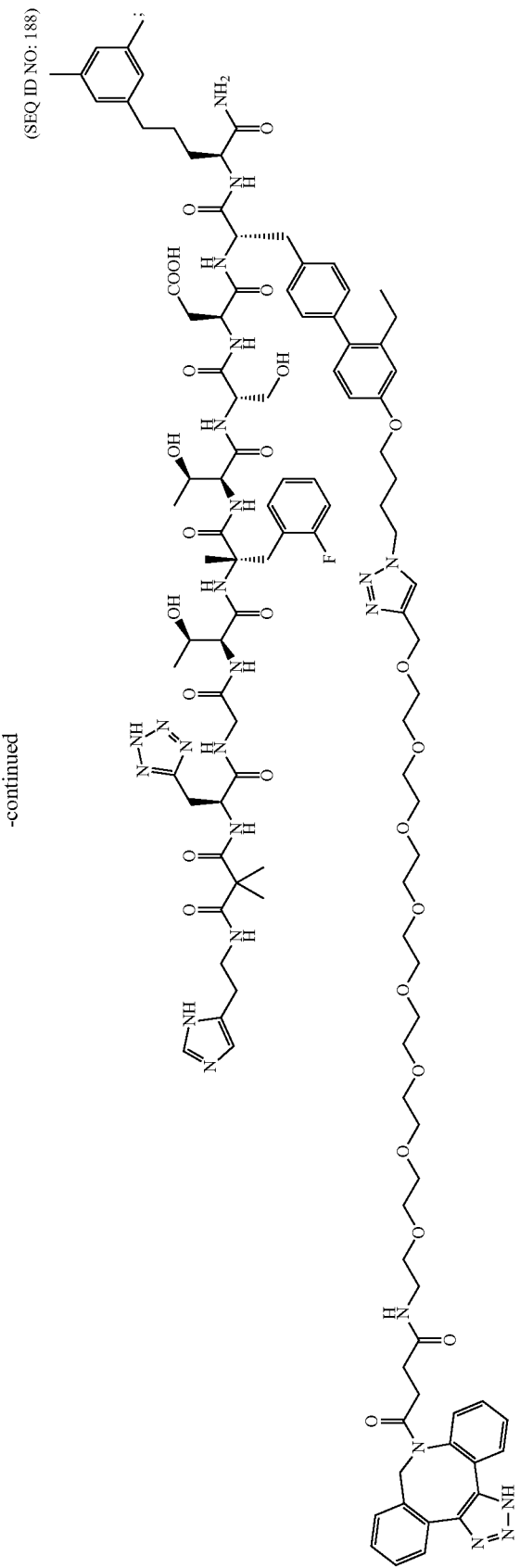
(SEQ ID NO: 188)
906
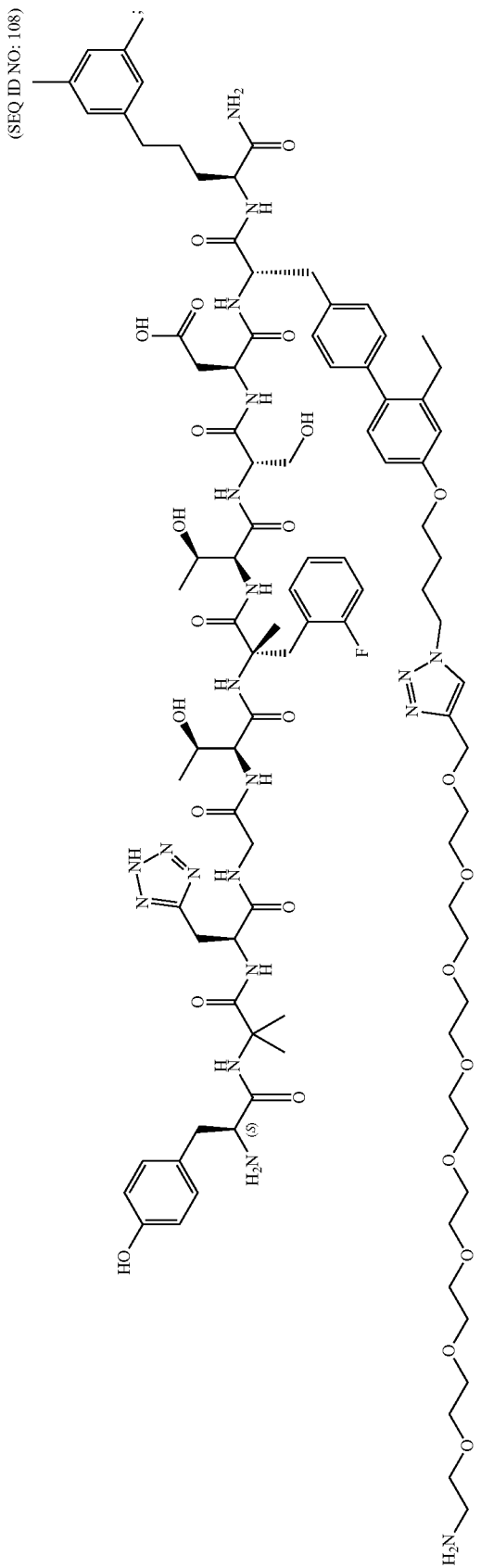
(SEQ ID NO: 108)

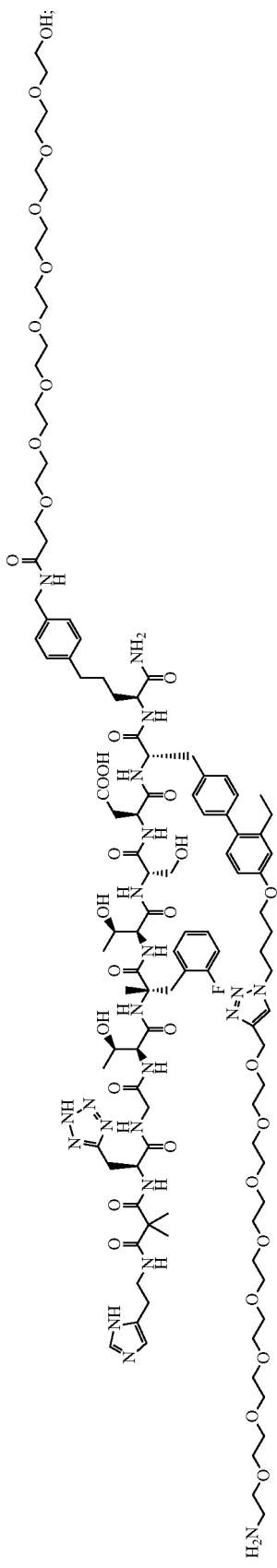
(SEQ ID NO: 109)
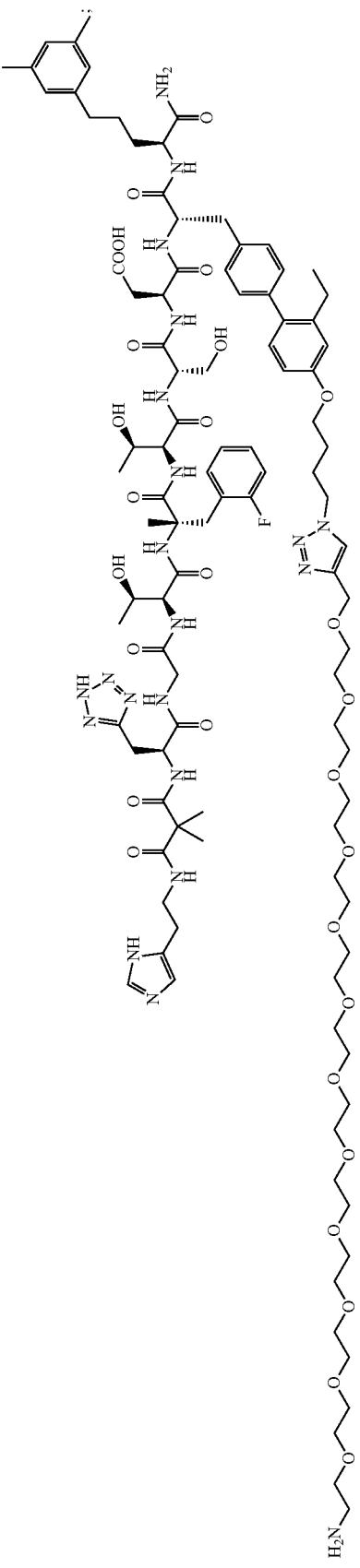
(SEQ ID NO: 110)

909 (SEQ ID NO: 189)
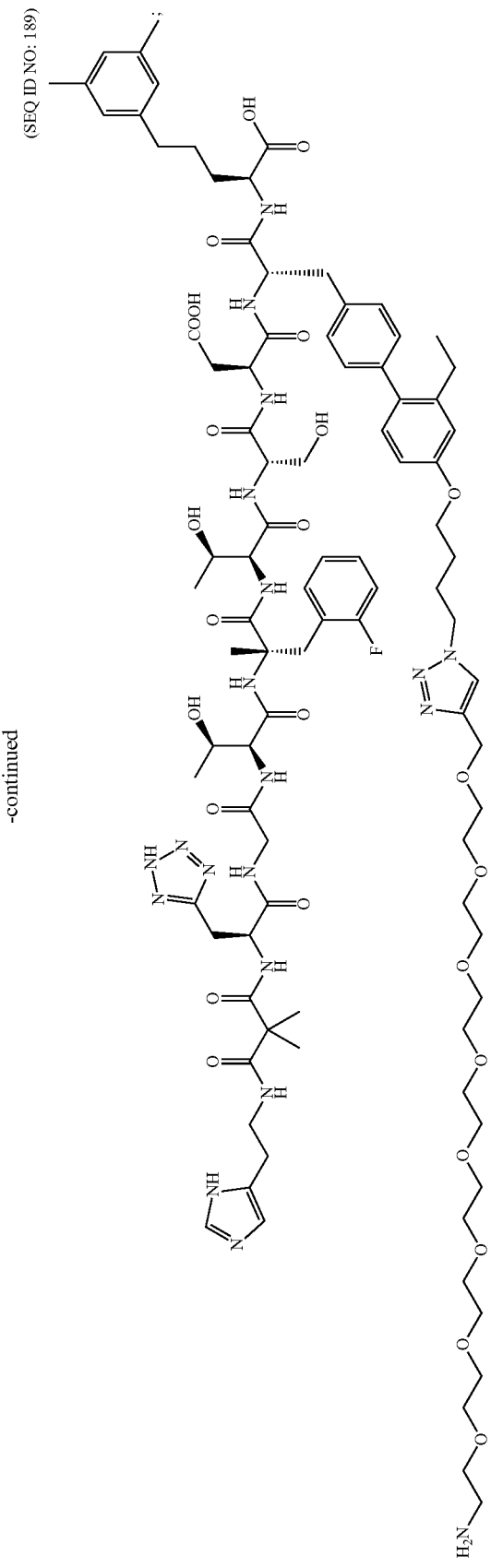
910 (SEQ ID NO: 190)
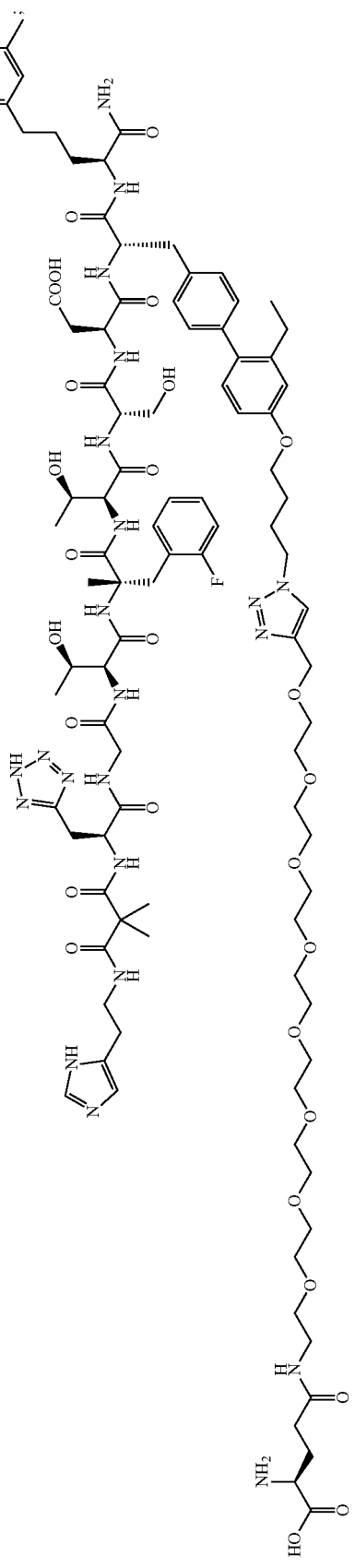

911 912
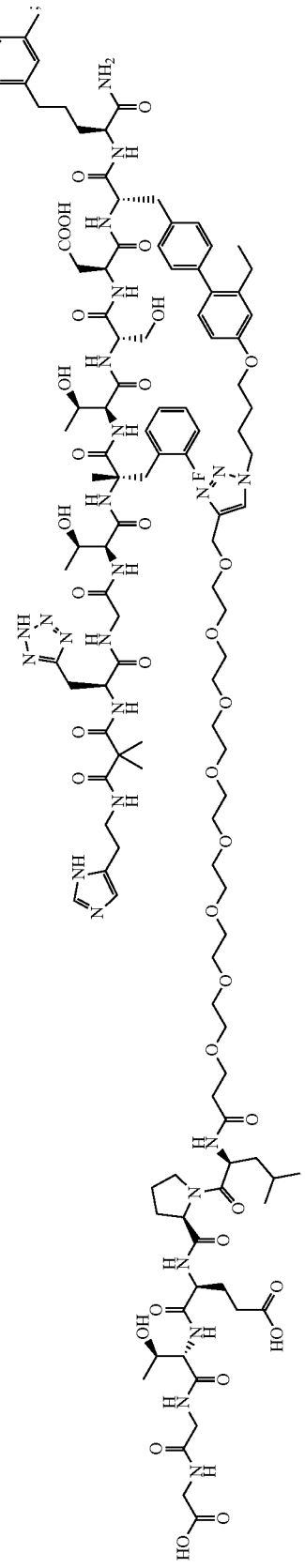
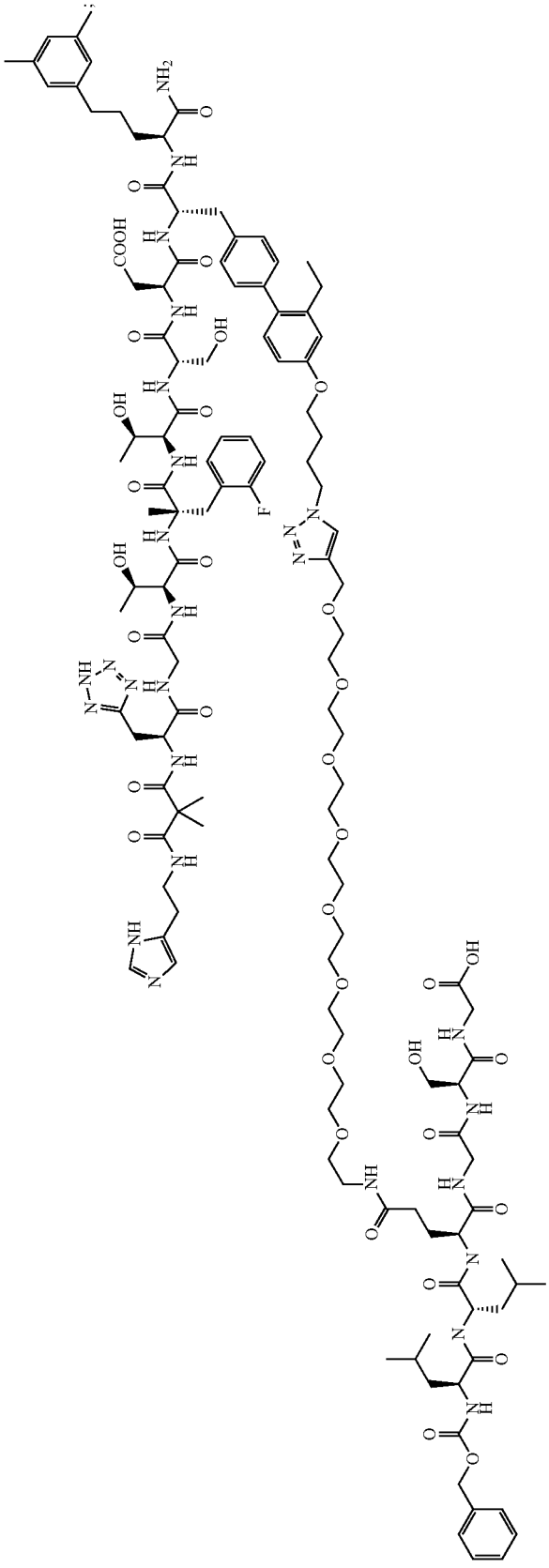

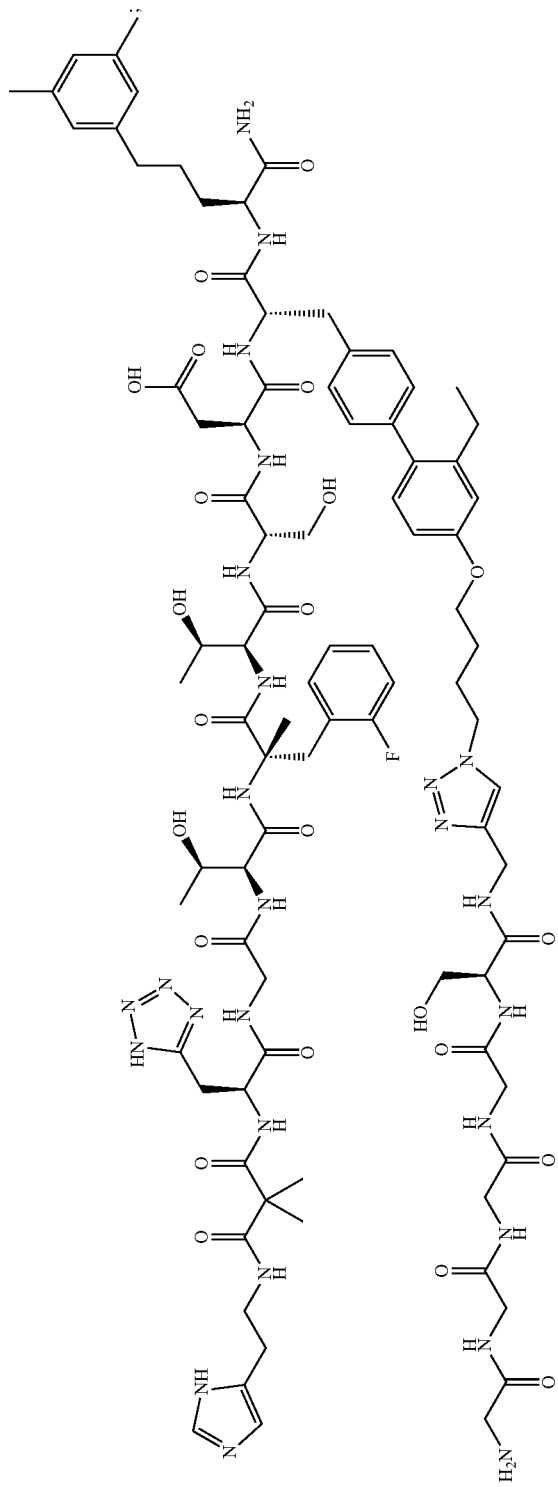
(Main Structure: SEQ ID NO: 114; Branched Sequence: SEQ ID NO: 168)

915
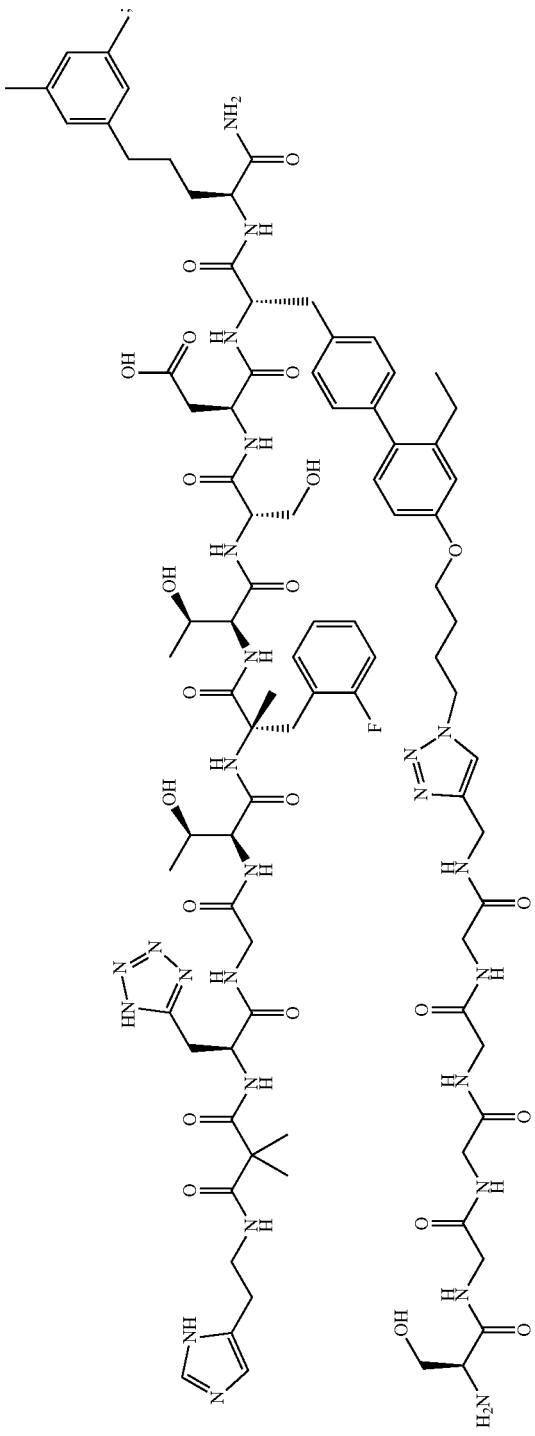
916
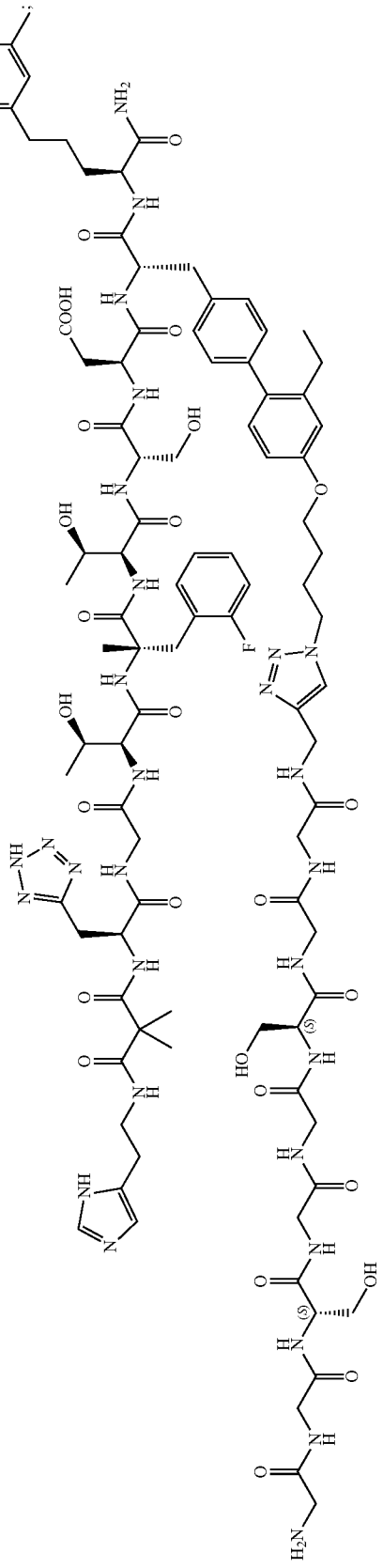

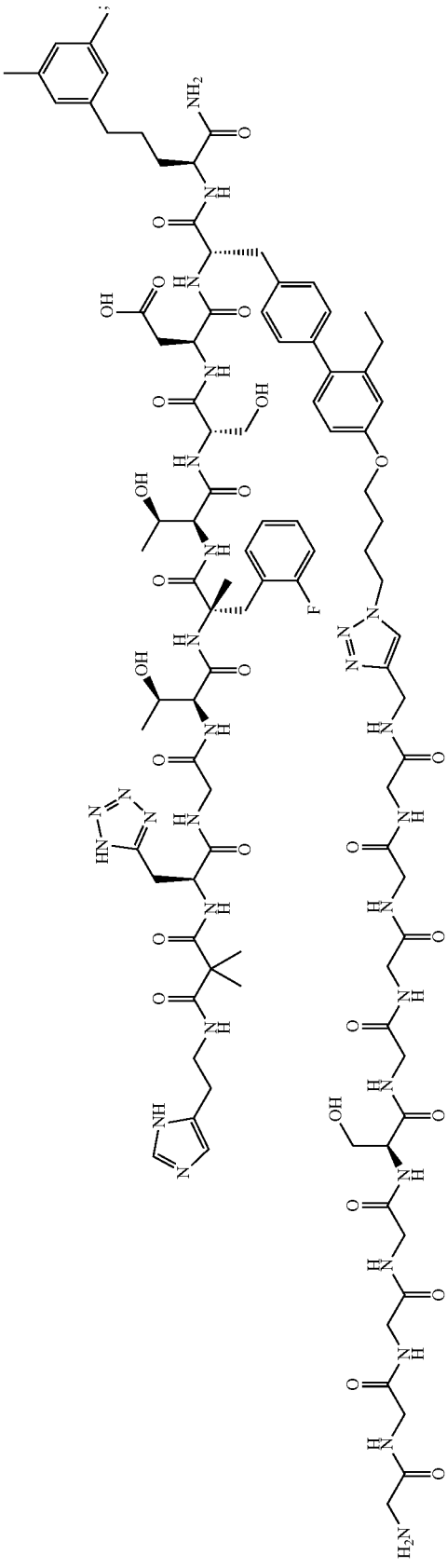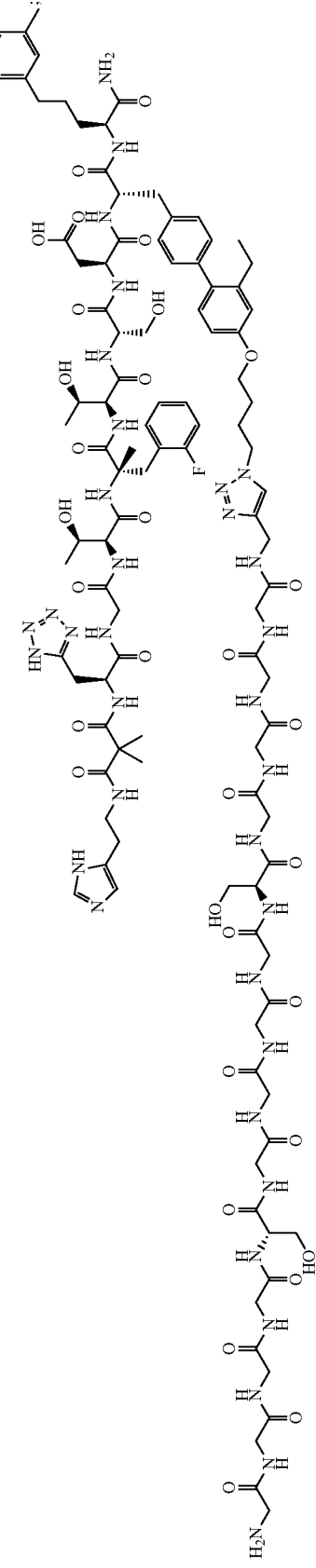

-continued
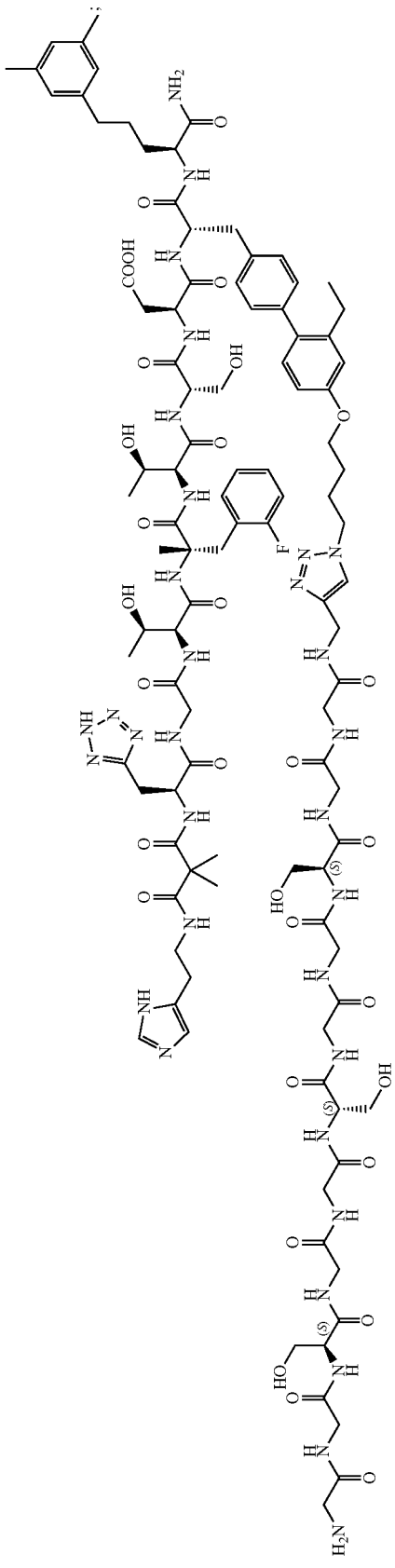
(Main Structure: SEQ ID NO: 119; Branched Sequence: SEQ ID NO: 173)
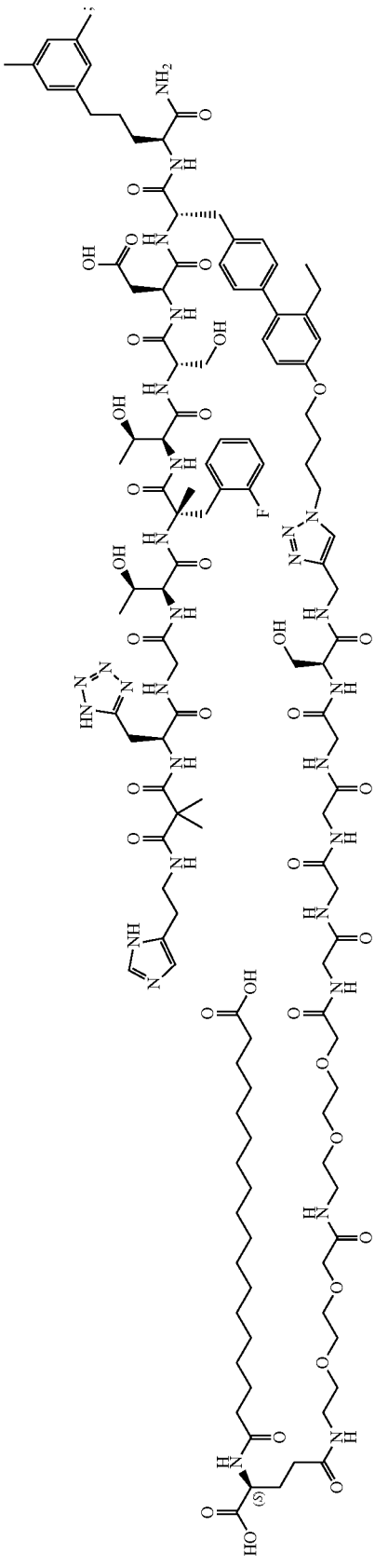
(Main Structure: SEQ ID NO: 120; Branched Sequence: SEQ ID NO: 174)

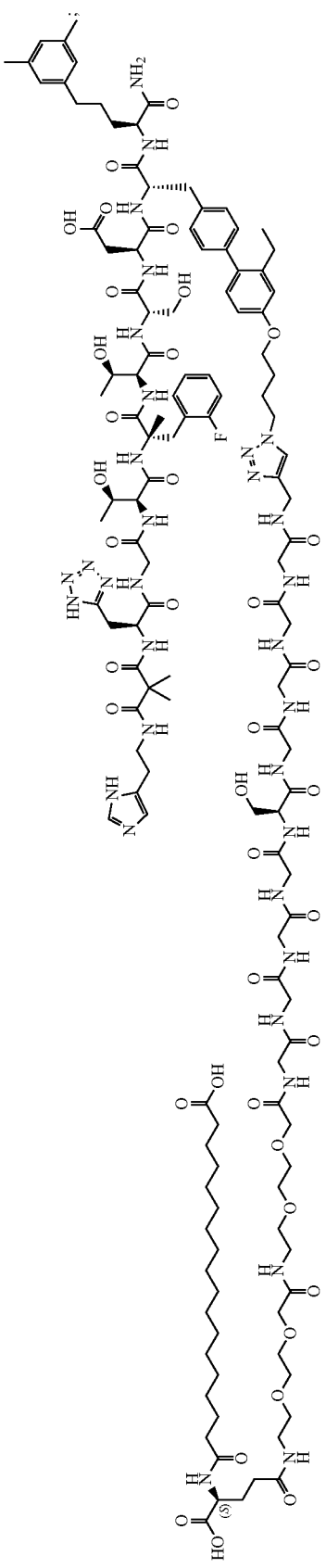
(Main Structure: SEQ ID NO: 121; Branched Sequence: SEQ ID NO: 175)
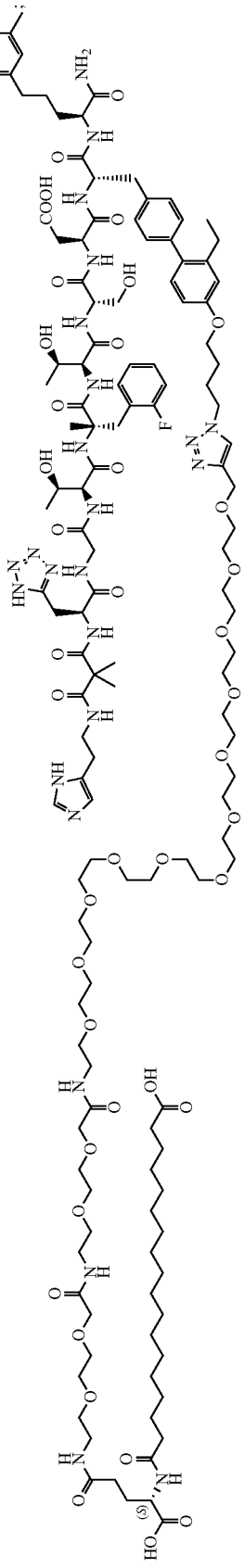
(SEQ ID NO: 122)

-continued
(SEQ ID NO: 123)
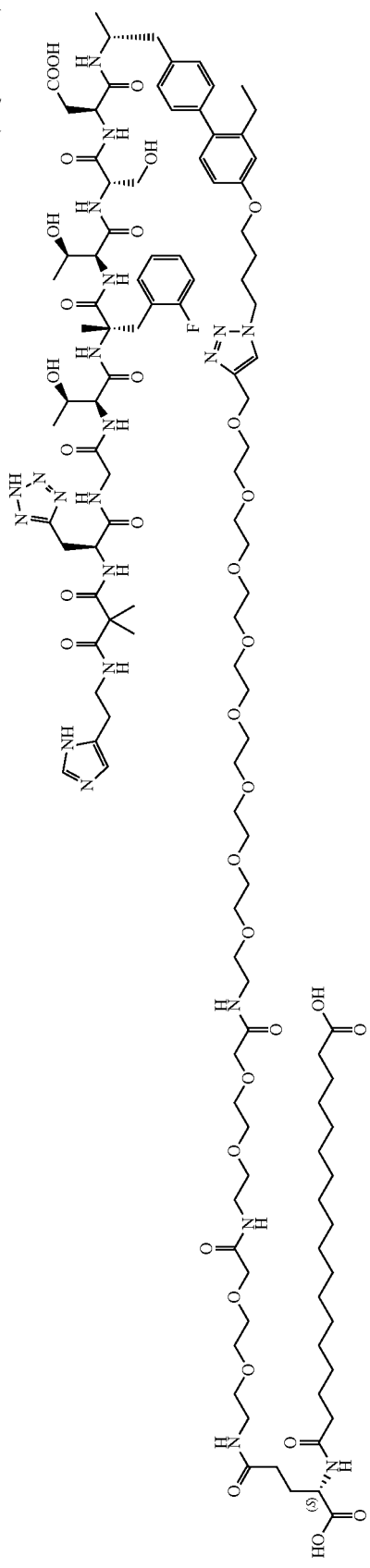
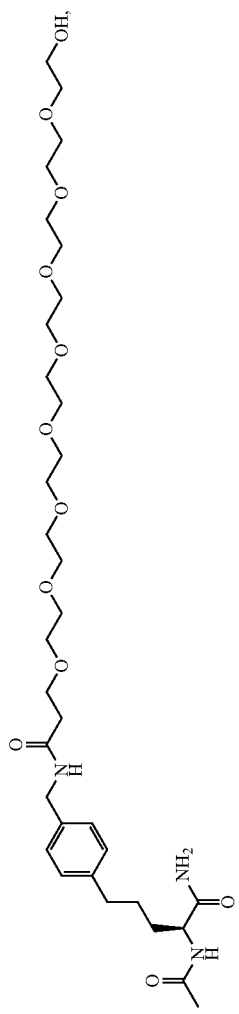

or a pharmaceutically acceptable salt thereof.
29. An antibody-drug conjugate comprising a glucagon-like peptide-1 receptor (GLP1R)-targeting antibody or an antigen-binding fragment thereof conjugated, optionally through a linker, to a payload selected from the group consisting of:
(SEQ ID NO: 41)
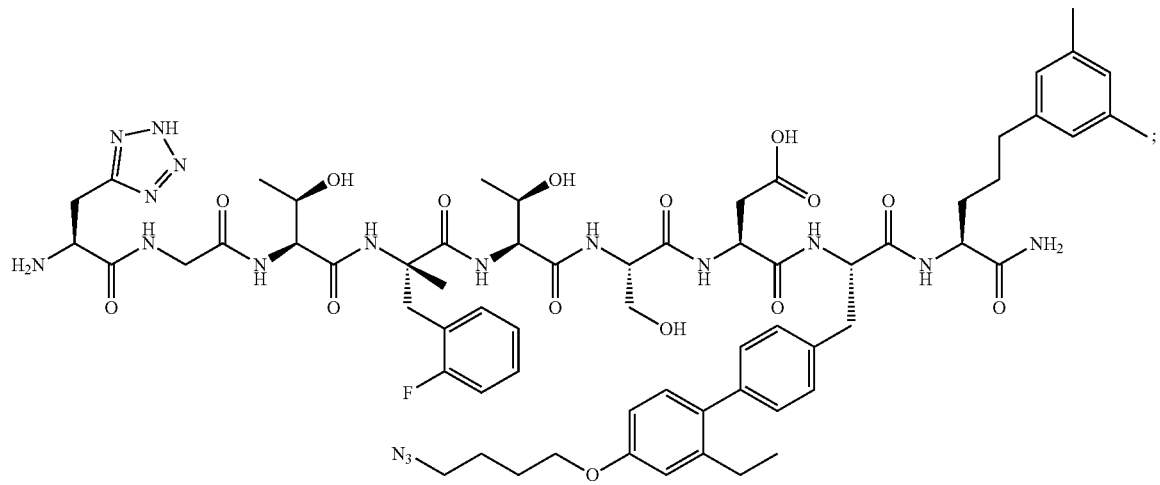
(SEQ ID NO: 42)
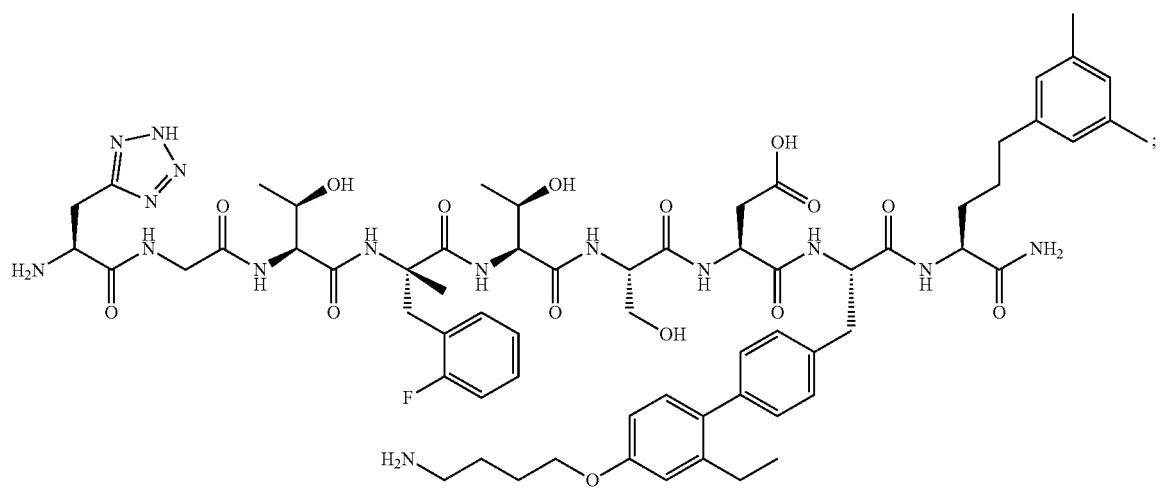
(SEQ ID NO: 43)
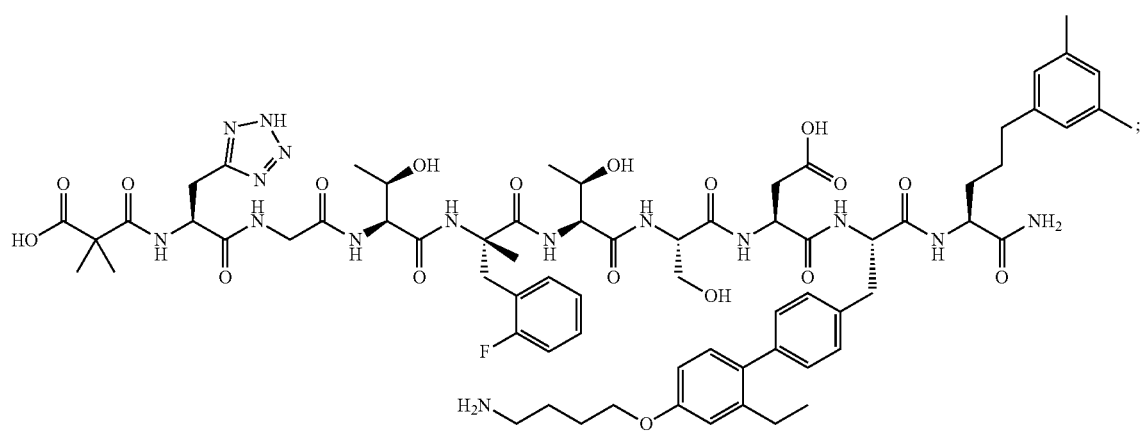

(SEQ ID NO: 44)
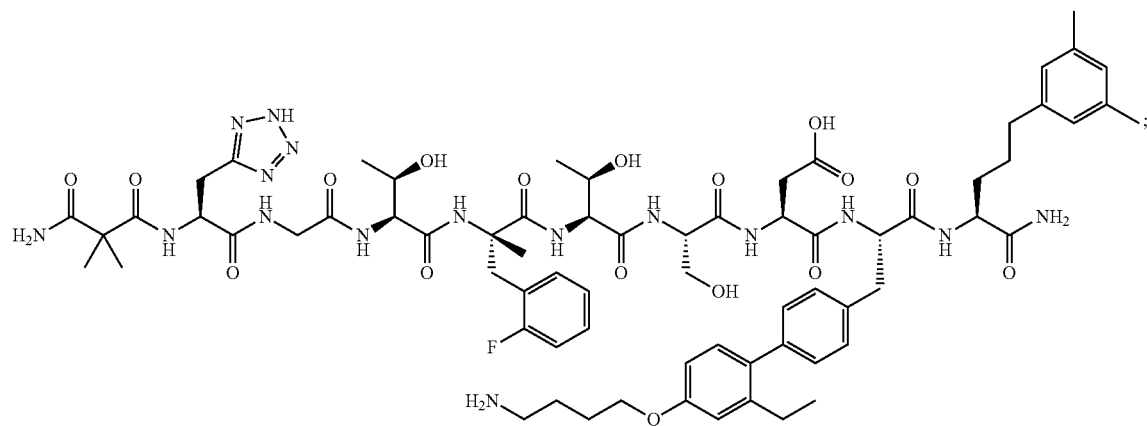
(SEQ ID NO: 45)
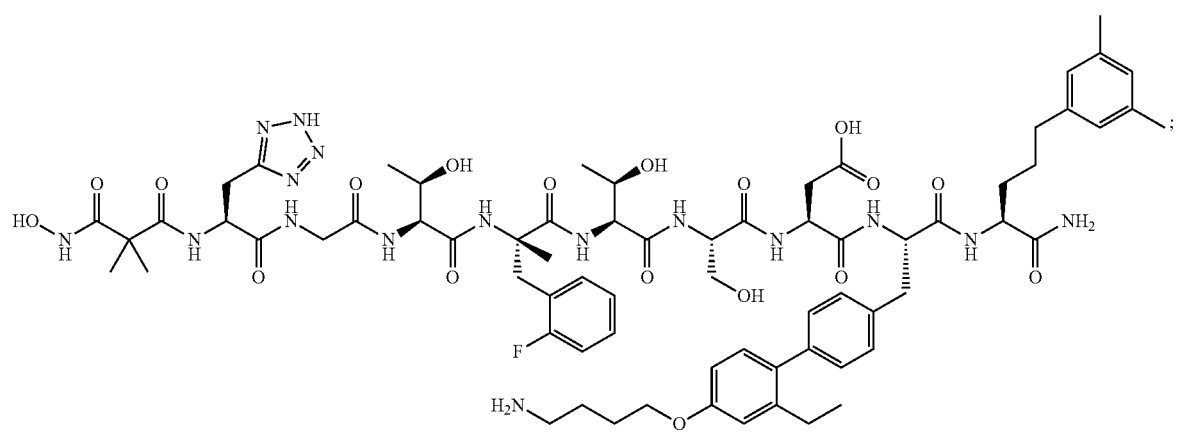
(SEQ ID NO: 46)
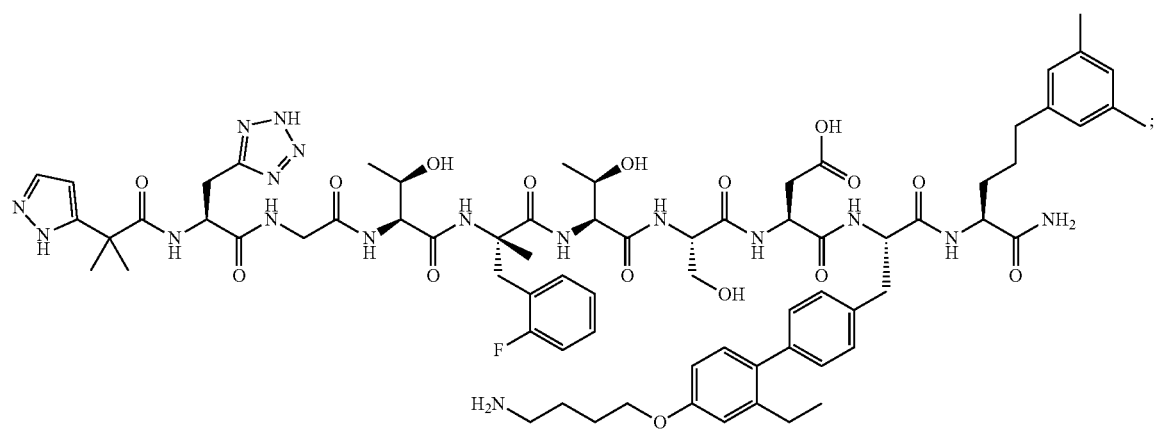

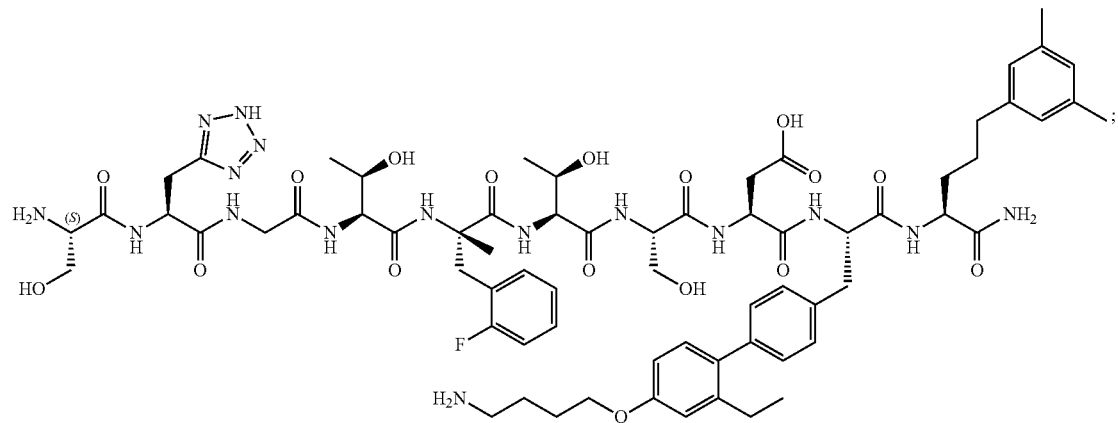
(SEQ ID NO: 47)
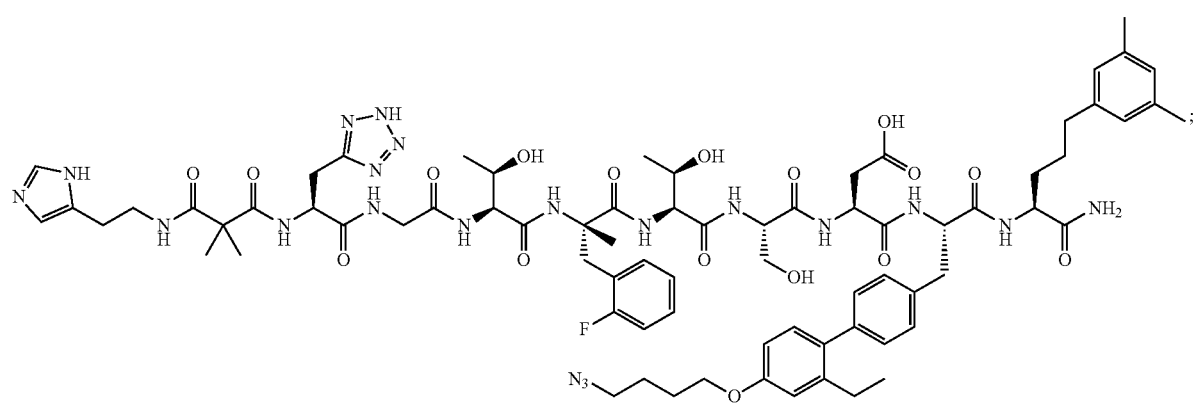
(SEQ ID NO: 48)
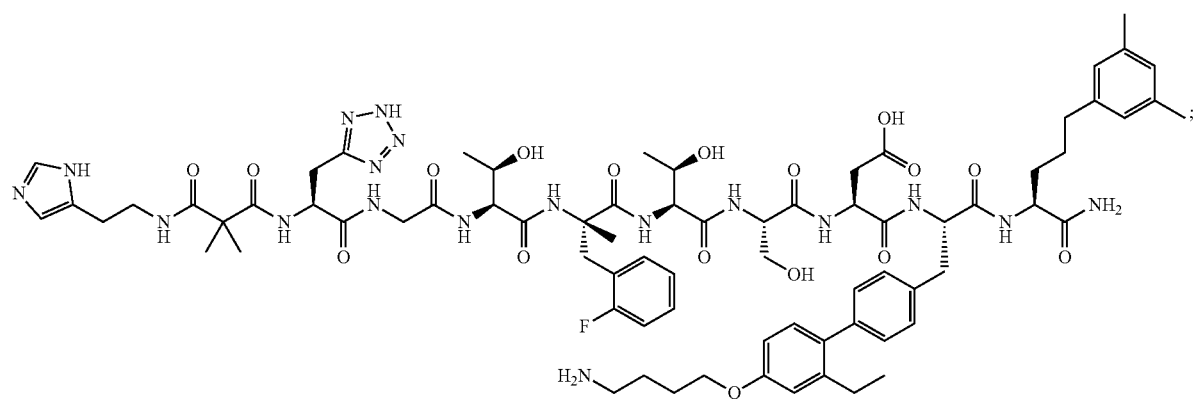
(SEQ ID NO: 49)

931 932
-continued
(SEQ ID NO: 50)
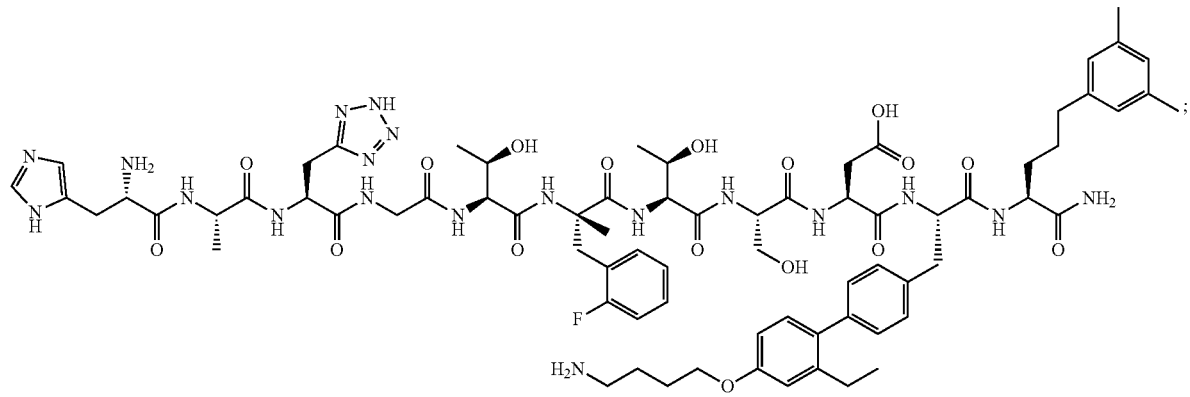
(SEQ ID NO: 51)
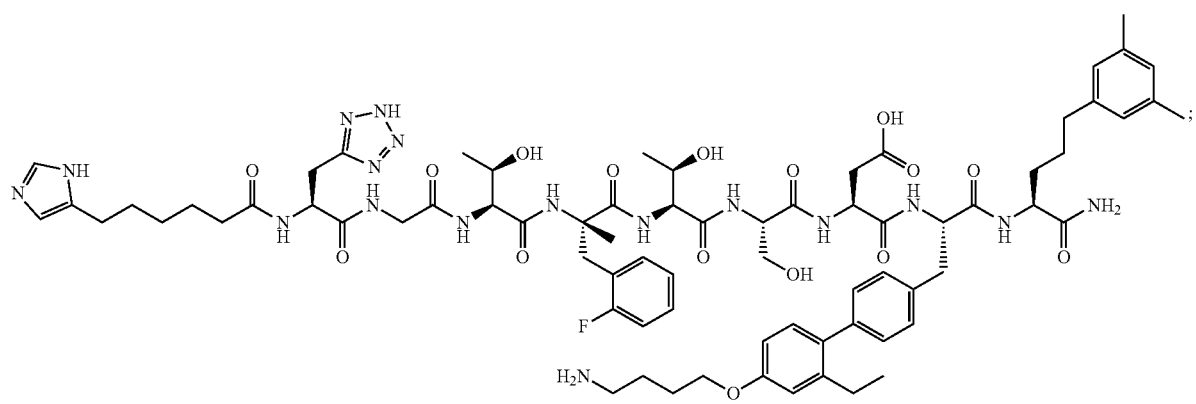
(SEQ ID NO: 52)
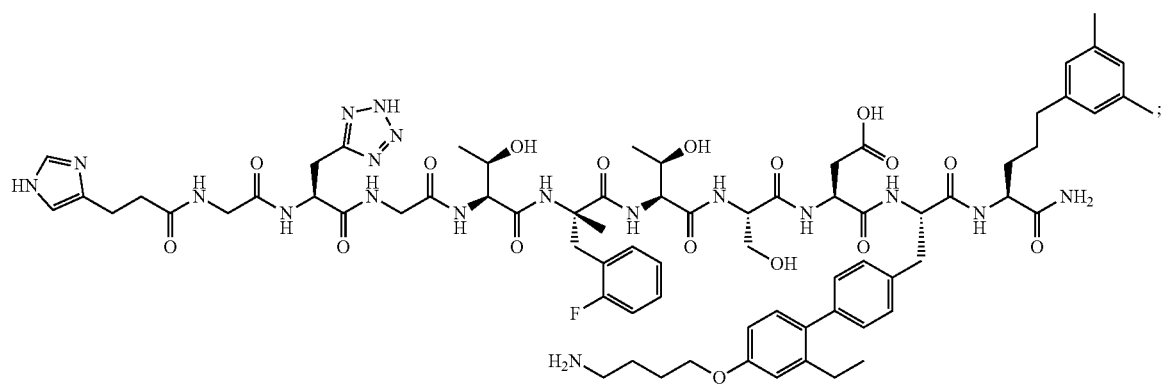
(SEQ ID NO: 53)
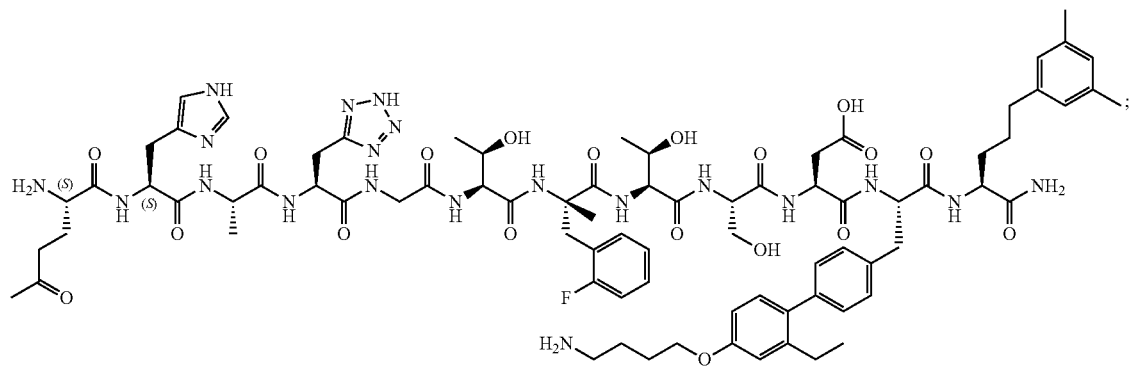

(SEQ ID NO: 54)
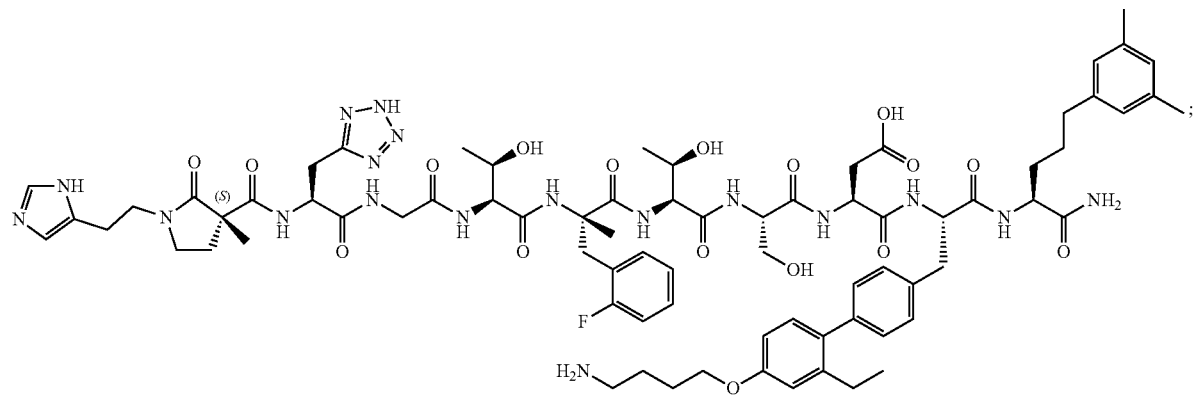
(SEQ ID NO: 55)
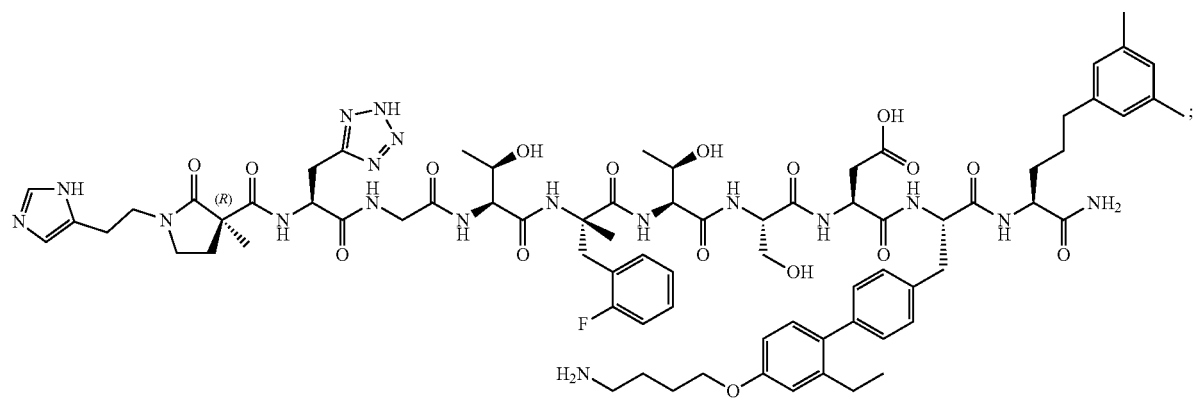
(SEQ ID NO: 56)
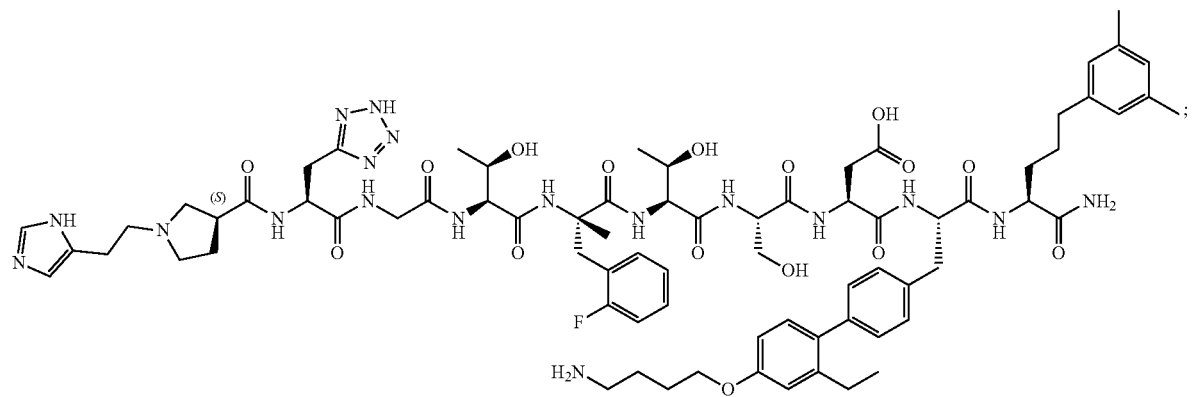

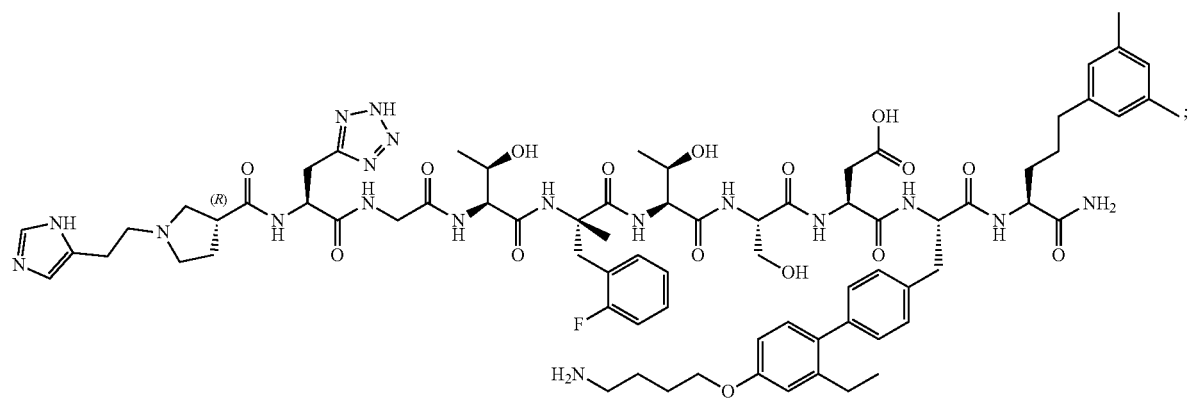
(SEQ ID NO: 57)
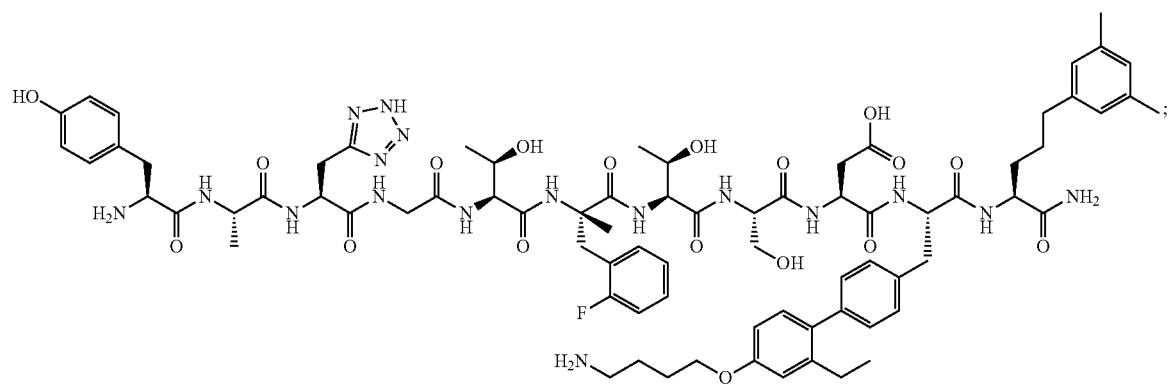
(SEQ ID NO: 58)
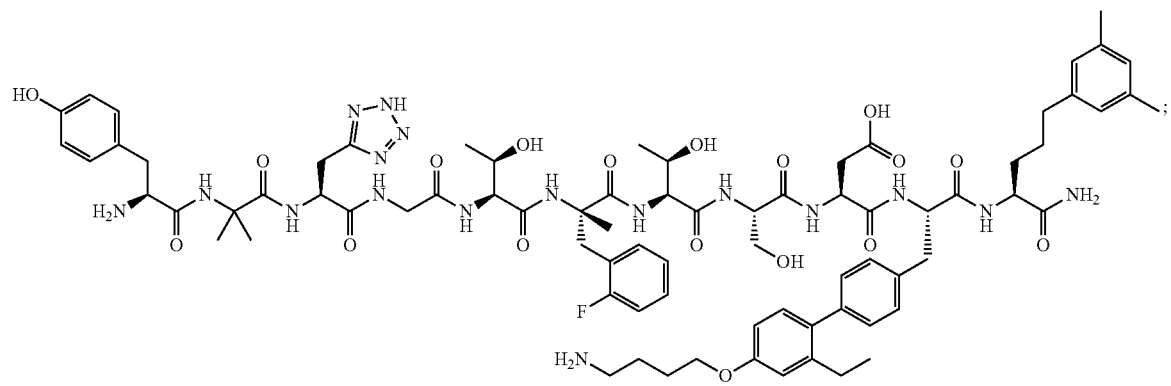
(SEQ ID NO: 59)

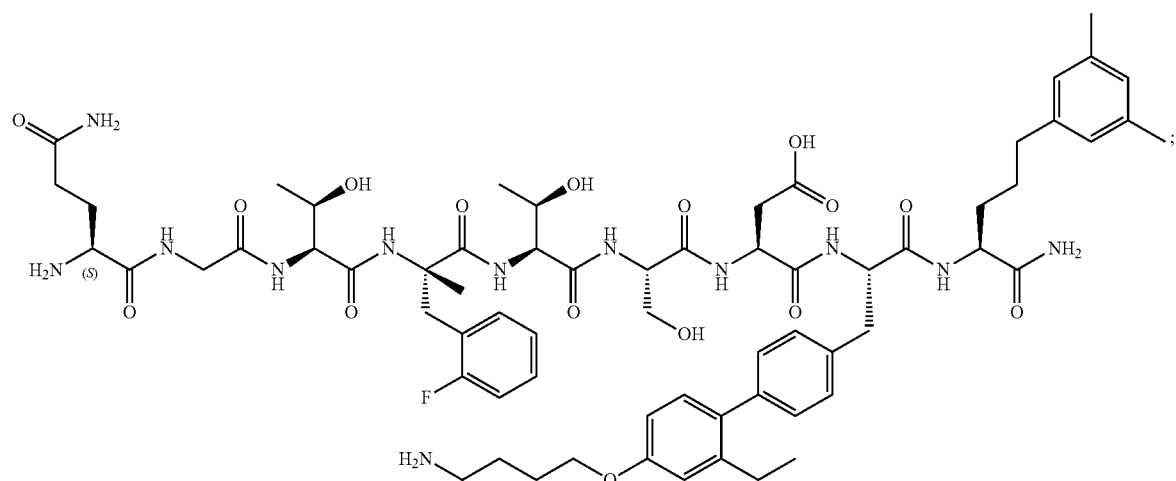
(SEQ ID NO: 60)
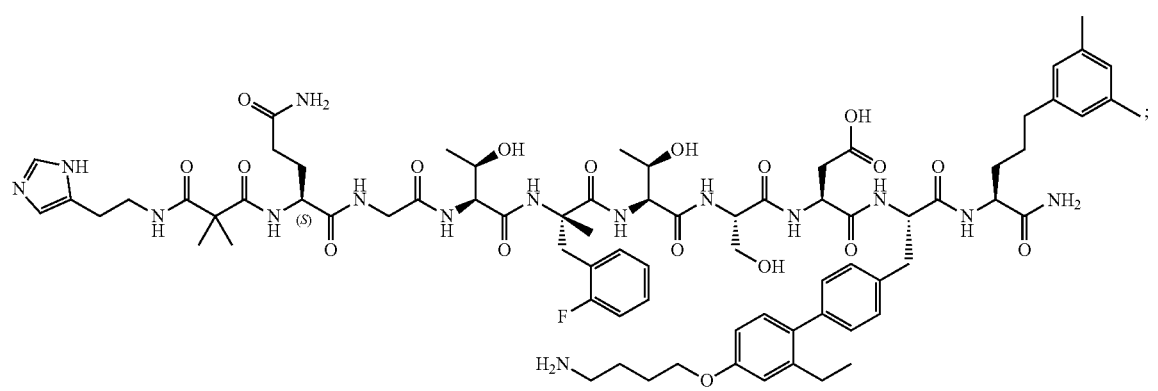
(SEQ ID NO: 61)
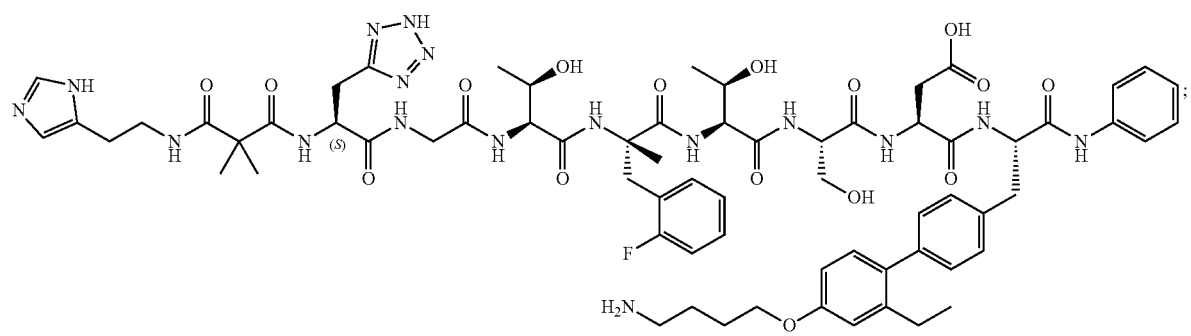
(SEQ ID NO: 62)
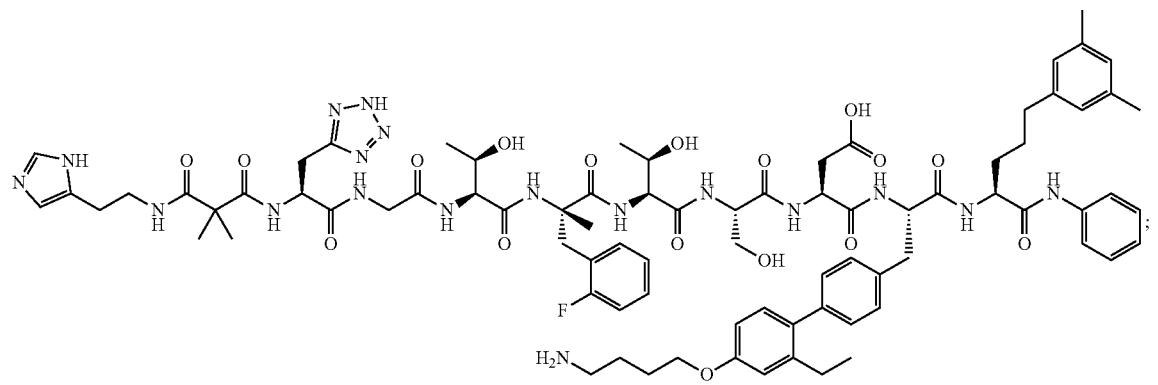
(SEQ ID NO: 63)

(SEQ ID NO: 64)
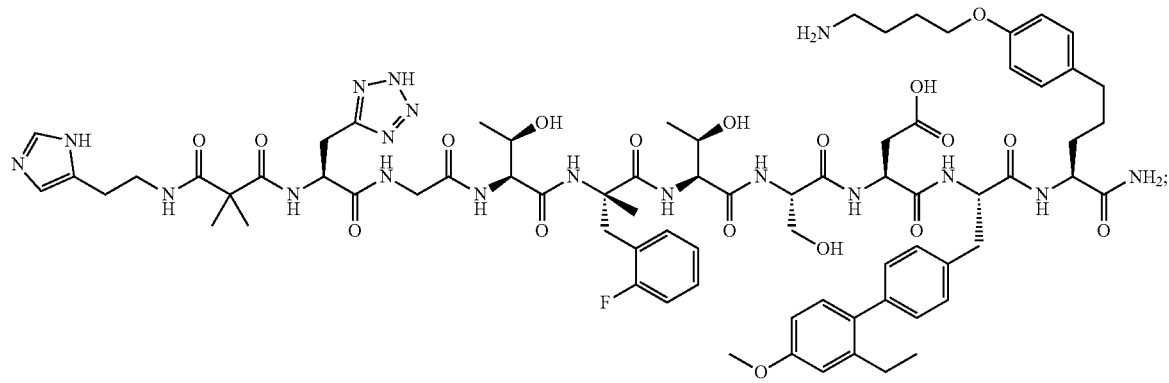
(SEQ ID NO: 65)
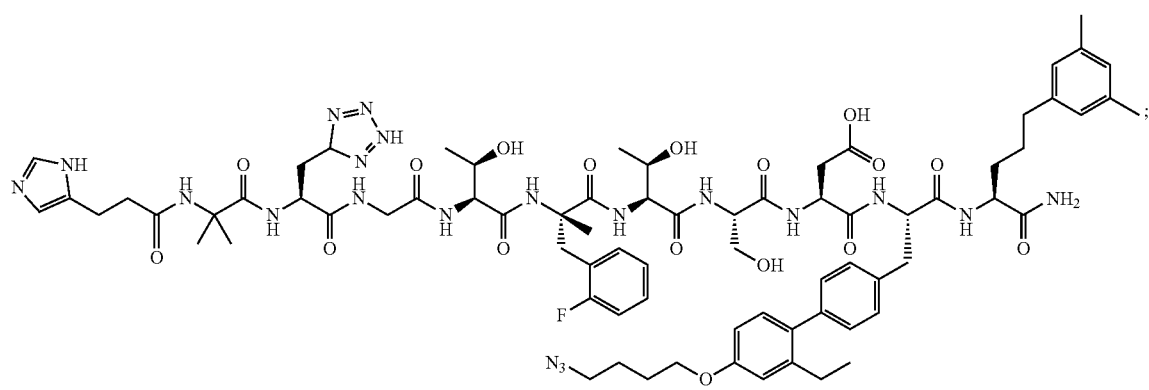
(SEQ ID NO: 66)
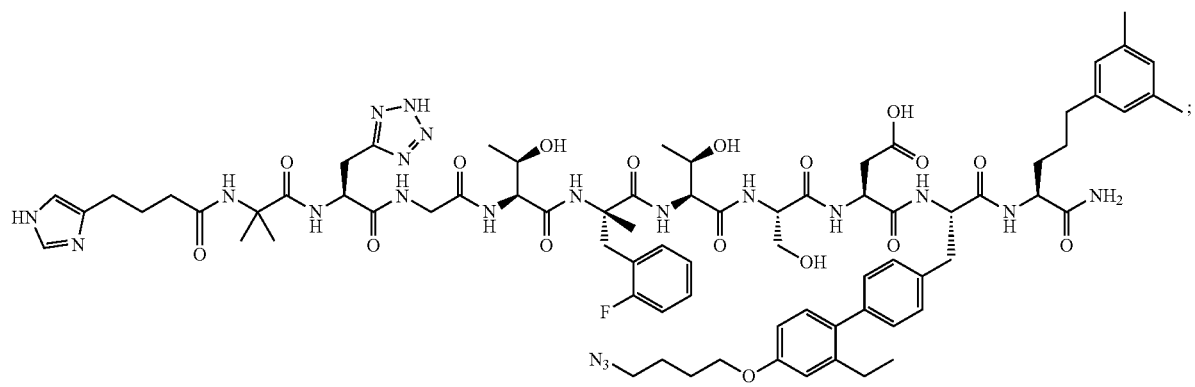
(SEQ ID NO: 67)
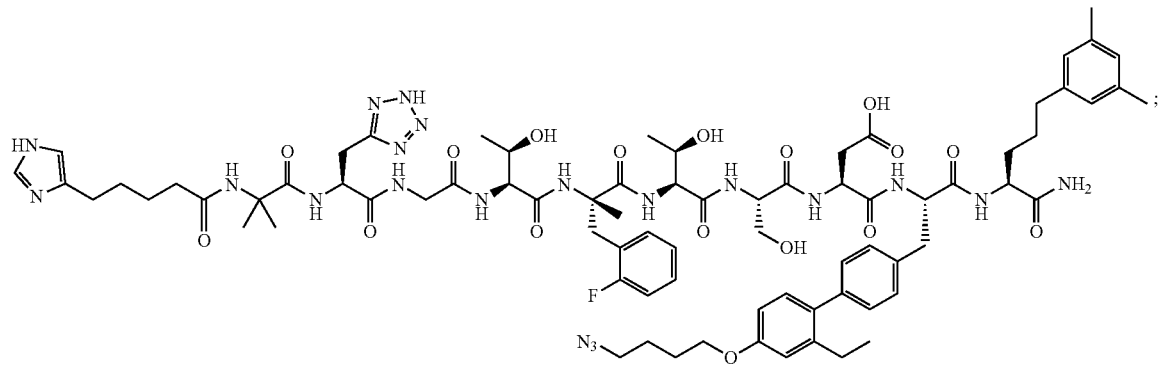

-continued
(SEQ ID NO: 68)
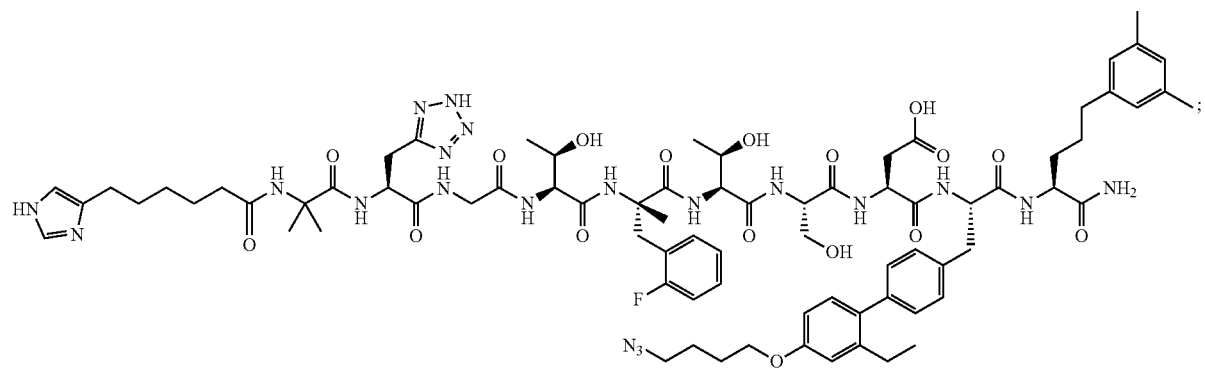
(SEQ ID NO: 69)
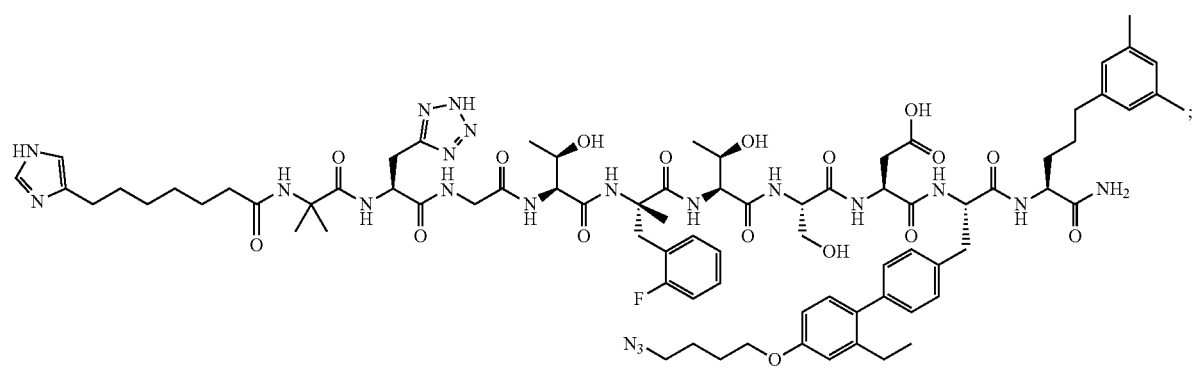
(SEQ ID NO: 70)
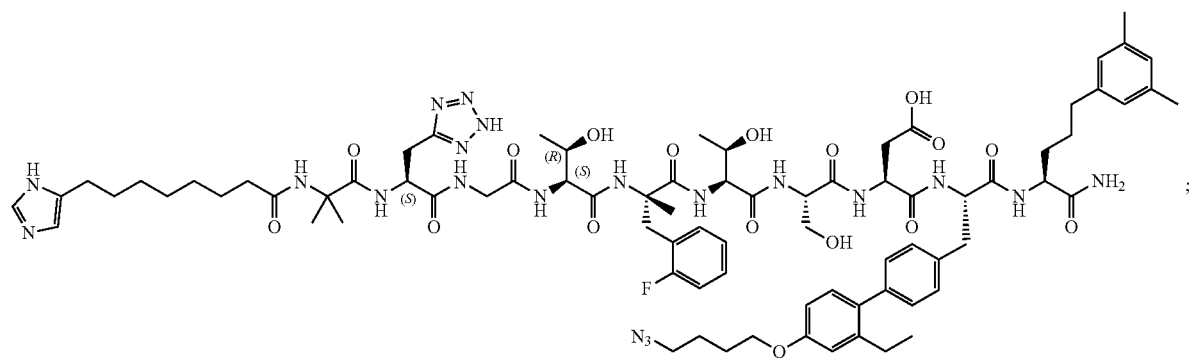
(SEQ ID NO: 71)
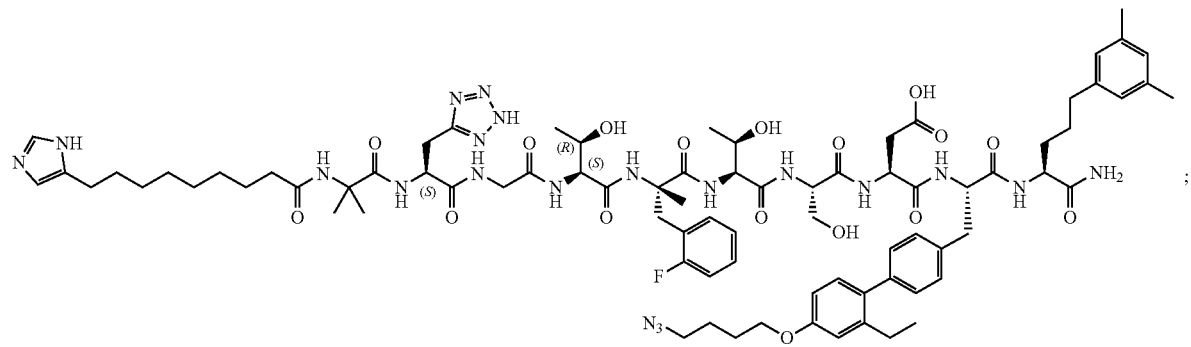

(Main Structure SEQ ID NO: 72; Branched Sequence: SEQ ID NO: 154)
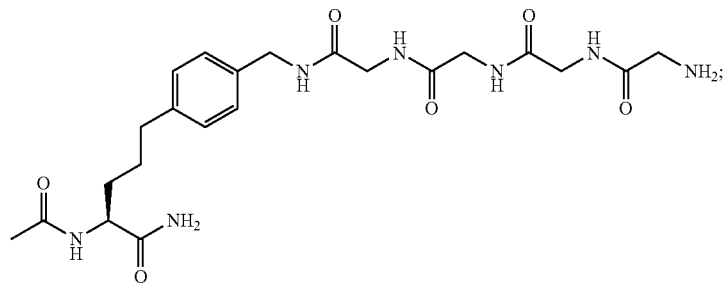
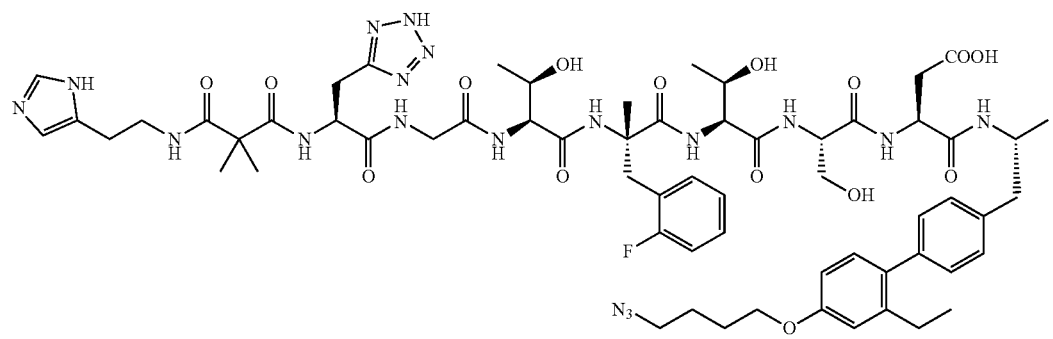
(SEQ ID NO: 73)
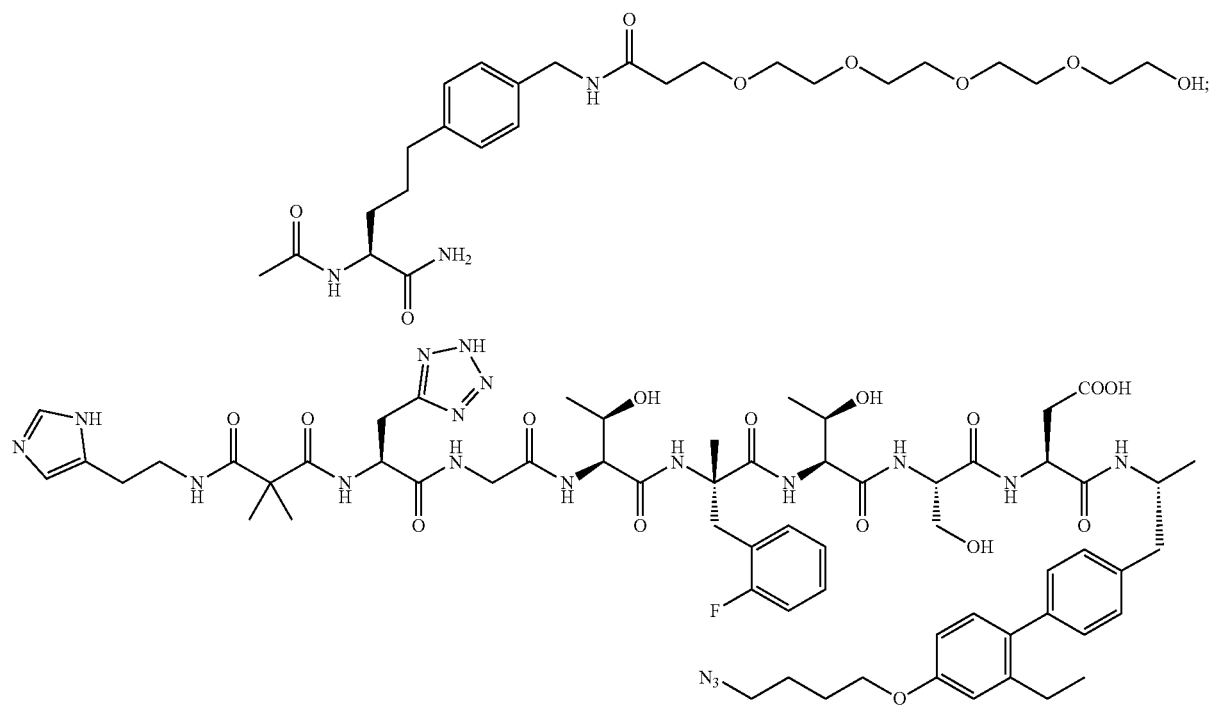

945
946
-continued
(Main Structure SEQ ID NO: 74; Branched Sequence: SEQ ID NO: 155)
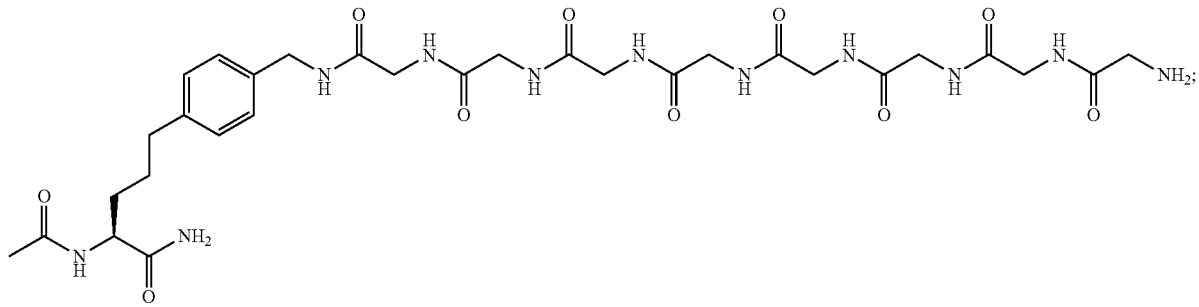
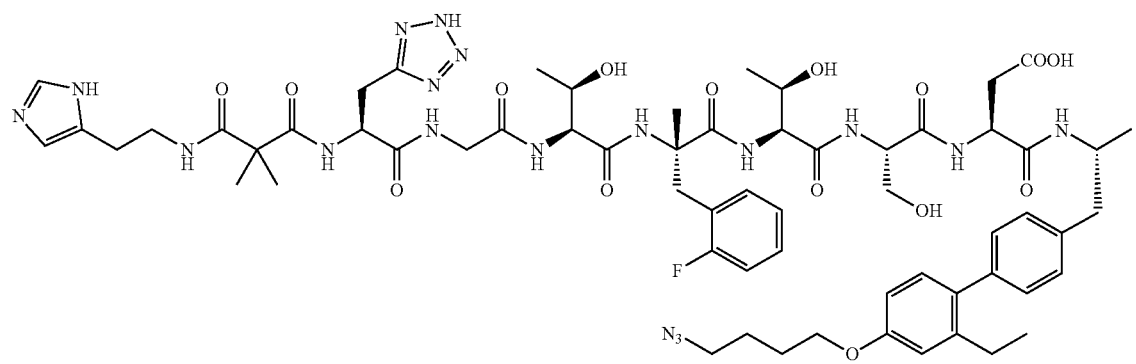
(SEQ ID NO: 75)
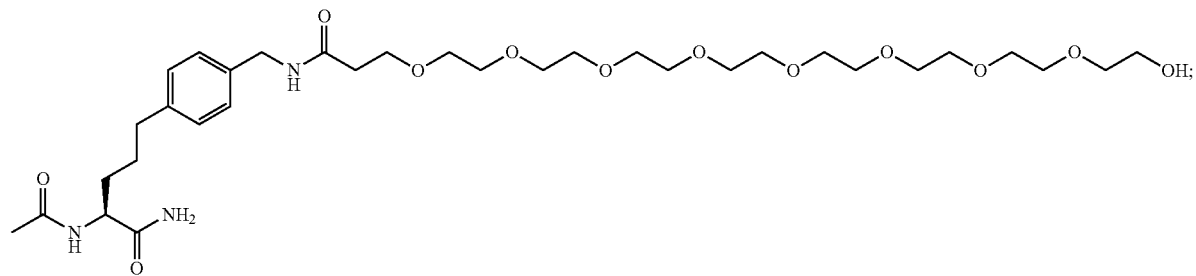
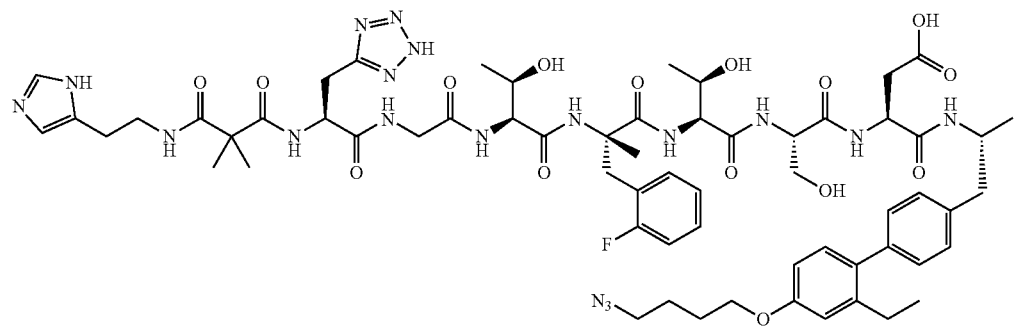

(SEQ ID NO: 76)
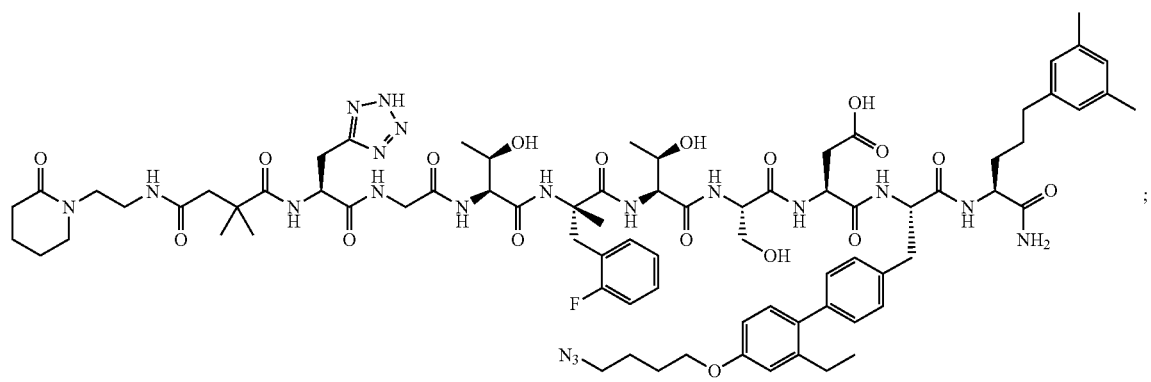
(SEQ ID NO: 77)
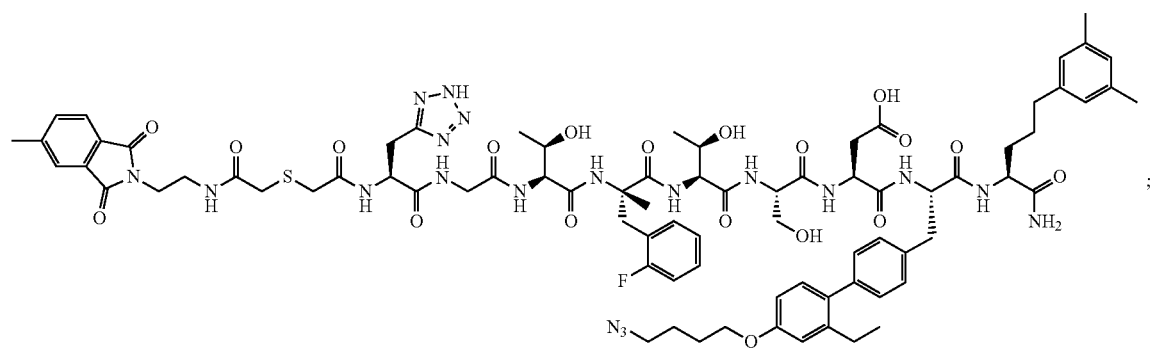
(SEQ ID NO: 78)
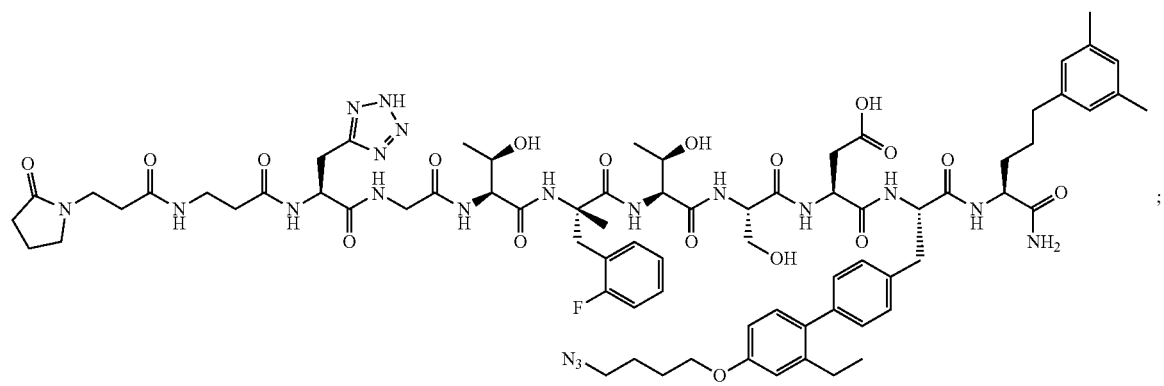
(SEQ ID NO: 80)
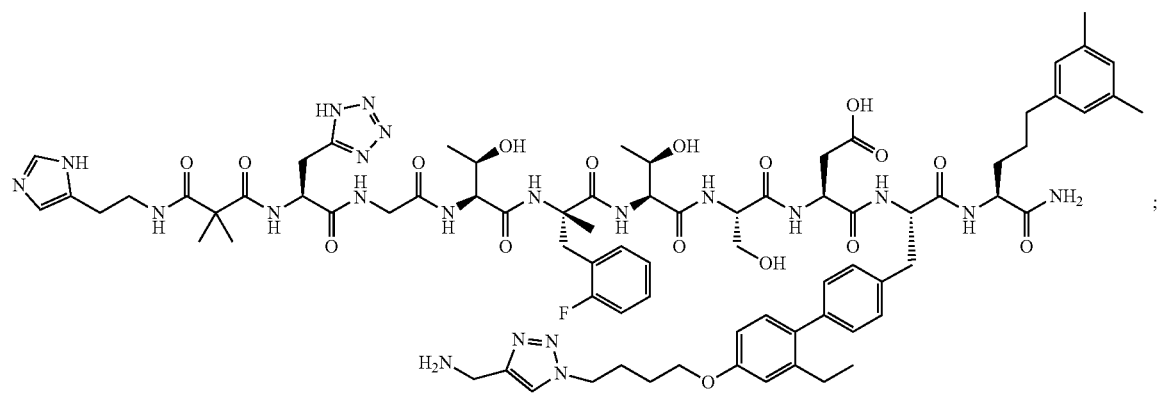

(SEQ ID NO: 81)
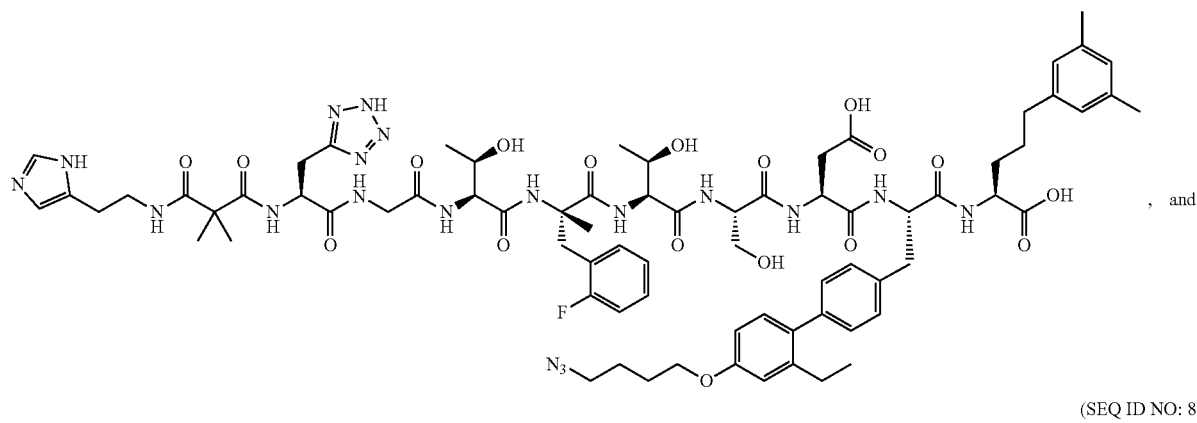
(SEQ ID NO: 82)
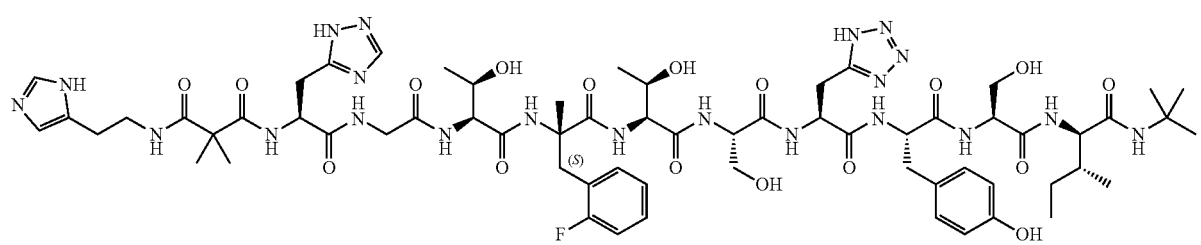
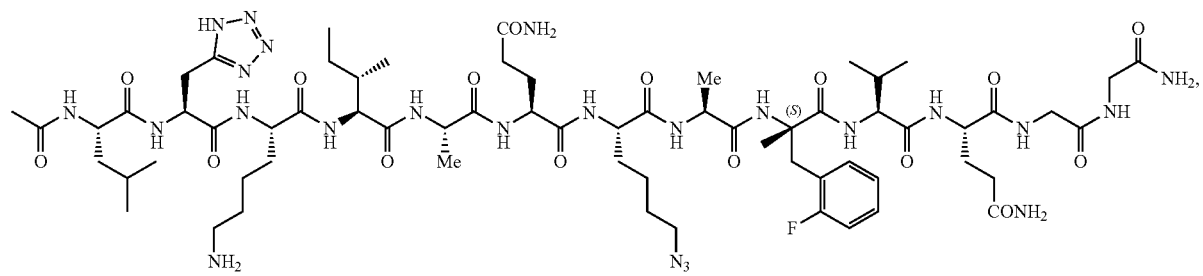
or a pharmaceutically acceptable salt thereof.
30. An antibody-drug conjugate comprising a glucagon-like peptide-1 receptor (GLP1R)-targeting antibody or an antigen-binding fragment thereof and a payload with the structure:
(SEQ ID NO: 124)
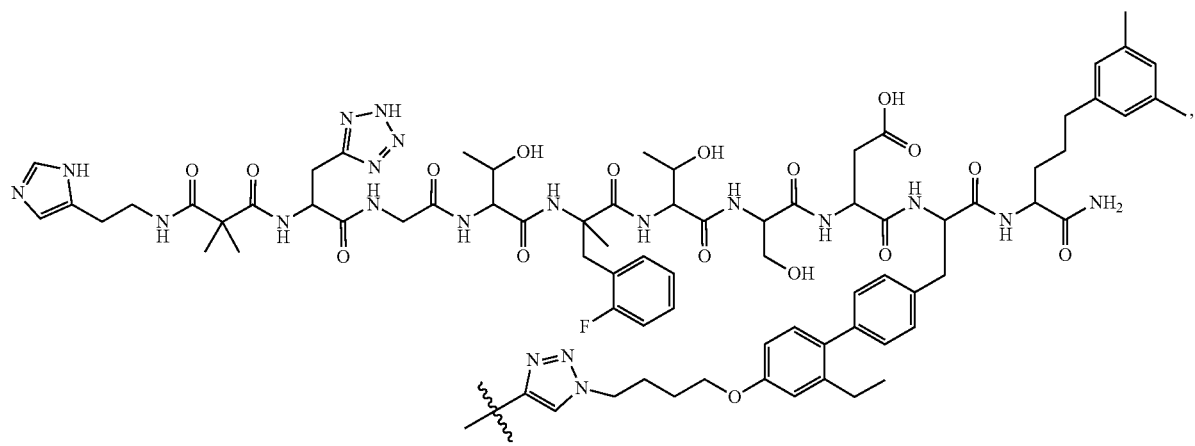

wherein

is the point of attachment of the payload to the antibody or the antigen-binding fragment thereof directly or through a linker.

31. The antibody-drug conjugate of claim 30, wherein the payload is:

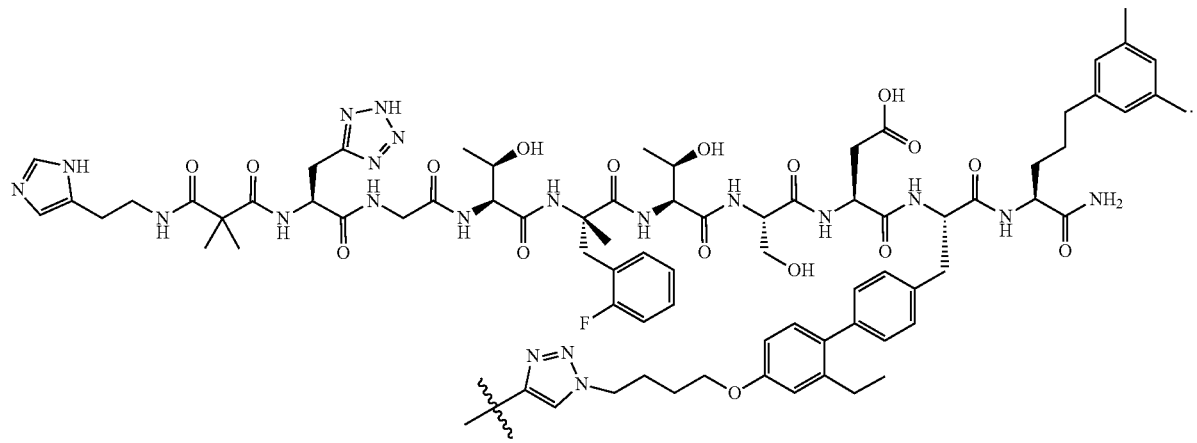

(SEQ ID NO: 90)

32. An antibody-drug conjugate comprising a glucagon-like peptide-1 receptor (GLP1R)-targeting antibody or an antigen-binding fragment thereof and a linker-payload with the structure:

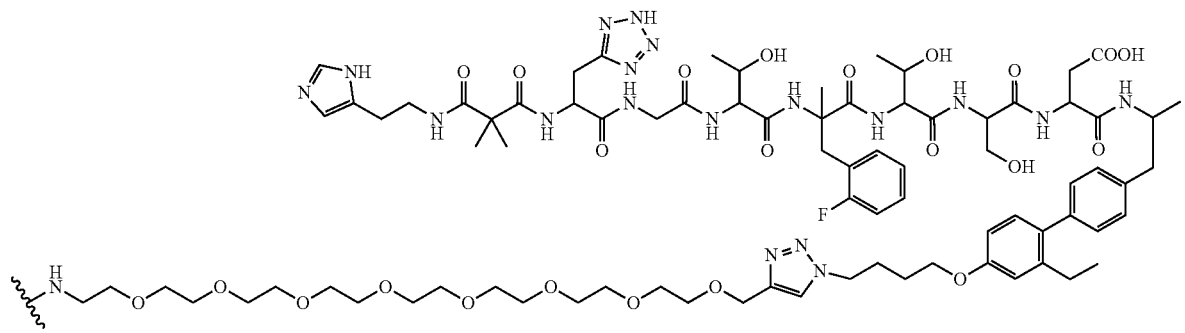

(SEQ ID NO: 125)

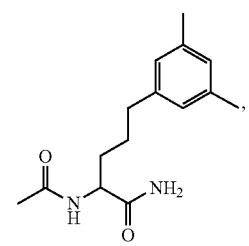

wherein
is the point of attachment of the linker-payload to the antibody or the antigen-binding fragment thereof.
33. The antibody-drug conjugate of claim 32, wherein the linker-payload has the is:
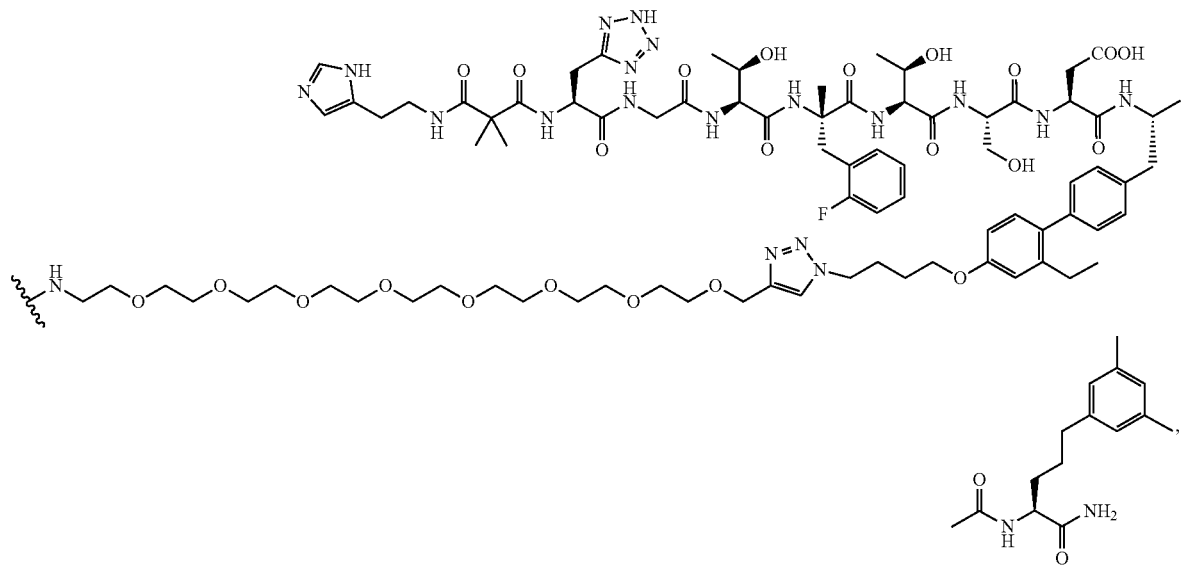
(SEQ ID NO: 126)

UNITED STATES PATENT AND TRADEMARK OFFICE
CERTIFICATE OF CORRECTION

| | | |
|---|---|---|
| PATENT NO. | : 12,280,124 B2 | Page 1 of 17 |
| APPLICATION NO. | : 17/475248 | |
| DATED | : April 22, 2025 | |
| INVENTOR(S) | : Han et al. | |

It is certified that error appears in the above-identified patent and that said Letters Patent is hereby corrected as shown below:

In the Claims

At Claim 1, Column 801, Line 61, please delete ":" after "a carbamate group" and insert --;-- in its place.

At Claim 1, Column 801, Line 63, please delete ":" after "chain" and insert --;-- in its place.

At Claim 1, Column 801, Line 63, please delete ":" after "triazole" and insert --;-- in its place.

At Claim 1, Column 803, please delete the following chemical formula:

"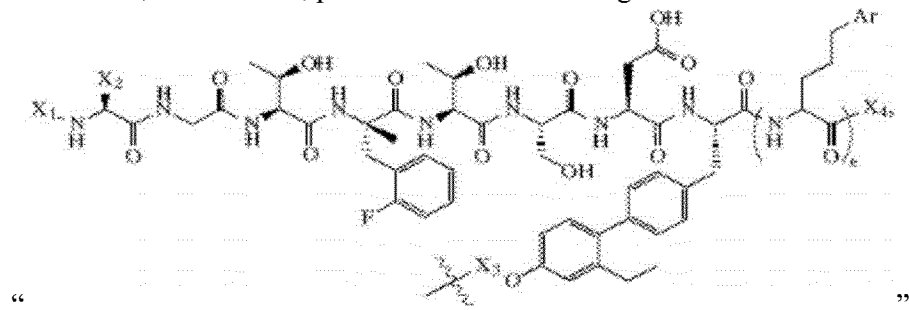"

And insert in its place the following chemical formula:

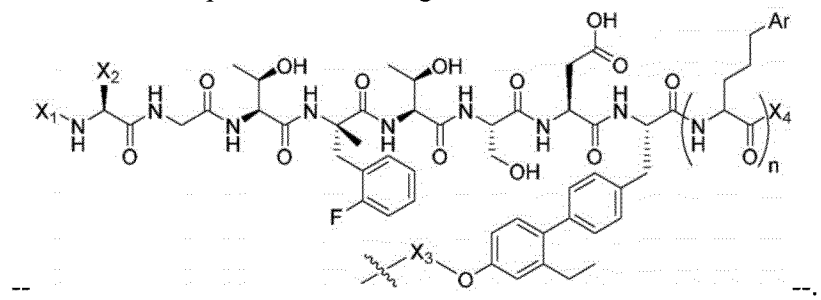

-- --.

Signed and Sealed this
Ninth Day of December, 2025

John A. Squires
*Director of the United States Patent and Trademark Office*

At Claim 1, Column 803-804, please delete the following chemical formula:

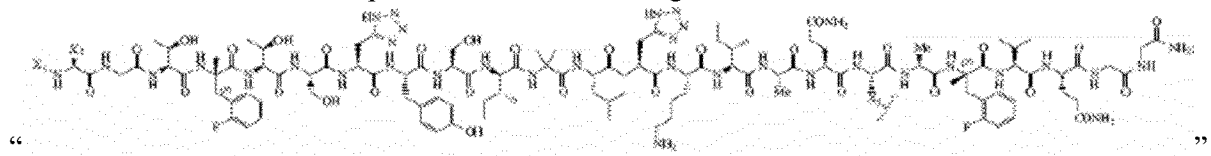
" "

And insert in its place the following chemical formula:

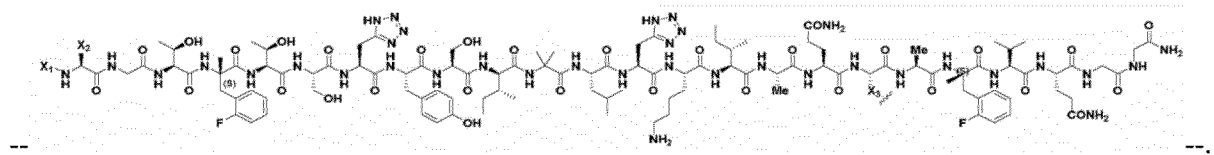
-- --.

At Claim 1, Column 805, Line 10, please insert --,-- after "H".

At Claim 1, Column 805, Line 59, please delete "—NH2" and insert -- —NH$_2$-- in its place.

At Claim 1, Column 806, Line 3, please insert --,-- after "H".

At Claim 1, Column 807, Line 1, please insert --,-- after "—NH$_2$".

At Claim 2, Column 807, Line 18, please delete "glucagon like" and insert --glucagon-like-- in its place.

At Claim 8, Column 808, Line 12, please delete "has-" before "comprises".

At Claim 21, Column 808, Line 65, please delete ":" after "chain" and insert --;-- in its place.

At Claim 21, Column 808, Line 65, please delete ":" after "triazole" and insert --;-- in its place.

At Claim 21, Column 809, Line 55, please insert --,-- after "H".

At Claim 21, Column 811, Line 12, please insert a space between "–(CH$_2$)$_{2-6}$–NH–" and "and".

At Claim 21, Column 811, Line 16, please insert --and-- after "—NH—OH,".

At Claim 21, Column 811, Line 26, please insert --,-- after "H".

At Claim 22, Column 812, Line 36, please delete ":" after "cyclodextrin" and insert --;-- in its place.

At Claim 22, Column 812, Line 38, please delete ":" after "chain" and insert --;-- in its place.

At Claim 22, Column 812, Line 38, please delete ":" after "triazole" and insert --;-- in its place.

At Claim 22, Column 821-822, please delete the first chemical formula:
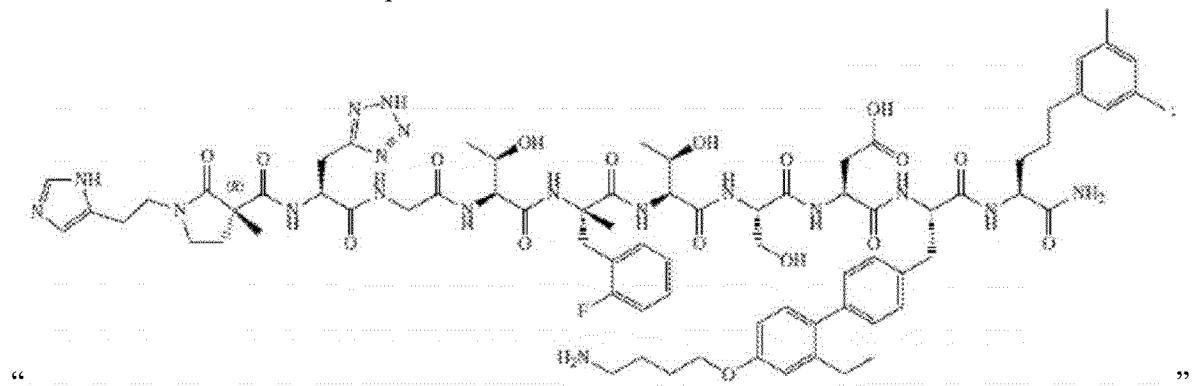
" "
And insert in its place the following chemical formula:
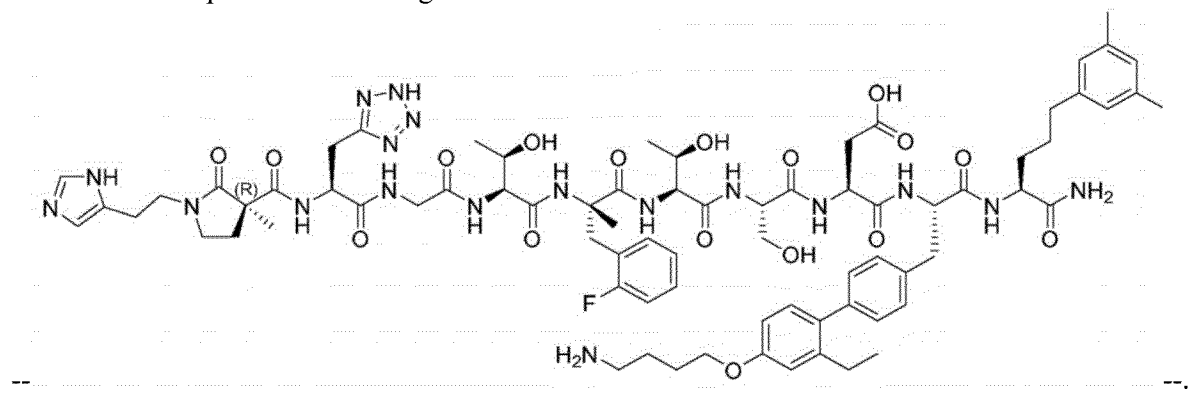
-- --.
At Claim 22, Column 829-830, please delete the last chemical formula:
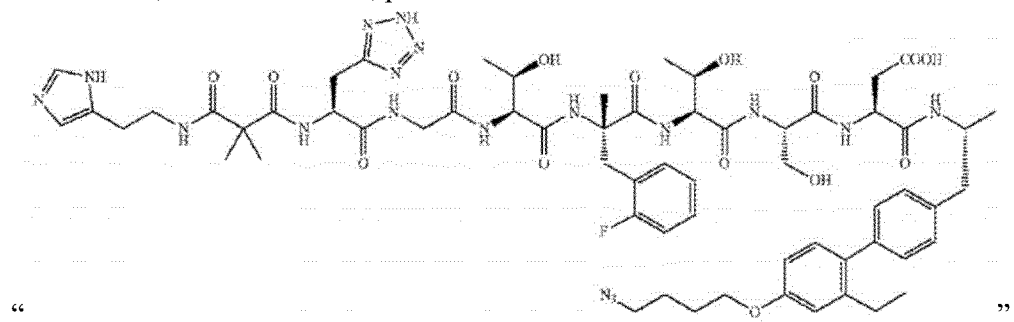
" "
And Column 831-832, please delete the first chemical formula:
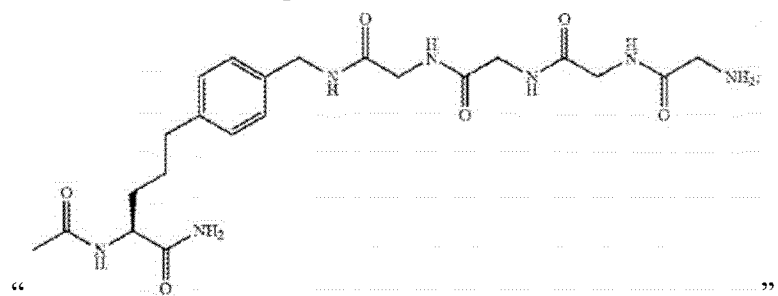
" "

CERTIFICATE OF CORRECTION (continued)
U.S. Pat. No. 12,280,124 B2

And insert in their place the following chemical formula:

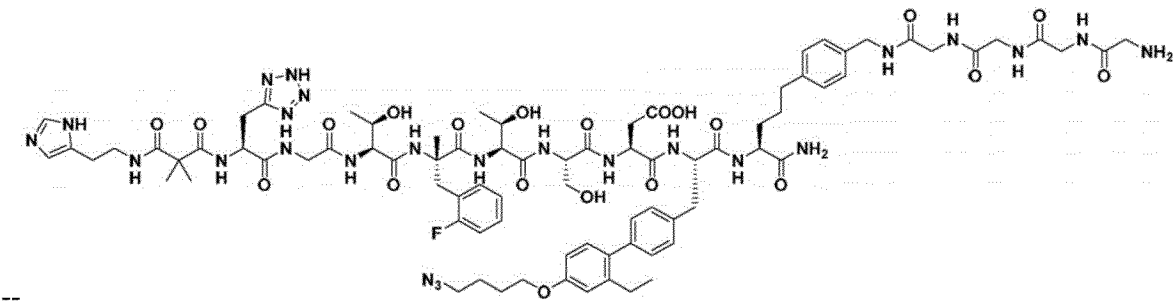

--                                                                                              --.

At Claim 22, Column 831-832, please delete the second and third chemical formulas:

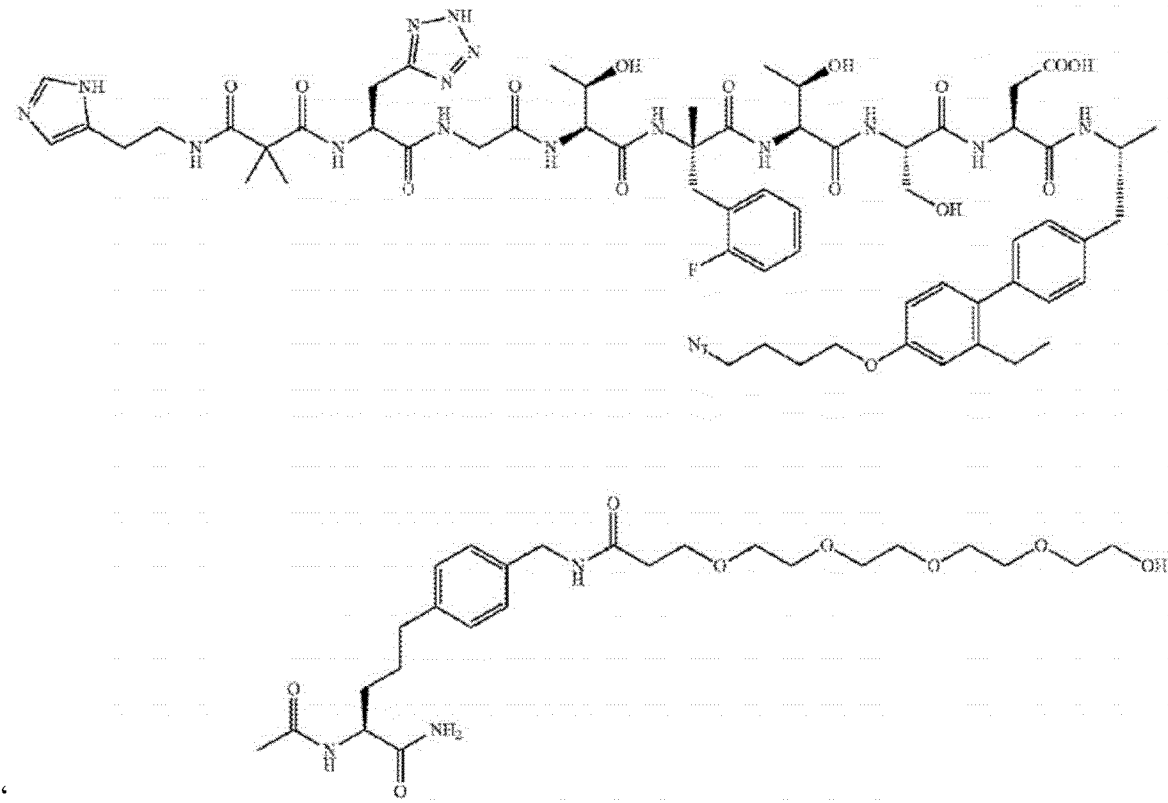

"                                                                                              "

And insert in their place the following chemical formula:

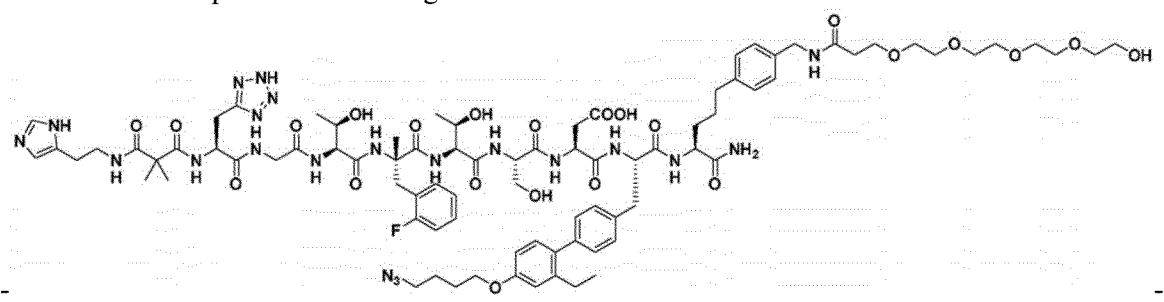

--                                                                                              --.

At Claim 22, Column 831-832, please delete the last chemical formula:
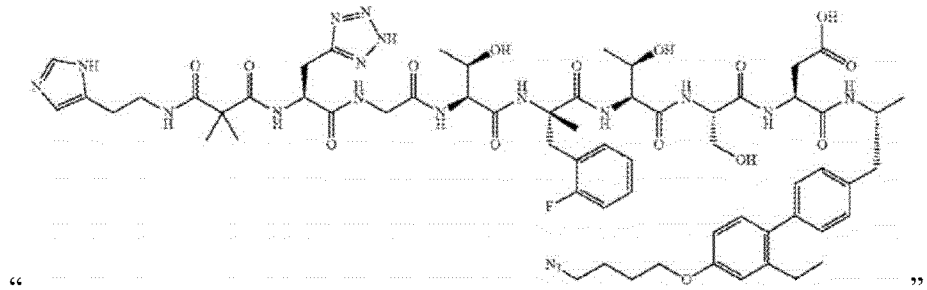
"  "
And Column 833-834, please delete the first chemical formula:
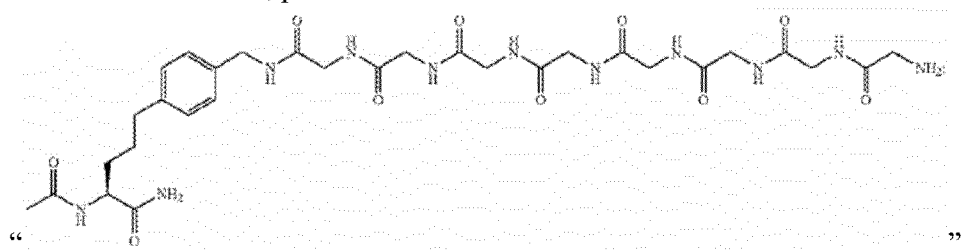
"  "
And insert in their place the following chemical formula:
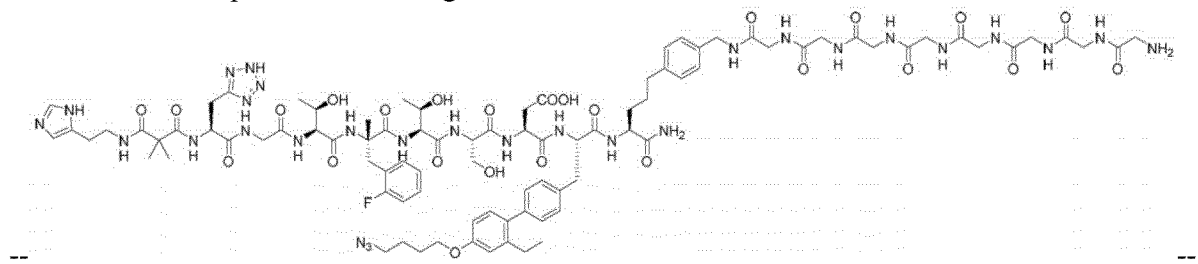
--                                                                              --.
At Claim 22, Column 833-834, please delete the second and third chemical formulas:
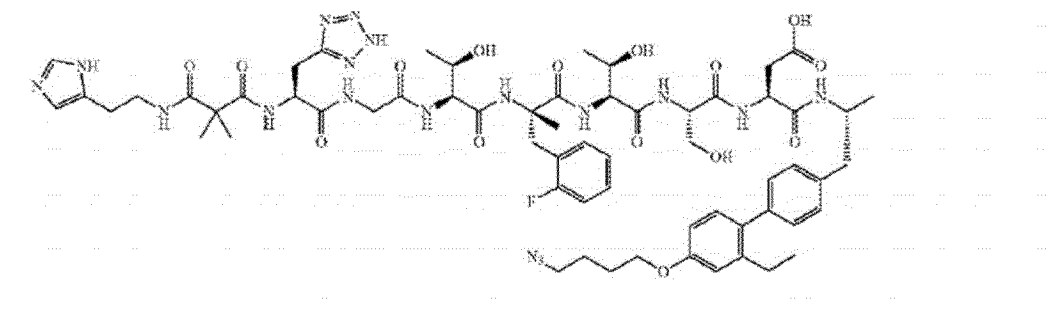
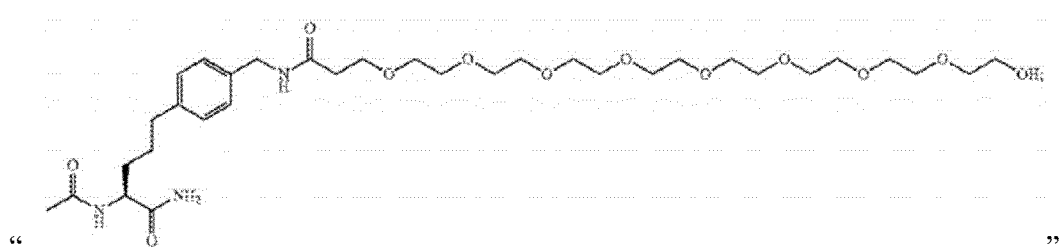
"  "
And insert in their place the following chemical formula:

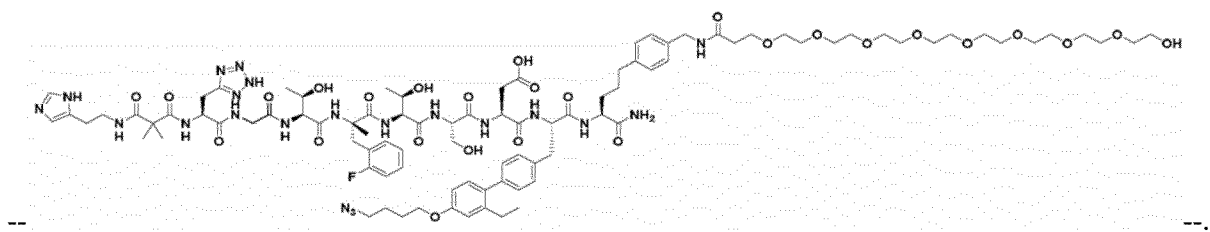
--                                                                     --.
At Claim 22, Column 835-836, please delete the third chemical formula:
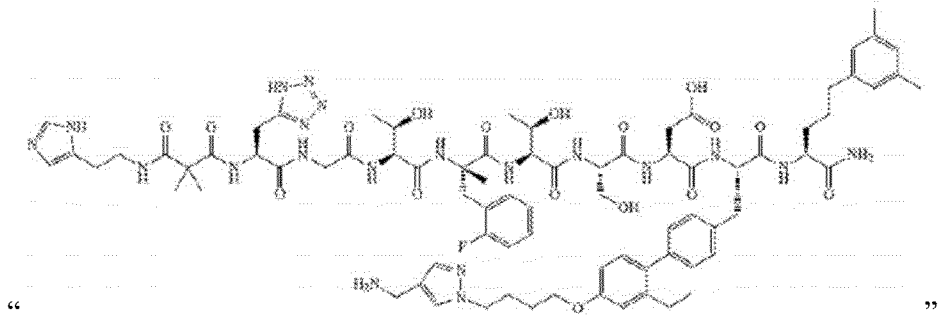
"                                                                     "
And insert in its place the following chemical formula:
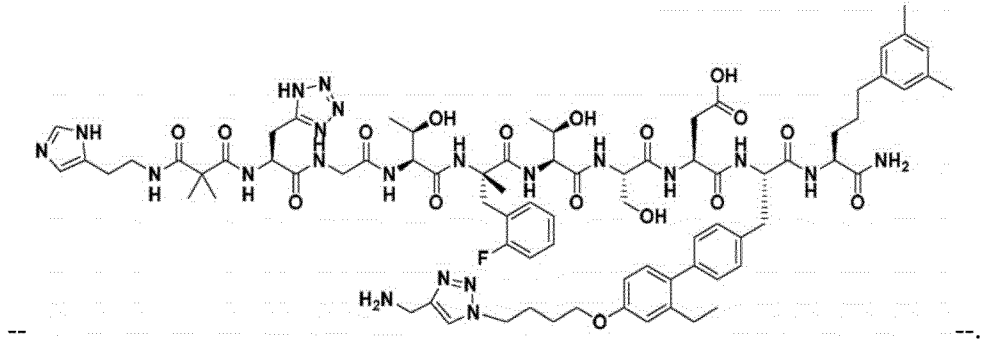
--                                                                     --.
At Claim 22, Column 837-838, please delete the first and second chemical formulas:
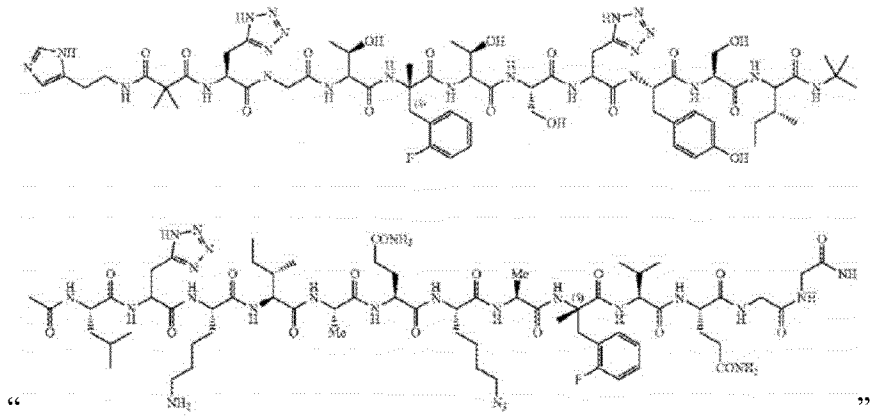
"                                                                     "
And insert in their place the following chemical formula:

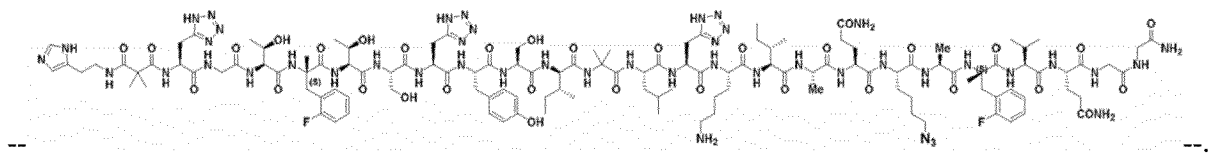
--.

At Claim 23, Column 839, Line 41, please insert --,-- after "H".

At Claim 23, Column 839-840, please delete the first, second, and third chemical formulas:

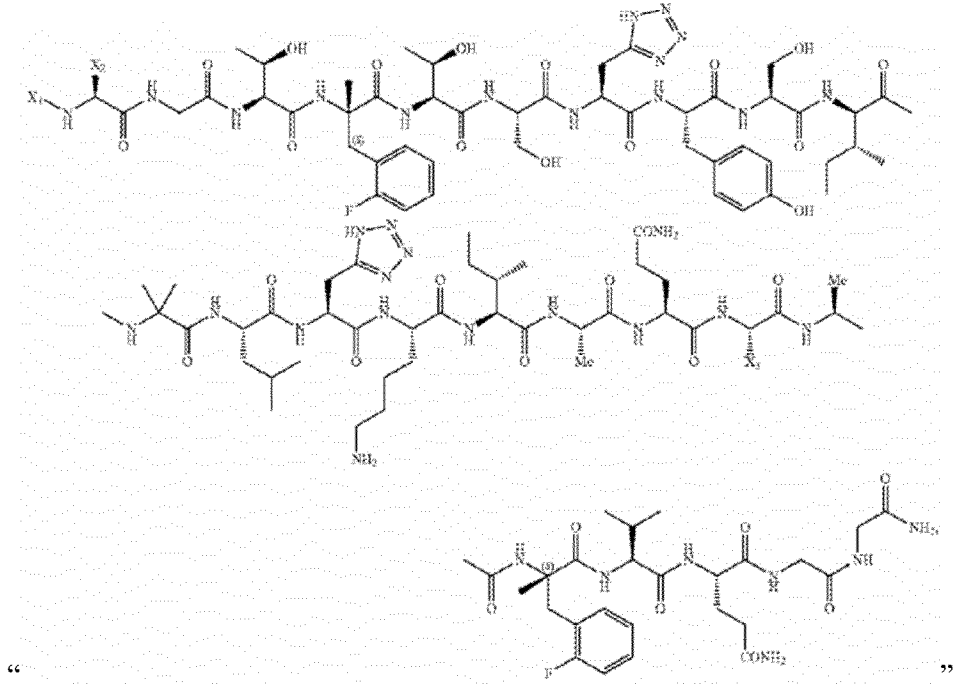
" "

And insert in their place the following chemical formula:

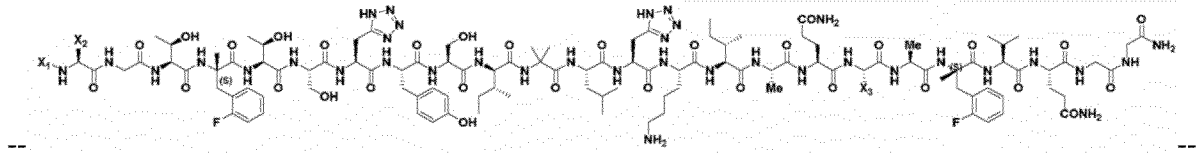
--.

At Claim 23, Column 840, Line 1, please delete "(P-IIIB (SEQ ID NO: 84))" and insert --(P-IIIB (SEQ ID NO: 29))-- in its place.

At Claim 24, Column 843, Line 2, please insert --,-- after "H".

At Claim 24, Column 843, Line 65, please delete "–(CH$_2$)$_{2-6}$–NH-$_2$" and insert -- –(CH$_2$)$_{2-6}$–NH$_2$-- in its place.

At Claim 25, Column 853-854, please delete the second chemical formula:

CERTIFICATE OF CORRECTION (continued)
U.S. Pat. No. 12,280,124 B2

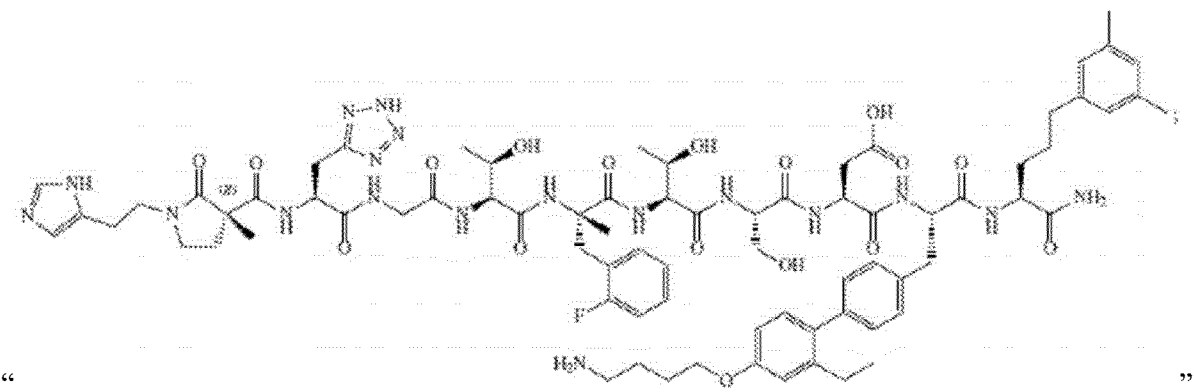

"

And insert in its place the following chemical formula:

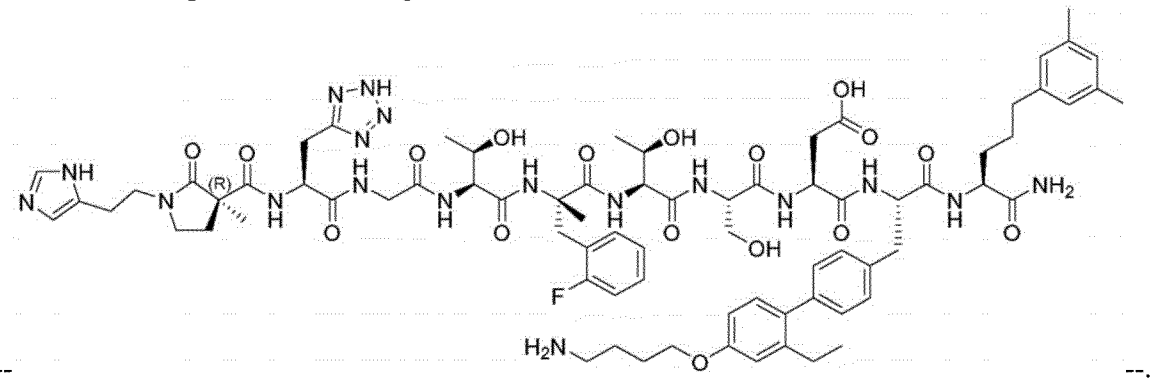

--                                                                                                    --.

At Claim 26, Column 874, Line 23, please insert --,-- after "H".

At Claim 26, Column 876, Line 32, please insert --,-- after "—NH₂".

At Claim 27, Column 877, Line 54, please insert --,-- after "H".

At Claim 28, Column 881-882, please delete the third chemical formula:

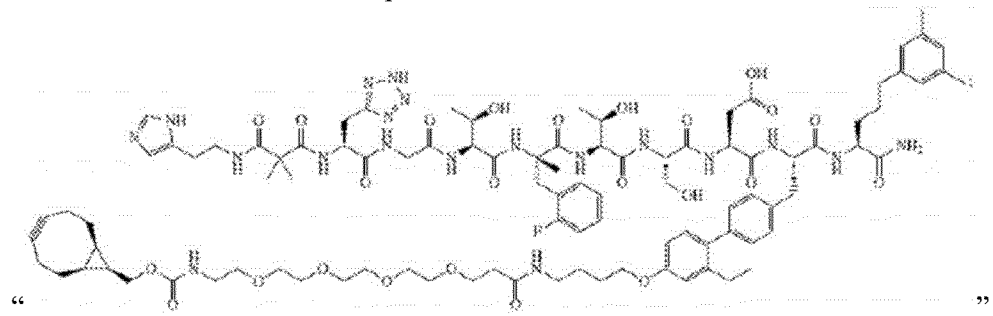

"

And insert in its place the following chemical formula:

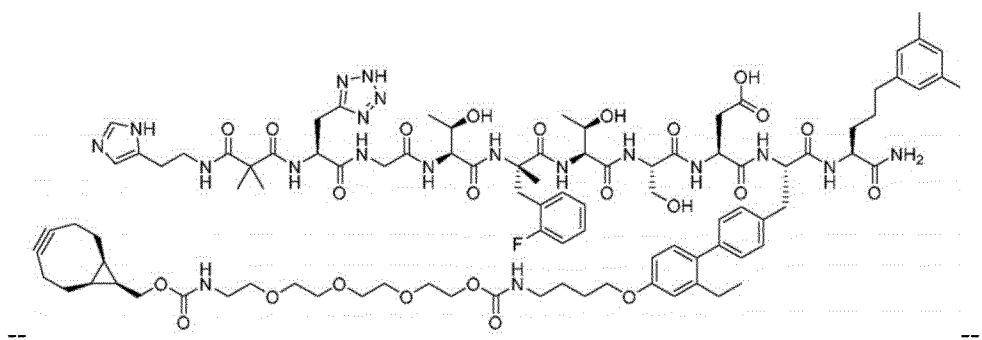
--  --.
At Claim 28, Column 885-886, please delete the third chemical formula:
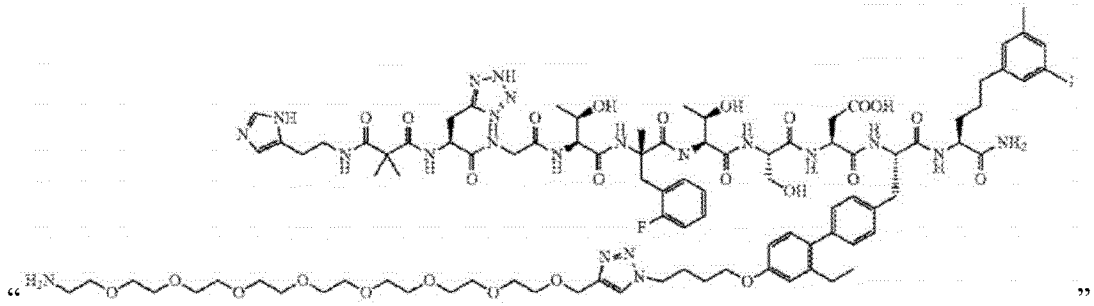
And insert in its place the following chemical formula:
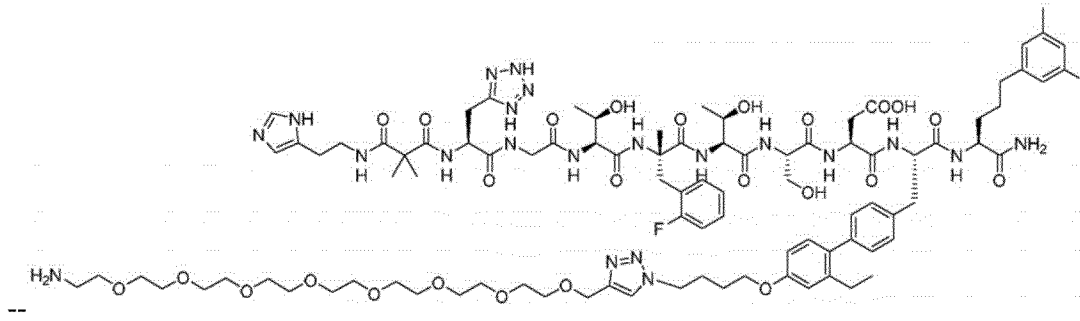
--  --.
At Claim 28, Column 889-890, please delete the third and fourth chemical formulas:
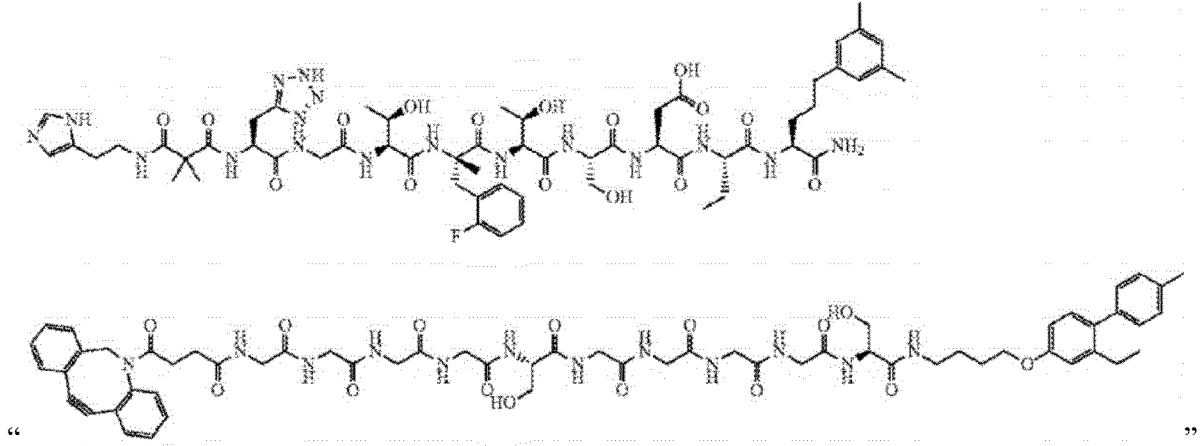
And insert in their place the following chemical formula:

CERTIFICATE OF CORRECTION (continued)
U.S. Pat. No. 12,280,124 B2

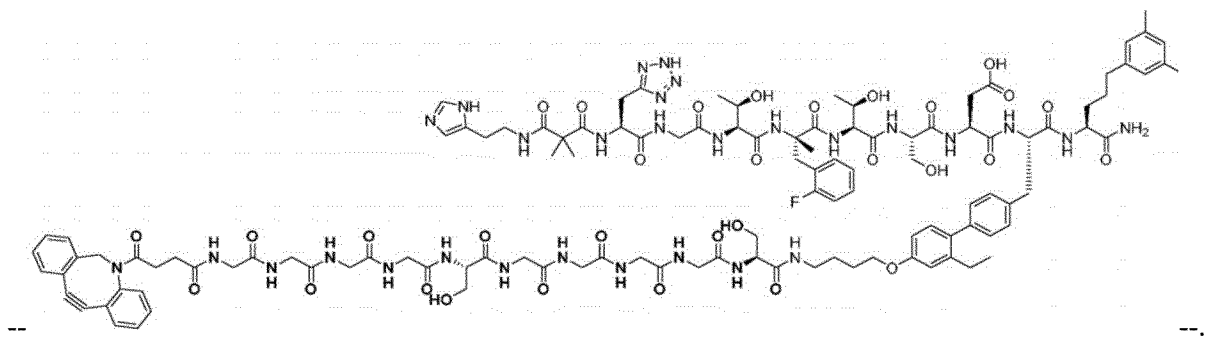

--.

At Claim 28, Column 911-912, please delete the second chemical formula:

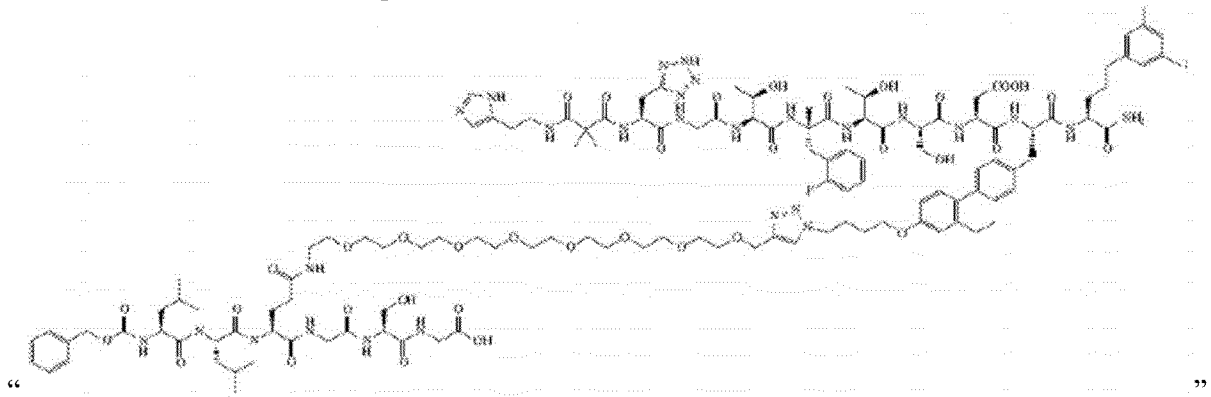

"                                                                                                                                    "

And insert in its place the following chemical formula:

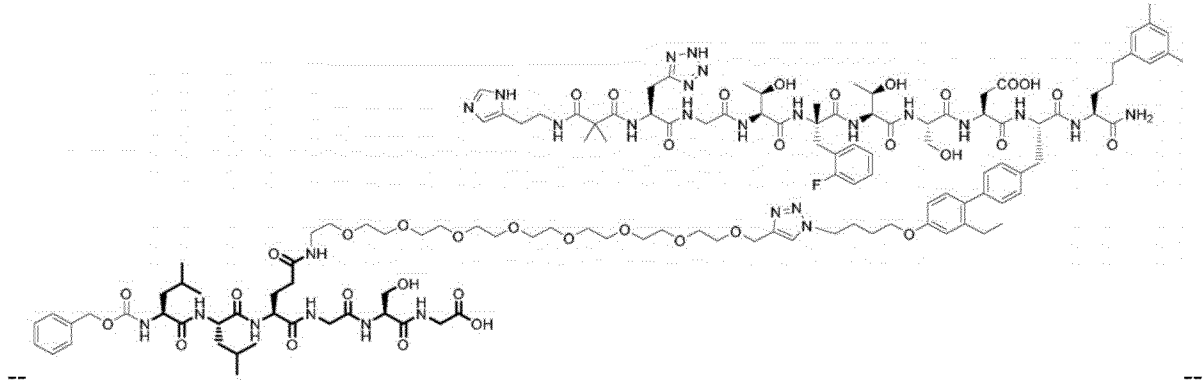

--                                                                                                                                    --.

At Claim 28, Column 923-924, please delete the following chemical formulas:

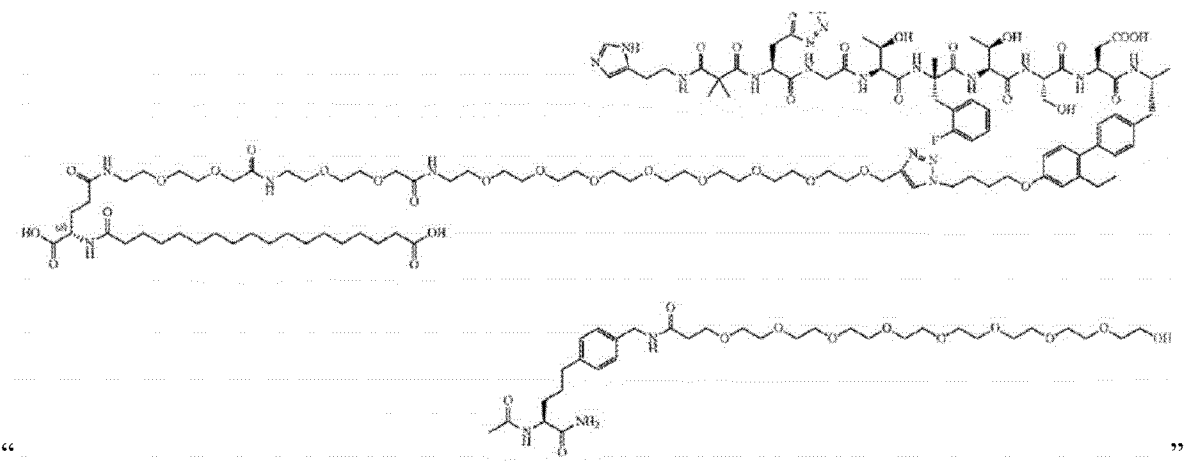
"
And insert in their place the following chemical formula:
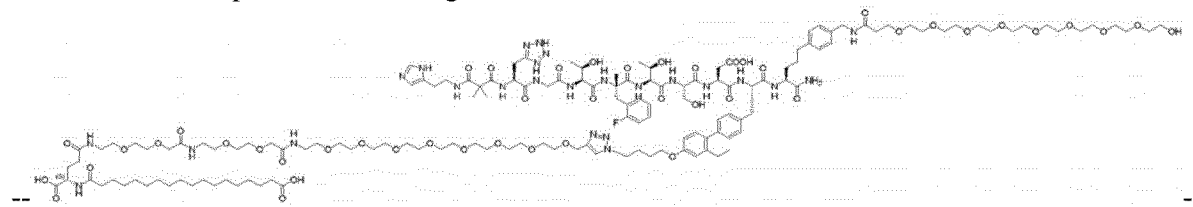
--.
At Claim 29, Column 931-932, please delete the fourth chemical formula:
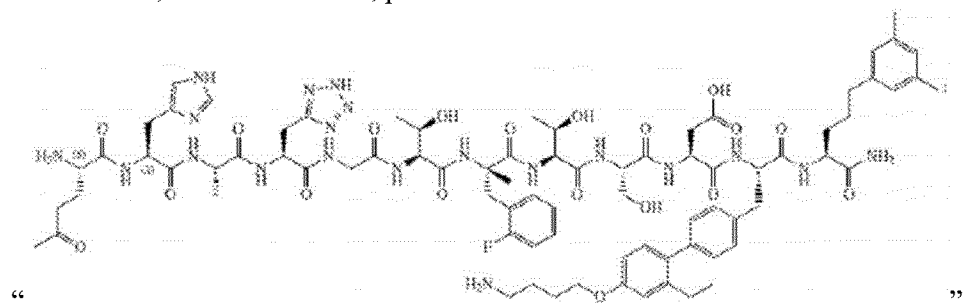
"
And insert in its place the following chemical formula:
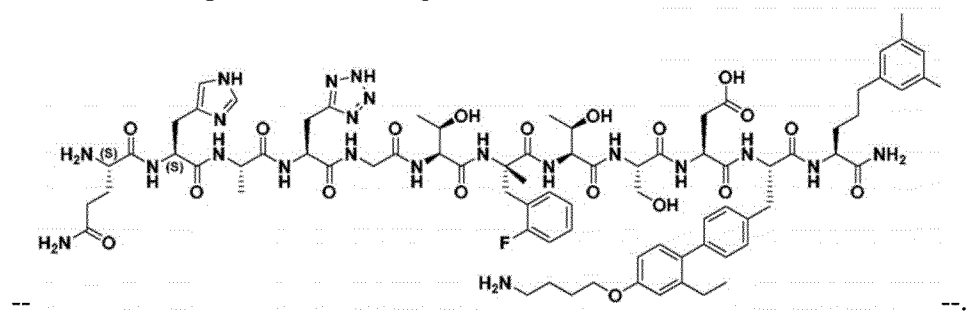
--.
At Claim 29, Column 939-940, please delete the second chemical formula:

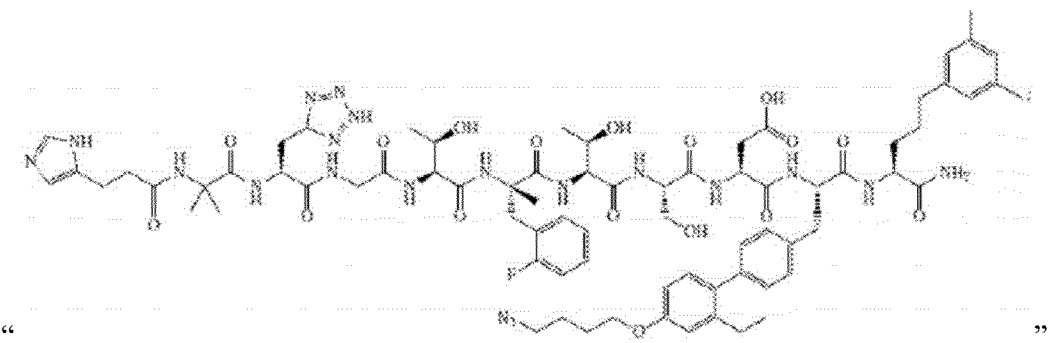
"
And insert in its place the following chemical formula:
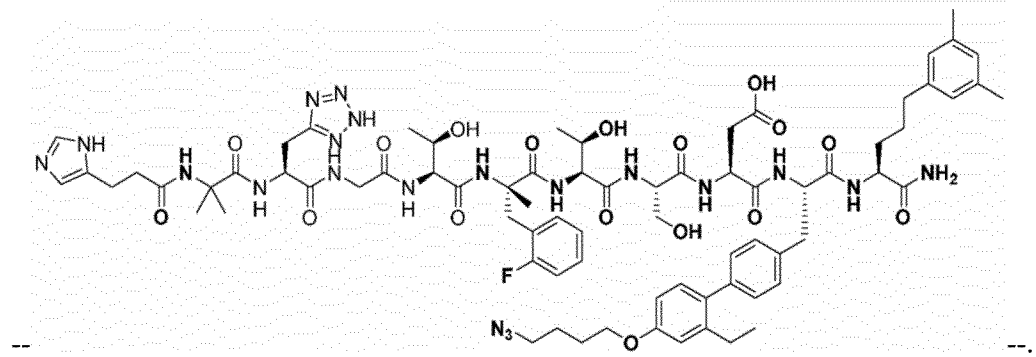
--  --.
At Claim 29, Column 943-944, please delete the first and second chemical formulas:
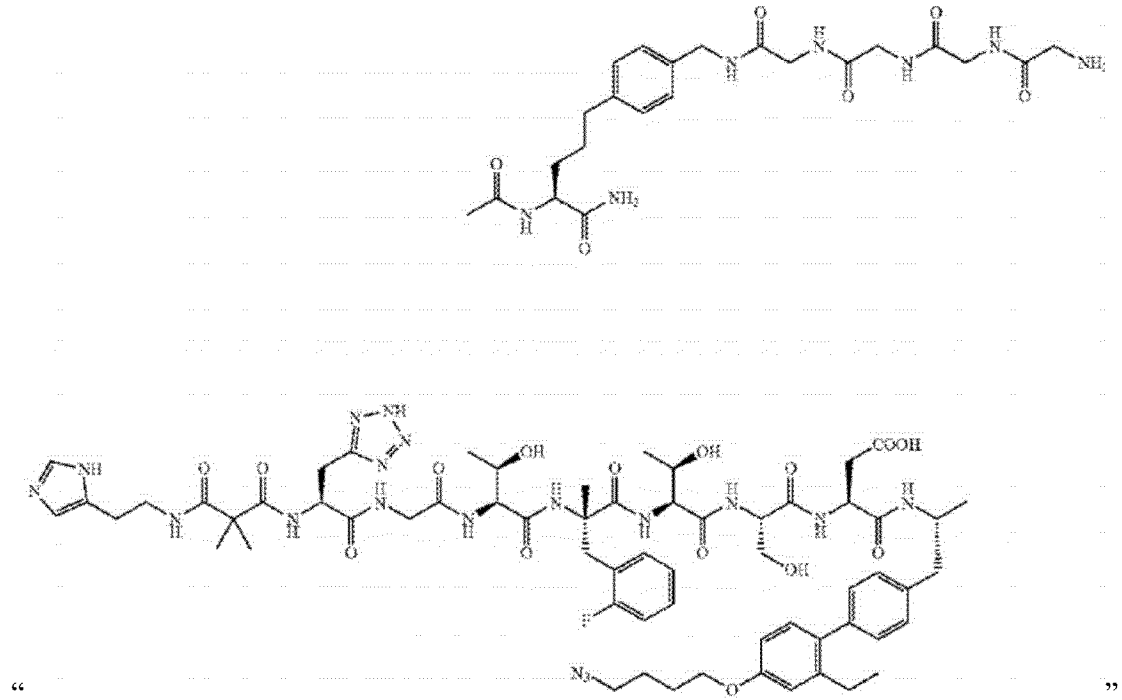
"
And insert in their place the following chemical formula:

CERTIFICATE OF CORRECTION (continued)
U.S. Pat. No. 12,280,124 B2

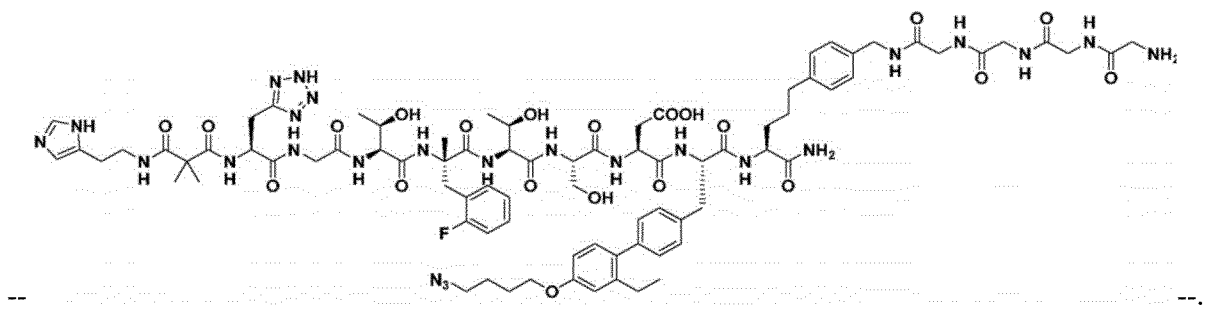

--.

At Claim 29, Column 943-944, please delete the third and fourth chemical formulas:

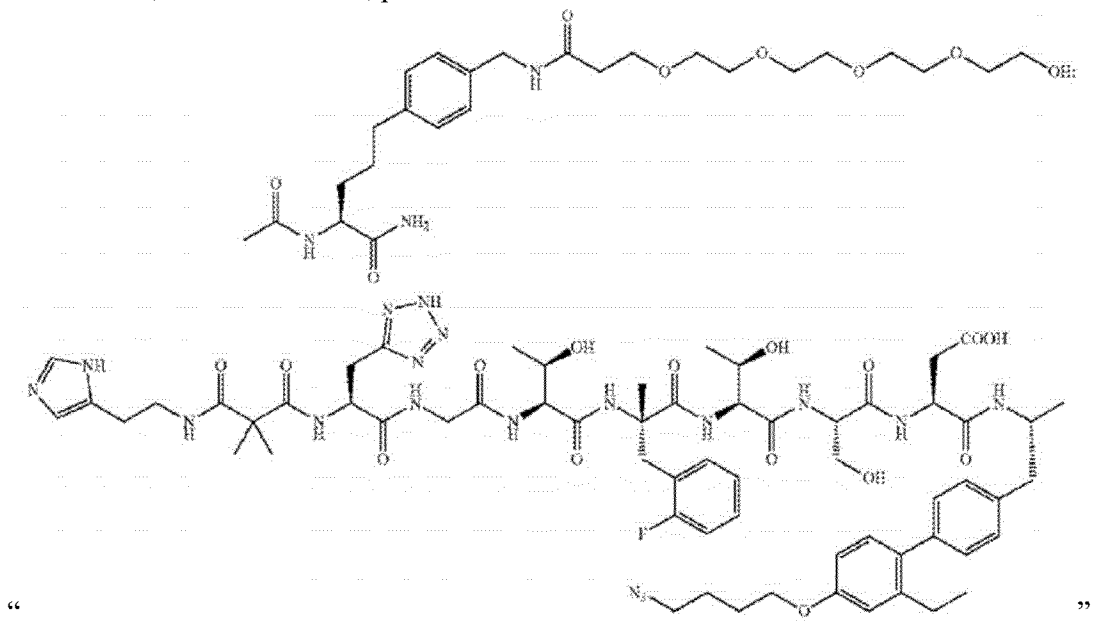

"

"

And insert in their place the following chemical formula:

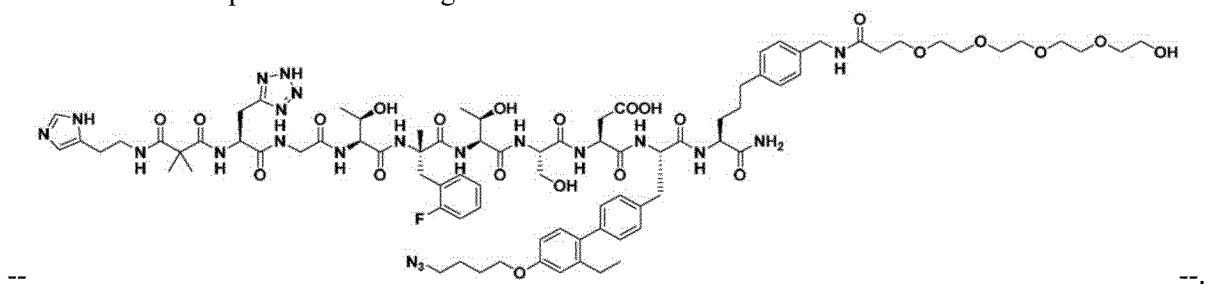

-- --.

At Claim 29, Column 945-946, please delete the first and second chemical formulas:

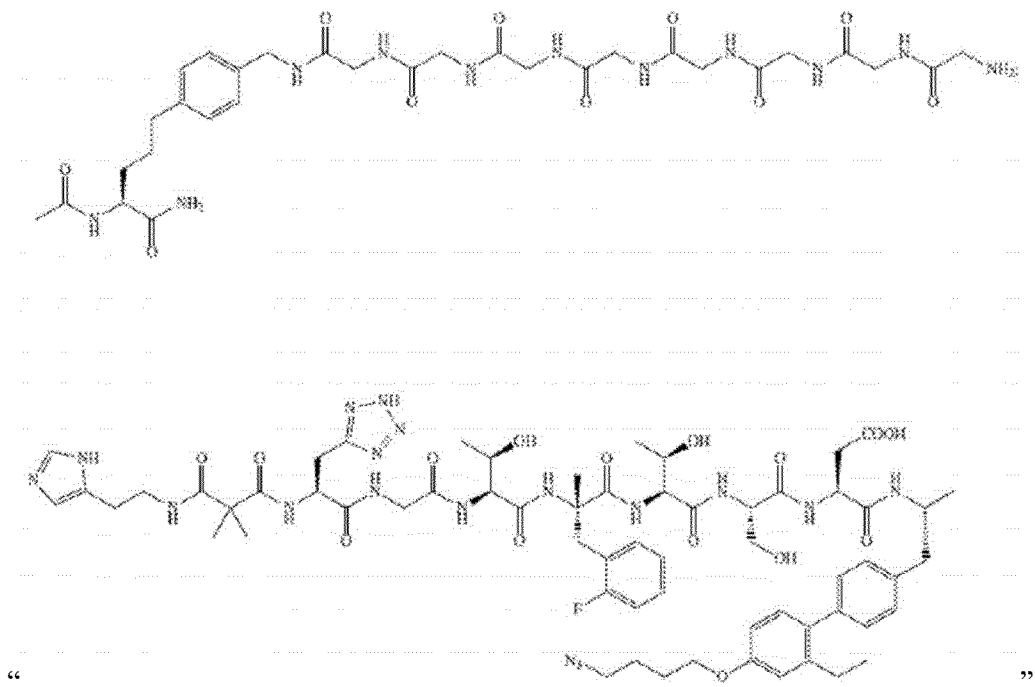
And insert in their place the following chemical formula:
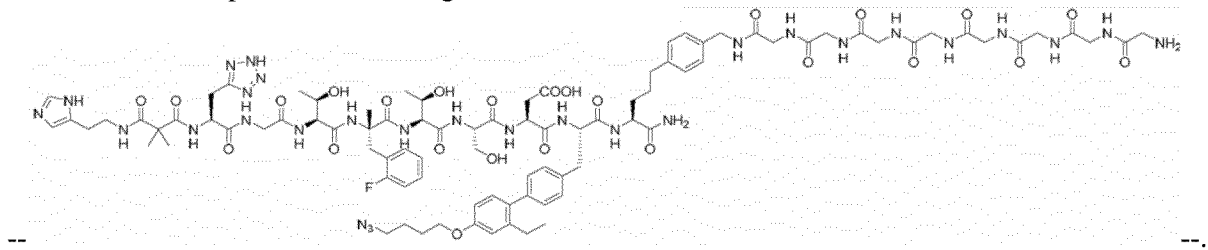
At Claim 29, Column 945-946, please delete the third and fourth chemical formulas:

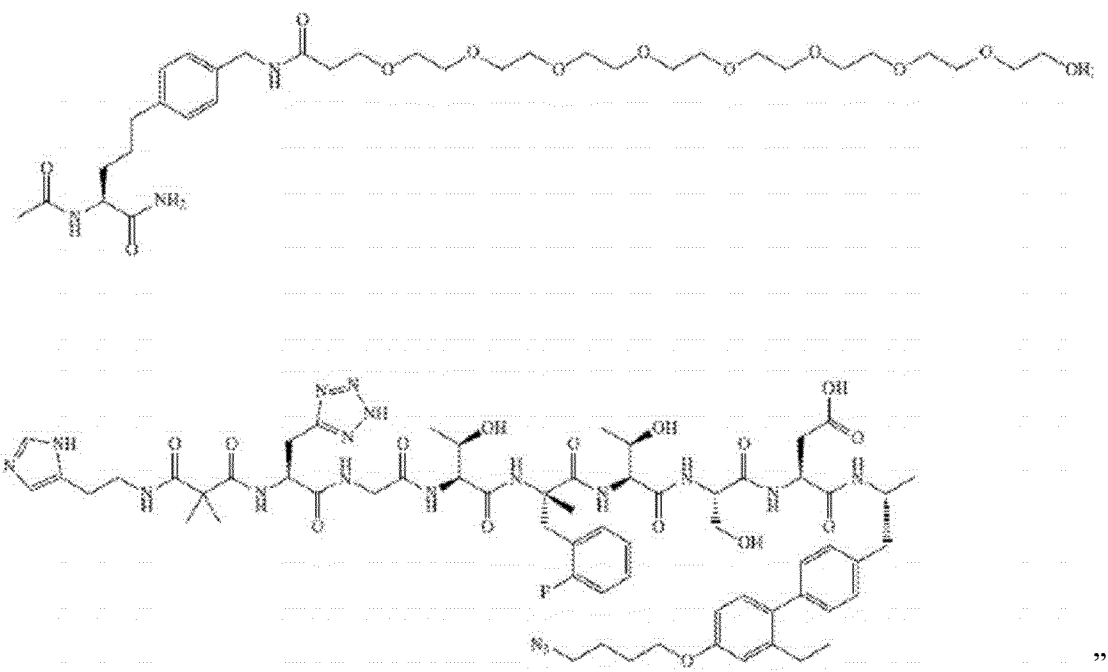
"
And insert in their place the following chemical formula:
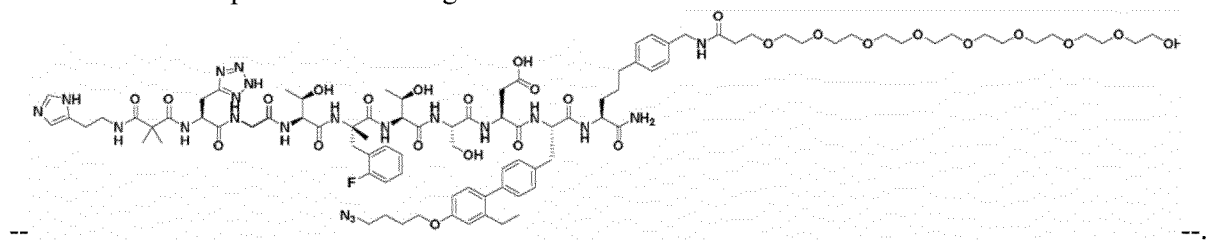
--.
At Claim 29, Column 949-950, please delete the second and third chemical formulas:
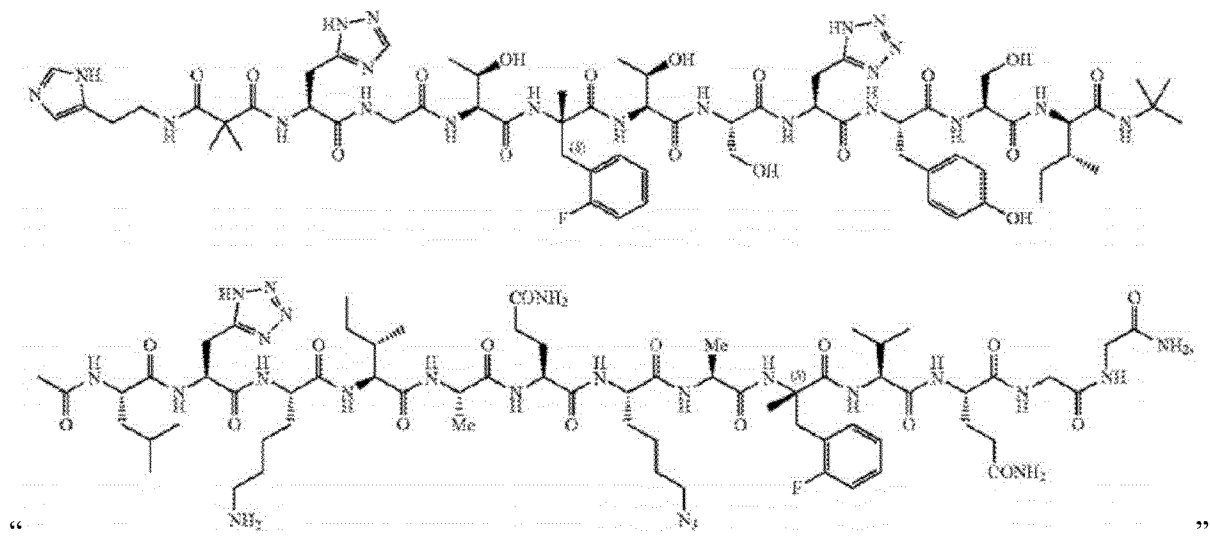
"
And insert in their place the following chemical formula:

CERTIFICATE OF CORRECTION (continued)

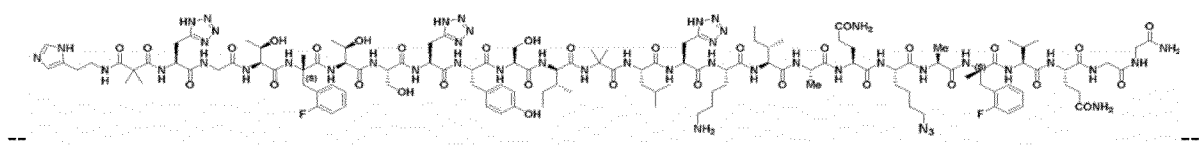
--.

At Claim 32, Column 951-952, please delete the second and third chemical formulas:

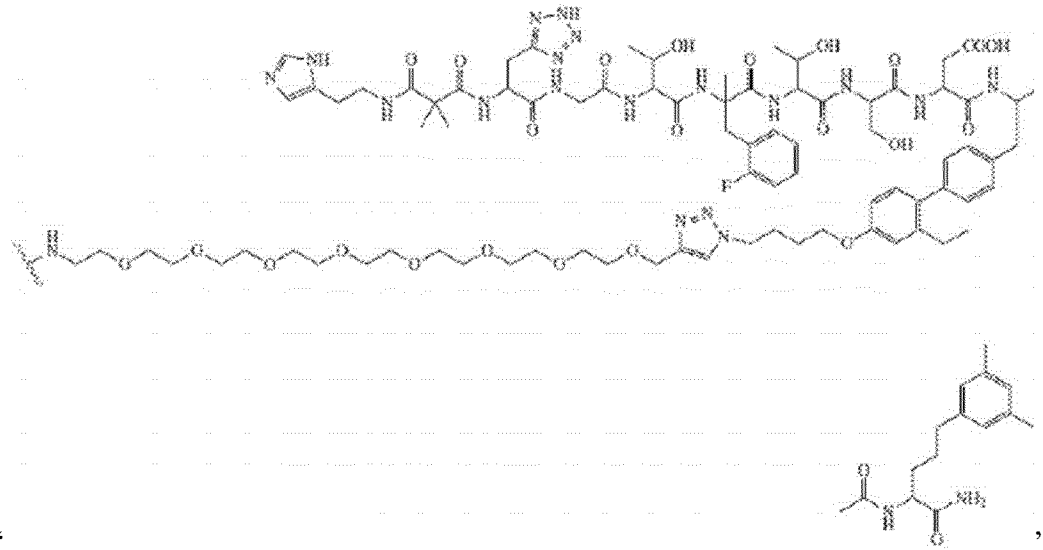
" "

And insert in their place the following chemical formula:

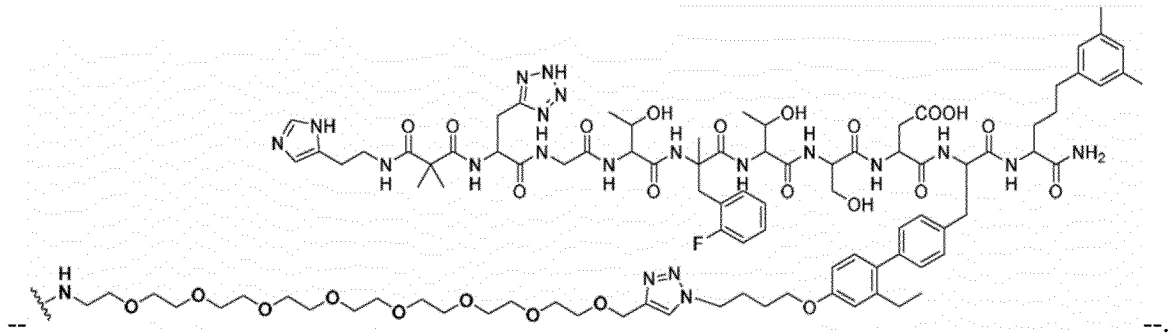
--.

At Claim 33, Column 953-954, please delete the first and second chemical formulas:

CERTIFICATE OF CORRECTION (continued)
U.S. Pat. No. 12,280,124 B2

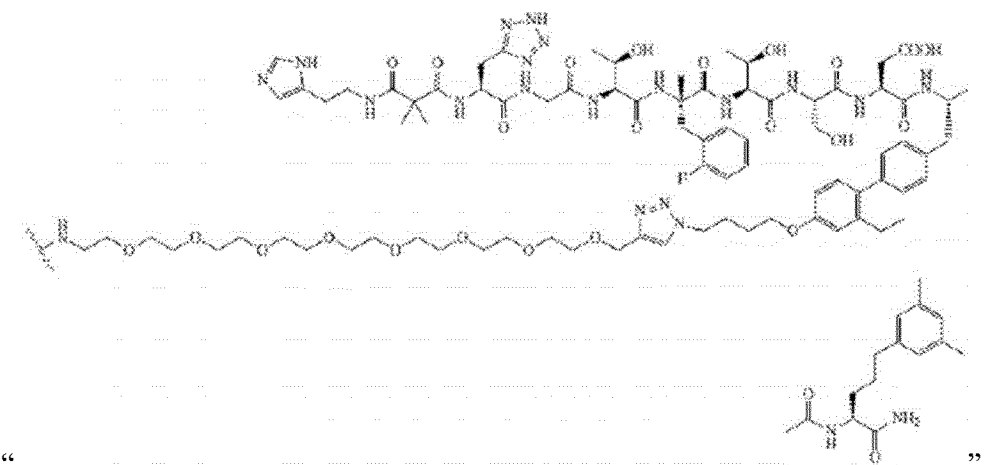

"                                                                                               "

And insert in their place the following chemical formula:

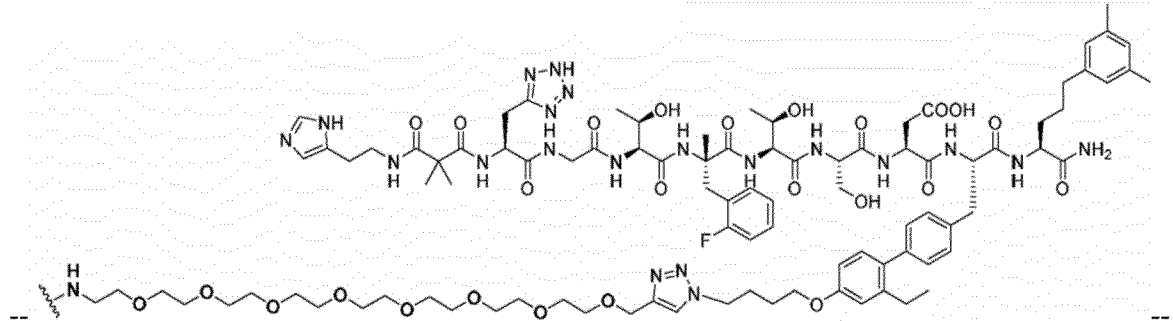

--                                                                                              --.

```
                         SEQUENCE LISTING

<160> NUMBER OF SEQ ID NOS: 190

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Ser Gly Gly Gly Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser
1               5                   10

<210> SEQ ID NO 4
<211> LENGTH: 30
<212> TYPE: PRT
<213> ORGANISM: Homo sapiens
<220> FEATURE:
<223> OTHER INFORMATION: C-term NH2

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-aminoisobutyric acid
<220> FEATURE:
<221> NAME/KEY: MOD_RES
<222> LOCATION: (2)..(2)
<223> OTHER INFORMATION: C-linked tetrazolyl-Ala
<220> FEATURE:
<221> NAME/KEY: MOD_RES
<222> LOCATION: (5)..(5)
<223> OTHER INFORMATION: Alpha-methyl-o-fluoro-Phe

<400> SEQUENCE: 5

Xaa Xaa Gly Thr Phe Thr Ser Asp
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Leu Gln Gly Gly
1               5

<210> SEQ ID NO 7
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Leu Leu Gln Gly
1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Leu Ser Gln Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Leu Leu Gln Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Leu Gln Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Pro Leu Ala Gln Ser His Gly Gly
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Leu Leu Gln Gly Gly Gly
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Leu Gln Gly Gly
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Leu Gln
1

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Leu Gln Leu Leu Gln Gly Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Leu Gln Gly Ala
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Gln Tyr Gln Gly Ala
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Leu Leu Gln Gly Ser Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Gln Tyr Gln Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Leu Gln Leu Leu Gln Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Leu Leu Gln Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Leu Gln Leu Gln
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Leu Gln Leu Leu Gln
1               5

<210> SEQ ID NO 24
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 24

Leu Leu Gln Gly Arg
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Gly Gly Ser Gly Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Gly
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (9)..(9)
<223> OTHER INFORMATION: (S)-2-amino-5-(3,5-dimethylphenyl)pentanoic
      acid, or optionally substituted (S)-2-amino-5-phenylpentanoic acid

<400> SEQUENCE: 27

Xaa Gly Thr Xaa Thr Ser Asp Xaa Xaa
1               5

<210> SEQ ID NO 28
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (9)..(9)
<223> OTHER INFORMATION: (S)-2-amino-5-phenylpentanoic acid linker

<400> SEQUENCE: 28

Xaa Gly Thr Xaa Thr Ser Asp Xaa Xaa
1               5

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (7)..(7)
<223> OTHER INFORMATION: (S)-2-amino-3-(1H-tetrazol-5-yl)propanoic acid
<220> FEATURE:
<221> NAME/KEY: MOD_RES
<222> LOCATION: (11)..(11)
<223> OTHER INFORMATION: 2-amino-2-methylpropanoic acid
<220> FEATURE:
<221> NAME/KEY: MOD_RES
<222> LOCATION: (13)..(13)
<223> OTHER INFORMATION: (S)-2-amino-3-(1H-tetrazol-5-yl)propanoic acid
<220> FEATURE:
<221> NAME/KEY: MOD_RES
<222> LOCATION: (18)..(18)
<223> OTHER INFORMATION: 2-amino-2-lambda-3-ethanoic acid
<220> FEATURE:
<221> NAME/KEY: MOD_RES
<222> LOCATION: (20)..(20)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (24)..(24)
<223> OTHER INFORMATION: 2-aminoacetamide

<400> SEQUENCE: 29

Xaa Gly Thr Xaa Thr Ser Xaa Tyr Ser Ile Xaa Leu Xaa Lys Ile Ala
1               5                   10                  15

Gln Xaa Ala Xaa Val Gln Gly Xaa
            20
```

```
<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (9)..(9)
<223> OTHER INFORMATION: (S)-2-amino-5-(3,5-dimethylphenyl)pentanoic
      acid

<400> SEQUENCE: 30

Xaa Gly Thr Xaa Thr Ser Asp Xaa Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 9H-1-lambda-2,8-lambda-2-
      dibenzo[b,f][1,2,3]triazolo[4,5-d]azocine oxopentanoic acid

<400> SEQUENCE: 31

Xaa Gly Gly Gly Gly Ser
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 9H-1-lambda-2,8-lambda-2-
      dibenzo[b,f][1,2,3]triazolo[4,5-d]azocine oxopentanoic acid

<400> SEQUENCE: 32

Xaa Ser Gly Gly Gly Gly
1               5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 9H-1-lambda-2,8-lambda-2-
      dibenzo[b,f][1,2,3]triazolo[4,5-d]azocine oxopentanoic acid

<400> SEQUENCE: 33

Xaa Gly Gly Gly Gly Ser Gly Gly Gly Gly Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (((5aR,6S,6aS)-5,5a,6,6a,7,8-hexahydro-4H-1-
      lambda-2-cyclopropa[5,6]cycloocta[1,2-d][1,2,3]triazol-6-
      yl)methoxy)-lambda-3-methanone
<220> FEATURE:
<221> NAME/KEY: MOD_RES
<222> LOCATION: (3)..(3)
<223> OTHER INFORMATION: glucosyl serine

<400> SEQUENCE: 34

Xaa Gly Ser Gly Gly Gly Gly
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-((4,5,6,7,8,9-hexahydro-1-lambda-2-
      cycloocta[d][1,2,3]triazol-4-yl)oxy)-1-lambda-3-ethan-1-one

<400> SEQUENCE: 35

Xaa Gly Gly Gly Gly Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 9H-1-lambda-2,8-lambda-2-
      dibenzo[b,f][1,2,3]triazolo[4,5-d]azocine oxopentanoic acid
<220> FEATURE:
<221> NAME/KEY: MOD_RES
<222> LOCATION: (2)..(2)
<223> OTHER INFORMATION: glucosyl serine

<400> SEQUENCE: 36

Xaa Ser Gly Gly Gly Gly
1               5

<210> SEQ ID NO 37
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Ser Glu Pro Leu
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl hydrogen carbonate Leucine

<400> SEQUENCE: 38

Leu Leu Gln Gly Ser Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-(2-(2-aminoethoxy)ethoxy)acetic acid
<220> FEATURE:
<221> NAME/KEY: MOD_RES
<222> LOCATION: (3)..(3)
<223> OTHER INFORMATION: 2-(2-(2-aminoethoxy)ethoxy)acetic acid

<400> SEQUENCE: 39

Glu Xaa Xaa Gly Gly Gly Gly Ser
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-(2-(2-aminoethoxy)ethoxy)acetic acid
<220> FEATURE:
<221> NAME/KEY: MOD_RES
<222> LOCATION: (3)..(3)
<223> OTHER INFORMATION: 2-(2-(2-aminoethoxy)ethoxy)acetic acid

<400> SEQUENCE: 40

Glu Xaa Xaa Gly Gly Gly Gly Ser Gly Gly Gly Gly
1               5                   10

<210> SEQ ID NO 41
<211> LENGTH: 9
<212> TYPE: PRT
<213> ORGANISM: Artificial Sequence
```

```
-continued

<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanamide

<400> SEQUENCE: 41

Xaa Gly Thr Xaa Thr Ser Asp Xaa Xaa
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanamide

<400> SEQUENCE: 42

Xaa Gly Thr Xaa Thr Ser Asp Xaa Xaa
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2,2-dimethylmalonic acid (S)-2-amino-3-(2H-
      tetrazol-5-yl)propanoic acid
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
```

```
<222> LOCATION: (8)..(8)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanamide

<400> SEQUENCE: 43

Xaa Gly Thr Xaa Thr Ser Asp Xaa Xaa
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-amino-2,2-dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 44

Xaa Xaa Gly Thr Xaa Thr Ser Asp Xaa Xaa
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(hydroxyamino)-2,2-dimethyl-3-oxopropanoic
      acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
```

<223> OTHER INFORMATION: (S)-2-amino-5-(3,5-dimethylphenyl)pentanamide

<400> SEQUENCE: 45

Xaa Xaa Gly Thr Xaa Thr Ser Asp Xaa Xaa
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-methyl-2-(1H-pyrazol-5-yl)propanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 46

Xaa Xaa Gly Thr Xaa Thr Ser Asp Xaa Xaa
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 47

Ser Xaa Gly Thr Xaa Thr Ser Asp Xaa Xaa
1               5                   10

<210> SEQ ID NO 48
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 48

Xaa Xaa Gly Thr Xaa Thr Ser Asp Xaa Xaa
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 49

Xaa Xaa Gly Thr Xaa Thr Ser Asp Xaa Xaa
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 50

His Ala Xaa Gly Thr Xaa Thr Ser Asp Xaa Xaa
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-5-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 51

Xaa Xaa Gly Thr Xaa Thr Ser Asp Xaa Xaa
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(1H-imidazol-4-yl)propanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
```

<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 52

Xaa Gly Xaa Gly Thr Xaa Thr Ser Asp Xaa Xaa
 1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-amino-3-(2H-tetrazol-5-yl)propanoic acid
<220> FEATURE:
<221> NAME/KEY: MOD_RES
<222> LOCATION: (7)..(7)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (11)..(11)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (12)..(12)
<223> OTHER INFORMATION: (S)-2-amino-5-(3,5-dimethylphenyl)pentanamide

<400> SEQUENCE: 53

Gln His Ala Xaa Gly Thr Xaa Thr Ser Asp Xaa Xaa
 1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-1-(2-(1H-imidazol-5-yl)ethyl)-3-methyl-2-
      oxopyrrolidine-3-carboxylic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)

<223> OTHER INFORMATION: (S)-2-amino-5-(3,5-dimethylphenyl)pentanamide

<400> SEQUENCE: 54

Xaa Xaa Gly Thr Xaa Thr Ser Asp Xaa Xaa
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-1-(2-(1H-imidazol-5-yl)ethyl)-3-methyl-2-
      oxopyrrolidine-3-carboxylic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 55

Xaa Xaa Gly Thr Xaa Thr Ser Asp Xaa Xaa
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-1-(2-(1H-imidazol-5-yl)ethyl)pyrrolidine-3-
      carboxylic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 56

Xaa Xaa Gly Thr Xaa Thr Ser Asp Xaa Xaa
1               5                   10

```
<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (R)-1-(2-(1H-imidazol-5-yl)ethyl)pyrrolidine-3-
      carboxylic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 57

Xaa Xaa Gly Thr Xaa Thr Ser Asp Xaa Xaa
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 58

Tyr Ala Xaa Gly Thr Xaa Thr Ser Asp Xaa Xaa
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: 3-amino-2,2-dimethyl-3-oxopropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 59

Tyr Xaa Xaa Gly Thr Xaa Thr Ser Asp Xaa Xaa
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanamide

<400> SEQUENCE: 60

Gln Gly Thr Xaa Thr Ser Asp Xaa Xaa
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
```

```
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 61

Xaa Gln Gly Thr Xaa Thr Ser Asp Xaa Xaa
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid

<400> SEQUENCE: 62

Xaa Xaa Gly Thr Xaa Thr Ser Asp Xaa
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanoic
      acid

<400> SEQUENCE: 63

Xaa Xaa Gly Thr Xaa Thr Ser Asp Xaa Xaa
1               5                   10
```

```
<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-(4-
      aminobutoxy)phenyl)pentanamide

<400> SEQUENCE: 64

Xaa Xaa Gly Thr Xaa Thr Ser Asp Xaa Xaa
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(1H-imidazol-5-yl)propanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 65

Xaa Xaa Xaa Gly Thr Xaa Thr Ser Asp Xaa Xaa
1               5                   10
```

```
<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(1H-imidazol-4-yl)butanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 66

Xaa Xaa Xaa Gly Thr Xaa Thr Ser Asp Xaa Xaa
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-(1H-imidazol-4-yl)pentanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 67

Xaa Xaa Xaa Gly Thr Xaa Thr Ser Asp Xaa Xaa
1               5                   10
```

```
<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 68

Xaa Xaa Xaa Gly Thr Xaa Thr Ser Asp Xaa Xaa
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 7-(1H-imidazol-4-yl)heptonic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide
```

```
<400> SEQUENCE: 69

Xaa Xaa Xaa Gly Thr Xaa Thr Ser Asp Xaa Xaa
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 9-(1H-imidazol-5-yl)nonanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 70

Xaa Xaa Xaa Gly Thr Xaa Thr Ser Asp Xaa Xaa
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-(1H-imidazol-4-yl)octanoic acid
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
```

<223> OTHER INFORMATION: (S)-2-amino-5-(3,5-dimethylphenyl)pentanamide

<400> SEQUENCE: 71

Xaa Xaa Xaa Gly Thr Xaa Thr Ser Asp Xaa Xaa
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-
      (aminomethyl)phenyl)pentanamide attached to GGGG via the side
      chain

<400> SEQUENCE: 72

Xaa Xaa Gly Thr Xaa Thr Ser Asp Xaa Xaa
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-N-(4-(4,5-diamino-5-oxopentyl)benzyl)-1-
      hydroxy-3,6,9,12-tetraoxapentadecan-15-amide

```
<400> SEQUENCE: 73

Xaa Xaa Gly Thr Xaa Thr Ser Asp Xaa Xaa
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-
      (aminomethyl)phenyl)pentanamide attached to GGGGGGGG via the side
      chain

<400> SEQUENCE: 74

Xaa Xaa Gly Thr Xaa Thr Ser Asp Xaa Xaa
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-(29-hydroxy-6,9,12,15,18,21,
      24,27-octaoxa-2-azanonacosyl)phenyl)pentanamide
```

```
<400> SEQUENCE: 75

Xaa Xaa Gly Thr Xaa Thr Ser Asp Xaa Xaa
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2,2-dimethyl-4-oxo-4-((2-(2-oxopiperidin-1-
      yl)ethyl)amino)butanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 76

Xaa Xaa Gly Thr Xaa Thr Ser Asp Xaa Xaa
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-((2-((2-(5-methyl-1,3-dioxoisoindolin-2-
      yl)ethyl)amino)-2-oxoethyl)thio)acetic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 77

Xaa Xaa Gly Thr Xaa Thr Ser Asp Xaa Xaa
1               5                   10
```

```
<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(2-oxopyrrolidin-1-yl)propanoic acid
<220> FEATURE:
<221> NAME/KEY: MOD_RES
<222> LOCATION: (2)..(2)
<223> OTHER INFORMATION: 3-aminopropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 78

Xaa Xaa Xaa Gly Thr Xaa Thr Ser Asp Xaa Xaa
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 79

Tyr Xaa Xaa Gly Thr Xaa Thr Ser Asp Tyr Xaa
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(1H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(aminomethyl)-1H-1,2,3-
      triazol-1-yl)butoxy)-2'-ethyl-[1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 80

Xaa Xaa Gly Thr Xaa Thr Ser Asp Xaa Xaa
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanoic
      acid

<400> SEQUENCE: 81

Xaa Xaa Gly Thr Xaa Thr Ser Asp Xaa Xaa
1               5                   10

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(1H-tetrazol-5-yl)propanoic acid
<220> FEATURE:
<221> NAME/KEY: MOD_RES
<222> LOCATION: (12)..(12)
<223> OTHER INFORMATION: 2-amino-2-methylpropanoic acid
<220> FEATURE:
<221> NAME/KEY: MOD_RES
<222> LOCATION: (14)..(14)
<223> OTHER INFORMATION: (S)-2-amino-3-(1H-tetrazol-5-yl)propanoic acid
<220> FEATURE:
<221> NAME/KEY: MOD_RES
<222> LOCATION: (19)..(19)
<223> OTHER INFORMATION: 2-amino-2-lambda-3-ethanoic acid
<220> FEATURE:
<221> NAME/KEY: MOD_RES
<222> LOCATION: (21)..(21)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (25)..(25)
<223> OTHER INFORMATION: 2-aminoacetamide

<400> SEQUENCE: 82

Xaa Xaa Gly Thr Xaa Thr Ser Xaa Tyr Ser Ile Xaa Leu Xaa Lys Ile
1               5                   10                  15

Ala Gln Xaa Ala Xaa Val Gln Gly Xaa
            20                  25

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: Substituted (S)-2-amino-3-(2'-ethyl-4'-
      methoxy-[1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanoic
      acid, or optionally substituted (S)-2-amino-5-phenylpentanoic acid

<400> SEQUENCE: 83

Xaa Gly Thr Xaa Thr Ser Asp Xaa Xaa
1               5
```

```
<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (9)..(9)
<223> OTHER INFORMATION: substituted (S)-2-amino-5-phenylpentanoic acid

<400> SEQUENCE: 84

Xaa Gly Thr Xaa Thr Ser Asp Xaa Xaa
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: Substituted (S)-2-amino-3-(2'-ethyl-4'-methoxy-
      [1,1'-biphenyl]-4-yl)propanoic acid
<220> FEATURE:
<221> NAME/KEY: MOD_RES
<222> LOCATION: (9)..(9)
<223> OTHER INFORMATION: substituted (S)-2-amino-5-phenylpentanoic acid

<400> SEQUENCE: 85

Xaa Gly Thr Xaa Thr Ser Asp Xaa Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
      or Glu
<220> FEATURE:
```

```
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (9)..(9)
<223> OTHER INFORMATION: substituted (S)-2-amino-5-phenylpentanoic acid

<400> SEQUENCE: 86

Xaa Gly Thr Xaa Thr Ser Asp Xaa Xaa
1               5

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: pegylated (S)-2-amino-3-(2'-ethyl-4'-methoxy-
      [1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 87

Xaa Xaa Gly Thr Xaa Thr Ser Asp Xaa Xaa
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
```

```
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGS via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 88

Xaa Xaa Gly Thr Xaa Thr Ser Asp Xaa Xaa
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to SGGGG via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 89

Xaa Xaa Gly Thr Xaa Thr Ser Asp Xaa Xaa
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
```

```
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 90

Xaa Xaa Gly Thr Xaa Thr Ser Asp Xaa Xaa
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 91

Xaa Xaa Gly Thr Xaa Thr Ser Asp Xaa Xaa
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide
```

<400> SEQUENCE: 92

Xaa Xaa Gly Thr Xaa Thr Ser Asp Xaa Xaa
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-amino-2,2-dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 93

Xaa Xaa Gly Thr Xaa Thr Ser Asp Xaa Xaa
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-amino-2,2-dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGS via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 94

Xaa Xaa Gly Thr Xaa Thr Ser Asp Xaa Xaa
1               5                   10

```
<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGS via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 95

Xaa Xaa Gly Thr Xaa Thr Ser Asp Xaa Xaa
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to SGGGG via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 96

Xaa Xaa Gly Thr Xaa Thr Ser Asp Xaa Xaa
1               5                   10

<210> SEQ ID NO 97
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGSGGGGS via
      the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 97

Xaa Xaa Gly Thr Xaa Thr Ser Asp Xaa Xaa
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGG via the side
      chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 98

Xaa Xaa Gly Thr Xaa Thr Ser Asp Xaa Xaa
1               5                   10

<210> SEQ ID NO 99
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGS via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 99

Xaa Xaa Gly Thr Xaa Thr Ser Asp Xaa Xaa
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to Glucosyl
      Serine-GGGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 100

Xaa Xaa Gly Thr Xaa Thr Ser Asp Xaa Xaa
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (10)..(10)
<223> OTHER INFORMATION: (S)-2-amino-5-phenylpentanamide linker

<400> SEQUENCE: 101

Xaa Xaa Gly Thr Xaa Thr Ser Asp Xaa Xaa
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 102

Xaa Xaa Gly Thr Xaa Thr Ser Asp Xaa Xaa
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
```

```
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGSGGGGS via
      the side chain
<220> FEATURE:
<221> NAME/KEY: MOD_RES
<222> LOCATION: (10)..(10)
<223> OTHER INFORMATION: (S)-2-amino-5-phenylpentanamide linker

<400> SEQUENCE: 103

Xaa Xaa Gly Thr Xaa Thr Ser Asp Xaa Xaa
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker
<220> FEATURE:
<221> NAME/KEY: MOD_RES
<222> LOCATION: (10)..(10)
<223> OTHER INFORMATION: (S)-2-amino-5-phenylpentanamide linker

<400> SEQUENCE: 104

Xaa Xaa Gly Thr Xaa Thr Ser Asp Xaa Xaa
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
```

```
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 105

Xaa Xaa Gly Thr Xaa Thr Ser Asp Xaa Xaa
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker attached to GGGGS via the
      side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 106

Xaa Xaa Gly Thr Xaa Thr Ser Asp Xaa Xaa
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
```

-continued

```
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 107

Xaa Xaa Gly Thr Xaa Thr Ser Asp Xaa Xaa
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 2-amino-2-methylpropanoic acid
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide

<400> SEQUENCE: 108

Tyr Xaa Xaa Gly Thr Xaa Thr Ser Asp Xaa Xaa
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid
<220> FEATURE:
<221> NAME/KEY: MOD_RES
<222> LOCATION: (10)..(10)
```

<223> OTHER INFORMATION: (S)-N-(4-(4,5-diamino-5-oxopentyl)benzyl)-1-
      hydroxy-3,6,9,12,15,18,21,24-octaoxaheptacosan-27-amide

<400> SEQUENCE: 109

Xaa Xaa Gly Thr Xaa Thr Ser Asp Xaa Xaa
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 110

Xaa Xaa Gly Thr Xaa Thr Ser Asp Xaa Xaa
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanoic
      acid

```
<400> SEQUENCE: 111

Xaa Xaa Gly Thr Xaa Thr Ser Asp Xaa Xaa
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid linker attached to
      GGTEPL via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 112

Xaa Xaa Gly Thr Xaa Thr Ser Asp Xaa Xaa
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid linker attached to
      benzyl hydrogen carbonate Leucine-LQGSG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide
```

```
<400> SEQUENCE: 113

Xaa Xaa Gly Thr Xaa Thr Ser Asp Xaa Xaa
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to GGGGS via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 114

Xaa Xaa Gly Thr Xaa Thr Ser Asp Xaa Xaa
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to SGGGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 115

Xaa Xaa Gly Thr Xaa Thr Ser Asp Xaa Xaa
1               5                   10
```

```
<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to GGSGGSGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 116

Xaa Xaa Gly Thr Xaa Thr Ser Asp Xaa Xaa
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to GGGGSGGGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 117

Xaa Xaa Gly Thr Xaa Thr Ser Asp Xaa Xaa
1               5                   10

<210> SEQ ID NO 118
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to GGGGSGGGGSGGGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 118

Xaa Xaa Gly Thr Xaa Thr Ser Asp Xaa Xaa
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to GGSGGSGGSGG via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 119

Xaa Xaa Gly Thr Xaa Thr Ser Asp Xaa Xaa
1               5                   10

<210> SEQ ID NO 120
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to pegylated Glycine-GGGS via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 120

Xaa Xaa Gly Thr Xaa Thr Ser Asp Xaa Xaa
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-3-(4'-(4-(1H-1,2,3-triazol-1-yl)butoxy)-2'-
      ethyl-[1,1'-biphenyl]-4-yl)-2-aminopropanoic acid linker attached
      to pegylated Glycine-GGGSGGGS via the side chain
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 121

Xaa Xaa Gly Thr Xaa Thr Ser Asp Xaa Xaa
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: pegylated (S)-3-(4'-(4-(1H-1,2,3-triazol-1-
      yl)butoxy)-2'-ethyl-[1,1'-biphenyl]-4-yl)-2-aminopropanoic acid
      linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 122

Xaa Xaa Gly Thr Xaa Thr Ser Asp Xaa Xaa
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: pegylated (S)-3-(4'-(4-(1H-1,2,3-triazol-1-
      yl)butoxy)-2'-ethyl-[1,1'-biphenyl]-4-yl)-2-aminopropanoic acid
      linker
<220> FEATURE:
<221> NAME/KEY: MOD_RES
<222> LOCATION: (10)..(10)
<223> OTHER INFORMATION: (S)-N-(4-(4,5-diamino-5-oxopentyl)benzyl)-1-
      hydroxy-3,6,9,12,15,18,21,24-octaoxaheptacosan-27-amide

<400> SEQUENCE: 123

Xaa Xaa Gly Thr Xaa Thr Ser Asp Xaa Xaa
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: 2-amino-3-(2H-tetrazol-5-yl)propanoic acid
<220> FEATURE:
<221> NAME/KEY: MOD_RES
<222> LOCATION: (5)..(5)
<223> OTHER INFORMATION: 2-amino-3-(2-fluorophenyl)-2-methylpropanoic
      acid
<220> FEATURE:
<221> NAME/KEY: MOD_RES
<222> LOCATION: (9)..(9)
<223> OTHER INFORMATION: 3-(4'-(4-(1H-1,2,3-triazol-1-yl)butoxy)-2'-
      ethyl-[1,1'-biphenyl]-4-yl)-2-aminopropanoic acid linker
<220> FEATURE:
<221> NAME/KEY: MOD_RES
<222> LOCATION: (10)..(10)
<223> OTHER INFORMATION: 2-amino-5-(3,5-dimethylphenyl)pentanamide

<400> SEQUENCE: 124

Xaa Xaa Gly Thr Xaa Thr Ser Asp Xaa Xaa
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: 2-amino-3-(2H-tetrazol-5-yl)propanoic acid
<220> FEATURE:
<221> NAME/KEY: MOD_RES
<222> LOCATION: (5)..(5)
<223> OTHER INFORMATION: 2-amino-3-(2-fluorophenyl)-2-methylpropanoic
      acid
<220> FEATURE:
<221> NAME/KEY: MOD_RES
<222> LOCATION: (9)..(9)
<223> OTHER INFORMATION: 2-amino-3-(4'-(4-(4-(25-amino-2,5,8,11,14,17,
      20,23-octaoxapentacosyl)-1H-1,2,3-triazol-1-yl)butoxy)-2'-ethyl-
      [1,1'-biphenyl]-4-yl)propanoic acid linker
<220> FEATURE:
<221> NAME/KEY: MOD_RES
<222> LOCATION: (10)..(10)
<223> OTHER INFORMATION: 2-amino-5-(3,5-dimethylphenyl)pentanamide

<400> SEQUENCE: 125

Xaa Xaa Gly Thr Xaa Thr Ser Asp Xaa Xaa
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
```

```
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 126

Xaa Xaa Gly Thr Xaa Thr Ser Asp Xaa Xaa
1               5                   10

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pegylated Glycine

<400> SEQUENCE: 127

Gly Gly Gly Gly Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pegylated Glycine

<400> SEQUENCE: 128

Gly Gly Gly Gly Ser Gly Gly Gly Gly
1               5

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
```

```
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(2'-ethyl-4'-methoxy-[1,1'-
      biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 129

Xaa Xaa Gly Thr Xaa Thr Ser Asp Xaa Xaa
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (6)..(6)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (7)..(7)
<223> OTHER INFORMATION: (S)-2-amino-5-(3,5-dimethylphenyl)pentanamide

<400> SEQUENCE: 130

Thr Xaa Thr Ser Asp Xaa Xaa
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (7)..(7)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (8)..(8)
<223> OTHER INFORMATION: (S)-2-amino-5-(3,5-dimethylphenyl)pentanamide

<400> SEQUENCE: 131

Gly Thr Xaa Thr Ser Asp Xaa Xaa
1               5

<210> SEQ ID NO 132
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (6)..(6)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (7)..(7)
<223> OTHER INFORMATION: (S)-2-amino-5-(3,5-dimethylphenyl)pentanamide

<400> SEQUENCE: 132

Thr Xaa Thr Ser Asp Xaa Xaa
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (7)..(7)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (8)..(8)
<223> OTHER INFORMATION: (S)-2-amino-5-(3,5-dimethylphenyl)pentanamide

<400> SEQUENCE: 133

Gly Thr Xaa Thr Ser Asp Xaa Xaa
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2,2-dimethylmalonic acid (S)-2-amino-3-(2H-
      tetrazol-5-yl)propanoic acid
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(3,5-dimethylphenyl)pentanamide
```

```
<400> SEQUENCE: 134

Xaa Gly Thr Xaa Thr Ser Asp Xaa Xaa
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-amino-2,2-dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 135

Xaa Xaa Gly Thr Xaa Thr Ser Asp Xaa Xaa
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(hydroxyamino)-2,2-dimethyl-3-oxopropanoic
      acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 136

Xaa Xaa Gly Thr Xaa Thr Ser Asp Xaa Xaa
1               5                   10
```

```
<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-methyl-2-(1H-pyrazol-5-yl)propanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 137

Xaa Xaa Gly Thr Xaa Thr Ser Asp Xaa Xaa
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 138

Ser Xaa Gly Thr Xaa Thr Ser Asp Xaa Xaa
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
```

```
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 139

Ala Xaa Gly Thr Xaa Thr Ser Asp Xaa Xaa
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 140

Gly Xaa Gly Thr Xaa Thr Ser Asp Xaa Xaa
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-amino-3-(2H-tetrazol-5-yl)propanoic acid
<220> FEATURE:
<221> NAME/KEY: MOD_RES
<222> LOCATION: (6)..(6)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (10)..(10)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (11)..(11)
<223> OTHER INFORMATION: (S)-2-amino-5-(3,5-dimethylphenyl)pentanamide
```

```
<400> SEQUENCE: 141

Tyr Ala Xaa Gly Thr Xaa Thr Ser Asp Xaa Xaa
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-amino-2-methylpropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-aminobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 142

Xaa Xaa Gly Thr Xaa Thr Ser Asp Xaa Xaa
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-amino-2-methylpropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 143

Xaa Xaa Gly Thr Xaa Thr Ser Asp Xaa Xaa
1               5                   10

<210> SEQ ID NO 144
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (7)..(7)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (8)..(8)
<223> OTHER INFORMATION: (S)-2-amino-5-(4-(4-
      aminobutoxy)phenyl)pentanamide

<400> SEQUENCE: 144

Gly Thr Xaa Thr Ser Asp Xaa Xaa
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-amino-3-(2H-tetrazol-5-yl)propanoic acid
<220> FEATURE:
<221> NAME/KEY: MOD_RES
<222> LOCATION: (4)..(4)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (8)..(8)
<223> OTHER INFORMATION: (S)-2-amino-3-(2'-ethyl-4'-methoxy-[1,1'-
      biphenyl]-4-yl)propanoic acid
<220> FEATURE:
<221> NAME/KEY: MOD_RES
<222> LOCATION: (9)..(9)
<223> OTHER INFORMATION: (S)-2-amino-5-(4-(4-
      aminobutoxy)phenyl)pentanamide

<400> SEQUENCE: 145

Xaa Gly Thr Xaa Thr Ser Asp Xaa Xaa
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
```

```
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-
      (aminomethyl)phenyl)pentanamide

<400> SEQUENCE: 146

Xaa Xaa Gly Thr Xaa Thr Ser Asp Xaa Xaa
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-(13-amino-3,6,9,12-tetraoxo-
      2,5,8,11-tetraazatridecyl)phenyl)pentanamide attached to GGGG
      via the side chain

<400> SEQUENCE: 147

Xaa Xaa Gly Thr Xaa Thr Ser Asp Xaa Xaa
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
```

```
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-N-(4-(4,5-diamino-5-oxopentyl)benzyl)-1-
      hydroxy-3,6,9,12-tetraoxapentadecan-15-amide

<400> SEQUENCE: 148

Xaa Xaa Gly Thr Xaa Thr Ser Asp Xaa Xaa
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-azidobutoxy)-2'-ethyl-
      [1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(4-(25-amino-3,6,9,12,15,18,21,
      24-octaoxo-2,5,8,11,14,17,20,23-
      octaazapentacosyl)phenyl)pentanamide attached to GGGGGGGG via the
      side chain

<400> SEQUENCE: 149

Xaa Xaa Gly Thr Xaa Thr Ser Asp Xaa Xaa
1               5                   10

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-(tert-butoxycarbonyl)-O-(tert-butyl)-L-serine

<400> SEQUENCE: 150

Ser Gly Gly Gly Gly
1               5

<210> SEQ ID NO 151
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-(((9H-fluoren-9-yl)methoxy)carbonyl)-O-
      ((2R,3R,4S,5R,6R)-3,4,5-triacetoxy-6-(acetoxymethyl)tetrahydro-2H-
      pyran-2-yl)-L-serine

<400> SEQUENCE: 151

Ser Gly Gly Gly Gly
1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Pro Ser Thr Gly Gly
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (4,7,10,13,16,19,22,25-octaoxaoctacos-27-
      ynoyl)-L-leucine-(S)-5-(((2S,3R)-1-((2-((carboxymethyl)amino)-2-
      oxoethyl)amino)-3-hydroxy-1-oxobutan-2-yl)amino)-5-oxo-4-((S)-
      pyrrolidine-2-carboxamido)pentanoic acid

<400> SEQUENCE: 153

Leu Pro Ser Thr Gly Gly
1               5

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glycine attached to the side chain of position
      10 of XXGTXTSDXX

<400> SEQUENCE: 154

Gly Gly Gly Gly
1

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: Glycine attached to the side chain of position
      10 of XXGTXTSDXX

<400> SEQUENCE: 155

Gly Gly Gly Gly Gly Gly Gly Gly
1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Serine attached to the side chain of position 9
      of XXGTXTSDXX

<400> SEQUENCE: 156

Gly Gly Gly Gly Ser
1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glycine attached to the side chain of position
      9 of XXGTXTSDXX

<400> SEQUENCE: 157

Ser Gly Gly Gly Gly
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Serine attached to the side chain of position 9
      of XXGTXTSDXX

<400> SEQUENCE: 158

Gly Gly Gly Gly Ser
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
```

```
<223> OTHER INFORMATION: Serine attached to the side chain of position 9
      of XXGTXTSDXX

<400> SEQUENCE: 159

Gly Gly Gly Gly Ser
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glycine attached to the side chain of position
      9 of XXGTXTSDXX

<400> SEQUENCE: 160

Ser Gly Gly Gly Gly
1               5

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Serine attached to the side chain of position 9
      of XXGTXTSDXX

<400> SEQUENCE: 161

Gly Gly Gly Gly Ser Gly Gly Gly Gly Ser
1               5                   10

<210> SEQ ID NO 162
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glycine attached to the side chain of position
      9 of XXGTXTSDXX

<400> SEQUENCE: 162

Gly Gly Gly Gly
1

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Serine attached to the side chain of position 9
      of XXGTXTSDXX
```

```
<400> SEQUENCE: 163

Gly Gly Gly Gly Ser
1               5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glucosyl Serine
<220> FEATURE:
<221> NAME/KEY: MOD_RES
<222> LOCATION: (5)..(5)
<223> OTHER INFORMATION: Glycine attached to the side chain of position
      9 of XXGTXTSDXX

<400> SEQUENCE: 164

Ser Gly Gly Gly Gly
1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Serine attached to the side chain of position 9
      of XXGTXTSDXX

<400> SEQUENCE: 165

Gly Gly Gly Gly Ser
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Leucine attached to the side chain of position
      9 of XXGTXTSDXX

<400> SEQUENCE: 166

Gly Gly Thr Glu Pro Leu
1               5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: benzyl hydrogen carbonate Leucine
<220> FEATURE:
<221> NAME/KEY: MOD_RES
```

```
<222> LOCATION: (3)..(3)
<223> OTHER INFORMATION: Glutamine attached to the side chain of
      position 9 of XXGTXTSDXX

<400> SEQUENCE: 167

Leu Leu Gln Gly Ser Gly
1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Serine attached to the side chain of position 9
      of XXGTXTSDXX

<400> SEQUENCE: 168

Gly Gly Gly Gly Ser
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glycine attached to the side chain of position
      9 of XXGTXTSDXX

<400> SEQUENCE: 169

Ser Gly Gly Gly Gly
1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Glycine attached to the side chain of position
      9 of XXGTXTSDXX

<400> SEQUENCE: 170

Gly Gly Ser Gly Gly Ser Gly Gly
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Glycine attached to the side chain of position
      9 of XXGTXTSDXX
```

```
<400> SEQUENCE: 171

Gly Gly Gly Gly Ser Gly Gly Gly Gly
1               5

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Glycine attached to the side chain of position
      9 of XXGTXTSDXX

<400> SEQUENCE: 172

Gly Gly Gly Gly Ser Gly Gly Gly Gly Ser Gly Gly Gly Gly
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Glycine attached to the side chain of position
      9 of XXGTXTSDXX

<400> SEQUENCE: 173

Gly Gly Ser Gly Gly Ser Gly Gly Ser Gly Gly
1               5                   10

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pegylated Glycine
<220> FEATURE:
<221> NAME/KEY: MOD_RES
<222> LOCATION: (5)..(5)
<223> OTHER INFORMATION: Serine attached to the side chain of position 9
      of XXGTXTSDXX

<400> SEQUENCE: 174

Gly Gly Gly Gly Ser
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pegylated Glycine
```

```
<220> FEATURE:
<221> NAME/KEY: MOD_RES
<222> LOCATION: (9)..(9)
<223> OTHER INFORMATION: Serine attached to the side chain of position 9
      of XXGTXTSDXX

<400> SEQUENCE: 175

Gly Gly Gly Gly Ser Gly Gly Gly Ser
1               5

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glycine attached to the side chain of position
      10 of XXGTXTSDXX

<400> SEQUENCE: 176

Gly Gly Gly Gly
1

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Glycine attached to the side chain of position
      10 of XXGTXTSDXX

<400> SEQUENCE: 177

Gly Gly Gly Gly Gly Gly Gly Gly
1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Serine attached to the side chain of position 9
      of XXGTXTSDXX

<400> SEQUENCE: 178

Gly Gly Gly Gly Ser Gly Gly Gly Gly Ser
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic-(PEG)4-pegylated (S)-2-amino-3-(2'-
      ethyl-4'-methoxy-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 179

Xaa Xaa Gly Thr Xaa Thr Ser Asp Xaa Xaa
 1               5                   10

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic-(PEG)8-pegylated (S)-2-amino-3-(2'-
      ethyl-4'-methoxy-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 180

Xaa Xaa Gly Thr Xaa Thr Ser Asp Xaa Xaa
 1               5                   10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
```

```
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic-(PEG)12-pegylated (S)-2-amino-3-(2'-
      ethyl-4'-methoxy-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 181

Xaa Xaa Gly Thr Xaa Thr Ser Asp Xaa Xaa
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic-(PEG)24-pegylated (S)-2-amino-3-(2'-
      ethyl-4'-methoxy-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 182

Xaa Xaa Gly Thr Xaa Thr Ser Asp Xaa Xaa
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
```

```
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Bicyclic-(PEG)4-pegylated (S)-2-amino-3-(2'-
      ethyl-4'-methoxy-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 183

Xaa Xaa Gly Thr Xaa Thr Ser Asp Xaa Xaa
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic-(PEG)4-pegylated (S)-3-(4'-(4-(1H-
      1,2,3-triazol-1-yl)butoxy)-2'-ethyl-[1,1'-biphenyl]-4-yl)-2-
      aminopropanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 184

Xaa Xaa Gly Thr Xaa Thr Ser Asp Xaa Xaa
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
```

```
<223> OTHER INFORMATION: Bicyclic-(PEG)4-pegylated (S)-3-(4'-(4-(1H-
      1,2,3-triazol-1-yl)butoxy)-2'-ethyl-[1,1'-biphenyl]-4-yl)-2-
      aminopropanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 185

Xaa Xaa Gly Thr Xaa Thr Ser Asp Xaa Xaa
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Monocyclic-(PEG)4-pegylated (S)-3-(4'-(4-(1H-
      1,2,3-triazol-1-yl)butoxy)-2'-ethyl-[1,1'-biphenyl]-4-yl)-2-
      aminopropanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 186

Xaa Xaa Gly Thr Xaa Thr Ser Asp Xaa Xaa
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tricyclic (S)-2-amino-3-(4'-(4-(4-(25-amino-
      2,5,8,11,14,17,20,23-octaoxapentacosyl)-1H-1,2,3-triazol-1-yl)
      butoxy)-2'-ethyl-[1,1'-biphenyl]-4-yl)propanoic acid linker
<220> FEATURE:
```

```
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 187

Xaa Xaa Gly Thr Xaa Thr Ser Asp Xaa Xaa
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 6-(1H-imidazol-4-yl)hexanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: Tetracyclic (S)-2-amino-3-(4'-(4-(4-(25-amino-
      2,5,8,11,14,17,20,23-octaoxapentacosyl)-1H-1,2,3-triazol-1-yl)
      butoxy)-2'-ethyl-[1,1'-biphenyl]-4-yl)propanoic acid linker
<220> FEATURE:
<221> NAME/KEY: MOD_RES
<222> LOCATION: (10)..(10)
<223> OTHER INFORMATION: (S)-2-amino-5-(3,5-dimethylphenyl)pentanamide

<400> SEQUENCE: 188

Xaa Xaa Gly Thr Xaa Thr Ser Asp Xaa Xaa
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanoic
      acid
```

```
<400> SEQUENCE: 189

Xaa Xaa Gly Thr Xaa Thr Ser Asp Xaa Xaa
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-((2-(1H-imidazol-5-yl)ethyl)amino)-2,2-
      dimethyl-3-oxopropanoic acid
<220> FEATURE:
<221> NAME/KEY: MOD_RES
<222> LOCATION: (2)..(2)
<223> OTHER INFORMATION: (S)-2-amino-3-(2H-tetrazol-5-yl)propanoic acid
<220> FEATURE:
<221> NAME/KEY: MOD_RES
<222> LOCATION: (5)..(5)
<223> OTHER INFORMATION: (S)-2-amino-3-(2-fluorophenyl)-2-
      methylpropanoic acid
<220> FEATURE:
<221> NAME/KEY: MOD_RES
<222> LOCATION: (9)..(9)
<223> OTHER INFORMATION: (S)-2-amino-3-(4'-(4-(4-(25-amino-2,5,8,11,14,
      17,20,23-octaoxapentacosyl)-1H-1,2,3-triazol-1-yl)butoxy)-2'-
      ethyl-[1,1'-biphenyl]-4-yl)propanoic acid linker attached to a
      glutamic acid
<220> FEATURE:
<221> NAME/KEY: MOD_RES
<222> LOCATION: (10)..(10)
<223> OTHER INFORMATION: (S)-2-amino-5-(3,5-dimethylphenyl)pentanoic
      acid

<400> SEQUENCE: 190

Xaa Xaa Gly Thr Xaa Thr Ser Asp Xaa Xaa
1               5                   10
```